United States Patent
Short

(10) Patent No.: US 7,033,781 B1
(45) Date of Patent: Apr. 25, 2006

(54) WHOLE CELL ENGINEERING BY MUTAGENIZING A SUBSTANTIAL PORTION OF A STARTING GENOME, COMBINING MUTATIONS, AND OPTIONALLY REPEATING

(75) Inventor: Jay M. Short, Rancho Santa Fe, CA (US)

(73) Assignee: Diversa Corporation, San Diego, CA (US)

(*) Notice: Subject to any disclaimer, the term of this patent is extended or adjusted under 35 U.S.C. 154(b) by 698 days.

(21) Appl. No.: 09/677,584

(22) Filed: Sep. 30, 2000

Related U.S. Application Data

(63) Continuation-in-part of application No. 09/594,459, filed on Jun. 14, 2000, which is a continuation-in-part of application No. 09/552,289, filed on Mar. 9, 2000, now Pat. No. 6,358,709, which is a continuation-in-part of application No. 09/498,557, filed on Feb. 4, 2000, which is a continuation-in-part of application No. 09/495,052, filed on Jan. 31, 2000, said application No. 09/677,584.

(60) Provisional application No. 60/156,815, filed on Sep. 29, 1999.

(51) Int. Cl.
C12P 21/06 (2006.01)
C12Q 1/68 (2006.01)

(52) U.S. Cl. .......................... 435/69.1; 435/6
(58) Field of Classification Search .............. 435/6, 435/69.1
See application file for complete search history.

(56) References Cited

FOREIGN PATENT DOCUMENTS

| | | |
|---|---|---|
| FR | 2 761 576 | 10/1998 |
| WO | WO 97 26334 | 7/1997 |
| WO | WO 98/31837 | 7/1998 |
| WO | WO 00/04190 | 1/2000 |
| WO | WO 00/18906 | 4/2000 |
| WO | WO 00/55346 | 9/2000 |
| WO | WO 01/02555 | 1/2001 |

OTHER PUBLICATIONS

Hutchison et al., "Global Transposon Mutagenesis and a Minimal Mycoplasma Genome," Science, vol. 286, No. 5447, Dec. 10, 1999, pp 2165–2169.

"Defined Oligonucleotide Tag Pools and PCR Screening in Signature–Tagged Mutagenesis of Essential Genes From Bacteria," Biotechniques, Eaton Publishing, vol. 26, No. 3, Mar. 1999, pp 473–474, 476, 478–480.

Hensel et al., "Simultaneous Identification of Bacterial Virulence Genes by Negative Selection," Science, vol. 269, Jul. 21, 1995, pp 400–403.

Primary Examiner—Hankyel T. Park
(74) Attorney, Agent, or Firm—Jane M. Love; Hale and Dorr LLP

(57) ABSTRACT

An invention comprising cellular transformation, directed evolution, and screening methods for creating novel transgenic organisms having desirable properties. Thus in one aspect, this invention relates to a method of generating a transgenic organism, such as a microbe or a plant, having a plurality of traits that are differentially activatable. Also, a method of retooling genes and gene pathways by the introduction of regulatory sequences, such as promoters, that are operable in an intended host, thus conferring operability to a novel gene pathway when it is introduced into an intended host. For example a novel man-made gene pathway, generated based on microbially-derived progenitor templates, that is operable in a plant cell. Furthermore, a method of generating novel host organisms having increased expression of desirable traits, recombinant genes, and gene products.

24 Claims, 28 Drawing Sheets

Panel A.
Panel B.
Panel C.
Panel D.
FIG. 3

Figure 4B:
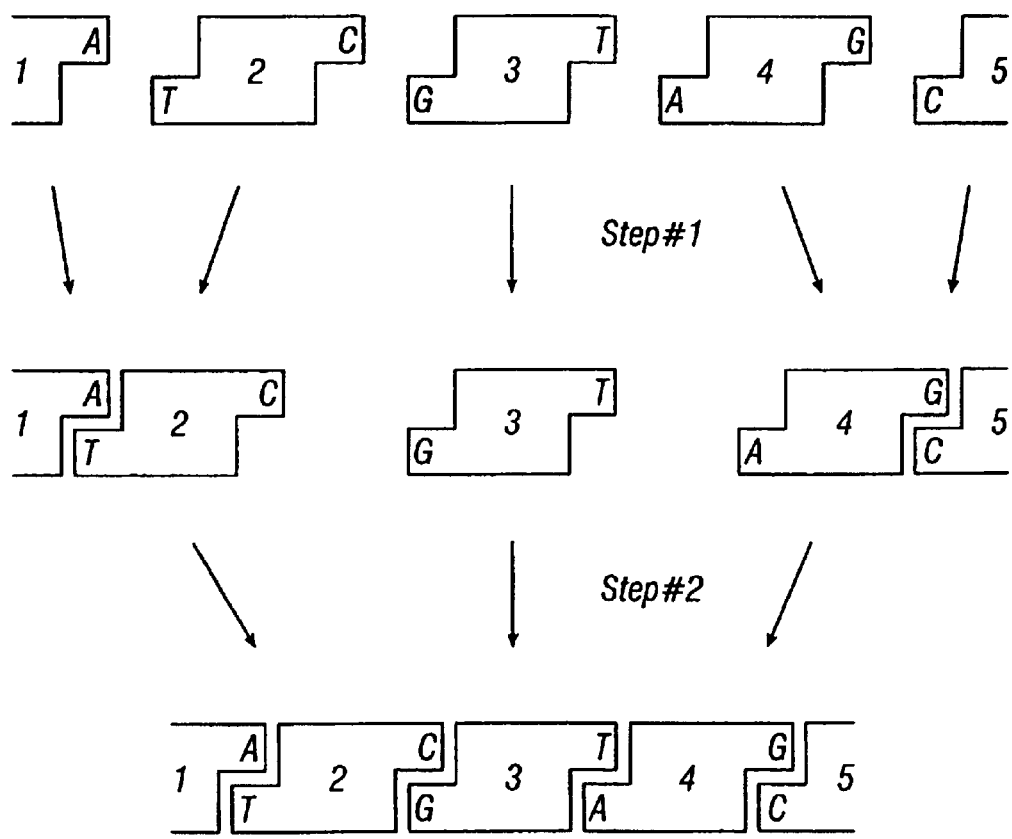

Panel A.
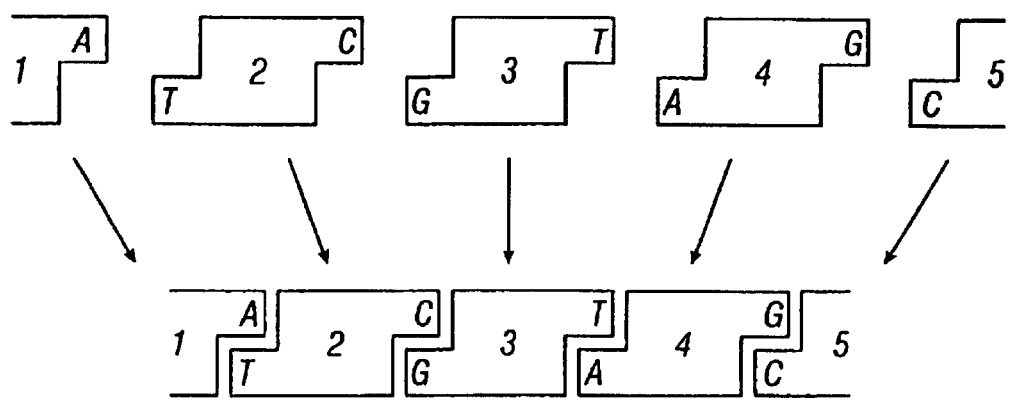
Panel B.
FIG. 4A

FIG. 5

```
                                                                    100
ACACGGGCCA  GGGTGATTCC  GTTCTGTTTC  TTCACGGCAA  CCCGACGTCG
ACGTGGGAGA  GGGCGACCCG  ATCGTGTTCC  TCCACGGAAA  TCCCACGTCG
AGATGGGCGA  GGGTGATCCC  ATCATTTTCC  AACACGGCAA  TCCGACCTCA
ACGAAGGCAA  GGGTGACGCC  ATCGTCTTTC  AGCACGGCAA  CCCCACGTCG
AAGTGGGACG  GGGCGACCCC  ATCGTACTCT  TGCACGGCAA  CCCCACCTCG
ATACCGGCGA  GGGAGCGCCG  ATCGTGTTCC  TTCACGGCAA  CCCGACTTCC
GCGTCGGCGA  T...CTTCCC  GTCGTGTTCC  TGCACGGCAA  CCCCACGTCG
GACCGCGGGA  TGGCACGCCT  GTGCTGTTCC  TGCACGGTAA  CCCGACCTCG
----------  ----------  -T--T--T-.  --CACGG-AA  -CC-AC-TC-

FIG. 6B

150
TCGTATCTGT  GGAGGGGCGT  AATGCCTTTT  GTGACGGACG  TCGCCCGATG
TCGTACCTGT  GGCGGAACGT  GATTCCCCAC  GTTGCCGGCT  TGGGACGCTG
TCGTACCTGT  GGCGCAACAT  CATGCCCCAT  GTGCAACAGC  TCGGTCGCTG
TCGTACCTGT  GGCGCAACAT  CATGCCCGCA  TTGGAAGGGC  TGGGCCGGCT
TCTTACTTGT  GGCGCAACGT  GTTGCCGCAC  CTGGCGCCGT  TAGGCCGCTG
TCGTACCTCT  GGCGCAACAT  CATCCCCTAT  CTCGCGCGGA  ACGGCAGATG
TCCTATCTTT  GGCGCAACGT  CATCCCGCAC  GTCGCTGGCC  AGCACCGGTG
TCTCACGTCT  GGCGCAACAT  GATCCCCGCA  GTCGCTGGCC  AGCACCGGTG
TCCTACCTGT  GGCGCAACAT  CATCCCGCAT  GTAGCACCGA  GTCATCGGTG
TC--A--T-T  GG-G----C-T  --T-CC----  --T------  ------G---

Represents 15% of gene

FIG. 6C
```

```
                                                                                                      CCGT
            NcoI
150am13_00  cATGATGCACG GCGATATTTC ATCGAGCAAT GACACGGTCG GCGTTGCCGT
150AM7_001  cATGCATCACG GCGACATTTC ATCGAGCAAT GACACGGTCG GCGTTGCCGT
431am7_002  cATGAGACACG GAGATATCTC CAGCAGCAAC GATTGCGTGG GCGTGGCCGT

GAG GT
150am13_00  CGTGAACTAC AAGATGCCTC GCCTTCATAC CAAGGCGAG  GTTTTAGCGA
150AM7_001  CGTGAACTAC AAGATGCCGC GGCTTCACAC CAAGGCTGAG GTGCTGGCCA
431am7_002  CGTGAACTAC AAGATGCCGC GGCTGCATAC CCGCGCGAG  GTGATGGAGA

CGG
150am13_00  ACGCCAGAAA GATCGGCGAG ATGATCGTCG GCATGAAGAC CGGCCTGCCC
150AM7_001  ACTGCCCGCA GATCGCCGAC ATGCTGGTCG GCATGAAGAG CGGCCTGCCG
431am7_002  ACGCCCGCAA GATCGCCGAC ATGGTCGTGG GCATGAAGCG CGGCCTGCCC

CCACG
150am13_00  GGAATGGATC TGGTGATCTT CCCGGAATAT TCGACCCTGCCC GCATCATGTA
150AM7_001  GGAATGGATC TGGTGATCTT CCCGGAATAT TCCACCCACG GCATCATGTA
431am7_002  GGCATGGACC TGGTCATCTT CCCCGAGTAC TCCACCCACG GCATCATGTA

CCC  GG
150am13_00  CGACTCCAAG GAAATGTACG ATACCGCGTC CGTCGTGCCC GGCGAGGAGA
150AM7_001  CGACTCCAAG GAGATGTACG ACACGGCGTC GACGGTGCCG GGTGAAGAGA
431am7_002  CGACGCCAAG GAAATGTACG AAACCGCTTC GGCCATTCCG GGCGAAGAGA

G GGG
150am13_00  CCGAGATTTT TGCCGAAGCC TGCCGCAAGG CGAAAGTCTG GGGCGTGTTC
150AM7_001  CCGAGATTTT CGCCGAGGCC TGCCGCAAGG CCAAGGTCTG GGGCGTGTTC
431am7_002  CTGCTGTGTT CGCCGACGCC TGCCGCAAGG CCAACGTATG GGGCGTGTTT
```

FIG. 7A

```
                                                                              AAAG   C
150am13_00   TCGCTCACCG GCGAACGTCA CGAGGAACAT CCGAAGAAGG CGCCCTACAA
150AM7_001   TCGCTGACCG GCGAGCGCCA CGAGGAGCAT CCCAATAAAG CGCCGTACAA
431am7_002   TCGCTGACGG GCGAGCGCCA CGAAGAGCAC CCGAACAAGG CGCCGTACAA
                                                         CAG   AA
150am13_00   CACGCTGATC CTGATGAACG ACAAGGGCGA GGTGGTCCAG AAATACCGCA
150AM7_001   CACCCTGATC CTGATGAACG ACAAGGGTGA AGTCGTTCAG AAATATCGCA
431am7_002   CACGCTCATC CTGATGAACA ACAAGGGCGA GATCGTGCAG AAGTACCGCA
                                                   GGTA
150am13_00   AGATCATGCC GTGGGTTCCG ATCGAGGGCT GGTACCCCGG CAACTGCACC
150AM7_001   AGATCATGCC GTGGGTGCCG ATCGAAGGCT GGTATCCCGG CAACTGCACG
431am7_002   AGATCATGCC CTGGGTGCCG ATCGAAGGCT GGTATCCGGG CGATTGCACC
                                        TGAAG
150am13_00   TACGTCTCCG ACGGGCCGAA GGGCATGAAG GTTTCGCTGA TCATCTGCGA
150AM7_001   TACGTCTCCG AAGGCCCGAA GGGCATGAAG ATGTCGCTGA TCATCTGCGA
431am7_002   TATGTGTCGG AAGGCCCCAA GGGACTGAAG CGATTGCACC TCATCTGCGA
                                        TCTGGCG
150am13_00   TGACGGCAAC TATCCGGAAA GGGCATGAAG CTGCGCCATG AAGGGCGCCG
150AM7_001   CGACGGCAAC TACCCGGAAA TCTGGCGCGA CTGCGCGATG AAGGGCGCCG
431am7_002   CGACGGCAAT TACCCCGAGA TCTGGCGCGA TTGCGCCATG CGCGGCGCCG
                         CCAG
150am13_00   AGCTGATCGT GCGCTGCCAG GGCTACATGT ATCCGGCCAA GGACCAGCAG
150AM7_001   AACTGATCAT CCGCTGCCAG GGCTACATGT ATCCCGGCCAA GGATCAGCAG
431am7_002   AGCTGATCGT GCGTTGCCAG GGATACATGT ACCCGGCCAA GGACCAGCAG
```

*FIG. 7B*

```
150am13_00   GTCATCATGG  CGAAGGCGAT  GGCGTGGGCG  AATAATTGTT  ACGTCGCGGT
150AM7_001   GTGCTGATGG  CGAAAGCAAT  GGCCTGGGCC  AACAACGTTT  ATGTCGCGGT
431am7_002   GTCATGGTGT  CCAAGCCAT   GGCGTGGATG  AACAACGTCT  ACGTGGCGGT
                             GC
                         GGGCTTCG
150am13_00   TTCCAATGCC  GCGGGCTTCG  ATGGCGTCTA  TTCGTATTTC  GGCCACTCGG
150AM7_001   CGCCAATGCC  TCGGGCTTCG  ACGGCGTCTA  CTCGTATTTC  GGCCATTCGG
431am7_002   GGCCAATGCC  GCGGGCTTCG  ACGGCGTGTA  TTCCTACTTC  GGCCATTCGG
                           TTCGA
150am13_00   CGATCATCGG  CTTCGATGGC  CGCACGCTCG  GCGAATGCGG  CGAGGAAGAA
150AM7_001   CGATCATCGG  CTTCGACGGC  CGTACCCCTC  GCGAATGCGG  CGAGGAGGAT
431am7_002   CCATCATCGG  CTTCGACGGC  CGCACGCTGG  GCGAATGCGG  TGAAGAAGAC
                         C AGTA
150am13_00   TACGGCATCC  AGTATGCCCA  GCTTTCGAAG  ATGCTGATCC  GCGACGCCCG
150AM7_001   TATGGCATCC  AGTATGCCGC  CATCTCCAAG  TCGCTGATCC  GCGACGGCG
431am7_002   ATGGGCGTGC  AGTACGCCGA  GCTCTCCACC  AGCCTGATCC  GCGACGCGCG
                         CAATC
150am13_00   CCGCACCGGA  CAATGGAAA   ACCATCTCTT  CAAGCTGGTG  CATCGTGGCT
150AM7_001   CCGCACCGGC  CAATGGAAA   ACCATCTCTT  CAAGCTGGTG  CACCGTGGCT
431am7_002   CAAGAACATG  CAGTGCAGA   ACCACTTGTT  CAAGCTGGTG  CACCGGCT
             GATCAA
150am13_00   ACACCGGGTT  GATCAACTCC  GGCGAGGGCG  ACCGCGGTCT  CGCGGCCTGT
150AM7_001   ACACCGGCAT  GATCAATTCC  GGCGAGGGCG  ACCGCGGTGT  CGCGGCTTGC
431am7_002   ACACCGGCAA  GATCAATTCC  GGCGAAGAGG  CCACCGGCGT  CGCGGCATGC
```

*FIG. 7C*

```
150am13_00   CCTTATGAGT  TCTACAACAA  ATGGATCGCC  GATCCGGAAG  GCACCCGCGA
150AM7_001   CCGTATGATT  TCTATTCGAA  ATGGATCGCC  GATCCCGAGG  GTACACGCGA
431am7_002   CCGTACAACT  TCTACGCCAA  CTGGATCAAC  GATCCGGAGG  GCACGCGCAA

150am13_00   AATGGTCGAG  TCCTTTACCC  GGCCGACGGT  GGGAACCGAT  GAAGCGCCCA
150AM7_001   GATGGTGGAA  TCCTTCACGC  GTCCGACGGT  GGGTGTGGAG  GAATGCCCGA
431am7_002   GATGGTCGAA  TCCTTCACCC  GGTCCACCGT  GGGCACGCCG  GAGTGCCCCA

150am13_00   TCGAAGGCAT  CCCGAACAAG  GTCGCGGTGC  ACCGCTGA   aagct
150AM7_001   TCGAGGGCAT  TCCGAACAAG  GCCACCACGC  ACCGCTGA   aagct
431am7_002   TGGACGGCAT  CCCCAACGAG  GACGCCAAGC  ACCGCTAG   aagct
                                                            HindIII
```

FIG. 7D

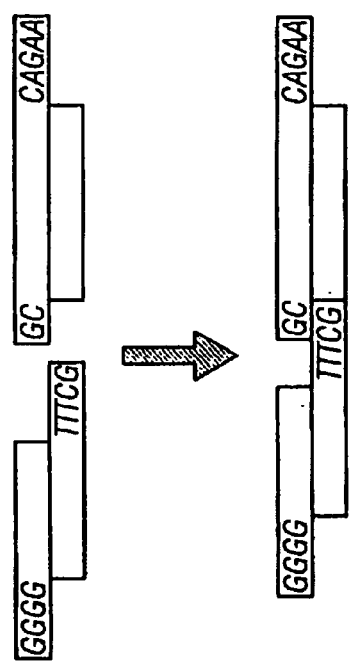
FIG. 9
FIG. 10
Gap Ligation

SEQUENCE LISTING

<160> NUMBER OF SEQ ID NOS: 33

<210> SEQ ID NO 1
<211> LENGTH: 5818
<212> TYPE: DNA
<213> ORGANISM: Escherichia coli

<400> SEQUENCE: 1

| | | | | | |
|---|---|---|---|---|---|
| ctgactctta | tacacaagta | gcgtcctgaa | cggaaccttt | cccgttttcc | aggatctgac | 60 |
| ttccatgtga | cctcctaaca | tggtaacgtt | catgataact | tctgctcttc | atcgtgcggc | 120 |
| cgactgggct | aaatctgtgt | tctcttcggc | ggcgctgggt | gatcctcgcc | gtactgcccg | 180 |
| cttggttaac | gtcgccgccc | aattggcaaa | atattctggt | aaatcaataa | ccatctcatc | 240 |
| agagggtagt | gaagccatgc | aggaaggcgc | ttaccgattt | taccgcaatc | ccaacgtttc | 300 |
| tgccgaggcg | atcagaaagg | ctggcgccat | gcaaacagtc | aagttggctc | aggagtttcc | 360 |
| cgaactgctg | gccattgagg | acaccacctc | tttgagttat | cgccaccagg | tcgccgaaga | 420 |
| gcttggcaag | ctgggctcta | ttcaggataa | atcccgcgga | tggtgggttc | actccgttct | 480 |
| cttgctcgag | gccaccacat | tccgcaccgt | aggattactg | catcaggagt | ggtggatgcg | 540 |
| cccggatgac | cctgccgatg | cggatgaaaa | ggagagtggc | aaatggctgg | cagcggccgc | 600 |
| aactagccgg | ttacgcatgg | gcagcatgat | gagcaacgtg | attgcggtct | gtgaccgcga | 660 |
| agccgatatt | catgcttatc | tgcaggacag | gctggcgcat | aacgagcgct | tcgtggtgcg | 720 |
| ctccaagcac | ccacgcaagg | acgtagagtc | tgggttgtat | ctgatcgacc | atctgaagaa | 780 |
| ccaaccggag | ttgggtggct | atcagatcag | cattccgcaa | aagggcgtgg | tggataaacg | 840 |
| cggtaaacgt | aaaaatcgac | cagcccgcaa | ggcgagcttg | agcctgcgca | gtgggcgcat | 900 |
| cacgctaaaa | caggggaata | tcacgctcaa | cgcggtgctg | gccgaggaga | ttaacccgcc | 960 |
| caagggtgag | accccgttga | aatggttgtt | gctgaccggc | gaaccggtcg | agtcgctagc | 1020 |
| ccaagccttg | cgcgtcatcg | acatttatac | ccatcgctgg | cggatcgagg | agttccataa | 1080 |
| ggcatggaaa | accggagcag | gagccgagag | gcaacgcatg | gaggagccgg | ataatctgga | 1140 |
| gcggatggtc | tcgatcctct | cgtttgttgc | ggtcaggctg | ttacagctca | gagaaagctt | 1200 |
| cacgctgccg | caagcactca | gggcgcaagg | gctgctaaag | gaagcggaac | acgtagaaag | 1260 |
| ccagtccgca | gaaacggtgc | tgaccccgga | tgaatgtcag | ctactgggct | atctggacaa | 1320 |
| gggaaaacgc | aagcgcaaag | agaaagcagg | tagcttgcag | tgggcttaca | tggcgatagc | 1380 |
| tagactgggc | ggttttatgg | acagcaagcg | aaccggaatt | gccagctggg | gcgccctctg | 1440 |
| gtaaggttgg | gaagccctgc | aaagtaaact | ggatggcttt | cttgccgcca | aggatctgat | 1500 |
| ggcgcagggg | atcaagatct | gatcaagaga | caggatgagg | atcgtttcgc | atgattgaac | 1560 |
| aagatggatt | gcacgcaggt | tctccggccg | cttgggtgga | gaggctattc | ggctatgact | 1620 |
| gggcacaaca | gacaatcggc | tgctctgatg | ccgccgtgtt | ccggctgtca | gcgcagggc | 1680 |
| gcccggttct | ttttgtcaag | accgacctgt | ccggtgccct | gaatgaactg | caggacgagg | 1740 |
| cagcgcggct | atcgtggctg | gccacgacgg | gcgttccttg | cgcagctgtg | ctcgacgttg | 1800 |
| tcactgaagc | gggaagggac | tggctgctat | tgggcgaagt | gccggggcag | gatctcctgt | 1860 |
| catctcacct | tgctcctgcc | gagaaagtat | ccatcatggc | tgatgcaatg | cggcggctgc | 1920 |
| atacgcttga | tccggctacc | tgcccattcg | accaccaagc | gaaacatcgc | atcgagcgag | 1980 |
| cacgtactcg | gatggaagcc | ggtcttgtcg | atcaggatga | tctggacgaa | gagcatcagg | 2040 |

-continued

```
ggctcgcgcc agccgaactg ttcgccaggc tcaaggcgcg catgcccgac ggcgaggatc    2100
tcgtcgtgac ccatggcgat gcctgcttgc cgaatatcat ggtggaaaat ggccgctttt    2160
ctggattcat cgactgtggc cggctgggtg tggcggaccg ctatcaggac atagcgttgg    2220
ctacccgtga tattgctgaa gagcttggcg gcgaatgggc tgaccgcttc ctcgtgcttt    2280
acggtatcgc cgctcccgat tcgcagcgca tcgccttcta tcgccttctt gacgagttct    2340
tctgagcggg actctggggt tcgaaatgac cgaccaagcg acgcccaacc tgccatcacg    2400
agatttcgat tccaccgccg ccttctatga aggttgggc ttcggaatcg ttttccggga     2460
cgccggctgg atgatcctcc agcgcgggga tctcatgctg gagttcttcg cccacccccgg   2520 gctcgatccc ctcgcgagtt ggttcagctg ctgcctgagg ctggacgacc tcgcggagtt    2580
ctaccggcag tgcaaatccg tcggcatcca ggaaaccagc agcggctatc cgcgcatcca    2640 tgccccgaa ctgcaggagt gggaggcac gatggccgct ttggtcgacc cggacgggac     2700
gctcctgcgc ctgatacaga acgaattgct tgcaggcatc tcatgagtgt gtcttcccgt    2760
tttccgcctg aggtcactgc gtggatggag cgctggcgcc tgctgcgcga cggcgagctg    2820
ctcaccaccc actcgagctg gatacttccc gtccgccagg gggacatgcc ggcgatgctg    2880
aaggtcgcgc gcattcccga tgaagaggcc ggttaccgcc tgttgacctg gtgggacggg    2940
cagggcgccg cccgagtctt cgcctcggcg gcgggcgctc tgctcatgga gcgcgcgtcc    3000
ggggccgggg accttgcaca gatagcgtgg tccggccagg acgacgaggc ttgcaggatc    3060
ctctgcgaca ccgccgctcg tctgcacgcg ccgcggtccg gaccgccgcc cgatctccat    3120
ccgctacagg aatggttcca gccgcttttc cggttggccg ctgagcacgc ggcacttgcg    3180
cccgccgcca gcgtagcgcg ccaacttctg gcggcgccgc gcgaggtgtg cccgctccac    3240
ggcgacctgc accacgagaa cgtgctcgac ttcgcgacc cggctggct ggccatcgac      3300 ccgcacggac tgctcggcga gcgcaccttc gactatgcca acatcttcac gaatcccgat    3360
ctcagcgacc ccggtcgccc gcttgcgatc ctgccgggca ggctggaggc tcgactcagc    3420
attgtggtcg cgacgaccgg gtttgagccc gaacggcttc ttcgctggat cattgcatgg    3480
acgggcttgt cggcagcctg gttcatcggc gacggcgacg gcgagggcga gggcgctgcg    3540
attgatctgg ccgtaaacgc catggcacgc cggttgcttg actagcgcgg tcaccgatct    3600
cacctggtcg tcgagctagg tcaggccgtg tcgggcgtga tccgctggaa gtcgttgcgg    3660
gccacacccg ccgcctcgaa gccctgcacc aggccggcat cgtggtgtgc gtggccgagg    3720
gactatggaa ggtgccggac gatctgcccg agcagggccg ccgctatgac gcccagcgtc    3780
ttggtggcgt gacggtggag ctgaaatcgc acctgcccat cgagcggcag gcccgcgtga    3840
tcggtgccac ctggcttgac cagcagttga tcgacggtgg ctcgggcttg ggcgacctgg    3900
gctttagcag tgaggccaag taggcgatac agcagcgcgc ggacttcctg gccgaacagg    3960
gactggccga gcggcgcggg cagcgcgtga tcctcaccgg aatctgctcg gcagcagcgg    4020
gctcgggaac tggcgcaggc cgcgaaggac attgccgccg ataccggcct ggagcatcgc    4080
cccgtggccg acgccagcg cgttgccggc gtctaccggc gccccgtcat gctcgccagc     4140
gggcgaaatg ggatgcttga tgacgccaag gggtccagcc tcgtgcggtg aagcccatc     4200 gaacagcggc ttggggagca gctcgccgcg acggtgcgcg gtgcggcgt gtcttgggag     4260 attggacgac agcgtgggcc ggcccctgtc tcttgatcag atcttgatcc cctgcgccat    4320
cagatccttg gcggcaagaa agccatccag tttactttgc agggcttccc aaccttccca    4380
```

-continued

```
gagggcgccc cagctggcaa ttccggttcg cttgctgtcc ataaaaccgc ccagtctagc    4440
tatcgccatg taagcccact gcaagctacc tgctttctct ttgcgcttgc gttttccctt    4500
gtccagatag cccagtagct gacattcatc cggggtcagc accgtttctg cggactggct    4560
ttctacgtgt tccgcttcct ttagcagccc ttgcgccctg agtgcttgcg gcagcgtgaa    4620
gctttctctg agctgtaaca gcctgaccgc aacaaacgag aggatcgaga ccatccgctc    4680
cagattatcc ggctcctcca tgcgttgcct ctcggctcct gctccggttt tccatgcctt    4740
atggaactcc tcgatccgcc agcgatgggt ataaatgtcg atgacgcgca aggcttgggc    4800
tagcgactcg accggttcgc cggtcagcaa caaccatttc aacggggtct cacccttggg    4860
cgggttaatc tcctcggcca gcaccgcgtt gagcgtgata ttcccctgtt ttagcgtgat    4920
gcgcccactg cgcaggctca agctcgcctt gcgggctggt cgatttttac gtttaccgcg    4980
tttatccacc acgcccttttt gcggaatgct gatctgatag ccacccaact ccggttggtt    5040
cttcagatgg tcgatcagat acaacccaga ctctacgtcc ttgcgtgggt gcttggagcg    5100
caccacgaag cgctcgttat gcgccagcct gtcctgcaga taagcatgaa tatcggcttc    5160
gcggtcacag accgcaatca cgttgctcat catgctgccc atgcgtaacc ggctagttgc    5220
ggccgctgcc agccatttgc cactctcctt ttcatccgca tcggcagggt catccgggcg    5280
catccaccac tcctgatgca gtaatcctac ggtgcggaat gtggtggcct cgagcaagag    5340
aacggagtga acccaccatc cgcgggattt atcctgaata gagcccagct tgccaagctc    5400
ttcggcgacc tggtggcgat aactcaaaga ggtggtgtcc tcaatggcca gcagttcggg    5460
aaactcctga gccaacttga ctgtttgcat ggcgccagcc tttctgatcg cctcggcaga    5520
aacgttggga ttgcggtaaa atcggtaagc gccttcctgc atggcttcac taccctctga    5580
tgagatggtt attgatttac cagaatattt tgccaattgg gcggcgacgt taaccaagcg    5640
ggcagtacgg cgaggatcac ccagcgccgc cgaagagaac acagatttag cccagtcggc    5700
cgcacgatga agagcagaag ttatcatgaa cgttaccatg ttaggaggtc acatggaagt    5760
cagatcctgg aaaacgggaa aggttccgtt caggacgcta cttgtgtata agagtcag    5818
```

<210> SEQ ID NO 2
<211> LENGTH: 476
<212> TYPE: PRT
<213> ORGANISM: Escherichia coli

<400> SEQUENCE: 2

```
Met Ile Thr Ser Ala Leu His Arg Ala Ala Asp Trp Ala Lys Ser Val
1               5                  10                  15

Phe Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Glu Ala Met Gln Glu Gly Ala Tyr Arg Phe Tyr
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125
```

```
Val Leu Leu Leu Glu Ala Thr Thr Phe Arg Thr Val Gly Leu Leu His
        130                 135                 140

Gln Glu Trp Trp Met Arg Pro Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Arg Leu Ala His Asn Glu Arg Phe Val
        195                 200                 205

Val Arg Ser Lys His Pro Arg Lys Asp Val Glu Ser Gly Leu Tyr Leu
        210                 215                 220

Ile Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Thr Gly Glu
290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Leu Pro Gln Ala Leu Arg Ala Gln Gly Leu Leu Lys Glu
370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
450                 455                 460

Ala Ala Lys Asp Leu Met Ala Gln Gly Ile Lys Ile
465                 470                 475

<210> SEQ ID NO 3
<211> LENGTH: 30
<212> TYPE: DNA
<213> ORGANISM: Artificial sequence
<220> FEATURE:
<223> OTHER INFORMATION: Defined sequence kernel
<220> FEATURE:
<221> NAME/KEY: misc_feature
<222> LOCATION: (1)..(30)
<223> OTHER INFORMATION: n is A, T, G, or C
```

```
<400> SEQUENCE: 3
nnknnknnkn nknnknnkkn knnknnknnk                               30

<210> SEQ ID NO 4
<211> LENGTH: 30
<212> TYPE: DNA
<213> ORGANISM: Artificial sequence
<220> FEATURE:
<223> OTHER INFORMATION: Defined sequence kernel
<220> FEATURE:
<221> NAME/KEY: misc_feature
<222> LOCATION: (1)..(30)
<223> OTHER INFORMATION: n is A, T, G, or C

<400> SEQUENCE: 4
nnmnnmnnmn nmnnmnnmnn mnnmnnmnnm                               30

<210> SEQ ID NO 5
<211> LENGTH: 5
<212> TYPE: PRT
<213> ORGANISM: Artificial sequence
<220> FEATURE:
<223> OTHER INFORMATION: Antibody spacer peptide.  The entire peptide
      sequence can be repeated more than one time

<400> SEQUENCE: 5

Gly Gly Gly Gly Ser
1               5

<210> SEQ ID NO 6
<211> LENGTH: 14
<212> TYPE: DNA
<213> ORGANISM: Artificial sequence
<220> FEATURE:
<223> OTHER INFORMATION: Tetradecanucleotide d

<400> SEQUENCE: 6
catgccatgg catg                                                14

<210> SEQ ID NO 7
<211> LENGTH: 21
<212> TYPE: DNA
<213> ORGANISM: Artificial sequence
<220> FEATURE:
<223> OTHER INFORMATION: 21-mer d

<400> SEQUENCE: 7
aaattgtgca catcctgcag c                                        21

<210> SEQ ID NO 8
<211> LENGTH: 12
<212> TYPE: DNA
<213> ORGANISM: Artificial sequence
<220> FEATURE:
<223> OTHER INFORMATION: 12-mer target DNA

<400> SEQUENCE: 8
agcctagctg aa                                                  12

<210> SEQ ID NO 9
<211> LENGTH: 12
<212> TYPE: DNA
<213> ORGANISM: Artificial sequence
<220> FEATURE:
<223> OTHER INFORMATION: Complement of the original 12-mer target

<400> SEQUENCE: 9
```

```
tcggatcgac tt                                                          12

<210> SEQ ID NO 10
<211> LENGTH: 4
<212> TYPE: PRT
<213> ORGANISM: Artificial sequence
<220> FEATURE:
<223> OTHER INFORMATION: Target sequence
<220> FEATURE:
<221> NAME/KEY: VARIANT
<222> LOCATION: (3)..(3)
<223> OTHER INFORMATION: Xaa is any Amino Acid

<400> SEQUENCE: 10

Tyr Tyr Xaa Tyr
 1

<210> SEQ ID NO 11
<211> LENGTH: 4
<212> TYPE: PRT
<213> ORGANISM: Artificial sequence
<220> FEATURE:
<223> OTHER INFORMATION: Single base mismatched probe

<400> SEQUENCE: 11

Tyr Tyr Tyr Tyr
 1

<210> SEQ ID NO 12
<211> LENGTH: 4
<212> TYPE: PRT
<213> ORGANISM: Artificial sequence
<220> FEATURE:
<223> OTHER INFORMATION: 4-mer extemtion probe
<220> FEATURE:
<221> NAME/KEY: VARIANT
<222> LOCATION: (2)..(2)
<223> OTHER INFORMATION: Xaa is any Amino Acid

<400> SEQUENCE: 12

Tyr Xaa Tyr Tyr
 1

<210> SEQ ID NO 13
<211> LENGTH: 10
<212> TYPE: DNA
<213> ORGANISM: Artificial sequence
<220> FEATURE:
<223> OTHER INFORMATION: BstNB I cleaves btw. nucleotide 9 & 10 of
      target sequence
<220> FEATURE:
<221> NAME/KEY: misc_feature
<222> LOCATION: (6)..(10)
<223> OTHER INFORMATION: n is any nucleotide

<400> SEQUENCE: 13 gagtcnnnnn                                                             10

<210> SEQ ID NO 14
<211> LENGTH: 223
<212> TYPE: DNA
<213> ORGANISM: Artificial sequence
<220> FEATURE:
<223> OTHER INFORMATION: Forward primer
<220> FEATURE:
<221> NAME/KEY: misc_feature
<222> LOCATION: (1)..(223)
<223> OTHER INFORMATION: n is any nucleotide
<220> FEATURE:
```

```
<221> NAME/KEY: misc_feature
<222> LOCATION: (1)..(10)
<223> OTHER INFORMATION: at least one nt. of nt. 1-10 is present
<220> FEATURE:
<221> NAME/KEY: misc_feature
<222> LOCATION: (21)..(120)
<223> OTHER INFORMATION: at least one nt. of nt. 21-120 is present
<220> FEATURE:
<221> NAME/KEY: misc_feature
<222> LOCATION: (124)..(223)
<223> OTHER INFORMATION: nt. 124-223 are optionally present

<400> SEQUENCE: 14
nnnnnnnnnn aagggaggag nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
atgnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnn                       223

<210> SEQ ID NO 15
<211> LENGTH: 215
<212> TYPE: DNA
<213> ORGANISM: Artificial sequence
<220> FEATURE:
<223> OTHER INFORMATION: Revers primer
<220> FEATURE:
<221> NAME/KEY: misc_feature
<222> LOCATION: (1)..(215)
<223> OTHER INFORMATION: n is any nucleotide
<220> FEATURE:
<221> NAME/KEY: misc_feature
<222> LOCATION: (1)..(10)
<223> OTHER INFORMATION: at least one nt. of nt. 1-10 is present
<220> FEATURE:
<221> NAME/KEY: misc_feature
<222> LOCATION: (16)..(115)
<223> OTHER INFORMATION: at least one nt. of 16-115 is present
<220> FEATURE:
<221> NAME/KEY: misc_feature
<222> LOCATION: (116)..(215)
<223> OTHER INFORMATION: nt. 116-215 are optionally present

<400> SEQUENCE: 15
nnnnnnnnnn aagggnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnn                                215

<210> SEQ ID NO 16
<211> LENGTH: 123
<212> TYPE: DNA
<213> ORGANISM: Artificial sequence
<220> FEATURE:
<223> OTHER INFORMATION: Forward primer with 10-100 template specific
      sequence
<220> FEATURE:
<221> NAME/KEY: misc_feature
<222> LOCATION: (24)..(123)
<223> OTHER INFORMATION: n is any nucleotide
<220> FEATURE:
<221> NAME/KEY: misc_feature
<222> LOCATION: (34)..(123)
<223> OTHER INFORMATION: nt. 34-123 are each optionally present

<400> SEQUENCE: 16
ctagaagaga ggagaaaacc atgnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
```

```
nnn                                                                    123

<210> SEQ ID NO 17
<211> LENGTH: 121
<212> TYPE: DNA
<213> ORGANISM: Artificial sequence
<220> FEATURE:
<223> OTHER INFORMATION: Reverse primer with 10-100 nt long template
      specific sequence
<220> FEATURE:
<221> NAME/KEY: misc_feature
<222> LOCATION: (22)..(121)
<223> OTHER INFORMATION: n is any nucleotide
<220> FEATURE:
<221> NAME/KEY: misc_feature
<222> LOCATION: (32)..(121)
<223> OTHER INFORMATION: nt. 32-121 are each optionally present

<400> SEQUENCE: 17
gatcaaaggc gcgcctgcag gnnnnnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120 n                                                                    121

<210> SEQ ID NO 18
<211> LENGTH: 23
<212> TYPE: DNA
<213> ORGANISM: Artificial sequence
<220> FEATURE:
<223> OTHER INFORMATION: Forward primer

<400> SEQUENCE: 18
ctagaaggga ggagaaaacc atg                                             23

<210> SEQ ID NO 19
<211> LENGTH: 21
<212> TYPE: DNA
<213> ORGANISM: Artificial sequence
<220> FEATURE:
<223> OTHER INFORMATION: Reverse primer

<400> SEQUENCE: 19
gatcaaaggc gcgcctgcag g                                               21

<210> SEQ ID NO 20
<211> LENGTH: 15
<212> TYPE: PRT
<213> ORGANISM: Artificial sequence
<220> FEATURE:
<223> OTHER INFORMATION: Linker peptide

<400> SEQUENCE: 20

Gly Gly Gly Gly Ser Gly Gly Gly Gly Ser Gly Gly Gly Gly Ser
1               5                   10                  15

<210> SEQ ID NO 21
<211> LENGTH: 150
<212> TYPE: DNA
<213> ORGANISM: Artificial sequence
<220> FEATURE:
<223> OTHER INFORMATION: Protogenitor template 124-2d

<400> SEQUENCE: 21
aatggacaag aaacgtgtcc gtgtgtacaa cgcggagatg gcctatgtcg acacgggcca     60
gggtgattcc gttctgtttc ttcacggcaa cccgacgtcg tcgtatctgt ggaggggcgt    120
aatgcctttt gtgacggacg tcgcccgatg                                     150
```

<210> SEQ ID NO 22
<211> LENGTH: 149
<212> TYPE: DNA
<213> ORGANISM: Artificial sequence
<220> FEATURE:
<223> OTHER INFORMATION: Protogenitor template 12412

<400> SEQUENCE: 22

```
atggagaaac accgcgtaga agttctcggt tcggagatgg cctacatcga cgtgggagag      60
ggcgacccga tcgtgttcct ccacggaaat cccacgtcgt cgtacctgtg gcggaacgtg     120
attccccacg ttgccggctt gggacgctg                                        149
```

<210> SEQ ID NO 23
<211> LENGTH: 150
<212> TYPE: DNA
<213> ORGANISM: Artificial sequence
<220> FEATURE:
<223> OTHER INFORMATION: Protogenitor template 124-1d

<400> SEQUENCE: 23

```
acacgacaag cgctacatcg aggtgctggg taagcgaatg gcctatgtcg agatgggcga      60
gggtgatccc atcattttcc aacacggcaa tccgacctca tcgtacctgt ggcgcaacat     120
catgccccat gtgcaacagc tcggtcgctg                                       150
```

<210> SEQ ID NO 24
<211> LENGTH: 150
<212> TYPE: DNA
<213> ORGANISM: Artificial sequence
<220> FEATURE:
<223> OTHER INFORMATION: Protogenitor template myco1

<400> SEQUENCE: 24

```
cgggcagccg aagtacctag aaatcgccgg gaagcgcatg gcgtatatcg acgaaggcaa      60
gggtgacgcc atcgtctttc agcacggcaa ccccacgtcg tcttacttgt ggcgcaacat     120
catgccgcac ttggaagggc tgggccggct                                       150
```

<210> SEQ ID NO 25
<211> LENGTH: 150
<212> TYPE: DNA
<213> ORGANISM: Artificial sequence
<220> FEATURE:
<223> OTHER INFORMATION: Protogenitor template b3

<400> SEQUENCE: 25

```
ctacccaaaa tttcggcggt cggtcttcgg ccgcgagatg gcgtacgtgg aagtgggacg      60
gggcgacccc atcgtactct tgcacggcaa ccccacctcg tcgtacctct ggcgcaacgt     120
gttgccgcac ctggcgccgt taggccgctg                                       150
```

<210> SEQ ID NO 26
<211> LENGTH: 150
<212> TYPE: DNA
<213> ORGANISM: Artificial sequence
<220> FEATURE:
<223> OTHER INFORMATION: Protogenitor template b1

<400> SEQUENCE: 26

```
gcatccgaga aagcggatcg ccgtgctcga ttcggagatg agctacgtcg ataccggcga      60
gggagcgccg atcgtgttcc ttcacggcaa cccgacttcc tcctatcttt ggcgcaacat     120
```

```
catccctat ctcgcggatc acggcagatg                                    150

<210> SEQ ID NO 27
<211> LENGTH: 146
<212> TYPE: DNA
<213> ORGANISM: Artificial sequence
<220> FEATURE:
<223> OTHER INFORMATION: Protogenitor template 15112

<400> SEQUENCE: 27
atgccagcga ttgagctatt ggattcgttc atgaactacc gcgacacggg cgtcggcgat    60
cttcccgtcg tgttcctgca cggcaacccc acgtcgtctc acgtctggcg caacgtgatc   120
ccgcacgtcg ctggccagca ccggtg                                       146

<210> SEQ ID NO 28
<211> LENGTH: 150
<212> TYPE: DNA
<213> ORGANISM: Artificial sequence
<220> FEATURE:
<223> OTHER INFORMATION: Protogenitor template rhod2

<400> SEQUENCE: 28
cccccattat gtggaagtcc tgggcgagcg tatgcactac gtcgatgttg gaccgcggga    60
tggcacgcct gtgctgttcc tgcacggtaa cccgacctcg tcctacctgt ggcgcaacat   120
catcccgcat gtagcaccga gtcatcggtg                                   150

<210> SEQ ID NO 29
<211> LENGTH: 35
<212> TYPE: DNA
<213> ORGANISM: Artificial sequence
<220> FEATURE:
<223> OTHER INFORMATION: Consensus sequence

<400> SEQUENCE: 29
aggctttcac ggaaccactc tcattgggct tcctg                              35

<210> SEQ ID NO 30
<211> LENGTH: 100
<212> TYPE: DNA
<213> ORGANISM: Artificial sequence
<220> FEATURE:
<223> OTHER INFORMATION: Derived nucleic acid building block sequence

<400> SEQUENCE: 30
ccgtgaggtc ggccacgccc gggggggaaag ccagaaggta tgaagtctgg cgccaggcgg    60
gcttcgttcg acagtacaat cgatcaatta atggttcgag                        100

<210> SEQ ID NO 31
<211> LENGTH: 1044
<212> TYPE: DNA
<213> ORGANISM: Artificial sequence
<220> FEATURE:
<223> OTHER INFORMATION: Polynucleotide progenitor template 150am13_00

<400> SEQUENCE: 31
catgatgcac ggcgatattt catcgagcaa tgacacggtc ggcgttgccg tcgtgaacta    60
caagatgcct cgccttcata ccaaggcgga ggttttagcg aacgccagaa agatcggcga   120
gatgatcgtc ggcatgaaga ccggcctgcc cggaatggat ctggtgatct cccggaata   180 ttcgacccac ggcatcatgt acgactccaa ggaaatgtac gataccgcgt ccgtcgtgcc   240
cggcgaggag accgagattt ttgccgaagc ctgccgcaag gcgaaagtct ggggcgtgtt   300
```

```
ctcgctcacc ggcgaacgtc acgaggaaca tccgaagaag gcgccctaca acacgctgat    360
cctgatgaac gacaagggcg aggtggtcca gaaataccgc aagatcatgc cgtgggttcc    420
gatcgagggc tggtaccccg gcaactgcac ctacgtctcc gacgggccga agggcatgaa    480
ggtttcgctg atcatctgcg atgacggcaa ctatccggaa atctggcgcg actgcgccat    540
gaagggcgcc gagctgatcg tgcgctgcca gggctacatg tatccggcca aggaccagca    600
ggtcatcatg gcgaaggcga tggcgtgggc gaataattgt tacgtcgcgg tttccaatgc    660
cgcgggcttc gatggcgtct attcgtattt cggccactcg gcgatcatcg gcttcgatgg    720
ccgcacgctc ggcgaatgcg gcgaggaaga atacggcatc cagtatgccc agctttcgaa    780
gatgctgatc cgcgacgccc gccgcaccgg acaatcggaa aaccatctct tcaagctggt    840
gcatcgtggc tacaccgggt tgatcaactc cggcgagggc gaccgcggtc tcgcggcctg    900
tccttatgag ttctacaaca aatggatcgc cgatccggaa ggcacccgcg aaatggtcga    960
gtcctttacc cggccgacgg tgggaaccga tgaagcgccc atcgaaggca tcccgaacaa   1020
ggtcgcggtg caccgctgaa agct                                          1044

<210> SEQ ID NO 32
<211> LENGTH: 1044
<212> TYPE: DNA
<213> ORGANISM: Artificial sequence
<220> FEATURE:
<223> OTHER INFORMATION: Polynucleotide progenitor template 150AM7_001

<400> SEQUENCE: 32
catgcatcac ggcgacattt catcgagcaa tgacacggtc ggcgttgccg tcgtgaacta    60
caagatgccg cggcttcaca ccaaggctga ggtgctggcc aactgccgca agatcgccga   120
catgctggtc ggcatgaaga gcggcctgcc gggaatggat ctggtgatct cccggaata   180 ttccacccac ggcatcatgt acgactccaa ggagatgtac gacacggcgt cgacggtgcc   240
gggtgaagag accgagattt cgccgaggc ctgccgcaag gccaaggtct ggggcgtgtt   300
ctcgctgacc ggcgagcgcc acgaggagca tcccaataaa gcgccgtaca acaccctgat   360
cctgatgaac gacaagggtg aagtcgttca gaaatatcgc aagatcatgc cgtgggtgcc   420
gatcgaaggc tggtatcccg gcaactgcac gtacgtctcc gaaggcccga agggcatgaa   480
gatgtcgctg atcatctgcg acgacggcaa ctacccggaa atctggcgtg actgcgcgat   540
gaagggcgcc gaactgatca tccgctgcca gggctacatg tatcccgcca aggatcagca   600
ggtgctgatg gcgaaagcaa tggcctgggc caacaacgtt tatgtcgcgg tcgccaatgc   660
ctcgggcttc gacggcgtct actcgtattt cggccattcg gcgatcatcg gcttcgacgg   720
ccgtaccctc ggcgaatgcg gcgaggagga ttatggcatc cagtatgccg ccatctccaa   780
gtcgctgatc cgcgacgcgc gccgcaccgg ccaatcggaa aaccatctct tcaagctggt   840
gcaccgtggc tacaccggca tgatcaattc cggcgagggc gaccgcggtg tcgcggcttg    900
cccgtatgat ttctattcga aatggatcgc cgatcccgag ggtacacgcg agatggtgga   960
atccttcacg cgtccgacgg tgggtgtgga ggaatgcccg atcgagggca ttccgaacaa   1020
ggccaccacg caccgctgaa agct                                          1044

<210> SEQ ID NO 33
<211> LENGTH: 1044
<212> TYPE: DNA
<213> ORGANISM: Artificial sequence
<220> FEATURE:
```

-continued

<223> OTHER INFORMATION: Polynucleotide progenitor template 431am7_002

<400> SEQUENCE: 33

```
catgagacac ggagatatct ccagcagcaa cgattgcgtg ggcgtggccg tcgtgaacta        60
caagatgccg cggctgcata cccgcgcgga ggtgatggag aacgcccgca agatcgccga       120
catggtcgtg ggcatgaagc gcggcctgcc cggcatggac ctggtcatct tccccgagta       180
ctccacccac ggcatcatgt acgacgccaa ggaaatgtac gaaaccgctt cggccattcc       240
gggcgaagag actgctgtgt tcgccgacgc ctgccgcaag gccaacgtat ggggcgtgtt       300
ttcgctgacg ggcgagcgcc acgaagagca cccgaacaag gcgccgtaca acacgctcat       360
cctgatgaac aacaagggcg agatcgtgca gaagtaccgc aagatcatgc cctgggtgcc       420
gatcgaaggc tggtatccgg gcgattgcac ctatgtgtcg gaaggcccca agggactgaa       480
gatcagcctc atcatctgcg acgacggcaa ttaccccgag atctggcgcg attgcgccat       540
gcgcggcgcc gagctgatcg tgcgttgcca gggatacatg tacccggcca aggaccagca       600
ggtcatggtg tccaaggcca tggcgtggat gaacaacgtc tacgtggcgg tggccaatgc       660
cgcgggcttc gacggcgtgt attcctactt cggccattcg gccatcatcg gcttcgacgg       720
ccgcacgctg ggcgaatgcg gtgaagaaga catgggcgtg cagtacgccg agctctccac       780
cagcctgatc cgcgacgcgc gcaagaacat gcagtcgcag aaccacttgt tcaagctggt       840
gcaccgcggc tacaccggca agatcaattc cggcgaagag gccaccggcg tcgcggcatg       900
cccgtacaac ttctacgcca actggatcaa cgatccggag ggcacgcgca agatggtcga       960
atccttcacc cggtccaccg tgggcacgcc ggagtgcccc atggacggca tccccaacga      1020
ggacgccaag caccgctaga agct                                              1044
```

US 7,033,781 B1

WHOLE CELL ENGINEERING BY MUTAGENIZING A SUBSTANTIAL PORTION OF A STARTING GENOME, COMBINING MUTATIONS, AND OPTIONALLY REPEATING

CROSS-REFERENCE TO RELATED APPLICATIONS

This application is a continuation-in-part under Section 120 to U.S. patent application Ser. No. 09/594,459, filed Jun. 14, 2000, which is a continuation-in-part of U.S. patent application Ser. No. 09/522,289, filed Mar. 9, 2000 which is a continuation-in-part of U.S. patent application Ser. No. 09/498,557, filed Feb. 4, 2000, which is a continuation-in-part of U.S. patent application Ser. No. 09/495,052, filed Jan. 31, 2000. This application also claims priority under Section 119(e)(1) to U.S. Provisional Patent Application No. 60/156,815, filed Sep. 29, 1999.

A—FIELD OF THE INVENTION

This invention relates to the field of cellular and whole organism engineering. Specifically, this invention relates to a cellular transformation, directed evolution, and screening method for creating novel transgenic organisms having desirable properties. Thus in one aspect, this invention relates to a method of generating a transgenic organism, such as a microbe or a plant, having a plurality of traits that are differentially activatable.

This invention also relates to the field of protein engineering. Specifically, this invention relates to a directed evolution method for preparing a polynucleotide encoding a polypeptide. More specifically, this invention relates to a method of using mutagenesis to generate a novel polynucleotide encoding a novel polypeptide, which novel polypeptide is itself an improved biological molecule &/or contributes to the generation of another improved biological molecule. More specifically still, this invention relates to a method of performing both non-stochastic polynucleotide chimerization and non-stochastic site-directed point mutagenesis.

Thus, in one aspect, this invention relates to a method of generating a progeny set of chimeric polynucleotide(s) by means that are synthetic, and non-stochastic, and where the design of the progeny polynucleotide(s) is derived by analysis of a parental set of polynucleotides &/or of the polypeptides correspondingly encoded by the parental polynucleotides. In another aspect this invention relates to a method of performing site-directed mutagenesis using means that are exhaustive, systematic, and non-stochastic.

Furthermore this invention relates to a step of selecting from among a generated set of progeny molecules a subset comprised of particularly desirable species, including by a process termed end-selection, which subset may then be screened further. This invention also relates to the step of screening a set of polynucleotides for the production of a polypeptide &/or of another expressed biological molecule having a useful property.

Novel biological molecules whose manufacture is taught by this invention include genes, gene pathways, and any molecules whose expression is affected thereby, including directly encoded polypetides &/or any molecules affected by such polypeptides. Said novel biological molecules include those that contain a carbohydrate, a lipid, a nucleic acid, &/or a protein component, and specific but non-limiting examples of these include antibiotics, antibodies, enzymes, and steroidal and non-steroidal hormones.

In a particular non-limiting aspect, the present invention relates to enzymes, particularly to thermostable enzymes, and to their generation by directed evolution. More particularly, the present invention relates to thermostable enzymes which are stable at high temperatures and which have improved activity at lower temperatures.

B—BACKGROUND

General Overview of the Problem to Be Solved

Brief Summary: It is instantly appreciated that the process of performing a genetic manipulation on a organism to achieve a genetic alteration, whether it is on a unicellular or on a multi-cellular organism, can lead to harmful, toxic, noxious, or even lethal effects on the manipulated organism. This is particularly true when the genetic manipulation becomes sizable. From a technical point of view, this problem is seen as one of the current obstacles that hinder the creation of genetically altered organisms having a large number of transgenic traits.

On the marketing side, is instantly appreciated that the purchase price of a genetically altered organism is often dictated by, or proportional to, the number of transgenic traits that have been introduced into the organism. Consequently, a genetically altered organism having a large number of stacked transgenic traits can be quite costly to produce and purchase and economically in low demand.

On the other hand, the generation of organism having but a single genetically introduced trait can also lead to the incurrence of undesirable costs, although for other reasons. It is thus appreciated that the separate production, marketing, & storage of genetically altered organisms each having a single transgenic traits can incur costs, including inventory costs, that are undesirable. For example, the storage of such organisms may require a separate bin to be used for each trait. Furthermore, the value of an organisms having a single particular trait is often intimately tied to the marketability of that particular trait, and when that marketability diminishes, inventories of such organisms cannot be sold in other markets.

The instant invention solves these and other problems by providing a method of producing genetically altered organisms having a large number of stacked traits that are differentially activatable. Upon purchasing such a genetically altered organism (having a large number of differentially activatable stacked traits), the purchasing customer has the option of selecting and paying for particular traits among the total that can then be activated differentially. One economic advantage provided by this invention is that the storage of such genetically altered organisms is simplified since, for example, one bin could be used to store a large number of traits. Moreover, a single organism of this type can satisfy the demands for a variety of traits; consequently, such an organism can be sold in a variety of markets.

To achieve the production of genetically altered organisms having a large number of stacked traits that are differentially activatable, this invention provides—in one specific aspect—a process comprising the step of monitoring a cell or organism at holistic level. This serves as a way of collecting holistic—rather than isolated—information about a working cell or organism that is being subjected to a substantial amount of genetic manipulation. This invention further provides that this type of holistic monitoring can include the detection of all morphological, behavioral, and physical parameters.

Accordingly, the holistic monitoring provided by this invention can include the identification &/or quantification of all the genetic material contained in a working cell or organism (e.g. all nucleic acids including the entire genome, messenger RNA's, tRNA's, rRNA's, and mitochondrial nucleic acids, plasmids, phages, phagemids, viruses, as well as all episomal nucleic acids and endosymbiont nucleic acids). Furthermore this invention provides that this type of holistic monitoring can include all gene products produced by the working cell or organisms.

Furthermore, the holistic monitoring provided by this invention can include the identification &/or quantification of all molecules that are chemically at least in part protein in a working cell or organism. The holistic monitoring provided by this invention can also include the identification &/or quantification of all molecules that are chemically at least in part carbohydrate in a working cell or organism. The holistic monitoring provided by this invention can also include the identification &/or quantification of all molecules that are chemically at least in part proteoglycan in a working cell or organism. The holistic monitoring provided by this invention can also include the identification &/or quantification of all molecules that are chemically at least in part glycoprotein in a working cell or organism. The holistic monitoring provided by this invention can also include the identification &/or quantification of all molecules that are chemically at least in part nucleic acids in a working cell or organism. The holistic monitoring provided by this invention can also include the identification &/or quantification of all molecules that are chemically at least in part lipids in a working cell or organism.

In one aspect, this invention provides that the ability to differentially activate a trait from among many, such as a enzyme from among many enzymes, depends the enzyme(s) to be activated having a unique activity profile (or activity fingerprint). An enzyme's activity profile includes the reaction(s) it catalyzes and its specificity. Thus, an enzymes activity profile includes its:

Catalyzed reaction(s)
Reaction type
Natural substrate(s)
Substrate spectrum
Product spectrum
Inhibitor(s)
Cofactor(s)/prostetic group(s).
Metal compounds/salts that affect it
Turnover number
Specific activity
Km value
pH optimum
pH range
Temperature optimum
Temperature range It is also instantly appreciated that enzymes are differentially affected by exposure to varying degrees of processing (e.g. upon extraction &/or purification) and exposure (e.g. to suboptimal storage conditions). Accordingly, enzyme differences may surface after exposure to:

Isolation/Preparation
Purification
Crystallization
Renaturation

It is instantly appreciated that differences in molecular stability can also be used advantageously to differentially activate or inactivate selected enzymes, by exposing the enzymes for an appropriate time to variations in:

pH
Temperature
Oxidation
Organic solvent(s)
Miscellaneous storage conditions

It is thus appreciated that in order to be able to differentially activate selected traits among a plurality of stacked traits, it is desirable to introduce into a working cell or organism traits conferred by molecules (e.g. enzymes) having very unique profiles (e.g. unique enzyme fingerprints). Furthermore, it is appreciated that in order to obtain the molecules having a representation of a wide range of molecular fingerprints, it is advantageous to harvest molecules from the widest possible reaches nature's diversity. Thus, it is beneficial to harvest molecules not only from cultured mesophilic organisms, but also from extremophiles that are largely uncultured.

In another aspect, it is instantly appreciated that harvesting the full potential of nature's diversity can include both the step of discovery and the step of optimizing what is discovered. For example, the step of discovery allows one to mine biological molecules that have commercial utility. It is instantly appreciated that the ability to harvest the full richness of biodiversity, i.e. to mine biological molecules from a wide range of environmental conditions, is critical to the ability to discover novel molecules adapted to funtion under a wide variety of conditions, including extremes of conditions, such as may be found in a commercial application.

However, it is also instantly appreciated that only occassionally are there criteria for selection &/or survival in nature that point in the exact direction of particular commercial needs. Instead, it is often the case that a naturally occurring molecule will require a certain amount of change—from fine tuning to sweeping modification—in order to fulfill a particular unmet commercial need. Thus, to meet certain commercial needs (e.g., a need for a molecule that is fucntional under a specific set of commercial processing conditions) it is sometimes advantageous to experimentally modify a naturally expressed molecule to achieve properties beyond what natural evolution has provided &/or is likely to provide in the near future.

The approach, termed directed evolution, of experimentally modifying a biological molecule towards a desirable property, can be achieved by mutagenizing one or more parental molecular templates and by idenifying any desirable molecules among the progeny molecules. Currently available technologies in directed evolution include methods for achieving stochastic (i.e. random) mutagenesis and methods for achieving non-stochastic (non-random) mutagenesis. However, critical shortfalls in both types of methods are identified in the instant disclosure.

In prelude, it is noteworthy that it may be argued philosophically by some that all mutagenesis—if considered from an objective point of view—is non-stochastic; and furthermore that the entire universe is undergoing a process that—if considered from an objective point of view—is non-stochastic. Whether this is true is outside of the scope of the instant consideration. Accordingly, as used herein, the terms "randomness", "uncertainty", and "unpredictability" have subjective meanings, and the knowledge, particularly the predictive knowledge, of the designer of an experimental process is a determinant of whether the process is stochastic or non-stochastic.

By way of illustration, stochastic or random mutagenesis is exemplified by a situation in which a progenitor molecular template is mutated (modified or changed) to yield a set of progeny molecules having mutation(s) that are not predetermined. Thus, in an in vitro stochastic mutagenesis reaction, for example, there is not a particular predetermined product whose production is intended; rather there is an uncertainty—hence randomness—regarding the exact nature of the mutations achieved, and thus also regarding the products generated. In contrast, non-stochastic or non-random mutagenesis is exemplified by a situation in which a progenitor molecular template is mutated (modified or changed) to yield a progeny molecule having one or more predetermined mutations. It is appreciated that the presence of background products in some quantity is a reality in many reactions where molecular processing occurs, and the presence of these background products does not detract from the non-stochastic nature of a mutagenesis process having a predetermined product.

Thus, as used herein, stochastic mutagenesis is manifested in processes such as error-prone PCR and stochastic shuffling, where the mutation(s) achieved are random or not predetermined. In contrast, as used herein, non-stochastic mutagenesis is manifested in instantly disclosed processes such as gene site-saturation mutagenesis and synthetic ligation reassembly, where the exact chemical structure(s) of the intended product(s) are predetermined.

In brief, existing mutagenesis methods that are non-stochastic have been serviceable in generating from one to only a very small number of predetermined mutations per method application, and thus produce per method application from one to only a few progeny molecules that have predetermined molecular structures. Moreover, the types of mutations currently available by the application of these non-stochastic methods are also limited, and thus so are the types of progeny mutant molecules.

In contrast, existing methods for mutagenesis that are stochastic in nature have been serviceable for generating somewhat larger numbers of mutations per method application—though in a random fashion & usually with a large but unavoidable contingency of undesirable background products. Thus, these existing stochastic methods can produce per method application larger numbers of progeny molecules, but that have undetermined molecular structures. The types of mutations that can be achieved by application of these current stochastic methods are also limited, and thus so are the types of progeny mutant molecules.

It is instantly appreciated that there is a need for the development of non-stochastic mutagenesis methods that:

1) Can be used to generate large numbers of progeny molecules that have predetermined molecular structures;
2) Can be used to readily generate more types of mutations;
3) Can produce a correspondingly larger variety of progeny mutant molecules;
4) Produce decreased unwanted background products;
5) Can be used in a manner that is exhaustive of all possibilities; and
6) Can produce progeny molecules in a systematic & non-repetitive way.

The instant invention satisfies all of these needs.

Directed Evolution Supplements Natural Evolution:

Natural evolution has been a springboard for directed or experimental evolution, serving both as a reservoir of methods to be mimicked and of molecular templates to be mutagenized. It is appreciated that, despite its intrinsic process-related limitations (in the types of favored &/or allowed mutagenesis processes) and in its speed, natural evolution has had the advantage of having been in process for millions of years & and throughout a wide diversity of environments. Accordingly, natural evolution (molecular mutagenesis and selection in nature) has resulted in the generation of a wealth of biological compounds that have shown usefulness in certain commercial applications.

However, it is instantly appreciated that many unmet commercial needs are discordant with any evolutionary pressure &/or direction that can be found in nature. Moreover, it is often the case that when commercially useful mutations would otherwise be favored at the molecular level in nature, natural evolution often overrides the positive selection of such mutations, e.g. when there is a concurrent detriment to an organism as a whole (such as when a favorable mutation is accompanied by a detrimental mutation). Additionally, natural evolution is often slow, and favors fidelity in many types of replication. Additionally still, natural evolution often favors a path paved mainly by consecutive beneficial mutations while tending to avoid a plurality of successive negative mutations, even though such negative mutations may prove beneficial when combined, or may lead—through a circuitous route—to final state that is beneficial.

Moreover, natural evolution advances through specific steps (e.g. specific mutagenesis and selection processes), with avoidance of less favored steps. For example, many nucleic acids do not reach close enough proximity to each other in a operative environment to undergo chimerization or incorporation or other types of transfers from one species to another. Thus, e.g., when sexual intercourse between 2 particular species is avoided in nature, the chimerization of nucleic acids from these 2 species is likewise unlikely, with parasites common to the two species serving as an example of a very slow passageway for inter-molecular encounters and exchanges of DNA. For another example, the generation of a molecule causing self-toxicity or self-lethality or sexual sterility is avoided in nature. For yet another example, the propagation of a molecule having no particular immediate benefit to an organism is prone to vanish in subsequent generations of the organism. Furthermore, e.g., there is no selection pressure for improving the performance of molecule under conditions other than those to which it is exposed in its endogenous environment; e.g. a cytoplasmic molecule is not likely to acquire functional features extending beyond what is required of it in the cytoplasm. Furthermore still, the propagation of a biological molecule is susceptible to any global detrimental effects—whether caused by itself or not—on its ecosystem. These and other characteristics greatly limit the types of mutations that can be propagated in nature.

On the other hand, directed (or experimental) evolution—particularly as provided herein—can be performed much more rapidly and can be directed in a more streamlined manner at evolving a predetermined molecular property that is commercially desirable where nature does not provide one &/or is not likely to provide. Moreover, the directed evolution invention provided herein can provide more wide-ranging possibilities in the types of steps that can be used in mutagenesis and selection processes. Accordingly, using templates harvested from nature, the instant directed evolution invention provides more wide-ranging possibilities in the types of progeny molecules that can be generated and in the speed at which they can be generated than often nature itself might be expected to in the same length of time.

In a particular exemplification, the instantly disclosed directed evolution methods can be applied iteratively to produce a lineage of progeny molecules (e.g. comprising successive sets of progeny molecules) that would not likely be propagated (i.e., generated &/or selected for) in nature, but that could lead to the generation of a desirable downstream mutagenesis product that is not achievable by natural evolution.

Previous Directed Evolution Methods Are Suboptimal

Mutagenesis has been attempted in the past on many occasions, but by methods that are inadequate for the purpose of this invention. For example, previously described non-stochastic methods have been serviceable in the generation of only very small sets of progeny molecules (comprised often of merely a solitary progeny molecule). By way of illustration, a chimeric gene has been made by joining 2 polynucleotide fragments using compatible sticky ends generated by restriction enzyme(s), where each fragment is derived from a separate progenitor (or parental) molecule. Another example might be the mutagenesis of a single codon position (i.e. to achieve a codon substitution, addition, or deletion) in a parental polynucleotide to generate a single progeny polynucleotide encoding for a single site-mutagenized polypeptide.

Previous non-stochastic approaches have only been serviceable in the generation of but one to a few mutations per method application. Thus, these previously described non-stochastic methods thus fail to address one of the central goals of this invention, namely the exhaustive and non-stochastic chimerization of nucleic acids. Accordingly previous non-stochastic methods leave untapped the vast majority of the possible point mutations, chimerizations, and combinations thereof, which may lead to the generation of highly desirable progeny molecules.

In contrast, stochastic methods have been used to achieve larger numbers of point mutations and/or chimerizations than non-stochastic methods; for this reason, stochastic methods have comprised the predominant approach for generating a set of progeny molecules that can be subjected to screening, and amongst which a desirable molecular species might hopefully be found. However, a major drawback of these approaches is that—because of their stochastic nature—there is a randomness to the exact components in each set of progeny molecules that is produced. Accordingly, the experimentalist typically has little or no idea what exact progeny molecular species are represented in a particular reaction vessel prior to their generation. Thus, when a stochastic procedure is repeated (e.g. in a continuation of a search for a desirable progeny molecule), the re-generation and re-screening of previously discarded undesirable molecular species becomes a labor-intensive obstruction to progress, causing a circuitous—if not circular—path to be taken. The drawbacks of such a highly suboptimal path can be addressed by subjecting a stochastically generated set of progeny molecules to a labor-incurring process, such as sequencing, in order to identify their molecular structures, but even this is an incomplete remedy.

Moreover, current stochastic approaches are highly unsuitable for comprehensively or exhaustively generating all the molecular species within a particular grouping of mutations, for attributing functionality to specific structural groups in a template molecule (e.g. a specific single amino acid position or a sequence comprised of two or more amino acids positions), and for categorizing and comparing specific grouping of mutations. Accordingly, current stochastic approaches do not inherently enable the systematic elimination of unwanted mutagenesis results, and are, in sum, burdened by too many inherently shortcomings to be optimal for directed evolution.

In a non-limiting aspect, the instant invention addresses these problems by providing non-stochastic means for comprehensively and exhaustively generating all possible point mutations in a parental template. In another non-limiting aspect, the instant invention further provides means for exhaustively generating all possible chimerizations within a group of chimerizations. Thus, the aforementioned problems are solved by the instant invention.

Specific shortfalls in the technological landscape addressed by this invention include:

1) Site-directed mutagenesis technologies, such as sloppy or low-fidelity PCR, are ineffective for systematically achieving at each position (site) along a polypeptide sequence the full (saturated) range of possible mutations (i.e. all possible amino acid substitutions).
2) There is no relatively easy systematic means for rapidly analyzing the large amount of information that can be contained in a molecular sequence and in the potentially colossal number or progeny molecules that could be conceivably obtained by the directed evolution of one or more molecular templates.
3) There is no relatively easy systematic means for providing comprehensive empirical information relating structure to function for molecular positions.
4) There is no easy systematic means for incorporating internal controls, such as positive controls, for key steps in certain mutagenesis (e.g. chimerization) procedures.
5) There is no easy systematic means to select for a specific group of progeny molecules, such as full-length chimeras, from among smaller partial sequences.

An exceedingly large number of possibilities exist for the purposeful and random combination of amino acids within a protein to produce useful hybrid proteins and their corresponding biological molecules encoding for these hybrid proteins, i.e., DNA, RNA. Accordingly, there is a need to produce and screen a wide variety of such hybrid proteins for a desirable utility, particularly widely varying random proteins.

The complexity of an active sequence of a biological macromolecule (e.g., polynucleotides, polypeptides, and molecules that are comprised of both polynucleotide and polypeptide sequences) has been called its information content ("IC"), which has been defined as the resistance of the active protein to amino acid sequence variation (calculated from the minimum number of invariable amino acids (bits) required to describe a family of related sequences with the same function). Proteins that are more sensitive to random mutagenesis have a high information content.

Molecular biology developments, such as molecular libraries, have allowed the identification of quite a large number of variable bases, and even provide ways to select functional sequences from random libraries. In such libraries, most residues can be varied (although typically not all at the same time) depending on compensating changes in the context. Thus, while a 100 amino acid protein can contain only 2,000 different mutations, $20^{100}$ sequence combinations are possible.

Information density is the IC per unit length of a sequence. Active sites of enzymes tend to have a high information density. By contrast, flexible linkers of information in enzymes have a low information density.

Current methods in widespread use for creating alternative proteins in a library format are error-prone polymerase chain reactions and cassette mutagenesis, in which the specific region to be optimized is replaced with a synthetically mutagenized oligonucleotide. In both cases, a substantial number of mutant sites are generated around certain sites in the original sequence.

Error-prone PCR uses low-fidelity polymerization conditions to introduce a low level of point mutations randomly over a long sequence. In a mixture of fragments of unknown sequence, error-prone PCR can be used to mutagenize the mixture. The published error-prone PCR protocols suffer from a low processivity of the polymerase. Therefore, the protocol is unable to result in the random mutagenesis of an average-sized gene. This inability limits the practical application of error-prone PCR. Some computer simulations have suggested that point mutagenesis alone may often be too gradual to allow the large-scale block changes that are required for continued and dramatic sequence evolution. Further, the published error-prone PCR protocols do not allow for amplification of DNA fragments greater than 0.5 to 1.0 kb, limiting their practical application.. In addition, repeated cycles of error-prone PCR can lead to an accumulation of neutral mutations with undesired results, such as affecting a protein's immunogenicity but not its binding affinity.

In oligonucleotide-directed mutagenesis, a short sequence is replaced with a synthetically mutagenized oligonucleotide. This approach does not generate combinations of distant mutations and is thus not combinatorial. The limited library size relative to the vast sequence length means that many rounds of selection are unavoidable for protein optimization. Mutagenesis with synthetic oligonucleotides requires sequencing of individual clones after each selection round followed by grouping them into families, arbitrarily choosing a single family, and reducing it to a consensus motif. Such motif is re-synthesized and reinserted into a single gene followed by additional selection. This step process constitutes a statistical bottleneck, is labor intensive, and is not practical for many rounds of mutagenesis.

Error-prone PCR and oligonucleotide-directed mutagenesis are thus useful for single cycles of sequence fine-tuning, but rapidly become too limiting when they are applied for multiple cycles.

Another limitation of error-prone PCR is that the rate of down-mutations grows with the information content of the sequence. As the information content, library size, and mutagenesis rate increase, the balance of down-mutations to up-mutations will statistically prevent the selection of further improvements (statistical ceiling).

In cassette mutagenesis, a sequence block of a single template is typically replaced by a (partially) randomized sequence. Therefore, the maximum information content that can be obtained is statistically limited by the number of random sequences (i.e., library size). This eliminates other sequence families which are not currently best, but which may have greater long term potential.

Also, mutagenesis with synthetic oligonucleotides requires sequencing of individual clones after each selection round. Thus, such an approach is tedious and impractical for many rounds of mutagenesis.

Thus, error-prone PCR and cassette mutagenesis are best suited, and have been widely used, for fine-tuning areas of comparatively low information content. One apparent exception is the selection of an RNA ligase ribozyme from a random library using many rounds of amplification by error-prone PCR and selection.

In nature, the evolution of most organisms occurs by natural selection and sexual reproduction. Sexual reproduction ensures mixing and combining of the genes in the offspring of the selected individuals. During meiosis, homologous chromosomes from the parents line up with one another and cross-over part way along their length, thus randomly swapping genetic material. Such swapping or shuffling of the DNA allows organisms to evolve more rapidly.

In recombination, because the inserted sequences were of proven utility in a homologous environment, the inserted sequences are likely to still have substantial information content once they are inserted into the new sequence.

Theoretically there are 2,000 different single mutants of a 100 amino acid protein. However, a protein of 100 amino acids has $20^{100}$ possible sequence combinations, a number which is too large to exhaustively explore by conventional methods. It would be advantageous to develop a system which would allow generation and screening of all of these possible combination mutations.

Some workers in the art have utilized an in vivo site specific recombination system to generate hybrids of combine light chain antibody genes with heavy chain antibody genes for expression in a phage system. However, their system relies on specific sites of recombination and is limited accordingly. Simultaneous mutagenesis of antibody CDR regions in single chain antibodies (scFv) by overlapping extension and PCR have been reported.

Others have described a method for generating a large population of multiple hybrids using random in vivo recombination. This method requires the recombination of two different libraries of plasmids, each library having a different selectable marker. The method is limited to a finite number of recombinations equal to the number of selectable markers existing, and produces a concomitant linear increase in the number of marker genes linked to the selected sequence(s).

In vivo recombination between two homologous, but truncated, insect-toxin genes on a plasmid has been reported as a method of producing a hybrid gene. The in vivo recombination of substantially mismatched DNA sequences in a host cell having defective mismatch repair enzymes, resulting in hybrid molecule formation has been reported.

C—SUMMARY OF THE INVENTION

This invention relates generally to the field of cellular and whole organism engineering. Specifically, this invention relates to a cellular transformation, directed evolution, and screening method for creating novel transgenic organisms having desirable properties. Thus in one aspect, this invention relates to a method of generating a transgenic organism, such as a microbe or a plant, having a plurality of traits that are differentially activatable.

In one embodiment, this invention is directed to a method of producing an improved organism having a desirable trait to by: a) obtaining an initial population of organisms, b) generating a set of mutagenized organisms, such that when all the genetic mutations in the set of mutagenized organisms are taken as a whole, there is represented a set of substantial genetic mutations, and c) detecting the presence of said improved organism. This invention provides that any of steps a), b), and c) can be further repeated in any particular order and any number of times; accordingly, this invention specifically provides methods comprised of any iterative combination of steps a), b), and c), with a number of iterations.

In another embodiment, this invention is directed to a method of producing an improved organism having a desirable trait to by: a) obtaining an initial population of organisms, which can be a clonal population or otherwise, b) generating a set of mutagenized organisms each having at least one genetic mutation, such that when all the genetic mutations in the set of mutagenized organisms are taken as a whole, there is represented a set of substantial genetic mutations c) detecting the manifestation of at least two genetic mutations, and d) introducing at least two detected genetic mutations into one organism. Additionally, this invention provides that any of steps a), b), c), and d) can be further repeated in any particular order and any number of times; accordingly, this invention specifically provides methods comprised of any iterative combination of steps a), b), c), and d), with a total number of iterations can be from one up to one million, including specifically every integer value in between.

In a preferred aspect of embodiments specified herein the step of b) generating a second set of mutagenized organisms is comprised of generating a plurality of organisms, each of which organisms has a particular transgenic mutation.

As used herein, "generating a set of mutagenized organisms having genetic mutations" can be achieved by any means known in the art to mutagenized including any radiation known to mutagenized, such as ionizing and ultra violet. Further examples of serviceable mutagenizing methods include site-saturation mutagenesis, transposon-based methods, and homologous recombination.

"Combining" means incorporating a plurality of different genetic mutations in the genetic makeup (e.g. the genome) of the same organism; and methods to achieve this "combining" step including sexual recombination, homologous recombination, and transposon-based methods.

As used herein, an "initial population of organisms" means a "working population of organisms", which refers simply to a population of organisms with which one is working, and which is comprised of at least one organism. An "initial population of organisms" which can be a clonal population or otherwise.

Accordingly, in step 1) an "initial population of organisms" may be a population of multicellular organisms or of unicellular organisms or of both. An "initial population of organisms" may be comprised of unicellular organisms or multicellular organisms or both. An "initial population of organisms" may be comprised of prokaryotic organisms or eukaryotic organisms or both. This invention provides that an "initial population of organisms" is comprised of at least one organism, and preferred embodiments include at least that.

By "organism" is meant any biological form or thing that is capable of self replication or replication in a host. Examples of "organisms" include the following kinds of organisms (which kinds are not necessarily mutually-exclusive): animals, plants, insects, cyanobacteria, microorganisms, fungi, bacteria, eukaryotes, prokaryotes, mycoplasma, viral organisms (including DNA viruses, RNA viruses), and prions.

Non-limiting particularly preferred examples of kinds of "organisms" also include Archaea (archaebacteria) and Bacteria (eubacteria). Non-limiting examples of Archaea (archaebacteria) include Crenarchaeota, Euryarchaeota, and Korarchaeota. Non-limiting examples Bacteria (eubacteria) include Aquificales, CFB/Green sulfur bacteria group, Chlamydiales/Verrucomicrobia group, Chrysiogenes group, Coprothermobacter group, Cyanobacteria & chloroplasts, Cytophaga/Flexibacter /Bacteriods group, Dictyoglomus group, Fibrobacter/Acidobacteria group, Firmicutes, Flexistipes group, Fusobacteria, Green non-sulfur bacteria, Nitrospira group, Planctomycetales, Proteobacteria, Spirochaetales, Synergistes group, Thermodesulfobacterium group, Thermotogales, Thermus/Deinococcus group. As non-limiting examples, particularly preferred kinds of organisms include Aquifex, Aspergillus, Bacillus, Clostridium, *E. coli,* Lactobacillus, Mycobacterium, Pseudomonas, Streptomyces, and Thermotoga. As additional non-limiting examples, particularly preferred organisms include cultivated organisms such as CHO, VERO, BHK, HeLa, COS, MDCK, Jurkat, HEK-293, and W138. Particularly preferred non-limiting examples of organisms further include host organisms that are serviceable for the expression of recombinant molecules. Organisms further include primary cultures (e.g. cells from harvested mammalian tissues), immortalized cells, all cultivated and culturable cells and multicellular organisms, and all uncultivated and uculturable cells and multicellular organisms.

In a preferred embodiment, knowledge of genomic information is useful for performing the claimed methods; thus, this invention provides the following as preferred but non-limiting examples of organisms that are particularly serviceable for this invention, because there is a significant amount of—if not complete—genomic sequence information (in terms of primary sequence &/or annotation) for these organisms: Human, Insect (e.g. *Drosophila melanogaster*), Higher plants (e.g. *Arabidopsis thaliana*), Protozoan (e.g. *Plasmodium falciparum*), Nematode (e.g. *Caenorhabditis elegans*), Fungi(e.g. *Saccharomyces cerevisiae*), Proteobacteria gamma subdivision (e.g. *Escherichia coli* K-12*Haemophilus influenzae* Rd, *Xylella fastidiosa* 9a5c, *Vibrio cholerae* E1 Tor N16961, *Pseudomonas aeruginosa* PA01, Buchnera sp. APS), Proteobacteria beta subdivision (e.g. *Neisseria meningitidis* MC58 (serogroup B), *Neisseria meningitidis* Z2491 (serogroup A)), Proteobacteria other subdivisions (e.g. *Helicobacter pylori* 26695, *Helicobacter pylori* J99, *Campylobacter jejuni* NCTC11168, *Rickettsia prowazekii*), Gram-positive bacteria (e.g. *Bacillus subtilis, Mycoplasma genitalium, Mycoplasma pneumoniae, Ureaplasma urealyticum, Mycobacterium tuberculosis* H37Rv), Chlamydia (e.g. *Chlamydia trachomatisserovar* D, *Chlamydia muridarum (Chlamydia trachomatis* MoPn), *Chlamydia pneumoniae* CWL029, *Chlamydia pneumoniae* AR39, *Chlamydia pneumoniae* J138), Spirochete (e.g. *Borrelia burgdorferi* B31, *Treponema pallidum*), Cyanobacteria (e.g. Synechocystis sp. PCC6803), Radioresistant bacteria (e.g. *Deinococcus radiodurans* R1), Hyperthermophilic bacteria (e.g. *Aquifex aeolicus* VF5, *Thermotoga maritima* MSB8), and Archaea (e.g. *Methanococcus jannaschii, Methanobacterium thermoautotrophicum* deltaH, *Archaeoglobus fulgidus, Pyrococcus horikoshii* OT3, *Pyrococcus abyssi, Aeropyrum pernix* K1).

Non-limiting particularly preferred examples of kinds of plant "organisms" include those listed in Table 1.

TABLE 1

Non-limiting examples of plant organisms and sources of transgenic molecules (e.g. nucleic acids & nucleic acid products)

| | |
|---|---|
| 1. Alfalfa | 39. Pepper |
| 2. Amelanchier laevis | 40. Persimmon |
| 3. Apple | 41. Petunia |
| 4. Arab. thaliana | 42. Pine |
| 5. Arabidopsis | 43. Pineapple |
| 6. Aspergillus flavus | 44. Pink bollworm |
| 7. Barley | 45. Plum |
| 8. Beet | 46. Poplar |
| 9. Belladonna | 47. Potato |
| 10. Brassica oleracea | 48. Pseudomonas |
| 11. Carrot | 49. Pseudomonas putida |
| 12. Chrysanthemum | 50. Pseudomonas syringae |

TABLE 1-continued

Non-limiting examples of plant organisms and sources of transgenic molecules (e.g. nucleic acids & nucleic acid products)

| | |
|---|---|
| 13. Cichorium intybus | 51. Rapeseed |
| 14. Clavibacter | 52. Rhizobium |
| 15. Clavibacter xyli | 53. Rhizobium etli |
| 16. Coffee | 54. Rhizobium fredii |
| 17. Corn | 55. Rhizobium leguminosarum |
| 18. Cotton | 56. Rhizobium meliloti |
| 19. Cranberry | 57. Rice |
| 20. Creeping bentgrass | 58. Rubus idaeus |
| 21. Cryphonectria parasitica | 59. Spruce |
| 22. Eggplant | 60. Soybean |
| 23. Festuca arundinacea | 61. Squash |
| 24. Fusarium graminearum | 62. Squash-cucumber |
| 25. Fusarium moniliforme | 63. Squash-cucurbita texana |
| 26. Fusarium sporotrichioides | 64. Strawberry |
| 27. Gladiolus | 65. Sugarcane |
| 28. Grape | 66. Sunflower |
| 29. Heterorhabditis bacteriophora | 67. Sweet potato |
| 30. Kentucky bluegrass | 68. Sweetgum |
| 31. Lettuce | 69. TMV |
| 32. Melon | 70. Tobacco |
| 33. Oat | 71. Tomato |
| 34. Onion | 72. Walnut |
| 35. Papaya | 73. Watermelon |
| 36. Pea | 74. Wheat |
| 37. Peanut | 75. Xanthomonas |
| 38. Pelargonium | 76. Xanthomonas campestris |

As used herein, the meaning of "generating a set of mutagenized organisms having genetic mutations" includes the steps of substituting, deleting, as well as introducing a nucleotide sequence into organism; and this invention provides a nucleotide sequence that serviceable for this purpose may be a single-stranded or double-stranded and the fact that its length may be from one nucleotide up to 10,000,000,000 nucleotides in length including specifically every integer value in between.

A mutation in an organism includes any alteration in the structure of one or more molecules that encode the organism. These molecules include nucleic acid, DNA, RNA, prionic molecules, and may be exemplified by a variety of molecules in an organism such as a DNA that is genomic, episomal, or nucleic, or by a nucleic acid that is vectoral (e.g. viral, cosmid, phage, phagemid).

In one aspect, as used herein, a "set of substantial genetic mutations" is preferably a disruption (e.g. a functional knock-out) of at least about 15 to about 150,000 genomic locations or nucleotide sequences (e.g. genes, promoters, regulatory sequences, codons etc.), including specifically every integer value in between. In another aspect, as used herein, a "set of substantial genetic mutations" is preferably an alteration in an expression level (e.g. decreased or increased expression level) or an alteration in the expression pattern (e.g. throughout a period of time) of at least about 15 to about 150,000 genes, including specifically every integer value in between. Corresponding to another aspect, as used herein, a "set of substantial genetic mutations" is preferably an alteration in an expression level (e.g. decreased or increased expression level) or an alteration in the expression pattern (e.g. throughout a period of time) of at least about 15 to about 150,000 gene products &/or phenotypes &/or traits, including specifically every integer value in between.

In another aspect, as used herein, a "set of substantial genetic mutations" with respect to an organism (or type of organism) is preferably a disruption (e.g. a functional knock-out) of at least about 1% to about 100% of genomic locations or nucleotide sequences (e.g. genes, promoters, regulatory sequences, codons etc.) in the organism (or type of organism), including specifically percentages of every integer value in between. In another aspect, as used herein, a "set of substantial genetic mutations" is preferably an alteration in an expression level (e.g. decreased or increased expression level) or an alteration in the expression pattern (e.g. throughout a period of time) of at least about 1% to about 100% of genes in an organism (or type of organism), including specifically percentages of every integer value in between. Corresponding to another aspect, as used herein, a "set of substantial genetic mutations" is preferably an alteration in an expression level (e.g. decreased or increased expression level) or an alteration in the expression pattern (e.g. throughout a period of time) of at least about 1% to about 100% of the gene products &/or phenotypes &/or traits of an organism (or type of organism), including specifically every integer value in between.

In yet another aspect, as used herein, a "set of substantial genetic mutations" is preferably an introduction or deletion of at least about 15 to 150,000 genes promoters or other nucleotide sequences (where each sequence is from 1 base to 10,000,000 bases), including specifically every integer value in between. For example, one can introduce a library of at least about 15 to 150,000 nucleotides (genes or promoters) produced by "site-saturation mutagenesis" &/or by "ligation reassembly" (including any specific aspect thereof provided herein) into an "initial population of organisms".

It is provided that wherever the manipulation of a plurality of "genes" is mentioned herein, gene pathways (e.g. that ultimately lead to the production of small molecules) are also included. It is appreciated herein that knocking-out, altering expression level, and altering expression pattern can be achieved, by non-limiting exemplification, by mutagenizing a nucleotide sequence corresponding gene as well as a corresponding promoter that affects the expression of the gene.

As used herein, a "mutagenized organism" includes any organism that has been altered by a genetic mutation.

A "genetic mutation" can be, by way of non-limiting and non-mutually exclusive exemplification, and change in the nucleotide sequence (DNA or RNA) with respect to genomic, extra-genomic, episomal, mitochondrial, and any nucleotide sequence associated with (e.g. contained within or considered part of) an organism.

According to this invention, detecting the manifestation of a "genetic mutation" means "detecting the manifestation of a detectable parameter", including but not limited to a change in the genomic sequence. Accordingly, this invention provides that a step of sequencing (&/or annotating) of and organism's genomic DNA is necessary for some methods of this invention, and exemplary but non-limiting aspects of this sequencing (&/or annotating) step are provided herein.

A detectable "trait", as used herein, is any detectable parameter associated with the organism. Accordingly, such a detectable "parameter" includes, by way of non-limiting exemplification, any detectable "nucleotide knock-in", any detectable "nucleotide knock-outs", any detectable "phenotype", and any detectable "genotype". By way of further illustration, a "trait" includes any substance produced or not produced by the organism. Accordingly, a "trait" includes viability or non-viability, behavior, growth rate, size, morphology. "Trait" includes increased (or alternatively decreased) expression of a gene product or gene pathway product. "Trait" also includes small molecule production (including vitamins, antibiotics), herbicide resistance, drought resistance, pest resistance, production of any recombinant biomolecule (ie.g. vaccines, enzymes, protein therapeutics, chiral enzymes). Additional examples of serviceable traits for this invention are shown in Table 2.

TABLE 2—Non-limiting examples of serviceable genes, gene products, phenotypes, or traits according to the methods of this invention (e.g. knockouts, knockins, increased or decreased expression level, increased or decreased expression pattern)

TABLE 2

Non-limiting examples of serviceable genes, gene products, phenotypes, or traits according to the methods of this invention (e.g. knockouts, knockins, increased or decreased expression level, increased or decreased expression pattern)

Part 1.
Non-limiting examples of genes or gene products

| | |
|---|---|
| 1. | 17 kDa protein |
| 2. | 3-hydroxy-3-methylglutaryl Coenzyme A reductase |
| 3 | 4-Coumarate:CoA ligase knockout |
| 4. | 60 kDa protein |
| 5. | Ac transposable element |
| 6 | ACC deaminase |
| 7. | ACC oxidase knockout |
| 8. | ACC synthase |
| 9. | ACC synthase knockout |
| 10. | Acetohydroxyacid synthase variant |
| 11. | Acetolactate synthase |
| 12. | Acetyl CoA carboxylase |
| 13. | ACP acyl-ACP thioesterase |
| 14. | ACP thioesterase |
| 15. | Acyl CoA reductase |
| 16. | Acyl-ACP knockout |
| 17. | Acyl-ACP desaturase |
| 18. | Acyl-ACP desaturase knockout |
| 19. | Acyl-ACP thioesterase |
| 20. | ADP glucose pyrophosphorylase |
| 21. | ADP glucose pyrophosphorylase knockout |
| 22. | Agglutinin |
| 23. | Aleurone 1 |
| 24. | Alpha hordothinonin |
| 25. | Alpha-amylase |
| 26. | Alpha-hemoglobin |
| 27. | Aminoglycoside 3'-adenylytransferase |
| 28. | Amylase |
| 29. | Anionic peroxidase |
| 30. | Antibody |
| 31. | Antifungal protein |
| 32. | Antithrombin |
| 33. | Antitrypsin |
| 34. | Antiviral protein |
| 35. | Aspartokinase |
| 36. | Attacin E |
| 37. | B1 regulatory gene |
| 38. | B-1,3-glucanase knockout |
| 39. | B-1,4-endoglucanase knockout |
| 40. | Bacteropsin |
| 41. | Barnase |
| 42. | Barstar |
| 43. | Beta-hemoglobin |
| 44. | B-glucuronidase |
| 45. | C1 knockout |
| 46. | C1 regulatory gene |
| 47. | C2 knockout |
| 48. | C3 knockout |
| 49. | Caffeate O-methylthransferase |
| 50. | Caffeate O-methyltransferase knockout |
| 51. | Caffeoyl CoA O-methyltransferase knockout |
| 52. | Casein |
| 53 | Cecropin |
| 54. | Cecropin B |
| 55. | Cellulose binding protein |
| 56. | Chalcone synthase knockout |
| 57. | Chitinase |
| 58. | Chitobiosidase |
| 59. | Chloramphenicol acetyltransferase |
| 60. | Cholera toxin B |
| 61. | Choline oxidase |

TABLE 2-continued

Non-limiting examples of serviceable genes, gene products, phenotypes, or traits according to the methods of this invention (e.g. knockouts, knockins, increased or decreased expression level, increased or decreased expression pattern)

| | |
|---|---|
| 62. | Cinnamate 4-hydroxylase |
| 63. | Cinnamate 4-hydroxylase knockout |
| 64. | Coat protein |
| 65. | Coat protein knockout |
| 66. | Conglycinin |
| 67. | CryIA |
| 68. | CryIAb |
| 69. | CryIAc |
| 70. | CryIB |
| 71. | CryIIA |
| 72. | CryIIIA |
| 73. | CryVIA |
| 74. | Cyclin dependent kinase |
| 75. | Cyclodextrin glycosyltransferase |
| 76. | Cylindrical inclusion protein |
| 77. | Cystathionine synthase |
| 78. | Delta-12 desaturase |
| 79. | Delta-12 desaturase knockout |
| 80. | Delta-12 saturase |
| 81. | Delta-12 saturase knockout |
| 82. | Delta-15 desaturase |
| 83. | Delta-15 desaturase knockout |
| 84. | Delta-9 desaturase |
| 85. | Delta-9 desaturase knockout |
| 86. | Deoxyhypusine synthase (DHS) |
| 87. | Deoxyhypusine synthase knockout |
| 88. | Diacylglyceryl acetyl tansferase |
| 89. | Dihydrodipicolinate synthase |
| 90. | Dihydrofolate reductase |
| 91. | Diptheria toxin A |
| 92. | Disease resistance response gene 49 |
| 93. | Double stranded ribonuclease |
| 94. | Ds transposable element |
| 95. | Elongase |
| 96. | EPSPS |
| 97. | Ethylene forming enzyme knockout |
| 98. | Ethylene receptor protein |
| 99. | Ethylene receptor protein knockout |
| 100. | Fatty acid elongase |
| 101. | Fluorescent protein |
| 102. | G glycoprotein |
| 103. | Galactanase |
| 104. | Galanthus nivalis agglutinin |

Non-limiting examples of transgenic genes & gene knockouts

| | |
|---|---|
| 105. | Genome-linked protein |
| 106. | Glucanase |
| 107. | Glucanase knockout |
| 108. | Glucose oxidase |
| 109. | Glutamate dehydrogenase |
| 110. | Glutamine binding protein |
| 111. | Glutamine synthetase |
| 112. | Glutenin |
| 113. | Glycerol-3-phosphate acetyl transferase |
| 114. | Glyphosate exidoreductase |
| 115. | Glyphosate oxidoreductase |
| 116. | Green fluorescent protein |
| 117. | Helper component |
| 118. | Hemicellulase |
| 119. | Hup locus |
| 120. | Hygromycin phosphotransferase |
| 121. | Hyoscamine 6B-hydroxylase |
| 122. | IAA monooxygenase |
| 123. | Invertase |
| 124. | Invertase knockout |
| 125. | Isopentenyl transferase |
| 126. | Ketoacyl-ACP synthase |
| 127. | Ketoacyl-ACP synthase knockout |
| 128. | Larval serum protein |
| 129. | Leafy homeotic regulatory gene |
| 130. | Lectin |
| 131. | Lignin peroxidase |
| 132. | Luciferase |

TABLE 2-continued

Non-limiting examples of serviceable genes, gene products, phenotypes, or traits according to the methods of this invention (e.g. knockouts, knockins, increased or decreased expression level, increased or decreased expression pattern)

| | |
|---|---|
| 133. | Lysine-2 gene |
| 134. | Lysophosphatidic acid acetyl transferase |
| 135. | Lysozyme |
| 136. | Mabinlin |
| 137. | Male sterility protein |
| 138. | Metallothionein |
| 139. | Modified ethylene receptor protein |
| 140. | Modified ethylene receptor protein knockout |
| 141. | Monooxygenase |
| 142. | Movement protein |
| 143. | Movement protein nonfunctional |
| 144. | N gene for TMV resistance |
| 145. | N-acetyl glucosidase |
| 146. | Nitrilase |
| 147. | Nopaline synthase |
| 148. | Notch |
| 149. | NptII |
| 150. | Nuclear inclusion protein a |
| 151. | Nuclear inclusion protein b |
| 152. | Nucleocapsid |
| 153. | Nucleoprotein |
| 154. | O-acyl transferase |
| 155. | Oleayl-ACP thioesterase |
| 156. | Omega 3 desaturase |
| 157. | Omega 3 desaturease knockout |
| 158. | Omega 6 desaturase |
| 159. | Omega 6 desaturase knockout |
| 160. | O-methyltransferase |
| 161. | Osmotin |
| 162. | Oxalate oxidase |
| 163. | Par locus |
| 164. | Pathogenesis protein 1a |
| 165. | Pectate lyase |
| 166. | Pectin esterase |
| 167. | Pectin esterase knockout |
| 168. | Pectin methylesterase |
| 169. | Pectin methylesterase knockout |
| 170. | Pentenlypyrophosphate isomerase |
| 171. | Phosphinothricin |
| 172. | Phosphinothricin acetyl transferase |
| 173. | Phytochrome A |
| 174. | Phytoene synthase |
| 175. | Phleomycin binding protein |
| 176. | Polygalacturonase |
| 177. | Polygalacturonase knockout |
| 178. | Polygalacturonase inhibitor protein |
| 179. | Prf regulatory gene |
| 180. | Prosystemin |
| 181. | Protease |
| 182. | Protein A |
| 183. | Protein kinase |
| 184. | Proteinase inhibitor 1 |
| 185. | Pti5 transcription factor |
| 186. | R regulatory gene |
| 187. | Receptor kinase |
| 188. | Recombinase |
| 189. | Reductase |
| 190. | Replicase |
| 191. | Resveratrol synthase |
| 192. | Ribonuclease |
| 193. | rolc |
| 194. | Rol hormone gene |
| 195. | S-adenosylmethione decarboxylase |
| 196. | S-adenosylmethione hydrolase |
| 197. | S-adenosylmethionine transferase |
| 198. | Salicylate hydroxylase |
| 199. | Satellite RNA |
| 200. | Seed storage protein |
| 201. | Serine-threonine protein kinase |
| 202. | Serum albumin |
| 203. | Shrunken 2 |
| 204. | Sorbitol dehydrogenase |
| 205. | Sorbitol synthase |
| 206. | Stilbene synthase |
| 207. | Storage protein |
| 208. | Sucrose phosphate synthase |
| 209. | Systemic acquired resistance gene 8.2 |
| 210. | Tetracycline binding protein |
| 211. | Thioesterase (x2) |
| 212. | Thiolase |
| 213. | TobRB7 |
| 214. | Transcriptional activator |
| 215. | Transposon Tn5 |
| 216. | Trehalase |
| 217. | Trehalase knockout |
| 218. | Trichodiene synthase |
| 219. | Trichosanthin |
| 220. | Trifolitoxin |
| 221. | Trypsin inhibitor |
| 222. | T-URF13 mitochondrial |
| 223. | UDP glucose glucosyltransferase |
| 224. | Violaxanthin de-epoxidase |
| 225. | Violaxanthin de-epoxidase knockout |
| 226. | Wheat germ agglutinin |
| 227. | Xanthosine-N7-methyltransferase knockout |
| 228. | Zein storage protein |

Part 2.
Non-limiting examples of input traits/phenotypes

| | |
|---|---|
| 1. | 2,4-D tolerant |
| 2. | Alernaria resistant |
| 3. | Altered amino acid composition |
| 4. | *Alternaria solani* resistant |
| 5. | Ammonium assimilation increased |
| 6. | AMV resistant |
| 7. | Aphid resistant |
| 8. | Apple scab resistant |
| 9. | Aspergillus resistant |
| 10. | B-1,4-endoglucanase |
| 11. | Bacterial leaf blight resistant |
| 12. | Bacterial speck resistant |
| 13. | BCTV resistant |
| 14. | Blackspot bruise resistant |
| 15. | BLRV resistant |
| 16. | BNYVV Resistant |
| 17. | *Botrytis cinerea* resistant |
| 18. | Botrytis resistant |
| 19. | BPMV resistant |
| 20. | Bromoxynil tolerant |
| 21. | BYDV resistant |
| 22. | BYMV resistant |
| 23. | Carbohydrate metabolism altered |
| 24. | Cell wall altered |
| 25. | Chlorsulfuron tolerant |
| 26. | Clavibacter resistant |
| 27. | CLRV resistant |
| 28. | CMV resistant |
| 29. | Cold tolerant |
| 30. | Coleopteran resistant |
| 31. | Colletotrichum resistant |
| 32. | Colorado potato beetle resistant |
| 33. | Constitutive expression of glutamine synthetase |
| 34. | *Corynebacterium sepedonicum* resistant |
| 35. | Cottonwood leaf beetle resistant |
| 36. | Crown gall resistant |
| 37. | Crown rot resistant |
| 38. | Cucumovirus resistant |
| 39. | Cutting rootability increased |
| 40. | Downy mildew resistant |
| 41. | Drought tolerant |
| 42. | *Erwinia carotovora* resistant |
| 43. | Ethylene production reduced |
| 44. | European Corn Borer resistant |
| 45. | Female sterile |
| 46. | Fenthion susceptible |
| 47. | Fertility altered |
| 48. | Fire blight resistant |

TABLE 2-continued

Non-limiting examples of serviceable genes, gene products, phenotypes, or traits according to the methods of this invention (e.g. knockouts, knockins, increased or decreased expression level, increased or decreased expression pattern)

| | |
|---|---|
| 49. | Flower and fruit abscission reduced |
| 50. | Flower and fruit set altered |
| 51. | Flowering altered |
| 52. | Flowering time altered |
| 53. | Frogeye leaf spot resistant |
| 54. | Fruit ripening altered |
| 55. | Fruit ripening delayed |
| 56. | Fruit rot resistant |
| 57. | Fruit solids increased |
| 58. | Fruit sweetness increased |
| 59. | Fungal post-harvest resistant |
| 60. | Fungal resistant |
| 61. | Fungal resistant general |
| 62. | Fusarium resistant |
| 63. | Glyphosate tolerant |
| 64. | Growth rate altered |
| 65. | Growth rate reduced |
| 66. | Heat stable glucanase produced |
| 67. | Hordothionin produced |
| 68. | Imidazolinone tolerant |
| 69. | Insect resistant general |
| 70. | Kanamycin resistant |
| 71. | Lepidopteran resistant |
| 72. | Lesser cornstalk borer resistant |
| 73. | LMV resistant |
| 74. | Loss of systemic resistance |
| 75. | Male sterile |
| 76. | Marssonina resistant |
| 77. | MCDV resistant |
| 78. | MCMV resistant |
| 79. | MDMV resistant |
| 80. | MDMV-B resistant |
| 81. | Mealybug wilt virus resistant |
| 82. | Melamtsora resistant |
| 83. | Melodgyne resistant |
| 84. | Methotrexate resistant |
| 85. | Mexican Rice Borer resistant |
| 86. | Nucleocapsid protein produced |
| 87. | Oblique banded leafroller resistant |
| 88. | PEMV resistant |
| 89. | PeSV resistant |
| 90. | Phoma resistant |
| 91. | Phosphinothricin tolerant |
| 92. | Phratora leaf beetle resistant |
| 93. | Phytophthora resistant |
| 94. | PLRV resistant |
| 95. | Polyamine metabolism altered |
| 96. | Potyvirus resistant |
| 97. | Powdery mildew resistant |
| 98. | PPV resistant |
| 99. | *Pratylenchus vulnus* resistant |
| 100. | Proteinase inhibitors level constitutive |
| 101. | PRSV resistant |
| 102. | PRV resistant |

Non-limiting examples of transgenic input traits/phenotypes

| | |
|---|---|
| 103. | PSbMV resistant |
| 104. | *Pseudomonas syringae* resistant |
| 105. | PStV resistant |
| 106. | PVX resistant |
| 107. | PVY resistant |
| 108. | RBDV resistant |
| 109. | Rhizoctonia resistant |
| 110. | *Rhizoctonia solani* resistant |
| 111. | Ring rot resistance |
| 112. | Root-knot nematode resistant |
| 113. | SbMV resistant |
| 114. | Sclerotinia resistant |
| 115. | SCMV resistant |
| 116. | SCYLV resistant |
| 117. | Secondary metabolite increased |
| 118. | Seed set reduced |
| 119. | Selectable marker |

TABLE 2-continued

Non-limiting examples of serviceable genes, gene products, phenotypes, or traits according to the methods of this invention (e.g. knockouts, knockins, increased or decreased expression level, increased or decreased expression pattern)

| | |
|---|---|
| 120. | Senescence altered |
| 121. | Septoria resistant |
| 122. | Shorter stems |
| 123. | Soft rot fungal resistant |
| 124. | Soft rot resistant |
| 125. | SqMV resistant |
| 126. | SrMV resistant |
| 127. | Storage protein altered |
| 128. | *Streptomyces scabies* resistant |
| 129. | Sulfonylurea tolerant |
| 130. | Tetracycline binding protein produced |
| 131. | TEV resistant |
| 132. | Thelaviopsis resistant |
| 133. | TMV resistant |
| 134. | Tobamovirus resistant |
| 135. | ToMoV resistant |
| 136. | ToMV resistant |
| 137. | Transposon activator |
| 138. | Transposon inserted |
| 139. | TRV resistant |
| 140. | TSWV resistant |
| 141. | TVMV resistant |
| 142. | TYLCV resistant |
| 143. | Tyrosine level increased |
| 144. | Venturia resistant |
| 145. | *Verticillium dahliae* resistant |
| 146. | Verticillium resistant |
| 147. | Visual marker |
| 148. | WMV2 resistant |
| 149. | WSMV resistant |
| 150. | Yield increased |
| 151. | ZYMV resistant |

Part 3.
Non-limiting examples of output traits/phenotypes

| | |
|---|---|
| 1. | ACC oxidase level decreased |
| 2. | Altered lignin biosynthesis |
| 3. | B-1,4-endoglucanase |
| 4. | Botrytis resistant |
| 5. | Carbohydrate metabolism altered |
| 6. | Carotenoid content altered |
| 7. | Cell wall altered |
| 8. | CMV resistant |
| 9. | Coleopteran resistant |
| 10. | Dry matter content increased |
| 11. | Ethylene production reduced |
| 12. | Ethylene synthesis reduced |
| 13. | Fatty acid metabolism altered |
| 14. | Fire blight resistant |
| 15. | Flower and fruit abscission reduced |
| 16. | Flower and fruit set altered |
| 17. | Flowering time altered |
| 18. | Fruit firmness increased |
| 19. | Fruit pectin esterasse levels decreased |
| 20. | Fruit ripening altered |
| 21. | Fruit ripening delayed |
| 22. | Fruit solids increased |
| 23. | Fruit sugar profile altered |
| 24. | Fruit sweetness increased |
| 25. | Glucuronidase expressing |
| 26. | Heat stable glucanase produced |
| 27. | Heavy metals sequestered |
| 28. | Hordothionin produced |
| 29. | Improved fruit quality |
| 30. | Industrial enzyme produced |
| 31. | Lepidopteran resistant |
| 32. | Lysine level increased |
| 33. | Mealybug wilt virus resistant |
| 34. | Methionine level increased |
| 35. | Nucleocapsid protein produced |
| 36. | Oil profile altered |
| 37. | Pectin esterase level reduced |
| 38. | Phamaceutical proteins produced |

TABLE 2-continued

Non-limiting examples of serviceable genes, gene products, phenotypes, or traits according to the methods of this invention (e.g. knockouts, knockins, increased or decreased expression level, increased or decreased expression pattern)

| | |
|---|---|
| 39. | Phosphinothricin tolerant |
| 40. | Phytoene synthase activity increased |
| 41. | Pigment metabolism altered |
| 42. | Polygalacturonase level reduced |
| 43. | Processing characteristics altered |
| 44. | Prolonged shelf life |
| 45. | Protein altered |
| 46. | Protein quality altered |
| 47. | PRSV resistant |
| 48. | Root-knot nematode resistant |
| 49. | Sclerotinia resistant |
| 50. | Seed composition altered |
| 51. | Seed methionine storage increased |
| 52. | Seed set reduced |
| 53. | Seed storage protein |
| 54. | Senescence altered (e.g. Shelf life increased) |
| 55. | Shorter stems |
| 56. | Solids increased |
| 57. | SqMV resistant |
| 58. | Starch level increased |
| 59. | Starch metabolism altered |
| 60. | Starch reduced |
| 61. | Sterols increased |
| 62. | Storage protein altered |
| 63. | Sugar alcohol levels increased |
| 64. | Tetracycline binding protein produced |
| 65. | Tyrosine level increased |
| 66. | Verticillium resistant |
| 67. | Visual marker |
| 68. | WMV2 resistant |
| 69. | Yield increased |
| 70. | ZYMV resistant |

Part 4.
Non-limiting examples of traits/phenotypes with agronomic properties

| | |
|---|---|
| 1. | ACC oxidase level decreased |
| 2. | Altered amino acid composition |
| 3. | Altered lignin biosynthesis |
| 4. | Altered maturing |
| 5. | Altered plant development |
| 6. | Aluminum tolerant |
| 7. | Ammonium assimilation increased |
| 8. | Anthocyanin produced in seed |
| 9. | B-1,4-endoglucanase |
| 10. | Calmodulin level altered |
| 11. | Carbohydrate metabolism altered |
| 12. | Carotenoid content altered |
| 13. | Cell wall altered |
| 14. | Cold tolerant |
| 15. | Constitutive expression of glutamine synthetase |
| 16. | Cutting root ability increased |
| 17. | Development altered |
| 18. | Drought tolerant |
| 19. | Dry matter content increased |
| 20. | Environmental stress reduced |
| 21. | Ethylene metabolism altered |
| 22. | Ethylene production reduced |
| 23. | Ethylene synthesis reduced |
| 24. | Fatty acid metabolism altered |
| 25. | Female sterile |
| 26. | Fenthion susceptible |
| 27. | Fertility altered |
| 28. | Fiber quality altered |
| 29. | Flower and fruit abscission reduced |
| 30. | Flower and fruit set altered |
| 31. | Flowering altered |
| 32. | Flower color altered |
| 33. | Flowering time altered |
| 34. | Fruit firmness increased |
| 35. | Fruit pectin esterase and levels decreased |
| 36. | Fruit polygalacturonase level decreased |
| 37. | Fruit ripening altered |
| 38. | Fruit ripening delayed |

TABLE 2-continued

Non-limiting examples of serviceable genes, gene products, phenotypes, or traits according to the methods of this invention (e.g. knockouts, knockins, increased or decreased expression level, increased or decreased expression pattern)

| | |
|---|---|
| 39. | Fruit solids increased |
| 40. | Fruit sugar profile altered |
| 41. | Fruit sweetness increased |
| 42. | Glucuronidase expressing |
| 43. | Growth rate altered |
| 44. | Growth rate increased |
| 45. | Growth rate reduced |
| 46. | Heat stable glucanase produced |
| 47. | Heat tolerant |
| 48. | Heavy metals sequestered |
| 49. | Hordothionin produced |
| 50. | Improved fruit quality |
| 51. | Increased phosphorus |
| 52. | Increased stalk strength |
| 53. | Industrial enzyme produced |
| 54. | Lignin levels decreased |
| 55. | Lipase expressed in seeds |
| 56. | Lysine level increased |
| 57. | Male sterile |
| 58. | Male sterile reversible |
| 59. | Methionine level increased |
| 60. | Modified growth characteristics |
| 61. | Mycotoxin degradation |
| 62. | Nitrogen metabolism altered |
| 63. | Nucleocapsid protein produced |
| 64. | Oil profile altered |
| 65. | Oil quality altered |
| 66. | Oxidative stress tolerant |
| 67. | Pectin esterase level reduced |
| 68. | Pharmaceutical proteins produced |
| 69. | Photosynthesis enhanced |
| 70. | Phytoene synthase activity increased |
| 71. | Pigment metabolism altered |
| 72. | Polyamine metabolism altered |
| 73. | Polygalacturonase level reduced |
| 74. | *Pratylenchus vulnus* resistant |
| 75. | Processing characteristics altered |
| 76. | Prolonged shelf life |
| 77. | Protein altered |
| 78. | Protein lysine level increased |
| 79. | Protein quality altered |
| 80. | Proteinase inhibitors level constitutive |
| 81. | Salt tolerance increased |
| 82. | Seed composition altered |
| 83. | Seed methionine storage increased |
| 84. | Seed set reduced |
| 85. | Selectable marker |
| 86. | Senescence altered |
| 87. | Shorter stems |
| 88. | Solids increased |
| 89. | Starch level increased |
| 90. | Starch metabolism altered |
| 91. | Starch reduced |
| 92. | Sterols increased |
| 93. | Storage protein altered |
| 94. | Stress tolerant |
| 95. | Sugar alcohol levels increased |
| 96. | Tetracycline binding protein produced |
| 97. | Thermostable protein produced |
| 98. | Transposon activator |
| 99. | Transposon inserted |
| 100. | Tyrosine level increased |
| 101. | Visual marker |
| 102. | Vivipary increased |
| 103. | Yield increased |

Part 5.
Non-limiting examples of traits/phenotypes with product quality properties

| | |
|---|---|
| 1. | 2,4-D tolerant |
| 2. | ACC oxidase level decreased |
| 3. | Altered amino acid composition |
| 4. | Altered lignin biosynthesis |
| 5. | Anthocyanin produced in seed |

TABLE 2-continued

Non-limiting examples of serviceable genes, gene products, phenotypes, or traits according to the methods of this invention (e.g. knockouts, knockins, increased or decreased expression level, increased or decreased expression pattern)

| | |
|---|---|
| 6. | Antioxidant enzyme increased |
| 7. | Auxin metabolism and increased tuber solids |
| 8. | B-1,4-endoglucanase |
| 9. | Blackspot bruise resistant |
| 10. | Brown spot resistant |
| 11. | Bruising reduced |
| 12. | Caffeine levels reduced |
| 13. | Carbohydrate metabolism altered |
| 14. | Carotenoid content altered |
| 15. | Cell wall altered |
| 16. | Cold tolerant |
| 17. | Delayed softening |
| 18. | Disulfides reduced in endosperm |
| 19. | Dry matter content increased |
| 20. | Ear mold resistant |
| 21. | Ethylene production reduced |
| 22. | Ethylene synthesis reduced |
| 23. | Extended flower life |
| 24. | Fatty acid metabolism altered |
| 25. | Fiber quality altered |
| 26. | Fiber strength altered |
| 27. | Flavor enhancer |
| 28. | Flower and fruit abscission reduced |
| 29. | Fruit firmness increased |
| 30. | Fruit invertase level decreased |
| 31. | Fruit polygalacturonase level decreased |
| 32. | Fruit ripening altered |
| 33. | Fruit ripening delayed |
| 34. | Fruit solids increased |
| 35. | Fruit sugar profile altered |
| 36. | Fruit sweetness increased |
| 37. | Glyphosate tolerant |
| 38. | Heat stable glucanase produced |
| 39. | Improved fruit quality |
| 40. | Increased phosphorus |
| 41. | Increased protein levels |
| 42. | Lignin levels decreased |
| 43. | Lysine level increased |
| 44. | Male sterile |
| 45. | Melanin produced in cotton fibers |
| 46. | Metabolism altered |
| 47. | Methionine level increased |
| 48. | Mycotoxin degradation |
| 49. | Mycotoxin production inhibited |
| 50. | Nicotine levels reduced |
| 51. | Nitrogen metabolism altered |
| 52. | Novel protein produced |
| 53. | Nutritional quality altered |
| 54. | Oil profile altered |
| 55. | Oil quality altered |
| 56. | Pectin esterase level reduced |
| 57. | Photosynthesis enhanced |
| 58. | Phytoene synthase activity increased |
| 59. | Pigment metabolism altered |
| 60. | Polyamine metabolism altered |
| 61. | Polygalacturonase level reduced |
| 62. | Processing characteristics altered |
| 63. | Prolonged shelf life |
| 64. | Protein altered |
| 65. | Protein lysine level increased |
| 66. | Protein quality altered |
| 67. | Proteinase inhibitors level constitutive |
| 68. | Rust resistant |
| 69. | Seed composition altered |
| 70. | Seed methionine storage increased |
| 71. | Seed number increased |
| 72. | Seed quality altered |
| 73. | Seed set reduced |
| 74. | Seed weight increased |
| 75. | Senescence altered |
| 76. | Solids increased |
| 77. | Starch level increased |
| 78. | Starch metabolism altered |
| 79. | Starch reduced |
| 80. | Steroidal glycoalkaloids reduced |
| 81. | Sterols increased |
| 82. | Storage protein altered |
| 83. | Sugar alcohol levels increased |
| 84. | Thermostable protein produced |
| 85. | Tryptophan level increased |
| 86. | Tuber solids increased |
| 87. | Yield increased |

Part 6.
Non-limiting examples of traits/phenotypes with herbicide tolerance properties

| | |
|---|---|
| 1. | 2,4D tolerant |
| 2. | Chloroacetanilide tolerant |
| 3. | Fertility altered |
| 4. | Protein altered |
| 5. | Lignin levels decreased |
| 6. | Methionine level increased |
| 7. | Bromoxynil tolerant |
| 8. | Metabolism altered |
| 9. | Imidazole tolerant |
| 10. | Imidazolinone tolerant |
| 11. | Sulfonylurea tolerant |
| 12. | Northern corn leaf blight resistant |
| 13. | Herbicide tolerant |
| 14. | Isoxazole tolerant |
| 15. | Chlorsulfuron tolerant |
| 16. | Glyphosate tolerant |
| 17. | Lepidopteran resistant |
| 18. | Phosphinothricin tolerant |
| 19. | Sulfonylurea tolerant |

Part 7.
Non-limiting exaples of traits/phenotypes with pest resistance properties Legend BR - Bacterial Resistant
FR - Fungal Resistant
IR - Insent Resistant
NR - Nematode Resistant
VR - Viral Resistant

| | |
|---|---|
| 1. | Agrobacterium resistant - BR |
| 2. | Alternaria resistant - FR |
| 3. | *Alternaria daucii* resistant - FR |
| 4. | *Alternaria solani* resistant - FR |
| 5. | AMV resistant - VR |
| 6. | Anthracnose resistant - FR |
| 7. | Aphid resistant - IR |
| 8. | Apple scab resistant - FR |
| 9. | Aspergillus resistant - FR |
| 10. | Bacterial leaf blight resistant - BR |
| 11. | Bacterial resistant - BR |
| 12. | Bacterial soft rot resistant - BR |
| 13. | Bacterial soft rot resistant - VR |
| 14. | Bacterial speck resistant - BR |
| 15. | BCTV resistant - VR |
| 16. | Black shank resistant - FR |
| 17. | BLRV resistant - VR |
| 18. | BNYVV resistant - VR |
| 19. | *Botrytis cinerea* resistant - FR |
| 20. | Botrytis resistant - FR |
| 21. | BPMV resistant - VR |
| 22. | Brown spot resistant - FR |
| 23. | BYDV resistant - VR |
| 24. | BYMV resistant - VR |
| 25. | CaMV resistant - VR |
| 26. | Cercospora resistant - FR |
| 27. | Clavibacter resistant - BR |
| 28. | Closteroviurs resistant - BR |
| 29. | CLRV resistant - VR |
| 30. | CMV resistant - FR |
| 31. | Coleopteran resistant - IR |
| 32. | Colletotrichum resistant - FR |

TABLE 2-continued

Non-limiting examples of serviceable genes, gene products, phenotypes, or traits according to the methods of this invention (e.g. knockouts, knockins, increased or decreased expression level, increased or decreased expression pattern)

| | |
|---|---|
| 33. | Colorado potato beetle resistant - IR |
| 34. | Corn earworm resistant - IR |
| 35. | *Corynebacterium sepedonicum* resistant - BR |
| 36. | Cottonwood leaf beetle resistant - IR |
| 37. | Criconhemella resistant - NR |
| 38. | Crown gall resistant - BR |
| 39. | Cucumovirus resistant - VR |
| 40. | Cylindrosporium resistant - FR |
| 41. | Disease resistant general - FR |
| 42. | Dollar spot resistant - FR |
| 43. | Downy mildew resistant - FR |
| 44. | Ear mold resistant - FR |
| 45. | *Erwinia carotovora* resistant - BR |
| 46. | European Corn Borer resistant - IR |
| 47. | Eyespot resistant - FR |
| 48. | Fall armyworm resistant - IR |
| 49. | Fire blight resistant - BR |
| 50. | Frogeye leaf spot resistanT - FR |
| 51. | Fruit rot resistant - FR |
| 52. | Fungal post-harvest resistant - FR |
| 53. | Fungal resistant - FR |
| 54. | Fungal resistant general - FR |
| 55. | *Fusarium dehlae* resistant - FR |
| 56. | Fusarium resistant - FR |
| 57. | Geminivirus resistant - VR |
| 58. | Gray lead spot resistant - FR |
| 59. | Helminthosporium resistant - FR |
| 60. | Hordothionin produced - BR |
| 61. | Insect predator resistant - IR |
| 62. | Insect resistant general - IR |
| 63. | Late blight resistant - FR |
| 64. | Leaf blight resistant - FR |
| 65. | Leaf spot resistant - FR |
| 66. | Lepidopteran resistant - IR |
| 67. | Lesser cornstalk borer resistant - IR |
| 68. | LMV resistant - VR |
| 69. | Loss of systemic resistance - VR |
| 70. | Marssonina resistant - FR |
| 71. | MCDV resistant - VR |
| 72. | MCMV resistant - VR |
| 73. | MDMV resistant - VR |
| 74. | MDMV-B resistant - VR |
| 75. | Mealybug wilt virus resistant - VR |
| 76. | Melamtsora resistant - FR |
| 77. | Melodgyne resistant - NR |
| 78. | Meloidogyne resistant - NR |
| 79. | Mexican Rice Borer resistant - IR |
| 80. | Mycotoxin degradation - FR |
| 81. | Nepovirus resistant - VR |
| 82. | Northern corn leaf blight resistant - IR |
| 83. | Nucleocapsid protein produced - VR |
| 84. | Oblique banded leafroller resistant - IR |
| 85. | Oomycete resistant - FR |
| 86. | Pathogenesis related proteins level increased - FR |
| 87. | PEMV resistant - VR |
| 88. | PeSV Resistant - VR |
| 89. | Phatora leaf beetle resistant - IR |
| 90. | Phoma resistant - FR |
| 91. | Phytophthora resistant - FR |
| 92. | PLRV resistant - VR |
| 93. | Potyvirus resistant - VR |
| 94. | Powdery mildew resistant - FR |
| 95. | PPV resistant - VR |
| 96. | *Pratylenchus vulnus* resistant - NR |
| 97. | PRSV resistant - VR |
| 98. | PRV resistant - VR |
| 99. | PSbMV resistant - VR |
| 100. | *Pseudomonas syringae* resistant - BR |
| 101. | PStV resistant - VR |
| 102. | PVX resistant - VR |
| 103. | PVY resistant - VR |
| 104. | RBDV resistant - VR |
| 105. | Rhizoctonia resistant - FR |
| 106. | *Rhizoctonia solani* resistant - FR |
| 107. | Ring rot resistance - BR |
| 108. | Root-knot nematode resistant - NR |
| 109. | Rust resistant - FR |
| 110. | SbMV resistant - VR |
| 111. | Sclerotinia resistant - FR |
| 112. | SCMV resistant - VR |
| 113. | SCYLV resistant - VR |
| 114. | Septoria resistant - FR |
| 115. | Smut resistant - FR |
| 116. | SMV resistant - VR |
| 117. | Sod web worm resistant - IR |
| 118. | Soft rot fungal resistant - FR |
| 119. | Soft rot resistant - BR |
| 120. | Southwestern corn borer resistant - IR |
| 121. | SPFMV resistant - VR |
| 122. | Sphaeropsis fruit rot resistant - FR |
| 123. | SqMV resistant - VR |
| 124. | SrMV resistant - VR |
| 125. | *Streptomyces scabies* resistant - BR |
| 126. | Sugar cane borer resistant - IR |
| 127. | TEV resistant - VR |
| 128. | Thelaviopsis resistant - FR |
| 129. | TMV resistant - FR |
| 130. | Tobamovirus resistant - VR |
| 131. | ToMoV resistant - VR |
| 132. | ToMV resistant - VR |
| 133. | TRV resistant - VR |
| 134. | TSWV resistant - VR |
| 135. | TVMV resistant - VR |
| 136. | TYLCV resistant - VR |
| 137. | Venturia resistant - FR |
| 138. | *Verticillium dahliae* resistant - FR |
| 139. | Verticillium resistant - FR |
| 140. | Western corn root worm resistant - IR |
| 141. | WMV2 resistant - VR |
| 142. | WSMV resistant - VR |
| 143. | ZYMV resistant - VR |

Part 8.
Non-limiting examples of miscellaneous traits/phenotypes with properties

| | |
|---|---|
| 1. | Antibiotic produced |
| 2. | Antiprotease producing |
| 3. | Capable of growth on defined synthetic media |
| 4. | Carbohydrate metabolism altered |
| 5. | Cell wall altered |
| 6. | Cold tolerant |
| 7. | Coleopteran resistant |
| 8. | Color altered |
| 9. | Color sectors in seeds |
| 10. | Colored sectors in leaves |
| 11. | Constitutive expression of glutamine synthetase |
| 12. | Cre recombinase produced |
| 13. | Dalapon tolerant |
| 14. | Development altered |
| 15. | Disease resistant general |
| 16. | Ethylene metabolism altered |
| 17. | Expression optimization |
| 18. | Fenthion susceptible |
| 19. | Glucuronidase expressing |
| 20. | Glyphosate tolerant |
| 21. | Growth rate reduced |
| 22. | Heavy metals sequestered |
| 23. | Hygromycin tolerant |
| 24. | Inducible DNA modification |
| 25. | Industrial enzyme produced |
| 26. | Kanamycin resistant |
| 27. | Lipase expressed in seeds |
| 28. | Methotrexate resistant |
| 29. | Modified growth characteristics |
| 30. | Mycotoxin deficient |
| 31. | Mycotoxin production inhibited |
| 32. | Mycotoxin restored |
| 33. | Non-lesion forming mutant |

TABLE 2-continued

Non-limiting examples of serviceable genes, gene products, phenotypes, or traits according to the methods of this invention (e.g. knockouts, knockins, increased or decreased expression level, increased or decreased expression pattern)

| | |
|---|---|
| 34. | Novel protein produced |
| 35. | Oil quality altered |
| 36. | Peroxidase levels increased |
| 37. | Pharmaceutical proteins produced |
| 38. | Phosphinothricin tolerant |
| 39. | Pigment metabolism altered |
| 40. | Pollen visual marker |
| 41. | Polyamine metablosim altered |
| 42. | Polymer produced |
| 43. | Recombinase produced |
| 44. | Secondary metabolite increased |
| 45. | Seed color altered |
| 46. | Seed weight increased |
| 47. | Selectable marker |
| 48. | Spectromycin resistant |
| 49. | Sterile |
| 50. | Sterols increased |
| 51. | Sulfonylurea susceptible |
| 52. | Syringomycin deficient |
| 53. | Transposon activator |
| 54. | Transposon elements inserted |
| 55. | Transposon inserted |
| 56. | Trifolitoxin producing |
| 57. | Trifolitoxin resistant |
| 58. | Virulence reduced |
| 59. | Visual marker |
| 60. | Visual marker inactive |

In a particular examplification, "producing an organism having a desirable trait" includes an organism that is with respect to an organ or a part of an organ but not necessarily altered anywhere else.

By "trait" is meant any detectable parameter associated with an organism under a set of conditions. Examples of "detectable parameters" include the ability to produce a substance, the ability to not produce a substance, an altered pattern of (such as an increased or a decreased) ability to produce a substance, viability, non-viability, behaviour, growth rate, size, morphology or morphological characteristic, In another embodiment, this invention is directed to a method of producing an organism having a desirable trait or a desirable improvement in a trait by: a) obtaining an initial population of organisms comprised of at least one starting organism, b) mutagenizing the population such that mutations occur throughout a substantial part of the genome of at least one initial organism, c) selecting at least one mutagenized organism having a desirable trait or a desirable improvement in a trait, and d) optionally repeating the method by subjecting one or more mutagenized organisms to a repetition of the method. A mutagenized organism having a desirable trait or a desirable improvement in a trait can be referred to as an "up-mutant", and the associated mutation(s) contained in an up-mutant organism can be referred to as up-mutation(s).

In one embodiment, step c) is comprised of selecting at least two different mutagenized organisms, each having a different mutagenized genome, and the method of producing an organism having a desirable trait or a desirable improvement in a trait is comprised of a) obtaining a starting population of organisms comprised of at least one starting organism, b) mutagenizing the population such that mutations occur throughout a substantial part of the genome of at least one starting organism, c) selecting at least two mutagenized organism having a desirable trait or a desirable improvement in a trait, d) creating combinations of the mutations of the two or more mutagenized organisms, e) selecting at least one mutagenized organism having a desirable trait or a desirable improvement in a trait, and f) optionally repeating the method by subjecting one or more mutagenized organisms to a repetition of the method.

In one embodiment, the method is repeated. Thus, for example, an up-mutant organism can serve as a starting organism for the above method. Also, for example, an up mutant organism having a combination of two or more up-mutations in its genome can serve as a starting organism for the above method.

Thus, in one embodiment, this invention is directed to a method of producing an organism having a desirable trait or a desirable improvement in a trait by: a) obtaining a starting population of organisms comprised of at least one starting organism, b) mutagenizing the population such that mutations occur throughout a substantial part of the genome of at least one starting organism, c) selecting at least one mutagenized organism having a desirable trait or a desirable improvement in a trait, and d) optionally repeating the method by subjecting one or more mutagenized organisms to a repetition of the method. A mutagenized organism having a desirable trait or a desirable improvement in a trait can be referred to as an "up-mutant", and the associated mutation(s) contained in an up-mutant organism can be referred to as up-mutation(s).

Mutagenizing a starting population such that mutations occur throughout a substantial part of the genome of at least one starting organism refers to mutagenizing at least approximately 1% of the genes of a genome, or at least approximately 10% of the genes of a genome, or at least approximately 20% of the genes of a genome, or at least approximately 30% of the genes of a genome, or at least approximately 40% of the genes of a genome, or at least approximately 50% of the genes of a genome, or at least approximately 60% of the genes of a genome, or at least approximately 70% of the genes of a genome, or at least approximately 80% of the genes of a genome, or at least approximately 90% of the genes of a genome, or at least approximately 95% of the genes of a genome, or at least approximately 98% of the genes of a genome.

In a particular embodiment, this invention provides a method of producing an organism having a desirable trait or a desirable improvement in a trait by: a) obtaining sequence information of a genome; b) annotating the genomic sequence obtained; c) mutagenizing a substantial part of the genome the genome; d) selecting at least one mutagenized genome having a desirable trait or a desirable improvement in a trait; and e) optionally repeating the method by subjecting one or more mutagenized genomes to a repetition of the method.

Thus in one aspect, this invention provides a process comprised of:

1.) Subjecting a working cell or organism to holistic monitoring (which can include the detection and/or measurement of all detectable functions and physical parameters). Examples of such parameters include morphology, behavior, growth, responsiveness to stimuli (e.g., antibiotics, different environment, etc.). Additional examples include all measurable molecules, including molecules that are chemically at least in part a nucleic acids, proteins, carbohydrates, proteoglycans, glycoproteins, or lipids. In a particular aspect, performing holistic monitoring is comprised of using a microarray-based method. In another aspect, performing holistic monitoring is comprised of sequencing a substantial portion of the genome, i.e. for example at least approximately 10% of the genome, or for example at least approximately 20% of the genome, or for example at least approximately 30% of the genome, or for example at least approximately 40% of the genome, or for example at least approximately 50% of the genome, or for example at least approximately 60% of the genome, or for example at least approximately 70% of the genome, or for example at least approximately 80% of the genome, or for example at least approximately 90% of the genome, or for example at least approximately 95% of the genome, or for example at least approximately 98% of the genome.

2) Introducing into the working cell or organism a plurality of traits (stacked traits), including selectively and differentially activatable traits. Serviceable traits for this purpose include traits conferred by genes and traits conferred by gene pathways.

3) Subjecting the working cell or organism to holistic monitoring.

4) Compiling the information obtained from steps 1) and 3), and processing &/or analyzing it to better understand the changes introduced into the working cell or organisms. Such data processing includes identifying correlations between and/or among the measured parameters.

5) Repeating any number or all of steps 2), 3), and 4).

This invention provides that molecules serviceable for introducing transgenic traits into a plant include all known genes and nucleic acids. By way of non-limiting exemplification, this invention specifically names any number &/or combination of genes listed herein or listed in any reference incorporated herein by reference. Furthermore, by way of non-limiting exemplification, this invention specifically names any number &/or combination of genes & gene pathways listed herein as well as in any reference incorporated by reference herein. This invention provides that molecules serviceable as detectable parameters include molecule, any enzyme, substrate thereof, product thereof, and any gene or gene pathway listed herein including in any figure or table herein as well as in any reference incorporated by reference herein.

This invention also relates generally to the field of nucleic acid engineering and correspondingly encoded recombinant protein engineering. More particularly, the invention relates to the directed evolution of nucleic acids and screening of clones containing the evolved nucleic acids for resultant activity(ies) of interest, such nucleic acid activity(ies) &/or specified protein, particularly enzyme, activity(ies) of interest.

Mutagenized molecules provided by this invention may have chimeric molecules and molecules with point mutations, including biological molecules that contain a carbohydrate, a lipid, a nucleic acid, &/or a protein component, and specific but non-limiting examples of these include antibiotics, antibodies, enzymes, and steroidal and non-steroidal hormones.

This invention relates generally to a method of: 1) preparing a progeny generation of molecule(s) (including a molecule that is comprised of a polynucleotide sequence, a molecule that is comprised of a polypeptide sequence, and a molecules that is comprised in part of a polynucleotide sequence and in part of a polypeptide sequence), that is mutagenized to achieve at least one point mutation, addition, deletion, &/or chimerization, from one or more ancestral or parental generation template(s); 2) screening the progeny generation molecule(s)—preferably using a high throughput method—for at least one property of interest (such as an improvement in an enzyme activity or an increase in stability or a novel chemotherapeutic effect); 3) optionally obtaining &/or cataloguing structural &/or and functional information regarding the parental &/or progeny generation molecules; and 4) optionally repeating any of steps 1) to 3).

In a preferred embodiment, there is generated (e.g. from a parent polynucleotide template)—in what is termed "codon site-saturation mutagenesis"—a progeny generation of polynucleotides, each having at least one set of up to three contiguous point mutations (i.e. different bases comprising a new codon), such that every codon (or every family of degenerate codons encoding the same amino acid) is represented at each codon position. Corresponding to—and encoded by—this progeny generation of polynucleotides, there is also generated a set of progeny polypeptides, each having at least one single amino acid point mutation. In a preferred aspect, there is generated—in what is termed "amino acid site-saturation mutagenesis"—one such mutant polypeptide for each of the 19 naturally encoded polypeptide-forming alpha-amino acid substitutions at each and every amino acid position along the polypeptide. This yields—for each and every amino acid position along the parental polypeptide—a total of 20 distinct progeny polypeptides including the original amino acid, or potentially more than 21 distinct progeny polypeptides if additional amino acids are used either instead of or in addition to the 20 naturally encoded amino acids Thus, in another aspect, this approach is also serviceable for generating mutants containing—in addition to &/or in combination with the 20 naturally encoded polypeptide-forming alpha-amino acids—other rare &/or not naturally-encoded amino acids and amino acid derivatives. In yet another aspect, this approach is also serviceable for generating mutants by the use of—in addition to &/or in combination with natural or unaltered codon recognition systems of suitable hosts—altered, mutagenized, &/or designer codon recognition systems (such as in a host cell with one or more altered tRNA molecules).

In yet another aspect, this invention relates to recombination and more specifically to a method for preparing polynucleotides encoding a polypeptide by a method of in vivo re-assortment of polynucleotide sequences containing regions of partial homology, assembling the polynucleotides to form at least one polynucleotide and screening the polynucleotides for the production of polypeptide(s) having a useful property.

In yet another preferred embodiment, this invention is serviceable for analyzing and cataloguing—with respect to any molecular property (e.g. an enzymatic activity) or combination of properties allowed by current technology—the effects of any mutational change achieved (including particularly saturation mutagenesis). Thus, a comprehensive method is provided for determining the effect of changing each amino acid in a parental polypeptide into each of at least 19 possible substitutions. This allows each amino acid in a parental polypeptide to be characterized and catalogued according to its spectrum of potential effects on a measurable property of the polypeptide.

In another aspect, the method of the present invention utilizes the natural property of cells to recombine molecules and/or to mediate reductive processes that reduce the complexity of sequences and extent of repeated or consecutive sequences possessing regions of homology.

It is an object of the present invention to provide a method for generating hybrid polynucleotides encoding biologically active hybrid polypeptides with enhanced activities. In accomplishing these and other objects, there has been provided, in accordance with one aspect of the invention, a method for introducing polynucleotides into a suitable host cell and growing the host cell under conditions that produce a hybrid polynucleotide.

In another aspect of the invention, the invention provides a method for screening for biologically active hybrid polypeptides encoded by hybrid polynucleotides. The present method allows for the identification of biologically active hybrid polypeptides with enhanced biological activities.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

In yet another aspect, this invention relates to a method of discovering which phenotype corresponds to a gene by disrupting every gene in the organism.

Accordingly, this invention provides a method for determining a gene that alters a characteristic of an organism, comprising: a) obtaining an initial population of organisms, b) generating a set of mutagenized organisms, such that when all the genetic mutations in the set of mutagenized organisms are taken as a whole, there is represented a set of substantial genetic mutations, and c) detecting the presence an organism having an altered trait, and d) determining the nucleotide sequence of a gene that has been mutagenized in the organism having the altered trait.

In yet another aspect, this invention relates to a method of improving a trait in an organism by functionally knocking out a particular gene in the organism, and then transferring a library of genes, which only vary from the wild-type at one codon position, into the organism.

Accordingly, this invention provides a method method for producing an organism with an improved trait, comprising:

a) functionally knocking out an enogenous gene in a substantially clonal population of organisms;

b) transferring the set of altered genes into the clonal population of organisms, wherein each altered gene differs from the endogenous gene at only one codon; and c) detecting a mutagenized organism having an improved trait; and d) determining the nucleotide sequence of a gene that has been transferred into the detected organism.

D. BRIEF DESCRIPTION OF THE DRAWINGS

Figure 1:
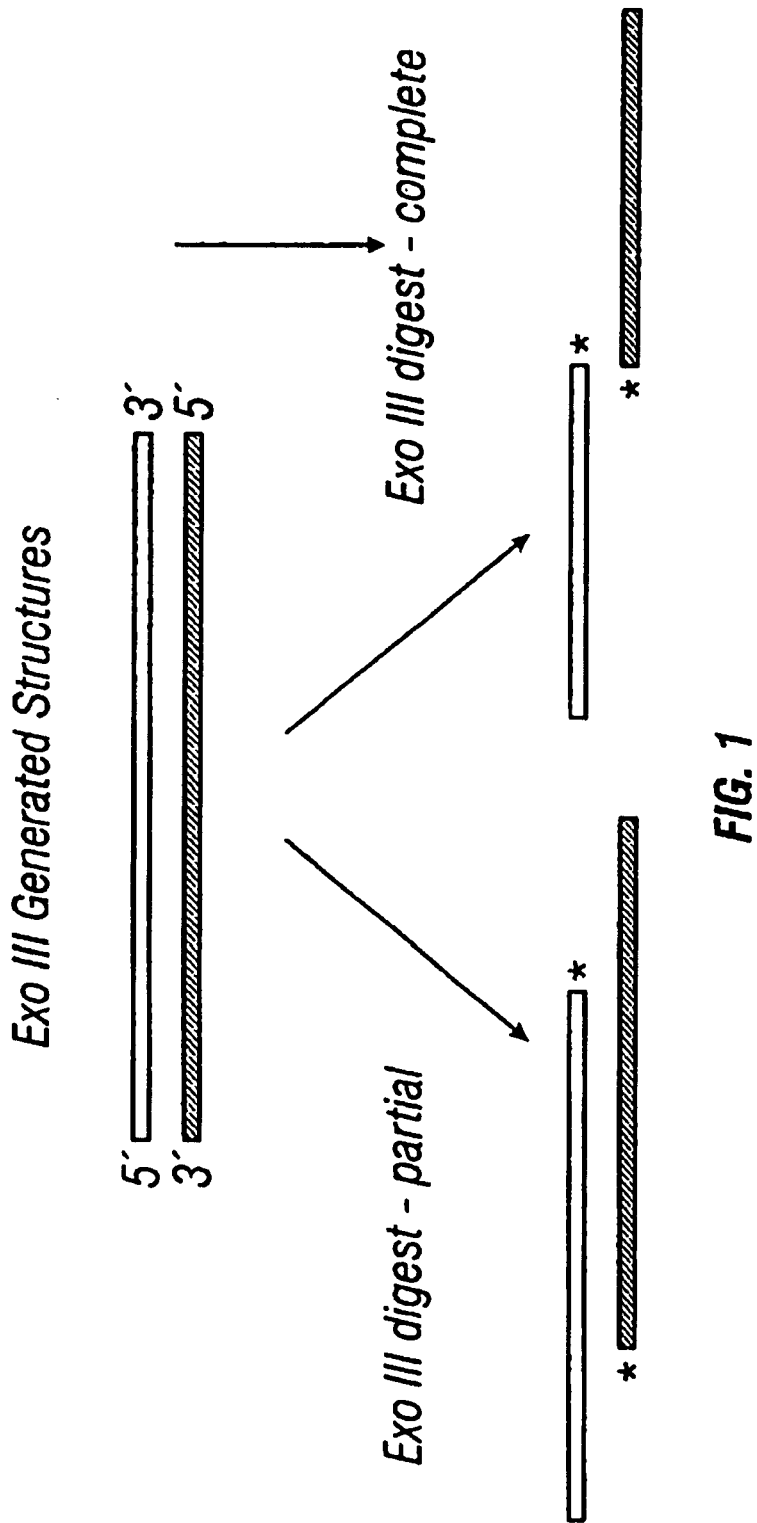

FIG. 1. Exonuclease Activity. FIG. 1 shows the activity of the enzyme exonuclease III. This is an exemplary enzyme that can be used to shuffle, assemble, reassemble, recombine, and/or concatenate polynucleotide building blocks. The asterisk indicates that the enzyme acts from the 3' direction towards the 5' direction of the polynucleotide substrate.

Figure 2:
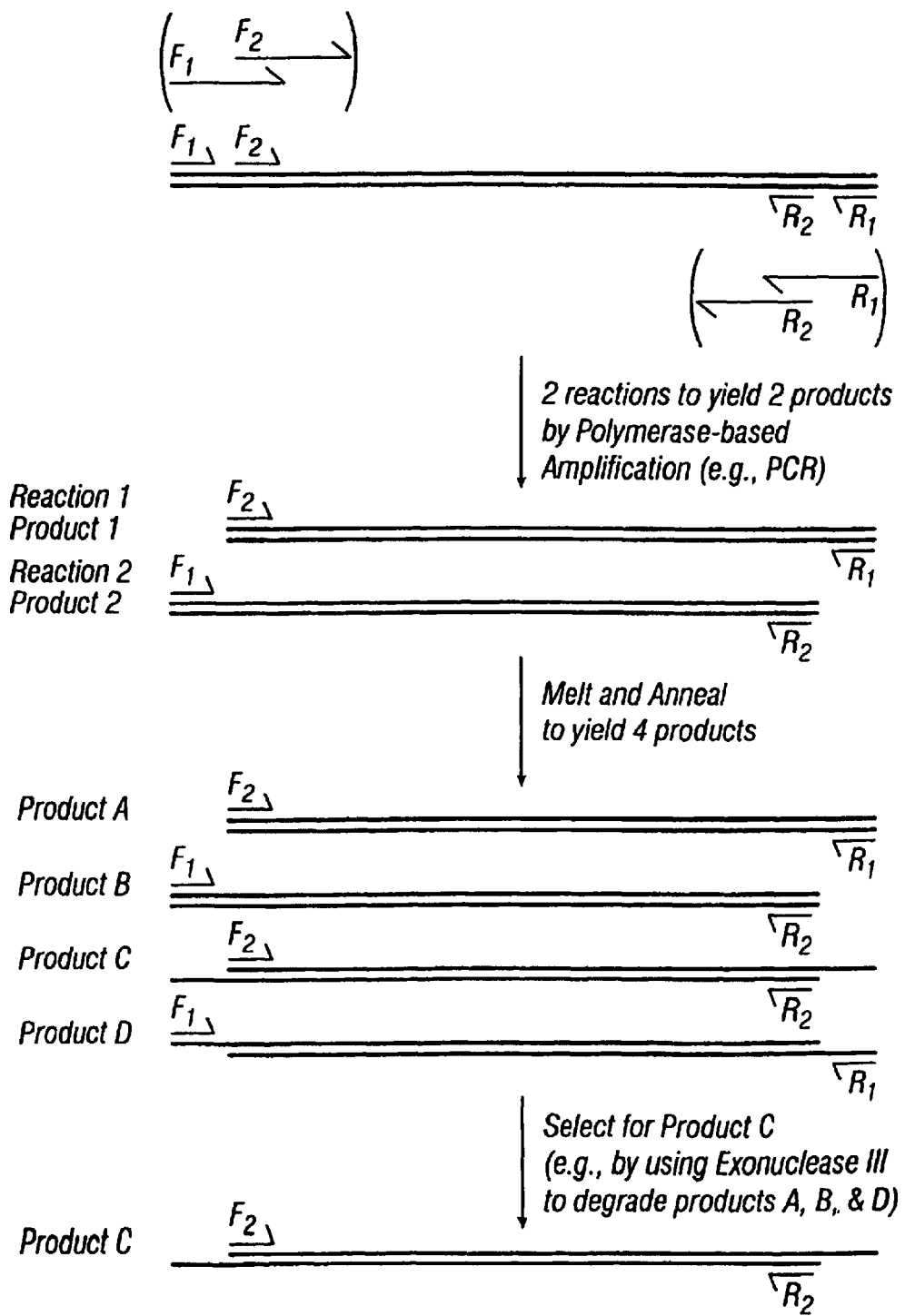

FIG. 2. Generation of A Nucleic Acid Building Block by Polymerase-Based Amplification. FIG. 2 illustrates a method of generating a double-stranded nucleic acid building block with two overhangs using a polymerase-based amplification reaction (e.g., PCR). As illustrated, a first polymerase-based amplification reaction using a first set of primers, $F_2$ and $R_1$, is used to generate a blunt-ended product (labeled Reaction 1, Product 1), which is essentially identical to Product A. A second polymerase-based amplification reaction using a second set of primers, $F_1$ and $R_2$, is used to generate a blunt-ended product (labeled Reaction 2, Product 2), which is essentially identical to Product B. These two products are then mixed and allowed to melt and anneal, generating a potentially useful double-stranded nucleic acid building block with two overhangs. In the example of FIG. 1, the product with the 3' overhangs (Product C) is selected for by nuclease-based degradation of the other 3 products using a 3' acting exonuclease, such as exonuclease III. Alternate primers are shown in parenthesis to illustrate serviceable primers may overlap, and additionally that serviceable primers may be of different lengths, as shown.

FIG. 3. Unique Overhangs And Unique Couplings. FIG. 3 illustrates the point that the number of unique overhangs of each size (e.g. the total number of unique overhangs composed of 1 or 2 or 3, etc. nucleotides) exceeds the number of unique couplings that can result from the use of all the unique overhangs of that size. For example, there are 4 unique 3' overhangs composed of a single nucleotide, and 4 unique 5' overhangs composed of a single nucleotide. Yet the total number of unique couplings that can be made using all the 8 unique single-nucleotide 3' overhangs and single-nucleotide 5' overhangs is 4.

FIG. 4. Unique Overall Assembly Order Achieved by Sequentially Coupling the Building Blocks FIG. 4 illustrates the fact that in order to assemble a total of "n" nucleic acid building blocks, "n–1" couplings are needed. Yet it is sometimes the case that the number of unique couplings available for use is fewer that the "n–1" value. Under these, and other, circumstances a stringent non-stochastic overall assembly order can still be achieved by performing the assembly process in sequential steps. In this example, 2 sequential steps are used to achieve a designed overall assembly order for five nucleic acid building blocks. In this illustration the designed overall assembly order for the five nucleic acid building blocks is: 5'-(#1-#2-#3-#4-#5)-3', where #1 represents building block number 1, etc.

Figure 5:
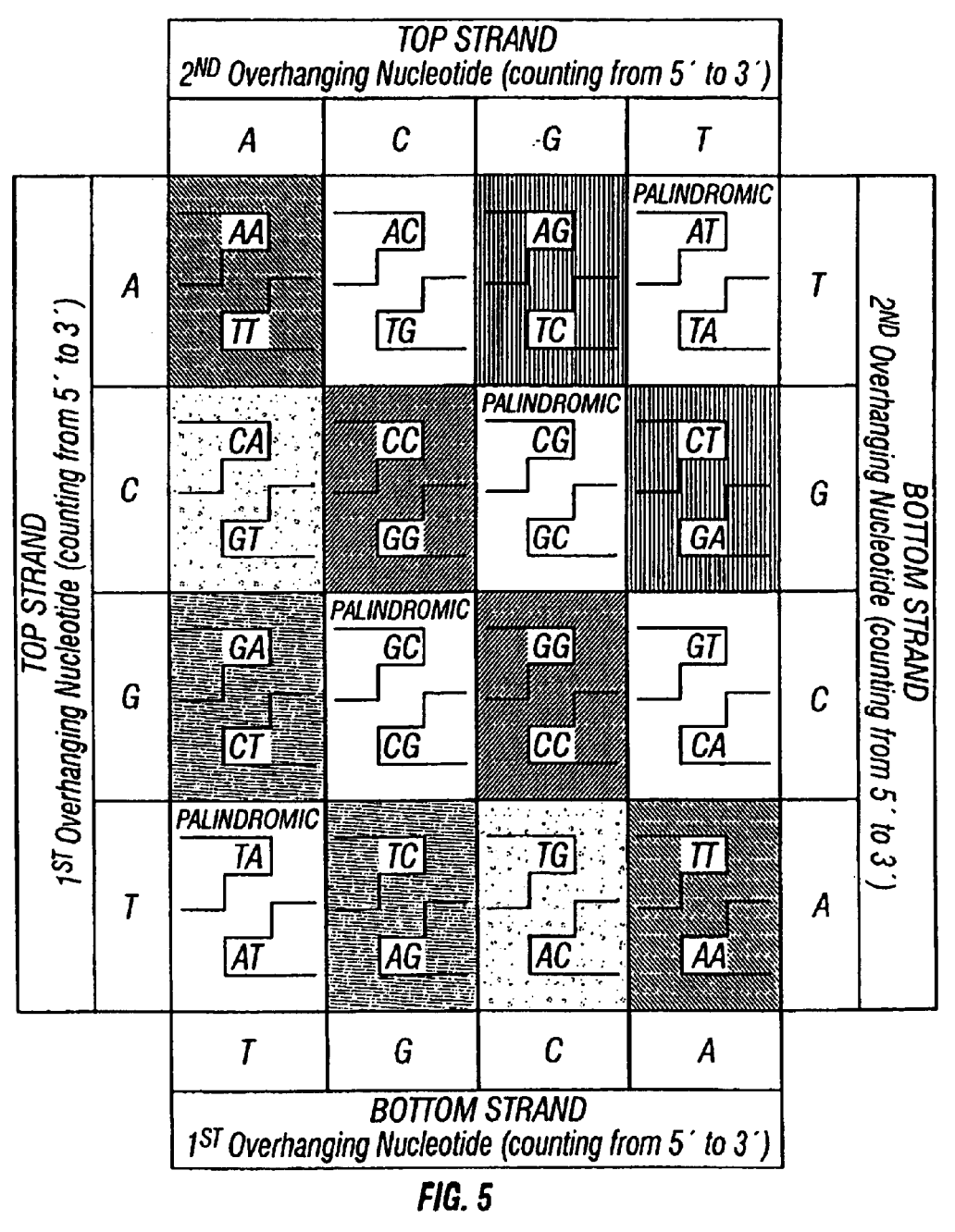

FIG. 5. Unique Couplings Available Using a Two-Nucleotide 3' Overhang. FIG. 5 further illustrates the point that the number of unique overhangs of each size (here, e.g. the total number of unique overhangs composed of 2 nucleotides) exceeds the number of unique couplings that can result from the use of all the unique overhangs of that size. For example, there are 16 unique 3' overhangs composed of two nucleotides, and another 16 unique 5' overhangs composed of two nucleotides, for a total of 32 as shown. Yet the total number of couplings that are unique and not self-binding that can be made using all the 32 unique double-nucleotide 3' overhangs and double-nucleotide 5' overhangs is 12. Some apparently unique couplings have "identical twins" (marked in the same shading), which are visually obvious in this illustration. Still other overhangs contain nucleotide sequences that can self-bind in a palindromic fashion, as shown and labeled in this figure; thus they not contribute the high stringency to the overall assembly order.

Figure 6A:
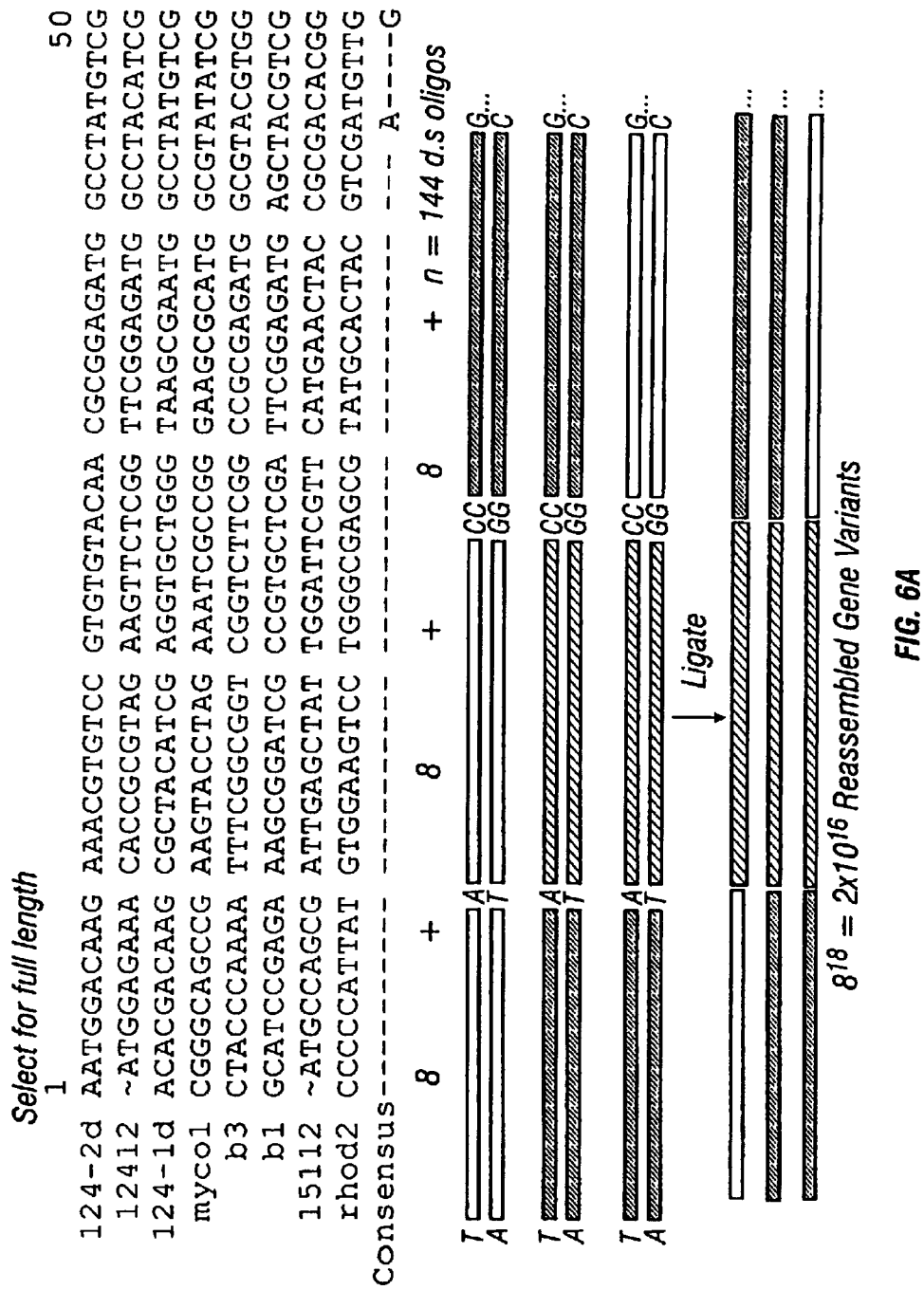

FIG. 6. Generation of an Exhaustive Set of Chimeric Combinations by Synthetic Ligation Reassembly. FIG. 6 showcases the power of this invention in its ability to generate exhaustively and systematically all possible combinations of the nucleic acid building blocks designed in this example. Particularly large sets (or libraries) of progeny chimeric molecules can be generated. Because this method can be performed exhaustively and systematically, the method application can be repeated by choosing new demarcation points and with correspondingly newly designed nucleic acid building blocks, bypassing the burden of re-generating and re-screening previously examined and rejected molecular species. It is appreciated that, codon wobble can be used to advantage to increase the frequency of a demarcation point. In other words, a particular base can often be substituted into a nucleic acid building block without altering the amino acid encoded by progenitor codon (that is now altered codon) because of codon degeneracy. As illustrated, demarcation points are chosen upon alignment of 8 progenitor templates. Nucleic acid building blocks including their overhangs (which are serviceable for the formation of ordered couplings) are then designed and synthesized. In this instance, 18 nucleic acid building blocks are generated based on the sequence of each of the 8 progenitor templates, for a total of 144 nucleic acid building blocks (or double-stranded oligos). Performing the ligation synthesis procedure will then produce a library of progeny molecules comprised of yield of $8^{18}$ (or over $1.8 \times 10^{16}$) chimeras.

FIG. 7. Synthetic genes from oligos:. According to one embodiment of this invention, double-stranded nucleic acid building blocks are designed by aligning a plurality of progenitor nucleic acid templates. Preferably these templates contain some homology and some heterology. The nucleic acids may encode related proteins, such as related enzymes, which relationship may be based on function or structure or both. FIG. 7 shows the alignment of three polynucleotide progenitor templates and the selection of demarcation points (boxed) shared by all the progenitor molecules. In this particular example, the nucleic acid building blocks derived from each of the progenitor templates were chosen to be approximately 30 to 50 nucleotides in length.

Figure 8:
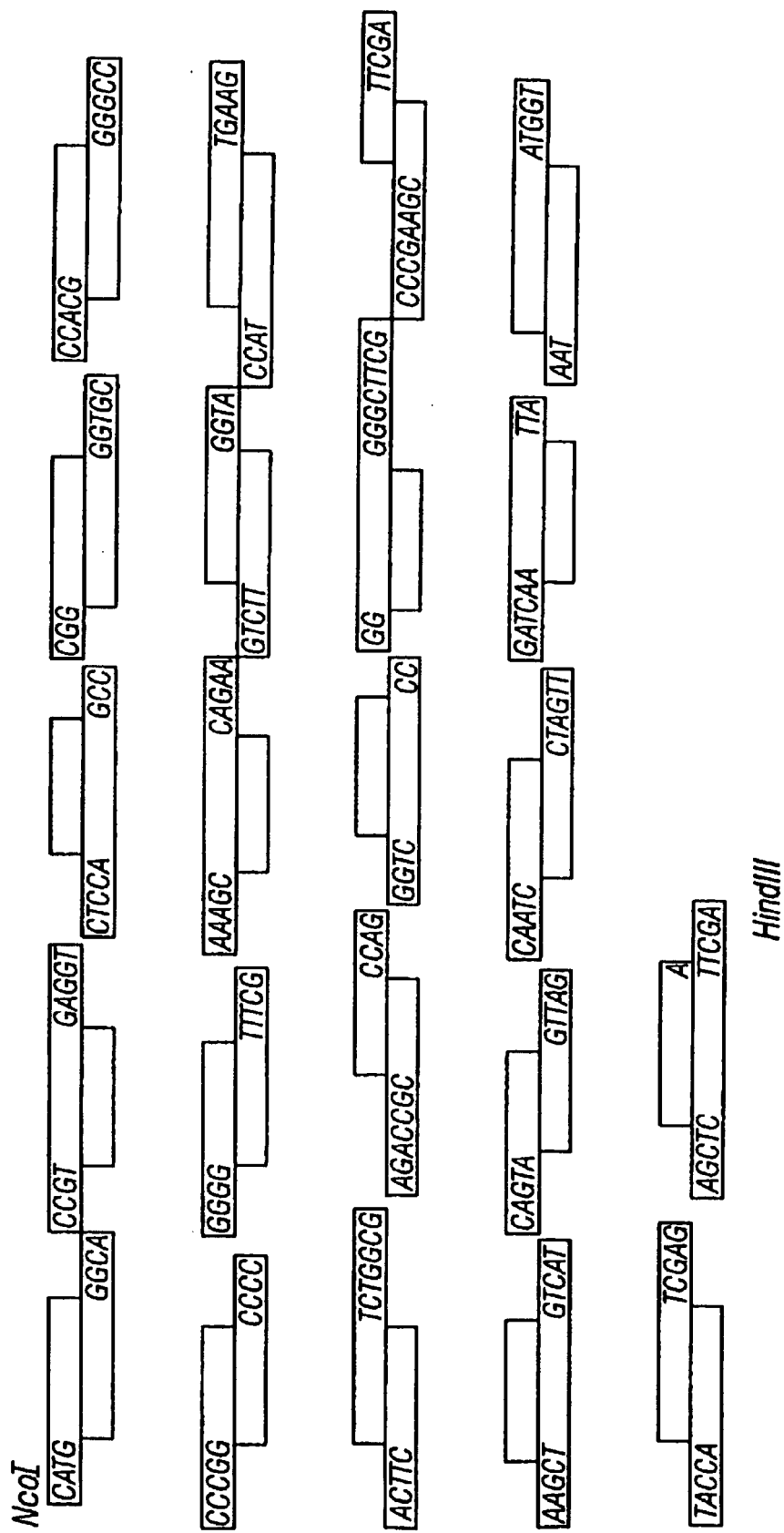

FIG. 8. Nucleic acid building blocks for synthetic ligation gene reassembly. FIG. 8 shows the nucleic acid building blocks from the example in FIG. 7. The nucleic acid building blocks are shown here in generic cartoon form, with their compatible overhangs, including both 5' and 3' overhangs. There are 22 total nucleic acid building blocks derived from each of the 3 progenitor templates. Thus, the ligation synthesis procedure can produce a library of progeny molecules comprised of yield of $3^{22}$ (or over $3.1 \times 10^{10}$)chimeras.

FIG. 9. Addition of Introns by Synthetic Ligation Reassembly. FIG. 9 shows in generic cartoon form that an intron may be introduced into a chimeric progeny molecule by way of a nucleic acid building block. It is appreciated that introns often have consensus sequences at both termini in order to render them operational. It is also appreciated that, in addition to enabling gene splicing, introns may serve an additional purpose by providing sites of homology to other nucleic acids to enable homologous recombination. For this purpose, and potentially others, it may be sometimes desirable to generate a large nucleic acid building block for introducing an intron. If the size is overly large easily genrating by direct chemical synthesis of two single stranded oligos, such a specialized nucleic acid building block may also be generated by direct chemical synthesis of more than two single stranded oligos or by using a polymerase-based amplification reaction as shown in FIG. 2.

FIG. 10. Ligation Reassembly Using Fewer Than All The Nucleotides Of An Overhang. FIG. 10 shows that coupling can occur in a manner that does not make use of every nucleotide in a participating overhang. The coupling is particularly lively to survive (e.g. in a transformed host) if the coupling reinforced by treatment with a ligase enzyme to form what may be referred to as a "gap ligation" or a "gapped ligation". It is appreciated that, as shown, this type of coupling can contribute to generation of unwanted background product(s), but it can also be used advantageously increase the diversity of the progeny library generated by the designed ligation reassembly.

Figure 11:
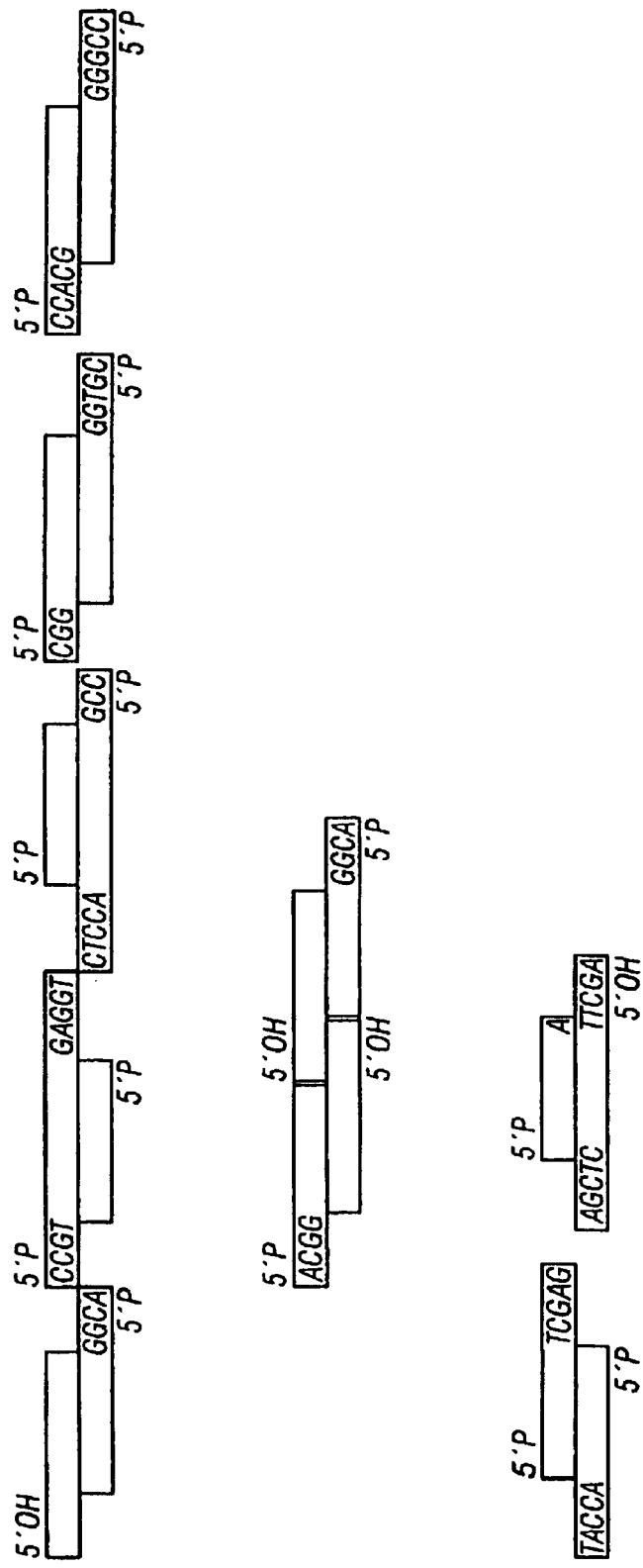

FIG. 11. Avoidance of unwanted self-ligation in palindromic couplings. As mentioned before and shown in FIG. 5, certain overhangs are able to undergo self-coupling to form a palindromic coupling. A coupling is strengthened substantially if it is reinforced by treatment with a ligase enzyme. Accordingly, it is appreciated that the lack of 5' phosphates on these overhangs, as shown, can be used advantageously to prevent this type of palindromic self-ligation. Accordingly, this invention provides that nucleic acid building blocks can be chemically made (or ordered) that lack a 5' phosphate group (or alternatively they can be remove—e.g. by treatment with a phosphatase enzyme such as a calf intestinal alkaline phosphatase (CIAP)—in order to prevent palindromic self-ligations in ligation reassembly processes.

Figure 12:
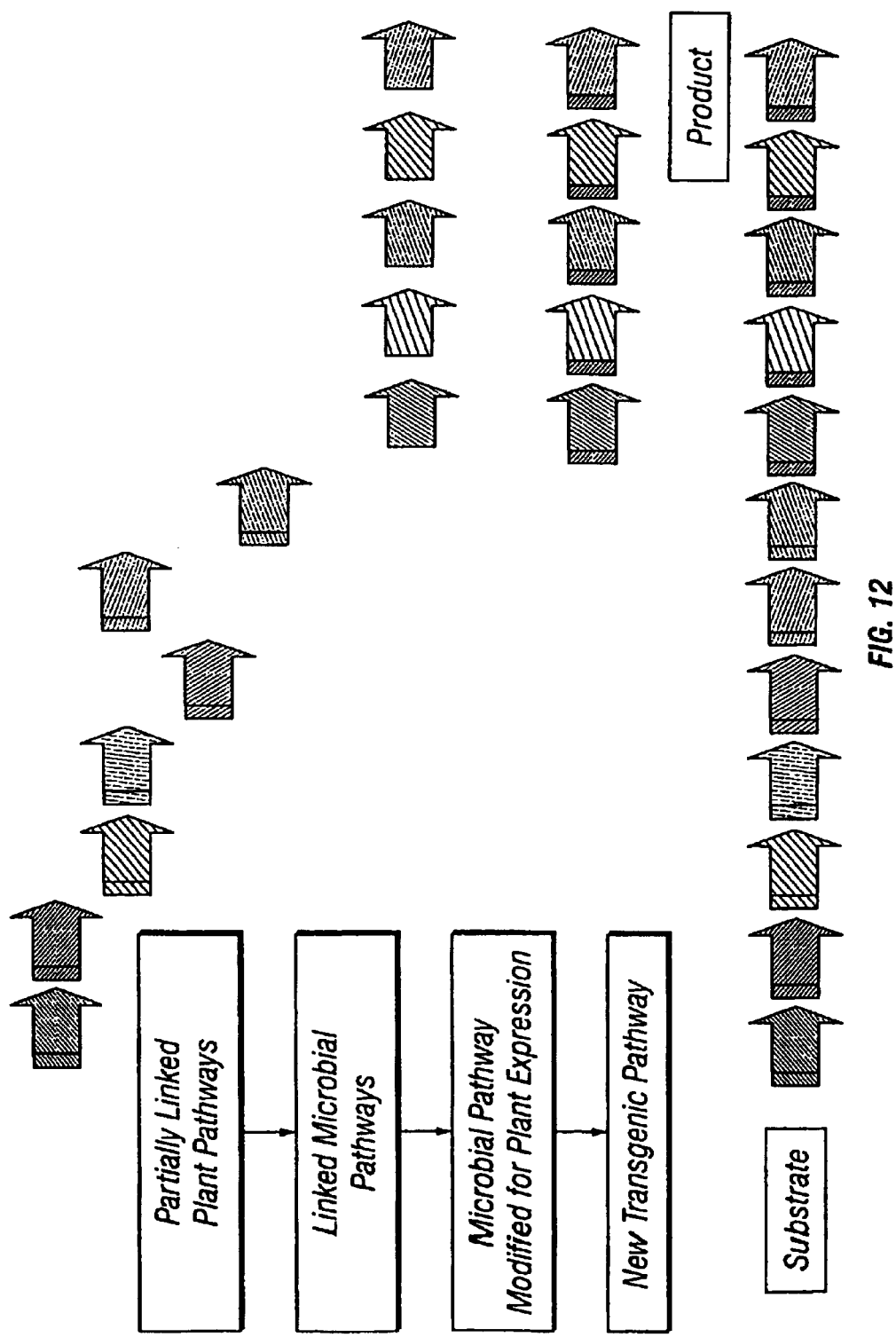

FIG. 12. Pathway Engineering. It is a goal of this invention to provide ways of making new gene pathways using ligation reassembly, optionally with other directed evolution methods such as saturation mutagenesis. FIG. 12 illustrates a preferred approach that may be taken to achieve this goal. It is appreciated that naturally-occurring microbial gene pathways are linked more often than naturally-occurring eukaryotic (e.g. plant) gene pathways, which are sometime only partially linked. In a particular embodiment, this invention provides that regulatory gene sequences (including promoters) can be introduced in the form of nucleic acid building blocks into progeny gene pathways generated by ligation reassembly processes. Thus, originally linked microbial gene pathways, as well as originally unlinked genes and gene pathways, can be thus converted to acquire operability in plants and other eukaryotes.

Figure 13:
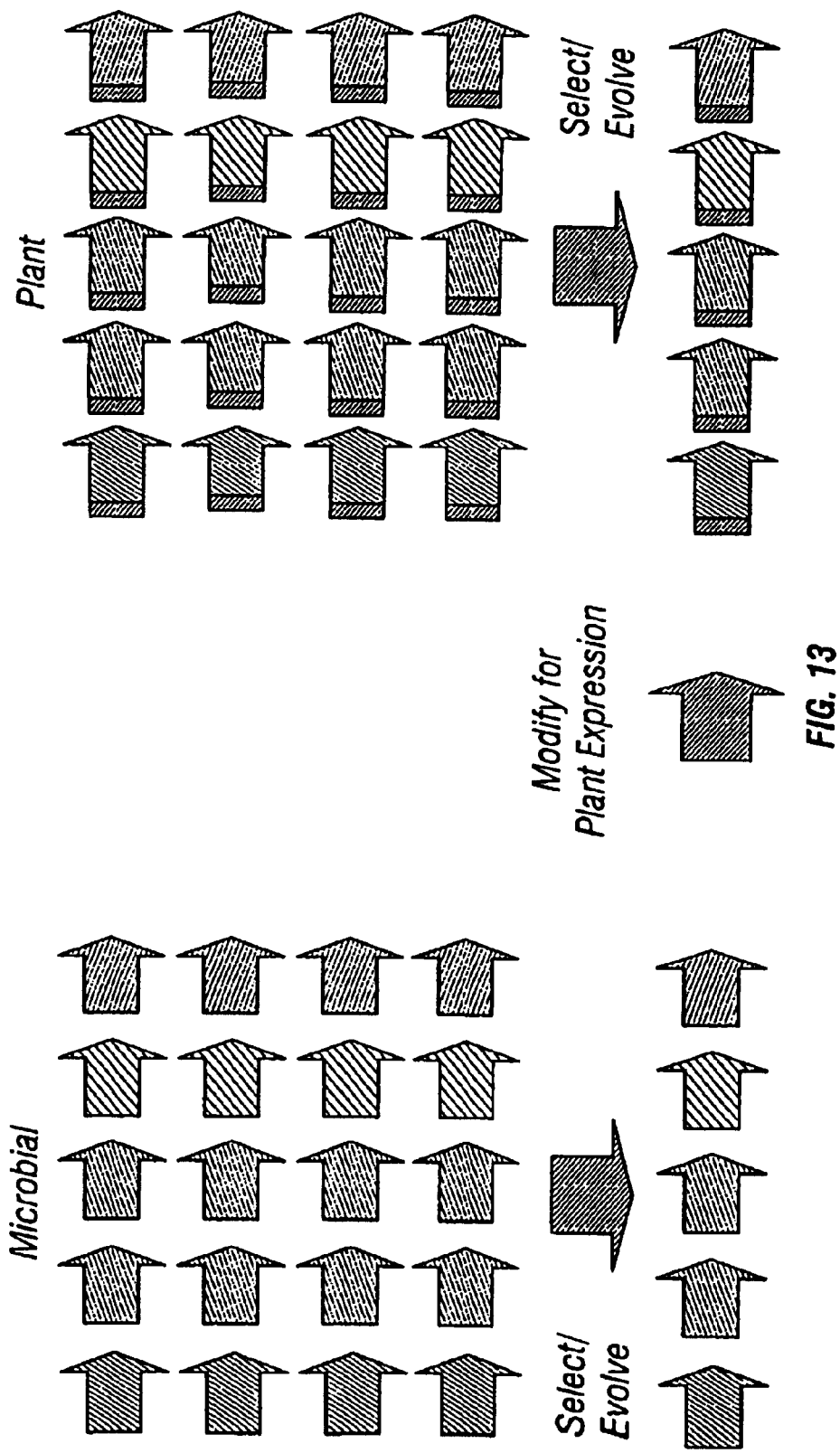

FIG. 13. Avoidance of unwanted self-ligation in palindromic couplings. FIG. 13 illustrates that another goal of this invention, in addition to the generation of novel gene pathways, is the subjection of gene pathways—both naturally occurring and man-made—to mutagenesis and selection in order to achieve improved progeny molecules using the instantly disclosed methods of directed evolution (including saturation mutagenesis and synthetic ligation reassembly). In a particular embodiment, as provided by the instant invention, both microbial and plant pathways can be improved by directed evolution, and as shown, the directed evolution process can be performed both on genes prior to linking them into pathways, and on gene pathways themselves.

Figure 14:
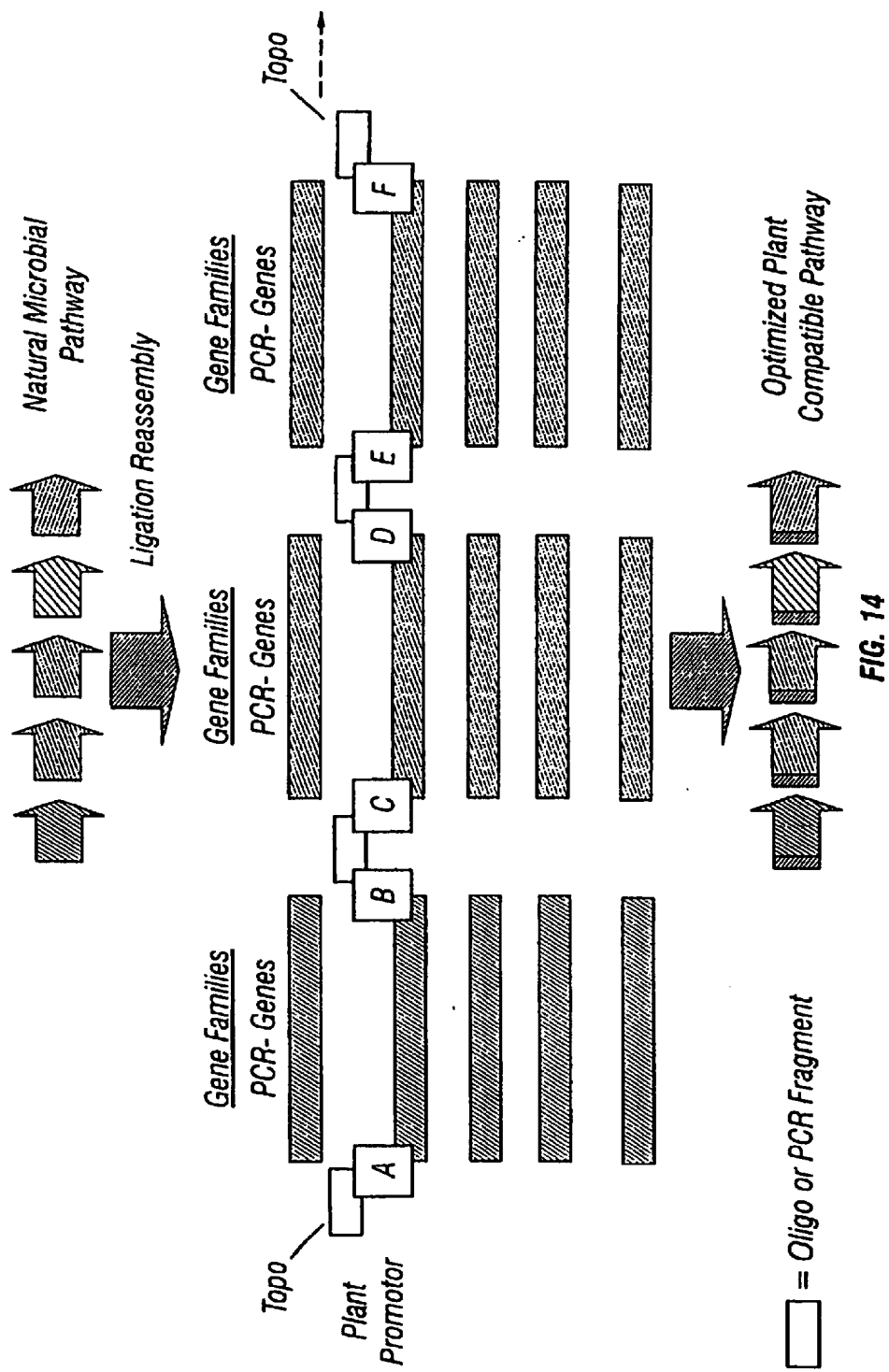

FIG. 14. Conversion of Microbial Pathways to Eukaryotic Pathways. In a particular embodiment, this invention provides that microbial pathways can be converted to pathways operable in plants and other eukaryotic species by the introduction of regulatory sequences that function in those species. Preferred regulatory sequences include promoters, operators, and activator binding sites. As shown, a preferred method of achieving the introduction of such serviceable regulatory sequences is in the form of nucleic acid building blocks, particularly through the use of couplings in ligation reassembly processes. These couplings in FIG. 14 are marked with the letters A, B, C, D and F.

Figure 15:
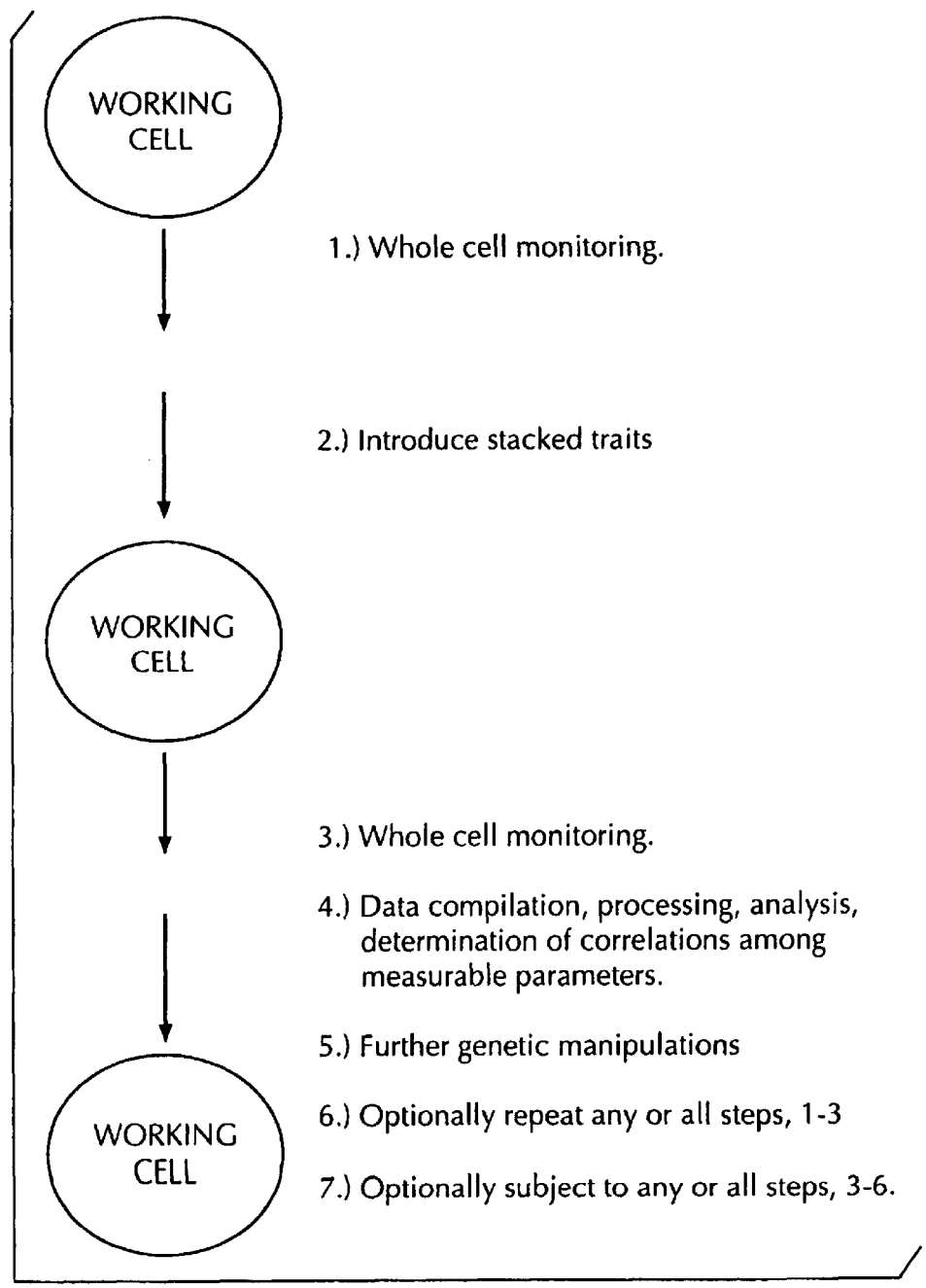

FIG. 15. Holistic engineering of differentially activatable stacked traits in noveltransgenic plants using directed evolution and whole cell monitoring.

Figure 16:
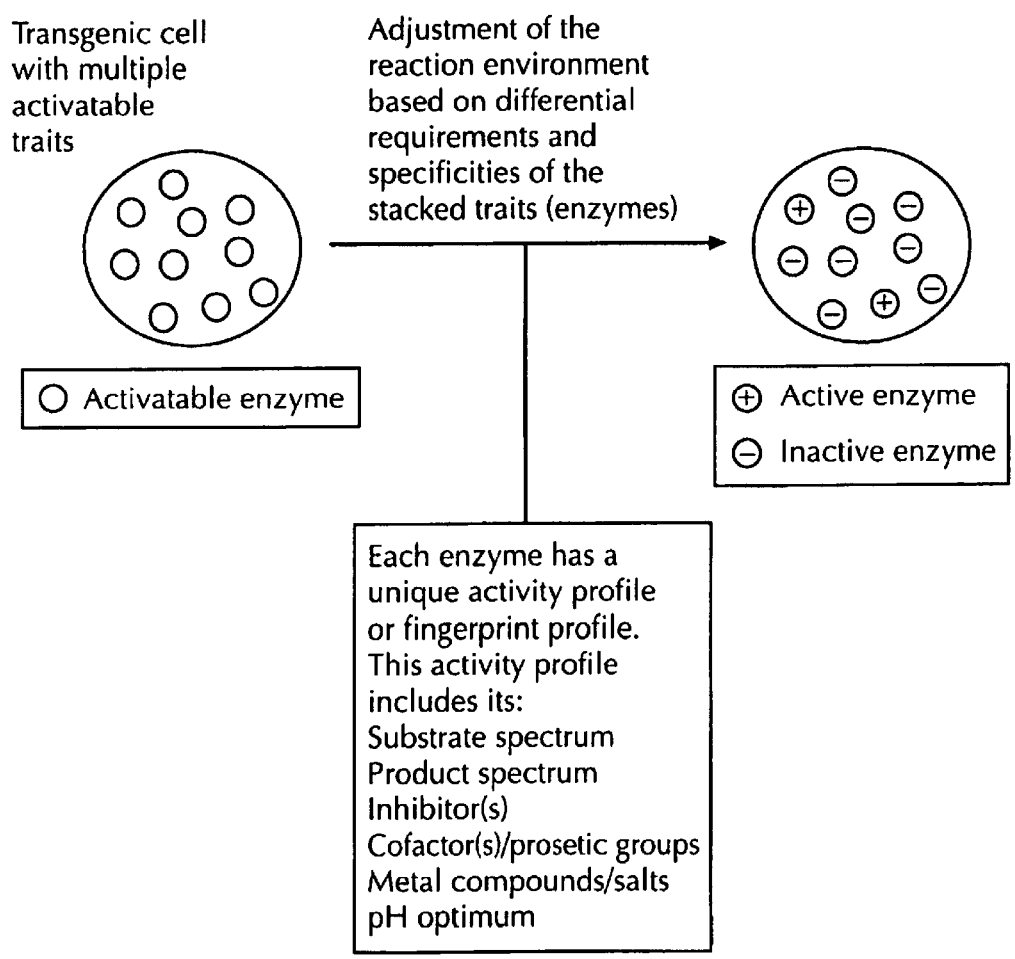

FIG. 16. Differential Activation of Selected Traits Can Be Achieved by Adjusting and Controlling the Environment of the Traits.

Figure 17:
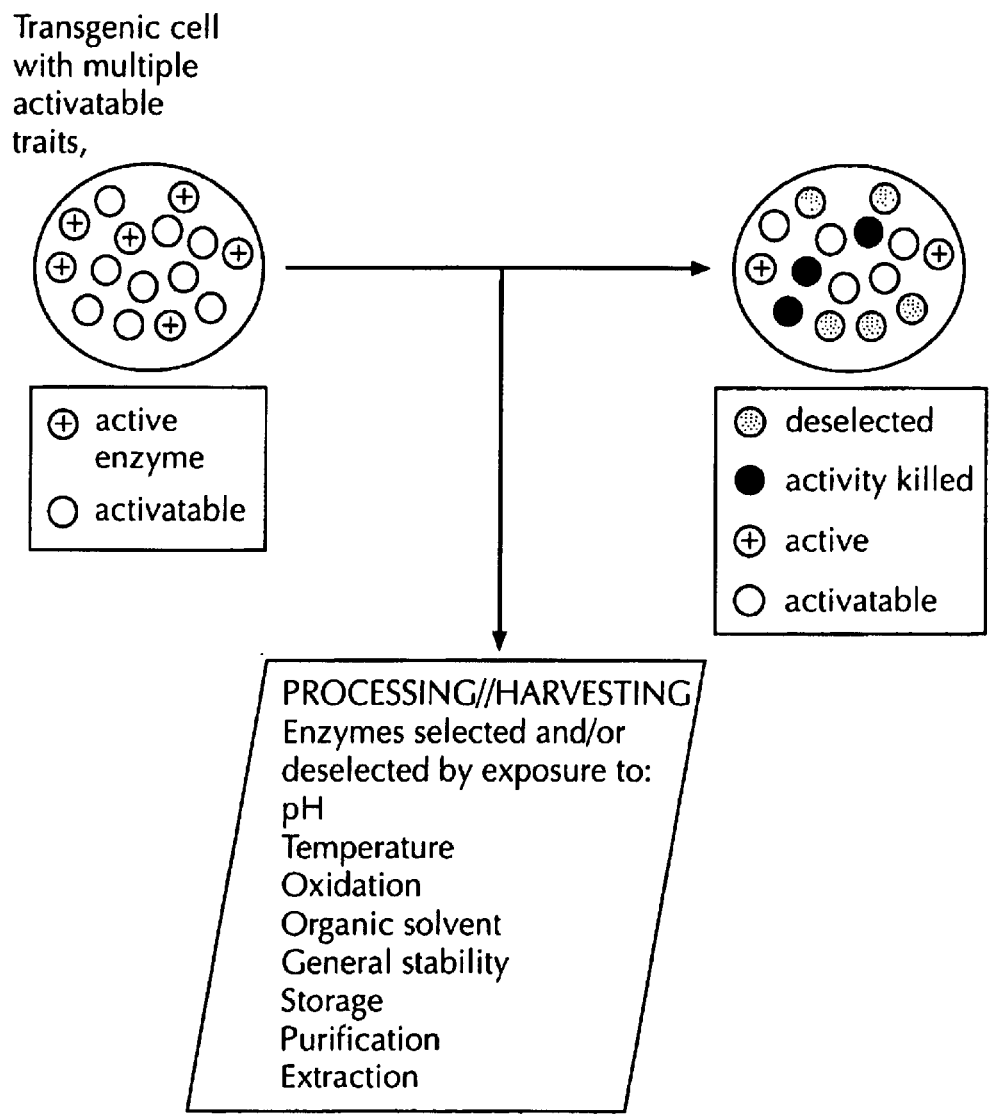

FIG. 17. Harvesting, Processing, Storage.

Figure 18:
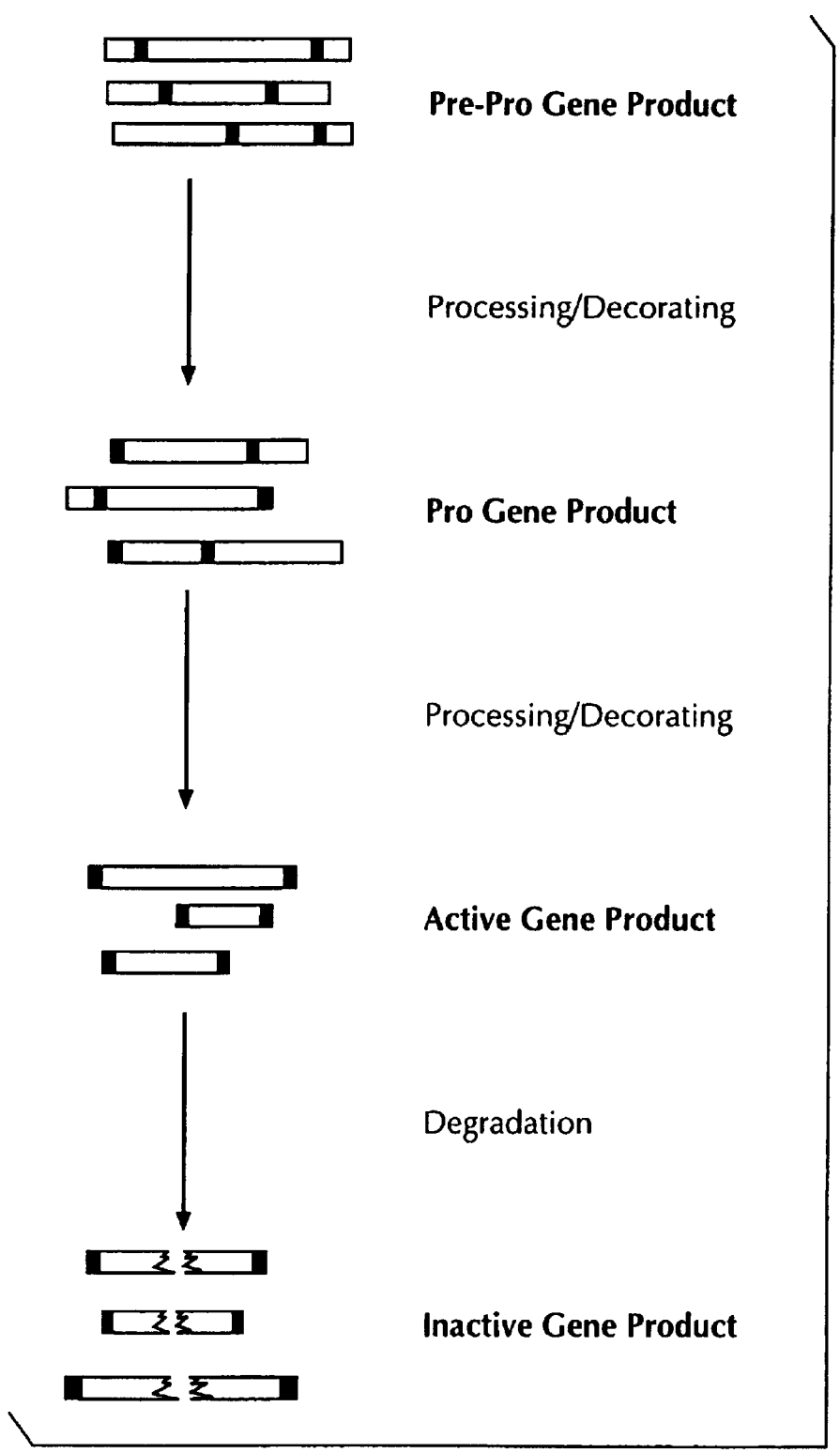

FIG. 18. Processing.

Figure 19:
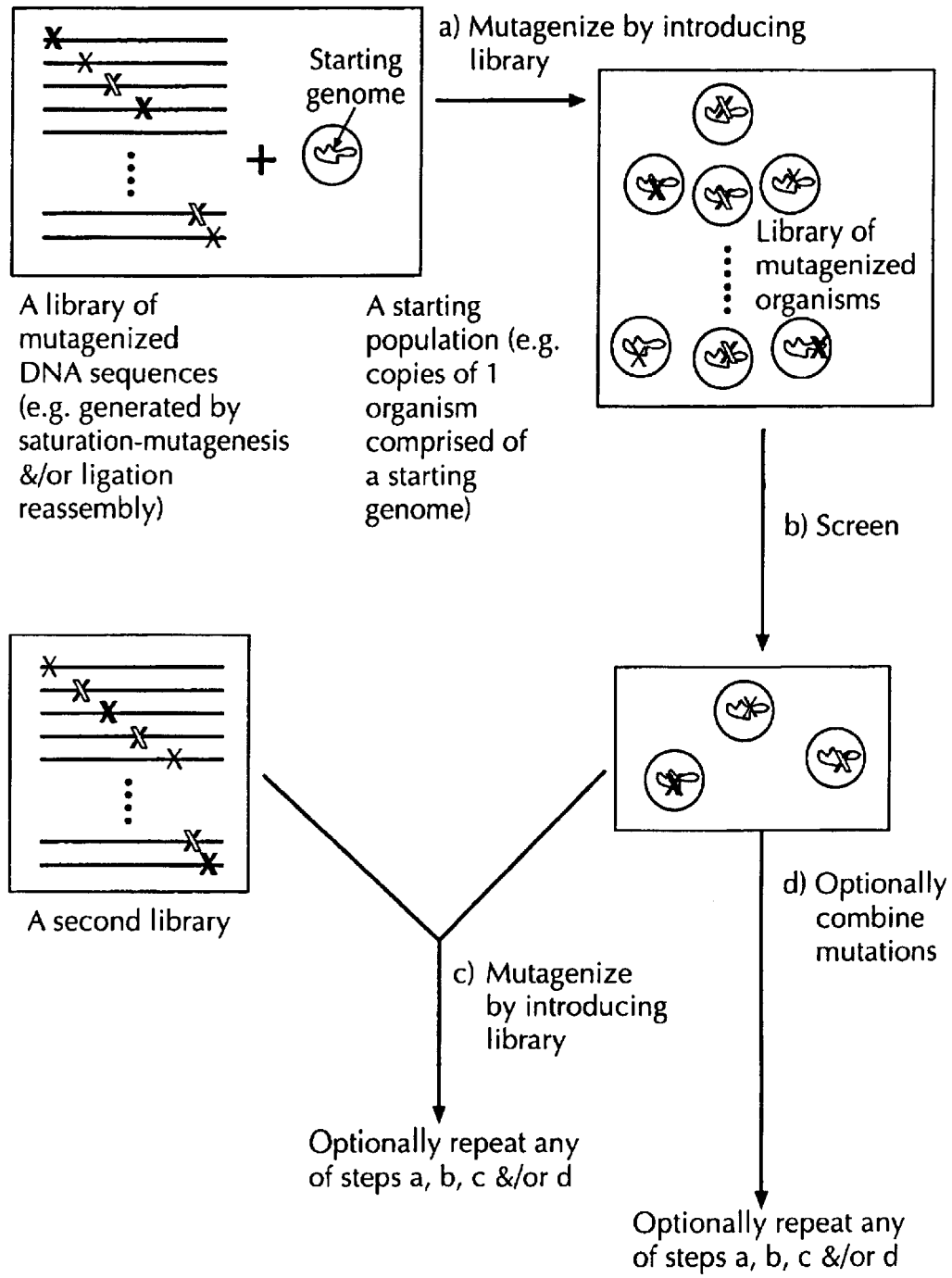

FIG. 19. Cellular Mutagenesis.

Figure 20:
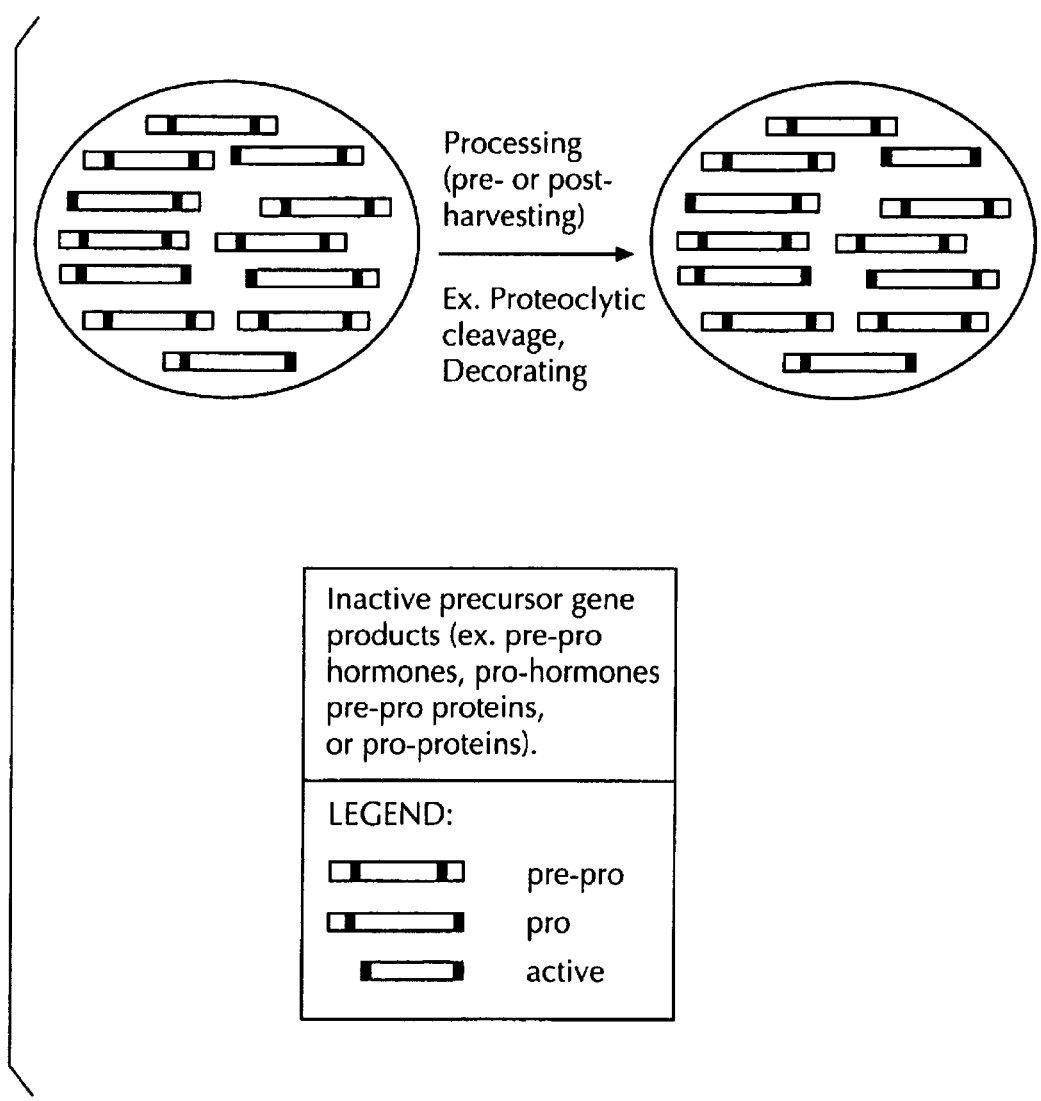

FIG. 20. Differential Activation of Selected Precursor (Inactive) Gene Products.

Figure 21:
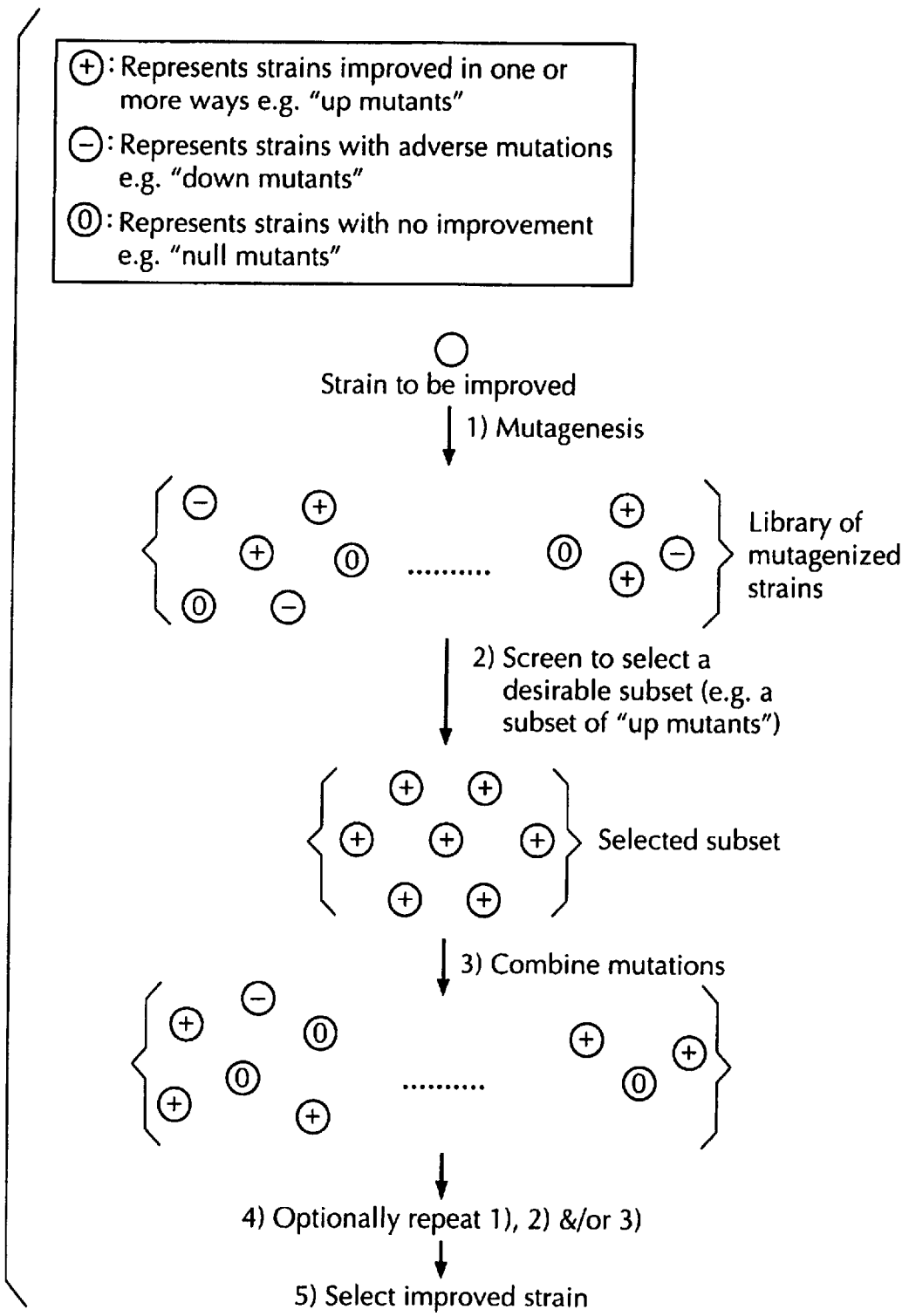

FIG. 21. Starting population comprised of an organism strain to be subjected to improvement or evolution in order to produce a resultant population comprised of an improved organism strain that has a desired trait.

Figure 22:
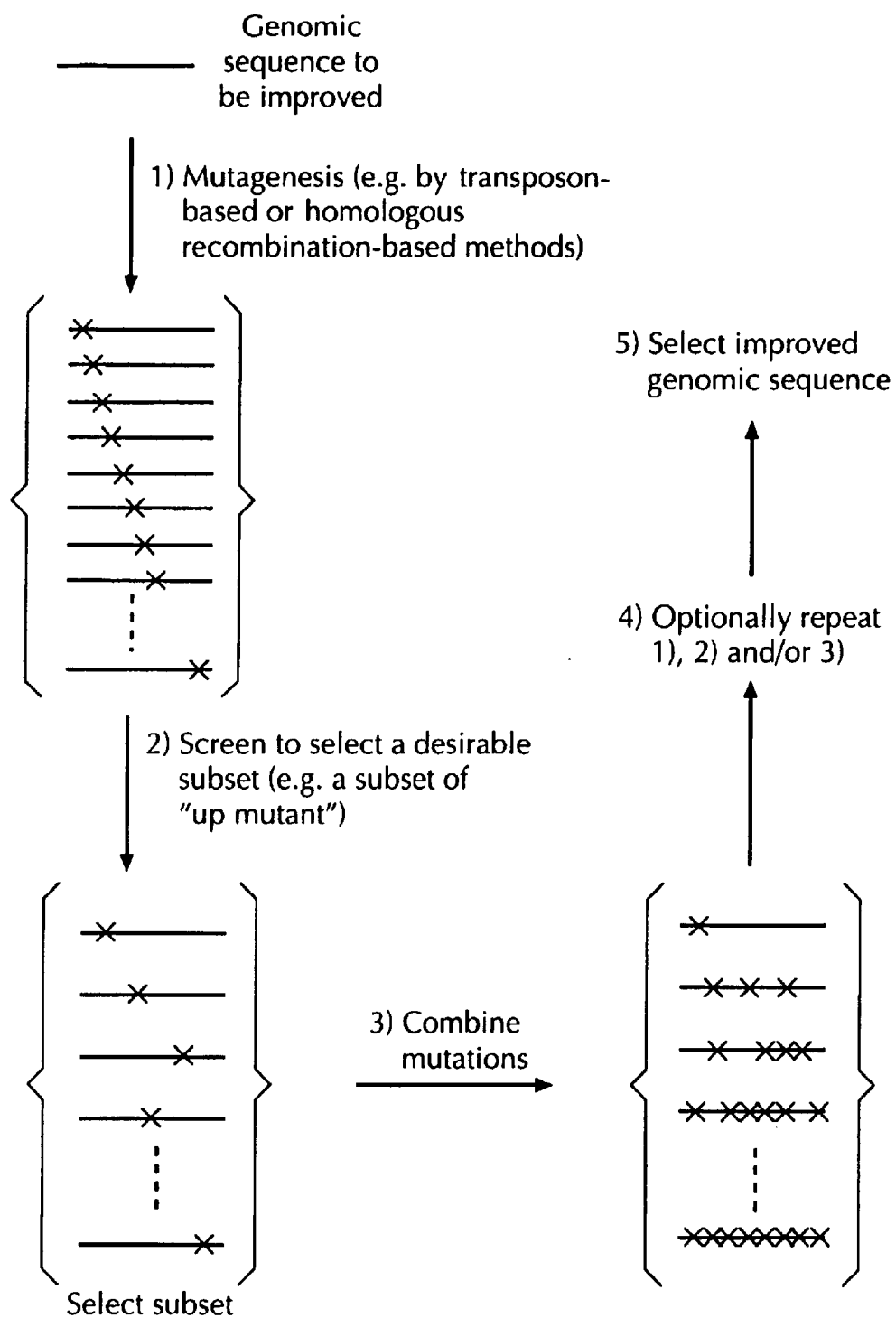

FIG. 22. Starting population comprised of a genomic sequence to be subjected to improvement or evolution in order to produce a resultant population comprised of an improved genomic sequence that has a desired trait.

Figure 23:
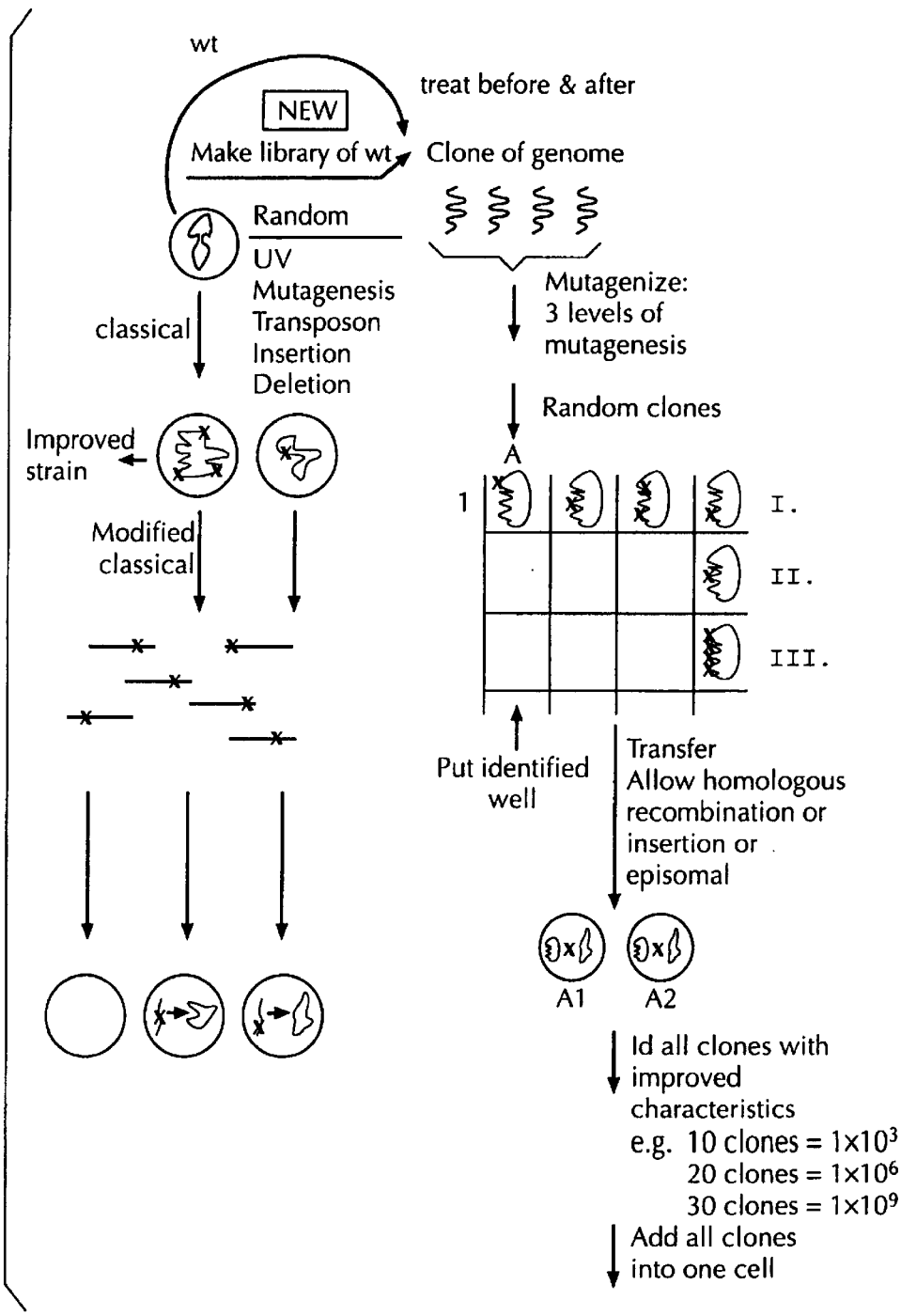

FIG. 23. Strain Improvement.

Figure 24:
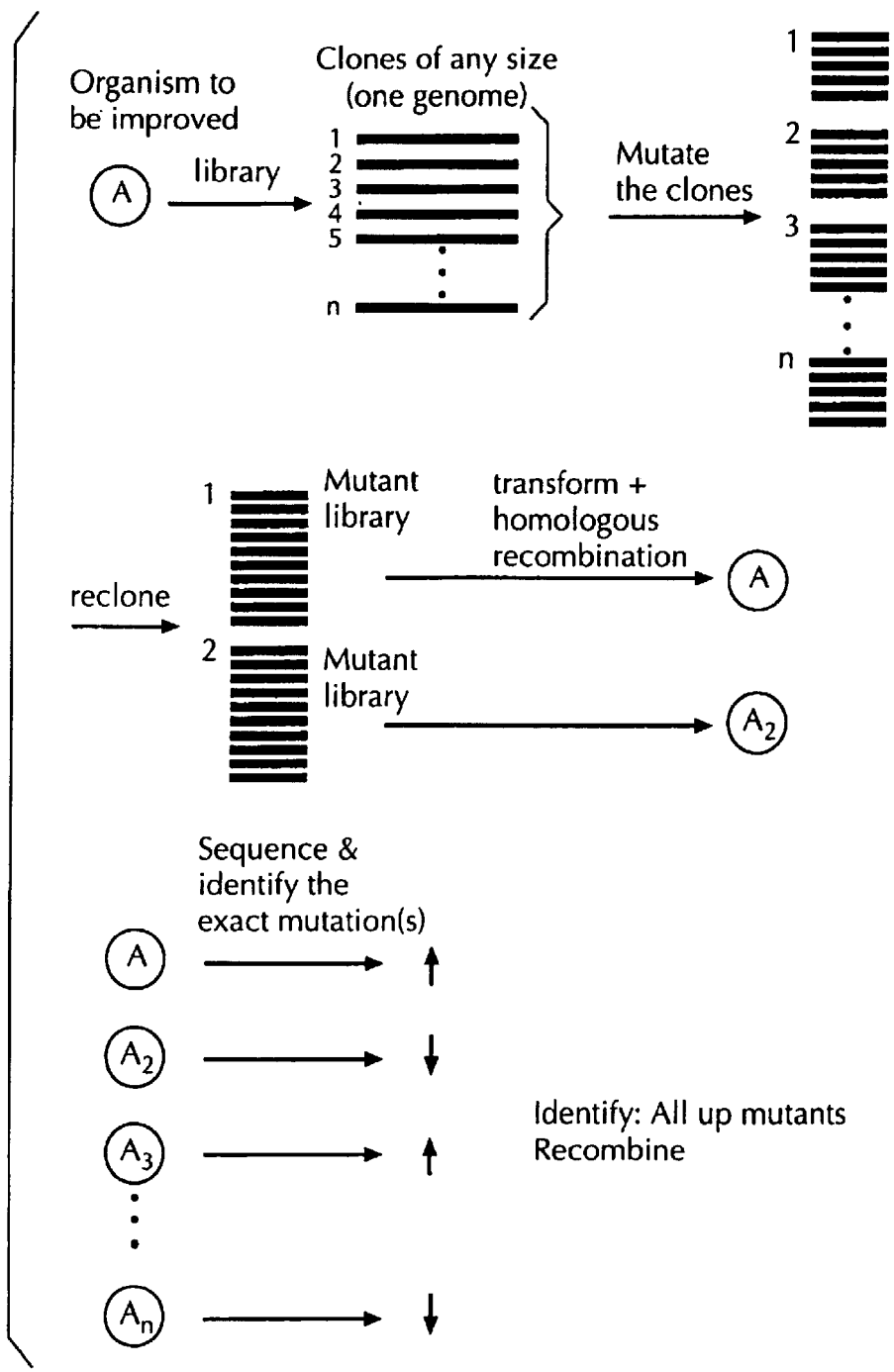

FIG. 24. Iterative Strain Improvement.

E. DEFINITIONS OF TERMS

In order to facilitate understanding of the examples provided herein, certain frequently occurring methods and/or terms will be described.

The term "agent" is used herein to denote a chemical compound, a mixture of chemical compounds, an array of spatially localized compounds (e.g., a VLSIPS peptide array, polynucleotide array, and/or combinatorial small molecule array), biological macromolecule, a bacteriophage peptide display library, a bacteriophage antibody (e.g., scFv) display library, a polysome peptide display library, or an extract made form biological materials such as bacteria, plants, fungi, or animal (particular mammalian) cells or tissues. Agents are evaluated for potential activity as anti-neoplastics, anti-inflammatories or apoptosis modulators by inclusion in screening assays described hereinbelow. Agents are evaluated for potential activity as specific protein interaction inhibitors (i.e., an agent which selectively inhibits a binding interaction between two predetermined polypeptides but which doe snot substantially interfere with cell viability) by inclusion in screening assays described hereinbelow.

An "ambiguous base requirement" in a restriction site refers to a nucleotide base requirement that is not specified to the fullest extent, i.e. that is not a specific base (such as, in a non-limiting exemplification, a specific base selected from A, C, G, and T), but rather may be any one of at least two or more bases. Commonly accepted abbreviations that are used in the art as well as herein to represent ambiguity in bases include the following: R=G or A; Y=C or T; M=A or C; K=G or T; S=G or C; W=A or T; H=A or C or T; B=G or T or C; V=G or C or A; D=G or A or T; N=A or C or G or T.

The term "amino acid" as used herein refers to any organic compound that contains an amino group (—NH$_2$) and a carboxyl group (—COOH); preferably either as free groups or alternatively after condensation as part of peptide bonds. The "twenty naturally encoded polypeptide-forming alpha-amino acids" are understood in the art and refer to: alanine (ala or A), arginine (arg or R), asparagine (asn or N), aspartic acid (asp or D), cysteine (cys or C), gluatamic acid (glu or E), glutamine (gln or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (trp or W), tyrosine (tyr or Y), and valine (val or V).

The term "amplification" means that the number of copies of a polynucleotide is increased.

The term "antibody", as used herein, refers to intact immunoglobulin molecules, as well as fragments of immunoglobulin molecules, such as Fab, Fab', (Fab')$_2$, Fv, and SCA fragments, that are capable of binding to an epitope of an antigen. These antibody fragments, which retain some ability to selectively bind to an antigen (e.g., a polypeptide antigen) of the antibody from which they are derived, can be made using well known methods in the art (see, e.g., Harlow and Lane, supra), and are described further, as follows.

(1) An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) An (Fab')$_2$ fragment of an antibody can be obtained by treating a whole antibody molecule with the enzyme pepsin, without subsequent reduction. A (Fab')$_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) An single chain antibody ("SCA") is a genetically engineered single chain molecule containing the variable region of a light chain and the variable region of a heavy chain, linked by a suitable, flexible polypeptide linker.

The term "Applied Molecular Evolution" ("AME") means the application of an evolutionary design algorithm to a specific, useful goal. While many different library formats for AME have been reported for polynucleotides, peptides and proteins (phage, lacI and polysomes), none of these formats have provided for recombination by random crossovers to deliberately create a combinatorial library.

A molecule that has a "chimeric property" is a molecule that is: 1) in part homologous and in part heterologous to a first reference molecule; while 2) at the same time being in part homologous and in part heterologous to a second reference molecule; without 3) precluding the possibility of being at the same time in part homologous and in part heterologous to still one or more additional reference molecules. In a non-limiting embodiment, a chimeric molecule may be prepared by assemblying a reassortment of partial molecular sequences. In a non-limiting aspect, a chimeric polynucleotide molecule may be prepared by synthesizing the chimeric polynucleotide using plurality of molecular templates, such that the resultant chimeric polynucleotide has properties of a plurality of templates.

The term "cognate" as used herein refers to a gene sequence that is evolutionarily and functionally related between species. For example, but not limitation, in the human genome the human CD4 gene is the cognate gene to the mouse 3d4 gene, since the sequences and structures of these two genes indicate that they are highly homologous and both genes encode a protein which functions in signaling T cell activation through MHC class II-restricted antigen recognition.

A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith (Smith and Waterman, *Adv Appl Math*, 1981; Smith and Waterman, J Teor Biol, 1981; Smith and Waterman, *J Mol Biol*, 1981; Smith et al, *J Mol Evol*, 1981), by the homology alignment algorithm of Needleman (Needleman and Wuncsch, 1970), by the search of similarity method of Pearson (Pearson and Lipman, 1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

As used herein, the term "complementarity-determining region" and "CDR" refer to the art-recognized term as exemplified by the Kabat and Chothia CDR definitions also generally known as supervariable regions or hypervariable loops (Chothia and Lesk, 1987; Clothia et al, 1989; Kabat et al, 1987; and Tramontano et al, 1990). Variable region domains typically comprise the amino-terminal approximately 105–115 amino acids of a naturally-occurring immunoglobulin chain (e.g., amino acids 1–110), although variable domains somewhat shorter or longer are also suitable for forming single-chain antibodies.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are : valine-leucine-isoleucine, phenylalanine-tyrosine, lysine-arginine, alanine-valine, and asparagine-glutamine.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference "TATAC" and is complementary to a reference sequence "GTATA."

The term "degrading effective" amount refers to the amount of enzyme which is required to process at least 50% of the substrate, as compared to substrate not contacted with the enzyme. Preferably, at least 80% of the substrate is degraded.

As used herein, the term "defined sequence framework" refers to a set of defined sequences that are selected on a non-random basis, generally on the basis of experimental data or structural data; for example, a defined sequence framework may comprise a set of amino acid sequences that are predicted to form a β-sheet structure or may comprise a leucine zipper heptad repeat motif, a zinc-finger domain, among other variations. A "defined sequence kemal" is a set of sequences which encompass a limited scope of variability. Whereas (1) a completely random 10-mer sequence of the 20 conventional amino acids can be any of $(20)^{10}$ sequences, and (2) a pseudorandom 10-mer sequence of the 20 conventional amino acids can be any of $(20)^{10}$ sequences but will exhibit a bias for certain residues at certain positions and/or overall, (3) a defined sequence kernal is a subset of sequences if each residue position was allowed to be any of the allowable 20 conventional amino acids (and/or allowable unconventional amino/imino acids). A defined sequence kernal generally comprises variant and invariant residue positions and/or comprises variant residue positions which can comprise a residue selected from a defined subset of amino acid residues), and the like, either segmentally or over the entire length of the individual selected library member sequence. Defined sequence kernels can refer to either amino acid sequences or polynucleotide sequences. Of illustration and not limitation, the sequences $(NNK)_{10}$ and $(NNM)_{10}$, wherein N represents A, T, G, or C; K represents G or T; and M represents A or C, are defined sequence kernels.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a gel to isolate the desired fragment.

"Directional ligation" refers to a ligation in which a 5' end and a 3' end of a polynuclotide are different enough to specify a preferred ligation orientation. For example, an otherwise untreated and undigested PCR product that has two blunt ends will typically not have a preferred ligation orientation when ligated into a cloning vector digested to produce blunt ends in its multiple cloning site; thus, directional ligation will typically not be displayed under these circumstances. In contrast, directional ligation will typically displayed when a digested PCR product having a 5' EcoR I-treated end and a 3' BamH I-is ligated into a cloning vector that has a multiple cloning site digested with EcoR I and BamH I.

The term "DNA shuffling" is used herein to indicate recombination between substantially homologous but non-identical sequences, in some embodiments DNA shuffling may involve crossover via non-homologous recombination, such as via cer/lox and/or flp/frt systems and the like.

As used in this invention, the term "epitope" refers to an antigenic determinant on an antigen, such as a phytase polypeptide, to which the paratope of an antibody, such as an phytase-specific antibody, binds. Antigenic determinants usually consist of chemically active surface groupings of molecules, such as amino acids or sugar side chains, and can have specific three-dimensional structural characteristics, as well as specific charge characteristics. As used herein "epitope" refers to that portion of an antigen or other macromolecule capable of forming a binding interaction that interacts with the variable region binding body of an antibody. Typically, such binding interaction is manifested as an intermolecular contact with one or more amino acid residues of a CDR.

The terms "fragment", "derivative" and "analog" when referring to a reference polypeptide comprise a polypeptide which retains at least one biological function or activity that is at least essentially same as that of the reference polypeptide. Furthermore, the terms "fragment", "derivative" or "analog" are exemplified by a "pro-form" molecule, such as a low activity proprotein that can be modified by cleavage to produce a mature enzyme with significantly higher activity.

A method is provided herein for producing from a template polypeptide a set of progeny polypeptides in which a "full range of single amino acid substitutions" is represented at each amino acid position. As used herein, "full range of single amino acid substitutions" is in reference to the naturally encoded 20 naturally encoded polypeptide-forming alpha-amino acids, as described herein.

The term "gene" means the segment of DNA involved in producing a polypeptide chain; it includes regions preceding and following the coding region (leader and trailer) as well as intervening sequences (introns) between individual coding segments (exons).

"Genetic instability", as used herein, refers to the natural tendency of highly repetitive sequences to be lost through a process of reductive events generally involving sequence simplification through the loss of repeated sequences. Deletions tend to involve the loss of one copy of a repeat and everything between the repeats.

The term "heterologous" means that one single-stranded nucleic acid sequence is unable to hybridize to another single-stranded nucleic acid sequence or its complement. Thus areas of heterology means that areas of polynucleotides or polynucleotides have areas or regions within their sequence which are unable to hybridize to another nucleic acid or polynucleotide. Such regions or areas are for example areas of mutations.

The term "homologous" or "homeologous" means that one single-stranded nucleic acid nucleic acid sequence may hybridize to a complementary single-stranded nucleic acid sequence. The degree of hybridization may depend on a number of factors including the amount of identity between the sequences and the hybridization conditions such as temperature and salt concentrations as discussed later. Preferably the region of identity is greater than about 5 bp, more preferably the region of identity is greater than 10 bp.

An immunoglobulin light or heavy chain variable region consists of a "framework" region interrupted by three hypervariable regions, also called CDR's. The extent of the framework region and CDR's have been precisely defined; see "Sequences of Proteins of Immunological Interest" (Kabat et al, 1987). The sequences of the framework regions of different light or heavy chains are relatively conserved within a specie. As used herein, a "human framework region" is a framework region that is substantially identical (about 85 or more, usually 90–95 or more) to the framework region of a naturally occurring human immunoglobulin. the framework region of an antibody, that is the combined framework regions of the constituent light and heavy chains, serves to position and align the CDR's. The CDR's are primarily responsible for binding to an epitope of an antigen.

The benefits of this invention extend to "commercial applications" (or commercial processes), which term is used to include applications in commercial industry proper (or simply industry) as well as non-commercial commercial applications (e.g. biomedical research at a non-profit institution). Relevant applications include those in areas of diagnosis, medicine, agriculture, manufacturing, and academia.

The term "identical" or "identity" means that two nucleic acid sequences have the same sequence or a complementary sequence. Thus, "areas of identity" means that regions or areas of a polynucleotide or the overall polynucleotide are identical or complementary to areas of another polynucleotide or the polynucleotide.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

By "isolated nucleic acid" is meant a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

As used herein "ligand" refers to a molecule, such as a random peptide or variable segment sequence, that is recognized by a particular receptor. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

"Ligation" refers to the process of forming phosphodiester bonds between two double stranded nucleic acid fragments (Sambrook et al, 1982, p. 146; Sambrook, 1989). Unless otherwise provided, ligation may be accomplished using known buffers and conditions with 10 units of T4 DNA ligase ("ligase") per 0.5 µg of approximately equimolar amounts of the DNA fragments to be ligated.

As used herein, "linker" or "spacer" refers to a molecule or group of molecules that connects two molecules, such as a DNA binding protein and a random peptide, and serves to place the two molecules in a preferred configuration, e.g., so that the random peptide can bind to a receptor with minimal steric hindrance from the DNA binding protein.

As used herein, a "molecular property to be evolved" includes reference to molecules comprised of a polynucleotide sequence, molecules comprised of a polypeptide sequence, and molecules comprised in part of a polynucleotide sequence and in part of a polypeptide sequence. Particularly relevant—but by no means limiting—examples of molecular properties to be evolved include enzymatic activities at specified conditions, such as related to temperature; salinity; pressure; pH; and concentration of glycerol, DMSO, detergent, &/or any other molecular species with which contact is made in a reaction environment. Additional particularly relevant—but by no means limiting—examples of molecular properties to be evolved include stabilities— e.g. the amount of a residual molecular property that is present after a specified exposure time to a specified environment, such as may be encountered during storage.

The term "mutations" includes changes in the sequence of a wild-type or parental nucleic acid sequence or changes in the sequence of a peptide. Such mutations may be point mutations such as transitions or transversions. The mutations may be deletions, insertions or duplications. A mutation can also be a "chimerization", which is exemplified in a progeny molecule that is generated to contain part or all of a sequence of one parental molecule as well as part or all of a sequence of at least one other parental molecule. This invention provides for both chimeric polynucleotides and chimeric polypeptides.

As used herein, the degenerate "N,N,G/T" nucleotide sequence represents 32 possible triplets, where "N" can be A, C, G or T.

The term "naturally-occurring" as used herein as applied to the object refers to the fact that an object can be found in nature. For example, a polypeptide or polynucleotide sequence that is present in an organism (including viruses) that can be isolated from a source in nature and which has not been intentionally modified by man in the laboratory is naturally occurring. Generally, the term naturally occurring refers to an object as present in a non-pathological (undiseased) individual, such as would be typical for the species.

As used herein, a "nucleic acid molecule" is comprised of at least one base or one base pair, depending on whether it is single-stranded or double-stranded, respectively. Furthermore, a nucleic acid molecule may belong exclusively or chimerically to any group of nucleotide-containing molecules, as exemplified by, but not limited to, the following groups of nucleic acid molecules: RNA, DNA, genomic nucleic acids, non-genomic nucleic acids, naturally occurring and not naturally occurring nucleic acids, and synthetic nucleic acids. This includes, by way of non-limiting example, nucleic acids associated with any organelle, such as the mitochondria, ribosomal RNA, and nucleic acid molecules comprised chimerically of one or more components that are not naturally occurring along with naturally occurring components.

Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule".

In addition, by way of example, but not limitation, a nucleic acid molecule that is labeled with a detectable moiety, such as a radioactive or alternatively a non-radioactive label, is likewise considered a "nucleic acid molecule".

The terms "nucleic acid sequence coding for" or a "DNA coding sequence of" or a "nucleotide sequence encoding" a particular enzyme—as well as other synonymous terms— refer to a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The terms "nucleic acid encoding an enzyme (protein)" or "DNA encoding an enzyme (protein)" or "polynucleotide encoding an enzyme (protein)" and other synonymous terms encompasses a polynucleotide which includes only coding sequence for the enzyme as well as a polynucleotide which includes additional coding and/or non-coding sequence.

In one preferred embodiment, a "specific nucleic acid molecule species" is defined by its chemical structure, as exemplified by, but not limited to, its primary sequence. In another preferred embodiment, a specific "nucleic acid molecule species" is defined by a function of the nucleic acid species or by a function of a product derived from the nucleic acid species. Thus, by way of non-limiting example, a "specific nucleic acid molecule species" may be defined by one or more activities or properties attributable to it, including activities or properties attributable its expressed product.

The instant definition of "assembling a working nucleic acid sample into a nucleic acid library" includes the process of incorporating a nucleic acid sample into a vector-based collection, such as by ligation into a vector and transformation of a host. A description of relevant vectors, hosts, and other reagents as well as specific non-limiting examples thereof are provided hereinafter. The instant definition of "assembling a working nucleic acid sample into a nucleic acid library" also includes the process of incorporating a nucleic acid sample into a non-vector-based collection, such as by ligation to adaptors. Preferably the adaptors can anneal to PCR primers to facilitate amplification by PCR.

Accordingly, in a non-limiting embodiment, a "nucleic acid library" is comprised of a vector-based collection of one or more nucleic acid molecules. In another preferred embodiment a "nucleic acid library" is comprised of a non-vector-based collection of nucleic acid molecules. In yet another preferred embodiment a "nucleic acid library" is comprised of a combined collection of nucleic acid molecules that is in part vector-based and in part non-vector-based. Preferably, the collection of molecules comprising a library is searchable and separable according to individual nucleic acid molecule species.

The present invention provides a "nucleic acid construct" or alternatively a "nucleotide construct" or alternatively a "DNA construct". The term "construct" is used herein to describe a molecule, such as a polynucleotide (e.g., a phytase polynucleotide) may optionally be chemically bonded to one or more additional molecular moieties, such as a vector, or parts of a vector. In a specific—but by no means limiting—aspect, a nucleotide construct is exemplified by a DNA expression DNA expression constructs suitable for the transformation of a host cell.

An "oligonucleotide" (or synonymously an "oligo") refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated. To achieve polymerase-based amplification (such as with PCR), a "32-fold degenerate oligonucleotide that is comprised of, in series, at least a first homologous sequence, a degenerate N,N,G/T sequence, and a second homologous sequence" is mentioned. As used in this context, "homologous" is in reference to homology between the oligo and the parental polynucleotide that is subjected to the polymerase-based amplification.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

As used herein the term "parental polynucleotide set" is a set comprised of one or more distinct polynucleotide species. Usually this term fis used in reference to a progeny polynucleotide set which is preferably obtained by mutagenization of the parental set, in which case the terms "parental", "starting" and "template" are used interchangeably.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50–200 mM NaCl or KCl, pH 6.5–8.5, 20–45 C and 0.001–10 mM divalent cation (e.g., $Mg^{++}$, $Ca^{++}$); preferably about 150 mM NaCl or KCl, pH 7.2–7.6, 5 mM divalent cation, and often include 0.01–1.0 percent nonspecific protein (e.g., BSA). A non-ionic detergent (Tween, NP-40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s) and/or metal chelators and/or non-ionic detergents and/or membrane fractions and/or anti-foam agents and/or scintillants.

Standard convention (5' to 3') is used herein to describe the sequence of double standed polynucleotides.

The term "population" as used herein means a collection of components such as polynucleotides, portions or polynucleotides or proteins. A "mixed population: means a collection of components which belong to the same family of nucleic acids or proteins (i.e., are related) but which differ in their sequence (i.e., are not identical) and hence in their biological activity.

A molecule having a "pro-form" refers to a molecule that undergoes any combination of one or more covalent and noncovalent chemical modifications (e.g. glycosylation, proteolytic cleavage, dimerization or oligomerization, temperature-induced or pH-induced conformational change, association with a co-factor, etc.) en route to attain a more mature molecular form having a property difference (e.g. an increase in activity) in comparison with the reference pro-form molecule. When two or more chemical modification (e.g. two proteolytic cleavages, or a proteolytic cleavage and a deglycosylation) can be distinguished en route to the production of a mature molecule, the referemce precursor molecule may be termed a "pre-pro-form" molecule.

As used herein, the term "pseudorandom" refers to a set of sequences that have limited variability, such that, for example, the degree of residue variability at another position, but any pseudorandom position is allowed some degree of residue variation, however circumscribed.

"Quasi-repeated units", as used herein, refers to the repeats to be re-assorted and are by definition not identical. Indeed the method is proposed not only for practically identical encoding units produced by mutagenesis of the identical starting sequence, but also the reassortment of similar or related sequences which may diverge significantly in some regions. Nevertheless, if the sequences contain sufficient homologies to be reassorted by this approach, they can be referred to as "quasi-repeated" units.

As used herein "random peptide library" refers to a set of polynucleotide sequences that encodes a set of random peptides, and to the set of random peptides encoded by those polynucleotide sequences, as well as the fusion proteins contain those random peptides.

As used herein, "random peptide sequence" refers to an amino acid sequence composed of two or more amino acid monomers and constructed by a stochastic or random process. A random peptide can include framework or scaffolding motifs, which may comprise invariant sequences.

As used herein, "receptor" refers to a molecule that has an affinity for a given ligand. Receptors can be naturally occurring or synthetic molecules. Receptors can be employed in an unaltered state or as aggregates with other species. Receptors can be attached, covalently or non-covalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

"Recombinant" enzymes refer to enzymes produced by recombinant DNA techniques, i.e., produced from cells transformed by an exogenous DNA construct encoding the desired enzyme. "Synthetic" enzymes are those prepared by chemical synthesis.

The term "related polynucleotides" means that regions or areas of the polynucleotides are identical and regions or areas of the polynucleotides are heterologous.

"Reductive reassortment", as used herein, refers to the increase in molecular diversity that is accrued through deletion (and/or insertion) events that are mediated by repeated sequences.

The following terms are used to describe the sequence relationships between two or more polynucleotides: "reference sequence," "comparison window," "sequence identity," "percentage of sequence identity," and "substantial identity."

A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

"Repetitive Index (RI)", as used herein, is the average number of copies of the quasi-repeated units contained in the cloning vector.

The term "restriction site" refers to a recognition sequence that is necessary for the manifestation of the action of a restriction enzyme, and includes a site of catalytic cleavage. It is appreciated that a site of cleavage may or may not be contained within a portion of a restriction site that comprises a low ambiguity sequence (i.e. a sequence containing the principal determinant of the frequency of occurrence of the restriction site). Thus, in many cases, relevant restriction sites contain only a low ambiguity sequence with an internal cleavage site (e.g. G/AATTC in the EcoR I site) or an immediately adjacent cleavage site (e.g. /CCWGG in the EcoR II site). In other cases, relevant restriction enzymes [e.g. the Eco57 I site or CTGAAG(16/14)] contain a low ambiguity sequence (e.g. the CTGAAG sequence in the Eco57 I site) with an external cleavage site (e.g. in the $N_{16}$ portion of the Eco57 I site). When an enzyme (e.g. a restriction enzyme) is said to "cleave" a polynucleotide, it is understood to mean that the restriction enzyme catalyzes or facilitates a cleavage of a polynucleotide.

In a non-limiting aspect, a "selectable polynucleotide" is comprised of a 5' terminal region (or end region), an intermediate region (i.e. an internal or central region), and a 3' terminal region (or end region). As used in this aspect, a 5' terminal region is a region that is located towards a 5' polynucleotide terminus (or a 5' polynucleotide end); thus it is either partially or entirely in a 5' half of a polynucleotide. Likewise, a 3' terminal region is a region that is located towards a 3' polynucleotide terminus (or a 3' polynucleotide end); thus it is either partially or entirely in a 3' half of a polynucleotide. As used in this non-limiting exemplification, there may be sequence overlap between any two regions or even among all three regions.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. This "substantial identity", as used herein, denotes a characteristic of a polynucleotide sequence, wherein the polynucleotide comprises a sequence having at least 80 percent sequence identity, preferably at least 85 percent identity, often 90 to 95 percent sequence identity, and most commonly at least 99 percent sequence identity as compared to a reference sequence of a comparison window of at least 25–50 nucleotides, wherein the percentage of sequence identity is calculated by comparing the reference sequence to the polynucleotide sequence which may include deletions or additions which total 20 percent or less of the reference sequence over the window of comparison.

As known in the art "similarity" between two enzymes is determined by comparing the amino acid sequence and its conserved amino acid substitutes of one enzyme to the sequence of a second enzyme. Similarity may be determined by procedures which are well-known in the art, for example, a BLAST program (Basic Local Alignment Search Tool at the National Center for Biological Information).

As used herein, the term "single-chain antibody" refers to a polypeptide comprising a $V_H$ domain and a $V_L$ domain in polypeptide linkage, generally liked via a spacer peptide (e.g., [Gly-Gly-Gly-Gly-Ser]$_x$), and which may comprise additional amino acid sequences at the amino- and/or carboxy- termini. For example, a single-chain antibody may comprise a tether segment for linking to the encoding polynucleotide. As an example, a scFv is a single-chain antibody. Single-chain antibodies are generally proteins consisting of one or more polypeptide segments of at least 10 contiguous amino substantially encoded by genes of the immunoglobulin superfamily (e.g., see Williams and Barclay, 1989, pp. 361–368, which is incorporated herein by reference), most frequently encoded by a rodent, non-human primate, avian, porcine bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions (see above).)

"Specific hybridization" is defined herein as the formation of hybrids between a first polynucleotide and a second polynucleotide (e.g., a polynucleotide having a distinct but substantially identical sequence to the first polynucleotide), wherein substantially unrelated polynucleotide sequences do not form hybrids in the mixture.

The term "specific polynucleotide" means a polynucleotide having certain end points and having a certain nucleic acid sequence. Two polynucleotides wherein one polynucleotide has the identical sequence as a portion of the second polynucleotide but different ends comprises two different specific polynucleotides.

"Stringent hybridization conditions" means hybridization will occur only if there is at least 90% identity, preferably at least 95% identity and most preferably at least 97% identity between the sequences. See Sambrook et al, 1989, which is hereby incorporated by reference in its entirety.

Also included in the invention are polypeptides having sequences that are "substantially identical" to the sequence of a phytase polypeptide, such as one of SEQ ID 1. A "substantially identical" amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine).

Additionally a "substantially identical" amino acid sequence is a sequence that differs from a reference sequence or by one or more non-conservative substitutions, deletions, or insertions, particularly when such a substitution occurs at a site that is not the active site the molecule, and provided that the polypeptide essentially retains its behavioural properties. For example, one or more amino acids can be deleted from a phytase polypeptide, resulting in modification of the structure of the polypeptide, without significantly altering its biological activity. For example, amino- or carboxyl-terminal amino acids that are not required for phytase biological activity can be removed. Such modifications can result in the development of smaller active phytase polypeptides.

The present invention provides a "substantially pure enzyme". The term "substantially pure enzyme" is used herein to describe a molecule, such as a polypeptide (e.g., a phytase polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. The purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

As used herein, "substantially pure" means an object species is the predominant species present (i.e., on a molar basis it is more abundant than any other individual macromolecular species in the composition), and preferably substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

As used herein, the term "variable segment" refers to a portion of a nascent peptide which comprises a random, pseudorandom, or defined kemal sequence. A variable segment" refers to a portion of a nascent peptide which comprises a random pseudorandom, or defined kemal sequence. A variable segment can comprise both variant and invariant residue positions, and the degree of residue variation at a variant residue position may be limited: both options are selected at the discretion of the practitioner. Typically, variable segments are about 5 to 20 amino acid residues in length (e.g., 8 to 10), although variable segments may be longer and may comprise antibody portions or receptor proteins, such as an antibody fragment, a nucleic acid binding protein, a receptor protein, and the like.

The term "wild-type" means that the polynucleotide does not comprise any mutations. A "wild type" protein means that the protein will be active at a level of activity found in nature and will comprise the amino acid sequence found in nature.

The term "working", as in "working sample", for example, is simply a sample with which one is working. Likewise, a "working molecule", for example is a molecule with which one is working.

F. Detailed Description of the Invention

1. Genomic Characterization Methods

In one aspect, this invention describes a new method to sequence DNA. The improvements over the existing DNA sequencing technologies are high speed, high throughput, no electrophoresis and gel reading artifacts due to the complete absence of an electrophoretic step, and no costly reagents involving various substitutions with stable isotopes. The invention utilizes the Sanger sequencing strategy and assembles the sequence information by analysis of the nested fragments obtained by basespecific chain termination via their different molecular masses using mass spectrometry, as for example, MALDI or ES mass spectrometry. A futher increase in throughput can be obtained by introducing massmodifications in the oligonucleotide primer, chain-terminating nucleoside triphosphates and/or in the chainelongating nucleoside triphosphates, as well as using integrated tag sequences which allow multiplexing by hybridization of tag specific probes with mass differentiated molecular weights.

The present invention pertains to a method for sequencing genomes. The method comprises the steps of obtaining nucleic acid material from a genome. Then there is the step of constructing a clone library and one or more probe libraries from the nucleic acid material. Next there is the step of comparing the libraries to form comparisons. Then there is the step of combining the comparisons to construct a map of the clones relative to the genome. Next there is the step of determining the sequence of the genome by means of the map.

The present invention also pertains to a system for sequencing a genome. The system comprises a mechanism for obtaining nucleic acid material from a genome. The system also comprises a mechanism for constructing a clone library and one or more probe libraries. The constructing mechanism is in communication with the nucleic acid material from a genome. Additionally, the system comprises a mechanism for comparing said libraries to form comparisons. The comparing mechanism is in communication with the said libraries. The system also comprises a mechanism for combining the comparisons to construct a map of the clones relative to the genome. The said combining mechanism is in communication with the comparisons. Further, the system comprises a mechanism for determining the sequence of the genome by means of said map. The said determining mechanism is in communication with said map. The present invention additionally pertains to a method for producing a gene of a genome.

An efficient method for sequencing large fragments of DNA is described. A subclone path through the fragment is first identified; the collection of subclones that define this path is then sequenced using transposon-mediated direct sequencing techniques to an extent sufficient to provide the complete sequence of the fragment.

Improved techniques are provided for DNA sequencing, and particularly for sequencing of the entire human genome.

Different base-specific reactions are utilized to use different sets of DNA fragments from a piece of DNA of unknown sequence. Each of the different sets of DNA fragments has a common origin and terminates at a particular base along the unknown sequence. The molecular weight of the DNA fragments in each of the different sets is detected by a matrix assisted laser absorption mass spectrometer to determine the sequence of the different bases in the DNA. The methods and apparatus of the present invention provide a relatively simple and low cost technique which may be automated to sequence thousands of gene bases per hour, and eliminates the tedious and time consuming gel electrophoresis separation technique conventionally used to determine the masses of DNA fragments.

Processes and kits for simultaneously amplifying and sequencing nucleic acid molecules, and performing high throughput DNA sequencing are described.

A new contiguous genome sequencing method is described which allows the contiguous sequencing of a very long DNA without need to be subcloned. It uses the basic PCR technique but circumvents the usual need of this technique for the knowledge two primers for contiguous sequencing, enabling the knowledge of only one primer sufficient. The present invention makes it possible to PCR amplify a DNA adjacent to a known sequence with which one primer can be made without the knowledge of the second primer binding site present in the unknown sequence. The present invention could thus be used to contiguously sequence a very long DNA such as that contained in a YAC clone or a cosmid clone, without the need for subcloning smaller fragments, using the standard PCR technique. It can also be used to sequence a whole chromosome or genome without any need to subclone it.

Methods and means are provided for the massively parallel characterization of complex molecules and of molecular recognition phenomena with parallelism and redundancy attained through single molecule examination methods. Applications include ultra-rapid genome sequencing, affinity characterization, pathogen characterization and detection means for clinical use and use in the development and construction of cybernetic immune systems. Novel methods for single molecule examination and manipulation are provided, including scanned beam light microscopic means and methods, and detection means availing of optoelectronic array devices. Various apparatus for rate control, including stepping control for various reactions are combined with molecular recognition, signal amplification and single molecule examination methods. Inclusion of internal control in samples, algorithm-based dynamically responsive manipulation controls, and sample redundancy, are availed to provide an arbitrarily high degree of accuracy in final data.

1.1 Sequencing

The present invention relates to sequencing of DNA and is in the field of determining the nucleotide sequence of large segments of DNA. More specifically, the invention provides an improved method to obtain the complete nucleotide sequence of genomic DNA provided in fragments of over 30 kb.

The present invention pertains to a process for determining the DNA sequence of the genome of an organism. And more particularly, the invention relates to the sequencing of the entire human genome.

More specifically, the present invention is related to constructing clone maps of organisms, and then using these maps to direct the sequencing effort. The invention also pertains to systems that can effectively use this sequence and map information.

The invention relates to the massively parallel single molecule examination of associations or reactions between large numbers of first complex molecules, which may be diverse, and second single or plural probing molecules, which may or may not be diverse, with applications to biology, biotechnology, pharmacology, immunology, the novel field of cybernetic immunology, molecular evolution, cybernetic molecular evolution, genomics, comparative genomics, enzymology, clinical enzymology, pathology, medical research, and clinical medicine.

The present invention has applications in the area of polynucleotide sequence determination, including DNA sequencing.

1.2 Sequencing Methods 1.2.1 Importance of DNA Sequencing

Current knowledge regarding gene structure, the control of gene activity and the function of cells on a molecular level all arose based on the determination of the base sequence of millions of DNA molecules. DNA sequencing is still critically important in research and for genetic therapies and diagnostics, (e.g., to verify recombinant clones and mutations).

DNA, a polymer of deoxyribonucleotides, is found in all living cells and some viruses. DNA is the carrier of genetic information, which is passed from one generation to the next by homologous replication of the DNA molecule. Information for the synthesis of all proteins is encoded in the sequence of bases in the DNA. DNA sequence information represents the information required for gene organization and regulation of most life forms. Accordingly, the development of reliable methodology for sequencing DNA has contributed significantly to an understanding of gene structure and function.

Since the genetic information is represented by the sequence of the four DNA building blocks deoxyadenosine- (dpA), deoxyguanosine- (dpG), deoxycytidine- (dpC) and deoxythyraidine-5'-phosphate (dpT), DNA sequencing is one of the most fundamental technologies in molecular biology and the life sciences in general. The ease and the rate by which DNA sequences can be obtained greatly affects related technologies such as development and production of new therapeutic agents and new and useful varieties of plants and microorganisms via recombinant DNA technology. In particular, unraveling the DNA sequence helps in understanding human pathological conditions including genetic disorders, cancer and AIDS. In some cases, very subtle differences such as a one nucleotide deletion, addition or substitution can create serious, in some cases even fatal., consequences. Recently, DNA sequencing has become the core technology of the Human Genome Sequencing Project (e.g., J. E. Bishop and M. Waldholz, 1991, Genome: The Story of the Most Astonishing Scientific Adventure of Our Time—The Attempt to Map All the Genes in the Human Body, Simon & Schuster, New York). Knowledge of the complete human genome DNA sequence will certainly help to understand, to diagnose, to prevent and to treat human diseases. To be able to tackle successfully the determination of the approximately 3 billion base pairs of the human genome in a reasonable time frame and in an economical way, rapid, reliable, sensitive and inexpensive methods need to be developed, which also offer the possibility of automation. The present invention provides such a technology. The need for highly rapid, accurate, and inexpensive sequencing technology is nowhere more apparent than in a demanding sequencing project such as the human genome project.

The present invention relates to the field of nucleic acid analysis, detection, and sequencing. More specifically, in one embodiment the invention provides improved techniques for synthesizing arrays of nucleic acids, hybridizing nucleic acids, detecting mismatches in a double-stranded nucleic acid composed of a single-stranded probe and a target nucleic acid, and determining the sequence of DNA or RNA or other polymers.

A human being has 23 pairs of chromosomes consisting of a total of about 100,000 genes. The human genome consists of those genes. A single gene which is defective may cause an inheritable disease, such as Huntington's disease, Tay-Sachs disease or cystic fibrosis. The human chromosomes consist of large organic linear molecules of double-strand DNA (deoxyribonucleic acid) with a total length of about 3.3 billion "base pairs". The base pairs are the chemicals that encode information along DNA. A typical gene may have about 30,000 base pairs. By correlating the inheritance of a "marker" (a distinctive segment of DNA) with the inheritance of a disease, one can find a mutant (abnormal) gene to within one or two million base pairs. This opens the way to clone the DNA segment, test is activity, follow its inheritance, and diagnose carriers and future disease victims.

The mapping of the human genome is to accurately determine the location and composition of each of the 3.3 billion bases. The complexity and large scale of such a mapping has placed it, in terms of cost, effort and scientific potential of such projects, as one of the largest and most important projects of the 1990's and beyond.

Recent reviews of today's methods together with future directions and trends are given by Barrell (The FASEB Journal 1, 40–45 (1991)), and Trainor (Anal. Chem. 62, 418–26 (1990)).

1.2.2 Previously Developed Methods

The problem of DNA sequence analysis is that of determining the order of the four bases on the DNA strands. DNA sequencing is a technique by which the four DNA nucleotides (characters) in a linear DNA sequence is ordered by chemical and biochemical means. Generally, strategies for determining the nucleotide sequence of DNA involve the generation of a DNA substrate i.e., DNA fragments suitable for sequencing a region of the DNA, enzymatic or chemical reactions, and analysis of DNA fragments that have been separated according to their lengths to yield sequence information. More specifically, to sequence a given region of DNA, labeled DNA fragments are typically generated in four separate reactions. In each of the four reactions, the DNA fragments typically have one fixed end and one end that terminates sequentially at each of the four nucleotide bases, respectively. The products of each reaction are fractionated by gel electropheresis on adjacent lanes of a polyacrylamide gel. As all of the nucleotides are represented among the four lanes, the sequence of a given region of DNA can be determined from the four "ladders" of DNA fragments. The present status of techniques for determining such sequences is described in some detail in an article by Lloyd M. Smith published in the American Biotechnology Laboratory, Volume 7, Number 5, May 1989, pp 10–17. Since the early 1970's, two methods have been developed for the determination of DNA sequence: (1) the enzymatic chain-termination sequencing method, which relies on the template directed incorporation of nucleotides which themselves do not supply the necessary chemical functionalities required for subsequent enzymatic polymerization of a daughter strand polynucleotide, developed by Sanger and colleagues (F. Sanger, S. Nicklen, and A. R. Coulson, "DNA sequencing with chain- terminating inhibitors." Proc. Nati. Acad. Sci, USA, 74:5463–5467 (1977)), which is most commonly used for sequence determination; and (2) the base-specific chemical degradation (modification and cleavage) method, developed by Maxam and Gilbert (A. M. Maxam, and W. Gilbert, "A new method of sequencing DNA." Proceedings of the National Academy of Sciences, USA, 74:560–564 (1977)), which similarly yields polynucleotide molecules terminated at sites containing a specific base according to the chemical treatment applied to the sample. Both of these techniques are based on similar principals, and employ gel electrophoresis to separate DNA fragments of different lengths with high resolution. On these gels it is thus possible to separate a DNA fragment 600 bases in length from one 601 bases in length. No distinct method preferable to these has yet been validated. Both methods require a large number of complex manipulations, such as isolation of homogeneous DNA fragments, elaborate and tedious preparation of samples, preparation of a separating gel, application of samples to the gel, electrophoresing the samples on the gel, working up of the finjshed gel, and analysis of the results of the procedure.

1.2.2.1 Chemical/Maxam and Gilbert Method for Sequencing

In the chemical method, the DNA strand is isotropically labeled on one end, broken down into smaller fragments at sequence locations ending with a particular nucleotide (A, T, C, or G) by chemical means, and the fragments ordered based on this information. Base specific modifications result in a base specific cleavage of the radioactive or fluorescently labeled DNA fragment. After the DNA substrate is end labeled, it is subjected to chemical reactions designed to cleave the DNA at positions adjacent to a given base or bases. The labeled DNA fragments will, therefore, have a common labeled terminus while the unlabeled termini will be defined by the positions of chemical cleavage. This results in the generation of DNA fragments (four sets of nested fragments) which can be separated according to length by polyacrylamide gel electrophoresis (PAGE) and identified. Alternatively, unlabeled DNA fragments can be separated after complete restriction digestion and partial chemical cleavage of the DNA, and hybridized with probes homologous to a region near the region of the DNA to be sequenced. See, Church et al., Proc. Natl. Acad. Sci., 81:1991 (1984). After autoradiography, the sequence can be read directly since each band (fragment) in the gel originates from a base specific cleavage event. Thus, the fragment lengths in the four "ladders" directly translate into a specific position in the DNA sequence.

1.2.2.2 Enzymatic/Sanger Method for Sequencing

In the enzymatic method, the four base specific sets of DNA fragments are formed by starting with a primer/template system elongating the primer into the unknown DNA sequence area and thereby copying the template and synthesizing complementary strands using a DNA polymerase in the presence of chain-terminating reagents. The chain-terminating event is achieved by incorporating into the four separate reaction mixtures in addition to the four normal deoxynucleoside triphosphates, dATP, dGTP, dTTP and dCTP, only one of the chain-terminating dideoxynucleoside triphosphates, ddATP, ddGTP, ddTTP or ddCTP, respectively, in a limiting small concentration. The incorporation of a ddNTP lacking the 3' hydroxyl function into the growing DNA strand by the enzyme DNA polymerase leads to chain termination through preventing the formation of a 3'-5'-phosphodiester bond by DNA polymerase. Due to the random incorporation of the ddNTPs, each reaction leads to a population of base specific terminated fragments of different lengths, which all together represent the sequenced DNA-molecule. The four sets of resulting fragments produce, after electrophoresis, four base specific ladders from which the DNA sequence can be determined.

In the enzymatic method, the following basic steps are involved:

(i) annealing an oligonucleotide primer to a suitable single or denatured double stranded DNA template; (ii) extending the primer with DNA polymerase in four separate reactions, each containing one—labeled dNTP or ddNTP (alternatively a labeled primer can be used), a mixture of unlabeled dNTPs, and one chain-terminating dideoxynucleoside-5'-triphosphate (ddNTP); (iii) resolving the four sets of reaction products, which include a distribution of DNA fragments having primer-defined 5' termini and differing dideoxynucleotides at the 3' termini, on a high resolution polyacrylamide-urea gel; and (iv) producing an auto radiographic image of the gel that can be examined to infer the DNA sequence. Alternatively, fluorescently labeled primers or nucleotides can be used to identify the reaction products. Known dideoxy sequencing methods utilize a DNA polymerase such as the Klenow fragment of E. coli DNA polymerase, a DNA polymerase from Thermus aquaticus, reverse transcriptase, a modified T7 DNA polymerase, or the Taq polymerase.

1.2.2.3 Similarities, Differences and Other Details of the Two Methods

The two sequencing methods differ in the techniques employed to produce the DNA fragments, but are otherwise similar. In the Maxam-Gilbert method, four different base-specific reactions are performed on portions of the DNA molecules to be sequenced, to produce four sets of radiolabeled DNA fragments. These four fragment sets are each loaded in adjacent lanes of a polyacrylamide slab gel, and are separated by electrophoresis. Autoradiographic imaging of the pattern of the radiolabeled DNA bands in the gel reveals the relative size, corresponding to band mobilities, of the fragments in each lane, and the DNA sequence is deduced from this pattern.

While numerous modifications and improvements to the strategies referred to above have been developed, most sequencing techniques require the presence of a known primer binding site for every 300 to 500 nucleotides to be sequenced either, for example, for initiation of DNA synthesis or for hybridization to different length DNA fragments having a common end. However, as such approaches utilize a "ladder" of DNA fragments containing the primer binding site (or its complement), the amount of sequence information that can be obtained is limited by the present inability to resolve DNA fragments greater than 500 nucleotides in length on sequencing gels.

Both of these methods yield a population of molecules comprising a nested set which together may be analyzed to determine the base sequence of the sample. At least one of these two techniques is employed in essentially every laboratory concerned with molecular biology, and together they have been employed to sequence more than 26 million bases of DNA. Currently a skilled biologist can produce about 30,000 bases of finished DNA sequence per year under ideal conditions.

These methods and several variations thereupon, as well as their severe limitations with respect to the economy and rapidity of accumulation of sequence data, are well known to those in the relevant arts. Various lower resolution techniques, generally falling within the category termed genome mapping, have been developed to circumvent these limitations for applications where more "broad spectrum" examination of genetic material is required but less detailed information about sequence will suffice.

1.2.2.4 Cloning/Subcloning Steps

On the upfront end, the DNA to be sequenced has to be fragmented into sequencable pieces of currently not more than 500 to 1000 nucleotides. Starting from a genome, this is a multi-step process involving cloning and subcloning steps using different and appropriate cloning vectors such as YAC, cosmids, plasmids and M13vectors (Sambrook et al., Molecular Cloning: A Laboratory Manual. Cold Spring Harbor Laboratory Press, 1989). Finally, for Sanger sequencing, the fragments of about 500 to 1000 base pairs are integrated into a specific restriction site of the replicative form I (RF I) of a derivative of the M13 bacteriophage (Vieria and Messing, Gene 19, 259(1982)) and then the double-stranded form is transformed to the single-stranded circular form to serve as a template for the Sanger sequencing process having a binding site for a universal primer obtained by chemical DNA synthesis (Sinha, Biernat, McManus and Köster, Nucleic Acids Res. 12, 4539–57 (1984); U.S. Pat. No. 4,725,677 upstream of the restriction site into which the unknown DNA fragment has been inserted. Under specific conditions, unknown DNA sequences integrated into supercoiled double-stranded plasmid DNA can be sequenced directly by the Sanger method (Chen and Seeburg, DNA 4, 165–170 (1985)) and Lim et al., Gene Anal., Techn. 5, 32–39 (1988), and, with the Polymerase Chain Reaction (PCR) (PCR Protocols—A Guide to Methods and Applications. Innis et al., editors, Academic Press, San Diego (1990)) cloning or subcloning steps could be omitted by directly sequencing off chromosomal DNA by first amplifying the DNA segment by PCR and then applying the Sanger sequencing method (Innis et al., Proc. Nad. Acad. Sci. USA 85, 9436–9440 (1988)). In this case, however, the DNA sequence in the interested region most be known at least to the extent to bind a sequencing primer.

1.2.2.5 Methodology Described by Guo and Wu

Methodology described by Guo and Wu, Nucleic Acids Res., 10:2065 (1982); and Meth. Enz., 100:60 (1983), which is not dependent upon primer binding sites, is highly desirable for sequencing DNA greater than 500 nucleotides. This method involves partially digesting linear double stranded DNA with E. coli exonuclease III to produce DNA fragments with 3' ends shortened to varying lengths, performing the dideoxy primer extension reactions of Sanger, supra, with the shortened 3' ends as primers for DNA synthesis, and digesting the DNA with a selected restriction enzyme that cleaves near one end of the molecule adjacent to, but not within, the labeled region of DNA. By digestion of the DNA with a selected restriction enzyme, the labeled DNA strands from one end of the molecule are made small enough to be resolved on a sequencing gel. Each successive deletion in length, therefore, brings "new" regions of the target DNA into sequencing range.

However, certain disadvantages inherent in the methodology of Guo and Wu, supra, limit its usefulness for the large scale sequencing of DNA. For example, this approach depends upon the selection of appropriate restriction enzymes which cleave at restriction sites in close proximity to particular E. coli exonuclease III endpoints, but not within the labeled DNA as this would result in two or more superimposed sequence ladders. The selection of appropriate restriction enzymes generally requires, therefore, the restriction mapping of DNA fragments to identify sites in close proximity to the numerous exonuclease III endpoints. However, the determination of restriction maps tends to be both time consuming and labor intensive. Specifically, restriction mapping to the resolution needed for DNA sequencing involves the digestion of each region of DNA with combinations of 20 or more enzymes to uncover the relative position of restriction sites. This may require over 100 enzymatic reactions followed by numerous electrophoretic separations. Further, significant amounts of DNA are consumed in the mapping process and interpretation of the data generally requires a substantial amount of time.

1.2.3 3'-hydroxy-protected and Labeled Nucleotides

A modified nucleotide compound possessing two properties particularly useful for purposes of the present invention has been described by N. Williams and P. S. Colemanl. This compound is 3'-O-(4-benzoyl)benzoyl adenosine 5'-triphosphate. This nucleotide bears a 3' protecting group linked via an ester function which should be susceptible to hydrolysis by appropriate chemical treatments. The protecting moiety is suitable for photoactivation, and this property was utilized by those investigators to probe the structure of mitochondrial $F_1$-ATPase, indicating that this analog will interact properly with at least some enzymes. Under appropriate circumstances, the protecting moiety may also serve as a label.

Very recently, B Canard and R. S. Sarfati have described similar nucleotides, here comprising all four nucleobases, with chemically removable 3'-hydroxyl protecting groups. Said protecting groups comprise various fluorescent dye moieties. These investigators have shown that these compounds may be added to appropriately primed polynucleotides by polymerases according to Watson-Crick base-pairing rules, and serve to terminate chain elongation in a manner which may be reversed by removal of said protecting groups by appropriate chemical treatments, admitting resumption of polymerization. These workers propose that such compounds may form the basis of a novel sequencing methodology availing steppinq control by means of said removable protecting groups and detection of labels following their release from the nascent strand by appropriate chemical treatment. Such a method, while a potential advance over electrophoretic resolution methods, does not avail of great parallelism because only one molecule or an identical population of molecules may be sequenced at once (within a single vessel) by such a method, due to the release of the labeling moiety prior to detection, according to this proposed scheme. Further, this limitation requires that any attempt to avail of parallelism entail elaborate parallel fluidics. Low or no parallelism entails that stepping rate will be critical to the throughput attained with such a sequencing scheme. The results published by these authors suggests that the rate of chemical removal of 3'-hydroxy protecting groups (less than 90% removal after 10 minutes of treatment with 0.1M NaOH) will be unacceptably low for such an inherently serial sequencing scheme.

Additional references regarding such compounds and in most instances their properties as substrates for various enzymes including polymerases have been found in the biological literature: Churchich, J. E.; 1995. Eur. J. Biochem., 231:736. Metzket, M. L.; Gibbs, R. A.; et al.; 1994. Nucleic Acids Research, 22:4259. Beabealashvilli, R. S.; Kukhanova, M. K.; et al.; 1986. Biochimica et Biophysica Acta, 868:136. Chidgeavadze, Z. G.; Kukhanova, M. K.; et al.; 1986. Biochimica et Biophysica Acta, 868:145. Hiratsuka, T; 1983. Biochimica et Biophysica Acta, 742:496. Jeng, S. J.; Guillory, R. J.; 1975. J. Supramolecular Structure, 3:448.

1.2.4 Related Base Addition Sequencing Schemes

Various other investigators have also independently devised polynucleotide sequencing methodologies which depend on the addition of a polymerization terminating labeled nucleotide to a primed or elongated daughter strand on a polynucleotide sample with template dependent polynucleotide polymerases. Most, but not all, of these methods (referred to herein as previously disclosed base-addition sequencing schemes) avail nucleotide triphosphate monomers with some base-specific label which may be removed by some deprotection treatment. It must be emphasized that all of these other previously disclosed base-addition sequencing schemes examine not single molecules individually but rather large homogeneous populations of substantially identical molecules, wherein the observed signal used to identify label type originates from the totality of such a population of molecules rather than an individual molecule. It must be further emphasized that conventional usage does not generally reveal this distinction: phrases such a "a molecule" or "a sample molecule" refer not to an individual molecule considered separately or in isolation from other molecules including separately from other molecules of identical composition and structure, but to populations comprising millions or more molecules of identical structure. A careful reading of these prior disclosures reveals that these investigators are not working with samples consisting of single molecules but rather with samples comprising a plurality of identical molecules. In particular, even where these investigators do not (as is consistent with conventional usage) explicitly note this point, they take measures which would apply only to samples of pluralities of identical molecules, and do not take measures associated with working with single molecules.

1.2.5 Labeling 1.2.5.1 Sequencing from Page Using Radioisotopes

In order to be able to read the sequence from PAGE, detectable labels have to be used in either the primer (very often at the 5'-end) or in one of the deoxynucleoside triphosphates, dNTP. Using radioisotopes such as $^{32}P$, $^{33}P$, or $^{35}S$ is still the most frequently used technique. After PAGE, the gels are exposed to X-ray films and silver grain exposure is analyzed. The use of radioisotopic labeling creates several problems. Most labels useful for autoradiographic detection of sequencing fragments have relatively short half-lives which can limit the useful time of the labels. The emission high energy beta radiation, particularly from $^{32}P$, can lead to breakdown of the products via radiolysis so that the sample should be used very quickly after labeling. In addition, high energy radiation can also cause a deterioration of band sharpness by scattering. Some of these problems can be reduced by using the less energetic isotopes such as $^{33}P$ or $^{35}S$ (see, e.g., Ornstein et al., Biotechniques 2, 476 (1985)). Here, however, longer exposure times have to be tolerated. Above all, the use of radioisotopes poses significant health risks to the experimentalist and, in heavy sequencing projects, decontamination and handling the radioactive waste are other severe problems and burdens.

1.2.5.2 Integration of Non-radioactive Labeling Techniques into Partly Automated DNA Sequencing In response to the above mentioned problems related to the use of radioactive labels, non-radioactive labeling techniques have been explored and, in recent years, integrated into partly automated DNA sequencing procedures. All these improvements utilize the Sanger sequencing strategy. The fluorescent label can be tagged to the primer (Smith et al., Nature M, 674–679 (1986) and EPO Patent No. 873 00998.9; Du Pont De Nemours EPO Application No. 03 59225; Ansorge et al., L Biochem. Biophys. Method 13, 325–32 (1986)) or to the chain-terminating dideoxynucloside triphosphates (Prober et al. Science M, 336–41 (1987);

Applied Biosystems, PCT Application WO 91/05060). Based on either labeling the primer or the ddNTP, systems have been developed by Applied Biosystems (Smith et al., Science 235, G89 (1987); U.S. Pat. Nos. 570,973 and 689,013), Du Pont De Nemours (Prober et al., Science 238, 336–341 (1987); U.S. Pat. Nos. 881,372 and 57,566), Pharmacia-LKB (Ansorge et al. Nucleic Acids Res. 15-, 4593–4602 (1987) and EMBL Patent Application DE P3724442 and P3805808.1) and Hitachi (JP 1-90844 and DE 4011991 A1). A somewhat similar approach was developed by Brumbaugh et al. (Proc. Natl. Sci. USA 85, 5610–14 (1988) and U.S. Pat. No. 4,729,947). An improved method for the Du Pont system using two electrophoretic lanes with two different specific labels per lane is described (PCT Application W092/02635). A different approach uses fluorescently labeled avidin and biotin labeled primers. Here, the sequencing ladders ending with biotin are reacted during electrophoresis with the labeled avidin which results in the detection of the individual sequencing bands (Brumbaugh et al., U.S. Pat. No. 594,676).

More recently even more sensitive non-radioactive labeling techniques for DNA using chemiluminescence triggerable and amplifyable by enzymes have been developed (Beck, O'Keefe, Coull and Köster, Nucleic Acids Res. 7, 5115–5123 (1989) .L7 and Beck and Köster, Anal. Chem. 62 2258–2270 (1990)). These labeling methods were combined with multiplex DNA sequencing (Church et al., Science 240, 185–188 (1988) to provide for a strategy aimed at high throughput DNA sequencing (Köster et al., Nucleic Acids Res. Symposium Ser. No. 24, 318–321 (1991), University of Utah, PCT Application No. WO 90/15883); this strategy still suffers from the disadvantage of being very laborious and difficult to automate.

1.2.5.2.1 Fluorescent Labeling in Methods for Automated DNA Sequencing

Of particular interest in DNA sequencing are methods of automated sequencing, in which fluorescent labels are employed to label the size separated fragments or primer extension products of the enzymatic method. Currently, three different methods are used for automated DNA sequencing. In the first method, the DNA fragments are labeled with one fluorophore and then run in adjacent sequencing lanes, one lane for each base. See Ansorge et al., Nucleic Acids Res. (1987)15:4593–4602. In the second methods, the DNA fragments are labeled with oligonucleotide primers tagged with four fluorophores and all of the fragments are run in one lane. See Smith et al., Nature (1986) 321:674–679. In the third method, each of the different chain terminatina dideoxynucleotides is labeled with a different fluorophore and all of the fragments are run in one lane. See Prober et al., Science (1987) 238:336–341. The first method has the potential problems of lane-to-lane variations as well as a low throughput. The second and third methods require that the four dyes be well excited by one laser source, and that they have distinctly different emission spectra. Otherwise, multiple lasers have to be used, increasing the complexity and the cost of the detection instrument.

With the development of Energy Transfer primers which offer strong fluorescent signals upon excitation at a common wavelength, the second method produces robust sequencing data in currently commercial available sequencers. However, even with the use of Energy Transfer primers, the second method is not entirely satisfactory. In the second method, all of the false terminated or false stop fragments are detected resulting in high backgrounds. Furthermore, with the second method it is difficult to obtain accurate sequences for DNA templates with long repetitive sequences. See Robbins et al., Biotechniques (1996) 20: 862–868.

The third method has the advantage of only detecting DNA fragments incorporated with a terminator. Therefore, backgrounds caused by the detection of false stops are not detected. However, the fluorescence signals offered by the dye-labeled terminators are not very bright and it is still tedious to completely clear up the excess of dye-terminators even with AmpliTaq DNA Polymerase (FS enzyme). Furthermore, non-sequencing fragments are detected, which contributes to background signal. Applied Biosystems Model 373 A DNA Sequencing System User Bulletin, November 17,P3,August 1990.

Thus, there is a need for the development of improved methodology which is capable of providing for highly accurate sequencing data, even for long repetitive sequences. Such methodology would ideally include a means for isolating the DNA sequencing fragments from the remaining components of the sequencing reaction mixtures such as salts, enzymes, excess primers, template and the like, as well as false stopped sequencing fragments and non-sequencing fragments resulting from contaminated RNA and nicked DNA templates.

1.2.6 Simplifying DNA Sequencing Using Solid Supports

In an attempt to simplify DNA sequencing, solid supports have been introduced. In most cases published so far, the template strand for sequencing (with or without PCR amplification) is immobilized on a solid support most frequently utilizing the strong biotin-avidin/streptavidin interaction (Orion-Yhtyma Oy, U.S. Pat. No. 277,643; M. Uhlen et al. Nucleic Acids Res. 16, 3025–38 (1988); Cemu Bioteknik, PCT Application No. WO 89/09282 and Medical Research Council, GB, PCT Application No. WO 92/03575). The primer extension products synthesized on the immobilized template strand are purified of enzymes, other sequencing reagents and by-products by a washing step and then released under denaturing conditions by loosing the hydrogen bonds between the Watson-Crick base pairs and subjected to PAGE separation. In a different approach, the primer extension products (not the template) from a DNA sequencing reaction are bound to a solid support via biotin/avidin (Du Pont De Nemours, PCT Application WO 91/11533). In contrast to the above mentioned methods, here, the interaction between biotin and avidin is overcome by employing denaturing conditions (formamide/EDTA) to release the primer extension products of the sequencing reaction from the solid support for PAGE separation. As solid supports, beads, (e. g., magnetic beads (Dynabeads) and Sepharose beads), filters, capillaries, plastic dipsticks (e.g., polystyrene strips) and microtiter wells are being proposed.

1.2.7 Electrophoresis 1.2.7.1 Drawbacks and Limitations of Polyacrylamide Gel Electrophoresis (PAGE)

All methods discussed so far have one central step in common: polyacrylamide gel electrophoresis (PAGE). In many instances, this represents a major drawback and limitation for each of these methods. Preparing a homogeneous gel by polymerization, loading of the samples, the electrophoresis itself, detection of the sequence pattern (e.g., by autoradiography), removing the gel and cleaning the glass plates to prepare another gel are very laborious and time-consuming procedures.

Moreover, the whole process is error-prone, difficult to automate, and, in order to improve reproducibility and reliability, highly trained and skilled personnel are required.

In the case of radioactive labeling, autoradiography itself can consume from hours to days. In the case of fluorescent labeling, at least the detection of the sequencing bands is being performed automatically when using the laser-scanning devices integrated into commercial available DNA sequencers. One problem related to the fluorescent labeling is the influence of the four different base-specific fluorescent tags on the mobility of the fragments during electrophoresis and a possible overlap in the spectral bandwidth of the four specific dyes reducing the discriminating power between neighboring bands, hence, increasing the probability of sequence ambiguities. Artifacts are also produced by base-specific interactions with the polyacrylamide gel matrix (Frank and Köster, Nucleic Acids Res. —6, 2069 (1979)) and by the formation of secondary structures which result in "band compressions" and hence do not allow one to read the sequence. This problem has, in part, been overcome by using 7-deazadeoxyguanosine triphosphates (Barr et al., Biotechniques 4,428 (1986)). However, the reasons for some artifacts and conspicuous bands are still under investigation and need further improvement of the gel electrophoretic procedure.

1.2.7.2 Capillary Zone Electrophoresis (CZE)

A recent innovation in electrophoresis is capillary zone electrophoresis (CZE) (Jorgenson et al., J. Chromatography 352, 337 (1986); Gesteland et al., Nucleic Acids Res. 18, 1415–1419 (1990)) which, compared to slab gel electrophoresis (PAGE), significantly increases the resolution of the separation, reduces the time for an electrophoretic run and allows the analysis of very small samples. Here, however, other problems arise due to the miniaturization of the whole system such as wall effects and the necessity of highly sensitive on-line detection methods. Compared to PAGE, another drawback is created by the fact that CZE is only a "one-lane" process, whereas in PAGE samples in multiple lanes can be electrophoresed simultaneously.

1.2.7.3 DNA Sequencing without the Electrophoretic Step

Analysis methods have heretofore relied on electrophoretic separation and resolution of the products of Sanger or Maxam and Gilbert reactions according to the length of said products. Analysis thus suffers all of the limitations associated with electrophoresis including limited separation range (i.e. limited dynamic range, where separative resolution is related exponentially to fractional differences in molecular length), limitations on parallelism, time requirements, etc., despite much effort in improving these separative methodologies. With presently available equipment and trained personnel, sequencing the human genome would require about 100 years of total effort if no other sequencing projects were done. While very useful, the present sequencing methods are extremely tedious and expensive, yet require the services of highly skilled scientists. Moreover, these methods utilize hazardous chemicals and radioactive isotopes, which have inhibited their consideration and further development. Large scale sequencing projects, as that of the human genome, thus appear to be impractical using these well-established techniques.

In addition to being slow, the present DNA sequencing techniques involve a large number of cumbersome handling steps which are difficult to automate. Recent improvements include replacing the radioactive labels with fluorescent tags. These developments have improved the speed of the process and have removed some of the tedious manual steps, although present technology continues to employ the relatively slow gel electrophoresis technique for separating the DNA fragments.

Due to the severe limitations and problems related to having PAGE as an integral and central part in the standard DNA sequencing protocol, several methods have been proposed to do DNA sequencing without an electrophoretic step. One approach calls for hybridization or fragmentation sequencing (Bains, Biotechnology 10, 757–58 (1992) and Mirzabekov et al., FEBS Letters 256, 118–122 (1989)) utilizing the specific hybridization of known short oligo-nucleotides (e.g., octadeoxynucleotides which gives 65,536 different sequences) to a complementary DNA sequence. Positive hybridization reveals a short stretch of the unknown sequence. Repeating this process by performing hybridizations with all possible octadeoxynucleotides should theoretically determine the sequence. In a completely different approach, rapid sequencing of DNA is done by unilaterally degrading one single, immobilized DNA fragment by an exonuclease in a moving flow stream and detecting the cleaved nucleotides by their specific fluorescent tag via laser excitation (Jett et al., J. Biomolecular Structure & D3mamics 7, 301–309, (1989), United States Department of Energy, PCT Application No. WO 89/03432). In another system proposed by Hyman Anal. Biochem. 174, 423–436 (1988)), the pyrophosphate generated when the correct nucleotide is attached to the growing chain on a primer-template system is used to determine the DNA sequence. The enzymes used and the DNA are held in place by solid phases (DEAE-Sepharose and Sepharose) either by ionic interactions or by covalent attachment. In a continuous flow—through system, the amount of pyrophosphate is determined via bioluminescence (luciferase). A synthesis approach to DNA sequencing is also used by Tsien et al. (PCT Application No. WO 91/06678). Here, the incoming dNTP's are protected at the T-end by various blocking groups such as acetyl or phosphate groups and are removed before the next elongation step, which makes this process very slow compared to standard sequencing methods.

The template DNA is immobilized on a polymer support. To detect incorporation, a fluorescent or radioactive label is additionally incorporated into the modified dNTP's.

1.2.7.4 Apparatus to Automate DNA Sequencing without Electrophoretic Step(Mass Spectrometry)

PCT Application No. WO 91/06678 also describes an apparatus designed to automate the sequencing process.

Mass Spectrometry is a well known analytical technique which can provide fast and accurate molecular weight information on relatively complex mixtures of organic molecules. Mass spectrometry has historically had neither the sensitivity nor resolution to be useful for analyzing mixtures at high mass. A series of articles in 1988 by Hillenkamp and Karas do suggest that large organic molecules of about 10, 000 to 100,000 Daltons may be analyzed in a time of flight mass spectrometer, although resolution at lower molecular weights is not as sharp as conventional magnetic field mass spectrometry. Moreover, the Hillenkamp and Karas technique is very time-consuming, and requires complex and costly instrumentation.

Mass spectrometry, in general., provides a means of "weighing" individual molecules by ionizing the molecules in vacuo and making them "fly" by volatilization.

Under the influence of combinations of electric and magnetic fields, the ions follow trajectories depending on their individual mass (m) and charge (z). In the range of molecules with low molecular weight, mass spectrometry has long been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collision induced dissociation (CID). The fragmentation pattern/pathway very often allows the derivation of detailed structural information. Many applications of mass spectrometric methods in the known in the art, particularly in biosciences, and can be found summarized in Methods in Enzymology, Vol. 193: "Mass Spectrometry" Q. A. McCloskey, editor), 1990, Academic Press, New York.

Due to the apparent analytical advantages of mass spectrometry in providing high detection sensitivity, accuracy of mass measurements, detailed structural information by CID in conjunction with an MS/MS configuration and speed, as well as on-line data transfer to a computer, there has been considerable interest in the use of mass spectrometry for the structural analysis of nucleic acids. Recent reviews summarizing this field include K. H. Schram, "Mass Spectrometry of Nucleic Acid Components, Biomedical Applications of Mass Spectrometry" 34, 203–287 (1990); and P. F. Crain, "Mass Spectrometric Techniques in Nucleic Acid Research," Mass Spectrometry Reviews 9, 505–554 (1990). The biggest hurdle to applying mass spectrometry to nucleic acids is the difficulty of volatilizing these very polar biopolymers.

1.2.8 Mass Spectrometry 1.2.8.1 Limitation in Applying Mass Spectrometry Due to the Difficulty of Volatilizing Nucleic Acids:

Therefore, "sequencing" has been limited to low molecular weight synthetic oligonucleotides by determining the mass of the parent molecular ion and through this, confirming the already known sequence, or alternatively, confirming the known sequence through the generation of secondary ions (fragment ions) via CID in an MS/MS configuration utilizing, in particular, for the ionization and volatilization, the method of fast atomic bombardment (FAB mass spectrometry) or plasma desorption (PD mass spectrometry). As an example, the application of FAB to the analysis of protected dimeric blocks for chemical synthesis of oligodeoxynucleotides has been described (Koster et al., Bioedical Environmental Mass SpectrometricE 14, 111–116 (1987)).

1.2.8.2 Two More Ionization/desorption Techniques (ES and MALDI)

Two more recent ionization/desorption techniques are electrospray/ionspray (ES) and matrix-assisted laser desorption/ionization (MALDI). ES mass spectrometry has been introduced by Fenn et al. J. Phys. Chem. 18, 4451–59 (1984); PCT Application No. WO 90/14148) and current applications are summarized in recent review articles (R. D. Smith et al., Anal. Chem. 62, 882–89 (1990) and B. Ardrey, Electrospray Mass Spectrometry, Spectroscopy Europe 4, 10–18 (1992)). The molecular weights of the tetradecanucleotide d(CATGCCATGGCATG) (Covey et al. "The Determination of Protein, Oligonucleotide and Peptide Molecular Weights by Ionspray Mass Spectrometry," Rapid Communications in Mass SpectrometJ3~, 2, 249–256 (1988)), of the 21-mer d(AAATTGTGCACATCCTGCAGC) and without giving details of that of a tRNA with 76 nucleotides Methods in Enzymolop-L 1.23, "Mass Spectrometry" (McCloskey, editor), p. 425, 1990, Academic Press, New York) have been published. As a mass analyzer, a quadrupole is most frequently used. The determination of molecular weights in ferntomole amounts of sample is very accurate due to the presence of multiple ion peaks which all could be used for the mass calculation.

MALDI mass spectrometry, in contrast, can be particularly attractive when a time-of-flight (TOF) configuration is used as a mass analyzer. The MALDI-TOF mass spectrometry has been introduced by Hillenkamp et al. ("Matrix Assisted UV-Laser Desorption/Ionization: A New Approach to Mass Spectrometry of Large Biomolecules, Biological Mass Spectrometry (Burlingame and McCloskey, editors), Elsevier Science Publishers, Amsterdam, pp. 49–60, 1990.) Since, in most cases, no multiple molecular ion peaks are produced with this technique, the mass spectra, in principle, look simpler compared to ES mass spectrometry. Although DNA molecules up to a molecular weight of 410,000 daltons could be desorbed and volatilized (Williams et al., "Volatilization of High Molecular Weight DNA by Pulsed Laser Ablation of Frozen Aqueous Solutions," Science, 246, 1585–87 (1989)), this technique has so far only been used to determine the molecular weights of relatively small oligonucleotides of known sequence, e.g., oligothymidylic acids up to 18 nucleotides (Huth-Fehre et al., "Matrix- Assisted Laser Desorption Mass Spectrometry of Oligodeoxythymidylic Acids," Rapid Communications in Mass Spectrometry, 6, 209–13 (1992)) and a double-stranded DNA of 28 base pairs (Williams et al., "Time-of-Flight Mass Spectrometry of Nucleic Acids by Laser Ablation and Ionization from a Frozen Aqueous Matrix," Rapid Communications in Mass Spectrometry, 4, 348–351 (1990)). In one publication (Huth-Fehre et al., 1992, supra), it was shown that a mixture of all the oligothymidylic acids from n=12 to n=18 nucleotides could be resolved.

1.2.8.3 Producing Fragments, Separating by Electrophoresis and Using Matrix Method to Sequence In U.S. Pat. No. 5,064,754, RNA transcripts extended by DNA both of which are complementary to the DNA to be sequenced are prepared by incorporating NTP's, dNTP's and, as terminating nucleotides, ddNTP's which are substituted at the 5'-position of the sugar moiety with one or a combination of the isotopes $^{12}C$, $^{13}C$, $^{14}C$, $^{1}H$, $^{2}H$, $^{3}H$, $^{16}O$, $^{17}O$ and $^{18}O$. The polynucleotides obtained are degraded to 3'-nucleotides, cleaved at the N-glycosidic linkage and the isotopically labeled 5'-functionality removed by periodate oxidation and the resulting formaldehyde species determined by mass spectrometry. A specific combination of isotopes serves to discriminate base-specifically between internal nucleotides originating from the incorporation of NTPs and dNTP's and terminal nucleotides caused by linking ddNTP's to the end of the polynucleotide chain. A series of RNA/DNA fragments is produced, and in one embodiment, separated by electrophoresis, and, with the aid of the so-called matrix method of analysis, the sequence is deduced.

1.2.8.4 Mass Spectrometry Using Atoms Which Normally do not Occur in DNA

In Japanese Patent No. 59-131909, an instrument is described which detects nucleic acid fragments separated either by electrophoresis, liquid chromatography or high speed gel filtration. Mass spectrometric detection is achieved by incorporating into the nucleic acids atoms which normally do not occur in DNA such as S, Br, I or Ag, Au, Pt, Os, Hg. The method, however, is not applied to sequencing of DNA using the Sanger method. In particular, it does not propose a base-specific correlation of such elements to an individual ddNTP.

1.2.8.5 Sequencing with the Sanger Method by Using Four Stable Isotopes to Label the ddNTP's PCT Application No. WO 89/12694 (Brennan et al., Proc. SPIE-Int. Soc. Opt. Eng. 1206, (New Technol. Cytom. Mot. Biol.), pp. 60–77 (1990); and Brennan, U.S. Pat. No. 5,003, 059) employs the Sanger methodology for DNA sequencing by using a combination of either the four stable isotopes $^{32}S$, $^{33}S$, $^{34}S$, $^{36}S$ or $^{35}Cl$, $^{37}Cl$, $^{79}Br$, $^{81}Br$ to specifically label the chain-terminating ddNTP's. The sulfur isotopes can be located either in the base or at the alpha-position of the triphosphate moiety whereas the halogen isotopes are located either at the base or at the 3'-position of the sugar ring.

The sequencing reaction mixtures are separated by an electrophoretic technique such as CZE, transferred to a combustion unit in which the sulfur isotopes of the incorporated ddNTP's are transformed at about 900° C. in an oxygen atmosphere. The $SO_2$ generate with masses of 64, 65, 66 or 68 is determined on-line by mass spectrometry using, e.g., mass analyzer, a quadrupole with a single ion-multiplier to detect the ion current.

1.2.8.6 Using Resonance Ionization Spectroscopy in Conjunction with a Magnetic Sector Mass Analyzer A similar approach is proposed in U.S. Pat. No. 5,002,868 (Jacobson e al., Proc. SPIE-Int. Soc. Opt. Eng. 1435, 9pt. Methods Ultrasensitive Detect. Anal. Tech. 26–35 (1991)) using Sanger sequencing with four ddNTP's specifically substituted at the alpha-position of the triphosphate moiety with one of the four stable sulfur isotopes as described above and subsequent separation of the four sets of nested sequences by tube gel electrophoresis. The only difference is the use of resonance ionization spectroscopy (RIS) in conjunction with a magnetic sector mass analyzer as disclosed in U.S. Pat. No. 4,442,354 to detect the sulfur isotopes corresponding to th specific nucleotide terminators, and by this, allowing the assignment of the DNA sequence.

1.2.8.7 Using Tube Gel Electrophoresis, a Nebulizer and a Mass Analyzer to Sequence EPO Patent Applications No. 0360676 A1 and 0360677 A1 also describe Sanger sequencing using stable isotope substitutions in the ddNTP's such as D, $^{13}C$, $^{15}N$, $^{17}O$, $^{18}O$, $^{32}S$, $^{33}S$, $^{34}S$, $^{36}S$, $^{19}F$, $^{35}Cl$, $^{37}Cl$, $^{79}Br$, $^{81}Br$ and $^{127}I$ or function groups such as $CF_3$ or $Si(CH_3)_3$ at the base, the sugar or the alpha position of the triphosphate moiety according to chemical functionality. The Sanger sequencing reaction mixtures are separated by tube gel electrophoresis. The effluent is converted into an aerosol by the electrospray/thermospray nebulizer method and then atomized and ionize by a hot plasma (7000 to 8000° K.) and analyzed by a simple mass analyzer. An instrument is proposed which enables one to automate the analysis of the Sanger sequencing reaction mixture consisting of tube electrophoresis, a nebulizer and a mass analyzer.

The application of mass spectrometry to perform DNA sequencing by the hybridization/fragment method (see above) has been recently suggested (Bains, "DNA Sequencing by Mass Spectrometry: Outline of a Potential Future Application, Chimicaoiggi 2, 13–16 (1991)).

1.2.9 Probes 1.2.9.1 Using Large Arrays of Nucleic Acid Probes on a Substrate

Alternative techniques have been proposed for sequencing a nucleic acid. PCT patent Publication No. 92/10588, incorporated herein by reference for all purposes, describes one improved technique in which the sequence of a labeled, target nucleic acid is determined by hybridization to an array of nucleic acid probes on a substrate. Each probe is located at a positionally distinguishable location on the substrate. When the labeled target is exposed to the substrate, it binds at locations that contain complementary nucleotide sequences. Through knowledge of the sequence of the probes at the binding locations, one can determine the nucleotide sequence of the target nucleic acid. The technique is particularly efficient when very large arrays of nuleic acid probes are utilized.

Such arrays can be formed according to the techniques described in U.S. Pat. No. 5,143,854 issued to Pirrung et al. See also U.S. application Ser. No. 07/805,727, both incorporated herein by reference for all purposes.

1.2.9.2 Employing Sequencing by Hybridization When the Probes are Shorter than the Target When the nucleic acid probes are of a length shorter than the target, one can employ a reconstruction technique to determine the sequence of the larger target based on affinity data from the shorter probes. See U.S. Pat. No. 5,202,231 to Drmanac-et al., and PCT patent Publication No. 89/10977 to Southern. One technique for overcoming this difficulty has been termed sequencing by hybridization or SBH. For example, assume that a 12-mer target DNA 5'-AGCCTAGCTGAA is mixed with an array of all octanucleotide probes. If the target binds only to those probes having an exactly complementary nucleotide sequence, only five of the 65,536 octamer probes (3'-TCGGATCG, CGGATCGA, GGATCGAC, GATCGACT, and ATCGACTT) will hybridize to the target. Alignment of the overlapping sequences from the hybridizing probes reconstructs the complement of the original 12-mer target:

TCGGATCG
  CGGATCGA
    GGATCGAC
      GATCGACT
        ATCGACTT
TCGGATCGACTT

While meeting with much optimism, prior techniques have also met with certain limitations. For example, practitioners have 45 encountered substantial difficulty in analyzing probe arrays hybridized to a target nucleic acid due to the hybridization of partially mismatched sequences, among other difficulties. The present invention provides significant advances in sequencing with such arrays.

1.2.10 DNA Amplification

DNA can be amplified by a variety of procedures including cloning (Sambrook et at., Molecular Cloning: A Laboratory Manual., Cold Spring Harbor Laboratory Press, 1989), polymerase chain reaction (PCR) (C. R. Newton and A. Graham, PCF, BIOS Publishers, 1994), ligase chain reaction (LCR) (F. Barany Proc. Natl. Acad Sci USA 88, 189–93 (1991), strand displacement amplification (SDA) (G. Terrance Walker et al., Nucleic Acids Res. 22, 2670–77 (1994)) and variations such as RT-PCR, allele-specific amplification (ASA) etc.

The polymerase chain reaction (Mullis, K. et al., Methods Enzymol., 155:335–350 1987) permits the selective in vitro amplification of a particular DNA region by mimicking the phenomena of in vivo DNA replication. Required reaction components are single stranded DNA, primers (oligonucleotide sequences complementary to the 5'and 3' ends of a defined sequence of the DNA template), deoxynucleotidetriphosphates and a DNA polymerase enzyme. Typically, the single stranded DNA is generated by heat denaturation of provided double strand DNA. The reaction buffers contain magnesium ions and co-solvents for optimum enzyme stability and activity.

The amplification results from a repetition of such cycles in the following manner: The two different primers, which bind selectively each to one of the complementary strands, are extended in the first cycle of amplification. Each newly synthesized DNA then contains a binding site for the other primer. Therefore each new DNA strand becomes a template for any further cycle of amplification enlarging the template pool from cycle to cycle. Repeated cycles theoretically lead to exponential synthesis of a DNA-fragment with a length defined by the 5' termini of the primer.

The PCR amplification procedure has been used to sequence the DNA being amplified (e.g. "Introduction to the AmpliTaq Cycle Sequencing Kit Protocol", a booklet from Perkin Elmer Cetus Corporation). The DNA could be first amplified and then it could be sequenced using the two conventional DNA sequencing techniques. Modified methods for sequencing PCR-amplified DNA have also been developed (e.g. Bevan et al., "Sequencing of PCR-Amplified DNA" PCR Meth. App. 4:222 (1992)).

1.2.11 Additional Sequencing Methods 1.2.11.1 Sanger Sequencing Using the Degradation of Phosphorothioate-containing DNA Fragments A recent modification of the Sanger sequencing strategy involves the degradation of phosphorothioate-containing DNA fragments obtained by using alpha-thio dNTP instead of the normally used ddNTPs during the primer extension reaction mediated by DNA polymerase (Labeit et al., MA 5, 173–177 (1986); Amersham, PCT- Application GB86/00349; Eckstein et al., Nucleic Acids Res. 1~, 9947 (1988)). Here, the four sets of base-specific sequencing ladders are obtained by limited digestion with exonuclease III or snake venom phosphodiesterase, subsequent separation on PAGE and visualization by radioisotopic labeling of either the primer or one of the dNTPs. In a further modification, the base-specific cleavage is achieved by alkylating the sulphur atom in the modified phosphodiester bond followed by a heat treatment (Max- Planck- Geselischaft, DE 3930312 A1). Both methods can be combined with the amplification of the DNA via the Polymerase Chain Reaction (PCR).

1.2.11.2 Sanger Sequencing Using Modified Polymerization Reation (at High Temperature)

Initial PCR experiments used thermolabile DNA polymerase. However, thermolabile DNA polymerase must be continually added to the reaction mixture after each denaturation cycle. Major advances in PCR practice were the development of a polymerase, which is stable at the near-boiling temperature (Saiki, R. et al., Science 239:487–491 1998) and the development of automated thermal cyclers.

The discovery of thermostable polymerases also allowed modification of the Sanger sequencing reaction with significant advantages. The polymerization reaction could be carried out at high temperature with the use of thermostable DNA polymerase in a cyclic manner (cycle sequencing). The conditions of the cycles are similar to those of the PCR technique and comprise denaturation, annealing, and extension steps. Depending on the length of the primers only one annealing step at the beginning of the reaction may be sufficient. Carrying out a sequencing reaction at high temperature in a cyclic manner provides the advantage that each DNA strand can serve as template in every new cycle of extension which reduces the amount of DNA necessary for sequencing, thereby providing access to minimal volumes of DNA, as well as resulting in improved specificity of primer hybridization at higher temperature and the reduction of secondary structures of the template strand.

1.2.11.3 Semi-exponential Cycle Sequencing Using a Second Reverse Primer in the Sequencing Reaction However, amplification of the terminated fragments is linear in conventional cycle sequencing approaches. A recently developed method, called semi-exponential cycle sequencing shortens the time required and increases the extent of amplification obtained from conventional cycle sequencing by using a second reverse primer in the sequencing reaction. However, the reverse primer only generates additional template strands if it avoids being terminated prior to reaching the sequencing primer binding site. Needless to say, terminated fragments generated by the reverse primer can not serve as a sufficient template. Therefore, in practice, amplification by the semi-exponential approach is not entirely exponential. (Sarkat, G. and Bolander Mark E., Semi Exponential Cycle Sequencing Nucleic Acids Research, 1995, Vol. 23, No. 7, p. 1269–1270).

1.2.11.4 Need to Facilitate Highthroughput Sequencing

In addition to the foregoing limitations inherent in current sequencing techniques, the generation of DNA substrate molecules for each 300 to 500 nucleotides to be sequenced is presently required. Assuming no overlapping sequence between substrate molecules, the sequencing of both strands of an entire mammalian genome would, therefore, require the generation of at least 20 million DNA substrate molecules.

As pointed out above, current nucleic acid sequencing methods require relatively large amounts (typically about 1 g) of highly purified DNA template. Often, however, only a small amount of template DNA is available. Although amplifications may be performed, amplification procedures are typically time consuming, can be limited in the amount of amplified template produced and the amplified DNA must be purified prior to sequencing. A streamlined process for amplifying and sequencing DNA is needed, particularly to facilitate highthroughput nucleic acid sequencing.

1.2.12 Strategies for Obtaining the Initial Sequence

Methods currently used to sequence large segments of DNA do not lend themselves to large-scale determination of genomic sequences. In general., the initial determination of a genomic clone sequence results in ambiguities and discrepancies that are resolved by assembling and editing the raw sequencing data into a consensus sequence. There are also, generally, holes in the sequence that need to be filled in in order to create a finished sequence. There are two general strategies for obtaining the initial sequence: shotgun sequencing and transposon-mediated directed sequencing.

1.2.12.1 Shotgun Sequencing

In the currently existing methods for sequencing very long DNA of millions of nucleotides, the DNA is fragmented into smaller, overlapping fragments, and sub-cloned to produce numerous clones containing overlapping DNA sequences. These clones are sequenced randomly and the sequences assembled by "overlap sequence-matching" to produce the contiguous sequence. In this shot-gun sequencing method, approx. ten times more sequencing than the length of the DNA being sequenced is required to assemble the contiguous sequence. Shotgun sequencing is reasonably appropriate for generating the initial sequences of the genomic clone. In this method, the clone is digested with a multiplicity of restriction enzymes and the individual fragments are sequenced. When sufficient sequence is obtained to putatively cover the length of the genomic clone (1×total sequence length) statistically 65% of the genomic clone sequence will have successfully been determined. The shotgun strategy relies on assembly algorithms to piece together a final sequence by determining relationships between a selected set of random templates. Although this assembly process is semiautomated, it remains labor-intensive, especially in complex regions that contain highly related tandem repeats. In addition, since the selection of subclones is not random, gaps of unknown distance are included between islands of known sequence. Linking up the islands requires either sequencing additional subclones or ordering custom oligonucleotides to generate sequence into the gaps. The weaknesses of shotgun sequencing performed on substantial lengths of nucleotide sequence are thus 1) the difficulties involved in sequence assembly and 2) the need for hole-filling.

A non-ordered approach to sequencing, e.g., shotgun sequencing, would require the generation of 100 to 200 million DNA templates. Although there has been effort directed to automating the steps presently involved in DNA substrate generation, e.g., restriction mapping, preparation of subfragments for subcloning, identification of subclones, growing bacterial cultures, and purifying nucleic acids, it is unlikely that human intervention can be substantially eliminated from the process. Current approaches, therefore, are less than optimal for the large scale sequencing of DNA, particularly sequencing the human genome.

Although the problems enumerated above are not intended to be exhaustive, the limitations inherent in methods presently available for sequencing DNA are readily apparent. Accordingly, there exists a need for an improved method of sequencing DNA that circumvents the need for primer binding sites as well as the need to determine restriction maps. Additionally, there exists a need for an improved method which extends the amount of sequence information obtainable from a DNA substrate, thus substantially reducing the number of DNA substrate molecules required to sequence a given region of DNA. The present invention meets these needs.

1.2.12.2 Transposon-mediated Directed Sequencing

On the other hand, the transposon-mediated sequencing method described by Strathmann, M. et al. Proc Natl Acad Sci USA (1991) 88:1247–1250, provides an orderly approach to generating subclones for sequencing. The method uses a .gamma..delta. bacterial transposable element bracketed by sequencing primers. The primer-flanked transposon permits the introduction of evenly spaced priming sites across a fragment with an unknown DNA sequence. The number of template sequences required to obtain the complete sequence information can be calculated from the length of the fragment. In the "directed" sequencing method, the linear order of the DNA clones has to be first determined by "physical mapping" of the clones. As the transposon insertions are random, the positions of the insertions are mapped, for example, using the polymerase chain reaction (PCR) using primers that amplify the intervening sequence between the transposon insertion site and the vector sequences at each end of the inserted fragment to be sequenced. The lengths of the amplified products thus define a map position for the transposon. Sequencing can be conducted based on the sequencing primers flanking the transposon, and since the position of the transposon has been mapped prior to sequencing, a fully automated assembly process is possible. There are no gaps since an ordered set of sequencing templates which cover the DNA fragment is produced.

1.2.12.3 Drawbacks of These Two Strategies, "Primer-walking" Method

However, transposon sequencing can only be used on fragments containing 2–5 kb; preferably 3–4 kb. Thus, to use the transposon method on larger fragments, smaller subclones of the original fragment must be generated and organized into an ordered overlapping set. The shotgun strategy is not completely appropriate for this purpose. Neither is an alternative strategy termed dog-tagging. Dog-tagging is a "walking" process, a contiguous DNA sequencing method called the "primer-walking" method using the Sanger's DNA polymerase enzymatic sequencing procedure, that scans through a 30-hit subclone library for sequences that are near the end of the last walking step. It is labor-intensive and does not always succeed. In this method, the DNA copying has to occur always from the template DNA during DNA sequencing. In contrast, in the PCR procedure, the target DNA amplified in the first rounds from the original input template DNA will function as the template DNA in subsequent cycles of amplification. After a certain cycles of amplification, the DNA sequencing reaction will be started by adding the sequencing "cocktail". Thus in the PCR reaction, only one copy of template DNA is theoretically sufficient to amplify into millions of copies, and therefore a very little genomic (or template) DNA is sufficient for sequencing. The advantage of DNA amplification that exists in PCR is lacking in the conventional Sanger procedure. Thus, this primer-walking method will require a larger amount of template DNA compared to the PCR sequencing method. Also, because the long DNA has a tendency to re-anneal back to duplex DNA, the sequencing gel pattern may not be as clean as in a PCR procedure, when a very long DNA is being sequenced. This may limit the length of the DNA, that could be contiguously sequenced without breaking the DNA, using the primer-walking procedure. The PCR method also enables the reduction of non-specific binding of the primers to the template DNA because the enzymes used in these protocols function at high-temperatures, and thus allow "stringent" reaction conditions to be used to improve sequencing.

The present method of contiguous DNA sequencing using the basic PCR technique has thus many advantages over the primer walking method. Also, so far no method exists for contiguously sequencing a very long DNA using PCR technique. The present invention thus offers a unique and very advantageous procedure for contiguous DNA sequencing.

1.2.12.4 Amplification and Equencing a Long Genomic DNA without Subcloning into Smaller Fragments In one embodiment, the present invention provides a method for contiguous sequencing of very long DNA using a modification of the standard PCR technique without the need for breaking down and subcloning the long DNA.

The PCR technique enables the amplification of DNA which lies between two regions of known sequence (K. B. Mullis et al., U.S. Pat. Nos. 4,683,202; 7/1987; 435/91; and 4,683,195, 7/1987; 435/6). Oligonucleotides complementary to these known sequences at both ends serve as "primers" in the PCR procedure. Double stranded target DNA is first melted to separate the DNA strands, and then oligonucleotide (oligo) primers complementary to the ends of the segment which is desired to be amplified are annealed to the template DNA. The oligos serve as primers for the synthesis of new complementary DNA strands, using a DNA polymerase enzyme and a process known as primer extension. The orientation of the primers with respect to one another is such that the 5' to 3' extension product from each primer contains, when extended far enough, the sequence which is complementary to the other oligo. Thus, each newly synthesized DNA strand becomes a template for synthesis of another DNA strand beginning with the other oligo as primer. Repeated cycles of melting, annealing of oligo primers, and primer extension lead to a (near) doubling, with each cycle, of DNA strands containing the sequence of the template beginning with the sequence of one oligo and ending with the sequence of the other oligo.

The key requirement for this exponential increase of template DNA is the two oligo primers complementary to the ends of the sequence desired to be amplified, and oriented such that their 3' extension products proceed toward each other. If the sequence at both ends of the segment to be amplified is not known, complementary oligos cannot be made and standard PCR cannot be performed. The object of the present invention is to overcome the need for sequence information at both ends of the segment to be amplified, i.e. to provide a method which allows PCR to be performed when sequence is known for only a single region, and to provide a method for the contiguous sequencing of a very long DNA without the need for subcloning of the DNA.

Amplifying and sequencing using the PCR procedure requires that the sequences at the ends of the DNA (the two primer sequences) be known in advance. Thus, this procedure is limited in utility, and cannot be extended to contiguously sequence a long DNA strand. If the knowledge of only one primer is sufficient without anything known about the other primer, it would be greatly advantageous for sequencing very long DNA molecules using the PCR procedure. It would then be possible to use such a method for contiguously sequencing a long genomic DNA without the need for subcloning it into smaller fragments, and knowing only the very first, beginning primer in the whole long DNA.

1.2.12.5 Large-scale Sequencing Throught the Generation of a Subclone Path

In another embodiment, the present invention provides a large-scale sequencing method which combines efficient method to generate a subclone path through the large original fragment, such as a genomic clone, wherein the subclones are accessible to transposon sequencing, in combination with sequencing these subclones using the transposon method.

1.2.13 Constructing Ordered Clone Maps of DNA Sequences

A primary goal of the human genome project is to determine the entire DNA sequence for the genomes of human, model, and other useful organisms. A related goal is to construct ordered clone maps of DNA sequences at 100 kilobase (kb) resolution for these organisms (D. R. Cox, E. D. Green, E. S. Lander, D. Cohen, and R. M. Myers, "Assessing mapping progress in the Human Genome Project," Science, vol. 265, no. 5181, pp. 2031–2, 1994), incorporated by reference. Integrated maps that localize clones together with polymorphic genetic markers (J. Weber and P. May, "Abundant class of human DNA polymorphisms which can be typed using the polymerase chain reaction," Am. J. Hum. Genet., vol. 44, pp. 388–396, 1989), incorporated by reference, are particularly useful for positionally cloning human disease genes (F. Collins, "Positional cloning: lets not call it reverse anymore," Nature Genet., vol. 1, no. 1, pp. 3–6, 1992), incorporated by reference. The greatest need, however, is for sequence-ready maps. Also useful are maps of expressed sequences. Mapping techniques include restriction enzyme analysis of genetic material, and the hybridization and detection of specific oligonucleotides which test for the presence or absence of particular alleles or loci, and may further be used to gain spatial information about the occurrence of their targets when appropriate analytic techniques are subsequently applied. Note that such characterizations presently are methodologically and operationally distinct from other processes comprehended within the biotechnological and related arts. Human DNA sequences now exist as genomic libraries in a variety of small- and large-insert capacity cloning vectors, with yeast artificial chromosomes (YACs) (D. T. Burke, G. F. Carle, and M. V. Olson, "Cloning of large exogenous DNA into yeast by means of artificial chromosomes," Science, vol. 236, pp. 806–812, 1987), incorporated by reference, used extensively in mapping large regions. Efficient strategies for performing the requisite experimentation are critical for sequencing and mapping chromosomes or entire genomes.

1.2.13.1 Sequence-tagged Site

The starting point for an effective sequencing method is a complete ordered clone map of a genome. Current strategies for ordering clones build contiguous sequences (contigs) using short-range comparison data. Sequence-tagged site (STS) (M. Olson, L. Hood, C. Cantor, and D. Botstein, "A common language for physical mapping of the human genome," Science, vol. 245, pp. 1434–35, 1989), incorporated by reference, comparisons with clones are used in STS-content mapping (SCM) (E. D. Green and P. Green, "Sequence-tagged site (STS) content mapping of human chromosomes: theoretical considerations and early experiences," PCR Methods and Applications, vol. 1, pp. 77–90, 1991), incorporated by reference. For chromosomal or genome-wide SCM, very large YACs (megaYACs) are required for the currently available STS densities (R. Arratia, E. S. Lander, S. Tavare, and M. S. Waterman, "Genomic mapping by anchoring random clones: a mathematical analysis," Genomics, vol. 11, pp. 806–827, 1991; W. J. Ewens, C. J. Bell, P. J. Donnelly, P. Dunn, E. Matallana, and J. R. Ecker, "Genome mapping with anchored clones: theoretical aspects," Genomics, vol. 11, pp. 799–805, 1991), incorporated by reference; these large YACs are often chimeric or contain gaps. Restriction fragment fingerprint mapping has been done with hybridization (C. Bellanne-Chantelot, B. Lacroix, P. Ougen, A. Billault, S. Beaufils, S. Bertrand, S. Georges, F. Gliberr, I. Gros, G. Lucotte, L. Susini, J.-J. Codani, P. Gesnouin, S. Pook, G. Vaysseix, J. Lu-Kuo, T. Ried, D. Ward, I. Chumakov, D. Le Paslier, E. Barillot, and D. Cohen, "Mapping the whole genome by fingerprinting yeast artificial chromosomes," Cell, vol. 70, pp. 1059–1068, 1992; R. L. Stallings, D. C. Torney, C. E. Hildebrand, J. L. Longmire, L. L. Deaven, J. H. Jett, N. A. Doggert, and R. K. Moyzis, "Physical mapping of human chromosomes by repetitive sequence hybridization," Proc. Natl. Acad. Sci. USA, vol. 87, pp. 6218–6222, 1990), incorporated by reference, or without hybridization (A. Coulson, J. Sulston, S. Brenner, and J. Karn, "Toward a physical map of the genome of the nematode Caenorhaboditis elegans," Proc. Natl. Acad. Sci. USA, vol. 83, pp. 7821–7825, 1986), incorporated by reference. With hybridization fingerprinting, path analysis of YAC fingerprints is not always reliable when constructing contigs. Hybridizing an internal clone sequence (e.g., end-clone sequence, Alu-PCR probes) against a library to determine neighboring sequences builds unpositioned YAC contigs (M. T. Ross and V. P. J. Stanton, "Screening large-insert libraries by hybridization," in Current Protocols in Human Genetics, vol. 1, N. J. Dracopoli, J. L. Haines, B. R. Korf, C. C. Morton, C. E. Seidman, J. G. Seidman, D. T. Moir, and D. Smith, ed. New York: John Wiley and Sons, 1995, pp. 5.6.1–5.6.34), incorporated by reference, although walking techniques are generally reserved for closing gaps.

1.2.13.2 Gridding Library onto Nylon Filters, and Hybridizing with Probes to Reduce Cost, Increase Throughput The number of experiments needed for these short-range clone mapping approaches increases with the number of clones in the library. While considerable efficiency is gained by using multiplexed experiments with pooled reagents (G. A. Evans and K. A. Lewis, "Physical mapping of complex genomes by cosmid multiplex analysis," Proc. Natl. Acad. Sci. USA, vol. 86, no. 13, pp. 5030–4, 1989; E. D. Green and M. V. Olson, "Systematic screening of yeast artificial-chromosome libraries by use of the polymerase chain reaction," Proc. Natl. Acad. Sci. USA, vol. 87, no. 3, pp. 1213–7, 1990), incorporated by reference, the experimental requirements are at least proportional to the number of clones. A useful goal is to significantly reduce cost and increase throughput by achieving a number of required experiments largely independent of library size. One step toward this independence has been achieved by gridding an entire library onto nylon filters, and then hybridizing these filters with a set of probes (H. Lehrach, A. Drmanac, J. Hoheisel, Z. Larin, G. Lennon, A. P. Monaco, D. Nizetic, G. Zehetner, and A. Poustka, "Hybridization fingerprinting in genome mapping and sequencing," in Genetic and Physical Mapping I: Genome Analysis, K. E. Davies and S. M. Tilghman, ed. Cold Spring Harbor, N.Y.: Cold Spring Harbor Laboratory, 1990, pp. 39–81; A. P. Monaco, V. M. S. Lam, G. Zehetner, G. G. Lennon, C. Douglas, D. Nizetic, P. N. Goodfellow, and H. Lehrach, "Mapping irradiation hybrids to cosmid and yeast artificial chromosome libraries by direct hybridization of Alu-PCR products," Nucleic Acids Res., vol. 19, no. 12, pp. 3315–3318, 1991), incorporated by reference. For example, contigs of small genomic regions have been constructed by oligonucleotide fingerprinting of gridded cosmid filters (A. G. Craig, D. Nizetic, J. D. Hoheisel, G. Zehetner, and H. Lehrach, "Ordering of cosmid clones covering the herpes simplex virus type I," Nucleic Acids Res., vol. 18, no. 9, pp. 2653–60, 1990; A. J. Cuticchia, J. Arnold, and W. E. Timberlake, "ODS: ordering DNA sequences, a physical mapping algorithm based on simulated annealing," CABIOS, vol. 9, no. 2, pp. 215–219, 1992), incorporated by reference.

1.2.13.3 Radiation Hybrid Mapping

To efficiently span larger genomic regions, radiation hybrid (RH) mapping (D. R. Cox, M. Burmeister, E. R. Price, S. Kim, and R. M. Myers, "Radiation hybrid mapping: a somatic cell genetic method for constructing high-resolution maps of mammalian chromosomes," Science, vol. 250, pp. 245–250, 1990), incorporated by reference, has been used to localize small DNA sequences (though not clones) into high-resolution bins. Relatively few PCR experiments with one 96-well plate library of RHs generally suffice for mapping STSs or genes to unique bins having 250 kb to 1 Mb average resolution. The very large multiple fragments in each RH clone efficiently cover much of a chromosome (or genome). Assaying a sequence for intersection against a set of RHs provides long-range relational information for localization much akin to somatic cell hybrid (SCH) mapping (M. C. Weiss and H. Green, "Human-mouse hybrid cell lines containing partial complements of human chromosomes and functioning human genes," Proc. Natl. Acad. Sci. USA, vol. 58, pp. 104–1111, 1976), incorporated by reference. However, RH mapping offers much greater resolution than SCH or fluorescent in situ hybridization (FISH) mapping.

1.2.13.4 Combining RH Mapping with Filter Hybridization Techniques

For highly optimized experimentation, it would be desirable to combine high-resolution long-range RH mapping with low-cost high-throughput filter hybridization techniques to map clones. One can serially probe a gridded clone library with a set of RHs (H. Lehrach, A. Drmanac, J. Hoheisel, Z. Larin, G. Lennon, A. P. Monaco, D. Nizetic, G. Zehetner, and A. Poustka, "Hybridization fingerprinting in genome mapping and sequencing," in Genetic and Physical Mapping I: Genome Analysis, K. E. Davies and S. M. Tilghman, ed. Cold Spring Harbor, N.Y.: Cold Spring Harbor Laboratory, 1990, pp. 39–81), in principle requiring a number of experiments that is independent of the clone library size and logarithmically related to the desired map resolution. However, complex hybridization probes such as RHs (or their Alu-PCR products) generate data containing considerable noise. This inherent uncertainty, together with the large clone insert size (which complicates conventional RH analysis), has thus far precluded high-resolution mapping of clones using RHs (J. Kumlien, T. Labella, G. Zehetner, R. Vatcheva, D. Nizetic, and H. Lehrach, "Efficient identification and regional positioning of YAC and cosmid clones to human chromosome 21 by radiation fusion hybrids," Mammalian Genome, vol. 5, no. 6, pp. 365–71, 1994), incorporated by reference.

1.2.13.5 Inner Product Mapping

Inner product mapping (IPM) is a hybridization-based method for achieving high-throughput, high-resolution RH mapping of clones (M. W. Perlin and A. Chakravarti, "Efficient construction of high-resolution physical maps from yeast artificial chromosomes using radiation hybrids: inner product mapping," Genomics, vol. 18, pp. 283–289, 1993), incorporated by reference, that overcomes this barrier. Experimental data have established that IPM is a highly rapid, inexpensive, accurate, and precise large-scale long-range mapping method, particularly when preexisting RH maps are available, and that IPM can replace or complement more conventional short-range mapping methods.

1.2.13.6 Obtaining Improved Mapping Results

Improved mapping results can be obtained incrementally by gradually enlarging the data tables, a process which provides useful feedback to both experimentation and analysis. With additional RHs, the signal-to-noise characteristics of the clone profiles improve. This incremental process, and the relatively few RHs required for accurate mapping, follows the logarithmic number of the probes needed for IPM. For best mapping results, as many STS-typed RHs as feasible are used: with currently available high-throughput, robotically-assisted hybridization methods, the localization benefits of performing many filter hybridizations outweigh the relatively low experimentation costs. The incremental construction also highlights IPM's indirect inference of map location: STS-content mapping directly compares clones with STSs, and can not map small-insert clones against STSs which are insufficiently dense .

1.2.13.7 Building Accurate Maps and Partitioning Data Noise

IPM builds accurate maps from low-confidence data. IPM's partitioning of the experiments into two data tables of (A) clones vs. RHs and (B) RHs vs. STSs also partitions the data noise. Table B is formed from relatively noiseless PCR-based comparisons of STSs against RH DNA, and can thus accurately order and position the STS bins using combinatorial mapping procedures (M. Boehnke, "Radiation hybrid mapping by minimization of the number of obligate chromosome breaks," Genetic Analysis Workshop 7: Issues in Gene Mapping and the Detection of Major Genes. Cytogenet Cell Genet, vol. 59, pp. 96–98, 1992; M. Boehnke, K. Lange, and D. R. Cox, "Statistical methods for multipoint radiation hybrid mapping," Am. J. Hum. Genet., vol. 49, pp. 1174–1188, 1991), incorporated by reference. Table A is formed from inherently unreliable and inconsistently replicated hybridizations of complex RH probes against gridded filters. Inner product mapping uses the table B data matrix to ameliorate these data errors and robustly translate a clones's noisy RH signature vector (a row of table A) into a chromosomal profile, whose peak bins the clone.

1.2.13.8 Mapping YAC's Using IPM

IPM is a proven approach for mapping YACs (C. W. Richard III, D. J. Duggan, K. Davis, J. E. Farr, M. J. Higgins, S. Qin, L. Zhang, T. B. Shows, M. R. James, and M. W. Perlin, "Rapid construction of physical maps using inner product mapping: YAC coverage of chromosome 11," in Fourth International Conference on Human Chromosome 11, September 22–24, Oxford, England, 1994), incorporated by reference, and is a candidate method for mapping PACs (P. A. Ioannou, C. T. Amemiya, J. Games, P. M. Kroisel, H. Shizuya, C. Chen, M. A. Batzer, and P. J. de Jong, "A new bacterophage P1-derived vector for the propagation of large human DNA fragments," Nature Genet., vol. 6, no. 1, pp. 84–89, 1994), incorporated by reference, cosmids, expressed sequences (M. D. Adams, J. M. Kelley, J. D. Gocayne, M. Dubnick, M. H. Polymeropoulos, H. Xiao, C. R. Merril, A. Wu, B. Olde, R. F. Moreno, A. R. Kerlavage, W. R. McCombie, and J. C. Venter, "Complementary DNA sequencing: Expressed sequence tags and human genome project," Science, vol. 252, pp. 1651–1656, 1991), incorporated by reference, and other physical reagents (J. D. McPherson, C. Wagner-McPherson, M. Perlin, and J. J. Wasmuth, "A physical map of human chromosome 5 (Abstract)," Amer. J. Hum. Genet., vol. 55, no. 3 Supplement, pp. A265, 1994), incorporated by reference. Hybridization efficiency for table A can be improved by using long and IRE-bubble PCR (D. J. Munroe, M. Haas, E. Bric, T. Wiirton, H. Aburatani, K. Hunter, D. Ward, and D. E. Housman, "IRE-bubble PCR: a rapid method for efficient and representative amplification of human genomic DNA sequences from complex sources," Genomics, vol. 19, no. 3, pp. 506–14, 1994), incorporated by reference, to reduce false negative errors, providing controls and redundant DNA spotting for internal calibration, and directly acquiring signals (e.g., via a phosphorimager, Molecular Dynamics, Sunnyvale, Calif.) to facilitate automated scoring. Current robotic technologies enable the high-throughput construction of gridded filters (A. Copeland and G. Lennon, "Rapid arrayed filter production using the 'ORCA' robot," Nature, vol. 369, no. 6479, pp. 421–422, 1994), incorporated by reference; single use of these filters would reduce the time and error related to stripping and reprobing. Robots similarly provide high-throughput PCR comparisons for constructing table B. Alternatively, existing RH mapping data can be rapidly extended (at low cost) into inner product maps of libraries (U. Francke, E. Chang, K. Comeau, E.-M. Geigl, J. Giacalone, X. Li, J. Luna, A. Moon, S. Welch, and P. Wilgenbus, "A radiation hybrid map of human chromosome 18," Cytogenet. Cell Genet., vol. 66, pp. 196–213, 1994), incorporated by reference.

1.2.13.9 Whole Genome RH Libraries

Whole human genome RH (WG-RH) libraries of 0.5 and 1.0 Mb resolution have been constructed (D. R. Cox, K. O'Connor, S. Hebert, M. Harris, R. Lee, B. Stewart, G. DiSibio, M. Boehnke, K. Lange, R. Goold, and R. M. Myers, "Construction and analysis of a panel of 'whole genome' radiation hybrids (Abstract)," Amer. J. Hum. Genet., vol. 55, no. 3 Supplement, pp. A23, 1994; M. A. Walter, D. J. Spilleir, P. Thomas, J. Weissenbach, and P. N. Goodfellow, "A method for constructing radiation hybrid maps of whole genomes," Nature Genet., vol. 7, no. 1, pp. 22–28, 1994), incorporated by reference, and have been characterized for the STSs used in the genome-wide CEPH megaYAC STS-content map (T. Hudson, S. Foote, S. Gerety, J. Ma, S.-h. Xu, X. Hu, J. Bae, J. Silva, J. Valle, S. Maitra, A. Colbert, L. Horton, M. Anderson, M. P. Reeve, M. Daly, A. Kaufman, C. Rosenberg, L. Stein, N. Goodman, J. Orlin, D. C. Page, and E. S. Lander, "Towards an STS-content map of the human genome (Abstract)," Amer. J. Hum. Genet., vol. 55, no. 3 Supplement, pp. A23, 1994), incorporated by reference. The availability of this WG-RH table B resource suggests that constructing table A by performing hybridizations between species specific (e.g., Alu-PCR) products of these RHs and gridded clones or expressed sequences, and then combining tables A and B to build a genome-wide inner product map, is a fast, accurate, and inexpensive approach to whole genome physical mapping. IPM has localized the components of chimeric YACs as distinct multiple peaks. IPM is therefore useful in verifying and extending current mega YAC mapping projects, and in multiplexed experimental designs that pool sequences from well-separated bins.

1.2.13.10 Using Short-range Data to Determine the Orders and Distances of Clone Subsets in Proximate Bins IPM provides long-range mapping information for DNA sequences relative to RH bins through DNA hybridization. This binning information can be complemented with short-range mapping data, such as oligonucleotide fingerprint hybridizations (H. Lehrach, A. Drmanac, J. Hoheisel, Z. Larin, G. Lennon, A. P. Monaco, D. Nizetic, G. Zehetner, and A. Poustka, "Hybridization fingerprinting in genome mapping and sequencing," in Genetic and Physical Mapping I: Genome Analysis, K. E. Davies and S. M. Tilghman, ed. Cold Spring Harbor, N.Y.: Cold Spring Harbor Laboratory, 1990, pp. 39–81), incorporated by reference, and (R. Drmanac, Z. Strezoska, I. Labat, S. Drmanac, and R. Crkvenjakov, "Reliable hybridization of oligonucleotides as short as six nucleotides," DNA Cell Biol., vol. 9, no. 7, pp. 527–534, 1990), incorporated by reference. Combining the data from these two high-throughput hybridization studies enables a two-pass BIN-SORT (A. V. Aho, J. E. Hopcroft, and J. D. Ullman, Data Structures and Algorithms. Reading, Mass.: Addison-Wesley, 1983), incorporated by reference, strategy to high-resolution mapping: first use IPM to bin the clones, and then use short-range data to determine the orders and distances of clone subsets in proximate bins. This strategy can rapidly construct minimum-length paths of sequence-ready clones that tile the genome. Crucially, such IPM-derived contigs overcome the short-range limitations of all other known mapping methods, and enable the coordinated sequencing of the human genome, which is a well-recognized goal (F. Collins and D. Galas, "A new five-year plan for the U.S. Human Genome Project," Science, vol. 262, pp. 43–46, 1993), incorporated by reference. Such combination approaches can be highly effective for other purposes, such as using short-range proximity data to sharpen long-range inner product map results. IPM's experimental efficiencies enable effective determination of genome-wide DNA sequences, and the construction of high-resolution integrated genome maps for human, model organism, and agricultural species.

In one embodiment, this invention pertains to determining the sequence of the genome of an organism or species through the use of a novel, unobvious, and highly effective clone mapping strategy. Such sequence information can be used for finding genes of known utility, determining structure/function properties of genes and their products, elucidating metabolic networks, understanding the growth and development of humans and other organisms, and making comparisons of genetic information between species. From these studies, diagnostic tests and pharmacological agents can be developed of great utility for preventing and treating human and other disease.

Disclosures of this Type, Yielded in a Search, Are

Patent Number: Inventor Issued* U.S. Pat. No. 5,302,509 Cheeseman, Peter C. Apr. 12, 1994 WO 93/2134 Rosenthal., A; et al. Oct. 28, 1993 DE 41 41 178 A1 Ansorge, Wilhelm Jun. 16, 1993 Wo 93/01583 Gibbs, Richard A.; et al. Mar. 18, 1993 Wo 91/06678 Tsien, Roger Y.; et al. May 16, 1991 WO 90/13666 Garland, Peter B.; et al. Nov. 15, 1990 Included in some of these above disclosures are descriptions of nucleotide triphosphates comprising removable fluorescent 3' protecting groups.

1.3 Alternative Sequencing Methods

The present invention provides an improved method of determining the nucleotide base sequence of DNA. In one embodiment, the method of the invention involves the preparation of a DNA substrate comprising at a set of molecules, each having a template strand and a primer strand, wherein the 3' ends of the primer strands of the molecules terminate at about the same nucleotide position on the template strands of the molecules within each set. Preferably, the template and primer strands of the molecules are of unequal lengths wherein the 3' ends of the primer strands of the molecules terminate at about the same nucleotide position on the template strands of the molecules within each set. DNA synthesis is induced to obtain labeled reaction products comprising newly sythesized DNA complementary to the template strands using the 3' ends of the primer strands to prime DNA synthesis, labeled nucleoside triphosphates, at least one modified nucleoside triphosphate, and preferably, a suitable chain terminator, wherein the modified nucleoside triphosphate is selected to substantially protect newly synthesized DNA from cleavage. Thereafter, the labeled reaction products are cleaved at one or more selected sines to obtain labeled DNA fragments wherein newly synthesized DNA is substantially protected from cleavage by the incorporation of the modified nucleotide. The labeled DNA fragments obtained in the preceding step are separated and their nucleotide base sequence is identified by suitable means. The advantages of the present invention over prior art methods will become apparent after consideration of the accompanying drawings and the following detailed description of the invention.

1.3.1 One-step Process for Generating from a DNA Template

According to one process of the invention, a combined amplification and termination reaction is performed using at least two different polymerase enzymes, each having a different affinity for the chain terminating nucleotide, so that polymerization by an enzyme with relatively low affinity for the chain terminating nucleotide leads to exponential amplification whereas an enzyme with relatively high affinity for the chain terminating nucleotide terminates the polymerization and yields sequencing products.

In another aspect, the invention features kits for directly amplifying nucleic acid templates and generating base specifically terminated fragments. In one embodiment, the kit can comprise an appropriate amount of: i) a complete set of chain-elongating nucleotides; ii) at least one chain-terminating nucleotide; (iii) a first DNA polymerase, which has a relatively low affinity towards the chain terminating nucleotide, and (iv) a second DNA polymerase, which has a relatively high affinity towards the chain terminating nucleotide. The kit can also optionally include an appropriate primer or primers, appropriate buffers as well as instructions for use.

The instant invention allows DNA amplification and termination to be performed in one reaction vessel. Due to the use of two polymerases with different affinities for dideoxy nucleotide triphosphates, exponential amplification of the target sequence can be accomplished in combination with a termination reaction nucleotide. In addition, the process obviates the purification procedures, which are required when amplification is performed separately from base terminated fragment generation. Further, the instant process requires less time to accomplish than separate amplification and base specific termination reactions.

When combined with a detection means, the process can be used to detect and/or quantitate a particular nucleic acid sequence where only small amounts of template are available and fast and accurate sequence data acquisition is desirable. For example, when combined with a detection means, the process is useful for sequencing unknown genes or other nucleic acid sequences and for diagnosing or monitoring certain diseases or conditions, such as genetic diseases, chromosomal abnormalities, genetic predispositions to certain diseases (e.g. cancer, obesity, artherosclerosis) and pathogenic (e.g. bacterial, viral, fungal, protistal) infections. Further, when double stranded DNA molecules are used as the starting material, the instant process provides an opportunity to simultaneously sequence both strands, thereby providing greater certainty of the sequence data obtained or acquiring sequence information from both ends of a longer template.

1.3.2 Base-specific Reactions Used on DNA Fragments from a Piece of an Unknown Sequence In accordance with the present invention, there is also provided a method and apparatus for determining the sequence of the bases in DNA by measuring the molecular mass of each of the DNA fragments in mixtures prepared by either the Maxam-Gilbert or Sanger-Coulson techniques. The fragments are preferably prepared as in these standard techniques, although the fragments need not be tagged with radioactive tracers. These standard procedures produce from each section of DNA to be sequenced four separate collections of DNA fragments, each set containing fragments terminating at only one or two of the four bases. In the Maxam-Gilbert method, the four separated collections contain fragments terminating at G, both G and A, both C and T, or C positions, respectively. Each of these collections is sequentially loaded into an ultraviolet laser desorption mass spectrometer, and the mass spectrum of each collection is recorded and stored in the memory of a computer. These spectra are recorded under conditions such that essentially no fragmentation occurs in the mass spectrometer, so that the mass of each ion measured corresponds to the molecular weight of one of the DNA fragments in the collection, plus a proton in the positive ion spectrum, and minus a proton in the negative ion spectrum. Spectra obtained from the four spectra are compared using a computer algorithm, and the location of each of the four bases in the sequence is unambiguously determined.

It is also possible, in principle, to obtain the DNA sequence from a single mass spectrum obtained from a more complex single mixture containing all possible fragments, but both the resolution and mass accuracy required are much higher than in the preferred method described above. As a result the accuracy of the DNA sequence obtained from the single spectrum method will generally be inferior, and the gain in raw sequence speed will be counterbalanced by the need for more repetitions to assure accuracy of the sequence.

The DNA fragments to be analyzed are dissolved in a liquid solvent containing a matrix material. Each sample is radiated with a UV laser beam at a wavelength of between 260 nm to 560 nm, and pulses of from 1 to 20 ns pulsewidth.

It is an objective of the present invention to provide a method and apparatus for the rapid and accurate sequencing of human genome and other DNA material.

It is a further objective of the present invention to provide an instrument and method which are relatively simple to operate, relatively low in cost, and which may be automated to sequence thousands of gene bases per hour.

It is a further objective of the present invention to obtain much faster and more accurate DNA sequence data by eliminating the gel electrophoresis separation technique used in conventional DNA sequencing methods to determine the masses of the DNA fragments in a mixture.

1.3.3 Sequencing Through Exposure to Immobilized Probes of Shorter Length

According to one embodiment of the invention, a target oligonucleotide is exposed to a large number of immobilized probes of shorter length. The probes are collectively referred to as an "array." In the method, one identifies whether a target nucleic acid is complementary to a probe in the array by identifying first a core probe having high affinity to the target, and then evaluating the binding characteristics of all probes with a single base mismatch as compared to the core probe. If the single base mismatch probes exhibit a characteristic binding or affinity pattern, then the core probe is exactly complementary to at least a portion of the target nucleic acid.

The method can be extended to sequence a target nucleic acid larger than any probe in the array by evaluating the binding affinity of probes that can be termed "left" and "right" extensions of the core probe. The correct left and right extensions of the core are those that exhibit the strongest binding affinity and/or a specific hybridization pattern of single base mismatch probes.

The binding affinity characteristics of single base mismatch probes follow a characteristic pattern in which probe/target complexes with mismatches on the 3' or 5' termini are more stable than probe/target complexes with internal mismatches. The process is then repeated to determine additional left and right extensions of the core probe to provide the sequence of a nucleic acid target.

In some embodiments, such as in diagnostics, a target is expected to have a particular sequence. To determine if the target has the expected sequence, an array of probes is synthesized that includes a complementary probe and all or some subset of all single base mismatch probes. Through analysis of the hybridization pattern of the target to such probes, it can be determined if the target has the expected sequence and, if not, the sequence of the target may optionally be determined.

Kits for analysis of nucleic acid targets are also provided by virtue of the present invention. According to one embodiment, a kit includes an array of nucleic acid probes. The probes may include a perfect complement to a target nucleic acid.

The probes also include probes that are single base substitutions of the perfect complement probe. The kit may include one or more of the A, C, T, G, and/or U substitutions of the perfect complement. Such kits will have a variety of uses, including analysis of targets for a particular genetic sequence, such as in analysis for genetic diseases.

A further understanding of the nature and advantages of the inventions herein may be realized by reference to the remaining portions of the specification and the attached drawings.

1.3.4 Sequencing Contiguously, without the Need for Fragmenting and Sub-cloning the DNA The present invention also enables the amplification of a DNA adjacent to a known sequence using the PCR, without the knowledge of the sequence for a second primer.

The present primary invention also provides a new method for sequencing a contiguously very long DNA sequence using the PCR technique, thereby enabling contiguous genomic sequencing. It will avoid the need for mapping or sub-cloning of shorter DNA fragments from haploid genomes such as the bacterial genomes. This method can be used on very large DNA inserts into vectors such as the YAC. Thus, diploid genomes can be sequenced without any further need to sub-clone from the YAC clones. The cloned inserts can be of any length, of several million nucleotides. Alternatively, wherever purified chromosomes are available, this method can be directly applied to sequence the whole chromosome without any need to fragment the chromosome or obtain YAC clones from the chromosome. This method can also be used on whole unpurified genomes with appropriate modifications to account for the allelic variations of the two alleles present on the two chromosomes. In essence, using the method of the present invention, one can generate contiguous genomic sequence information in a manner not possible with any other known protocol using PCR.

The extended invention that enables the sequencing of an unknown region of very long DNA (e.g. genomic DNA) of totally unknown sequence would also find many applications in biology and medicine. For instance, it can be used to physically "map" a chromosome or genome. It would, for example, enable the production of an inventory of many about 500 nucleotide long sequences and the exact primer associated with each of them. This method would also enable the cloning of the amplified DNA sequences from arbitrary regions from a genomic DNA without the need for breaking down the DNA. Using appropriately longer partly fixed primers (as the second primers), very long DNA pieces (several kilobases long) could be amplified and cloned by using this method.

1.3.4.1 PCR Technique with 1 Primer

In one embodiment, the present invention enables the amplification of a DNA stretch using the PCR procedure with the knowledge of only one primer. Using this basic method, the present invention describes a procedure by which a very long DNA of the order of millions of nucleotides can be sequenced contiguously, without the need for fragmenting and sub-cloning the DNA. In this method, the general PCR technique is used, but the knowledge of only one primer is sufficient, and the knowledge of the other primer is derived from the statistics of the distributions of oligonucleotide sequences of specified lengths.

Present DNA sequencing methods using the separation of DNA fragments on a gel has a limitation of resolving the products of length up to about 1000 nucleotides. Thus, in a single step, the sequence of a DNA fragment up to a length of only about 1000 nucleotides can be obtained by the two conventional DNA sequencing methods. A DNA sequence of a few nucleotides up to many thousand nucleotides can be amplified by the PCR procedure. Thus the PCR procedure can be combined with the DNA sequencing procedure successfully.

A primer is usually of length twelve nucleotides and longer. Let the sequence of one primer is known in a long DNA sequence from which the DNA sequence is to be worked out. From this primer sequence, a specific sequence of four nucleotides occurs statistically at an average distance of 256 nucleotides. It has been worked out by Senapathy that a particular sequence of four characters would occur anywhere from zero distance up to about 1500 characters with a 99.9% probability (P. Senapathy, "Distribution and repetition of sequence elements in eukaryotic DNA: New insights by computer aided statistical analysis," Molecular Genetics (Life Sciences Advances), 7:53–65 (1988)). The mean distance for such an occurrence is 256 characters and the median is 180 characters. Similarly, a 5 nucleotide long specific sequence will occur at a mean distance of 1024 characters, with 99.99% of them occurring within 6000 characters from the first primer. The median distance for the occurrence of a 5-nucleotide specific sequence is ~730 nucleotides. Similarly, a particular 6 nucleotide long sequence will occur at a mean distance of 4096 nucleotides and a median distance of ~2800 nucleotides. A primer of known length, say length 14 can be prepared with a known sequence of 6 characters and the rest of the sequence being random in sequence. It means that any of the four nucleotides can occur at the "random" sequence locations. With a fixed 5, 6 or 7 nucleotide sequence within the second primer, a primer of length 12–18 can be prepared with high specificity of binding.

1.3.4.2 Non-Random Primer (Partly Fixed Primer)

Such a partially non-random primer (hereafter called the partly fixed primer, or partly non-random primer, meaning that part of its sequence is fixed) can "anneal" to only the sequence at which the fixed sequence exists. That is, from the first primer, the partly fixed primer will bind at an average distance of 1024 characters (for a fixed five nucleotide characters). This primer will bind specifically only at the location of the occurrence of the particular five nucleotide sequence with respect to the first primer. The average distance between the first primer and the second non-random primer is ideal for DNA amplification and DNA sequencing. In this situation, the first primer is labeled. Thus, although there would be many locations in the long DNA molecule at which the non-random primer can bind, it would not affect the DNA sequencing because it is dependent only upon the labeled primer.

1.3.4.3 Partly Fixed $2^{nd}$ Primer

Although the partly fixed second primer has a random sequence component in it, a sub-population of the primer molecules will have the exact sequence that would bind with the exact target sequence. The proportion of the molecules with exact sequence that would bind with the exact target sequence will vary depending on the number of random characters in the partly fixed second primer. For example, in a second primer 11 nucleotides long with 6 characters fixed and 5 characters random, one in ~1000 molecules will have the exact sequence complementary to the target sequence on the template. By increasing the concentration of the partly fixed second primer appropriately, a comfortable level of PCR amplification required for sequencing can be achieved. When primer concentration is increased, it requires an increase in the concentration of Magnesium, which is required for the function of the polymerase enzyme. The excess primers (and "primer-dimers" formed due to excess of primers) can be removed after amplification reaction by a gel-purification step.

Any non-specific binding by any population of the second primers to non-target sequences could be avoided by adjusting (increasing) the temperature of re-annealing appropriately during DNA amplification. It is well known that the change of even one nucleotide due to point-mutation in some cancer genes can be detected by DNA-hybridization. This technique is routinely used for diagnosing particular cancer genes (e.g. John Lyons, "Analysis of ras gene point mutations by PCR and oligonucleotide hybridization," in PCR Protocols: A guide to methods and applications, edited by Michael A Innis et al., (1990), Academic Press, New York). This is done by adjusting the "re-annealing" or "melting-temperature", and fine-tuning the reaction conditions. Thus the binding of non-specific sequences even with just one nucleotide difference compared to the target binding-site in the template sequence can be avoided.

It should also be noted that non-specific binding sites for the partly fixed second primers could be expected to occur statistically on a long genomic DNA at many places other than the target site which is close to the first primer. Amplification of non-specific DNA between these primer binding sites that could occur on opposite strands of the template DNA could happen. However, this would not affect the objective of the present invention of specific DNA sequencing of the target sequence. Because only the first primer is labeled radioactivity or fluorescently, only the reaction products of the target DNA will be visualized on the sequencing gel pattern. The presence of such non-specific amplification products in the reaction mixture will also not affect the DNA sequencing reaction.

Amplification of DNA will occur not only between the first primer and the partly fixed second primer that occurs closest downstream from the first primer, but also between the first primer and one or two subsequently occurring second primers, depending upon the distance at which they occur. However, these amplification products will all start from the first primer and will proceed up to these second primers. Since the DNA sequencing products are visualized by labeling the first primer, and since the DNA synthesis during the sequencing reaction proceeds from the first primer, the presence of two or three amplification products that start from the first primer will not affect the DNA sequencing products and their visualization on gels. At the most, the intensity of the bands that are subsets of different amplification products will vary slightly on the gel, but not affect the gel pattern. In fact, it is expected that this phenomenon will enable the sequencing of a longer DNA strand where the closest downstream primer is too close to the first primer—thereby avoiding the need for sequencing from the first primer again using another partly fixed second primer.

The minimum length of primer for highly specific amplification between primers on a template DNA is usually considered to be about 15 nucleotides. However, in the present invention, this length can be reduced by increasing the G/C content of the fixed sequence to 12–14 nucleotides.

In essence, the basic procedure of the present invention is fully viable and feasible, and any non-specificity can be avoided by fine-tuning the reaction conditions such as adjusting the annealing temperature and reaction temperature during amplification, and/or adjusting the length and G/C content of the primers, which are routinely done in the standard PCR amplification protocol.

1.3.4.4 Sequence DNA of $2^{nd}$ Primer

The primary advantage of the present invention is to provide an extremely specific second primer that would bind precisely to a sequence at an appropriate distance from the first primer resulting in the ability to sequence a DNA without the prior knowledge of the second primer. From the newly worked out DNA sequence, a primer sequence can be made complementary to a sequence located close to the downstream end. This can be used as the first primer in the next DNA amplification-sequencing reaction, and the unknown sequence downstream from it can be obtained by again using the same partly fixed primer that was used in the first round of sequencing as the second primer. Thus, knowing only one short sequence in a contiguously long DNA molecule, the entire sequence can be worked out using the present invention.

When the length of the fixed sequence in the partly fixed second primer is increased in the present invention, the distance from the first primer at which the second primer will bind on the template will also be correspondingly increased. For a 6 nucleotide fixed sequence, the median length of DNA amplified will be ~2800 nucleotides (mean 4096 nucleotides), and for a 7 nucleotide fixed sequence, the median length of amplified DNA will be ~11,000 nucleotides (mean=~16,000 nucleotides). However, even if the length of amplified DNA is several thousand nucleotides, still this DNA can be used in DNA sequencing procedures.

Furthermore, the present invention can be used to amplify a DNA of length which is limited only by the inherent ability of PCR amplification. A technique known as "long PCR" is used to amplify long DNA sequences (Kainz et al., "In vitro amplification of DNA Fragments >10 kb," Anal Biochem., 202:46 (1992); Ponce & Micol, "PCR amplification of long DNA fragments" Nucleic Acids Research, 20:623 (1992)).

Existing genome sequencing methods employ the breaking down of a very long genomic DNA into many small fragments, sub-cloning them, sequencing them, and then assembling the sequence of the long DNA. Typically, a genomic DNA is broken down and cloned into overlapping fragments of approx. one million nucleotides in "YAC" (Yeast Artificial Chromosome) clones, each YAC clone is again fragmented and sub-cloned into overlapping fragments of ~25,000 nucleotides in "cosmid" clones, and each cosmid clone in turn sub-cloned into overlapping fragments of ~1000 nucleotides in "M13 phage" or "plasmid" clones. These are sequenced randomly to assemble the larger sequences in the hierarchy. The present invention circumvents the need for breaking down and sub-cloning steps, making it greatly advantageous for contiguously sequencing long genomic DNA.

1.3.4.5 The $2^{nd}$ Partly Fixed Primer Enabling Sequencing

Extending the above invention, another invention is presented here. This extended invention would enable the sequencing of ~500 nucleotide long sequence somewhere within a given long DNA with no prior information of any sequence at all within the long DNA. The probability that any specific primer of length 10 nucleotides would occur somewhere in a DNA of about one million nucleotides is approximately 1. The probability that any primer of length 15 nucleotides occur somewhere in a genome of about one billion nucleotides is approximately 1. Thus, use of any exact primer of about 15 nucleotide sequence on a genomic DNA in the present invention as the first primer, and the use of the second partly fixed primer will enable the sequencing of the DNA sequence bracketed by the two primers somewhere in the genome. Thus, this procedure can be used to obtain an exact sequence of about 500 characters somewhere from a genome without the prior knowledge of any of its sequence at all. Thus, by using many different primers with arbitrary but exact sequences, one can obtain many ~500-nucleotide sequences at random locations within a genome. Using these sequences as the starting points for contiguous genome sequencing in the present invention, the whole genomic sequence can be closed and completed. Thus an advantage of the present invention is that without any prior knowledge of any sequence in a genome, the whole sequence of a genome can be obtained.

It must be noted that every 15-nucleotide arbitrary primer may not always have a complementary sequence in a genome (of ~one billion nucleotides long). However, most often it would be present and would be useful in performing the above-mentioned sequencing. In some cases, there may be more than one occurrence of the primer sequence in the genome, and so may not be useful in obtaining the sequence. However, the frequency of successful single-hits can be extremely high (~90%) and can be further refined by using an appropriate length of the arbitrary primer. For genomes (or long DNAs) that are shorter than a billion nucleotides, shorter exact sequences in the first primers (say 10 characters) could be used, and the rest could be random or "degenerate" nucleotides. While this primer will still bind at the sequence complementary to the exact sequence, the longer primer will aid in avoiding non-specific DNA amplification. The length of the first primer can thus be increased using degenerate nucleotides at the ends to a desired extent, without affecting any specificity. Once a sequence is known in an unknown genomic DNA, then the present method can be performed to extend a contiguous sequence in both directions of the DNA from this starting point.

The present invention can also be useful to amplify the DNA between the first primer and the partly fixed second primer, with an aim to using this amplified DNA for purposes other than DNA sequencing, such as cloning. Although there would be sufficient quantity of the target specific amplified DNA in the reaction products, the reaction products will, however, contain the population of non-specific DNA amplified between the non-specifically occurring second primer binding sites on opposite strands. However, by introducing a purification step from this reaction mixture, such as using an immobilized column containing only the first primer, the amplified target DNA can be purified and used for any other purposes.

1.3.5 Sequencing Large Fragments of DNA (End-sequencing-based Method of Subclone Pathway Generation Through the Fragment with Efficient Transposon-based Sequencing of the Identified Subclones)

The invention also provides a systematic and efficient way to sequence large fragments of DNA, in particular genomic DNA. It combines an end-sequencing-based method of subclone pathway generation through the fragment with efficient transposon-based sequencing of the identified subclones.

Thus, in one aspect, the invention is directed to a method to sequence a fragment of DNA, said fragment typically having a length of more than about 30 kb. The method comprises the following steps.

First, the fragment is provided in a host cloning vector capable of accommodating it. The size of the fragment that can be sequenced will depend on the nature of the host cloning vector. Cloning vectors are available that can accommodate large fragments of DNA; even the approximately 30–40 kb fragments that are suitable for insertion into cosmids are of sufficient length that the method of the invention is usefully applicable to them.

A composition comprising said vector containing the inserted fragment is then randomly sheared, such as by sonication, to obtain subfragments of approximately 3 kb. The length of the subfragments is appropriate to the transposon-mediated directed sequencing method that will ultimately be applied. The 3 kb length is an approximation; it is intended only as an order of magnitude. Generally speaking, subfragments of 2–5 kb are susceptible to this approach.

The subfragments are then inserted into host cloning vectors to obtain a library of subclones. These host cloning vectors are ideally of minimal size, containing only a selectable marker, an origin of replication, and appropriate insertion sites for the subfragments. The desirability of minimizing the available plasmid DNA in the performance of transposon-mediated sequencing is described by Strathmann, et al. (supra).

Sufficient subclones that contain subfragments derived from the original fragment are then recovered to provide 1× coverage of the fragment when the end of each subfragment is sequenced. A stretch of about 400–450 bases can be sequenced with assurance using available automated sequencing techniques. Thus, the sequencing can be conducted using the sequencing primers based on the vector sequences adjacent the inserts to proceed into the insert to approximately this distance. For a 1× coverage of the original fragment, the number of subclones required can be calculated by dividing the length of the original fragment by the intended sequencing distance—i.e., by approximately 400–450.

There should also be sufficient subclones in the library so that when the complete sequence of each is determined, the coverage of the original fragment will be about 7–8×. This provides, as described below, a high probability that every nucleotide present in the fragment will be present in the library. This number can, of course, be determined by multiplying the length of the fragment by 7 or 8 and dividing by the length of the subfragments generated.

It is preferable to assure that all of the subclones in the library contain pieces of the original fragment. This can be done by recovering only those subclones that hybridize to the fragments.

A sufficient portion of one of the ends of each recovered subclone containing fragment-derived DNA is then sequenced and this sequence information is placed into a searchable database. The database is searched for subclones that contain subfragments with nucleotide sequences matching those that characterize the host vector that accommodated the original fragment. To the extent that these subfragments also contain sequence from the original fragment, that sequence must be at one or the other end of the original fragment. This illustrates why the efficiency of the method is improved by introducing a prescreening step which eliminates any subclones which do not contain portions of the original fragment. If the prescreening has been done, these subclones contain oligonucleotide sequence from either end of the original fragment. The identified subclones are recovered.

1.3.5.1 "Second End" Sequence

A partial sequence of each of the identified subclones is determined from the opposite end of the subfragment insert from that originally placed in the database. This provides "second end" sequence information concerning sequence further removed from the end of the original fragment. This information is then used to search the database in order to identify subclones containing nucleotide sequence that matches this second end sequence. Such subclones are likely to represent regions of the original fragment that are farther removed from the ends and provide further progress in constructing a path across the fragment. These subclones are recovered as well, and sequenced from the end opposite to that which was sequenced to provide the information for the database and this new information, in turn, used to search the database for a matching sequence. The steps of second end sequencing, searching the database with the resulting sequence information, and recovery of subclones which contain a match are repeated sequentially until subclones have been identified that represent the complete original fragment. The resulting collection of subclones consists of an ordered minimum set that collectively represent the original fragment. The appropriate sequence of such subclones to span the original fragment from end to end is also known.

It remains only to obtain sufficient portions of the complete nucleotide sequence of each subclone from the subclone collection using transposon-mediated sequencing to provide the complete sequence of the original fragment.

In another aspect, the invention is directed to kits suitable for conducting the method of the invention.

1.3.6 Improvements in High Speed, High Throughput, no Required Electrophoresis (and, Thus, No Gel Reading Artifacts Due to the Complete Absence of an Electrophoretic Step)

The invention also describes a new method to sequence DNA. The improvements over the existing DNA sequencing technologies include high speed, high throughput, no required electrophoresis (and, thus, no gel reading artifacts due to the complete absence of an electrophoretic step), and no costly reagents involving various substitutions with stable isotopes. The invention utilizes the Sanger sequencing strategy and assembles the sequence information by analysis of the nested fragments obtained by base-specific chain termination via their different molecular masses using mass spectrometry, for example, MALDI or ES mass spectrometry. A further increase in throughput can be obtained by introducing mass modifications in the oligonucleotide primer, the chain-terminating nucleoside triphosphates and/or the chain-elongating nucleoside triphosphates, as well as using integrated tag sequences which allow multiplexing by hybridization of tag specific probes with mass differentiated molecular weights.

1.3.7 A Method and a System for Sequencing a Genome

The present invention pertains to a method for sequencing genomes. The method comprises the steps of obtaining nucleic acid material from a genome. Then there is the step of constructing a clone library and one or more probe libraries from the nucleic acid material. Next there is the step of comparing the libraries to form comparisons. Then there is the step of combining the comparisons to construct a map of the clones relative to the genome. Next there is the step of determining the sequence of the genome by means of the map.

The present invention pertains to a system for sequencing a genome. The system comprises a mechanism for obtaining nucleic acid material from a genome. The system also comprises a mechanism for constructing a clone library and one or more probe libraries. The constructing mechanism is in communication with the nucleic acid material from a genome. Additionally, the system comprises a mechanism for comparing said libraries to form comparisons. The comparing mechanism is in communication with the said libraries. The system also comprises a mechanism for combining the comparisons to construct a map of the clones relative to the genome. The said combining mechanism is in communication with the comparisons. Further, the system comprises a mechanism for determining the sequence of the genome by means of said map. The said determining mechanism is in communication with said map.

1.3.7.1 A Method for Producing a Gene of a Genome

The present invention additionally pertains to a method for producing a gene of a genome. The method comprises the steps of obtaining nucleic acid material from a genome. Then there is the step of constructing libraries from the nucleic acid material. Next there is the step of comparing the libraries to form comparisons. Then there is the step of combining the comparisons to construct a map of the clones relative to the genome. Next there is the step of localizing a gene on the map. Then there is the step of cloning the gene from the map.

1.3.8 Methods and Means for the Massively Parallel Characterization of Complex Molecules and of Molecular Recognition Phenomena with Parallelism and Redundancy Attained Through Single Molecule Examination Methods In another embodiment, the present invention approaches the vastness of biological complexity through massive parallelism, which may conveniently be attained through various single molecule examination (SME) methods variously referred to heretofore as single molecule detection (SMD), single molecule visualization (SMV) and single molecule spectroscopy (SMS) techniques.

Used within appropriate procedures, single molecule examination methods can enable molecular parallelism.

Molecular parallelism may be applied to the examination of the composition of complex molecules (including co-polymers of natural or of synthetic origin) or to determinations of interactions between large numbers of molecules. The former case may be applied to genome-scale sequencing methods. The latter case may be applied to rapid determination of molecular complementarity, with applications in (biological or non-biological) affinity characterization, immulogical study, clinical pathology, molecular evolution (e.g. in vitro evolution), and the construction of a cybernetic immune system as well as prostheses based thereupon. In both cases, molecular recognition phenomena are observed with molecular parallelism.

Note that within said affinity characterization applications, both kinetics of both binding association and dissociation, and binding equilibria, may be examined. Kinetics may be examined by observing the rates of occupation of appropriate sites or diverse populations thereof by some homogenous or heterogeneous sample, and the rates of vacancy formation from occupied sites. Equilibria constants may be determined by observing the proportion (number of occupied sites divided by number of total sites) of sites occupied under equilibrium conditions, with greater quantitative confidence yielded by, for example, examining more binding sites.

Sequencing of polynucleotide molecules may be effected by the (preferably end-wise) immobilization of a library of such molecules to a surface at a density convenient for detection, which will vary according to the detection methodology availed. Several methods capable of effecting such immobilization will be obvious to those skilled in the arts of recombinant DNA technology and molecular biology, among others. Priming, which may be random or non-random, is effected by any of a variety of methods, most of which are obvious to those skilled in the relevant arts.

Genome sequencing applications availing of enzymatic polymerization's and corresponding embodiments of the present invention, rely upon control over polymerization rate and nucleotide incorporation specificity, consistent with the well-known Watson-Crick base pairing rules which may be enforced (upon single nucleotides in a processive manner, as conditions permit) by the use of DNA polymerases or analogs thereof, in combination with repeatable single molecule detection applied to a large population of diverse molecules. A sequencing cycle comprises the steps of: (1.) polymerizing one or less nucleotides, which carry some removable or neutralizable molecular label and may optionally be reversibly 3' protected (or otherwise protected in any manner which modulates polymerization rate onto each sample molecule at the primer or at subsequent extensions thereof and in opposition to (and pairing with) a single, unique, base of the template polynucleotide strand; (2.) optionally washing away any unreacted labeled nucleotides; (3.) detecting, by either direct or indirect methods, said labeled nucleotides incorporated into said sample molecules, in a manner which repeatably associates information obtained about the type of label observed with the unique identity of the template molecule under observation, which may be uniquely distinguished by a variety of methods (which include: a mappable location of immobilization of the sample template molecule on a substrate surface; a mappable location of immobilization of the sample template molecule within some matrix volume element; microscopic labeling with some readily identifiable, e.g. combinatorially or permutationally diverse and readily examined particle or molecule or group of molecules and detection of the thus marked identity of individual free molecules in solution; and, scanning of a liquid sample volume where sample molecules and sample conditions are matched to ensure manageably slow free diffusion of sample molecules permitting tracking of the motions of free individual molecules in solution, in which instance unreacted labeled monomers may be removed, for instance, by filtration), and recording the information obtained by said detections, especially in a manner which may be conveniently recalled according to the unique identity template molecule to which it refers; (4.) removing or neutralizing said incorporated label; (5.) optionally removing (by appropriate means) any 3' protecting groups (or any other protecting groups which may serve to modulate monomer addition rate to the strand being copied from the template molecule) from the nucleotide added during the present cycle, if these are distinct from any cleavably linked labeling moieties; (6.) optionally checking that the removal or neutralization of said label in step (4) was successful for any particular molecule of the sample, by repeating a similar detection procedure. Said sequencing cycle comprising an appropriate subset of steps 1–6 may be repeated as many times as convenient, but must be repeated a sufficient number of times to obtain sequence information of sufficient complexity from each individual molecule to permit unambiguous alignment of all such sequence information determined for all of the molecules of the sample. This minimum number of cycles will be approximately related to the complexity C of the sample to be treatated as part of the same macroscopic reaction (i.e. a macroscopic sample preparation subjected to unitary macroscopic manipulations) by the formula $C<4^n$ where n is the number of cycles. Beyond this minimum, there are tradeoffs between the number of cycles to be performed and the number of molecules to be examined, and the confidence for sequence data obtained.

Note that unused reagents and enzymes may be recovered from washes and recycled.

1.3.8.1 Advantages of Parallelism

In contrast to the previously disclosed base-addition sequencinq schemes, the sequence determination applications of the present invention enjoys substantial advantages deriving from sample manipulation in the single-molecule-regime. Working instead in the distinct single-molecule-regime rather than with populations of identical molecules provides substantial advantages of parallelism, facility of use and implementatiol, (including automated implementation,) and operability. Among these are unanticipated advantages: (1) because a single molecule is necessarily monodisperse, failure of a molecule to undergo addition in a cycle does not cause a loss of sample monodispersion (i.e. lead to uneven sample molecules dispersity or polydispersion); such addition failure is unproblematic when single molecules are examined individually because it is readily detected and accounted for in data analysis; in contrast, samples comprising multiple identical molecules may thus take on non-identical lengths, complicating data collection and analysis; (2) samples comprising a plurality of individually distinct single molecules (species) may be handled unitarily without requiring any handling measures to keep distinct molecules apart, providing a large reduction in manipulations required on a per-species basis and not requiring the use of many separate, parallel fluid handling steps or means; (3) inadvertent multiple base additions are more readily detected and their extent is more readily quantified because these changes in quantity are large compared to the signal expected from the incorporation of a single base (i.e. single label) into a single molecular species; (4) deprotection or delabeling failures may also be readily detected and noted for the correct single molecule, such that addition failure, the presence of a label, or overlabeling in the subsequent cycle may be correctly interpreted (according to the unlabeling and single stepping methods used in a particular embodiment.) These advantages are expected to be important in the competitiveness of these present methods over conventional polynucleotide sequencing methods.

Various techniques are included to address any non-idealities encountered which may arise because of deviations from conventional polymerization or detection methods. These generally take the form of different types of redundancy, which may be employed to either prevent or resolve any such errors. Prominent among these redundancies is oversampling, i.e. the examination of some multiple (j) of the number (m) of sample molecules suggested by combinatoric computations to be minimally sufficient for full alignment of data from a sample of a given complexity.

Such oversampling redundancy will increase the confidence interval for accuracy of collected data and reduce the likelihood of artifacts arising from sequence duplications which may occur in any given sample.

1.3.8.2 Oversampling Redundancy

Oversampling redundancy may be availed to increase data confidence by providing the opportunity to score and match multiple occurrences of the same sequence segment and thus detect and eliminate erroneous sequence segment information by virtue of its less frequent occurrence. Erroneous sequence segment information may arise, for instance, by nucleotide incorporation errors which are an inevitable feature of polymerization with polymerases having a characteristic fidelity, i.e. displaying a characteristic nucleotide misincorporation rate, Such methods will be particularly useful where polynucleotide polymerases fidelity would otherwise be unacceptably low. It should be noted that an error rate of one percent or more has been deemed conventionally acceptable for genome informatic purposes.

1.3.8.3 Controls/Data

Further, known molecules having sequences that are highly unrelated to the sample may be included as internal controls to monitor the efficiency and accuracy of a particular sequence collection process; such internal control sequences will present negligibly small overhead because molecular parallelism may easily accommodate any such comparatively small increase in sample complexity, even though it might be considered large with respect to pre-existing methods.

After raw data have been collected for each molecule, these are all mutually compared by some appropriate matching algorithm and aligned so as to reconstruct the full sequence of the sample. The computational complexity of completing such an alignment may be estimated as the multi-phase comparison and sorting of (j)(m) strings each of length n.

Alternatively, data alignment may be performed in tandem or parallel with later cycles and may be monitored by appropriate computational algorithms for data quality and confidence of sequence information, and cycling may continue till desired criteria are satisfied. Computer, microprocessor, electronic or other automated control of instrumentation, including fluidics and robotics for the manipulation of samples, and the automated effectuation of the various methods of the present invention, all according to parameterized algorithms, may be accomplished by means obvious from the present disclosure to those skilled in the relevant arts (e.g. fluidics, robotics, electronics, microelectronics, computer science and engineering, and mechanical engineering). Concurrent data alignment and monitoring will permit modifications of the sequencing cycle described above, such as dynamic adjustment of polymerization reaction conditions and durations, label removal or neutralization procedure parameters, polymerization deprotection conditions, and any other desired parameter, so as to permit optimization of procedures and results.

With appropriately flexible design, automated systems and instruments such as those described above for genome applications may readily be adapted, with appropriate changes in samples and labeling methods and reagents, to cybernetic molecular evolution, cybernetic immune system, broad spectrum pathogen characterization and other applications of the present invention.

1.3.8.4 Double/Single Stranded Polynucleotide Sequencing Method

According to the embodiment availed, double or single stranded polynucleotides may be examined. Where single stranded polynucleotide molecules are preferred, second strands may be removed by performing said immobilization so as to only involve only one strand in covalent linkage with said surface and then performing a denaturation of the sample with washing. Priming means required by any particular enzyme must then be provided, usually by hybridization of a complementary oligo- or polynucleotide to the sample template molecules, though other means are possible. Other methods which will be obvious to those skilled in the arts of recombinant DNA technology may also be employed to yield immobilized or otherwise uniquely identifiable single stranded polynucleotide samples.

Where double stranded molecules are preferred, said second strands may be treated with an appropriate exonuclease under appropriate conditions and for an appropriate lengths of time to provide a good distribution of lengths of said second strands such that the termini of the undegraded portions of said second strands provide convenient priming for enzymatic nucleotide polymerization (i.e. DNA directed DNA synthesis or DNA replication, DNA directed RNA synthesis or transcription, RNA directed DNA synthesis or reverse transcription, or RNA directed RNA synthesis or RNA replication).

Note that the polynucleotide sequencing methods of the present invention represent the converse of conventional enzymatic and chemical sequencing methods in that those conventional methods rely upon the production of multiple homogeneous sub-populations of DNA molecules which together comprise a nested set, and the detection of each of such sub-population (with deviant chain terminator misincorporation molecules arising with significantly lower frequency and thus constituting a poorly detected population), while the present invention relies on alignment of information from a highly inhomogeneous population molecules and repeatable detection of single molecules. Further note that by previous methods, each species yields information about only one base at one position within the sample sequence, while with the methods of the present invention, each individual sample template molecule may yield information about the identity of several bases. Note also that under conventional methods, some effort has been expended in increasing the number of bases yielding information per sample, i.e. lengthening the linear sequence information obtained from any one segment of a sample, which is substantially frustrated by the inherent limitations of electrophoretic separation and particularly gel electrophoresis, while the present invention readily accomplishes the information yielded per unitary manipulation through increases in the facility and practicable extent of parallelism.

There are several levels of parallelism and pipelining possible with the methods of the present invention. An arbitrarily large number of molecules may be subjected to any given manipulation at once if they are part of the same unitary sample. Detection will have constraints entailed by the particular instrumentation and method used, but many degrees of freedom exist with regard to means of providing parallelism in detection instrumentation (e.g. multiple microscopy instruments or appropriately arranged objective lenses and controlled light paths for light microscopic based detection, multiple optoelectronic device arrays [e.g. CCDs or SLMs] for the respective types of detection; multiple probes [i.e. in arrays with parallel detection provided] for scanning probe microscopic detection methods with various degrees of freedom with respect to eachother during scanning, etc.) Means for pipelining the steps of the methods disclosed herein will be readily apparent when one considers that dedicated instrumentation or robotics may perform each relevant step, and that the ensemble of such instrumentation may readily be integrated to form a coordinated system, for example matching throughput at different stages by adjusting the parallelism of appropriate stages. Thus economy, throughput and data accuracy are tradeoffs, but may individually vastly exceed any such measures attainable with conventional methods.

1.4 Exemplary Genomic Characterization Methods 1.4.1 Employing Mass Spectrometry to Analyze the Sanger Sequencing Reaction Mixtures In one embodiment, this invention describes an improved method of sequencing DNA. In particular, this invention employs mass spectrometry to analyze the Sanger sequencing reaction mixtures.

In Sanger sequencing, four families of chain-terminated fragments are obtained. The mass difference per nucleotide addition is 289.19 for dpC, 313.21 for dpA, 329.21 for dpG and 304.2 for dpT, respectively.

1.4.1.1 Mass Modified

In one embodiment, through the separate determination of the molecular weights of the four base-specifically terminated fragment families, the DNA sequence can be assigned via superposition (e.g., interpolation) of the molecular weight peaks of the four individual experiments. In another embodiment, the molecular weights of the four specifically terminated fragment families can be determined simultaneously by MS, either by mixing the products of all four reactions run in at least two separate reaction vessels (i.e., all run separately, or two together, or three together) or by running one reaction having all four chain-terminating nucleotides (e.g., a reaction mixture comprising dTTP, ddTTP, dATP, ddATP, dCTP, ddCTP, dGTP, ddGTP) in one reaction vessel. By simultaneously analyzing all four base-specifically terminated reaction products, the molecular weight values have been, in effect, interpolated. Comparison of the mass difference measured between fragments with the known masses of each chain-terminating nucleotide allows the assignment of sequence to be carried out. In some instances, it may be desirable to mass modify, as discussed below, the chain-terminating nucleotides so as to expand the difference in molecular weight between each nucleotide. It will be apparent to those skilled in the art when mass-modification of the chain-terminating nucleotides is desirable and can depend, for instance, on the resolving ability of the particular spectrometer employed. By way of example, it may be desirable to produce four chain-1 2 3 1 terminating nucleotides, ddTTP, ddCTP, ddATP and ddGTP where ddCTP ddATP 2 and ddGTP 3 have each been mass-modified so as to have molecular weights resolvable from one another by the particular spectrometer being used.

The terms chain-elongating nucleotides and chain-terminating nucleotides are well known in the art. For DNA, chain-elongating nucleotides include 2'-deoxyribonucleotides and chain-terminating nucleotides include 2', 3'-dideoxyribonucleotides. For RNA, chain-elongating nucleotides include ribonucelotides and chain-terminating nucleotides include 3'-deoxyribonucleotides. The term nucleotide is also well known in the art. For the purposes of this invention, nucleotides include nucleoside mono-, di-, and triphosphates. Nucleotides also include modified nucleotides such as phosphorothioate nucleotides.

Since mass spectrometry is a serial method, in contrast to currently used slab gel electrophoresis which allows several samples to be processed in parallel, in another embodiment of this invention, a further improvement can be achieved by multiplex mass spectrometric DNA sequencing to allow simultaneous sequencing of more than one DNA or RNA fragment. As described in more detail below, the range of about 300 mass units between one nucleotide addition can be utilized by employing either mass modified nucleic acid sequencing primers or chain-elongating and/or terminating nucleoside triphosphates so as to shift the molecular weight of the base-specifically terminated fragments of a particular DNA or RNA species being sequenced in a predetermined manner. For the first time, several sequencing reactions can be mass spectrometrically analyzed in parallel. In yet another embodiment of this invention, multiplex mass spectrometric DNA sequencing can be performed by mass modifying the fragment families through specific oligonucleotides (tag probes) which hybridize to specific tag sequences within each of the fragment families. In another embodiment, the tag probe can be covalently attached to the individual and specific tag sequence prior to mass spectrometry.

1.4.1.2 Mass Spectrometer Formats Used (MALDI, ES, ICR, Fourier Transform)

Preferred mass spectrometer formats for use in the invention are matrix assisted laser desorption ionization (MALDI), electrospray (ES), ion cyclotron resonance (ICR) and Fourier Transform. For ES, the samples, dissolved in water or in a volatile buffer, are injected either continuously or discontinuously into an atmospheric pressure ionization interface (API) and then mass analyzed by a quadrupole. The generation of multiple ion peaks which can be obtained using ES mass spectrometry can increase the accuracy of the mass determination. Even more detailed information on the specific structure can be obtained using an MS/N4S quadrupole configuration In MALDI mass spectrometry, various mass analyzers can be used, e.g., magnetic sector/magnetic deflection instruments in single or triple quadrupole mode (MS/MS), Fourier transform and time-of-flight (TOF) configurations as is known in the art of mass spectrometry. For the desorption/ionization process, numerous matrix/laser combinations can be used. Ion-trap and reflectron configurations can also be employed.

In one embodiment of the invention, the molecular weight values of at least two base-specifically terminated fragments are determined concurrently using mass spectrometry. The molecular weight values of preferably at least five and more preferably at least ten base-specifically terminated fragments are determined by mass spectrometry. Also included in the invention are determinations of the molecular weight values of at least 20 base-specifically terminated fragments and at least 30 base-specifically terminated fragments. Further, the nested base-specifically terminated fragments in a specific set can be purified of all reactants and by-products but are not separated from one another. The entire set of nested base-specifically terminated fragments is analyzed concurrently and the molecular weight values are determined. At least two base-specifically terminated fragments are analyzed concurrently by mass spectrometry when the fragments are contained in the same sample.

1.4.1.3 Process of Mass Spectrometric DNA Sequencing

In general, the overall mass spectrometric DNA sequencing process will start with a library of small genomic fragments obtained after first randomly or specifically cutting the genomic DNA into large pieces which then, in several subcloning steps, are reduced in size and inserted into vectors like derivatives of M13 or pUC (e.g., M13mp18 or M13mp19). In a different approach, the fragments inserted in vectors, such as M13, are obtained via subcloning starting with a cDNA library. In yet another approach, the DNA fragments to be sequenced are generated by the polymerase chain reaction (e.g., Higuchi et al., "A General Method of in vitro Preparation and Mutagenesis of DNA Fragments: Study of Protein and DNA Interactions," Nucleic Acids Res., 16, 7351–67 (1988)). As is known in the art, Sanger sequencing can start from one nucleic acid primer (UP) binding to the plus-strand or from another nucleic acid primer binding to the opposite minus-strand. Thus, either the complementary sequence of both strands of a given unknown DNA sequence can be obtained (providing for reduction of ambiguity in the sequence determination) or the length of the sequence information obtainable from one clone can be extended by generating sequence information from both ends of the unknown vector-inserted DNA fragment.

The nucleic acid primer carries, preferentially at the 5'-end, a linking functionality, L, which can include a spacer of sufficient length and which can interact with a suitable functionality, L', on a solid support to form a reversible linkage such as a photocleavable bond. Since each of the four Sanger sequencing families starts with a nucleic acid primer this fragment family can be bound to the solid support by reacting with functional groups, L', on the surface of a solid support and then intensively washed to remove all buffer salts, triphosphates, enzymes, reaction by-products, etc. Furthermore, for mass spectrometric analysis, it can be of importance at this stage to exchange the cation at the phosphate backbone of the DNA fragments in order to eliminate peak broadening due to a heterogeneity in the cations bound per nucleotideunit. Since the L-L' linkage is only of a temporary nature with the purpose to capture the nested Sanger DNA or RNA fragments to properly condition them for mass spectrometric analysis, there are different chemistries which can serve this purpose. In addition to the examples given in which the nested fragments are coupled covalently to the solid support, washed, and cleaved off the support for mass spectrometric analysis, the temporary linkage can be such that it is cleaved under the conditions of mass spectrometry, i.e., a photocleavable bond such as a charge transfer complex or a stable organic radical. Furthermore, the linkage can be formed with L' being a quaternary ammonium group. In this case, preferably, the surface of the solid support carries negative charges which repel the negatively charged nucleic acid backbone and thus facilitates desorption. Desorption will take place either by the heat created by the laser pulse and/or, depending on L,' by specific absorption of laser energy which is in resonance with the L' chromophore. The functionalities, L and L,' can also form a charge transfer complex and thereby form the temporary L-L' linkage. Various examples for appropriate functionalities with either acceptor or donator properties are depicted without limitation herein. Since in many cases the "charge-transfer band" can be determined by UV/vis spectrometry (see e.g. Organic Charge Transfer Complexes by R. Foster, Academic Press, 1969), the laser energy can be tuned to the corresponding energy of the charge-transfer wavelength and, thus, a specific desorption off the solid support can be initiated. Those skilled in the art will recognize that several combinations can serve this purpose and that the donor functionality can be either on the solid support or coupled to the nested Sanger DNA/RNA fragments or vice versa.

In yet another approach, the temporary linkage L-L' can be generated by homolytically forming relatively stable radicals. As described herein, a combination of the approaches using charge-transfer complexes and stable organic radicals is shown. Here, the nested Sanger DNA/RNA fragments are captured via the formation of a charge transfer complex. Under the influence of the laser pulse, desorption (as discussed above) as well as ionization will take place at the radical position. In other examples described herein, under the influence of the laser pulse, the L-L' linkage will be cleaved and the nested Sanger DNA/RNA fragments desorbed and subsequently ionized at the radical position formed. Those skilled in the art will recognize that other organic radicals can be selected and that, in relation to the dissociation energies needed to homolytically cleave the bond between them, a corresponding laser wavelength can be selected (see e.g. Reactive Molecules by C. Wentrup, John Wiley & Sons, 1984). In yet another approach, the nested Sanger DNA/RNA fragments are captured via Watson-Crick base pairing to a solid support-bound oligonucleotide complementary to either the sequence of the nucleic acid primer or the tag oligonucleotide sequence. The duplex formed will be cleaved under the influence of the laser pulse and desorption can be initiated. The solid support-bound base sequence can be presented through natural oligoribo- or oligodeoxyribonucleotide as well as analogs (e.g. thio-modified phosphodiester or phosphotriester backbone) or employing oligonucleotide mimetics such as PNA analogs (see e.g. Nielsen et al., Science, 254, 1497 (1991)) which render the base sequence less susceptible to enzymatic degradation and hence increases overall stability of the solid support-bound capture base sequence. With appropriate bonds, L-L', a cleavage can be obtained directly with a laser tuned to the energy necessary for bond cleavage. Thus, the immobilized nested Sanger fragments can be directly ablated during mass spectrometric analysis.

1.4.1.3.1 Conditioning

Prior to mass spectrometric analysis, it may be useful to "condition" nucleic acid molecules, for example to decrease the laser energy required for volatization, to minimize fragmentation or to otherwise increase the sensitivity of mass spectrometeric detection. For example, nucleic acids can be "conditioned" by adding positive or negative charges, i.e. charge tags (CTs). CTs increase the mass spectrometer detection sensitivity by increasing the degree of ionization during the mass spectrometric (e.g.MALDI) process. A CT can be linked either to the external 3' or 5' position or internally e.g. at the 2' position or at the base, e.g. at C-5 in uracil, C-5 methyl group of thymine, C-5 at cytosine, at $C^7$ or $C^8$ guanine, adenine and hypoxanthine or at the phosphate ester moiety. Charge tags, CTs, can function molecules with permanent (i.e. pH-independent) ionization, such as:

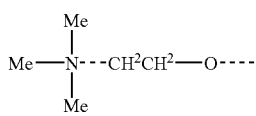

or molecules which generate a positive charge upon MALD1 and which are stabilized by delocalization of the positive charge by mesomeric effects in unsaturated and/or aromatic systems such as:

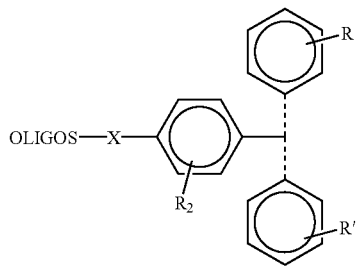

wherein, R, R', R'=H,OA1 (wherein A1=e.g. lower alky], methyl, ethyl, propyl), $NO_2$,CN, $CO_2H$, $CO_2$ active ester, or halogen; and X=—O—, —NH—, —S—, C=O, OCO either in the para or meta position.

For example, the positive charge of a trityl cation is produced during MALDI by the removal of a moiety such as: —OR, where R=a lower alkyl, or an anion such as $ClO_4$, $SbF_6$—, $BF_4$—and the like.

In an alternative scheme, the trityl group is used to anchor the oligonucleotide to a solid support via the tertiary carbon and this bond is cleaved during mass spectrometry (e.g. MALDI), leaving a positive charge on the desorbing and high vacuum flying oligonucleotide.

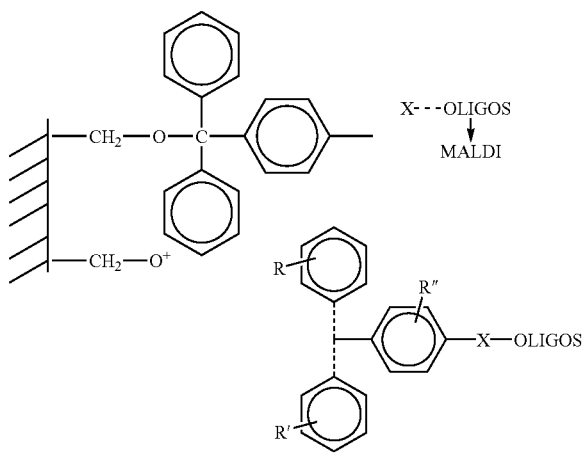

One of skill in the art can readily appreciate several variations to the schemes described above. In addition to employing the charge tag array alone, one of skill in the art can employ a charge tag array in conjunction with another conditioning means. Particularly preferred means to be used in conjunction with the CT include treating the phosphodiester bond with trialkylsilyl halides or the phosphomonothiodiester bond with alkyliodides to render the polyanionic backbone neutral.

1.4.1.3.1.1 Modification of Phosphodiester Backbone of Nucleic Acid Molecule

Another example of conditioning is modification of the phosphodiester backbone of the nucleic acid molecule (e.g. cation exchange), which can be useful for eliminating peak broadening due to a heterogeneity in the cations bound per nucleotide unit. In addition, a nucleic acid molecule can be contacted with an alkylating agent such as alkyliodide, iodoacetamide, 13-iodoethanol, or 2,3-epoxy-1-propanol, the monothio phosphodiester bonds of a nucleic acid molecule can be transformed into a phosphotriester bond. Likewise, phosphodiester bonds may be transformed to uncharged derivatives employing trialkylsilyl chlorides. Further conditioning involves incorporating nucleotides which reduce sensitivity for depurination (fragmentation during MS) such as N7- or N9-deazapurine nucleotides, or RNA building blocks or using oligonucleotide triesters or incorporating phosphorothioate functions which are alkylated or employing oligonucleotide mimetics such as PNA.

Modification of the phosphodiester backbone can be accomplished by, for example, using alpha-thio modified nucleotides for chain elongation and termination. With alkylating agents such as akyliodides, iodoacetarnide, β-iodoethanol, 2,3-epoxy-1-propanol, the monothio phosphodiester bonds of the nested Sanger fragments are transformed into phosphotriester bonds. Multiplexing by mass modification in this case is obtained by mass-modifying the nucleic acid primer (UP) or the nucleoside triphosphates at the sugar or the base moiety. To those skilled in the art, other modifications of the nested Sanger fragments can be envisioned. In one embodiment of the invention, the linking chemistry allows one to cleave off the so-purified nested DNA enzymatically, chemically or physically. By way of example, the L-L' chemistry can be of a type of disulfide bond (chemically cleavable, for example, by mcrcaptoethanol or dithioerythrol), a biotin/streptavidin system, a heterobifunctional derivative of a trityl ether group (K6ster et al., "A Versatile Acid-Labile Linker for Modification of Synthetic Biomolecules," Tetrahedron Letters 31, 7095 (1990)) which can be cleaved under mildly acidic conditions, a levulinyl group cleavable under almost neutral conditions with a hydrazinium/acetate buffer, an arginine- arginine or lysine-lysine bond cleavable by an endopeptidase enzyme like trypsin or a pyrophosphate bond cleavable by a pyrophosphatase, a photocleavable bond which can be, for example, physically cleaved and the like. Optionally, another cation exchange can be performed prior to mass spectrometric analysis. In the instance that an enzyme-cleavable bond is utilized to immobilize the nested fragments, the enzyme used to cleave the bond can serve as an internal mass standard during MS analysis.

1.4.1.3.2 Purification Process

The purification process and/or ion exchange process can be carried out by a number of other methods instead of, or in conjunction with, immobilization on a solid support. For example, the base-specifically terrainated products can be separated from the reactants by dialysis, filtration (including ultrafiltration), and chromatography.

Likewise, these techniques can be used to exchange the cation of the phosphate backbone with a counter-ion which reduces peak broadening.

The base-specifically terminated fragment families can be generated by standard Sanger sequencing using the Large Klenow fragment of E. coli DNA polymerase I, by Sequenase, Taq DNA polymerase and other DNA polymerases suitable for this purpose, thus generating nested DNA fragments for the mass spectrometric analysis. It is, however, part of this invention that base-specifically terminated RNA transcripts of the DNA fragments to be sequenced can also be utilized for mass spectrometric sequence determination. In this case, various RNA polymerases such as the SP6 or the T7 RNA polymerase can be used on appropriate vectors containing, for example, the SP6 or the T7 promoters (e.g. Axelrod et al., "Transcription from Bacteriophage T7 and SP6 RNA Polymerase Promoters in the Presence of 3' Deoxyribonucleoside 5' triphosphate Chain Terminators," Biochemistry 24, 5716–23 (1985)). In this case, the unknown DNA sequence fragments are inserted downstream from such promoters. Transcription can also be initiated by a nucleic acid primer (Pitulle et al., "Initiator Oligonucleotides for the Combination of Chemical and Enzymatic RNA Synthesis," Gene 112, 101–105 (1992)) which carries, as one embodiment of this invention, appropriate linking functionalities, L, which allow the immobilization of the nested RNA fragments, as outlined above, prior to mass spectrometric analysis for purification and/or appropriate modification and/or conditioning.

1.4.1.3.3 Immobilization Process

For this immobilization process of the DNA/RNA sequencing products for mass spectrometric analysis, various solid supports can be used, e.g., beads (silica gel, controlled pore glass, magnetic beads, Sephadex/Sepharose beads, cellulose beads, etc.), capillaries, glass fiber filters, glass surfaces, metal surfaces or plastic material. Examples of useful plastic materials include membranes in filter or microtiter plate formats, the latter allowing the automation of the purification process by employing microtiter plates which, as one embodiment of the invention, carry a permeable membrane in the bottom of the well functionalized with L'. Membranes can be based on polyethylene, polypropylene, polyamide, polyvinylidenedifluoride and the like. Examples of suitable metal surfaces include steel, gold, silver, aluminum, and copper. After purification, cation exchange, and/or modification of the phosphodiester backbone of the L-L' bound nested Sanger fragments, they can be cleaved off the solid support chemically, enzymatically or physically. Also, the L-L' bound fragments can be cleaved from the support when they are subjected to mass spectrometric analysis by using appropriately chosen L-L linkages and corresponding laser energies/intensities as described above and herein.

1.4.1.4 Data Analysis (ES, MALDI)

The highly purified, four base-specifically terminated DNA or RNA fragment families are then analyzed with regard to their fragment lengths via determination of their respective molecular weights by MALDI or ES mass spectrometry.

For ES, the samples, dissolved in water or in a volatile buffer, are injected either continuously or discontinuously into an atmospheric pressure ionization interface (API) and then mass analyzed by a quadrupole. With the aid of a computer program, the molecular weight peaks are searched for the known molecular weight of the nucleic acid primer (UP) and determined which of the four chain terminating nucleotides has been added to the UP. This represents the first nucleotide of the unknown sequence. Then, the second, the third, the n extension product can be identified in a similar manner and, by this, the nucleotide sequence is assigned. The generation of multiple ion peaks which can be obtained using ES mass spectrometry can increase the accuracy of the mass determination.

1.4.1.5 Process for Multiplex Mass Spectrometric DNA Sequencing Employing Mass Modiefied Reagents As illustrative embodiments of this invention, three different basic processes for multiplex mass spectrometric DNA sequencing employing the described mass-modified reagents are described below:

A) Multiplexing by the use of mass-modified nucleic acid primers (UP) for Sanger DNA or RNA sequencing, B) Multiplexing by the use of mass-modified nucleoside triphosphates as chain elongators and/or chain terminators for Sanger DNA or RNA sequencing, and C) Multiplexing by the use of tag probes which specifically hybridize to tag sequences which are integrated into part of the four Sanger DNA/RNA base-specifically terminated fragment families. Mass modification here can be achieved as described hereing, or alternately, by designing different oligonucleotide sequences having the same or different length with unmodified nucleotides which, in a predetermined way, generate appropriately differentiated molecular weights.

The process of multiplexing by mass-modified nucleic acid primers (UP) is illustrated by way of example herein for mass analyzing four different DNA clones simultaneously. The first reaction mixture is obtained by standard Sanger DNA sequencing having unknown DNA fragment 1 (clone 1) integrated in an appropriate vector (e.g., M13mp18), employing an unmodified nucleic acid primer $UP^0$, and a standard mixture of the four unmodified deoxynucleoside triphosphates, $dNTP^0$ and with 1/10th of one of the four dideoxynucleoside triphosphates, ddNTP. A second reaction mixture for DNA fragment 2 (clone 2) is obtained by employing a mass-modified nucleic acid primer $UP^1$ and, as before, the four unmodified nucleoside triphosphates, 0 dNTP, containing in each separate Sanger reaction $1/10^{th}$ of the chain-terminating unmodified dideoxynucleoside triphosphates ddNTP. In the other two experiments, the four Sanger reactions have the following compositions: DNA fragment 3 (clone 3 ), $UP^2$, $dNTP^0$, $ddNTP^0$ and DNA fragment 4 (clone 4), $UP^3$, $dNTP^0$, $ddNTP^0$. For mass spectrometric DNA sequencing, all base-specifically terminated reactions of the four clones are pooled and mass analyzed. The various mass peaks belonging to the four dideoxy-terminated (e.g., ddT-terminated) fragment families are assigned to specifically elongated and ddT-terminated fragments by searching (such as by a computer program) for the known molecular ion peaks of $UP^0$, $UP^1$, $Up^2$ and $UP^3$ extended by either one of the four dideoxynucleoside triphosphates, $UP^0$ $ddN^0$, $UP^1$ $ddN^0$, $UP^2$ $ddN^0$ and $UP^3$-$ddN^0$. In this way, the first nucleotides of the four unknown DNA sequences of clone 1 to 4 are determined. The process is repeated, having memorized the molecular masses of the four specific first extension products, until the four sequences are assigned. Unambiguous mass/sequence assignments are possible even in the worst case scenario in which the four mass-modified nucleic acid primers are extended by the same dideoxynucleoside triphosphate, the extension products then being, for example, $UP^0$ ddT, $UP^1$-ddT, $UP^2$ -ddT and $UP^3$ -ddT, which differ by the known mass increment differentiating the four nucleic acid primers. In another embodiment of this invention, an analogous technique is employed using different vectors containing, for example, the SP6 and/or T7 promoter sequences, and performing transcription with the nucleic acid primers $UP^0$, $UP^1$, $Up^2$ and $UP^3$ and either an RNA polymerase (e.g., SP6 or T7 RNA polymerase) with chain-elongating and terminating unmodified nucleoside triphosphates $NTP^0$ and 3'-$dNTP^0$. Here, the DNA sequence is being determined by Sanger RNA sequencing.

Illustrated herein is the process of multiplexing by mass-modified chain-elongating or/and terminating nucleoside triphosphates in which three different DNA fragments (3 clones) are mass analyzed simultaneously. The first DNA Sanger sequencing reaction (DNA fragment 1, clone 1) is the standard mixture employing unmodified nucleic acid primer $UP^0$, $dNTP^0$ and in each of the four reactions one of the four $ddNTP^0$. The second (DNA fragment 2, clone 2) and the third (DNA fragment 3, clone 3) have the following contents: $UP^0$, $dNTP^0$, $ddNTP^1$ and $UP^0$, $dNTP^0$, $ddNTP^2$, respectively. In a variation of this process, an amplification of the mass increment in mass-modifying the extended DNA fragments can be achieved by either using an equally mass-modified deoxynucleoside triphosphate (i.e., $dNTP^1$, $dNTP^2$) for chain elongation alone or in conjunction with the homologous equally mass-modified dideoxynucleoside triphosphate. For the three clones depicted above, the contents of the reaction mixtures can be as follows: either $UP^0/dNTP^0/ddNTP^0$, $UP^0/dNTP^1/ddNTP^0$ and $UP^0/dNTP^2/ddNTP^0$ or $UP^0/dNTP^0/ddNTP^0$, $UP^0/dNTP^1/ddNTP^1$ and $UP^0/dNTP^2/ddNTP^2$. As described above, DNA sequencing can be performed by Sanger RNA sequencing employing unmodified nucleic acid primers, UP, and an appropriate mixture of chain-elongating and terminating nucleoside triphosphates. The mass-modification can be again either in the chain-terminating nucleoside triphosphate alone or in conjunction with mass-modified chain-elongating nucleoside triphosphates. Multiplexing is achieved by pooling the three base-specifically terminated sequencing reactions (e.g., the ddTTP terminated products) and simultaneously analyzing the pooled products by mass spectrometry. Again, the first extension products of the known nucleic acid primer sequence are assigned, e.g., via a computer program. Mass/sequence assignments are possible even in the worst case in which the nucleic acid primer is extended/terminated by the same nucleotide, e.g., ddT, in all three clones. The following configurations thus obtained can be well differentiated by their different mass modifications: $UP^0\ ddT^0$, $UP^0\ ddT^1$, $UP^0\ ddT^2$.

In yet another embodiment of this invention, DNA sequencing by multiplex mass spectrometry can be achieved by cloning the DNA fragments to be sequenced in "plex-vectors" containing vector specific "tag sequences" as described (Köster et al., "Oligonucleotide Synthesis and Multiplex DNA Sequencing Using Chemiluminescent Detection," Nucleic Acids Re. Symposium Ser. No. 24, 318–321 (1991)); then pooling clones from different plex-vectors for DNA preparation and the four separate Sanger sequencing reactions using standard $dNTP^0/ddNTP^0$ and nucleic acid primer $UP^0$ purifying the four multiplex fragment families via linking to a solid support through the linking group, L, at the 5'-end of $UP^0$; washing out all by-products, and cleaving the purified multiplex DNA fragments off the support or using the L-L' bound nested Sanger fragments as such for mass spectrometric analysis as described above; performing de-multiplexing by one-by-one hybridization of specific "tag probes"; and subsequently analyzing by mass spectrometry. As a reference point, the four base-specifically terminated multiplex DNA fragment families are run by the mass spectrometer and all $ddT^0$, $ddA\ ddC$ and $ddG^0$ terminated molecular ion peaks are respectively detected and memorized. Assignment of, for example, $ddT^0$ terminated DNA fragments to a specific fragment family is accomplished by another mass spectrometric analysis after hybridization of the specific tag probe (TP) to the corresponding tag sequence contained in the sequence of this specific fragment family.

Only those molecular ion peaks which are capable of hybridizing to the specific tag probe are shifted to a higher molecular mass by the same known mass increment (e.g. of the tag probe). These shifted ion peaks, by virtue of all hybridizing to a specific tag probe, belong to the same fragment family. For a given fragment family, this is repeated for the remaining chain terminated fragment families with the same tag probe to assign the complete DNA sequence. This process is repeated i–I times corresponding to i clones multiplexed (the i-th clone is identified by default).

The differentiation of the tag probes for the different multiplexed clones can be obtained just by the DNA sequence and its ability to Watson-Crick base pair to the tag sequence. It is well known in the art how to calculate stringency conditions to provide for specific hybridization of a given tag probe with a given tag sequence (see, for example, Molecular Cloning: A laboratory manual 2ed, ed. by Sambrook, Fritsch and Maniatis (Cold Spring Harbor Laboratory Press: NY, 1989, Chapter 11). Furthermore, differentiation can be obtained by designing the tag sequence for each plex-vector to have a sufficient mass difference so as to be unique just by changing the length or base composition or by mass-modifications. In order to keep the duplex between the tag sequence and the tag probe intact during mass spectrometric analysis, it is another embodiment of the invention to provide for a covalent attachment mediated by, for example, photoreactive groups such as psoralen and ellipticine and by other methods known to those skilled in the art (see, for example, Helene et al., Nature 344, 358 (1990) and Thuong et at. "Oligonucleotides Attached to Intercalators, Photoreactive and Cleavage Agents" in F. Eckstein, Oligonucleotides and Analogues A Practical Approach, IRL Press, Oxford 1991, 283–306).

The DNA sequence is unraveled again by searching for the lowest molecular weight molecular ion peak corresponding to the known $UP^0$ -tag sequence/tag probe molecular weight plus the first extension product, e.g., $ddT^0$, then the second, the third, etc.

In a combination of the latter approach with the previously described multiplexing processes, a further increase in multiplexing can be achieved by using, in addition to the tag probe/tag sequence interaction, mass-modified nucleic acid primers and/or mass-modified deoxynucleoside, $dNTP^{0-i}$, and/or dideoxynucleoside triphosphates, $ddNTP^{0-i}$. Those skilled in the art will realize that the tag sequence/tag probe multiplexing approach is not limited to Sanger DNA sequencing generating nested DNA fragments with DNA polymerases. The DNA sequence can also be determined by transcribing the unknown DNA sequence from appropriate promoter-containing vectors (see above) with various RNA polymerases and mixtures of $NTP^{0-I}\ 3'\ dNTP^{0-1}$, thus generating nested RNA fragments.

In yet another embodiment of this invention, the mass-modifying functionality can be introduced by a two or multiple step process. In this case, the nucleic acid primer, the chain-elongating or terminating nucleoside triphosphates and/or the tag probes are, in a first step, modified by a precursor functionality such as azido, $-N_3$, or modified with a functional group in which the R in XR is H thus providing temporary functions, e.g., but not limited to $-OH$, $-NH_2$, $-NHR$, $-SH$, $-NCS$, $-OCO(CH_2)$ $rCOOH$ (r=1–20), $-NHCO(CH_2)rCOOH$ (r=1–20), $-OSO_2OH$, $-OCO(CH_2)r'$(r=1–20), $-OP(O-Alkyl)N$ $(Alkyl)_2$. These less bulky functionalities result in better substrate properties for the enzymatic DNA or RNA synthesis reactions of the DNA sequencing process. The appropriate mass-modifying functionality is then introduced after the generation of the nested base-specifically terminated DNA or RNA fragments prior to mass spectrometry. Several examples of compounds which can serve as mass-modifying functionalities are depicted herein without limiting the scope of this invention.

1.4.1.6 Kits for Sequencing Nucleic Acid by Mass Spectrometry

Another aspect of this invention concerns kits for sequencing nucleic acids by mass spectrometry which include combinations of the above-described sequencing reactants. For instance, in one embodiment, the kit comprises reactants for multiplex mass spectrometric sequencing of several different species of nucleic acid. The kit can include a solid support having a linking functionality (L1) for immobilization of the base-specifically terminated products; at least one nucleic acid primer having a linking group (L) for reversibly and temporarily linking the primer and solid support through, for example, a photocleavable bond; a set of chain-elongating nucleotides (e. g., dATP, dCTP, dGTP and dTTP, or ATP, CTP, GTP and UTP); a set of chain-terminating nucleotides (such as 2',3'-dideoxynucleotides for DNA synthesis or 3' deoxynucleotides for RNA synthesis); and an appropriate polymerase for synthesizing complementary nucleotides. Primers and/or terminating nucleotides can be mass-modified so that the base-specifically terminated fragments generated from one of the species of nucleic acids to be sequenced can be distinguished by mass spectrometry from all of the others. Alternative to the use of mass-modified synthesis reactants, a set of tag probes (as described above) can be included in the kit. The kit can also include appropriate buffers as well as instructions for performing multiplex mass spectrometry to concurrently sequence multiple species of nucleic acids.

In another embodiment, a nucleic acid sequencing kit can comprise a solid support as described above, a primer for initiating synthesis of complementary nucleic acid fragments, a set of chain-elongating nucleotides and an appropriate polymerase. The mass-modified chain-terminating nucleotides are selected so that the addition of one of the chain terminators to a growing complementary nucleic acid can be distinguished by mass spectrometry.

1.4.2 A Method and System for Determining the Sequence of Genomes 1.4.2.1 A Process for Directly Amplifying and Base Specifically Terminating a Nucleic Acid Molecule for Sequencing In general, the invention features a process for directly amplifying and base specifically terminating a nucleic acid molecule. According to the process of the invention, a combined amplification and termination reaction is performed on a nucleic acid template using: i) a complete set of chain-elongating nucleotides; ii) at least one chain-terminating nucleotide; and (iii) a first DNA polymerase, which has a relatively low affinity towards the chain terminating nucleotide; and (iv) a second DNA polymerase, which has a relatively high affinity towards the chain terminating nucleotide, so that polymerization by the enzyme with relatively low affinity for the chain terminating nucleotide leads to amplification of the template, whereas the enzyme with relatively high affinity for the chain terminating nucleotide terminates the polymerization and yields sequencing products.

The combined amplification and sequencing can be based on any amplification procedure that employs an enzyme with polynucleotide synthetic ability (e.g. polymerase). One preferred process, based on the polymerase chain reaction (PCR), is comprised of the following three thermal steps: 1) denaturing a double stranded (ds) DNA molecule at an appropriate temperature and for an appropriate period of time to obtain the two single stranded (ss) DNA molecules (the template: sense and antisense strand); 2) contacting the template with at least one primer that hybridizes to at least one ss DNA template at an appropriate temperature and for an appropriate period of time to obtain a primer containing ss DNA template; 3) contacting the primer containing template at an appropriate temperature and for an appropriate period of time with: (i) a complete set of chain elongating nucleotides, (ii) at least one chain terminating nucleotide, (iii) a first DNA polymerase, which has a relatively low affinity towards the chain terminating nucleotide; and (iv) a second DNA polymerase, which has a relatively high affinity towards the chain terminating nucleotide.

Steps 1)–3) can be sequentially performed for an appropriate number of times (cycles) to obtain the desired amount of amplified sequencing ladders. The quantity of the base specifically terminated fragment desired dictates how many cycles are performed. Although an increased number of cycles results in an increased level of amplification, it may also detract from the sensitivity of a subsequent detection. It is therefore generally undesirable to perform more than about 50 cycles, and is more preferable to perform less than about 40 cycles (e.g. about 20–30 cycles). In a preferred embodiment, the first denaturation step is performed at a temperature in the range of about 85° C. to about 100° C. (most preferably about 92° C. to about 96° C.) for about 20 seconds (s) to about 2 minutes (most preferably about 30 s–1 minute). The second hybridization step is preferably performed at a temperature, which is in the range of about 40° C. to about 80° C. (most preferably about 45° C. to about 72° C.) for about 20 s to about 2 minutes (most preferably about 30s–1 minute). The third, primer extension step is preferably performed at about 65° C. to about 80° C. (most preferably about 70° C. to about 74° C.) for about 30 s to about 3 minutes (most preferably about 1 to about 2 minutes).

In order to obtain sequence information on both the sense and antisense strands of a DNA molecule simultaneously, each of the single stranded sense and antisense templates generated from the denaturing step can be contacted with appropriate primers in step 2), so that amplified and chain terminated nucleic acid molecules generated in step 3), are complementary to both strands.

Another preferred process for simulataneously amplifying and chain terminating a nucleic acid sequence is based on strand displacement amplification (SDA) (G. Terrance Walker et al., Nucleic Acids Res. 22, 2670–77 (1994); European Patent Publication Number 0 684 315 entitled Strand Displacement Amplification Using Thermophilic Enzymes). In essence, this process involves the following three steps, which altogether comprise a cycle: 1) denaturing a double stranded (ds) DNA molecule containing the sequence to be amplified at an appropriate temperature and for an appropriate period of time to obtain the two single stranded (ss) DNA molecules (the template: sense and antisense strand); 2) contacting the template with at least one primer (P), that contains a recognition/cleavage site for a restriction endonuclease (RE) and that hybridizes to at least one ss DNA template at an appropriate temperature and for an appropriate period of time to obtain a primer containing ss DNA template; 3) contacting the primer containing template at an appropriate temperature and for an appropriate period of time with: (i) a complete set of chain elongating nucleotides; (ii) at least one chain terminating nucleotide, (iii) a first DNA polymerase, which has a relatively low affinity towards the chain terminating nucleotide; (iv) a second DNA polymerase, which has a relatively high affinity towards the chain terminating nucleotide; and (v) an RE that nicks the primer recognition/cleavage site.

Steps 1)–3) can be sequentially performed for an appropriate number of times (cycles) to obtain the desired amount of amplified sequencing ladders. As with the PCR based process, the quantity of the base specifically terminated fragment desired dictates how many cycles are performed. Preferably, less than 50 cycles, more preferably less than about 40 cycles and most preferably about 20 to 30 cycles are performed.

The amplified sequencing ladders obtained as described above, can be separated and detected and/or quantitated using well established methods, such as polyacrylamide gel electrophoresis (PAGE), or capillary zone electrophoresis (CZE) (Jorgenson et al., J. Chromatography 352, 337 (1986); Gesteland et al., Nucleic Acids Res. L8, 1415–1419 (1990)); or direct blotting electrophoresis (DBE) (Beck and Pohl, EMBO J, vol. 3: Pp. 2905–2909 (1984)) in conjunction with, for example, colorimetry, fluorimetry, chemiluminescence and radioactivity.

Dye-terminator chemistry can be employed in the combined amplification and sequencing reaction to enable the simultaneous generation of forward and reverse sequence ladders, which can be separated based on the streptavidin-biotin system when one biotinylated primer is provided.

Depicted herein is a scheme for the combined amplification and sequencing using two polymerases and dye-labeled chain terminating nucleotide (ddNTP) for detection and two reverse oriented primers. A means of separation for the simultaneously generated forward and reverse sequence ladders is shown. Step A represents the exponential amplification of a target sequence by the polymerase with a low affinity for ddNTPs. One of the sequence specific oligonucleotide primers is biotinylated. Step B represents the generation of a sequence ladder either from the original template or the simultaneously generated amplification product carried out by the polymerase with a high affinity for ddNTPs. After completion of the reaction, the products are incubated with a streptavidin coated solid support (Step C). Biotinylated forward sequencing products and reverse products hybridized to the forward template are immobilized. In order to obtain readable sequence information, the forward and reverse sequence ladders are separated in Step D. The immobilized strands are washed and separated by denaturation with ammonium hydroxide at room temperature. The non-biotinylated reverse sequencing products are removed from the beads with ammonium hydroxide supernatant during this procedure. The biotinylated forward sequencing products remain immobilized to the beads and are re-solubilized with ammonium hydroxide at 60° C. After ethanol precipitation, both sequencing species can be resuspended in loading dye and run on an automated sequencer, for example.

When mass spectrometry is used in conjunction with the direct amplification and chain termination processes, the sequencing ladders can be directly detected without first being separated using several mass spectrometer formats.

Amenable formats for use in the invention include ionization techniques such as matrix-assisted laser desorption (MALDI), continuous or pulsed electrospray (ESI) and related methods (e.g. Ionspray or Thermospray), and massive cluster impact (MSI); these ion sources can be matched with a detection format, such as linear or reflectron time-of-flight (TOF), single or multiple quadrupole, single or multiple magnetic sector, Fourier Transform ion cyclotron resonance (FTICR), ion trap, or combinations of these to give a hybrid detector (e.g. ion trap-TOF). For ionization, numerous matrix/wavelength combinations (MALDI) or solvent combinations (ESI) can be employed.

The above-described process can be performed using virtually any nucleic acid molecule as the source of the DNA template. For example, the nucleic acid molecule can be: a) single stranded or double stranded; b) linear or covalently closed circular in supercoiled or relaxed form; or c) RNA if combined with reverse transcription to generate a cDNA. For example, reverse transcription can be performed using a suitable reverse transcriptase (e.g. Moloney murine leukemia virus reverse transcriptase) using standard techniques (e.g. Kawasaki (1990) in PCR Protocols: A Guide to Methods and Applications, Innis et al., eds., Academic Press, Berkeley, CA pp21–27).

Sources of nucleic acid templates can include: a) plasmids (naturally occurring or recombinant); b) RNA- or DNA-viruses and bacteriophages (naturally occurring or recombinant); c) chromosomal or episomal replicating DNA (e. g. from tissue, a blood sample, or a biopsy); d) a nucleic acid fragment (e.g. derived by exonuclease, unspecific endonuclease or restriction endonuclease digestion or by physical disruption (e.g. sonication or nebulization)); and e) RNA or RNA transcripts like mRNAs.

The nucleic acid to be amplified and sequenced can be obtained from virtually any biological sample. As used herein, the term "biological sample" refers to any material obtained from any living source (e.g. human, animal, plant, bacteria, fungi, protist, virus). Examples of appropriate biological samples for use in the instant invention include: solid materials (e.g tissue, cell pellets, biopsies) and biological fluids (e.g. urine, blood, saliva, amniotic fluid, mouth wash, spinal fluid). The nucleic acid to be amplified and sequenced can be provided by unpurified whole cells, bacteria or virus.

Alternatively, the nucleic acid can first be purified from a sample using standard techniques, such as: a) cesium chloride gradient centrifugation; b) alkaline lysis with or without RNAse treatment; c) ion exchange chromatography; d) phenol/chloroform extraction; e) isolation by hybridization to bound oligonucleotides; f) gel electrophoresis and elution; alcohol precipitation and h) combinations of the above.

As used herein, the phrases "chain-elongating nucleotides" and "chain-terminating nucleotides" are used in accordance with their art recognized meaning. For example, for DNA, chain-elongating nucleotides include 2'-deoxyribonucleotides (e.g. dATP, dCTP, dGTP and dTTP) and chain-terminating nucleotides include 2', 3'-dideoxyribonucleotides, (e.g. ddATP, ddCTP, ddGTP, ddTTP). For RNA, chain-elongating nucleotides include ribonucleotides (e.g., ATP, CTP, GTP and UTP) and chain-terminating nucleotides include 3'-deoxyribonucleotides (e.g. 3'dA, 3'dC, 3'dG and 3'dU). A complete set of chain elongating nuclectides refers to dATP, dCTP, dGTP and dTTP. The term "nucleotide" is also well known in the art. For the purposes of this invention, nucleotides include nucleoside mono-, di-, and triphosphates. Nucleotides also include modified nucleotides, such as phosphorothioate nucleotides and deazapurine nucleotides. A complete set of chain-elongating nucleotides refers to four different nucleotides that can hybridize to each of the four different bases comprising the DNA template.

If the amplified sequencing ladders are to be detected by mass spectrometric analysis, it may be useful to "condition" nucleic acid molecules, for example to decrease the laser energy required for volatization and/or to minimize fragmentation. Conditioning is preferably performed while the sequencing ladders are immobilized. An example of conditioning is modification of the phosphodiester backbone of the nucleic acid molecule (e.g. cation "change), which can be useful for eliminating peak broadening due to a heterogeneity in the cations bound per nucleotide unit.

Contacting a nucleic acid molecule, which contains an -thio-nucleoside-triphosphate during polymerization with an alkylating agent such as akyliodide, iodoacetamide, -iodoethanol, or 2,3-epoxy-1-propanol, the monothio phosphodiester bonds of a nucleic acid molecule can be transformed into a phosphotriester bond. Further conditioning involves incorporating nucleotides which reduce sensitivity for depurination (fragmentation during MS), e.g. a purine analog such as N7- or N9-deazapurine nucleotides, and partial RNA containing oligodeoxynucleotide to be able to remove the unmodified primer from the amplified and modified sequencing ladders by RNAse or alkaline treatment. In DNA sequencing using fluorescent detection and gel electrophoretic separation, the N7 deazapurine nucleotides reduce the formation of secondary structure resulting in band compression from which no sequencing information can be generated.

1.4.2.2 The Use of Two Polymerase Enzymes Each Having Different Affinities for the Chain Terminating Nucleotides Critical to the novel process of the invention is the use of appropriate amounts of two different polymerase enzymes, each having a different affinity for the particular chain terminating nucleotide, so that polymerization by the enzyme with relatively low affinity for the chain terminating nucleotide leads to amplification whereas the enzyme with relatively high affinity for the chain terminating nucleotide terminates the polymerization and yields sequencing products. Preferably about 0.5 to about 3 units of polymerase is used in the combined amplification and chain termination reaction. Most preferably about 1 to 2 units is used. Particularly preferred polymerases for use in conjunction with PCR or other thermal amplification process are thermostable polymerases, such as Taq DNA polymerase (Boehringer Mannheim), AmpliTaq FS DNA polymerase (Perkin-Elmer), Deep Vent (exo-), Vent, Vent (exo-) and Deep Vent DNA polymerases (New England Biolabs), Thermo Sequenase (Amersham) or exo(-) Pseudococcusfuriosus (Pfu) DNA polymerase (Stratagene, Heidelberg Germany). AmpliTaq, Ultman, 9 degree Nm, Tth, Hot Tub, and Pyrococcusfuriosus. In addition, preferably the polymerase does not have 5'-3' exonuclease activity.

The process of the invention can be carried out using AmpliTaq FS DNA polymerase (Perkin-Elmer), which has a relatively high affinity and Taq DNA polymerase, which has a relatively low affinity for chain terminating nucleotides. Other appropriate polymerase pairs for use in the instant invention can be determined by one of skill in the art. (See e.g. S. Tabor and C. C. Richardson (1995) Proc. Nat. Acad. Sci. (USA), vol. 92: Pp. 6339–6343.) in addition to polymerases, which have a relatively high and a relatively low affinity to the chain terminating nucleotide, a third polymerase, which has proofreading capacity (e.g. Pyrococcus woesei (Pwo)) DNA polymerase may also be added to the amplification mixture to enhance the fidelity of amplification.

Oligonucleotide primers, for use in the invention, can be designed based on knowledge of the 5' and/or 3' regions of the nucleotide sequence to be amplified and sequenced, e.g., insert flanking regions of cloning and sequencing vectors (such as M13, pUC, phagemid, costaid). Optionally, at least one primer used in the chain extension and termination reaction can be linked to a solid support to facilitate purification of amplified product from primers and other reactants, thereby increasing yield or to separate the Sanger ladders from the sense and antisense template strand where simultaneous amplification-sequencing of both a sense and antisense strand of the template DNA has been performed.

Examples of appropriate solid supports include beads (silica gel, controlled pore glass, magnetic beads, Sephadex/Sepharose beads, cellulose beads, etc.), capillaries, flat supports such as glass fiber filters, glass surfaces, metal surfaces (steel, gold, silver, aluminum, and copper), plastic materials or membranes (polyethylene, polypropylene, polyamide, polyvinylidenedifluoride) or beads in pits of flat surfaces such as wafers (e.g. silicon wafers), with or without filter plates.

1.4.2.3 Immobilization Based on Hybridization

Immobilization can be accomplished, for example, based on hybridization between a capture nucleic acid sequence, which has already been immobilized to the support and a complementary nucleic acid sequence, which is also contained within the nucleic acid molecule containing the nucleic acid sequence to be detected. So that hybridization between the complementary nucleic acid molecules is not hindered by the support, the capture nucleic acid can include a spacer region of at least about five nucleotides in length between the solid support and the capture nucleic acid sequence. The duplex formed will be cleaved under the influence of the laser pulse and desorption can be initiated. The solid support-bound base sequence can be presented through natural oligoribo- or oligodeoxyribo-nucleotide as well as analogs (e.g. thio-modified phosphodiester or phosphotriester backbone) or employing oligonucleotide mimetics such as PNA analogs (see e.g. Nielsen et al., Science, 254, 1497 (1991)) which render the base sequence less susceptible to enzymatic degradation and hence increases overall stability of the solid support-bound capture base sequence.

1.4.2.4 Linkage

Alternatively, a target detection site can be directly linked to a solid support via a reversible or irreversible bond between an appropriate functionality (L') on the target nucleic acid molecule and an appropriate functionality (L) on the capture molecule. A reversible linkage can be such that it is cleaved under the conditions of mass spectrometry (i.e., a photocleavable bond such as a trityl ether bond or a charge transfer complex or a labile bond being formed between relatively stable organic radicals). Furthermore, the linkage can be formed with L' being a quaternary ammonium group, in which case, preferably, the surface of the solid support carries negative charges which repel the negatively charged nucleic acid backbone and thus facilitate the desorption required for analysis by a mass spectrometer. Desorption can occur either by the heat created by the laser pulse and/or, depending on L,' by specific absorption of laser energy which is in resonance with the L' chromophore.

By way of example, the L-L' chemistry can be of a type of disulfide bond (chemically cleavable, for example, by mercaptoethanol or dithioerythrol), a biotin/streptavidin system, a heterobifluctional derivative of a trityl ether group (Koster et al., "A Versatile Acid-Labile Linker for Modification of Synthetic Biomolecules," Tetrahedron Letters 31, 7095 (1990)) which can be cleaved under mildly acidic conditions as well as under conditions of mass spectrometry, a levulinyl group cleavable under almost neutral conditions with a hydrazinium/acetate buffer, an arginine-arginine or lysine-lysine bond cleavable by an endopeptidase enzyme like trypsin or a pyrophosphate bond cleavable by a pyrophosphatase or a ribonucleotide in between a deoxynucleotide sequence cleavable by an RNAse or alkali.

The functionalities, L and L,' can also form a charge transfer complex and thereby form the temporary L-L' linkage. Since in many cases the "charge-transfer band" can be determined by UV/vis spectrometry (see e.g. Organic Charge Transfer Complexes by R. Foster, Academic Press, 1969), the laser energy can be tuned to the corresponding energy of the charge-transfer wavelength and, thus, a specific desorption off the solid support can be initiated. Those skilled in the art will recognize that several combinations can serve this purpose and that the donor functionality can be either on the solid support or coupled to the nucleic acid molecule to be detected or vice versa.

In yet another approach, a reversible L-L' linkage can be generated by homolytically forming relatively stable radicals. Under the influence of the laser pulse, desorption (as discussed above) as well as ionization will take place at the radical position. Those skilled in the art will recognize that other organic radicals can be selected and that, in relation to the dissociation energies needed to homolytically cleave the bond between them, a corresponding laser wavelength can be selected (see e.g. Reactive Molecules by C. Wentrup, John Wiley & Sons, 1984). An anchoring function L' can also be incorporated into a target capturing sequence by using appropriate primers during an amplification procedure, such as PCR, LCR or transcription amplification.

For certain applications, it may be useful to simultaneously amplify and chain terminate more than one (mutated) loci on a particular captured nucleic acid fragment (on one spot of an array) or it may be useful to perform parallel processing by using oligonucleotide or oligonucleotide mimetic arrays on various solid supports.

"Multiplexing" can be achieved either by the sequence itself (composition or length) or by the introduction of mass-modifying functionalities into the primer oligonucleotide. Such multiplexing is particularly useful in conjunction with mass spectrometric DNA sequencing or mobility modified gel based fluorescence sequencing.

1.4.2.5 Mass or Mobility Modification

Without limiting the scope of the invention, the mass or mobility modification can be introduced by using oligo/polyethylene glycol derivatives. The oligo/polyethylene glycols can also be monoalkylated by a lower alkyl such as methyl, ethyl, propyl, isopropyl, t-butyl and the like. Other chemistries can be used in the mass-modified compounds, as for example, those described recently in Oligonucleotides and Analogues—A Practical Approach, F. Eckstein, editor IRL Press, Oxford, 1991.

In yet another embodiment, various mass or mobility modifying functionalities, other than oligo/polyethylene glycols, can be selected and attached via appropriate linking chemistries. A simple modification can be achieved by using different alkyl, aryl or aralkyl moieties such as methyl, ethyl, propyl, isopropyl, t-butyl, hexyl, phenyl, substituted phenyl or benzyl. Yet another modification can be obtained by attaching homo- or heteropeptides to the nucleic acid molecule (e.g., primer) or nucleoside triphosphates. Simple oligoamides also can be used. Numerous other possibilities, in addition to those mentioned above, can be performed by one skilled in the art.

Different mass or mobility modified primers allow for multiplex sequencing via simultaneous detection of primer-modified Sanger sequencing ladders.

Mass or mobility modifications can be incorporated during the amplification process through nucleoside triphosphates or modified primers.

1.4.2.6 Kits for Amplified Base Specifically Terminated Fragments

Another aspect of this invention concerns kits for directly generating from a nucleic acid template, amplified base specifically terminated fragments. Such kits include combinations of the above-described reactants. For instance, in one embodiment, the kit can comprise: i) a set of chain-elongating nucleotides; ii) a set of chain-terminating nucleotides; and (iii) a first DNA polymerase, which has a relatively low affinity towards the chain terminating nucleotide; and (iv) a second DNA polymerase, which has a relatively high affinity towards the chain terminating nucleotide. The kit can also include appropriate solid supports for capture/purification and buffers as well as instructions for use.

For use with certain detection means, such as polyacrylamide gel electrophoresis (PAGE), detectable labels must be used in either the primer (typically at the 5'-end) or in one of the chain extending nucleotides, or chain terminating nucleotides.

Using radioisotopes such as $^{32}P$, $^{33}P$, or $^{31}S$ is still the most frequently used technique. After PAGE, the gels are exposed to X-ray films and silver grain exposure is analyzed.

1.4.3 Hybridization

Oligonucleotide arrays can be used in a wide variety of applications, including hybridization studies. In a hybridization study, the array can be exposed to a receptor (R) of interest. The receptor can be labelled with an appropriate label (*), such as fluorescein. The locations on the substrate where the receptor has bound are determined and, through knowledge of the sequence of the oligonucleotide probe at that location one can then determine, if the receptor is an oligonucleotide, the sequence of the receptor.

Sequencing by hybridization (SBH) is most efficiently practiced by attaching many probes to a surface to form an array in which the identity of the probe at each site is known. A labeled target DNA or RNA is then hybridized to the array, and the hybridization pattern is examined to determine the identity of all complementary probes in the array. Contrary to the teachings of the prior art, which teaches that mismatched probe/target complexes are not of interest, the present invention provides an analytical method in which the hybridization signal of mismatched probe/target complexes identifies or confirms the identity of the perfectly matched probe/target complexes on the array.

Arrays of oligonucleotides are efficiently generated for the hybridization studies using light-directed synthesis techniques.

1.4.3.1 Light Directed Synthesis

As discussed below, an array of all tetranucleotides was produced in sixteen cycles, which required only 4 hours to complete. Because combinatorial strategies are used, the number of different compounds on the array increases exponentially during synthesis, while the number of chemical coupling cycles increases only linearly. For example, expanding the synthesis to the complete set of $4^8$ (65,536) octanucleotides adds only 4 hours (or less) to the synthesis due to the 16 additional cycles required. Furthermore, combinatorial synthesis strategies can be implemented to generate arrays of any desired probe composition. For example, because the entire set of dodecamers ($4^{12}$) can be produced in 48 photolysis and coupling cycles or less (b" compounds requires no more than b×n cycles), any subset of the dodecamers (including any subset of shorter oligonucleotides) can be constructed in 48 or fewer chemical coupling steps. The number of compounds in an array is limited only by the density of synthesis sites and the overall array size. The present invention has been practiced with arrays with probes synthesized in square sites 25 microns on a side. At this resolution, the entire set of 65,536 octanucleotides can be placed in an array measuring only 0.64 cm$^2$. The set of 1,048,576 dodecanucleotides requires only a 2.56 cm$^2$ array at this individual probe site size.

The success of genome sequencing projects depends on efficient DNA sequencing technologies. Current methods are highly reliant on complex procedures and require substantial manual effort. SBH offers the potential for automating many of the manual efforts in current practice. Light-directed sythesis offers an efficient means for large scale production of miniaturized arrays not only for SBH but for many other applications as well.

Although oligonucleotide arrays can be used for primary sequencing applications, many diagnostic methods involve the analysis of only a few nucleotide positions in a target nucleic acid sequence. Because single base changes cause multiple changes in the hybridization pattern of the target on a probe array, the oligonucleotide arrays and methods of the present invention enable one to check the accuracy of previously elucidated DNA sequences, or to scan for changes or mutations in certain specific sequences within a target nucleic acid. The latter as is important, for example, for genetic disease, quality control, and forensic analysis. With an octanucleotide probe set, a single base change in a target nucleic acid can be detected by the loss of eight perfect hybrids, and the generation of eight new perfect hybrids. The single base change can also be detected through altered mismatch probe/target complex formation on the array. Perhaps even more surprisingly, such single base changes in a complex nucleic acid dramatically alter the overall hybridization pattern of the target to the array. According to the present invention such changes in the overall hybridization pattern are used to actually simplify the analysis.

The high information content of light-directed oligonucleotide arrays greatly benefits genetic diagnostic testing. Sequence comparisons of hundreds to thousands of different mutations can be assayed simultaneously instead of in a one-at-a-time format.

1.4.3.2 Arrays Constructed to Contain Genetic Markers

Arrays can also be constructed to contain genetic markers for the rapid identification of a wide variety of pathogenic organisms, and to study the sequence specificity of RNA/RNA, RNA/DNA, protein/RNA or protein/DNA, interactions. One can use non Watson-Crick oligonucleotides and novel synthetic nucleoside analogs for antisense, triple helix, or other applications. Suitably protected RNA monomers can be employed for RNA synthesis, and a wide variety of synthetic and non-naturally occurring nucleic acid analogues can be used, depending upon the motivations of the practitioner. See, e.g., PCT patent Publication Nos. 91/19813, 92/05285, and 92/14843, incorporated herein by reference. In addition, the oligonucleotide arrays can be used to deduce thermodynamic and kinetic rules governing the formation and stability of oligonucleotide complexes.

1.4.3.2.1 Hybridization of Targets to Surface Oligonucleotides

The support bound octanucleotide probes discussed above were hybridized to a target of 5'GCGTAGGC-fluorescein in the hybridization chamber by incubation for 15 minutes at 15° C.

The array surface was then interrogated with an epifluorescence microscope (488 nm argon ion excitation). The fluorescence intensity pattern matches the 800×1280 µm stripe used to direct the synthesis of the probe. Furthermore, the signal intensities are high (four times over the background of the glass substrate), demonstrating specific binding of the target to the probe.

The behavior of the target-probe complex was investigated by increasing the temperature of the hybridization solution. After a minute equilibration at each temperature, the substrate was scanned for signal. The duplex melted in the temperature range expected for the sequence under study ($T_m$~28° C. obtained from the rule $T_m=[2°(A+T)+4°(G+C)]$). The probes in the array were stable to temperature denaturation of the target-probe complex as demonstrated by rehybridization of target DNA.

1.4.3.2.2 Sequence Specificity of Target Hybridization

To demonstrate the sequence specificity of target hybridization, two different probes were synthesized in 800×1280 µm stripes. The probe S-3'-CGCATCCG was synthesized in stripes 1, 3 and 5. The probe S-3'-CGCTTCCG was synthesized in stripes 2, 4 and 6. The results of hybridizing a 5'-GCGTAGGC-fluorescein target to the substrate at 15° C. are depicted herein. Although the probes differ by only one internal base, the target hybridizes specifically to its complementary sequence (~500 counts above background in stripes 1, 3 and 5) with little or no detectable signal in positions 2, 4 and 6 (~10 counts).

1.4.3.2.3 Combinatorial Synthesis of, and Hybridization of a Nucleic Acid Target to, a Probe Matrix In a light-directed synthesis, the location and composition of products depends on the pattern of illumination and the order of chemical coupling reagents (see Fodor et al., Science (1991) 251:767–773, for a complete description). Consider the synthesis of 256 tetranucleotides. Mask 1 activates one fourth of the substrate surface for coupling with the first of four nucleosides in the first round of synthesis. In cycle 2, mask 2 activates a different quarter of the substrate for coupling with the second nucleoside. The process is continued to build four regions of mononucleotides. The masks of round 2 are perpendicular to those of round 1, and each cycle of round 2 generates four new dinucleotides. The process continues through round 2 to form sixteen dinucleotides. The masks of round 3 further subdivide the synthesis regions so that each coupling cycle generates 16 trimers. The subdivision of the substrate is continued through round 4 to form the tetranucleotides. The synthesis of this probe matrix can be compactly represented in polynomial notation as $(A+C+G+T)^4$. Expansion of this polynomial yields the 256 tetranucleotides.

The application of an array of 256 probes synthesized by light-directed combinatorial synthesis to generate a probe matrix is illustrated herein. The polynomial for this synthesis is given by: 3'-CG(A+G+C+T)$^4$CG. All possible tetranucleotides were synthesized flanked by CG at the 3'- and 5'-ends. Hybridization of target 5'-GCGGCGGC-fluorescein to this array at 15° C. correctly yielded the S-3'-CGCCGCCG complementary probe as the most intense position (2,698 counts). Significant intensity was also observed for the following mismatches: S-3'-CGCAGCCG (554 counts), S-3'-CGCCGACG (317 counts), S-3'-CGCCGTCG (272 counts), S-3'-CGACGCCG (242 counts), S-3'-CGTCGCCG (203 counts), S-3'-CGCCCCCG (180 counts), S-3'-CGCTGCCG (163 counts), S-3'-CGCCACCG (125 counts), and S-3'-CGCCTCCG (78 counts).

1.4.3.3 Mismatch Analysis 1.4.3.3.1 Arrays Used to Determine the Gene Sequence of Oligos of Length "n" Using Array of Probes of Shorter Length "k"

The arrays discussed herein can be utilized in the present method to determine the nucleic acid sequence of an oligonucleotide of length n using an array of probes of shorter length k. In a simple example, the target has a sequence 5'-XXYXY-3', where X and Y are complementary nucleic acids such as A and T or C and G. For discussion purposes, the example is simplified by using only two bases and very short sequences, but the technique can easily be extended to larger nucleic acids with, for example, all 4 RNA or DNA bases.

The sequence of the target is, generally, not known ab initio. One can determine the sequence of the target using the present method with an array of shorter probes. In this example, an array of all possible X and Y 4-mers is synthesized and then used to determine the sequence of a 5-mer target.

Initially, a "core" probe is identified. The core probe is exactly complementary to a sequence in the target using the mismatch analysis method of the present invention. The core probe is identified using one or both of the following criteria:

1. The core probe exhibits stronger binding affinity to the target than other probes, typically the strongest binding affinity of any probe in the array (that has not been identified as a core probe in a previous cycle of analysis).
2. Probes that are mismatched with the target, as compared to the core probe sequence, exhibit a characteristic pattern, discussed in greater detail below, in which probes that mismatch at the 3'- and 5'-end of the probe bind more strongly to the target than probes that mismatch at interior positions.

In this particular example, selection criteria #1 identifies a core 4-mer probe with the strongest binding affinity to the target that has the sequence 3'-YYXY. The probe 3'-YYXY (corresponding to the 5'-XXYX position of the target) is, therefore, chosen as the "core" probe.

Selection criteria #2 is utilized as a "check" to ensure the core probe is exactly complementary to the target nucleic acid.

The second selection criteria evaluates hybridization data (such as the fluorescence intensity of a labeled target hybridized to an array of probes on a substrate, although other techniques are well known to those of skill in the art) of probes that have single base mismatches as compared to the core probe. In this particular case, the core probe has been selected as S-3'-YYXY. The single base mismatched probes of this core probe are: S-3'-XYXY, S-3'-YXXY, S-3'-YYYY, and S-3'-YYXX. The binding affinity characteristics of these single base mismatches are utilized to ensure that a "correct" core has been selected, or to select the core probe from among a set of probes exhibiting similar binding affinities.

1.4.3.3.2 Binding Affinity vs. Mismatch Position

An illustrative, hypothetical plot of expected binding affintity versus mismatch position is provided herein. The binding affinity values (typically fluorescence intensity of labeled target hybridized to probe, although many other factors relating to affinity may be utilized) are all normalized to the binding affinity of S-3'-YYXY to the target, which is plotted as a value of 1. Because only two nucleotides are involved in this example, the value plotted for a probe mismatched at position 1 (the nucleotide at the 3'-end of the probe) is the normalized binding affinity of S-3'-XYXY. The value plotted for mismatch at position 2 is the normalized affinity of S-3'-YXXY. The value plotted for mismatch at position 3 is the normalized affinity of S-3'-YYYY, and the value plotted for mismatch position 4 is the normalized affinity of S-3'-YYYX. As noted above, "affinity" may be measured in a number of ways including, for example, the number of photon counts from fluorescence markers on the target.

The affinity of all three mismatches is lower than the core in this illustration. Moreover, the affinity plot shows that a mismatch at the 3'-end of the probe has less impact than a mismatch at the 51-end of the probe in this particular case, although this may not always be the case. Further, mismatches at the end of the probe result in less disturbance than mismatches at the center of the probe. These features, which result in a "smile" shaped graph when plotted, will be found in most plots of single base mismatch after selection of a "correct" core probe, or after accounting for a mismatched probe that is a core probe with respect to another portion of the target sequence. This information will be utilized in either selecting the core probe initially or in checking to ensure that an exactly matched core probe has been selected.

Of course, in certain situations, as noted in in the section above, identification of a core is all that is required such as in, for example, forensic or genetic studies, and the like.

In sequencing studies, this process is then repeated for left and/or right extensions of the core probe. In one example, only right extensions of the core probe are possible. The possible 4-mer extension probes of the core probe are 3'-YXYY and 31-YXYX. Again, the same selection criteria are utilized. Between 31-YXYY and 3'-YXYX, it would normally be found that 31-YXYX would have the strongest binding affinity, and this probe is selected as the correct probe extension. This selection may be confirmed by again plotting the normalized binding affinity of probes with single base mismatches as compared to the core probe.

When a hypothetical plot is illustrated, again, the characteristic "smile" pattern is observed, indicating that the "correct" extension has been selected, i.e., 3'-YXYX. From this information, one would correctly conclude that the sequence of the target is 51-XXYXY.

1.4.4 A Method for Sequencing Genomes

In one embodiment, a method is described for sequencing genomes that is comprised of the steps:

(1) Obtaining a clone library to be sequenced and mapped;
(2) Preparing DNA from individual clones in the clone library for comparison experiments;
(3) Obtaining a long-range probe library relative to the clone library;
(4) Preparing DNA from members of the long-range probe library for comparison experiments;
(5) Comparing DNA from the clone library with DNA from the long-range probe library;
(6) Producing a clone library characterized by long-range probes;
(7) Obtaining a bin probe library suitable for positioning the DNA sequences of long-range probes relative to the genome;
(8) Comparing DNA from the bin probe library with DNA from the long-range probe library;
(9) Producing a long-range probe library whose DNA sequences have been characterized by binning information relative to the genome;
(10) Combining the clone vs. long-range probe characterization from step 6, together with the long-range probe vs. genome binning characterization from step 9;
(11) Producing a binning of the clone library;
(12) Obtaining a short-range probe library relative to the clone library;
(13) Comparing DNA from the clone library with DNA from the short-range probe library;

(14) Producing a clone library characterized by short-range probes;

(15) Combining the long-range binning of the clone library, together with the short-range probing of the clone library from;

(16) Producing a contig of the clone library which bins and orders clones relative to the genome;

(17) Forming a tiling path of clones that span genome regions;

(18) Determining the sequence of said clones, and of the entire genome.

1.4.4.1 Obtaining a Clone Library to be Sequenced and Mapped

The clones may be comprised of large-sized clones that have genomic inserts greater than 250 kb (e.g., YACS), medium-sized clones that have genomic inserts greater than 50 kb, but less than 250 kb (e.g., PACs, BACs, PI s, or YACs), or small-sized clones that have genomic inserts less than 50 kb (e.g., cosmids, plasmids, phage, phagemids, or cDNAs). In the preferred embodiment, the clone library has at least two-fold redundancy relative to the genome. The technology for constructing these clones is well described (F. M. Ausubel, R. Brent, R. E. Kingston, D. D. Moore, J. G. Seidman, J. A. Smith, and K. Struhl, ed., Current Protocols in Molecular Biology. New York, N.Y.: John Wiley and Sons, 1995; N. J. Dracopoli, J. L. Haines, B. R. Korf, C. C. Morton, C. E. Seidman, J. G. Seidman, D. T. Moir, and D. Smith, ed., Current Protocols in Human Generics. New York: John Wiley and Sons, 1995; J. Sambrook, E. F. Fritsch, and T. Maniatis, Molecular Cloning, Second Edition. Plainview, N.Y.: Cold Spring Harbor Press, 1989), incorporated by reference. Chromosome-specific cosmid clones are available from Los Alamos National Laboratories (Los Alamos, N. Mex.), genome-wide PAC clones from Pieter de Jong (Roswell Park, Buffalo, N.Y.), and the Genethon YAC libraries from the national genome center GESTECs, including the Whitehead Institute (Cambridge, Mass.). Libraries are also provided by commercial vendors, including cDNA libraries (ATCC, Rockville, Md.), P1 libraries (DuPont/Merck Pharmaceuticals, Glenolden, Pa.), BAC libraries (Research Genetics, Huntsville, Ala.), and cDNAs and other genome-wide resources (BIOS Labs, New Haven, Conn.).

1.4.4.1.1 Preparing DNA from Individual Clones in the Clone Library for Comparison Experiments In the preferred embodiment, DNA from the clones is prepared for DNA hybridization experiments. For DNA derived from bacterial clones (cosmids, PACs, etc.), two straightforward protocols are: (a) growing up colonies for each clone, and then lysing the bacterial cells to expose the cloned insert DNA, or (b) specifically extracting the DNA material from the clone using DNA prep such as an ion exchange column (Qiagen, Chatsworth, Calif.). When using vectors with more complex genomes (e.g., yeast cells), a species-specific DNA prep (e.g., Alu-PCR or IRE-bubble PCR) is preferred. This DNA from each clone is then gridded onto nylon membranes such as Hybond N+ (Amersham, Arlington Heights, Ill.) to prepare for subsequent DNA hybridization experiments (Hybond N+ product protocol, ver. 2), incorporated by reference.

1.4.4.1.2 Obtaining A Long-range Probe Library Relative to the Clone Library.

The preferred long-range multiplexed probe is the radiation hybrid (RH)(D. R. Cox, M. Burmeister, E. R. Price, S. Kim, and R. M. Myers, "Radiation hybrid mapping: a somatic cell genetic method for constructing high-resolution maps of mammalian chromosomes," Science, vol. 250, pp. 245–250, 1990; S. J. Goss and H. Harris, "New method for mapping genes in human chromosomes," Nature, vol. 255, pp. 680–684, 1975; S. J. Goss and H. Harris, "Gene transfer by means of cell fusion: statistical mapping of the human X-chromosome by analysis of radiation-induced gene segregation," J. Cell. Sci., vol. 25, pp. 17–37, 1977), incorporated by reference. Chromosome-specific RH libraries have been constructed for other human chromosomes (M. R. James, C. W. Richard III, J.-J. Schott, C. Yousry, K. Clark, J. Bell, J. Hazan, C. Dubay, A. Vignal., M. Agrapart, T. Imai, Y. Nakamiura, M. Polymeropoulos, J. Weissenbach, D. R. Cox, and G. M. Lathrop, "A radiation hybrid map of 506 STS markers spanning human chromosome 11," Nature Genetics, vol. 8, no. 1, pp. 70–76, 1994; S. H. Shaw, J. E. W. Farr, B. A. Thiel, T. C. Matise, J. Weissenbach, A. Chakravarti, and C. W. Richard, "A radiation hybrid map of 95 STSs spanning human chromosome 13q," Genomics, vol. 27, no. 3, pp. 502–510, 1995; U. Francke, E. Chang, K. Comeau, E.-M. Geigl, J. Giacalone, X. Li, J. Luna, A. Moon, S. Welch, and P. wilgenbus, "A radiation hybrid map of human chromosome 18," Cytogenet. Cell Genet., vol. 66, pp. 196–213, 1994), incorporated by reference. Whole-genome RHs (WG-RHs) for humans and other mammalian genomes have also been developed (M. A. Walter, D. J. Spillett, P. Thomas, J. Weissenbach, and P. N. Goodfellow, "A method for constructing radiation hybrid maps of whole genomes," Nature Genet., vol. 7, no. 1, pp. 22–28, 1994), incorporated by reference, including the high-energy Stanford set (David Cox, Stanford, Calif.) and the low-energy Genethon set; the DNAs from both WG-RH sets are available (Research Genetics, Huntsville, Ala.).

There are alternative embodiments that can construct long-range multiplexed probes. One alternative embodiment is the use of rare cutter restriction enzymes (e.g., Not1 partial digests) to develop large DNA sequences from genomes. These fragments can be purified using pulsed-field gel electrophoresis (D. C. Schwartz and C. R. Cantor, "Separation of yeast chromosome-sized DNAs by pulsed field gradient gel electrophoresis," Cell, vol. 37, pp. 67–75, 1984), incorporated by reference, and then selectively pooled. A second alternative embodiment is the use of a second clone library that has a larger average insert size than the first clone library in step 1. Subsets of these larger insert clones can be pooled together to form a long-range probe library (relative to the first clone library). A third alternative embodiment which is particularly useful in animal models is the use of genetically inbred strains. With an F1 backcross between strains A and B, the meiotic events produce an interleaving of large chromosomal fragments of strains A and B. A subtractive hybridization can selectively remove the DNA from strain B, leaving behind just the large chromosomal regions of strain A for each backcross individual. This procedure constructs a long-range probe library (relative to the strain A clone library). The subtractive hybridization can be performed by first digesting the backcross individual genome with restriction enzymes, and then using whole genome DNA from strain B bound to solid support to selectively remove the strain B DNA.

1.4.4.1.3 Preparing DNA from Members of the Long-range Probe Library for Comparison Experiments The long-range probe DNA often resides in a complex background genome. In the RH embodiment, the background is murine genome, while in the pooled YAC embodiment, the background is the yeast genome. Therefore, the DNA preparations for these long-range probe embodiments preferably use a species-specific DNA extraction and amplification. The particular assay often depends on the clone library used.

When the clonal inserts reside in a complex background genome, such as YACs, inter-Alu hybridization is the preferred approach in step 5. In this case, Alu-PCR preparation of the long-range probes (M. T. Ross and V. P. J. Stanton, "Screening large-insert libraries by hybridization," in Current Protocols in Human Genetics, vol. 1, N. J. Dracopoli, J. L. Haines, B. R. Korf, C. C. Morton, C. E. Seidman, J. G. Seidman, D. T. Moir, and D. Smith, ed. New York: John Wiley and Sons, 1995, pp. 5.6.1–5.6.34), incorporated by reference, is the preferred embodiment. An alternative embodiment when background hybridization noise may be greater is IRE-bubble PCR (D. J. Munroe, M. Haas, E. Bric, T. Whirton, H. Aburatani, K. Hunter, D. Ward, and D. E. Housman, "IRE-bubble PCR: a rapid method for efficient and representative amplification of human genomic DNA sequences from complex sources," Genomics, vol. 19, no. 3, pp. 506–14, 1994), incorporated by reference.

When the clonal inserts are sufficiently large to contain inter-Alu regions, and the vector genome is not complex (e.g., bacterial), then IRE-bubble PCR is the preferred embodiment. This situation applies to many clone libraries, including cosmids, PACs, BACs, and P1s.

When the clonal inserts are too small to contain inter-Alu subsequences detectable by hybridization (such as cDNAs), an assay that provides for more uniform DNA expression from the long-range probes may be needed. The most preferred embodiment is then to use a multiplicity of restriction enzyme digests, each followed by long PCR between Alu repeats, and to then pool the PCR products to construct a probe. A second approach is a variation on direct selection (M. Lovett, J. Kere, and L. M. Hinton, "Direct selection: a method for the isolation of cDNAs encoded by large genomic regions," Proc. Natl. Acad. Sci. U.S.A., vol. 88, pp. 9628–9632, 1991), incorporated by reference. In this approach, Lovett's cDNAs are replaced by a full restriction digest with a frequent-cutter of the long-range probe DNA, and Lovett's genomic contig is replaced with repetitive DNA (e.g., Alu or Cot-1) that selects for the same genome as the species-specific long-range probe. The result is a PCR amplification (via the end priming sites) of the long-range probe that is species specific (via the Alu selection).

The species-specific DNA is then amplified and labeled for use as a hybridization probe. In the preferred embodiment, this amplification and labeling is performed using a labeled dNTP with the random primer method (A. P. Feinberg and B. Vogelstein, "A technique for radiolabeling DNA restriction endonuclease fragments to high specific activity," Analyt. Biochem., vol. 132, pp. 6–13, 1983; N. J. Dracopoli, J. L. Haines, B. R. Korf, C. C. Morton, C. E. Seidman, J. G. Seidman, D. T. Moir, and D. Smith, ed., Current Protocols in Human Genetics. New York: John Wiley and Sons, 1995), incorporated by reference. In one embodiment, $^{32}$P-dNTP is incorporated into a random primer PCR amplification, possibly using a kit such as the DECprime II DNA labeling kit (Ambion, Austin, Tex.). Other isotopes such as $^{35}$S or $^{33}$P can be used. In alternative embodiments, nonisotopic labeling is performed (L. J. Kricka, ed., Nonisotopic Probing, Blotting, and Sequencing, Second Edition. San Diego, Calif.: Academic Press, 1995), incorporated by reference.

1.4.4.1.4 Comparing DNA from the Clone Library with DNA from the Long-range Probe Library The labeled long-range probe DNA is hybridized against the gridded clone library (A. P. Monaco, V. M. S. Lam, G. Zehetner, G. G. Lennon, C. Douglas, D. Nizetic, P. N. Goodfellow, and H. Lehrach, "Mapping irradiation hybrids to cosmid and yeast artificial chromosome libraries by direct hybridization of Alu-PCR products," Nucleic Acids Res., vol. 19, no. 12, pp. 3315–3318, 1991), incorporated by reference. In an alterative embodiment, the roles of the long-range probe library and the clone library are reversed, with the long-range probe immobilized on the membrane and the label on the clone.

The hybridization comparison is done by preannealing the probe with 25 ng of Cot-1 DNA (Gibco-BRL, Grand Island, N.Y.) for 2 hours at 37° C. before adding to the prehybridization mix. The nylon filters containing the spotted clone DNA is then prehybridized overnight per manufacturer's instructions (Amersham, Arlingon Heights, Ill.), except for the addition of sheared, denatured human placental DNA at a final concentration of 50 ng/ml. Filters are hybridized overnight at 68° C., washed three times with final wash of 0.1 SSPE/0.1% SDS at 72° C., before exposing to autoradiographic film for 1 to 8 days. The exposed film image is then electronically scanned into a computer with memory. A phosphorimager (Molecular Dynamics, Sunnyvale, Calif.) or other electronic device can be used for imaging without the use of film.

For every RH hybridization probing, each of the clone positions on the autoradiographs of the gridded filters are scored on a numerical scale, such as 1–5, with 1 negative, 2 equivocal, 3 weakly positive, 4 positive, and 5 strongly positive. When duplicate typings are available, the maximum of the two scores is used, since there is a very high false-negative rate in the hybridization data. This data entry can be facilitated by use of an interactive computer program that presents the electronic image of the filter on a computer display, or by automated computer interpretation of the scanned image.

1.4.4.2 Producing a Clone Library Characterized by Long-range Probes

The hybridization experiments construct a table of scores that compare the DNA from clones against DNA from long-range probes for detectable sequence similarity, and thus presumed genomic colocalization. The scores are rescaled so that the new scaling is approximately linear (C. C. Clogg and E. S. Shihadeh, Statistical Models for Ordinal Variables. Thousand Oaks, Calif.: Sage Press, 1994), incorporated by reference. That is, a unit increase in the scaling indicates a unit increase in the confidence one holds that the clone actually hybridized with the long-range probe. An equivocal event is scored as a 0, since it was equally likely to be negative or positive. A negative event is scored as −1, since there is high confidence that no observable hybridization has occurred; both positive and strongly positive events are scored as 1, since there is certainty that a hybridization event has occurred. A weakly positive event can be scored at 0.67 when a single typing is available, since there is considerably more confidence that it is positive than negative, and is considered equivocal when duplicate typings were available. For any scale used, the data is scored in a manner determined by the laboratory investigator and data analyst. This rescaled clone vs. probe comparison table A is stored in the memory of a computational device.

With perfectly clean comparison data (i.e., very low false negative and false positive rates), this table A might suffice for ordering the clones using conventional RH mapping methods. However, the high-throughput hybridization experiments incur a large noise cost. Therefore, some correction data is required to accurately map the clones. This correction stage is performed in the following steps.

1.4.4.2.1 Obtaining a Bin Probe Library Suitable for Positioning the DNA Sequences of Long-range Probes Relative to the Genome In the preferred embodiment, the bin probe library is comprised of sequence-tagged sites (STSs). For positional cloning applications, many of the STSs are preferably made polymorphic. The genetic or physical markers to be used for each STS are obtained as PCR primer sequences pairs and PCR reaction conditions from available Internet databases (Genbank, Bethseda, Md.; GDB, Baltimore, Md.; EMBL, Cambridge, UK; Genethon, Ervy, France; Stanford Genome Center, Stanford, Calif.; Whitehead Institute Genome Center, Cambridge, Mass.; G. Gyapay, J. Morissette, A. Vignal., C. Dib, C. Fizames, P. Millasseau, S. Marc, G. Bernardi, M. Lathrop, and J. Weissenbach, "The 1993–94 Genethon Human Genetic Linkage Map," Nature Genetics, vol. 7, no. 2, pp. 246–339, 1994; Hilliard, Davison, Doolittle, and Roderick, Jackson laboratory mouse genome database, Bar Harbor, Me.; MapPairs, Research Genetics, Huntsville, Ala.), incorporated by reference. Alternatively, STSs can be constructed using existing techniques (Sambrook, J., Fritsch, E. F., and Manjarls, T. 1989. Molecular Cloning, second edition. Plainview, N.Y.: Cold Spring Harbor Press; N. J. Dracopoli, J. L. Haines, B. R. Korf, C. C. Morton, C. E. Seidman, J. G. Seidman, D. T. Moir, and D. Smith, ed., Current Protocols in Human Genetics. New York: John Wiley and Sons, 1995), incorporated by reference.

In a first alternative embodiment, the locations of the long-range probe fragments are localized on the genome by fluorescence in situ hybridization (FISH) studies. In these FISH studies, the nuclear DNA of the genome serves as the bin probe. In a second alternative embodiment, the binning is effected by comparison with previously positioned DNA probes, including mapped clone libraries, ESTs, or PCR primers.

1.4.4.2.2 Comparing DNA from the Bin Probe Library with DNA from the Long-range Probe Library In the preferred embodiment, PCR amplifications are carried out between the STSs in the bin probe library and the RH (or other) DNAs in the long-range probe library. Subsequent detection for presence or absence of PCR products (+/−scores) is carried out either by gel electrophoresis or by internal oligonucleotide hybridizations.

The orders of the STSs relative to the genome are then determined using computational or statistical methods (M. Boehnke, "Radiation hybrid mapping by minimization of the number of obligate chromosome breaks," Genetic Analysis Workshop 7: Issues in Gene Mapping and the Detection of Major Genes. Cytogenet Cell Genet, vol. 59, pp. 96–98, 1992; M. Boehnke, K. Lange, and D. R. Cox, "Statistical methods for multipoint radiation hybrid mapping," Am. J. Hum. Genet., vol. 49, pp. 1174–1188, 1991; A. Chakravarti and J. E. Reefer, "A theory for radiation hybrid (Goss-Harris) mapping: application to proximal 21q markers," Generic Analysis Workshop 7: Issues in Gene Mapping and the Detection of Major Genes. Cytogenet Cell Genet, vol. 59, pp. 99–101, 1992), incorporated by reference. Physical distances are then computed using maximum likelihood estimation.

In the first alternative FISH embodiment of step 7, DNA from the long-range probes (e.g., species-specific PCR products) are fluorescently labeled, and then hybridized back onto the genome. The fragment positions on the genome of the probes are then visualized using fluorescent microscopic imaging. Linear fractional length measurements on the metaphase spreads of chromosomes are then performed to determine the bin positions of the fragments. In the second alternative embodiment of step 7, DNA from the previously positioned bin probes is hybridized to DNA from the long-range probes.

Detailed protocols for these methods have been described (F. M. Ausubel, R. Brent, R. E. Kingston, D. D. Moore, J. G. Seidman, J. A. Smith, and K. Struhl, ed., Current Protocols in Molecular Biology. New York, N.Y.: John Wiley and Sons, 1995; N. J. Dracopoli, J. L. Haines, B. R. Korf, C. C. Morton, C. E. Seidman, J. G. Seidman, D. T. Moir, and D. Smith, ed., Current Protocols in Human Genetics. New York: John Wiley and Sons, 1995), incorporated by reference.

1.4.4.2.3. Producing a Long-range Probe Library Whose DNA Sequences Have Been Characterized by Binning Information Relative to the Genome The procedures produce a data table which compares the DNA content of the long-range probes to bins on the genome. In the preferred embodiment, this is a table B of long-range probes (the rows of B) vs. ordered STSs (the columns of B). The pairwise distance information between the ordered STSs is also recorded. In alternative embodiments, the table can be arranged similarly.

Knowledge of the genomic positions of the RH fragments enables the desired correction of noisy RH hybridization data, as described next.

1.4.4.3 Producing a Binning of the Clone Library

The procedures of step 10 produce a table which bins each clone relative to the genome. In the preferred embodiment, this is a table C of clones (the rows of C) vs. ordered bins (the columns of C). Each entry in the table describes the confidence that the clone is located in the bin.

Note that this result C is a binning of clones, not a contig. To form the desired set of mapped overlapping clones, a short-range probing is preferrably performed. This probing and contig formation is performed in the following steps.

1.4.4.3.1 Obtaining a Short-range Probe Library Relative to the Clone Library Since current clone mapping technology is based on short-range probing, there is a large number of workable approaches. The preferred embodiment uses hybridization assays based on oligonucleotide probes. The design of such experiments has been described (A. J. Cuticchia, J. Arnold, and W. E. Timberlake, "PCAP: probe choice and analysis package, a set of programs to aid in choosing synthetic oligomers for contig mapping," CABIOS, vol. 9, no. 2, pp. 201–203, 1992; Y.-X. Fu, E. W. Timberlake, and J. Arnold, "On the design of genome mapping experiments using short synthetic oligoncletides," Biometrics, vol. 48, pp. 337–359, 1992; H. Lehrach, A. Drmanac, J. Hoheisel, Z. Larin, G. Lennon, A. P. Monaco, D. Nizetic, G. Zehetner, and A. Poustka, "Hybridization fingerprinting in genome mapping and sequencing," in Genetic and Physical Mapping I: Genome Analysis, K. E. Davies and S. M. Tilghman, ed. Cold Spring Harbor, N.Y.: Cold Spring Harbor Laboratory, 1990, pp. 39–81; A. Poustka, T. Pohl, D. P. Barlow, G. Zehetner, A. Craig, F. Michiels, E. Erlich, A.-M. Frischauf, and H. Lehrach, "Molecular approaches to mammalian genetics," in Cold Spring Harbor Symp. Quant. Biol., vol. 51. 1986, pp. 131–139), incorporated by reference.

An efficient design produces 25 to 200 small (preferrably 5 bp–15 bp) oligonucleotides which each hybridize, on average, to 5%–95% of the clones. The oligonucleotide sequences are generally designed to preferentially detect sequences that are related to the genes in the genome, rather than to repetitive elements in the genome or to the cloning vector. This selective bias can be achieved either by experimental probings, or by examination of the sequences to be compared. Once designed, these oligonucleotides are preferably ordered from a DNA synthesis service (Research Genetics, Huntsville, Ala.). Alternatively, they can be synthesized on a DNA synthesizer (Applied Biosystems, Foster City, Calif.).

Alternative hybridization embodiments include using clones (or their PCR products) to probe clone libraries, using pools of clones as hybridization probes, and using Southern blotting of digested clones with repetitive element hybridization probes. Enzymatic methods include gel electrophoresis of restriction endonuclease digests of clones, PCR-based STS comparisons, and hybrid methods such as Alu fingerprinting. Other short-range probes can be formed by selective or random retention of fragments produced by genome cutting.

For experimental efficiency, many of these short-range probes work in a multiplexed way, and probe one or more genome regions simultaneously. These probes include oligonucleotides, pooled clones, and repetitive-element fingerprint probes.

1.4.4.3.2 Comparing DNA from the Clone Library with DNA from the Short-Range Probe Library This is done by comparison experiments using standard protocols. In the preferred embodiment, DNA from the clones in the clone library is spotted onto nylon membranes. This DNA is comprised of lysed colonies, DNA preps, or species-specific PCR products. The membranes are then prepared for hybridization. Each oligonucleotide short-range probe is then labeled, preferably with $^{32}P$ using a kinase. The labeled probe is then hybridized to the membranes, followed by rinsing, stringent washing, and autoradiography. The filters may be stripped for subsequent reuse. The autoradiograph spots are then scored on a binary or more continuous (e.g., 0–255) scale.

Specific oligonucleotide hybridization protocols for particular clone libraries and oligonucleotides have been described (A. G. Craig, D. Nizetic, J. D. Hoheisel, G. Zehetner, and H. Lehrach, "Ordering of cosmid clones covering the herpes simplex virus type I," Nucleic Acids Res., vol. 18, no. 9, 2653–60, 1990; R. Drmanac, Z. Strezoska, I. Labat, S. Drmanac, and R. Crkvenjakov, "Reliable hybridization of oligonucleotides as short as six nucleotides," DNA Cell Biol., vol. 9, no. 7 pp. 527–534, 1990; J. D. Hoheisel, G. G. Lennon, G. Zehetner, and J. Lehrach, "Use of high coverage reference libraries of Drosophila melanogaster for relational analysis," J. Mol. Biol., vol. 220, pp. 903–914, 1991; F. Michiels, A. G. Craig, G. Zehetner, G. P. Smith, and H. Lehrach, "Molecular approaches to genome analysis: a strategy for the construction of ordered overlapping clone libraries," CABIOS, vol. 3, pp. 203–210, 1987; D. Nizetic, R. Drmanac, and J. Lehrach, "An improved bacterial colony lysis procedure enables direct DNA hybridization using short (10, 11 bases) oligonucleotides to cosmids," Nucleic Acids Res., vol. 19, pp. 182, 1991), incorporated by reference.

For alternative short-range probes, the comparison protocols are described (see cited references above).

1.4.4.3.3 Producing a Clone Library Characterized by Short-range Probes

The comparison experiments of the previous step construct a table D of scores that compare the DNA from clones against DNA from short-range probes. These provide measures of genomic colocalization and distance.

In this step, or in the following step 15, contigs can be formed from the short-range characterization data of the clones. In the preferred embodiment, each clone's score signature relative to the oligonucleotides is compared against other clones' score signatures. Pairs of clones having similar score signatures are inferred to be close, and their distances can be estimated. The preferred ordering method is simulated annealing (W. H. Press, B. P. Flannery, S. A. Teukolsky, and W. T. Vetterling, Numerical Recipes in C: The Art of Scientific Computing. Cambridge: Cambridge University Press, 1988), incorporated by reference. Effective contiging algorithms have been described (A. J. Cuticchia, J. Arnold, and W. E. Timberlake, "ODS: ordering DNA sequences, a physical mapping algorithm based on simulated annealing," CABIOS, vol. 9, no. 2, pp. 215–219, 1992; A. J. Cuticchia, J. Arnold, and W. E. Timberlake, "The Use of Simulated Annealing in Chromosome Reconstruction Experiments Based on Binary Scoring," Genetics, vol. 132, pp. 591–601, 1992; A. Milosavljevic, Z. Strezoska, M. Zeremski, D. Grujic, T. Paunesku, and R. Crkvenjakov, "Clone clustering by hybridization," Genomics, vol. 27, no. 1, pp. 83–89, 1995), incorporated by reference.

For alternative short-range probes, the contiging analysis procedures use analogous comparison data and search procedures, and have been described (D. O. Nelson and T. P. Speed, "Statistical issues in constructing high resolution physical maps," Statistical Science, vol. 9, no. 3, pp. 334–354, 1994; E. Branscomb, T. Slezak, R. Pae, D. Galas, and al., "Optimizing restriction fragment fingerprinting methods for ordering large genomic libraries," Genomics, vol. 8, pp. 351–366, 1990; S. G. Fisher, E. Cayanis, J. J. Russo, 1. Sunjevaric, B. Boukhgalter, P. Zhang, M.-T. Yu, R. Rothstein, D. Warburton, I. S. Edelman, and A. Efstratiadis, "Assembly of ordered contigs of cosmids selected with YACs of human chromosome 13," Genomics, vol. 21, pp. 525–537, 1994; R. Mort, A. Grigoriev, E. Maier, J. Hoheisel, and H. Lehrach, "Algorithms and software tools for ordering clone libraries: application to the mapping of the genome of Schizosaccharomyces pombe," Nucleic Acids Research, vol. 21, no. 8, pp. 1965–1974, 1993), incorporated by reference.

1.4.4.3.4 Forming a Tiling Path of Clones that Span Genome Regions

From an accurate clone map of a genome, a (not necessarily unique) subset of clones that cover the genome can be identified. This identification is done by starting from a leftmost clone by moving rightward from a selected clone A, selecting a neighbor B which overlaps A, and then iteratively continuing from B. A constraint can be placed on this process to find tiling paths having small or minimal length, where length is defined as the sum of the insert sizes of the component clones.

In the preferred embodiment, (minimal) tiling paths have immediately utility for finding genes. This is because the inner product map integrates genetic markers (polymorphic STSs) together with the clones that fully cover the genome region containing the gene of interest. This considerably reduces the search effort for cloning the gene. Even greater utility for positional/candidate cloning (F. S. Collins, "Positional cloning moves from perditional to traditional.," Nature Genet., vol. 9, no. 4, pp. 347–350, 1995), incorporated by reference, is present when a map of ESTs, expressed cDNAs, or exons is also integrated into the map.

1.4.4.3.5 Determining the Sequence of Said Clones, and of the Entire Genome

In the preferred embodiment, each mapped clone is selected in turn from a minimum tiling path. This clone is then subcloned into M13 sequencing vectors. For each M13 subclone, nested deletions are constructed for use in DNA sequencing. For each deletion clone, a DNA sequencing template is prepared. This template is then sequenced by the dideoxy method, preferably using an automated DNA sequencer, such as an A. L. F. (Pharmacia Biotech, Piscataway, N.J.) or an ABI/373 or ABI/377 (Applied Biosystems, Foster City, Calif.), and 100–500 bp of sequence determined. In addition to this "shotgun" phase, in which an initial read is taken from each subclone using a universal primer, a "walking" phase takes additional reads from selected subclones by use of custom primers. Complete protocols for these and related sequencing steps have been described (F. M. Ausubel, R. Brent, R. E. Kingston, D. D. Moore, J. G. Seidman, J. A. Smith, and K. Struhl, ed., Current Protocols in Molecular Biology. New York, N.Y.: John Wiley and Sons, 1995; N. J. Dracopoli, J. L. Haines, B. R. Korf, C. C. Morton, C. E. Seidman, J. G. Seidman, D. T. Moir, and D. Smith, ed., Current Protocols in Human Genetics. New York: John Wiley and Sons, 1995).

The sequences of the nested deletion clones are assembled into the complete sequence of the subclone by matching overlaps. The subclone sequences are then assembled into the sequence of the mapped clone. The sequences of the mapped clones are assembled into the complete sequence of the genome by matching overlaps. Computer programs are available for these tasks (Rodger Staden programs, Cambridge, UK; DNAStar, Madison, Wis.). Following sequence assembly, current analysis practice includes similarity and homology searches relative to sequence databases (Genbank, Bethesda, Md.; EMBL, Cambridge, UK; Phil Green's GENEFINDER, Seattle, Wash.) to identify genes and repetitive elements, infer function, and determine the sequence's relation to other parts of the genome and cell.

1.4.4.4.6 Application of Strategies

Such strategies have been successfully applied to sequencing the genomes of several bacteria (Human Genome Sciences, Gaithersburg, Md.), including *E. coli* (G. Plunkerr and al., "Analysis of the *Escherichia coli* genome. III. DNA sequence of the region from 87.2 to 89.2 minutes," Nucl. Acids Res., vol. 21, pp. 3391–3398, 1993), incorporated by reference, and higher organisms, including yeast (S. G. Oliver and al., "The complete sequence of yeast chromosome III," Nature, vol. 357, pp. 38–46, 1992), incorporated by reference, human (A. Martin-Gallardo and al., "Automated DNA sequencing and analysis of 106 kilobases from human chromosome 19 q13.3," Nature Genet., vol. 1, pp. 34–39, 1992), incorporated by reference, mouse (R. K. Wilson and al., "Nucleotide sequence analysis of 95 kb near the 3' end the murine T-cell receptor alpha/delta chain locus: strategy and methodology," Genomics, vol. 13, pp. 1198–1208, 1992), incorporated by reference, and C. elegans (R. Wilson and al., "2.2 Mb of contiguous nucleotide sequence from chromosome III of C. elegans," Nature, vol. 368, pp. 32–38, 1994; J. Sulston, Z. Du, K. Thomas, R. Wilson, L. Hillier, R. Staden, N. Halloran, P. Green, J. Thierry-Mieg, L. Qiu, S. Dear, A. Coulson, M. Craxton, M. Durbin, M. Berks, M. Metzstein, T. Hawkins, R. Ainscough, and R. Waterston, "The C. elegans genome sequencing project: a beginning," Nature, vol. 356, pp. 37–41, 1992), incorporated by reference. The automated sequencing of large genome regions from mapped cosmid (or other) clones is now routine in several centers (Sanger Center, Cambridge, UK; Washington University, St. Louis, Mo.), with very low error at an average cost of $0.50 or less per base. Specific strategies and protocols for these efforts have been detailed (H. G. Griffin and A. M. Griffin, ed., DNA Sequencing: Laboratory Protocols. New Jersey: Humana, 1992), incorporated by reference.

The current best mode for sequencing is gel electrophoresis on polyacrylamide gels, possibly using fluorescence detection. Newer technologies for DNA size separation are being developed that are applicable to DNA sequencing, including ultrathin gel slabs (A. J. Kostichka, M. L. Marchbanks, R. L. Brumley Jr., H. Drossman, and L. M. Smith, "High speed automated DNA sequencing in ultrathin slab gels," Bio/Technology, vol. 10, pp. 78–81, 1992), incorporated by reference, capillary arrays (R. A. Mathies and X. C. Huang, "Capillary array electrophoresis: an approach to high-speed, high-throughput DNA sequencing," Nature, vol. 359, pp. 167–169, 1992), incorporated by reference, and mass spectrometry (K. J. Wu, A. Stedding, and C. H. Becker, "Matrix-assisted laser desorption time-of-flight mass spectrometry of oligonucleotides using 3-hydroxypicolinic acid as an ultraviolet-sensitive matrix," Rapid Commun. Mass Spectrom., vol. 7, pp. 142–146, 1993), incorporated by reference. DNA sequencing without the use of gel electrophoresis has also been done using sequencing by hybridization methodologies (R. Drmanac, S. Drmanac, Z. Strezoska, T. Paunesku, l. Labat, M. Zeremski, J. Snoddy, W. K. Funkhouser, B. Koop, and L. Hood, "DNA sequence determination by hybridization: a strategy for efficient large-scale sequencing," Science, vol. 260, pp. 1649–1652, 1993; E. M. Southern, U. Maskos, and J. K. Elder, "Analyzing and comparing nucleic acid sequences by hybridization to arrays of oligonucleotides: evaluation using experimental models," Genomics, vol. 13, pp. 1008–10017, 1991; S. P. A. Fodor, J. L. Read, M. C. Pirrung, L. Stryer, A. T. Lu, and D. Solas, "Light-directed spatially addressable parallel chemical synthesis," Science, vol. 251, pp. 767–773, 1991), incorporated by reference. Another approach is base addition sequencing strategy (BASS), which uses synchronized DNA polymer construction to determine the sequence of unknown DNA templates (P. C. Cheeseman, "Method for sequencing polynucleotides," U.S. Pat. No. 5,302,509; filed Feb. 27, 1991, published Apr. 12, 1994; A. Rosenthal., K. Close, and S. Brenner, "DNA sequencing method," Patent #PCT WO 93/21340; filed Apr. 22, 1992, published Oct. 28, 1993; R. Y. Tsien, P. Ross, M. Fahenstock, and A. J. Johnston, "DNA sequencing," Patent #PCT WO 91/06678; filed Oct. 26, 1990, published May 16, 1991), incorporated by reference.

1.4.5 Insertion of a Genomic Fragment into an Appropriate Host Vector

In another embodiment, the process begins with a fragment of DNA, such as a genomic fragment, which is inserted into an appropriate host vector capable of accommodating it. For example, a BAC vector can accommodate approximately 140 kb of DNA; a cosmid vector can accommodate approximately 40 kb. A composition comprised of these insert-containing vectors is randomly sheared using standard methods, such as sonication, to obtain fragments suitable for transposon-based sequencing—i.e., about 2–5 kb, preferably 3–4 kb, on the average.

The resulting subfragments are ligated into cloning vectors to create a first library of subclones representing the original fragment. Because the subclones in this library will be used as target plasmids for transposon-mediated sequencing, the size of the cloning vector should be minimized; preferably it should contain only a selectable marker, an origin of replication, and an insertion site. A suitable host plasmid is pOT2; the subfragments obtained by shearing the original composition are end-repaired, ligated to suitable restriction site containing adapters, and inserted into the host vector. Suitable adapters for the pOT2 vector contain BstXI sites.

The resulting cloning vectors with their inserts are then transfected into bacteria, typically *E. coli*, for clonal growth.

This first library should contain a 15–20-fold representation of the original fragment of DNA. For example, if the original fragment is approximately 40 kb, and the subclones contain inserts of approximately 4 kb, 200 such clones would be required for a 20-fold representation of the original fragment.

1.4.5.1 Hybridization Screening

As pointed out above, this first library will contain subclones which do not contain DNA derived from the original fragment to be sequenced. In order to eliminate these subclones, a preliminary hybridization screen is conducted. The required number of subclones is prepared for hybridization screening, for example, by plating in 96-well plates and transferring to filters. The filters are then probed with the original fragment insert to weed out any colonies which do not contain DNA which represents portions of the original fragment. This checks the quality of the library and eliminates subclones that contain only host cloning vector for the original fragment or contaminating bacterial DNA.

1.4.5.2 $2^{nd}$ Library Formation by Subclones that Contain Inserts

The subclones confirmed to contain inserts derived from the fragment to be sequenced form a second library. The number of subclones in this library should be sufficient to contain a 7–8× times. representation of the fragment. Each subclone is individually sequenced from one end of the insert. This is straightforward, since the sequence information in the cloning vector provides sufficient information to design appropriate primers. Typically, about 400–450 nucleotides into the insert is read. In addition to the requirement for 7–8× times. coverage of the fragment when the complete insert sequences of the subclones are obtained, there must be sufficient sequence information available from this end sequencing to represent a 1× times. coverage of the fragment. Thus, if the original fragment contained 40 kb and 400 nucleotides into the insert is read, 100 clones would be required. The resulting sequence information is organized into a computer-readable form for searching. A DNA sequence comparison algorithm can be used for subsequent comparisons, such as the NCBI program BLASTN.

The criteria used to determine the number of subclones used to establish the database in the method described above are that low sequencing redundancy must be maintained and a complete path must be available within the set of subclones chosen to provide complete coverage of the original fragment. In addition, the number must be chosen so that there is a high probability of finding the next subclone when searching with the newly sequenced end sequence.

A method similar to that employed by Chen, E. et al. Genomics (1993) 17:651–666, is used. Lander and Waterman (cite) conclude that the maximum number of sequence islands occurs at $C=(1-\theta)^{-1}$, where C is the sequence coverage and theta is the ratio of the number of bases required to detect the true overlap to the sequence read length. As theta approaches zero, sequence coverage of 1 will produce the maximum number of sequence islands. In order to achieve the highest efficiency database, enough end-sequence data should be generated to obtain about 1× times. coverage.

In addition, the subclone coverage—i.e., the redundancy based on the complete sequence contained in the number of subclones chosen—is important. A subclone coverage factor of 7×–8× times provides a 99.9% probability that each nucleotide in the fragment will actually reside in the library. This requires only about 100 subclones averaging 3 kb in size for a 40 kb fragment.

Sequence information from the host vector for the original fragment is used as the first query and reveals which subclones in the library are hybrid vector/fragment insert subclones. These will identify the two ends of the original fragment. One subclone representing each end, preferably that containing the least amount of vector sequence, is selected for further sequencing. The insert of the identified subclone will be sequenced from the opposite end from that previously sequenced—i.e., opposite the end containing the vector sequence. The new sequence information (which is now derived from the fragment) is used as the next query. This identifies additional subclones which contain additional nucleotide sequence farther in from the end of the original fragment. The next identified subclone is then also sequenced from the opposite end of the insert from that used to place it in the database and the new sequence information used as the next query. The process is continued sequentially until a subclone path through the fragment is obtained. The subclone path will represent the collection of subclones which completely define the fragment from which they originated, and their correct relative positions are known.

At any point in this process, if there are no responses to the query, additional sequence can be obtained from the subclones already identified and this sequence used as the query.

Once the subclone path is determined, it remains only to complete the sequencing of the subclones involved in the path. According to the method of the invention, this is accomplished using the transposon-mediated method of Strathmann incorporated by reference hereinabove. Use of this method to complete the sequence information for the fragment has been designated "minimal assembled path" (MAP) sequencing. The name is apt because the information provided by the subclone path can be used to determine the minimal sequencing path through the identified subclones. For example, if two subclones overlap over 1 kb, transposon insertions can be selected so that the overlap region is sequenced only once. Thus, although theoretically each of the subclones obtained to define the path can be completely sequenced using the transposon-mediated method, only sufficient portions of these subclones need be sequenced to obtain the complete sequence of the original fragment.

1.4.6 Methods of Determining a Nucleic Acid Sequence through Enzymatic Sequencing In another embodiment, improved methods of determining a nucleic acid sequence through enzymatic sequencing are provided. In the subject methods, primers are used in combination with capturable chain terminators to produce primer extension products capable of being captured on a solid phase, where the primer extension products may be labeled, e. g. by employing labeled primers to generate the primer extension products. Following generation of the primer extension products, the primer extension products are isolated through capture on a solid phase. The isolated primer extension products are then released from the solid phase, size separated and detected to yield sequencing data from which the nucleic acid sequence is determined.

Methods of determining the sequence of a nucleic acid, e.g. DNA, by enzymatic sequencing are well known in the art and described in Sambrook et al., Molecular Cloning: A Laboratory Manual (Cold Spring Harbor Laboratory Press, 1989) and Griffin and Griffin, "DNA Sequencings, Recent Innovations and Future Trends," Applied Biochemistry and Biotechnology (1993) 38: 147–159, the disclosures of which are herein incorporated by reference. The Sanger method is shown schematically herein. Generally, in enzymatic sequencing methods, which are also referred to as Sanger dideoxy or chain termination methods, differently sized oligonucleotide fragments representing termination at each of the bases of the template DNA are enzymatically produced and then size separated yielding sequencing data from which the sequence of the nucleic acid is determined. The results of such size separations are shown herein. The first step in such methods is to produce a family of differently sized oligonucleotides for each of the different bases in the nucleic acid to be sequenced, e.g. for a strand of DNA comprising all four bases (A, G, C, and T) four families of differently sized oligonucleotides are produced, one for each base. To produce the family of differently sized oligonucleotides, each base in the sequenced nucleic acid, i.e. template nucleic acid, is combined with an oligonucleotide primer, a polymerase, nucleotides and a dideoxynucleotide corresponding to one of the bases in the template nucleic acid. Each of the families of oligonucleotides are then size separated, e.g. by electrophoresis, and detected to obtain sequencing data, e.g. a separation pattern or electropherogram, from which the nucleic acid sequence is determined.

Before further describing the subject methods in greater detail, the critical chain terminator reagents employed in the subject methods will be discussed. Critical to the subject methods is the use of capturable chain terminators to produce the families of different sized oligonucleotide fragments (hereinafter referred to as primer extension products) comprising a capture moiety at the 3' terminus. The primer sequences employed to generate the primer extension products will be sufficiently long to hybridize the nucleic acid comprising the target or template nucleic acid under chain extension conditions, where the length of the primer will generally range from 6 to 40, usually 15 to 30 nucleotides in length. The primer will generally be a synthetic oligonucleotide, analogue or mimetic thereof, e.g. a peptide nucleic acid. Although the primer may hybridize directly to the 3' terminus of the target nucleic acid where a sufficient portion of this terminus of the target nucleic acid is known, conveniently a universal primer may be employed which anneals to a known vector sequence flanking the target sequence. Universal primers which are known in the art and commercially available include pUC/M 13, gt10, gt 11 and the like.

1.4.6.1 Primers Comprise a Detectable Label

In one preferred embodiment of the subject invention, the primers employed in the subject invention will comprise a detectable label. A variety of labels are known in the art and suitable for use in the subject invention, including radioisotopic, chemiluminescent and fluorescent labels. As the subject methods are particularly suited for use with methods employing automated detection of primer extension products, fluorescent labels are preferred. Fluorescently labeled primers employed in the subject methods will generally comprise at least one fluorescent moiety stably attached to one of the bases of the oligonucleotide.

The primers employed in the subject invention may be labeled with a variety of different fluorescent moieties, where the fluorescer or fluorophore should have a high molar absorbance, where the molar absorbance will generally be at least $10^4 cm^{-1}M^{-1}$, usually at least $10^4 cm^{-1}M^{-1}$ and preferably at least $10^5 cm^{-1}M^{-1}$, and a high fluorescence quantum yield, where the fluorescence quantum yield will generally be at least about 0.1, usually at least about 0.2 and preferably at least about 0.5.

For primers labeled with a single fluorescer, the wavelength of light absorbed by the fluorescer will generally range from about 300 to 900 nm, usually from about 400 to 800 run, where the absorbance maximum will typically occur at a wavelength ranging from about 500 to 800 nm. Specific fluorescers of interest for use in singly labeled primers include: fluorescein, rhodamine, BODIPY, cyanine dyes and the like, and are farther described in Smith et al., Nature (1986) 321: 647–679, the disclosure of which is herein incorporated by reference.

Of particular interest for use in the subject methods are energy transfer labeled fluorescent primers, in which the primer comprises both a donor and acceptor fluorescer component in energy transfer relationship. Energy transfer labeled primers are described in PCT/US95/01205 and PCT/US96/13134, as well as in Ju et al., Nature Medicine (1996)2:246–249, the disclosures of which are herein incorporated by reference.

In an alternative embodiment of the subject invention, instead of using labeled primers labeled deoxynucleotides are employed, such as fluorescently labeled dUTP, which are incorporated into the primer extension product resulting in a labeled primer extension product.

The dideoxynucleotides employed as capturable chain terminators in the subject methods will comprise a functionality capable of binding to a functionality present on a solid phase. The bond arising from reaction of the two flnctionalities should be sufficiently strong so as to be stable under washing conditions and yet be readily disruptable by specific chemical or physical means. Generally, the chain terminator dideoxynucleotide will comprise a member of a specific binding pair which is capable of specifically binding to the other member of the specific binding pair present on the solid phase. Specific binding pairs of interest include ligands and receptors, such as antibodies and antigens, biotin and strept/avidin, sulfide and gold (Cheng & Brajter-Toth, Anal.Chem. (1996)68:4180–4185, and the like, where either the ligand or the receptor, but usually the ligand, member of the pair will be present on the chain terminator. Of particular interest for use as chain terminators are biotinylated dideoxymicleotides, where such dideoxymicleotides are known in the art and available commercially, e. g. biotin-II-ddATP, biotin-II-ddGTP, biotin-II-ddCTP and biotin-11-ddTTP, and the like.

1.4.6.2 Subject Methods

Turning now to the subject methods, the nucleic acids which are capable of being sequenced by the subject methods are generally deoxyribonucleic acids that have been cloned in appropriate vector, where a variety of vectors are known in the art and commercially available, and include M13mp 18, pGEM, pSport and the like. The first step in the subject method is to prepare a reaction mixture for each of the four different bases of the sequence to be sequenced or target DNA. Each of the reaction mixtures comprises an enzymatically generated family of primer extension products, usually labeled primer extension products, terminating in the same base. In other words, in practicing the subject method, one will first generate an "A", G," "C," and "T," family of differently sized primer extension products using the target DNA as template. To generate the four families of differently sized primer extension products, template DNA, a DNA polymerase, primer (which may be labeled), the four different deoxynucleotides, and capturable dideoxynucleotides are combined in a primer extension reaction mixture. The components are reacted under conditions sufficient to produce primer extension products which are differently sized due to the random incorporation of the capturable dideoxynucleotide and subsequent chain termination. Thus, to generate the "A" family of differently sized primer extension products, the above listed reagents will be combined into a reaction mixture, where the dideoxynucleotide is ddATP modified to comprise a capturable moiety, e.g. biotinylated ddATP, such as biotin-11-ddATP. The remaining "G", C," and "T" families of differently sized primer extension products will be generated in an analogous manner using the appropriate dideoxynucleotide.

Where labeled primers are employed to generate each of the families of primer extension products, the labeled primers may be the same or different. Preferably, the labeled primer employed will be different for production of each of the four families of primer extension products, where the labels will be capable of being excited at substantially the same wavelength and yet will provide a distinguishable signal. The use of labels with distinguishable signals affords the opportunity of separating the differently sized primer extension products when such products are together in the same separation medium. This results in superior sequencing data and therefore more accurate sequence determination. For example, one can prepare the "A" family of primer extension products with a first fluorescent label capable of excitation at a wavelength from about 470 to 480 nm which fluoresces at 525 nm. The label used in production of "G," "C," and "T" families will be excitable at the same wavelength as that used in the "A" family, but will emit at 555 nm, 580 nm, and 605 nm respectively. Accordingly, the primer extension labels are designed so that all four of the labels absorb at substantially the same wavelength but emit at different wavelengths, where the wavelengths of the emitted light differ in detectable and differentiatable amounts, e.g. differ by at least 15 nm. The next step in the subject method is isolation of the primer extension products. The primer extension products are isolated by first capturing the primer extension products on a solid phase through the capture moiety at the 3' terminus of the primer extension product and then separating the solid phase from the remaining components of the reaction mixture.

Capture of the primer extension products occurs by contacting the reaction mixture comprising the family of primer extension products with a solid phase. The solid phase has a member of a specific binding pair on its surface. The other member of the specific binding pair is bonded to the primer extension products, as described above. Contact will occur under conditions sufficient to provide for stable binding of the specific binding pair members. A variety of different solid-phases are suitable for use in the subject methods, such phases being known in the art and commercially available. Specific solid phases of interest include polystyrene pegs, sheets, beads, magnetic beads, gold surface and the like. The surfaces of such solid phases have been modified to comprise the specific binding pair member, e.g. for biotinylated primer extension products, streptavidin coated magnetic bead may be employed as the solid phase.

Following capture of the primer extension reaction products on the solid phase, the solid phase is then separated from the remaining components of the reaction mixture, such as template DNA, excess primer, excess deoxy- and dideoxymicleotides, polymerase, salts, extension products which do not have the capture moiety, and the like. Separation can be accomplished using any convenient methodology. The methodology will typically comprise washing the solid phase, where further steps can include centrifugation, and the like. The particular method employed to separate the solid-phase is not critical to the subject invention, as long as the method employed does not disrupt the bond linking the primer extension reaction product from the solid-phase.

The primer extension products are then released from the solid phase. The products may be released using any convenient means, including both chemical and physical means, depending on the nature of the bond between the specific binding pair members. For example, where the bond is a biotin-streptavidin bond, the bond may be disrupted by contacting the solid phase with a chemical disruption agent, such as formamide, and the like, which disrupts the biotin-streptavidin bond and thereby releases the primer extension product from the solid phase. The released primer extension products are then separated from the solid phase using any convenient means, including elution, centrifugation and the like.

The next step in the subject method is to size separate the primer extension products. Size separation of the primer extension products will generally be accomplished through electrophoresis, in which the primer extension products are moved through a separation medium under the influence of an electric field applied to the medium, as is known in the art. Alternatively, for sequencing with Mass Spectrometry (MS) where unlabeled primer extension products are detected, the sequencing fragments are separated by the time of the flight chamber and detected by the mass of the fragments. See Roskey et al., Proc. Natl. Acad. Sci. USA (1996) 93: 4724–4729. The subject methodology is especially important for obtaining accurate sequencing data with MS, because the subject methodology offers a means to load only the primer extension products terminated with the capturable chain terminators, eliminating all other masses, thereby producing accurate results.

In methods in which the fragments are size separated, the size separated primer extension products are then detected, where detection of the size separated products yields sequencing data from which the sequence of the target or template DNA is determined. For example, where the families of fragments are separated in a traditional slab gel in four separate lanes, one corresponding to each base of the target DNA, sequencing data in the form of a separation pattern is obtained. From the separation pattern, the target DNA sequence is then determined, e.g. by reading up the gel. Alternatively, where automated detectors are employed and all of the reaction products are separated in the same electrophoretic medium, the sequencing data may take the form of an electropherogram, as is known in the art, from which the DNA sequence is determined.

Where labeled primers are employed, the nature of the labeled primers will, in part, determine whether the families of labeled primer extension products may be separated in the same electrophoretic medium, e.g. in a single lane of slab gel or in the same capillary, or in different electophoretic media, e.g. in different lanes of a slab gel or in different capillaries. Where the same labeled primer generating the same detectable single is employed to generate the primer extension products in each of the different families, the families of primer extension products will be electrophoretically separated in different electrophoretic media, so that the families of primers extension products corresponding to each base in the nucleic acid can be distinguished.

Where different labeled primers are used for generating each family of primer extension products, the families of products may be grouped together and electrophoretically separated in the same electrophoretic medium. In this preferred method, the families of primer extension products may be combined or pooled together at any convenient point following the primer extension product generation step. Thus, the primer extension products can be pooled either prior to contact with the solid phase, while bound to the solid phase or after separation from the solid phase but prior to electrophoretic separation.

Kits for practicing the subject sequencing methods are also provided. At a minimum such kits will comprise capturable chain terminators, e.g. biotinylated-ddATP; -ddTTP; -ddCTP and -ddGTP. For embodiments in which the primer extension products are labeled, the kits will further comprise a means for generating labeled primer extension products, such as labeled deoxynucleotides, or preferably labeled primers, where the labeled primers are preferably Energy Transfer labeled primers which absorb at the same wavelength and provide distinguishable fluorescent signals. Conveniently, the kits may further comprise one or more additional reagents useful in enzymatic sequencing, such as vector, polymerase, deoxynucleotides, buffers, and the like. The kits may further comprise a plurality of containers, wherein each contain may comprise one or more of the necessary reagents, such as labeled primer, unlabled primer or degenerate primer, dNTPs, dNTPs containing a fraction of fluorescent dNTPs, capturable ddNTP, polymerase and the like. The kits may also further comprise solid phase comprising a moiety capable of binding with the capturable ddNTP, such as streptavidin coated magnetic beads and the like.

1.4.7 Production of the DNA Fragments

In another embodiment, the DNA fragments are preferably prepared according to either the enzymatic or chemical degradation sequencing techniques previously described, but the fragments are not tagged with radioactive tracers. These standard procedures produce, from each section of DNA to be sequenced, four separate collections of DNA fragments, each set containing fragments terminating at only one of the four bases. These four samples, suitably identified, are provided as a few microliters of liquid solution.

1.4.7.1 Sample Preparation and Introduction

To obtain intact molecular ions from large molecules, such as DNA fragments, by UV laser desorption mass spectrometry, the samples should be dispersed in a solid matrix that strongly absorbs light at the laser wavelength. Suitable matrices for this purpose include cinnamic acid derivatives such as (4-hydroxy, 3-methoxy) cinnamic acid (ferulic acid), (3,4-dihydroxy) cinnamic acid (caffeic acid) and (3,5-dimethoxy, 4-hydroxy) cinnamic acid (sinapinic acid). These materials may be dissolved in a suitable solvent such as 3:2 mixture of 0.1% aqueous trifluoroacetic acid and acetonitrile at concentrations which are near saturation at room temperature.

One technique for introducing samples into the vacuum of the mass spectrometer is to deposit each sample and matrix as a liquid solution at specific spots on a disk or other media having a planar surface. To prepare a sample for deposit, approximately 1 microliter of the sample solution is mixed with 5–10 microliters of the matrix solution. An aliquot of this mixed solution for each DNA sample is placed on the disk at a specific location or spot, and the volatile solvents are removed by room temperature evaporation. When the solution containing the samples and thousand-fold or more excess of matrix is dried on the disk, the result should be a solid solution of samples each in the matrix at a specific site on the disk.

Each molecule of the sample should be fully encased in matrix molecules and isolated from other sample molecules. Aggregation of sample molecules should not occur. The matrix need not be volatile, but it must be rapidly vaporized following absorption of photons. This can occur as the result of photochemical conversion to more volatile substances. In addition, the matrix must transfer ionization to the sample. To form protonated positive molecular ions from the sample, the proton affinity of the matrix must be less than that of the basic sites on the molecule, and to form deprotonated negative ions, the gas phase acidity of the matrix must be less than that of acidic sites on the sample molecule. Although it is necessary for the matrix to strongly absorb photons at the laser wavelength, it is preferable that the sample does not absorb laser photons to avoid radiation damage and fragmentation of the sample. Therefore, matrices which have absorption bands at longer wavelengths are preferred, such as at 355 nm, since DNA fragment molecules do not absorb at the longer wavelengths.

Depicted herein is a suitable automated DNA sample preparation and loading technique. In this approach, a commercially available autosampler is used to add matrix solution from container to the separated DNA samples. A large number of DNA fragment samples, for example 120 samples, may be loaded into a sample tray. The matrix solution may be added automatically to each sample using procedures available on such an autosampler, and the samples may then be spotted sequentially as sample spots on an appropriate surface, such as the planar surface of the disk rotated by stepper motor. Sample spot identification is entered into the data storage and computing system which controls both the autosampler and the mass spectrometer. The location of each spot relative to a reference mark is thus recorded in the computer. Sample preparation and loading onto the solid surface is done off-line from the mass spectrometer, and multiple stations may be employed for each mass spectrometer if the time required for sample preparation is longer than the measurement time.

Once the samples in suitable matrix are deposited on the disk, the disk may be inserted into the ion source of a mass spectrometer through the vacuum lock. Any gas introduced in this procedure must be removed prior to measuring the mass spectrum. Loading and pump down of the spectrometer typically requires two to three minutes, and the total time for measurement of each sample to obtain a spectrum is typically one minute or less. Thus 50 or more complete DNA spectrum may be determined per hour according to the present invention. Even if the samples were manually loaded, less than one hour would be required to obtain sequence data on a particular segment of DNA, which might be from 400 to 600 bases in length. Even this latter technique is much faster than the conventional DNA sequencing techniques, and compares favorably with the newer automated sequencers using fluorescence labeling. The technique of the present invention does not, however, require the full-time attention of a dedicated, trained operator to prepare and load the samples, and preferably is automated to produce 50 or more spectrum per hour.

Greater detail of the preferred technique for DNA sequencing is depicted herein. Under the control of the computer, the disk may be rotated by another stepper motor relative to the reference mark to sequentially bring any selected sample to the position for measurement. If the disk contains 120 samples, operator intervention is only required approximately once every two hours to insert a new sample disk, and less than five minutes of each two hour period is required for loading and pumpdown. With this approach, a single operator can service several spectrometers. The particular disk geometry shown for the automated system is chosen for illustrative purposes only. Other geometries, employing for example linear translation of the planar surface, could also be used.

1.4.7.2 The Mass Spectrometer

The present invention preferably utilizes a laser desorption time of flight (TOF) mass spectrometer. The disk has a planar face containing a plurality of sample spots, each being approximately equal to the laser beam diameter. The disk is maintained at a voltage $V_1$ and may be manually inserted and removed from the spectrometer. Ions are formed by sequentially radiating each spot on the disk with a laser beam from source.

The ions extracted from the face of the disk are attracted and pass through the grid covered holes in the metal plates. The plates are at voltages $V_2$ and $V_3$. Preferably $V_3$ is at ground, and $V_1$ and $V_2$ are varied to set the accelerating electrical potential, which typically is in the range of 15,000–50,000 volts. A suitable voltage $V_1$–$V_2$ is 5000 volts and a suitable range of voltages $V_2$–$V_3$ is 10,000 to 45,000 volts.

The low mass ions are almost entirely prevented from reaching the detector by the deflection plates. The ions travel as a beam between the deflection plates which suitably are spaced 1 cm. apart and are 3–10 cm long. The first plate is at ground and a second plate receives square wave pulses, for example, at 700 volts with a pulse width in the order of 1 microsecond after the laser strikes the tip. Such pulses suppress the unwanted low mass ions, for example, those under 1,000 Daltons, by deflecting them, so that the low weight ions do not reach the detector, while the higher weight ions pass between the plates after the pulse is off, so they are not deflected, and are detected by detector.

An ion detector is positioned at the end of the spectrometer tube and has its front face maintained at voltage $V_d$. The gain of the ion detector is set by $V_d$ which typically is in the range of −1500 to −2500 volts. The detector is a chevron-type tandem microchannel plate array with a front plate at about −2000 volts. The spectrometer tube is straight and provides a linear flight path, for example, ½ to 4 meters in length, and preferably about two meters in length. The ions are accelerated in two stages and the total acceleration is in the range of about 15,000–50,000 volts, positive or negative. The spectrometer is held under high vacuum, typically 10 uPa, which may be obtained, for example, after 2 minutes of introduction of the samples.

The face of the disk is struck with a laser beam to form the ions. Preferably the laser beam is from a solid laser. A suitable laser is an HY-400 Nd-YAG laser (available from Lumonics Inc., Kanata (Ottawa), Ontario, Canada), with a 2nd, 3rd and 4th harmonic generation/selection option. The laser is tuned and operated to produce maximum temporal and energy stability. Typically, the laser is operated with an output pulse width of 10 ns and an energy of 15 mj of UV per pulse. To improve the spatial homogeneity of the beam, the amplifier rod is removed from the laser.

The output of the laser is attenuated with a 935–5 variable attenuator (available from Newport Corp., Fountain Valley, Calif.), and focused onto the sample on the face, using a 12-in. focal length fused-slica lens. The incident angle of the laser beam, with respect to the normal of the disk's sample surface, is 70°. The spot illuminated on the disk is not circular, but a stripe of approximate dimensions 100×300 um or larger. The start time for the data system (i.e., the time the laser actually fired) is determined using a beam splitter and a P5-01 fast pyroelectric detector (available from Molectron Detector Inc., Campbell, Calif.). The laser is operated in the Q switched mode, internally triggering at 5 Hz, using the Pockels cell Q-switch to divide that frequency to a 2.5 Hz output.

The data system for recording the mass spectra produced is a combination of a TR8828D transient recorder and a 6010 CAMAC crate controller (both manufactured by Lecroy, Chestnut Ridge, N.Y.). The transient recorder has a selectable time resolution of 5–20 ns. Spectra may be accumulated for up to 256 laser shots in 131,000 channels, with the capability of running at up to 3 Hz, or with fewer channels up to 10 Hz. The data is read from the CAMAC crate using a Proteus IBM AT compatible computer. During the operation of the spectrometer, the spectra (shot-to-shot) may be readily observed on a 2465A 350 MHz oscilloscope (available from Tektronix, Inc., Beaverton, Oreg.). A suitable autosampler for mixing the matrix solution and each of the separated DNA samples and for depositing the mixture on a solid planar surface is the Model 738 Autosampler (available from Alcott Co., Norcoss, Ga.).

This linear TOF system may be switched from positive to negative ions easily, and both modes may be used to look at a single sample. The sample preparation was optimized for the production of homogeneous samples in order to produce similar signals from each DNA sample spot.

1.4.7.3 Data Analysis and Determination of Sequence

The raw data obtained from the laser desorption mass spectrometer 30 consists of ion current as a function of time after the laser pulse strikes the target containing the sample and matrix. This time delay corresponds to the "time-of-flight" required for an ion to travel from the point of formation in the ion source to the detector, and is proportional to the mass-to-charge ratio of the ion. By reference to results obtained for materials whose molecular weights are known, this time scale can be converted to mass with a precision of 0.01% or better.

In a graph of intensity v. time-of-flight of the pseudomolecularion region of a TOF mass spectrum of Not I Linker (DNA) in which the matrix is ferulic acid and the wavelength is 355 nm, four consecutive spectra can be obtained using the present invention by the successive measurement of the four collections of DNA fragments obtained from fragmentation of each sample of DNA. Each of these spectra will correspond to the set of fragments ending in a particular base or bases G, G and A, C and T, or C. To determine the order of the peaks in the four spectra, a simple computer algorithm may be utilized. It should be noted that the data obtained from the mass spectra contains significantly more useful information that the corresponding traces from electrophoresis. Not only can the mass order of the peaks be determined with good accuracy and precision, but also the absolute mass differences between adjacent peaks, both in individual spectra and between spectra, can be determined with high accuracy and precision. This information may be used to detect and correct sequence errors which might otherwise go undetected. For example, a common source of error which often occurs in conventional sequencing results from variations the amounts of the individual fragments present in a mixture due to variations in the cleavage chemistry. Because of this variation it is possible for a small peak to go undetected using conventional sequencing techniques. With the present invention, such errors can be immediately detected by noting that the mass differences between detected peaks do not match the apparent sequence. In many cases, the error can be quickly corrected by calculating the apparent mass of the missing base from the observed mass differences across the gap. As a result, the present invention provides sequence data not only much faster than conventional techniques, but also data which is more accurate and reliable. This correction technique will reduce the number of extra runs which are required to establish the validity of the result.

1.4.8 The Amplification of a DNA Stretch Using the per Procedure with the Knowledge of Only One Primer In another embodiment, the present invention enables the amplification of a DNA stretch using the PCR procedure with the knowledge of only one primer. Using this basic method, the present invention describes a procedure by which a very long DNA of the order of millions of nucleotides can be sequenced contiguously, without the need for fragmenting and sub-cloning the DNA. In this method, the general PCR technique is used, but the knowledge of only one primer is sufficient, and the knowledge of the other primer is derived from the statistics of the distributions of oligonucleotide sequences of specified lengths.

1.4.8.1 Method of Sequencing without the Need for Fragmenting or Subcloning

The objects and advantages of the present invention are also achieved by a method comprising:

a) synthesizing a partly fixed primer, with 4, 5, 6 nucleotide, or longer sequence characters fixed within it. The fixed sequence can be any sequence, with some preferred sequences such as those containing many G-C pairs that increases binding affinity. The fixed position within the primer can be anywhere, with some preferred positions;

b) taking a very long genomic DNA, either uncloned or a cloned large insert such as the YAC or cosmid in which a short sequence of about 20 characters somewhere within the DNA is known;

c) synthesizing a primer from the sequence known from the DNA in step b;

d) radiolabeling the primer in step c;

e) annealing the primers (from step a, and step d or step g as appropriate) to the DNA in step b, and amplifying the DNA between the attached primers;

f) performing DNA sequencing of the amplified DNA by the chemical degradation method of Maxam and Gilbert, or carrying out DNA sequencing by the Sanger method, or by modified PCR-sequencing method;

g) after obtaining the DNA sequence from step f, selecting an appropriate first primer towards the 3' end of the sequence, synthesizing it, and radiolabeling it;

h) repeating the steps e through g with the two primers (the same partly fixed unknown primer as the second primer and the newly synthesized primer from step g as the first primer);

i) if the sequence obtained in step f is too short to be of value, using another partly fixed primer with a different fixed sequence and the same first primer to obtain a longer DNA sequence.

Unless defined otherwise, all technical and scientific terms used herein have the same meaning as commonly understood by one of ordinary skill in the art to which this invention belongs. All publications mentioned hereunder are incorporated herein by reference. Unless mentioned otherwise, the techniques employed herein are standard methodologies well known to one of ordinary skill in the art.

The partly fixed primer used to perform DNA amplification and sequencing are, of course, not limited to those described under the examples. Further modification in the method may be made by varying the length, content and position of the fixed sequence and the length of the random sequence. Additional obvious modifications include using different DNA polymerases and altering the reaction conditions of DNA amplification and DNA sequencing. Furthermore, the basic technique can be used for sequencing RNA using appropriate enzymes.

Instead of preparing the first primer completely, it can also be prepared as follows. Two or three shorter oligonucleotides that would comprise the complete primer could be ligated, by joining end-to-end after annealing to the template DNA, as described under another patent (Helmut Blocker, U.S. Pat. No. 5,114,839, 435/6, 5/1992) or as described in the publication (L. E. Kotler, et al., Proceedings of the National Academy of Science, USA, 90:4241–4245 (1993)). Alternatively, it can be synthesized using the single-stranded DNA binding protein, the subject of another invention (J. Kieleczawa, et al., Science, 258:1787–1791 (1992)). One of such procedures, or an improved version thereof, can be used to make the first primer in the present invention. All in all, the first primer need not be synthesized at every PCR reaction while contiguously sequencing a long DNA, and can be directly constructed from an oligonucleotide bank. Based on the present invention, the second primer also can be chosen from a set of only a few pre-prepared primers. This enables the direct automation of sequencing the whole long DNA by incorporating the primer elements into the series of sequential PCR reactions.

1.4.8.2 Advantages of Method

An advantage of the present invention is that from a known sequence in a very long DNA, sequencing can be performed in both directions on the DNA. Two first primers can be prepared, one on each strand, running in the opposite directions, and the sequence can be extended on both directions until the two very ends of the long DNA are reached by the present invention, using a small set of pre-prepared partly fixed second primers.

One of the major advantages of the present invention is that it is highly amenable to various kinds of automation. Instead of radiolabeling the first known primer, it can be fluorescently labeled, and with this the DNA sequencing can be performed in an automated procedure on machines such as that marketed by the Applied Biosystems ("373 DNA Sequencer: Automated sequencing, sizing, and quantitation", a pamphlet from the Applied Biosystems, A Division of Perkin-Elmer Corporation (1994)). In the present invention there is no need to newly synthesize any primers to sequence a very long DNA. Thus, with the pre-prepared set of partly fixed second primers, an oligonucleotide bank for the synthesis of the first primer, and a large supply of the template genomic DNA (or any long DNA), the sequencing of the whole long DNA can be automated using robots almost without any human intervention, except for changing the sequencing gels.

1.4.8.3 Applications of Method

The following processes can be computer controlled: 1) the selection of the appropriate sequence for constructing the first primer close to the 3' end of the newly worked out sequence, 2) determining whether the sequence obtained is too short and selection of a different partly fixed second primer, 3) assembling the contiguous DNA sequences from the various lanes and various gels and appending to a database, and other such processes. Thus the present invention enables the construction of a fully automated contiguous DNA sequencing system. Any such automations are obvious modifications to the present invention.

The present invention is not limited to only unknown genomic DNA, and can be used to sequence any DNA under any situations. DNAs or RNAs of many different origins (e.g. viral, cDNA, mRNA) can be sequenced not only limited to research or information gathering purposes, but also to other purposes such as disease diagnosis and treatment, DNA testing, and forensic applications.

It is understood that the examples and embodiments described herein are for illustrative purposes only and that various modifications or changes in light thereof will be suggested to persons skilled in the art and are to be included within the spirit and purview of this application and scope of the appended claims.

It should be noted that any kit or process used for research, diagnostic, forensic, treatment, production or other purposes that uses the present invention is covered under these claims. Furthermore, the various sequences of the partly fixed second primers that can be used in the present invention are covered under this patent. Thus, any kit or process that uses this method and/or the DNA strands with the sequences that would comprise the partly fixed second primers will also be covered under this.

In addition to contiguous DNA sequencing, the present invention will cover the amplification of the DNA strands that are bounded between the known primer and the partly fixed second primer (either from claim 1 or from claim 2). The DNA amplification can also be performed for long DNA strands using the long PCR amplification protocols.

1.4.9 Polynucleotide Sequencing with Random Surface Immobilization and Light Microscopic Detection of Affinity Labels Coupled to Microscopic Beads A DNA sample is prepared by shearing or digestion at a first sequence with a first restriction enzyme producing a 3' overhang terminus, to some appropriate, known size distribution, and labeled with a digoxigenin bearing nucleotide by the action of terminal deoxynucleotidyl transferase.

After such digoxigenin labeling, said DNA sample is then subjected to random internal cleavage, for example by shearing so as to produce a population of molecules with an average length half that produced in the previous sizing step, or digestion with a second restriction enzyme recognizing a distinct, second recognition sequence. Sample molecules of said sample are then bound at some convenient surface density to a transparent surface modified with a monolayer or a sub-monolayer density of anti-digoxigenin antibody. Said sample molecules, which will thus be bound to said transparent surface by the 3' termini of one strand, are then subjected to treatment by a 3' to 5' exonuclease, which will only act at the 3' terminus which does not bear the digoxigenin moiety due to the hindrance of this latter 3' terminus by its interaction with the surface, preferably not to completion of digestion of susceptible strands. Thus primed DNA sample template molecules bound to a transparent surface in an end-wise manner are prepared.

Using a single nucleotide labeling affinity moiety in a manner similar to the example provided for one-bit binary labeling systems, utilizing for example each of the four nucleotides derrivatized to effect communication of said nucleotides with a biotin moiety via a chemically cleavable linker, such as those described by S.W. Ruby et al.34 polymerization directed by the template provided by each involved DNA sample template molecule is effected with an appropriate DNA polymerase lacking a 3' to 5' exonuclease activity, such as Sequenase 2.0,35 with only one nucleotide type present during each polymerization step sub-cycle, at sufficiently low concentration to effect equilibrium controlled stepping. Polymerization reagents are then washed away, and may favorably be recycled after quantitation and readjustment of respective labeled nucleotide content.

After each such polymerization sub-cycle step, which will add a biotin labeled nucleotide to only a fraction of those sample template molecules having only the base complementary to the nucleotide of said sub-cycle located immediately 5' to the base opposite the 3' terminal base of the strand priming this nucleotide addition, biotin bearing molecules may be labeled with microscopic streptavidin coated beads. Unbound beads are then washed away. Bead labeled molecules may then be observed by a video microscope, and the position of said bead labeled molecules within a sample may be recorded by image analysis of digital images thus obtained, in a manner similar to that used by Finzi and Gelles. Dithiothreitol or other reagents capable of cleaving said linker holding said biotin in communication with said nucleotide incorporated during the previous polymerization sub-cycle are then used to treat sample molecules to cleave said linkers and thus release said biotin labeling moieties and the beads which have bound to them. A wash step is then performed to remove said beads. The extent of bead removal may be checked with another video microscopy detection step if needed; and further cleavage treatment may be performed if decoupling was not adequate. The same sub-cycle (comprising polymerization, bead association, video microscopic examination, bead and label cleavage and removal by washing, and optionally a bead removal confirmation video microscopic examination step) is then repeated in succession for each of the three remaining nucleotide types, to complete a full base sequencing cycle (which as noted may yield information about more than one base location for some template molecules according to the sequence composition and the order of sub-cycles, and no information for other sample template molecules). Multiple said base sequence cycles are repeated until enough data have been accumulated relative to the total complexity of the initial DNA sample. Recorded data are then used to reconstruct sequence information for a segment of each sample template molecule, and segment sequence data are then aligned by appropriate computational algorithms.

Note that this embodiment avails only existing and generally available materials and devices, relies on relatively simple manipulations which are known to be highly reproducible according to their general use in the relevant fields, but due to the novel process of the present invention may yield genome sequence information far more rapidly and inexpensively than highly complex robotic instruments with sequencing methods utilizing electrophoretic separation.

Note that microscopic detection may be performed with a computer controlled stepable sample stage to effect the automated examination of large surface areas and hence very large numbers of sample molecules.

Alternatively, the transparent substrate providing the surface for immobilization may be that of a spooled film, which may be advanced at an appropriate rate before the objective of said video microscope of the present embodiment. Further, with such a spooled sample arrangement, said film may be circular, and continuously advanced through multiple video microscope apparata and wells effecting polymerization sub-cycles, all in appropriate order such that benefit of full pipelining of each step may be enjoyed. The construction of such instrumentation and rudimentary robotic actuation systems will be straightforward to those skilled in the relevant engineering arts.

Surface immobilization with single photon detection of plural fluorescent labels coupled to photodetachable 31-hydroxyl protecting groups. Sequence determination may additionally effected by the random immobilization at some appropriate density of appropriately prepared and primed sample molecules on the surface of a transparent film, and stepwise polymerization with some appropriate polymerase, of all four nucleotides, all of which are protected at the 3'-hydroxyl with a photolabile (and hence photoremovable) protecting group in communication with labeling moieties which distinctly correspond to each nucleoside base type of the respective nucleotide. Label incorporation is detected, for example by the scanned beam light microscopic methods of the present invention, or with highly sensitive CCDs, and assigned to the spatial region occupied by a particular molecule. Said film is translated appropriately such that the full complexity of the sample may be examined after each polymerization cycle.

Data are recorded electronically and according to the molecule for which they are obtained. Illumination of the sample with an appropriate frequency and intensity of light to effect 3'-hydroxy deprotection and hence also labeling moiety removal is performed, and a wash step is performed to remove freed label. Such polymerization, detection and deprotection cycles are repeated until the sample is sufficiently well characterized.

1.4.9.1 Random and Non-Random Immobilization to Optical Detection Array Devices with Optical Labels 1.4.9.1.1 Detection and Classification of Pathogens in Clinical Samples Methods of the present invention may be combined with the immobilization of highly diverse libraries of binding specificities with either encoding labels or phenogenocouples, which may therefore be characterized dynamically and related to any detected binding of particles of interest from a sample. Clinical samples are interacted with said libraries. All retained material is then interacted with some general label such as a polynucleotide binding dye (e.g. ethidium bromide, DAPI) or some chromophorigenic or photoemissive or labeled competitive inhibitor analog reagent detecting some metabolically fundamental reaction such as ATP hydrolysis, or the presence enzymes catalyzing said metabolically fundamental reaction. Pathogens containing polynucleotides or capable of said metabolically fundamental reaction may thus be detected.

The essential features of such a system are massively parallel screening for affinity interactions, generalized labeling methodology, and automated sample characterization. Because pathogen culturing is not required, and many types of highly specific information may be obtained in one assay procedure, without any previous knowledge of the state of the organism from which said clinical sample was obtained, this represents the basis for extremely powerful diagnostic methods.

Note that various implementations may distribute binding specificities of known composition in a spatially controlled manner, and thus rely on spatial information to encode specificity type and hence, if known, composition of each specificity type. Note also that said libraries may comprise known mimetics or small molecules of known binding specificity.

The profile of any sample type from an individual organism according to such an assay may be monitored over time, and a profile is preferably obtained for a state of presumed health for comparison to samples correlated to states of disease, deficiency or degeneration or other states of ill health (i.e. longtitudinal tracking of individuals stratified by sample type). Samples of similar type may also be compared across populations and subpopulations, and the profile of these samples also correlated with state of health of the respective individuals (cross-sectional comparison).

For additional selectivity of detection, such a sample characterized as above may be further characterized according to the immunocharacterization method below.

1.4.9.1.2 Automated Immunocharacterization and Cyber-Immune Detection

Such a system resembles that used for the detection and characterization of clinical samples, except that said highly libraries of binding specificities comprises a large number of immunoglobulin specificities. Libraries comprising immunoglobulin specificities may include such specificities in the form of immunoglobulins expressed on bacteriophages, viruses, or in the form of the phenogenocouples of the present invention.

Banks comprising all of the specificities of a library may be maintained as monoclones, and upon detection of a pathogen in association with one or more binding specificity contained in some library, and the identification and/or characterization of said one or more binding specificity, an alignment of the respective said monoclone, from one of said banks, may can be provided to the organism. Such analysis and provision of one or more monoclones be automated and controlled by algorithms.

Similar rapidity and broad characterization advantages are attained as with the preceding method for the characterization of clinical sample.

1.4.9.1.3 Massively Parallel Enzymological Assays

In a manner similar to the preceding embodiments, several enzymes contained within some sample may be analyzed according to their binding probability, binding duration or dissociation rate and conformational or phosphorylation or other status. Such assays may favorably be performed by the methods of the present invention, with immobilized libraries which may include competitive inhibitors, and with pre- or post-binding labeling of sample enzymes by encoded label antibodies, to permit classification of sample enzyme type on a molecule by molecule basis, which classification data may be combined with the data obtained in this assay.

1.4.9.2 Hybridization Based Detection of Polynucleotide Sequences

Various methods have been developed to test for the presence of short polynucleotide sequences and combinations of such sequences (according to stringency) in polynucleotide samples by hybridizing oligonucleotides or polynucleotides of known sequence to said polynucleotide samples. Such methods are sometimes termed 'gene-probe" methods and often involve the use of immobilized, ordered arrays of oligonucleotides of known composition.

Said ordered arrays have been formed on the surfaces of integrated electronic devices. It has been shown that, provided stringency can be made sufficiently high to prevent binding with even one base mismatch, such methods may be used to obtain sequence information about a sufficiently small sample.

The methods of the present invention provide a more rapid and convenient method for testing for the binding of known oligonucleotides to a complex polynucleotide sample, owing largely to the higher degree of parallelism which may be accomplished with single molecule methods. Here, each oligonucleotide, of known sequence, to be used as a specific gene probe, is synthesized with some perceptible encoded label, as described above, where the codes assigned to the sequence of said each oligonucleotide are known (due to the synthetic scheme by which they are produced and concurrently labeled). These are then hybridized to sample polynucleotide molecules, which either have previously been or will subsequently be immobilized, or may otherwise be separated from probe oligonucleotides, and the presence or absence of said each oligonucleotide in the sample polynucleotide containing fraction, which is a direct result of the success or failure of said each oligonuclectide to bind said sample polynucleotide molecules, will be readily ascertained through the detection and discrimination of the perceptible encoding labels corresponding to said each oligonucleotide. Contrary to the conventional gene-probe methodology, known probing molecules are generally unbound in this variation of the method as may be used with the present invention.

If the complexity of the polynucleotide sample is not too large, and the population made up of said oligonucleotides is sufficiently large and complex, preferably exhaustively enumerating all possible oligonucleotides of the respective and sufficiently long length, and provided hybridization may be sufficiently stringent, which stringency is affected by a large number of known factors but also has sequence dependent components, information about the binding of said each oligonucleotide, which may be related to the respective known sequence and by Watson-Crick pairing rules to the respective sample polynucleotide sequence segment (or by identity with the strand complementary to the strand to which said each oligonucleotide has bound) may thus be obtained. As with other methods, alignment of such data may yield information about the sequence of the sample. The methods of the present invention further provide for the quantitation of such oligonucleotide hybridization by way of counting the number of times a particular perceptible encoded label is retained by a said polynucleotide sample, which may be availed both in the monitoring and correcting of errors and in the modulation of binding (hybridization) conditions.

Alternatively, probing may be accomplished by oligomeric sequences immobilized in some known configuration, for example by spatially patterned methods such as those of S.P.A. Fodor et al.37 or by the lattices produced hierarchically by the method of N. C. Seeman noted above but comprising an ordered array (the order of which is predetermined by the incorporation or association of single stranded oligonucleotides or other single stranded termini of known sequence into or with modular components used to build up said lattices) of short single stranded regions of known sequence and preferably one free terminus (so as not to hinder conformational changes required for hybridization), but detected by the methods of the present invention, where sample polynucleotides are labeled with some appropriate discernible label, such as the dye YOYO-I, to facilitate the detection of their presence in association with each of said oligomeric sequences.

A yet further variation for effecting the spatially predetermined distribution of, for example and exhaustively enumerated population of single stranded oligonucleotides, may be effected by the used of the methods of N. C. Seeman to produce a uniform two dimensional lattice with a repeating pattern of short single stranded sequences with photo protected termini, for example all of the 256 possible 4-mers. Such a lattice may have a periodicity substantially smaller than the wavelength of visible light. Said short single stranded sequences may be comprise some synthetic backbone so as to be resistant to enzymatic cleavage, which backbone preferably also is non-ionic (for example, of alkyl or beta-cyanoethyl derivation, peptide-nucleic-acid composition, or methylphosphonate composition) so as to denature from a complementary sequence only at markedly elevated temperatures relative to ordinary oligonucleotides. Thus, a pattern of oligonucleotide complexity may be distributed in a predetermined manner below the resolution of light directed patterning.

Light patterning techniques may then be availed to spatially direct the photodeprotection of said short single stranded sequences at lower resolution. Such light directed syntheses are preferably terminated with some comonomer which will prevent exonucleolytic degradation of said short single stranded sequences, or all of said short single stranded sequences are of a polarity opposite to that specified by the exonuclease to be subsequently used. By this combination of methods, patterning resolution is not limited by the properties of light, but may avail of the convenience of light directed patterning at lower resolutions. After a known distribution of all possible single stranded sequences of sufficient complexity has thus been produced, a denatured, labeled polynucleotide sample produced by extensive nick translation, with fluorescent labeled nucleotides, of a naturally occurring polynucleotide sample is hybridized to said lattice. Hybridized molecules are treated mildly with a single strand specific nuclease, followed by an exonuclease, to degrade or by the same process to free those regions which are not bound to the probing said short single stranded sequences. Label incorporated into the nick translation products of said polynucleotide sample is then detected and spatially mapped by the methods of the present invention, and binding is thus scored according to the known probing said short single stranded sequences. This method thus avails the molecular parallelism made possible by the molecular recognition, high density and high resolution detection methods availed with the present invention.

Note, finally, that higher density patterning than attainable by conventional light patterning methods may also be effected by scanning probe lithographic methods, such as the use of NFSOM lithography with photodeprotectable groups.

1.4.9.2.1 Methods for Repeatable Detection and Identification of Single Molecules Repeatable detection and identification of single:molecules is achievable by microscopic labeling with some readily identifiable, e.g. combinatorially or permutationally diverse and readily examined particle or molecule or group of molecules and detection of the thus marked identity of individual free molecules in solution, with removal of excess nucleotides (e.g. by filtration); and, scanning of a liquid sample volume where sample molecules and sample conditions are matched to ensure manageably slow free diffusion of sample molecules permitting tracking of the motions of free individual molecules in solution, as observed by T. T. Perkins et al. for reptation of DNA in solution, in which instance unreacted labeled monomers may be removed, for instance, according to their more rapid diffusion, possibly through a filter, and detection may favorably comprise observation of reduced mobility of a labeling moiety after it has become attached to a sample molecule.)

According to the labeling methods employed, various detection methods may satisfy the requirements of signal detection with repeatable assignability to a particular unique sample template molecule.

Prominent among these detection methods are microscopy methods such as video microscopy including confocal fluorescence microscopy with or without enhancement, and with or without variations incorporated into the present invention near field scanning optical microscopy (NFSOM) and variations thereof; contact and non-contact varieties of scanning force microscopy (SFM; also termed atomic force microscopy (AFMI) and variations thereof; other scanning probe microscopies including scanning tunneling microscopy (STM), scanning tunneling spectroscopy (STS), and so-called field emission mode STM (which is more accurately described as microscopy by field emission from a scanned conductive probe, or scanning field emission microscopy, SFEM, because no tunneling actually occurs). Any enhancements of scanning probe microscopy, including multiple probe parallelism, may readily be availed in the practice of the present invention.

Additionally, optical detection methods employing optoelectronic array devices (OADs), such as spatial light modulators (SLMs), laser diode arrays (LDAs), light-emitting diode arrays, or charge coupled photo-diode arrays (conventionally termed CCDs), in combination with appropriately high sensitivity detection methods, may also be employed, particularly with samples immobilized such that the maximal proportion of pixel elements of said array will be involved with the detection of a signal from exactly one sample molecule. CCD and SLM array device are presently available at pixel densities of approximately $10^5$ to $10^6$ per $cm^2$. LDAs of comparable density are currently under development. Device level constraints upon parallelism will thus be significant, but may be overcome by increasing the data obtained per molecule (i.e. processivity or sequence segment length.) Such devices may be employed remotely, i.e. in some arrangement where light passes through the sample under study and is detected by some apparatus involving said array devices, or in close or direct contact with said sample, as for instance, polynucleotides have been immobilized to integrated circuits for other applications. Appropriate arrangements of such devices for the appropriate detection scheme in which each device type is appropriately used will be obvious to those skilled in the arts of optics and optoelectronics.

Note that for purposes of those variations of the present invention involving the immobilization of sample molecules, said immobilization may be conveniently effected in a random manner, relying upon some appropriate surface or volume density which yields a corresponding random surface or volume distribution, and appropriate detection methods to permit repeatable resolution of most sample molecules from each other. The length of the molecules in question will be an important factor in the determination of a desirable said density. Generally speaking, for random surface immobilization and without the use of measures to orient or order sample molecules, for molecules of length L (which may additionally account for any labeling bead diameter), and detection methods relying on spatial resolution R, maximum practical molecule number density will generally be the less than $1/(2L+R)^2$. This assumes the worst case configuration of two end immobilized molecules extending directly towards each other and both labeled near their respective termini. Similar calculations may be applied to three dimensional cases. Alternatively, one may consider $(2L+R)^2$ or $(2L+R)^3$ to be an average bin size, and determine via the Poison distribution the optimal molecular number density corresponding to the largest number of bins being occupied by precisely one sample template molecule.

Alternatively, molecules may be labeled by a first label, for example with a particular fluorescent dye incorporated by nick translation, in a manner identifying a portion of the molecule near the site of polymerization, and proximity of said first label to the perceptibly distinct labeling moieties used for nucleotide incorporation detection and discrimination will permit the detection of unacceptable proximity of two distinct sample molecules. Such a method is consistent with the tracking methods described below for free sample molecules. in such a case, the data collected during the cycle in which said unacceptable proximity is observed for the affected molecules may be ignored, and lack of information from this cycle noted for the respective molecules. Conditions, such as solution viscosity, sample molecule diffusion rate, sample molecule concentration, sample dimensions, etc., may be optimized to reduce the occurrence of such unacceptable proximity, and oversampling methods described in other portions of the present disclosure may be applied to preclude this form of error from degrading final data quality. These methods may be applied to either immobilized or unimmobilized sample molecules.

1.4.9.2.1.1 Microscopy Based Detection

Light microscopic visualization represents a particularly convenient and technically simple detection and unique molecule localization method. A visualization method of particular interest for purposes of the present invention in higher performance or more demanding applications is video enhanced confocal fluorescence microscopy (VECFM), preferably utilizing optics well matched to the refractive index of the reaction or detection medium.

As discussed above, various scanning probe microscopies may also be advantageously used within the present invention according to labeling agents and methods used. Most prominent among these are NFSOM and variations thereof, and both contact and non-contact SFM, and variations thereof.

Generally speaking, a microscopy based detection method must be sufficiently convenient, capable of use with a stepper translated or otherwise translatable sample, not destructive of the sample, and capable of detection of any labeling methodology to be used with it. Thus, it is quite likely that many microscopy methodologies not yet developed may readily be employed with the present invention. Further, microscopy and corresponding apparata shall comprehend any miniaturized or microfabricated microscopy devices or other comparable integrated detection means.

1.4.9.2.1.2 High Sensitivity and Scanned Excitation Beam Fluorescence Confocal Microscopy A modification of VECFM which is particularly suited for SMD and SMV relies upon selective fluorescent excitation of an appropriate dye molecule label (or of molecules within a sample with appropriate fluorescent properties independent of labeling) in some sample by means of some tightly defined beam, with dimensions at or near the resolution limit of the apparatus, of an appropriate frequency, or of parametrically controllable frequency, where said beam is caused to scan in a controlled manner through the sample region within the visual field. This microscopy, including numerous variations, may be termed either scanned beam confocal microscopy or steered beam confocal microscopy (in either case, SBCM). Scanning of said beam through the sample within the visual field may be accomplished by introducing said beam into the optical path of the VECFM via mobile mirrors which may effect said controlled scanning, or by first producing said beam with a pinhole which is itself scanned, before deflection towards the sample via said mirrors, which in the present case may be fixed in position, through the use of pinholes in a rotating disk arranged in one or more spiral arms to effect an approximately rastering illumination of the sample as said disk rotates, or by other means which will be obvious to those skilled in the design of optical instrumentation and microscopy. Said beam will excite fluorescence in any appropriately responsive molecules which occur in its path. An optical splitter may then redirect a fraction of the light transmitted from the sample through the objective lens, and direct it through a narrow bandwidth, high transmissiveness filter, which may be specific for a fixed or for a parametrically controllable variable frequency, to uniquely select the appropriate fluorescent emission frequency, to a highly sensitive photodetector, which may record either intensity as intensity information or as the number of photons detected per unit time, as a function of the region being subjected to fluorescence exiting illumination or being distinctly observed (see below). Thus a high resolution map of the fluorescence of the sample may be reconstructed, and further overlayed images obtained for the same sample and sample location by conventional VECFM means.

Alternatively, the entire sample of visual field may be subjected to illumination by an appropriate excitation frequency, and a pinhole scanned through the portion of the output of said optical splitter, such that light passing through said pinhole will reach said highly sensitive photodetector.

In yet a third, albeit technically more complex implementation, an SLM, may be used in place of said pinhole (in either configuration), and fluorescent excitatory illumination may be either broadly distributed or scanned.

In a fourth, albeit technically more complex implementation, sensitive photodetection may be accomplished with a highly sensitive CCD, and fluorescent excitatory illumination may be either broadly distributed or scanned. At present, CCD sensitivity approaching single photon detection is technically possible though is not practical for high volume applications.

In a fifth implementation, said scanned beam may originate from a laser diode array device or a light emitting diode array device, where only one of, or a contiguous group of elements of, such an array is active at any particular time so as to produce a particular beam, and the group of active elements of said such an array is changed as a function of time to effect scanning of the sample by the coordinated activation and deactivation of the plural beams thus produced.

In all of the above implementations, spatial information is gained about any particular fluorescent emission, and this may then be combined with other visual information obtained via the same VECFM apparatus.

Note that for scanned beam methodologies, where beams are used for excitation or detection, even where said beams may have inhomogeneous but invariant distribution of internal flux density, known samples such as individual dye molecules may be imaged for calibration purposes and information useful for algorithmic enhancement may be collected. This information represents the characterization of the convolution of the beam and optics properties with the signal actually owing to the known sample, and thus localization of fluorescent sample features may be accomplished at better than optical resolution limitations. For example, a single, immobilized fluorescent molecule may be examined by such an apparatus, and the intensity as a function of beam position may be recorded for the full duration of its presence within the beam's path as said beam scans the sample, and the data thus obtained may then be used to determine the change in observed intensity as the sample molecule enters the extremity of the beam, traverses the beam and exits the beam. This information may then be subjected, for instance to averaging or other computations to determine the relationship between the location of the molecule within the beam and the intensity observed, and finally that information used to estimate the intensity which would be observed when such a calibration sample molecule is in the precise center of the beam. This information may then be used in image enhancement of unknown samples. Note, however, that localization to below optical resolution limitations is distinct from increasing the resolution capability for two nearby objects.

Scanning beam microscopies will be of particular advantage where it is desirable to use particular illumination frequencies to modify the sample. For purposes of the present invention, a beam of predetermined frequency, for instance delimited and scanned by means of a pinhole as described above, may be used to selectively modify a particular sample molecule. For example, a beam of predetermined frequency may be used to effect the photobleaching of the labeling moiety on a particular sample molecule. to selectively remove a photocleavable protecting group on a particular sample molecule, to selectively remove a moiety joined to a sample molecule by a photocleavable linker, or selectively control any photochemical reactions in a highly localized but non-invasive manner.

Note that implementations permitting variations of illumination frequency and/or variations of the frequency or frequencies selected b,,. * filters for detection purposes constitute microspectroscopy or microfluorimetry, and may be applied to any of the various light microscopies.

1.4.9.2.1.3 Repeatability by Immobilization with Discernible Location

Surface Immobilization

A large number of methods presently exist to effect the immobilization of macromolecules and other molecules to various surfaces including the, surfaces of optically transparent materials. In general, such methods on the chemical modification of said surfaces such that they will be reactive with or have specific affinity for particular chemical functional groups placed on said macromolecules or molecules.

Applicable methods include those described by S. P. A. Fodor et al effect micropatterned surface immobilization and controlled synthesis polypeptides and polynucleotides, those described by M. Hegner et al. 14' effect the end-wise immobilization of terminally thiol modified double helical DNA molecules to a gold coated surface, or those methods recently used by L. Finzi and J. Gelles 15 to effect end-wise attachment of DNA molecules to an antibody coated glass surface. Many alternative methods will be obvious to those skilled in the relevant arts.

For purposes of genome sequencing applications of the present invention, DNA from a cosmid library which may have been prepared from total genomic material., from a cDNA library derived from a particular tissue type, from a cosmid library which may have been prepared for a single chromosome or group of chromosomes or particular chromosome segments, or directly purified genomic DNA or directly purified RNA from a particular cell type, etc., may be subjected to fragmentation. Physical methods such as shearing with a hypodermic apparatus may be suitable. Where the sample is in the form of duplex DNA, it may be treated with restriction enzymes, which preferably restrict either 6- or 4-base recognition sequences, so as to produce sample molecules of mean length of either 4 kilobases or 256 bases, respectively. Such lengths are sufficiently short to yield a high number density of sample molecules. Said sample molecules may then be appropriately derrivatized, for example by fill-in reactions at 5' overhang cohesive termini produced by said restriction enzymes with nucleotides bearing an affinity label or an appropriately reactive chemical functional group.

1.4.9.2.1.4 Matrix Immobilization

There has been increasing interest and progress in the field of affinity chromatography which relies upon varyingly specific affinity interactions between molecules immobilized to a chromatographic matrix or polymeric matrix and the molecules contained in some sample. Of particular relevance are matrices with polynucleotides immobilized thereupon. An example which is widely known and used within the relevant fields is oligo-dT cellulose. Further, many chemistries and methods used to immobilize macromolecules to surfaces will be similarly applicable to immobilization to a polymeric matrix provided said matrix is chosen so as to have appropriate reactivities and not pose any difficulties associated with non-specific interactions. Most methods capable of effecting such matrix immobilization will be acceptable for purposes of the present invention. Note, however, that any matrix used in the present invention must admit the sufficiently rapid transport or diffusion of reaqents, enzvmes and buffers, as required by the particular embodiment.

1.4.9.2.1.5 Focal Plane Scanning

For detection an discrimination within a volume, whether for matrix immobilized samples or diffusion constrained free molecules in solution, especially where fluorescent labeling of one form or another has been employed, a sample may be examined by microscopy with reconstruction of three-dimensional spatial information by scanning the focal plane through the depth of the sample and collecting image data at appropriate intervals. Such methods of three-dimensional reconstruction are well known within the art of microscopy.

1.4.9.2.1.6 Plane Excitatory Illumination

Alternatively, optical means such as moving slits or SLMs or laser diode arrays may be employed to selectively illuminate a particular region, preferably a single plane (of thickness similar to the wavelength of light employed or feature size of integrated device means employed), to examine a particular subset of sample template molecules and labels associated with them, providing spatial reconstructability of the data thus collected.

1.4.9.2.2 Two Beam Methods Including Plane Illumination

Volume distributed samples may also be examined with methods closely analogous to those recommended for three dimensional optical mass data storage, for instance, by Sadik Esener in U.S. Pat. No. 5,325,324. Here, labels requiring excitation by photons of two distinct frequencies for photoemission may be employed. Alternatively, the related methods of illuminating an entire plane of a sample with one of said distinct frequencies may be availed as a mechanism for imaging with spatial reconstructability.

1.4.9.2.3 Immobilization via Concatenation

For the various applications of the present invention involving the interaction of enzymes with extended linear macromolecules such as polynucleotides, when said extended linear molecules may be conveniently circularized by appropriate treatments (which will generally be obvious to those skilled in the relevant arts), immobilization of said extended linear molecules may be conveniently effected by their concatenation with second extended linear molecules which are likewise conveniently circularized by appropriate treatments (which will again generally be obvious to those skilled in the relevant arts) bearing chemical properties (i.e. functional groups such as thiols or affinity moieties such as biotin) favorable for convenient, specific immobilization to a surface, matrix or other solid support. For purposes of, for example, certain sequencing applications of the present invention, said second extended linear molecules are favorably bound (with methods which will generally be obvious to those skilled in the relevant arts) at a predetermined location along their length, to some protein, which may be an enzyme such as a polymerase, before immobilization. Said second extended linear molecules may have termini with reactive chemical functional groups which may be bound together by the addition of some appropriate reagent such as a chemical cross-linking agent, or with some affinity, moiety such as an oligo- or polynucleotide which may be bound together by an appropriately complementary oligonucleotide or polynucleotide (with or without ligation thereof), or some appropriate multifuctional binding protein or receptor. Such an arrangement permits the following steps to be performed: said second extended linear molecule is bound to said enzyme; said protein is caused to bind to said first extended linear molecule (which may be circularized either in a prior or subsequent step); said second extended linear molecule to which said protein has been bound is caused to circularize by appropriate treatment; and if said first extended linear molecule is at this stage linear, it is caused to circularize. Without any special measures, there is a fifty percent chance that such a process will result in concatenation of the first extended linear molecule with the second extended linear molecule. Numerous methods, such as size separation followed by retention by immobilization, may be used to purify the resulting desired concatenate. Where said second extended linear molecule was chosen to be relatively short, such an assemblage will provide for the retention of said first extended linear molecule, now in concatenated circular form, in proximity to said protein, with specific immobilization or convenient immobilizability. Thus, said protein and said first extended linear molecule now in concatenated circular form have a high effective concentration with respect to eachother upon dissociation, and said protein and said first extended linear molecule now in concatenated circular form will not interact with the molecules of other such assemblages when said assemblages are at sufficiently low density or said second extended linear molecule now in concatenated circular form is particularly short (i.e. effectively shackles said first extended linear molecule now in concatenated circular form to said protein whether or not said first extended linear molecule now in concatenated circular form is bound by said protein.)

Such an immobilization scheme will be particularly desirable in, for example, sequencing applications of the present invention where a polymerase must perform a cycle, in which it binds, modifies and releases a sample molecule, at a high rate. A particular instance in which such desirability obtains is for samples to be analyzed with long sequence segments (e.g. hundreds or thousands of bases) where dissociation of the polymerase is necessary to permit either 3' hydroxy deprotection (e.g. removal of a photolabile protecting group) and or labeling moiety removal by appropriate means. Note that by immobilizing the enzyme, and hence the spatial location at which the labeling moiety first comes into physical communication with a sample molecule, the above stated limitation on sample molecule density may be overcome, with the new limit being that imposed by the detection method, thus increasing sample density and in some embodiments the parallelism that thence may readily be achieved with detection methods such as microscopy. It is therefore feasible, with such assemblages, to collect sequence data dynamically from each molecule at a rate approaching the limits imposed by the slower of: the characteristic nucleotide incorporation rate of the polymerase; or, the diffusion rate limit of nucleotide association with the nucleotide binding site of the polymerase (divided by four) when nucleotides are at a sufficiently low concentration that their presence as labeled but free molecules in the detection field does not interfere with the detection (which may be time averaged according to the particular instrumentation used) of incorporated labeled nucleotides, which concentration will be dependent in part on the geometry of the liquid volume; or, the maximum rate of single label detection (but note that such a rate need not be low because detection rate will increase for multimeric labels, which may be employed). Such an immobilization method will favorably be employed for embodiments locating sample molecules on or near the surface of a CCD or SLM. Note that kinetic control of polymerization rate (and hence stepping rate, e.g. by adjusting nucleotide concentration) is also enhanced by the use of such a concatenation methodology.

1.4.9.3 Immobilization with Non-random Distribution

While the above methods are convenient precisely because they require only the simple optimization of sample molecule density, the resulting random distribution will less than fully utilize available substrate or matrix space and fewer than all sample molecules will be sufficiently well separated for unambiguous resolution of two adjacent sample molecules. Due to the inherent advantages provided by molecular parallelism, this will not in general be a significant constraint. For applications in which a high degree of instrumentation miniaturization is desired, however, a better effective density of usable sample molecules, distributed in either two or three dimensions, may be effected as needed by non-random immobilization methods.

One such random immobilization method may avail of the invention of N. C. Seeman, described in U.S. Pat. No. 5,278,05 1, which provides a process for the construction of complex geometrical objects. These methods may be applied to the production of regular two- and three-dimensional molecular lattices from polynucleotide compositions. The process of this invention may be extended by the incorporation of appropriate affinity groups at predetermined locations within the objects, which for present purposes may favorably be small ligands such as biotin or digoxigenin, which may then be used as the target for a sample molecule which has been terminally labeled by a similar small ligand which has subsequently been bound by (an excess of) an appropriate multimeric receptor. Said multimeric receptor will then recognize and bind the complementary small molecule ligand incorporated into the structure of said lattice, and thus effect sample molecule immobilization according to the non-random pattern predetermined by the precise structure of said lattice and the precise distribution of ligands thereupon. Note that because the objects provided by the invention of N. C. Seeman comprise polynucleotide structures, care must be taken in using such a sample substrate with the methods of the present invention to ensure that said objects will be stable to all treatments which are to be applied to sample molecules, including denaturation, exonucleolytic degradation, primer hybridization, exposure to active polymerases, etc. Generally, these constraints may be met by effecting topological closure of all strands such that no free polynucleotide terminus is carried on such a lattice, and no denaturation procedures will result in matrix dissociation; the methods of the invention of N. C. Seeman may be availed in a manner meeting these constrains.

Note that to ensure complete regularity of lattices constructed by such means, or any other molecular lattices which do not have complete internal rigidity, the extremities of these lattices may be bound to solid supports which are then positioned so as to apply tensile stresses to said molecular lattices which will enforce constraints limiting flexural internal degrees of freedom and enforcing substantial spatial regularity on sample molecule distributions.

Any other method which provides a regular array of binding sites to which sample molecules may selectively be associated will also suffice for the purpose of non-random immobilization of sample molecules in two- or three-dimensions for the present invention.

Note also that said appropriate affinity groups incorporated (directly or, by conjugation or other methods, indirectly) at appropriate sites in a lattice may be chosen so as to interact directly with polynucleotide sample molecules in a sequence dependent or independent manner. Sequence dependent affinity binding may be effected with oligonucleotides or analogs thereof capable of forming double-, triple- or quadruple helices with said sample polynucleotides, ribozymes, or sequence dependent binding proteins including but not limited to: transcriptional activators (e.g. TATA-Binding Protein), enhancers and repressors; integrases; restriction enzymes; replicator proteins (e.g. DnaA); DNA repair proteins; anti-polynucleotide antibodies, RNA processing complexes (e.g. snRNPs); and RNA binding proteins all under conditions permitting desired selectivity, specificity or stringency but, where appropriate, preventing polynucleotide cleavage or degradation. Where sequence specific binding is desired, and hierarchically prepared lattices are used, the distribution of particular specificities may be controlled by the staged incorporation of said affinity groups at various hierachial levels of the synthetic procedure. This will permit classification of sequence data according to the location of the sample template molecule from which it is obtained in the lattice (i.e. on the surface or within the matrix). Sequence independent binding of polynucleotides may be effected by the use of proteins such as RecA, histones, U1, etc.

1.4.9.3.1 Repeatable Identification of Unimmobilized Molecules

Single molecule tracking with controlled diffusion—For samples under continuous observation, e.g. continuously within as visual field of a video microscope, molecules may be perceptibly labeled, for example by perceptible microscopic beads or the incorporation of a first fluorescent label, and tracked by the use of image analysis algorithms. Said algorithms will recognize only the appropriate type of label and track the motions of the respective sample molecule as it slowly diffuses in solution, so as to permit the unambiguous direct correlation or assignment of the signal associated with the addition of a labeled nucleotide to said respective sample molecule. For these methods, nucleotide labeling does not necessitate the use of large beads or other complexes for detection. Instead, single or oligomeric fluorescent labeling moieties, or enzymatic label affinity conjugation are preferred, such that labels may be removed without greatly disturbing the trajectory of said respective sample molecules. Either the direct colocalization (to within the resolution of the imaging method) of nucleotide label with said first fluorescent label or reductions in the Brownian motion of said nucleotide label sufficiently near (e.g. closest to) said first fluorescent label may be exploited in the detection of nucleotide label incorporation.

Note that manipulation with a laser trap, as for instance described by T. T. Perkins et al. for reptation of DNA in solution, may be employed with such free molecules.

1.4.9.3.2 Unique Labeling of Sample Molecules and Identification Methods

Various methods may be employed to uniquely label individual sample molecules. The complexity of such unique labels must be greater than the number of sample molecules contained within a unitary sample preparation, such that any label is highly unlikely to occur more than once within said unitary sample preparation.

Labels may be visually discriminatable, or may be diverse affinity labels or combinations thereof. Labels of this type may conveniently be random combinations of some basis set of distinct labels, formed for example, by a random coupling or polymerization of such labeling moieties to a defined chemical site provided by chemical modification of sample molecules.

Visual labeling may be accomplished by the use of a sufficient number of distinguishable fluorescent dye molecules, or other visual labels, such that the presence or absence of association of any one of said distinguishable fluorescent dye molecules may comprise the state of a bit in a binary code. Such labeling is similar to the combinatorial encoding described by S. Brenner and R. A. Lerner, but differs in that: perceptible labels may be used for encoding; labels need not be genetic material or linear copolymers;

where only unique identifiability is required, the label moiety employed for encoding may be synthesized separately and possibly randomly, and bound possibly randomly with sample molecules; the information contained by each labeling moiety need not depend on its precise spatial association with sample molecules, or its location within a sequence, only its sufficient proximity; and, because ol such modes of independence between the encoding, which serves here only for purposes of unique labeling, difficulties which may arise for particular orthogonal polymerization chemistries of different copolymer types may be avoided either by separate synthesis. Alternatively, for biopolymers, and, possibly for specifically encoded libraries, the use of specific enzymes which may for example ligate polynucleotides or polypeptides, may be used to specifically control reactions and prevent polymerizations of one biopolymer from affecting a second, linked biopolymer. Note that moieties different from biologically occurring comonomers may be used as encoding: label moieties, via functionalization of appropriate biopolymer segment with such moieties, in synthetic manners which will be obvious to those skilled in the relevant arts, or may be used, similarly, as constitutes the random library thus encoded. This latter case is, for example accomplished with the use of multiple distinct short double stranded DNA molecules with appropriately complementary cohesive termini which each carry some particular affinity or photolabel type, and which may be ligated together in a manner stepped by the addition of appropriate adaptor linkers, even in the presence of other biopolymers (such synthetic methods being further favorably facilitated by the use of solid phase synthetic methodologies). Depending on the sensitivity of the detection methods used, multimers of each single type of fluorescent dye moiety, or detectable multiplications of other photolabels, may be used to effect higher modulo coding of labels.

1.4.9.4 Encoding by Synthesis with Multimacromonomers

Note that the labeling methods of the present invention suggest a convenient solution to the problem recognized by Brenner and Lerner, as limiting the facility of their encoding system, i.e. the requirement of separate distinct comonomer (or co-oligomer) type addition steps for each polymer type. This prevents the use of highly random (but step-controlled) synthetic preparation of such encoded libraries, because the information encoded is realized by individual preparative synthetic steps, i.e. all of the information content of the encoding is conferred upon these compounds by the intervention or agency of a chemist (or automated systems) at each step. Such encoded libraries, of either the sequence encoded or modulo encoded types, including compounds comprising more than two polymer types, may be prepared with the following stepped random method in one container (with or without the favorable use of solid phase synthetic methodologies). Note that the term random here refers to the mixture of two or more multimacromonomers in each addition step, such that addition to all compounds under preparation will occur in a random manner within the reaction mixture, in a manner weighted according to the relative concentration of each such multimacromonomer. Such multimacromonomers may also be used in more directly controlled addition schemes with advantages which will be obvious to those skilled in the relevant arts.

Multimacromonomers comprising two or more monomer (or macromonomer) types (e.g. comprising an amino acid monomer and a trinucleotide oligomer, or an amino acid monomer, a trinucleotide oligomer and a fluorescent or affinity labeling moiety) may be prepared by joining some or all of said two or more monomer (or macromonomer) types by cleavable linkers such as those described in other sections of the present disclosure. Thus, each multimacromonomer may be added to compounds under synthesis by addition of one of the monomer or macromonomer types to the corresponding polymer or macropolymer types of said compounds under synthesis by appropriate polymer synthesis chemistry, followed by addition of some or all of each of the remaining monomer or macromonomer types to the respective corresponding polymer or macropolymer types of said compounds under synthesis by appropriate polymer synthesis chemistry. Control over the details of such additions may be effected by control over, for example, removal of distinct protecting groups from distinct polymer or macropolymer types of said compounds under synthesis by appropriate polymer synthesis chemistry. Linkers or specific linker branches may be cleaved at appropriate steps or after synthesis has otherwise been completed. Thus, correspondence between the composition of each polymer or macropolymer type comprised within each molecule of the compound under synthesis (which final composition may vary widely from molecule to molecule of the compound under synthesis, but strictly observe the correspondence between composition of some or all of each of the polymers or macropolymers comprised within each molecule of the compound under synthesis) is provided by the communication of the distinct monomer or macromonomer types comprised within each multimacromonomer. The first bond formed between a first monomer or first macromonomer of a multimacromonomer and a molecule of the compound under synthesis will thus ensure that other monomer or macromonomer types of the multimacromonomer which will be added at the respective multimacromonomer addition stage will correspond to the identity of the first monomer or first macromonomer thus added. Thus correspondence of some or all of each of the polymer or macropolymer types of final compounds is enforced (by the communication effected by, for example, linkers) even where the composition of some or all of the polymer or macropolymer types is respectively random.

Preferably, such linkers (which may be multiply branched, each of such branches possibly comprising cleavable groups susceptible to distinct cleaving treatments) are held in communication with some or all of the two or more distinct monomer or macromonomer types (which are added to the compounds under synthesis with distinct and mutually non-interfering addition or polymerization, deprotection and/or activation chemistries, termed "orthogonal" chemistries in the respective art) by attachment to the protecting groups used to effect the stepping of additions of each such multimacromonomer. Said diverse affinity labels may be used in conjunction with multiple affinity separation paths and nucleotide label detection that associates the detected said nucleotide label with the resolved location of the respective affinity labeled sample molecule, thus accomplishing the required assignment of detection and discrimination of the appropriate nucleotide label precisely to the correct respective sample molecule. Alternatively, said diverse affinity labels may be added to sample molecules so as to be independently recognizable by appropriate receptor molecules or other affinity means, each complementarity type of which is respectively labeled with some distinct independently perceptible label.

Such labeling methods permit the processing of samples in fluid flow based apparata without the loss of single molecule identifiability or assignability of results. Also note that manipulation with a laser trap, as for instance described by T. T. Perkins et al., may be employed with such uniquely labeled molecules.

Note that a case of encoding of particular interest is that of a functional molecule coupled to an informational molecule which is sufficient to direct the synthesis of said functional molecule in an appropriate, (e.g. biological or biological derived) system. Libraries of polypeptides expressed on the surface of, for example, bacteriophages carrying genetic material specifying said polypeptides, have found great use in the in vitro selection of binding specificities. Encoding which may additionally direct synthesis may be availed in the affinity characterization and molecular evolution applications of the present invention. The communication of a synthesis directing informational molecule (favorably DNA or RNA) with the correspondingly synthesized one or more functional molecules (generally a polypeptide) may be effected by the in vivo coupling or otherwise compartmentally enforced unique one-to-one corresponding coupling of said informational and said functional molecule. A particularly convenient instance of such a molecules comprises the fused expression of said functional molecule or molecules as segments of the terminal proteins of the informational molecules (i.e. DNA) of various virus (e.g. adenovirus) or bacteriophage (e.g. PRD1 or phi29) genomes. Alternatively, said functional molecules may be fused with some molecule which associates in a specific manner with said terminal proteins, and which has sufficient opportunity during its in vivo synthesis, without or preferably with concurrent viral or bacteriophage replication, to associate with the terminal protein of the genomic material which determines the composition of said functional molecules, such that upon purification or lysis functional molecules remain in communication with the genetic material that determines their composition. Because biosynthesis of functional and informational moieties may favorably occur within the confines of a single cell, cross-coupling of inappropriate molecules may be readily avoided. Alternatively, the communication between polypeptide and polynucleotide moieties may be effected with some intermediate snRNP or snRNP-like moiety, where such an intermediate moiety may be targeted on the one hand by an appropriate affinity characteristic of one or more polypeptides to which said functional molecules are fused, and on the other hand by a polynucleotide sequence complementary (according to appropriate rules for double-, triple- or quadruple-helix formation) with the polynucleotide moiety of said intermediate snRNP or snRNP-like moiety.

Such complexes comprising an intermediate snRNP or snRNP-like moiety may also favorably be formed within the confines of a single cell.

1.4.9.5 Cybernetic Molecular Evolution and Algorithm Mediated Cybernetic Molecular Evolution of Phenogenocouples Such polynucleotide-polypeptide chimera, or other molecule types comprising thus communicating and informationally corresponding chimera (e.g. where the polypeptide moiety has further been subjected to post-translational modification such as specific glycosylation and has been associated by some method to the respective genetic material determining its composition, for example by the sorting of individual cells carrying said genetic material in the form of a DNA vector with terminal proteins and expressing and processing said polypeptide, into distinct wells or vessels followed by disruption of membranes such that terminal proteins fused with peptides having affinity for the particular polypeptide of interest may come into contact with the processed polypeptide of interest, comprising a method for the molecular evolution of multiple-biopolymer containing macromolecules), which may be termed phenogenocouples, may be used as sample molecules with the broad methods of the present invention to effect the affinity characterization (including either or both equilibrium and kinetic characterization of molecular recognition including catalytic recognition and catalysis) of functional moieties and then the characterization and transcription of informational moieties thus determined to be of interest. Where algorithms control such a process, cybernetic molecular evolution is embodied.

Selected informational molecules may be selectively replicated or transcribed by activatable (e.g. photodeprotectable and especially 3' hydroxyl photodeprotectable) primers with appropriate complementarity to some region which bounds the informational content specifying said functional molecule or molecules. Alternatively, immobilization of a sample to be subjected to such manipulations may be effected so as to comprise some photolabile linkage, which may then be subjected to selective photodegradation to effect specific release. For immobilized samples, informational molecules which carry the relevant genetic component of a phenogenocouple may thus be released by either of these methods either singly, or as the population of multiple such molecules simultaneousl, copied or otherwise released according to the pattern of deprotection.

Alternatively, successive generations of molecules need only be related informationally, by analysis of composition of one generation, by, for example, the massively parallel characterization methods of the present invention, followed by de novo synthesis of molecules carrying the desired complexity and diversity of the succeeding generation. This is a particular distinguishing feature of cybernetic molecular evolution; selection, amplification and mutation may be directed strictly by algorithms which manipulate data gathered about one generation to determine the composition of a succeeding generation.

Released molecules may then be recovered for subsequent amplification, mutation and subsequent rounds of selection by similar or other methods, as will be obvious to those skilled in the art of in vitro molecular evolution.

Note that post transcriptionally modified polypeptide moieties or other phenogenocouples may also be selected and otherwise subjected to in vitro evolution by conventional means as well as by the massively parallel examination and modification methods of the present invention.

Because of the correspondence between the diversity generation and selection aspects of molecular evolution, and immunological recognition and memory, all of these methods may be directly applied to cybernetic immune system applications of the present invention.

Labeled reagents and signal amplification and elimination techniques:

The categories enumerated below are included for description and not limitation; other appropriate labeling methods will be obvious to those skilled in the arts of biotechnology, cell biology and cytology, microscopy, organic chemistry, biochemistry or recombinant DNA techniques.

Each category will comprehend a variety of specific variations, as will be obvious to those skilled in the relevant arts. Various labeling methods will generally correspond best to various detection methods.

1.4.10 Detection Methods for the Present Invention

Non-radioactive labeling techniques have been explored and, in recent years, integrated into partly automated DNA sequencing procedures. These improvements utilize the Sanger sequencing strategy. The label (e.g. fluorescent dye) can be tagged to the primer (Smith et al., Nature M, 674–679 (1986) and EPO Patent No. 87300998.9; Du Pont De Nemours EPO Application No. 0359225; Ansorge et al., J. Biochem. Biophys. Methods 13, 325–32 (1986)) or to the chain-terminating dideoxynucloside triphosphates (Prober et al. Science 218, 336–41 (1987); Applied Biosystems, PCT Application WO 91/05060). Based on either labeling the primer or the ddNTP, systems have been developed by Applied Biosystems (Smith et al., Science 23 5, G89 (1987); U.S. Pat. Nos. 570,973 and 689,013), Du Pont De Nemours (Prober et al., Science 238, 336–341 (1987); U.S. Pat. Nos. 881,372 and 57,566), Pharmacia-LKB (Ansorge et al., Nucleic Acids Res. 11, 4593–4602 (1987) and EMBL Patent Application DE P3 724442 and P3 805 808. 1) and Hitachi (JP I-90844 and DE 4011991 AI). A somewhat similar approach was developed by Brumbaugh et al., (Proc. Nad. Sci. US A85 5610–14 (1988) and U.S. Pat. No. 4,729,947). An improved method for the Du Pont system using two electrophoretic lanes with two different specific labels per lane is described (PCT Application WO92/02635). A different approach uses fluorescently labeled avidin and biotin labeled primers. Here, the sequencing ladders ending with biotin are reacted during electrophoresis with the labeled avidin which results in the detection of the individual sequencing bands (Brumbaugh et al., U.S. Pat. No. 594, 676).

More recently even more sensitive non-radioactive labeling techniques for DNA using chemiluminescence triggerable and amplifyable by enzymes have been developed (Beck, OKeefe, Coull and Köster, Nucleic Acids Res. 12, 5115–5123 (1989) and Beck and Köster, Anal. Chem. Q 2258–2270 (1990)). These labeling methods were combined with multiplex DNA sequencing (Church et al., Science 240, 185–188 (1988) and direct blotting electrophoresis (DBE) (Beck and Pohl, EMBO I Vol. 3: p 2905–2909 (1984)) to provide for a strategy aimed at high throughput DNA sequencing (Köster et al., Nucleic Acids Res. Symposium Ser. No. 2,4, 318–321 (1991), University of Utah, PCT Application No. WO 90/15883). However, this strategy still suffers from the disadvantage of being very laborious and difficult to automate.

Multiple distinctly labeled primers can be used to discriminate sequencing patterns. For example, four differently labeled sequencing primers specific for the single termination reactions, e.g. with fluorescent dyes and online detection using laser excitation in an automated sequencing device. The use of eight differently labeled primers allow the discrimination of the sequencing pattern from both strands. Instead of labeled primers, labeled ddNTP may be used for detection, if separation of the sequencing fragments derived from both strand is provided, With one biotin labeled primer, sequencing fragments from one strand can be isolated for example via biotin-streptavidin coated magnetic beads. Possible is also the isolation via immunoaffinity chromatography in the case of a digoxigenin labeled primer or with affinity chromatography in case of complementary oligonucleotides bound to a solid support.

1.4.10.1 Fluorescent Labels

In automated sequencing, fluorescence labeled DNA fragments are detected during migration through the sequencing gel by laser excitation. Fluorescence label is incorporated during the sequencing reaction via labeled primers or chain extending nucleotides (Smith, L. et. al., Fluorescence detection in automated DNA sequence analysis, Nature 321.674–89 1986), (Knight, P., Automated DNA sequencers, Biotechnology 6:1095–96 1988).

Detection methods for the present invention may favorably exploit fluorescent labeling techniques. Genome sequencing applications of the present invention may thus avail of established fluorescent modification and detection methods. Other applications of the present invention may also benefit from the application of fluorescence modification and detection methods.

Much effort has already been invested in the development of fluorescently labeled nucleotide triphosphate compounds and analogs thereof. Many such compounds are acceptable substrates for polynucleotide polymerase molecules. These compounds have therefore proven suitable for use in various electrophoresis based DNA sequencing methodologies utilizing fluorescence detection, as well as in other applications such as chromatin mapping. There are therefore various compounds comprising a fluorescent dye moiety and a nucleotide triphosphate moiety commercially available.

Fluorescent labels find use in variety of different biological, chemical, medical and biotechnological applications. One example of where such labels find use is in polynucleotide sequencing, particularly in automated DNA sequencing, which is becoming of critical importance to large scale DNA sequencing projects, such as the Human Genome Project.

In methods of automated DNA sequencing, differently sized fluorescently labeled DNA fragments which terminate at each base in the sequence are enzymatically produced using the DNA to be sequenced as a template. Each group of fragments corresponding to termination at one of the four labeled bases are labeled with the same label. Thus, those fragments terminating in A are labeled with a first label, while those terminating in G, C and T are labeled with second, third and fourth labels respectively. The labeled fragments are then separated by size in an electrophoretic medium and an electropherogram is generated, from which the DNA sequence is determined.

As methods of automated DNA sequencing have become more advanced, of increasing interest is the use of sets of fluorescent labels in which all of the labels are excited at a common wavelength and yet emit one of four different detectable signals, one for each of the four different bases. Such labels provide for a number of advantages, including high fluorescence signals and the ability to electrophoretically separate all of the labeled fragments in a single lane of an electrophoretic medium which avoids problems associated with lane to lane mobility variation.

Although such sets of labels have been developed for use in automated DNA sequencing applications, heretofore the differently labeled members of such sets have each emitted at a different wavelength. Thus, conventional automated detection devices currently employed in methods in which all of the enzymatically produced fragments or primer extension products are separated in the same lane must be able to detect emitted fluorescent light at four different wavelengths. This requirement can prove to be an undesirable limitation. More specifically, carrying out sequencing on vast numbers of different DNA templates simultaneously increases the number of different fragments and corresponding labels required. At the same time, there is a need for a reduction in the complexity of the detection device, e.g. a device which can operate with light detection at only two wavelengths is preferable.

Sets of fluorescent labels, particularly sets of fluorescently labeled primers, and methods for their use in multi component analysis applications, particularly nucleic acid enzymatic sequencing applications, are provided. At least two of the label members of the set are energy transfer labels having a common donor and acceptor fluorophore separated by sufficiently different distances so that the two labels provide distinguishable fluorescent signals upon excitation at a common wavelength. In further describing the subject invention, the subject sets will first be described in greater detail followed by a discussion of methods for their use in multi component analysis applications.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

The subject sets of fluorescent labels comprise a plurality of different types of labels, wherein each type of label in a given set is capable of producing a distinguishable fluorescent signal from that of the other types of labels in different sets. Labels in the different sets generate different signals, preferably, though not necessarily upon excitation at a common excitation wavelength. For DNA sequencing applications, the subject sets will comprise at least 2 different types of labels, and may comprise 8 or more different types of labels, where for many applications the number of different types of labels in the set will not exceed 6, and will usually not exceed four, where at least two of the different types of labels are energy transfer labels sharing a common donor and acceptor fluorescer, as described in greater detail below. For other applications, such as fluorescence in situ hybridization (FISH), substantially more than 8 labels are ideal so that multiple targets can be analyzed.

The distinguishable signals generated by the "at least two energy transfer labels" will at least comprise the intensity of emitted light at one to two wavelengths. Preferably, the distinguishable signals produced by the "at least two energy transfer labels" will comprise distinguishable fluorescence emission patterns, which patterns are generated by plotting the intensity of emitted light from differently sized fragments at two wavelengths with respect to time as differently labeled fragments move relative to a detector, which patterns are known in the art as electropherograms. For analyses not based on electrophoresis, such as micro-array chip based assays, different targets tagged with a specific label can be differentiated from each other by the unique fluorescence patterns. For example, in one type of label of a set the intensity of emitted light at a first wavelength may be twice that of the intensity of emitted light at a second wavelength and in the second label the magnitude of the intensities of light emitted at the two wavelengths may be reversed, or light may be emitted at only one intensity. The different patterns are generated by varying the distance between the donor and acceptor. These patterns emitted from each of these labels are thus distinguishable.

The subject sets will comprise a plurality of different types of fluorescent labels, where at least two of the labels and usually all of the labels are energy transfer labels which comprise at least one acceptor fluorophore and at least one donor fluorophore in energy transfer relationship, where such labels may have more complex configurations, such as multiple donors and/or multiple acceptors, e.g. donor 1, acceptor I and acceptor 2. Critical to the subject sets is that at least two of the labels of the sets have common donor and accceptor fluorophores, where the only difference between the labels is the distance between these common acceptor and donor fluorophores. Thus, for sets of labels in which each label comprises a single donor and a single acceptor, at least one of the energy transfer labels will have a donor fluorophore and acceptor fluorophore in energy transfer relationship separated by a distance x and at least one of the energy transfer labels will comprise the same donor and acceptor fluorophores in energy transfer relationship separated by a different distance y, where the distances x and y are sufficiently different to provide for distinguishable fluorescence emission patterns upon excitation at a common wavelength, as described above.

In those sets comprising a third label having the same donor and acceptor fluorophores as the first and second label, the distance z between the donor and acceptor fluorophore will be sufficiently different from x and y to ensure that the third label is capable of providing a distinguishable fluorescence emission pattern from the first and second labels. Thus, in a particular set of labels, one may have a plurality of labels having the same donor and acceptor fluorophores, where the only difference among the labels is the distance between the donor and acceptor fluorophores. To ensure that different types of labels of a set having common donor and acceptor fluorophores yield distinguishable fluorescence emission patterns, the distances between the donor and acceptor fluorophores will differ by at least about 5%, usually by at least about 10% and more usually by at least about 20% and will generally range from about from about 4 to 200 Å, usually from about 12 to 100 Å and more usually from about 15 to 80 Å, where the minimums in such distances are determined based on currently available detection devices and may be reduced as detection technology becomes more sensitive, therefore more distinct labels can be generated.

In one preferred embodiment, at least a portion of, up to and including all of, the labels of the subject sets will comprise a donor and acceptor fluorescer component in energy transfer relationship and covalently bonded to a spacer component, i.e. energy transfer labels. Thus, one could have a set of a plurality of labels in which only two of the labels comprise the above mentioned donor and acceptor fluorescer components and the remainder of the labels comprise a single fluorescer component. Preferably, however, all of the labels will comprise a donor and acceptor fluorescer component. Generally, for one donor and one acceptor ET systems, if a set comprises n types of energy transfer labels, the number of different types of acceptor fluorophores present in the energy transfer labels of the set will not exceed n−1. Thus, if the number of different types of energy transfer labels in the set is four, the number of different acceptor fluorophores in the set will not exceed 3, and will usually not exceed 2.

In other preferred embodiments, additional combinations of labels are possible. Thus, in a set of labels, two of the labels could be energy transfer labels sharing common donor and acceptor fluorophores separated by different distances and the remaining labels could be additional energy transfer labels with different donor and/or acceptor fluorophores, non-energy transfer fluorescent labels, and the like.

In the energy transfer labels of the subject sets, the spacer component to which the fluorescer components are covalently bound will typically be a polymeric chain or other chemical moiety capable of acting as a spacer for the donor and acceptor fluorophore components, such as a rigid chemical moiety, such as chemicals with cyclic ring or chain structures which can separate the donor and acceptor and which also can be incorporated with an active group for attaching to the targets to be analyzed, where the spacer component will generally be a polymeric chain, where the fluorescer components are covalently bonded through linking groups to monomeric units of the chain, where these monomeric units of the chain are separated by a plurality of monomeric units sufficient so that energy transfer can occur from the donor to acceptor fluorescer components. The polymeric chains will generally be either polynucleotides, analogues or mimetics thereof-, or peptides, peptide analogues or mimetics thereof, e.g. peptoids. For polynucleotides, polynucleotide analogues or mimetics thereof, the polymeric chain will generally comprise sugar moieties which may or may not be covalently bonded to a heterocyclic nitrogenous base, e.g. adenine, guanine, cytosine, thymine, uracil etc., and are linked by a linking group. The sugar moieties will generally be five membered rings, e.g. ribose, or six membered rings, e. g. hexose, with five membered rings such as ribose being preferred. A number of different sugar linking groups may be employed, where illustrative linking groups include phosphodiester, phosphorothioate, methylene(methyl imino)(MMI), methophosphonate, phosphoramadite, guanidine, and the like. See Matteucci & Wagner, Nature (1996) Supp 84: 20–22. Peptide, peptide analogues and mimetics thereof suitable for use as the polymeric spacer include peptoids as described in WO 91/19735, the disclosure of which is herein incorporated by reference, where the individual monomeric units which are joined through amide bonds may or may not be bonded to a heterocyclic nitrogenous base, e.g, peptide nucleic acids. See Matteucci & Wagner supra. Generally, the polymeric spacer components of the subject labels will be peptide nucleic acid, polysugarphosphate as found in energy transfer cassettes as described in PCT/US96/13134, the disclosure of which is herein incorporated by reference, and polynucleotides as described in PCT/US95/01205, the disclosure of which is herein incorporated by reference.

Both the donor and acceptor fluorescer components of the subject labels will be covalently bonded to the spacer component, e.g. the polymeric spacer chain, through a linking group. The linking group can be varied widely and is not critical to this invention. The linking groups may be aliphatic, alicyclic, aromatic or heterocyclic, or combinations thereof. Functionalities or heteroatoms which may be present in the linking group include oxygen, nitrogen, sulfur, or the like, where the heteroatom functionality which may be present is oxy, oxo, thio, thiono, amino, amido and the like. Any of a variety of the linking groups may be employed which do not interfere with the energy transfer and gel electrophoresis, which may include purines or pyrimidines, particularly uridine, thymidine, cytosine, where substitution will be at an annular member, particularly carbon, or a side chain, e.g. methyl in thymidine. The donor and/or fluorescer component may be bonded directly to a base or through a linking group of from 1 to 6, more usually from 1 to 3 atoms, particularly carbon atoms. The linking group may be saturated or unsaturated, usually having not more than about one site of aliphatic unsaturation.

Though not absolutely necessarily, generally for DNA sequencing applications at least one of the donor and acceptor fluorescer components will be linked to a terminus of the polymeric spacer chain, where usually the donor fluorescer component will be bonded to the terminus of the chain, and the acceptor fluorescer component bonded to a monomeric unit internal to the chain. For labels comprising polynucleotides, analogues or mimetics thereof as the polymeric chain, the donor fluorescer component will generally be at the 5' terminus of the polymeric chain and the acceptor fluorescer component will be bonded to the polymeric chain at a position 3' position to the 5' terminus of the chain. For other applications, such as FISH, a variety of labeling approaches are possible.

The donor fluorescer components will generally be compounds which absorb in the range of about 300 to 900 nm, usually in the range of about 350 to 800 nm, and are capable of transferring energy to the acceptor fluorescer component. The donor component will have a strong molar absorbance co-efficient at the desired excitation wavelength, desirably greater than about $10^4$ preferably greater than about $10^5$ cm$^{-1}$M$^{-1}$. The molecular weight of the donor component will usually be less than about 2.0 kD, more usually less than about 1.5 kD. A variety of compounds may be employed as donor fluorescer components, including fluorescein, phycoerythrin, BODIPY, DAPI, Indo-1, cournarin, dansyl, cyanine dyes, and the like. Specific donor compounds of interest include fluorescein, rhodamine, cyanine dyes and the like.

Although the donor and acceptor fluorescer component may be the same, e. g both may be FAM, where they are different the acceptor fluorescer moiety will generally absorb light at a wavelength which is usually at least 10 nm higher, more usually at least 20 nm or higher, than the maximum absorbance wavelength of the donor, and will have a fluorescence emission maximum at a wavelength ranging from about 400 to 900 run. As with the donor component, the acceptor fluorescer component will have a molecular weight of less than about 2.0 kD, usually less than about 1.5 kD. Acceptor fluorescer moieties may be rhodamines, fluorescein derivatives, BODIPY and cyanine dyes and the like. Specific acceptor fluorescer moieties include FAM, JOE, TAM, ROX, BODIPY and cyanine dyes.

The distance between the donor and acceptor fluorescer components will be chosen to provide for energy transfer from the donor to acceptor fluorescer, where the efficiency of energy transfer will be from 20 to 100%. Depending on the donor and acceptor fluorescer components, the distance between the two will generally range from 4 to 200 Å, usually from 12 to 100 Å and more usually from 15 to 80 Å, as described above.

For the most part the labels of the subject sets will be described by the following formula:

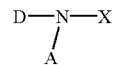

wherein:
D is the donor fluorescer component, which may consist of more than two different donors separated by a spacer;
N is the spacer component, which may be a polymeric chain or rigid chemical moiety, where when N is a polymeric spacer that comprises nucleotides, analogues or mimetics thereof, the number of monomeric units in N will generally range from about 1 to 50, usually from about 4 to 20 and more usually from about 4 to 16;
A is the acceptor fluorescer component, which may consist of more than two different acceptors separated by a spacer; and X is optional and is generally present when the labels are incorporated into oligonucleotide primers, where X is a functionality, e.g an activated phosphate group, for linking to a mono- or polynucleotide, analogue or mimetic thereof, particularly a deoxyribonucleotide, generally of from 1 to 50, more usually from 1 to 25 nucleotides.

For sets to be employed in nucleic acid enzymatic sequencing in which the labels are to be employed as primers, the labels of the subject sets will comprise either the donor and acceptor fluorescer components attached directly to a hybridizing polymeric backbone, e.g. a polynucleotide, peptide nucleic acid and the like, or the donor and acceptor fluorescer components will be present in an energy transfer cassette attached to a hybridizable component, where the energy transfer cassette comprises the fluorescer components attached to a non-hybridizing polymeric backbone, e.g. a universal spacer. See PCT/US96/13134 and Ju et al., Nat. Med. (1996) supra, the disclosures of which are herein incorporated by reference. The hybridizable component will typically comprise from about 8 to 40, more usually from about 8 to 25 nucleotides, where the hybridizable component will generally be complementary to various commercially available vector sequences such that during use, synthesis proceeds from the vector into the cloned sequence. The vectors may include single-stranded filamentous bacteriophage vectors, the bacteriophage lambda vector, pUC vectors, pGEM vectors, or the like. Conveniently, the primer may be derived from a universal primer, such as pUC/M13, g tIO, gt11, and the like, (See Sambrook et al., Molecular Cloning: A Laboratory Manual., 2nd ed., CSHL, 1989, Section 13), where the universal primer will have been modified as described above, e.g. by either directly attaching the donor and acceptor fluorescer components to bases of the primer or by attaching an energy transfer cassette comprising the fluorescer components to the primer.

Sets of preferred energy transfer labels comprising donor and acceptor fluorescers covalently attached to a polynucleotide backbone in the above D-N-A format include: (1) F6R, F 13R, F16R and F16F; where different formats can be employed as long as the four primers display distinct fluorescence emission patterns.

The fluorescent labels of the subject sets can be readily synthesized according to known methods, where the subject labels will generally be synthesized by oligomerizing monomeric units of the polymeric chain of the label, where certain of the monomeric units will be covalently attached to a fluorescer component.

The subject sets of fluorescent labels find use in applications where at least two components of a sample or mixture of components are to be distinguishably detected. In such applications, the set will be combined with the sample comprising the to be detected components under conditions in which at least two of the components of the sample if present at all will be labeled with first and second labels of the set, where the first and second labels of the set comprise the same donor and acceptor fluorescer components which are separated by different distances. Thus, a first component of the sample is labeled with a first label of the set comprising donor and acceptor fluorescer components separated by a first distance X. A second component of the sample is labeled with a second label comprising the same donor and fluorescer components separated by a second distance Y, where X and Y are as described above. The labeled first and second components, which may or may not have been separated from the remaining components of the sample, are then irradiated by light at a wavelength capable of a being absorbed by the donor fluorescer components, generally at a wavelength which is maximally absorbed by the donor fluorescer components. Irradiation of the labeled components results in the generation of distinguishable fluorescence emission patterns from the labeled components, a first fluorescence emission pattern generated by the first label and second pattern being attributable to the second label. The distinguishable fluorescence emission patterns are then detected. Applications in which the subject labels find use include a variety of multicomponent analysis applications in which fluorescent labels are employed, including FISH, micro-array chip based assays where the labels may be used as probes which specifically bind to target components, DNA sequencing where the labels may be present as primers, and the like.

The subject sets of labels find particular use in polynucleotide enzymatic sequencing applications, where four different sets of differently sized polynucleotide fragments terminating at a different base are generated (with the members of each set terminating at the same base) and one wishes to distinguish the sets of fragments from each other. In such applications, the sets will generally comprise four different labels which are capable of acting as primers for enzymatic extension, where at least two of the labels will be energy transfer labels comprising differently spaced common donor and acceptor fluorescer components that are capable of generating distinguishable fluorescence emission patterns upon excitation at a common wavelength of light. Using methods known in the art, a first set of primer extension products all ending in A will be generated by using a first of the labels of the set as a primer. Second, third and fourth sets of primer extension products terminating in G, C and T will be also be enzymatically produced. The four different sets of primer extension products will then be combined and size separated, usually in an electrophoretic medium. The separated fragments will then be moved relative to a detector (where usually either the fragments or the detector will be stationary). The intensity of emitted light from each labeled fragment as it passes relative to the detector will be plotted as a function of time, i.e. an electropherogram will be produced. Since, the labels of the subject sets will generally emit light in only two wavelengths, the plotted electropherogram will comprise light emitted in two wavelengths. Each peak in the electropherogram will correspond to a particular type of primer extension product (i.e. A, G, C or T), where each peak will comprise one of four different fluorescence emission patterns. To determine the DNA sequence, the electropherogram will be read, with each different fluorescence emission pattern related to one of the four different bases in the DNA chain.

Where desired, two sets of labels according to the subject invention may be employed, where the distinguishable fluorescence emission patterns produced by the labels in the first set will comprise emissions at a first and second wavelength and the patterns produced by the second set of labels will comprise emissions at a third and fourth wavelength. By using two such sets in conjunction with one another, one could detect primer extension products produced from two different template DNA strands at essentially the same time in a conventional four color detector, thereby doubling the throughput of the detector.

The subject sets of labels may be sold in kits, where the kits may or may not comprise additional reagents or components necessary for the particular application in which the label set is to be employed. Thus, for sequencing applications, the subject sets may be sold in a kit which further comprises one or more of the additional requisite sequencing reagents, such as polymerase, nucleotides, dideoxymicleotides and the like.

The following examples are offered by way of illustration and not by way of limitation. The following examples are put forth so as to provide those of ordinary skill in the art with a complete disclosure and description of how to make and use the subject sets of fluorescent labels.

1.4.10.2 Affinity Labels

Other single molecule detection methods have availed of compounds having well studied affinity interactions with other molecules, such as receptor-ligand interactions.

Genome sequencing applications of the present invention may thus avail of established affinity labeling and detection methods. Other applications of the present invention my also benefit from the application of affinity labeling and detection methods.

Various compounds comprising a nucleotide triphosphate moiety and a small molecule affinity moiety are commercially available and suitable as substrates for DNA polymerases. Said compounds have been used, in conjunction with DNA polymerases, to effect the affinity labeling of various polynucleotide molecules, and thus labeled polynucleotides are routinely subjected to manipulations comprising the formation of an affinity association with an appropriate receptor molecule. Two common examples are the use of biotin as said affinity moiety and streptavidin as said receptor molecule, and digoxigenin as said affinity moiety and anti-digoxigenin antibodies or fragments thereof as the respective said receptor molecule, it will be obvious to those skilled in the relevant arts that there are numerous other possible ligand-receptor interactions which may be exploited for affinity labeling purposes as well as immobilization purposes of the present invention, and that multiple distinct affinity interactions may be employed simultaneously.

For detection purposes, said affinity labels may be used to bind a microscopic colloid or bead which has been modified with an appropriate complementary affinity group such as a receptor.

1.4.10.1 Affinity Label Detection with Microscopic Beads

In recent years a number of different methods and materials have been developed to permit the affinity binding of beads to molecules. Such binding is commonly accomplished by coating said beads with receptor molecules, such as streptavidin or Protein A (also known as Staph A, to which immunoglobulin G antibodies may subsequently be bound). Bead types include polymeric spheres of micron or submicron dimensions, metallic colloids such as colloidal gold, silica beads and magnetic beads. As will be obvious to those skilled in the art of polymer chemistry, polymer beads including dendrimers may incorporate dyes or liquid crystal molecules as side chains or within polymeric backbones, and these may facilitate optical detection methods. Attachment of appropriate receptor or affinity molecules to the surfaces of such beads yields a reagent suitable for the detection of an affinity labeled molecule. One such detection scheme was utilized by Finzi and Gelles, albeit for different purposes.

1.4.10.3 Multimeric Labels

Where sensitivity to a single labeling moiety is insufficient, labeled reagents may comprise multiple occurrences of said labeling moiety in a manner that does not interfere with the corresponding molecular recognition and monomer addition processes, to increase the likelihood of correct signal amplification of any labeled molecule. For example, the ordinary single biotin moiety attached to a nucleotide by a linker may be replaced with a polymer having multiple biotin moieties as side chains, such that the likelihood of a streptavidin molecule interacting with this multimeric affinity label is increased. Fluorescent labels may similarly multiplied, as may any other labeling moieties. Measures must be taken in the design and synthesis of such multimerically labeled reagents to ensure that solubility is retained. This may be accomplished by choosing a highly soluble polymer as the backbone carrying said labeling moieties comprising the multimeric label.

1.4.10.4 Polymerization Nucleating Labels

Any compound capable of serving as an initiator for some aqueous polymerization may also serve as a labeling moiety. This initiator nucleates the formation of a perceptible polymer attached to the sample molecule. Such a polymer, may, for example, comprise multiple fluorescent moieties, or simple effect a local change in transmitance of light or a local change of refractive index. After detection has been accomplished, said perceptible polymer is degraded or otherwise removed from the sample molecule. Such polymerizations may be self-limiting, as is the case for some dendrimeric polymers.

For this label detection methodology, polymerization is caused to occur in a step after the labeled nucleotide is added to the sample molecule, and must proceed via a chemistry that leaves the sample molecule in tact. Degradation or removal of said perceptible polymer must also leave the sample molecule in tact. Subject to the above stated limitation, any polymer and respective detection method may be employed.

1.4.10.5 Enzymatic Labels and Conjugates Thereof 1.4.10.5.1 Photochemical Labeling Various methods have been developed for the photochemical labeling of molecules and especially biological macromolecules. These include detection of affinity labels such as biotin with conjugates of streptavidin and an appropriate enzyme capable of catalysing the formation of a chromophore from a chromophorigenic substrate, or capable of catalysing a photon liberating chemical reaction, as with the enzyme luciferase. Such photochemical labeling methods will be readily applicable as detection methods for various embodiments of the present invention.

Note that multimeric affinity labels accessible for simultaneous association with multiple such enzymes will enable greater signal amplification, as will secondary enzyme amplification techniques and other techniques known within the molecular biological and microscopic arts.

1.4.10.5.2 Cleavable Linkers

Labeling moieties are favorably in communication with or coupled to nucleotides via a linker of sufficient length to ensure that the presence of said labeling moieties on said nucleotides will not interfere with the action of a polymerase enzyme on said nucleotides. Linkers will also necessarily be of some minimal length when stepping control is effected through the use of various preformed enzyme-nucleotide complexes (as described below). Once a nucleotide has been added by polymerization to (the daughter strand of) a sample molecule, and the accompanying label has been detected, proper detection and discrimination of subsequent nucleotides requires the elimination of said accompanying label. This may favorably be accomplished through the cleavage of said linkers which have been designed and synthesized to admit of cleavage by treatments which will not degrade or otherwise modify the relevant state or information content of sample molecules.

Cleavability may be provided for in a number of ways which will be obvious to those skilled in the arts of organic and synthetic chemistry. For example, said linker may include along its length one or more ester linkages, which will be susceptible to hydrolysis, which may be sufficiently mild for various ester functional groups. Amide linkages may similarly be employed. Linkages comprising disulfide bonds within their length have been developed to provide for cleavability; reagents comprising such linkages are commercially available and have been used to modify nucleotides in a manner which may be conveniently reversed by treatment with mild reducing agents such as dithiothreitol. Cleavable linkages may be provided so as to minimize the portion of the linker which remains on the sample molecule. Because polymerases are relatively tolerant of linkers which may extend from various atoms of nucleotide molecules, it is not, however, critical that all of said linkers be cleaved away from the nucleotides incorporated into said sample molecules in the process of label removal.

Note that commercially available biotin derived nucleotides frequently contain, along the linker joining said biotin moiety to said nucleotide moiety, one or more ester or amide bonds, which is susceptible to cleavage by various chemical treatments.

Note also that for linkers comprising appropriate bonds along their length, enzymatic cleavage may be performed.

1.4.10.5.3 Dissociative Cleavage

Note that cleavage of a labeling moiety may also be effected by the disruption of some affinity interaction which effects the communication between said labeling moiety and the nucleotide moiety. In such cases, moieties joined by non-covalent associations may, for example, be dissociated by physical or chemical changes which do not necessarily cleave covalent bonds.

Photocleavable moieties may also comprise an intermediate portion of linkers joining labeling moieties to nucleotide moieties, such that upon photocleavage of said photocleavable moieties, communication between the termini of said linker is disrupted and the label moiety is liberated from the nucleotide moiety. Because photodeprotection or photocleavage reactions generally proceed quite rapidly, with appropriate detection and photoexcitation means, detection, label removal and nucleotide incorporation rates per sample molecule may approach the limit imposed by any particular polymerase enzyme and the processivity of said enzyme. Long linkers with photocleavable termini have been synthesized.

Similarly, compounds which thermally degrade into two or more portions may comprise an intermediate portion of such linkers, such that thermal cycling may be employed to effect linker cleavage. Thermostable polymerases may be conveniently employed in embodiments availing thermolabile linkers.

1.4.10.5.4 Photomodification

Single dye molecule photobleaching has been directly observed. Fluorescent labels of nucleotides, particularly when only one or a small number of such moieties are used for labeling, may be neutralized by photobleaching, such that while some product of said fluorescent label may remain in communication with the sample molecule (e.g. the daughter strand of a polynucleotide being sequenced) it will no longer provide a signal sufficiently strong to interfere with the detection and discrimination of subsequently added labels.

Beyond photobleaching of fluorescent labels, affinity labels with appropriate photochemical properties may be subjected to photochemical modification rendering them inert to binding, generally subsequent to dissociation of the corresponding receptor by appropriate means.

For affinity labels, fluorescent labels or any other labeling moieties, chemical modification appropriate to the chemistries of said labels which effects a change or reduction in the detectable signal provided by said label may be availed to prevent interference of said labels with similar or distinct labels subsequently added to sample molecules or complexes thereof.

1.4.10.5.5 Labeling with Activation and Thermodynamic Decay

Compounds such as spirobenzopyran, which have labile, structurally and photochemically distinct but interconvertible isomers, may be used as labeling moieties. Here, an excited state of such a moiety may be used as a means of detection. After said detection has been successfully effected, chemical modification of one or another state of such interconvertible molecules may then neutralize it. Alternatively, activation may cause such a label to convert to some unstable but discernible state, which then irreversibly degrades according to characterizable kinetics. Such molecules must be chosen so as to remain in said discernible state for a sufficient time period to permit detection, but reliably degrade (to completion for a population of such molecules) within a practical time period.

1.4.10.5.6 Binding Reaction Inhibition Detection Methods

Agents which specifically inhibit binding reactions may be identified rapidly through the detection of molecules, of a diverse library each molecular species of which is uniquely labeled, not bound by particles some sample which may comprise many different species, in the presence test reagent, which is labeled, and permitted to associate with said sample (preferably during a preincubation step before the addition of said diverse library to said sample,) in analogy to blocking antibody assays. Results are compared to those obtained with an aliquot of said diverse library and another portion of the same said sample. Such an assay may be performed for increasing concentrations of said test reagent.

1.4.10.5.7 Enzymatically Enforced Associations at Defined Molecular Sites

Methods are provided to enforce highly specific associations and reactions, including molecular recognition processes, on individual sample molecules or on populations and subpopulations of sample molecules. These are described for genome sequencing applications, but the methods included thereunder have broad applicability, including to any molecular affinity interaction.

1.4.10.5.8 Enzymatically Enforced Template Directed Copolymer Addition at Defined Site Controlled comonomer addition Various methods may be used to accomplish the controlled addition of monomers, including nucleotides and especially labeled or protected nucleotides, to the daughter strand of a sample template molecule.

1.4.10.6 Rate Control or Accommodation

Means of slowing the time required for the addition of a single nucleotide to a sample molecule will circumvent the requirement of stepping control. This will be particularly applicable for detection mechanisms not requiring separate manipulation steps (such as the separate association of beads to affinity labeled sample molecules). For example, the four nucleotides, each respectively labeled with unique, removable or neutralizable fluorescent labels, may be added to appropriately primed sample template molecules in the presence of polymerases, at low concentrations. Said concentrations must be sufficiently low that two nucleotides are not added to the sample molecule in less than the time required to accomplish the detection of the first such addition. Because all labels are present in the observation field, detection is accomplished through the observation of the reduction of the Brownian motion of a fluorescent moiety due to its addition to the sample molecule, in close analogy to the experiments of Finzi and Gelles, but it will be noted that the change in mobility is much larger in the present case. Alternatively detection may be understood to depend on an increase in the net residence of some fluorescent moiety within a defined region or the occupancy of said a region, above the occupancy arising from the background of unbound labeled nucleotides.

Such detection is preferably conducted with a scanning excitation beat fluorescence confocal microscopic method as described above, or with a scanning detection light path, as also described above. Conditions (particularly nucleotide concentration) are chosen such that on average less than one labeled nucleotide will be present within the area illuminated by such a beam or thus observed, so that a light pulse of appropriate frequency passing through, for example, the pinhole which effects the scanning of the excitation beam, may be used to photobleach or photocleave the fluorescent label from the sample molecule after it has been detected to have been added to the sample molecule, without the appreciable accumulation of incidentally unlabeled nucleotides. Alternatively, an SLM may be used to spatially control illumination of the sample by an appropriate frequency of light to effect photochemical unlabeling, and thus permit the simultaneous unlabaling of multiple sample molecules.

This method may be understood as concentration modulated control of the kinetics of polymerization processivity, which is used to facilitate direct observation of successive addition of individual (labeled) nucleotides, with controlled unlabeling. Scanning rate and other instrumentation dependent parameters will influence optimal conditions and concentrations. Thus, direct observation of the addition of comonomers is dynamically observed, and sequence information for the respective sample molecule may be reconstructed accordingly.

1.4.10.7 Stepping Control By Equilibrium Means

A simple method to effect adequate stepping control for sequencing applications of the present invention relies on equilibrium control. In this method, nucleotides (which are labeled) are limiting, and there is a relative excess of sample molecules. Exonuclease activity intrinsic to most polynucleotide polymerases is circumvented by the use of alpha-phosphorothioate nucleotides (which are appropriately labeled) which are resistant to such degradation, in this method. Other nucleotide derivatives or analogs suitable as substrates for polymerases and yielding exonuclease resistant polynucleotides may likewise be employed.

As an example of equilibrium controlled stepping, a thirty-three-fold excess of sample molecules relative to labeled complementary nucleotides per cycle may be chosen. Polymerase molecules are preferably provided in excess of sample template molecules. Each sample molecule has a three percent chance of undergoing a single nucleotide addition. Nucleotides are rapidly depleted. Any sample molecule which has undergone one nucleotide addition has a further three percent chance, or in total approximately a 0.1% chance of undergoing a second nucleotide addition. For a sequencing segment run of 20 bases per sample molecule, each segment will experience an error contribution of $(20)(0.1\%)$ or 2% from multiple additions within a cycle. Such erroneous segment data will be conspicuous when oversampling is performed due to the correspondingly low frequency with which it occurs.

Alternatively, for tenfold excess of sample molecules with respect to labeled complementary nucleotides, there is a 1% chance per base of multiple additions to the same molecule, or, again for sequencing runs of bases, a 20% chance that a segment experiences at least one duplicate addition event. For five-fold oversampling, the binomial distribution indicates that there is approximately a 94.2% chance that three or more segments including a particular base contain correct data regarding that base. Any specific individual data error is highly unlikely to occur more than once for fivefold oversampling. Note that in practice such calculations will also have to account for label amplification error and label detection error, but these error contributions should be susceptible to reduction to manageably low levels.

More generally, for a ratio x of nucleotide molecules to sample template molecules with a complementary base properly located relative to the primer, for $x<1$ there is a probability p equal to x that a particular sample molecule will experience the addition of at least one nucleotide and a probability pk that any sample molecule will experience at least k nucleotide additions within the same sequencing cycle. Multiple nucleotide additions to a sample molecule within the same sequencing cycle will result in erroneous sequence information being obtained from said sample molecule. The probability (d) of such a multiple incorporation error occurring within the sequence segment data obtained from a particular sample molecule in a sequencing run of n bases will be less than $2(n)(p2)$. The net sequence information per sample molecule obtained per sequencing cycle will be x bases, and the net sequence information for a sample with N molecules will be $(x)(N)$ bases, which will be large for large N. For example, with $x=0.03$ and $N=3.3\times10^{10}$, there will be a net raw data accumulation of approximately $10^9$ bases per cycle, which, with one-hundred-fold oversampling (i.e. due to each sequence being represented 100 times in the sample) will yield $10^7$ bases of data per cycle; for a desired segment length of $n=15$ bases, $n/x=(15)/(0.03)$ or approximately 500 sequencing cycles will be required per run, and the run will yield $1.5\times10^8$ bases of information. For polymerase fidelity of 95% (an extremely low value chosen for purposes of illustration) there will be a 5% error rate (e) per base or a segment error rate of $(n)(e)=75\%$ per molecule, but the probability of two erroneous sequence segments having identical sequences will be $e2(1-e)^{n-1}$ for segments with a single base error, which will be the most frequent error species. For this example, this yields a 0.12% frequency. Methods similar to those used to determine consensus sequences may thus be employed to obtain highly accurate data in spite of less than perfect polymerization fidelity. Thus, fidelity error components will be negligible compared to multiple base incorporation errors. For this example, multiple base incorporation error components will yield an error rate of less than $(2)(15)(0.03)^2$ or about 3% per molecule. Again, oversampling will readily detect such errors, which will occur identically for two molecules with only $d2=(0.03)^2$ or less than 0.1% probability, yielding a far lower error rate for over sampled data.

1.4.10.8 Stepping Control by Removable Protecting Groups

Stepping control may favorably be applied to any polymerization process useful within the scope of the present invention, including both genome sequencing and affinity characterization applications.

Template directed polymerization depends on the processive addition of comonomers at the terminus of a growing daughter strand as specified by the respective complementary base of the parent template strand. Complementarity may be enforced through molecular recognition of said complementarity of protected analogs of said comonomers with the appropriate base of a template molecule, by the action upon such protected comonomers of appropriate polymerase enzymes.

Numerous monomers which may thus be added but do not provide an appropriate chemical functional group for subsequent elongation of the polynucleotide strand to which they have been enzymatically added are known within the relevant arts, and are generally referred to as chain terminators. Any such terminators which may be chemically or photochemically modified, particularly in a manner not disrupting the sample molecule, to a form which may support subsequent addition of comonomers in the usual manner, may be employed to effect controlled stepping of polymerization addition.

Removable protecting groups are particularly advantageous for the genome sequencing applications of the present invention because they may be utilized to permit and ensure that exactly one nucleotide is added to a sample molecule per sequencing cycle. This will permit an even greater rate of data accumulation than may be achieved by equilibrium control methods, with which only a fraction of the sample molecule population per cycle yields data.

Photoremovable protecting groups may be used to gain similar advantage but further permit controlled spatial localization of deprotection. Examples of such nucleosides have been prepared.31 Because photodeprotection reactions generally proceed rapidly, with appropriate detection and photoexcitation means, processivity and nucleotide incorporation rates per sample molecule may approach the limit imposed by any particular polymerase enzyme.

Nucleotide analogs comprising such removable protecting groups preferably further comprise labeling moieties. A particularly convenient category of such compounds comprises a labeling moiety or multimer thereof in communication with the nucleotide moiety exclusively through said removable protecting group. For such compounds, removal of said removable protecting group will simultaneously effect removal of said labeling moiety. Simultaneous removal of both protecting moiety and labeling moiety will conveniently prepare a sample molecule for the next sequencing cycle in a single step.

Enzymological evidence concerning binding of 3' acetate esterified nucleotides and 5'-triphosphate-3'-(nucleoside-5'-monophosphate) to the triphosphate binding site of E. coli Polymerase I supports the acceptability of 3' modified nucleotides as substrates for this enzyme. Such protecting groups should therefore be compatible with either naturally occurring or genetically modified polymerases.

Note that in other applications of the present invention, primers comprising a photodeprotectable 3' bydroxyl terminus (which may be synthesized by the polymerization of an appropriate 3' protected nucleotide onto the unprotected 3' hydroxyl of an oligo- or poly-nucleotide, for instance, by the action of terminal deoxynucleotidyl transferase) may provide for the selective polymerization of a polynucleotide moiety selectable by control over illumination of the appropriate region of the sample. A polynucleotide moiety to which such a primer is hybridized and then selectively deprotected may thus be subjected to amplification techniques such as PCR in a selectable manner. Such modified primers shall simply be referred to as photoactivatable primers.

The 3' deprotectable nucleotides employed in some variations on the present invention may also find other uses in molecular biology and biotechnology. They may be used as chain terminators in conventional enzymatic sequencing methods. If such manipulations are performed, any species terminating in a particular base may be extracted from the resolution medium (conventionally polyacrylamide gel), deprotected and then subjected to other manipulations requiring an active 3' hydroxyl group, such as ligation.

1.4.10.9 Enzyme Adaptation to Specific Substrates

The emergence of resistance to chain terminating nucleotide analogs by various viral polynucleotide polymerases suggests a convenient method for the in vitro evolution of polymerases capable of using reversibly 3' protected nucleotide analogs, or nucleotide analogs which otherwise serve as chain terminators which may be reactively modified to form an elongation competent molecule after incorporation into a polynucleotide. Further selection constraints may be concurrently or subsequently applied to fidelity, as the inclusion of non-sense condons in the coding region of a dominant lethal protein coding gene which is carried by the same genetic material carrying the polymerase gene under selection, such that misreading of the non-sense codon, by the polymerase under selection, will effect lethality to the host and thus select against low-fidelity polymerases.

As stated above, such deprotectable compounds may serve as a convenient stepping control means for polymerization. Included among such deprotectable nucleotides are nucleotides with photocleavable protecting groups, including those which reside on the 3' hydroxyl of a nucleotide.

1.4.10.10 Label Encoding and Labeling Methods for Data Collection

Various systems may be used to represent the data corresponding to the occurrence of an affinity interaction. The complexity required of such a representational system will be determined by the types of molecules and associations being examined and the extent to which manipulative steps are to be minimized.

The most rudimentary encoding system will be a one-bit binary labeling system, consisting of only one label moiety type, indicating whether or not an association of only one resolvable type occurred during the preceding association step.

For example, consider a sequencing application employing only a single nucleotide labeling moiety. Such a system may avail each of the four nucleotides modified with a biotin moiety attached by a sufficiently long, cleavable linker arm. In such a case, a polymerization sub-cycle comprises: the incubation of sample template molecules bearing appropriate primers with an appropriate polymerase and limiting quantities of only one labeled nucleotide (and no unlabeled nucleotides) such that this monomer will be added only if the template molecule has the complementary base in the template position immediately 5' to the base opposite the 3' terminal base of the primer, and no monomers will be added otherwise; sample molecules are then washed to remove any remaining free nuclectides; the sample is then exposed to excess quantities of streptavidin modified fluorescently labeled beads for a sufficient length of time to ensure that all biotin moieties are bound by said labeled beads, and then all unbound beads are washed away; detection is then performed and data recorded; linkers are then cleaved. Said sub-cycle is repeated for the remaining three nucleotides, to constitute a cycle which successively tests for tile presence in the sample template molecule of each type of base immediately to the base opposite the 3' terminal base of the primer. If a sample molecule does not bind any label through such a cycle, then it was most likely "missed" due to the limiting concentration of nucleotides used to effect stepping of polymerization. If a sample molecule is labeled multiply during such a cycle, then the respective subsequent bases are detected as occurring in the template according to the pattern of labeling.

A somewhat more efficient encoding system is provided if two distinct labeling moieties may be availed. Each nucleotide will be indicated by the presence or absence of each of the two moiety types, as a binary code. The moieties may, for instance be biotin (B) and digoxigenin (D). For example, the representation may be: A=B+D; T=B; G=D. These three nucleotides are added for a first polymerization sub-cycle, and all unbound reagents then washed away. Either two perceptibly distinct bead types may be used for simultaneous detection, provided distinct affinity labels are sufficiently well separated by extended linkers for simultaneous binding, or a single bead type with two distinct receptor molecules may be used in two separate binding and release cycles, in which case the release of one bead type will have to leave the remaining affinity moiety bound to sample molecules.

After detection of bead labels, all remaining beads are removed and a second subcycle with C nucleotides affinity labeled with only one moiety are then polymerized onto sample molecules and appropriate detection is performed. Where protecting groups are used to effect stepping control, only one sub-cycle is needed and C may be unlabeled. In such cases unlabeled molecules will be detected as having added a cytidine.

More conveniently, nucleotides of each of the four types distinctly labeled with a fluorescent dye moiety may be used with fluorescence detection means, and a sequencing cycle consisting of only one sub-cycle. Alternatively, four antibodies (or four other appropriate receptor molecules or affinity reagents) which each bind each of the four distinct dye moieties may be bound to each of four perceptibly distinct beads. In another arrangement, nucleotides may each be labeled with some distinct combination of multiple dye moieties, again encoding a unique binary label.

1.4.11 Utility of the Sequence of a Genome

The present invention provides methods of detection and discrimination which address the complexity found in biological systems, though they may further be applied to non-natural systems including but not limited to mimetics. Much of this complexity derives from combinations or permutations of simple units such as the four nucleotide bases of polydeoxyribonucleic acids and polyribonucleic acids, or the twenty common amino acids found in polypeptides and proteins.

This complexity, which underlies the most diverse and nuanced of biological processes, has presented both the promise that ultimately much mechanistic knowledge of biological processes may be gained through the accumulation of greater information about underlying structures and biopolymer sequences, and the correspondingly motivated challenge of full enumeration and determination of these structures and sequences.

Because typical eukarvotic qenomes contain between $10^7$ and $10^{10}$ DNA base pairs, and because there are several well studied organisms of particular interest, economical and technically simple methods capable of determining the full genome sequence of an individual organism over a convenientl~short period of time would be particularly desirable.

The present invention can find applications in many fields, for instance, medical, diagnostic, forensic, genetics, biotechnology, and genome research. It should be noted that this technique would be applicable in many other fields and instances, and such applications would be discernible by people of ordinary skills in the respective fields.

The availability of such sequencing methods would enable greater clinical applications of molecular medicine, would facilitate greater and safer application of gene therapy, would permit timely completion of the several genome projects within fiscal constraints, and would enable facile gathering of genome information on populations of individuals, which would have applications in such areas as the study of polygenic diseases, epidemiology and field ecology. Such applications are presently limited by the cost and cumbersome nature of existing sequencing methodologies.

Combinatorial chemistry, affinity characterization, therapeutic synthetic immunochemistry, pharmacology and drug development, in vitro evolution and other fields concerned with the elaboration of a diverse population of molecules, their characterization according to desired properties, and recovery or identification of molecules displaying suitable characteristics may be favorably improved by the availability of methods which permit the introduction of and both qualitative and quantitative characterization of kinetic and equilibrium properties of molecular recognition and binding phenomena, particularly where such parameters may be used as selective constraints.

There has further been some interest in rebuilding or supplementing the immune systems of immunocompromized individuals, and in the development of highly specific antibiotic agents targeted to antibiotic, antifungal or antiviral resistant or otherwise poorly treatable pathogens. Both of these goals may be furthered by the use of the methods of the present invention as they may readily be applied to the determination of pathogen specificity and antigenicity.

1.4.11.1. Application: Gene Finding

An integrated clone map is constructed by the method described herein. When the bin probes include polymorphic genetic markers, and these markers are typed against the DNAs of member of families carrying a genetic trait, that trait can be genetically localized on the map relative to one or more bin probes. Depending on the study design, this genetic localization can be carried out using one of a variety of methods (G. M. Lathrop and J.-M. Lalouel, "Efficient computations in multilocus linkage analysis," Amer. J. Hum. Genet., vol. 42, pp. 498–505, 1988; T. C. Matise, M. W. Perlin, and A. Chakravarti, "Automated construction of genetic linkage maps using an expert system (MultiMap): application to 1268 human microsatellite markers," Nature Genetics, vol. 6, no. 4, pp. 384–390, 1994; E. S. Lander and D. Botstein, "Mapping Complex Genetic Traits in Humans: New Methods Using a Complete RFLP Linkage Map," in Cold Spring Harbor Symposia on Quantitative Biology, vol. LI, Cold Spring Harbor, Cold Spring Harbor Laboratory, 1986, pp. 49–62; L. Penrose, Ann. Eugenics, vol. 18, pp. 120–124, 1953; N. E. Morton, Am. J. Hum. Genet., vol. 35, pp. 201–213, 1983; N. Risch, Am. J. Hum. Genet., vol. 40, pp. 1–14, 1987; E. Lander and D. Botstein, Genetics, vol. 121, pp. 185–199, 1989; N. Risch, "Linkage strategies for genetically complex traits," in three parts, Am. J. Hum. Genet., vol. 46, pp. 222–253, 1990; N. Risch, Genet. Epidemiol., vol. 7, pp. 3–16, 1990; N. Risch, Am. J. Hum. Genet., vol. 48, pp. 1058–1064, 1991; P. Holmans, "Asymptotic Properties of Affected-Sib-Pair Linkage Analysis," Am. J. Hum. Genet., vol. 52, pp. 362–374, 1993; N. Risch, S. Ghosh, and J. A. Todd, "Statistical Evaluation of Multiple-Locus Linkage Data in Experimental Species and Its Relevance to Human Studies: Application to Nonobese Diabetic (NOD) Mouse and Human Insulin-dependent Diabetes Mellitus (IDDM)," Am. J. Hum. Genet., vol. 53, pp. 702–714, 1993; R. C. Elston, in Genetic Approaches So Mental Disorders, E. S. Gershon and C. R. Cloninger, ed. Washington DC: American Psychiatric Press, 1994, pp. 3–21), incorporated by reference.

Following genetic localization relative to the bin probes, the integrated contiged clone map provides an immediate means to proceed with positional cloning procedures. (D. Cohen, I. Chumakov, and J. Weissenbach, Nature, vol. 366, pp. 698–701, 1993; B.-S. Kerem, J. M. Rommens, J. A. Buchanan, D. Markiewicz, T. K. Cox, A. Chakravarti, M. Buchwald, and L.-C.Tsui, "Identification of the cystic fibrosis gene: genetic analysis," Science, vol. 245, pp.

1073–1080, 1989; J. R. Riordan, J. M. Rommens, B.-S. Kerem, N. Alon, R. Rozmahel, Z. Grzelczak, J. Zielenski, S. Lok, N. Playsic, J.-L. Chou, M. L. Drumm, M. C. lannuzzi, F. S. Collins, and L.-C. Tsui, "Identification of the cystic fibrosis gene: cloning and characterization of complementary DNA," Science, vol. 245, pp. 1066–1073, 1989), incorporated by reference. When an expression of candidate genes is included in the mapping resource (e.g., ESTs, cDNAs), the search may proceed more rapidly. When the genome sequences of the clones in the region have been determined, the gene search may be done in part using computer searches for candidate genes.

1.4.11.2 Application: Structure/function Relation

The sequence of a genome is determined by the method described herein. From this genome sequence, the relation of a gene or its promoters to other known functions may be determined using similarity or homology searches. Protocols for these determinations are well described (N. J. Dracopoli, J. L. Haines, B. R. Korf, C. C. Morton, C. E. Seidman, J. G. Seidman, D. T. Moir, and D. Smith, ed., Current Protocols in Human Genetics. New York: John Wiley and Sons, 1995), incorporated by reference. The use of expressed sequence tag (EST) databases (Merck Gene Index, St. Louis, Mo.; Human Genome Sciences, Gathersburg, Md.) together with the genome sequence provides a highly effective means for rapidly correlating a gene's sequence with the structure and function of its protein products.

1.4.11.3 Application: Metabolic Network Determination

The sequence of a genome is determined by the method described herein. Using the RT-PCR technique of differential display, perturbations on the cell state can be assayed in terms of DNA expression. Select perturbations can elucidate the metabolic networks of coupled enzyme systems in the cell. Reference back to the DNA sequence of the genome provides information about local control and gene/promoter interactions. This information can be used to understand disease mechanisms and to develop new pharmaceutical agenst to alleviate said diseases.

1.4.11.4 Application: Growth and Development

The sequence of a genome is determined by the method described herein. A method is described for constructing an integrated genetic-physical-expression map that includes the genome sequence and cDNAs. It is currently impractical to map very large numbers of cDNAs at high resolution, due to the currently used technology of sequencing each cDNA, constructing PCR primers for it, and then performing multiple PCR amplifications and detections relative to a panel of RHs to accurately map even a single cDNA. However unobvious it may currently seem to those skilled in the art, it would nonetheless be extremely desirable for elucidating the mechanism of cell growth and organism development to construct and map tissue-specific cDNA expression libraries at numerous points (e.g., at least every 24 hours) early in organism development. Further, the mapping of these expressed sequences back to their genomic locations would provide information on candidate genes, local gene expression, the coordination of normal and diseased cellular function under genetic control, and the time course of development in different tissues that would be highly useful in developing new diagnostic tests and therapeutic treatments for human disease. The method of the said examples provides such a novel means for practical rapid and high-resolution mapping of many expression libraries that would otherwise be neither constructed nor mapped.

1.4.11.5 Application: Drug Development

A sequence and map of a genome is determined by the method described herein. The sequence of the human genome or integrated clone maps can be used to identify genes that are causative for human disease. From such genes, and their DNA promoters and protein products, mechanisms of diseases related to said genes can be determined. Pharmacological agents that intervene at key junctures in gene-related functions can then be devised to specifically circumvent and treat diseases related to these genes.

1.4.11.6 Application: Diagnostic Testing

A sequence and map of a genome is determined by the method described herein. The sequence of the human genome or integrated clone maps can be used to identify genes that are causative for human disease. From such genes, and their DNA promoters and protein products, mechanisms of diseases related to said genes can be determined. Diagnostic tests that detect key junctures in gene-related structures and functions can then be devised to diagnose diseases related to these genes, and develop kits.

1.4.11.7 Application: Animal Models

The sequence of a genome is determined by the method described herein. In the current art, sequencing even one complete mammalian genome is a highly debated and very expensive proposition (estimated to cost around one billion dollars) which is not likely to be performed more than once. However, the novel sequencing method described renders sequencing more practical., since it produces a high-resolution clone map which can be used to cost-effectively direct the sequencing effort and to practically assemble the resulting sequences. Given the pressing medical need for sequencing a mammalian genome, and the absence of any such useful coordinating map, clearly the described invention is highly nonobvious.

By constructing a map as described in the method described herein, the upfront burden of building maps for mammalian species other than humans is considerably reduced. Further, since the cost per base of sequencing is expected to diminish, particularly as newer sequencing technologies become established, the described method provides the first useful starting point for beginning (and eventually completing) the DNA sequence determination of model animal genomes. Comparison of the DNA sequences and genes between human and model organisms is a well-established route for understanding and treating human disease.

1.4.11.8 Application: Somatic Cell Hybrids

The method described herein describes an inner product mapping analysis mechanism. Localization profiles are produced that can localize DNA sequences to high resolution. This inner product operation can be applied to somatic cell hybrid deletion panel data, thereby increasing the utility of such data by providing more confident and higher resolution localizations.

1.4.11.9 Application: Genome Mismatch Scanning

Genome mismatch scanning (GMS) (S. F. Nelson, J. H. McCusker, M. A. Sander, Y. Kee, P. Modrich, and P. O. Brown, "Genomic mismatch scanning: a new approach to genetic linkage mapping," Nature Genetics, vol. 4, no. May, pp. 11–18, 1993), incorporated by reference, has been described as powerful hybridization-based approach to genetic linkage mapping. GMS has applications both in the mapping of genetic traits and in the diagnosis and prevention of disease. What is currently impeding practical application of the GMS method is the lack of a sequence or map of the human (or animal model) genome that would provide densely spaced (e.g., 1 Mb) hybridization probes for the genome sampling step that scans the mismatched genome DNAs. Applicant's invention discloses a practical method for constructing such a sequence or map of a genome using the method described in the specification. In a preferred embodiment, densely spaced subsequences from the constructed sequence of a genome are used as hybridization probes in GMS. In an alternative embodiment, densely spaced clones (or subsequences therefrom) from the constructed map of a genome are used as hybridization probes in GMS.

1.4.1110 Application: Reliable Maps from Unreliable Data

A sequence and map of a genome is determined by the method described herein. It is generally believed that such maps can be reliably constructed only from highly reliable and relatively complete data. This belief adds considerably to the time, expense, and effort currently expended in constructing genome maps. However, the method described herein discloses a novel mechanism for constructing highly reliable maps from unreliable and incomplete data (J. von Neumann, "Probabilistic logics and the synthesis of reliable organisms from unreliable components," in Automata Studies, C. E. Shannon and J. McCarthy, ed. Princeton, N. J.: Princeton University Press, 1956, pp. 43–98), incorporated by reference.

Specifically:

In step 6, table A's long-range characterization of the clone library can be comprised of very noisy, highly unreliable hybridization data exhibiting large error rates.

In step 9, table B's characterization of the long-range probe library can be sparsely sampled. In some embodiments, a.gtoreq.1 Mb average inter-bin distance suffices for accurate mapping and contig construction.

In step 14, table D's short-range characterization of the clone library has a high tolerance for data errors.

This unobvious result is due to the considerable redundancy in the three data tables, and to the noise filtering and consistency cross- checking capabilities of the analysis methods:

In step 11, table C is a highly reliable binning because the clean PCR-based data table B is used as a global corrective for the noisy complex hybridization-based data table A. This has been empirically demonstrated for human chromosome 11.

In step 16, table E is a highly reliable contiging because every clone has been probed with both long-range and short-range data. Therefore, the global binning information relaxes the requirements on the short-range probings: useful comparisons can be made within a relatively small bin region using imperfect data.

1.4.11.11 Application: Mutation Detection

The techniques described herein will have a wide range of applications, particularly wherever desired to determine if a target nucleic acid has a particular nucleotide sequence or some other sequence differing from a known sequence. For example, one application of the inventions herein is found in mutation detection. These techniques may be applied in a wide variety of fields including diagnostics, forensics, bioanalytics, and others.

For example, assume a "wild-type" nucleic acid has the sequence 5'-$N_1N_2N_3N_4$ where, again, N refers to a monomer such as a nucleotide in a nucleic acid and the subscript refers to position number. Assume that a target nucleic acid is to be evaluated to determine if it is the same as 51 -$N_1N_2N_3N_4$ or if it differs from this sequence, and so contains a mutation or mutant sequence. The target nucleic acid is initially exposed to an array of typically shorter probes, as discussed above. Thereafter, one or more "core" sequences are identified, each of which would be expected to have a high binding affinity to the target, if the target does not contain a mutant sequence or mutation. In this particular example, one probe that would be expected to exhibit high binding affinity would be the complement to 5'-$N_1N_2N_3$ 3'-$P_1P_2P_3$, assuming a 3-mer array is utilized. Again, it will be recognized that the probes and/or the target may be part of a longer nucleic acid molecule.

As an initial screening tool, the absolute binding affinity of the target to the 3'-$P_1P_2P_3$ probe will be utilized to determine if the first three positions of the target are of the expected sequence. If the complement to 5'-$N_1N_2N_3$ does not exhibit strong binding to the target, it can be properly concluded that the target is not of the wild-type.

The single base mismatch profile can also be utilized according to the present invention to determine if the target contains a mutant or wild-type sequence. As shown herein, the single base mismatch plots for wild-type targets generally follow the typical., smile-shaped plot. Conversely, when the target has a mutation at a particular position, not only will the absolute binding affinity of the target to a particular core probe be less, but the single base mismatch characteristics will deviate from expected behavior.

According to one aspect of the invention, a substrate having a selected group of nucleic acids (otherwise referred to herein as a "library" of nucleic acids") is used in the determination of whether a particular nucleic acid is the same or different than a wild-type or other expected nucleic acid. Libraries of nUcleic acids will normally be provided as an array of probes or "probe array." Such probe arrays are preferably formed on a single substrate in which the identity of a probe is determined by ways of its location on the substrate. Optionally, such substrates will not only determine if the nucleotide sequence of a target is the same as the wild-type, but it will also provide sequence information regarding the target. Such substrates will find use in fields noted above such as in forensics, diagnostics, and others. Merely by way of specific example, the invention may be utilized in diagnostics associated with sickle cell anemia detection, detection of any of the large number of P-53 mutations, for any of the large number of cystic fibrosis mutations, for any particular variant sequence associated with the highly polymorphic HLA class 1 or class 2 genes (particularly class 2 DP, DQ and DR beta genes), as well as many other sequences associated with genetic diseases, genetic predisposition, and genetic evaluation.

When a substrate is to be used in such applications, it is not necessary to provide all of the possible nucleic acids of a particular length on the substrate. Instead, it will be necessary using the present invention to provide only a relatively small subset 45 of all the possible sequences. For example, suppose a target nucleic acid comprises a 5-base sequence of particular interest and that one wishes to develop a substrate that may be used to detect a single substitution in the 5-base sequence. According to one aspect of the invention, the substrate will be formed with the expected 5-base sequence formed on a surface thereof, along with all or most of the single base mismatch probes of the 5-base sequence. Accordingly, it will not be necessary to include all possible 5-base sequences on the substrate, although larger arrays will often be preferred. Typically, the length of the nucleic acid probes on the substrate according to the present invention will be between about 5 and 100 bases, between about 5 and 50 bases, between about 8 and 30 bases, or between about 8 and 15 bases.

By selection of the single base mismatch probes among all possible probes of a certain length, the number of probes on the substrate can be greatly limited. For example, in a 3-base sequence there are 69 possible DNA base sequences, but there will be only one exact complement to an expected sequence and 9 possible single base mismatch probes. By selecting only these probes, the diversity necessary for screening will be reduced. Preferably, but not necessarily, all of such single base mismatch probes are synthesized on a single substrate. While substrates will often be formed including other probes of interest in addition to the single base mismatches, such substrates will normally still have less than 50% of all the possible probes of n-bases, often less than 30% of all the possible probes of n-bases, often less than 20% of all the possible probes of n-bases, often less than 10% of the possible probes of n-bases, and often less than 5% of the possible probes of n-bases.

Nucleic acid probes will often be provided in a kit for analysis of a specific genetic sequence. According to one embodiment the kits will include a probe complementary to a target nucleic acid of interest. In addition, the kit will include single base mismatches of the target. The kit will normally include one or more of C, G, T, A and/or U single base mismatches of such probe. Such kits will often be provided with appropriate instructions for use of the complementary probe and single base mismatches in determining the sequence of a particular nucleic acid sample in accordance with the teachings herein. According to one aspect of the invention, the kit provides for the complement to the target, along with only the single base mismatches. Such kits will often be utilized in assessing a particular sample of genetic material to determine if it indicates a particular genetic characteristic. For example, such kits may be utilized in the evaluation of a sample as mentioned above in the detection of sickle cell anemia, detection of any of the large number of P-53 mutations, detection of the large number of cystic fibrosis mutations, detection of particular variant sequence associated with the highly polymorphic HLA class 1 or class 2 genes (particularly class 2 DP, DQ and DR beta genes), as well as detection of many other sequences associated with genetic diseases, genetic predisposition, and genetic evaluation.

Accordingly, it is seen that substrates with probes selected according to the present invention will be capable of performing many mutation detection and other functions, but will need only a limited number of probes to perform such functions.

2. Annotating

In one aspect this invention discloses the use of a relational database system for storing and manipulating biomolecular sequence information and storing and displaying genetic information, the database including genomic libraries for a plurality of types of organisms, the libraries having multiple genomic sequences, at least some of which represent open reading frames located along a contiguous sequence on each the plurality of organisms' genomes, and a user interface capable of receiving a selection of two or more of the genomic libraries for comparison and displaying the results of the comparison. Associated with the database is a software system that allows a user to determine the relative position of a selected gene sequence within a genome. The system allows execution of a method of displaying the genetic locus of a biomolecular sequence. The method involves providing a database including multiple biomolecular sequences, at least some of which represent open reading frames located along a contiguous sequence on an organism's genome. The system also provides a user interface capable of receiving a selection of one or more probe open reading frames for use in determining homologous matches between such probe open reading frame(s) and the open reading frames in the genomic libraries, and displaying the results of the determination. An open reading frame for the sequence is selected and displayed together with adjacent open reading frames located upstream and downstream in the relative positions in which they occur on the contiguous sequence.

Also disclosed is a relational database system for storing biomolecular sequence information in a manner that allows sequences to be catalogued and searched according to one or more protein function hierarchies. The hierarchies allow searches for sequences based upon a protein's biological function or molecular function. Also disclosed is a mechanism for automatically grouping new sequences into protein function hierarchies. This mechanism uses descriptive information obtained from "external hits" which are matches of stored sequences against gene sequences stored in an external database such as GenBank. The descriptive information provided with the external database is evaluated according to a specific algorithm and used to automatically group the external hits (or the sequences associated with the hits) in the categories. Ultimately, the biomolecular sequences stored in databases of this invention are provided with both descriptive information from the external hit and category information from a relevant hierarchy or hierarchies.

Disclosed is a relational database system for storing biomolecular sequence information in a manner that allows sequences to be catalogued and searched according to association with one or more projects for obtaining full-length biomolecular sequences from shorter sequences. The relational database has sequence records containing information identifying one or more projects to which each of the sequence records belong. Each project groups together one or more biomolecular sequences generated during work to obtain a full-length gene sequence from a shorter sequence. The computer system has a user interface allowing a user to selectively view information regarding one or more projects. The relational database also provides interfaces and methods for accessing and manipulating and analyzing project-based information.

Polymer sequences are assembled into bins. A first number of bins are populated with polymer sequences. The polymer sequences in each bin are assembled into one or more consensus sequences representative of the polymer sequences of the bin. The consensus sequences of the bins are compared to determine relationships, if any, between the consensus sequences of the bins. The bins are modified based on the relationships between the consensus sequences of the bins. The polymer sequences are reassembled in the modified bins to generate one or more modified consensus sequences for each bin representative of the modified bins. In another aspect of the invention, sequence similarities and dissimilarities are analyzed in a set of polymer sequences. Pairwise alignment data is generated for pairs of the polymer sequences. The pairwise alignment data defines regions of similarity between the pairs of polymer sequences with boundaries. Additional boundaries in particular polymer sequences are determined by applying at least one boundary from at least one pairwise alignment for one pair of polymer sequences to at least one other pairwise alignment for another pair of polymer sequences including one of the particular polymer sequences. Additional regions of similarity are generated based on the boundaries.

2.1. Annotating—General Methodology

In one aspect this present invention relates generally to relational databases for storing and retrieving biological information. More particularly the invention relates to systems and methods for providing sequences of biological molecules in a relational format allowing retrieval in a client-server environment and for providing full-length cDNA sequences in a relational format allowing retrieval in a client-server environment.

Informatics is the study and application of computer and statistical techniques to the management of information. In genome projects, bioinformatics includes the development of methods to search databases quickly, to analyze nucleic acid sequence information, and to predict protein sequence, structure and function from DNA sequence data.

Increasingly, molecular biology is shifting from the laboratory bench to the computer desktop. Today's researchers require advanced quantitative analyses, database comparisons, and computational algorithms to explore the relationships between sequence and phenotype. Thus, by all accounts, researchers can not and will not be able to avoid using computer resources to explore gene expression, gene sequencing and molecular structure.

One use of bioinformatics involves studying an organism's genome to determine the sequence and placement of its genes and their relationship to other sequences and genes within the genome or to genes in other organisms. Another use of bioinformatics involves studying genes differentially or commonly expressed in different tissues or cell lines (e.g. normal and cancerous tissue).

Such information is of significant interest in biomedical and pharmaceutical research, for instance to assist in the evaluation of drug efficacy and resistance.

The sequence tag method involves generation of a large number (e.g., thousands) of Expressed Sequence Tags ("ESTs") from cDNA libraries (each produced from a different tissue or sample). ESTs are partial transcript sequences that may cover different parts of the cDNA(s) of a gene, depending on cloning and sequencing strategy. Each EST includes about 50 to 300 nucleotides. If it is assumed that the number of tags is proportional to the abundance of transcripts in the tissue or cell type used to make the cDNA library, then any variation in the relative frequency of those tags, stored in computer databases, can be used to detect the differential abundance and potentially the expression of the corresponding genes.

To make genomic and EST information manipulation easy to perform and understand, sophisticated computer database systems have been developed. In one database system, developed by Incyte Pharmaceuticals, Inc. of Palo Alto, Calif., genomic sequence data and the abundance levels of mRNA species represented in a given sample is electronically recorded and annotated with information available from public sequence databases such as GenBank. Examples of such databases include GenBank (NCBI) and TIGR. The resulting information is stored in a relational database that may be employed to determine relationships between sequences and genes within and among genomes and establish a cDNA profile for a given tissue and to evaluate changes in gene expression caused by disease progression, pharmacological treatment, aging, etc.

In one database system, developed by Incyte Pharmaceuticals, Inc. of Palo Alto, Calif., abundance levels of mRNA species represented in a given sample are electronically recorded and annotated with information available from public sequence databases such as GenBank. The resulting information is stored in a relational database that may be employed to establish a cDNA profile for a given tissue and to evaluate changes in gene expression caused by disease progression, pharmacological treatment, aging, etc.

Genetic information for a number of organisms has been catalogued in computer databases. Genetic databases for organisms such as *Eschericia coli*, *Haemophilus influenzae*, *Mycoplasma genitalium*, and *Mycoplasma pneumoniae*, among others, are publicly available. At present, however, complete sequence data is available for relatively few species, and the ability to manipulate sequence data within and between species and databases is limited.

While genetic data processing and relational database systems such as those developed by Incyte Pharmaceuticals, Inc. provide great power and flexibility in analyzing genetic information and gene expression information, this area of technology is still in its infancy and further improvements in genetic data processing and relational database systems and their content will help accelerate biological research for numerous applications.

In genome projects, bioinformatics includes the development of methods to search databases quickly, to analyze nucleic acid sequence information, and to predict protein sequence and structure from DNA sequence data. Increasingly, molecular biology is shifting from the laboratory bench to the computer desktop. Advanced quantitative analyses, database comparisons, and computational algorithms are needed to explore the relationships between sequence and phenotype.

2.2. Annotating—Exemplary Aspects

The annotation methods of this invention include those described in PCT patent publication Nos. 98/26407, 98/26408, and 99/49403 and U.S. Pat. Nos. 6,023,659 and 5,953,727 and are herein incorporated by reference in their entirety to the same extent as if each individual patent or patent application were specifically and individually indicated to be incorporated by reference in its entirety.

Thus, in one aspect, this present invention provides relational database systems for storing and analyzing biomolecular sequence information together with biological annotations detailing the source and interpretation the sequence data. The present invention provides a powerful database tool for drug development and other research and development purposes.

The present invention provides relational database systems for storing and analyzing biomolecular sequence information together with biological detailing the source and interpretation the sequence data. Disclosed is a relational database systems for storing and displaying genetic information.

Associated with the database is a software system the allows a user to determine the relative position of a selected gene sequence within a genome. The system allows execution of a method of displaying the genetic locus of a biomolecular sequence. The method involves providing a database including multiple biomolecular sequences, at least some of which represent open reading frames located along a contiguous sequence on an organism's genome. An open reading frame for the sequence is selected and displayed together with adjacent open reading frames located upstream and downstream in the relative positions in which they occur on the contiguous sequence.

The invention provides a method of displaying the genetic locus of a biomolecular sequence. The method involve providing a database including multiple biomolecular sequences, at least some of which represent open reading frames located along a contiguous sequence on an organism's genome. The method further involves identifying a selected open reading frame, and displaying the selected open reading frame together with adjacent open reading frames located upstream and downstream from the selected open reading frame.

The adjacent open reading frames and the selected open reading frame are displayed in the relative positions in which they occur on the contiguous sequence, textually and/or graphically. The method of the invention may be practiced with sequences from microbial organisms, and the sequences may include nucleic acid or protein sequences.

The invention also provides a computer system including a database having multiple biomolecular sequences, at least some of which represent open reading frames located along a contiguous sequence on an organism's genome.

The computer system also includes a user interface capable of identifying a selected open reading frame, and displaying the selected open reading frame together with adjacent open reading frames located upstream and downstream from the selected open reading frame. The adjacent the open reading frames and the selected open reading frame are displayed in the relative positions in which they occur on the contiguous sequence. The user interface may also capable of detecting a scrolling command, and based upon the direction and magnitude of the scrolling command, identifying a new selected open reading frame from the contiguous sequence.

The invention further provides a computer program product comprising a computer-usable medium having computer-readable program code embodied thereon relating to a database including multiple biomolecular sequences, at least some of which represent open reading frames located along a contiguous sequence on an organism's genome. The computer program product includes computer-readable program code for identifying a selected open reading frame, and displaying the selected open reading frame together with adjacent open reading frames located upstream and downstream from the selected open reading frame. The adjacent open reading frames and the selected open reading frame are displayed in the relative positions in which they occur on the contiguous sequence.

Comparative Genomics is a feature of the database system of the present invention which allows a user to compare the sequence data of sets of different organism types. Comparative searches may be formulated in a number of ways using the Comparative Genomics feature. For example, genes common to a set of organisms may be identified through a "commonality" query, and genes unique to one of a set of organisms may be identified through a "subtraction" query.

Electronic Southern is a feature of the present database system which is useful for identifying genomic libraries in which a given gene or ORF exists.

A Southern analysis is a conventional molecular biology technique in which a nucleic acid of known sequence is used to identify matching (complementary) sequences in a sample of nucleic acid to be analyzed. Like their laboratory counterparts, Electronic Southerns according to the present invention may be used to locate homologous matches between a "probe" DNA sequence and a large number of DNA sequences in one or more libraries.

The present invention provides a method of comparing genetic complements of different types of organisms. The method involves providing a database having sequence libraries with multiple biomolecular sequences for different types of organisms, where at least some of the sequences represent open reading frames located along one or more contiguous sequences on each of the organisms' genomes. The method further involves receiving a selection of two or more of the sequence libraries for comparison, determining open reading frames common or unique to the selected sequence libraries, and displaying the results of the determination.

The invention also provides a method of comparing genomic complements of different types of organisms. The method involves providing a database having genomic sequence libraries with multiple biomolecular sequences for different types of organisms, where at least some of the sequences represent open reading frames located along one or more contiguous sequences on each of the organisms' genomes. The method further involves receiving a selection of two or more of the sequence libraries for comparison, determining sequences common or unique to the selected sequence libraries, and displaying the results of the determination.

The invention further provides a computer system including a database containing genomic libraries for different types of organisms, which libraries have multiple genomic sequences, at least some of which representing open reading frames located along one or more contiguous sequences on each the organisms' genomes. The system also includes a user interface capable of receiving a selection of two or more genomic libraries for comparison and displaying the results of the comparison.

Another aspect of the present invention provides a method of identifying libraries in which a given gene exists. The method involves providing a database including genomic libraries for one or more types of organisms. The libraries have multiple genomic sequences, at least some of which represent open reading frames located along one or more contiguous sequences on each the organisms' genomes. The method further involves receiving a selection of one or more probe sequences, determining homologous matches between the selected probe sequences and the sequences in the genomic libraries, and displaying the results of the determination.

The invention also provides a computer system including a database including genomic libraries for one or more types of organisms, which libraries have multiple genomic sequences, at least some of which represent open reading frames located along one or more contiguous sequences on each the organisms' genomes. The system also includes a user interface capable of receiving a selection of one or more probe sequences for use in determining homologous matches between one or more probe sequences and the sequences in the genomic libraries, and displaying the results of the determination.

Also provided is a computer program product including a computer-usable medium having computer-readable program code embodied thereon relating to a database including genomic libraries for one or more types of organisms. The libraries have multiple genomic sequences, at least some of which represent open reading frames located along one or more contiguous sequences on each the organisms' genomes. The computer program product includes computer-readable program code for providing, within a computing system, an interface for receiving a selection of two or more genomic libraries for comparison, determining sequences common or unique to the selected genomic libraries, and displaying the results of the determination.

Additionally provided is a computer program product including a computer-usable medium having computer-readable program code embodied thereon relating to a database including genomic libraries for one or more types of organisms. The libraries have multiple genomic sequences, at least some of which represent open reading frames located along one or more contiguous sequences on each the organisms' genomes. The computer program product includes computer-readable program code for providing, within a computing system, an interface for receiving a selection of one or more probe open reading frames, determining homologous matches between the probe sequences and the sequences in the genomic libraries, and displaying the results of the determination.

The invention further provides a method of presenting the genetic complement of an organism. The method involves providing a database including sequence libraries for a plurality of types of organisms, where the libraries have multiple biomolecular sequences, at least some of which represent open reading frames located along one or more contiguous sequences on each of the organisms' genomes. The method further involves receiving a selection of one of the sequence libraries, determining open reading frames within the selected sequence library, and displaying the results as one or more unique identifiers for groups of related opening reading frames.

The present invention provides relational database systems for storing biomolecular sequence information in a manner that allows sequences to be catalogued and searched according to one or more protein function hierarchies. The hierarchies are provided to allow carefully tailored searches for sequences based upon a protein's biological function or molecular function. To make this capability available in large sequence databases, the invention provides a mechanism for automatically grouping new sequences into protein function hierarchies. This mechanism takes advantage of descriptive information obtained from "external hits" which are matches of stored sequences against gene sequences stored in an external database such as GenBank. The descriptive information provided with GenBank is evaluated according to a specific algorithm and used to automatically group the external hits (or the sequences associated with the hits) in the categories. Ultimately, the biomolecular sequences stored in databases of this invention are provided with both descriptive information from the external hit and category information from a relevant hierarchy or hierarchies.

The invention provides a computer system having a database containing records pertaining to a plurality of biomolecular sequences. At least some of the biomolecular sequences are grouped into a first hierarchy of protein function categories, the protein function categories specifying biological functions of proteins corresponding to the biomolecular sequences and the first hierarchy. The hierarchy includes a first set of protein function categories specifying biological functions at a cellular level, and a second set of protein function categories specifying biological functions at a level above the cellular level. The computer system of the invention also includes a user interface allowing a user to selectively view information regarding the plurality of biomolecular sequences as it relates to the first hierarchy. The computer system may also include additional protein function categories based, for example, on molecular or enzymatic function of proteins. The biomolecular sequences may include nucleic acid or amino acid sequences. Some of said biomolecular sequences may be provided as part of one or more projects for obtaining full-length gene sequences from shorter sequences, and the database records may contain information about such projects.

The invention also provides a method of using a computer system to present information pertaining to a plurality of biomolecular sequence records stored in a database. The method involves displaying a list of the records or a field for entering information identifying one or more of the records, identifying one or more of the records that a user has selected from the list or field, matching the one or more selected records with one or more protein function categories from a first hierarchy of protein function categories into which at least some of the biomolecular sequence records are grouped, and displaying the one or more categories matching the one or more selected records. The protein function categories specify biological functions of proteins corresponding to the biomolecular sequences and the first hierarchy includes a first set of protein function categories specifying biological functions at a cellular level, and a second set of protein function categories specifying biological functions at a tissue level. The method may also involve matching the records against other protein function hierarchies, such as hierarchies based on molecular and/or enzymatic function, and displaying the results. At least some of the biomolecular sequences may be provided as part of one or more projects for obtaining full-length gene sequences from shorter sequences, and the database records may contain information about those projects.

Additionally, the invention provides a method of using a computer system to present information pertaining to a plurality of biomolecular sequence records stored in a database. The method involves displaying a list of one or more protein biological function categories from a first hierarchy of protein biological function categories into which at least some of the biomolecular sequence records are grouped, identifying one or more of the protein biological function categories that a user has selected from the list, matching the one or more selected protein biological function categories with one or more biomolecular sequence records which are grouped in the selected protein biological function categories, and displaying the one or more sequence records matching the one or more selected protein biological function categories. The protein biological function categories specify biological functions of proteins corresponding to the biomolecular sequences and the first hierarchy includes a first set of protein biological function categories specifying biological functions at a cellular level, and a second set of protein biological function categories specifying biological functions at a tissue level. The method may also involve matching the records against other protein function hierarchies, such as hierarchies based on molecular and/or enzymatic function, and displaying the results. At least some of the biomolecular sequences may be provided as part of one or more projects for obtaining full-length gene sequences from shorter sequences, and the database records may contain information about those projects.

Another aspect of the invention provides a database system having a plurality of internal records. The database includes a plurality of sequence records specifying biomolecular sequences, at least some of which records reference hits to an external database, which hits specify genes having sequences that at least partially match those of the biomolecular sequences. The database also includes a plurality of external hit records specifying the hits to the external database, and at least some of the records reference protein function hierarchy categories which specify at least one of biological functions of proteins or molecular functions of proteins. At least some of the biomolecular sequences may be provided as part of one or more projects for obtaining full-length gene sequences from shorter sequences, and the database records may contain information about those projects.

Further aspects of the present invention provide a method of using a computer system and a computer readable medium having program instructions to automatically categorize biomolecular sequence records into protein function categories in an internal database. The method and program involve receiving descriptive information about a biomolecular sequence in the internal database from a record in an external database pertaining to a gene having a sequence that at least partially matches that of the biomolecular sequence. Next, a determination is made whether the descriptive information contains one or more terms matching one or more keywords associated with a first protein function category, the keywords being terms consistent with a classification in the first protein function category. When at least one keyword is found to match a term in the descriptive information, a determination is made whether the descriptive information contains a term matching one or more anti-keywords associated with the first protein function category, the anti-keywords being terms inconsistent with a classification in the first protein function category. Then, the biomolecular sequence is grouped in the first protein function category when the descriptive information contains a term matching a keyword but contains no term matching an anti-keyword, with reference to the drawings, The present invention provides relational database systems for storing biomolecular sequence information in a manner that allows sequences to be catalogued and searched according to one or more characteristics. The sequence information of the database is generated by one or more "projects" which are concerned with identifying the full-length coding sequence of a gene (i.e., mRNA). The projects involve the extension of an initial sequenced portion of a clone of a gene of interest (e.g., an EST) by a variety of methods which use conventional molecular biological techniques, recently developed adaptations of these techniques, and certain novel database applications. Data accumulated in these projects may be provided to the database of the present invention throughout the course of the projects and may be available to database users (subscribers) throughout the course of these projects for research, product (i.e., drug) development, and other purposes.

In a preferred embodiment, the database of the present invention and its associated projects may provide sequence and related data in amounts and forms not previously available. The present invention preferably makes partial and full-length sequence information for a given gene available to a user both during the course of the data acquisition and once the full-length sequence of the gene has been elucidated. The database also preferably provides a variety of tools for analysis and manipulation of the data, including Northern analysis and Expression summaries. The present invention should permit more complete and accurate annotation of sequence data, as well as the study of relationships between genes of different tissues, systems or organisms, and ultimately detailed expression studies of full-length gene sequences.

The invention provides a computer system including a database having sequence records containing information identifying one or more projects to which each of the sequence records belong. Each project groups together one or more biomolecular sequences generated during work to obtain a full-length gene sequence from a shorter sequence. The computer system also has a user interface allowing a user to selectively view information regarding one or more projects. The biomolecular sequences may include nucleic acid or amino acid sequences. The user interface may allow users to view at least three levels of project information including a project information results level listing at least some of the projects in said database, a sequence information results level listing at least some of the sequences associated with a given project, and a sequence retrieval results level sequentially listing monomers which comprise a given sequence.

A method of using a computer system and a computer program product to present information pertaining to a plurality of sequence records stored in a database are also provided by the present invention. The sequence records contain information identifying one or more projects to which each of the sequence records belong. Each of the projects groups one or more biomolecular sequences generated during work to obtain a full-length gene sequence from a shorter sequence. The method and program involve providing an interface for entering query information relating to one or more projects, locating data corresponding to the entered query information, and displaying the data corresponding to the entered query information.

Additionally, the invention provides a method of using a computer system to present information pertaining to a plurality of sequence records stored in a database. The sequence records contains information identifying one or more projects to which each of the sequence records belong. Each of the projects groups one or more biomolecular sequences generated during work to obtain a full-length gene sequence from a shorter sequence. The method involves displaying a list of one or more project identifiers, determining which project identifier or identifiers from the list is selected by a user, then displaying a second list of one or more biomolecular sequence identifiers associated with the selected project identifier or identifiers, determining which sequence identifier or identifiers from the second list has been selected by a user, and displaying a third list of one or more sequences corresponding to the selected sequence identifier or identifiers. Following the display of the third list, a determination may be made whether and which sequence from the third list has been selected by a user. If a sequence is selected, a sequence alignment search of the selected sequence against other databased sequences may be initiated, and the results of the alignment search displayed.

For Electronic Northern analysis, the invention further provides a computer system including a database having sequence records containing information identifying one or more projects to which each of the sequence records belong, each of said projects grouping one or more biomolecular sequences generated during work to obtain a full-length gene sequence from a shorter sequence. The system also has a user interface capable of allowing a user to select one or more project identifiers or project member identifiers specifying one or more sequences to be compared with one or more cDNA sequence libraries, and displaying matches resulting from that comparison.

A method of using a computer system to present comparative information pertaining to a plurality of sequence records stored in a database is also provided by the present invention. The sequence records contain information identifying one or more projects to which each of the sequence records belong, each of the projects grouping one or more biomolecular sequences generated during work to obtain a full-length gene sequence from a shorter sequence. The method involves providing an interface capable of allowing a user to select one or more project identifiers or project member identifiers specifying one or more sequences, comparing the one or more specified sequences with one or more cDNA sequence libraries, and displaying matches resulting from the comparison.

In addition, for Expression analysis, the invention provides a computer system including a database having sequence records containing information identifying one or more projects to which each of the sequence records belong, each of the projects grouping one or more biomolecular sequences generated during work to obtain a full-length gene sequence from a shorter sequence. The system also has a user interface allowing a user to view expression information pertaining to the projects by selecting one or more expression categories for a query, and displaying the result of the query.

A method of using a computer system to view expression information pertaining to one or more projects, each of the projects grouping one or more biomolecular sequences generated during work to obtain a full-length gene sequence from a shorter sequence, is also provided in accordance with the present invention. The computer system includes a database storing a plurality of sequence records, the sequence records containing information identifying one or more projects to which each of the sequence records belong. The method involves providing an interface which allows a user to select one or more expression categories as a query, locating projects belonging to the selected one or more expression categories, and displaying a list of located projects.

Finally, the present invention provides a computer system including a database having sequence records containing information identifying one or more projects to which each of the sequence records belong, each of the projects grouping one or more biomolecular sequences generated during work to obtain a full-length gene sequence from a shorter sequence. This computer system has a user interface allowing a user to selectively view information regarding said one or more projects and which displays information to a user in a format common to one or more other sequence databases. These and other features and advantages of the invention will be described in more detail below with reference to the drawings.

Polymer sequences are assembled into bins. A first number of bins are populated with polymer sequences. The polymer sequences in each bin are assembled into one or more consensus sequences representative of the polymer sequences of the bin. The consensus sequences of the bins are compared to determine relationships, if any, between the consensus sequences. The bins are modified based on the relationships between the consensus sequences. The polymer sequences are reassembled in the modified bins to generate one or more modified consensus sequences for each bin representative of the modified bins.

In another aspect of the invention, sequence similarities and dissimilarities are analyzed in a set of polymer sequences. Pairwise alignment data is generated for pairs of the polymer sequences. The pairwise alignment data defines regions of similarity between the pairs of polymer sequences with boundaries. Additional boundaries in particular polymer sequences are determined by applying at least one boundary from at least one pairwise alignment for one pair of polymer sequences to at least one other pairwise alignment for another pair of polymer sequences including one of the particular polymer sequences. Additional regions of similarity are generated based on the boundaries 2.3. Annotating—Preferred Embodiments Generally, the present invention provides an improved relational database for storing and manipulating genomic sequence information. While the invention is described in terms of a database optimized for microbial data, it is by no means so limited. The invention may be employed to investigate data from various sources. For example, the invention covers databases optimized for other sources of sequence data, such as animal sequences (e.g., human, primate, rodent, amphibian, insect, etc.), plant sequences and microbial sequences. In the following description, numerous specific details are set forth in order to provide a thorough understanding of the present invention. It will be apparent, however, that the present invention may be practiced without limitation to some of the specific details presented herein.

Generally, the present invention provides an improved relational database for storing sequence information. The invention may be employed to investigate data from various sources. For example, it may catalogue animal sequences (e.g., human, primate, rodent, amphibian, insect, etc.), plant sequences, and microbial sequences.

3. Directed Evolution Methods

In one aspect the invention described herein is directed to the use of repeated cycles of reductive reassortment, recombination and selection which allow for the directed molecular evolution of highly complex linear sequences, such as DNA, RNA or proteins thorough recombination.

In vivo shuffling of molecules can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In a preferred embodiment, the invention relates to a method for producing a hybrid polynucleotide from at least a first polynucleotide and a second polynucleotide. The present invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

The invention provides a means for generating hybrid polynucleotides which may encode biologically active hybrid polypeptides. In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism may, for example, function effectively under a particular environmental condition, e.g. high salinity. An enzyme encoded by a second polynucleotide from a different organism may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

Enzymes encoded by the original polynucleotides of the invention include, but are not limited to; oxidoreductases, transferases, hydrolases, lyases, isomerases and ligases. A hybrid polypeptide resulting from the method of the invention may exhibit specialized enzyme activity not displayed in the original enzymes. For example, following recombination and/or reductive reassortment of polynucleotides encoding hydrolase activities, the resulting hybrid polypeptide encoded by a hybrid polynucleotide can be screened for specialized hydrolase activities obtained from each of the original enzymes, i.e. the type of bond on which the hydrolase acts and the temperature at which the hydrolase functions. Thus, for example, the hydrolase may be screened to ascertain those chemical functionalities which distinguish the hybrid hydrolase from the original hydrolyases, such as: (a) amide (peptide bonds), i.e. proteases; (b) ester bonds, i.e. esterases and lipases; (c) acetals, i.e., glycosidases and, for example, the temperature, pH or salt concentration at which the hybrid polypeptide functions.

Sources of the original polynucleotides may be isolated from individual organisms ("isolates"), collections of organisms that have been grown in defined media ("enrichment cultures"), or, most preferably, uncultivated organisms ("environmental samples"). The use of a culture-independent approach to derive polynucleotides encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

The microorganisms from which the polynucleotide may be prepared include prokaryotic microorganisms, such as Eubacteria and Archaebacteria, and lower eukaryotic microorganisms such as fungi, some algae and protozoa. Polynucleotides may be isolated from environmental samples in which case the nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. Polynucleotides encoding enzymes isolated from extremophilic microorganisms are particularly preferred. Such enzymes may function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. For example, several esterases and lipases cloned and expressed from extremophilic organisms show high activity throughout a wide range of temperatures and pHs.

Polynucleotides selected and isolated as hereinabove described are introduced into a suitable host cell. A suitable host cell is any cell which is capable of promoting recombination and/or reductive reassortment. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (Davis et al, 1986).

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9; animal cells such as CHO, COS or Bowes melanoma; adenoviruses; and plant cells. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified enzyme activity may then be sequenced to identify the polynucleotide sequence encoding an enzyme having the enhanced activity.

In another aspect, it is envisioned the method of the present invention can be used to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function. An example of a biochemical pathway encoded by gene clusters are polyketides. Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of an enormous variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

The ability to select and combine desired components from a library of polyketides, or fragments thereof, and postpolyketide biosynthesis genes for generation of novel polyketides for study is appealing. The method of the present invention makes it possible to facilitate the production of novel polyketide synthases through intermolecular recombination.

Preferably, gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of $E.$ $coli$. This f-factor of $E.$ $coli$ is a plasmid which affect high-frequency transfer of itself during conjugation and is ideal to achieve and stably propagate large DNA fragments, such as gene clusters from mixed microbial samples. Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Therefore, in a preferred embodiment, the present invention relates to a method for producing a biologically active hybrid polypeptide and screening such a polypeptide for enhanced activity by:

1) introducing at least a first polynucleotide in operable linkage and a second polynucleotide in operable linkage, said at least first polynucleotide and second polynucleotide sharing at least one region of partial sequence homology, into a suitable host cell;
2) growing the host cell under conditions which promote sequence reorganization resulting in a hybrid polynucleotide in operable linkage;
3) expressing a hybrid polypeptide encoded by the hybrid polynucleotide;
4) screening the hybrid polypeptide under conditions which promote identification of enhanced biological activity; and
5) isolating the a polynucleotide encoding the hybrid polypeptide.

Methods for screening for various enzyme activities are known to those of skill in the art and discussed throughout the present specification. Such methods may be employed when isolating the polypeptides and polynucleotides of the present invention.

As representative examples of expression vectors which may be used there may be mentioned viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used as long as they are replicable and viable in the host. Low copy number or high copy number vectors may be employed with the present invention.

A preferred type of vector for use in the present invention contains an f-factor origin replication. The f-factor (or fertility factor) in $E.$ $coli$ is a plasmid which effects high frequency transfer of itself during conjugation and less frequent transfer of the bacterial chromosome itself. A particularly preferred embodiment is to use cloning vectors, referred to as "fosmids" or bacterial artificial chromosome (BAC) vectors. These are derived from $E.$ $coli$ f-factor which is able to stably integrate large segments of genomic DNA. When integrated with DNA from a mixed uncultured environmental sample, this makes it possible to achieve large genomic fragments in the form of a stable "environmental DNA library."

Another preferred type of vector for use in the present invention is a cosmid vector. Cosmid vectors were originally designed to clone and propagate large segments of genomic DNA. Cloning into cosmid vectors is described in detail in "Molecular Cloning: A laboratory Manual" (Sambrook et al, 1989).

The DNA sequence in the expression vector is operatively linked to an appropriate expression control sequence(s) (promoter) to direct RNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli$.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), -factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

The cloning strategy permits expression via both vector driven and endogenous promoters; vector promotion may be important with expression of genes whose endogenous promoter will not function in *E. coli*.

The DNA isolated or derived from microorganisms can preferably be inserted into a vector or a plasmid prior to probing for selected DNA. Such vectors or plasmids are preferably those containing expression regulatory sequences, including promoters, enhancers and the like. Such polynucleotides can be part of a vector and/or a composition and still be isolated, in that such vector or composition is not part of its natural environment. Particularly preferred phage or plasmid and methods for introduction and packaging into them are described in detail in the protocol set forth herein.

The selection of the cloning vector depends upon the approach taken, for example, the vector can be any cloning vector with an adequate capacity to multiply repeated copies of a sequence, or multiple sequences that can be successfully transformed and selected in a host cell. One example of such a vector is described in "Polycos vectors: a system for packaging filamentous phage and phagemid vectors using lambda phage packaging extracts" (Alting-Mecs and Short, 1993). Propagation/maintenance can be by an antibiotic resistance carried by the cloning vector. After a period of growth, the naturally abbreviated molecules are recovered and identified by size fractionation on a gel or column, or amplified directly. The cloning vector utilized may contain a selectable gene that is disrupted by the insertion of the lengthy construct. As reductive reassortment progresses, the number of repeated units is reduced and the interrupted gene is again expressed and hence selection for the processed construct can be applied. The vector may be an expression/selection vector which will allow for the selection of an expressed product possessing desirable biologically properties. The insert may be positioned downstream of a functional promoter and the desirable property screened by appropriate means.

In vivo reassortment is focused on "inter-molecular" processes collectively referred to as "recombination" which in bacteria, is generally viewed as a "RecA-dependent" phenomenon. The present invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process.

Therefore, in another aspect of the present invention, novel polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In the present invention, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:
a) Primers that include a poly-A head and poly-T tail which when made single-stranded would provide orientation can be utilized. This is accomplished by having the first few bases of the primers made from RNA and hence easily removed RNAseH.
b) Primers that include unique restriction cleavage sites can be utilized. Multiple sites, a battery of unique sequences, and repeated synthesis and ligation steps would be required.
c) The inner few bases of the primer could be thiolated and an exonuclease used to produce properly tailed molecules.

The recovery of the re-assorted sequences relies on the identification of cloning vectors with a reduced RI. The re-assorted encoding sequences can then be recovered by amplification. The products are re-cloned and expressed. The recovery of cloning vectors with reduced RI can be effected by:

1) The use of vectors only stably maintained when the construct is reduced in complexity.
2) The physical recovery of shortened vectors by physical procedures. In this case, the cloning vector would be recovered using standard plasmid isolation procedures and size fractionated on either an agarose gel, or column with a low molecular weight cut off utilizing standard procedures.
3) The recovery of vectors containing interrupted genes which can be selected when insert size decreases.
4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates the method of the invention. Encoding nucleic acid sequences (quasi-repeats) derived from three (3) unique species are depicted. Each sequence encodes a protein with a distinct set of properties. Each of the sequences differs by a single or a few base pairs at a unique position in the sequence which are designated "A", "B" and "C". The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may, or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations.

Optionally, the method comprises the additional step of screening the library members of the shuffled pool to identify individual shuffled library members having the ability to bind or otherwise interact (e.g., such as catalytic antibodies) with a predetermined macromolecule, such as for example a proteinaceous receptor, peptide oligosaccharide, viron, or other predetermined compound or structure.

The displayed polypeptides, antibodies, peptidomimetic antibodies, and variable region sequences that are identified from such libraries can be used for therapeutic, diagnostic, research and related purposes (e.g., catalysts, solutes for increasing osmolarity of an aqueous solution, and the like), and/or can be subjected to one or more additional cycles of shuffling and/or affinity selection. The method can be modified such that the step of selecting for a phenotypic characteristic can be other than of binding affinity for a predetermined molecule (e.g., for catalytic activity, stability oxidation resistance, drug resistance, or detectable phenotype conferred upon a host cell).

The present invention provides a method for generating libraries of displayed antibodies suitable for affinity interactions screening. The method comprises (1) obtaining first a plurality of selected library members comprising a displayed antibody and an associated polynucleotide encoding said displayed antibody, and obtaining said associated polynucleotide encoding for said displayed antibody and obtaining said associated polynucleotides or copies thereof, wherein said associated polynucleotides comprise a region of substantially identical variable region framework sequence, and (2) introducing said polynucleotides into a suitable host cell and growing the cells under conditions which promote recombination and reductive reassortment resulting in shuffled polynucleotides. CDR combinations comprised by the shuffled pool are not present in the first plurality of selected library members, said shuffled pool composing a library of displayed antibodies comprising CDR permutations and suitable for affinity interaction screening. Optionally, the shuffled pool is subjected to affinity screening to select shuffled library members which bind to a predetermined epitope (antigen) and thereby selecting a plurality of selected shuffled library members. Further, the plurality of selectively shuffled library members can be shuffled and screened iteratively, from 1 to about 1000 cycles or as desired until library members having a desired binding affinity are obtained.

In another aspect of the invention, it is envisioned that prior to or during recombination or reassortment, polynucleotides generated by the method of the present invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N3-Adenine, see Sun and Hurley, 1992); an N-acelylated or deacetylated 4'-fluro-4-aminobiphenyl adduct capable of inhibiting DNA synthesis (see, for example, van de Poll et al, 1992); or a N-acetylated or deacetylated 4-aminobiphenyl adduct capable of inhibiting DNA synthesis (see also, van de Poll et al, 1992, pp. 751–758); trivalent chromium, a trivalent chromium salt, a polycyclic aromatic hydrocarbon ("PAH") DNA adduct capable of inhibiting DNA replication, such as 7-bromomethyl-benz[$\alpha$] anthracene ("BMA"), tris(2,3-dibromopropyl)phosphate ("Tris-BP"), 1,2-dibromo-3-chloropropane ("DBCP"), 2-bromoacrolein (2BA), benzo[$\alpha$]pyrene-7,8-dihydrodiol-9-10-epoxide ("BPDE"), a platinum(II) halogen salt, N-hydroxy-2-amino-3-methylimidazo[4,5-f]-quinoline ("N-hydroxy-IQ"), and N-hydroxy-2-amino-1-methyl-6-phenylimidazo[4,5-f]-pyridine ("N-hydroxy-PhIP"). Especially preferred "means for slowing or halting PCR amplification consist of UV light (+)-CC-1065 and (+)-CC-1065-(N3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect the present invention is directed to a method of producing recombinant proteins having biological activity by treating a sample comprising double-stranded template polynucleotides encoding a wild-type protein under conditions according to the present invention which provide for the production of hybrid or re-assorted polynucleotides.

The invention also provides the use of polynucleotide shuffling to shuffle a population of viral genes (e.g., capsid proteins, spike glycoproteins, polymerases, and proteases) or viral genomes (e.g., paramyxoviridae, orthomyxoviridae, herpesviruses, retroviruses, reoviruses and rhinoviruses). In an embodiment, the invention provides a method for shuffling sequences encoding all or portions of immunogenic viral proteins to generate novel combinations of epitopes as well as novel epitopes created by recombination; such shuffled viral proteins may comprise epitopes or combinations of epitopes as well as novel epitopes created by recombination; such shuffled viral proteins may comprise epitopes or combinations of epitopes which are likely to arise in the natural environment as a consequence of viral evolution; (e.g., such as recombination of influenza virus strains).

The invention also provides a method suitable for shuffling polynucleotide sequences for generating gene therapy vectors and replication-defective gene therapy constructs, such as may be used for human gene therapy, including but not limited to vaccination vectors for DNA-based vaccination, as well as anti-neoplastic gene therapy and other general therapy formats.

In the polypeptide notation used herein, the left-hand direction is the amino terminal direction and the right-hand direction is the carboxy-terminal direction, in accordance with standard usage and convention. Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the coding RNA transcript are referred to as "downstream sequences".

3.1. Saturation Mutagenesis

In one aspect, this invention provides for the use of proprietary codon primers (containing a degenerate N,N,G/T sequence) to introduce point mutations into a polynucleotide, so as to generate a set of progeny polypeptides in which a full range of single amino acid substitutions is represented at each amino acid position. The oligos used are comprised contiguously of a first homologous sequence, a degenerate N,N,G/T sequence, and preferably but not necessarily a second homologous sequence. The downstream progeny translational products from the use of such oligos include all possible amino acid changes at each amino acid site along the polypeptide, because the degeneracy of the N,N,G/T sequence includes codons for all 20 amino acids.

In one aspect, one such degenerate oligo (comprised of one degenerate N,N,G/T cassette) is used for subjecting each original codon in a parental polynucleotide template to a full range of codon substitutions. In another aspect, at least two degenerate N,N,G/T cassettes are used—either in the same oligo or not, for subjecting at least two original codons in a parental polynucleotide template to a full range of codon substitutions. Thus, more than one N,N,G/T sequence can be contained in one oligo to introduce amino acid mutations at more than one site. This plurality of N,N,G/T sequences can be directly contiguous, or separated by one or more additional nucleotide sequence(s). In another aspect, oligos serviceable for introducing additions and deletions can be used either alone or in combination with the codons containing an N,N,G/T sequence, to introduce any combination or permutation of amino acid additions, deletions, and/or substitutions.

In a particular exemplification, it is possible to simultaneously mutagenize two or more contiguous amino acid positions using an oligo that contains contiguous N,N,G/T triplets, i.e. a degenerate $(N,N,G/T)_n$ sequence.

In another aspect, the present invention provides for the use of degenerate cassettes having less degeneracy than the N,N,G/T sequence. For example, it may be desirable in some instances to use (e.g. in an oligo) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N,N,N triplet sequence, or an N,N, G/C triplet sequence.

It is appreciated, however, that the use of a degenerate triplet (such as N,N,G/T or an N,N, G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the instant invention provides a way to systematically and fairly easily generate 2000 distinct species (i.e. 20 possible amino acids per position X 100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes, and point mutations that cause the generation of stop codons and the corresponding expression of polypeptide fragments.

Thus, in a preferred embodiment of this invention, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g. cloned into a suitable *E. coli* host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e. 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

Thus, in a non-limiting exemplification, this invention provides for the use of saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, the instant invention provides that mutagenesis can be use to replace each of any number of bases in a polynucleotide sequence, wherein the number of bases to be mutagenized is preferably every integer from 15 to 100,000. Thus, instead of mutagenizing every position along a molecule, one can subject every a discrete number of bases (preferably a subset totaling from 15 to 100,000) to mutagenesis. Preferably, a separate nucleotide is used for mutagenizing each position or group of positions along a polynucleotide sequence. A group of 3 positions to be mutagenized may be a codon. The mutations are preferably introduced using a mutagenic primer, containing a heterologous cassette, also referred to as a mutagenic cassette. Preferred cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo). The tables below show exemplary tri-nucleotide cassettes (there are over 3000 possibilities in addition to N,N,G/T and N,N,N and N,N,A/C).

In a general sense, saturation mutagenesis is comprised of mutagenizing a complete set of mutagenic cassettes (wherein each cassette is preferably 1–500 bases in length) in defined polynucleotide sequence to be mutagenized (wherein the sequence to be mutagenized is preferably from 15 to 100,000 bases in length). Thusly, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Defined sequences to be mutagenized (see FIG. 20) include preferably a whole gene, pathway, cDNA, an entire open reading frame (ORF), and entire promoter, enhancer, repressor/transactivator, origin of replication, intron, operator, or any polynucleotide functional group. Generally, a preferred "defined sequences" for this purpose may be any polynucleotide that a 15 base-polynucleotide sequence, and polynucleotide sequences of lengths between 15 bases and 15,000 bases (this invention specifically names every integer in between). Considerations in choosing groupings of codons include types of amino acids encoded by a degenerate mutagenic cassette.

In a particularly preferred exemplification a grouping of mutations that can be introduced into a mutagenic cassette (see Tables 1–85), this invention specifically provides for degenerate codon substitutions (using degenerate oligos) that code for 2, 3, 4, 5, 6, 7, 8, 9, 10, 11, 12, 13, 14, 15, 16, 17, 18, 19, and 20 amino acids at each position, and a library of polypeptides encoded thereby.

3.2. Chimerizations
3.2.1 "Shuffling"

Nucleic acid shuffling is a method for in vitro or in vivo homologous recombination of pools of shorter or smaller polynucleotides to produce a polynucleotide or polynucleotides. Mixtures of related nucleic acid sequences or polynucleotides are subjected to sexual PCR to provide random polynucleotides, and reassembled to yield a library or mixed population of recombinant hybrid nucleic acid molecules or polynucleotides.

In contrast to cassette mutagenesis, only shuffling and error-prone PCR allow one to mutate a pool of sequences blindly (without sequence information other than primers).

The advantage of the mutagenic shuffling of this invention over error-prone PCR alone for repeated selection can best be explained with an example from antibody engineering. Consider DNA shuffling as compared with error-prone PCR (not sexual PCR). The initial library of selected pooled sequences can consist of related sequences of diverse origin (i.e. antibodies from naive mRNA) or can be derived by any type of mutagenesis (including shuffling) of a single antibody gene. A collection of selected complementarity determining regions ("CDRs") is obtained after the first round of affinity selection. In the diagram the thick CDRs confer onto the antibody molecule increased affinity for the antigen. Shuffling allows the free combinatorial association of all of the CDR1s with all of the CDR2s with all of the CDR3s, for example.

This method differs from error-prone PCR, in that it is an inverse chain reaction. In error-prone PCR, the number of polymerase start sites and the number of molecules grows exponentially. However, the sequence of the polymerase start sites and the sequence of the molecules remains essentially the same. In contrast, in nucleic acid reassembly or shuffling of random polynucleotides the number of start sites and the number (but not size) of the random polynucleotides decreases over time. For polynucleotides derived from whole plasmids the theoretical endpoint is a single, large concatemeric molecule.

Since cross-overs occur at regions of homology, recombination will primarily occur between members of the same sequence family. This discourages combinations of CDRs that are grossly incompatible (e.g., directed against different epitopes of the same antigen). It is contemplated that multiple families of sequences can be shuffled in the same reaction. Further, shuffling generally conserves the relative order, such that, for example, CDR1 will not be found in the position of CDR2.

Rare shufflants will contain a large number of the best (eg. highest affinity) CDRs and these rare shufflants may be selected based on their superior affinity.

CDRs from a pool of 100 different selected antibody sequences can be permutated in up to 1006 different ways. This large number of permutations cannot be represented in a single library of DNA sequences. Accordingly, it is contemplated that multiple cycles of DNA shuffling and selection may be required depending on the length of the sequence and the sequence diversity desired.

Error-prone PCR, in contrast, keeps all the selected CDRs in the same relative sequence, generating a much smaller mutant cloud.

The template polynucleotide which may be used in the methods of this invention may be DNA or RNA. It may be of various lengths depending on the size of the gene or shorter or smaller polynucleotide to be recombined or reassembled. Preferably, the template polynucleotide is from 50 bp to 50 kb. It is contemplated that entire vectors containing the nucleic acid encoding the protein of interest can be used in the methods of this invention, and in fact have been successfully used.

The template polynucleotide may be obtained by amplification using the PCR reaction (U.S. Pat. Nos. 4,683,202 and 4,683,195) or other amplification or cloning methods. However, the removal of free primers from the PCR products before subjecting them to pooling of the PCR products and sexual PCR may provide more efficient results. Failure to adequately remove the primers from the original pool before sexual PCR can lead to a low frequency of crossover clones.

The template polynucleotide often should be double-stranded. A double-stranded nucleic acid molecule is recommended to ensure that regions of the resulting single-stranded polynucleotides are complementary to each other and thus can hybridize to form a double-stranded molecule.

It is contemplated that single-stranded or double-stranded nucleic acid polynucleotides having regions of identity to the template polynucleotide and regions of heterology to the template polynucleotide may be added to the template polynucleotide, at this step. It is also contemplated that two different but related polynucleotide templates can be mixed at this step.

The double-stranded polynucleotide template and any added double- or single-stranded polynucleotides are subjected to sexual PCR which includes slowing or halting to provide a mixture of from about 5 bp to 5 kb or more. Preferably the size of the random polynucleotides is from about 10 bp to 1000 bp, more preferably the size of the polynucleotides is from about 20 bp to 500 bp.

Alternatively, it is also contemplated that double-stranded nucleic acid having multiple nicks may be used in the methods of this invention. A nick is a break in one strand of the double-stranded nucleic acid. The distance between such nicks is preferably 5 bp to 5 kb, more preferably between 10 bp to 1000 bp. This can provide areas of self-priming to produce shorter or smaller polynucleotides to be included with the polynucleotides resulting from random primers, for example.

The concentration of any one specific polynucleotide will not be greater than 1% by weight of the total polynucleotides, more preferably the concentration of any one specific nucleic acid sequence will not be greater than 0.1% by weight of the total nucleic acid.

The number of different specific polynucleotides in the mixture will be at least about 100, preferably at least about 500, and more preferably at least about 1000.

At this step single-stranded or double-stranded polynucleotides, either synthetic or natural, may be added to the random double-stranded shorter or smaller polynucleotides in order to increase the heterogeneity of the mixture of polynucleotides.

It is also contemplated that populations of double-stranded randomly broken polynucleotides may be mixed or combined at this step with the polynucleotides from the sexual PCR process and optionally subjected to one or more additional sexual PCR cycles.

Where insertion of mutations into the template polynucleotide is desired, single-stranded or double-stranded polynucleotides having a region of identity to the template polynucleotide and a region of heterology to the template polynucleotide may be added in a 20 fold excess by weight as compared to the total nucleic acid, more preferably the single-stranded polynucleotides may be added in a 10 fold excess by weight as compared to the total nucleic acid.

Where a mixture of different but related template polynucleotides is desired, populations of polynucleotides from each of the templates may be combined at a ratio of less than about 1:100, more preferably the ratio is less than about 1:40. For example, a backcross of the wild-type polynucleotide with a population of mutated polynucleotide may be desired to eliminate neutral mutations (e.g., mutations yielding an insubstantial alteration in the phenotypic property being selected for). In such an example, the ratio of randomly provided wild-type polynucleotides which may be added to the randomly provided sexual PCR cycle hybrid polynucleotides is approximately 1:1 to about 100:1, and more preferably from 1:1 to 40:1.

The mixed population of random polynucleotides are denatured to form single-stranded polynucleotides and then re-annealed. Only those single-stranded polynucleotides having regions of homology with other single-stranded polynucleotides will re-anneal.

The random polynucleotides may be denatured by heating. One skilled in the art could determine the conditions necessary to completely denature the double-stranded nucleic acid. Preferably the temperature is from 80° C. to 100° C., more preferably the temperature is from 90° C. to 96° C. other methods which may be used to denature the polynucleotides include pressure (36) and pH.

The polynucleotides may be re-annealed by cooling. Preferably the temperature is from 20° C. to 75° C., more preferably the temperature is from 40° C. to 65° C. If a high frequency of crossovers is needed based on an average of only 4 consecutive bases of homology, recombination can be forced by using a low annealing temperature, although the process becomes more difficult. The degree of renaturation which occurs will depend on the degree of homology between the population of single-stranded polynucleotides.

Renaturation can be accelerated by the addition of polyethylene glycol ("PEG") or salt. The salt concentration is preferably from 0 mM to 200 mM, more preferably the salt concentration is from 10 mM to 100 mm. The salt may be KCl or NaCl. The concentration of PEG is preferably from 0% to 20%, more preferably from 5% to 10%.

The annealed polynucleotides are next incubated in the presence of a nucleic acid polymerase and dNTP's (i.e. dATP, dCTP, DGTP and dTTP). The nucleic acid polymerase may be the Klenow fragment, the Taq polymerase or any other DNA polymerase known in the art.

The approach to be used for the assembly depends on the minimum degree of homology that should still yield crossovers. If the areas of identity are large, Taq polymerase can be used with an annealing temperature of between 45–65° C. If the areas of identity are small, Klenow polymerase can be used with an annealing temperature of between 20–30° C. One skilled in the art could vary the temperature of annealing to increase the number of cross-overs achieved.

The polymerase may be added to the random polynucleotides prior to annealing, simultaneously with annealing or after annealing.

The cycle of denaturation, renaturation and incubation in the presence of polymerase is referred to herein as shuffling or reassembly of the nucleic acid. This cycle is repeated for a desired number of times. Preferably the cycle is repeated from 2 to 50 times, more preferably the sequence is repeated from 10 to 40 times.

The resulting nucleic acid is a larger double-stranded polynucleotide of from about 50 bp to about 100 kb, preferably the larger polynucleotide is from 500 bp to 50 kb.

This larger polynucleotide may contain a number of copies of a polynucleotide having the same size as the template polynucleotide in tandem. This concatemeric polynucleotide is then denatured into single copies of the template polynucleotide. The result will be a population of polynucleotides of approximately the same size as the template polynucleotide. The population will be a mixed population where single or double-stranded polynucleotides having an area of identity and an area of heterology have been added to the template polynucleotide prior to shuffling. These polynucleotides are then cloned into the appropriate vector and the ligation mixture used to transform bacteria.

It is contemplated that the single polynucleotides may be obtained from the larger concatemeric polynucleotide by amplification of the single polynucleotide prior to cloning by a variety of methods including PCR (U.S. Pat. Nos. 4,683,195 and 4,683,202), rather than by digestion of the concatemer.

The vector used for cloning is not critical provided that it will accept a polynucleotide of the desired size. If expression of the particular polynucleotide is desired, the cloning vehicle should further comprise transcription and translation signals next to the site of insertion of the polynucleotide to allow expression of the polynucleotide in the host cell. Preferred vectors include the pUC series and the pBR series of plasmids.

The resulting bacterial population will include a number of recombinant polynucleotides having random mutations. This mixed population may be tested to identify the desired recombinant polynucleotides. The method of selection will depend on the polynucleotide desired.

For example, if a polynucleotide which encodes a protein with increased binding efficiency to a ligand is desired, the proteins expressed by each of the portions of the polynucleotides in the population or library may be tested for their ability to bind to the ligand by methods known in the art (i.e. panning, affinity chromatography). If a polynucleotide which encodes for a protein with increased drug resistance is desired, the proteins expressed by each of the polynucleotides in the population or library may be tested for their ability to confer drug resistance to the host organism. One skilled in the art, given knowledge of the desired protein, could readily test the population to identify polynucleotides which confer the desired properties onto the protein.

It is contemplated that one skilled in the art could use a phage display system in which fragments of the protein are expressed as fusion proteins on the phage surface (Pharmacia, Milwaukee Wis.). The recombinant DNA molecules are cloned into the phage DNA at a site which results in the transcription of a fusion protein a portion of which is encoded by the recombinant DNA molecule. The phage containing the recombinant nucleic acid molecule undergoes replication and transcription in the cell. The leader sequence of the fusion protein directs the transport of the fusion protein to the tip of the phage particle. Thus the fusion protein which is partially encoded by the recombinant DNA molecule is displayed on the phage particle for detection and selection by the methods described above.

It is further contemplated that a number of cycles of nucleic acid shuffling may be conducted with polynucleotides from a sub-population of the first population, which sub-population contains DNA encoding the desired recombinant protein. In this manner, proteins with even higher binding affinities or enzymatic activity could be achieved.

It is also contemplated that a number of cycles of nucleic acid shuffling may be conducted with a mixture of wild-type polynucleotides and a sub-population of nucleic acid from the first or subsequent rounds of nucleic acid shuffling in order to remove any silent mutations from the sub-population.

Any source of nucleic acid, in purified form can be utilized as the starting nucleic acid. Thus the process may employ DNA or RNA including messenger RNA, which DNA or RNA may be single or double stranded. In addition, a DNA-RNA hybrid which contains one strand of each may be utilized. The nucleic acid sequence may be of various lengths depending on the size of the nucleic acid sequence to be mutated. Preferably the specific nucleic acid sequence is from 50 to 50000 base pairs. It is contemplated that entire vectors containing the nucleic acid encoding the protein of interest may be used in the methods of this invention.

The nucleic acid may be obtained from any source, for example, from plasmids such a pBR322, from cloned DNA or RNA or from natural DNA or RNA from any source including bacteria, yeast, viruses and higher organisms such as plants or animals. DNA or RNA may be extracted from blood or tissue material. The template polynucleotide may be obtained by amplification using the polynucleotide chain reaction (PCR, see U.S. Pat. Nos. 4,683,202 and 4,683,195). Alternatively, the polynucleotide may be present in a vector present in a cell and sufficient nucleic acid may be obtained by culturing the cell and extracting the nucleic acid from the cell by methods known in the art.

Any specific nucleic acid sequence can be used to produce the population of hybrids by the present process. It is only necessary that a small population of hybrid sequences of the specific nucleic acid sequence exist or be created prior to the present process.

The initial small population of the specific nucleic acid sequences having mutations may be created by a number of different methods. Mutations may be created by error-prone PCR. Error-prone PCR uses low-fidelity polymerization conditions to introduce a low level of point mutations randomly over a long sequence. Alternatively, mutations can be introduced into the template polynucleotide by oligonucleotide-directed mutagenesis. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be altered by chemical mutagenesis. Chemical mutagens include, for example, sodium bisulfite, nitrous acid, hydroxylamine, hydrazine or formic acid. Other agents which are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light. Generally, plasmid polynucleotides so mutagenized are introduced into *E. coli* and propagated as a pool or library of hybrid plasmids.

Alternatively the small mixed population of specific nucleic acids may be found in nature in that they may consist of different alleles of the same gene or the same gene from different related species (i.e., cognate genes). Alternatively, they may be related DNA sequences found within one species, for example, the immunoglobulin genes.

Once the mixed population of the specific nucleic acid sequences is generated, the polynucleotides can be used directly or inserted into an appropriate cloning vector, using techniques well-known in the art.

The choice of vector depends on the size of the polynucleotide sequence and the host cell to be employed in the methods of this invention. The templates of this invention may be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are preferred where the specific nucleic acid sequence to be mutated is larger because these vectors are able to stably propagate large polynucleotides.

If the mixed population of the specific nucleic acid sequence is cloned into a vector it can be clonally amplified by inserting each vector into a host cell and allowing the host cell to amplify the vector. This is referred to as clonal amplification because while the absolute number of nucleic acid sequences increases, the number of hybrids does not increase. Utility can be readily determined by screening expressed polypeptides.

The DNA shuffling method of this invention can be performed blindly on a pool of unknown sequences. By adding to the reassembly mixture oligonucleotides (with ends that are homologous to the sequences being reassembled) any sequence mixture can be incorporated at any specific position into another sequence mixture. Thus, it is contemplated that mixtures of synthetic oligonucleotides, PCR polynucleotides or even whole genes can be mixed into another sequence library at defined positions. The insertion of one sequence (mixture) is independent from the insertion of a sequence in another part of the template. Thus, the degree of recombination, the homology required, and the diversity of the library can be independently and simultaneously varied along the length of the reassembled DNA.

This approach of mixing two genes may be useful for the humanization of antibodies from murine hybridomas. The approach of mixing two genes or inserting alternative sequences into genes may be useful for any therapeutically used protein, for example, interleukin I, antibodies, tPA and growth hormone. The approach may also be useful in any nucleic acid for example, promoters or introns or 3' untranslated region or 5' untranslated regions of genes to increase expression or alter specificity of expression of proteins. The approach may also be used to mutate ribozymes or aptamers.

Shuffling requires the presence of homologous regions separating regions of diversity. Scaffold-like protein structures may be particularly suitable for shuffling. The conserved scaffold determines the overall folding by self-association, while displaying relatively unrestricted loops that mediate the specific binding. Examples of such scaffolds are the immunoglobulin beta-barrel, and the four-helix bundle which are well-known in the art. This shuffling can be used to create scaffold-like proteins with various combinations of mutated sequences for binding.

In vitro Shuffling

The equivalents of some standard genetic matings may also be performed by shuffling in vitro. For example, a "molecular backcross" can be performed by repeatedly mixing the hybrid's nucleic acid with the wild-type nucleic acid while selecting for the mutations of interest. As in traditional breeding, this approach can be used to combine phenotypes from different sources into a background of choice. It is useful, for example, for the removal of neutral mutations that affect unselected characteristics (i.e. immunogenicity). Thus it can be useful to determine which mutations in a protein are involved in the enhanced biological activity and which are not, an advantage which cannot be achieved by error-prone mutagenesis or cassette mutagenesis methods.

Large, functional genes can be assembled correctly from a mixture of small random polynucleotides. This reaction may be of use for the reassembly of genes from the highly fragmented DNA of fossils. In addition random nucleic acid fragments from fossils may be combined with polynucleotides from similar genes from related species.

It is also contemplated that the method of this invention can be used for the in vitro amplification of a whole genome from a single cell as is needed for a variety of research and diagnostic applications. DNA amplification by PCR is in practice limited to a length of about 40 kb. Amplification of a whole genome such as that of *E. coli* (5, 000 kb) by PCR would require about 250 primers yielding 125 forty kb polynucleotides. This approach is not practical due to the unavailability of sufficient sequence data. On the other hand, random production of polynucleotides of the genome with sexual PCR cycles, followed by gel purification of small polynucleotides will provide a multitude of possible primers. Use of this mix of random small polynucleotides as primers in a PCR reaction alone or with the whole genome as the template should result in an inverse chain reaction with the theoretical endpoint of a single concatamer containing many copies of the genome.

100 fold amplification in the copy number and an average polynucleotide size of greater than 50 kb may be obtained when only random polynucleotides are used. It is thought that the larger concatamer is generated by overlap of many smaller polynucleotides. The quality of specific PCR products obtained using synthetic primers will be indistinguishable from the product obtained from unamplified DNA. It is expected that this approach will be useful for the mapping of genomes.

The polynucleotide to be shuffled can be produced as random or non-random polynucleotides, at the discretion of the practitioner. Moreover, this invention provides a method of shuffling that is applicable to a wide range of polynucleotide sizes and types, including the step of generating polynucleotide monomers to be used as building blocks in the reassembly of a larger polynucleotide. For example, the building blocks can be fragments of genes or they can be comprised of entire genes or gene pathways, or any combination thereof.

In vivo Shuffling

In an embodiment of in vivo shuffling, the mixed population of the specific nucleic acid sequence is introduced into bacterial or eukaryotic cells under conditions such that at least two different nucleic acid sequences are present in each host cell. The polynucleotides can be introduced into the host cells by a variety of different methods. The host cells can be transformed with the smaller polynucleotides using methods known in the art, for example treatment with calcium chloride. If the polynucleotides are inserted into a phage genome, the host cell can be transfected with the recombinant phage genome having the specific nucleic acid sequences. Alternatively, the nucleic acid sequences can be introduced into the host cell using electroporation, transfection, lipofection, biolistics, conjugation, and the like.

In general, in this embodiment, the specific nucleic acids sequences will be present in vectors which are capable of stably replicating the sequence in the host cell. In addition, it is contemplated that the vectors will encode a marker gene such that host cells having the vector can be selected. This ensures that the mutated specific nucleic acid sequence can be recovered after introduction into the host cell. However, it is contemplated that the entire mixed population of the specific nucleic acid sequences need not be present on a vector sequence. Rather only a sufficient number of sequences need be cloned into vectors to ensure that after introduction of the polynucleotides into the host cells each host cell contains one vector having at least one specific nucleic acid sequence present therein. It is also contemplated that rather than having a subset of the population of the specific nucleic acids sequences cloned into vectors, this subset may be already stably integrated into the host cell.

It has been found that when two polynucleotides which have regions of identity are inserted into the host cells homologous recombination occurs between the two polynucleotides. Such recombination between the two mutated specific nucleic acid sequences will result in the production of double or triple hybrids in some situations.

It has also been found that the frequency of recombination is increased if some of the mutated specific nucleic acid sequences are present on linear nucleic acid molecules. Therefore, in a preferred embodiment, some of the specific nucleic acid sequences are present on linear polynucleotides.

After transformation, the host cell transformants are placed under selection to identify those host cell transformants which contain mutated specific nucleic acid sequences having the qualities desired. For example, if increased resistance to a particular drug is desired then the transformed host cells may be subjected to increased concentrations of the particular drug and those transformants producing mutated proteins able to confer increased drug resistance will be selected. If the enhanced ability of a particular protein to bind to a receptor is desired, then expression of the protein can be induced from the transformants and the resulting protein assayed in a ligand binding assay by methods known in the art to identify that subset of the mutated population which shows enhanced binding to the ligand. Alternatively, the protein can be expressed in another system to ensure proper processing.

Once a subset of the first recombined specific nucleic acid sequences (daughter sequences) having the desired characteristics are identified, they are then subject to a second round of recombination.

In the second cycle of recombination, the recombined specific nucleic acid sequences may be mixed with the original mutated specific nucleic acid sequences (parent sequences) and the cycle repeated as described above. In this way a set of second recombined specific nucleic acids sequences can be identified which have enhanced characteristics or encode for proteins having enhanced properties. This cycle can be repeated a number of times as desired.

It is also contemplated that in the second or subsequent recombination cycle, a backcross can be performed. A molecular backcross can be performed by mixing the desired specific nucleic acid sequences with a large number of the wild-type sequence, such that at least one wild-type nucleic acid sequence and a mutated nucleic acid sequence are present in the same host cell after transformation. Recombination with the wild-type specific nucleic acid sequence will eliminate those neutral mutations that may affect unselected characteristics such as immunogenicity but not the selected characteristics.

In another embodiment of this invention, it is contemplated that during the first round a subset of the specific nucleic acid sequences can be generated as smaller polynucleotides by slowing or halting their PCR amplification prior to introduction into the host cell. The size of the polynucleotides must be large enough to contain some regions of identity with the other sequences so as to homologously recombine with the other sequences. The size of the polynucleotides will range from 0.03 kb to 100 kb more preferably from 0.2 kb to 10 kb. It is also contemplated that in subsequent rounds, all of the specific nucleic acid sequences other than the sequences selected from the previous round may be utilized to generate PCR polynucleotides prior to introduction into the host cells.

The shorter polynucleotide sequences can be single-stranded or double-stranded. If the sequences were originally single-stranded and have become double-stranded they can be denatured with heat, chemicals or enzymes prior to insertion into the host cell. The reaction conditions suitable for separating the strands of nucleic acid are well known in the art.

The steps of this process can be repeated indefinitely, being limited only by the number of possible hybrids which can be achieved. After a certain number of cycles, all possible hybrids will have been achieved and further cycles are redundant.

In an embodiment the same mutated template nucleic acid is repeatedly recombined and the resulting recombinants selected for the desired characteristic.

Therefore, the initial pool or population of mutated template nucleic acid is cloned into a vector capable of replicating in a bacteria such as *E. coli*. The particular vector is not essential, so long as it is capable of autonomous replication in *E. coli*. In a preferred embodiment, the vector is designed to allow the expression and production of any protein encoded by the mutated specific nucleic acid linked to the vector. It is also preferred that the vector contain a gene encoding for a selectable marker.

The population of vectors containing the pool of mutated nucleic acid sequences is introduced into the *E. coli* host cells. The vector nucleic acid sequences may be introduced by transformation, transfection or infection in the case of phage. The concentration of vectors used to transform the bacteria is such that a number of vectors is introduced into each cell. Once present in the cell, the efficiency of homologous recombination is such that homologous recombination occurs between the various vectors. This results in the generation of hybrids (daughters) having a combination of mutations which differ from the original parent mutated sequences.

The host cells are then clonally replicated and selected for the marker gene present on the vector. Only those cells having a plasmid will grow under the selection.

The host cells which contain a vector are then tested for the presence of favorable mutations. Such testing may consist of placing the cells under selective pressure, for example, if the gene to be selected is an improved drug resistance gene. If the vector allows expression of the protein encoded by the mutated nucleic acid sequence, then such selection may include allowing expression of the protein so encoded, isolation of the protein and testing of the protein to determine whether, for example, it binds with increased efficiency to the ligand of interest.

Once a particular daughter mutated nucleic acid sequence has been identified which confers the desired characteristics, the nucleic acid is isolated either already linked to the vector or separated from the vector. This nucleic acid is then mixed with the first or parent population of nucleic acids and the cycle is repeated.

It has been shown that by this method nucleic acid sequences having enhanced desired properties can be selected.

In an alternate embodiment, the first generation of hybrids are retained in the cells and the parental mutated sequences are added again to the cells. Accordingly, the first cycle of Embodiment I is conducted as described above. However, after the daughter nucleic acid sequences are identified, the host cells containing these sequences are retained.

The parent mutated specific nucleic acid population, either as polynucleotides or cloned into the same vector is introduced into the host cells already containing the daughter nucleic acids. Recombination is allowed to occur in the cells and the next generation of recombinants, or granddaughters are selected by the methods described above.

This cycle can be repeated a number of times until the nucleic acid or peptide having the desired characteristics is obtained. It is contemplated that in subsequent cycles, the population of mutated sequences which are added to the preferred hybrids may come from the parental hybrids or any subsequent generation.

In an alternative embodiment, the invention provides a method of conducting a "molecular" backcross of the obtained recombinant specific nucleic acid in order to eliminate any neutral mutations. Neutral mutations are those mutations which do not confer onto the nucleic acid or peptide the desired properties. Such mutations may however confer on the nucleic acid or peptide undesirable characteristics. Accordingly, it is desirable to eliminate such neutral mutations. The method of this invention provide a means of doing so.

In this embodiment, after the hybrid nucleic acid, having the desired characteristics, is obtained by the methods of the embodiments, the nucleic acid, the vector having the nucleic acid or the host cell containing the vector and nucleic acid is isolated.

The nucleic acid or vector is then introduced into the host cell with a large excess of the wild-type nucleic acid. The nucleic acid of the hybrid and the nucleic acid of the wild-type sequence are allowed to recombine. The resulting recombinants are placed under the same selection as the hybrid nucleic acid. Only those recombinants which retained the desired characteristics will be selected. Any silent mutations which do not provide the desired characteristics will be lost through recombination with the wild-type DNA. This cycle can be repeated a number of times until all of the silent mutations are eliminated.

Thus the methods of this invention can be used in a molecular backcross to eliminate unnecessary or silent mutations.

3.2.2. Exonuclease-Mediated Reassembly

In a particular embodiment, this invention provides for a method for shuffling, assembling, reassembling, recombining, &/or concatenating at least two polynucleotides to form a progeny polynucleotide (e.g. a chimeric progeny polynucleotide that can be expressed to produce a polypeptide or a gene pathway). In a particular embodiment, a double stranded polynucleotide end (e.g. two single stranded sequences hybridized to each other as hybridization partners) is treated with an exonuclease to liberate nucleotides from one of the two strands, leaving the remaining strand free of its original partner so that, if desired, the remaining strand may be used to achieve hybridization to another partner.

In a particular aspect, a double stranded polynucleotide end (that may be part of—or connected to—a polynucleotide or a nonpolynucleotide sequence) is subjected to a source of exonuclease activity. Serviceable sources of exonuclease activity may be an enzyme with 3' exonuclease activity, an enzyme with 5' exonuclease activity, an enzyme with both 3' exonuclease activity and 5' exonuclease activity, and any combination thereof. An exonuclease can be used to liberate nucleotides from one or both ends of a linear double stranded polynucleotide, and from one to all ends of a branched polynucleotide having more than two ends. The mechanism of action of this liberation is believed to be comprised of an enzymatically-catalyzed hydrolysis of terminal nucleotides, and can be allowed to proceed in a time-dependent fashion, allowing experimental control of the progression of the enzymatic process.

By contrast, a non-enzymatic step may be used to shuffle, assemble, reassemble, recombine, and/or concatenate polynucleotide building blocks that is comprised of subjecting a working sample to denaturing (or "melting") conditions (for example, by changing temperature, pH, and /or salinity conditions) so as to melt a working set of double stranded polynucleotides into single polynucleotide strands. For shuffling, it is desirable that the single polynucleotide strands participate to some extent in annealment with different hybridization partners (i.e. and not merely revert to exclusive reannealment between what were former partners before the denaturation step). The presence of the former hybridization partners in the reaction vessel, however, does not preclude, and may sometimes even favor, reannealment of a single stranded polynucleotide with its former partner, to recreate an original double stranded polynucleotide.

In contrast to this non-enzymatic shuffling step comprised of subjecting double stranded polynucleotide building blocks to denaturation, followed by annealment, the instant invention further provides an exonuclease-based approach requiring no denaturation—rather, the avoidance of denaturing conditions and the maintenance of double stranded polynucleotide substrates in annealed (i.e. non-denatured) state are necessary conditions for the action of exonucleases (e.g., exonuclease III and red alpha gene product). Additionally in contrast, the generation of single stranded polynucleotide sequences capable of hybridizing to other single stranded polynucleotide sequences is the result of covalent cleavage—and hence sequence destruction—in one of the hybridization partners. For example, an exonuclease III enzyme may be used to enzymatically liberate 3' terminal nucleotides in one hybridization strand (to achieve covalent hydrolysis in that polynucleotide strand); and this favors hybridization of the remaining single strand to a new partner (since its former partner was subjected to covalent cleavage).

By way of further illustration, a specific exonuclease, namely exonuclease III is provided herein as an example of a 3' exonuclease; however, other exonucleases may also be used, including enzymes with 5' exonuclease activity and enzymes with 3' exonuclease activity, and including enzymes not yet discovered and enzymes not yet developed. It is particularly appreciated that enzymes can be discovered, optimized (e.g. engineered by directed evolution), or both discovered and optimized specifically for the instantly disclosed approach that have more optimal rates &/or more highly specific activities &/or greater lack of unwanted activities. In fact it is expected that the instant invention may encourage the discovery &/or development of such designer enzymes. In sum, this invention may be practiced with a variety of currently available exonuclease enzymes, as well as enzymes not yet discovered and enzymes not yet developed.

The exonuclease action of exonuclease III requires a working double stranded polynucleotide end that is either blunt or has a 5' overhang, and the exonuclease action is comprised of enzymatically liberating 3' terminal nucleotides, leaving a single stranded 5' end that becomes longer and longer as the exonuclease action proceeds (see FIG. 1). Any 5' overhangs produced by this approach may be used to hybridize to another single stranded polynucleotide sequence (which may also be a single stranded polynucleotide or a terminal overhang of a partially double stranded polynucleotide) that shares enough homology to allow hybridization. The ability of these exonuclease III-generated single stranded sequences (e.g. in 5' overhangs) to hybridize to other single stranded sequences allows two or more polynucleotides to be shuffled, assembled, reassembled, &/or concatenated.

Furthermore, it is appreciated that one can protect the end of a double stranded polynucleotide or render it susceptible to a desired enzymatic action of a serviceable exonuclease as necessary. For example, a double stranded polynucleotide end having a 3' overhang is not susceptible to the exonuclease action of exonuclease III. However, it may be rendered susceptible to the exonuclease action of exonuclease III by a variety of means; for example, it may be blunted by treatment with a polymerase, cleaved to provide a blunt end or a 5' overhang, joined (ligated or hybridized) to another double stranded polynucleotide to provide a blunt end or a 5' overhang, hybridized to a single stranded polynucleotide to provide a blunt end or a 5' overhang, or modified by any of a variety of means).

According to one aspect, an exonuclease may be allowed to act on one or on both ends of a linear double stranded polynucleotide and proceed to completion, to near completion, or to partial completion. When the exonuclease action is allowed to go to completion, the result will be that the length of each 5' overhang will extend far towards the middle region of the polynucleotide in the direction of what might be considered a "rendezvous point" (which may be somewhere near the polynucleotide midpoint). Ultimately, this results in the production of single stranded polynucleotides (that can become dissociated) that are each about half the length of the original double stranded polynucleotide (see FIG. 1). Alternatively, an exonuclease-mediated reaction can be terminated before proceeding to completion.

Thus this exonuclease-mediated approach is serviceable for shuffling, assembling &/or reassembling, recombining, and concatenating polynucleotide building blocks, which polynucleotide building blocks can be up to ten bases long or tens of bases long or hundreds of bases long or thousands of bases long or tens of thousands of bases long or hundreds of thousands of bases long or millions of bases long or even longer.

This exonuclease-mediated approach is based on the action of double stranded DNA specific exodeoxyribonuclease activity of *E. coli* exonuclease III. Substrates for exonuclease III may be generated by subjecting a double stranded polynucleotide to fragmentation. Fragmentation may be achieved by mechanical means (e.g., shearing, sonication, etc.), by enzymatic means (e.g. using restriction enzymes), and by any combination thereof. Fragments of a larger polynucleotide may also be generated by polymerase-mediated synthesis.

Exonuclease III is a 28K monomeric enzyme, product of the xthA gene of *E. coli* with four known activities: exodeoxyribonuclease (alternatively referred to as exonuclease herein), RNaseH, DNA-3'-phosphatase, and AP endonuclease. The exodeoxyribonuclease activity is specific for double stranded DNA. The mechanism of action is thought to involve enzymatic hydrolysis of DNA from a 3' end progressively towards a 5' direction, with formation of nucleoside 5'-phosphates and a residual single strand. The enzyme does not display efficient hydrolysis of single stranded DNA, single-stranded RNA, or double-stranded RNA; however it degrades RNA in an DNA-RNA hybrid releasing nucleoside 5'-phosphates. The enzyme also releases inorganic phosphate specifically from 3' phosphomonoester groups on DNA, but not from RNA or short oligonucleotides. Removal of these groups converts the terminus into a primer for DNA polymerase action.

Additional examples of enzymes with exonuclease activity include red-alpha and venom phosphodiesterases. Red alpha (red□gene product (also referred to as lambda exonuclease) is of bacteriophage origin. The red gene is transcribed from the leftward promoter and its product is involved (24 kD) in recombination. Red alpha gene product acts processively from 5'-phosphorylated termini to liberate mononucleotides from duplex DNA (Takahashi & Kobayashi, 1990). Venom phosphodiesterases (Laskowski, 1980) is capable of rapidly opening supercoiled DNA.

3.2.3. Non-Stochastic Ligation Reassembly

In one aspect, the present invention provides a non-stochastic method termed synthetic ligation reassembly (SLR), that is somewhat related to stochastic shuffling, save that the nucleic acid building blocks are not shuffled or concatenated or chimerized randomly, but rather are assembled non-stochastically.

A particularly glaring difference is that the instant SLR method does not depend on the presence of a high level of homology between polynucleotides to be shuffled. In contrast, prior methods, particularly prior stochastic shuffling methods require that presence of a high level of homology, particularly at coupling sites, between polynucleotides to be shuffled. Accordingly these prior methods favor the regeneration of the original progenitor molecules, and are suboptimal for generating large numbers of novel progeny chimeras, particularly full-length progenies. The instant invention, on the other hand, can be used to non-stochastically generate libraries (or sets) of progeny molecules comprised of over $10^{100}$ different chimeras. Conceivably, SLR can even be used to generate libraries comprised of over $10^{1000}$ different progeny chimeras with (no upper limit in sight).

Thus, in one aspect, the present invention provides a method, which method is non-stochastic, of producing a set of finalized chimeric nucleic acid molecules having an overall assembly order that is chosen by design, which method is comprised of the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). FIG. 4, Panel C illustrates an exemplary assembly process comprised of 2 sequential steps to achieve a designed (non-stochastic) overall assembly order for five nucleic acid building blocks. In a preferred embodiment of this invention, the annealed building pieces are treated with an enzyme, such as a ligase (e.g. T4 DNA ligase), achieve covalent bonding of the building pieces.

In a preferred embodiment, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, this invention provides for the chimerization of a family of related genes and their encoded family of related products. In a particular exemplification, the encoded products are enzymes. As a representative list of families of enzymes which may be mutagenized in accordance with the aspects of the present invention, there may be mentioned, the following enzymes and their functions:

1 Lipase/Esterase
   a. Enantioselective hydrolysis of esters (lipids)/thioesters
      1) Resolution of racemic mixtures
      2) Synthesis of optically active acids or alcohols from meso-diesters
   b. Selective syntheses
      1) Regiospecific hydrolysis of carbohydrate esters
      2) Selective hydrolysis of cyclic secondary alcohols
   c. Synthesis of optically active esters, lactones, acids, alcohols
      1) Transesterification of activated/nonactivated esters
      2) Interesterification
      3) Optically active lactones from hydroxyesters
      4) Regio- and enantioselective ring opening of anhydrides
   d. Detergents
   e. Fat/Oil conversion
   f. Cheese ripening 2 Protease
   a. Ester/amide synthesis
   b. Peptide synthesis
   c. Resolution of racemic mixtures of amino acid esters
   d. Synthesis of non-natural amino acids
   e. Detergents/protein hydrolysis 3 Glycosidase/Glycosyl Transferase
   a. Sugar/polymer synthesis
   b. Cleavage of glycosidic linkages to form mono, di-and oligosaccharides
   c. Synthesis of complex oligosaccharides
   d. Glycoside synthesis using UDP-galactosyl transferase
   e. Transglycosylation of disaccharides, glycosyl fluorides, aryl galactosides
   f. Glycosyl transfer in oligosaccharide synthesis
   g. Diastereoselective cleavage of -glucosylsulfoxides
   h. Asymmetric glycosylations
   i. Food processing
   j. Paper processing 4 Phosphatase/Kinase
   a. Synthesis/hydrolysis of phosphate esters
      1) Regio-, enantioselective phosphorylation
      2) Introduction of phosphate esters
      3) Synthesize phospholipid precursors
      4) Controlled polynucleotide synthesis
   b. Activate biological molecule
   c. Selective phosphate bond formation without protecting groups Mono/Dioxygenase
   a. Direct oxyfunctionalization of unactivated organic substrates
   b. Hydroxylation of alkane, aromatics, steroids
   c. Epoxidation of alkenes
   d. Enantioselective sulphoxidation
   e. Regio- and stereoselective Bayer-Villiger oxidations Haloperoxidase
   a. Oxidative addition of halide ion to nucleophilic sites
   b. Addition of hypohalous acids to olefinic bonds
   c. Ring cleavage of cyclopropanes
   d. Activated aromatic substrates converted to ortho and para derivatives
   e. 1.3 diketones converted to 2-halo-derivatives
   f. Heteroatom oxidation of sulfur and nitrogen containing substrates
   g. Oxidation of enol acetates, alkynes and activated aromatic rings Lignin Peroxidase/Diarylpropane Peroxidase
   a. Oxidative cleavage of C-C bonds
   b. Oxidation of benzylic alcohols to aldehydes
   c. Hydroxylation of benzylic carbons
   d. Phenol dimerization
   e. Hydroxylation of double bonds to form diols
   f. Cleavage of lignin aldehydes Epoxide Hydrolase
   a. Synthesis of enantiomerically pure bioactive compounds
   b. Regio- and enantioselective hydrolysis of epoxide
   c. Aromatic and olefinic epoxidation by monooxygenases to form epoxides
   d. Resolution of racemic epoxides
   e. Hydrolysis of steroid epoxides Nitrile Hydratase/Nitrilase
   a. Hydrolysis of aliphatic nitriles to carboxamides
   b. Hydrolysis of aromatic, heterocyclic, unsaturated aliphatic nitrites to corresponding acids
   c. Hydrolysis of acrylonitrile
   d. Production of aromatic and carboxamides, carboxylic acids (nicotinamide, picolinamide, isonicotinamide)
   e. Regioselective hydrolysis of acrylic dinitrile
   f. -amino acids from -hydroxynitriles 10 Transaminase
   a. Transfer of amino groups into oxo-acids 11 Amidase/Acylase
   a. Hydrolysis of amides, amidines, and other C—N bonds
   b. Non-natural amino acid resolution and synthesis These exemplifications, while illustrating certain specific aspects of the invention, do not portray the limitations or circumscribe the scope of the disclosed invention.

Thus according to one aspect of this invention, the sequences of a plurality of progenitor nucleic acid templates are aligned in order to select one or more demarcation points, which demarcation points can be located at an area of homology, and are comprised of one or more nucleotides, and which demarcation points are shared by at least two of the progenitor templates. The demarcation points can be used to delineate the boundaries of nucleic acid building blocks to be generated. Thus, the demarcation points identified and selected in the progenitor molecules serve as potential chimerization points in the assembly of the progeny molecules.

Preferably a serviceable demarcation point is an area of homology (comprised of at least one homologous nucleotide base) shared by at least two progenitor templates. More preferably a serviceable demarcation point is an area of homology that is shared by at least half of the progenitor templates. More preferably still a serviceable demarcation point is an area of homology that is shared by at least two thirds of the progenitor templates. Even more preferably a serviceable demarcation points is an area of homology that is shared by at least three fourths of the progenitor templates. Even more preferably still a serviceable demarcation points is an area of homology that is shared by at almost all of the progenitor templates. Even more preferably still a serviceable demarcation point is an area of homology that is shared by all of the progenitor templates.

The process of designing nucleic acid building blocks and of designing the mutually compatible ligatable ends of the nucleic acid building blocks to be assembled is illustrated in FIGS. 6 and 7. As shown, the alignment of a set of progenitor templates reveals several naturally occurring demarcation points, and the identification of demarcation points shared by these templates helps to non-stochastically determine the building blocks to be generated and used for the generation of the progeny chimeric molecules.

In a preferred embodiment, this invention provides that the ligation reassembly process is performed exhaustively in order to generate an exhaustive library. In other words, all possible ordered combinations of the nucleic acid building blocks are represented in the set of finalized chimeric nucleic acid molecules. At the same time, in a particularly preferred embodiment, the assembly order (i.e. the order of assembly of each building block in the 5' to 3' sequence of each finalized chimeric nucleic acid) in each combination is by design (or non-stochastic). Because of the non-stochastic nature of this invention, the possibility of unwanted side products is greatly reduced.

In another preferred embodiment, this invention provides that the ligation reassembly process is performed systematically, for example in order to generate a systematically compartmentalized library, with compartments that can be screened systematically, e.g. one by one. In other words this invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. In a particularly preferred embodiment of this invention, such a generated library is comprised of preferably greater than $10^3$ different progeny molecular species, more preferably greater than $10^5$ different progeny molecular species, more preferably still greater than $10^{10}$ different progeny molecular species, more preferably still greater than $10^{15}$ different progeny molecular species, more preferably still greater than $10^{20}$ different progeny molecular species, more preferably still greater than $10^{30}$ different progeny molecular species, more preferably still greater than $10^{40}$ different progeny molecular species, more preferably still greater than $10^{50}$ different progeny molecular species, more preferably still greater than $10^{60}$ different progeny molecular species, more preferably still greater than $10^{70}$ different progeny molecular species, more preferably still greater than $10^{80}$ different progeny molecular species, more preferably still greater than $10^{100}$ different progeny molecular species, more preferably still greater than $10^{110}$ different progeny molecular species, more preferably still greater than $10^{120}$ different progeny molecular species, more preferably still greater than $10^{130}$ different progeny molecular species, more preferably still greater than $10^{140}$ different progeny molecular species, more preferably still greater than $10^{150}$ different progeny molecular species, more preferably still greater than $10^{175}$ different progeny molecular species, more preferably still greater than $10^{200}$ different progeny molecular species, more preferably still greater than $10^{300}$ different progeny molecular species, more preferably still greater than $10^{400}$ different progeny molecular species, more preferably still greater than $10^{500}$ different progeny molecular species, and even more preferably still greater than $10^{1000}$ different progeny molecular species.

In one aspect, a set of finalized chimeric nucleic acid molecules, produced as described is comprised of a polynucleotide encoding a polypeptide. According to one preferred embodiment, this polynucleotide is a gene, which may be a man-made gene. According to another preferred embodiment, this polynucleotide is a gene pathway, which may be a man-made gene pathway. This invention provides that one or more man-made genes generated by this invention may be incorporated into a man-made gene pathway, such as a pathway operable in a eukaryotic organism (including a plant).

It is appreciated that the power of this invention is exceptional, as there is much freedom of choice and control regarding the selection of demarcation points, the size and number of the nucleic acid building blocks, and the size and design of the couplings. It is appreciated, furthermore, that the requirement for intermolecular homology is highly relaxed for the operability of this invention. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template. Alternatively, a codon can be altered such that the coding for an originally amino acid is altered. This invention provides that such substitutions can be introduced into the nucleic acid building block in order to increase the incidence of intermolecularly homologous demarcation points and thus to allow an increased number of couplings to be achieved among the building blocks, which in turn allows a greater number of progeny chimeric molecules to be generated.

In another exemplifaction, the synthetic nature of the step in which the building blocks are generated allows the design and introduction of nucleotides (e.g. one or more nucleotides, which may be, for example, codons or introns or regulatory sequences) that can later be optionally removed in an in vitro process (e.g. by mutageneis) or in an in vivo process (e.g. by utilizing the gene splicing ability of a host organism). It is appreciated that in many instances the introduction of these nucleotides may also be desirable for many other reasons in addition to the potential benefit of creating a serviceable demarcation point.

Thus, according to another embodiment, this invention provides that a nucleic acid building block can be used to introduce an intron. Thus, this invention provides that functional introns may be introduced into a man-made gene of this invention. This invention also provides that functional introns may be introduced into a man-made gene pathway of this invention. Accordingly, this invention provides for the generation of a chimeric polynucleotide that is a man-made gene containing one (or more) artificially introduced intron(s).

Accordingly, this invention also provides for the generation of a chimeric polynucleotide that is a man-made gene pathway containing one (or more) artificially introduced intron(s). Preferably, the artificially introduced intron(s) are functional in one or more host cells for gene splicing much in the way that naturally-occurring introns serve functionally in gene splicing. This invention provides a process of producing man-made intron-containing polynucleotides to be introduced into host organisms for recombination and/or splicing.

The ability to achieve chimerizations, using couplings as described herein, in areas of little or no homology among the progenitor molecules, is particularly useful, and in fact critical, for the assembly of novel gene pathways. This invention thus provides for the generation of novel man-made gene pathways using synthetic ligation reassembly. In a particular aspect, this is achieved by the introduction of regulatory sequences, such as promoters, that are operable in an intended host, to confer operability to a novel gene pathway when it is introduced into the intended host. In a particular exemplification, this invention provides for the generation of novel man-made gene pathways that is operable in a plurality of intended hosts (e.g. in a microbial organism as well as in a plant cell). This can be achieved, for example, by the introduction of a plurality of regulatory sequences, comprised of a regulatory sequence that is operable in a first intended host and a regulatory sequence that is operable in a second intended host. A similar process can be performed to achieve operability of a gene pathway in a third intended host species, etc. The number of intended host species can be each integer from 1 to 10 or alternatively over 10. Alternatively, for example, operability of a gene pathway in a plurality of intended hosts can be achieved by the introduction of a regulatory sequence having intrinsic operability in a plurality of intended hosts.

Thus, according to a particular embodiment, this invention provides that a nucleic acid building block can be used to introduce a regulatory sequence, particularly a regulatory sequence for gene expression. Preferred regulatory sequences include, but are not limited to, those that are man-made, and those found in archeal, bacterial, eukaryotic (including mitochondrial), viral, and prionic or prion-like organisms. Preferred regulatory sequences include but are not limited to, promoters, operators, and activator binding sites. Thus, this invention provides that functional regulatory sequences may be introduced into a man-made gene of this invention. This invention also provides that functional regulatory sequences may be introduced into a man-made gene pathway of this invention.

Accordingly, this invention provides for the generation of a chimeric polynucleotide that is a man-made gene containing one (or more) artificially introduced regulatory sequence(s). Accordingly, this invention also provides for the generation of a chimeric polynucleotide that is a man-made gene pathway containing one (or more) artificially introduced regulatory sequence(s). Preferably, an artificially introduced regulatory sequence(s) is operatively linked to one or more genes in the man-made polynucleotide, and are functional in one or more host cells.

Preferred bacterial promoters that are serviceable for this invention include lacI, lacZ, T3, T7, gpt, lambda $P_R$, $P_L$ and trp. Serviceable eukaryotic promoters include CMV immediate early, HSV thymidine kinase, early and late SV40, LTRs from retrovirus, and mouse metallothionein-I. Particular plant regulatory sequences include promoters active in directing transcription in plants, either constitutively or stage and/or tissue specific, depending on the use of the plant or parts thereof. These promoters include, but are not limited to promoters showing constitutive expression, such as the 35S promoter of Cauliflower Mosaic Virus (CaMV) (Guilley et al., 1982), those for leaf-specific expression, such as the promoter of the ribulose bisphosphate carboxylase small subunit gene (Coruzzi et al., 1984), those for root-specific expression, such as the promoter from the glutamin synthase gene (Tingey et al., 1987), those for seed-specific expression, such as the cruciferin A promoter from *Brassica napus* (Ryan et al., 1989), those for tuber-specific expression, such as the class-I patatin promoter from potato (Rocha-Sasa et al., 1989; Wenzler et al., 1989) or those for fruit-specific expression, such as the polygalacturonase (PG) promoter from tomato (Bird et al., 1988).

Other regulatory sequences that are preferred for this invention include terminator sequences and polyadenylation signals and any such sequence functioning as such in plants, the choice of which is within the level of the skilled artisan. An example of such sequences is the 3' flanking region of the nopaline synthase (nos) gene of *Agrobacterium tumefaciens* (Bevan, 1984). The regulatory sequences may also include enhancer sequences, such as found in the 35S promoter of CaMV, and mRNA stabilizing sequences such as the leader sequence of Alfalfa Mosaic Cirus (AlMV) RNA4 (Brederode et al., 1980) or any other sequences functioning in a like manner.

Man-made genes produced using this invention can also serve as a substrate for recombination with another nucleic acid. Likewise, a man-made gene pathway produced using this invention can also serve as a substrate for recombination with another nucleic acid. In a preferred instance, the recombination is facilitated by, or occurs at, areas of homology between the man-made intron-containing gene and a nucleic acid with serves as a recombination partner. In a particularly preferred instance, the recombination partner may also be a nucleic acid generated by this invention, including a man-made gene or a man-made gene pathway. Recombination may be facilitated by or may occur at areas of homology that exist at the one (or more) artificially introduced intron(s) in the man-made gene.

The synthetic ligation reassembly method of this invention utilizes a plurality of nucleic acid building blocks, each of which preferably has two ligatable ends. The two ligatable ends on each nucleic acid building block may be two blunt ends (i.e. each having an overhang of zero nucleotides), or preferably one blunt end and one overhang, or more preferably still two overhangs.

A serviceable overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

According to one preferred embodiment, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large depending on the choice of the experimenter. Preferred sizes for building block range from 1 base pair (not including any overhangs) to 100,000 base pairs (not including any overhangs). Other preferred size ranges are also provided, which have lower limits of from 1 bp to 10,000 bp (including every integer value in between), and upper limits of from 2 bp to 100,000 bp (including every integer value in between).

It is appreciated that current methods of polymerase-based amplification can be used to generate double-stranded nucleic acids of up to thousands of base pairs, if not tens of thousands of base pairs, in length with high fidelity. Chemical synthesis (e.g. phosphoramidite-based) can be used to generate nucleic acids of up to hundreds of nucleotides in length with high fidelity; however, these can be assembled, e.g. using overhangs or sticky ends, to form double-stranded nucleic acids of up to thousands of base pairs, if not tens of thousands of base pairs, in length if so desired.

A combination of methods (e.g. phosphoramidite-based chemical synthesis and PCR) can also be used according to this invention. Thus, nucleic acid building block made by different methods can also be used in combination to generate a progeny molecule of this invention.

The use of chemical synthesis to generate nucleic acid building blocks is particularly preferred in this invention & is advantageous for other reasons as well, including procedural safety and ease. No cloning or harvesting or actual handling of any biological samples is required. The design of the nucleic acid building blocks can be accomplished on paper. Accordingly, this invention teaches an advance in procedural safety in recombinant technologies.

Nonetheless, according to one preferred embodiment, a double-stranded nucleic acid building block according to this invention may also be generated by polymerase-based amplification of a polynucleotide template. In a non-limiting exemplification, as illustrated in FIG. 2, a first polymerase-based amplification reaction using a first set of primers, $F_2$ and $R_1$, is used to generate a blunt-ended product (labeled Reaction 1, Product 1), which is essentially identical to Product A. A second polymerase-based amplification reaction using a second set of primers, $F_1$, and $R_2$, is used to generate a blunt-ended product (labeled Reaction 2, Product 2), which is essentially identical to Product B. These two products are mixed and allowed to melt and anneal, generating potentially useful double-stranded nucleic acid building blocks with two overhangs. In the example of FIG. 2, the product with the 3' overhangs (Product C) is selected by nuclease-based degradation of the other 3 products using a 3' acting exonuclease, such as exonuclease III. It is appreciated that a 5' acting exonuclease (e.g. red alpha) may be also be used, for example to select Product D instead. It is also appreciated that other selection means can also be used, including hybridization-based means, and that these means can incorporate a further means, such as a magnetic bead-based means, to facilitate separation of the desired product.

Many other methods exist by which a double-stranded nucleic acid building block can be generated that is serviceable for this invention; and these are known in the art and can be readily performed by the skilled artisan.

According to particularly preferred embodiment, a double-stranded nucleic acid building block that is serviceable for this invention is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another embodiment, the two strands of a double-stranded nucleic acid building block are complementary at fewer than every nucleotide apart from any that form an overhang. Thus, according to this embodiment, a double-stranded nucleic acid building block can be used to introduce codon degeneracy. Preferably the codon degeneracy is introduced using the site-saturation mutagenesis described herein, using one or more N,N,G/T cassettes or alternatively using one or more N,N,N cassettes.

Contained within an exemplary experimental design for achieving an ordered assembly according to this invention are:

1) The design of specific nucleic acid building blocks.
2) The design of specific ligatable ends on each nucleic acid building block.
3) The design of a particular order of assembly of the nucleic acid building blocks.

An overhang may be a 3' overhang or a 5' overhang. An overhang may also have a terminal phosphate group or alternatively may be devoid of a terminal phosphate group (having, e.g., a hydroxyl group instead). An overhang may be comprised of any number of nucleotides. Preferably an overhang is comprised of 0 nucleotides (as in a blunt end) to 10,000 nucleotides. Thus, a wide range of overhang sizes may be serviceable. Accordingly, the lower limit may be each integer from 1–200 and the upper limit may be each integer from 2–10,000. According to a particular exemplification, an overhang may consist of anywhere from 1 nucleotide to 200 nucleotides (including every integer value in between).

The final chimeric nucleic acid molecule may be generated by sequentially assembling 2 or more building blocks at a time until all the designated building blocks have been assembled. A working sample may optionally be subjected to a process for size selection or purification or other selection or enrichment process between the performance of two assembly steps. Alternatively, the final chimeric nucleic acid molecule may be generated by assembling all the designated building blocks at once in one step.

Utility

The in vivo recombination method of this invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 3' untranslated regions or 5' untranslated regions of genes. Thus this approach may be used to generate genes having increased rates of expression. This approach may also be useful in the study of repetitive DNA sequences. Finally, this approach may be useful to mutate ribozymes or aptamers.

Scaffold-like regions separating regions of diversity in proteins may be particularly suitable for the methods of this invention. The conserved scaffold determines the overall folding by self-association, while displaying relatively unrestricted loops that mediate the specific binding. Examples of such scaffolds are the immunoglobulin beta barrel, and the four-helix bundle. The methods of this invention can be used to create scaffold-like proteins with various combinations of mutated sequences for binding.

The equivalents of some standard genetic matings may also be performed by the methods of this invention. For example, a "molecular" backcross can be performed by repeated mixing of the hybrid's nucleic acid with the wild-type nucleic acid while selecting for the mutations of interest. As in traditional breeding, this approach can be used to combine phenotypes from different sources into a background of choice. It is useful, for example, for the removal of neutral mutations that affect unselected characteristics (i.e. immunogenicity). Thus it can be useful to determine which mutations in a protein are involved in the enhanced biological activity and which are not.

3.2.4. End-Selection

This invention provides a method for selecting a subset of polynucleotides from a starting set of polynucleotides, which method is based on the ability to discriminate one or more selectable features (or selection markers) present anywhere in a working polynucleotide, so as to allow one to perform selection for (positive selection) &/or against (negative selection) each selectable polynucleotide. In a preferred aspect, a method is provided termed end-selection, which method is based on the use of a selection marker located in part or entirely in a terminal region of a selectable polynucleotide, and such a selection marker may be termed an "end-selection marker".

End-selection may be based on detection of naturally occurring sequences or on detection of sequences introduced experimentally (including by any mutagenesis procedure mentioned herein and not mentioned herein) or on both, even within the same polynucleotide. An end-selection marker can be a structural selection marker or a functional selection marker or both a structural and a functional selection marker. An end-selection marker may be comprised of a polynucleotide sequence or of a polypeptide sequence or of any chemical structure or of any biological or biochemical tag, including markers that can be selected using methods based on the detection of radioactivity, of enzymatic activity, of fluorescence, of any optical feature, of a magnetic property (e.g. using magnetic beads), of immunoreactivity, and of hybridization.

End-selection may be applied in combination with any method serviceable for performing mutagenesis. Such mutagenesis methods include, but are not limited to, methods described herein (supra and infra). Such methods include, by way of non-limiting exemplification, any method that may be referred herein or by others in the art by any of the following terms: "saturation mutagenesis", "shuffling", "recombination", "re-assembly", "error-prone PCR", "assembly PCR", "sexual PCR", "crossover PCR", "oligonucleotide primer-directed mutagenesis", "recursive (&/or exponential) ensemble mutagenesis (see Arkin and Youvan, 1992)", "cassette mutagenesis", "in vivo mutagenesis", and "in vitro mutagenesis". Moreover, end-selection may be performed on molecules produced by any mutagenesis &/or amplification method (see, e.g., Arnold, 1993; Caldwell and Joyce, 1992; Stemmer, 1994; following which method it is desirable to select for (including to screen for the presence of) desirable progeny molecules.

In addition, end-selection may be applied to a polynucleotide apart from any mutagenesis method. In a preferred embodiment, end-selection, as provided herein, can be used in order to facilitate a cloning step, such as a step of ligation to another polynucleotide (including ligation to a vector). This invention thus provides for end-selection as a serviceable means to facilitate library construction, selection &/or enrichment for desirable polynucleotides, and cloning in general.

In a particularly preferred embodiment, end-selection can be based on (positive) selection for a polynucleotide; alternatively end-selection can be based on (negative) selection against a polynucleotide; and alternatively still, end-selection can be based on both (positive) selection for, and on (negative) selection against, a polynucleotide. End-selection, along with other methods of selection &/or screening, can be performed in an iterative fashion, with any combination of like or unlike selection &/or screening methods and serviceable mutagenesis methods, all of which can be performed in an iterative fashion and in any order, combination, and permutation.

It is also appreciated that, according to one embodiment of this invention, end-selection may also be used to select a polynucleotide that is at least in part: circular (e.g. a plasmid or any other circular vector or any other polynucleotide that is partly circular), &/or branched, &/or modified or substituted with any chemical group or moiety. In accord with this embodiment, a polynucleotide may be a circular molecule comprised of an intermediate or central region, which region is flanked on a 5' side by a 5' flanking region (which, for the purpose of end-selection, serves in like manner to a 5' terminal region of a non-circular polynucleotide) and on a 3' side by a 3' terminal region (which, for the purpose of end-selection, serves in like manner to a 3' terminal region of a non-circular polynucleotide). As used in this non-limiting exemplification, there may be sequence overlap between any two regions or even among all three regions.

In one non-limiting aspect of this invention, end-selection of a linear polynucleotide is performed using a general approach based on the presence of at least one end-selection marker located at or near a polynucleotide end or terminus (that can be either a 5' end or a 3' end). In one particular non-limiting exemplification, end-selection is based on selection for a specific sequence at or near a terminus such as, but not limited to, a sequence recognized by an enzyme that recognizes a polynucleotide sequence. An enzyme that recognizes and catalyzes a chemical modification of a polynucleotide is referred to herein as a polynucleotide-acting enzyme. In a preferred embodiment, serviceable polynucleotide-acting enzymes are exemplified non-exclusively by enzymes with polynucleotide-cleaving activity, enzymes with polynucleotide-methylating activity, enzymes with polynucleotide-ligating activity, and enzymes with a plurality of distinguishable enzymatic activities (including non-exclusively, e.g., both polynucleotide-cleaving activity and polynucleotide-ligating activity).

Relevant polynucleotide-acting enzymes thus also include any commercially available or non-commercially available polynucleotide endonucleases and their companion methylases including those catalogued at the website http://www.neb.com/rebase, and those mentioned in the following cited reference (Roberts and Macelis, 1996). Preferred polynucleotide endonucleases include—but are not limited to—type II restriction enzymes (including type IIS), and include enzymes that cleave both strands of a double stranded polynucleotide (e.g. Not I, which cleaves both strands at 5' . . . GC/GGCCGC . . . 3') and enzymes that cleave only one strand of a double stranded polynucleotide, i.e. enzymes that have polynucleotide-nicking activity, (e.g. N. BstNB I, which cleaves only one strand at 5' . . . GAGTCNNNN/N . . . 3'). Relevant polynucleotide-acting enzymes also include type III restriction enzymes.

It is appreciated that relevant polynucleotide-acting enzymes also include any enzymes that may be developed in the future, though currently unavailable, that are serviceable for generating a ligation compatible end, preferably a sticky end, in a polynucleotide.

In one preferred exemplification, a serviceable selection marker is a restriction site in a polynucleotide that allows a corresponding type II (or type IIS) restriction enzyme to cleave an end of the polynucleotide so as to provide a ligatable end (including a blunt end or alternatively a sticky end with at least a one base overhang) that is serviceable for a desirable ligation reaction without cleaving the polynucleotide internally in a manner that destroys a desired internal sequence in the polynucleotide. Thus it is provided that, among relevant restriction sites, those sites that do not occur internally (i.e. that do not occur apart from the termini) in a specific working polynucleotide are preferred when the use of a corresponding restriction enzyme(s) is not intended to cut the working polynucleotide internally. This allows one to perform restriction digestion reactions to completion or to near completion without incurring unwanted internal cleavage in a working polynucleotide.

According to a preferred aspect, it is thus preferable to use restriction sites that are not contained, or alternatively that are not expected to be contained, or alternatively that are unlikely to be contained (e.g. when sequence information regarding a working polynucleotide is incomplete) internally in a polynucleotide to be subjected to end-selection. In accordance with this aspect, it is appreciated that restriction sites that occur relatively infrequently are usually preferred over those that occur more frequently. On the other hand it is also appreciated that there are occasions where internal cleavage of a polypeptide is desired, e.g. to achieve recombination or other mutagenic procedures along with endselection.

In accord with this invention, it is also appreciated that methods (e.g. mutagenesis methods) can be used to remove unwanted internal restriction sites. It is also appreciated that a partial digestion reaction (i.e. a digestion reaction that proceeds to partial completion) can be used to achieve digestion at a recognition site in a terminal region while sparing a susceptible restriction site that occurs internally in a polynucleotide and that is recognized by the same enzyme. In one aspect, partial digest are useful because it is appreciated that certain enzymes show preferential cleavage of the same recognition sequence depending on the location and environment in which the recognition sequence occurs. For example, it is appreciated that, while lambda DNA has 5 EcoR I sites, cleavage of the site nearest to the right terminus has been reported to occur 10 times faster than the sites in the middle of the molecule. Also, for example, it has been reported that, while Sac II has four sites on lambda DNA, the three clustered centrally in lambda are cleaved 50 times faster than the remaining site near the terminus (at nucleotide 40,386). Summarily, site preferences have been reported for various enzymes by many investigators (e.g., Thomas and Davis, 1975; Forsblum et al, 1976; Nath and Azzolina, 1981; Brown and Smith, 1977; Gingeras and Brooks, 1983; Krüiger et al, 1988; Conrad and Topal, 1989; Oller et al, 1991; Topal, 1991; and Pein, 1991; to name but a few). It is appreciated that any empirical observations as well as any mechanistic understandings of site preferences by any serviceable polynucleotide-acting enzymes, whether currently available or to be procured in the future, may be serviceable in end-selection according to this invention.

It is also appreciated that protection methods can be used to selectively protect specified restriction sites (e.g. internal sites) against unwanted digestion by enzymes that would otherwise cut a working polypeptide in response to the presence of those sites; and that such protection methods include modifications such as methylations and base substitutions (e.g. U instead of T) that inhibit an unwanted enzyme activity. It is appreciated that there are limited numbers of available restriction enzymes that are rare enough (e.g. having very long recognition sequences) to create large (e.g. megabase-long) restriction fragments, and that protection approaches (e.g. by methylation) are serviceable for increasing the rarity of enzyme cleavage sites. The use of M.Fnu II (mCGCG) to increase the apparent rarity of Not I approximately twofold is but one example among many (Qiang et al, 1990; Nelson et al, 1984; Maxam and Gilbert, 1980; Raleigh and Wilson, 1986).

According to a preferred aspect of this invention, it is provided that, in general, the use of rare restriction sites is preferred. It is appreciated that, in general, the frequency of occurrence of a restriction site is determined by the number of nucleotides contained therein, as well as by the ambiguity of the base requirements contained therein. Thus, in a non-limiting exemplification, it is appreciated that, in general, a restriction site composed of, for example, 8 specific nucleotides (e.g. the Not I site or GC/GGCCGC, with an estimated relative occurrence of 1 in $4^8$, i.e. 1 in 65,536, random 8-mers) is relatively more infrequent than one composed of, for example, 6 nucleotides (e.g. the Sma I site or CCC/GGG, having an estimated relative occurrence of 1 in $4^6$, i.e. 1 in 4,096, random 6-mers), which in turn is relatively more infrequent than one composed of, for example, 4 nucleotides (e.g. the Msp I site or C/CGG, having an estimated relative occurrence of 1 in $4^4$, i.e. 1 in 256, random 4-mers). Moreover, in another non-limiting exemplification, it is appreciated that, in general, a restriction site having no ambiguous (but only specific) base requirements (e.g. the Fin I site or GTCCC, having an estimated relative occurrence of 1 in $4^5$, i.e. 1 in 1024, random 5-mers) is relatively more infrequent than one having an ambiguous W (where W=A or T) base requirement (e.g. the Ava II site or G/GWCC, having an estimated relative occurrence of 1 in 4×4×2×4×4 - i.e. 1 in 512— random 5-mers), which in turn is relatively more infrequent than one having an ambiguous N (where N=A or C or G or T) base requirement (e.g. the Asu I site or G/GNCC, having an estimated relative occurrence of 1 in 4×4×1×4×4, i.e. 1 in 25613 random 5-mers). These relative occurrences are considered general estimates for actual polynucleotides, because it is appreciated that specific nucleotide bases (not to mention specific nucleotide sequences) occur with dissimilar frequencies in specific polynucleotides, in specific species of organisms, and in specific groupings of organisms. For example, it is appreciated that the % G+C contents of different species of organisms are often very different and wide ranging.

The use of relatively more infrequent restriction sites as a selection marker include—in a non-limiting fashion— preferably those sites composed at least a 4 nucleotide sequence, more preferably those composed of at least a 5 nucleotide sequence, more preferably still those composed at least a 6 nucleotide sequence (e.g. the BamH I site or G/GATCC, the Bgl II site or A/GATCT, the Pst I site or CTGCA/G, and the Xba I site or T/CTAGA), more preferably still those composed at least a 7 nucleotide sequence, more preferably still those composed of an 8 nucleotide sequence nucle6tide sequence (e.g. the Asc I site or GG/CGCGCC, the Not I site or GC/GGCCGC, the Pac I site or TTAAT/TAA, the Pme I site or GTTT/AAAC, the Srf I site or GCCC/GGGC, the Sse838 I site or CCTGCA/GG, and the Swa I site or ATTT/AAAT), more preferably still those composed of a 9 nucleotide sequence, and even more preferably still those composed of at least a 10 nucleotide sequence (e.g. the BspG I site or CG/CGCTGGAC). It is further appreciated that some restriction sites (e.g. for class IIS enzymes) are comprised of a portion of relatively high specificity (i.e. a portion containing a principal determinant of the frequency of occurrence of the restriction site) and a portion of relatively low specificity; and that a site of cleavage may or may not be contained within a portion of relatively low specificity. For example, in the Eco57 I site or CTGAAG(16/14), there is a portion of relatively high specificity (i.e. the CTGAAG portion) and a portion of relatively low specificity (i.e. the N16 sequence) that contains a site of cleavage.

In another preferred embodiment of this invention, a serviceable end-selection marker is a terminal sequence that is recognized by a polynucleotide-acting enzyme that recognizes a specific polynucleotide sequence. In a preferred aspect of this invention, serviceable polynucleotide-acting enzymes also include other enzymes in addition to classic type II restriction enzymes. According to this preferred aspect of this invention, serviceable polynucleotide-acting enzymes also include gyrases, helicases, recombinases, relaxases, and any enzymes related thereto.

Among preferred examples are topoisomerases (which have been categorized by some as a subset of the gyrases) and any other enzymes that have polynucleotide-cleaving activity (including preferably polynucleotide-nicking activity) &/or polynucleotide-ligating activity. Among preferred topoisomerase enzymes are topoisomerase I enzymes, which is available from many commercial sources (Epicentre Technologies, Madison, Wis.; Invitrogen, Carlsbad, Calif.; Life Technologies , Gathesburg, Md.) and conceivably even more private sources. It is appreciated that similar enzymes may be developed in the future that are serviceable for end-selection as provided herein. A particularly preferred topoisomerase I enzyme is a topoisomerase I enzyme of vaccinia virus origin, that has a specific recognition sequence (e.g. 5' . . . AAGGG . . . 3') and has both polynucleotide-nicking activity and polynucleotide-ligating activity. Due to the specific nicking-activity of this enzyme (cleavage of one strand), internal recognition sites are not prone to polynucleotide destruction resulting from the nicking activity (but rather remain annealed) at a temperature that causes denaturation of a terminal site that has been nicked. Thus for use in end-selection, it is preferable that a nicking site for topoisomerase-based end-selection be no more than 100 nucleotides from a terminus, more preferably no more than 50 nucleotides from a terminus, more preferably still no more than 25 nucloetides from a terminus, even more preferably still no more than 20 nucleotides from a terminus, even more preferably still no more than 15 nucleotides from a terminus, even more preferably still no more than 10 nucleotides from a terminus, even more preferably still no more than 8 nucleotides from a terminus, even more preferably still no more than 6 nucleotides from a terminus, and even more preferably still no more than 4 nucleotides from a terminus.

In a particularly preferred exemplification that is non-limiting yet clearly illustrative , it is appreciated that when a nicking site for topoisomerase-based end-selection is 4 nucleotides from a terminus, nicking produces a single stranded oligo of 4 bases (in a terminal region) that can be denatured from its complementary strand in an end-selectable polynucleotide; this provides a sticky end (comprised of4 bases) in a polynucleotide that is serviceable for an ensuing ligation reaction. To accomplish ligation to a cloning vector (preferably an expression vector), compatible sticky ends can be generated in a cloning vector by any means including by restriction enzyme-based means. The terminal nucleotides (comprised of 4 terminal bases in this specific example) in an end-selectable polynucleotide terminus are thus wisely chosen to provide compatibility with a sticky end generated in a cloning vector to which the polynucleotide is to be ligated.

On the other hand, internal nicking of an end-selectable polynucleotide, e.g. 500 bases from a terminus, produces a single stranded oligo of 500 bases that is not easily denatured from its complementary strand, but rather is serviceable for repair (e.g. by the same topoisomerase enzyme that produced the nick).

This invention thus provides a method—e.g. that is vaccinia topoisomerase-based &/or type II (or IIS) restriction endonuclease-based &/or type III restriction endonuclease-based &/or nicking enzyme-based (e.g. using N. BstNB I)—for producing a sticky end in a working polynucleotide, which end is ligation compatible, and which end can be comprised of at least a 1 base overhang. Preferably such a sticky end is comprised of at least a 2-base overhang, more preferably such a sticky end is comprised of at least a 3-base overhang, more preferably still such a sticky end is comprised of at least a 4- base overhang, even more preferably still such a sticky end is comprised of at least a 5-base overhang, even more preferably still such a sticky end is comprised of at least a 6-base overhang. Such a sticky end may also be comprised of at least a 7-base overhang, or at least an 8-base overhang, or at least a 9-base overhang, or at least a 10-base overhang, or at least 15-base overhang, or at least a 20-base overhang, or at least a 25-base overhang, or at least a 30-base overhang. These overhangs can be comprised of any bases, including A, C, G, or T.

It is appreciated that sticky end overhangs introduced using topoisomerase or a nicking enzyme (e.g. using N. BstNB I) can be designed to be unique in a ligation environment, so as to prevent unwanted fragment reassemblies, such as self-dimerizations and other unwanted concatamerizations.

According to one aspect of this invention, a plurality of sequences (which may but do not necessarily overlap) can be introduced into a terminal region of an end-selectable polynucleotide by the use of an oligo in a polymerase-based reaction. In a relevant, but by no means limiting example, such an oligo can be used to provide a preferred 5' terminal region that is serviceable for topoisomerase I-based end-selection, which oligo is comprised of: a 1–10 base sequence that is convertible into a sticky end (preferably by a vaccinia topoisomerase 1), a ribosome binding site (i.e. and "RBS", that is preferably serviceable for expression cloning), and optional linker sequence followed by an ATG start site and a template-specific sequence of 0–100 bases (to facilitate annealment to the template in the polymerase-based reaction). Thus, according to this example, a serviceable oligo (which may be termed a forward primer) can have the sequence: 5'[terminal sequence=$(N)_{1-10}$][topoisomerase I site & RBS=AAGGGAGGAG][linker=$(N)_{1-100}$][start codon and template-specific sequence=ATG$(N)_{0-100}$]3'.

Analogously, in a relevant, but by no means limiting example, an oligo can be used to provide a preferred 3' terminal region that is serviceable for topoisomerase I-based end-selection, which oligo is comprised of: a 1–10 base sequence that is convertible into a sticky end (preferably by a vaccinia topoisomerase I), and optional linker sequence followed by a template-specific sequence of 0–100 bases (to facilitate annealment to the template in the polymerase-based reaction). Thus, according to this example, a serviceable oligo (which may be termed a reverse primer) can have the sequence: 5'[terminal sequence=$(N)_{1-10}$][topoisomerase I site=AAGGG][linker=$(N)_{1-100}$][template-specific sequence=$(N)_{0-100}$]3'.

It is appreciated that, end-selection can be used to distinguish and separate parental template molecules (e.g. to be subjected to mutagenesis) from progeny molecules (e.g. generated by mutagenesis). For example, a first set of primers, lacking in a topoisomerase I recognition site, can be used to modify the terminal regions of the parental molecules (e.g. in polymerase-based amplification). A different second set of primers (e.g. having a topoisomerase I recognition site) can then be used to generate mutated progeny molecules (e.g. using any polynucleotide chimerization method, such as interrupted synthesis, template-switching polymerase-based amplification, or interrupted synthesis; or using saturation mutagenesis; or using any other method for introducing a topoisomerase I recognition site into a mutagenized progeny molecule as disclosed herein) from the amplified template molecules. The use of topoisomerase I-based end-selection can then facilitate, not only discernment, but selective topoisomerase I-based ligation of the desired progeny molecules.

Annealment of a second set of primers to thusly amplified parental molecules can be facilitated by including sequences in a first set of primers (i.e. primers used for amplifying a set parental molecules) that are similar to a toposiomerase I recognition site, yet different enough to prevent functional toposiomerase I enzyme recognition. For example, sequences that diverge from the AAGGG site by anywhere from 1 base to all 5 bases can be incorporated into a first set of primers (to be used for amplifying the parental templates prior to subjection to mutagenesis). In a specific, but non-limiting aspect, it is thus provided that a parental molecule can be amplified using the following exemplary—but by no means limiting—set of forward and reverse primers:

Forward Primer: 5' CTAGAAGAGAGGAGAAAACCATG$(N)_{10-100}$ 3', and

Reverse Primer: 5' GATCAAAGGCGCGCCTGCAGG $(N)_{10-100}$ 3'

According to this specific example of a first set of primers, $(N)_{10-100}$ represents preferably a 10 to 100 nucleotide-long template-specific sequence, more preferably a 10 to 50 nucleotide-long template-specific sequence, more preferably still a 10 to 30 nucleotide-long template-specific sequence, and even more preferably still a 15 to 25 nucleotide-long template-specific sequence.

According to a specific, but non-limiting aspect, it is thus provided that, after this amplification (using a disclosed first set of primers lacking in a true topoisomerase I recognition site), amplified parental molecules can then be subjected to mutagenesis using one or more sets of forward and reverse primers that do have a true topoisomerase I recognition site. In a specific, but non-limiting aspect, it is thus provided that a parental molecule can be used as templates for the generation of a mutagenized progeny molecule using the following exemplary—but by no means limiting—second set of forward and reverse primers:

Forward Primer: 5' CTAGAAGGGAGGAGAAAAC-CATG 3'

Reverse Primer: 5' GATCAAAGGCGCGCCTGCAGG 3' (contains Asc I recognition sequence)

It is appreciated that any number of different primers sets not specifically mentioned can be used as first, second, or subsequent sets of primers for end-selection consistent with this invention. Notice that type II restriction enzyme sites can be incorporated (e.g. an Asc I site in the above example). It is provided that, in addition to the other sequences mentioned, the experimentalist can incorporate one or more N,N,G/T triplets into a serviceable primer in order to subject a working polynucleotide to saturation mutagenesis. Summarily, use of a second and/or subsequent set of primers can achieve dual goals of introducing a topoisomerase I site and of generating mutations in a progeny polynucleotide.

Thus, according to one use provided, a serviceable end-selection marker is an enzyme recognition site that allows an enzyme to cleave (including nick) a polynucleotide at a specified site, to produce a ligation-compatible end upon denaturation of a generated single stranded oligo. Ligation of the produced polynucleotide end can then be accomplished by the same enzyme (e.g. in the case of vaccinia virus topoisomerase I), or alternatively with the use of a different enzyme. According to one aspect of this invention, any serviceable end-selection markers, whether like (e.g. two vaccinia virus topoisomerase I recognition sites) or unlike (e.g. a class II restriction enzyme recognition site and a vaccinia virus topoisomerase I recognition site) can be used in combination to select a polynucleotide. Each selectable polynucleotide can thus have one or more end-selection markers, and they can be like or unlike end-selection markers. In a particular aspect, a plurality of end-selection markers can be located on one end of a polynucleotide and can have overlapping sequences with each other.

It is important to emphasize that any number of enzymes, whether currently in existence or to be developed, can be serviceable in end-selection according to this invention. For example, in a particular aspect of this invention, a nicking enzyme (e.g. N. BstNB I, which cleaves only one strand at 5' . . . GAGTCNNNN/N . . . 3') can be used in conjunction with a source of polynucleotide-ligating activity in order to achieve end-selection. According to this embodiment, a recognition site for N. BstNB I—instead of a recognition site for topoisomerase I—should be incorporated into an end-selectable polynucleotide (whether end-selection is used for selection of a mutagenized progeny molecule or whether end-selection is used apart from any mutagenesis procedure). It is appreciated that the instantly disclosed end-selection approach using topoisomerase-based nicking and ligation has several advantages over previously available selection methods. In sum, this approach allows one to achieve direction cloning (including expression cloning). Specifically, this approach can be used for the achievement of: direct ligation (i.e. without subjection to a classic restriction-purification-ligation reaction, that is susceptible to a multitude of potential problems from an initial restriction reaction to a ligation reaction dependent on the use of T4 DNA ligase); separation of progeny molecules from original template molecules (e.g. original template molecules lack topoisomerase I sites that not introduced until after mutagenesis), obviation of the need for size separation steps (e.g. by gel chromatography or by other electrophoretic means or by the use of size-exclusion membranes), preservation of internal sequences (even when topoisomerase I sites are present), obviation of concerns about unsuccessful ligation reactions (e.g. dependent on the use of T4 DNA ligase, particularly in the presence of unwanted residual restriction enzyme activity), and facilitated expression cloning (including obviation of frame shift concerns). Concerns about unwanted restriction enzyme-based cleavages—especially at internal restriction sites (or even at often unpredictable sites of unwanted star activity) in a working polynucleotide—that are potential sites of destruction of a working polynucleotide can also be obviated by the instantly disclosed end-selection approach using topoisomerase-based nicking and ligation.

3.3. Additional Screening Methods

Peptide Display Methods

The present method can be used to shuffle, by in vitro and/or in vivo recombination by any of the disclosed methods, and in any combination, polynucleotide sequences selected by peptide display methods, wherein an associated polynucleotide encodes a displayed peptide which is screened for a phenotype (e.g., for affinity for a predetermined receptor (ligand).

An increasingly important aspect of bio-pharmaceutical drug development and molecular biology is the identification of peptide structures, including the primary amino acid sequences, of peptides or peptidomimetics that interact with biological macromolecules. one method of identifying peptides that possess a desired structure or functional property, such as binding to a predetermined biological macromolecule (e.g., a receptor), involves the screening of a large library or peptides for individual library members which possess the desired structure or functional property conferred by the amino acid sequence of the peptide.

In addition to direct chemical synthesis methods for generating peptide libraries, several recombinant DNA methods also have been reported. One type involves the display of a peptide sequence, antibody, or other protein on the surface of a bacteriophage particle or cell. Generally, in these methods each bacteriophage particle or cell serves as an individual library member displaying a single species of displayed peptide in addition to the natural bacteriophage or cell protein sequences. Each bacteriophage or cell contains the nucleotide sequence information encoding the particular displayed peptide sequence; thus, the displayed peptide sequence can be ascertained by nucleotide sequence determination of an isolated library member.

A well-known peptide display method involves the presentation of a peptide sequence on the surface of a filamentous bacteriophage, typically as a fusion with a bacteriophage coat protein. The bacteriophage library can be incubated with an immobilized, predetermined macromolecule or small molecule (e.g., a receptor) so that bacteriophage particles which present a peptide sequence that binds to the immobilized macromolecule can be differentially partitioned from those that do not present peptide sequences that bind to the predetermined macromolecule. The bacteriophage particles (i.e., library members) which are bound to the immobilized macromolecule are then recovered and replicated to amplify the selected bacteriophage sub-population for a subsequent round of affinity enrichment and phage replication. After several rounds of affinity enrichment and phage replication, the bacteriophage library members that are thus selected are isolated and the nucleotide sequence encoding the displayed peptide sequence is determined, thereby identifying the sequence(s) of peptides that bind to the predetermined macromolecule (e.g., receptor). Such methods are further described in PCT patent publications WO 91/17271, WO 91/18980, WO 91/19818 and WO 93/08278.

The latter PCT publication describes a recombinant DNA method for the display of peptide ligands that involves the production of a library of fusion proteins with each fusion protein composed of a first polypeptide portion, typically comprising a variable sequence, that is available for potential binding to a predetermined macromolecule, and a second polypeptide portion that binds to DNA, such as the DNA vector encoding the individual fusion protein. When transformed host cells are cultured under conditions that allow for expression of the fusion protein, the fusion protein binds to the DNA vector encoding it. Upon lysis of the host cell, the fusion protein/vector DNA complexes can be screened against a predetermined macromolecule in much the same way as bacteriophage particles are screened in the phage-based display system, with the replication and sequencing of the DNA vectors in the selected fusion protein/vector DNA complexes serving as the basis for identification of the selected library peptide sequence(s).

Other systems for generating libraries of peptides and like polymers have aspects of both the recombinant and in vitro chemical synthesis methods. In these hybrid methods, cell-free enzymatic machinery is employed to accomplish the in vitro synthesis of the library members (i.e., peptides or polynucleotides). In one type of method, RNA molecules with the ability to bind a predetermined protein or a predetermined dye molecule were selected by alternate rounds of selection and PCR amplification (Tuerk and Gold, 1990; Ellington and Szostak, 1990). A similar technique was used to identify DNA sequences which bind a predetermined human transcription factor (Thiesen and Bach, 1990; Beaudry and Joyce, 1992; PCT patent publications WO 92/05258 and WO 92/14843). In a similar fashion, the technique of in vitro translation has been used to synthesize proteins of interest and has been proposed as a method for generating large libraries of peptides. These methods which rely upon in vitro translation, generally comprising stabilized polysome complexes, are described further in PCT patent publications WO 88/08453, WO 90/05785, WO 90/07003, WO 91/02076, WO 91/05058, and WO 92/02536. Applicants have described methods in which library members comprise a fusion protein having a first polypeptide portion with DNA binding activity and a second polypeptide portion having the library member unique peptide sequence; such methods are suitable for use in cell-free in vitro selection formats, among others.

The displayed peptide sequences can be of varying lengths, typically from 3–5000 amino acids long or longer, frequently from 5–100 amino acids long, and often from about 8–15 amino acids long. A library can comprise library members having varying lengths of displayed peptide sequence, or may comprise library members having a fixed length of displayed peptide sequence. Portions or all of the displayed peptide sequence(s) can be random, pseudorandom, defined set kemal, fixed, or the like. The present display methods include methods for in vitro and in vivo display of single-chain antibodies, such as nascent scFv on polysomes or scfv displayed on phage, which enable large-scale screening of scfv libraries having broad diversity of variable region sequences and binding specificities.

The present invention also provides random, pseudorandom, and defined sequence framework peptide libraries and methods for generating and screening those libraries to identify useful compounds (e.g., peptides, including single-chain antibodies) that bind to receptor molecules or epitopes of interest or gene products that modify peptides or RNA in a desired fashion. The random, pseudorandom, and defined sequence framework peptides are produced from libraries of peptide library members that comprise displayed peptides or displayed single-chain antibodies attached to a polynucleotide template from which the displayed peptide was synthesized. The mode of attachment may vary according to the specific embodiment of the invention selected, and can include encapsulation in a phage particle or incorporation in a cell.

A method of affinity enrichment allows a very large library of peptides and single-chain antibodies to be screened and the polynucleotide sequence encoding the desired peptide(s) or single-chain antibodies to be selected. The polynucleotide can then be isolated and shuffled to recombine combinatorially the amino acid sequence of the selected peptide(s) (or predetermined portions thereof) or single-chain antibodies (or just VHI, VLI or CDR portions thereof). Using these methods, one can identify a peptide or single-chain antibody as having a desired binding affinity for a molecule and can exploit the process of shuffling to converge rapidly to a desired high-affinity peptide or scfv. The peptide or antibody can then be synthesized in bulk by conventional means for any suitable use (e.g., as a therapeutic or diagnostic agent).

A significant advantage of the present invention is that no prior information regarding an expected ligand structure is required to isolate peptide ligands or antibodies of interest. The peptide identified can have biological activity, which is meant to include at least specific binding affinity for a selected receptor molecule and, in some instances, will further include the ability to block the binding of other compounds, to stimulate or inhibit metabolic pathways, to act as a signal or messenger, to stimulate or inhibit cellular activity, and the like.

The present invention also provides a method for shuffling a pool of polynucleotide sequences selected by affinity screening a library of polysomes displaying nascent peptides (including single-chain antibodies) for library members which bind to a predetermined receptor (e.g., a marnmalian proteinaceous receptor such as, for example, a peptidergic hormone receptor, a cell surface receptor, an intracellular protein which binds to other protein(s) to form intracellular protein complexes such as hetero-dimers and the like) or epitope (e.g., an immobilized protein, glycoprotein, oligosaccharide, and the like).

Polynucleotide sequences selected in a first selection round (typically by affinity selection for binding to a receptor (e.g., a ligand)) by any of these methods are pooled and the pool(s) is/are shuffled by in vitro and/or in vivo recombination to produce a shuffled pool comprising a population of recombined selected polynucleotide sequences. The recombined selected polynucleotide sequences are subjected to at least one subsequent selection round. The polynucleotide sequences selected in the subsequent selection round (s) can be used directly, sequenced, and/or subjected to one or more additional rounds of shuffling and subsequent selection. Selected sequences can also be back-crossed with polynucleotide sequences encoding neutral sequences (i.e., having insubstantial functional effect on binding), such as for example by back-crossing with a wild-type or naturally-occurring sequence substantially identical to a selected sequence to produce native-like functional peptides, which may be less immunogenic. Generally, during back-crossing subsequent selection is applied to retain the property of binding to the predetermined receptor (ligand).

Prior to or concomitant with the shuffling of selected sequences, the sequences can be mutagenized. In one embodiment, selected library members are cloned in a prokaryotic vector (e.g., plasmid, phagemid, or bacteriophage) wherein a collection of individual colonies (or plaques) representing discrete library members are produced. Individual selected library members can then be manipulated (e.g., by site-directed mutagenesis, cassette mutagenesis, chemical mutagenesis, PCR mutagenesis, and the like) to generate a collection of library members representing a kernal of sequence diversity based on the sequence of the selected library member. The sequence of an individual selected library member or pool can be manipulated to incorporate random mutation, pseudorandom mutation, defined kernal mutation (i.e., comprising variant and invariant residue positions and/or comprising variant residue positions which can comprise a residue selected from a defined subset of amino acid residues), codon-based mutation, and the like, either segmentally or over the entire length of the individual selected library member sequence. The mutagenized selected library members are then shuffled by in vitro and/or in vivo recombinatorial shuffling as disclosed herein.

The invention also provides peptide libraries comprising a plurality of individual library members of the invention, wherein (1) each individual library member of said plurality comprises a sequence produced by shuffling of a pool of selected sequences, and (2) each individual library member comprises a variable peptide segment sequence or single-chain antibody segment sequence which is distinct from the variable peptide segment sequences or single-chain antibody sequences of other individual library members in said plurality (although some library members may be present in more than one copy per library due to uneven amplification, stochastic probability, or the like).

The invention also provides a product-by-process, wherein selected polynucleotide sequences having (or encoding a peptide having) a predetermined binding specificity are formed by the process of: (1) screening a displayed peptide or displayed single-chain antibody library against a predetermined receptor (e.g., ligand) or epitope (e.g., antigen macromolecule) and identifying and/or enriching library members which bind to the predetermined receptor or epitope to produce a pool of selected library members, (2) shuffling by recombination the selected library members (or amplified or cloned copies thereof) which binds the predetermined epitope and has been thereby isolated and/or enriched from the library to generate a shuffled library, and (3) screening the shuffled library against the predetermined receptor (e.g., ligand) or epitope (e.g., antigen macromolecule) and identifying and/or enriching shuffled library members which bind to the predetermined receptor or epitope to produce a pool of selected shuffled library members.

Antibody Display and Screening Methods

The present method can be used to shuffle, by in vitro and/or in vivo recombination by any of the disclosed methods, and in any combination, polynucleotide sequences selected by antibody display methods, wherein an associated polynucleotide encodes a displayed antibody which is screened for a phenotype (e.g., for affinity for binding a predetermined antigen (ligand)).

Various molecular genetic approaches have been devised to capture the vast immunological repertoire represented by the extremely large number of distinct variable regions which can be present in immunoglobulin chains. The naturally-occurring germ line immunoglobulin heavy chain locus is composed of separate tandem arrays of variable segment genes located upstream of a tandem array of diversity segment genes, which are themselves located upstream of a tandem array of joining (i) region genes, which are located upstream of the constant region genes. During B lymphocyte development, V-D-J rearrangement occurs wherein a heavy chain variable region gene (VH) is formed by rearrangement to form a fused D segment followed by rearrangement with a V segment to form a V-D-J joined product gene which, if productively rearranged, encodes a functional variable region (VH) of a heavy chain. Similarly, light chain loci rearrange one of several V segments with one of several J segments to form a gene encoding the variable region (VL) of a light chain.

The vast repertoire of variable regions possible in immunoglobulins derives in part from the numerous combinatorial possibilities of joining V and i segments (and, in the case of heavy chain loci, D segments) during rearrangement in B cell development. Additional sequence diversity in the heavy chain variable regions arises from non-uniform rearrangements of the D segments during V-D-J joining and from N region addition. Further, antigen-selection of specific B cell clones selects for higher affinity variants having non-germline mutations in one or both of the heavy and light chain variable regions; a phenomenon referred to as "affinity maturation" or "affinity sharpening". Typically, these "affinity sharpening" mutations cluster in specific areas of the variable region, most commonly in the complementarity-determining regions (CDRs).

In order to overcome many of the limitations in producing and identifying high-affinity immunoglobulins through antigen-stimulated β cell development (i.e., immunization), various prokaryotic expression systems have been developed that can be manipulated to produce combinatorial antibody libraries which may be screened for high-affinity antibodies to specific antigens. Recent advances in the expression of antibodies in *Escherichia coli* and bacteriophage systems (see "alternative peptide display methods", infra) have raised the possibility that virtually any specificity can be obtained by either cloning antibody genes from characterized hybridomas or by de novo selection using antibody gene libraries (e.g., from Ig cDNA).

Combinatorial libraries of antibodies have been generated in bacteriophage lambda expression systems which may be screened as bacteriophage plaques or as colonies of lysogens (Huse et al, 1989); Caton and Koprowski, 1990; Mullinax et al, 1990; Persson et al, 1991). Various embodiments of bacteriophage antibody display libraries and lambda phage expression libraries have been described (Kang et al, 1991; Clackson et al, 1991; McCafferty et al, 1990; Burton et al, 1991; Hoogenboom et al, 1991; Chang et al, 1991; Breitling et al, 1991; Marks et al, 1991, p. 581; Barbas et al, 1992; Hawkins and Winter, 1992; Marks et al, 1992, p. 779; Marks et al, 1992, p. 16007; and Lowman et al, 1991; Lerner et al, 1992; all incorporated herein by reference). Typically, a bacteriophage antibody display library is screened with a receptor (e.g., polypeptide, carbohydrate, glycoprotein, nucleic acid) that is immobilized (e.g., by covalent linkage to a chromatography resin to enrich for reactive phage by affinity chromatography) and/or labeled (e.g., to screen plaque or colony lifts).

One particularly advantageous approach has been the use of so-called single-chain fragment variable (scfv) libraries (Marks et al, 1992, p. 779; Winter and Milstein, 1991; Clackson et al, 1991; Marks et al, 1991, p. 581; Chaudhary et al, 1990; Chiswell et al, 1992; McCafferty et al, 1990; and Huston et al, 1988). Various embodiments of scfv libraries displayed on bacteriophage coat proteins have been described.

Beginning in 1988, single-chain analogues of Fv fragments and their fusion proteins have been reliably generated by antibody engineering methods. The first step generally involves obtaining the genes encoding VH and VL domains with desired binding properties; these V genes may be isolated from a specific hybridoma cell line, selected from a combinatorial V-gene library, or made by V gene synthesis. The single-chain Fv is formed by connecting the component V genes with an oligonucleotide that encodes an appropriately designed linker peptide, such as (Gly-Gly-Gly-Gly-Ser)3 or equivalent linker peptide(s). The linker bridges the C-terminus of the first V region and N-terminus of the second, ordered as either VH-linker-VL or VL-linker-VH' In principle, the scfv binding site can faithfully replicate both the affinity and specificity of its parent antibody combining site.

Thus, scfv fragments are comprised of VH and VL domains linked into a single polypeptide chain by a flexible linker peptide. After the scfv genes are assembled, they are cloned into a phagemid and expressed at the tip of the M13 phage (or similar filamentous bacteriophage) as fusion proteins with the bacteriophage PIII (gene 3) coat protein. Enriching for phage expressing an antibody of interest is accomplished by panning the recombinant phage displaying a population scfv for binding to a predetermined epitope (e.g., target antigen, receptor).

The linked polynucleotide of a library member provides the basis for replication of the library member after a screening or selection procedure, and also provides the basis for the determination, by nucleotide sequencing, of the identity of the displayed peptide sequence or VH and VL amino acid sequence. The displayed peptide (s) or single-chain antibody (e. g., scfv) and/or its VH and VL domains or their CDRs can be cloned and expressed in a suitable expression system. Often polynucleotides encoding the isolated VH and VL domains will be ligated to polynucleotides encoding constant regions (CH and CL) to form polynucleotides encoding complete antibodies (e.g., chimeric or fully-human), antibody fragments, and the like. Often polynucleotides encoding the isolated CDRs will be grafted into polynucleotides encoding a suitable variable region framework (and optionally constant regions) to form polynucleotides encoding complete antibodies (e.g., humanized or fully-human), antibody fragments, and the like. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like.

Various methods have been reported for increasing the combinatorial diversity of a scfv library to broaden the repertoire of binding species (idiotype spectrum) The use of PCR has permitted the variable regions to be rapidly cloned either from a specific hybridoma source or as a gene library from non-immunized cells, affording combinatorial diversity in the assortment of VH and VL cassettes which can be combined. Furthermore, the VH and VL cassettes can themselves be diversified, such as by random, pseudorandom, or directed mutagenesis. Typically, VH and VL cassettes are diversified in or near the complementarity-determining regions (CDRS), often the third CDR, CDR3. Enzymatic inverse PCR mutagenesis has been shown to be a simple and reliable method for constructing relatively large libraries of scfv site-directed hybrids (Stemmer et al, 1993), as has error-prone PCR and chemical mutagenesis (Deng et al, 1994). Riechmann (Riechmann et al, 1993) showed semi-rational design of an antibody scfv fragment using site-directed randomization by degenerate oligonucleotide PCR and subsequent phage display of the resultant scfv hybrids. Barbas (Barbas et al, 1992) attempted to circumvent the problem of limited repertoire sizes resulting from using biased variable region sequences by randomizing the sequence in a synthetic CDR region of a human tetanus toxoid-binding Fab.

CDR randomization has the potential to create approximately $1 \times 10^{20}$ CDRs for the heavy chain CDR3 alone, and a roughly similar number of variants of the heavy chain CDR1 and CDR2, and light chain CDR1–3 variants. Taken individually or together, the combination possibilities of CDR randomization of heavy and/or light chains requires generating a prohibitive number of bacteriophage clones to produce a clone library representing all possible combinations, the vast majority of which will be non-binding. Generation of such large numbers of primary transformants is not feasible with current transformation technology and bacteriophage display systems. For example, Barbas (Barbas et al, 1992) only generated $5 \times 10^7$ transformants, which represents only a tiny fraction of the potential diversity of a library of thoroughly randomized CDRS.

Despite these substantial limitations, bacteriophage display of scfv have already yielded a variety of useful antibodies and antibody fusion proteins. A bispecific single chain antibody has been shown to mediate efficient tumor cell lysis (Gruber et al, 1994). Intracellular expression of an anti-Rev scfv has been shown to inhibit HIV-1 virus replication in vitro (Duan et al, 1994), and intracellular expression of an anti-p21rar, scfv has been shown to inhibit meiotic maturation of Xenopus oocytes (Biocca et al, 1993). Recombinant scfv which can be used to diagnose HIV infection have also been reported, demonstrating the diagnostic utility of scfv (Lilley et al, 1994). Fusion proteins wherein an scFv is linked to a second polypeptide, such as a toxin or fibrinolytic activator protein, have also been reported (Holvost et al, 1992; Nicholls et al, 1993).

If it were possible to generate scfv libraries having broader antibody diversity and overcoming many of the limitations of conventional CDR mutagenesis and randomization methods which can cover only a very tiny fraction of the potential sequence combinations, the number and quality of scfv antibodies suitable for therapeutic and diagnostic use could be vastly improved. To address this, the in vitro and in vivo shuffling methods of the invention are used to recombine CDRs which have been obtained (typically via PCR amplification or cloning) from nucleic acids obtained from selected displayed antibodies. Such displayed antibodies can be displayed on cells, on bacteriophage particles, on polysomes, or any suitable antibody display system wherein the antibody is associated with its encoding nucleic acid(s). In a variation, the CDRs are initially obtained from mRNA (or cDNA) from antibody-producing cells (e.g., plasma cells/splenocytes from an immunized wild-type mouse, a human, or a transgenic mouse capable of making a human antibody as in WO 92/03918, WO 93/12227, and WO 94/25585), including hybridomas derived therefrom.

Polynucleotide sequences selected in a first selection round (typically by affinity selection for displayed antibody binding to an antigen (e.g., a ligand) by any of these methods are pooled and the pool(s) is/are shuffled by in vitro and/or in vivo recombination, especially shuffling of CDRs (typically shuffling heavy chain CDRs with other heavy chain CDRs and light chain CDRs with other light chain CDRs) to produce a shuffled pool comprising a population of recombined selected polynucleotide sequences. The recombined selected polynucleotide sequences are expressed in a selection format as a displayed antibody and subjected to at least one subsequent selection round. The polynucleotide sequences selected in the subsequent selection round(s) can be used directly, sequenced, and/or subjected to one or more additional rounds of shuffling and subsequent selection until an antibody of the desired binding affinity is obtained. Selected sequences can also be back-crossed with polynucleotide sequences encoding neutral antibody framework sequences (i.e., having insubstantial functional effect on antigen binding), such as for example by back-crossing with a human variable region framework to produce human-like sequence antibodies. Generally, during back-crossing subsequent selection is applied to retain the property of binding to the predetermined antigen.

Alternatively, or in combination with the noted variations, the valency of the target epitope may be varied to control the average binding affinity of selected scfv library members. The target epitope can be bound to a surface or substrate at varying densities, such as by including a competitor epitope, by dilution, or by other method known to those in the art. A high density (valency) of predetermined epitope can be used to enrich for scfv library members which have relatively low affinity, whereas a low density (valency) can preferentially enrich for higher affinity scfv library members.

For generating diverse variable segments, a collection of synthetic oligonucleotides encoding random, pseudorandom, or a defined sequence kernal set of peptide sequences can be inserted by ligation into a predetermined site (e.g., a CDR). Similarly, the sequence diversity of one or more CDRs of the single-chain antibody cassette(s) can be expanded by mutating the CDR(s) with site-directed mutagenesis, CDR-replacement, and the like. The resultant DNA molecules can be propagated in a host for cloning and amplification prior to shuffling, or can be used directly (i.e., may avoid loss of diversity which may occur upon propagation in a host cell) and the selected library members subsequently shuffled.

Displayed peptide/polynucleotide complexes (library members) which encode a variable segment peptide sequence of interest or a single-chain antibody of interest are selected from the library by an affinity enrichment technique. This is accomplished by means of a immobilized macromolecule or epitope specific for the peptide sequence of interest, such as a receptor, other macromolecule, or other epitope species. Repeating the affinity selection procedure provides an enrichment of library members encoding the desired sequences, which may then be isolated for pooling and shuffling, for sequencing, and/or for further propagation and affinity enrichment.

The library members without the desired specificity are removed by washing. The degree and stringency of washing required will be determined for each peptide sequence or single-chain antibody of interest and the immobilized predetermined macromolecule or epitope. A certain degree of control can be exerted over the binding characteristics of the nascent peptide/DNA complexes recovered by adjusting the conditions of the binding incubation and the subsequent washing. The temperature, pH, ionic strength, divalent cations concentration, and the volume and duration of the washing will select for nascent peptide/DNA complexes within particular ranges of affinity for the immobilized macromolecule. Selection based on slow dissociation rate, which is usually predictive of high affinity, is often the most practical route. This may be done either by continued incubation in the presence of a saturating amount of free predetermined macromolecule, or by increasing the volume, number, and length of the washes. In each case, the rebinding of dissociated nascent peptide/DNA or peptide/RNA complex is prevented, and with increasing time, nascent peptide/DNA or peptide/RNA complexes of higher and higher affinity are recovered.

Additional modifications of the binding and washing procedures may be applied to find peptides with special characteristics. The affinities of some peptides are dependent on ionic strength or cation concentration. This is a useful characteristic for peptides that will be used in affinity purification of various proteins when gentle conditions for removing the protein from the peptides are required.

One variation involves the use of multiple binding targets (multiple epitope species, multiple receptor species), such that a scfv library can be simultaneously screened for a multiplicity of scfv which have different binding specificities. Given that the size of a scfv library often limits the diversity of potential scfv sequences, it is typically desirable to us scfv libraries of as large a size as possible. The time and economic considerations of generating a number of very large polysome scFv-display libraries can become prohibitive. To avoid this substantial problem, multiple predetermined epitope species (receptor species) can be concomitantly screened in a single library, or sequential screening against a number of epitope species can be used. In one variation, multiple target epitope species, each encoded on a separate bead (or subset of beads), can be mixed and incubated with a polysome-display scfv library under suitable binding conditions. The collection of beads, comprising multiple epitope species, can then be used to isolate, by affinity selection, scfv library members. Generally, subsequent affinity screening rounds can include the same mixture of beads, subsets thereof, or beads containing only one or two individual epitope species. This approach affords efficient screening, and is compatible with laboratory automation, batch processing, and high throughput screening methods.

A variety of techniques can be used in the present invention to diversify a peptide library or single-chain antibody library, or to diversify, prior to or concomitant with shuffling, around variable segment peptides found in early rounds of panning to have sufficient binding activity to the predetermined macromolecule or epitope. In one approach, the positive selected peptide/polynucleotide complexes (those identified in an early round of affinity enrichment) are sequenced to determine the identity of the active peptides. Oligonucleotides are then synthesized based on these active peptide sequences, employing a low level of all bases incorporated at each step to produce slight variations of the primary oligonucleotide sequences. This mixture of (slightly) degenerate oligonucleotides is then cloned into the variable segment sequences at the appropriate locations. This method produces systematic, controlled variations of the starting peptide sequences, which can then be shuffled. It requires, however, that individual positive nascent peptide/polynucleotide complexes be sequenced before mutagenesis, and thus is useful for expanding the diversity of small numbers of recovered complexes and selecting variants having higher binding affinity and/or higher binding specificity. In a variation, mutagenic PCR amplification of positive selected peptide/polynucleotide complexes (especially of the variable region sequences, the amplification products of which are shuffled in vitro and/or in vivo and one or more additional rounds of screening is done prior to sequencing. The same general approach can be employed with single-chain antibodies in order to expand the diversity and enhance the binding affinity/specificity, typically by diversifying CDRs or adjacent framework regions prior to or concomitant with shuffling. If desired, shuffling reactions can be spiked with mutagenic oligonucleotides capable of in vitro recombination with the selected library members can be included. Thus, mixtures of synthetic oligonucleotides and PCR produced polynucleotides (synthesized by error-prone or high-fidelity methods) can be added to the in vitro shuffling mix and be incorporated into resulting shuffled library members (shufflants).

The present invention of shuffling enables the generation of a vast library of CER-variant single-chain antibodies. One way to generate such antibodies is to insert synthetic CDRs into the single-chain antibody and/or CDR randomization prior to or concomitant with shuffling. The sequences of the synthetic CDR cassettes are selected by referring to known sequence data of human CDR and are selected in the discretion of the practitioner according to the following guidelines: synthetic CDRs will have at least 40 percent positional sequence identity to known CDR sequences, and preferably will have at least 50 to 70 percent positional sequence identity to known CDR sequences. For example, a collection of synthetic CDR sequences can be generated by synthesizing a collection of oligonucleotide sequences on the basis of naturally-occurring human CDR sequences listed in Kabat (Kabat et al, 1991); the pool (s) of synthetic CDR sequences are calculated to encode CDR peptide sequences having at least 40 percent sequence identity to at least one known naturally-occurring human CDR sequence. Alternatively, a collection of naturally-occurring CDR sequences may be compared to generate consensus sequences so that amino acids used at a residue position frequently (i.e., in at least 5 percent of known CDR sequences) are incorporated into the synthetic CDRs at the corresponding position(s). Typically, several (e.g., 3 to about 50) known CDR sequences are compared and observed natural sequence variations between the known CDRs are tabulated, and a collection of oligonucleotides encoding CDR peptide sequences encompassing all or most permutations of the observed natural sequence variations is synthesized. For example but not for limitation, if a collection of human VH CDR sequences have carboxy-terminal amino acids which are either Tyr, Val, Phe, or Asp, then the pool(s) of synthetic CDR oligonucleotide sequences are designed to allow the carboxy-terminal CDR residue to be any of these amino acids. In some embodiments, residues other than those which naturally-occur at a residue position in the collection of CDR sequences are incorporated: conservative amino acid substitutions are frequently incorporated and up to 5 residue positions may be varied to incorporate non-conservative amino acid substitutions as compared to known naturally-occurring CDR sequences. Such sequences can be used in primary library members (prior to first round screening) and/or can be used to spike in vitro shuffling reactions of selected library member sequences. Construction of such pools of defined and/or degenerate sequences will be readily accomplished by those of ordinary skill in the art.

The collection of synthetic CDR sequences comprises at least one member that is not known to be a naturally-occurring CDR sequence. It is within the discretion of the practitioner to include or not include a portion of random or pseudorandom sequence corresponding to N region addition in the heavy chain CDR; the N region sequence ranges from 1 nucleotide to about 4 nucleotides occurring at V-D and D-J junctions. A collection of synthetic heavy chain CDR sequences comprises at least about 100 unique CDR sequences, typically at least about 1,000 unique CDR sequences, preferably at least about 10,000 unique CDR sequences, frequently more than 50,000 unique CDR sequences; however, usually not more than about 1×106 unique CDR sequences are included in the collection, although occasionally $1 \times 10^7$ to $1 \times 10^8$ unique CDR sequences are present, especially if conservative amino acid substitutions are permitted at positions where the conservative amino acid substituent is not present or is rare (i.e., less than 0.1 percent) in that position in naturally-occurring human CDRS. In general, the number of unique CDR sequences included in a library should not exceed the expected number of primary transformants in the library by more than a factor of 10. Such single-chain antibodies generally bind of about at least $1 \times 10$ m-, preferably with an affinity of about at least $5 \times 10^7$ M-1, more preferably with an affinity of at least $1 \times 10^8$ M-1 to $1 \times 10^9$ M-1 or more, sometimes up to $1 \times 10^{10}$ M-1 or more. Frequently, the predetermined antigen is a human protein, such as for example a human cell surface antigen (e. g., CD4, CD8, IL-2 receptor, EGF receptor, PDGF receptor), other human biological macromolecule (e.g., thrombomodulin, protein C, carbohydrate antigen, sialyl Lewis antigen, Lselectin), or nonhuman disease associated macromolecule (e.g., bacterial LPS, virion capsid protein or envelope glycoprotein) and the like.

High affinity single-chain antibodies of the desired specificity can be engineered and expressed in a variety of systems. For example, scfv have been produced in plants (Fiirek et al, 1993) and can be readily made in prokaryotic systems (Owens and Young, 1994; Johnson and Bird, 1991). Furthermore, the single-chain antibodies can be used as a basis for constructing whole antibodies or various fragments thereof (Kettleborough et al, 1994). The variable region encoding sequence may be isolated (e.g., by PCR amplification or subcloning) and spliced to a sequence encoding a desired human constant region to encode a human sequence antibody more suitable for human therapeutic uses where immunogenicity is preferably minimized. The polynucleotide(s) having the resultant fully human encoding sequence(s) can be expressed in a host cell (e.g., from an expression vector in a mammalian cell) and purified for pharmaceutical formulation.

The DNA expression constructs will typically include an expression control DNA sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the mutant "engineered" antibodies.

As stated previously, the DNA sequences will be expressed in hosts after the sequences have been operably linked to an expression control sequence (i.e., positioned to ensure the transcription and translation of the structural gene). These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

In addition to eukaryotic microorganisms such as yeast, mammalian tissue cell culture may also be used to produce the polypeptides of the present invention (see Winnacker, 1987), which is incorporated herein by reference). Eukaryotic cells are actually preferred, because a number of suitable host cell lines capable of secreting intact immunoglobulins have been developed in the art, and include the CHO cell lines, various COS cell lines, HeLa cells, and myeloma cell lines, but preferably transformed Bcells or hybridomas. Expression vectors for these cells can include expression control sequences, such as an origin of replication, a promoter, an enhancer (Queen et al, 1986), and necessary processing information sites, such as ribosome binding sites, RNA splice sites, polyadenylation sites, and transcriptional terminator sequences. Preferred expression control sequences are promoters derived from immunoglobulin genes, cytomegalovirus, SV40, Adenovirus, Bovine Papilloma Virus, and the like.

Eukaryotic DNA transcription can be increased by inserting an enhancer sequence into the vector. Enhancers are cis-acting sequences of between 10 to 300 bp that increase transcription by a promoter. Enhancers can effectively increase transcription when either 5' or 3' to the transcription unit. They are also effective if located within an intron or within the coding sequence itself. Typically, viral enhancers are used, including SV40 enhancers, cytomegalovirus enhancers, polyoma enhancers, and adenovirus enhancers. Enhancer sequences from mammalian systems are also commonly used, such as the mouse immunoglobulin heavy chain enhancer.

Mammalian expression vector systems will also typically include a selectable marker gene. Examples of suitable markers include, the dihydrofolate reductase gene (DHFR), the thymidine kinase gene (TK), or prokaryotic genes conferring drug resistance. The first two marker genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The vectors containing the DNA segments of interest can be transferred into the host cell by well-known methods, depending on the type of cellular host. For example, calcium chloride transfection is commonly utilized for prokaryotic cells, whereas calcium phosphate treatment. lipofection, or electroporation may be used for other cellular hosts. Other methods used to transform mammalian cells include the use of Polybrene, protoplast fusion, liposomes, electroporation, and micro-injection (see, generally, Sambrook et al, 1982 and 1989).

Once expressed, the antibodies, individual mutated immunoglobulin chains, mutated antibody fragments, and other immunoglobulin polypeptides of the invention can be purified according to standard procedures of the art, including ammonium sulfate precipitation, fraction column chromatography, gel electrophoresis and the like (see, generally, Scopes, 1982). Once purified, partially or to homogeneity as desired, the polypeptides may then be used therapeutically or in developing and performing assay procedures, immunofluorescent stainings, and the like (see, generally, Lefkovits and Pernis, 1979 and 1981; Lefkovits, 1997).

The antibodies generated by the method of the present invention can be used for diagnosis and therapy. By way of illustration and not limitation, they can be used to treat cancer, autoimmune diseases, or viral infections. For treatment of cancer, the antibodies will typically bind to an antigen expressed preferentially on cancer cells, such as erbB-2, CEA, CD33, and many other antigens and binding members well known to those skilled in the art.

Two-Hybrid Based Screening Assays

Shuffling can also be used to recombinatorially diversify a pool of selected library members obtained by screening a two-hybrid screening system to identify library members which bind a predetermined polypeptide sequence. The selected library members are pooled and shuffled by in vitro and/or in vivo recombination. The shuffled pool can then be screened in a yeast two hybrid system to select library members which bind said predetermined polypeptide sequence (e. g., and SH2 domain) or which bind an alternate predetermined polypeptide sequence (e.g., an SH2 domain from another protein species).

An approach to identifying polypeptide sequences which bind to a predetermined polypeptide sequence has been to use a so-called "two-hybrid" system wherein the predetermined polypeptide sequence is present in a fusion protein (Chien et al, 1991). This approach identifies protein-protein interactions in vivo through reconstitution of a transcriptional activator (Fields and Song, 1989), the yeast Gal4 transcription protein. Typically, the method is based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacz, HIS3) which is operably linked to a Gal4 binding site. Typically, the two-hybrid method is used to identify novel polypeptide sequences which interact with a known protein (Silver and Hunt, 1993; Durfee et al, 1993; Yang et al, 1992; Luban et al, 1993; Hardy et al, 1992; Bartel et al, 1993; and Vojtek et al, 1993). However, variations of the two-hybrid method have been used to identify mutations of a known protein that affect its binding to a second known protein (Li and Fields, 1993; Lalo et al, 1993; Jackson et al, 1993; and Madura et al, 1993). Two-hybrid systems have also been used to identify interacting structural domains of two known proteins (Bardwell et al, 1993; Chakrabarty et al, 1992; Staudinger et al, 1993; and Milne and Weaver 1993) or domains responsible for oligomerization of a single protein (Iwabuchi et al, 1993; Bogerd et al, 1993). Variations of two-hybrid systems have been used to study the in vivo activity of a proteolytic enzyme (Dasmahapatra et al, 1992). Alternatively, an *E. coli*/BCCP interactive screening system (Germino et al, 1993; Guarente, 1993) can be used to identify interacting protein sequences (i.e., protein sequences which heterodimerize or form higher order heteromultimers). Sequences selected by a two-hybrid system can be pooled and shuffled and introduced into a two-hybrid system for one or more subsequent rounds of screening to identify polypeptide sequences which bind to the hybrid containing the predetermined binding sequence. The sequences thus identified can be compared to identify consensus sequence(s) and consensus sequence kernals.

In general, standard techniques of recombination DNA technology are described in various publications (e.g. Sambrook et al, 1989; Ausubel et al, 1987; and Berger and Kimmel, 1987) each of which is incorporated herein in its entirety by reference. Polynucleotide modifying enzymes were used according to the manufacturer's recommendations. Oligonucleotides were synthesized on an Applied Biosystems Inc. Model 394 DNA synthesizer using ABI chemicals. If desired, PCR amplimers for amplifying a predetermined DNA sequence may be selected at the discretion of the practitioner.

One microgram samples of template DNA are obtained and treated with U.V. light to cause the formation of dimers, including TT dimers, particularly purine dimers. U.V. exposure is limited so that only a few photoproducts are generated per gene on the template DNA sample. Multiple samples are treated with U.V. light for varying periods of time to obtain template DNA samples with varying numbers of dimers from U.V. exposure.

A random priming kit which utilizes a non-proofreading polymease (for example, Prime-It II Random Primer Labeling kit by Stratagene Cloning Systems) is utilized to generate different size polynucleotides by priming at random sites on templates which are prepared by U.V. light (as described above) and extending along the templates. The priming protocols such as described in the Prime-It II Random Primer Labeling kit may be utilized to extend the primers. The dimers formed by U.V. exposure serve as a roadblock for the extension by the non-proofreading polymerase. Thus, a pool of random size polynucleotides is present after extension with the random primers is finished.

The present invention is further directed to a method for generating a selected mutant polynucleotide sequence (or a population of selected polynucleotide sequences) typically in the form of amplified and/or cloned polynucleotides, whereby the selected polynucleotide sequences(s) possess at least one desired phenotypic characteristic (e.g., encodes a polypeptide, promotes transcription of linked polynucleotides, binds a protein, and the like) which can be selected for. One method for identifying hybrid polypeptides that possess a desired structure or functional property, such as binding to a predetermined biological macromolecule (e.g., a receptor), involves the screening of a large library of polypeptides for individual library members which possess the desired structure or functional property conferred by the amino acid sequence of the polypeptide.

In one embodiment, the present invention provides a method for generating libraries of displayed polypeptides or displayed antibodies suitable for affinity interaction screening or phenotypic screening. The method comprises (1) obtaining a first plurality of selected library members comprising a displayed polypeptide or displayed antibody and an associated polynucleotide encoding said displayed polypeptide or displayed antibody, and obtaining said associated polynucleotides or copies thereof wherein said associated polynucleotides comprise a region of substantially identical sequences, optimally introducing mutations into said polynucleotides or copies, (2) pooling the polynucleotides or copies, (3) producing smaller or shorter polynucleotides by interrupting a random or particularized priming and synthesis process or an amplification process, and (4) performing amplification, preferably PCR amplification, and optionally mutagenesis to homologously recombine the newly synthesized polynucleotides.

It is a particularly preferred object of the invention to provide a process for producing hybrid polynucleotides which express a useful hybrid polypeptide by a series of steps comprising:

(a) producing polynucleotides by interrupting a polynucleotide amplification or synthesis process with a means for blocking or interrupting the amplification or synthesis process and thus providing a plurality of smaller or shorter polynucleotides due to the replication of the polynucleotide being in various stages of completion;

(b) adding to the resultant population of single- or double-stranded polynucleotides one or more single- or double-stranded oligonucleotides, wherein said added oligonucleotides comprise an area of identity in an area of heterology to one or more of the single- or double-stranded polynucleotides of the population;

(c) denaturing the resulting single- or double-stranded oligonucleotides to produce a mixture of single-stranded polynucleotides, optionally separating the shorter or smaller polynucleotides into pools of polynucleotides having various lengths and further optionally subjecting said polynucleotides to a PCR procedure to amplify one or more oligonucleotides comprised by at least one of said polynucleotide pools;

(d) incubating a plurality of said polynucleotides or at least one pool of said polynucleotides with a polymerase under conditions which result in annealing of said single-stranded polynucleotides at regions of identity between the single-stranded polynucleotides and thus forming of a mutagenized double-stranded polynucleotide chain, (e) optionally repeating steps (c) and (d);

(f) expressing at least one hybrid polypeptide from said polynucleotide chain, or chains; and (g) screening said at least one hybrid polypeptide for a useful activity.

In a preferred aspect of the invention, the means for blocking or interrupting the amplification or synthesis process is by utilization of UV light, DNA adducts, DNA binding proteins.

In one embodiment of the invention, the DNA adducts, or polynucleotides comprising the DNA adducts, are removed from the polynucleotides or polynucleotide pool, such as by a process including heating the solution comprising the DNA fragments prior to further processing.

Having thus disclosed exemplary embodiments of the present invention, it should be noted by those skilled in the art that the disclosures are exemplary only and that various other alternatives, adaptations and modifications may be made within the scope of the present invention. Accordingly, the present invention is not limited to the specific embodiments as illustrated herein.

Without further elaboration, it is believed that one skilled in the art can, using the preceding description, utilize the present invention to its fullest extent. The following examples are to be considered illustrative and thus are not limiting of the remainder of the disclosure in any way whatsoever.

4. Transposons

4.1. General Applications

In one aspect, the present invention relates generally to the field of transposable nucleic acid and, more particularly to production and use of a modified transposase enzyme in a system for introducing genetic changes to nucleic acid.

The present invention relates to transposable elements isolated from maize and a process for using the same to identify and isolate genes and to insert desired gene sequences into plants in a heritable manner.

4.2. Specific Methodologies

4.2.1. Description of Transposable Elements

Transposable genetic elements are DNA sequences, found in a wide variety of prokaryotic and eukaryotic organisms, that can move or transpose from one position to another position in a genome. In vivo, intra-chromosomal transpositions as well as transpositions between chromosomal and non-chromosomal genetic material are known. In several systems, transposition is known to be under the control of a transposase enzyme that is typically encoded by the transposable element. The genetic structures and transposition mechanisms of various transposable elements are summarized, for example, in "Transposable Genetic Elements" in "The Encyclopedia of Molecular Biology," Kendrew and Lawrence, Eds., Blackwell Science, Ltd., Oxford (1994), incorporated herein by reference.

Transposable elements (hereinafter "transposons") are natural gene transfer vectors in bacteria, yeast, *Drosophila melanogaster* and other organisms. The best documented examples of transposons in bacteria are those carrying genes that confer antibiotic resistance on the bacterium in which they reside. These transposons tend to accumulate and become a part of bacterial plasmids. The biological properties of the plasmids permit the spread of the plasmids and their passengers, e.g., drug resistance transposons, in bacterial populations.

Transposons have also been used to identify and isolate otherwise inaccessible genes (See Bingham, P. M., Kidwell, M. G. and Rubin, G. M., Cell 29:995–1004 (1982)). That is, the White locus of *Drosophila melanogaster* has been isolated by virtue of the existence of an insertion mutation at the locus caused by a transposon that has been isolated and studied using recombinant DNA technology. Such applications are receiving increasing attention in plants and animals.

The use of transposable elements as deliberate gene transfer vectors evolved from work in bacteria and yeast and, as stated above, has recently been developed into a useful research tool in *Drosophila melanogaster* (See Rubin, G. M. and Spradling, A. C., Science 218:348–353 (1982)). The basic principle on which such applications are based is that transposons are compact genetic units that contain within their sequences essentially all of the coding information required for transposition. Although the transposition functions are only now beginning to be identified in higher organisms, in bacteria, they are known to include enzymes termed transposases, as well as molecules which regulate expression of the transposase and other genes encoding transposition-specific proteins.

Transposable elements are mobile stretches of DNA which are defined by two end terminals, usually denoted attL and attR at the left and right attachment ends respectively. Natural transposable elements contain DNA coding for transposases, and often portable genes conferring traits such as resistance to antibiotics. Some transposable elements can insert randomly into targeted DNA while others are sequence specific in their insertion sites. Transposons have been implicated as having a major role in evolution, and there is evidence for natural multifunctional enzymes having originated from the natural fusion of different protein domains.

Scientists have taken advantage of transposons to transport reporter genes for use in studying gene expression. These include transcriptional (Type I) fusions and translational (Type II) fusions. Transcriptional fusions, unlike translational fusions, place a reporter gene under the control of another promoter, but do not translationally fuse two protein domains. Translational fusions have generally been made to link a reporter gene carried inside the transposon to the translational frame of the target gene so that the reporter gene is expressed under direct control of the transcription and translation signals of the target gene of interest to study gene regulation. This requires that an open reading frame extend through the end of the transposable element to join an internal reporter protein to external translational sequences. This usually results in complete inactivation of the target gene.

4.2.2. Rational Protein Design

The main goal of modern protein chemistry is to be able to design proteins with desired functions. The approach taken by the majority of scientists has been called rational protein design, which is highly dependent on knowledge of protein structure in three dimensions and protein folding. While an extremely powerful tool, rational protein design is currently limited to a small subset of enzymes: those with well defined three dimensional structures. The classic examples include proteins such as subtilisin from several Bacillus sp. (Wells, Powers et al. Proc Natl Acad Sci USA. (1987). 84: 1219–1223.) and T4 lysozyme (Matsumura, Becktel et al. (1989). Proc Natl Acad Sci USA. 86: 6562–6566.). The three dimensional organization of the amino acid side chains of the protein must be known at high resolution, and often protein/substrate and mutant structures must be known as well. While this method is useful, it is expensive, time consuming and requires difficult predictions. Even with a complete three dimensional X- ray crystallography structure in hand, it has proven difficult to design proteins with specific desired activities. To address these problems, methods which allow the accelerated evolution of proteins in vivo or in vitro can take advantage of natural mutagenic mechanisms and their resulting variability.

4.2.2.1. Protein Fusions

Protein (translational) fusion can be created by the joining of translational sequences from two different genes to create a hybrid protein molecule. These applications have traditionally included the study of gene expression in microorganisms and eukaryotes (Casadaban, Martinez-Arias et al. (1983). Recombinant DNA. Methods in Enzymology. 100: 293–308.).

The use of protein fusion in vitro to generate hybrid (chimeric) proteins has gained importance in the development of novel or multifunctional enzyme activities. Applications include using protein domains to aid in protein purification (Sherwood. (1991). TIBTECH. 9: 1–3.) or to tag proteins for delivery to specific cellular locations (Crozel, Lazdunski et al. (1984). FEBS Lett. 172: 183–188; Moore and Kelly. (1986). Nature. 321: 443–446; Roitsch and Lehle. (1991). Eur J Biochem. 195: 145–50.). Domain shuffling between different proteins shows promise to create protein products with unique uses, often to bind a particular enzymatic activity to a site of interest (Panayotatos, Fontaine et al. (1988). Molecular genetics of bacteria and phages: prokaryotic gene regulation. 174.), as a reporter system for protein- protein interactions (Fields and Song. (1989). Nature. 340: 245–246.), to study the relatedness of different proteins (Caramori, Albertini et al. (1991). Gene. 98: 37–44.) or as targeted pharmaceuticals (Pastan and FitzGerald. (1991). Science. 254: 1173–1177.). Finally, another promising application of protein fusion to biotechnology is in creating multi-catalytic enzymes which are important in biocatalysis since they represent an alternative to co-immobilization and chemical crosslinking to create multienzyme systems (Bulow and Mosbach. (1991). TIBTECH. 9: 226–231.).

4.2.2.2. Problems in the Development of Protein Fusions

Unfortunately, the construction of functional hybrid proteins can require an extensive knowledge of a protein's structure and functional domains in order to select a proper site for fusion. Many attempts have failed to produce the desired properties (Bowie and Sauer. (1989). J Bio Chem. 264: 7596–7602; Ellis, Morgan et al. (1986). Proc Natl Acad Sci, USA. 83: 8137–8141; Guan and Rose. (1984). Cell. 37: 779–787; Hellebust, Murby et al. (1989). BioTech. 7: 165–168.). Random deletions can be made to fuse two domains, but this is typically done for only one domain at a time, and the cost and time involved in such trial and error efforts can be substantial. In addition, while some gene fusions can be used to stabilize proteins, unstable structures are often formed which are recognized by the cellular degrading machinery (Bowie and Sauer. (1989). J Bio Chem. 264: 7596–7602; Hellebust, Murby et al. (1989). BioTech. 7: 165–168.). Also, even with the advanced level of molecular biological techniques available today, cloning remains a labor-intensive procedure, the results of which are not trivially predictable. Several tools have been developed to make the construction of protein fusions simpler. These tools include new plasmid systems with convenient restriction sites (Shapira, Chou et al. (1983). Gene. 25: 71–82.), and a method for making gene fusions using the Polymerase Chain Reaction (PCR) so that convenient restriction sites are not required (Horton, Hunt et al. (1989). Gene. 77: 61–8.). None of these approaches, however, offers a truly simple way of making random protein fusions which eliminates the labor-intensive, trial and error aspects of traditional techniques, especially in the case when at least one of the two domains being studied has not yet been well characterized.

4.2.3. In vitro Transposition Systems

In vitro transposition systems that utilize the particular transposable elements of bacteriophage Mu and bacterial transposon Tn10 have been described, by the research groups of Kiyoshi Mizuuchi and Nancy Kleckner, respectively.

The bacteriophage Mu system was first described by Mizuuchi, K., "In Vitro Transposition of Bacteria Phage Mu: A Biochemical Approach to a Novel Replication Reaction," Cell:785–794 (1983) and Craigie, R. et al., "A Defined System for the DNA Strand-Transfer Reaction at the Initiation of Bacteriophage Mu Transposition: Protein and DNA Substrate Requirements," P.N.A.S. U.S.A. 82:7570–7574 (1985). The DNA donor substrate (mini-Mu) for Mu in vitro reaction normally requires six Mu transposase binding sites (three of about 30 bp at each end) and an enhancer sequence located about 1 kb from the left end. The donor plasmid must be supercoiled. Proteins required are Mu-encoded A and B proteins and host-encoded HU and IHF proteins. Lavoie, B. D, and G. Chaconas, "Transposition of phage Mu DNA," Curr. Topics Microbiol. Immunol. 204:83–99 (1995). The Mu-based system is disfavored for in vitro transposition system applications because the Mu termini are complex and sophisticated and because transposition requires additional proteins above and beyond the transposase.

The Tn10 system was described by Morisato, D. and N. Kleckner, "Tn10 Transposition and Circle Formation in vitro," Cell 51:101–111 (1987) and by Benjamin, H. W. and N. Kleckner, "Excision Of Tn10 from the Donor Site During Transposition Occurs By Flush Double-Strand Cleavages at the Transposon Termini," P.N.A.S. U.S.A. 89:4648–4652 (1992). The Tn10 system involves a supercoiled circular DNA molecule carrying the transposable element (or a linear DNA molecule plus *E. Coli* IHF protein). The transposable element is defined by complex 42 bp terminal sequences with IHF binding site adjacent to the inverted repeat. In fact, even longer (81 bp) ends of Tn10 were used in reported experiments. Sakai, J. et al., "Identification and Characterization of Pre-Cleavage Synaptic Complex that is an Early Intermediate in Tn10 transposition," E.M.B.O. J. 14:4374–4383 (1995). In the Tn10 system, chemical treatment of the transposase protein is essential to support active transposition. In addition, the termini of the Tn10 element limit its utility in a generalized in vitro transposition system.

Both the Mu- and Tn10-based in vitro transposition systems are further limited in that they are active only on covalently closed circular, supercoiled DNA targets. What is desired is a more broadly applicable in vitro transposition system that utilizes shorter, more well defined termini and which is active on target DNA of any structure (linear, relaxed circular, and supercoiled circular DNA).

4.2.4. Importance of Transposons in Agriculture

Currently, there is a great deal of interest in the development of gene transfer vectors for use with agriculturally important plants (See Outlook for Science and Technology, The Next Five Years, Vol. III (National Science Foundation (1982); and O.T.A. Report, Impact of Applied Genetics (1981)).

Although the United States presently has an excess productivity in the agricultural sector, this is recognized as a local and short term condition. Thus, agricultural research and planning must be based on long term considerations. The variety of problems surrounding increases in population, degradation of prime farm land and decreasing availability of good farm land necessitates the increased use of marginal land, as well as exogenous fertilizers and chemical pest control compositions.

Classical plant breeding programs have thus far been successful in increasing agricultural productivity. However, a substantial fraction of the increase in farm productivity experienced in the United States in the past 40 years is attributable to the use of fertilizers and modem energy intensive cultivation practices, both of which are increasingly costly. The ability of plant breeding alone to sustain productivity is a matter of some question. Plant breeders are divided in their views on whether genetic improvements will continue at the rate that has occurred over the past few decades or will begin to level out. Since such questions cannot be resolved a priori, it is prudent to explore a variety of additional means by which agronomically useful traits can be accumulated and improved in major crop plants. The unconventional areas that are presently receiving the most attention in the academic research establishment, as well as in both small and large firms with plant-oriented research programs are wide genetic crosses, tissue culture and the development of gene transfer systems that circumvent fertility barriers.

In the past, many attempts have been made to transform plant cells with DNA from a variety of sources. The first unequivocal demonstration that DNA transfer can and does occur in plants emerged from the work described above on *Agrobacterium tumefaciens* Ti plasmid. However, Ti-plasmid mediated gene transfer is presently accomplished only in dicotyledonous plants that interact with the plasmid's natural host bacterium. Since most major crop species are monocotyledonous, ti-plasmid mediated gene transfer has limited applications.

4.2.4.1. Use of Transposons on the Ti Plasmid of Agrobacterium

In higher organisms, transposons have been, or are being, used in several ways. For example, transposons are used as mutagens on the Ti plasmid of *Agrobacterium tumefaciens*. That is, a method for using bacterial transposons to cause insertion mutations in the *Agrobacterium tumefaciens* Ti plasmid, the causative agent of crown gall disease in dicotyledonous plants, has been developed. (See Zambriski, P., Goodman, H., Van Montagu, M. and Schell, J., Mobile Genetic Elements, J. Shapiro, Ed., (Academic Press) New York, pp. 506–535 (1983)). By this technique, it has become possible to identify the plasmid-borne genes that are responsible for virulence, as well as those that are responsible for the tumorous transformation of plant cells caused by the Ti plasmid. Further, it has become possible to show by using transposable elements, that a portion of the Ti plasmid can be integrated into plant genomes and can act as a vehicle for transferring genes from virtually any organism to any dicotyledonous plant that is susceptible to *Agrobacterium tumefaciens*.

4.2.4.2. Use of Transposons in Maize

In maize, a monocotyledon, transposable elements were first genetically identified in the mid-1940s. These elements have been studied extensively and their genetic behavior has been extensively reviewed (See McClintock, B., Cold Spring Harbor Symp. Quant. Biol. 16:13–47 (1951); McClintock, B., Cold Spring Harbor Symp. Quant. Biol. 21:197–216 (1956); McClintock, B., Brookhaven Symp. Biol. 18:162–184 (1965); Fincham, J. R. S., and Sastry, G. R. K., Ann. Rev. Genet. 8:15–50 (1974); and Fedoroff, N., Mobile Genetic Elements, J. Shapiro, Ed., (Academic Press) New York, pp. 1–63 (1983)).

It has been demonstrated that transposons are normal, although cryptic, residents of the maize genome and that upon activation, they are responsible for various types of genetic rearrangements, including chromosome breakage, deletions, duplications, inversions and translocations. In addition, it has been shown that certain common types of unstable mutations, which have been studied for decades in both maize and in other organisms, are attributable to the insertion of transposons into genes or genetic loci.

4.2.5. Mu and the Transposing Bacteriophage

Bacteriophage Mu represents a class of transposons known as transposable bacteriophage which both function as a virus and a transposon. Mu replicates itself by transposing at high frequency, but can also integrate randomly into its host's genome as a lysogen. Mu is a model system for other transposable bacteriophage which are generally highly homologous. These include the Pseudomonas phage D3112, D108, and several other phage.

Because of the randomness of Mu insertions, and the high levels of transposition which can be generated by Mu strains containing a temperature sensitive transposition repressor (Mucts strains), Mu has been developed into a genetic tool to study gene expression in bacterial systems. Transposition of Mu derivatives has allowed scientists to perturb and examine the basic components critical to protein expression and translation. The most commonly used Mu derivatives include reporter genes which have been integrated into the Mu genome.

4.2.5.1. Type I Fusions

Type I transcriptional fusions have been used to study gene expression and regulation by co-opting the native transcriptional signal to express the exogenous reporter gene. For example for gene expression in *E. coli*, yeast, and Drosophila development.

4.2.5.2. Type II Fusions

Type II fusions have also been used to study gene expression and regulation, but in this case not only co-opt the transcriptional signals, but any translational signals as well to express the reporter gene. In this type of system the protein product usually only expresses the activity of the reporter exogenous gene. MudII elements are mini-Mu deletion elements which are type II Mu transposable elements. Examples of these include beta-galactosidase fusion elements, where a beta-galactosidase (lacZ) reporter gene is inserted via transposable elements to detect transcription and translation of regulated gene systems. This usually results in the inactivation of the targeted gene.

Two types of Mu protein fusions have been developed, lacZ fusion elements and nptI fusion elements (Symonds, Toussaint et al. (1987). Phage Mu) The lacZ elements have been used to study translation regulation, determination of the translation phase of target genes, infer the location of a protein fusion by hybrid protein size, determine amino terminal sequence, and raise antibodies to regions of the protein of interest. By far the major goal of these studies has been to determine mechanisms of gene expression in the studied organisms.

The nptI system was designed to perform transposon-tagging since nptI is known to function as an aminoglycoside resistance gene in a variety of organisms. Transposon tagging is a method of creating an mutant by inserting a transposon with a selectable marker into the gene of interest so that mutants which inactivate the gene can be identified and maintained. This element is useful since it allows the nptI to be directly linked to the transcription/translation system of the organism being studied.

In these studies there has been no emphasis on creating novel proteins with new activities using these transposable elements. More importantly, these Mu elements are restricted to making amino-terminal fusions to the reporter protein. In these cases the inserted reporter gene is fused to the carboxy-end of the truncated targeted protein, terminating inside the Mu. If the transposable element were to insert before the amino terminal of a targeted gene, functional translation could only occur on the marker gene by itself, and no translation of the target gene would occur.

4.2.5.3. Problems with Mu

Unfortunately, available Mu elements had several problems. First, it has not been demonstrated that Mu elements can be readily used as a general method for the development of fusion proteins with two active domains. Second, the Mu elements used thus far for creation of protein fusions can not be used for construction of "carboxy-terminal" fusions since they did not have an open reading frame extending into the element. Third, the Mu elements previously used have long linker regions which incorporate a 40 amino acid linker between the fused domains. This could create protein folding problems or unwanted domain interactions. Fourth the currently existing Mu elements had only a single restriction site for the insertion of protein domains. Finally, although Mu elements which had deleted ends existed, it was not known whether they would transpose well with additional sequences added in such close proximity to the right end and whether the intervening linker region which would join the two protein domains would interfere with the construction of active chimeric proteins.

4.2.6. Other Transposons

Other transposons have been used in a similar manner as Mu to create lac fusions to study gene expression. These include Tn10 and Tn917 (Berg and Howe. (1989). Mobile DNA). The Tn5 element has also been used to construct phoA fusions in vivo. Fusions with alkaline phosphatase (phoA) have also been used to probe the structure of membrane bound proteins (Lloyd and Kadner. (1990). J Bacteriol. 172: 1688–93.). In general, these transposons have been used to study the membrane topology structure of a particular gene and protein secretion. The resultant fusion proteins are also limited to amino-terminal fusion of the reporter PhoA reporter protein resulting in fusion at the carboxy end of the targeted gene.

In general, these types of fusions have been applied to the study of gene expression. These elements were constructed with truncated marker proteins that extend through the end of the transposon. Transposition of the element can create an in-frame fusion with a target gene, thereby activating expression. Mini-Mu elements are used because they transpose at high frequencies, insert randomly, and can be packaged along with a target plasmid and transduced to a new cell (Symonds, Toussaint et al. (1987). Phage Mu). Some of the more pertinent work that has been done in the area of transposable elements are detailed in the following.

Namgoong et al., (1994), teach that the Mu transposition reaction attachment sites attL and attR can promote the assembly of higher order complexes held together by non-covalent protein-DNA and protein-protein interactions. (Namgoong, Jayaram et al. (1994). J Mol Biol. 238: 514–527.)

Harel et al., (1990), teach that in Mu helper-mediated transposition packaging the left end contains an essential domain defined by nucleotides 1 to 54 of the left end (attL). At the right end (attR), they teach that the essential sequences for transposition require not more than the first 62 base pairs (bp), although the presence of sequences between 63 and 117 bp from the right end increase transposition frequency about 15-fold. (Harel, Dupliessis et al. (1990). Arch Microbiol. 154: 67–72.)

Groenen and van de Putte (1986), teach that the Mu A protein binds weakly to sequences between nucleotides 1 to 30 on the right end (R1) and between nucleotides 110 and 135 on the left end (L2). Mutations in these weak A binding sites have a greater effect on transposition than mutations of corresponding base pairs in the stronger A binding sites, located adjacent to these weak A binding sites. (Groenen and van de Putte. (1986). J Mol Biol. 189: 597–602.)

Groenen and et al. (1985) teach the DNA sequences at the end of the genome of bacteriophage Mu that are essential for transposition. (Groenen, Timmers et al. (1985). Proc Natl Acad Sci, USA. 82: 2087–2091.)

Lloyd and Kadner teach the how to probe the topology of the uhpT sugar phosphate transporter using a Tn5phoA element. (Lloyd and Kadner. (1990). J Bacteriol. 172: 1688–93.)

Phage Mu (1987), Cold Spring Harbor Laboratory Press (Symonds, et al eds.) teaches general methods for handling and working with bacteriophage Mu as a transposon, and describes the various uses of mini- Mu elements including the construction of Mu transcriptional and translational fusions.

Silhavy and Beckwith (1985) teaches the various uses of lac fusions for the study of biological problems. (Silhavy and Beckwith. (1985). Microbiol Rev. 49: 398–418.) Mobile DNA, (1989), American Society for Microbiology, Publishers. (Berg, Howe, eds) describes transposons.

Casadaban, et al. (1983) Methods in Enzymol, provides a good general review of beta-galactosidase gene fusions for the study of gene expression. (Casadaban, Martinez-Arias et al. (1983). Recombinant DNA. Methods in Enzymology. 100: 293–308.)

4.3.1. In vitro Transposition System

The present invention is summarized in that an in vitro transposition system comprises a preparation of a suitably modified transposase of bacterial transposon Tn5, a donor DNA molecule that includes a transposable element, a target DNA molecule into which the transposable element can transpose, all provided in a suitable reaction buffer.

4.3.1.1. Donor DNA Molecule: Transposable DNA Sequence of Interest

The transposable element of the donor DNA molecule is characterized as a transposable DNA sequence of interest, the DNA sequence of interest being flanked at its 5'- and 3'-ends by short repeat sequences that are acted upon in trans by Tn5 transposase.

4.3.1.1.1. Modified Transposase Enzyme Comprises Two Classes of Differences from Wild Type Tn5 Transposase The invention is further summarized in that the suitably modified transposase enzyme comprises two classes of differences from wild type Tn5 transposase, where each class has a separate measurable effect upon the overall transposition activity of the enzyme and where a greater effect is observed when both modifications are present. The suitably modified enzyme both (1) binds to the repeat sequences of the donor DNA with greater avidity than wild type Tn5 transposase ("class (1) mutation") and (2) is less likely than the wild type protein to assume an inactive multimeric form ("class (2) mutation"). A suitably modified Tn5 transposase of the present invention that contains both class (1) and class (2) modifications induces at least about 100-fold (.+/−.10%) more transposition than the wild type enzyme, when tested in combination in an in vivo conjugation assay as described by Weinreich, M. D., "Evidence that the cis Preference of the Tn5 Transposase is Caused by Nonproductive Multimerization," Genes and Development 8:2363–2374 (1994), incorporated herein by reference. Under optimal conditions, transposition using the modified transposase may be higher. A modified transposase containing only a class (1) mutation binds to the repeat sequences with sufficiently greater avidity than the wild type Tn5 transposase that such a Tn5 transposase induces about 5- to 50-fold more transposition than the wild type enzyme, when measured in vivo. A modified transposase containing only a class (2) mutation is sufficiently less likely than the wild type Tn5 transposase to assume the multimeric form that such a Tn5 transposase also induces about 5- to 50-fold more transposition than the wild type enzyme, when measured in vivo.

4.3.1.1.2. Method for Transposing the Transposable Element

In mother aspect, the invention is summarized in that a method for transposing the transposable element from the donor DNA into the target DNA in vitro includes the steps of mixing together the suitably modified Tn5 transposase protein, the donor DNA, and the target DNA in a suitable reaction buffer, allowing the enzyme to bind to the flanking repeat sequences of the donor DNA at a temperature greater than 0 degree C., but no higher than about 28° C., and then raising the temperature to physiological temperature (about 37° C., whereupon cleavage and strand transfer can occur.

It is an object of the present invention to provide a useful in vitro transposition system having few structural requirements and high efficiency.

It is another object of the present invention to provide a method that can be broadly applied in various ways, such as to create absolute defective mutants, to provide selective markers to target DNA, to provide portable regions of homology to a target DNA, to facilitate insertion of specialized DNA sequences into target DNA, to provide primer binding sites or tags for DNA sequencing, to facilitate production of genetic fusions for gene expression studies and protein domain mapping, as well as to bring together other desired combinations of DNA sequences (combinatorial genetics).

4.3.1.1.3. Modified Transposase Advantages Over Wild Type Tn5 Transposase

It is a feature of the present invention that the modified transposase enzyme binds more tightly to DNA than does wild type Tn5 transposase.

It is an advantage of the present invention that the modified transposase facilitates in vitro transposition reaction rates of at least about 100-fold higher than can be achieved using wild type transposase (as measured in vivo).

It is noted that the wild-type Tn5 transposase shows no detectable in vitro activity in the system of the present invention. Thus, while it is difficult to calculate an upper limit to the increase in activity, it is clear that hundreds, if not thousands, of colonies are observed when the products of in vitro transposition are assayed in vivo.

It is, another advantage of the present invention that in vitro transposition using this system can utilize donor DNA and target DNA that is circular or linear.

It is yet another advantage of the present invention that in vitro transposition using this system requires no outside high energy source and no other protein other than the modified transposase.

Other objects, features, and advantages of the present invention will become apparent upon consideration of the following detailed description.

4.3.2. Transposable Elements for Generating Functional Fusion Proteins

The instant invention encompasses transposable elements for generating functional fusion proteins comprising at least a left attachment site and a right attachment site where there is an open reading frame in both directions through at least one of the ends. In one embodiment the instant invention encompasses a transposable element containing a polylinker that is located adjacent to one end of the transposable element, while still allowing for open translational reading frames to enter and exit the near end. In another embodiment, the invention encompasses a transposable element as in containing a polylinker with an inserted exogenous DNA sequence. This exogenous DNA can encode for a complete protein, a functional portion of a protein, an expressible or inducible segment of DNA, or any other suitable DNA sequence. Also encompassed by the instant invention is a transposable element, where the expression of the exogenous DNA is under controlled regulation of a promoter, enhancer, or repressor which target sequences can be a part of the exogenous DNA segment, or a part of the transposable element construct. In a preferred embodiment, the instant invention encompasses a transposable element of containing a right attachment site of 50 to 62 nucleotides. The instant invention encompasses a transposable element for generating functional fusion proteins comprising at least a left attachment site and a right attachment site where there is an open translational reading frame extending out through one of the ends of the element. The instant invention also encompasses, in one embodiment, full-length attachment sites, in which translational open reading frame interrupting stop codons, which prevent the reading frame from extending out of the transposable element through a attachment site that is within 400 bases, have been removed by selective substitution of nucleotides in the nucleic acid sequence. Thus the instant invention also encompasses a transposable element for generating functional fusion proteins comprising at least a left attachment site and a right attachment site where the endogenous stop codons that would prevent translation through the ends have been removed by point mutation.

4.3.2.1. Transposable Element Containing the Protein A Domain

In another particular embodiment of constructs of the instant invention is a transposable element containing the Protein A domain which allows functional protein fusion with a target protein. The instant invention also embodies a transposable element which allows for functional carboxy or amino terminal fusion of the Protein A domain to a targeted protein sequence. Thus the instant invention provides for methods of making Protein A fusion proteins which are either amino- or carboxy-terminal fusion proteins.

4.3.2.2. A Cell wherein a Transposable Element for Generating Functional Fusion Proteins The methods and constructs of the instant invention also provide for a cell wherein a transposable element for generating functional fusion proteins, comprising at least a left attachment site and a right attachment site with a protein domain whose translational open reading frame extends through one of the ends of the element, is integrated into the cell genome. In one embodiment, the transposable element is integrated into an autonomously replicating DNA form within a cell of the instant invention.

The instant invention encompasses a method for generating functional fusion proteins, with a transposable element which contains at least a left attachment site and a right attachment site where there is an open reading frame in both directions through at least one of the ends, comprising insertion of an exogenous DNA sequence into the transposable element, transposing into a target DNA sequence with the transposable element, detecting the presence of the exogenous DNA insert, and selecting for the presence of the exogenous DNA insert. Another embodiment of the instant invention encompasses a method for in vitro or in vivo protein fusion in a target organism genome comprising constructing a transposable element with a left attachment site, a polylinker, and a right attachment site of between 50 and 62 nucleic acid base pairs, inserting within the polylinker an exogenous DNA sequence, transposing the transposable element into a target organism genome, expanding the target organism, isolating protein, and screening for fusion protein containing the translated exogenous DNA. In particular the instant invention encompasses a right attachment site of 58 nucleotides in length.

4.3.2.3. In vitro or in vivo Carboxy Terminal Translational Protein Fusion in a Target Organism Genome Another particular embodiment of the instant invention encompasses a method for in vitro or in vivo carboxy terminal translational protein fusion in a target organism genome comprising constructing a transposable element with a left attachment site and a right attachment site of between 50 and 62 nucleic acid base pairs, inserting within the transposable element an exogenous DNA sequence, transposing the transposable element into a target organism genome, expanding the target organism, isolating protein, and screening for fusion protein containing the translated exogenous DNA. In a particular embodiment the right attachment site is 58 nucleotides in length. The instant invention also provides for a method for in vitro or in vivo amino terminal translational protein fusion in a target organism genome comprising constructing a transposable element with a left attachment site attL and a right attachment site attR of between 50 and 62 nucleic acid base pairs, inserting within the transposable element an exogenous DNA sequence, transposing the transposable element into a target organism genome, expanding the target organism, isolating protein, and screening for fusion protein containing the translated exogenous DNA. In a preferred embodiment of the instant invention, the attachment sites arc derived from the Mu family of transposable elements. In another preferred embodiment of the instant invention, the right attachment site is 58 nucleotides in length.

4.3.2.4. A Plasmid for Inserting Target Sequences for Protein Fusion

The instant invention also encompasses a plasmid for inserting target sequences for protein fusion which comprises in the following order, a transcription termination site, an extended translational target region with no stop codons, and a polylinker sequence for cloning protein domains into containing no stop codons in frame with the translational target region. In another embodiment, the plasmid additionally contains a screenable marker fused to the translational target region, and the polylinker reading frame located after the polylinker region.

Thus the instant invention teaches the use of transposable elements with deletions in an end terminal attachment site which result in multiple reading frames in both directions through the end, and allows for the generation of functional protein fusions. In one particular embodiment the particular end is the right end attachment site of Mu known as attR. The invention specifically teaches constructs which allow for carboxy-terminal and/or amino-terminal fusion events to occur. In one embodiment, the instant invention encompasses a transposable element comprising a left attachment site attL, and a right attachment site of no more than 58 nucleic acid base pairs which will transpose an exogenous DNA sequence into a target DNA sequence. In a preferred embodiment, the attachment sites are derived from the Mu family of transposable elements. The teachings of the instant invention can also be applied to create similar constructs which allow for similar translation reading frames via the left attachment site. The instant invention also encompasses transposable elements comprising a left attachment site attL, a polylinker, and a right attachment site. In this embodiment, the polylinker allows for multiple restriction sites which allow for the convenient insertion of exogenous DNA segments. In a preferred embodiment, the transposable element is constructed such that it allows for open reading frames in both orientations. In a further embodiment, the exogenous DNA inserted within the transposable element is under controlled expression by a promoter, enhancer or repressor element. In a preferred embodiment, the instant invention encompasses a transposable element comprising a left attachment site attL, a polylinker region, and a right attachment site of no more than 58 nucleic acid base pairs derived from the Mu family of transposable elements, which will transpose an exogenous DNA sequence into a target DNA sequence and allow for open reading frames in both orientations.

4.3.2.5. Transposable Element Comprising a Left Attachment Site

The instant invention provides for the use of a transposable element comprising a left attachment site attL, an exogenous DNA, and a right attachment site for generating in vivo protein fusions in a target DNA. The target DNA can be plasmid DNA, DNA segments, genomic DNA, or other DNA targets. In a preferred embodiment of the instant invention, the right end of the transposable element consists of no more than 58 nucleic acid base pairs derived from the Mu family of transposable elements. The instant invention encompasses methods for using transposable element constructs with deletions in the right end for generating fusion proteins in vitro and in vivo. A method of the instant invention allows for the rapid and efficient generation of alternatively fused proteins suitable for screening for activity. In one embodiment of the method of the instant invention generates fusion proteins in which the exogenous DNA segment has been transposed such that the resultant fusion protein functionally expresses the exogenous protein as a amino- terminal fusion to the carboxy end of a targeted protein. In a further embodiment of a method of the instant invention, the transposable element causes the insertion of the exogenous DNA such that the functionally expressed fusion protein consists of the exogenous protein at the amino end, linked to the endogenous protein at the carboxy end of the fusion protein.

The instant invention provides for a method for in vivo protein fusion in a target organism genome comprising constructing a transposable element with a left attachment site attL, a polylinker, and a right attachment site of no more than 58 nucleic acid base pairs, inserting within the polylinker an exogenous DNA sequence, transposing the transposable element into a target organism genome, expanding the target organism, isolating protein, and screening for fusion protein containing the translated exogenous DNA. In a preferred embodiment, the instant invention provides for the in vivo carboxy terminal translational protein fusion in a target organism genome comprising constructing a transposable element with a left attachment site attL and a right attachment site attR of no more than 58 nucleic acid base pairs, inserting within the transposable element an exogenous DNA sequence, transposing the transposable element into a target organism genome, expanding the target organism, isolating protein, and screening for fusion protein containing the translated exogenous DNA. In another preferred embodiment, the instant invention provides for in vivo amino terminal translational protein fusion in a target organism genome comprising constructing a transposable element with a left attachment site attL and a right attachment site attR of no more than 58 nucleic acid base pairs, inserting within the transposable element an exogenous DNA sequence, transposing the transposable element into a target organism genome, expanding the target organism, isolating protein, and screening for fusion protein containing the translated exogenous DNA.

4.3.2.6. Transposable Elements in which the Stop Codons Have Been Removed

In a further embodiment of the instant invention, the method for generating novel fusion proteins encompasses the use of transposable elements in which the stop codons present in the attR region have been removed by point mutation such that there is an open reading frame leading out of the transposable element, allowing for the amino-terminal or carboxy-terminal fusion of the exogenous protein with the targeted protein by a linker which is translated from the attR region.

The constructs and methods of the instant invention are useful for the rapid and efficient generation of functional fusion proteins. The constructs and methods of the instant invention are useful in that they reduce the labor intensive burdens that accompany generation of protein fusions by traditional molecular cloning techniques. The following descriptions and examples are meant only by way of illustration of the instant invention, and are in no way intended to limit the scope of the instant invention. One with ordinary skill in the art will be able to understand and use the descriptions of the instant specification to use all of the embodiments which are contemplated and encompassed by the constructs and methods of the instant invention.

4.4. Transposons—Specialized Applications 4.4.1. In vitro System for Introducing any Transposable Element from a Donor DNA into a Target DNA It will be appreciated that this technique provides a simple, in vitro system for introducing any transposable element from a donor DNA into a target DNA. It is generally accepted and understood that Tn5 transposition requires only a pair of OE termini, located to either side of the transposable element. These OE termini are generally thought to be 18 or 19 bases in length and are inverted repeats relative to one another. Johnson, R. C., and W. S. Reznikoff, Nature 304:280 (1983), incorporated herein by reference. The Tn5 inverted repeat sequences, which are referred to as "termini" even though they need not be at the termini of the donor DNA molecule, are well known and understood.

Apart from the need to flank the desired transposable element with standard Tn5 outside end ("OE") termini, few other requirements on either the donor DNA or the target DNA are envisioned. It is thought that Tn5 has few, if any, preferences for insertion sites, so it is possible to use the system to introduce desired sequences at random into target DNA. Therefore, it is believed that this method, employing the modified transposase described herein and a simple donor DNA, is broadly applicable to introduce changes into any target DNA, without regard to its nucleotide sequence. It will, thus, be applied to many problems of interest to those skilled in the art of molecular biology.

4.4.1.1. Modified Transposase Protein is Combined in a Suitable Reaction Buffer with the Donor DNA and the Target DNA In the method, the modified transposase protein is combined in a suitable reaction buffer with the donor DNA and the target DNA. A suitable reaction buffer permits the transposition reaction to occur. A preferred, but not necessarily optimized, buffer contains spermidine to condense the DNA, glutamate, and magnesium, as well as a detergent, which is preferably 3-[(3-cholamidopropyl) dimethylammonio]-1-propane sulfonate ("CHAPS"). The mixture can be incubated at a temperature greater than 0° C. and as high as about 28° C. to facilitate binding of the enzyme to the OE termini. A preferred temperature range is between 16° C. and 28° C. A most preferred pretreatment temperature is about 20° C. Under different buffer conditions, however, it may be possible to use other below-physiological temperatures for the binding step. After a short pretreatment period of time (which has not been optimized, but which may be as little as 30 minutes or as much as 2 hours, and is typically 1 hour), the reaction mixture is diluted with 2 volumes of a suitable reaction buffer and shifted to physiological conditions for several more hours (say 2–3 hours) to permit cleavage and strand transfer to occur. A temperature of 37° C., or thereabouts, is adequate. After about 3 hours, the rate of transposition decreases markedly. The reaction can be stopped by phenol-chloroform extraction and can then be desalted by ethanol precipitation.

Following the reaction and subsequent extraction steps, transposition can be assayed by introducing the nucleic acid reaction products into suitable bacterial host cells (e.g., *E. coli* K-12 DH5α cells (recA-); commercially available from Life Technologies (Gibco-BRL)) preferably by electroporation, described by Dower et al., Nuc. Acids. Res. 16:6127 (1988), and monitoring for evidence of transposition, as is described elsewhere herein.

Those persons skilled in the art will appreciate that apart from the changes noted herein, the transposition reaction can proceed under much the same conditions as would be found in an in vivo reaction. Yet, the modified transposase described herein so increases the level of transposition activity that it is now possible to carry out this reaction in vitro where this has not previously been possible. The rates of reaction are even greater when the modified transposase is coupled with an optimized buffer and temperature conditions noted herein.

4.4.1.1.1. Preparation of a Modified Tn5 Transposase Enzyme that Differs from Wild Type Tn5 Transposase In another aspect, the present invention is a preparation of a modified Tn5 transposase enzyme that differs from wild type Tn5 transposase in that it (1) binds to the repeat sequences of the donor DNA with greater avidity than wild type Tn5 transposase and (2) is less likely than the wild type protein to assume an inactive multimeric form. An enzyme having these requirements can be obtained from a bacterial host cell containing an expressible gene for the modified enzyme that is under the control of a promoter active in the host cell. Genetic material that encodes the modified Tn5 transposase can be introduced (e.g., by electroporation) into suitable bacterial host cells capable of supporting expression of the genetic material. Known methods for overproducing and preparing other Tn5 transposase mutants are suitably employed. For example, Weinreich, M. D., et al., supra, describes a suitable method for overproducing a Tn5 transposase. A second method for purifying Tn5 transposase was described in de la Cruz, N. B., et al., "Characterization of the Tn5 Transposase and Inhibitor Proteins: A Model for the Inhibition of Transposition," J. Bact. 175:6932–6938 (1993), also incorporated herein by reference. It is noted that induction can be carried out at temperatures below 37° C., which is the temperature used by de la Cruz, et al. Temperatures at least in the range of 33 to 37° C. are suitable. The inventors have determined that the method for preparing the modified transposase of the present invention is not critical to success of the method, as various preparation strategies have been used with equal success.

Alternatively, the protein can be chemically synthesized, in a manner known to the art, using the amino acid sequence attached hereto as SEQ ID NO:2 as a guide. It is also possible to prepare a genetic construct that encodes the modified protein (and associated transcription and translation signals) by using standard recombinant DNA methods familiar to molecular biologists. The genetic material useful for preparing such constructs can be obtained from existing Tn5 constructs, or can be prepared using known methods for introducing mutations into genetic material (e.g., random mutagenesis PCR or site-directed mutagenesis) or some combination of both methods. The genetic sequence that encodes the protein shown in SEQ ID NO:2 is set forth in SEQ ID NO: 1.

The nucleic acid and amino acid sequence of wild type Tn5 transposase are known and published. N.C.B.I. Accession Number U00004 L19385, incorporated herein by reference.

4.4.1.1.2. Differences Observed in Modified Tn5 Transposase Enzyme from Wildtype 4.4.1.1.2.1. Higher Binding Preference of the Transposase for Outside End ("OE") Termini In a preferred embodiment, the improved avidity of the modified transposase for the repeat sequences for OE termini (class (1) mutation) can be achieved by providing a lysine residue at amino acid 54, which is glutamic acid in wild type Tn5 transposase. The mutation strongly alters the preference of the transposase for OE termini, as opposed to inside end ("IE") termini. The higher binding of this mutation, known as EK54, to OE termini results in a transposition rate that is about 10-fold higher than is seen with wild type transposase. A similar change at position 54 to valine (mutant EV54) also results in somewhat increased preference (about 3-fold higher than wild type) for OE termini, as does a threonine-to-proline change at position 47 (mutant TP47; about 10-fold higher). It is believed that other, comparable transposase mutations (in one or more amino acids) that increase binding avidity for OE termini may also be obtained which would function as well or better in the in vitro assay described herein.

One of ordinary skill will also appreciate that changes to the nucleotide sequences of the short repeat sequences of the donor DNA may coordinate with other mutation(s) in or near the binding region of the transposase enzyme to achieve the same increased binding effect, and the resulting 5- to 50-fold increase in transposition rate. Thus, while the applicants have exemplified one case of a mutation that improves binding of the exemplified transposase, it will be understood that other mutations in the transposase, or in the short repeat sequences, or in both, will also yield transposases that fall within the scope and spirit of the present invention. A suitable method for determining the relative avidity for Tn5 OE termini has been published by Jilk, R. A., et al., "The Organization of the Outside end of Transposon Tn5," J. Bact. 178:1671–79 (1996).

4.4.1.1.2.2. Less Likely than the Wild Type Protein to Assume an Inactive Multimeric Form The transposase of the present invention is also less likely than the wild type protein to assume an inactive multimeric form. In the preferred embodiment, that class (2) mutation from wild type can be achieved by modifying amino acid 372 (leucine) of wild type Tn5 transposase to a proline (and, likewise by modifying the corresponding DNA to encode proline). This mutation, referred to as LP372, has previously been characterized as a mutation in the dimerization region of the transposase. Weinreich, et al., supra. It was noted by Weinreich et al. that this mutation at position 372 maps to a region shown previously to be critical for interaction with an inhibitor of Tn5 transposition. The inhibitor is a protein encoded by the same gene that encodes the transposase, but which is truncated at the N-terminal end of the protein, relative to the transposase. The approach of Weinreich et al. for determining the extent to which multimers are formed is suitable for determining whether a mutation falls within the scope of this element.

4.4.1.1.2.3. Reduced Inhibitory Activity Leading to Higher Levels of Transposition It is thought that when wild type Tn5 transposase multimerizes, its activity in trans is reduced. Presumably, a mutation in the dimerization region reduces or prevents multimerization, thereby reducing inhibitory activity and leading to levels of transposition 5- to 50-fold higher than are seen with the wild type transposase. The LP372 mutation achieves about 10-fold higher transposition levels than wild type. Likewise, other mutations (including mutations at a one or more amino acid) that reduce the ability of the transposase to multimerize would also function in the same manner as the single mutation at position 372, and would also be suitable in a transposase of the present invention. It may also be possible to reduce the ability of a Tn5 transposase to multimerize without altering the wild type sequence in the so-called dimerization region, for example by adding into the system another protein or non-protein agent that blocks the dimerization site. Alternatively, the dimerization region could be removed entirely from the transposase protein.

4.4.1.1.2.3.1. Inhibitor Protein

As was noted above, the inhibitor protein, encoded in partially overlapping sequence with the transposase, can interfere with transposase activity. As such, it is desired that the amount of inhibitor protein be reduced over the amount observed in wild type in vivo. For the present assay, the transposase is used in purified form, and it may be possible to separate the transposase from the inhibitor (for example, according to differences in size) before use. However, it is also possible to genetically eliminate the possibility of having any contaminating inhibitor protein present by removing its start codon from the gene that encodes the transposase.

An AUG in the wild type Tn5 transposase gene that encodes methionine at transposase amino acid 56 is the first codon of the inhibitor protein. However, it has already been shown that replacement of the methionine at position 56 has no apparent effect upon the transposase activity, but at the same time prevents translation of the inhibitor protein, thus resulting in a somewhat higher transposition rate. Weigand, T. W. and W. S. Reznikoff, "Characterization of Two Hyper-transposing Tn5 Mutants," J. Bact. 174:1229–1239 (1992), incorporated herein by reference. In particular, the present inventors have replaced the methionine with an alanine in the preferred embodiment (and have replaced the methionine-encoding AUG codon with an alanine-encoding GCC). A preferred transposase of the present invention therefore includes an amino acid other than methionine at amino acid position 56, although this change can be considered merely technically advantageous (since it ensures the absence of the inhibitor from the in vitro system) and not essential to the invention (since other means can be used to eliminate the inhibitor protein from the in vitro system).

4.4.1.2. Preferred Transposase Amino Acid Sequence

The most preferred transposase amino acid sequence known to the inventors differs from the wild type at amino acid positions 54, 56, and 372. The mutations at positions 54 and 372 separately contribute approximately a 10-fold increase to the rate of transposition reaction in vivo. When the mutations are combined using standard recombinant techniques into a single molecule containing both classes of mutations, reaction rates of at least about 100-fold higher than can be achieved using wild type transposase are observed when the products of the in vitro system are tested in vivo. The mutation at position 56 does not directly affect the transposase activity.

Other mutants from wild type that are contemplated to be likely to contribute to high transposase activity in vitro include, but are not limited to glutamic acid-to-lysine at position 110, and glutamic acid to lysine at position 345.

It is, of course, understood that other changes apart from these noted positions can be made to the modified transposase (or to a construct encoding the modified transposase) without adversely affecting the transposase activity. For example, it is well understood that a construct encoding such a transposase could include changes in the third position of codons such that the encoded amino acid does not differ from that described herein. In addition, certain codon changes have little or no functional effect upon the transposition activity of the encoded protein. Finally, other changes may be introduced which provide yet higher transposition activity in the encoded protein. It is also specifically envisioned that combinations of mutations can be combined to encode a modified transposase having even higher transposition activity than has been exemplified herein. All of these changes are within the scope of the present invention. It is noted, however, that a modified transposase containing the EK110 and EK345 mutations (both described by Weigand and Reznikoff, supra, had lower transposase activity than a transposase containing either mutation alone.

4.4.1.3. Introduction of any Desired Transposable Element

After the enzyme is prepared and purified, as described supra, it can be used in the in vitro transposition reaction described above to introduce any desired transposable element from a donor DNA into a target DNA. The donor DNA can be circular or can be linear. If the donor DNA is linear, it is preferred that the repeat sequences flanking the transposable element should not be at the termini of the linear fragment but should rather include some DNA upstream and downstream from the region flanked by the repeat sequences.

The transposable element between the OE termini can include any desired nucleotide sequence. The length of the transposable element between the termini should be at least about 50 base pairs, although smaller inserts may work. No upper limit to the insert size is known. However, it is known that a donor DNA portion of about 300 nucleotides in length can function well. By way of non-limiting examples, the transposable element can include a coding region that encodes a detectable or selectable protein, with or without associated regulatory elements such as promoter, terminator, or the like.

If the element includes such a detectable or selectable coding region without a promoter, it will be possible to identify and map promoters in the target DNA that are uncovered by transposition of the coding region into a position downstream thereof, followed by analysis of the nucleic acid sequences upstream from the transposition site.

Likewise, the element can include a primer binding site that can be transposed into the target DNA, to facilitate sequencing methods or other methods that rely upon the use of primers distributed throughout the target genetic material. Similarly, the method can be used to introduce a desired restriction enzyme site or polylinker, or a site suitable for another type of recombination, such as a cre-lox, into the target.

The invention can be better understood upon consideration of the following examples which are intended to be exemplary and not limiting on the invention.

4.4.2. Generation of Functional Fusion Protein Products

The instant invention provides constructs and methods for the rapid and efficient generation of functional fusion protein products with either carboxy-terminal or amino-terminal fusions. Functional fusion proteins are those which retain some of the activity of the original domains, and/or those which have a newly created activity. Throughout this specification, reference is made to two types of fusions: carboxy terminal fusions and amino terminal fusions. In this text we use amino and carboxy terminal fusions to refer to the end of the domain inside of the Mu elements which is fused to the target molecule. Thus, carboxy terminal fusion elements are those with a protein domain inside of the Mu which extends out of the Mu element such that the exogenous protein is fused to the amino end of the endogenous protein. The amino terminal fusion elements are those that create fusions with a target gene extending into the element such that the exogenous protein is fused to the carboxy terminal of the endogenous protein. An overview for generating both amino- and carboxy-terminal fusion proteins with the transposable elements is outlined. A domain of interest is inserted in one of two possible orientations into the end of a transposable element, such that a continuing open reading frame extends out through the element (for carboxy-terminal fusions) or in through the element (for amino-terminal fusions). Transposition into a target sequence allows random generation of hybrid proteins. Functional fusions can be selected or screened for.

4.4.2.1. Mini-Mu Transposon Elements & Macro-Mu Elements

The instant invention provides for mini-Mu transposon elements with convenient polylinker sites for inserting protein domains into the transposable element. The instant invention also provides for macro-Mu elements. The transposable elements of the instant invention have been designed to have a shorter transposon end which becomes incorporated into the fusion product while still retaining their high transposition frequencies. Unlike other elements used to date they can be used to make both amino and carboxy-terminal fusions since they have open reading frames extending in both directions. The examples below demonstrate the application of the teachings of the instant invention for using the new elements to create protein fusions with two fully active domains and their usefulness as a general tool for protein fusion. Other examples demonstrate new features such as regulatable promoters incorporated into the transposable element, which can allow control of expression for promoterless domains or domains which may exhibit some degree of lethality to the cell. The constructs and methods described here allow high frequency random fusion of two domains at multiple sites so that the optimal fusion junctions can be selected.

4.4.2.2. The Constructs

The constructs and teachings of the instant invention provide a powerful tool which will aid in the development of new enzymes for biocatalytic applications such as bioremediation and industrial biocatalysis, and for other industrial applications such as biosensors and strain development. Many different combinations of fusions between two domains can be generated rapidly and screened for activity. As an extension of protein evolution, this will be a powerful technique for production of novel chimeric proteins. In contrast to the difficulties inherent in a traditional rational protein design approach which employs traditional molecular biological techniques to generate fusion proteins, the instant invention provides for rapid and efficient "randomized experimentation" whereby the transposon fusion events are utilized to generate a panel of fusion proteins. From this panel of fusion proteins, selection for functionally expressed products, results in efficient screening for successful fusions.

While traditional experimentation with transposable elements resulted in the ablation of endogenous protein translation, and substitution of the translation and expression of the reporter gene for study of gene expression and regulation, the instant invention teaches modifications of these elements which allow for the generation of functional fusion proteins which can contain novel activities. The instant invention teaches for the first time the construction of transposable elements which can transpose exogenous DNA into target DNA in both orientations which can result in the functional expression of fusion proteins which have the exogenous protein linked either on the amino-end, or at the carboxy-end of the target protein.

The constructs and methods of the instant invention are not limited to the use of proteins with known crystal structures, but is capable of generating functional fusion proteins from the randomized combination of functional domains. Instead of being limited to the mere tethering of functional domains, the constructs and methods of the instant invention allow for the fusion protein product to occur at randomized "truncated" sites of the target protein. This allows for the rapid generation of and screening for functional fusion proteins that are incorporated into a truncated form of the targeted protein. Thus the instant invention has provided for creating new mini-Mu elements with polylinkers for domain insertion and open reading frames both into and out of the element. The elements have reduced ends while maintaining their high transposition frequency. The constructs of the instant invention and examples below show the ability of these elements to make carboxy-terminal protein fusions between a Protein A domain carried on the element and both selectable (chloramphenicol-acetyl transferase) and screenable (beta-galactosidase) proteins.

The constructs of the instant invention are useful for making amino-terminal fusions and demonstration of kinetic observations with beta-galactosidase showing that the Km value is maintained even if it is fused to different locations.

4.4.2.3. In vivo Settings for Generating Functional Fusion Proteins

While the constructs and methods of the instant invention are functional in an in vitro setting, a major advantage of the instant invention is the application of in vivo settings for generating functional fusion proteins. The development of an in vivo protein engineering system that is both versatile and easy to use will have a significant impact on the way proteins with specific activities are defined. This invention results in the development of a refined system for the in vivo engineering of proteins. The constructs and methods of the instant invention are powerful enhancements to the genetic tools available to the molecular biologist. The constructs of the instant invention can be provided as kits for the engineering of proteins.

One might imagine that an in vivo system may have problems since biological systems are limited to the properties of the particular system. One of the advantages of the Mu transposition system is that it is the most general and well defined of the transposition systems available (Symonds, Toussaint et al. (1987). Phage Mu.). The biological properties of the system are advantages which make Mu simple to use. Mu provides very convenient methods for isolating independent insertion events by transducing them to a new cell. Creation of insertions requires only a temperature shift. We have favored the Mu transposition system from the start because an untrained technician may be taught to reproducibly use the Mu system in just a few days. While the initial design and construction of a Mu system can be difficult, the finished system's simplicity lends itself to commercialization. There is much to be said for in vitro systems. The in vivo system of the instant invention was intended to be an additional protein engineering tool to enhance the methods of producing novel active protein fusions when used in conjunction with basic in vitro methods, or with additional novel in vitro methods of the instant invention. There has been no previous demonstration of the altered transcription through the end of a Mu element. Specifically, transcription through the end of the Mu element might reduce transposition frequencies. Surprisingly we have found that the transcription of the Protein A gene through the end of Mu did not alter transposition frequencies.

The instant invention encompasses both the amino and carboxy-terminal fusion elements because they are useful in different applications. The carboxy-terminal element is more useful for making fusions with a cDNA which has been cloned from a eukaryotic organism, especially if one wants to ultimately express it in another organism. Amino-terminal elements are more useful for some applications because they can only be activated by a fusion event if they are missing the start codon. The instant specification teaches new Mu elements with promoters for expression in the experimental design. One of the main commercial applications of the system is to generate new enzymes for medical or industrial uses both in vivo and in vitro. E. coli will likely be the production organism if there are no post-translational modification problems associated with the enzymes. But it is possible to use any Mu compatible strain as the production organism.

4.5. Additional Applications

It is envisioned that in addition to the uses specifically noted herein, other applications will be apparent to the skilled molecular biologist. In particular, methods for introducing desired mutations into prokaryotic or eukaryotic DNA are very desirable. For example, at present it is difficult to knock out a functional eukaryotic gene by homologous recombination with an inactive version of the gene that resides on a plasmid. The difficulty arises from the need to flank the gene on the plasmid with extensive upstream and downstream sequences. Using this system, however, an inactivating transposable element containing a selectable marker gene (e.g., neo) can be introduced in vitro into a plasmid that contains the gene that one desires to inactivate. After transposition, the products can be introduced into suitable host cells. Using standard selection means, one can recover only cell colonies that contain a plasmid having the transposable element. Such plasmids can be screened, for example by restriction analysis, to recover those that contain a disrupted gene. Such clones can then be introduced directly into eukaryotic cells for homologous recombination and selection using the same marker gene.

Also, one can use the system to readily insert a PCR-amplified DNA fragment into a vector, thus avoiding traditional cloning steps entirely. This can be accomplished by (1) providing suitable a pair of PCR primers containing OE termini adjacent to the sequence-specific parts of the primers, (2) performing standard PCR amplification of a desired nucleic acid fragment, (3) performing the in vitro transposition reaction of the present invention using the double-stranded products of PCR amplification as the donor DNA.

The invention is not intended to be limited to the foregoing examples, but to encompass all such modifications and variations as come within the scope of the appended claims.

5. Homologous Recombination disease as well as to identify new targets for drug or pathogen screening.

5.1.1. Evolution of Genes

In nature, the evolution of genes and their encoded proteins occurs through an equilibrium between recombination or mutation and selection. While evolution in nature takes millions of years, in vitro methods and compositions have been developed to evolve proteins, with improved and novel functions, in a matter of hours to days.

5.1.1.1. Through Mutagenesis

Current in vitro gene evolution methods utilize repeated cycles of random mutagenesis or random nicking and mixing of related genes containing mutations in PCR-based random recombination. These methods couple multiple rounds of in vitro mutagenesis with screening systems to produce and identify the desired mutants or recombinants (Stemmer 1994. Nature 370:389–391; Arnold 1996. Chemical Engineering Science 51:5091–5102). Research has shown, however, that the mutations of interest tend to occur in those regions or domains that are directly related to function (Chen and Arnold. 1993. PNAS USA 90:5618–5622).

However, these mutagenesis methods produce random mutations throughout the gene of interest which requires the need to screen large numbers of uninteresting or deleterious mutants. The labor-intensive and time consuming aspects of these methods are further complicated by the necessity of multiple rounds of subcloning and can be extremely challenging if the screening system is complex and does not utilize a selection system.

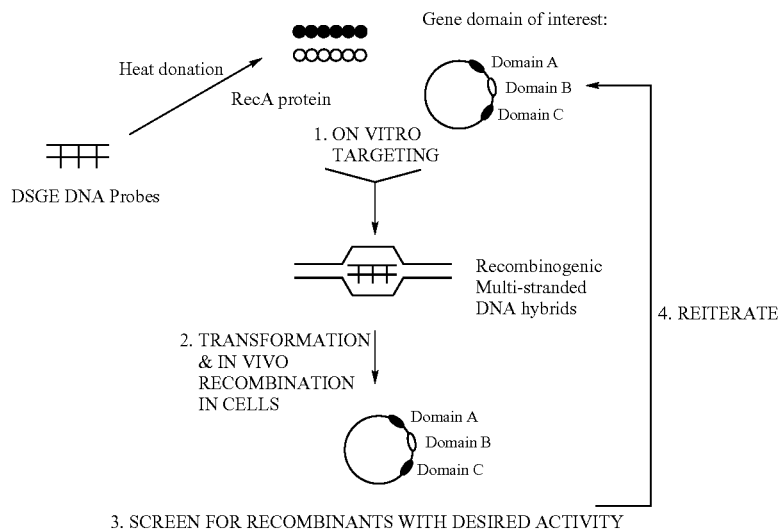

5.1 Homologous Recombination for the Generation of Deletions and Insertions

The invention relates to compositions and methods of rapidly evolving specific protein domains using a library of nucleic acid filaments and a recombinase polypeptide or peptide. The invention relates to compositions and methods for targeting sequence modifications in one or more genes of a related family of genes using enhanced homologous recombination techniques. The invention also relates to compositions and methods for isolating and identifying novel members of homologous sequences families. These techniques may be used to create animal or plant models of 5.1.1.2. Homologous Recombination (HR)

Homologous recombination (HR) is defined as the exchange of homologous or similar DNA sequences between two DNA molecules. As essential feature of HR is that the enzymes responsible for the recombination event can pair any homologous sequences as substrates. The ability of HR to transfer genetic information between DNA molecules makes targeted homologous recombination a very powerful method in genetic engineering and gene manipulation. Both genetic and cytological studies have indicated that such a crossing-over process occurs between pairs of homologous chromosomes during meiosis in higher organisms.

5.1.1.3. Site-Specific Recombination

Alternatively, in site-specific recombination, exchange occurs at a specific site, as in the integration of phage A into the *E coli* chromosome and the excision of lambda DNA from it. Site-specific recombination involves specific inverted repeat sequences; e.g. the Cre-loxP and FLP-FRT systems. Within these sequences there is only a short stretch of homology necessary for the recombination event, but not sufficient for it. The enzymes involved in this event generally cannot recombine other pairs of homologous (or nonhomologous) sequences, but act specifically.

5.1.1.4. Advantage of Homologous Recombination over Site-Specific Recombination Although both site-specific recombination and homologous recombination are useful mechanisms for genetic engineering of DNA sequences, targeted homologous recombination provides a basis for targeting and altering essentially any desired sequence in a duplex DNA molecule, such as targeting a DNA sequence in a chromosome for replacement by another sequence. Site- specific recombination has been proposed as one method to integrate transfected DNA at chromosomal locations having specific recognition sites (O'Gorman et al. (1991) Science 251: 1351; Onouchi et al. (1991) Nucleic Acids Res. 19: 6373). Unfortunately, since this approach requires the presence of specific target sequences and recombinases, its utility for targeting recombination events at any particular chromosomal location is severely limited in comparison to targeted general recombination.

5.1.1.5. HR to Create Transgenic Plants, Animals, and Organisms

Homologous recombination has also been used to create transgenic plants and animals. Transgenic organisms contain stably integrated copies of genes or gene constructs derived from another species in the chromosome of the transgenic organism. In addition, gene targeted animals can be generated by introducing cloned DNA constructs of the foreign genes into totipotent cells by a variety of methods, including homologous recombination. For example, animals that develop from genetically altered totipotent cells can contain the foreign gene in all somatic cells and also in germ-line cells.

5.1.1.5.1. Current Methods using Embryonic Stem Cells

Currently methods for producing transgenic and targeted animals have been performed on totipotent embryonic stem cells (ES) and with fertilized zygotes. ES cells have an advantage in that large numbers of cells can be manipulated easily by homologous recombination in vitro before they are used to generate targeted animals. Currently, however, only embryonic stem cells from mice have been shown to contribute to the germ line. Alternatively, DNA can also be introduced into fertilized oocytes by micro-injection into pronuclei which are then transferred into the uterus of a pseudo-pregnant recipient animal to develop to term. The ability of mammalian and human cells to incorporate exogenous genetic material into genes residing on chromosomes has demonstrated that these cells have the general enzymatic machinery for carrying out homologous recombination required between resident and introduced sequences. These targeted recombination events can be used to correct mutations at known sites, replace genes or gene segments with defective ones, or introduce foreign genes into cells.

5.1.1.5.2. Frequency and Efficiency of HR

HR can be used to add subtle mutations at known sites, replace wild type genes or gene segments or introduce completely foreign genes into cells. However, HR efficiency is very low in living cells and is dependent on several parameters, including the method of DNA delivery, how it is packaged, its size and conformation, DNA length and position of sequences homologous to the target, and the efficiency of hybridization and recombination at chromosomal sites. These variables severely limit the use of conventional HR approaches for gene evolution in cell based systems. (Kucherlapati et al., 1984. PNAS; USA 81:3153–3157; Smithies et al. 1985. Nature 317:230–234; Song et al. 1987. PNAS USA 84:6820–6824; Doetschman et al. 1987. Nature 330:576–578; Kim and Smithies. 1988. Nuc. Acids. Res. 16:8887–8903; Koller and Smithies. 1989. PNAS USA 86:8932–8935; Shesely et al. 1991. PNAS USA 88:4294–4298; Kim et al. 1991. Gene 103:227–233).

5.1.1.5.2.1. Enhancement by the Presence of Recombinase Activities

The frequency of HR is significantly enhanced by the presence of recombinase activities in cellular and cell free systems. Several proteins or purified extracts that promote HR (i.e., recombinase activity) have been identified in prokaryotes and eukaryotes (Cox and Lehman., 1987. Annu. Rev. Biochem. 56:229–262; Radding. 1982. Annual Review of Genetics 16:405–547; McCarthy et al. 1988. PNAS; USA 85:5854–5858). These recombinases promote one or more steps in the formation of homologously-paired intermediates, strand-exchange, and/or other steps. Recent advances have resulted in techniques allowing enhanced homologous recombination (EHR) using recombinases such as recA and Rad51and single-stranded nucleic acids that have sequence heterologies. This allows sequence modifications to be specifically targeted to virtually any genomic position. See for example, PCT US93/03868 and PCT US98/05223, both of which are expressly incorporated herein by reference.

5.1.1.5.2.1.1. Recombinase Rec A: A Bacterial Protein that Catalyses Homologous Pairing and Strand Exchange between Two Homologous DNA Molecules The most studied recombinase to date is the RecA recombinase of *E coli*, which is involved in homology search and strand exchange reactions (Cox and Lehman, 1987, supra). The bacterial RecA protein (Mr 37,842) catalyses homologous pairing and strand exchange between two homologous DNA molecules (Kowalczykowski et al. 1994. Microbiol. Rev. 58:401–465; West. 1992. Annu. Rev. Biochem. 61:603–640); Roca and Cox. 1990. CRC Cit. Rev. Biochem. Mol. Biol. :415–455; Radding. 1989. Biochim. Biophys. Acta. 1008:131–145; Smith. 1989. Cell 58:807–809).

RecA protein binds cooperatively to any given sequence of single-stranded DNA with a stochiometry of one RecA protein monomer for every three to four nucleotides in DNA (Cox and Lehman, 1987, supra). This forms unique right handed helical nucleoprotein filaments in which the DNA is extended by 1.5 times its usual length (Yu and Egelman 1992. J. Mol. Biol. 227:334–346). These nucleoprotein filaments, which are referred to as DNA probes, are crucial "homology search engines" which catalyze DNA pairing. Once the filament finds its homologous target gene sequence, the DNA probe strand invades the target and forms a hybrid DNA structure, referred to as a joint molecule or D-loop (DNA displacement loop) (McEntee et al. 1979. PNAS USA 76:2615–2619; Shibata et al. 1979. PNAS USA 76:1638–1642). The phosphate backbone of DNA inside the RecA nucleoprotein filaments is protected against digestion by phosphodiesterases and nucleases.

RecA protein is the prototype of a universal class of recombinase enzymes which promote probe-target pairing reactions. Recently, genes homologous to *E.coli* RecA (the Rad51 family of proteins) were isolated from all groups of eukaryotes, including yeast and humans. Rad51 protein promotes homologous pairing and strand invasion and exchange between homologous DNA molecules in a similar manner to RecA protein (Sung. 1994. Science 265:1241–1243; Sung and Robberson. 1995. Cell 82:453–461; Gupta et al. 1997. PNAS USA 94:463–468; Baumann et al. 1996. Cell 87:757–766).

5.1.1.5.3. Functional Genomics: The Correlation of Genotype and Phenotype

One area of pressing interest in biology is within the area of "functional genomics", i.e. the correlation of genotype and phenotype. This requires animal systems, since phenotypic changes must be evaluated in vivo. Similarly, and related to this idea, is the elucidation and characterization of gene families, i.e. genes or proteins that are structurally related, i.e. they have sequence homologies between the members of the family. Since presumably many, if not most, disease states are caused by multiple gene interactions, the ability to evaluate interactions among genes, and particularly within or between gene families, at the phenotype level, would be extremely valuable.

The functional genomics tools that allow facile identification and engineering of gene family members in animals and cells, however, are not yet available. While the amino acid sequence motifs shared between gene family members may be identical, due to degeneracy in the DNA code, the DNA sequence identity may be significantly less. Hence, one criterion necessary for genetic modifications of gene family members is development of homologous recombination technologies that can be used to clone and modify similar DNA sequences that share little sequence identity. This is particularly important since homologous recombination in cells normally requires significant sequence identity to work efficiently. Relaxing the amount of sequence identity needed for homologous recombination allows greater flexibility to target related genes for creating transgenic animals and cells containing modifications in gene family consensus sequences, and also will allow the rapid cloning, generation of gene family specific libraries, and evolution of gene family members. Accordingly, it is an object of the invention to provide an efficient method of domain specific gene evolution that generates maximal diversity but increases the probability of identifying a gene of interest.

5.2. Domain Specific Gene Evolution 5.2.1.1. Domain Specific Gene Evolution-Comprising Forming a Plurality of Recombination Intermediates Comprising a Target Nucleic Acid Encoding an Amino Acid Sequence of Interest, a Recombinase and a Plurality of Targeting Polnucleotides The present invention provides methods of domain specific gene evolution comprising forming a plurality of recombination intermediates comprising a target nucleic acid encoding an amino acid sequence of interest, a recombinase and a plurality of targeting polynucleotides. The targeting polynucleotides are substantially complementary to each other and each comprises a homology clamp that substantially correspond to or is substantially complementary to a predetermined sequence of the target nucleic acid and comprise random or degenerate sequences. The predetermined sequence encodes a domain of the amino acid sequence. The method further comprises contacting the intermediate with a recombination proficient cell, whereby a library of altered target nucleic acids are produced. The altered target nucleic acids are expressed in the cell to generate a pool of variant amino acid sequences. The method further comprises selecting and isolating a cell comprising an altered target nucleic acid that expressed a variant amino acid having a desired activity.

5.2.1.2. Comprising Forming a Recombination Intermediate Comprising a Target Nucleic Acid Encoding an Amino Acid Sequence of Interest, a Recombinase and a Pair of Targeting Poly Nucleotides In another aspect of the invention, a method of domain specific gene evolution comprises forming a recombination intermediate comprising a target nucleic acid encoding an amino acid sequence of interest, a recombinase and a pair of targeting polynucleotides. The targeting polynucleotides are substantially complementary to each other and each comprises a homology clamp that substantially corresponds to or is substantially complementary to a predetermined sequence of the target nucleic acid. The predetermined sequence encodes a domain of the amino acid sequence. The method further comprises contacting the intermediate with a single-strand specific nuclease or junction-specific nuclease to form a nicked or open-ended target nucleic acid. The regions adjacent to the hybridized region or junctions are susceptible to nucleases. The target nucleic acid is reassembled and recombined to produce a library of altered target nucleic acids. The target nucleic acids are expressed to generate a pool of variant amino acid sequences. The variant amino acid sequences are selected and characterized to identify an altered target nucleic acid encoding a variant amino acid sequence of interest.

In a further aspect, each method is repeated one or more times to further evolve a variant amino acid sequence having a desired activity. In yet another aspect, more than one domain or a protein is evolved simultaneously.

5.2.1.3. Compositions

It is an object of the present invention to provide compositions comprising at least one recombinase and at least two single-stranded targeting polynucleotides which are substantially complementary to each other and each having a consensus homology clamp for a gene family.

In an additional aspect, the invention provides compositions comprising at least one recombinase and a plurality of pairs of single stranded targeting polynucleotides, where the plurality of pairs comprises a set of degenerate probes encoding the consensus sequence.

In a further aspect, the invention provides kits comprising the compositions of the invention and at least one reagent.

5.2.1.4. Methods for Targeting a Sequence Modification in at Least One Member of a Consensus Family of Genes in a Cell by Homologous Recombination.

In an additional aspect, the invention provides methods for targeting a sequence modification in at least one member of a consensus family of genes in a cell by homologous recombination. The method comprises introducing into at least one cell at least one recombinase and at least two single-stranded targeting polynucleotides which are substantially complementary to each other and each having a consensus homology clamp for the family. The method can additionally comprise identifying a target cell having a targeted sequence modification.

5.2.1.4.1. Methods of Making a Non-Human Organism with a Targeted Sequence Modification in at Least One Member of a Gene Family In a further aspect, the invention provides methods of making a non-human organism with a targeted sequence modification in at least one member of a gene family. The method comprises introducing into a cell at least one recombinase and at least two single-stranded targeting polynucleotides which are substantially complementary to each other and each having a consensus homology clamp for said family. The cell is then subjected to conditions that result in the formation of an animal, and the animal has at least one modification in at least one member of a consensus family of genes.

In a further aspect, the invention provides non-human organisms containing a sequence. modification in an endogenous consensus functional domain of a gene member of a gene family.

5.2.1.5. Methods of Isolating a Member of a Gene Family Comprising a Protein Consensus Sequence In an additional aspect, the invention provides methods of isolating a member of a gene family comprising a protein consensus sequence. The method comprises adding to a complex mixture of nucleic acids at least one recombinase and at least two single-stranded targeting polynucleotides which are substantially complementary to each other and each having a consensus homology clamp for said family. At least one of the targeting polynucleotides comprises a purification tag. The method is done under conditions whereby the targeting polynucleotides form a complex with the member, and the family member is isolated using said purification tag. The complex nucleic acid mixture may be a cDNA library, a cell, RNA or a restriction endonucleases genomic digest.

5.3. Targeting a Predetermined Nucleic Acid Sequence that Encodes a Specific Protein Domain, to Make a Plurality of Targeted Sequence Modifications The present invention provides methods and compositions for domain specific gene evolution. In one aspect of the invention, the method comprises targeting a predetermined nucleic acid sequence that encodes a specific protein domain, to make a plurality of targeted sequence modifications. That is, by targeting the recombinogenic probes of the invention to particular protein domains, gene evolution and selection are targeted to specific domains known or believed to harbor specific activities or functions. These methods create maximal diversity in specific domains of interest, thereby, decreasing the size of the library of mutations that are to be screened and increasing the probability of finding a gene with improved or desired attributes. Therefore, the libraries of the present invention are enriched for advantageous or interesting mutations or recombinant sequence(s).

5.3.1. Combining a Plurality of Pairs of Single-Stranded Targeting Poly Nucleotides, a Predetermined Target Nucleic Acid, and a Recombinase to Form a Polynucleotide: Target Nucleic Acid Complex Accordingly, the methods comprise combining a plurality of pairs of single-stranded targeting poly nucleotides, a predetermined target nucleic acid, and a recombinase to form a polynucleotide: target nucleic acid complex. The targeting polynucleotides comprise at least one homology clamp for targeting a predetermined domain of a target nucleic acid and randomized or degenerate sequences. The complex is optionally introduced into a plurality of recombination proficient cells which catalyze strand exchange and homologous recombination intracellularly to produce a library of modified nucleic acids. Cells are selected and isolated that comprise a modified nucleic acid that encodes a polypeptide having a desired property. The process is preferably repeated iteratively to further evolve the target domain of interest.

5.3.2. Domain Specific DNA Nicking

In another aspect of the invention, methods of domain specific DNA nicking are provided for domain specific gene evolution. This method comprises combining a pair of single-stranded targeting polynucleotides, a predetermined target nucleic acid, and a recombinase to firm a polynucleotide: target nucleic acid complex. The targeting polynucleotides are substantially complementary and comprise at least one homology clamp for targeting a predetermined domain of a target nucleic acid. The polynucleotide:target nucleic acid complex is treated with a single-strand specific nuclease, which preferentially nicks the regions flanking the polynucleotide:target nucleic acid complex region (Ferrin and Camerini-Otero. 1991. Science. 254 1494–1497). That is, the domain is protected from recombination by the initial presence of the recombinase in the complex. The nuclease is inactivated and the complex dissociated. The nicked target nucleic acid is reassembled and recombined by PCR to produce a library of nucleic acids with preferential modifications in the nicked regions. The library of modified nucleic acids can be introduced into a host cell and expressed. Cells are selected and isolated that comprise a modified nucleic acid that encodes a polypeptide having a desired property. This process is repeated iteratively to further evolve the predetermined targeted domain of interest.

In each of the methods described above, single domains and optionally multiple domains are targeted. The methods and compositions described above are optionally used in combination for domain specific gene evolution. For example, individual or multiple rounds of domain specific DNA nicking are followed or interspersed with one or more rounds of domain specific evolution employing a plurality of targeting polynucleotides described above.

The methods of the present invention also avoid multiple subcloning steps. This is particularly relevant when large complex vectors such as lambda, BACS, PACS, YACS, MACS and other genomic DNAs are used and where multiple subcloning steps make mutagenesis and shuffling of unique sites in large vectors particularly tedious and time consuming.

5.3.3. Generating Homologous Recombination Intermediates in vitro, Panels or Libraries of Mutagenized and Shuffled Genes to Generate in vitro Evolution Accordingly, the present invention provides methods to introduce recombinogenic probe or hybrid complexes into recombination proficient cells to link in vitro and in vivo recombination and evolution processes. By generating homologous recombination intermediates in vitro, panels or libraries of mutagenized and shuffled genes are generated for in vitro evolution. The link to in vivo systems allows in vivo selection of evolved genes encoding proteins of a desired characteristic. The present invention can thus be used in a variety of important ways.

5.3.3.1. Methods Can Be used in the Creation of Transgenic Organisms, Animal, and Plant Models of Disease First, these methods can be used in the creation of transgenic organisms, animal, and plant models of disease. Thus, for example, domain-specific targeting polynucleotides used in homologous recombination methods can generate animals that have a wide variety of mutations in a wide variety of functionally related genes, potentially resulting in a wide variety of phenotypes, including phenotypes related to disease states. This may also be done on a cellular level, to identify genes involved in cellular phenotypes, i.e. target identification.

5.3.3.2. Identify "Reversion" Genes, Genes that can Modulate Disease States

Secondly, domain targeting can be used in cells or animals that are diseased or altered; in essence, domain targeting can be done to identify "reversion" genes, genes that can modulate disease states caused by different genes, either genes within the same gene family or a completely different gene family. Thus, for example the loss of one type of enzymatic activity, resulting in a disease phenotype, may be compensated by alterations in a different but homologous enzymatic activity.

5.3.3.3. Creation of Libraries of Altered Nucleic Acids

In addition, the methods may be used in the creation of libraries of altered nucleic acids, including extrachromosomal sequences, and can be expressed in cells to produce libraries of altered proteins, which then can be screened for any number of useful or interesting properties, including, but not limited to, increased or altered stability (thermal, pH, oxidants, to proteases, etc.); altered specificity (for example, in the case of enzymes); altered binding; modified activity and other desirable properties, such as, altered immunogenicity.

5.3.4. Use of Homology Motif Tags (HMTs) in Targeted Homologous Recombination to Elucidate Disease Mechanisms and to Identify Disease Targets Contained within Gene Families The present invention is directed to the use of homology motif tags (HMTs) in targeted homologous recombination to elucidate disease mechanisms and to identify disease targets contained within gene families related by the presence of one or more common domains. That is, there are a large number of gene families that contain genes related by the presence of similar functional domains, i.e. binding domains for substrates or other proteins, enzymatic domains such as kinase or protease domains, signaling and regulator domains, receptor binding domains, ATP binding domains, leucine zipper domains, zinc finger domains, etc. These functional domains frequently result in primary sequence homology; that is, related functional domains have related sequences. Many of these functional domains have been studied and so-called "consensus sequences" identified; that is, an average sequence derived from a number of related sequences. Each residue (or set of residues) of the consensus sequence is the most frequent at that position in the set under consideration. Consensus sequences can be either amino acid or nucleic acid consensus sequences, with amino acid sequences being used to generate nucleic acid consensus sequences.

Interestingly, while a wide variety of gene families are known, the majority of drug targets come from only four of these gene families. These are the G-protein coupled or seven-transmembrane domain receptors, nuclear (hormone) receptors, ion channels, esterases. Other important gene families are enzymes, including recombinases. Of the top 100 pharmaceutical drugs, 18 bind to seven-transmembrane receptors, 10 to nuclear receptors and 16 to ion channels.

By using HMTs directed to the consensus sequences of gene families for homologous recombination and particularly enhanced homologous recombination methods, sequence modifications may be made to any number of targeted genes in a related family.

5.3.4.1. Methods and Compositions Utilizing Homology Motif Tags (HMTs) or Consensus Sequences Accordingly, the present invention provides methods and compositions utilizing homology motif tags (HMTs) or consensus sequences. By "homology motif tag" or "protein consensus sequence" herein is meant an amino acid consensus sequence of a gene family. By "consensus nucleic acid sequence" herein is meant a nucleic acid that encodes a consensus protein sequence of a functional domain of a gene family. In addition, "consensus nucleic acid sequence" can also refer to cis sequences that are non-coding but can serve a regulatory or other role. As outlined below, generally a library of consensus nucleic acid sequences are used, that comprises a set of degenerate nucleic acids encoding the protein consensus sequence. A wide variety of protein consensus sequences for a number of gene families are known. A "gene family" therefore is a set of genes that encode proteins that contain a functional is domain for which a consensus sequence can be identified. However, in some instances, a gene family includes non-coding sequences; for example, consensus regulatory regions can be identified. For example, gene family/consensus sequences pairs are known for the G-protein coupled receptor family, the AAA-protein family, the bZIP transcription factor family, the mutS family, the recA family, the Rad51 family, the dmel family, the recF family, the SH2 domain family, the Bcl-2 family, the single-stranded binding protein family, the TFIID transcription family, the TGF-beta family, the TNF family, the XPA family, the XPG family, actin binding proteins, bromo-domain GDP exchange factors, MCM family, ser/thr phosphatase family, etc.

As will be appreciated by those in the art, the proteins of the gene families generally do not contain the exact consensus sequences; generally consensus sequences are artificial sequences that represent the best comparison of a variety of sequences. The actual sequence that corresponds to the functional sequence within a particular protein is termed a "consensus functional domain" herein; that is, a consensus functional domain is the actual sequence within a protein that corresponds to the consensus sequence. A consensus functional domain may also be a "predetermined endogenous DNA sequence" (also referred to herein as a "predetermined target sequence") that is a polynucleotide sequence contained in a target cell. Such sequences can include, for example, chromosomal sequences (e.g., structural genes, regulatory sequences including promoters and enhancers, recombinatorial hotspots, repeat sequences, integrated proviral sequences, hairpins, palindromes), episomal or extrachromosomal sequences (e.g., replicable plasmids or viral replication intermediates) including chloroplast and mitochondrial DNA sequences. By "predetermined" or "preselected" it is meant that the consensus functional domain target sequence may be selected at the discretion of the practitioner on the basis of known or predicted sequence information, and is not constrained to specific sites recognized by certain site-specific recombinases (e.g., FLP recombinase or CRE recombinase). In some embodiments, the predetermined endogenous DNA target sequence will be other than a naturally occurring germline DNA sequence (e.g., a transgene, parasitic, mycoplasmal or viral sequence).

5.3.4.1.1. Gene Family is the G-Protein Coupled Receptor Family

5.3.4.1.1.1. Subfamily 1 also Called R7G Proteins

In a preferred embodiment, the gene family is the G-protein coupled receptor family, which has over 900 identified members, including several subfamilies. In a preferred embodiment, the G-protein coupled receptors are from subfamily 1 and are also called R7G proteins. They are an extensive group of receptors which recognize hormones, neurotransmitters, odorants and light and transduce extracellular signals by interaction with guanine (G) nucleotide-binding proteins. The structure of all these receptors is thought to be virtually identical, and they contain seven hydrophobic regions, each of which putatively spans the membrane. The N-terminus is extracellular and is frequently glycosylated, and the C-terminus is cytoplasmic and generally phosphorylated. Three extracellular loops alternate with three cytoplasmic loops to link the seven transmembrane regions. G-protein coupled receptors include, but are not limited to: the class A rhodopsin first subfamily, including amine (acetylcholine (muscarinic), adrenoceptors, domamine, histamine, serotonin, octopamine), peptides (angiotensin, bombesin, bradykinin, C5a anaphylatoxin, Fmet-leu-phe, interleukin-8, chemokine, CCK, endothelin, mealnocortin, neuropeptide Y, neurotensin, opioid, somatostatin, tachykinin, thrombin, vasopressin-like, galanin, proteinase activated), hormone proteins (follicle stimulating hormone, lutropin-choriogonadotropic hormone, thyrotropin), rhodopsin (vertebrate), olfactory (olfactory type 1–11, gustatory), prostanoid (prostaglandin, prostacyclin, thromboxane), nucleotide (adenosine, purinoceptors), cannabis, platelet activating factor, gonadotropin-releasing hormone (gonadotropin releasing hormone, thyrotropin-releasing hormone, growth hormone secretagogue), melatonin, viral proteins, MHC receptor, Mas proto-oncogene, EBV-induced and glucocorticoid induced; the class B secretin second subfamily, including calcitonin, corticotropin releasing factor, gastric inhibitory peptide, glucagon, growth hormone releasing hormone, parathyroid hormone, secretin, vasoactive intestinal polypeptide, and diuretic hormone; the class C metabotropic glutamate third subfamily, including metabrotropic glutamate and extracellular calcium-sensing agents; and the class D pheromone fourth subfamily. Because of the large number of family members, these large classes of GPCRs can be further subdivided into subfamilies. Examples of these subfamilies are calcitonin, glucagon, vasoactive and parathyroid are from class B; and acetylcholine, histamine angiotensin, alpha2- and beta-adrenergic are from class A. From each subfamily small protein consensus sequences can be derived from sequence alignments. For example, there are 6 motifs for the metabotripic glutamate like GPRCs derived from the indicated number of family members. Using the protein consensus sequence, degenerate nucleic acid probes are made to encode the protein consensus sequence, as is well known in the art. The protein sequence is encoded by DNA triplets which are deduced using standard tables. In some cases additional degeneracy is used to enable production in one oligonucleotide synthesis. In many cases motifs were chosen to minimize degeneracy. Amplification of neighboring sequences can utilize two motifs as indicated by faithful or error prone amplification. Alternatively outside sequences can be used as is indicated using vector sequence. In addition degenerate oligos can be synthesized and used directly in the procedure without amplification. Double stranded (ds) DNA probes are denatured and coated with RecA or another recombinase such as Rad51. This material can be used to bind to and allow capture of specific clones from cDNA or genomic libraries. Alternatively this material can be introduced into cells producing transgenic cells or animals with alterations in related family members.

5.3.4.1.1.2. Second Subfamily Encoding Receptors that Bind Peptide Hormones that do not Show Sequence Similarity to the First R7G Subfamily In addition to the first subfamily of G-protein coupled receptors, there is a second subfamily encoding receptors that bind peptide hormones that do not show sequence similarity to the first R7G subfamily. All the characterized receptors in this subfamily are coupled to G-proteins that activate both adenylyl cyclase and the phosphatidylinositol-calcium pathway. However, they are structurally similar; like classical R7G proteins they putatively contain seven transmembrane regions, a glycosylated extracellular N-terminus and a cytoplasmic C-terminus. Known receptors in this subfamily are encoded on multiple exons, and several of these genes are alternatively spliced to yield functionally distinct products. The N-terminus contains five conserved cysteine residues putatively important in disulfide bonds. Known G-protein coupled receptors in this subfamily are listed above.

5.3.4.1.1.3. Third Subfamily Encoding Receptors that Bind Glutamate and Calcium but do not Show Sequence Similarity to Either of the Other Subfamilies In addition to the first and second subfamilies of G-protein coupled receptors, there is a third subfamily encoding receptors that bind glutamate and calcium but do not show sequence similarity to either of the other subfamilies. Structurally, this subfamily has signal sequences, very large hydrophobic extracellular regions of about 540 to 600 amino acids that contain 17 conserved cysteines (putatively involved in disulfides), a region of about 250 residues that appear to contain seven transmembrane domains, and a C-terminal cytoplasmic domain of variable length (50 to 350 residues). Known G-protein coupled receptors of this subfamily are listed above.

5.3.4.1.2. Gene Family is the bZIP Transcription Factor Family

In a preferred embodiment, the gene family is the bZIP transcription factor family. This eukaryotic gene family encodes DNA binding transcription factors that contain a basic region that mediates sequence specific DNA binding, and a leucine zipper, required for dimerization. The bZIP family includes, but is not limited to, AP-1, ATF, CREB, CREM, FOS, FRA, GBF, GCN4, HBP, JUN, MET4, OCS1, OP, TAF1, XBP1, and YBBO. In a preferred embodiment, the gene family is involved in DNA mismatch repair, such as mutL, hexB and PMS1. Members of this family include, but are not limited to, MLH 1, PMS 1, PMS2, HexB and Mu1L. The protein consensus sequence is G-F-R-G-E-A-L. In a preferred embodiment, the gene family is the mutS family, also involved in mismatch repair of DNA, directed to the correction of mismatched base pairs that have been missed by the proofreading element of the DNA polymerase complex. MutS gene family members include, but are not limited to, MSH2, MSH3, MSH6 and MutS. In a preferred embodiment, the gene family is the recA family. The bacterial recA is essential for homologous recombination and recombinatorial repair of DNA damage. RecA has many activities, including the formation of nucleoprotein filaments, binding to single stranded and double stranded DNA, binding and hydrolyzing ATP, recombinase activity and interaction with lexA causing lexa activation and autocatalytic cleavage. RecA family members include those from *E. coli*, drosophila, human, lily, etc. specifically including but not limited to, *E. coli* recA, Rec1, Rec2, Rad51, Rad51B, Rad51C, Rad51D, Rad51E, XRCC2 and DMC 1.

5.3.4.1.3. Gene Family is the RecF Family

In a preferred embodiment, the gene family is the recF family. The prokaryotic recF protein is a single-stranded DNA binding protein which also putatively binds ATP. RecF is involved in DNA metabolism; it is required for recombinatorial. DNA repair and for induction of the SOS response. RecF is a protein of about 350 to 370 amino acid residues; there is a conserved ATP-binding site motif "A" in the N-terminal section of the protein as well as two other conserved regions, one located in the central section and the other in the C-terminal section.

5.3.4.1.4. Gene Family is the Bcl-2 Family

In a preferred embodiment, the gene family is the Bcl-2 family. Programmed cell death (PCD), or apoptosis, is induced by events such as growth factor withdrawal and toxins. It is generally controlled by regulators, which have either an inhibitory effect (i.e. anti-apoptotic) or block the protective effect of inhibitors (pro-apoptotic). Many viruses have found a way of countering defensive apoptosis by encoding their own anti-apoptotic genes thereby preventing their target cells from dying too soon.

All proteins belonging to the Bcl-2 family contain at least one of a BH1, BH2, BH3 or BH4 domain. All anti-apoptotic proteins contain BH1 and BH2 domains, some of them contain an additional N-terminal BH4 domain (such as Bcl-2, Bcl-x(L), Bcl-W, etc.), which is generally not found in pro-apoptotic proteins (with the exception of Bcl-x(S). Generally all pro-apoptotic proteins contain a BH3 domain (except for Bad), thought to be crucial for the dimerization of the proteins with other Bcl-2 family members and crucial for their killing activity. In addition, some of the pro-apoptotic proteins contain BH1 and BH2 domains (such as Bax and Bak). The BH3 domain is also present in some anti-apoptosis proteins, such as Bcl-2 and Bcl-x(L). Known Bcl-2 proteins include, but are not limited to, Bcl-2, Bcl-x (L), Bcl-W, Bcl-x(S), Bad, Bax, and Bak.

5.3.4.1.5. Gene Family is the Site-Specific Recombinase Family

In a preferred embodiment, the gene family is the site-specific recombinase family. Site-specific recombination plays an important role in DNA rearrangement in prokaryotic organisms. Two types of site-specific recombination are known to occur: a) recombination between inverted repeats resulting in the reversal of a DNA segment; and b) recombination between repeat sequences on two DNA molecules resulting in their cointegration, or between repeats on one DNA molecule resulting the excision of a DNA fragment. Site-specific recombination is characterized by a strand exchange mechanism that requires no DNA synthesis or high energy cofactor; the phosphodiester bond energy is conserved in a phospho-protein linkage during strand cleavage and re-ligation.

Two unrelated families of recombinases are currently known. The first, called the "phage integrase" family, groups a number of bacterial, phage and yeast plasmid enzymes. The second, called the "resolvase" family, groups enzymes which share the following structural characteristics: an N-terminal catalytic and dimerization domain that contains a conserved serine residue involved in the transient covalent attachment to DNA, and a C-terminal helix-turn-helix DNA-binding domain.

5.3.4.1.6. Gene Family is the Single-Stranded Binding Protein Family

In a preferred embodiment, the gene family is the single-stranded binding protein family. The E coli single-stranded binding protein (ssb), also known as the helix-destabilizing protein, is a protein of 177 amino acids. It binds tightly as a homotetramer to a single-stranded DNA ss-DNA) and plays an important role in DNA replication, recombination and repair. Members of the ssb family include, but are not limited to, *E. coli* ssb and eukaryotic RPA proteins.

5.3.4.1.7. Gene Family is the TFIID Transcription Family

In a preferred embodiment, the gene family is the TFIID transcription family. Transcription factor TRID (or TATA-binding protein, TBP), is a general factor that plays a major role in the activation of eukaryotic genes transcribed by RNA polymerase II. TRID binds specifically to the TATA box promoter element which lies close to the position of transcription initiation. There is a remarkable degree of sequence conservation of a C-terminal domain of about 180 residues in TFIID from various eukaryotic sources. This region is necessary and sufficient for TATA box binding. The most significant structural feature of this domain is the presence of two conserved repeats of a 77 amino-acid region.

5.3.4.1.8. Gene Family is the TGF-beta Family

In a preferred embodiment, the gene family is the TGF-beta family. Transforming growth factor-beta (TGF-beta) is a multifunctional protein that controls proliferation, differentiation and other functions in many cell types. TGF-beta-1 is a protein of 112 amino acid residues derived by proteolytic cleavage from the C-terminal portion of the precursor protein. Members of the TGF-beta family include, but are not limited to, the TGF-1–3 subfamily (including TGF1, TGF2, and TGF3); the BMP3 subfamily (BM3B, BMP3); the BMP5–8 subfamily (BM8A, BMP5, BMP6, BMP7, and BMP8); and the BMP 2 & 4 subfamily (BMP2, BMP4, DECA).

In a preferred embodiment, the gene family is the TNF family. A number of cytokines can be grouped into a family on the basis of amino acid sequence, as well as structural and functional similarities. These include (1) tumor necrosis factor (TNF), also known as cachectin or TNF-alpha, which is a cytokine with a wide variety of functions. TNF-alpha can cause cytolysis of certain tumor cell lines; it is involved in the induction of cachexia; it is a potent pyrogen, causing fever by direct action or by stimulation of interleukin-1 secretion; and it can stimulate cell proliferation and induce cell differentiation under certain conditions; (2) lymphotoxin-alpha (LT-alpha) and lymphotoxin-beta (LT-beta), two related cytokines produced by lymphocytes and which are cytotoxic for a wide range of tumor cells in vitro and in vivo; (3) T cell antigen gp39 (CD40L), a cytokine that seems to be important in B-cell development and activation; (4) CD27L, a cytokine that plays a role in T-cell activation; it induces the proliferation of costimulated T cells and enhances the generation of cytolytic T cells; (5) CD30L, a cytokine that induces proliferation of T-cells; (6) FASL, a cytokine involved in cell death; (8) 4-1 BBL, an inducible T cell surface molecule that contributes to T-cell stimulation; (9) OX40L, a cytokine that co-stimulates T cell proliferation and cytokine production; and (10), TNF-related apoptosis inducing ligand (TRAIL), a cytokine that induces apoptosis.

5.3.4.1.9. Gene Family is the XPA Family

In a preferred embodiment, the gene family is the XPA family. Xerodenna pigmentosa (XP) is a human autosomal recessive disease, characterized by a high incidence of sunlight-induced skin cancer. Skin cells associated with this condition are hypersensitive to ultaviolet light, due to defects in the incision step of DNA excision repair. There are a minimum of 7 genetic complementation groups involved in this disorder: XPA to XPG. XPA is the most common form of the disease and is due to defects in a 30 kD nuclear protein called XPA or (XPAC). The sequence of XPA is conserved from higher eukaryotes to yeast (gene RAD14). XPA is a hydrophilic protein of 247 to 296 amino acid residues that has a C4-type zinc finger motif in its central section.

5.3.4.1.10. Gene Family is the XPG Family

In a preferred embodiment, the gene family is the XPG family. The defect in XPG can be corrected by a 133 kD nuclear protein called XPG (or XPGC). Members of the XPG family include, but are not limited to, FEN1, XPG, RAD2, EXO1, and DIN7.

Once having identified a gene family and a consensus sequence, the compositions of the invention can be made. The compositions of the invention comprise at least one recombinase and at least two single-stranded targeting polynucleotides which are substantially complementary to each other and each have a consensus homology clamp for a gene family.

5.3.5. Homologous Recombination

Accordingly, the present invention provides methods of homologous recombination. By "homologous recombination" (HR) herein is meant an exchange of homologous or similar DNA sequence between two DNA molecules. An essential feature of HR is that the enzyme responsible for the recombination event can pair any homologous sequences as substrates. The ability of HR to transfer genetic information between DNA molecules makes targeted homologous recombination a very powerful method in genetic engineering and gene manipulation. HR can be used to insert, delete, and/or substitute any one or more nucleotides in a gene or gene segment or to introduce or delete genes in a targeted nucleic acid.

Once having identified a protein domain, the compositions of the invention can be made. The compositions of the invention comprise at least one recombinase and at least two single-stranded targeting polynucleotides which are substantially complementary to each other and each have a domain homology clamp.

5.3.6. Recombinase

By "recombinase" herein is meant a protein or peptide (e.g. L2 peptide) that, when included with an exogenous targeting polynucleotide, provide a measurable increase in the recombination frequency and/or localization frequency between the targeting polynucleotide and an endogenous predetermined DNA sequence. Thus, in a preferred embodiment, increases in recombination frequency from the normal range of $10^{-8}$ to $10^{-4}$, to $10^{-4}$ to $10^{1}$, preferably $10^{-3}$ to $10_{1}$, and most preferably $10^{-2}$ to $10^{0}$, may be achieved.

In the present invention, recombinase refers to a family of RecA-like and Rad51-like recombination proteins all having essentially all or most of the same functions, particularly: (i) the recombinase protein's ability to properly bind to and position targeting polynucleotides on their homologous targets and (ii) the ability of recombinase protein/targeting polynucleotide complexes to efficiently find and bind to complementary endogenous sequences. The best characterized RecA protein is from $E$ $coli$, in addition to the wild-type protein a number of mutant RecA proteins have been identified (e.g., RecA803; see Madiraju et al., PNAS USA 85(18):6592 (1988); Madiraju et al, Biochem. 31:10529 (1992); Lavery et al., J. Biol. Chem. 267:20648 (1992)). Further, many organisms have RecA-like recombinases with strand-transfer activities (e.g., Fugisawa et al., (1985) Nucl. Acids Res. 13:7473; Hsieh et al., (1986) Cell 44: 885; Hsieh et al., (1989) J. Biol. Chem. 264: 5089; Fishel et al., (1988) Proc. Natl. Acad. Sci. (USA) 85: 3683; Cassuto et al., (1987) Mol. Gen. Genet. 208: 10; Ganea et al., (1987) Mol. Cell Biol. 7: 3124; Moore et al., (1990) J. Biol. Chem. 19:11108; Keene et al., (1984) Nucl. Acids Res. 12: 3057; Kimeic, (1984) Cold Spring Harbor Symp. 48: 675; Kmeic, (1986) Cell 44: 545; Kolodner et al., (1987) Proc. Natl. Acad. Sci. USA 84: 5560; Sugino et al., (1 985) Proc. Natl. Acad. Sci. USA 85: 3683; Halbrook et al., (1989) J. Biol. Chem. 264: 21403; Eisen et al., (1988) Proc. Natl. Acad. Sci. USA 85: 7481; McCarthy et al., (1988) Proc. Natl. Acad. Sci. US 85: 5854; Lowenhaupt et al., (1989) J. Biol. Chem 264: 20568, which are incorporated herein by reference. Examples of such recombinase proteins include, for example but not limited to: RecA, RecA803, uvsX, and other RecA mutants and RecA-like recombinases (Roca, A. 1. (1990) Crit. Rev. Biochem. Molec. Biol. 25: 415), sep1 (Kolodner et al. (1987) Proc. Natl. Acad. Sci. (U.S.6.1 B4:5560; Tishkoff et al. Molec. Cell. Biol. 11:2593), RuvC (Dunderdale et al. (1991) Nature 354: 506), DST2, KEM1, XRN 1 (Dykstra et al. (1991) Molec. Cell. Biol. 11: 2583), STPalpha/DST1 (Clark et al. (1991) Molec. Cell. Biol. 11: 2576), HPP-1 (Moore et al. (1991) Proc. Natl. Acad. Sci. (U.S.A.1 B8:9067), other target recombinases (Bishop et al. (1992) Cell 69 439; Shinohara et al. (1992) Cell 69 457); incorporated herein by reference. RecA may be purified from $E$ $coli$ strains, such as $E$ $coli$ strains JC 12772 and JC1 5369 (available from A. J. Clark and M. Madiraju, University of California-Berkeley, or purchased commercially). These strains contain the RecA coding sequences on a "runaway" replicating plasmid vector present at a high copy numbers per cell. The RecA803 protein is a high-activity mutant of wild-type RecA. The art teaches several examples of recombinase proteins, for example, from Drosophila, yeast, plant, human, and non-human mammalian cells, including proteins with biological properties similar to RecA (i.e., RecA-like recombinases), such as Rad51, Rad55, Rad57, dmc1 from mammals and yeast. In addition, the recombinase may actually be a complex of proteins, i.e. a "recombinosome". In addition, included within the definition of a recombinase are portions or fragments of recombinases which retain recombinase biological activity, as well as variants or mutants of wild-type recombinases which retain biological activity, such as the $E$. $coli$ RecA803 mutant with enhanced recombinase activity.

5.3.6.1. RecA or rad51

In a preferred embodiment, RecA or rad51 is used. For example, RecA protein is typically obtained from bacterial strains that overproduce the protein: wild-type $E$ $coli$ RecA protein and mutant RecA803 protein may be purified from such strains. Alternatively, RecA protein can also be purchased from, for example, Pharmacia (Piscataway, N.J.) or Boehringer Mannheim (Indianapolis, Ind.). RecA proteins, and its homologs, form a nucleoprotein filament when it coats a single-stranded DNA. In this nucleoprotein filament, one monomer of RecA protein is bound to about 3 nucleotides. This property of RecA to coat single-stranded DNA is essentially sequence independent, although particular sequences favor initial loading of RecA onto a polynucleotide (e.g., nucleation sequences). The nucleoprotein filament(s) can be formed on essentially any DNA molecule and can be formed in cells (e.g., mammalian cells), forming complexes with both single- stranded and double-stranded DNA, although the loading conditions for dsDNA are somewhat different than for ssDNA.

5.3.6.1.1. The Recombinase is Combined with Targeting Polynucleotides

The recombinase is combined with targeting polynucleotides as is more fully outlined below. By "nucleic acid" or "oligonucleotide" or "polynucleotide" or grammatical equivalents herein means at least two nucleotides covalently linked together. A nucleic acid of the present invention will generally contain phosphodiester bonds, although in some cases nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); SprinzI et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate, phosphorodithioate, O-methylphophoroamidete linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). These modifications of the ribose-phosphate backbone or bases may be done to facilitate the addition of other moieties such as chemical constituents, including 2' O-methyl and 5' modified substituents, as discussed below, or to increase the stability and half-life of such molecules in physiological environments.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo-and ribo-nucleotides, and any combination of bases, including uracil, adenine, thymine, cytosine, guanine, inosine, xathanine and hypoxathanine, etc. Thus, for example, chimeric DNA-RNA molecules may be used such as described in Cole-Strauss et al., Science 273:1386 (1996) and Yoon et al., PNAS USA 93:2071 (1996), both of which are hereby incorporated by reference.

In general, the targeting polynucleotides may comprise any number of structures, as long as the changes do not substantially effect the functional ability of the targeting polynucleotide to result in homologous recombination. For example, recombinase coating of alternate structures should still be able to occur.

By "targeting polynucleotides" herein is meant the polynucleotides used to make alterations in the protein domains as described herein. Targeting polynucleotides are generally ssDNA or dsDNA, most preferably two complementary single-stranded DNAs.

Targeting polynucleotides are generally at least about 5 to 2000 nucleotides long, preferably about 12 to 200 nucleotides long, at least about 200 to 500 nucleotides long, more preferably at least about 500 to 2000 nucleotides long, or longer; however, as the length of a targeting polynucleotide increases beyond about 20,000 to 50,000 to 400,000 nucleotides, the efficiency or transferring an intact targeting polynucleotide into the cell decreases. The length of homology may be selected at the discretion of the practitioner on the basis of the sequence composition and complexity of the predetermined endogenous target DNA sequence(s) and guidance provided in the art, which generally indicates that 1.3 to 6.8 kilobase segments of homology are preferred when non-recombinase mediated methods are utilized (Hasty et al. (1991) Molec. Cell. Biol. 11: 5586; Shulman et al. (1990) Molec. Cell. Biol. 10: 4466, which are incorporated herein by reference).

Targeting polynucleotides have at least one sequence that substantially corresponds to, or is substantially complementary to, a predetermined endogenous DNA sequence. As used herein, the terms "predetermined target nucleic acid" and "predetermined target sequence" and "predetermined domain of a target nucleic acid" refer to polynucleotide sequences contained in a target nucleic acid. Such sequences include, for example, chromosomal sequences (e.g., structural genes, regulatory sequences including promoters and enhancers, recombinatorial hotspots, repeat sequences, integrated proviral sequences, hairpins, palindromes), episomal or extrachromosomal sequences (e.g., replicable plasmids or viral replication intermediates) including chloroplast and mitochondrial DNA sequences. By "predetermined" or "preselected" it is meant that the target sequence maybe selected at the discretion of the practitioner on the basis of known or predicted sequence information, and is not constrained to specific sites recognized by certain site-specific recombinases (e.g., FLIP recombinase or CRE recombinase). In some embodiments, the predetermined endogenous DNA target sequence will be other than a naturally occurring germline DNA sequence (e.g., a transgene, parasitic, mycoplasmal or viral sequence). An exogenous polynucleotide is a polynucleotide which is transferred into a target cell but which has not been replicated in that host cell; for example, a virus genome polynucleotide that enters a cell by fusion of a virion to the cell is an exogenous polynucleotide, however, replicated copies of the viral polynucleotide subsequently made in the infected cell are endogenous sequences (and may, for example, become integrated into a cell chromosome). Similarly, transgenes which are microinjected or transfected into a cell are exogenous polynucleotides, however integrated and replicated copies of the transgene(s) are endogenous sequences.

5.3.6.1.1.1. Target Nucleic Acid Comprises a Nucleotide Sequence Encoding a Protein or Polypeptide or Can Be Made to Comprise Non-Coding Regions as Well In a preferred embodiment, the target nucleic acid comprises a nucleotide sequence encoding a protein or polypeptide, although as outlined herein, target nucleic acids may be made to non-coding regions as well. By "protein" herein is meant at least two covalently attached amino acids, which includes proteins, polypeptides, oligopeptides and peptides. Thus "amino acid" or "peptide residue", as used herein means naturally occurring and naturally modified amino acids. For example, "amino acid" also includes imino acid residues such as proline and hydroxyproline. A "naturally modified amino acid" includes for examples, amino acids that are modified to contain carbohydrate structures, such as high-mannose or complex carbohydrates, phosphate, or lipids. In the preferred embodiment, the amino acids are in the (S) or L-configuration.

The nucleotide sequence encoding the polypeptide is preferably operably linked to transcription and translation control elements operable in a host cell of interest, such that, introduction of the target nucleic acid results in expression of the encoded protein. The transcription control elements include a promoter, such as, a constitutive or inducible promoter. When the host cell of interest is a eukaryotic cell, enhancer elements are optionally employed. In a preferred embodiment the target nucleic acid is an extrachromosomal vector such as a plasmid. In other embodiments, the target nucleic acid is a viral vector, such as, a retrovirus, a phage, a BAC, PAC, YAC, MAC or other types of genomic and chromosomal DNA.

The term "naturally-occurring" as used herein as applied to an object refers to the fact that an object can be found in nature. For example, a polynucleotide sequence that is present in an organism (including viruses) that can be isolated from a source in nature and which has not been intentionally modified by man in the laboratory is naturally-occurring.

5.3.6.1.1.2. The Target Nucleic Acid Comprises a Nucleic Acid Encoding a Protein Domain The methods of the invention are used for alteration and evolution of protein domains; that is, in a preferred embodiment, the target nucleic acid comprises a nucleic acid encoding a protein domain. By "protein domain" and grammatical equivalents as used herein are meant a region of a protein that provides a specific structural and/or functional characteristic. Accordingly, a protein domain is an enzymatic active site, a ligand binding site, an allosteric effector region, an epitope, a region of a protein that is modified, such as, by addition of a carbohydrate, phosphate or lipid. A domain also relates to the hydrophobicity or hydrophilicity of a region and, therefore, also includes extracellular, intracellular, and transmembrane domains. Cell targeting sequences, such as, a signal peptide, nuclear localization sequence, mitochondrial localization sequences, etc. that direct proteins to either an extracellular or subcellular locale are domains. Additional domains include regions of proteins that interact with other proteins or nucleic acids, for example, include multimerization sequences, zinc-finger motifs, and the like. In another aspect, a protein domain is a region encoded by an exon.

Targeting polynucleotides have at least one sequence that substantially corresponds to, or is substantially complementary to, a target nucleic acid; in a preferred embodiment, it corresponds or complements a nucleic acid encoding a protein domain. By "corresponds to" herein is meant that a polynucleotide sequence is homologous (i.e., may be similar or identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence can hybridize to all or a portion of a reference polynucleotide sequence. Thus, one of the complementary single stranded targeting polynucleotides is complementary to one strand of the endogenous target domain sequence (i.e. Watson) and corresponds to the other strand of the endogenous target domain sequence (i.e. Crick). Thus, the complementarity between two single-stranded targeting polynucleotides need not be perfect. For illustration, the nucleotide sequence "TATAC" corresponds to a reference sequence "TATAC" and is perfectly complementary to a reference sequence "GTATA".

The terms "substantially corresponds to" or "substantial identity" or "homologous" as used herein denotes a characteristic of a nucleic acid sequence, wherein a nucleic acid sequence has at least about 50 percent sequence identity as compared to a reference sequence, typically at least about 70 percent sequence identity, and preferably at least about 85 percent sequence identity as compared to a reference sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long.

"Substantially complementary" as used herein refers to a sequence that is complementary to a sequence that substantially corresponds to a reference sequence. In general, targeting efficiency increases with the length of the targeting polynucleotide portion that is substantially complementary to a reference sequence present in the target DNA. By "sequence homology" herein is meant sequence similarity or sequence identity. Nucleic acid similarity can be determined using, for example, BLASTN (Altschul et aL 1990. J. Mol. Biol. 147:195–197). BLASTN uses a simple scoring system in which matches count +5 and mismatches –4. To achieve computational efficiency, the default parameters have been incorporated directly into the source code.

5.3.7. Percent Nucleic Acid Sequence Identity is Determined

In an alternative embodiment, percent nucleic acid sequence identity is determined. In percent identity calculations relative weight is not assigned to the various types of sequence variation, such as, insertions, deletions, substitutions, etc. Only identities are scored positively (+1) and all forms of sequence variation given a value of "0", which obviates the need for a weighted scale or parameters as described above for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

5.3.8. Domain Homology Clamps: A Portion of the Targeting Polynucleotide that Can Specifically Hybridize to a Nucleic Acid Encoding a Domain Within a Gene of Interest These corresponding/complementary sequences are sometimes referred to herein as "domain homology clamps", as they serve as templates for homologous pairing with the predetermined endogenous sequence(s). Thus, a "domain homology clamp" is a portion of the targeting polynucleotide that can specifically hybridize to a nucleic acid encoding a domain within a gene of interest. "Specific hybridization" is defined herein as the formation of hybrids between a targeting polynucleotide (e.g., a polynucleotide of the invention which may include substitutions, deletion, and/or additions as compared to the predetermined target nucleic acid sequence) and a predetermined target nucleic acid, wherein the targeting polynucleotide preferentially hybridizes to the predetermined target nucleic acid such that, for example, at least one discrete band can be identified on a Southern blot of nucleic acid prepared from target cells that contain the target nucleic acid sequence, and/or a targeting polynucleotide in an intact nucleus localizes to a discrete chromosomal location characteristic of a unique or repetitive sequence. As will be appreciated by those in the art, a target domain sequence may be present in more than one target polynucleotide species (e.g., a particular target sequence may occur in multiple members of a gene family). It is evident that optimal hybridization conditions will vary depending upon the sequence composition and length(s) of the targeting polynucleotide(s) and target(s), and the experimental method selected by the practitioner. Various guidelines may be used to select appropriate hybridization conditions (see, Maniatis et al., Molecular Cloning: A Laboratory Manual (1989), 2nd Ed., Cold Spring Harbor, N.Y. and Berger and Kimmel, Methods in Enzymology. Volume 152, Guide to Molecular Cloning Technigues (1987), Academic Press, Inc., San Diego, Calif.), which are incorporated herein by reference. Methods for hybridizing a targeting polynucleotide to a discrete chromosomal location in intact nuclei are known in the art, see for example WO 93/05177 and Kowalczykowski and Zarling (1994) in Gene Targeting, Ed. Manuel Vega.

In targeting polynucleotides, domain homology clamps are typically located at or near the 5' or 3' end, preferably domain homology clamps are internal or located at each end of the polynucleotide (Berinstein et al. (1992) Molec, Cell. Biol. 12: 360, which is incorporated herein by reference). Without wishing to be bound by any particular theory, it is believed that the addition of recombinases permits efficient gene targeting with targeting polynucleotides having short (i. e., about 10 to 1000 basepair long) segments of homology, as well as with targeting polynucleotides having longer segments of homology.

5.3.9. Targeting Polynucleotides 5.3.9.1. Targeting Polynucleotides that have Domain Homology Clamps that are Highly Homologous to the Predetermined Target Endogenous Domain Functional Domain Nucleic Acid Sequence Therefore, it is preferred that targeting polynucleotides of the invention have domain homology clamps that are highly homologous to the predetermined target endogenous domain functional domain nucleic acid sequence(s). Typically, targeting polynucleotides of the invention have at least one domain homology clamp that is at least about 18 to 35 nucleotides long, and it is preferable that domain homology clamps are at least about 20 to 100 nucleotides long, and more preferably at least about 100–500 nucleotides long, although the degree of sequence homology between the domain homology clamp and the targeted sequence and the base composition of the targeted sequence will determine the optimal and minimal clamp lengths (e.g., G-C rich sequences are typically more thermodynamically stable and will generally require shorter clamp length). Therefore, both domain homology clamp length and the degree of sequence homology can only be determined with reference to a particular predetermined sequence, but domain homology clamps generally must be at least about 10 nucleotides long and must also substantially correspond or be substantially complementary to a predetermined target sequence. Preferably, a homology clamp is at least about 10, and preferably at least about 50 nucleotides long and is substantially identical to or complementary to a predetermined target sequence. Without wishing to be bound by a particular theory, it is believed that the addition of recombinases to a targeting polynucleotide enhances the efficiency of homologous recombination between homologous, nonisogenic sequences (e.g., between an exon 2 sequence of an albumin gene of a Balb/c mouse and a homologous albumin gene exon 2 sequence of a C57/BL6 mouse), as well as between isogenic sequences.

5.3.9.2. Targeting Polynucleotides Comprising a Plurality of Targeting Polynucleotides Comprising at Least One Shared Homology Clamp and a Degenerate Sequence In one aspect of the invention, the targeting polynucleotides comprise a plurality of targeting polynucleotides comprising at least one shared homology clamp and a degenerate sequence. By "plurality" herein is meant more than one. The targeting polynucleotides find use in the mutagenesis and evolution of a target nucleic acid sequence that encodes specific protein domain by insertion, deletion and/or substitution of the nucleic acid sequence encoding the domain. In one embodiment the degenerate sequence is completely randomized, representing all possible combinations of nucleotides. In another embodiment, the degenerate sequence is biased, for example, to eliminate sequences encoding for transcriptional or translational stop signals. In another embodiment, the degenerate sequence is biased, to represent the codon bias of a host cell or class of organisms. The degenerate sequence is optionally biased to randomize specific sequence while maintaining other sequences constant. The length of the degenerate sequence is determined by the practitioner and is based on the desired number of nucleotides within the predetermined sequence to be modified.

5.3.9.3. Targeting Polynucleotides Substantially Identical to the Predetermined Target Sequence In an alternative embodiment, the targeting polynucleotides are substantially identical to the predetermined target sequence. In the presence of a recombinase, the targeting polynucleotides form complexes with a predetermined target sequence of a target nucleic acid. As a part of the complex, the predetermined target sequence is resistant to nuclease digestion. The regions flanking the polynucleotide-:target complex are susceptible to single-strand specific exonucleases. Accordingly, to effect domain specific evolution, these regions are nicked and the resultant fragments are reassembled and recombined by PCR as described below and by Stemmer et al. Nature. 370:389–391 and Stemmer et al. PNAS USA 91:10747–10751, hereby incorporated by reference.

The formation of heteroduplex joints is not a stringent process; genetic evidence supports the view that the classical phenomena of meiotic gene conversion and aberrant meiotic segregation results in part from the inclusion of mismatched base pairs in heteroduplex joints, and the subsequent correction of some of these mismatched base pairs before replication. Observations on RecA protein have provided information on parameters that affect the discrimination of relatedness from perfect or near-perfect homology and that affect the inclusion of mismatched base pairs in heteroduplex joints. The ability of RecA protein to drive strand exchange past all single base-pair mismatches and to form extensively mismatched joints in superhelical DNA reflect its role in recombination and gene conversion. This error-prone process may also be related to its role in mutagenesis. RecA-mediated pairing reactions involving DNA of X 1 74 and G4, which are about 70 percent homologous, have yielded homologous recombinants (Cunningham et al. (1981) Cell 24: 213), although RecA preferentially forms homologous joints between highly homologous sequences, and is implicated as mediating a homology search process between an invading DNA strand and a recipient DNA strand, producing relatively stable heteroduplexes at regions of high homology. Accordingly, it is the fact that recombinases can drive the homologous recombination reaction between strands which are significantly, but not perfectly, homologous, which allows gene conversion and the modification of target sequences. Thus, targeting polynucleotides may be used to introduce nucleotide substitutions, insertions and deletions into an endogenous functional domain nucleic acid sequence, and thus the corresponding amino acid substitutions, insertions and deletions in proteins expressed from the endogenous domain functional domain nucleic acid sequence. By "endogenous" in this context herein is meant the naturally occurring sequence, i.e. sequences or substances originating from within a cell or organism. Similarly, "exogenous" refers to sequences or substances originating outside the cell or organism.

5.3.9.4. Method Where Two Substantially Complementary Targeting Polynucleotides are Used In a preferred embodiment, two substantially complementary targeting polynucleotides are used.

5.3.9.5. Method Where the Targeting Polynucleotides Form a Double Stranded Hybrid, Which may Be Coated with Recombinase In one embodiment, the targeting polynucleotides form a double stranded hybrid, which may be coated with recombinase, although when the recombinase is RecA, the loading conditions may be somewhat different from those used for single stranded nucleic acids.

5.3.9.6. Method Where Two Substantially Complementary Single-Stranded Targeting Polynucleotides are Used In a preferred embodiment, two substantially complementary single-stranded targeting polynucleotides are used. The two complementary single-stranded targeting polynucleotides are usually of equal length, although this is not required. However, as noted below, the stability of the four strand hybrids of the invention is putatively related, in part, to the lack of significant unhybridized single-stranded nucleic acid, and thus significant unpaired sequences are not preferred. Furthermore, as noted above, the complementarity between the two targeting polynucleotides need not be perfect. The two complementary single-stranded targeting polynucleotides are simultaneously or contemporaneously introduced into a target cell harboring a predetermined endogenous target sequence, generally with at lease one recombinase protein (e.g., RecA). Under most circumstances, it is preferred that the targeting polynucleotides are incubated with RecA or other recombinase prior to introduction into a target cell, so that the recombinase protein(s) may be "loaded" onto the targeting polynucleotide (s), to coat the nucleic acid, as is described below. Incubation conditions for such recombinase loading are described infra. A targeting polynucleotide may contain a sequence that enhances the loading process of a recombinase, for example a RecA loading sequence is the recombinogenic nucleation sequence poly[d(A-C)], and its complement, poly [d(G-T)]. The duplex sequence poly[d(A-C)*d(G-T)n, where n is from 5 to 25, is a middle repetitive element in target DNA.

There appears to be a fundamental difference in the stability of RecA-protein-mediated D-loops formed between one single-stranded DNA (ssDNA) probe hybridized to negatively supercoiled DNA targets in comparison to relaxed or linear duplex DNA targets. Internally located dsDNA target sequences on relaxed linear DNA targets hybridized by ssDNA probes produce single D-loops, which are unstable after removal of RecA protein (Adzuma, Genes Devel. 6:1679 (1992); Hsieh et al, PNAS USA 89:6492 (1992); Chiu et al., Biochemistry 32:13146 (1993)). This probe DNA instability of hybrids formed with linear duplex DNA targets is most probably due to the incoming ssDNA probe W-C base pairing with the complementary DNA strand of the duplex target and disrupting the base pairing in the other DNA strand. The required high free-energy of maintaining a disrupted DNA strand in an unpaired ssDNA conformation in a protein-free single-D-loop apparently can only be compensated for either by the stored free energy inherent in negatively supercoiled DNA targets or by base pairing initiated at the distal ends of the joint DNA molecule, allowing the exchanged strands to freely intertwine. However, the addition of a second complementary ssDNA to the three-strand-containing single-D-loop stabilizes the deproteinized hybrid joint molecules by allowing W-C base pairing of the probe with the displaced target DNA strand. The addition of a second RecA-coated complementary ssDNA (cssDNA) strand to the three-strand containing single D-loop stabilizes deproteinized hybrid joints located away from the free ends of the duplex target DNA (Sena & Zarling, Nature Genetics 3:365 (1993); Revet et al. J. Mol. Biol. 232:779 (1993); Jayasena and Johnston, J. Mol. Bio. 230:1015 (1993)). The resulting four-stranded structure, named a double D-loop by analogy with the three-stranded single D-loop hybrid has been shown to be stable in the absence of RecA protein. This stability likely occurs because the restoration of W-C basepairing in the parental duplex would require disruption of two W-C basepairs in the double-D-loop (one W-C pair in each heteroduplex D-loop).

Since each base-pairing in the reverse transition (double-D-loop to duplex) is less favorable by the energy of one W-C basepair, the pair of cssDNA probes are thus kinetically trapped in duplex DNA targets in stable hybrid structures. The stability of the double-D loop joint molecule within internally located probe: target hybrids is an intermediate stage prior to the progression of the homologous recombination reaction to the strand exchange phase. The double D-loop permits isolation of stable multistranded DNA recombination intermediates.

In addition, when the targeting polynucleotides are used to generate insertions or deletions in an endogenous nucleic acid sequence, as is described herein, the use of two complementary single-stranded targeting polynucleotides allows the use of internal homology clamps. The use of internal homology clamps allows the formation of stable deproteinized cssDNA:probe target hybrids with homologous DNA sequences containing either relatively small or large insertions and deletions within a homologous DNA target. Without being bound by theory, it appears that these probe:target hybrids, with heterologous inserts in the cssDNA probe, are stabilized by the re-annealing of cssDNA probes to each other within the double-D-loop hybrid, forming a novel DNA structure with an internal homology clamp. Similarly stable double-D-loop hybrids formed at internal sites with heterologous inserts in the linear DNA targets (with respect to the cssDNA probe) are equally stable. Because cssDNA probes are kinetically trapped within the duplex target, the multi-stranded DNA intermediates of homologous DNA pairing are stabilized and strand exchange is facilitated.

5.3.10. Length of the Internal Homology Clamp (i.e. The Length of the Insertion or Deletion)

In a preferred embodiment, the length of the internal homology clamp (i.e. the length of the insertion or deletion) is from about 1 to 50% of the total length of the targeting polynucleotide, with from about 1 to about 20% being preferred and from about 1 to about 10% being especially preferred, although in some cases the length of the deletion or insertion may be significantly larger. As for the domain homology clamps, the complementarity within the internal homology clamp need not be perfect. A targeting polynucleotide used in a method of the invention typically is a single-stranded nucleic acid, usually a DNA strand, or derived by denaturation of a duplex DNA, which is complementary to one (or both) strand(s) of the target duplex nucleic acid. Thus, one of the complementary single stranded targeting polynucleotides is complementary to one strand of the endogenous target sequence (i.e. Watson) and the other complementary single stranded targeting polynucleotide is complementary to the other strand of the endogenous target sequence (i.e. Crick). The domain homology clamp sequence preferably contains at least 90–95% sequence homology with the target sequence (although as outlined above, less sequence homology can be tolerated), to insure sequence-specific targeting of the targeting polynucleotide to the endogenous DNA domain target. Each single-stranded targeting polynucleotide is typically about 50–600 bases long, although a shorter or longer polynucleotide may also be employed.

5.3.11. Method for Making the Targeting Polynucleotides

Once the gene family and domain sequence is selected, the targeting polynucleotides are made, as will be appreciated by those in the art. For example, for large targeting polynucleotides, plasmids are engineered to contain an appropriately sized gene sequence with a deletion or insertion in the gene of interest and at least one flanking homology clamp which substantially corresponds or is substantially complementary to an endogenous target DNA sequence. Vectors containing a targeting polynucleotide sequence are typically grown in *E coli* and then isolated using standard molecular biology methods. Alternatively, targeting polynucleotides may be prepared in single-stranded form by oligonucleotide synthesis methods, which may first require, especially with larger targeting polynucleotides, formation of subfragments of the targeting polynucleotide, typically followed by splicing of the subfragments together, typically by enzymatic ligation. In general, as will be appreciated by those in the art, targeting polynucleotides may be produced by chemical synthesis of oligonucleotides, nick-translation of a double-stranded DNA template, polymerase chain-reaction amplification of a sequence (or ligase chain reaction amplification), purification of prokaryotic or target cloning vectors harboring a sequence of interest (e.g., a cloned cDNA or genomic clone, or portion thereof) such as plasmids, phagemids, YACs, cosmids, bacteriophage DNA, other viral DNA or replication intermediates, or purified restriction fragments thereof, as well as other sources of single and double-stranded polynucleotides having a desired nucleotide sequence. When using microinjection procedures it may be preferable to use a transfection technique with linearized sequences containing only modified target gene sequence and without vector or selectable sequences. The modified gene site is such that a homologous recombinant between the exogenous targeting polynucleotide and the endogenous DNA target sequence can be identified by using carefully chosen primers and PCR, followed by analysis to detect if PCR products specific to the desired targeted event are present (Erlich et al., (1991) Science 252: 1643, which is incorporated herein by reference). Several studies have already used PCR to successfully identify and then clone the desired transfected cell lines (Zimmer and Gruss, (1989) Nature 338: 150; Mouellic et al., (1990) Proc. Natl. Acad. Sci. USA 87: 4712; Shesely et al., (1991) Proc. Natl. Acad. Sci. USA 88: 4294, which are incorporated herein by reference). This approach is very effective when the number of cells receiving exogenous targeting polynucleotide(s) is high (i.e., with microinjection, or with liposomes) and the treated cell populations are allowed to expand to cell groups of approximately $1 \times 10^4$ cells (Capecchi, (11989) Science 244: 1288). When the target gene is not on a sex chromosome, or the cells are derived from a female, both alleles of a gene can be targeted by sequential inactivation (Mortensen et al., (1991) Proc. Natl. Acad. Sci. US 88: 7036). Alternatively, animals heterologous for the target gene can be bred to homologously as is known in the art.

The invention may also be practiced with individual targeting polynucleotides which do not comprise part of a complementary pair. In each case, a targeting polynucleotide is introduced into a target cell simultaneously or contemporaneously with a recombinase protein, typically in the form of a recombinase coated targeting polynucleotide as outlined herein (i.e., a polynucleotide pre-incubated with recombinase wherein the recombinase is noncovalently bound to the polynucleotide; generally referred to in the art as a nucleoprotein filament).

5.3.12. Alterations in the Target Nucleic Acid Comprising a Domain or Domains of Interest The present invention allows for the introduction of alterations in the target nucleic acid comprising a domain or domains of interest. That is, the fact that heterologies are tolerated in targeting polynucleotides allows for two things: first, the use of a heterologous domain homology clamps that may target genes encoding functional domains of a protein or multiple proteins, resulting in a variety of genotypes and phenotypes, and secondly, the introduction of alterations to the target sequence. Thus typically, a targeting polynucleotide (or complementary polynucleotide pair) has a portion or region having a sequence that is not present in the preselected endogenous targeted sequence(s) (i.e., a nonhomologous portion or mismatch) which may be as small as a single mismatched nucleotide, several mismatches, or may span up to about several kilobases or more of nonhomologous sequence.

5.3.12.1. Methods and Compositions for Inactivation of a Domain of a Gene

Accordingly, in a preferred embodiment, the methods and compositions of the invention are used for inactivation of a domain of a gene. That is, exogenous targeting polynucleotides can be used to inactivate, decrease or alter the biological activity of one or more domains in a gene of a cell (or transgenic nonhuman animal or plant). This finds particular use in the generation of animal models of disease states, or in the elucidation of gene function and activity, similar to "knock out" experiments. Alternatively, the biological activity of the wild-type gene may be either decreased, or the wild-type activity altered to mimic disease states. This includes genetic manipulation of non-coding gene sequences that affect the transcription of genes, including, promoters, repressors, enhancers and transcriptional activating sequences.

5.3.12.1.1. Amino Acid Substitutions, Insertions or Deletions in the Endogenous Target Sequences Thus in a preferred embodiment, homologous recombination of the targeting polynucleotide and endogenous target sequence will result in amino acid substitutions, insertions or deletions in the endogenous target sequences, potentially both within the functional domain region and outside of it, for example as a result of the incorporation of PCR tags. This will generally result in modulated or altered gene function of the endogenous gene, including both a decrease or elimination of function as well as an enhancement of function. Nonhomologous portions are used to make insertions, deletions, and/or replacements in a predetermined endogenous targeted DNA sequence, and/or to make single or multiple nucleotide substitutions in a predetermined endogenous target DNA sequence so that the resultant recombined sequence (i.e., a targeted recombinant endogenous sequence) incorporates some or all of the sequence information of the nonhomologous portion of the targeting polynucleotide(s). Thus, the nonhomologous regions are used to make variant sequences, i.e. targeted sequence modifications. In this way, site directed modifications may be done in a variety of systems for a variety of purposes.

5.3.12.1.1.1. Disruption by Either the Substitution, Insertion, Deletion or Frame Shifting of Nucleotides The endogenous target sequence, generally nucleic acid encoding a domain, may be disrupted in a variety of ways. The term "disrupt" as used herein comprises a change in the coding or non-coding sequence of an endogenous nucleic acid. In one preferred embodiment, a disrupted gene will no longer produce a functional gene product. In another preferred embodiment, a disrupted gene produces a variant gene product. Generally, disruption may occur by either the substitution, insertion, deletion or frame shifting of nucleotides.

5.3.12.1.1.2. Disruption by Amino Acid Substitutions

In one embodiment, amino acid substitutions are made. This can be the result of either the incorporation of a non-naturally occurring domain sequence into a target, or of more specific changes to a particular sequence outside of the domain sequence. 5.3.12.1.1.3. Disruption by an Insertion Sequence In one embodiment, the endogenous sequence is disrupted by an insertion sequence. The term "insertion sequence" as used herein means one or more nucleotides which are inserted into an endogenous gene to disrupt it. In general, insertion sequences can be as short as 1 nucleotide or as long as a gene, as outlined herein. For non-gene insertion sequences, the sequences are at least 1 nucleotide, with from about 1 to about 50 nucleotides being preferred, and from about 10 to 25 nucleotides being particularly preferred. An insertion sequence may comprise a polylinker sequence, with from about 1 to about 50 nucleotides being preferred, and from about 10 to 25 nucleotides being particularly preferred. Insertion sequence may be a PCR tag used for identification of the first gene. In a preferred embodiment, an insertion sequence comprises a gene which not only disrupts the endogenous gene, thus preventing its expression, but also can result in the expression of a new gene product. Thus, in a preferred embodiment, the disruption of an endogenous gene by an insertion sequence gene is done in such a manner to allow the transcription and translation of the insertion gene. An insertion sequence that encodes a gene may range from about 50 bp to 5000 bp of cDNA or about 5000 bp to 50000 bp of genomic DNA. As will be appreciated by those in the art, this can be done in a variety of ways. In a preferred embodiment, the insertion gene is targeted to the endogenous gene in such a manner as to utilize endogenous regulatory sequences, including promoters, enhancers or a regulatory sequence. In an alternate embodiment, the insertion sequence gene includes its own regulatory sequences, such as a promoter, enhancer or other regulatory sequence etc.

Particularly preferred insertion sequence genes include, but are not limited to, genes which encode selection or reporter proteins. In addition, the insertion sequence genes may be modified or variant genes.

5.3.12.1.1.4. Disruption by Deletions

The term "deletion" as used herein comprises removal of a portion of the nucleic acid sequence of an endogenous gene. Deletions range from about 1 to about 100 nucleotides, with from about 1 to 50 nucleotides being preferred and from about 1 to about 25 nucleotides being particularly preferred, although in some cases deletions may be much larger, and may effectively comprise the removal of the entire functional domain, the entire endogenous gene and/or its regulatory sequences. Deletions may occur in combination with substitutions or modifications to arrive at a final modified endogenous gene.

5.3.12.1.1.5. Disruption Simultaneously by an Insertion and a Deletion

In a preferred embodiment, endogenous genes may be disrupted simultaneously by an insertion and a deletion. For example, a domain of an endogenous gene, with or without its regulatory sequences, may be removed and replaced with an insertion sequence gene. Thus, for example, all but the regulatory sequences of an endogenous gene may be removed, and replaced with an insertion sequence gene, which is now under the control of the endogenous gene's regulatory elements.

The term "regulatory element" is used herein to describe a non-coding sequence which affects the transcription or translation of a gene including, but are not limited to, promoter sequences, ribosomal binding sites, transcriptional start and stop sequences, translational start and stop sequences, enhancer or activator sequences, dimerizing sequences, etc. In a preferred embodiment, the regulatory sequences include a promoter and transcriptional start and stop sequence. Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition to domain homology clamps and optional internal homology clamps, the targeting polynucleotides of the invention may comprise additional components, such as cell-uptake components, chemical substituents, purification tags, etc.

5.3.12.2. Targeting Polynucleotide Comprising a Cell-Uptake Component

In a preferred embodiment, at least one of the targeting polynucleotides comprises at least one cell-uptake component. As used herein, the term "cell-uptake component" refers to an agent which, when bound, either directly or indirectly, to a targeting polynucleotide, enhances the intracellular uptake of the targeting polynucleotide into at least one cell type (e.g., hepatocytes). A targeting polynucleotide of the invention may optionally be conjugated, typically by covalently or preferably noncovalent , binding, to a cell-uptake component. Various methods have been described in the art for targeting DNA to specific cell types. A targeting polynucleotide of the invention can be conjugated to essentially any of several cell-uptake components known in the art. For targeting to hepatocytes, a targeting polynucleotide can be conjugated to an asialoorosomucoid (ASOR)-poly-L-lysine conjugate by methods described in the art and incorporated herein by reference (Wu GY and Wu CH (1987) J. Biol. Chem. 262:4429; Wu GY and Wu CH (1988) Biochemistry 27:887; Wu GY and Wu CH (1988) J. Biol. Chem. 263: 1462 1; Wu GY and Wu CH (1992) J. Biol. Chem. 267: 12436; Wu et al. (1991) J. Biol. Chem. 266: 14338; and Wilson et al. 0 992) J. Biol. Chem. 267: 963, W092/06180; W092/05250; and W091/17761, which are incorporated herein by reference).

Alternatively, a cell-uptake component may be formed by incubating the targeting polynucleotide with at least one lipid species and at least one protein species to form protein-lipid-polynucleotide complexes consisting essentially of the targeting polynucleotide and the lipid-protein cell-uptake component. Lipid vesicles made according to Feigner (W091/17424, incorporated herein by reference) and/or cationic lipidization (WO91/16024, incorporated herein by reference) or other forms for polynucleotide administration (EP 465,529, incorporated herein by reference) may also be employed as cell-uptake components. Nucleases, DNA damaging chemicals, UV radiation or gamma-radiation may also be used.

In addition to cell-uptake components, targeting components such as nuclear localization signals may be used, as is known in the art. See for example Kido et al., Exper. Cell Res. 198:107–114 (1992), hereby expressly incorporated by reference. Typically, a targeting polynucleotide of the invention is coated with at least one recombinase and is conjugated to a cell-uptake component, and the resulting cell targeting complex is contacted with a target cell under uptake conditions (e.g., physiological conditions) so that the targeting polynucleotide and the recombinase(s) are internalized in the target cell. A targeting polynucleotide may be contacted simultaneously or sequentially with a cell-uptake component and also with a recombinase; preferably the targeting polynucleotide is contacted first with a recombinase, or with a mixture comprising both a cell-uptake component and a recombinase under conditions whereby, on average, at least about one molecule of recombinase is noncovalently attached per targeting polynucleotide molecule and at least about one cell-uptake component also is noncovalently attached. Most preferably, coating of both recombinase and cell-uptake component saturates essentially all of the available binding sites on the targeting polynucleotide. A targeting polynucleotide may be preferentially coated with a cell-uptake component so that the resultant targeting complex comprises, on a molar basis, more cell-uptake component than recombinase(s). Alternatively, a targeting polynucleotide may be preferentially coated with recombinase(s) so that the resultant targeting complex comprises, on a molar basis, more recombinase(s) than cell-uptake component.

Cell-uptake components are included with recombinase-coated targeting polynucleotides of the invention to enhance the uptake of the recombinase-coated targeting polynucleotide(s) into cells, particularly for in vivo gene targeting applications, such as gene therapy to treat genetic diseases, including neoplasia, and targeted homologous recombination to treat viral infections wherein a viral sequence (e.g., an integrated hepatitis B virus (HBV) genome or genome fragment) may be targeted by homologous sequence targeting and inactivated. Alternatively, a targeting polynucleotide may be coated with the cell-uptake component and targeted to cells with a contemporaneous or simultaneous administration of a recombinase (e.g., liposomes or immunoliposomes containing a recombinase, a viral-based vector encoding and expressing a recombinase).

In addition to recombinase and cellular uptake components, at least one of the targeting polynucleotides may include chemical substituents. Exogenous targeting polynucleotides that have been modified with appended chemical substituents may be introduced along with recombinase (e.g., RecA) into a metabolically active target cell to homologously pair with a predetermined endogenous DNA target sequence in the cell. In a preferred embodiment, the exogenous targeting polynucleotides are derivatized, and additional chemical substituents are attached, either during or after polynucleotide synthesis, respectively, and are thus localized to a specific endogenous target sequence where they produce an alteration or chemical modification to a local DNA sequence. Preferred attached chemical substituents include, but are not limited to: cross-linking agents (see Podyminogin et al., Biochem. 34:13098 (1995) and 35:7267 (1996), both of which are hereby incorporated by reference), nucleic acid cleavage agents, metal chelates (e.g., iron/EDTA chelate for iron catalyzed cleavage), topoisomerases, endonucleases, exonucleases, ligases, phosphodiesterases, photodynamic porphyrins, chemotherapeutic drugs (e.g., adriamycin, doxirubicin), intercalating agents, labels, base-modification agents, agents which normally bind to nucleic acids such as labels, etc. (see for example Afonina et al., PNAS USA 93:3199 (1996), incorporated herein by reference) immunoglobulin chains, and oligonucleotides. Iron/EDTA chelates are particularly preferred chemical substituents where local cleavage of a DNA sequence is desired (Hertzberg et al. (1982) J. Am. Chem. Soc. 104: 313; Hertzberg and Dervan (1984) Biochemistry 23: 3934; Taylor et al. (1984) Tetrahedron 40: 457; Dervan, PB ( 1986) Science 232: 464, which are incorporated herein by reference). Further preferred are groups that prevent hybridization of the complementary single stranded nucleic acids to each other but not to unmodified nucleic acids; see for example Kutryavin et al., Biochem. 35:11170 (1996) and Woo et al., Nucleic Acid. Res. 24(13):2470 (1996), both of which are incorporated by reference. 2'-0 methyl groups are also preferred; see Cole-Strauss et al., Science 273:1386 (1996); Yoon et al., PNAS 93:2071 (1996)). Additional preferred chemical substituents include labeling moieties, including fluorescent labels. Preferred attachment chemistries include: direct linkage, e.g., via an appended reactive amino group (Corey and Schultz (1988) Science 238:1401, which is incorporated herein by reference) and other direct linkage chemistries, although streptavidin/biotin and digoxigenin/antidigoxigenin antibody linkage methods may also be used. Methods for linking chemical substituents are provided in U.S. Pat. Nos. 5,135,720, 5,093,245, and 5,055,556, which are incorporated herein by reference. Other linkage chemistries may be used at the discretion of the practitioner.

5.3.12.3. Targeting Polynucleotides Comprises at Least One Purification Tag or Capture Moiety In a preferred embodiment, at least one of the targeting polynucleotides comprises at least one purification tag or capture moiety, some of which are discussed above as chemical substituents, for example biotin, digoxigenin, psoralen, etc. Alternatively, the domain oligonucleotide could be directly attached to beads with the targeting reaction performed on a solid phase support.

5.3.12.4. Targeting Polynucleotides are Coated with Recombinase Prior to Introduction to the Domain Target In a preferred embodiment, the targeting polynucleotides are coated with recombinase prior to introduction to the domain target. The procedures below are directed to the use of E. coli RecA, although as will be appreciated by those in the art, other recombinases may be used as well. Targeting polynucleotides can be coated using GTPgammaS, mixes of ATPgammaS with rATP, rGTP and/or dATP, or dATP or rATP alone in the presence of an rATP generating system (Boehringer Mannheim). Various mixtures of GTPgammaS, ATPgammaS, ATP, AIDP, DATP and/or rATP or other nucleosides may be used, particularly preferred are mixes of ATPgammaS and ATP or ATPgammaS and ADP. The targeting polynucleotide, whether double-stranded or single-stranded, is denatured by heating in an aqueous solution at 95–100' C. for five minutes, then placed in an ice bath for 20 seconds to about one minute followed by centrifugation at 0' C. for approximately 20 sec, before use. When denatured targeting polynucleotides are not placed in a freezer at –20' C. they are usually immediately added to standard RecA coating reaction buffer containing ATPgammaS, at room temperature, and to this is added the RecA protein.

Alternatively, RecA protein may be included with the buffer components and ATPgammaS before the polynucleotides are added.

RecA coating of targeting polynucleotide(s) is initiated by incubating polynucleotide-RecA mixtures at 37' C. for 10–15 min. RecA protein concentration tested during reaction with polynucleotide varies depending upon polynucleotide size and the amount of added polynucleotide, and the ratio of RecA molecule: nucleotide preferably ranges between about 3:1 and 1:3. When single-stranded polynucleotides are RecA coated independently of their homologous polynucleotide strands, the mM and microM concentrations of ATPgammaS and RecA, respectively, can be reduced to one-half those used with double-stranded targeting polynucleotides (i.e., RecA and ATPgammaS concentration ratios are usually kept constant at a specific concentration of individual polynucleotide strand, depending on whether a single- or double-stranded polynucleotide is used).

RecA protein coating of targeting polynucleotides is normally carried out in a standard 10×RecA coating reaction buffer. 10×RecA reaction buffer (i.e., 10×AC buffer) consists of 100 mM Tris acetate (pH 7.5 at 37' C.), 20 mM magnesium acetate, 500 mM sodium acetate, 10 mM DTT, and 50% glycerol). All of the targeting polynucleotides, whether double-stranded or single-stranded, typically are denatured before use by heating to 95–100' C. for five minutes, placed on ice for one minute, and subjected to centrifugation (10,000 rpm) at 0' C. for approximately 20 seconds (e.g., in a Tomy centrifuge). Denatured targeting polynucleotides usually are added immediately to room temperature RecA coating reaction buffer mixed with ATPgammaS and diluted with double-distilled H20 as necessary.

A reaction mixture typically contains the following components: (i) 0.2–4.8 mM ATPgammaS; and (ii) between 1–100 ng/ul of targeting polynucleotide. To this mixture is added about 1–20, ul of RecA protein per 10–100 ul of reaction mixture, usually at about 2–10 mg/ml (purchased from Pharmacia or purified), and is rapidly added and mixed. The final reaction volume-for RecA coating of targeting polynucleotide is usually in the range of about 10–500 ul. RecA coating of targeting polynucleotide is usually initiated by incubating targeting polynucleotide-RecA mixtures at 37' C. for about 10–15 min. RecA protein concentrations in coating reactions varies depending upon targeting polynucleotide size and the amount of added targeting polynucleotide: RecA protein concentrations are typically in the range of 5 to 50 uM. When single-stranded targeting polynucleotides are coated with RecA, independently of their complementary strands, the concentrations of ATPgammaS and RecA protein may optionally be reduced to about one-half of the concentrations used with double-stranded targeting polynucleotides of the same length: that is, the RecA protein and ATPgammaS concentration ratios are generally kept constant for a given concentration of individual polynucleotide strands.

5.3.12.4.1. Evaluation of Coating of Targeting Polynucleotides with RecA Protein The coating of targeting polynucleotides with RecA protein can be evaluated in a number of ways. First, protein binding to DNA can be examined using band-shift gel assays (McEntee et al., (1981) 1. Biol. Chem. 256: 8835). Labeled polynucleotides can be coated with RecA protein in the presence of ATPgammaS and the products of the coating reactions may be separated by agarose gel electrophoresis.

Following incubation of RecA protein with denatured duplex DNAs the RecA protein effectively coats single-stranded targeting polynucleotides derived from denaturing a duplex DNA. As the ratio of RecA protein monomers to nucleotides in the targeting polynucleotide increases from 0, 1:27, 1:2.7 to 3.7:1 for 121-mer and 0, 1:22, 1:2.2 to 4.5:1 for 159-mer, targeting polynucleotide's electrophoretic mobility decreases, i.e., is retarded, due to RecA-binding to the targeting polynucleotide. Retardation of the coated polynucleotide's mobility reflects the saturation of targeting polynucleotide with RecA protein. An excess of RecA monomers to DNA nucleotides is required for efficient RecA coating of short targeting polynucleotides (Leahy et al., (1986) J. Biol. Chem. 261: 954).

A second method for evaluating protein binding to DNA is in the use of nitrocellulose fiber binding assays (Leahy et al., (1986) J. Biol. Chem. 261:6954; Woodbury, et al., (1983) Biochemistry 22(20):4730–4737. The nitrocellulose filter binding method is particularly useful in determining the dissociation-rates for protein:DNA complexes using labeled DNA. In the filter binding assay, DNA:protein complexes are retained on a filter while free DNA passes through the filter. This assay method is more quantitative for dissociation-rate determinations because the separation of DNA:protein complexes from free targeting polynucleotide is very rapid.

Alternatively, recombinase protein(s) (prokaryotic, eukaryotic or endogeneous to the target cell) may be exogenously induced or administered to a target cell simultaneously or contemporaneously (i.e., within about a few hours) with the targeting polynucleotide(s). Such administration is typically done by micro-injection, although electroporation, lipofection, and other transfection methods known in the art may also be used. Alternatively, recombinase-proteins may be produced in vivo. For example, they may be produced from a homologous or heterologous expression cassette in a transfected cell or targeted cell, such as a transgenic totipotent cell (e.g. a fertilized zygote) or an embryonal stem cell (e.g., a murine ES cell such as AB-1) used to generate a transgenic non-human animal line or a somatic cell or a pluripotent hematopoietic stem cell for reconstituting all or part of a particular stem cell population (e.g. hematopoietic) of an individual. Conveniently, a heterologous expression cassette includes a modulatable promoter, such as an ecdysone-inducible promoter-enhancer combination, an estrogen-induced promoter-enhancer combination, a CMV promoter-enhancer, an insulin gene promoter, or other cell-type specific, developmental stage-specific, hormone-inducible drug inducible, or other modulatable promoter construct so that expression of at least one species of recombinase protein from the cassette can by modulated for transiently producing recombinase(s) in vivo simultaneous or contemporaneous with introduction of a targeting polynucleotide into the cell. When a hormone-inducible promoter-enhancer combination is used, the cell must have the required hormone receptor present, either naturally or as a consequence of expression a co-transfected expression vector encoding such receptor. Alternatively, the recombinase may be endogeneous and produced in high levels. In this embodiment, preferably in eukaryotic target cells such as tumor cells, the target cells produce an elevated level of recombinase. In other embodiments the level of recombinase may be induced by DNA damaging agents, such as mitomycin C, UV or gamma-irradiation. Alternatively, recombinase, levels may be elevated by transfection of a plasmid encoding the recombinase gene into the cell.

5.3.13. Specialized Applications 5.3.13.1. Identification of New Members of Gene Families which may be Useful in Functional Genomic Studies as well as in the Identification of New Drug Targets Once made, the compositions of the invention find use in a number of applications upon administration to target cells. In general, the compositions and methods of the invention are useful to identify new members of gene families which may be useful in functional genomic studies as well as in the identification of new drug targets; both of these may be accomplished through the generation of "knock out" animal models. In addition, the present invention allows the modification of functional domain targets, the creation of transgenic plants and animals, the cloning of genes containing domain functional domains, etc.

5.3.13.2. Domain Specific Gene Evolution

Once made and administered to a target host cell, the compositions of the invention find use in a number of applications, including domain specific gene evolution. The polypeptide or protein encoded by the targeted nucleic undergoes homologous recombination with the plurality of polynucleotides to produce a plurality of modified target nucleic acids that are expressed to produce a plurality of modified proteins. Selection systems are employed to identify and isolate host cells expressing proteins having a desired property or phenotype. For example, if the expressed protein is an enzyme, cells having a modified enzyme activity are identified. The desired activity can be an increased or decreased or altered activity. Proteins having the desired phenotype are selected and isolated, the modified nucleic acid is sequenced to identify sequences effecting the desired activity, and the process is repeated iteratively as needed to produce a protein having a desired activity or property. In this and other embodiments, suitable target sequences include nucleic acid sequences encoding therapeutically or commercially relevant proteins, including, but not limited to, enzymes (proteases, recombinases, lipases, kinases, carbohydrases, isomerases, tautomerases, nucleases etc.), hormones, receptors, transcription factors, growth factors, cytokines, globin genes, immunosupppressive genes, tumor suppressors, oncogenes, complement-activating genes, milk proteins (casein, alpha-lactalbumin, beta-lactoglobulin, bovine and human serum albumin), immunoglobulins, milk proteins, and pharmaceutical proteins and vaccines.

In a preferred embodiment, the methods of the invention are used to generate pools or libraries of variant nucleic acid sequences, and cellular libraries containing the variant sequences. This idea is somewhat similar to the "gene shuffling" techniques of the literature (see Stemmer et al., 1994, Natuere 370:389 which attempt to rapidly "evolve" genes by making multiple random changes simultaneously. In the present invention, this end is accomplished by using at least one cycle, and preferably reiterative cycles, of enhanced homologous recombination with targeting polynucleotides containing random mismatches, substitutions, insertions, or deletions. By using a library of targeting polynucleotides comprising a plurality of random mutations, and repeating the homologous recombination steps as many times as needed, a rapid "gene evolution" can occur, wherein the new genes may contain large numbers of mutations.

Thus, in this embodiment, a plurality of targeting polynucleotides are used. The targeting polynucleotides each have at least one homology clamp that substantially corresponds to or is substantially complementary to the target sequence. Generally, the targeting polynucleotides are generated in pairs; that is, pairs of two single stranded targeting polynucleotides that are substantially complementary to each other are made (i.e. a Watson strand and a Crick strand). However, as will be appreciated by those in the art, less than a one to one ratio of Watson to Crick strands may be used; for example, an excess of one of the single stranded target polynucleotides (i.e. Watson) may be used. Preferably, sufficient numbers of each of Watson and Crick strands are used to allow the majority of the targeting polynucleotides to form double D-loops, which are preferred over single D-loops as outlined above. In addition, the pairs need not have perfect complementarity; for example, an excess of one of the single stranded target polynucleotides (i.e. Watson), which may or may not contain mismatches, may be paired to a large number of variant Crick strands, etc. Due to the random nature of the pairing, one or both of any particular pair of single-stranded targeting polynucleotides may not contain any mismatches. However, generally, at least one of the strands will contain at least one mismatch.

The plurality of pairs preferably comprise a pool or library of mismatches. The size of the library will depend on a number of factors, including the number of residues to be mutagenized, the susceptibility of the protein to mutation, etc., as will be appreciated by those in the art. Generally, a library in this instance preferably comprises at least 10% different mismatches over the length of the targeting polynucleotides, with at least 30% mismatches being preferred and at least 40% being particularly preferred, although as will be appreciated by those in the art, lower (1, 2, 5%, etc.) or higher amounts of mismatches being both possible and desirable in some instances. That is, the plurality of pairs comprise a pool of random and preferably degenerate mismatches over some regions or all of the entire targeting sequence. As outlined herein, "mismatches" include substitutions, insertions and deletions, with the former being preferred. Thus, for example, a pool of degenerate variant targeting polynucleotides covering some, or preferably all, possible mismatches over some region are generated, as outlined above, using techniques well known in the art. Preferably, but not required, the variant targeting polynucleotides each comprise only one or a few mismatches (less than 10), to allow complete multiple randomization. That is, by repeating the homologous recombination steps any number of times, as is more fully outlined below, the mismatches from a plurality of probes can be incorporated into a single target sequence.

The mismatches can be either non-random (i.e. targeted) or random, including biased randomness. That is, in some instances specific changes are desirable, and thus the sequence of the targeting polynucleotides are specifically chosen. In a preferred embodiment, the mismatches are random. The targeting polynucleotides can be chemically synthesized, and thus may incorporate any nucleotide at any position. The synthetic process can be designed to generate randomized nucleic acids, to allow the formation of all or most of the possible combinations over the length of the nucleic acid, thus forming a library of randomized targeting polynucleotides. Preferred methods maximize library size and diversity.

It is important to understand that in any library system encoded by oligonucleotide synthesis one cannot have complete control over the codons that will eventually be incorporated into the peptide structure. This is especially true in the case of codons encoding stop signals (TAA, TGA, TAG). In a synthesis with NNN as the random region, there is a 3/64, or 4.69%, chance that the codon will be a stop codon. To alleviate this, random residues are encoded as NNK, where K=T or G. This allows for encoding of all potential amino acids (changing their relative representation slightly), but importantly preventing the encoding of two stop residues TAA and TGA.

5.3.13.2.1. Mismatches are Fully Randomized, with no Sequence Preferences or Constants at any Position In one embodiment, the mismatches are fully randomized, with no sequence preferences or constants at any position.

5.3.13.2.2. Biased Library

In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

As will be appreciated by those in the art, the introduction of a pool of variant targeting polynucleotides (in combination with recombinase) to a target sequence, in vitro to an extrachromosomal sequence, can result in a large number of homologous recombination reactions occuring over time. That is, any number of homologous recombination reactions can occur on a single target sequence, to generate a wide variety of single and multiple mismatches within a single target sequence, and a library of such variant target sequences, most of which will contain mismatches and be different from other members of the library. This thus works to generate a library of mismatches.

5.3.13.2.2.1. Generating a Large Number of Different Variants within a Particular Region of a Sequence, Similar to Cassette Mutagenesis but not Limited by Sequence Length In a preferred embodiment, the variant targeting polynucleotides are made to a particular region or domain of a sequence (i.e. a nucleotide sequence that encodes a particular protein domain). For example, it may be desirable to generate a library of all possible variants of a binding domain of a protein, without affecting a different biologically functional domain, etc. Thus, the methods of the present invention find particular use in generating a large number of different variants within a particular region of a sequence, similar to cassette mutagenesis but not limited by sequence length. This idea is sometimes referred to herein as "domain specific gene evolution". In addition, two or more regions may also be altered simultaneously using these techniques; thus "single domain" and "multi-domain" shuffling can be done. Suitable domains include, but are not limited to, kinase domains, nucleotide-binding sites, DNA binding sites, signaling domains, receptor binding domains, transcriptional activating regions, promoters, origins, leader sequences, terminators, localization signal domains, and, in immunoglobulin genes, the complementarity determining regions (CDR), Fc, $V_H$, and $V_L$.

In a preferred embodiment, the variant targeting polynucleotides are made to the entire target sequence. In this way, a large number of single and multiple mismatches may be made in an entire sequence.

Thus, this embodiment proceeds as follows. A pool of, targeting polynucleotides are made each containing one or more mismatches. The probes are coated with recombinase as generally described herein, and introduced to the target sequence. Upon binding of the probes to form D-loops, the recombinase is preferably removed. These polynucleotide-:target sequences can then introduced into recombinant proficient cells, to produce target protein which can then be tested for biological activity, based on the identification of the target sequence. Depending on the results, the altered target sequence can be used as the starting target sequence in reiterative rounds of homologous recombination, generally using the same library. Preferred embodiments utilize at least two rounds of homologous recombination, with at least 5 rounds being preferred and at least 10 rounds being particularly preferred. Again, the number of reiterative rounds that are performed will depend on the desired endpoint, the resistance or susceptibility of the protein to mutation, the number of mismatches in each probe, etc.

5.3.14. Target Sequence 5.3.14.1. Target Sequences—An Immunoglobulin

In a preferred embodiment, the target sequence is an immunoglobulin. The amino terminal region of the light and heavy chains of an antibody that come together to form the antigen binding site and the variability of their amino acid sequences provides the structural basis for the diversity of antigen binding sites. The variability of the variable regions of both the heavy and light chains is for the most part restricted to three small hypervariable regions in each chain. The remianing part of the variable regions, known as framework regions, is relatively constant. Each of the hypervariable regions consists of only about 5 to 10 amino acids; the corresponding regions in the DNA encoding these regions are known as the complementarity determining regions, or CDRs. Thus to engineer an antibody library, for example an antibody phage library, one can change the sequences in the CDR regions of both the heavy and light chains. Different permutations and combinations of CDRs can be changed and evolved to engineer antibody-phage libraries.

5.3.14.2. Target Sequence—A Single-Chain Fv Framework for Any Number of Specific Antigens In a preferred embodiment, the target sequence is a single-chain Fv framework for any number of specific antigens. Single chain Fv (scFv) consists of $V_L$ and $V_H$ domains of an immunoglobulin linked by a peptide spacer and thus contains the minimal antigen-binding domains of an antibody.

5.3.14.3. Target Sequence—An Antibody-Phage Fusion

In a preferred embodiment, antibody-phage fusions are used as the target sequence. As is known in the art, single-chain Fv fusions with the pIII minor coat protein allows expression of the antibody on the surface of a phage, wherein it is available to bind antigen. Five copies of pIII are expressed on the surface of the phage. It is therefor possible to express five scFv on the phage. This antibody-phage display system has been used previously to isolate novel antibodies. By starting with antibodies to any antigen, higher affinity antibodies may be made, as well as novel antibodies.

5.3.14.4. Target Sequence—The Coding Sequence for Beta-Lactamase

In a preferred embodiment, the target sequence is the coding sequence for beta-lactamase.

Thus, the methods of the invention may be used to create superior recombinant reporter genes such as 1 acZ and green fluorescent protein (GFP); superior antibiotic and drug resistance genes; superior recombinase genes; superior recombinant vectors; and other superior recombinant genes and proteins, including immunoglobulins, vaccines or other proteins with therapeutic value. For example, targeting polynucleotides containing any number of alterations may be made to one or more functional or structural domains of a protein, and then the products of homologous recombination evaluated.

Once made and administered to target cells, the target cells may be screened to identify a cell that contains the targeted sequence modification. This will be done in any number of ways, and will depend on the target gene and targeting polynucleotides as will be appreciated by those in the art. The screen may be based on phenotypic, biochemical, genotypic, or other functional changes, depending on the target sequence. In an additional embodiment, as will be appreciated by those in the art, selectable markers or marker sequences may be included in the targeting polynucleotides to facilitate later identification.

5.3.15. Kits Containing the Compositions of the Invention are Provided

In a preferred embodiment, kits containing the compositions of the invention are provided. The kits include the compositions, particularly those of libraries or pools of degenerate cssDNA probes, along with any number of reagents or buffers, including recombinases, buffers, ATP, etc.

5.3.16. Targeting Polynucleotide: Target Nucleic Acid Complexes Serve As Substrates for Single-Stranded Endonucleases In an alternate embodiment, the targeting polynucleotide: target nucleic acid complexes serve as substrates for single-stranded endonucleases, such as, S1 and mung bean nuclease. Preferably the targeting polynucleotides are substantially complementary and form double D-loops with the target nucleic acid. The junctions of the complexes are single-stranded in nature, and thus are suceptible to single-strand specific nucleases and junction-specific nucleases. Accordingly, treatment of the complex with a single-strand nuclease results in defined nicks in the selected region encoding a predetermined domain of a protein encoded by the target nucleic acid. The nicked target nucleic acid is disassociated from the targeting polynucleotides and are reassembled and "shuffled" in vitro by PCR (Stemmer. 1994. Nature 370:389–391) to produce a plurality modified nucleic acids. The modified nucleic acids are introduced into an appropriate host cell, as described above, for expression of the plurality of modified proteins. Selection techniques are used as described herein to identify and isolate a cell expressing a modified protein. The process is repeated iteratively as needed to further evolve the targeted nucleic acid.

5.3.17. Isolation of New Members of Gene Families That Comprise Particular Domains In a preferred embodiment, the present invention finds use in the isolation of new members of gene families that comprise particular domains. The use of domain filaments (i.e. domain homology clamps preferably containing a purification tag such as biotin, disoxisenin, or one purification method such as the use of a RecA antibody), allows the identification of genes containing the domain. Once identified, the new genes can be cloned, sequenced and the protein gene products purified. As will be appreciated by those in the art, the functional importance of the new genes can be assessed in a number of ways, including functional studies on the protein level, as well as the generation of "knock out" animal models. By choosing domain sequences for therapeutically relevant protein domains, novel targets can be identified that can be used in screening of drug candidates.

5.3.18. Utilizing the Purification Tag to Isolate the Gene(s)

Thus, in a preferred embodiment, the present invention provides methods for isolating new members of gene families containing protein domains comprising introducing targeting polynucleotides comprising domain homology clamps and at least one purification tag, preferably biotin, to a mix of nucleic acid, such as a plasmid cDNA library or a cell, and then utilizing the purification tag to isolate the gene(s). The exact methods will depend on the purification tag; a preferred method utilizes the attachment of the binding ligand for the tag to a bead, which is then used to pull out the sequence. Alternatively anti-RecA antibodies could be used to capture RecA-coated probes. The genes are then cloned, sequenced, and reassembled if necessary, as is well known in the art.

5.3.19. Use in Functional Genomic Studies, by Providing the Creation of Transgenic Animal Models of Disease In an alternate preferred embodiment, the present invention finds use in fuctional genomic studies, by providing the creation of transgenic animal models of disease. Thus, for example, domain sequences used in homologous recombination methods can generate animals that have a wide variety of mutations in a wide variety of related domains of genes, potentially resulting in a wide variety of phenotypes, including phenotypes related to disease states. That is, by targeting a domain family, one, two or multiple genes in the family may be altered in any given experiment, thus creating a wide variety of genotypes and phenotypes to evaluate. Thus, in a preferred embodiment, the compositions and methods of the invention are used to generate pools or libraries of variant nucleic acid sequences, wherein the mutations are within the functional domain coding region, cellular libraries containing the variant libraries, and libraries of animals containing the variant libraries.

Furthermore, domain targeting can be used in cells or animals that are diseased or altered; in essence, domain targeting can be done to identify "reversion" genes, genes that can modulate disease states caused by domains of different genes. Thus for example the loss of one type of enzymatic activity, resulting in a disease phenotype, may be compensated by alterations in a different but homologous enzymatic activity. Accordingly, once the recombinase-targeting polynucleotide compositions are formulated, they are introduced or administered into target cells. The administration is typically done as is known for the administration of nucleic acids into cells, and, as those skilled in the art will appreciate, the methods may depend on the choice of the target cell. Suitable methods include, but are not limited to, microinjection, electroporation, lipofection, etc. By "target cells" herein is meant prokaryotic or eukaryotic cells. Suitable prokaryotic cells include, but are not limited to, bacteria such as E. coli, Bacillus species, and the extremophile bacteria such as thermophiles, halophiles, etc. Preferably, the procaryotic target cells are recombination competent. Suitable eukaryotic cells include, but are not limited to, fungi such as yeast and filamentous fungi, including species of Aspergillus, Trichoderma, and Neurospora; plant cells including those of corn, sorghum, tobacco, canola, soybean, cotton, tomato, potato, alfalfa, sunflower, etc.; and animal cells, including fish, reptiles, amphibia, birds and mammals. Suitable fish cells include, but are not limited to, those from species of salmon, trout, tilapia, tuna, carp, flounder, halibut, swordfish, cod and zebrafish. Suitable bird cells include, but are not limited to, those of chickens, ducks, quail, pheasants, ostrich, and turkeys, and other jungle foul or game birds. Suitable mammalian cells include, but are not limited to, cells from horses, cows, buffalo, deer, sheep, rabbits, rodents such as mice, rats, hamsters and guinea pigs, goats, pigs, primates, marine mammals including dolphins and whales, as well as cell lines, such as human cell lines of any tissue or stem cell type, and stem cells, including pluripotent and non-pluripotent, and non-human zygotes. Particular human cells including, but not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells, osteoclasts, chondrocytes and other connective tissue cells, keratinocytes, melanocytes, liver cells, kidney cells, and adipocytes. Suitable cells also include known research cells, including, but not limited to, Jurkat T cells, mouse La, HT1080, C127, Rat2, CV-1, NIH3T3 cells, CHO, COS, 293 cells, etc. See the ATCC cell line catalog, hereby expressly incorporated by reference.

5.3.20. Procaryotic Cells Are Used to Identify, Clone, or Alter Target Sequences In a preferred embodiment, procaryotic cells are used to identify, clone, or alter target sequences, preferably protein domains. In this embodiment, a pre-selected target DNA sequence is chosen for alteration. Preferably, the pre-selected target DNA sequence is contained within an extrachromosomal sequence. By "extrachromosomal sequence" herein is meant a sequence separate from the chromosomal or genomic sequences. Preferred extrachromosomal sequences include plasmids (particularly procaryotic plasmids such as bacterial plasmids), pl vectors, viral genomes, yeast, bacterial and mammalian artificial chromosomes (YAC, BAC and MAC, respectively), and other autonomously self-replicating sequences, although this is not required. As described herein, a recombinase and at least two single stranded targeting polynucleotides which are substantially complementary to each other, each of which contain a homology clamp to the target sequence contained on the extrachromosomal sequence, are added to the extrachromosomal sequence, preferably in vitro. The two single stranded targeting polynucleotides are preferably coated with recombinase, and at least one of the targeting polynucleotides contain at least one nucleotide substitution, insertion or deletion. The targeting polynucleotides then bind to the target sequence in the extrachromosomal sequence to effect homologous recombination and form an altered extrachromosomal sequence which contains the substitution, insertion or deletion. The altered extrachromosomal sequence is then introduced into the procaryotic cell using techniques known in the art. Preferably, the recombinase is removed prior to introduction into the target cell, using techniques known in the art. For example, the reaction may be treated with proteases such as proteinase K, detergents such as SDS, and phenol extraction (including phenol:chloroform:isoamyl alcohol extraction). These methods may also be used for eukaryotic cells. The cells are then grown under conditions which allow the expression of the variant nucleic acids to form variant proteins, particularly with alterations in domains.

5.3.20.1. Proteins Having the Desired Phenotype Are Selected and Isolated

In a preferred embodiment, proteins having the desired phenotype are selected and isolated, the modified nucleic acid is sequenced to identify sequences effecting the desired activity, and the process is repeated iteratively as needed to produce a protein having a desired activity or property. Thus, in a preferred embodiment, the methods of the invention are repeated until the desired protein or phenotype is seen.

Alternatively, the pre-selected target DNA sequence is a chromosomal sequence. In this embodiment, the recombinase with the targeting polynucleotides are introduced into the target cell, preferably eukaryotic target cells. In this embodiment, it may be desirable to bind (generally non-covalently) a nuclear localization signal to the targeting polynucleotides to facilitate localization of the complexes in the nucleus. See for example Kido et al., Exper. Cell Res. 198:107–114 (1992), hereby expressly incorporated by reference. The targeting polynucleotides and the recombinase function to effect homologous recombination, resulting in altered chromosomal or genomic sequences.

5.3.21. Eukaryotic Cells Are Used

In a preferred embodiment, eukaryotic cells are used. Basically, any mammalian cells may be used, with mouse, rat, primate and human cells being particularly preferred. Accordingly, suitable cell types include, but are not limited to, tumor cells of all types, i.e., fibroblasts, epithelial cells (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH 3T3 cells, CHO, Cos, etc. See the ATCC cell line catalog, hereby expressly incorporated by reference.

For making transgenic non-human animals (which include homologously targeted non-human animals) embryonal stem cells (ES cells), donor cells for nuclear transfer and fertilized zygotes are preferred. In a preferred embodiment, embryonal stem cells are used. Murine ES cells, such as AB-1 line grown on mitotically inactive SNL76/7 cell feeder layers (McMahon and Bradley, Cell 62: 1073–1085 (1990)) essentially as described (Robertson, E. J. (1987) in Teratocarcinomas and Embcyonic Stem Cells: A Practical Approach. E. J. Robertson, ed. (oxford: IRL Press), p. 71–112; Zjilstra et al., Nature 342:435–438 (1989); and Schwartzberg et al., Science 246:799–803 (1989), each of which is incorporated herein by reference) may be used for homologous gene targeting. Other suitable ES lines include, but are not limited to, the E14 line (Hooper et al. (1987) Nature 326: 292–295), theD3 line (Doetschman et al. (1985) J. Embryol. Exp. Morph. 87: 21–45), and the CCE line (Robertson et al. (1986) Nature 323: 445–448). The success of generating a mouse line from ES cells bearing a specific targeted mutation depends on the pluripotence of the ES cells (i.e., their ability, once injected into a host blastocyst, to participate in embryogenesis and contribute to the germ cells of the resulting animal).

The pluripotence of any given ES cell line can vary with time in culture and the care with which it has been handled. The only definitive assay for pluripotence is to determine whether the specific population of ES cells to be used for targeting can give rise to chimeras capable of germline transmission of the ES genome. For this reason, prior to gene targeting, a portion of the parental population of AB-1 cells is injected into C57B1/6J blastocysts to ascertain whether the cells are capable of generating chimeric mice with extensive ES cell contribution and whether the majority of these chimeras can transmit the ES genome to progeny.

5.3.22. Non-Human Zygotes Are Used

In a preferred embodiment, non-human zygotes are used, for example to make transgenic animals, using techniques known in the art (see U.S. Pat. No. 4,873,191; Brinster et al., PNAS 86:7007 (1989); Susulic et al., J. Biol. Chem. 49:29483 (1995), and Cavard et al., Nucleic Acids Res. 16:2099 (1988), hereby incorporated by reference). Preferred zygotes include, but are not limited to, animal zygotes, including fish, avian, reptilian, amphibian and mammalian zygotes. Suitable fish zygotes include, but are not limited to, those from species of salmon, trout, tuna, carp, flounder, halibut, swordfish, cod, tilapia and zebrafish. Suitable bird zygotes include, but are not limited to, those of chickens, ducks, quail, pheasant, turkeys, and other jungle fowl and game birds. Suitable mammalian zygotes include, but are not limited to, cells from horses, cows, buffalo, deer, sheep, rabbits, rodents such as mice, rats, hamsters and guinea pigs, goats, pigs, primates, and marine mammals including dolphins and whales. See Hogan et al., Manipulating the Mouse Embryo (A Laboratory Manual), 2nd Ed. Cold Spring Harbor Press, 1994, incorporated by reference.

The vectors containing the DNA segments of interest can be transferred into the host cell by well-known methods, depending on the type of cellular host. For example, microinjection is commonly utilized for target cells, although calcium phosphate treatment, electroporation, lipofection, biolistics or viral-based transfection also may be used. Other methods used to transform mammalian cells include the use of Polybrene, protoplast fusion, and others (see, generally, Sambrook et al. Molecular Cloning: A Laboratory Manual, 2d ed., 1989, Cold Spring Harbor Laboratory Press, Cold Spring Harbor, N.Y., which is incorporated herein by reference). Direct injection of DNA and/or recombinase-coated targeting polynucleotides into target cells, such as skeletal or muscle cells also may be used (Wolff et al. (1990) Science 247: 1465, which is incorporated herein by reference).

5.3.23. Precursor Animals or Cells Already Contain a Disease Allele

In a preferred embodiment, the precursor animals or cells already contain a disease allele. As used herein, the term "disease allele" refers to an allele of a gene which is capable of producing a recognizable disease. A disease allele may be dominant or recessive and may produce disease directly or when present in combination with a specific genetic background or pre-existing pathological condition. A disease allele may be present in the gene pool or may be generated de novo in an individual by somatic mutation. For example and not limitation, disease alleles include: activated oncogenes, a sickle cell anemia allele, a Tay-Sachs allele, a cystic fibrosis allele, a Lesch-Nyhan allele, a retinoblastoma-susceptibility allele, a Fabry's disease allele, a Huntington's chorea allele, and a xenoderma pigmentosa allele. As used herein, a disease allele encompasses both alleles associated with human diseases and alleles associated with recognized veterinary diseases. For example, the deltaF508 CFTR allele in a human disease allele which is associated with cystic fibrosis in North Americans.

Once made and administered to target cells, new domains of genes may be isolated as outlined herein.

Alternatively, the target cells may be screened to identify a cell that contains the targeted functional domain sequence modification. This will be done in any number of ways, and will depend on the target domain and targeting polynucleotides as will be appreciated by those in the art. The screen may be based on phenotypic, biochemical, genotypic, or other functional changes, depending on the target sequence. For example, IgE levels may be evaluated for inflammation or asthma; vascular tone or blood pressure can be evaluated for hypertension, behavior screens can be done for neurologic effects, lipoprotein profiles can be screened for cardiovascular effects; secreted molecules can be evaluated for endocrine processes; CBCs can be done for hematology studies, etc. In an additional embodiment, as will be appreciated by those in the art, selectable markers or marker sequences may be included in the targeting polynucleotides to facilitate later identification.

The broad scope of this invention is best understood with reference to the following examples, which are not intended to limit the invention in any manner. All patents, patent applications, and publications cited herein are expressly incorporated by reference in their entirety.

5.4. Gene Deletion in Bacteria

This invention relates to a method and means for deleting a gene from a bacterial chromosome in a single step.

5.4.1 Applications 5.4.1.1 The Construction of Special Bacterial Strains Which Have a Particular Genetic Background Many applications require the construction of special bacterial strains which have a particular genetic background. These genetic backgrounds are the framework in which specific recombinant DNA plasmid constructions are tested to determine whether they can provide functions which are missing from the background of the bacteria. If such functions are provided by the recombinant plasmid, then there is positive evidence that a particular genetic locus or loci is encoded by the plasmid. The construction of genetic backgrounds is therefore a vital step in the subsequent cloning and investigation of specific genes.

5.4.1.2. The Gene in Question Has Been Deleted, So There Is No Production Whatsoever of a Mutant Protein Making Analysis Much Less Ambiguous The most common backgrounds are those in which a single mutation is present in a specific gene on the bacterial chromosome. This may result in synthesis of a defective version of the protein encoded by that gene, resulting in a specific cellular dysfunction. Correction of the cellular dysfunction, by introduction of a specific recombinant plasmid, is evidence that the relevant gene has been cloned onto the specific plasmid. However, a mutant protein may not be silent and may undergo interactions with other components, thereby creating the appearance that the plasmid gene encodes the entire active protein when it does not. This can seriously confuse the analysis. A much less ambiguous and therefore more desirable approach is one in which the gene in question has been deleted. In these circumstances, there is no production whatsoever of a mutant protein.

5.4.1.3. If Bacteria is Being Used to Genetically Engineer a Protein, Deletion of the Gene that Manufactures a Contaminating Protein Made by the Same Bacteria Can Reduce Purification Steps Another situation where it is desirable to delete a complete gene from the chromosome of a bacteria is when the bacteria is being used in the production of a genetically engineered protein. Examples of these situations include the expression of insulin, growth hormone, protein A, and various vaccines from recombinant genes inserted into E. coli. Many times the E. coli produces proteins which contaminate the purified product produced by the genetic engineering. Although it is possible to add additional purification steps to remove this contaminant, it would be preferable to avoid the problem entirely by deleting the gene encoding the contaminating protein. Methods that are presently used to alter a gene include random mutation or inactivation of the gene sequence by mutation, insertion, or deletion of some portion of the gene. However, this can still lead to the production of inactive protein fragments or deletion of more of the chromosome than is necessary or desirable.

It is therefore an object of the present invention to provide a method and means for deleting a specific gene from a bacteria.

It is another object of the present invention to provide a method and means for inserting and/or inactivating or deleting the recA gene in a variety of bacteria.

5.4.2. Miscellaneous Applications 5.4.2.1 Creating a Deletion in a Defined Target within the Bacterial Chromosome There are two obstacles which have to be overcome. One is to develope a method which will create a deletion in a defined target within the bacterial chromosome.

5.4.2.2 Generalizing the Approach So That Even Essential Genes Can Be Deleted

The second is to generalize the approach so that even essential genes can be deleted. This is because many of the genes of interest are essential ones. The deletion of an essential gene normally would result in cell death.

Essential proteins includes enzymes of glycolysis, enzymes associated with amino acid or sugar biosynthesis, enzymes and factors associated with protein and nucleic acid biosynthesis (including both RNA and DNA), enzymes required for the synthesis of cofactors for oxidation, reduction, methylation and transamination processes, and enzymes necessary for synthesis of essential lipids and polysaccharides or of any other essential molecule, including various nucleic acids, such as transfer or ribosomal RNAs, and segments of nucleic acids, such as gene regulatory elements.

It is therefore an object of the present invention to provide a method wherein an organism is produced which does not contain genetic material coding for the molecule which is to be cloned and expressed in the organism.

A further object of the present invention is to provide a method whereby a deficient organism which is to be used for cloning an essential gene remains viable even under restrictive conditions.

5.4.3 Specialized Applications 5.4.3.1. Method for the Deletion of a Gene from a Bacteria Using a Single Step Procedure That is Applicable to any Gene That Has Been Cloned Disclosed is a method for the deletion of a gene from a bacteria using a single step procedure that is applicable to any gene that has been cloned. The procedure depends upon site-directed recombination of linear DNA fragments with sequences on the chromosome as a function of recA in combination with the subsequent inactivation or deletion of the recA gene. The method is analogous to a procedure used to give insertions by homologous recombination into specific plasmid genes.

5.4.3.1.1. Strategy for Construction of Chromosomal Deletions

The basic strategy for construction of chromosomal deletions is to transform the bacteria with linear DNA fragments which contain an antibiotic resistant or other phenotypically detectable gene segment (a "marker") flanked by sequences homologous to a closely spaced region on the cell chromosome containing the gene to be deleted A double-crossover event within the homologous sequences, effectively deleting the entire gene, is selected for by screening for the antibiotic resistant phenotype.

The linear fragment is not integrated into the chromosome in the absence of enzymes expressed by the recA gene. Accordingly, if the gene is absent or inactive, a recA gene must be inserted into the cell prior to the linear recombination event, and then inactivated or removed to prevent subsequent incorporation of other non-chromosomal sequences into the chromosome. This is particularly important if the bacteria is used as a host for the expression of genetically engineered proteins from sequences carried on plasmids or other extrachromosomal elements. The recA gene can be provided either in the form of an extrachromosomal element such as a plasmid or through incorporation of the gene into the chromosome. The recA gene is preferably inactivated or deleted by means of a double reciprocal recombination event utilizing linear sequences containing sequences homologous to the flanking sequences on either side of the recA gene in the chromosome. This is essentially the same method used to delete or insert a gene into the chromosome by homologous recombination as described above.

The present invention includes isolated linear DNA fragments constructed for use in the method for deleting a gene from the chromosome and for inserting or deleting the recA gene.

The method and sequences are applicable to a variety of bacteria including strains of Escherichia, Pseudomonas, Agrobacterium, Proteus, Erwinia, Shigella, Bacillus, Rhizobium, Vibrio, Salmonella, Streptococcus, and Haemophilus.

A plasmid which has a temperature-sensitive replicon and a wild-type allele of the desired gene is used to restore or maintain the phenotype produced by the deleted gene. This plasmid maintains production of the desired protein, and therefore cell viability if the encoded protein is essential to cell growth, when the chromosomal copy of the desired gene has been deleted. However, since the resulting cells have a temperature-sensitive phototype, the expression of the plasmid gene may be easily prevented by culturing the host strain at an elevated temperature. The resulting deficient host strain may then be used to screen other mutated and cloned genes for their ability to produce the desired protein.

5.5. Additional Considerations 5.5.1. Maintaining the Viability of the Bacteria

The present invention is a method for deleting any gene from a bacterial strain, while maintaining the viability of the bacteria if the gene encodes an essential molecule and deletion of the essential gene results in a lethal phenotype. The gene to be deleted is provided on a plasmid with a temperature sensitive replicon. The cells now have a temperature sensitive phenotype. When the cells are grown at an elevated temperature under conditions which allow rapid detection of the absence of the desired molecule, complementation of this phenotype by introduction of a DNA fragment fused onto a stable plasmid is strong evidence for cloning of the gene which has been deleted from the chromosome.

5.5.2. Homologous Recombination

The present invention is a method for deleting any gene from a bacterial strain employing linear DNA fragments incorporating sequences homologous to the sequences flanking the gene to be deleted in the chromosome and sequences allowing insertion or removal/inactivation of recA in a variety of bacteria.

5.5.2.1. Roles for Several Enzymes Needed in Recombination

Homologous recombination has been detected in a wide variety of organisms, from simple bacteriophages to complex eukaryotic cells. Genetic and biochemical investigations have defined roles for several enzymes needed in recombination.

5.5.2.2. RecA 5.5.2.2.1. Alignment of DNA Molecules before Exchange

The RecA protein participates in the early steps of synapse, allowing alignment of DNA molecules before exchange, in strand transfer, where there is transfer of a single-stranded segment to a recipient duplex to form a limited heteroduplex region between the interacting DNAs and in the extension of this heteroduplex region by a reaction involving the concerted winding and unwinding of incoming and outgoing DNA chains, respectively. The hydrolysis of ATP by RecA protein is required for these events in vitro.

5.5.2.2.2. Controlling Expression of a Group of Unlinked Genes That Aid in Recovery of Cells After Exposure to DNA Damaging Agents The recA gene performs another equally important role in cell metabolism by controlling expression of a group of unlinked genes that aid in recovery of cells after exposure to DNA-damaging agents. This response, termed the SOS response, involves genes that participate in repair of DNA damage, mutagenesis, and coordination of cell division events.

5.5.2.2.3. Characterization

The purified RecA protein is a single polypeptide ranging in weight from about 37,000 to about 42,000. Although there is some variation in the sequences between bacterial strains, the recA proteins from a variety of bacteria in general have been isolated and characterized by interspecies complementation and assays utilizing comparisons with isolated, characterized proteins.

The present method and the linear fragments for use in the present method are not limited to organisms such as *E. coli*. The recA gene is found in a variety of bacteria including both gram negative and gram positive organisms. The recA gene has been isolated or identified and characterized in several organisms. It is possible to prepare a genomic library from any bacterial species and to isolate a clone containing a sequence homologous to a characterized recA gene by interspecific complementation using one of the available DNA clones containing a recA sequence or cross-reactivity with antisera to RecA proteins from a well-characterized organism such as *E. coli*.

RecA+ and RecA− strains are available from a variety of sources. For example, cloning and characterization of recA genes and recA proteins from *Proteus vulgaris, Erwinia carotovoria, Shigella flexneria* and *Escherichia coli* are described by S. L. Keener, et al., in J. Bacter. 160(1), 153–160 (1984). The RecA proteins produced by these organisms were demonstrated to be highly conserved among the species. In fact, the protein produced by one species could be introduced into another species where it complemented repair and regulatory defects of recA mutations. Other bacterial recA genes and gene products have been described by C. A. Miles, et al, in Mol. Gen.Genet. 204, 161–165 (1986) (Agrobacterium tumefaciens C58), I. Goldberg et al, J. Bacteriol. 165(3), 715–722(1986), (*Vibrio cholera*), M. Better et al, J. Bacteriol. 155(1), 311–316 (1983), (*Rhizobium meliloti*), T. A. Kokjohn et al, J. Bacteriol. 163(2), 568–572 ( 1985), (*Pseudomonas aeruginosa*), and C. M. Lovett, Jr. et al, J. Bio.Chem. 260(6), 3305–3313 (1985) (*Bacillus subtilis*). These articles detail the isolation and characterization of gene libraries and the proteins encoded by the recA genes using techniques known to those skilled in the art including construction of gene libraries, identification of homologous genes using hybridization to probes from other more well characterized species such as *E. coli*, isolation and characterization of RecA proteins using antisera to RecA proteins from *E. coli*, and interspecies complementation of deficient strains of *E. coli* using gene segments from the libraries. The isolated proteins were useful for in vitro complementation studies. RecA deficient strains and RecA clones are available from many of the laboratories cited in the above articles and from the *E. coli* Genetic Stock Center at Yale University run by Dr. Barbara Bachman.

5.5.2.3. Construction of Linear DNA Fragments Which Have Sequences Homologous to Closely Spaced Regions on the Chromosome in the Bacteria Which Flank Each Side of the Gene of Interest The method whereby the DNA fragment is introduced into the chromosome to delete a gene or to regulate recA involves the construction of linear DNA fragments which have sequences homologous to closely spaced regions on the chromosome in the bacteria which flank each side of the gene of interest. In general, they must contain at least 80 to 100 nucleotides homologous to sequences flanking the gene to be deleted or the recA gene. An antibiotic resistant locus such as Kan$^r$, which encodes a protein making the bacterial resistant to the antibiotic, or other marker, is placed between these flanking sequences.

The linear DNA segment is introduced into a specific cell strain and selection is done for a double, reciprocal recombination which will delete the target gene and insert the marker into its place. As a result of the insertion of the antibiotic resistant gene, the cells are now resistant to the antibiotic. Cells which do not contain the insertion are eliminated by growing the bacteria in a medium containing the antibiotic.

Any other gene which allows for rapid screening of the cells containing a double, reciprocal recombination may be used in place of a gene for antibiotic resistance. For example, any gene for an essential protein, including enzymes, cofactors, proteins which are necessary for the synthesis of essential lipids, polysaccharides, nucleic acids, and other protein molecules such as receptors, as well as nucleic acids which have functional activity such as ribozymes, may be used. Other genes which confer a detectable phenotype on the cell strain such as sensitivity to temperature or ultraviolet radiation, auxotrophism for a sugar, amino acid, protein or nucleotide, or any other phenotype which can be detected by chemical indicators either in vitro or in vivo assay, or an immunoassay for a specific cellular component may also be used. Such chemical, radioactive, or immunological screening assays are well known to those skilled in the art.

5.5.3. Eliminating Contamination from the Host Producing Its Own Protein by Deletion and Replacement In one application, in which the goal is to produce and purify a foreign protein, and the microorganism encodes its own version of the protein, the gene for the microorganism's own protein is eliminated. The gene for the foreign protein is then inserted and the protein produced. The purification process is thereby simplified since there is no contamination by the host protein, whether analogous to the protein being produced or unrelated which copurifies with, or interferes with the purification of, the protein being produced. For example, a protein may interfere with binding of the protein to be purified to a column.

5.5.4. A Plasmid is Used to Introduce a Mutated Gene into an Organism

In a second application, a plasmid is used to introduce a gene into an organism which typically contains a mutation in the gene to be investigated resulting in a negative phenotype for the product of the gene to be investigated. Failure of the organism to produce a biologically active form of the protein encoded by the mutated gene may confer a lethal phenotype under certain defined conditions. For example, this can be at a temperature, designated as the restrictive temperature, at which the mutant protein denatures or otherwise undergoes inactivation. The cloned gene which is introduced is selected for by virtue of its ability to confer cell viability or any other detectable phenotype for the desired protein at the restrictive temperature. The acquisition of viability or other detectable phenotype at the normally restrictive temperature is evidence that the gene of interest has been cloned.

5.5.4.1. Problems: The Defective Host Protein May Interact with a Protein Produced from the Introduced Plasmid The major problem with this second system is that, unless the inactive gene is deleted in entirety, the defective host protein may interact with a protein produced from the introduced plasmid. This interaction may stabilize the defective host protein enough so that its activity is restored even at the restrictive temperature. In this case, the restoration of growth at the restrictive temperature would be a false positive, that is, the growth would not be due to activity encoded by the cloned DNA segment. This problem holds true for all selections based on complementation of a phenotype which is due to a defect in a specific protein. Such phenotypes include temperature sensitivity, amino acid auxotrophies or any other auxotrophies which result from a lack of synthesis of a key ingredient such as a sugar, nucleotide, critical protein or nucleic acid, or cofactor used for oxidation, reduction, or transamination reactions.

5.5.5. False Positives

The problem of "false positives" also exists for cloned DNA pieces which are created to encode enzyme fragments as a means to define the catalytic core or to define any segment which achieves a specific purpose, such as a piece which undergoes self-association, binds to a specific ligand or receptor, or forms a specific complex or array with one or more additional components. In these cases, the engineering of protein fragments, which are tested in a host cell that encodes a defective version of the protein of interest, is seriously hampered if the defective host protein interacts in any way with the engineered pieces.

5.5.6. Use of Temperature Sensitive Replicons

In the present invention, specifically designed linear DNA fragments are used to create a deletion of a gene by site-specific recombination. These fragments are transformed into the host cell. Cell viability or the detectable phenotype can be maintained during the procedure by provision of the gene encoding the desired protein on a recombinant plasmid that has a temperature-sensitive replicon, so that the cells which contain the deletion have a temperature sensitive phenotype. To achieve the deletion by recombination with the linear DNA fragments, it is necessary for the cells to have a RecA+ phenotype which is derived from recA, or its equivalent. Once recombination has occurred, the cell must immediately be changed to RecA or else the temperature sensitive plasmid will recombine with homologous sequences on the chromosome. The same would apply to any other extrachromosomal element where integration into the host chromosome would be undesirable.

The RecA– phenotype may be achieved by simultaneous inactivation of recA during the transformation with linear fragments or, after the transformation, by immediately introducing RecA– by mating with an appropriate RecA– strain or by transduction with a phage which carries a RecA– gene segment. Although mutagenesis may also be an effective means of making the cell RecA–, this is a "hit or miss" approach. The preferred method is to use homologous recombination of linear DNA sequences bounded by sequences hybridizing to the sequences flanking the recA gene. The recA gene is necessary in order for the gene encoding the desired protein to be incorporated into the organism. However, any plasmids or other extrachromosomal elements in the cell will be incorporated unless the recA gene is immediately removed. This is a particular concern where the bacteria serves as a host for the expression of a genetically engineered protein from multicopy plasmids.

6. Detection Methods (Screening/Selection)

6.1. Basic Approach: Artificially Evolving Cells to Acquire a New or Improved Property by Stochastic &/or Non-stochasticly Mutagenizing 6.1.1. General: Successive Cycles of Recombination and Screening/selection The invention provides methods for artificially evolving cells to acquire a new or improved property by recursive sequence recombination. Briefly, recursive sequence recombination entails successive cycles of recombination to generate molecular diversity and screening/selection to take advantage of that molecular diversity. That is, a family of nucleic acid molecules is created showing substantial sequence and/or structural identity but differing as to the presence of mutations. These sequences are then recombined in any of the described formats so as to optimize the diversity of mutant combinations represented in the resulting recombined library. Typically, any resulting recombinant nucleic acids or genomes are recursively recombined for one or more cycles of recombination to increase the diversity of resulting products. After this recursive recombination procedure, the final resulting products are screened and/or selected for a desired trait or property.

Alternatively, each recombination cycle can be followed by at least one cycle of screening or selection for molecules having a desired characteristic. In this embodiment, the molecule(s) selected in one round form the starting materials for generating diversity in the next round.

The cells to be evolved can be bacteria, archaebacteria, or eukaryotic cells and can constitute a homogeneous cell line or mixed culture. Suitable cells for evolution include the bacterial and eukaryotic, cell lines commonly used in genetic engineering, protein expression, or the industrial production or conversion of proteins, enzymes, primary metabolites, secondary metabolites, fine, specialty or commodity chemicals. Suitable mammalian cells include those from, e.g., mouse, rat, hamster, primate, and human, both cell lines and primary cultures. Such cells include stem cells, including embryonic stem cells and hemopoietic stem cells, zygotes, fibroblasts, lymphocytes, Chinese hamster ovary (CHO), mouse fibroblasts (NIHM), kidney, liver, muscle, and skin cells. Other eukaryotic cells of interest include plant cells, such as maize, rice, wheat, cotton, soybean, sugarcane, tobacco, and arabidopsis; fish, algae, fungi (penicillium, aspergillus, podospora, neurospora, saccharomyces), insect (e.g., baculo lepidoptera), yeast (picchia and saccharomyces, Schizosaccharomycespombe). Also of interest are many bacterial cell types, both gram-negative and gram-positive, such as *Bacillus subtilis, B. licehniformis, B. cereus, Escherichia coli*, Streptomyces, Pseudomonas, Salmonella, Actinomycetes, Lactobacillius, Acelonitcbacter, Deinococcus, and Erwinia. The complete genome sequences of *E. coli* and *Bacillus subtilis* are described by Blattner et al., Science 277, 1454–1462 (1997); Kunst et al., Nature 390, 249–256 (1997).

6.2. Screening for Improved Strains

Strains showing viability in initial selections are assayed more quantitatively for improvements in the desired properties before being restochastic &/or non-stochasticly mutagenized with other strains.

Progeny resulting from mutagenesis of a strain, or those pre-selected for their ethanol tolerance and/or themostability, can be plated on non-selective agar. Colonies can be picked robotically into microtiter dishes and grown. Cultures are replicated to fresh microtiter plates, and the replicates are incubated under the appropriate stress condition(s). The growth or metabolic activity of individual clones may be monitored and ranked. Indicators of viability can range from the size of growing colonies on solid media, density of growing cultures, or color change of a metabolic activity indicator added to liquid media. Strains that show the greatest viability are then mixed and stochastic &/or non-stochasticly mutagenized, and the resulting progeny are rescreened under more stringent conditions.

6.3. Methods for Whole Genome Stochastic &/or Non-stochasticly Mutagenizing by Blind Family Stochastic &/or Non-stochasticly Mutagenizing of Parsed Genomes and Recursive Cycles of Forced Integration and Excision by Homologous Recombination, and Screening for Improved Phenotypes In vitro methods have been developed to stochastic &/or non-stochasticly mutagenize single genes and operons, as set forth, e.g., herein. "Family" stochastic &/or non-stochasticly mutagenizing of homologous genes within species and from different species is also an effective methods for accelerating molecular evolution. This section describes additional methods for extending these methods such that they can be applied to whole genomes.

In some cases, the genes that encode rate-limiting steps in a biochemical process, or that contribute to a phenotype of interest are known. This method can be used to target family stochastic &/or non-stochasticly mutagenized libraries to such loci, generating libraries of organisms with high quality family stochastic &/or non-stochasticly mutagenized libraries of alleles at the locus of interest. An example of such a gene would be the evolution of a host chaperonin to more efficiently chaperone the folding of an overexpressed protein in *E. coli*.

The goals of this process are to stochastic &/or non-stochasticly mutagenize homologous genes from two or more species and to then integrate the stochastic &/or non-stochastic mutagenized genes into the chromosome of a target organism.

Integration of multiple stochastic &/or non-stochastic mutagenized genes at multiple loci can be achieved using recursive cycles of integration (generating duplications), excision (leaving the improved allele in the chromosome) and transfer of additional evolved genes by serially applying the same procedure.

In the first step, genes to be stochastic &/or non-stochasticly mutagenized into suitable bacterial vectors are subcloned. These vectors can be plasmids, cosmids, BACS or the like. Thus, fragments from 100 bp to 100 kb can be handled. Homologous fragments are then "family stochastic &/or non-stochasticly mutagenized" together (i.e. homologous fragments from different species or chromosomal locations are homologously recombined). As a simple case, homologs from two species (say, *E. coli* and Salmonella) are cloned, family stochastic &/or non-stochasticly mutagenized in vitro and cloned into an allele replacement vector (e.g., a vector with a positively selectable marker, a negatively selectable marker and conditionally active origin of replication). The basic strategy for whole genome family stochastic &/or non-stochasticly mutagenizing of parsed (subcloned) genomes is additionally set forth in.

The vectors are transfected into *E. coli* and selected, e.g., for drug resistance. Most drug resistant cells should arise by homologous recombination between a family stochastic &/or non-stochasticly mutagenized insert and a chromosomal copy of the cloned insert. Colonies with improved phenotype are screened (e.g., by mass spectroscopy for enzyme activity or small molecule production, or a chromogenic screen, or the like, depending on the phenotype to be assayed). Negative selection (i.e. sue selection) is imposed to force excision of tandem duplication. Roughly half C, of the colonies should retain the improved phenotype. Importantly, this process regenerates a "clean" chromosome in which the wild type locus is replaced with a family stochastic &/or non-stochasticly mutagenized fragment that encodes a beneficial allele. Since the chromosome is "clean" (i.e., has no vector sequences), other improved alleles can also be moved into this point on the chromosome by homologous recombination.

Selection or screening for improved phenotype can occur either after step 3 or step 4. If selection or screening takes place after step 3, then the improved allele can be conveniently moved to other strains by, for example, PI transduction. One can then regenerate a strain containing the improved allele but lacking vector sequences by "negative selection" against the suc marker. In subsequent rounds, independently identified improved variants of the gene can be sequentially moved into the improved strain (e.g., by PI transduction of the drug marked tandem duplication above). Transductants are screened for further improvement in phenotype by virtue of receiving the transduced tandem duplication, which itself contains the family stochastic &/or non-stochasticly mutagenized genetic material. Negative selection is again imposed and the process of stochastic &/or non-stochasticly mutagenizing the improved strain is recursively repeated as desired.

Although this process was described with reference to targeting a gene or genes of interest, it can be used "blindly," making no assumptions about which locus is to be targeted. For example, the whole genome of an organism of interest is cloned into manageable fragments (e.g., 10 kb for plasmid-based methods). Homologous fragments are then isolated from related species. Forced recombination with chromosomal homologs creates chimeras.

6.4. Selection and Screening

Screening is, in general, a two-step process in which one first determines which cells do and do not express a screening marker and then physically separates the cells having the desired property. Selection is a form of screening in which identification and physical separation are achieved simultaneously, for example, by expression of a selectable marker, which, in some genetic circumstances, allows cells expressing the marker to survive while other cells die (or vice versa). Screening markers include, for example, luciferase, beta-galactosidase, and green fluorescent protein. Screening can also be done by observing such aspects of growth as colony size, halo formation, etc. Additionally, screening for production of a desired compound, such as a therapeutic drug or "designer chemical" can be accomplished by observing binding of cell products to a receptor or ligand, such as on a solid support or on a column. Such screening can additionally be accomplished by binding to antibodies, as in an ELISA. In some instances the screening process is preferably automated so as to allow screening of suitable numbers of colonies or cells. Some examples of automated screening devices include fluorescence activated cell sorting, especially in conjunction with cells immobilized in agarose (see Powell et. al. Bio/Technology 8:333–337 (1990); Weaver et. al. Methods 2:234–247 (1991)), automated ELISA assays, scintillation proximity assays (Hart, H. E. et al., Molecular Immunol. 16:265–267 (1979)) and the formation of fluorescent, coloured or UV absorbing compounds on agar plates or in microtitre wells (Krawiec, S., Devel. Indust. Microbiology 31:103–114 (1990)).

Selectable markers can include, for example, drug, toxin resistance, or nutrient synthesis genes. Selection is also done by such techniques as growth on a toxic substrate to select for hosts having the ability to detoxify a substrate, growth on a new nutrient source to select for hosts having the ability to utilize that nutrient source, competitive growth in culture based on ability to utilize a nutrient source, etc.

In particular, uncloned but differentially expressed proteins (e.g., those induced in response to new compounds, such as biodegradable pollutants in the medium) can be screened by differential display (Appleyard et al. Mol. Gen. Gent. 247:338–342 (1995)).

Hopwood (Phil Trans R. Soc. Lond B 324:549–562) provides a review of screens for antibiotic production. Omura (Microbio. Rev. 50:259–279 (1986) and Nisbet (Ann Rev. Med. Chem. 21:149–157 (1986)) disclose screens for antimicrobial agents, including supersensitive bacteria, detection of beta-lactamase and D,D- carboxypeptidase inhibition, beta-lactamase induction, chromogenic substrates and monoclonal antibody screens.

Antibiotic targets can also be used as screening targets in high throughput screening. Antifungals are typically screened by inhibition of fungal growth. Pharmacological agents can be identified as enzyme inhibitors using plates containing the enzyme and a chromogenic substrate, or by automated receptor assays. Hydrolytic enzymes (e.g., proteases, amylases) can be screened by including the substrate in an agar plate and scoring for a hydrolytic clear zone or by using a calorimetric indicator (Steele et al. Ann. Rev. Microbiol. 45:89–106 (1991)). This can be coupled with the use of stains to detect the effects of enzyme action (such as congo red to detect the extent of degradation of celluloses and hemicelluloses).

Tagged substrates can also be used. For example, lipases and esterases can be screened using different lengths of fatty acids linked to umbelliferyl. The action of lipases or esterases removes this tag from the fatty acid, resulting in a quenching or enhancement of umbelliferyl fluorescence. These enzymes can be screened in microtiter plates by a robotic device.

6.4.1. FACS

Fluorescence activated cell sorting (FACS) methods are also a powerful tool for selection/screening. In some instances a fluorescent molecule is made within a cell (e.g., green fluorescent protein). The cells producing the protein can simply be sorted by FACS. Gel microdrop technology allows screening of cells encapsulated in agarose microdrops (Weaver et al. Methods 2:234–247 (1991)). In this technique products secreted by the cell (such as antibodies or antigens) are immobilized with the cell that generated them. Sorting and collection of the drops containing the desired product thus also collects the cells that made the product, and provides a ready source for the cloning of the genes encoding the desired functions. Desired products can be detected by incubating the encapsulated cells with fluorescent antibodies (Powell et al. Bio/Technology 8:333–337 (1990)). FACS sorting can also be used by this technique to assay resistance to toxic compounds and antibiotics by selecting droplets that contain multiple cells (i.e., the product of continued division in the presence of a cytotoxic compound; Goguen et al. Nature 363:189–190 (1 995)). This method can select for any enzyme that can change the fluorescence of a substrate that can be immobilized in the agarose droplet.

6.4.2. Reporter Molecule

In some embodiments of the invention, screening can be accomplished by assaying reactivity with a reporter molecule reactive with a desired feature of, for example, a gene product. Thus, specific functionalities such as antigenic domains can be screened with antibodies specific for those determinants.

6.4.3. Cell-cell Indicator

In other embodiments of the invention, screening is preferably done with a cell-cell indicator assay. In this assay format, separate library cells (Cell A, the cell being assayed) and reporter cells (Cell B, the assay cell) are used.

Only one component of the system, the library cells, is allowed to evolve. The screening is generally carried out in a two-dimensional immobilized format, such as on plates. The products of the metabolic pathways encoded by these genes (in this case, usually secondary metabolites such as antibiotics, polyketides, carotenoids, etc.) diffuse out of the library cell to the reporter cell. The product of the library cell may affect the reporter cell in one of a number of ways.

The assay system (indicator cell) can have a simple readout (e.g., green fluorescent protein, luciferase, beta-galactosidase) which is induced by the library cell product but which does not affect the library cell. In these examples the desired product can be detected by calorimetric changes in the reporter cells adjacent to the library cell.

6.4.4. Feedback Mechanism

In other embodiments, indicator cells can in turn produce something that modifies the growth rate of the library cells via a feedback mechanism. Growth rate feedback can detect and accumulate very small differences. For example, if the library and reporter cells are competing for nutrients, library cells producing compounds to inhibit the growth of the reporter cells will have more available nutrients, and thus will have more opportunity for growth. This is a useful screen for antibiotics or a library of polyketide synthesis gene clusters where each of the library cells is expressing and exporting a different polyketide gene product.

6.4.5. Secretion

Another variation of this theme is that the reporter cell for an antibiotic selection can itself secrete a toxin or antibiotic that inhibits growth of the library cell. Production by the library cell of an antibiotic that is able to suppress growth of the reporter cell will thus allow uninhibited growth of the library cell.

Conversely, if the library is being screened for production of a compound that stimulates the growth of the reporter cell (for example, in improving chemical syntheses, the library cell may supply nutrients such as amino acids to an auxotrophic reporter, or growth factors to a growth-factor-dependent reporter. The reporter cell in turn should produce a compound that stimulates the growth of the library cell. Interleukins, growth factors, and nutrients are possibilities. Further possibilities include competition based on ability to kill surrounding cells, positive feedback loops in which the desired product made by the evolved cell stimulates the indicator cell to produce a positive growth factor for cell A, thus indirectly selecting for increased product formation.

In some embodiments of the invention it can be advantageous to use a different organism (or genetic background) for screening than the one that will be used in the final product. For example, markers can be added to DNA constructs used for recursive sequence recombination to make the microorganism dependent on the constructs during the improvement process, even though those markers may be undesirable in the final recombinant microorganism.

Likewise, in some embodiments it is advantageous to use a different substrate for screening an evolved enzyme than the one that will be used in the final product. For example, Evnin et al. (Proc. Natl. Acad. Sci. U.S.A. 87:6659–6663 (1990)) selected trypsin variants with altered substrate specificity by requiring that variant trypsin generate an essential amino acid for an arginine auxotroph by cleaving arginine beta-naphthylamide. This is thus a selection for arginine-specific trypsin, with the growth rate of the host being proportional to that of the enzyme activity.

The pool of cells surviving screening and/or selection is enriched for recombinant genes conferring the desired phenotype (e.g. altered substrate specificity, altered biosynthetic ability, etc.). Further enrichment can be obtained, if desired, by performing a second round of screening and/or selection without generating additional diversity.

The recombinant gene or pool of such genes surviving one round of screening/selection forms one or more of the substrates for a second round of recombination. Again, recombination can be performed in vivo or in vitro by any of the recursive sequence recombination formats described above.

If recursive sequence recombination is performed in vitro, the recombinant gene or genes to form the substrate for recombination should be extracted from the cells in which screening/selection was performed. Optionally, a subsequence of such gene or genes can be excised for more targeted subsequent recombination. If the recombinant gene (s) are contained within episomes, their isolation presents no difficulties. If the recombinant genes are chromosomally integrated, they can be isolated by amplification primed from known sequences flanking the regions in which recombination has occurred. Alternatively, whole genomic DNA can be isolated, optionally amplified, and used as the substrate for recombination. Small samples of genomic DNA can be amplified by whole genome amplification with degenerate primers (Barrett et al. Nucleic Acids Research 23:3488–3492 (1995)). These primers result in a large amount of random 3' ends, which can undergo homologous recombination when reintroduced into cells.

If the second round of recombination is to be performed in vivo, as is often the case, it can be performed in the cell surviving screening/selection, or the recombinant genes can be transferred to another cell type (e.g., a cell is type having a high frequency of mutation and/or recombination). In this situation, recombination can be effected by introducing additional DNA segment(s) into cells bearing the recombinant genes. In other methods, the cells can be induced to exchange genetic information with each other by, for example, electroporation. In some methods, the second round of recombination is performed by dividing a pool of cells surviving screening/selection in the first round into two subpopulations. DNA from one subpopulation is isolated and transfected into the other population, where the recombinant gene(s) from the two subpopulations recombine to form a further library of recombinant genes. In these methods, it is not necessary to isolate particular genes from the first subpopulation or to take steps to avoid random shearing of DNA during extraction. Rather, the whole genome of DNA sheared or otherwise cleaved into manageable sized fragments is transfected into the second subpopulation. This approach is particularly useful when several genes are being evolved simultaneously and/or the location and identity of such genes within chromosome are not known.

The second round of recombination is sometimes performed exclusively among the recombinant molecules surviving selection. However, in other embodiments, additional substrates can be introduced. The additional substrates can be of the same form as the substrates used in the first round of recombination, i.e., additional natural or induced mutants of the gene or cluster of genes, forming the substrates for the first round. Alternatively, the additional substrate(s) in the second round of recombination can be exactly the same as the substrate(s) in the first round of replication.

After the second round of recombination, recombinant genes conferring the desired phenotype are again selected. The selection process proceeds essentially as before. If a suicide vector bearing a selective marker was used in the first round of selection, the same vector can be used again. Again, a cell or pool of cells surviving selection is selected. If a pool of cells, the cells can be subject to further enrichment.

6.5. Factors Involved in Discovery and Development of New Drugs

In the discovery and development of new drugs, it is a common strategy to first try to identify molecules or complexes of molecules, naturally occurring within cells, that are involved in producing symptoms of a disease. These naturally occurring molecules can be thought of as "targets." A second major part of the strategy is then to find molecules that bind to the targets. These molecules are candidates for drug development, on the theory that a molecule that binds to a target can modulate (inhibit or enhance) the function of the target, thereby causing a change in the biological status of the cell containing the target. The change caused in the cell (e.g., a change in phenotype towards wild type, or a change in growth rate) may be therapeutically beneficial to the animal or human host of the cell.

The genomics revolution, by determining the DNA sequences of great numbers of genes from many different organisms, has considerably broadened the possibilities for drug discovery by identifying, large numbers of molecules that are potential targets of drug action. These technical advances in genomics however, have posed an entirely new set of challenges. Specifically, how can one prove that a chosen target molecule is essential to maintaining the disease or disorder to be treated? That is, how does one validate a target? Although methods currently available to validate targets do provide some guidelines in selection of drug targets, they are usually not conducted under the conditions in which a drug actually interacts with its target, and therefore provide a limited set of information. In addition, they do not directly address, among other things: 1) if a wild type (normal) target is essential for cell growth and viability during the disease state; 2) if the wild type gene products themselves are suitable targets for drug discovery; 3) if specific sites on a target are suitable for drug interaction (for example, in a pathogenic organism, there can be one gene coding for a single protein target with two activities—one activity essential for growth and infectivity, the second activity non-essential); 4) if a compensatory mechanism in the cell, either in vitro or in vivo, can overcome or compensate for target modulation or, 5) if a disease state can be cured by modulation of function of the candidate target. These methods also do not provide a direct route for testing wild type target proteins in high throughput screening assays.

An analysis of the discovery of novel antimicrobial agents illustrates the problems researchers in all fields of drug development face today. The increasing prevalence of drug-resistant pathogens (bacteria, fungi, parasites, etc.) has led to significantly higher mortality rates from infectious diseases and currently presents a serious crisis worldwide. Despite the introduction of second and third generation antimicrobial drugs, certain pathogens, such as vancomycin resistant strains of Enterococcus facieun, have developed resistance to all currently available drugs.

New antimicrobial drugs must be discovered to treat such infections by such organisms, and new methods are urgently needed to facilitate making such discoveries.

Neither whole cell screening, chemistry nor target based drug discovery approaches as currently applied, have met the challenge of controlling infectious diseases, particularly those caused by drug resistant microorganisms. Whole cell screening assays have been limited by the fact that they are unable to identify compounds that can effectively modulate a target function inside the cell but cannot permeate the cell membrane to get to the target. Therefore entire classes of potent, intracellular target modulators, which could be subsequently modified by medicinal chemistry to increase cell membrane permeability, go undetected. Chemistry based approaches have focused on chemically modifying the molecular structure of existing antimicrobial drugs or combining existing antimicrobials with another agent to circumvent established resistance mechanisms. Technical advances in molecular biology, automated methods for high throughput screening and chemical syntheses have led to an increase in the number of target based screens utilized for antimicrobial drug discovery and in the number of compounds being analyzed. However, despite these advances, only a limited number of antimicrobial drugs acting by a novel mechanism have been identified during recent years.

How does one efficiently establish screening assays for drugs that can be used with a variety of different targets having different properties, enzymatic activities, or even unknown functions? A number of potentially novel, valuable targets are incompatible with current methods to screen for drug candidates because either the target's exact function and molecular mechanism of action are unknown, or there are technical obstacles preventing the development of effective high throughput screening methods. It can take anywhere from six months to several years to develop a screening assay, which is impractical when the goal is to rapidly screen multiple targets in a cost-effective manner.

The path in the progression from target identification through assay development, high throughput screening, medicinal chemistry, lead optimization, preclinical and clinical drug development is expensive, time consuming and full of technical challenges. Many different targets must be screened against multiple chemical compounds to identify new lead compounds for drug development. New, efficient technologies are needed that can be broadly applied to a variety of different targets to validate targets in the direct context of the desired outcome of drug therapy and to rapidly develop screening assays using these targets for drug discovery. Such developments will allow the wealth of genomics information to be leveraged for drug discovery and will lower the risk and costs while expediting the timelines of the drug discovery process.

6.6. General Approach for Identifying Targets

The invention relates to methods that couple the validation of a target for drug discovery with the development of an assay to identify compounds that cause a phenotypic effect on the target cell. These procedures can be applied to identifying compounds that bind to and modulate the function of target components of a cell whose function is known or unknown, and cell components that are not amenable to other screening methods.

The invention relates to procedures for identifying a compound that binds to and modulates (inhibits or enhances) the function of a component of a cell, thereby producing a phenotypic effect in the cell. Within these procedures are methods for identifying a biomolecule that 1) binds to, in vitro, a component a cell that has been isolated from other constituents of the cell and that 2) causes, in vivo, as seen in an assay upon intracellular expression of the biomolecule, a phenotypic effect in the cell which is the usual producer and host of the target cell component. In an assay demonstrating characteristic 2) above, intracellular production of the biomolecule can be in cells grown in culture or in cells introduced into an animal. Further methods within these procedures are those methods comprising an assay for a phenotypic effect in the cell upon intracellular production of the biomolecule, either in cells in culture or in cells that have been introduced into one or more animals, and an assay to identify one or more compounds that behave as competitors of the biomolecule in an assay of binding to the target cell component.

6.6.1. Process for Identifying One or More Compounds that Produce a Phenotypic Effect on a Cell One procedure envisioned in the invention is a process for identifying one or more compounds that produce a phenotypic effect on a cell. The process is at the same time a method for target validation. The process is characterized by identifying a biomolecule which binds an isolated target cell component, constructing cells comprising the target cell component and further comprising a gene encoding the biomolecular binder which can be expressed to produce the biomolecular binder, testing the constructed cells for their ability to produce, upon expression of the gene encoding the biomolecular binder, a phenotypic effect in the cells (e.g., inhibition of growth), wherein the test of the constructed cells can be a test of the cells in culture or a test of the cells after introducing them into host animals, or both, and further, identifying, for a biomolecular binder that caused the phenotypic effect, one or more compounds that compete with the biomolecular binder for binding to the target cell component.

A test of the constructed cells after introducing them into host animals is especially well-suited to assessing whether a biomolecular binder can produce a particular phenotype by the expression (regulatable by the researcher) of a gene encoding the biomolecular binder. In this method, cells are constructed which have a gene encoding the biomolecular binder, and wherein the biomolecular binder can be produced by regulation of expression of the gene. The constructed cells are introduced into a set of animals. Expression of the gene encoding the biomolecular binder is regulated in one group of the animals (test animals) such that the biomolecular binder is produced. In another group of animals, the gene encoding the biomolecular binder is regulated such that the biomolecular binder is not produced (control animals). The cells in the two groups of animals are monitored for a phenotypic change (for example, a change in growth rate). If the phenotypic change is observed in cells in the test animals and not in the cells in the control animals, or to a lesser extent in the control animals, then the biomolecular binder has been proven to be effective in binding to its target cell component under in vivo conditions.

A further embodiment of the invention is a method for determining whether a target cell component of a particular cell type (a "first cell") is essential to producing a phenotypic effect on the first cell, the method having the steps: isolating the target component of the first cell; identifying a biomolecular binder of the isolated target component of the first cell; constructing a second type of cells ("second cell") comprising the target component and a regulable, exogenous gene encoding the biomolecular binder; and testing the second cell in culture for an altered phenotypic effect, upon production of the biomolecular binder in the second cell; whereby, if the second cell shows the altered phenotypic effect upon production of the biomolecular binder, then the target component of the first cell is essential to producing the phenotypic effect on the first cell. The target cell component in this embodiment and in other embodiments not limited to pathogens can be one that is found in mammalian cells, especially cells of a type found to cause or contribute to disease or the symptoms of disease (e.g., cells of tumors or cells of other types of hyperproliferative disorders).

6.6.1.1. Procedure for Identifying and/or Designing Compounds with Antimicrobial Activity Against a Pathogen The invention further relates to methods particularly well suited to a procedure for identifying and/or designing compounds with antimicrobial activity against a pathogen whose target cell component is the subject of studies to identify such compounds. A common mechanism of action of an antimicrobial agent is binding to a component of the cells of the pathogen treated with the antimicrobial.

The procedure includes methods for identifying biomolecules that bind to a chosen target in vitro, methods for identifying biomolecules that also bind to the chosen target and modulate its function during infection of a host mammal in vivo, and methods for identifying compounds that compete with the biomolecules for sites on the target in competitive binding assays. Compounds identified by this procedure are candidates for drugs with antimicrobial activity against the pathogen.

6.6.1.1.1. Identifying a Biomolecular Inhibitor of Growth of Pathogen Cells

One embodiment of the invention is a method for identifying a biomolecular inhibitor of growth of pathogen cells by using cell culture techniques, comprising contacting one or more types of biomolecules with isolated target cell component of the pathogen, applying a means of detecting bound complexes of biomolecules and target cell component, whereby, if the bound complexes are detected, one or more types of biomolecules have been identified as a biomolecular binder of the target cell component, constructing a pathogen strain having a regulable gene encoding the biomolecular binder, regulating expression of the gene encoding the biomolecular binder to express the gene; and monitoring growth of the pathogen cells in culture relative to suitable control cells, whereby, if growth of the pathogen cells is decreased compared to growth of suitable control cells, then the biomolecule is a biomolecular inhibitor of growth of the pathogen cells.

6.6.1.1.2. Identifying Compounds That Inhibit Infection of a Mammal by a Pathogen A further embodiment of the invention is a method, employing an animal test, for identifying one or more compounds that inhibit infection of a mammal by a pathogen by binding to a target cell component, comprising constructing a pathogen comprising a regulable gene encoding a biomolecule which binds to the target cell component, infecting test animals with the pathogen, regulating expression of the regulable gene to produce the biomolecule, monitoring the test animals and suitable control animals for signs of infection, wherein observing fewer or less severe signs of infection in the test animals than in suitable control animals indicates that the biomolecule is a biomolecular inhibitor of infection, and identifying one or more compounds that compete with the biomolecular inhibitor of growth for binding to the target cell component (as by employing a competitive binding assay), then the compound inhibits infection of a mammal by a pathogen by binding to a target.

The competitive binding assay to identify binding analogs of biomolecular binders, which have been proven to bind to their targets in an intracellular test of binding, can be applied to any target for which a biomolecular binder has been identified, including targets whose function is unknown or targets for which other types of assays are not easily developed and performed. Therefore, the method of the invention offers the advantage of decreasing assay development time when using a gene product of known function as a target cell component and the advantage of bypassing the major hurdle of gene function identification when using a gene product of unknown function as a target cell component.

Other embodiments of the invention are cells comprising a biomolecule and a target cell component, wherein the biomolecule is produced by expression of a regulable gene, and wherein the biomolecule modulates function of the target cell component, thereby causing a phenotypic change in the cells. Yet other embodiments are cells comprising a biomolecule and a target cell component, wherein the biomolecule is a biomolecular binder of the target cell component, and is encoded by a regulable gene. The cells can include mammalian cells or cells of a pathogen, for instance, and the phenotypic change can be a change in growth rate. The pathogen can be a species of bacteria, yeast, fungus, or parasite, for example.

6.6.2. Definitions

Target: (also, "target component of a cell," or "target cell component") a constituent of a cell which contributes to and is necessary for the production or maintenance of a phenotype of the cell in which it is found. A target can be a single type of molecule or can be a complex of molecules. A target can be the product of a single gene, but can also be a complex comprising more than one gene product (for example, an enzyme comprising alpha and beta subunits, mRNA, tRNA, ribosomal RNA or a ribonucleoprotein particle such as a snRNP). Targets can be the product of a characterized gene (gene of known function) or the product of an uncharacterized gene (gene of unknown function).

Target Validation: the process of determining whether a target is essential to the maintenance of a phenotype of the cell type in which the target normally occurs. For example, for pathogenic bacteria, researchers developing antimicrobials want to know if a compound which is potentially an antimicrobial agent not only binds to a target in vitro, but also binds to, and modulates the function of, a target in the bacteria in vivo, and especially under the conditions in which the bacteria are producing an infection—those conditions under which the antimicrobial agent must work to inhibit bacterial growth in an infected animal or human. If such compounds can be found that bind to a target in vitro and alter the target's function in cells resulting in an altered phenotype, as found by testing cells in culture and/or as found by testing cells in an animal, then the target is validated.

Phenotypic Effect: a change in an observable characteristic of a cell which can include, e.g., growth rate, level or activity of an enzyme produced by the cell, sensitivity to various agents, antigenic characteristics, and level of various metabolites of the cell. A phenotypic effect can be a change away from wild type (normal) phenotype, or can be a change towards wild type phenotype, for example.

A phenotypic effect can be the causing or curing of a disease state, especially where mammalian cells are referred to herein. For cells of a pathogen or tumor cells, especially, a phenotypic effect can be the slowing of growth rate or cessation of growth.

Biomolecule: a molecule which can be produced as a gene product in cells that have been appropriately constructed to comprise one or more genes encoding the biomolecule. Preferably, production of the biomolecule can be turned on, when desired, by an inducible promoter. A biomolecule can be a peptide, polypeptide, or an RNA or RNA oligonucleotide, a DNA or DNA oligonucleotide, but is preferably a peptide. The same biomolecules can also be made synthetically. For peptides, see Merrifield, J., J. Am. Chem. Soc. 85: 2140–2154 (1963). For instance, an Applied Biosystems 431 A Peptide Synthesizer (Perkin Elmer) can be used for peptide synthesis. Biomolecules produced as gene products intracellularly are tested for their interaction with a target in the intracellular steps described herein (tests performed with cells in culture and tests performed with cells that have been introduced into animals). The same biomolecules produced synthetically are tested for their binding to an isolated target in an initial in vitro method described herein.

Synthetically produced biomolecules can also be used for a final step of the method for finding compounds that are competitive binders of the target.

Biomolecular Binder (of a target): a biomolecule which has been tested for its ability to bind to an isolated target cell component in vitro and has been found to bind to the target.

Biomolecular Inhibitor of Growth: a biomolecule which has been tested for its ability to inhibit the growth of cells constructed to produce the biomolecule in an "in culture" test of the effect of the biomolecule on growth of the cells, and has been found, in fact, to inhibit the growth of the cells in this test in culture.

Biomolecular Inhibitor of Infection: a biomolecule which has been tested for its ability to ameliorate the effects of infection, and has been found to do so. In the test, pathogen cells constructed to regulably express the biomolecule are introduced into one or more animals, the gene encoding the biomolecule is regulated so as to allow production of the biomolecule in the cells, and the effects of production of the biomolecule are observed in the infected animals compared to one or more suitable control animals.

Isolated: term used herein to indicate that the material in question exists in a physical milieu distinct from that in which it occurs in nature. For example, an isolated target cell component of the invention may be substantially isolated with respect to the complex cellular milieu in which it naturally occurs. The absolute level of purity is not critical, and those skilled in the art can readily determine appropriate levels of purity according to the use to which the mat e rial is to be put.

In many circumstances the isolated material will form part of a composition (for example, a more or less crude extract containing other substances), buffer system or reagent mix. In other circumstances, the material may be purified to essential homogeneity, for example as determined by PAGE or column chromatography (for example, HPLC).

Pathogen or Pathogenic Organism: an organism which is capable of causing disease, detectable by signs of infection or symptoms characteristic of disease. Pathogens can include procaryotes (which include, for example, medically significant Gram- positive bacteria such as *Streptococcus pneumoniae, Enterococcus faecalis* and *Staphylococcus aureus,* Gram-negative bacteria such as *Escherichia coli, Pseudomonas aeroginosa* and *Klebsiella pneumoniae,* and "acid-fast" bacteria such as Mycobacteria, especially M. tuberculosis), eucaryotes such as yeast and fungi (for example, *Candida albicans* and *Aspergillus fumigatus*) and parasites. It should be recognized that pathogens can include such organisms as soil-dwelling organisms and "normal flora" of the skin, gut and orifices, if such organisms colonize and cause symptoms of infection in a human or other mammal, by abnormal proliferation or by growth at a site from which the organism cannot usually be cultured.

6.7. Target Validation

The present invention relates to methods that couple the validation of a target cell component for drug discovery with the development of a validated assay to identify compounds that cause a phenotypic effect on the target cell (cell harboring the target cell component). When the target cells are cells of a pathogenic organism, compounds identified by this procedure are candidates for drugs with antimicrobial activity against the pathogen.

The method utilized for target validation provides a test of how a biomolecule produced intracellularly binds to a specific site on a target cell component and alters the target's function in a cell during an established infection or disease. The technology to validate the target identifies a biomolecule specific to the target that can be used in a screening assay to identify drug leads, thereby coupling target validation with drug lead identification. The method also validates specific sites on a target molecule for drug discovery, which is especially important for proteins involved in multiple functions.

6.7.1. Intracellular Validation of a Biomolecule

Described herein are methods that result in the identification of compounds that cause a phenotypic effect on a cell. The general steps described herein to find a compound for drug development can be thought of as these: (1) identifying a biomolecule that can bind to an isolated target cell component in vitro, (2) confirming that the biomolecule, when produced in cells with the target cell component, can cause a desired phenotypic effect and (3) identifying, by an in vitro screening method, for example, compounds that compete with the biomolecule for binding to the target cell component. Advantages of the these steps are that it is not necessary to identify the function of the target cell component and it is not necessary to develop an assay tailored to the function (e.g., enzyme activity) of the target cell component.

Central to these methods is general step (2) above, intracellular validation of a biomolecule comprising one or more steps that determine whether a biomolecule can cause a phenotypic effect on a cell, when the biomolecule is produced by the expression (which can be regulable) of a gene in the cell. As used in general step (2), a biomolecule is a gene product (e.g., polypeptide, RNA, peptide or RNA oligonucleotide) of an exogenous gene—a gene which has been introduced in the course of construction of the cell.

Biomolecules that bind to and alter the function of a candidate target are identified by various in vitro methods. Upon production of the biomolecule within a cell either in vitro or within an animal model system, the biomolecule binds to a specific site on the target, alters its intracellular function, and hence produces a phenotypic change (e.g. cessation of growth, cell death). When the biomolecule is produced in engineered pathogen cells in an animal model of infection, cessation of growth or death of the engineered pathogen cells leads to the clearing of infection and animal survival, demonstrating the importance of the target in infection and thereby validating the target.

6.7.1.1. Comprising an Exogenous Regulable Gene Encoding the Biomolecule

A method for (1) identifying a biomolecule that produces a phenotypic effect on a cell (wherein the cell can be, for instance, a pathogen cell or a mammalian cell) and (2) simultaneous intracellular target validation, can comprise steps of introducing into an animal a cell comprising an exogenous regulable gene encoding the biomolecule, regulating expression of the gene to produce the biomolecule in the cell, and monitoring said cell in the animal for a phenotypic effect, compared to a suitable control cell. If the cell of this test manifests a phenotypic effect, this indicates that the biomolecule produced in the cell causes a phenotypic effect on the cell. If this phenotypic effect is the inhibition of growth of the cells, then the biomolecule can be termed a "biomolecular inhibitor" or a "biomolecular inhibitor of growth." It may be desirable to perform another test of intracellular function, using cell culturing techniques, wherein the cell comprising an exogenous regulable gene encoding the biomolecule of interest, and comprising the target cell component, is treated so as to turn on expression of the gene encoding the biomolecule, and one or more phenotypic characteristics of the cells in culture are monitored relative to suitable control cells, where the control cells do not produce the biomolecule. It may be preferable, where both "in culture" and "in animal" intracellular tests are performed, to do an "in culture" test first.

6.7.1.2. Advantages of Intracellular Validation

The purpose of intracellular validation for the combination of a potential target for drug action and molecule for drug development is two-fold. First, it demonstrates that the biomolecule under study produces a phenotypic effect on a living cell. In contrast with conditions in an in vitro binding test, the biomolecule in an intracellular test is exposed to a multitude of potential binding partners in the living cell, and interaction with one or more of these binding partners in the cell may be unproductive or result in undesirable effects. These effects are not detectable in an in vitro binding test. Second, where a biomolecule has been shown previously by in vitro tests to bind to a target cell component (that is, the biomolecule can be called a "biomolecular binder" of the target cell component, intracellular validation provides proof that the target cell component is essential to the maintenance of the original phenotype of the cell. Therefore, the target is validated for drug discovery and the biomolecule can then be utilized in a competitive binding assay to identify compounds that will have an effect on target molecule function.

Efficient binding between a biomolecule and a target cell component may be demonstrated in vitro; even binding, that inhibits activity of a target enzyme may be demonstrated in vitro. However, in the living cells, there could exist a redundant system that nullifies the effect of the biomolecule binding to the target cell component. For example, production of an enzyme having similar activity to that of the target cell component may be induced in the cells. By a mechanism such as this, the cell could escape any effect the biomolecule might otherwise cause by binding to the target cell component.

6.7.1.2.1. Ensures That the Target Cell Component Is in Its Natural Conformation as Seen in the Disease State Using an intracellular test to validate biomolecule/target cell component interaction is superior to using only an in vitro test using isolated molecules, because the intracellular test ensures that the target cell component is in its natural conformation and that the biomolecule "sees" the target cell component in that conformation, as that conformation occurs in a disease state. That in an intracellular test a biomolecule finds a site which ultimately causes a phenotypic effect on the cell indicates that the biomolecule is binding to a functionally relevant site on the target cell component (e.g., an active site of an enzyme). Thus, molecules that are found to be structural analogs of the biomolecule and to compete with the biomolecule for a binding site on the target will also interact with the functionally relevant site of the target cell component, as functional analogs. A functional analog of the biomolecule can be found through competitive binding assays of the biomolecule against compounds (as in a library of compounds) that are potential binders of the target cell component. Structural analogs can also be found by rational drug design once a biomolecular binder is identified, by designing drugs that mimic the structure of the biomolecular binder. These structural analogs can be tested for their binding properties by techniques described herein.

6.7.1.2.2. Biomolecule Does Not Have to Pass Through a Cell Membrane or Rely on Inefficient Uptake Mechanisms of the Cell A further advantage of the intracellular test in which the biomolecule is produced from one or more genes in the cell, is that the biomolecule does not have to pass through a cell membrane or rely on inefficient uptake mechanisms of the cell. Intracellular production of the biomolecule ensures that a biomolecule that interacts with a functional site on a target cell component to produce an effect will be detected, even if uptake of the biomolecule into the cell is limited. By the intracellular test, more biomolecules testing as being able to cause the desired phenotypic effect can be detected as candidates for further testing to find functional analogs for drug development. In a test employing extracellular addition of biomolecules. Biomolecules that bind the target cell component but are taken up by the cell only to a limited extent could be missed as candidates for further testing to find functional analogs for drug development. Limited uptake of a biomolecule which has been found to bind to a target in vitro is not necessarily a barrier to further steps towards drug development, as a structural portion of the ultimate compound to be administered as a drug can be selected for its stability, membrane solubility, efficient uptake, etc., and can be chemically combined with a compound whose structure mimics the active binding portion of the biomolecule. Intracellular production of the biomolecule, in an intracellular test of the effect of a biomolecule, as opposed to uptake from outside the cell, can also minimize degradation of the biomolecules from extracellular and intracellular degradative enzymes (e. g., proteases).

In further steps following one or more intracellular tests of the biomolecule/target cell component combination, one or more compounds that can also produce the phenotypic effect caused by the biomolecule can be identified in an in vitro competitive binding assay (which may be adapted for high-throughput screening) as compounds that compete with the biomolecule for a binding site on the target cell component. Target cell components can be isolated from the type of cell in which the phenotypic effect is desired (for instance, cells of pathogenic bacteria, yeast or fungi; mammalian cells, such as tumor cells), or from cells engineered to produce the cell component or a derivative of the cell component that would provide (at least some) structurally identical binding sites (e.g., a fusion protein). Compounds that produce the phenotypic effect observed with the biomolecule can be found in the competitive binding assay upon screening of libraries of compounds (for example, small molecule compounds or natural products or libraries that can be selected for having as their members compounds that have greater intracellular stability than biomolecules such as peptides or RNA oligonucleotides).

6.7.1.3. Methods for Identifying Compounds That Inhibit the Growth of Cells Having a Target Cell Component The invention includes methods for identifying compounds that inhibit the growth of cells having a target cell component. The target cell component can first be identified as essential to the growth of the cells in culture and/or under conditions in which it is desired that the growth of the cells be inhibited. These methods can be applied, for example, to various types of cells that undergo abnormal or undesirable proliferation, including cells of neoplasms (tumors or growths, either benign or malignant) which, as known in the art, can originate from a variety of different cell types. Such cells can be referred to, for example, as being from adenomas, carcinomas, lymphomas or leukemias. The method can also be applied to cells that proliferate abnormally in certain other diseases, such as arthritis, psoriasis or autoimmune diseases.

Described herein are similar methods for identifying inhibitors of target molecules or target cell components of pathogenic organisms. These methods can include a target validation procedure using an animal model for confirming that a cell component of a pathogenic organism is essential, after infection with the organism has been established in a host, and that the inhibitor is effective against the organism after the organism has established the infection. A goal of the procedure is to identify compounds and/or gain the knowledge required to design compounds that can be used as antimicrobial agents to treat a human or other mammal having an infection of the organism.

6.7.1.4. Methods for in Vitro and in Vivo Validation of Target and Assay Combinations The invention provides methods for in vitro and in vivo validation of target and assay combinations. Following selection of biomolecular binders to the isolated target cell component of interest, the invention can incorporate steps for (1) regulable (e.g., inducible) intracellular expression of a gene encoding the biomolecular binder and (2) monitoring cell viability in culture (e.g., cell growth in liquid media or agar plates) or in vivo (e.g., growth of introduced cells or pathogen virulence in an animal infection model) or both. If intracellular expression of the biomolecular binder inhibits the function of a target essential for growth (presumably by binding to the target at a biologically relevant site) cells monitored in step (2) will exhibit a slow growth or no growth phenotype. Targets found to be essential for growth by these methods are validated starting points for drug discovery, and can be incorporated into assays to identify more stable compounds that bind to the same site on the target as the biomolecule. Where the cells are pathogen cells and the desired phenotypic change to be monitored is inhibition of growth, the invention provides a procedure to examine the activity of target (pathogen) cell components in an animal infection model.

6.7.1.5. Mimicking the Environment for Traditional Antimicrobial Therapy

Controlled expression in cells of biomolecular binders to the target of interest mimics the environment for traditional antimicrobial therapy and validates targets as essential and appropriate for drug discovery. The technology facilitates choosing the best antimicrobial targets for drug discovery by facilitating, direct observation of the effect (phenotype) produced by target inhibition at a specific target subsite. The process is broadly applicable to a variety of targets. The process also validates target and biomolecular binder combinations as a direct path to high throughput screening for binding analogs of the biomolecular binder, and is equally facile with targets that are gene products of genes of unknown function or genes of known function. Validated target and biomolecular binder assay combinations can be used directly in in vitro or in vivo competitive binding assays for screening chemical compound files. Compounds that compete with the biomolecular binders are identified as potential medicinal chemistry leads.

6.7.1.6. Study as a Target Cell Component a Gene Product of a Particular Cell Type In the course of this method, it may be decided to study as a target cell component a gene product of a particular cell type (e.g., a type of pathogenic bacteria), wherein the target cell component is already known as being encoded by a characterized gene, as a potential target for a modulator to be identified. In this case, the target cell component can be isolated directly from the cell type of interest, assuming suitable culture methods are available to grow a sufficient number of cells, using methods appropriate to the type of cell component to be isolated (e.g., protein purification methods such as differential precipitation, ion exchange chromatography, gel chromatography, affinity chromatography, HPLC.

6.7.1.7. Target Cell Component Can Be Produced Recombinantly

Alternatively, the target cell component can be produced recombinantly, which requires that the gene encoding the target cell component be isolated from the cell type of interest. This can be done by any number of methods, for example known methods such as PCR, using template DNA isolated from the pathogen or a DNA library produced from the pathogen DNA, and using primers based on known sequences or combinations of known and unknown sequences within or external to the chosen gene. See, for example, methods described in "The Polymerase Chain Reaction," Chapter 15 of Current Protocols in Molecular Biology, (Ausubel, F. M. et al., eds), John Wiley & Sons, New York, 1998. Other methods include cloning a gene from a DNA library (e.g., a cDNA library from a eucaryotic pathogen) into a vector (e.g., plasmid, phage, phagemid, virus, etc.) and applying a means of selection or screening, to clones resulting from a transformation of vectors (including a population of vectors now having inserted genes) into appropriate host cells. The screening method can take advantage of properties given to the host cells by the expression of the inserted chosen gene (e.g., detection of the gene product by antibodies directed against it, detection of an enzymatic activity of the gene product), or can detect the presence of the gene itself (for instance, by methods employing nucleic acid hybridization). For methods of cloning genes in *E. coli*, which also may be applicable to cloning in other bacterial species, see, for example, "*Escherichia coli*, Plasmids and Bacteriophages," Chapter I of Current Protocols in Molecular Biology, (Ausubel, F. M. et al., eds), John Wiley & Sons, New York, 1998. For methods applicable to cloning genes of eukaryotic origin, see Chapter 5 ("Construction of Recombinant DNA Libraries"), Chapter 9 ("Introduction of DNA Into Mammalian Cells") and Chapter 6 ("Screening of Recombinant DNA Libraries") of Current Protocols in Molecular Biology, (Ausubel, F. M. et al., eds), John Wiley & Sons, New York, 1998.

Target proteins can be expressed with *E. coli* or other prokaryotic gene expression systems, or in eukaryotic gene expression systems. Since many eukaryotic proteins carry unique modifications that are required for their activities, e.g. glycosylation and methylation, protein expression can in some cases be better carried out in eukaryotic systems, such as yeast, insect, or mammalian cells that can perform these modifications. Examples of these expression systems have been reviewed in the following literature: Methods in Enzymology, Volume 185, eds D. V. Goeddel, Academic Press, San Diego, 1990; Geisse et al, Protein Expression and Purification 8:271–282, 1996; Simonsen and McGrogan, Biologicals 22: 85–94; Jones and Morikawa, Current Opinions in Biotechnologies 7: 512–516, 1996; Possee, Current Opinions in Biotechnologies 8:569–572.

Where a gene encoding a chosen target cell component has not been isolated previously, but is thought to exist because homologs of the gene product are known in other species, the gene can be identified and cloned by a method such as that used in Shiba et al., U.S. Pat. No. 5,759,833, Shiba et al., U.S. Pat. No. 5,629,188, Martinis et al., U.S. Pat. Nos. 5,656,470 and Sassanfar et al., 5,756,327. The teachings of these four patents are incorporated herein by reference in their entirety.

6.7.1.8. Method Should Be Used with Target Cell Components which Have Not Been Previously Isolated or Characterized and Whose Functions Are Unknown It is an advantage of the target validation method that it can be used with target cell components which have not been previously isolated or characterized and whose functions are unknown. In this case, a segment of DNA containing an open reading frame (ORF; a cDNA can also be used, as appropriate to a eukaryotic cell) which has been isolated from a cell of a type that is to be an object of drug action (e.g., tumor cell, pathogen cell) can be cloned into a vector, and the target gene product of the ORF can be produced in host cells harboring the vector. The gene product can be purified and further studied in a manner similar to that of a gene product that has been previously isolated and characterized.

In some cases, the open reading frame (in some cases, cDNA) can be isolated from a source of DNA of the cells of interest (genomic DNA or a library, as appropriate), and inserted into a fusion protein or fusion polypeptide construct. This construct can be a vector comprising a nucleic acid sequence which provides a control region (e.g., promoter, ribosome binding site) and a region which encodes a peptide or polypeptide portion of the fusion polypeptide wherein the polypeptide encoded by the fusion vector endows the fusion polypeptide with one or more properties that allow for the purification of the fusion polypeptide. For example, the vector can be one from the pGEX series of plasmids (Pharmacia) designed to produce fusions with glutathione S-transferase.

6.7.1.9. Host Cells

The isolated DNA having an open reading frame, whether encoding a known or an as yet unidentified gene product, when inserted into an expression construct, can be expressed to produce the target cell component in host cells. Host cells can be, for example, Gram-negative or Gram-positive bacterial cells such as *Escherichia coli* or *Bacillus subtilis*, respectively, or yeast cells such as *Saccharomyces cerevisiae, Schizosaccharomyces pombe* or *Pichia pastoris*. It is preferable that the target cell component to be used in target validation studies be produced in a host that is genetically related to the pathogen from which the gene encoding it was isolated. For example, for a Gram-negative bacterial pathogen, an *E. coli* host is preferred over a *Pichia pastoris* host. The target cell component so produced can then be isolated from the host cells. Many protein purification methods are known that separate proteins on the basis of, for instance, size, charge, or affinity for a binding partner (e.g., for an enzyme, a binding partner can be a substrate or substrate analog), and these methods can be combined in a sequence of steps by persons of skill in the art to produce an effective purification scheme. For methods to manipulate RNA, see, for example, Chapter 4 in Current Protocols in Molecular Biology (Ausubel, F. M. et al., eds), John Wiley & Sons, New York, 1998.

An isolated cell component or a fusion protein comprising the cell component can be used in a test to identify one or more biomolecular binders of the isolated product (general step (1)). A biomolecular binder of a target cell component can be identified by in vitro assays that test for the formation of complexes of target and biomolecular binder noncovalently, bound to each other. For example, the isolated target can be contacted with one or more types of biomolecules under conditions conducive to binding, the unbound biomolecules can be removed from the targets, and a means of detecting bound complexes of biomolecules and targets can be applied. The detection of the bound complexes can be facilitated by having either the potential biomolecular binders or the target labeled or tagged with an adduct that allows detection or separation (e. g., radioactive isotope or fluorescent label; streptavidin, avidin or biotin affinity label).

Alternatively, both the potential biomolecular binders and the target can be differentially labeled. For examples of such methods see, e.g., WO 98/19162.

6.7.1.10. Biomolecules to Be Tested and Means for Detection

The biomolecules to be tested for binding to a target can be from a library of candidate biomolecular binders, (e.g., a peptide or oligonucleotide library). For example, a peptide library can be displayed on the coat protein of a phage (see, for examples of the use of genetic packages such as phage display libraries, Koivunen, E. et al., J Biol. Chem. 268:20205–20210 (1993)). The biomolecules can be detected by means of a chemical tag or label attached to or integrated into the biomolecules before they are screened for binding properties. For example, the label can be a radioisotope, a biotin tag, or a fluorescent label. Those molecules that are found to bind to the target molecule can be called biomolecular binders.

6.7.1.11. Fusion Proteins

An isolated target cell component, an antigenically similar portion thereof, or a suitable fusion protein comprising all of or a portion of or the entire target can be used in a method to select and identify biomolecules which bind specifically to the target. Where the target cell component comprises a protein, fusion proteins comprising all of, or a portion of, the target linked to a second moiety not occurring in the target as found in nature, can be prepared for use in another embodiment of the method. Suitable fusion proteins for this purpose include those in which the second moiety comprises an affinity ligand (e.g., an enzyme, antigen, epitope). The fusion proteins can be produced by the insertion of a gene encoding a target or a suitable portion of such gene into a suitable expression vector, which encodes an affinity ligand (e.g., pGEX-4T-2 and pET-15b, encoding glutathione S-transferase and His-Tag affinity ligands, respectively). The expression vector can be introduced into a suitable host cell for expression. Host cells are lysed and the lysate, containing fusion protein, can be bound to a suitable affinity matrix by contacting the lysate with an affinity matrix under conditions sufficient for binding of the affinity ligand portion of the fusion protein to the affinity matrix.

6.7.1.11.1. Fusion Protein Can Be Immobilized

In one embodiment, the fusion protein can be immobilized on a suitable affinity matrix under conditions sufficient to bind the affinity ligand portion of the fusion protein to the matrix, and is contacted with one or more candidate biomolecules (e.g., a mixture of peptides) to be tested as biomolecular binders, under conditions suitable for binding of the biomolecules to the target portion of the bound fusion protein. Next, the affinity matrix with bound fusion protein can be washed with a suitable wash buffer to remove unbound biomolecules and non- specifically bound biomolecules. Biomolecules which remain bound can be released by contacting the affinity matrix with fusion protein bound thereto with a suitable elution buffer. Wash buffer can be formulated to permit binding of the fusion protein to the affinity matrix, without significantly disrupting binding of specifically bound biomolecules. In this aspect, elution buffer can be formulated to permit retention of the fusion protein by the affinity matrix, but can be formulated to interfere with binding of the test biomolecule(s) to the target portion of the fusion protein. For example, a change in the ionic strength or pH of the elution buffer can lead to release of biomolecules, or the elution buffer can comprise a release component or components designed to disrupt binding of biomolecules to the target portion of the fusion protein.

Immobilization can be performed prior to, simultaneous with, or after contacting, the fusion protein with biomolecule, as appropriate. Various permutations of the method are possible, depending upon factors such as the biomolecules tested, the affinity matrix-ligand pair selected, and elution buffer formulation. For example, after the wash step, fusion protein with biomolecules bound thereto can be eluted from the affinity matrix with a suitable elution buffer (a matrix elution buffer, such as glutathione for a GST fusion). Where the fusion protein comprises a cleavable linker, such as a thrombin cleavage site, cleavage from the affinity ligand can release a portion of the fusion with the biomolecules bound thereto. Bound biomolecule can then be released from the fusion protein or its cleavage product by an appropriate method, such as extraction.

6.7.1.12. Various Methods to Identify Biomolecular Binders

One or more candidate biomolecular binders can be tested simultaneously. Where a mixture of biomolecules is tested, the biomolecules selected by the foregoing processes can be separated (as appropriate) and identified by suitable methods (e.g., PCR, sequencing, chromatography). Large libraries of biomolecules (e.g., peptides, RNA oligonucleotides) produced by combinatorial chemical synthesis or other methods can be tested (see e. a., Ohlmeyer, M. H. J. et al., Proc. Natl. Acad. Sci. USA 90:10922–10926 (1993) and DeWitt, S. H. et al., Proc. Natl. Acad. Sci. USA 90:6909–6913 (1993), relating to tagged compounds; see also Rutter, W. J. et al. U.S. Pat. No. 5,010,175; Huebner, V. D. et al., U.S. Pat. No. 5,182,366; and Geysen, H. M., U.S. Pat. No. 4,833,092). Random sequence RNA libraries (see Ellington, A. D. et al., Nature 346:818–822 (1990); Bock, L. C. et al., Nature 355:584–566 (1992); and Szostak, J. W., Trends in Biochem. Sci. 17:89–93 (March, 1992)) can also be screened according to the present method to select RNA molecules which bind to a target. Where biomolecules selected from a combinatorial library by the present method carry unique tags, identification of individual biomolecules by chromatographic methods is possible. Where biomolecules do not carry tags, chromatographic separation, followed by mass spectrometry to ascertain structure, can be used to identify individual biomolecules selected by the method, for example.

Other methods to identify biomolecular binders of a target cell component can be used. For example, the two-hybrid system or interaction trap is an in vivo system that can be used to identify polypeptides, peptides or proteins (candidate biomolecular binders) that bind to a target protein. In this system, both candidate biomolecular binders and target cell component proteins are produced as fusion proteins. The two-hybrid system and variations on it have been described (U.S. Pat. Nos. 5,283,173 and 5,468,614; Golemis, E. A. et al., pages 20.1.1–20.1.35 In Current Protocols in Molecular Biology, F. M. Ausubel et al., eds., John Wiley and Sons, containing supplements up through Supplement 40, 1997; two-hybrid systems available from Clontech, Palo Alto, Calif.).

Once one or more biomolecular binders of a cell component have been identified, further steps can be combined with those taken to identify the biomolecular binder, to identify those biomolecular binders that produce a phenotypic effect on a cell (where "a cell" can mean cells of a cell strain or cell line).

Thus, a method for identifying a biomolecule that produces a phenotypic effect on a first cell can comprise the steps of identifying a biomolecular binder of an isolated target cell component of the first cell, constructing a second cell comprising the target cell component and a regulable exogenous gene encoding the biomolecular binder, and testing the second cell for the phenotypic effect, upon production of the biomolecular binder in the second cell, where the second cell can be maintained in culture or introduced into an experimental animal. If the second cell shows the phenotypic effect upon intracellular production of the biomolecular binder, then a biomolecule that produces a phenotypic effect on the first cell has been identified. Testing the second cell is general step (2) of the invention, as the three general steps were outlined above.

6.7.1.13. Host Cells: Engineered to Control Expression

Host cells (also, "second cells" in the terminology used above) of the cell type (e.g., species of pathogenic bacteria) the target was isolated from (or the gene encoding the target was originally isolated from, if the target is produced by recombinant methods), can be engineered to harbor a gene that can regulably express the biomolecular binder (e.g., under an inducible or repressible promoter). The ability to regulate the expression of the biomolecular binder is desirable because constitutive expression of the biomolecular binder could be lethal to the cell.

Therefore, inducible or regulated expression gives the researcher the ability to control if and when the biomolecular binder is expressed. The gene expressing the biomolecular binder can be present in one or more copies, either on an extra chromosomal structure, such as on a single or multi-copy plasmid, or integrated into the host cell genome. Plasmids that provide an inducible gene expression system in pathogenic organisms can be used. For example, plasmids allowing tetracycline-inducible expression of a gene in *Staphylococcus aureus* have been developed.

6.7.1.14. Genes for Expression

For intracellular expression of a biomolecule to be tested for its phenotypic effect in a eukaryotic cell (e.g., mammalian cell), the genes for expression can be carried on plasmid-based or virus-based vectors, or on a linear piece of DNA or RNA. For examples of expression vectors, see Hosfield and Lu, Biotechniques: 306–309, 1998; Stephens and Cockett, Nucleic Acid Research 17:7110, 1989; Wohlgemuth et al, Gene Therapy, 3:503–512, 1996; Ramirez-Solis et al, Gene 87:291–294, 1990, Dirks et al, Gene 149:387–388, 1994; Chenaalvala et al. Current Opinion in Biotechnologies 2:718–722, 1991; Methods in Enzymology, Volume 185, (D. V. Goeddel, ed.) Academic Press, San Diego, 1990. The genetic material can be introduced into cells using a variety of techniques, including whole cell or protoplast transformation, electroporation, calcium phosphate-DNA precipitation or DEAE-Dextran transfection, liposome mediated DNA or RNA transfer, or transduction with recombinant viral or retroviral vectors. Expression of the gene can be constitutive (e.g., ADHI promoter for expression in S. cerevisiae (Bennetzen, J. L. and Hall, B. D., J Biol. Chem 257:3026–3031 (1982)), or CMV immediate early promoter and RSV LTR for mammalian expression) or inducible, as the inducible GAL I promoter in yeast (Davis, L. I. and Fink, G. R., Cell 61:965–978 (1990)). A variety of inducible systems can be utilized, for example, *E. coli* Lac repressor/operator system and Tn10 Tet repressor/operator systems have been engineered to govern regulated expression in organisms from bacterial to mammalian cells. Regulated gene expression can also be achieved by activation. For example, gene expression governed by HIV LTR can be activated by HIV or SIV Tat proteins in human cells; GAL4 promoter can be activated by galactose in a nonglucose-containing medium. The location of the biomolecule binder genes can be extra chromosomal or chromosomally integrated. The chromosome integration can be mediated through homologous or nonhomologous recombinations.

For proper localization in the cells, it maybe desirable to tag the biomolecule binders with certain peptide signal sequences (for example, nuclear localization signal (NLS) sequences, mitochondria localization sequences). Secretion sequences have been well documented in the art.

6.7.1.15. Fused Biomolecular Binders

For presentation of the biomolecular binders in the intracellular system, they can be fused N-terminally, C-terminally, or internally in a carrier protein (if the biomolecular binder is a peptide), and can be fused (5', 3' or internally) in a carrier RNA or DNA molecule (if the biomolecular binder is a nucleic acid). The biomolecular binder can be presented with a protein or nucleic acid structural scaffold. Certain linkages (e.g., a 4-glycine linker for a peptide or a stretch of A's for an RNA can be inserted between the biomolecular binder and the carrier proteins or nucleic acids.

In such engineered cells, the effect of this biomolecular binder on the phenotype of the cells can be tested, as a manifestation of the binding (implying binding to a functionally relevant site, thus, an activator, or more likely, an inhibitory) effect of the biomolecular binder on the target used in an in vitro binding assay as described above. An intracellular test can not only determine which biomolecular binders have a phenotypic effect on the cells, but at the same time can assess whether the target in the cells is essential for maintaining the normal phenotype of the cells. For example, a culture of the engineered cells expressing a biomolecular binder can be divided into two aliquots. The first aliquot ("test" cells) can be treated in a suitable manner to regulate (e.g., induce or release repression of, as appropriate) the gene encoding the biomolecular binder, such that the biomolecular binder is produced in the cells. The second aliquot ("control" cells) can be left untreated so that the biomolecular binder is not produced in the cells. In a variation of this method of testing the effect of a biomolecular binder on the phenotype of the cells, a different strain of cells, not having a gene that can express the biomolecular binder, can be used as control cells. The phenotype of the cells in each culture ("test" and "control" cells grown under the same conditions, other than the expression of the biomolecular binder), can then be monitored by a suitable means (e.g., enzymatic activity, monitoring, a product of a biosynthetic pathway, antibody to test for presence of cell surface antigen, etc.). Where the change in phenotype is a change in growth rate, the growth of the cells in each culture ("test" and "control" cells grown under the same conditions, other than the expression of the biomolecular binder), can be monitored by a suitable means (e.g., turbidity of liquid cultures, cell count, etc). If the extent of growth, or rate of growth of the test cells is less than the extent of growth or rate of growth of the control cells, then the biomolecular binder can be concluded to be an inhibitor of the growth of the cells, or a biomolecular inhibitor.

If the phenotype of the test cells is altered relative to that of the control cells, then the biomolecular binder can be concluded to be one that causes a phenotypic effect. In an optional additional test, isolated target cell component having a known function (e.g., an enzyme activity) can be tested for modulation of this known function in the presence of biomolecular binder under conditions conducive to binding of the biomolecular binder to the target cell component. Positive results in these tests should encourage the investigator to continue in the drug discovery process with efforts to find a more stable compound (than a peptide, polypeptide or RNA biomolecule) that mimics the binding properties of the biomolecular binder on the tested target cell component.

6.7.1.16. Engineering Strain of Cells

A further test can, again, employ an engineered strain of cells that comprise both the target cell component and one or more genes encoding a biomolecule tested to be a biomolecular binder of the target cell component. The cells of the cell strain can be tested in animals to see if regulable expression of the biomolecular binder in the engineered cells produces an observable or testable change in phenotype of the cells. Both the "in culture" test for the effect of intracellular expression of the biomolecular binder and the "in animal" test (described below) for the effect of intracellular expression of the biomolecular binder can be applied not only towards drug discovery in the categories of antimicrobials and anticancer agents, but also towards the discovery of therapeutic agents to treat inflammatory diseases, cardiovascular diseases, diseases associated with metabolic pathways, and diseases associated with the central nervous system, for example.

Where the engineered strain of cells is a strain of pathogen cells or tumor cells, the object of the test is to see whether production of the biomolecular binder in the engineered strain inhibits growth of these cells after their introduction into an animal by the engineered pathogen. Such a test can not only determine which biomolecular binders are inhibitors of growth of the cells, but at the same time can assess whether the target in the cells is essential for maintaining growth of the cells (infection, for a pathogenic organism) in a host mammal. Suitable animals for such an experiment are, for example, mammals such as mice, rats, rabbits, guinea pigs, dogs, pigs, and the like. Small mammals are preferred for reasons of convenience.

The engineered cells are introduced into one or more animals ("test" animals) and into one or more animals in a separate group ("control" animals) by a route appropriate to cause symptoms of systemic or local growth of the engineered cells.

The route of introduction may be, for example, by oral feeding, by inhalation, by subdermal, intramuscular, intravenous, or intraperitoneal injection as appropriate to the desired result.

After the cell strain has been introduced into the test and control animals, expression of the gene encoding the biomolecular binder is regulated to allow production of the biomolecular binder in the engineered pathogen cells. This can be achieved, for instance, by administering to the test animals a treatment appropriate to the regulation system built into the cells, to cause the gene encoding the biomolecular binder to be expressed. The same treatment is not administered to the control animals, but the conditions under which they are maintained are otherwise identical to those of the test animals. The treatment to express the gene encoding the biomolecular binder can be the administration of an inducer substance (where expression of the biomolecular binder or gene is under the control of an inducible promoter) or the functional removal of a repressor substance (where expression of the biomolecular binder gene is under the control of a repressible promoter).

After such treatment, the test and control animals can be monitored for a phenotypic effect in the introduced cells. Where the introduced cells are constructed pathogen cells, the animals can be monitored for signs of infection (as the simplest endpoint, death of the animal, but also e.g., lethargy, lack of grooming behavior, hunched posture, not eating, diarrhea or other discharges; bacterial titer in samples of blood or other cultured fluids or tissues). In the case of testing engineered tumor cells, the test and control animals can be monitored for the development of tumors or for other indicators of the proliferation of the introduced engineered cells. If the test animals are observed to exhibit less growth of the introduced cells than the control animals, then the biomolecule can be also called a biomolecular inhibitor of growth, or biomolecular inhibitor of infection, as appropriate, as it can be concluded that the expression in vivo of the biomolecular inhibitor is the cause of the relative reduction in growth of the introduced cells in the test animals.

6.7.2. In vitro Assays

Further steps of the procedure involve in vitro assays to identify one or more compounds that have binding and activating or inhibitory properties that are similar to those of the biomolecules which have been found to have a phenotypic effect, such as inhibition of growth. That is, compounds that compete for binding to a target cell component with the biomolecule would then be structural analogs of the biomolecules. Assays to identify such compounds can take advantage of known methods to identify competing molecules in a binding assay. These steps comprise general step (3) of the method.

In one method to identify such compounds, a biomolecular inhibitor (or activator) can be contacted with the isolated target-cell component to allow binding, one or more compounds can be added to the milieu comprising the biomolecular inhibitor and the cell component under conditions that allow interaction and binding between the cell component and the biomolecular inhibitor, and any biomolecular inhibitor that is released from the cell component can be detected.

6.7.2.1. Fluorescence

One suitable system that allows the detection of released biomolecular inhibitor (or activator) is one in which fluorescence polarization of molecules in the milieu can be measured. The biomolecular inhibitor can have bound to it a fluorescent tag or label such as fluorescein or fluorescein attached to a linker.

Assays for inhibition of the binding of the biomolecular inhibitor to the cell component can be done in microtiter plates to conveniently test a set of compounds at the same time. In such assays, a majority of the fluorescently labeled biomolecular inhibitor must bind to the protein in the absence of competitor compound to allow for the detection of small changes in the bound versus free probe population when a compound which is a competitor with a biomolecular inhibitor is added (B. A. Lynch, et al., Analytical Biochemistry 247:77–82 (1997)). If a compound competes with the biomolecular inhibitor for a binding site on the target cell component, then fluorescently labeled biomolecular inhibitor is released from the target cell component, lowering the polarization measured in the milieu.

6.7.2.2. Radioactive Isotope

In a further method for identifying one or more compounds that compete with a biomolecular inhibitor (or activator) for a binding site on a target cell component, the target cell component can be attached to a solid support, contacted with one or more compounds, and contacted with the biomolecular inhibitor. One or more washing steps can be employed to remove biomolecular inhibitor and compound not bound to the cell component. Either the biomolecular inhibitor bound to the target cell component or the compound bound to the target cell component can be measured. Detection of biomolecular inhibitor or compound bound to the cell compound can be facilitated by the use of a label on either molecule type, wherein the label can be, for instance, a radioactive isotope either incorporated into the molecule itself or attached as an adduct, streptavidin or biotin, a fluorescent label or a substrate for an enzyme that can produce from the substrate a colored or fluorescent product. An appropriate means of detection of the labeled biomolecular inhibitor or compound moiety of the biomolecular inhibitor-cell component complex or the compound-cell component complex can be applied. For example, a scintillation counter can be used to measure radioactivity. Radio labeled streptavidin or biotin can be allowed to bind to biotin or streptavidin, respectively, and the resulting complexes detected in a scintillation counter. Alkaline phosphatase conjugated to streptavidin can be added to a biotin-labeled biomolecular inhibitor or compound. Detection and quantitation of a biotin-labeled complex can then be by addition of pNPP substrate of alkaline phosphatase and detection by spectrophotometry, of a product which absorbs UV light at a wavelength of 405 nm. A fluorescent label can also be used, in which case detection of fluorescent complexes can be by a fluorometer. Models are available that can read multiple samples, as in a microtiter plate.

For example, in one type of assay, the method for identifying compounds comprises attaching the target cell component to a solid support, contacting the biomolecular inhibitor with the target cell component under conditions suitable for binding of the biomolecular inhibitor to the cell component, removing unbound biomolecular inhibitor from the solid support, contacting one or more compounds (e.g., a mixture of compounds) with the cell component under conditions suitable for binding of the biomolecular inhibitor to the cell component, and testing for unbound biomolecular inhibitor released from the cell component, whereby if unbound biomolecular inhibitor is detected, one or more compounds that displace or compete with the biomolecular inhibitor for a particular site on the target cell component have been identified.

Other methods for identifying compounds that are competitive binders with the biomolecule for a target can employ adaptations of fluoresence polarization methods. See, for instance, Anal. Biochem. 253(2):210–218 (1997), Anal. Biochem. 249(1):29–36 (1997), Bio Techniques 17(3):585–589 (1994) and Nature 373:254–256 (1995).

Those compounds that bind competitively to the target cell component can be considered to be drug candidates. Further appropriate testing can confirm that those compounds which bind competitively with biomolecular inhibitors (or activators) possess the same activity as seen in an intracellular test of the effect of the biomolecular inhibitor or activator upon the phenotype of cells. Derivatives of these compounds having modifications to confer improved solubility, stability, etc., can also be tested for a desired phenotypic effect.

6.7.3. Combining Steps

Combining steps for testing the phenotypic effects of a biomolecule, as can be produced in an intracellular test, with steps for identifying compounds that compete with the biomolecule for sites on a target cell component, yields a method for identifying a compound which is a functional analog of a biomolecule which produces a phenotypic effect on a cell. These steps can be to test, for the phenotypic effect, either in culture or in an animal model, or in both, a cell which produces a biomolecule by regulable expression of an exogenous gene in the cell, and to identify, if the biomolecule caused the phenotypic effect, one or more compounds that compete with the biomolecule for binding to a target cell component. If a compound is found to compete with the biomolecule for binding to the target cell component, then the compound is a functional analog of a biomolecule which produces a phenotypic effect on the cell. Such a functional analog can cause qualitatively a similar effect on the cell, but to a similar degree, lesser degree or greater degree than the biomolecule.

6.7.3.1. Method for Determining Whether a Target Component of a Cell Is Essential to Producing a Phenotypic Effect on the Cell A further embodiment of the invention combining general steps (1) and (2) is a method for determining whether a target component of a cell is essential to producing a phenotypic effect on the cell, comprising isolating the target component from the cell, identifying a biomolecular binder of the isolated target component of the cell, constructing a second cell comprising the target component and a regulable, exogenous gene encoding the biomolecular binder, and testing the second cell in culture for an altered phenotypic effect, upon production of the biomolecular binder in the second cell, whereby, if the second cell shows the altered phenotypic effect upon production of the bimolecular binder, then the target component of the first cell is essential to producing the phenotypic effect on the first cell.

6.7.3.1.1. Inhibit the Proliferation of the Cells

The methods described herein are well suited to the identification of compounds that can inhibit the proliferation of the cells of infectious agents such as bacteria, fungi and the like. In addition, a procedure such as the one outlined below can be used in the identification of compounds to inhibit the proliferation of cancer cells. The two procedures described below further illustrate the use of the methods described herein and would provide proof of principle of these methods with a known target for anticancer therapy.

Mammalian dihydrofolate reductase (DHFR) is a proven target for anticancer therapy. Methotrexate (MTX) is one of many existing drugs that inhibit DHFR. It is widely used for anticancer chemotherapy.

NIH 3T3 is a mouse fibroblast cell line that is able to develop spontaneous transformed cells when cultured in low concentration (2%) of calf serum in molecular, cellular and developmental biology medium 402 (MCDB) (M. Chow and H. Rubin, Proc. Natl. Acad. Sci. USA 95(8):4550–4555 (1998)). The transformed cells, which can be selectively inhibited by MTX (Chow and Rubin), are isolated.

Both the normal and transformed NIH3T3 cells are transfected with pTet-On plasmid (Clontech; Palo Alto, Calif.). Stable cell lines that express high levels of reverse tetracycline-control led activator (rtTA) are isolated and characterized for their normal or transformed phenotype (Chow and Rubin).

The DHFR gene (Genbank Accession # L26316) from the NIH 3T3 cell line is amplified by reverse transcription-PCR (RT-PCR) using poly A' RNA isolated from NIH 3T3 cells (Sambrook, J. et al., Molecular Cloning: A Laboratory Manual, 2nd edition, Cold Spring Harbor Laboratory Press, 1989). Active DHFR is expressed using the BacPAK Baculovirus Expression System (Clontech) or other appropriate systems. The expressed DHFR is purified and biotinylated and subjected to peptide binder identification as exemplified for bacterial proteins. The identified peptides are biochemically characterized for in vitro inhibition of DHFR activity. Peptides that inhibit DHFR are identified. A nucleic acid encoding each peptide can be cloned into a vector such as pGEX-4T2 (Pharmacia) to yield a vector which encodes a fusion polypeptide having the peptide fused to the N-terminus of GST. This can also be done by PCR amplification as exemplified herein for the peptide Pro-3. The fusion genes are cloned into plasmid pTRE (Clontech) for regulated expression. The constructed plasmid or the vector is cotransfected with pTK-Hyg into the stable NIH 3T3 cell line that expresses rtTA. The resulting cell lines, termed 3T3N-VITA (normal 3T3 cells that express rtTA and the DHFR inhibitory peptides), 3T3T-VITA (transformed 3T3 cells that express rtTA and the DHFR inhibitory peptides), or 3T3T-VITA control (transformed 3T3 cells that express rtTA and GST), are characterized for their normal or transformed phenotype (loss of contact inhibition, change in morphology, immortalization, etc. ). $10^2$–$10^1$ of 3T3T-VITA or 3T3T-VITA control cells are mixed with $10^5$ 3T3N-VITA and are grown in MCD 402 medium with 10% calf serum at 37'C. for three days. Tetracycline is added to the medium to a final concentration of 0 to 1 ug/ml. In a control, 200 nM of MTX is added. The cultures are incubated for an additional eight days, and the number of foci formed are counted as described by M. Chow and H. Rubin, Proc. Natl. Acad Sci. USA 95(8):4550–4555 (1998). Peptides that specifically inhibit foci formation of 3T3 transformed cells are identified.

A murine model of fibroblastoma (Kogerman, P. et al., Oncogene (12):1407–1416 (1997)) is used for evaluating the DHFR/peptide combination for identification of compounds for cancer therapy. Various amounts of 3T3T-VITA or 3T3T-VITA control cells ($10^3$, $10^4$, $10^5$, $10^6$ cells) are injected subcutaneously into 5 groups (10 in each group) of athymic nude mice (4–6 weeks old, 18–22 g) to determine the minimal dose needed for development of fibroblastomas in all of the tested animals. Upon determination of the minimal tumorigenic dose, 6 groups of athymic nude mice (10 each) are injected subcutaneously (s.c.) with the minimal tumorigenic dose for 3T3T-VITA or 3T3T-VITA control cells to develop fibroblastoma. One week after injection, group I mice start receiving MTX s.c. at 2 mg/kg/day as positive control, group 2 to 5 start receiving 1, 2, 5, or 10 mg/kg/day of tetracycline, group 6 start receiving saline (vehicle) as control. Five weeks after the introduction of cells, all of the mice are sacrificed and tumors are removed from them. Tumor mass is measured and compared among the groups.

An effective peptide identified by these in vivo experiments can be used for screening libraries of compounds to identify those compounds that competitively bind to DHFR. One mechanism of tumorigenesis is overexpression of proto-oncogenes such as Ha-ras (Reviewed by Suarez, H. G., Anticancer Research 9(5):1331–1343 (1989)).

Compounds that inhibit the activities of the products of such proto-oncogenes can be used for cancer chemotherapy. What follows is a further illustration of the methods described herein, as applied to mammalian cells.

Transgenic mice that overexpress human Ha-ras have been produced. Such transgenic mice develop salivary and/or mammary adenocarcinomas (Nielsen, L. L. et al, In Vivo 8(5):1331–1343 (1994)). Secondary transgenic mice that express rtTA can be generated using the pTet-On plasmid from Clontech.

Human Ha-ras open reading frame cDNA (Genbank Accession #GO0277) is amplified by RT-PCR using polyA-RNA isolated from human mammary gland or other tissues. Active Ha-ras is expressed using the BacPAK Baculovirus Expression System (Clontech) or other appropriate systems. The expressed Ha-ras is purified and biotinylated and subjected to peptide binder identification as exemplified herein for bacterial proteins as target cell components. The identified peptides are biochemically characterized for in vitro inhibition of Ha-ras GTPase activity.

Peptides that inhibit Ha-ras are cloned into plasmid pTPE (Clontech) for regulated expression as an N-terminal fusion of GST. Such constructs are used to generate tertiary transgenic mice using the secondary transgenic mice. Transgenic mice that are able to overexpress peptide genes are identified by Northern and Western analysis. Control mice that express GST are also identified.

Various doses of tetracycline are administered to the tertiary transgenic mice by s.c. or i.p. injection before or after tumor onset. Prevention or regression of tumors resulting from expression of the peptide genes are analyzed as described above for murine fibroblastoma. Peptides found to be effective in in vivo experiments will be used to screen compounds that inhibit human Ha-ras activity for cancer therapy.

6.7.4. Disease Targets

The method of the invention can be applied more generally to mammalian diseases caused by: (1) loss or gain of protein function, (2) over-expression or loss of regulation of protein activity. In each case the starting point is the identification of a putative protein target or metabolic pathway involved in the disease. The protocol can sometimes vary with the disease indication, depending on the availability of cell culture and animal model systems to study the disease. In all cases the process can deliver a validated target and assay combination to support the initiation of drug discovery.

Appropriate disease indications include, but are not limited to, Alzheimer's, arthritis, cancer, cardiovascular diseases, central nervous system disorders, diabetes, depression, hypertension, inflammation, obesity and pain.

Appropriate protein targets putatively linked to disease indications include, but are not limited to (1) the leptin protein, putatively linked to obesity and diabetes; (2) a mitogen-activated protein kinase putatively linked to arthritis, osteoporosis and atherosclerosis; (3) the interleukin-1 beta converting protein putatively linked to arthritis, asthma and inflammation; (4) the caspase proteins putatively linked to neurodegenerative diseases such as Alzheimer's, Parkinson's and stroke, and (5) the tumor necrosis factor protein putatively linked to obesity and diabetes. Appropriate protein targets include also, but are not limited to, enzymes catalyzing the following types of reactions: (1) oxido-reductases, (2) transferases, (3) hydrolases, (4) lyases, (5) isomerases, and (6) ligases.

The arachidonic acid pathway constitutes one of the main mechanisms for the production of pain and inflammation. The pathway produces different classes of end products, including the prostaglandins, thromboxane and leukotrienes.

Prostaglandins, an end product of cyclooxygenase metabolism, modulate immune function, mediate vascular phases of inflammation and are potent vasodilators. The major therapeutic action of aspirin and other non-steroidal anti-inflammatory drugs (NSAIDs) is proposed to be inhibition of the enzyme cyclooxygenase (COX). Anti-inflammatory potencies of different NSAIDs have been shown to be proportional to their action as COX inhibitors. It has also been shown that COX inhibition produces toxic side effects such as erosive gastritis and renal toxicity. The knowledge base regarding the toxic side effects of COX inhibitors has been gained through years of monitoring human therapies and human suffering. Two kinds of COX enzymes are now known to exist, with inhibition of COX 1 related to toxicity, and inhibition of COX2 related to reduction of inflammation. Thus, selective COX2 inhibition is a desirable characteristic of new anti-inflammatory drugs. The method of the invention can provide a route from identification of potential drug targets to validating these targets (for example, COX1 and COX2) as playing a role in disease (pain and inflammation) to an examination of the phenotype for the inhibition of one or both target isozymes without human suffering. Importantly, this information can be collected in vivo.

As an alternative strategy, the method of the invention can be used to define the phenotype of "genes of unknown function" obtained from various human genome sequencing projects or to assess the phenotype resulting, from inhibition of one isozyme subtype or one member of a family of related protein targets.

6.8. Biological Chips 6.8.1. General Considerations

In one aspect the present invention provides arrays of oligonucleotide probes immobilized in microfabricated patterns on silica chips for analyzing molecular interactions of biological interest.

The invention therefore relates to diverse fields impacted by the nature of molecular interaction, including chemistry, biology, medicine, and medical diagnostics.

Oligonucleotide probes have long been used to detect complementary nucleic acid sequences in a nucleic acid of interest (the "target" nucleic acid). In some assay formats, the oligonucleotide probe is tethered, i.e., by covalent attachment, to a solid support, and arrays of oligonucleotide probes immobilized on solid supports have been used to detect specific nucleic acid sequences in a target nucleic acid.

See, e.g., PCT patent publication Nos. WO 89/10977 and 89/11548. Others have proposed the use of large numbers of oligonucleotide probes to provide the complete nucleic acid sequence of a target nucleic acid but failed to provide an enabling method for using arrays of immobilized probes for this purpose. See U.S. Pat. Nos. 5,202,231 and 5,002,867 and PCT patent publication No. WO 93/17126. See U.S. Pat. No. 5,143,854 and PCT patent publication Nos. WO 90/15070 and 92/10092, each of which is incorporated herein by reference. Microfabricated arrays of large numbers of oligonucleotide probes, called "DNA chips" offer great promise for a wide variety of applications. New methods and reagents are required to realize this promise, and the present invention helps meet that need.

6.8.2. General Strategies

The invention provides several strategies employing immobilized arrays of probes for comparing a reference sequence of known sequence with a target sequence showing substantial similarity with the reference sequence, but differing in the presence of, e.g., mutations. In a first embodiment, the invention provides a tiling strategy employing an array of immobilized oligonucleotide probes comprising at least two sets of probes. A first probe set comprises a plurality of probes, each probe comprising a segment of at least three nucleotides exactly complementary to a subsequence of the reference sequence, the segment including at least one interrogation position complementary to a corresponding nucleotide in the reference sequence. A second probe set comprises a corresponding probe for each probe in the first probe set, the corresponding probe in the second probe set being identical to a sequence comprising the corresponding probe from the first probe set or a subsequence of at least three nucleotides thereof that includes the at least one interrogation position, except that the at least one interrogation position is occupied by a different nucleotide in each of the two corresponding probes from the first and second probe sets. The probes in the first probe set have at least two interrogation positions corresponding to two contiguous nucleotides in the reference sequence. One interrogation position corresponds to one of the contiguous nucleotides, and the other interrogation position to the other.

In a second embodiment, the invention provides a tiling strategy employing an array comprising four probe sets. A first probe set comprises a plurality of probes, each probe comprising a segment of at least three nucleotides exactly complementary to a subsequence of the reference sequence, the segment including at least one interrogation position complementary to a corresponding nucleotide in the reference sequence. Second, third and fourth probe sets each comprise a corresponding probe for each probe in the first probe set.

The probes in the second, third and fourth probe sets are identical to a sequence comprising the corresponding probe from the first probe set or a subsequence of at least three nucleotides thereof that includes the at least one interrogation position, except that the at least one interrogation position is occupied by a different nucleotide in each of the four corresponding probes from the four probe sets. The first probe set often has at least 100 interrogation positions corresponding to 100 contiguous nucleotides in the reference sequence. Sometimes the first probe set has an interrogation position corresponding to every nucleotide in the reference sequence. The segment of complementarity within the probe set is usually about 9–21 nucleotides. Although probes may contain leading or trailing sequences in addition to the 9–21 sequences, many probes consist exclusively of a 9–21 segment of complementarity.

In a third embodiment, the invention provides immobilized arrays of probes tiled for multiple reference sequences. one such array comprises at least one pair of first and second probe groups, each group comprising first and second sets of probes as defined in the first embodiment. Each probe in the first probe set from the first group is exactly complementary to a subsequence of a first reference sequence, and each probe in the first probe set from the second group is exactly complementary to a subsequence of a second reference sequence.

Thus, the first group of probes are tiled with respect to a first reference sequence and the second group of probes with respect to a second reference sequence. Each group of probes can also include third and fourth sets of probes as defined in the second embodiment. In some arrays of this type, the second reference sequence is a mutated form of the first reference sequence.

In a fourth embodiment, the invention provides arrays for block tiling. Block tiling is a species of the general tiling strategies described above. The usual unit of a block tiling array is a group of probes comprising a wildtype probe, a first set of three mutant probes and a second set of three mutant probes. The wildtype probe comprises a segment of at least three nucleotides exactly complementary to a subsequence of a reference sequence. The segment has at least first and second interrogation positions corresponding to first and second nucleotides in the reference sequence. The probes in the first set of three mutant probes are each identical to a sequence comprising the wildtype probe or a subsequence of at least three nucleotides thereof including the first and second interrogation positions, except in the first interrogation position, which is occupied by a different nucleotide in each of the three mutant probes and the wildtype probe. The probes in the second set of three mutant probes are each identical to a sequence comprising the wildtype probes or a subsequence of at least three nucleotides thereof including the first and second interrogation positions, except in the second interrogation position, which is occupied by a different nucleotide in each of the three mutant probes and the wildtype probe.

In a fifth embodiment, the invention provides methods of comparing a target sequence with a reference sequence using arrays of immobilized pooled probes. The arrays employed in these methods represent a further species of the general tiling arrays noted above. In these methods, variants of a reference sequence differing from the reference sequence in at least one nucleotide are identified and each is assigned a designation. An array of pooled probes is provided, with each pool occupying a separate cell of the array. Each pool comprises a probe comprising a segment exactly complementary to each variant sequence assigned a particular designation.

The array is then contacted with a target sequence comprising a variant of the reference sequence. The relative hybridization intensities of the pools in the array to the target sequence are determined. The identity of the target sequence is deduced from the pattern of hybridization intensities. Often, each variant is assigned a designation having at least one digit and at least one value for the digit. In this case, each pool comprises a probe comprising a segment exactly complementary to each variant sequence assigned a particular value in a particular digit. When variants are assigned successive numbers in a numbering system of base m having n digits, n×(m−1) pooled probes are used are used to assign each variant a designation.

In a sixth embodiment, the invention provides a pooled probe for trellis tiling, a further species of the general tiling strategy. In trellis tiling, the identity of a nucleotide in a target sequence is determined from a comparison of hybridization intensities of three pooled trellis probes. A pooled trellis probe comprises a segment exactly complementary to a subsequence of a reference sequence except at a first interrogation position occupied by a pooled nucleotide N, a second interrogation position occupied by a pooled nucleotide selected from the group of three consisting of (1) M or K, (2) R or Y and (3) S or W, and a third interrogation position occupied by a second pooled nucleotide selected from the group. The pooled nucleotide occupying the second interrogation position comprises a nucleotide complementary to a corresponding nucleotide from the reference sequence when the second pooled probe and reference sequence are maximally aligned, and the pooled nucleotide occupying the third interrogation position comprises a nucleotide complementary to a corresponding nucleotide from the reference sequence when the third pooled probe and the reference sequence are maximally aligned. Standard IUPAC nomenclature is used for describing pooled nucleotides.

In trellis tiling, an array comprises at least first, second and third cells, respectively occupied by first, second and third pooled probes, each according to the generic description above. However, the segment of complementarity, location of interrogation positions, and selection of pooled nucleotide at each interrogation position may or may not differ between the three pooled probes subject to the following constraint. One of the three interrogation positions in each of the three pooled probes must align with the same corresponding nucleotide in the reference sequence.

This interrogation position must be occupied by a N in one of the pooled probes, and a different pooled nucleotide in each of the other two pooled probes.

In a seventh embodiment, the invention provides arrays for bridge tiling. Bridge tiling is a species of the general tiling strategies noted above, in which probes from the first probe set contain more than one segment of complementarity.

In bridge tiling, a nucleotide in a reference sequence is usually determined from a comparison of four probes. A first probe comprises at least first and second segments, each of at least three nucleotides and each exactly complementary to first and second subsequences of a reference sequences. The segments including at least one interrogation position corresponding to a nucleotide in the reference sequence.

Either (1) the first and second subsequences are noncontiguous in the reference sequence, or (2) the first and second subsequences are contiguous and the first and second segments are inverted relative to the first and second subsequences.

The arrays further comprises second, third and fourth probes, which are identical to a sequence comprising the first probe or a subsequence thereof comprising at least three nucleotides from each of the first and second segments, except in the at least one interrogation position, which differs in each of the probes. In a species of bridge tiling, referred to as deletion tiling, the first and second subsequences are separated by one or two nucleotides in the reference sequence.

In an eighth embodiment, the invention provides arrays of probes for multiplex tiling. Multiplex tiling is a strategy, in which the identity of two nucleotides in a target sequence is determined from a comparison of the hybridization intensities of four probes, each having two interrogation positions. Each of the probes comprising a segment of at least 7 nucleotides that is exactly complementary to a subsequence from a reference sequence, except that the segment may or may not be exactly complementary at two interrogation positions. The nucleotides occupying the interrogation positions are selected by the following rules: (1) the first interrogation position is occupied by a different nucleotide in each of the four probes, (2) the second interrogation position is occupied by a different nucleotide in each of the four probes, (3) in first and second probes, the segment is exactly complementary to the subsequence, except at no more than one of the interrogation positions, (4) in third and fourth probes, the segment is exactly complementary to the subsequence, except at both of the interrogation positions.

In a ninth embodiment, the invention provides arrays of immobilized probes including helper mutations. Helper mutations are useful for, e.g., preventing self-annealing of probes having inverted repeats. In this strategy, the identity of a nucleotide in a target sequence is usually determined from a comparison of four probes. A first probe comprises a segment of at least 7 nucleotides exactly complementary to a subsequence of a reference sequence except at one or two positions, the segment including an interrogation position not at the one or two positions. The one or two positions are occupied by helper mutations.

Second, third and fourth mutant probes are each identical to a sequence comprising the wildtype probe or a subsequence thereof including the interrogation position and the one or two positions, except in the interrogation position, which is occupied by a different nucleotide in each of the four probes.

In a tenth embodiment, the invention provides arrays of probes comprising at least two probe sets, but lacking a probe set comprising probes that are perfectly matched to a reference sequence. Such arrays are usually employed in methods in which both reference and target sequence are hybridized to the array. The first probe set comprising a plurality of probes, each probe comprising a segment exactly complementary to a subsequence of at least 3 nucleotides of a reference sequence except at an interrogation position. The second probe set comprises a corresponding probe for each probe in the first probe set, the corresponding probe in the second probe set being identical to a sequence comprising the corresponding probe from the first probe set or a subsequence of at least three nucleotides thereof that includes the interrogation position, except that the interrogation position is occupied by a different nucleotide in each of the two corresponding probes and the complement to the reference sequence.

In an eleventh embodiment, the invention provides methods of comparing a target sequence with a reference sequence comprising a predetermined sequence of nucleotides using any of the arrays described above. The methods comprise hybridizing the target nucleic acid to an array and determining which probes, relative to one another, in the array bind specifically to the target nucleic acid. The relative specific binding of the probes indicates whether the target sequence is the same or different from the reference sequence. In some such methods, the target sequence has a substituted nucleotide relative to the reference sequence in at least one undetermined position, and the relative specific binding of the probes indicates the location of the position and the nucleotide occupying the position in the target sequence. In some methods, a second target nucleic acid is also hybridized to the array. The relative specific binding of the probes then indicates both whether the target sequence is the same or different from the reference sequence, and whether the second target sequence is the same or different from the reference sequence. In some methods, when the array comprises two groups of probes tiled for first and second reference sequences, respectively, the relative specific binding of probes in the first group indicates whether the target sequence is the same or different from the first reference sequence. The relative specific binding of probes in the second group indicates whether the target sequence is the same or different from the second reference sequence. Such methods are particularly useful for analyzing heterologous alleles of a gene. Some methods entail hybridizing both a reference sequence and a target sequence to any of the arrays of probes described above. Comparison of the relative specific binding of the probes to the reference and target sequences indicates whether the target sequence is the same or different from the reference sequence.

In a twelfth embodiment, the invention provides arrays of immobilized probes in which the probes are designed to tile a reference sequence from a human immunodeficiency virus.

Reference sequences from either the reverse transcriptase gene or protease gene of HIV are of particular interest. Some chips further comprise arrays of probes tiling a reference sequence from a 16S RNA or DNA encoding the 16S RNA from a pathogenic microorganism. The invention further provides methods of using such arrays in analyzing a HIV target sequence. The methods are particularly useful where the target sequence has a substituted nucleotide relative to the reference sequence in at least one position, the substitution conferring resistance to a drug use in treating a patient infected with a HIV virus. The methods reveal the existence of the substituted nucleotide. The methods are also particularly useful for analyzing a mixture of undetermined proportions of first and second target sequences from different HIV variants. The relative specific binding of probes indicates the proportions of the first and second target sequences.

In a thirteenth embodiment, the invention provides arrays of probes tiled based on reference sequence from a CFTR gene. A preferred array comprises at least a group of probes comprising a wildtype probe, and five sets of three mutant probes. The wildtype probe is exactly complementary to a subsequence of a reference sequence from a cystic fibrosis gene, the segment having at least five interrogation positions corresponding to five contiguous nucleotides in the reference sequence. The probes in the first set of three mutant probes are each identical to the wildtype probe, except in a first of the five interrogation positions, which is occupied by a different nucleotide in each of the three mutant probes and the wildtype probe. The probes in the second set of three mutant probes are each identical to the wildtype probe, except in a second of the five interrogation positions, which is occupied by a different nucleotide in each of the three mutant probes and the wildtype probe. The probes in the third set of three mutant probes are each identical to the wildtype probe, except in a third of the five interrogation positions, which is occupied by a different nucleotide in each of the three mutant probes and the wildtype probe. The probes in the fourth set of three mutant probes are each identical to the wildtype probe, except in a fourth of the five interrogation positions, which is occupied by a different nucleotide in each of the three mutant probes and the wildtype probe. The probes in the fifth set of three mutant probes are each identical to the wildtype probe, except in a fifth of the five interrogation positions, which is occupied by a different nucleotide in each of the three mutant probes and the wildtype probe. Preferably, a chip comprises two such groups of probes. The first group comprises a wildtype probe exactly complementary to a first reference sequence, and the second group comprises a wildtype probe exactly complementary to a second reference sequence that is a mutated form of the first reference sequence.

The invention further provides methods of using the arrays of the invention for analyzing target sequences from a CFTR gene. The methods are capable of simultaneously analyzing first and second target sequences representing heterozygous alleles of a CFTR gene.

In a fourteenth embodiment, the invention provides arrays of probes tiling a reference sequence from a p53 gene, an hMLH1 gene and/or an MSH2 gene. The invention further provides methods of using the arrays described above to analyze these genes. The method are useful, e.g., for diagnosing patients susceptible to developing cancer.

In a fifteenth embodiment, the invention provides arrays of probes tiling a reference sequence from a mitochondrial genome. The reference sequence may comprise part or all of the D-loop region, or all, or substantially all, of the mitochondrial genome. The invention further provides method of using the arrays described above to analyze target sequences from a mitochondrial genome. The methods are useful for identifying mutations associated with disease, and for forensic, epidemiological and evolutionary studies.

6.8.3. Specific Strategies

The invention provides a number of strategies for comparing a polynucleotide of known sequence (a reference sequence) with variants of that sequence (target sequences).

The comparison can be performed at the level of entire genomes, chromosomes, genes, exons or introns, or can focus on individual mutant sites and immediately adjacent bases. The strategies allow detection of variations, such as mutations or polymorphisms, in the target sequence irrespective whether a particular variant has previously been characterized. The strategies both define the nature of a variant and identify its location in a target sequence.

The strategies employ arrays of oligonucleotide probes immobilized to a solid support. Target sequences are analyzed by determining the extent of hybridization at particular probes in the array. The strategy in selection of probes facilitates distinction between perfectly matched probes and probes showing single-base or other degrees of mismatches.

The strategy usually entails sampling each nucleotide of interest in a target sequence several times, thereby achieving a high degree of confidence in its identity. This level of confidence is further increased by sampling of adjacent nucleotides in the target sequence to nucleotides of interest.

The number of probes on the chip can be quite large (e.g., $10^5$–$10^6$). However, usually only a small proportion of the total number of probes of a given length are represented.

Some advantage of the use of only a small proportion of all possible probes of a given length include: (i) each position in the array is highly informative, whether or not hybridization occurs; (ii) nonspecific hybridization is minimized; (iii) it is straightforward to correlate hybridization differences with sequence differences, particularly with reference to the hybridization pattern of a known standard; and (iv) the ability to address each probe independently during synthesis, using high resolution photolithography, allows the array to be designed and optimized for any sequence. For example the length of any probe can be varied independently of the others.

The present tiling strategies result in sequencing and comparison methods suitable for routine large-scale practice with a high degree of confidence in the sequence output.

6.8.3.1. General Tiling Strategies 6.8.3.1.1. Selection of Reference Sequence

The chips are designed to contain probes exhibiting complementarity to one or more selected reference sequence whose sequence is known. The chips are used to read a target sequence comprising either the reference sequence itself or variants of that sequence. Target sequences may differ from the reference sequence at one or more positions but show a high overall degree of sequence identity with the reference sequence (e.g., at least 75, 90, 95, 99, 99.9 or 99–99%). Any polynucleotide of known sequence can be selected as a reference sequence. Reference sequences of interest include sequences known to include mutations or polymorphisms associated with phenotypic changes having clinical significance in human patients. For example, the CFTR gene and P53 gene in humans have been identified as the location of several mutations resulting in cystic fibrosis or cancer respectively. Other reference sequences of interest include those that serve to identify pathogenic microorganisms and/or are the site of mutations by which such microorganisms acquire drug resistance (e.g., the HIV reverse transcriptase gene). Other reference sequences of interest include regions where polymorphic variations are known to occur (e.g., the D-loop region of mitochondrial DNA). These reference sequences have utility for, e.g., forensic or epidemiological studies. Other reference sequences of interest include p34 (related to p53), p65 (implicated in breast, prostate and liver cancer), and DNA segments encoding cytochromes P450 (see Meyer et al., Pharmac. Ther. 46, 349–355 (1990)). Other reference sequences of interest include those from the genome of pathogenic viruses (e.g., hepatitis J, B, or Q, herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus. Other reference sequences of interest are from genomes or episomes of pathogenic bacteria, particularly regions that confer drug resistance or allow phylogenic characterization of the host (e.g., 16S rRNA or corresponding DNA). For example, such bacteria include chlanydia, rickettsial bacteria, mycobacteria, staphylococci, treptocci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lymes disease bacteria. Other reference sequences of interest include those in which mutations result in the following autosomal recessive disorders: sickle cell anemia, beta-thalassemia, phenylketonuria, galactosemia, Wilson's disease, hemochromatosis, severe combined immunodeficiency, alpha-1-antitrypsin deficiency, albinism, alkaptonuria, lysosomal storage diseases and Ehlers-Danlos syndrome. Other reference sequences of interest include those in which mutations result in X-linked recessive disorders: hemophilia, glucose-6-phosphate dehydrogenase, agammaglobulimenia, diabetes insipidus, Lesch-Nyhan syndrome, muscular dystrophy, Wiskott-Aldrich syndrome, Fabry's disease and fragile X-syndrome. Other reference sequences of interest includes those in which mutations result in the following autosomal dominant disorders: familial hypercholesterolemia, polycystic kidney disease, Huntingdon's disease, hereditary spherocytosis, Marfan's syndrome, von Willebrand's disease, neurofibromatosis, tuberous sclerosis, hereditary hemorrhagic telangiectasia, familial colonic polyposis, Ehlers-Danlos syndrome, myotonic dystrophy, muscular dystrophy, osteogenesis imperfecta, acute intermittent porphyria, and von Hippel-Lindau disease.

The length of a reference sequence can vary widely from a full-length genome, to an individual chromosome, episome, gene, component of a gene, such as an exon, intron or regulatory sequences, to a few nucleotides. A reference sequence of between about 2, 5, 10, 20, 50, 100, 5000, 1000, 5,000 or 10,000, 20,000 or 100,000 nucleotides is common.

Sometimes only particular regions of a sequence (e.g., exons of a gene) are of interest. In such situations, the particular regions can be considered as separate reference sequences or can be considered as components of a single reference sequence, as matter of arbitrary choice.

A reference sequence can be any naturally occurring, mutant, consensus or purely hypothetical sequence of nucleotides, RNA or DNA. For example, sequences can be obtained from computer data bases, publications or can be determined or conceived de novo. Usually, a reference sequence is selected to show a high degree of sequence identity to envisaged target sequences. Often, particularly, where a significant degree of divergence is anticipated between target sequences, more than one reference sequence is selected. Combinations of wildtype and mutant reference sequences are employed in several applications of the tiling strategy.

6.8.3.1.2. Chip Design 6.8.3.1.2.1. Basic Tiling Strategy

The basic tiling strategy provides an array of immobilized probes for analysis of target sequences showing a high degree of sequence identity to one or more selected reference sequences. The strategy is first illustrated for an array that is subdivided into four probe sets, although it will be apparent that in some situations, satisfactory results are obtained from only two probe sets. A first probe set comprises a plurality of probes exhibiting perfect complementarity with a selected reference sequence. The perfect complementarity usually exists throughout the length of the probe. However, probes having a segment or segments of perfect complementarity that is/are flanked by leading or trailing sequences lacking complementarity to the reference sequence can also be used. Within a segment of complementarity, each probe in the first probe set has at least one interrogation position that corresponds to a nucleotide in the reference sequence. That is, the interrogation position is aligned with the corresponding nucleotide in the reference sequence, when the probe and reference sequence are aligned to maximize complementarity between the two. If a probe has more than one interrogation position, each corresponds with a respective nucleotide in the reference sequence. The identity of an interrogation position and corresponding nucleotide in a particular probe in the first probe set cannot be determined simply by inspection of the probe in the first set. As will become apparent, an interrogation position and corresponding nucleotide is defined by the comparative structures of probes in the first probe set and corresponding probes from additional probe sets.

In principle, a probe could have an interrogation position at each position in the segment complementary to the reference sequence. Sometimes, interrogation positions provide more accurate data when located away from the ends of a segment of complementarity. Thus, typically a probe having a segment of complementarity of length x does not contain more than x-2 interrogation positions. Since probes are typically 9–21 nucleotides, and usually all of a probe is complementary, a probe typically has 1–19 interrogation positions. Often the probes contain a single interrogation position, at or near the center of probe.

For each probe in the first set, there are, for purposes of the present illustration, three corresponding probes from three additional probe sets. Thus, there are four probes corresponding to each nucleotide of interest in the reference sequence. Each of the four corresponding probes has an interrogation position aligned with that nucleotide of interest. Usually, the probes from the three additional probe sets are identical to the corresponding probe from the first probe set with one exception. The exception is that at least one (and often only one) interrogation position, which occurs in the same position in each of the four corresponding probes from the four probe sets, is occupied by a different nucleotide in the four probe sets. For example, for an A nucleotide in the reference sequence, the corresponding probe from the first probe set has its interrogation position occupied by a T, and the corresponding probes from the additional three probe sets have their respective interrogation positions occupied by A, C, or G, a different nucleotide in each probe. Of course, if a probe from the first probe set comprises trailing or flanking sequences lacking complementarity to the reference sequences, these sequences need not be present in corresponding probes from the three additional sets. Likewise corresponding probes from the three additional sets can contain leading or trailing sequences outside the segment of complementarity that are not present in the corresponding probe from the first probe set. Occasionally, the probes from the additional three probe set are identical (with the exception of interrogation position(s)) to a contiguous subsequence of the full complementary segment of the corresponding probe from the first probe set. In this case, the subsequence includes the interrogation position and usually differs from the full-length probe only in the omission of one or both terminal nucleotides from the termini of a segment of complementarity.

That is, if a probe from the first probe set has a segment of complementarity of length n, corresponding probes from the other sets will usually include a subsequence of the segment of at least length n-2. Thus, the subsequence is usually at least 3, 4, 7, 9, 15, 21, or 25 nucleotides long, most typically, in the range of 9–21 nucleotides. The subsequence should be sufficiently long to allow a probe to hybridize detectably more strongly to a variant of the reference sequence mutated at the interrogation position than to the reference sequence.

The probes can be oligodeoxyribonucleotides or oligoribonucleotides, or any modified forms of these polymers that are capable of hybridizing with a target nucleic sequence by complementary base-pairing. Complementary base pairing means sequence-specific base pairing which includes e.g., Watson-Crick base pairing as well as other forms of base pairing such as Hoogsteen base pairing. Modified forms include 2'-O-methyl oligoribonucleotides and so-called PNAs, in which oligodeoxyribonucleotides are linked via peptide bonds rather than phophodiester bonds. The probes can be attached by any linkage to a support (e.g., 3', 5' or via the base). 3' attachment is more usual as this orientation is compatible with the preferred chemistry for solid phase synthesis of oligonucleotides.

The number of probes in the first probe set (and as a consequence the number of probes in additional probe sets) depends on the length of the reference sequence, the number of nucleotides of interest in the reference sequence and the number of interrogation positions per probe. In general, each nucleotide of interest in the reference sequence requires the same interrogation position in the four sets of probes.

Consider, as an example, a reference sequence of 100 nucleotides, 50 of which are of interest, and probes each having a single interrogation position. In this situation, the first probe set requires fifty probes, each having one interrogation position corresponding to a nucleotide of interest in the reference sequence. The second, third and fourth probe sets each have a corresponding probe for each probe in the first probe set, and so each also contains a total of fifty probes. The identity of each nucleotide of interest in the reference sequence is determined by comparing the relative hybridization signals at four probes having interrogation positions corresponding to that nucleotide from the four probe sets.

In some reference sequences, every nucleotide is of interest. In other reference sequences, only certain portions in which variants (e.g., mutations or polymorphisms) are concentrated are of interest. In other reference sequences, only particular mutations or polymorphisms and immediately adjacent nucleotides are of interest. Usually, the first probe set has interrogation positions selected to correspond to at least a nucleotide (e.g., representing a point mutation) and one immediately adjacent nucleotide. Usually, the probes in the first set have interrogation positions corresponding to at least 3, 10, 50, 100, 1000, or 20,000 contiguous nucleotides. The probes usually have interrogation positions corresponding to at least 5, 10, 30, 50, 75, 90, 99 or sometimes 100% of the nucleotides in a reference sequence.

Frequently, the probes in the first probe set completely span the reference sequence and overlap with one another relative to the reference sequence. For example, in one common arrangement each probe in the first probe set differs from another probe in that set by the omission of a 3' base complementary to the reference sequence and the acquisition of a 5' base complementary to the reference sequence.

For conceptual simplicity, the probes in a set are usually arranged in order of the sequence in a lane across the chip. A lane contains a series of overlapping probes, which represent or tile across, the selected reference sequence. The components of the four sets of probes are usually laid down in four parallel lanes, collectively constituting a row in the horizontal direction and a series of 4-member columns in the vertical direction. Corresponding probes from the four probe sets (i.e., complementary to the same subsequence of the reference sequence) occupy a column.

Each probe in a lane usually differs from its predecessor in the lane by the omission of a base at one end and the inclusion of additional base at the other end. However, this orderly progression of probes can be interrupted by the inclusion of control probes or omission of probes in certain columns of the array. Such columns serve as controls to orient the chip, or gauge the background, which can include target sequence nonspecifically bound to the chip.

The probes sets are usually laid down in lanes such that all probes having an interrogation position occupied by an A form an-A-lane, all probes having an interrogation position occupied by a C form a C-lane, all probes having an interrogation position occupied by a G form a G-lane, and all probes having an interrogation position occupied by a T (or U) form a T lane (or a U lane). Note that in this arrangement there is not a unique correspondence between probe sets and lanes. Thus, the probe from the first probe set is laid down in the A-lane, C-lane, A-lane, A-lane and T-lane for the five columns. The interrogation position on a column of probes corresponds to the position in the target sequence whose identity is determined from analysis of hybridization to the probes in that column. The interrogation position can be anywhere in a probe but is usually at or near the central position of the probe to maximize differential hybridization signals between a perfect match and a single-base mismatch.

For example, for an 11 mer probe, the central position is the sixth nucleotide.

Although the array of probes is usually laid down in rows and columns as described above, such a physical arrangement of probes on the chip is not essential. Provided that the spatial location of each probe in an array is known, the data from the probes can be collected apd processed to yield the sequence of a target irrespective of the physical arrangement of the probes on a chip. In processing the data, the hybridization signals from the respective probes can be reasserted into any conceptual array desired for subsequent data reduction whatever the physical arrangement of probes on the chip.

A range of lengths of probes can be employed in the chips. As noted above, a probe may consist exclusively of a complementary segments, or may have one or more complementary segments juxtaposed by flanking, trailing and/or intervening segments. In the latter situation, the total length of complementary segment(s) is more important than the length of the probe. In functional terms, the complementarity segment(s) of the first probe sets should be sufficiently long to allow the probe to hybridize detectably more strongly to a reference sequence compared with a variant of the reference including a single base mutation at the nucleotide corresponding to the interrogation position of the probe.

Similarly, the complementarity segment(s) in corresponding probes from additional probe sets should be sufficiently long to allow a probe to hybridize detectably more strongly to a variant of the reference sequence having a single nucleotide substitution at the interrogation position relative to the reference sequence. A probe usually has a single complementary segment having a length of at least 3 nucleotides, and more usually at least 5, 6, 7, 8, 9, 10, 11, 12, 13, 14, 15, 16, 17, 18, 19, 20, 21, 22, 23, 24, 25 or bases exhibiting perfect complementarity (other than possibly at the interrogation position(s) depending on the probe set) to the reference sequence. In bridging strategies, where more than one segment of complementarity is present, each segment provides at least three complementary nucleotides to the reference sequence and the combined segments provide at least two segments of three or a total of six complementary nucleotides. As in the other strategies, the combined length of complementary segments is typically from 6–30 nucleotides, and preferably from about 9–21 nucleotides. The two segments are often approximately the same length. Often, the probes (or segment of complementarity within probes) have an odd number of bases, so that an interrogation position can occur in the exact center of the probe.

In some chips, all probes are the same length. Other chips employ different groups of probe sets, in which case the probes are of the same size within a group, but differ between different groups. For example, some chips have one group comprising four sets of probes as described above in which all the probes are 11 mers, together with a second group comprising four sets of probes in which all of the probes are 13 mers. Of course, additional groups of probes can be added.

Thus, some chips contain, e.g., four groups of probes having sizes of 11 mers, 13 mers, 15 mers and 17 mers. Other chips have different size probes within the same group of four probe sets. In these chips, the probes in the first set can vary in length independently of each other. Probes in the other sets are usually the same length as the probe occupying the same column from the first set. However, occasionally different lengths of probes can be included at the same column position in the four lanes. The different length probes are included to equalize hybridization signals from probes irrespective of whether A-T or C-G bonds are formed at the interrogation position.

The length of probe can be important in distinguishing between a perfectly matched probe and probes showing a single-base mismatch with the target sequence. The discrimination is usually greater for short probes. Shorter probes are usually also less susceptible to formation of secondary structures.

However, the absolute amount of target sequence bound, and hence the signal, is greater for larger probes. The probe length representing the optimum compromise between these competing considerations may vary depending on inter alia the GC content of a particular region of the target DNA sequence, secondary structure, synthesis efficiency and cross-hybridization. In some regions of the target, depending on hybridization conditions, short probes (e.g., 11 mers) may provide information that is inaccessible from longer probes (e.g., 19 mers) and vice versa. Maximum sequence information can be read by including several groups of different sized probes on the chip as noted above. However, for many regions of the target sequence, such a strategy provides redundant information in that the same sequence is read multiple times from the different groups of probes. Equivalent information can be obtained from a single group of different sized probes in which the sizes are selected to maximize readable sequence at particular regions of the target sequence. The strategy of customizing probe length within a single group of probe sets minimizes the total number of probes required to read a particular target sequence. This leaves ample capacity for the chip to include probes to other reference sequences.

The invention provides an optimization block which allows systematic variation of probe length and interrogation position to optimize the selection of probes for analyzing a particular nucleotide in a reference sequence. The block comprises alternating columns of probes complementary to the wildtype target and probes complementary to a specific mutation. The interrogation position is varied between columns and probe length is varied down a column.

Hybridization of the chip to the reference sequence or the mutant form of the reference sequence identifies the probe length and interrogation position providing the greatest differential hybridization signal.

The probes are designed to be complementary to either strand of the reference sequence (e.g., coding or noncoding). some chips contain separate groups of probes, one complementary to the coding strand, the other complementary to the noncoding strand. Independent analysis of coding and noncoding strands provides largely redundant information.

However, the regions of ambiguity in reading the coding strand are not always the same as those in reading the noncoding strand. Thus, combination of the information from coding and noncoding strands increases the overall accuracy of sequencing.

Some chips contain additional probes or groups of probes designed to be complementary to a second reference sequence.

The second reference sequence is often a subsequence of the first reference sequence bearing one or more commonly occurring mutations or interstrain variations. The second group of probes is designed by the same principles as described above except that the probes exhibit complementarity to the second reference sequence. The inclusion of a second group is particular useful for analyzing short subsequences of the primary reference sequence in which multiple mutations are expected to occur within a short distance commensurate with the length of the probes (i.e., two or more mutations within 9 to 21 bases). Of course, the same principle can be extended to provide chips containing groups of probes for any number of reference sequences. Alternatively, the chips may contain additional probe(s) that do not form part of a tiled array as noted above, but rather serves as probe(s) for a conventional reverse dot blot. For example, the presence of mutation can be detected from binding of a target sequence to a single oligomeric probe harboring the mutation. Preferably, an additional probe containing the equivalent region of the wildtype sequence is included as a control.

The chips are read by comparing the intensities of labelled target bound to the probes in an array.

Specifically, a comparison is performed between each lane of probes (e.g., A, C, G and T lanes) at each columnar position (physical or conceptual). For a particular columnar position, the lane showing the greatest hybridization signal is called as the nucleotide present at the position in the target sequence corresponding to the interrogation position in the probes. The corresponding position in the target sequence is that aligned with the interrogation position in corresponding probes when the probes and target are aligned to maximize complementarity. Of the four probes in a column, only one can exhibit a perfect match to the target sequence whereas the others usually exhibit at least a one base pair mismatch. The probe exhibiting a perfect match usually produces a substantially greater hybridization signal than the other three probes in the column and is thereby easily identified. However, in some regions of the target sequence, the distinction between a perfect match and a one-base mismatch is less clear. Thus, a call ratio is established to define the ratio of signal from the best hybridizing probes to the second best hybridizing probe that must be exceeded for a particular target position to be read from the probes. A high call ratio ensures that few if any errors are made in calling target nucleotides, but can result in some nucleotides being scored as ambiguous, which could in fact be accurately read.

A lower call ratio results in fewer ambiguous calls, but can result in more erroneous calls. It has been found that at a call ratio of 1.2 virtually all calls are accurate. However, a small but significant number of bases (e.g., up to about %) may have to be scored as ambiguous.

Although small regions of the target sequence can sometimes be ambiguous, these regions usually occur at the same or similar segments in different target sequences. Thus, for precharacterized mutations, it is known in advance whether that mutation is likely to occur within a region of unambiguously determinable sequence. An array of probes is most useful for analyzing the reference sequence from which the probes were designed and variants of that sequence exhibiting substantial sequence similarity with the reference sequence (e.g., several single-base mutants spaced over the reference sequence). When an array is used to analyze the exact reference sequence from which it was designed, one probe exhibits a perfect match to the reference sequence, and the other three probes in the same column exhibits single-base mismatches. Thus, discrimination between hybridization signals is usually high and accurate sequence is obtained. High accuracy is also obtained when an array is used for analyzing a target sequence comprising a variant of the reference sequence that has a single mutation relative to the reference sequence, or several widely spaced mutations relative to the reference sequence. At different mutant loci, one probe exhibits a perfect match to the target, and the other three probes occupying the same column exhibit single-base mismatches, the difference (with respect to analysis of the reference sequence) being the lane in which the perfect match occurs.

For target sequences showing a high degree of divergence from the reference strain or incorporating several closely spaced mutations from the reference strain, a single group of probes (i.e., designed with respect to a single reference sequence) will not always provide accurate sequence for the highly variant region of this sequence. At some particular columnar positions, it may be that no single probe exhibits perfect complementarity to the target and that any comparison must be based on different degrees of mismatch between the four probes. Such a comparison does not always allow the target nucleotide corresponding to that columnar position to be called. Deletions in target sequences can be detected by loss of signal from probes having interrogation positions encompassed by the deletion. However, signal may also be lost from probes having interrogation positions closely proximal to the deletion resulting in some regions of the target sequence that cannot be read. Target sequence bearing insertions will also exhibit short regions including and proximal to the insertion that usually cannot be read.

The presence of short regions of difficult-to-read target because of closely spaced mutations, insertions or deletion, does not prevent determination of the remaining sequence of the target as different regions of a target sequence are determined independently. Moreover, such ambiguities as might result from analysis of diverse variants with a single group of probes can be avoided by including multiple groups of probe sets on a chip. For example, one group of probes can be designed based on a full-length reference sequence, and the other groups on subsequences of the reference sequence incorporating frequently occurring mutations or strain variations.

A particular advantage of the present sequencing strategy over conventional sequencing methods is the capacity simultaneously to detect and quantify proportions of multiple target sequences. Such capacity is valuable, e.g., for diagnosis of patients who are heterozygous with respect to a gene or who are infected with a virus, such as HIV, which is usually present in several polymorphic forms. Such capacity is also useful in analyzing targets from biopsies of tumor cells and surrounding tissues. The presence of multiple target sequences is detected from the relative signals of the four probes at the array columns corresponding to the target nucleotides at which diversity occurs. The relative signals at the four probes for the mixture under test are compared with the corresponding signals from a homogeneous reference sequence. An increase in a signal from a probe that is mismatched with respect to the reference sequence, and a corresponding decrease in the signal from the probe which is matched with the reference sequence signal the presence of a mutant strain in the mixture. The extent in shift in hybridization signals of the probes is related to the proportion of a target sequence in the mixture. Shifts in relative hybridization signals can be quantitatively related to proportions of reference and mutant sequence by prior calibration of the chip with seeded mixtures of the mutant and reference sequences. By this means, a chip can be used to detect variant or mutant strains constituting as little as 1, 5, 20, or 25% of a mixture of stains.

Similar principles allow the simultaneous analysis of multiple target sequences even when none is identical to the reference sequence. For example, with a mixture of two target sequences bearing first and second mutations, there would be a variation in the hybridization patterns of probes having interrogation positions corresponding to the first and second mutations relative to the hybridization pattern with the reference sequence. At each position, one of the probes having a mismatched interrogation position relative to the reference sequence would show an increase in hybridization signal, and the probe having a matched interrogation position relative to the reference sequence would show a decrease in hybridization signal. Analysis of the hybridization pattern of the mixture of mutant target sequences, preferably in comparison with the hybridization pattern of the reference sequence, indicates the presence of two mutant target sequences, the position and nature of the mutation in each strain, and the relative proportions of each strain.

In a variation of the above method, the different components in a mixture of target sequences are differentially labelled before being applied to the array. For example, a variety of fluorescent labels emitting at different wavelength are available. The use of differential labels allows independent analysis of different targets bound simultaneously to the array. For example, the methods permit comparison of target sequences obtained from a patient at different stages of a disease.

6.8.3.1.2.2. Omission of Probes

The general strategy outlined above employs four probes to read each nucleotide of interest in a target sequence. One probe (from the first probe set) shows a perfect match to the reference sequence and the other three probes (from the second, third and fourth probe sets) exhibit a mismatch with the reference sequence and a perfect match with a target sequence bearing a mutation at the nucleotide of interest.

The provision of three probes from the second, third and fourth probe sets allows detection of each of the three possible nucleotide substitutions of any nucleotide of interest. However, in some reference sequences or regions of reference sequences, it is known in advance that only certain mutations are likely to occur. Thus, for example, at one site it might be known that an A nucleotide in the reference sequence may exist as a T mutant in some target sequences but is unlikely to exist as a C or G mutant. Accordingly, for analysis of this region of the reference sequence, one might include only the first and second probe sets, the first probe set exhibiting perfect complementarity to the reference sequence, and the second probe set having an interrogation position occupied by an invariant A residue (for detecting the T mutant). In other situations, one might include the first, second and third probes sets (but not the fourth) for detection of a wildtype nucleotide in the reference sequence and two mutant variants thereof in target sequences. In some chips, probes that would detect silent mutations (i.e., not affecting amino acid sequence) are omitted.

In some chips, the probes from the first probe set are omitted corresponding to some or all positions of the reference sequences. Such chips comprise at least two probe sets. The first probe set has a plurality of probes. Each probe comprises a segment exactly complementary to a subsequence of a reference sequence except in at least one interrogation position. A second probe set has a corresponding probe for each probe in the first probe set.

The corresponding probe in the second probe set is identical to a sequence comprising the corresponding probe form the first probe set or a subsequence thereof that includes the at least one (and usually only one) interrogation position except that the at least one interrogation position is occupied by a different nucleotide in each of the two corresponding probes from the first and second probe sets. A third probe set, if present, also comprises a corresponding probe for each probe in the first probe set except at the at least one interrogation position, which differs in the corresponding probes from the three sets. Omission of probes having a segment exhibiting perfect complementarity to the reference sequence results in loss of control information, i.e., the detection of nucleotides in a target sequence that are the same As those in a reference sequence. However, similar information can be obtained by hybridizing a chip lacking probes from the first probe set to both target and reference sequences. The hybridization can be performed sequentially, or concurrently, if the target and reference are differentially labelled. In this situation, the presence of a mutation is detected by a shift in the background hybridization intensity of the reference sequence to a perfectly matched hybridization signal of the target sequence, rather than by a comparison of the hybridization intensities of probes from the first set with corresponding probes from the second, third and fourth sets.

6.8.3.1.2.3. Wildtype Probe Lane

When the chips comprise four probe sets, as discussed supra, and the probe sets are laid down in four lanes, an A-lane, a C-lane, a G-lane and a T or U-lane, the probe having a segment exhibiting perfect complementarity to a reference sequence varies between the four lanes from one column to another. This does not present any significant difficulty in computer analysis of the data from the chip. However, visual inspection of the hybridization pattern of the chip is sometimes facilitated by provision of an extra lane of probes, in which each probe has a segment exhibiting perfect complementarity to the reference sequence. This segment-is identical to a segment from one of the probes in the other four lanes (which lane depending on the column position). The extra lane of probes (designated the wildtype lane) hybridizes to a target sequence at all nucleotide positions except those in which deviations from the reference sequence occurs. The hybridization pattern of the wildtype lane thereby provides a simple visual indication of mutations.

6.8.3.1.2.4. Deletion, Insertion and Multiple-Mutation Probes

Some chips provide an additional probe set specifically designed for analyzing deletion mutations. The additional probe set comprises a probe corresponding to each probe in the first probe set as described above. However, a probe from the additional probe set differs from the corresponding probe in the first probe set in that the nucleotide occupying the interrogation position is deleted in the probe from the additional probe set. Optionally, the probe from the additional probe set bears an additional nucleotide at one of its termini relative to the corresponding probe from the first probe set. The probe from the additional probe set will hybridize more strongly than the corresponding probe from the first probe set to a target sequence having a single base deletion at the nucleotide corresponding to the interrogation position. Additional probe sets are provided in which not only the interrogation position, but also an adjacent nucleotide is detected.

Similarly, other chips provide additional probe sets for analyzing insertions. For example, one additional probe set has a probe corresponding to each probe in the first probe set as described above. However, the probe in the additional probe set has an extra T nucleotide inserted adjacent to the interrogation position. Optionally, the probe has one fewer nucleotide at one of its termini relative to the corresponding probe from the first probe set. The probe from the additional probe set hybridizes more strongly than the corresponding probe from the first probe set to a target sequence having an A nucleotide inserted in a position adjacent to that corresponding to the interrogation position.

Similar additional probe sets are constructed having C, G or T/U nucleotides inserted adjacent to the interrogation position. Usually, four such probe sets, one for each nucleotide, are used in combination.

Other chips provide additional probes (multiple-mutation probes) for analyzing target sequences having multiple closely spaced mutations. A multiple-mutation probe is usually identical to a corresponding probe from the first set as described above, except in the base occupying the interrogation position, and except at one or more additional positions, corresponding to nucleotides in which substitution may occur in the reference sequence. The one or more additional positions in the multiple mutation probe are occupied by nucleotides complementary to the nucleotides occupying corresponding positions in the reference sequence when the possible substitutions have occurred.

6.8.3.1.2.5. Block Tiling

As noted in the discussion of the general tiling strategy, a probe in the first probe set sometimes has more than one interrogation position. In this situation, a probe in the first probe set is sometimes matched with multiple groups of at least one, and usually, three additional probe sets. Three additional probe sets are used to allow detection of the three possible nucleotide substitutions at any one position. If only certain types of substitution are likely to occur (e.g., transitions), only one or two additional probe sets are required (analogous to the use of probes in the basic tiling strategy). To illustrate for the situation where a group comprises three additional probe sets, a first such group comprises second, third and fourth probe sets, each of which has a probe corresponding to each probe in the first probe set. The corresponding probes from the second, third and fourth probes sets differ from the corresponding probe in the first set at a first of the interrogation positions. Thus, the relative hybridization signals from corresponding probes from the first, second, third and fourth probe sets indicate the identity of the nucleotide in a target sequence corresponding to the first interrogation position. A second group of three probe sets (designated fifth, sixth and seventh probe sets), each also have a probe corresponding to each probe in the first probe set. These corresponding probes differ from that in the first probe set at a second interrogation position. The relative hybridization signals from corresponding probes from the first, fifth, sixth, and seventh probe sets indicate the identity of the nucleotide in the target sequence corresponding to the second interrogation position. As noted above, the probes in the first probe set often have seven or more interrogation positions. If there are seven interrogation positions, there are seven groups of three additional probe sets, each group of three probe sets serving to identify the nucleotide corresponding to one of the seven interrogation positions.

Each block of probes allows short regions of a target sequence to be read. For example, for a block of probes having seven interrogation positions, seven nucleotides in the target sequence can be read. Of course, a chip can contain any number of blocks depending on how many nucleotides of the target are of interest. The hybridization signals for each block can be analyzed independently of any other block. The block tiling strategy can also be combined with other tiling strategies, with different parts of the same reference sequence being tiled by different strategies.

The block tiling strategy offers two advantages over the basic strategy in which each probe in the first set has a single interrogation position. One advantage is that the same sequence information can be obtained from fewer probes. A second advantage is that each of the probes constituting a block (i.e., a probe from the first probe set and a corresponding probe from each of the other probe sets) can have identical 3' and 5' sequences, with the variation confined to a central segment containing the interrogation positions. The identity of 3' sequence between different probes simplifies the strategy for solid phase synthesis of the probes on the chip and results in more uniform deposition of the different probes on the chip, thereby in turn increasing the uniformity of signal to noise ratio for different regions of the chip. A third advantage is that greater signal uniformity is achieved within a block.

6.8.3.1.2.6. Multiplex Tiling

In the block tiling strategy discussed above, the identity of a nucleotide in a target or reference sequence is determined by comparison of hybridization patterns of one probe having a segment showing a perfect match with that of other probes (usually three other probes) showing a single base mismatch. In multiplex tiling, the identity of at least two nucleotides in a reference or target sequence is determined by comparison of hybridization signal intensities of four probes, two of which have a segment showing perfect complementarity or a single base mismatch to the reference sequence, and two of which have a segment showing perfect complementarity or a double-base mismatch to a segment. The four probes whose hybridization patterns are to be compared each have a segment that is exactly complementary to a reference sequence except at two interrogation positions, in which the segment may or may not be complementary to the reference sequence. The interrogation positions correspond to the nucleotides in a reference or target sequence which are determined by the comparison of intensities. The nucleotides occupying the interrogation positions in the four probes are selected according to the following rule. The first interrogation position is occupied by a different nucleotide in each of the four probes.

The second interrogation position is also occupied by a different nucleotide in each of the four probes. In two of the four probes, designated the first and second probes, the segment is exactly complementary to the reference sequence except at not more than one of the two interrogation positions. In other words, one of the interrogation positions is occupied by a nucleotide that is complementary to the corresponding nuclectide from the reference sequence and the other interrogation position may or may not be so occupied. In the other two of the four probes, designated the third and fourth probes, the segment is exactly complementary to the reference sequence except that both interrogation positions are occupied by nucleotides which are noncomplementary to the respective corresponding nucleotides in the reference sequence.

There are number of ways of satisfying these conditions depending on whether the two nucleotides in the reference sequence corresponding to the two interrogation positions are the same or different. If these two nucleotides are different in the reference sequence (probability ¾), the conditions are satisfied by each of the two interrogation positions being occupied by the same nucleotide in any given probe. For example, in the first probe, the two interrogation positions would both be A, in the second probe, both would be C, in the third probe, each would be G, and in the fourth probe each would be T or U. If the two nucleotides in the reference sequence corresponding to the two interrogation positions are different, the conditions noted above are satisfied by each of the interrogation positions in any one of the four probes being occupied by complementary nucleotides. For example, in the first probe, the interrogation positions could be occupied by A and T, in the second probe by C and G, in the third probe by G and C and in the four probe, by T and A.

When the four probes are hybridized to a target that is the same as the reference sequence or differs from the reference sequence at one (but not both) of the interrogation positions, two of the four probes show a double-mismatch with the target and two probes show a single mismatch. The identity of probes showing these different degrees of mismatch can be determined from the different hybridization signals.

From the identity of the probes showing the different degrees of mismatch, the nucleotides occupying both of the interrogation positions in the target sequence can be deduced.

For ease of illustration, the multiplex strategy has been initially described for the situation where there are two nucleotides of interest in a reference sequence and only four probes in an array. Of course, the strategy can be extended to analyze any number of nucleotides in a target sequence by using additional probes. In one variation, each pair of interrogation positions is read from a unique group of four probes. In a block variation, different groups of four probes exhibit the same segment of complementarity with the reference sequence, but the interrogation positions move within a block.

The block and standard multiplex tiling variants can of course be used in combination for different regions of a reference sequence. Either or both variants can also be used in combination with any of the other tiling strategies described.

6.8.3.1.2.7. Helper Mutations

Occasionally small regions of a reference sequence give a low hybridization signal as a result of annealing of probes.

The self-annealing reduces the amount of probe effectively available for hybridizing to the target. Although such regions of the target are generally small and the reduction of hybridization signal is usually not so substantial as to obscure the sequence of this region, this concern can be avoided by the use of probes incorporating helper mutations.

The helper mutation(s) serve to break-up regions of internal complementarity within a probe and thereby prevent annealing.

Usually, one or two helper mutations are quite sufficient for this purpose. The inclusion of helper mutations can be beneficial in any of the tiling strategies noted above. In general each probe having a particular interrogation position has the same helper mutation(s). Thus, such probes have a segment in common which shows perfect complementarity with a reference sequence, except that the segment contains at least one helper mutation (the same in each of the probes) and at least one interrogation position (different in all of the probes). For example, in the basic tiling strategy, a probe from the first probe set comprises a segment containing an interrogation position and showing perfect complementarity with a reference sequence except for one or two helper mutations. The corresponding probes from the second, third and fourth probe sets usually comprise the same segment (or sometimes a subsequence thereof including the helper mutation(s) and interrogation position), except that the base occupying the interrogation position varies in each probe.

Usually, the helper mutation tiling strategy is used in conjunction with one of the tiling strategies described above.

The probes containing helper mutations are used to tile regions of a reference sequence otherwise giving low hybridization signal (e.g., because of self-complementarity), and the alternative tiling strategy is used to tile intervening regions.

6.8.3.1.2.8. Pooling Strategies

Pooling strategies also employ arrays of immobilized probes. Probes are immobilized in cells of an array, and the hybridization signal of each cell can be determined independently of any other cell. A particular cell may be occupied by pooled mixture of probes. Although the identity of each probe in the mixture is known, the individual probes in the pool are not separately addressable. Thus, the hybridization signal from a cell is the aggregate of that of the different probes occupying the cell. In general, a cell is scored as hybridizing to a target sequence if at least one probe occupying the cell comprises a segment exhibiting perfect complementarity to the target sequence.

A simple strategy to show the increased power of pooled strategies over a standard tiling is to create three cells each containing a pooled probe having a single pooled position, the pooled position being the same in each of the pooled probes. At the pooled position, there are two possible nucleotides, allowing the pooled probe to hybridize to two target sequences. In tiling terminology, the pooled position of each probe is an interrogation position. As will become apparent, comparison of the hybridization intensities of the pooled probes from the three cells reveals the identity of the nucleotide in the target sequence corresponding to the interrogation position (i.e., that is matched with the interrogation position when the target sequence and pooled probes are maximally aligned for complementarity).

The three cells are assigned probe pools that are perfectly complementary to the target except at the pooled position, which is occupied by a different pooled nucleotide in each probe.

With 3 pooled probes, all 4 possible single base pair states (wild and 3 mutants) are detected. A pool hybridizes with a target if some probe contained within that pool is complementary to that target.

A cell containing a pair (or more) of oligonucleotides lights up when a target complementary to any of the oligonucleotide in the cell is present. Using the simple strategy, each of the four possible targets (wild and three mutants) yields a unique hybridization pattern among the three cells.

Since a different pattern of hybridizing pools is obtained for each possible nucleotide in the target sequence corresponding to the pooled interrogation position in the probes, the identity of the nucleotide can be determined from the hybridization pattern of the pools. Whereas, a standard tiling requires four cells to detect and identify the possible single-base substitutions at one location, this simple pooled strategy only requires three cells.

A more efficient pooling strategy for sequence analysis is the 'Trellis' strategy. In this strategy, each pooled probe has a segment of perfect complementarity to a reference sequence except at three pooled positions. One pooled position is an N pool. The three pooled positions may or may not be contiguous in a probe. The other two pooled positions are selected from the group of three pools consisting of (1) M or K, (2) R or Y and (3) W or S, where the single letters are IUPAC standard ambiguity codes. The sequence of a pooled probe is thus, of the form XXXN[(M/K) or (R/Y) or (W/S)][(M/K) or (RIY) or (W/S)]XXXXX, where XXX represents bases complementary to the reference sequence. The three pooled positions may be in any order, and may be contiguous or separated by intervening nucleotides. For, the two positions occupied by [(M/K) or (R/Y) or (W/S)], two choices must be made. First, one must select one of the following three pairs of pooled nucleotides (1) M/K, (2) R/Y and (3) W/S. The one of three pooled nucleotides selected may be the same or different at the two pooled positions. Second, supposing, for example, one selects M/K at one position, one must then chose between M or K. This choice should result in selection of a pooled nucleotide comprising a nucleotide that complements the corresponding nucleotide in a reference sequence, when the probe and reference sequence are maximally aligned. The same principle governs the selection between R and Y, and between W and S. A trellis pool probe has one pooled position with four possibilities, and two pooled positions, each with two possibilities. Thus, a trellis pool probe comprises a mixture of 16 (4×2×2) probes. Since each pooled position includes one nucleotide that complements the corresponding nucleotide from the reference sequence, one of these 16 probes has a segment that is the exact complement of the reference sequence. A target sequence that is the same as the reference sequence (i.e., a wildtype target) gives a hybridization signal to each probe cell. Here, as in other tiling methods, the segment of complementarity should be sufficiently long to permit specific hybridization of a pooled probe to a reference sequence be detected relative to a variant of that reference sequence. Typically, the segment of complementarity is about 9–21 nucleotides.

A target sequence is analyzed by comparing hybridization intensities at three pooled probes, each having the structure described above. The segments complementary to the reference sequence present in the three pooled probes show some overlap.

Sometimes the segments are identical (other than at the interrogation positions). However, this need not be the case.

For example, the segments can tile across a reference sequence in increments of one nucleotide (i.e., one pooled probe differs from the next by the acquisition of one nucleotide at the 5' end and loss of a nucleotide at the 3' end). The three interrogation positions may or may not occur at the same relative positions within each pooled probe (i.e., spacing from a probe terminus). All that is required is that one of the three interrogation positions from each of the three pooled probes aligns with the same nucleotide in the reference sequence, and that this interrogation position is occupied by a different pooled nucleotide in each of the three probes. In one of the three probes, the interrogation position is occupied by an N. In the other two pooled probes the interrogation position is occupied by one of (M/K) or (R/Y) or (W/S).

In the simplest form of the trellis strategy, three pooled probes are used to analyze a single nucleotide in the reference sequence. Much greater economy of probes is achieved when more pooled probes are included in an array.

For example, consider an array of five pooled probes each having the general structure outlined above. Three of these pooled probes have an interrogation position that aligns with the same nucleotide in the reference sequence and are used to read that nucleotide. A different combination of three probes have an interrogation position that aligns with a different nucleotide in the reference sequence. Comparison of these three probe intensities allows analysis of this second nucleotide. Still another combination of three pooled probes from the set of five have an interrogation position that aligns with a third nucleotide in the reference sequence and these probes are used to analyze that nucleotide. Thus, three nucleotides in the reference sequence are fully analyzed from only five pooled probes. By comparison, the basic tiling strategy would require 12 probes for a similar analysis.

The trellis strategy employs an array of probes having at least three cells, each of which is occupied by a pooled probe as described above.

Consider the use of three such pooled probes for analyzing a target sequence, of which one position may contain any single base substitution to the reference sequence (i.e, there are four possible target sequences to be distinguished).

Three cells are occupied by pooled probes having a pooled interrogation position corresponding to the position of possible substitution in the target sequence, one cell with an 'N', one cell with one of 'M' or 'K', and one cell with 'R' or 'Y'. An interrogation position corresponds to a nucleotide in the target sequence if it aligns adjacent with that nucleotide when the probe and target sequence are aligned to maximize 45 complementarity. Note that although each of the pooled probes has two other pooled positions, these positions are not relevant for the present illustration. The positions are only relevant when more than one position in the target sequence is to be read, a circumstance that will be considered later. For present purposes, the cell with the 'N' in the interrogation position lights up for the wildtype sequence and any of the three single base substitutions of the target sequence.

A further class of strategies involving pooled probes are termed coding strategies. These strategies assign code words from some set of numbers to variants of a reference sequence. Any number of variants can be coded. The variants can include multiple closely spaced substitutions, deletions or insertions. The designation letters or other symbols assigned to each variant may be any arbitrary set of numbers, in any order. For example, a binary code is often used, but codes to other bases are entirely feasible. The numbers are often assigned such that each variant has a designation having at least one digit and at least one nonzero value for that digit.

For example, in a binary system, a variant assigned the number 101, has a designation of three digits, with one possible nonzero value for each digit.

The designation of the variants are coded into an array of pooled probes comprising a pooled probe for each nonzero value of each digit in the numbers assigned to the variants.

For example, if the variants are assigned successive number in a numbering system of base m, and the highest number assigned to a variant has n digits, the array would have about n x (m -1) pooled probes. In general, $\log_m$ (3N+1) probes are required to analyze all variants of N locations in a reference sequence, each having three possible mutant substitutions.

For example, 10 base pairs of sequence may be analyzed with only 5 pooled probes using a binary coding system.

Each pooled probe has a segment exactly complementary to the reference sequence except that certain positions are pooled.

The segment should be sufficiently long to allow specific hybridization of the pooled probe to the reference sequence relative to a mutated form of the reference sequence. As in other tiling strategies, segments lengths of 9–21 nucleotides are typical. Often the probe has no nucleotides other than the 9–21 nucleotide segment. The pooled positions comprise nucleotides that allow the pooled probe to hybridize to every variant assigned a particular nonzero value in a particular digit. Usually, the pooled positions further comprises a nucleotide that allows the pooled probe to hybridize to the reference sequence. Thus, a wildtype target (or reference sequence) is immediately recognizable from all the pooled probes being lit.

When a target is hybridized to the pools, only those pools comprising a component probe having a segment that is exactly complementary to the target light up. The identity of the target is then decoded from the pattern of hybridizing pools. Each pool that lights up is correlated with a particular value in a particular digit. Thus, the aggregate hybridization patterns of each lighting pool reveal the value of each digit in the code defining the identity of the target hybridized to the array.

6.8.3.1.2.9. Bridging Strategy

Probes that contain partial matches to two separate (i.e., non contiguous) subsequences of a target sequence sometimes hybridize strongly to the target sequence. In certain instances, such probes have generated stronger signals than probes of the same length which are perfect matches to the target sequence. It is believed (but not necessary to the invention) that this observation results from interactions of a single target sequence with two or more probes simultaneously. This invention exploits this observation to provide arrays of probes having at least first and second segments, which are respectively complementary to first and second subsequences of a reference sequence. Optionally, the probes may have a third or more complementary segments. These probes can be employed in any of the strategies noted above.

The two segments of such a probe can be complementary to disjoint subsequences of the reference sequences or contiguous subsequences. * If the latter, the two segments in the probe are inverted relative to the order of the complement of the reference sequence. The two subsequences of the reference sequence each typically comprises about 3 to 30 contiguous nucleotides. The subsequences of the reference sequence are sometimes separated by 0, 1, 2 or 3 bases. Often the sequences, are adjacent and nonoverlapping.

The bridging strategy offers the following advantages:
(1) Higher discrimination between matched and mismatched probes, (2) The possibility of using longer probes in a bridging tiling, thereby increasing the specificity of the hybridization, without sacrificing discrimination, (3) The use of probes in which an interrogation position is located very off-center relative to the regions of target complementarity. This may be of particular advantage when, for example, when a probe centered about one region of the target gives low hybridization signal. The low signal is overcome by using a probe centered about an adjoining region giving a higher hybridization signal. (4) Disruption of secondary structure that might result in annealing of certain probes (see previous discussion of helper mutations).

6.8.3.1.2.10. Deletion Tiling

Deletion tiling is related to both the bridging and helper mutant strategies described above. In the deletion strategy, comparisons are performed between probes sharing a common deletion but differing from each other at an interrogation position located outside the deletion. For example, a first probe comprises first and second segments, each exactly complementary to respective first and second subsequences of a reference sequence, wherein the first and second subsequences of the reference sequence are separated by a short distance (e.g., 1 or 2 nucleotides). The order of the first and second segments in the probe is usually the same as that of the complement to the first and second subsequences in the reference sequence.

Such tilings sometimes offer superior discrimination in hybridization intensities between the probe having an interrogation position complementary to the target and other probes. Thermodynamically, the difference between the hybridizations to matched and mismatched targets for the probe set shown above is the difference between a single-base bulge, and a large asymmetric loop (e.g., two bases of target, one of probe). This often results in a larger difference in stability than the comparison of a perfectly matched probe with a probe showing a single base mismatch in the basic tiling strategy.

The use of deletion or bridging probes is quite general. These probes can be used in any of the tiling strategies of the invention. As well as offering superior discrimination, the use of deletion or bridging strategies is advantageous for certain probes to avoid self-hybridization (either within a probe or between two probes of the same sequence)

6.8.3.1.3. Preparation of Target Samples

The target polynucleotide, whose sequence is to be determined, is usually isolated from a tissue sample. If the target is genomic, the sample may be from any tissue (except exclusively red blood cells). For example, whole blood, peripheral blood lymphocytes or PBMC, skin, hair or semen are convenient sources of clinical samples. These sources are also suitable if the target is RNA. Blood and other body fluids are also a convenient source for isolating viral nucleic acids. If the target is mRNA, the sample is obtained from a tissue in which the mRNA is expressed. If the polynucleotide in the sample is RNA, it is usually reverse transcribed to DNA. DNA samples or cDNA resulting from reverse transcription are usually amplified, e.g., by PCR. Depending on the selection of primers and amplifying enzyme(s), the amplification product can be RNA or DNA.

Paired primers are selected to flank the borders of a target polynucleotide of interest. More than one target can be simultaneously amplified by multiplex PCR in which multiple paired primers are employed. The target can be labelled at one or more nucleotides during or after amplification. For some target polynucleotides (depending on size of sample), e.g., episomal DNA, sufficient DNA is present in the tissue sample to dispense with the amplification step.

When the target strand is prepared in single-stranded form as in preparation of target RNA, the sense of the strand should of course be complementary to that of the probes on the chip. This is achieved by appropriate selection of primers.

The target is preferably fragmented before application to the chip to reduce or eliminate the formation of secondary structures in the target. The average size of targets segments following hybridization is usually larger than the size of probe on the chip.

6.8.3.2. Modes Of Practicing The Invention

In an exemplary method, light is shone through a mask to activate functional (for oligonucleotides, typically an -OH) groups protected with a photoremovable protecting group on a surface of a solid support. After light activation, a nucleoside building block, itself protected with a photoremovable protecting group (at the 5'-OH), is coupled to the activated areas of the support. The process can be repeated, using different masks or mask orientations and building blocks, to prepare very dense arrays of many different oligonucleotide probes. New methods for the combinatorial chemical synthesis of peptide, polycarbamate, and oligonucleotide arrays have recently been reported (see Fodor et al., 1991, Science 251: 767–773; Cho et al., 1993, Science 261: 1303–1305; and Southern et al., 1992, Genomics 13: 1008–10017, each of which is incorporated herein by reference). These arrays, or biological chips (see Fodor et al., 1993, Nature 364: 555–556, incorporated herein by reference), harbor specific chemical compounds at precise locations in a high-density, information rich format, and are a powerful tool for the study of biological recognition processes. A particularly exciting application of the array technology is in the field of DNA sequence analysis. The hybridization pattern of a DNA target to an array of shorter oligonucleotide probes is used to gain primary structure information of the DNA target. This format has important applications in sequencing by hybridization, DNA diagnostics and in elucidating the thermodynamic parameters affecting nucleic acid recognition.

Conventional DNA sequencing technology is a laborious procedure requiring electrophoretic size separation of labeled DNA fragments. An alternative approach, termed Sequencing By Hybridization (SBH), has been proposed (Lysov et al., 1988, Dokl. Akad. Nauk SSSR 303:1508–1511; Bains et al., 1988, J. Theor. Biol. 135:303–307; and Drmanac et al., 1989, Genomics 4:114–128, incorporated herein by reference). This method uses a set of short oligonucleotide probes of defined sequence to search for complementary sequences on a longer target strand of DNA. The hybridization pattern is used to reconstruct the target DNA sequence. It is envisioned that hybridization analysis of large numbers of probes can be used to sequence long stretches of DNA. In immediate applications of this hybridization methodology, a small number of probes can be used to interrogate local DNA sequence.

Hybridization methodology can be carried out by attaching target DNA to a surface. The target is interrogated with a set of oligonucleotide probes, one at a time (see Strezoska et al., 1991, Proc. Natl. Acad. Sci. USA 88:10089–10093, and Drmanac et al., 1993, Science 260:1649–1652, each of which is incorporated herein by reference). This approach can be implemented with well established methods of immobilization and hybridization detection, but involves a large number of manipulations. For example, to probe a sequence utilizing a full set of octanucleotides, tens of thousands of hybridization reactions must be performed. Alternatively, SBH can be carried out by attaching probes to a surface in an array format where the identity of the probes at each site is known. The target DNA is then added to the array of probes.

The hybridization pattern determined in a single experiment directly reveals the identity of all complementary probes.

As noted above, a preferred method of oligonucleotide probe array synthesis involves the use of light to direct the synthesis of oligonucleotide probes in high-density, miniaturized arrays. Photolabile 5'-protected N-acyl-deoxynucleoside phosphoramidites, surface linker chemistry, and versatile combinatorial synthesis strategies have been developed for this technology. Matrices of spatially-defined oligonucleotide probes have been generated, and the ability to use these arrays to identify complementary sequences has been demonstrated by hybridizing fluorescent labeled oligonucleotides to the DNA chips produced by the methods. The hybridization pattern demonstrates a high degree of base specificity and reveals the sequence of oligonucleotide targets.

The surface of a solid support modified with photolabile protecting groups is illuminated through a photolithographic mask, yielding reactive hydroxyl groups in the illuminated regions. A 3'-0-phosphoramidite activated deoxynucleoside (protected at the 51-hydroxyl with a photolabile group) is then presented to the surface and coupling occurs at sites that were exposed to light. Following capping, and oxidation, the substrate is rinsed and the surface illuminated through a second mask, to expose additional hydroxyl groups for coupling. A second 5'-protected, 3'-0-phosphoramidite activated deoxynucleoside is presented to the surface. The selective photodeprotection and coupling cycles are repeated until the desired set of products is obtained.

Light directed chemical synthesis lends itself to highly efficient synthesis strategies which will generate a maximum number of compounds in a minimum number of chemical steps.

To carry out hybridization of DNA targets to the probe arrays, the arrays are mounted in a thermostatically controlled hybridization chamber. Fluorescein labeled DNA targets are injected into the chamber and hybridization is allowed to proceed for 5 min to 24 hr. The surface of the matrix is scanned in an epifluorescence microscope (Zeiss Axioscop 20) equipped with photon counting electronics using 50–100 uW of 488 nm excitation from an Argon ion laser (Spectra Physics Model 2020). Measurements may be made with the target solution in contact with the probe matrix or after washing. Photon counts are stored and image files are presented after conversion to an eight bit image format.

Arrays of oligonucleotides can be efficiently generated by light-directed synthesis and can be used to determine the identity of DNA target sequences. Because combinatorial strategies are used, the number of compounds increases exponentially while the number of chemical coupling cycles increases only linearly. For example, synthesizing the complete set of $4^8$ (65,536) octanucleotides will add only four hours to the synthesis for the 16 additional cycles.

Furthermore, combinatorial synthesis strategies can be implemented to generate arrays of any desired composition. For example, because the entire set of dodecamers ($4^{12}$) can be produced in 48 photolysis and coupling cycles (b" compounds requires b×n cycles), any subset of the dodecamers (including any subset of shorter oligonucleotides) can be constructed with the correct lithographic mask design in 48 or fewer chemical coupling steps. In addition, the number of compounds in an array is limited only by the density of synthesis sites and the overall array size. Recent experiments have demonstrated hybridization to probes synthesized in 25 um sites. At this resolution, the entire set of 65,536 octanucleotides can be placed in an array measuring 0.64 cm square, and the set of 1,048,576 dodecanucleotides requires only a 2.56 cm array.

Genome sequencing projects will ultimately be limited by DNA sequencing technologies. Current sequencing methodologies are highly reliant on complex procedures and require substantial manual effort. Sequencing by hybridization has the potential for transforming many of the manual efforts into more efficient and automated formats. Light-directed synthesis is an efficient means for large scale production of miniaturized arrays for SBH. The oligonucleotide arrays are not limited to primary sequencing applications. Because single base changes cause multiple changes in the hybridization pattern, the oligonucleotide arrays provide a powerful means to check the accuracy of previously elucidated DNA sequence, or to scan for changes within a sequence. In the case of octanucleotides, a single base change in the target DNA results in the loss of eight complements, and generates eight new complements. Matching of hybridization patterns may be useful in resolving sequencing ambiguities from standard gel techniques, or for rapidly detecting DNA mutational events. The potentially very high information content of light-directed oligonucleotide arrays will change genetic diagnostic testing. Sequence comparisons of hundreds to thousands of different genes will be assayed simultaneously instead of the current one, or few at a time format. Custom arrays can also be constructed to contain genetic markers for the rapid identification of a wide variety of pathogenic organisms.

Oligonucleotide arrays can also be applied to study the sequence specificity of RNA or protein-DNA interactions.

Experiments can be designed to elucidate specificity rules of non Watson-Crick oligonucleotide structures or to investigate the use of novel synthetic nucleoside analogs for antisense or triple helix applications. Suitably protected RNA monomers may be employed for RNA synthesis. The oligonucleotide arrays should find broad application deducing the thermodynamic and kinetic rules governing formation and stability of oligonucleotide complexes.

Other than the use of photoremovable protecting groups, the nucleoside coupling chemistry is very similar to that used routinely today for oligonucleotide synthesis.

7 Plant Gene Expression

7. General Considerations

The present invention provides a chimeric recombinant DNA molecule comprising: a plurality of DNA sequences, each of which comprises a plant-functional promoter linked to a coding region, which encodes a virus-associated coat protein, wherein said DNA sequences are preferably linked in-tandem so that they are expressed in virus-susceptible plant cells transformed with said recombinant DNA molecule to impart resistance to said viruses; as well as methods for transforming plants with the chimeric constructs and for selecting plants which express at least one of said DNA sequences imparting viral resistance.

A method for making a genetically modified plant comprising regenerating a whole plant from a plant cell that has been transfected with DNA sequences comprising a first gene whose expression results in an altered plant phenotype linked to a transiently active promoter, the gene and promoter being separated by a blocking sequence flanked on either side by specific excision sequences, a second gene that encodes a recombinase specific for the specific excision sequences linked to a repressible promoter, and a third gene that encodes the repressor specific for the repressible promoter. Also a method for making a genetically modified hybrid plant by hybridizing a first plant regenerated from a plant cell that has been transfected with DNA sequences comprising a first gene whose expression results in an altered plant phenotype linked to a transiently active promoter, the gene and promoter being separated by a blocking sequence flanked on either side by specific excision sequences to a second plant regenerated from a second plant cell that has been transfected with DNA sequences comprising a second gene that encodes a recombinase specific for the specific excision sequences linked to a promoter that is active during seed germination, and growing a hybrid plant from the hybrid seed. Plant cells, plant tissues, plant seed and whole plants containing the above DNA sequences are also claimed.

The present invention is also directed to a DNA construct formed from a fusion gene which includes a trait DNA molecule and a silencer DNA molecule. The trait DNA molecule has a length that is insufficient to impart a desired trait to plants transformed with the trait DNA molecule. The silencer DNA molecule is operatively coupled to the trait DNA molecule with the trait and silencer DNA molecules collectively having sufficient length to impart the trait to plants transformed with the DNA construct. Expression systems, host cells, plants, and plant seeds containing the DNA construct are disclosed. The present invention is also directed to imparting multiple traits to a plant.

The present invention is also directed to methods of introgressing one or more desired quantitative traits into a plant comprising screening one or more restriction fragment length polymorphisms (RFLP) for association with desired quantitative traits (QT), selecting one or more RFLP's showing association with the desired QT's, developing a mathematical model based on the magnitude of the association of RFLP(s) to predict the degree of expression of the desired QT's, and using the thus-selected RFLP(s) and the mathematical model in a plant breeding program to predict the degree of introgression and expression of the desired QT's in plant progeny.

A method for producing one of the following proteins in transgenic monocot plant cells is disclosed: (i) mature, glycosylated $\alpha_1$-antitrypsin (AAT) having the same N-terminal amino acid sequence as mature AAT produced in humans and a glycosylation pattern which increases serum halflife substantially over that of mature non-glycosylated AAT; (ii) mature, glycosylated antithrombin III (ATIII) having the same N-terminal amino acid sequence as mature ATIII produced in humans; (iii) mature human serum albumin (HSA) having the same N-terminal amino acid sequence as mature HSA produced in humans and having the folding pattern of native mature HSA as evidenced by its bilirubin-binding characteristics; and (iv) mature, active subtilisin BPN' (BPN') having the same N-terminal amino acid sequence as BPN' produced in Bacillus. Monocot plants cells are transformed with a chimeric gene which includes a DNA coding sequence encoding a fusion protein having an (i) N-terminal moiety corresponding to a rice α-amylase signal sequence peptide and, (iii) immediately adjacent the C-terminal amino acid of said peptide, a protein moiety corresponding to the mature protein to be produced.

A process for commercially propagating plants by tissue culture in such a way as both to conserve desired plant morphology and to transform the plant with respect to one or more desired genes. The method includes the steps of (a) creating an Agrobacterium vector containing the gene sequence desired to be transferred to the propagated plant, preferably together with a marker gene; (b) taking one or more petiole explants from a mother plant and inoculating them with the Agrobacterium vector; (c) conducting callus formation in the petiole sections in culture, in the dark; and (d) culturing the resulting callus in growth medium containing a benzylamino growth regulator such as benzylaminopurine or, most preferably, benzylaminopurine-riboside. Additional optional growth regulators including auxins and cytokinins (indole butyric acid, benzylamine, benzyladenine, benzylaminopurine, alpha naphthylacetic acid and others known in the art) may also be present. Preferably, the petiole tissue is taken from *Pelargonium x domesticum* and the Agrobacterium vector contains an antisense gene for ACC synthase or ACC oxidase to prevent ACC synthase or ACC oxidase expression and, in turn, the ethylene formation for which these enzymes are precursors.

7.1 Experimental Approach

This invention is related to the genetic engineering of plants and to a means and method (use of DNA construct) for conferring a plurality of traits, including resistance to viruses, to a plant using a vector encoding a plurality of genes, such as coat protein genes, protease genes, or replicase genes. The field of the invention is plant genetics, including genetic mapping and restriction fragment length polymorphism technology.

The present invention also relates to:
(i) the production of mature proteins in plant cells, and in particular, to the production of proteins in mature secreted form.
(i) the development of techniques for the commercial production of transgenic plants.

7.2. Production of Virus Resistant Plants

The genetic manipulation of plants is centuries old, and modern crop yields and disease- and pest-resistances often owe much to traditional plant genetic engineering. Classical plant breeding methods are time-consuming and subject to chance, however, so the recent advent of recombinant DNA techniques is promising. This promise is encouraging especially with respect to enabling plant geneticists to identify and to clone specific genes for desirable traits, and to introduce such genes into already useful varieties of plants.

7.2.1 Infection of Crops by Plant Virus

Many agriculturally important crops are susceptible to infection by plant viruses, which can seriously damage a crop, reduce its economic value to the grower, and increase its cost to the consumer. Attempts to control or prevent infection of a crop by a plant virus have been made, yet viral pathogens continue to be a significant problem in agriculture.

7.2.2 Production of Virus Resistant Plants

Scientists have recently developed means to produce virus resistant plants using genetic engineering techniques. Such an approach is advantageous in that the genetic material which provides the protection is incorporated into the genome of the plant itself and can be passed on to its progeny. A host plant is resistant if it possesses the ability to suppress or retard the multiplication of a virus, or the development of pathogenic symptoms. "Resistant" is the opposite of "susceptible," and may be divided into: (1) high, (2) moderate, or (3) low resistance, depending upon its effectiveness. Essentially, a resistant plant shows reduced or no symptom expression, and virus multiplication within it is reduced or negligible.

Several different types of host resistance to viruses are recognized. The host may be resistant to: (1) establishment of infection, (2) virus multiplication, or (3) viral movement.

7.2.3 Example of Plant Virus: Potyvirus

Potyviruses are a distinct group of plant viruses which are pathogenic to various crops, and which demonstrate cross-infectivity between plant members of different families. Potyviruses include watermelon mosaic virus-2 (WMV); papaya ringspot virus strains papaya ringspot and watermelon mosaic I (PRV-p and PRV-w), two closely related members of the plant potyvirus group which were at one time classified as distinct virus types, but are presently classified as different strains of the same virus; zucchini yellow mosaic virus (ZYMV); potato virus Y; tobacco etch and many others.

These viruses consist of flexous, filamentous particles of dimensions approximately 780×12 nanometers. The viral particles contain a single-stranded RNA genome containing about 10,000 nucleotides of positive (+, coding, or sense) polarity. Translation of the RNA genome of potyviruses shows that the RNA encodes a single Large polyprotein of about 330 kD. This polyprotein contains several proteins, one of which is a 49 kD protease that is specific for the cleavage of the polyprotein into at least six (6) other peptides. These proteins can be found in the infected plant cell and form the necessary components for viral replication. One of the proteins contained within this polyprotein is a 35 kD capsid or coat protein which coats and protects the viral RNA from degradation. Another protein is the nuclear inclusion protein, also referred to as replicase, which is believed to function in the replication of the viral RNA. In the course of a potyviral infection, the replicase protein (60 kDa, also referred to as the nuclear inclusion B protein) and the protease protein (50 kDa, also referred to as the nuclear inclusion I or nuclear inclusion A protein) are posttranslationally transported across the nuclear membrane into the nucleus of the plant cell at the later stages of viral infection and accumulate to high levels.

Generally, the coat protein gene is located at the 3'-end of the RNA, just prior to a stretch of terminal adenine nucleotide residues (200 to 300 bases). The location of the 49 Kd protease gene appears to be conserved in these viruses. In the tobacco etch virus, the protease cleavage site has been determined to be the dipeptide Gln-Ser, Gln-Gly or Gln-Ala. Conservation of these dipeptides as the cleavage sites in these viral polyproteins is apparent from the sequences of the above-listed potyviruses.

Expression of the coat protein genes from tobacco mosaic virus, alfalfa mosaic virus, cucumber mosaic virus, and potato virus X, among others, in transgenic plants has resulted in plants which are resistant to infection by the respective virus. Some evidence of heterologous protection has also been reported. For example, Namba et al., *Phytopathology*, 82, 940 (1992) report that expression of coat protein genes from watermelon mosaic virus-2 or zucchini yellow mosaic virus in transgenic tobacco plants conferred protection against six other potyviruses: bean yellow mosaic virus, potato virus Y, pea mosaic virus, clover yellow vein virus, pepper mottle virus and tobacco etch virus. Stark et al., Biotechnology, 1, 1257 (1989) report that expression of the potyvirus soybean mosaic virus in transgenic plants provided protection against two serologically unrelated potyviluses: tobacco etch virus and potato virus Y.

However, expression of a preselected coat protein gene does not reliably confer heterologous protection to a plant. For example, transgenic squash plants containing the CMV-C coat protein gene and which have been shown to be resistant to CMV-C strain, are not protected against several highly virulent strains of CMV, including CW-V-27 and CARNA-5. Thus, a need exists for improved methods to impart potyvirus resistance to plants.

7.2.4 Using "Pathogen Driven Resistance" (PDR) for Developing Virus Resistant Transgenic Plants Control of plant virus diseases took a major step forward in the last decade when it was shown in 1986 that the tobacco mosaic virus ("TMV") coat protein gene that was expressed in transgenic tobacco conferred resistance to TMV (Powell-Abel, P., et al., "Delay of Disease Development in Transgenic Plants that Express the Tobacco Mosaic Virus Coat Protein Gene," *Science*, 232:738–43 (1986)). The concept of pathogen-derived resistance ("PDR"), which states that pathogen genes that are expressed in transgenic plants will confer resistance to infection by the homologous or related pathogens (Sanford, J. C., et al. "The Concept of Parasite-Derived Resistance—Deriving Resistance Genes from the Parasite's Own Genome," *J. Theor. Biol.*, 113:395–405 (1985)) was introduced at about the same time. Since then, numerous reports have confirmed that PDR is a useful strategy for developing transgenic plants that are resistant to many different viruses (Lomonossoff, G. P., "Pathogen-Derived Resistance to Plant Viruses," *Ann. Rev. Photopathol.*, 33:323–43 (1995)).

Only eight years after the report by Beachy and colleagues (Powell-Abel, P., et al., "Delay of Disease Development in Transgenic Plants that Express the Tobacco Mosaic Virus Coat Protein Gene," Science, 232:738–43 (1986)), Grumet, R., "Development of Virus Resistant Plants via Genetic Engineering," Plant Breedinq Reviews, 12:47–49 (1994) reviewed the PDR literature and listed the successful development of virus resistant transgenic plants to at least 11 different groups of plant viruses.

7.2.1.4.1 Utilizing the Coat Protein Genes

The vast majority of reports have utilized the coat protein genes of the viruses that are targeted for control. Although the testing of transgenic plants have been largely confined to laboratory and greenhouse experiments, a growing number of reports showed that resistance is effective under field conditions (e.g., Grumet, R., "Development of Virus Resistant Plants via Genetic Engineering," *Plant Breeding Reviews*, 12:47–49 (1994)). Two virus resistant crops have been deregulated by APHIS/USDA and thus are approved for unrestricted release into the environment in the U.S.A. Squash that are resistant to watermelon mosaic virus 2 and zucchini yellow mosaic potyviruses have been commercialized (Fuchs, M., et al., "Resistance of Transgenic Hybrid Squash ZW-20 Expressing the Coat Protein Genes of Zucchini Yellow Mosaic Virus and Watermelon Mosaic Virus 2 to Mixed Infections by Both Potyviruses," *Bio/Technology*, 13:1466–73 (1995); Tricoli, D. M., et al., "Field Evaluation of Transgenic Squash Containing Single or Multiple Virus Coat Protein Gene Constructs for Resistance to Cucumber Mosaic Virus, Watermelon Mosaic Virus 2, and Zucchini Yellow Mosaic Virus," *Bio/Technology*, 13:1458–65 (1995)). Also, a transgenic papaya that is resistant to papaya ringspot virus has been developed (Fitch, M. M. M., et al., "Virus Resistant Papaya Derived from Tissues Bombarded with the Coat Protein Gene of Papaya Ringspot Virus," *Bio/Technology*, :1466–72 (1992); Tennant, P. F., et al., "Differential Protection Against Papaya Ringspot Virus Isolates in Coat Protein Gene Transgenic Papaya and Classically Cross-Protected Papaya," *Phytopathology*, 84:1359–66 (1994)). This resistant transgenic papaya was recently deregulated by USDA/APHIS. Deregulation of the transgenic papaya is timely, because Hawaii3 s papaya industry is being devastated by papaya ringspot virus. Undoubtedly, more crops will be deregulated and commercialized in the near future.

7.2.1.4.2 Other Effective Viral Genes

Interestingly, remarkable progress has been made in developing virus resistant transgenic plants despite a poor understanding of the mechanisms involved in the various forms of pathogen-derived resistance (Lomonossoff, G. P., "Pathogen-Derived Resistance to Plant Viruses," *Ann.-Rev. Photopathol.*, 33:323–43 (1995)). Although most reports deal with the use of coat protein genes to confer resistance, a growing number of reports have shown that viral replicase (Golemboski, D. B., et al., "Plants Transformed with a Tobacco Mosaic Virus Nonstructural Gene Sequence are Resistant to the Virus," *Proc. Natl. Acad. Sci. USA*, 87:6311–15 (1990)), movement protein (e.g., Beck, D. L., et al., "Disruption of Virus Movement Confers Broad-Spectrum Resistance Against Systemic Infection by Plant Viruses with a Triple Gene Block," Proc. Natl. Acad. Sci. USA, 91:10310–14 (1994)), NIa proteases of potyviruses (e.g., Maiti, I. B., et al., "Plants that Express a Potyvirus Proteinase Gene are Resistant to Virus Infection," *Proc. Natl. Acad. Sci. USA*, 90:6110–14 (1993)), and other viral genes are effective. This led to the conclusion that any part of a plant viral genome gives rise to PDR. Furthermore, the viral genes can be effective in the translatable and nontranslatable sense forms, and less frequently antisense forms (e.g., Baulcombe, D. C., "Mechanisms of Pathogen-Derived Resistance to Viruses in Transgenic Plants," *Plant Cell*, 8:1833–44 (1996); Dougherty, W. G., et al., "Transgenes and Gene Suppression: Telling us Something New?," Current Opinion in Cell Biology, 7:399–05 (1995); Lomonossoff, G. P., "Pathogen-Derived Resistance to Plant Viruses," Ann. Rev. Photopathol. 33:323–43 (1995)).

7.2.1.5 RNA-Mediated Resistance 7.1.2.1.5.1 Description (A Form of PDR)

RNA-mediated resistance is the form of PDR where there is clear evidence that viral proteins do not play a role in conferring resistance to the transgenic plant. The first clear cases for RNA-mediated resistance were reported in 1992 for tobacco etch ("TEV") potyvirus (Lindbo, et al., "Pathogen-Derived Resistance to a Potyvirus Immune and Resistance Phenotypes in Transgenic Tobacco Expressing Altered Forms of a Potyvirus Coat Protein Nucleotide Sequence," *Mol. Plant Microbe Interact.,* 5:144–53 (1992)), for potato virus Y ("PVY") potyvirus by Van Der Vlugt, R. A. A., et al., "Evidence for Sense RNA-Mediated Protection to PVY in Tobacco Plants Transformed with the Viral Oat Protein Cistron," Plant *Mol. Biol.,* 20:631–39 (1992), and for tomato spotted wilt ("TSWV") tospovirus by de Haan, P., et al., "Characterization of RNA-Mediated Resistance to Tomato Spotted Wilt Virus in Transgenic Tobacco Plants," Bio/Technology, 10:1133–37 (1992). others confirmed the occurrence of RNA-mediated resistance with potyviruses (Smith, H. A., et al., "Transgenic Plant Virus Resistance Mediated by Untranslatable Sense RNAs: Expression, Regulation, and Fate of Nonessential RNAs," *Plant Cell,* 6:1441–53 (1994)), potexviruses (Mueller, E., et al., "Homology-Dependent Resistance: Transgenic Virus Resistance in Plants Related to Homology-Dependent Gene Silencing," *Plant Journal,* 7:1001–13 (1995)), and TSWV and other topsoviruses (Pang, S. Z., et al., "Resistance of Transgenic Nicotiana Benthamiana Plants to Tomato Spotted Wilt and Impatiens Necrotic Spot Tospoviruses: Evidence of Involvement of the N Protein and N Gene RNA in Resistance," Phytopathology, 84:243–49 (1994); Pang, S. -Z., et al., "Different Mechanisms Protect Transgenic Tobacco Against Tomato Spotted Wilt Virus and Impatiens Necrotic Spot Tospoviruses," BiolTechnology 11:819–24 (1993)). More recent work has shown that RNA-mediated resistance also occurs with the comovirus cowpea mosaic virus (Sijen, T., et al., "RNA-Mediated Virus Resistance: Role of Repeated Transgene and Delineation of Targeted Regions," Plant Cell, 8:2227–94 (1996)) and squash mosaic virus (Jan, F. -J., et al., "Genetic and Molecular Analysis of Squash Plants Transformed with Coat Protein Genes of Squash Mosaic Virus," Phytopathology, 86:S16–17 (1996)).

7.2.1.5.2 The Mechanism(s) of RNA-Mediated Resistance

Major advances towards understanding the mechanism(s) of RNA-mediated resistance were made by Dougherty and colleagues in a series of experiments with TEV and PVY. Using TEV, Lindbo, J. A., "Pathogen-Derived Resistance to a Potyvirus Immune and Resistant Phenotypes in Transgenic Tobacco Expressing Altered Forms of a Potyvirus Coat Protein Nucleotide Sequence," *Mol. Plant Microbe Interact.,* 5:144–53 (1992) and Lindbo, J. A., et al., "Untranslatable Transcripts of the Tobacco Etch Virus Coat Protein Gene Sequence can Interfere with Tobacco Etch Virus Replication in Transgenic Plants and Protoplasts," *Virology,* 189:725–33 (1992) showed that transgenic plants expressing translatable full length coat protein, truncated translatable coat protein, antisense coat protein genes, and nontranslatable coat protein gene had various phenotypic reactions after inoculation with TEV. Transgenic plants displayed resistance, recovery (inoculated plants initially show systemic infection but younger leaves that develop later are symptomless and resistant to the virus), or susceptible phenotypes. Furthermore, they showed that leaves of resistant plants and asymptomatic leaves of recovered plants had relatively low levels of steady state RNA when compared to those in leaves of susceptible plants (Lindbo, J. A., et al., "Induction of a Highly Specific Antiviral State in Transgenic Plants: Implications for Regulation of Gene Expression and Virus Resistance," *Plant Cell,* 5:1749–59 (1993)). However, nuclear run off experiments showed that those plants with low levels of steady state RNA had higher transcription rates of the viral transgene than those plants that were susceptible (and had high steady state RNA levels). To account for these observations, it was proposed "that the resistant state and reduced steady state levels of transgene transcript accumulation are mediated at the cellular level by a cytoplasmic activity that targets specific RNA sequences for inactivation," (Lindbo, J. A., et al., "Induction of a Highly Specific Antiviral State in Transgenic Plants: Implications for Regulation of Gene Expression and Virus Resistance," *Plant Cell,* 5:1749–59 (1993)). It was also suggested that the low steady state RNA levels may be due to post-transcriptional gene silencing, a phenomenon that was first proposed by de Carvalho, F., et al., "Suppression of beta-1,3-glucanase Transgene Expression in Homozygous Plants," *EMBO J.,* 11:2595–602 (1992) for the suppression of P-1,3-glucanase transgene in homozygous transgenic plants.

An RNA threshold model was proposed to account for the observations (Lindbo, J. A., et al., "Induction of a Highly Specific Antiviral State in Transgenic Plants: Implications for Regulation of Gene Expression and Virus Resistance," *Plant Cell,* 5:1749–59 (1993)). Basically, the model states that there is a cytoplasmic cellular degradation mechanism that acts to limit the RNA levels in plant cells, and that this mechanism is activated when the transgenic RNA transcript goes above a threshold level. The degradation mechanism is specific for the transcript that goes above the threshold level; and if the transcripts that go above a certain threshold is a viral transgene, the virus resistance state is observed in the plant, because the degradation mechanism also targets, for inactivation, the specific sequences of the incoming virus. The model also accounts for the 'recovery' of transgenic plants by suggesting that viral RNA from the systemically invading virus triggers the phenomenon in some transgenic plants that have two copies of the transgenes. Plants that had more than three copies of the transgenes caused the threshold level to be surpassed without the invasion of virus (Goodwin, J., et al., "Genetic and Biochemical Dissection of Transgenic RNA-Mediated Virus Resistance," *Plant Cell,* 8:95–105 (1996); Smith, H. A., et al., "Transgenic Plant Virus Resistance Mediated by Untranslatable Sense RNAs: Expression, Regulation, and Fate of Nonessential RNAs," *Plant Cell,* 6:1441–53 (1994)). Although the degradation mechanism is not clear, it is proposed that a cellular RNA dependent RNA polymerase ("RdRp") binds to the transcript and produces small fragments of anti sense RNA which then bind to other transcripts to form duplexes which are then degraded by nucleases that specifically recognize RNA-RNA duplexes. This degradation mechanism is sequence specific, which accounts for the specificity of RNA-mediated resistance.

Work on PVX by Baulcombe and colleagues (English, J. J., et al., "Suppression of Virus Accumulation in Transgenic Plants Exhibiting Silencing of Nuclear Genes," *Plant Cell,* 8: 179–88 (1996); Mueller, E., et al., "Homology-Dependent Resistance: Transgenic Virus Resistance in Plants Related to Homology-Dependent Gene Silencing, "*Plant Journal,* 7:1001–13 (1995)) confirmed and extended the results by Dougherty and colleagues. An aberrant RNA model which is a modification of the RNA threshold model proposed by Dougherty and colleagues was proposed. The features of the model are similar to Dougherty3 s except that it states that the RNA level is not the sole trigger to activate the cellular degradation mechanism, but instead aberrant RNA that are produced during the transcription of the transgene plays an important part in activating the cytoplasmic cellular mechanism that degrades specific RNA. The production of aberrant RNA may be enhanced by positional affects of the transgene on the chromosome and by methylation of the transgene DNA. The precise nature of the aberrant RNA is not defined, but it may contain a characteristic that makes it a preferred template for the production of antisense RNA by the host encoded RdRp (Baulcombe, D. C., "Mechanisms of Pathogen-Derived Resistance to Viruses in Transgenic Plants," Plant Cell, 8:1833–44 (1996); English, J. J., et al., "Suppression of Virus Accumulation in Transgenic Plants Exhibiting Silencing of Nuclear Genes," Plant Cell, 8: 179–88 (1996)). Thus, the model also proposes that RdRp and antisense molecules are involved in the degradation mechanism. Baulcombe and colleagues confirmed that plants which show low steady state transgene levels have multiple copies of transgenes and that the low steady state RNA and the accompanying resistant state is due to post-transcriptional gene silencing. The term homology-dependent resistance was proposed to describe the resistance in plants that show homology-dependent gene silencing (Mueller, E., et al., "Homology-Dependent Resistance: Transgenic Virus Resistance in Plants Related to Homology-Dependent Gene Silencing," Plant Journal, 7:1001–13 (1995)).

Experiments with TSWV tospovirus (Pang, S. Z., et al., "Post-Transcriptional Transgene Silencing and Consequent Tospovirus Resistance in Transgenic Lettuce are Affected by Transgene Dosage and Plant Development," Plant Journal, 9:899–09 (1996); Prins, M., et al., "Engineered RNA Mediated Resistance to Tomato Spotted Wilt Virus is Sequence Specific," Mol. Plant Microbe Interact., 9:416–18 (1996)) and cowpea mosaic comovirus (Sijen, T., et al., "RNA-Mediated Virus Resistance: Role of Repeated Transgene and Delineation of Targeted Regions," Plant Cell, 8:2227–94 (1996)) also showed that resistance in transgenic plants is a consequence of post-transcriptional gene silencing. Pang, S. Z., et al., "Post-Transcriptional Transgene Silencing and Consequent Tospovirus Resistance in Transgenic Lettuce are Affected by Transgene Dosage and Plant Development," Plant Journal, 9:899–09 (1996) showed that post-transcriptional gene silencing in transgenic lettuce expressing the N 1S gene of TSWV was influenced by gene dosage and by the developmental stage of the plant. The effect of developmental stage on post-transcriptional gene silencing of transgenes and their effect on resistance had not been previously shown for transgenic plants expressing viral genes, but had been shown to occur in plants expressing other transgenes (de Carvalho, F., et al., "Suppression of beta-1,3-glucanase Transgene Expression in Homozygous Plants," EMBO J., 11:2595–02 (1992)). Post-transcriptional gene silencing could also account for the correlation of low steady state level of N gene RNA in transgenic tobacco showing very high but specific resistance (Pang, S. Z., et al., "Different Mechanisms Protect Transgenic Tobacco Against Tomato Spotted Wilt and Impatiens Necrotic Spot Tospoviruses," Bio/Technology, 11:819–24 (1993)). Prins, M., et al., "Engineered RNA-Mediated Resistance to Tomato Spotted Wilt Virus is Sequence Specific," Molecular Plant Microbe Interactions, 9:416–18 (1 996) also reported that post-transcriptional gene silencing occurred with transgenic tobacco expressing the N gene and nonstructural gene of the mRNA. Interestingly, it was found that tobacco with other parts of the TSWV genome were not resistant. They suggested, as one explanation, that those gene fragments which did not confer resistance may not fit the criteria for inducing post-transcriptional gene silencing. Sijen, T., et al., "RNA-Mediated Virus Resistance: Role of Repeated Transgene and Delineation of Targeted Regions," Plant Cell, 8:2227–94 (1996) showed that resistance of transgenic plants expressing the movement protein, replicase, or coat protein were due to post-transcriptional gene silencing. This data also suggested that the 31 region of the movement protein transgene mRNA is the initial target of the silencing mechanism.

The present invention is directed to producing improved disease resistant plants.

7.2.2 Creating Transgenic Plants with Controllable Genes

This invention also relates to certain transgenic plants and involves a method of creating transgenic plants with controllable genes. More particularly, the invention relates to transgenic plants that have been modified such that expression of a desired introduced gene can be limited to a particular stage of plant development, a particular plant tissue, particular environmental conditions, or a particular time or location, or a combination of these situations.

7.2.2.1 Inducible Gene Promoter: "Gene Switch"

Various gene expression control elements that are operable in one or more species of organisms are known. For example, PCT Application WO 90/08826 (Bridges, et al.) discloses an inducible gene promoter that is responsive to an exogenous chemical inducer, called a "gene switch." This promoter can be linked to a gene and introduced into a plant. The gene can be selectively expressed by application of the chemical inducer to activate the promoter directly.

PCT application WO 94/03619 (Bright, et al.) discloses a gene cascade consisting of a gene switch linked to a repressor gene and a repressible operator linked to a disrupter protein capable of disrupting plant development. Growth of the plant can be controlled by the application or withholding of a chemical inducer. While the inducer is present, the repressor is expressed, the promoter attached to the disrupter gene is repressed, the disrupter protein is not expressed, thereby allowing the plant to grow normally. If the chemical inducer is withheld, the gene switch is turned off, the repressible promoter is not repressed, so the disrupter protein is expressed and plant development is disrupted. This system is said to be useful for controlling the escape of plants into the wild by making their continued growth and development dependent on the continued application of a chemical inducer, and to mitigate the problem of preharvest sprouting of grains by withholding the chemical inducer at the last stages of seed development.

7.2.2.2 Tetracycline-controlled Plant-active Repressor-operator System

Gatz and Quail (1988) and Gatz, et al. (1992), (Hoppe-Seyler), 372:659–660 (1991), disclose a plant-active repressor-operator system that is controlled by the application of tetracycline. The system consists of the Tn10 tet repressor gene, and a cauliflower mosaic virus (CaMV) 35S promoter, modified to contain two tet opetons and linked to the chloramphenicol acetyltransferase (cat) gene (Gatz and Quail, 1988), or modified to contain three tet operons and linked to the beta-glucuronidase (gus) gene (Gatz, et al., 1992). So long as the Tn10 tet repressor gene is active, the modified promoter is repressed by the interaction of the repressor with the tet operons, and the cat or gus gene is not expressed. The presence of tetracycline inhibits repressor binding, enabling expression of the cat or gus gene.

7.2.3 Recombinant Production of Proteins

A major commercial focus of biotechnology is the recombinant production of proteins, including both industrial enzymes and proteins that have important therapeutic uses.

7.2.3.1 Recombinant Proteins Produced in Microbial Hosts

Therapeutic proteins are commonly produced recombinantly by microbial expression systems, such as in E. coli and the yeast system S. cerevisiae. To date, the cost of recombinant proteins produced in a microbial host has limited the availability of a variety of therapeutically important proteins, such as human serum albumin (HSA) and $\alpha_1$-antitrypsin (AAT), to the extent that the proteins are in short supply.

7.2.31.1 Inability of Microbial Systems to Glycosylate (Properly) Mammalian Proteins Some therapeutic proteins appear to rely on glycosylation for optimal activity or stability, and the general inability of microbial systems to glycosylate or properly glycosylate mammalian proteins has also limited the usefulness of these recombinant expression systems. In some cases, proper protein folding cannot take place, because of the need for mammalian-specific foldases or other folding conditions.

7.2.3.1.2 Cost Per Weight Ratio and Other Problems of Mammalian Expression Systems To some extent, protein expression in cultured mammalian cells, or in transgenic animals may overcome the limitations of microbial expression systems. However, the cost per weight ratio of the protein is still high in mammalian expression systems, and the risk of protein contamination by mammalian viruses may be a significant regulatory problem. Protein production by transgenic animals also carries the risk of genetic variation from one generation to another. The attendant risk is variation in the recombinant protein produced, for example, variation in protein processing to yield a nature active protein with different N-terminal residue.

7.2.3.2 Alternative Protein Expression System to Overcome Problems of Microbial and Mammalian Systems It would therefore be desirable to produce selected therapeutic and industrial proteins in a protein expression system that largely overcomes problems associated with microbial and mammalian-cell systems. In particular, production of the proteins should allow large volume production at low cost, and yield properly processed and glycosylated proteins. The production system should also have a relatively stable genotype from generation to generation. These aims are achieved, in the present invention, for the therapeutic proteins AAT, HSA, and antithrombin III (ATIII), and the industrial enzyme subtilisin BPN'.

7.2.3.2.1 Use: Human $\alpha_1$-antitrypsin

Human $\alpha_1$-antitrypsin (AAT) is a monomer with a molecular weight of about 52 kd. Normal AAT contains 394 residues, with three complex oligosaccharide units exposed to the surface of the molecule, linked to asparagines 46, 83, and 247 (Carrell, P., et al., Nature (1992) 298:329).

AAT is the major plasma proteinase inhibitor whose primary function is to control the proteolytic activity of trypsin, elastase, and chyrnotrypsin in plasma. In particular, the protein is a potent inhibitor of neutrophil elastase, and a deficiency of AAT has been observed in a number of patients with chronic emphysema of the lungs. A proportion of individuals with serum deficiency of AAT may progress to cirrhosis and liver failure (e.g., Wu, Y., et al., BioEssays 13(4):163 (1991).

Because of the key role of AAT as an elastase inhibitor, and because of the prevalence of genetic diseases resulting in deficient serum levels of AAT, there has been an active interest in recombinant synthesis of AAT, for human therapeutic use. To date, this approach has not been satisfactory for AAT produced by recombinant methods, for the reasons discussed above.

7.2.3.2.2 Use: Human Antithrombin III

Antithrombin III (ATIII) is the major inhibitor of thrombin and factor Xa, and to a lesser extent, other serine proteases, generated during the coagulation process, e.g., factors IXa, XIA, and XIIa. The inhibitory effect of ATIII is accelerated dramatically by heparin. In patients with a history of deep vein thrombosis and pulmonary embolism, the prevalence of ATIII deficiency is 2–3%.

ATIII protein has been useful in treating hereditary ATIII deficiency and has wide clinical applications for the prevention of thrombosis in high risk situations, such as surgery and delivery, and for treating acute thrombotic episodes, when used in combination with heparin.

ATIII is a glycoprotein with a molecular weight of 58,200, having 432 amino acids and containing three disulfide linkages and four asparagine-linked biantennary carbohydrate chains. Because of the key role of ATIII as an anti-thrombotic agent, and because of the broad clinical potential in anti-thrombosis therapy, there has been an active interest in recombinant synthesis of ATIII, for human therapeutic use. To date, this approach has not been satisfactory for ATIII produced by microbial or mammalian recombinant methods, for the reasons discussed above.

7.2.3.2.3 Use: Human Serum Albumin

Serum albumin is the main protein component of plasma. Its main function is regulation of colloidal osmotic pressure in the bloodstream. Serum albumin binds numerous ions and small molecules, including $Ca^{2+}$, $Na^+$, $K^+$, fatty acids, hormones, bilirubin and certain drugs.

Human serum albumin (HSA) is expressed as a 609 amino acid prepro-protein which is further processed by removal of an amino-terminal peptide and an additional six amino acid residues to form the mature protein. The mature protein found in human serum is a monomeric, unglycosylated protein 585 amino acids in length (66 kDal), with a globular structure maintained by 17 disuffide bonds. The pattern of disulfide links forms a structural unit of one small and two large disulfide-linked double loops (Geisow, M. J. et al. (1977) Biochem. J. 163:477–484) which forms a high-affinity bilirubin binding site.

HSA is used to expand blood volume and raise low blood protein levels in cases of shock, trauma, and post-surgical recovery. HSA is often administered in emergency situations to stabilize blood pressure.

Because of the key role of HSA as an osmotic stabilizing agent, and because of its broad clinical potential in, e.g., plasma replacement therapy, there has been an active interest in recombinant synthesis of HSA for human therapeutic use. This approach has not been satisfactory for HSA produced by microbial or mammalian recombinant methods, for the reasons discussed above.

7.2.3.2.4 Use: Subtilisin BPN'

Subtilisin BPN' (BPN') is an important industrial enzyme, particularly for use as a detergent enzyme. Several groups have reported amino acid substitution modifications of the enzyme that are effective in enhancing the activity, pH optimum, stability and/or therapeutic use of the enzyme.

BPN' is expressed in as a 381 amino acid preproenzyme, including 35 amino acid sequence required for secretion and a 77 amino acid moiety which serves as a chaperon to facilitate folding. Studies indicate that the pro moiety acts in trans outside of cells.

To date, large-scale production of BPN' is predominantly by microbial fermentation, which has relatively high costs associated with it. In addition, the enzyme tends to auto-degrade at optimal fermentation growth-medium conditions.

7.2.4 Practical Method for the Commercial Production of Transgenic Plants

Translating genetic engineering theory into practice, however, and then furthermore into a commercially practical reality, requires ingenuity. Gene transplantation in plants has already been accomplished at this writing—and examples are cited below—but heretofore no practical method for the commercial production of transgenic plants has been perfected.

7.2.4.1 Tissue Culture Propagation

Apart from the transgenic plant technology per se, it is known to propagate plants by replicating plant cells in culture, or "tissue culture." An early motivating force in the development of tissue culture was the desire to improve upon the relatively slow and low yields of vegetative propagation with the quick and exponential proliferation of new plants from cell culture. Tissue culture methods are made possible by the plant physiological phenomenon of callus formation. When a plant is wounded, a patch of soft cells called a calli grows over the wound and, with time, phenolic compounds accumulate in the soft cells and harden, effectively sealing the wound. While hardened callus is the plant equivalent of scar tissue, callus is different from mammalian scar tissue with respect to its regenerative properties. If a piece of young, still-soft callus is removed and placed in a culture medium containing salts, sugars, vitamins, amino acids and the appropriate plant growth hormones, rather than harden, the cells will continue to divide and give rise to a disorganized mass of undifferentiated cells called a "callus culture." Plant or seedling "explants," or tissue samples, will likewise grow into similar cell cultures. The cultured cells can further be induced to redifferentiate into shoots, roots or whole plants by further culturing with the necessary hormones and growth media.

One of the most serious drawbacks with tissue culture propagation techniques has been the morphologic variation from generation to generation, a problem which is particularly notable in certain species and varieties. For example, as reported in Cassells, A. C., and Carney, B. F., "Adventitious regeneration in *Pelarcronium x domesticum Bailey,*" Acta Horticulturae, 212(11), 419–425 (1987), in stem and petiole tissue cultures of Grand Slam (as an example of *P. domesticum,* also known as Regal Pelargoniums or "Martha Washington" geraniums), up to 16% of the adventitious regenerants were variants, depending on the explant origin. The authors concluded that genome instability in Grand Slam and presumably other *P. domesticum* varieties may produce useful variation but mitigates against the use of adventitious regeneration in micropropagation.

The findings of Cassells et al. are consistent with the earlier work of Skirvin, R. M. and Janick, Jules, "Tissue Culture-Induced variation in Scented Pelargonium ssp.," *J. Amer. Soc. Hort. Sci .,* 101 (3), 281–290 (1976). Skirvin et al. compared tissue culture propagated Pelarcronium plants (from root cuttings, petiole cuttings or calliclones) with plants derived from vegetative propagation, i.e., stem cuttings. The plants derived from stem cuttings were all uniform and identical to the parental clone, whereas those from the root cuttings, petiole cuttings or calliclones were all morphologically distinct with the degree of variability depending upon the cultivar. The authors conclude that the variability associated with calliclones derived from tissue culture is a pool on which selection can be imposed, implying conversely that tissue culturing of this type is inappropriate for use in attempting reliable regeneration of *Pelarcronium x domesticum* varieties.

Other varieties and species, besides *Pelargonium x domesticum,* are known and/or believed to suffer morphologic variation when propagated using tissue culture. It can be easily appreciated that any substantial morphologic variation in propagation is unacceptable for commercial propagation of a desired variety or species. Thus, tissue culture methods are not always acceptable for commercial use, even with the potentially much larger yields achievable as compared with prior art vegetative propagation techniques.

7.2.4.2 Gene Transplantation

Apart from tissue culture considerations, gene transplantation in plants has achieved some success at this writing. Gene introduction is generally accomplished with a vector such as Agrobacterium. As this technology developed, it was noted that Crown Gall tumors of plants arose at the site of infection of some species of the bacterium Agrobacterium The cells of Crown Galls acquire the properties of independent, unregulated growth. In culture, such transformed cells grow in the absence of the plant hormones usually necessary for plant cell growth, and the cells retain the transformed phenotype even in the absence of the bacterium. The tumor-inducing agent in Agrobacterium is a plasmid that integrates some of its DNA into the chromosome of the host plant cells. Ti (tumor-inducing) plasmids exist in Agrobacterium cells as independently replicating genetic units.

Ti plasmids are maintained in Agrobacterium because part of the plasmid DNA, the T-DNA, carries the genes coding for the synthesis of amino acids called opines. The infected plant cell is induced to synthesize these amino acids, but the plant cannot use these amino acids. The Ti plasmid is believed to carry genes coding for enzymes that can degrade opines. Thus, Ti plasmids both make and degrade opines, within the plant cell, which the plant cell cannot metabolically use—presumably giving a selective advantage to the Agrobacterium at least with respect to utilization of the opine metabolites. A second set of genes in T-DNA codes for enzymes which lead to production of hormones which, in turn, cause the infected plant cell to divide in an unregulated way.

In summary terms, T-DNA enters a plant cell by what amounts to the equivalent of bacterial conjugation between the Agrobacterium and the plant cell. In other words, an Agrobacterium organism and a plant cell transfer their DNA in a process analogous to mating. Ultimately, T-DNA becomes incorporated into the genomic plant cell DNA in the plant cell nucleus.

All of the above background illustrates how Agrobacterium species can serve well as vectors for genetic transformation of plant cells. Early gene transfer using Ti plasmids, T-DNA and Agrobacterium was accomplished by the cointegration method, in which T-DNA was first cloned into a standard *E. coli* cloning vector, and the plant gene was subsequently cloned into a second cloning site carried by the vector. This intermediate vector was introduced into Agrobacterium organisms containing intact Ti plasmids. Recombination occurred between the homologous regions of the intermediate vector and the wild-type Ti plasmid, and on infection of a plant with the Agrobacterium the recombinant plasmid is transferred to the plant cells.

7.2.4.3 The Binary System

Despite the early use of the cointegration method described above—and certainly it still works—the standard method for T-DNA transfer as of this writing is called the "binary system." The binary system was devised when investigators realized that the essential functions for transfer are supplied separately by the T-DNA itself and by the Ti plasmid, and that the components can be carried on separate vectors. The binary vector contains the borders of the T-DNA—needed for excision and integration—and the hormone-producing region of the original T-DNA can be removed and replaced with the foreign gene sequence intended for transfer to the plant cell. One side benefit of the use of binary vectors is that, by removing the hormone-producing regions of the T-DNA, uncontrolled growth of the recipient cells is prevented—or in other words the tumor-causing aspect of the T-DNA is nullified. The vir genes of the Ti plasmid can be supplied on a separate plasmid and etc.; the binary vector technique for gene transfer into plants is well established at this writing.

An example of the use of binary vectors to introduce functional genes into plants came about through experiments to use antisense RNA to control plant gene expression. Early work used binary vectors to introduce antisense polygalacturonase genes into tomato plants, to turn off the polygalacturonase expression which in turn digests pectin, in attempts to reduce bruising of tomato fruit during shipment. The results of these trials were disappointing. However, when binary vectors have been used to transfer antisense ethylene precursor genes into tomato plants, the results have been favorable. The antisense gene prevents expression of the ethylene precursor, no ethylene production occurs during storage of the harvested tomatoes, and thus no ripening occurs until the time ripening is desired, when the fruit can be contacted with ethylene from another source.

Exemplary publications and patents which disclose transgenic plants and various techniques therefor are summarized below.

Pellegrineschi, A., et al., "Improvement of ornamental Characters and Fragrance Production in Lemon-scented Geranium Through Genetic Transformation by *Agrobacterium rhizocrenes*," Bio/Technology, Vol. 12 (January, 1994) discloses transformation of root cultures by inoculating stem and leaf fragments with *Agrobacterium rhizoaenes*. An important plasmid in this species of Agrobacterium is the root-inducing plasmid which can be used to transfer to the plant genome the genes necessary for improved root growth in culture. The use of sterilized petioles as the source of explant material for plant transformation and culture is disclosed.

U.S. Pat. No. 5,276,268 to Strauch et al., entitled 11 Phosphinothricin-Resistance Gene, and Its Use," is directed to the transfer of phosphinothricin-resistance gene into plants using Agrobacterium species. A modification of the binary vector method is discussed, and the phosphinothricin-resistance gene nucleic acid sequences are provided.

U.S. Pat. No. 5,283,184 to Jorgenson et al. is entitled "Genetic Engineering of Novel Plant Phenotypes" and discusses transgenote formation and propagation in tissue culture, as well mentioning Pelarcioniums and geraniums (and many other plants) by name. The tissue culture propagation of morphologically conserved transgenotes is not discussed.

U.S. Pat. No. 5,286,635 to Hanson et al., entitled "Genetically, Transformed Pea Plants and Methods for Their Production," discloses the transfer of desired gene sequences into pea plants by incubating pea plant explants (preferably not callus) with Agrobacterium vectors containing the desired gene sequence. Mature seed material is used as the explant source. The issue of total morphologic conservation is not addressed.

7.2.4.4 A Method for Commercially Viable Production of Transgenic Plants in Which Plants Undergo Minimal, and thus Commercially Acceptable, Morphologic Variation as a Result of Tissue Culture Propagation Thus while certain inroads have been made in the area of tissue culture plant propagation as well as in plant gene transfer, a need remains for a method for the commercially viable production of transgenic plants in which the plants undergo only minimal, and thus commercially acceptable, morphologic variation as a result of tissue culture propagation.

7.2.5 Method of Identifying and Characterizing the Role of Individual Plant Genes in Quantitative Trait Expression When considering the application of biotechnology to plant improvement, a great deal of emphasis is usually placed on the strategy of introducing novel variability into plants via genetic engineering techniques. Over the past decade, advances have been made in developing methods of transferring genes to plant cells (see Potrykus et al., Plant Mol. Bio. Rep. 3:117–128 (1985)). For example, transfer and expression of single genes improving insect and herbicide resistance has reportedly been achieved in plants (Abel et al., Science 232:738–743 (1986); Shah et al., Science 233:478–481 (1986)). While there is excitement over advances in plant genetic engineering, the prospects for the general use of these techniques for plant improvement are tempered by the realization that very few genes corresponding to plant traits of interest have been identified or cloned.

One procedure that has been used by plant breeders to increase efficiency in the testing of traits which are difficult or expensive to evaluate is the use of indirect selection criteria (Hallaver and Miranda, Quantitative Genetics in Corn Breeding (Iowa State University Press 1981). One indirect selection criterion, for example, might be an easily recognized morphological characteristic of the plant which is either genetically linked to the desired trait or perhaps a component of the desired trait, e.g., the association between leaf size and seed size in beans.

Agronomically important traits such as, for example, plant yield, height, maturity, and fruit and grain characteristics, are all attractive targets for manipulation in plant improvement programs, but often have very low heritabilities. Heritability is the ratio of genetic to total variation and, therefore, is important to the efficiency of the selection process. Influencing heritability of such traits, sometimes termed "quantitative" traits, is difficult, however, because expression of a number of different gene products generally influences the phenotype. Quantitative traits are characterized by continuous rather than discreet distribution of phenotypic expression. There is currently a poor understanding of how single genes influence the expression of complex traits and, in conventional plant breeding programs, selection for inheritance of quantitative traits is difficult due to the unrecognized genetic basis of the trait. The use of direct gene transfer in manipulating these traits, of course, is therefore difficult due to problems in pinpointing and then cloning those individual loci which contribute predominantly to the expression of the trait. Determination of genotypic information from phenotypic values is further imprecise because evaluation of the trait may frequently be confounded by environmental effects (Berger, "Multiple-Trait Selection Experiments: Current Status, Problem Areas and Experimental Approaches." In: Proceedings of the International Conference on Quantitative Genetics (Pollack et al., Eds.), p. 191–204 (Iowa St. Press 1977)).

Clearly, one area in which biotechnology may have a significant impact on plant improvement is in the development of new methods to identify and characterize the role of individual plant genes in quantitative trait expression. Following the development of a new class of plant molecular markers based on restriction fragment length polymorphisms, termed "RFLPs", (Helentjaris et al., Plant Mol. Bio. 5:109–118 (1985)) ("Helentjaris et al. I"), the processes to identify such loci and discriminate gene effects have been invented and are described and claimed herein. This and all other publications noted herein are hereby incorporated by reference. This will undoubtedly benefit plant improvement, not only within the context of conven-

7.3. Fusion Gene Including a Trait and a Silencer DNA Molecule

The present invention is directed to a DNA construct formed from a fusion gene which includes a trait DNA molecule and a silencer DNA molecule. The trait DNA molecule has a length that is insufficient to impart a desired trait to plants transformed with the trait DNA molecule. The silencer DNA molecule is operatively coupled to the trait DNA molecule with the trait and silencer DNA molecules collectively having sufficient length to impart the trait to plants transformed with the DNA construct. Expression systems, host cells, plants, and plant seeds containing the DNA construct are disclosed.

7.3.1 Fusion Gene Comprising a Plurality of Trait DNA Molecules

In an alternative embodiment of the present invention, the DNA construct can be a fusion gene comprising a plurality of trait DNA molecules at least some of which having a length that is insufficient to impart that trait to plants transformed with that trait DNA molecule. However, the plurality of trait DNA molecules collectively have a length sufficient to impart their traits to plants transformed with the DNA construct and to effect post-transcriptional silencing of the fusion gene. Expression systems, host cells, plants, and plant seeds containing this embodiment of the DNA construct are disclosed.

7.3.2 A Recombinant Chimeric Molecule

The present invention also provides a recombinant chimeric DNA molecule comprising a plurality of DNA sequences each of which comprises a promoter operably linked to a DNA sequence which encodes a virus-associated protein, such as a coat protein (cp), a protease, or a replicase, wherein said DNA sequences are expressed in virus-susceptible plant cells transformed with said recombinant DNA molecule to impart resistance to infection by each of said viruses. Preferably, the DNA sequences are linked in tandem, i.e., exist in head to tail orientation relative to one another. Also, preferably substantially equal levels of resistance to infection by each of said viruses occurs in plant cells transformed with said plurality of DNA sequences.

Preferably, each DNA sequence is also linked to a 3' non-translated DNA sequence which functions in plant cells to cause the termination of transcription and the addition of polyadenylated ribonucleotides to the 3' end of the transcribed mRNA sequences. Preferably, the virus is a plant-associated virus, such as a potyvirus.

Thus, the present DNA molecule can be employed as a chimeric recombinant "expression construct," or "expression cassette" to prepare transgenic plants that exhibit increased resistance to infection by at least two plant viruses, such as potyviruses. The present cassettes also preferably comprise at least one selectable marker gene or reporter gene which is stably integrated into the genome of the transformed plant cells in association with the viral genes. The selectable marker and/or reporter genes facilitate identification of transformed plant cells and plants. Preferably, the virus gene array is flanked by two or more selectable marker genes, reporter genes or a combination thereof.

Another aspect of the present invention is a method of preparing a virus-resistant plant, such as a dicot, comprising:
(a) transforming plant cells with a chimeric recombinant DNA molecule comprising a plurality of DNA sequences, each comprising a promoter functional in said plant cells, operably linked to a DNA sequence, which encodes a protein associated with a virus which is capable of infecting said plant; (b) regenerating said plant cells to provide a differentiated plant; and (c) identifying a transformed plant which expresses the DNA sequences so as to render the plant resistant to infection by said viruses, preferably at substantially equal levels of resistance to infection by each virus.

Yet another object of the present invention is to provide a method for providing resistance to infection by viruses in a susceptible Cucurbitaceae plant which comprises:
(a) transforming Cucurbitaceae plant cells with a DNA molecule encoding a plurality of proteins from viruses which are capable of infecting said Cucurbitaceae plant; (b) regenerating said plant cells to provide a differentiated plant; and (c) selecting a transformed Cucurbitaceae which expresses the virus proteins at levels sufficient to render the plant resistant to infection by said viruses.

It is a further object of the present invention to provide multi-virus resistant transformed plant which contains stably-integrated DNA sequences encoding virus proteins.

7.3.3 Controlling Gene Expression with External Stimulus

The present invention involves, in one embodiment, the creation of a transgenic plant that contains a gene whose expression can be controlled by application of an external stimulus. This system achieves a positive control of gene expression by an external stimulus, without the need for continued application of the external stimulus to maintain gene expression. The present invention also involves, in a second embodiment, the creation of transgenic parental plants that are hybridized to produce a progeny plant expressing a gene not expressed in either parent. By controlling the expression of genes that affect the plant phenotype, it is possible to grow plants under one set of conditions or in one environment where one phenotype is advantageous, then either move the plant or plant its seed under another set of conditions or in another environment where a different phenotype is advantageous. This technique has particular utility in agricultural and horticultural applications.

In accordance with one embodiment of the invention, a series of sequences is introduced into a plant that includes a transiently-active promoter linked to a structural gene, the promoter and structural gene being separated by a blocking sequence that is in turn bounded on either side by specific excision sequences, a repressible promoter operably linked to a gene encoding a site-specific recombinase capable of recognizing the specific excision sequences, and a gene encoding a repressor specific for the repressible promoter whose function is sensitive to an external stimulus. Without application of the external stimulus, the structural gene is not expressed. Upon application of the stimulus, repressor function is inhibited, the recombinase is expressed and effects the removal of the blocking sequence at the specific excision sequences, thereby directly linking the structural gene and the transiently-active promoter.

In a modification of this embodiment, the sequences encoding the recombinase can be introduced separately into the plant via a viral vector.

In an alternative embodiment, no repressor gene or repressible promotor is used. Instead, the recombinase gene is linked to a germination-specific promoter and introduced into a separate plant from the other sequences. The plant containing the transiently-active promoter, blocking sequence, and structural gene is then hybridized with the plant containing the recombinase gene, producing progeny that contain all of the sequences. When the second transiently-active promotor becomes active, the recombinase removes the blocking sequence in the progeny, allowing expression of the structural gene in the progeny, whereas it was not expressed in either parent.

In still another embodiment, the recombinase gene is simply linked to an inducible promoter. Exposure of the plant to the induce specific for the inducible promoter leads to the expression of the recombinase gene and the excision of the blocking sequence.

In all of these embodiments, the structural gene is expressed when the transiently-active promoter becomes active in the normal course of growth and development, and will continue to be expressed so long as the transiently-active promoter is active, without the necessity of continuous external stimulation. This system is particularly useful for developing seed, where a particular trait is only desired during the first generation of plants grown from that seed, or a trait is desired only in subsequent generations.

7.3.4 Preparing Plants Which are Resistant to Multiple Viruses

It is still a further object of the present invention to provide virus resistant transformed plant cells which contain a plurality of viral genes, i.e., 2–7 or more genes, which are expressed as virus proteins, such as coat proteins, proteases and/or replicases, from the same virus strain, from different virus strains as from different members of the virus group, such as the potyvirus group. Representative viruses from which these DNA sequences can be isolated include, but are not limited to, potato virus X (PVX), potyviruses such as potato virus Y (PVY), cucomovirus (CMV), tobacco vein mottling virus, watermelon mosaic virus (WMV), zucchini yellow mosaic virus (ZYMV), bean common mosaic virus, bean yellow mosaic virus, soybean mosaic virus, peanut mottle virus, beet mosaic virus, wheat streak mosaic virus, maize dwarf mosaic virus, sorghum mosaic virus, sugarcane mosaic virus, johnsongrass mosaic virus, plum pox virus, tobacco etch virus, sweet potato feathery mottle virus, yam mosaic virus, and papaya ringspot virus (PRV), cucomoviruses, including CMA and comovirus.

Generally, a potyvirus is a single-stranded RNA virus that is surrounded by a repeating proteinaceous monomer, which is termed the coat protein (CP). The encapsidated virus has a flexous rod morphology. The majority of the potyviruses are transmitted in a nonpersistent manner by aphids. As can be seen from the wide range of crops affected by potyviruses, the host range includes such diverse families of plants, but is not limited to Solanaceae, Chenopodiaceae, Gramineae, Compositae, Leguminosae, Dioscroeaceae, Cucurbitaceae, and Caricaceae.

The present invention is particularly directed to preparing plants which are resistant to multiple viruses. It is well known that particular plant types are often susceptible to more than one virus. Although PDR is an excellent approach to controlling the damaging effects of plant viruses, incorporating multiple virus resistance in a given plant can be challenging. For example, identifying and producing full length viral genes to transform plants can be expensive and time consuming. Further, such genes may be so large that they need to be incorporated in different expression systems which must be separately incorporated in plants.

7.3.4.1 Using Short Fragments of Viral Genes to Impart Resistance

Rather than attempting to incorporate full length viral genes in a plant, the present invention uses short fragments of such genes to impart resistance to the plant against a plurality of viral pathogens. These short fragments, which each by themselves have insufficient length to impart such resistance, are more easily and cost effectively produced than full length genes. There is no need to include in the plant separate promoters for each of the fragments; only a single promoter is required. Moreover, such viral gene fragments can preferably be incorporated in a single expression system to produce transgenic plants with a single transformation event.

7.3.4.1.1 Example: Papaya Ringspot Virus

The impact of this simple strategy for multiple virus resistant transgenic plants could have far reaching effects in agriculture. An example is the case of papaya ringspot virus ("PRV"). Transgenic papaya with the coat protein gene of the PRV strain from Hawaii have been developed and found to be highly resistant under greenhouse and long-term field conditions. However, that papaya is largely susceptible to strains from other parts of the world, including Jamaica, Thailand, and Brazil.

Apparently, PRV resistance in papaya is highly specific and a number of transgenic papaya lines will need to be developed with different coat protein genes of the target countries to control the virus worldwide. With the present invention, a transgenic papaya could be developed with resistance to all PRV strains using viral gene fragments that total less than 1,000 base pairs plus a silencer DNA of about 400 bp; by comparison, the PRV coat protein gene alone is about 1,000 bp.

7.3.4.1.2 Example: Potato Leaf Roll Virus, Potato Virus Y, and Potato Virus X

Another use of the present invention involves imparting resistance against a plurality of different viruses. For example, in potato, the present invention can be employed to impart resistance against potato leaf roll virus, potato virus Y, and potato virus X. To effect such resistance, in accordance with the present invention, a DNA construct, driven by a single promoter, and containing a portion of the potato leafroll virus replicase encoding gene, a portion of the potato virus Y coat protein encoding gene, and a portion of the gene encoding the movement protein of potato virus X can be produced and transformed into potato. As a result, transgenic potato with resistance to potato leafroll virus, potato virus Y, and potato virus X can be produced by a single transformation event. This constitutes a significant advance beyond incorporating full length versions of each of the genes with separate promoters together in a single expression vector or in separate vectors.

7.3.4.1.3 Example: Multiple Resistance

Another use of the present invention involves imparting resistance to cucurbits against a number of viruses. For example, in squash, the present invention can be utilized to impart multiple resistance to zuccinni yellow mosaic virus, papaya ringspot virus, watermelon mosaic virus IT, and squash mosaic virus. For example, a construct containing a portion of the coat protein encoding gene or a portion of the replicase encoding gene from each of these viruses, driven by a single promoter, can be produced and transformed into squash. The resulting transgenic squash is resistant to all of these viruses.

The present invention is exemplified primarily by the insertion of multiple virus cp expression cassettes into a binary plasmid and subsequent characterization of resulting plasmids. Combinations of CMV, ZYMV, WMV-2, SQMV, and PRV coat protein expression cassettes were placed in the binary plasmid pPRBN. Subsequently, binary plasmids harboring multiple cp expression cassettes were mobilized into Agrobacterium for use in plant transformation procedures. Binary plasmids harboring multiple expression cassettes are employed to transfer two or more virus coat protein transformation-susceptible genes into plants, such as members of the Cucurbitaceae family, along with the associated selectable marker and/or reporter genes.

7.3.5 Imparting other Traits to Plants

In addition to conferring on plants resistance to multiple viral diseases, the present invention can be utilized to impart other traits to plants. It is often desirable to incorporate a number of traits to a transgenic plant besides disease resistance. For example, color, enzyme production, etc. may be desirable traits to confer on a plant. However, transforming plants with a plurality of such traits encounter the same difficulties discussed above with respect to disease resistance. The present invention may be likewise useful in alleviating these problems with respect to traits other than disease resistance.

Thus, the present invention provides a genetic engineering methodology by which multiple traits can be manipulated and tracked as a single gene insert, i.e., as a construct which acts as a single gene which segregates as a single Mendelian locus. Although the invention is exemplified via virus resistance genes, in practice, any combination of genes could be linked. Therefore one could track a block of genes that provide traits such as disease resistance, plus enhanced herbicide resistance, plus extended shelf life, and the like, by simply tracking the linked selectable marker or reporter gene which has been incorporated into the transformation vector.

It was also discovered that when multiple tandem genes are inserted, they preferably all exhibit substantially the same degrees of efficacy, and more preferably substantially equal degrees of efficacy, wherein the term "substantial" as it relates to viral resistance is defined with reference to the assays described in the examples hereinbelow. For example, if one examines numerous transgenic lines containing an intact ZYMV and WMV-2 coat protein insert, one finds that if a line is immune to infection by ZYMV it is also immune to infection by WMV-2. Similarly, if a line exhibits a delay in symptom development to ZYMV it will also exhibit a delay in symptom development to WMV2. Finally, if a line is susceptible to ZYMV it win be susceptible to WMV-2. This phenomenon is unexpected. If there were not a correlation between the efficacy of each gene in these multiple gene constructs this approach as a tool in plant breeding would probably be prohibitively difficult to use. Even with single gene constructs, one must test numerous transgenic plant lines to find one that displays the appropriate level of efficacy. The probability of finding a line with useful levels of expression can range from 10–50% (depending on the species involved).

If the efficacy of individual genes in a Ti plasmid containing multiple genes were independent, the probability of finding a transgenic line that was resistant to each targeted virus would decrease dramatically. For example, in a species in which there is a 10% probability of identifying a line with resistance using a single gene insert, is transformed with a triple-gene construct CZW and each gene display an independent levels of efficacy, the probability of finding a line with resistance to CMV, ZYMV and WMV-2 would be 0.1×0.1×0.1=0.001 or 0.1%. However, since the efficacy of multivalent genes is not independent of each other the probability of finding a line with resistance to CMV, ZYMV and WMV-2 is still 10% rather than 0.1%. Obviously this advantage becomes more pronounced as constructs containing four or more genes are used.

7.3.6 Probability of Expression

One problem with transforming plants to contain multiple traits is the possibility that not all of them will be successfully imparted. For example, where there are 4 new traits to be imparted to a transgenic plant, there is a 10% likelihood that each expression event will occur, making the probability of imparting all traits in a plant produced in accordance with the present invention much higher than in a plant transformed with full length trait genes driven by separate promoters. More particularly, the probability of expressing all 4 traits in the latter is 0.0001 (i.e., 0.1 ×0.1×0.1×0.1), while the probability in the present invention is 0.1.

7.3.7 Commercially Viable Production Method

A need remains for a method for the commercially viable production of transgenic plants in which the plants undergo only minimal, and thus commercially acceptable, morphologic variation as a result of tissue culture propagation.

In order to meet this need, the present method is a process for commercially propagating plants by tissue culture in such a way as both to conserve desired plant morphology and to transform the plant with respect to one or more desired genes. The method includes the steps of (a) creating an Agrobacterium vector containing the gene sequence desired to be transferred to the propagated plant, preferably together with a marker gene; (b) taking one or more petiole explants from a mother plant and inoculating them with the Agrobacterium vector; (c) conducting callus formation in the petiole sections in culture, in the dark; and (d) culturing the resulting callus in growth medium having a benzylamino growth regulator such as benzylaminopurine or, most preferably, benzylaminopurine-riboside. Additional optional growth regulators including auxins and cytokinins (indole butyric acid, benzylamine, benzyladenine, benzylaminopurine, alpha naphthylacetic acid and others known in the art) may also be present.

Preferably, the petiole tissue is taken from Pelargonium x domesticum and the Agrobacterium vector contains an antisense gene for ACC synthase or ACC oxidase to prevent ACC synthase or ACC oxidase expression and, in turn, preventing ethylene formation. Pelargoniums propagated in culture using the present technique are resistant to wilting and petal shatter, and are morphologically conserved due to the use of petiole explants specifically and the particular culture media disclosed.

7.3.8 Production of a Mature Heterologous Protein in Transformed Monocot Plant Cells In one aspect, the invention includes a method of producing, in monocot plant cells, a mature heterologous protein selected from the group consisting of (i) mature, glycosylated $\alpha_1$-antitrypsin (AAT) having the same N-terminal amino acid sequence as mature AAT produced in humans and a glycosylation pattern which increases serum halflife substantially over that of non-glycosylated mature AAT; (ii) mature, glycosylated antithrombin III (ATIII) having the same N-terminal amino acid sequence as mature ATIII produced in humans; (iii) mature human serum albumin (HSA) having the same N-terminal amino acid sequence as mature HSA produced in humans and having the folding pattern of native mature HSA as evidenced by its bilirubin-binding characteristics; and (iv) mature, active subtilisin BPN' (BPN'), glycosylated or non-glycosylated, having the same N-terminal amino acid sequence as BPN' produced in Bacillus.

The method includes obtaining monocot cells transformed with a chimeric gene having (i) a monocot transcriptional regulatory region, inducible by addition or removal of a small molecule, or during seed maturation, (ii) a first DNA sequence encoding the heterologous protein, and (iii) a second DNA sequence encoding a signal peptide. The second DNA sequence is operably linked to the transcriptional regulatory region and to the first DNA sequence. The first DNA sequence is in translation-frame with the second DNA sequence, and the two sequences encode a fusion protein.

The transformed cells are cultivated under conditions effective to induce the transcriptional regulatory region, thereby promoting expression of the fusion protein and secretion of the mature heterologous protein from the transformed cells. The mature heterologous protein produced by the transformed cells is then isolated.

In one embodiment of the method, the first DNA sequence encodes pro-subtilisin BPN' (proBPN'), the cultivating includes cultivating the transformed cells at a pH between 5 and 6, and the isolating step includes incubating the proBPN' to under condition effective to allow its autoconversion to active mature BPN'. In another embodiment, the first DNA sequence encodes mature BPN', and the cells are transformed with a second chimeric gene containing (i) a transcriptional regulatory region inducible by addition or removal of a small molecule, (ii) a third DNA sequence encoding the pro-peptide moiety of BPN', and (iii) a fourth DNA sequence encoding a signal polypeptide. The fourth DNA sequence is operably linked to the transcriptional regulatory region and to the third DNA sequence, and the signal polypeptide is in translation-frame with the pro-peptide moiety and is effective to facilitate secretion of expressed pro-peptide moiety from the transformed cells. The cultivating step includes cultivating the transformed cells at a pH between 5 and 6, and the isolating step includes incubating the mature BPN and the pro-moiety under conditions effective to allow the conversion of BPN' by the pro-moiety to active mature BPN'.

7.3.8.1 Inducing the Transcriptional Regulatory Region

In other embodiments of the method, the transcriptional regulatory region may be a promoter derived from a rice or barley α-amylase gene, including RAmy1A, RAmy1B, RAmy2A, RAmy3A, RAmy3B, RAmy3C, RAmy3D, RAmy3E, pM/C, gKAmy141, gKAmy155, Amy32b, or HV18. The chimeric gene may further include, between the transcriptional regulatory region and the fusion protein coding sequence, the 5' untranslated region (5' UTR) of an inducible monocot gene such as one of the rice or barley α-amylase genes described above. One preferred 5' UTR is that from the RAmy1A gene, which is effective to enhance the stability of the gene transcript. The chimeric gene may further include, downstream of the coding sequence, the 3' untranslated region (3' UTR) from an inducible monocot gene, such as one of the rice or barley α-amylase genes mentionedabove. One preferred 3' UTR is from the RAmy1A gene.

7.3.8.2 Preferred Promoters

Where the method is employed in protein production in a monocot cell culture, preferred promoters are the RAmy3D and RAmy3E gene promoters, which are upregulated by sugar depletion in cell culture. Where the gene is employed in protein production in germinating seeds, a preferred promoter is the RAmy1A gene promoter, which is upregulated by gibberellic acid during seed germination. Where gene is upregulated during seed maturation, a preferred promoter is the barley endosperm-specific B1-hordein promoter.

7.3.8.3 Product: A Mature Heterologous Protein

The invention also includes a mature heterologous protein produced by the above method. The protein has a glycosylation pattern characteristic of the monocot plant in which the protein is produced. The glycosyated protein is selected from the group consisting of (i) mature glycosylated $\alpha_1$-antitrypsin (AAT) having the same N-terminal amino acid sequence as mature AAT produced in humans and having a glycosylation pattern which increases serum halflife substantially over that of non-glycosylated mature AAT; (ii) mature glycosylated antithrombin III (ATIII) having the same N-terminal amino acid sequence as mature ATIII produced in humans; and (iii) mature glycosylated subtilisin BPN' (BPN') having the same N-terminal amino acid sequence as BPN' produced in Bacillus.

The invention also includes plant cells and seeds capable of producing the mature heterologous proteins according to the above method.

These and other objects and features of the invention will be more fully understood when the following detailed description of the invention is read in conjunction with the accompanying drawings.

7.3.9 Indentifying such Loci and Discrinating Gene Effects of Restriction Fragment Length Polymorphisms The development of new methods to identify and characterize the role of individual plant genes in quantitative trait expression has significant impact on plant improvement. Following the development of a new class of plant molecular markers based on restriction fragment length polymorphisms, termed "RFLPs", (Helentjaris et al., Plant Mol. Bio. 5:109–118 (1985)) ("Helentjaris et al. I"), the processes to identify such loci and discriminate gene effects have been invented and are described and claimed herein.

RFLPs are differences observed between genotypes in the fragment lengths of restriction endonuclease-digested DNA. RFLPs occur as a result of base pair or positional changes in the restriction enzyme recognition sites which flank a chromosomal location and can be detected by hybridization of labelled DNA clones containing sequences that are homologous to a portion of the chromosomal fragment. Hybridization with a unique cloned sequence can permit the identification of a specific chromosomal region (locus).

This technology employs cloned DNA fragments to detect differences between individuals at the DNA sequence level. When genomic DNAs from two genetically distinct individuals are digested with a restriction enzyme, electrophoresed and probed with a labelled DNA clone, polymorphisms in the hybridization patterns sometimes result due to sequence differences between the individuals. The term "restriction fragment length polymorphism" has been coined to describe this variation.

7.3.9.1 Using RFLPs as Genectic Markers

Differences in fragment lengths which are revealed, for example, by agarose gel electophoresis, function as alleles of that RFLP. Thus, RFLPs can serve as genetic markers in a manner analogous to conventional morphological or isozyme markers. Unlike most genetic markers, however, they are not the products of transcription and translation. Additionally, RFLP possess certain additional advantages over previously available genetic markers. First, RFLPs reflect existing differences between genetically distinct individuals. The potential number of RFLPs for all practical purposes is thus unlimited, as digestion of the genomic DNA of any higher eukaryote with a six base recognition enzyme will generate more than a million fragments, many of which can be polymorphic. Additionally, over one hundred different restriction enzymes have now been described, each of which may generate a new and different set of fragments (Roberts, Nuc. Acids Res. 10:117–144 (1982)). The utility of isozyme markers or morphological markers in studies is frequently limited by a lack of informativeness in lines of interest or by an insufficient availability or chromosomal distribution of the loci.

7.3.9.2 Isozyme Variation in Plant Breeding

The use of isozyme variation in plant breeding is, like RFLP technology, one of indirect selection. (Tanskley and Orton, Isozymes in Plant Genetics and Breeding 1B (Elsevier, N.Y. 1983). The time required to backcross a trait from a donor to a recurrent parent is the product of the generation time by the number of generations. Therefore, screening for traits linked to isozymes, which may sometimes be identified in seeds or seedlings, can reduce the time required for evaluation, especially if the expression of that trait is controlled by recessive alleles. In addition, the number of backcross generations necessary to sufficiently recover the phenotype of the recurrent parent can be reduced by selection for isozymes associated with the recurrent parent.

In tomato, closely linked isozyme variation has been used to follow the inheritance of several simply inherited traits such as, for example, nematode resistance (Rick and Fobes, Rep. Tomato Genet. Coop. 24:25 (1974)). The inheritance of quantitative traits has also been followed by the use of multiple isozyme loci. For example, in tomato, eleven isozyme loci were used to survey eight of the 12 chromosomes and three independent genetic factors were detected in association with cold tolerance (Vallejos and Tanksley, Theor. Appl. Genet. 66:241–247 (1983)). In maize, changes in the frequency of eight isozyme loci were found to be associated with selection for improved grain yield (Stuber et al., Crop. Sci. 22:737–740 (1982)). Nevertheless, for a multigenic trait, only that portion of the genome closely linked to an isozyme marker can be considered, and many other major or minor genes may be associated with the expression of quantitative traits.

Maize is perhaps the best characterized plant system in terms of isozymes and yet only about two dozen isozyme loci have been located and it is rare for more than a dozen of these to be informative in any particular cross involving Corn Belt germplasm. By contrast, using the inventors' RFLP technology, over 300 RFLPs covering all ten maize chromosomes have been characterized (Helentjaris et al., Trends in Genetics. 3:217–221 (1987)). The level of informativeness of these RFLPs is great. In a study involving the maize cross Tx303X Co159, only 13 informative isozyme loci with very biased coverage of less than the 10 chromosomes were available. In contrast, using RFLP analysis, more than 99 informative RFLPs covering all 10 chromosomes can be analyzed in the same cross (unpublished data). In a recent comparative survey of Corn Belt germplasm RFLPs averaged greater than five alleles per locus while isozyme loci averaged less than two (M. Walton and T. Helentjaris, abstract).

7.3.9.3 RFLP Markers in Plant Breeding

RFLP markers rarely possess detectable phenotype effects of their own, so they can be utilized in economic lines without detriment and many can be evaluated at one time without the pleiotropic effects often seen with phenotypic markers. Evaluation can be performed on small amounts of DNA obtained from plant tissue at virtually any stage of plant development from roots, to shoots, to fruits, or even with tissue culture material. Evaluation of RFLPs is not affected by environmental factors and greenhouse-grown plants will not differ from field-grown plants when tested. Finally, the evaluation of RFLPs reveals the exact genotype, so the heterozygous state can be differentiated from the homozygous condition at any chromosomal location.

Many of the potential applications and theoretical advantages of RFLPs compared to more conventional phenotypic or isozyme marking systems have been described previously. Helentjaris et al. I. In one application of the use of RFLP markers in plant studies, genetic linkage maps based on these markers have been constructed for both maize and tomato (Helentjaris et al., Theor. Appl. Genet. 72:761–769 (1986)) ("Helentjaris et al. II"). Similar linkage maps are also being constructed for other crop species, such as Brassica Figdore et al., Theor. Appl. Genetics. 75:833–840 (1988); Slocum et al., In "Genetic Maps" (S. J. O'Brien, ed.), 5th Edition, Cold Spring Harbor Press, N.Y. (1990)). Close to 120 RFLPs in tomato have been arranged into linkage groups by comparing segregation patterns in an F2 population derived from homozygous parental lines. Approximately 70 RFLPs have been mapped by another group of workers. Bernatzky and Tanksley, Genetics 112:887–898 (1986). Over 300 RFLPs in maize have been arranged into linkage groups (Helentjaris et al., 1986; Helentjaris et al., 1987). The locations of the maize RFLP loci have been correlated to the conventional maize genetic map by analyzing the inheritance patterns of the RFLPs in maize lines monosomic for different chromosomes (Helentjaris et al., Proc. Nat. Acad. Sci. USA 83:6035–6039 (1986)) ("Helentjaris et al. II"), by establishing linkage relationships with isozyme markers, cloned genes, and morphological markers with previously identified chromosomal locations (Wright et al., MNL 61:89–90 (1987)), and by analyzing inheritance patterns in B-A translocation stocks (Helentjaris et al., Weber and Helentjaris, Genetics 121:583–590 (1989). The resulting map shows the resolution possible.

Numerous direct applications of RFLP technology to facilitate plant breeding programs have been suggested. Helentjaris et al. I. Because of the large numbers of RFLP markers available in a population of interest, one of the more important applications of RFLPs may be as markers linked to genes affecting the expression of quantitatively inherited traits. In this application, RFLPs function as indirect selection criteria for traits which are difficult or expensive to evaluate phenotypically. A prerequisite for the use of RFLPs as indirect selection criteria is the identification of RFLPs closely linked to the quantitative trait loci (QTL) affecting expression of the trait of interest.

Currently, the introgression of quantitative traits from one germplasm to another involves the identification of favorable genotypes in segregating generations followed by repeated backcrossing to commercially acceptable cultivars. This procedure is feasible for simply inherited quantitative traits, but as the number of genes controlling a trait increases, screening the number of F2 segregants required to identify at least one individual which represents the ideal (homozygous) genotype quickly becomes prohibitive. For example, with one gene and two alleles of equal frequency, the probability of recovering a desirable genotype in the F2 generation is 1/4. However, if the number of genes is increased to 5 or 10, the probability of recovering an ideal genotype in the F2 population is reduced to approximately one in one thousand and one in one million, respectively. Thus, to identify desirable segregants, one must either reduce the number of segregants needed or have available very efficient screening procedures. Additionally, in situations where enviromental effects interfere with the ability to draw accurate genotypic information from the phenotype, large allocations of time and resources are required to evaluate progeny in replicated trials within several target environments.

Described and claimed herein is the use of RFLPs to dissect multigenic traits into their individual genetic components. A genome, or portion thereof, saturated with RFLPs or probed with select RFLP markers, all of which can be evaluated together in individual plants, has been found to give the resolution necessary to break down traits of complex inheritance into individual loci, even those under a significant environmental influence. The procedure is equally workable with dominant or recessive traits and can be used to accelerate introgression of desired genes into a commercially acceptable cultivar. As used herein, "plants" includes all forms of plant life, such as crop plants, mushrooms and fungi, ferns, trees, flowers and so on. These examples are not intended to be limiting but are merely illustrative of the wide applications of the invention.

Particular Definitions

The terms below have the following meaning, unless indicated otherwise in the specification.

As used in this specification, a "transiently-active promoter" is any promoter that is active either during a particular phase of plant development or under particular environmental conditions, and is essentially inactive at other times.

A "plant active promoter" is any promoter that is active in cells of a plant of interest. Plant-active promoters can be of viral, bacterial, fungal, animal or plant origin.

A gene that results in an altered plant phenotype is any gene whose expression leads to the plant exhibiting a trait or traits that would distinguish it from a plant of the same species not expressing the gene. Examples of such altered phenotypes include a different growth habit, altered flower or fruit color or quality, premature or late flowering, increased or decreased yield, sterility, mortality, disease susceptibility, altered production of secondary metabolites, or an altered crop quality such as taste or appearance.

A gene and a promoter are to be considered to be operably linked if they are on the same strand of DNA, in the same orientation, and are located relative to one another such that the promoter directs transcription of the gene (i.e. in cis). The presence of intervening DNA sequences between the promoter and the gene does not preclude an operable relationship.

A "blocking sequence" is a DNA sequence of any length that blocks a promoter from effecting expression of a targeted gene.

A "specific excision sequence" is a DNA sequence that is recognized by a site-specific recombinase.

A "recombinase" is an enzyme that recognizes a specific excision sequence or set of specific excision sequences and effects the removal of, or otherwise alters, DNA between specific excision sequences.

A "repressor element" is a gene product that acts to prevent expression of an otherwise expressible gene. A repressor element can comprise protein, RNA or DNA.

A "repressible promoter" is a promoter that is affected by a repressor element, such that transcription of the gene linked to the repressible promoter is prevented.

"Expression" means transcription or transcription followed by translation of a particular DNA molecule.

As used herein, with respect to a DNA sequence or "gene", the term "isolated" is defined to mean that the sequence is either extracted from its context in the viral genome by chemical means and purified and/or modified to the extent that it can be introduced into the present vectors in the appropriate orientation, i.e., sense or antisense.

"Cell culture" refers to cells and cell clusters, typically callus cells, growing on or suspended in a suitable growth medium.

"Germination" refers to the breaking of dormancy in a seed and the resumption of metabolic activity in the seed, including the production of enzymes effective to break down starches in the seed endosperm.

"Inducible" means a promoter that is upregulated by the presence or absence of a small molecules. It includes both indirect and direct inducement.

"Inducible during germination" refers to promoters which are substantially silent but not totally silent prior to germination but are turned on substantially (greater than 25%) during germination and development in the seed. Examples of promoters that are inducible during germination are presented below.

"Small molecules", in the context of promoter induction, are typically small organic or bioorganic molecules less than about 1 kDal. Examples of such small molecules include sugars, sugar-derivatives (including phosphate derivatives), and plant hormones (such as, gibberellic or absissic acid).

"Specifically regulatable" refers to the ability of a small molecule to preferentially affect transcription from one promoter or group of promoters (e.g., the α-amylase gene family), as opposed to non-specific effects, such as, enhancement or reduction of global transcription within a cell by a small molecule.

"Seed maturation" or "grain development" refers to the period starting with fertilization in which metabolizable reserves, e.g., sugars, oligosaccharides, starch, phenolics, amino acids, and proteins, are deposited, with and without vacuole targeting, to various tissues in the seed (grain), e.g., endosperm, testa, aleurone layer, and scutellar epithelium, leading to grain enlargement, grain filling, and ending with grain desiccation.

"Inducible during seed maturation" refers to promoters which are turned on substantially (greater than 25%) during seed maturation.

"Heterologous" is defined to mean not identical, e.g. different in nucleotide and/or amino acid sequence, phenotype or an independent isolate.

"Heterologous DNA" or "foreign DNA" refers to DNA which has been introduced into plant cells from another source, or which is from a plant source, including the same plant source, but which is under the control of a promoter or terminator that does not normally regulate expression of the heterologous DNA.

"Heterologous protein" is a protein, including a polypeptide, encoded by a heterologous DNA. A "transcription regulatory region" or "promoter" refers to nucleic acid sequences that influence and/or promote initiation of transcription. Promoters are typically considered to include regulatory regions, such as enhancer or inducer elements.

"Chimeric" is defined to mean the linkage of two or more DNA sequences which are derived from different sources, strains or species, i.e., from bacteria and plants, or that two or more DNA sequences from the same species are linked in a way that does not occur in the native genome. Thus, the DNA sequences useful in the present invention may be naturally occurring, semi-synthetic or entirely synthetic. The DNA sequence may be linear or circular, Le, may be located on an intact or linearized plasmid, such as the binary plasmids described below.

A "chimeric gene," in the context of the present invention, typically comprises a promoter sequence operably linked to DNA sequence that encodes a heterologous gene product, e.g., a selectable marker gene or a fusion protein gene. A chimeric gene may also contain further transcription regulatory elements, such as transcription termination signals, as well as translation regulatory signals, such as, termination codons.

"Operably linked" refers to components of a chimeric gene or an expression cassette that function as a unit to express a heterologous protein. For example, a promoter operably linked to a heterologous DNA, which encodes a protein, promotes the production of functional mRNA corresponding to the heterologous DNA.

A "product" encoded by a DNA molecule includes, for example, RNA molecules and polypeptides.

"Removal" in the context of a metabolite includes both physical removal as by washing and the depletion of the metabolite through the absorption and metabolizing of the metabolite by the cells.

"Substantially isolated" is used in several contexts and typically refers to the at least partial purification of a protein or polypeptide away from unrelated or contaminating components.

Methods and procedures for the isolation or purification of proteins or polypeptides are known in the art.

"Stably transformed" as used herein refers to a cereal cell or plant that has foreign nucleic acid stably integrated into its genome which is transmitted through multiple generations.

"$\alpha_1$-antitrypsin" or "AAT" refers to the protease inhibitor which has an amino acid sequence substantially identical or homologous to AAT protein.

"Antithrombin III" or "ATIII" refers to the heparin-activated inhibitor of thrombin and factor Xa, and which has an amino acid sequence substantially identical or homologous to ATIII protein.

"Human serum albumin" or "HSA" refers to a protein which has an amino acid sequena substantially identical or homologous to the mature HSA protein.

"Subtilisin" or "subtilisin BPN'" or "BPN'" refers to the protease enzyme produced naturally by *B. amyloliquefaciens*.

"proBPN'" refers to a form of BPN' having an approximately 78 amino-acid "pro" moiety that functions as a chaperon polypeptide to assist in folding and activation of the BPN'.

"Codon optimization" refers to changes in the coding sequence of a gene to replace native codons with those corresponding to optimal codons in the host plant.

A DNA sequence is "derived from" a gene, such as a rice or barley α-amylase gene, if it corresponds in sequence to a segment or region of that gene. Segments of genes which may be derived from a gene include the promoter region, the 5' untranslated region, and the 3' untranslated region of the gene.

7.4.1 General Approach

Generally, the nomenclature and laboratory procedures with respect to standard recombinant DNA technology can be found in Sambrook, et al., MOLECULAR -CLONING—A LABORATORY MANUAL, Cold Spring Harbor Laboratory, Cold Spring Harbor, N.Y. 1989 and in S. B. Gelvin and R. A. Schilperoot, PLANT MOLECULAR BIOLOGY, 1988. Other general references are provided throughout this document. The procedures therein are known in the art and are provided for the convenience of the reader.

Most of the recombinant DNA methods employed in practicing the present invention are standard procedures, well known to those skilled in the art, and described in detail in, or example, European Patent Application Publication Number 223,452, published Nov. 29, 1986, which is incorporated herein by reference. Enzymes are obtained from commercial sources and are used according to the vendor's recommendations or other variations known in the art. General references containing such standard techniques include the following: R. Wu, ed. (1979) Methods Emzymology, Vol. 68; J. H. Miller (1972) Experiments in Molecular Genetics; J. Sambrook et al. (1989) Molecular Cloning: A Laboratory Manual 2nd Ed.; D. M. Glover, ed. (1985) DNA Cloning Vol. II;H. G. Polites and K. R. Marotti (1987) "A step-wise protocol for cDNA synthesis," Biotechniques 4; 514–520; S. B. Gelvin and R. A. Schilperoort, eds. Introduction, Expression, and Analysis of Gene Products in Plants, all of which are incorporated by reference.

7.4.2 Control of Plant Gene Expression 7.4.2.1 Using a Transiently-active Promoter This invention relates to a method of creating transgenic plants wherein the expression of certain plant traits is ultimately under external control. In one embodiment the control is achieved through application of an external stimulus; in another embodiment it is achieved through hybridization, in still another embodiment it is achieved by direct introduction of a recombinase or recombinase gene into a plant. The transgenic plants of the present invention are prepared by introducing into their genome a series of functionally interrelated DNA sequences, containing the following basic elements: a plant-active promoter that is active at a particular stage in plant development or under particular environmental conditions ("transiently-active promoter"), a gene whose expression results in an altered plant phenotype which is linked to the transiently-active promoter through a blocking sequence separating the transiently-active promoter and the gene, unique specific excision sequences flanking the blocking sequence, wherein the specific excision sequences are recognizable by a site-specific recombinase, a gene encoding the site-specific recombinase, an alternative repressible promoter linked to the recombinase gene, and an alternative gene that encodes the repressor specific for the repressible promoter, the action of the repressor being responsive to an applied or exogenous stimulus. While these elements may be arranged in any order that achieves the interactions described below, in one embodiment they are advantageously arranged as follows: a first DNA sequence contains the transiently-active promotor, a first specific excision sequence, the blocking sequence, a second specific excision sequence, and the gene whose expression results in an altered plant phenotype; a second DNA sequence contains the repressible promoter operably linked to the recombinase gene, and optionally an enhancer; and a third DNA sequence containing the gene encoding the repressor specific for the repressible promoter, itself linked to a promoter functional and constitutive in plants. The third DNA sequence can conveniently act as the blocking sequence located in the first DNA sequence, but can also occur separately without altering the function of the system. This embodiment can be modified such that the recombinase sequence is introduced separately via a viral vector. In an alternative embodiment, an advantageous arrangement is as follows: a first plant containing a DNA sequence comprising the transiently-active promotor, a first specific excision signal sequence, the blocking sequence, a second specific excision signal sequence, and the gene whose expression results in an altered plant phenotype; a second plant containing a DNA sequence comprising a constitutive plant-active promotor operably linked to the recombinase gene (the two plants being hybridized to produce progeny that contain all of the above sequences).

When a plant contains the basic elements of either embodiment, the gene whose expression results in an altered plant phenotype is not active, as it is separated from its promoter by the blocking sequence. In the first embodiment, absent the external stimulus, the repressor is active and represses the promoter that controls expression of the recombinase; in the alternative embodiment the recombinase is not present in the same plant as the first DNA sequence. Such a plant will not display the altered phenotype, and will produce seed that would give rise to plants that also do not display the altered phenotype. When the 5 stimulus to which the repressor is sensitive is applied to this seed or this plant, the repressor no longer functions, permitting the expression of the site-specific recombinase, or alternatively, when the recombinase is introduced via hybridization it is expressed during germination of the seed, either of which effects the removal of the blocking sequence between the specific excision signal sequences. Upon removal of the blocking sequence, the transiently-active promoter becomes directly linked to the gene whose expression results in an altered plant phenotype. A plant grown from either treated or hybrid seed, or a treated plant, will still not exhibit the altered phenotype, until the transiently-active promoter becomes active during the plant's development, after which the gene to which it is linked is expressed, and the plant will exhibit an altered phenotype.

7.4.2.2 Transgenic Plants that Produce Seeds that Cannot Germinate

In a preferred embodiment, the present invention involves a transgenic plant or seed which, upon treatment with an external stimulus produces plants that produce seed that cannot germinate (but that is unaltered in other respects). If the transiently-active promoter is one that is active only in late embryogenesis, the gene to which it is linked will be expressed only in the last stages of seed development or maturation. If the gene linked to this promoter is a lethal gene, it will render the seed produced by the plants incapable of germination. In the initially-transformed plant cells, this lethal gene is not expressed, not only because the promoter is intrinsically inactive, but because there is a blocking sequence separating the lethal gene from its promoter. Also within the genome of these cells are the genes for the recombinase, linked to a repressible promoter, and the gene coding for the repressor. The repressor is expressed constitutively and represses the expression of the recombinase. These plant cells can be regenerated into a whole plant and allowed to produce seed. The mature seed is exposed to a stimulus, such as a chemical agent, that inhibits the function of the repressor. Upon inhibition of the repressor, the promotor driving the recombinase gene is depressed and the recombinase gene is expressed. The resulting recombinase recognizes the specific excision sequences flanking the blocking sequence, and effects the removal of the blocking sequence. The late embryogenesis promoter and the lethal gene are then directly linked. The lethal gene is not expressed, however, because the promoter is not active at this time in the plant's life cycle. This seed can be planted, and grown to produce a desired crop of plants. As the crop matures and produces a second generation of seed, the late embryogenesis promoter becomes active, the lethal gene is expressed in the maturing second generation seed, which is rendered incapable of germination. In this way, accidental reseeding, escape of the crop plant to areas outside the area of cultivation, or germination of stored seed can be avoided.

7.4.2.3 Trangenic Plants Hybridized to Display Phenotype Not Seen in Either Parent In an alternative preferred embodiment, the present invention involves a pair of transgenic plants that are hybridized to produce progeny that display a phenotype not seen in either parent. In this alternative embodiment a transiently-active promotor that is active only in late embryogenesis can be linked to a lethal gene, with an intervening blocking sequence bounded by the specific excision sequences. These genetic sequences can be introduced into plant cells to produce one transgenic parent plant. The recombinase gene is linked to a germination-specific promoter and introduced into separate plant cells to produce a second transgenic parent plant. Both of these plants can produce viable seed if pollinated. If the first and second transgenic parent plants are hybridized, the progeny will contain both the blocked lethal gene and the recombinase gene. The recombinase is expressed upon germination of the seed and effects the removal of the blocking sequence, as in the first embodiment, thereby directly linking the lethal gene and the transiently-active promotor. As in the first embodiment, this promotor becomes active during maturation of the second generation seed, resulting in seed that is incapable of germination. Ideally, the first parent employs a male-sterility gene as the blocking sequence, and includes an herbicide resistance gene. In this way, self-pollination of the first transgenic parent plant is avoided, and self-pollinated second transgenic parent plants can be eliminated by application of the herbicide. In the hybrid progeny, the male-sterility gene is removed by the recombinase, resulting in hybrid progeny capable of self-pollination.

7.4.2.3.1 Linking the Recombinase Gene to an Inducible Promoter

In another embodiment, the recombinase gene is linked to an inducible promoter. Examples of such promoters include the copper, controllable gene expression system (Mett et al., 1993) and the steroid-inducible gene system (Schena et al., 1991). Exposure of the transgenic plant to the inducer specific for the inducible promoter leads to expression of the recombinase gene and the excision of the blocking sequence. The gene that results in an altered plant phenotype is then expressed when the transiently active promoter becomes active.

7.4.2.3.2 Selection of an Appropriate Promoter

Any appropriate transiently-active promoter can be used, and selection of an appropriate promoter will be governed by such considerations as plant type and the phenotypic trait over which control is sought. The transiently-active promoter is preferably not a "leaky" promoter, meaning that it is active substantially only during a well-defined phase of plant growth or under particular environmental conditions, and substantially inactive at all other times. This property prevents the premature "triggering" of the system. There are numerous published examples of transiently-active promoters, which can be applied in the present system. The principle consideration for selecting an appropriate promoter is the stage in the plant's life at which it is desired to have the altered phenotype expressed. If it is desired to have the phenotype expressed after the first generation, a promoter that is active during seed production is preferred, as it will not be active during the vegetative phase of first generation plant growth. If it is desired to have the altered phenotype expressed at some time during the first generation itself, a promoter that is active at an earlier stage would be appropriate. It will be readily apparent to workers conversant in the art that the timing of the application of the external stimulus to the plant to trigger the system, in those embodiments employing the repressible promotor system, should occur prior to the stage at which the selected transiently-active promotor is active for the generation of plant which is desired to display the altered phenotype. A promoter active in late embryogenesis, such as the LEA promoter, Hughes and Galau, 1989 and 1991, Galau, et al., 1991, 1992 and 1993, is ideal when it is desired to have the altered phenotype appear after the first generation, because it is active only during the formation of the embryo within the seed, after the first generation plant has completed a season of vegetative growth (embryogenesis is virtually the last stage in seed formation, after most other fruit and seed structures are formed).

7.4.2.3.3 Gene(s) Linked to the Plant Development Promoter

The gene or genes linked to the plant development promoter can be any gene or genes whose expression results in a desired detectable phenotype. This phenotype could be any trait that would be desired in a plant in one situation, but not desired in another, such as male sterility, drought resistance, insect resistance, early or late seed germination, or early or late flowering, to give a few examples. Often a plant can possess traits that are advantageous in some ways or under some conditions, but at a certain cost to the plant. For instance, a trait for insect resistance might involve the production of secondary plant metabolites or structures, at a certain metabolic expense to the plant. This is advantageous in an environment where pests are present, but essentially an unnecessary-burden where they are not. Another example is the production of seeds in an annual fruit crop, such as watermelon. Obviously, it is necessary for at least one generation of plants to produce seeds, so that a seed company can produce seed for sale to growers, but a seedless fruit crop grown from that seed is commercially desirable. Still another example is a trait that allows ready and rapid seed germination in a cereal crop. This is advantageous for getting a crop established as rapidly as possible and with a minimum of effort, but very undesirable if it leads to germination of the harvested grain in the grain bin. Still another example would be where the plant is desirable in one location or season (as a winter forage crop, for instance), but considered a weed in another. If the second generation seed were incapable of germination, it would prevent post-harvest germination, the "tescape" of a plant through natural seed dispersal into a location where it is not desired, or accidental reseeding. These last two examples could advantageously employ a lethal gene (meaning a gene whose expression somehow interferes in plant growth or development), so that the second generation seed simply will not germinate, or the last example could alternatively employ any gene that introduces a trait that decreases the plant's vigor, such as disease susceptibility, early flowering, low seed production, or seedless. A ribosomal inhibitor protein ("RIP") gene is a preferred lethal gene, the saponin 6 RIP, (GenBank ID SOSAPG, Accession No. X15655), being particularly preferred. RIP directly interferes in the expression of all protein in a plant cell, without being toxic to other organisms. Expression of RIP in the cells of the embryo would entirely prevent germination of the seed.

7.4.2.3.4 Blocking Sequence

The blocking sequence can be any sequence that prevents expression of the gene linked to the transiently-active promotor, such as a termination signal, but in those embodiments employing a repressible promoter is advantageously the sequence that codes for the repressor. In this way, when the blocking sequence is excised, the repressor gene is eliminated, thus further minimizing the chance of later inhibition of the system. In the hybrid embodiment, the blocking sequence is advantageously a gene that produces male sterility (such as a lethal gene linked to an anther-specific promotor). In this way, hybridization is facilitated, but hybrid progeny will be capable of self-pollination when the blocking sequence is removed by the recombinase.

7.4.2.3.5 Repressible Promoter System

In those embodiments employing a repressible promoter system, the gene encoding the repressor is responsive to an outside stimulus, or encodes a repressor element that is itself responsive to an outside stimulus, so that repressor function can be controlled by the outside stimulus. The stimulus is preferably one to which the plant is not normally exposed, such as a particular chemical, temperature shock, or osmotic shock. In this way, the simple application of the stimulus will block the repression of the recombinase, yet there will be a low probability of the repressor being accidentally or incidentally blocked. If the repressor is sensitive to a chemical stimulus, the chemical is preferably non-toxic to the crop and to non-pest animals. A preferred system is the Tn10 tet repressor system, which is responsive to tetracycline. Gatz and Quail (1988); Gatz, et al. (1992). In this system, a modified Cauliflower Mosaic Virus (CaMV) 35S promoter containing one or more, preferably three, tet operons is used; the Tn10 tet repressor gene produces a repressor protein that binds to the tet operon(s) and prevents the expression of the gene to which the promoter is linked. The presence of tetracycline inhibits binding of the Tn10 tet repressor to the tet operon(s), allowing free expression of the linked gene. This system is preferred because the stimulus, tetracycline, is not one to which the plant would normally be exposed, so its application can be controlled. Also, since tetracycline has no harmful effects on plants or animals, its presence would not otherwise impede the normal development of the plant, and residual amounts left on the seed or plant after treatment would have no significant environmental impact. Examples of other repressible promoter systems are described by Lanzer and Bujard (1988) and Ptashne, et al.

7.4.2.3.6 The Recombinase/Excision Sequence System

The recombinase/excision sequence system can be any one that selectively removes DNA in a plant genome. The excision sequences are preferably unique in the plant, so that unintended cleavage of the plant genome does not occur. Several examples of such systems are discussed in Sauer, U.S. Pat. No. 4,959,317 and in Sadowski (1993). A preferred system is the bacteriophage CRE/LOX system, wherein the CRE protein performs site-specific recombination of DNA at LOX sites. Other systems include the resolvases (Hall, 1993), FLP (Pan, et al., 1993), SSV1 encoded integrase (Muskhekishvili, et al., 1993), and the maize Ac/Ds transposon system (Shen and Hohn, 1992).

7.4.3 Conferring Viral Resistance to the Plant

To practice the present invention, a viral gene must be isolated from the viral genome and inserted into a vector containing the genetic regulatory sequences necessary to express the inserted gene. Accordingly, a vector must be constructed to provide the regulatory sequences such that they will be functional upon inserting a desired gene. When the expression vector/insert construct is assembled, it is used to transform plant cells which are then used to regenerate plants. These transgenic plants carry the viral gene in the expression vector/insert construct. The gene is expressed in the plant and increased resistance to viral infection is conferred thereby.

7.4.3.1 Isolation of a Viral Gene

Several different courses exist to isolate a viral gene. To do so, one having ordinary skill in the art can use information about the genomic organization of potyviruses, cucumoviruses or comoviruses to locate and isolate the coat protein gene or the nuclear inclusion body genes. The coat protein gene in potyviruses, is located at the 3' end of the RNA, just prior to a stretch of about 200–300 adenine nucleotide residues. The nuclear inclusion body B (NIb) gene is located just 5' to the coat protein gene, and the nuclear inclusion body A (NIa) gene is 5' to the NIb gene. Additionally, the information related to proteolytic cleavage sites is used to determine the N-terminus of the potyvirus coat protein gene and the N- and C-terminus of non-coat protein genes. The protease recognition sites are conserved in the potyviruses and have been determined to be either the dipeptide Gln-Ser, Gln-Gly or Gln-Ala. The nucleotide sequences which encode these dipeptides can be determined.

7.4.3.2 Insertion of the Viral Gene into a Vector

Using methods well known in the art, a quantity of virus is grown and harvested. The viral RNA is then separated and the viral gene isolated using a number of known procedures. A cDNA library is created using the viral RNA, by methods known to the art. The viral RNA is incubated with primers that hybridize to the viral RNA and reverse transcriptase, and a complementary DNA molecule is produced. A DNA complement of the complementary DNA molecule is produced and that sequence represents a DNA copy (cDNA) of the original viral RNA molecule. The DNA complement can be produced in a manner that results in a single double stranded cDNA or polymerase chain reactions can be used to amplify the DNA encoding the cDNA with the use of oligomer primers specific for the viral gene. These primers can include in addition to viral specific sequences, novel restriction sites used in subsequent cloning steps.

Thus, a double stranded DNA molecule is generated which contains the sequence information of the viral RNA. These DNA molecules can be cloned in *E. coli* plasmid vectors after the additions of restriction enzyme linker molecules by DNA ligase. The various fragments are inserted into cloning vectors, such as well-characterized plasmids, which are then used to transform *E. coli* to create a cDNA library.

Since potyvirus genes are generally conserved, oligonucleotides based on an analogous gene from a previous isolate or an analogous gene fragment from a previous isolate can be used as a hybridization probe to screen the cDNA library to determine if any of the transformed bacteria contain DNA fragments with the appropriate viral sequences. The cDNA inserts in any bacterial colonies which hybridize to these probes can be sequenced. The viral gene is present in its entirety in colonies which have sequences that extend 5' to sequences which encode a N-terminal proteolytic cleavage site and 3' to sequences which encode a C-terminal proteolytic cleavage site for the gene of interest.

Alternatively, cDNA fragments may be inserted in the sense orientation into expression vectors. Antibodies against a viral protein may be used to screen the cDNA expression library and the gene can be isolated from colonies which express the protein.

7.4.3.3 Table of Selected Literature References to Methods of Isolating, Cloning and Expressing Viral Genes The nucleotide sequences encoding the coat protein genes and nuclear inclusion genes of a number of viruses have been determined and the genes have been inserted into expression vectors. The expression vectors contain the necessary genetic regulatory sequences for expression of an inserted gene. The coat protein gene is inserted such that those regulatory sequences are functional and the genes can be expressed when incorporated into a plant genome. Selected literature references to methods of isolating, cloning and expressing viral genes are listed on Table 3, below.

TABLE 3

Cloned Genes From RNA Viruses

| Viral Gene | Reference |
|---|---|
| Papaya ringspot cp | M. M. Fitch et al., Bio/Technology, 10, 1466 (1992) |
| Potato virus X cp | K. Ling et al., Bio/Technology, 2, 752 (1991); A. Hoekema et al., Bio/Technology, 7, 273 (1989) |
| Watermelon Mosaic Virus II cp | H. Quemada et al., J. Gen. Virol., 71, 1451 (1990); S. Namba et al., Phytopathology, 82, 940 (1992) |
| Zucchini yellow Mosaic Virus cp | S. Namba et al., Phytopathology, 82, 940 (1992) |
| Tobacco Mosaic Virus cp | R. S. Nelson et al., Bio/Technology, 6, 403 (1988); P. Powell Abel et al., Science, 232, 738 (1986) |
| Alfalfa Mosaic Virus cp | Loesch-Fries et al., EMBO J., 6, 1845 (1987); N. E. Turner et al., EMBO J., 6, 1181 (1987) |
| Soybean Mosaic Virus cp | D. M. Stark et al., Biotechnology, 7, 1257 (1989) |
| Cucumber Mosaic Virus strain C cp | H. Q. Quemada et al., Molec. Plant Pathol., 81, 794 (1991) |
| Cucumber Mosaic Virus strain WL cp | UpJohn Co. (PCT WO90/02185) |
| Tobacco etch virus cp | Allison et al., Virology, 147, 309 (1985) |
| Tobacco etch virus nuclear inclusion protein | J. C. Carrington et al., J. Virol., 61, 2540 (1987) |
| Pepper Mottle Virus cp | W. G. Dougherty et al., Virology, 146, 282 (1985) |
| Potato virus Y cp | D. D. Shukla et al., Virology, 152, 118 (1986) |
| Potato virus Y nuclear inclusion protein | European Patent Application 578,627 |
| Potato virus X cp | C. Lawson et al., Biotechnology, 8, 127 (1990) |
| Tobacco streak virus (TSV) cp | C. M. Van Dun et al., Virology, 164, 383 (1988) |

7.4.4 Formation of a DNA Construct 7.4.4.1 Fusion Gene Including a Trait DNA Molecule and a Silencer DNA Molecule The present invention is directed to a DNA construct formed from a fusion gene which includes a trait DNA molecule and a silencer DNA molecule. The trait DNA molecule has a length that is insufficient to impart a desired trait to plants transformed with the trait DNA molecule. The silencer DNA molecule is operatively coupled to the trait DNA molecule with the trait and silencer DNA molecules collectively having sufficient length to impart the trait to plants transformed with the DNA construct.

7.4.4.2 Plurality of Trait DNA Molecules

In an alternative embodiment of the present invention, the DNA construct can be a fusion gene comprising plurality of trait DNA molecules at least some of which having a length that is insufficient to impart that trait to plants transformed with that trait DNA molecule. However, the plurality of trait DNA molecules collectively have a length sufficient to impart the traits to plants transformed with the DNA construct and to effect post-transcriptional silencing of the fusion gene.

A particularly preferred aspect of the present invention is where the DNA construct includes a plurality of trait DNA molecules each having a length insufficient to impart the trait to plants transformed with the trait DNA molecule alone. It is also possible for some of the trait DNA molecules to have a length sufficient to impart their respective trait; however, not all such DNA molecules will have such a length.

7.4.4.3 Transformed Plant Cells with Expression Constructs for Production of Mature Proteins Plant cells or tissues derived from the members of the family known as the Gramineae are transformed with expression constructs (i.e., plasmid DNA into which the gene of interest has been inserted) using a variety of standard techniques (e.g., electroporation, protoplast fusion or microparticle bombardment). The expression construct includes a transcription regulatory region (promoter) whose transcription is specifically upregulated by the presence or absence of a small molecule, such as the reduction or depletion of sugar, e.g., sucrose, in culture medium, or in plant tissues, e.g., germinating seeds. In the present invention, particle bombardment is the preferred transformation procedure.

The construct also includes a gene encoding a mature heterologous protein in a form suitable for secretion from plant cells. The gene encoding the recombinant heterologous protein is placed under the control of a metabolically regulated promoter. Metabolically regulated promoters are those in which mRNA synthesis or transcription, is repressed or upregulated by a small metabolite or hormone molecule, such as the rice RAmy3D and RAmy3E promoters, which are upregulated by sugar-depletion in cell culture. For protein production in germinating seeds from regenerated transgenic plants, a preferred promoter is the-Ramy 1A promoter, which is up-regulated by gibberellic acid during seed germination. The expression construct also utilizes additional regulatory DNA sequences e.g., preferred codons, termination sequences, to promote efficient translation of AAT, as will be described.

7.4.5 Disease Resistance

One aspect of the present invention relates to the use of trait DNA molecules which are heterologous to the plant— e.g., DNA molecules that confer disease resistance to plants transformed with the DNA construct. The present invention is useful in plants for imparting resistance to a wide variety of pathogens including viruses, bacteria, fungi, viroids, phytoplasmas, nematodes, and insects. The present invention may also be used in mammals to impart genetic traits. Resistance, inter alia, to the following viruses can be achieved by the method of the present invention: tomato spotted wilt virus, impatiens necrotic spot virus, groundnut ringspot virus, potato virus Y, potato virus X, tobacco mosaic virus, turnip mosaic virus, tobacco etch virus, papaya ringspot virus, tomato mottle virus, tomato yellow leaf curl virus, or-combinations thereof. Resistance, inter alia, to the following bacteria can also be imparted to plants in accordance with present invention: *Pseudomonas solancearum, Pseudomonas syringae* pv. *tabaci, Xanthamonas campestris* pv. *pelargonii,* and *Agrobacterium tumefaciens*. Plants can be made resistant, inter alia, to the following fungi by use of the method of the present invention: *Fusarium oxysporum* and *Phytophthora infestans*. Suitable DNA molecules include a DNA molecule encoding a coat protein, a replicase, a DNA molecule not encoding protein, a DNA molecule encoding a viral gene product, or combinations thereof.

7.4.5.1 Sense/Antisense Orientation

The DNA molecule conferring disease resistance can be positioned within the DNA construct in sense orientation. Alternatively, it can have an antisense orientation. Antisense RNA technology involves the production of an RNA molecule that is complementary to the messenger RNA molecule of a target gene; the antisense RNA can potentially block all expression of the targeted gene. In the anti-virus context, plants are made to express an antisense RNA molecule corresponding to a viral RNA (that is, the antisense RNA is an RNA molecule which is complementary to a plus sense RNA species encoded by an infecting virus). Such plants may show a slightly decreased susceptibility to infection by that virus. Such a complementary RNA molecule is termed antisense RNA.

7.4.6 Other Traits

The present invention is also used to confer traits other than disease resistance on plants. For example, DNA molecules which impart a plant genetic trait can be used as the DNA trait molecule of the present invention. In this aspect of the present invention, suitable trait DNA molecules encode for desired color, enzyme production, or combinations thereof.

7.4.6.1 Gene Silencing

The silencer DNA molecule of the present invention can be selected from virtually any nucleic acid which effects gene silencing. This involves the cellular mechanism to degrade mRNA homologous to the transgene mRNA. The silencer DNA molecule can be heterologous to the plant, need not interact with the trait DNA molecule in the plant, and can be positioned 3' to the trait DNA molecule. For example, the silencer DNA molecule can be a viral cDNA molecule, a jellyfish green fluorescence protein encoding DNA molecule, a plant DNA molecule, or combinations thereof.

While not wishing to be bound by theory, by use of the construct of the present invention, it is believed that post-transcriptional gene silencing is achieved. More particularly, the silencer DNA molecule is believed to boost the level of heterologous RNA within the cell above a threshold level. This activates the degradation mechanism by which viral resistance is achieved.

7.4.6.1.1 Trait & Silencer DNA Molecules Encoding RNA Molecules—Translatable

It is possible for the DNA construct of the present invention to be configured so that the trait and silencer DNA molecules encode RNA molecules which are translatable. As a result, that RNA molecule will be translated at the ribosomes to produce the protein encoded by the DNA construct. Production of proteins in this manner can be increased by joining the cloned gene encoding the DNA construct of interest with synthetic double-stranded oligonucleotides which represent a viral regulatory sequence (i.e., a 5' untranslated sequence). See U.S. Pat. No. 4,820,639 to Gehrke and U.S. Pat. No. 5,849,527 to Wilson which are hereby incorporated by reference.

7.4.6.1.2 Trait & Silencer DNA Molecules Encoding RNA Molecules—Not Translatable Alternatively, the DNA construct of the present invention can be configured so that the trait and silencer DNA molecules encode mRNA which is not translatable. This is achieved by introducing into the DNA molecule one or more premature stop codons, adding one or more bases (except multiples of 3 bases) to displace the reading frame, removing the translation initiation codon, etc. See U.S. Pat. No. 5,583,021 to Dougherty et al., which is hereby incorporated by reference.

7.4.7 Recombinant DNA Technology

The subject DNA construct can be incorporated in cells using conventional recombinant DNA technology. Generally, this involves inserting the DNA construct into an expression system to which the DNA construct is heterologous (i.e. not normally present). The heterologous DNA construct may be inserted into the expression system or vector in proper sense orientation and correct reading frame. The vector contains the necessary elements for the transcription of the inserted sequences.

7.4.7. Restriction Enzyme Cleavage and Ligation

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

7.4.7.2 Introduction to Viruses

Recombinant genes may also be introduced into viruses, such as vaccinia virus. Recombinant viruses can be generated by transfection of plasmids into cells infected with virus.

7.4.8 Incorporation into a Host Cell

Once the DNA construct has been cloned into an expression system, it is ready to be incorporated into a host cell. Such incorporation can be carried out by the various forms of transformation noted above, depending upon the vector/host cell system. Suitable host cells include, but are not limited to, bacteria, virus, plant, is and the like cells.

7.4.8.1 Plant Transformation—Production of Mature Proteins in Plants

Expression vectors for use in the present invention comprise a chimeric gene (or expression cassette), designed for operation in plants, with companion sequences upstream and downstream from the expression cassette. The companion sequences will be of plasmid or viral origin and provide necessary characteristics to the vector to permit the vectors to move DNA from bacteria to the desired plant host. For transformation of plants, the chimeric gene is placed in a suitable expression vector designed for operation in plants. The vector includes suitable elements of plasmid or viral origin that provide necessary characteristics to the vector to permit the vectors to move DNA from bacteria to the desired plant host. Suitable components of the expression vector, including an inducible promoter, coding sequence for a signal peptide, coding sequence for a mature heterologous protein, and suitable termination sequences, are discussed below. One exemplary vector is the p3Dv1.O (p3D(AAT) v1.0) vector described herein.

7.4.8.1.1 Transformation Vector

Vectors containing a chimeric gene of the present invention may also include selectable markers for use in plant cells (such as the nptI1 kanamycin resistance gene, for selection in kanamycin-containing or the phosphinothricin acetyltransferase gene, for selection in medium containing phosphinothricin (PPT).

The vectors may also include sequences that allow their selection and propagation in a secondary host, such as sequences containing an origin of replication and a selectable marker such as antibiotic or herbicide resistance genes, e.g., HPH (Hagio et al., Plant Cell Reports 14:329 (1995); van der Elzer, Plant Mol. Biol. 5:299–302 (1985)). Typical secondary hosts include bacteria and yeast. In one embodiment, the secondary host is *Escherichia coli,* the origin of replication is a colE1-type, and the selectable marker is a gene encoding ampicillin resistance. Such sequences are well known in the art and are commercially available as well (e.g., Clontech, Palo Alto, Calif.; Stratagene, La Jolla, Calif.).

The vectors of the present invention may also be modified to intermediate plant transformation plasmids that contain a region of homology to an *Agrobacterium tumefaciens* vector, a T-DNA border region from *Agrobacterium tumefaciens,* and chimeric genes or expression cassettes (described above). Further, the vectors of the invention may comprise a disarmed plant tumor inducing plasmid of *Agrobacterium tumefaciens.*

7.4.9 Plant Expression Vector Production of Mature Proteins in Plants

7.4.9.1 Suitable Vectors

Suitable vectors include, but are not limited to, the following viral vectors such as lambda vector system gt11, gt WFS.tB, Charon 4, and plasmid vectors such as pER322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," Gene Expression Technolog vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual,* Cold Springs Laboratory, Cold Springs Harbor, N.Y. (1989), which is hereby incorporated by reference.

7.4.9.2 Host-Vector Systems

A variety of host-vector systems may be utilized to carry out the present invention. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and, perhaps, translation elements can be used.

7.4.10 Genetic Signals and Processing Events

In order to express the viral gene, the necessary genetic regulatory sequences must be provided. Since the proteins encoded in a potyvirus, genome are produced by the post translational processing of a polyprotein, a viral gene isolated from viral RNA does not contain transcription and translation signals necessary for its expression once transferred and integrated into a plant genome. It must, therefore, be engineered to contain a plant expressible promoter, a translation initiation codon (ATG) and a plant functional poly(A) addition signal (AATAAA) 3' of its translation termination codon. In the present invention, a viral gene is inserted into a vector which contains cloning sites for insertion 3' of the initiation codon and 5' of the poly(A) signal. The promoter is 5' of the initiation codon such that when structural genes are inserted at the cloning site, a functional unit is formed in which the inserted genes are expressed under the control of the various genetic regulatory sequences.

Different genetic signals and processing events control many levels of gene expression (e.g., DNA transcription and messenger RNA (mRNA) translation).

7.4.10.1 Signal Sequences for Production of Mature Proteins

In addition to encoding the protein of interest, the chimeric gene encodes a signal sequence (or signal peptide) that allows processing and translocation of the protein, as appropriate. Suitable signal sequences are described in above-referenced PCT application WO 95/14099. The plant signal sequence is placed in frame with a heterologous nucleic acid encoding a mature protein, forming a construct which encodes a fusion protein having an N-terminal region corresponding to the signal peptide and, immediately adjacent to the C-terminal amino acid of the signal peptide, the N-terminal amino acid of the mature heterologous protein. The expressed fusion protein is subsequently secreted and processed by signal peptidase cleavage precisely at the junction of the signal peptide and the mature protein, to yield the mature heterologous protein.

In another embodiment of the invention, the coding sequence in the fusion protein gene, in at least the coding region for the signal sequence, may be codon-optimized for optimal expression in plant cells, e.g., rice cells, as described below.

7.4.10.2 Promoters

Transcription Dependent upon the Presence of a Promotor

Transcription of DNA is dependent upon the presence of a promotor which is a DNA sequence that directs the binding of RNA polymerase and thereby promotes mRNA synthesis. The DNA sequences of eucaryotic promoters differ from those of procaryotic promoters. Furthermore, eucaryotic promotors and accompanying genetic signals may not be recognized in or may not function in a procaryotic system, and, further, procaryotic promoters are not recognized and do not function in eucaryotic cells.

The segment of DNA referred to as the promoter is responsible for the regulation of the transcription of DNA into mRNA. A number of promoters which function in plant cells are known in the art and may be employed in the practice of the present invention. These promoters may be obtained from a variety of sources such as plants or plant viruses, and may include but are not limited to promoters isolated from the caulimovirus group such as the cauliflower mosaic virus 35S promoter (CaMV35S), the enhanced cauliflower mosaic virus 35S promoter (enh CaMV35S), the figwort mosaic virus full-length transcript promoter (FMV35S), and the promoter isolated from the chlorophyll alb binding protein. Other useful promoters include promoters which are capable of expressing the potyvirus proteins in an inducible manner or in a tissue-specific manner in certain cell types in which the infection is known to occur. For example, the inducible promoters from phenylalanine ammonia lyase, chalcone synthase, hydroxyproline rich glycoprotein, extensin, pathogenesis-related proteins (e.g. PR-1a), and wound-inducible protease inhibitor from potato may be useful.

Preferred promoters for use in the present viral gene expression cassettes include the constitutive promoters from CaMV, the Ti genes nopaline synthase (Bevan et al., Nucleic Acids Res. II, 369–385 (1983)) and octopine synthase (Depicker et al., J. Mol. Appl. Genet., 1, 561–564 (1982)), and the bean storage protein gene phaseolin. The poly(A) addition signals from these genes are also suitable for use in the present cassettes. The particular promoter selected is preferably capable of causing sufficient expression of the DNA coding sequences to which it is operably linked, to result in the production of amounts of the proteins or the RNAs effective to provide viral resistance, but not so much as to be detrimental to the cell in which they are expressed. The promoters selected should be capable of functioning in tissues including but not limited to epidermal, vascular, and mesophyll tissues. The actual choice of the promoter is not critical, as long as it has sufficient transcriptional activity to accomplish the expression of the preselected proteins or antisense RNA, and subsequent conferral of viral resistance to the plants.

Promotors vary in their "strength" (i.e. their ability to promote transcription). For the purposes of expressing a cloned gene, it is desirable to use strong promotors in order to obtain a high level of transcription and, hence, expression of the gene. Depending upon the host cell system utilized, any one of a number of suitable promotors may be used. For instance, when cloning in $E.\ coli$, its bacteriophages, or plasmids, promotors such as the T7 phage promoter, lac promotor, trp promotor, recA promotor, ribosomal RNA promotor, the $P_R$ and $P_L$ promotors of coliphage lambda and others, including but not limited, to lacUV5, ompF, bla, 1pp, and the like, may be used to direct high levels of transcription of adjacent DNA segments. Additionally, a hybrid trp-lacUV5 (tac) promotor or other $E.\ coli$ promotors produced by recombinant DNA or other synthetic DNA techniques may be used to provide for transcription of the inserted gene.

7.4.10.2.1 Promoters that Transcribe the Cereal a-amylase Genes and Sucrose Synthase Genes The transcription regulatory or promoter region is chosen to be regulated in a manner allowing for induction under selected cultivation conditions, e.g., sugar depletion in culture or water uptake followed by gibberellic acid production in germinating seeds. Suitable promoters, and their method of selection are detailed in above-cited PCT application WO 95/14099. Examples of such promoters include those that transcribe the cereal a-amylase genes and sucrose synthase genes, and are repressed or induced by small molecules, like sugars, sugar depletion or phytohormones such as gibberellic acid or absissic acid. Representative promoters include the promoters from the rice a-amylase RAmy1A, RAmy1B, RAmy2A, RAmy3A, RAmy3B, RAmy3C, RAmy3D, and RAmy3E genes, and from the pM/C, gKAmy141, gKAmy155, Amy32b, and HV18 barley (x-amylase genes. These promoters are described, for example, in ADVANCES IN PLANT BIOTECHNOLOGY Ryu, D. D. Y., et al, Eds., Elsevier, Amsterdam, 1994, p.37, and references cited therein. Other suitable promoters include the sucrose synthase and sucrose-6-phosphate-synthetase (SPS) promoters from rice and barley.

Other suitable promoters include promoters which are regulated in a manner allowing for induction under seed-maturation conditions. Examples of such promoters include those associated with the following monocot storage proteins: rice glutelins, oryzins, and prolamines, barley hordeins, wheat gliadins and glutelins, maize zeins and glutelins, oat glutelins, and sorghum kafirins, millet pennisetins, and rye secalins.

A preferred promoter for expression in germinating seeds is the rice a-amylase RAmy1A promoter, which is upregulated by gibberellic acid. Preferred promoters for expression in cell culture are the rice a-amylase RAmy3D and RAmy3E promoters which are strongly upregulated by sugar depletion in the culture. These promoters are also active during seed germination. A preferred promoter for expression in maturing seeds is the barley endosperm-specific BI-hordein promoter (Brandt, A., et al., (1985) Carlsberg Res. Commun. 50:333–345).

The chimeric gene may further include, between the promoter and coding sequences, the 5' untranslated region (5' UTR) of an inducible monocot gene, such as the 5' UTR derived from one of the rice or barley a-amylase genes mentioned above. One preferred 5' UTR is that derived from the RAmy1A gene, which is effective to enhance the stability of the gene transcript.

7.4.10.2.2 Use of Inducers

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

7.4.10.3 Transcription Initiation Signal

Specific initiation signals are also required for efficient gene transcription in procaryotic cells.

These transcription initiation signals may vary in "strength" as measured by the quantity of gene specific messenger RNA and protein synthesized, respectively. The DNA expression vector, which contains a promotor, may also contain any combination of various "strong" transcription initiation signals.

7.4.10.4 Translation Dependent on Shine-Dalgarno Sequence (in Procaryotes)

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 31-end of the 16S rRNA (ribosomal RNA) and probably promote binding of mRNA to ribosomes by duplexing with the rRNA to allow correct positioning of the ribosome. For a review on maximizing gene expression, see Roberts and Lauer, Methods in Enzvmology, 68:473 (1979), which is hereby incorporated by reference.

The non-translated leader sequence can be derived from any suitable source and can be specifically modified to increase the translation of the mRNA. The 5' non-translated region can be obtained from the promoter selected to express the gene, an unrelated promoter, the native leader sequence of the gene or coding region to be expressed, viral RNAs, suitable eucaryotic genes, or a synthetic gene sequence. The present invention is not limited to the constructs presented in the following examples.

7.4.10.5 Naturally-Occurring, Heterologous Protein Coding Sequences 7.4.10.5.1 (i) $\alpha_1$-Antitrypsin: Mature human AAT is composed of 394 amino acids. The protein has N-glycosylation sites at asparagines 46, 83 and 247.

7.4.10.5.2 (ii) Antithrombin III: Mature human ATIII is composed of 432 amino acids. The protein has N-glycosylation sites at the four asparagine residues 96, 135, 155, and 192.

7.4.10.5.3 (iii) Human serum albumin: Mature HSA as found in human serum is composed of 585 amino acids. The protein has no N-linked glycosylation sites.

7.4.10.5.4 (iv) Subtilisin BPN': Native proBPN' as produced in B. ainyloliquefaciens is composed of 352 amino acids. The proBPN' polypeptide contains a 77 amino acid "pro" moiety. The remainder of the polypeptide, which forms the mature active BPN', is a 275 amino acid sequence. Native 13PN' as produced in Bacillus is not glycosylated.

7.4.10.6 A4. Codon-Qptimized Coding Sequences

In accordance with one aspect of the invention, it has been discovered that a severalfold enhancement of expression level can be achieved in plant cell culture by modifying the native coding sequence of a heterologous gene by contain predominantly or exclusively, highest-frequency codons found in the plant cell host.

The method will be illustrated for expression of a heterologous gene in rice plant cells, it being recognized that the method is generally applicable to any monocot. As a first step, a representative set of known coding gene sequence from rice is assembled. The sequences are then analyzed for codon frequency for each amino acid, and the most frequent codon is selected for each amino acid. This approach differs from earlier reported codon matching methods, in which more than one frequent codon is selected for at least some of the amino acids. The optimal codons selected in this manner for rice and barley are shown in Table 4.

TABLE 4

| Amino Acid | Rice Preferred Codon | Barley Preferred Codon |
| --- | --- | --- |
| Ala A | GCC | |
| Arg R | CGC | |
| Asn N | AAC | |
| Asp D | GAC | |
| Cys C | UGC | |
| Gln Q | CAG | |
| Glu E | GAG | |
| Gly G | GGC | |
| His H | CAC | |
| Ile I | AUC | |
| Leu L | CUC | |
| Lys K | AAG | |
| Phe F | UUC | |
| Pro P | CCG | CCC |
| Ser S | AGC | UCC |
| Thr T | ACC | |
| Tyr Y | UAC | |
| Val V | GUC | GUG |
| stop | UAA | UGA |

As indicated above, the fusion protein coding sequence in the chimeric gene is constructed such that the final (C-terminal) codon in the signal sequence is immediately followed by the codon for the N-terminal amino acid in the mature form of the heterologous protein.

In a preferred embodiment, the BPN' coding sequence is further modified to eliminate potential N-glycosylation sites, as native BPN' is not glycosylated. Table 5 illustrates preferred codon substitutions, which eliminate all potential N-glycosylation sites in subtilisin BPN'.

TABLE 5

| N-Glycosylation Sites | Location (Asn) (in mature protein) | Amino Acid Substitution |
| --- | --- | --- |
| Asn Asn Ser | 61 | Thr Asn Ser |
| Asn Asn Ser | 76 | Thr Asn Ser |
| Asn Met Ser | 123 | Thr Met Ser |
| Asn Gly Thr | 218 | Ser Gly Thr¹ |
| Asn Trp Thr | 240 | Thr Trp Thr |

¹improved thermostability; Bryan, et al., Proteins: Structure, Function, and Genetics 1:326 (1986).

7.4.10.7 Termination Sequence Coupled to the Fusion End

The present invention can also utilize a termination sequence operatively coupled to the fusion gene to end transcription. Suitable transcription termination sequences include the termination region of a 3' non-translated region. This will cause the termination of transcription and the addition of polyadenylated ribonucleotides to the 3' end of the transcribed mRNA sequence. The termination region or 31 non-translated region will be additionally one of convenience. The termination region may be native with the promoter region or may be derived from another source, and preferably includes a terminator and a sequence coding for polyadenylation. Suitable 3' non-translated regions include but are not limited to: (1) the 3' transcribed, non-translated regions containing the polyadenylated signal of Agrobacterium tumor-inducing (Ti) plasmid genes, such as the nopaline synthase (NOS) gene or the 35S promoter terminator gene, and (2) plant genes like the soybean 7S storage protein genes and the pea small subunit of the ribulose 1,5-bisphosphate carboxylase-oxygenase (ssRUBISCO) E9 gene.

The termination region or 3' non-translated region which is employed is one which will cause the termination of transcription and the addition of polyadenylated ribonucleotides to the 3' end of the transcribed mRNA sequence. The termination region may be native with the promoter region, native with the structural gene, or may be derived from another source, and preferably include a terminator and a sequence coding for polyadenylation. Suitable 3' non-translated regions of the chimeric plant gene include but are not limited to: (1) the 3' transcribed, non-translated regions containing the polyadenylation signal of AgjQbacterium tumor-inducing (Ti) plasmid genes, such as the nopaline synthase (NOS) gene, and (2) plant genes like the soybean 7S storage protein genes. ps 7.4.10.8 Transcription and Translation Terminators for Production of Mature Proteins The chimeric gene may also include, downstream of the coding sequence, the 3' untranslated region (Y UTR) from an inducible monocot gene, such as one of the rice or barley a-amylase genes mentioned above. One preferred 3' UTR is that derived from the RAmy1A gene. This sequence includes non-coding sequence 5' to the polyadenylation site, the polyadenylation site, and the transcription termination sequence. The transcriptional termination region may be selected, particularly for stability of the mRNA to enhance expression. Polyadenylation tails (Alber and Kawasaki, 1982, Mol. and Appl. Genet. 1:419–434) are also commonly added to the expression cassette to optimize high levels of transcription and proper transcription termination, respectively. Polyadenylation sequences include but are not limited to the Agrobacterium octopine synthetase signal (Gielen, et al., EMBO J. 3:835–846 (1984) or the nopaline synthase of the same species (Depicker, et al., Mol. Appl. Genet. 1:561–573 (1982).

Since the ultimate expression of the heterologous protein will be in a eukaryotic cell (in this case, a member of the grass family), it is desirable to determine whether any portion of the cloned gene contains sequences which will be processed out as introns by the host's splicing machinery. If so, site-directed mutagenesis of the "intron" region may be conducted to prevent losing a portion of the genetic message as a false intron code (Reed and Maniatis, Cell 41:95–105 (1985).

7.4.11 Selectable Marker Gene

Selectable marker genes may be incorporated into the present expression cassettes and used to select for those cells or plants which have become transformed. The marker gene employed may express resistance to an antibiotic, such as kanamycin, gentamycin, G418, hygromycin, streptomycin, spectinomycin, tetracyline, chloramphenicol, and the like.

Other markers could be employed in addition to or in the alternative, such as, for example, a gene coding for herbicide tolerance such as tolerance to glyphosate, sulfonylurea, phosphinothricin, or bromoxynil. Additional means of selection could include resistance to methotrexate, heavy metals, complementation providing prototrophy to an auxotrophic host, and the like.

For example, see Table 1 of PCT WO/91/10725, cited above. The present invention also envisions replacing all of the virus-associated genes with an array of selectable marker genes.

The particular marker employed will be one which will allow for the selection of transformed cells as opposed to those cells which were not transformed. Depending on the number of different host species one or more markers may be employed, where different conditions of selection would be useful to select the different host, and would be known to those of skill in the art. A screenable marker or "reporter gene" such as the 0-glucuronidase gene or luciferase gene may be used in place of, or with, a selectable marker. Cells transformed with this gene may be identified by the production of a blue product on treatment with 5-bromo-4-chloro-3-indoyl-β-D-glucuronide (X-Gluc).

In developing the present expression construct, the various components of the expression construct such as the DNA sequences, linkers, or fragments thereof will normally be insetted into a convenient cloning vector, such as a plasmid or phage, which is capable of replication in a bacterial host, such as E. coli. Numerous cloning vectors exist that have been described in the literature. After each cloning, the cloning vector may be isolated and subjected to further manipulation, such as restriction, insertion of new fragments, ligation, deletion, resection, insertion, in vitro mutagenesis, addition of polylinker fragments, and the like, in order to provide a vector which will meet a particular need.

7.4.12 Transferring Recombinant DNA into Plant Cell 7.4.12.1 Use of Micropipettes or Polyethylene Glycol In producing transgenic plants, the DNA construct in a vector described above can be microinjected directly into plant cells by use of micropipettes to transfer mechanically the recombinant DNA. Crossway, Mol. Gen. Genetics, 202:179–85 (1985), which is hereby incorporated by reference. The genetic material may also be transferred into the plant cell using polyethylene glycol. Krens, et al., Nature, 296:72–74 (1982), which is hereby incorporated by reference.

7.4.12.2 Particle Bombardment (Biolistic Transformation)

Another approach to transforming plant cells with the DNA construct is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, a vector containing the DNA construct can be introduced into the cell by coating the particles with the vector containing that heterologous DNA construct. Alternatively, the target cell can be surrounded by the vector so that the vector is carried into the cell by the wake of the particle. Biologically active particles (e.g., dried bacterial cells containing the vector and heterologous DNA construct) can also be propelled into plant cells.

7.4.12.2 Fusion of Protoplasts with Other Entities

Yet another method of introduction is fusion of protoplasts with other entities,—either minicells, cells, lysosomes or other fusible lipid-surfaced bodies. Fraley, et al., Proc. Natl. Acad. Sci. USA, 79:1859–63 (1982), which is hereby incorporated by reference.

7.4.12.4 Electroporation

The DNA molecule may also be introduced into the plant cells by electroporation. Fromm et al., Proc. Natl. Acad. Sci. USA, 82:5824 (1985), which is hereby incorporated by reference. In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

7.4.12.5 Infection with *Agrobacterium tumefaciens* or *A. rhizogenes*

Another method of introducing the DNA molecule into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

Agrobacterium is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome. J. Schell, Science, 237:1176–83 (1987), which is hereby incorporated by reference.

For Agrobacterium-mediated transformation, the expression cassette will be included in a vector, and flanked by fragments of the Agrobacterium Ti or Ri plasmid, representing the right and, optionally the left, borders of the Ti or Ri plasmid transferred DNA (T-DNA). This facilitates integration of the present chimeric DNA sequences into the genome of the host plant cell. This vector will also contain sequences that facilitate replication of the plasmid in Agrobacterium cells, as well as in *E. coli* cells.

All DNA manipulations are typically carried out in *E. coli* cells, and the final plasmid bearing the potyvirus expression cassette is moved into Agrobacterium cells by direct DNA transformation, conjugation, and the like. These Agrobacterium cells will contain a second plasmid, also derived from Ti or Ri plasmids. This second plasmid will carry all the vir genes required for transfer of the foreign DNA into plant cells.

Suitable plant transformation cloning vectors include those derived from a Ti plasmid of *Agrobacterium turnefacien*, as generally disclosed in Glassman et al. (U.S. Pat. No. 5,258,300). In addition to those disclosed, for example, Herrera-Estrella, Nature, 303, 209 (1983), Biotechnica (published PCT application PCT WO/91/10725), and U.S. Pat. No. 4,940,838, issued to Schilperoort et al.

7.4.13 Method for Making Genetically Recombinant Plants in Commercially Feasible Numbers In one preferred embodiment, the invention provides for a process for propagating plants by tissue culture in such a way as both to conserve desired plant morphology and to transform the plant with respect to one or more desired genes. The method includes the steps of (a) creating an Agrobacterium vector containing the gene sequence desired to be transferred to the propagated plant, preferably together with a marker gene; (b) taking one or more petiole explants from a mother plant and inoculating them with the Agrobacterium vector; (c) conducting callus formation in the petiole sections in culture, in the dark; and (d) culturing the resulting callus in growth medium having a benzylamino growth regulator such as benzylaminopurine or, most preferably, benzylaminopurineriboside. Additional optional growth regulators including auxins and cytokinins (indole butyric acid, benzylamine, benzyladenine, benzylaminopurine, alpha naphthylacetic acid and others known in the art) may also be present. Preferably, the petiole tissue is taken from Pelarcronium x domesticum and the Acrobacterium vector contains an antisense gene for ACC synthase or ACC oxidase to prevent ACC synthase or ACC oxidase expression and, in turn, preventing ethylene formation. Pelargoniums propagated in culture using the present technique are resistant to wilting and petal shatter, and are morphologically conserved due to the use of petiole explants specifically and the particular culture media disclosed.

7.4.13.1 Using Petioles as the Explant Tissue

Although in theory any anatomic explants can be mixed with Agrobacterium containing the desired gene sequences to be transferred, followed by tissue culture propagation of transgenic transformed plants, in practice we have encountered unexpectedly good results using petioles as the explant tissue. We have found that morphologic conservation is virtually assured with the use of leaf petiole tissue, whereas morphologic variation-even is between two generations—can result when explants of other tissue, i.e. leaf tissue, are used. Moreover, the petiole explants should be taken from stock plants (mother plants) of which commercial propagation is desired. Commercial viability is attributable to the large number of transgenically transformed plants which can be produced from a relatively few petioles taken from the mother plant-particularly because leaf petioles can be harvested from a mother plant with impunity, without endangering the mother plant.

7.4.13.1.1 Cut Leaf Petioles

The process of the present invention generally proceeds as follows. Leaves are harvested from stock plants for which commercial propagation is desired. The petiole section of each leaf is sterilized with a soap-and-water wash followed by surface sterilization using a solution containing soap and hypochlorite bleach, or a sequence of ethanol and bleach rinses. A good sterilization protocol rinses the petiole tissue in 70% aqueous ethanol for 1 minute, followed by a 15 minute rinse with 10% aqueous bleach, followed by two rinses with sterile water.

After sterilization, the leaf petioles are cut into approximately 1 cm pieces. The cut leaf petioles are inoculated with Actrobacterium cells which contain the gene sequence desired to be transferred to the plant cells, preferably together with a marker gene such as the kanamycin resistance gene known in the art. The inoculation can be as simple as the physical mixing of the cut leaf petioles with the Agrobacterium cells, with an approximate 30 minute incubation at ambient room or greenhouse temperatures.

7.4.13.1.2 Use of a Marker Gene

Those skilled in the art know the significance of the use of a marker gene, but it is instructive to review that technology here. If a genetic sequence to be transplanted includes both the gene (or antisense gene) of interest adjacent a marker gene such as an antibiotic-resistance gene, the successfully genetically transformed cells can easily be separated from any cells in which the desired transformation did not occur. As a practical matter in plant propagation, a number of explants or other regenerative plant cells can be exposed to the gene/marker gene combination and then screened for successful transformants by, for example, inducing and growing the plantlets in culture medium containing the antibiotic for which the marker gene imparts resistance. If any plant grows in the antibiotic-containing medium, it will also have been transformed with respect to the desired gene adjacent the antibiotic-resistance gene. Explants or other cells which may not have underwent genetic transformation merely die in the culture medium—due to antibiotic susceptibility—and disappear.

7.4.13.1.3 Antisense Molecular Biology

Those skilled in the art also understand the significance of "antisense" molecular biology, but it should be borne in mind that primarily the present invention is intended to create transformants having antisense genes per se, and preferably not organisms containing vector-borne antisense mRNAs to prevent transcription of intact, or non-antisense, genes.

Transformation to create antisense genes is known in the art as exemplified by van der Krol, et al., "Antisense Chalcone Synthase Genes in Petunia Visualization of Variable Transgene Expression," Mol. Gen. Genet. (Molecular & General Genetics) Vol. 220, No. 2, pp. 204–212 (1990).

7.4.13.1.4 Growth Period 7.1.4.13.1.4.1 Transfer to Culture Medium

The inoculated petiole sections are then transferred to separate test tubes or vials containing culture medium. The culture medium contains vitamins, minerals, a food source and at least one growth regulator.

The food source usually includes the Murashige Skoog salt known in the art, and preferably also includes additional food/energy sources, most preferably fresh coconut milk, as well as Agrobacterium virulence enhancers such as acetosyringone. An essential growth regulator is a benzylamino compound chemically equivalent to the most preferred benzylaminopurineriboside or the benzylaminopurines generally. The use of this class of growth regulators gives unexpectedly good results over the use of other growth regulators such as 2,4- dichlorophenoxyacetic acid, kinetin, gibberellic acid, abscisic acid or 6-dimethylallylaminopurine ($N^6$-[2-isopentenyl]adenine). Additional auxin and/or cytokinin growth regulators (indole acetic acid, indole butyric acid, benzylamine, benzyladenine, additional benzylaminopurine, alpha naphthylacetic acid and others) may also be present if they are in addition to, and not in substitution for, the benzyl/amino growth regulator selected.

The test tubes or vials are maintained for five days to two weeks in complete darkness, at a temperature of about 25° C. Over the five day to two week period, the section enlarges slightly and the ends form callus.

Miniature shoots start forming intermittently on the callused ends of the petiole section.

7.4.13.1.4.2 Transfer to a Magenta Vial or Box Known in the Art

After five days to two weeks, the enlarged petiole section bearing the miniature shoots is transferred from the test tube or vial to a Magenta vial or box known in the art. The enlarged petiole sections are housed five- to-a-Magenta vial. The same growing medium as was originally charged to the test tube or vial is likewise charged to the Magenta vial, and in any event coconut milk should be present in the culture medium at this stage of the process. Also added to the medium is kanamycin (assuming the Agrobacterium contained the kanamycin resistance gene) and carbenicillin to kill any excess Agrobacterium. The Magenta vials are then maintained, under the same conditions as were the test tubes or vials, for an additional five to eight weeks in the dark and at about 25° C. The Magenta vials are then exposed to 5–10 weeks of 16 hours of light daily, in which the temperature is maintained at 72° F. with 690 foot candles (6900 lux) of cool fluorescent light. During this time the petiole is sections grow into enlarged clumps; the shoots elongate and turn into plantlets and many more shoots form. Once plantlets appear, they are transferred to fresh media containing kanamycin, carbenicillin and no growth hormones.

7.4.13.1.5 Rooting

After the total growth period has elapsed, the clumps are removed and placed in sterile water. The individual plants are dissected out of the clump with a sterile scalpel. Each individual plant essentially has a series of leaves and nodes and is at least ½" high, but usually no roots are present. The individual plants are placed in RUBBER DIRT™ or other soil or soil-like growth media or growth media plugs, where rooting then takes place. Many varieties of *Pelargonium x domesticum* have been successfully tissue cultured through leaf petioles and multiplied, both with and without transgenic transformation via Agrobacterium. Morphologic variation has been minimal and within commercially acceptable limits for finished plant material. Other plants may be propagated by this tissue culture technique/transgenic technique also.

7.4.13.2 Creating an Agrobacterium Cell Containing the Desired Vector

The creation of the Agrobacterium cell containing the desired vector can be accomplished by means known in the art. Structural and regulatory genes to be inserted may be obtained from depositories, such as the American Type Culture Collection, Rockville, Md., 20852, as well as by isolation from other organisms, typically by the screening of genomic or cDNA libraries using conventional hybridization techniques. Typical hybridization techniques are dislosed in Sambrook, et al., Molecular Cloning—Laboratory Manual, Cold Spring Harbor Laboratory, Cold Spring Harbor, N.Y. (1989). Screening may be performed by (1) nucleic acid hybridization using homologous genes or heterologous genes from other organisms, (2) probes synthetically produced to hybridize to particular sequences coding for desired protein sequences, or (3) DNA sequencing and comparison to known sequences. Sequences for specific genes may be found in various computer databases, including GenBank, National Institutes of Health, or the database maintained by the United States Patent and Trademark Office.

The genes of interest may also be identified by antibody screening of expression libraries with antibodies made against homologous proteins to identify genes encoding for homologous functions. Transposon tagging can also be used to aid the isolation of a desired gene. Transposon tagging typically involves mutation of the target gene. A mutant gene is isolated in which a transposon has inserted into the target gene and altered the resulting phenotype.

7.4.13.2.1 Isolation of the Mutated Gene

Using a probe for the transposon, the mutated gene can be isolated. Then, using the DNA adjacent to the transposon in the isolated, mutated gene as a probe, the normal wild-type allele of the target gene can be isolated. Such techniques are taught, for example, in McLaughlin and Walbot, Genetics, Vol. 117 pp. 771–776 (1987), as well as numerous other references.

7.4.13.2.2 Reporter Gene

In addition to the functional gene and the selectable marker gene, the DNA sequences may also contain a reporter gene which facilitates screening of the transformed shoots and plant material for the presence and expression of endogenous DNA sequences. Exemplary reporter genes include β-glucuronidase and luciferase.

7.4.13.2.3 Transfer Regions of a Suitable Plasmid

As described above, the exogenous DNA sequences are introduced into the area of the explants by incubation with Agrobacterium cells which carry the sequences to be transferred within a transfer DNA (T-DNA) region found on a suitable plasmid, typically the Ti plasmid. Ti plasmids contain two regions essential for the transformation of plant cells. One of these, the T-DNA region, is transferred to the plant nuclei and induces tumor formation. The other, referred to as the virulence (vir) region, is essential for the transfer of the T-DNA but is not itself transferred. By inserting the DNA sequence to be transferred into the T-DNA region, introduction of the DNA sequences to the plant genome can be effected. Usually, the Ti plasmid will be modified to delete or to inactivate the tumor-causing genes so that they are suitable for use as a vector for the transfer of the gene constructs of the present invention. Other plasmids may be utilized in conjunction with Agrobacterium for transferring the DNA sequences of the present invention to the plant cells.

The construction of recombinant Ti plasmids may be accomplished using conventional recombinant DNA techniques, such as those described by Sambrook et al. (1989). Frequently, the plasmids will include additional selective marker genes which permit manipulation and construction of the plasmids in suitable hosts, typically bacterial hosts other than Agrobacterium, such as *E. coli*. In addition to the above-described kanamycin resistance marker gene, other exemplary genes are the tetracycline resistance gene and the ampicillin resistance gene, among others.

7.4.13.2.4 Transcriptional and Translational Control Sequences

The genes within the DNA sequences will typically be linked to appropriate transcriptional and translational control sequences which are suitable for the Pelargonium plant host. For example, the gene will typically be situated at a distance from a promoter corresponding to the distance at which the promoter is normally effective in order to ensure transcriptional activity. Usually, a polyadenylation site and transcription termination site will be provided at the 3'-end of the gene coding sequence. Frequently, the necessary control functions can be obtained together with the structural gene when it is isolated from is a target plant or other host. Such intact genes will usually include coding sequences, intron (s), a promoter, enhancers, and all other regulatory elements either upstream (5') or downstream (3') of the coding sequences.

7.4.13.2.5 Using the Binary Vector System to Introduce the DNA Sequence

The binary vector system generally discussed above may be used to introduce the DNA sequence according to the present invention. A first plasmid vector strain would carry the T-DNA sequence while a second plasmid vector carries a virulence (vir) region. By incubating Agrobacterium cells carrying both plasmids with the explant, infection of the plant material is thus achieved.

7.4.13.2.6 The T-DNA Plasmid

Any one of a number of T-DNA plasmids can be used with such a binary vector system, the only requirement being that one be able to select independently for the two plasmids. The T-DNA plasmid in a preferred embodiment comprises a heterologous promoter which promotes the transcription of one or more genes within the exogenous DNA fragment (s) . An example is the Cauliflower Mosaic Virus 35S promoter (Odell et al., Nature, Vol. 313, pp. 810–812 (1985) among others.

7.4.13.2.7 Agrobacterium Species

Suitable Agrobacterium species include *Agrobacterium tumefaciens* and *Agrobacterium rhizocienes*. While the wild-type *Agrobacterium rhizocrenes* may be used, the *Agrobacterium tumefaciens* should be disarmed by deactivating its tumor activating capacity prior to use.

Preferred *Agrobacterium tumefaciens* strains include LBA4404, as described by Hoekema et al., Nature, Vol. 303, pp. 179–180 (1983) and EHA101 as described by Hood et al., J. Bacteriol., Vol. 168, pp. 1291–1301 (1986). A preferred *Agrobacterium rhizocrenes* strain is 15834, as described by Birot et al., Plant Physiol. Biochem., Vol. 25, pp. 323–325 (1987).

7.4.13.2.8 Antisense Sequences

As the Agrobacterium strains carrying the desired exogenous DNA sequences are being prepared, the following antisense sequences are preferred for use in the present process, and are particularly preferred in transforming regal Pelargonium petiole explants according to the present method. These sequences are the known sequences for ACC Synthase (1-aminocyclopropane-1-carboxylate synthase) and ACC Oxidase (1-aminocyclopropane-1-carboxylate oxidase) , reversed to create antisense sequences.

7.4.13.2.9 Culturing the Agrobacterium Strains

After the Agrobacterium strains carrying the desired exogenous DNA sequences have been prepared, they will usually be cultured for a period of time prior to incubation with the explant material. Initially, the Agrobacterium may be cultured on a solid media including nutrients, an energy source and a gelling agent. Suitable nutrients include salts, tryptone and yeast extracts, while most sugars are suitable as the energy source and the gelling agent can be TC agar or bactoagar or other similar products. The Agrobacterium cells are typically cultured for about two to five days, preferably in the dark at about 23–280° C., and are collected by scraping before browning (while still a white color). The cells are scraped from the medium and suspended in a liquid medium such as L-broth, pH 6.9–7.1, preferably 7.0. The bacteria are cultured in liquid medium for 8–36 hours, preferably 12–20, on a shaker (50–220 rpm, preferably 100–120 rpm) at 23–280° C. At the end of this period the bacteria are diluted to an optical density of 0.3 and cultured for 2–6, preferably 4, hours (on a shaker, 23–28° C.). The Agrobacterium cells thus incubated are ready for inoculation onto explant material such as Pelargonium petiole sections.

When Agrobacterium cells are inoculated onto *Pelargonium x domesticum* petiole explants, and after the coincubation discussed above, the tissue culture method will proceed generally in accordance with the disclosure of U.S. application Ser. No. 08/149,702 filed Nov. 9, 1993, which is a Continuation of U.S. application Ser. No. 07/690,073 filed Apr. 23, 1991, by Wendy Oglevee- O'Donovan and Eleanor Stoots, both of which applications are hereby incorporated herein by reference. By means known in the art, carbenicillin can be added to the coincubated petiole/Agrobacterium cells to kill excess Agrobacterium cells, after transfection has taken place.

7.4.13.2.10 Selecting an Antibiotic

The key is to select an antibiotic which will kill the Agrobacterium without harming the explant material. An additional amount of the same antibiotic may be provided in the ensuing tissue culture method, to assure final removal of any viable Agrobacterium cells.

7.4.13.2.11 Confirming Transformation

After green transformed shoots are approximately ½" tall, they can then be transplanted to soil within a greenhouse or elsewhere in a conventional manner for tissue culture plantlets. Transformation of the resulting plantlets can be confirmed by assaying activity for the selection marker, or by assaying the plant material for any of the phenotypes which have been introduced by the exogenous DNA. Suitable assay techniques include polymerase chain reaction (PCR), restriction enzyme digestion, Southern blot hybridization and Northern blot hybridization.

7.4.13.3 Commercial Production

The present invention represents a breakthrough in the commercial production and genetically transformed plants. Because the method uses petiole tissue from a grower's mother plant (a stock plant), the starting petiole explants have a commercially desirable morphology to begin with— by definition. However, if the mother plant could be improved by genetic transformation of some type, for example to deactivate a gene which expresses an enzyme in the ethylene synthesis pathway, the progeny of the mother plant may thus be improved in this one way over their parent stock. The petiole tissue from the stock plant, plus the genetic transformation from the Agrobacterium, yield both an improved genetic makeup of the commercially produced plants—although with preserved desired morphology from the mother plant—and at the same time the high yields possible only with the generation of many plantlets in a single generation's growth in tissue culture. In summary, with the present method a single genetically transformed mother plant can yield literally thousands of offspring plants. No one in the prior art has attempted to combine these two previously disparate technologies to achieve a unique method in which the result is no less than a commercially viable technique for making genetically recombinant plants in commercially feasible numbers.

7.4.14 Transformation of Plant Cells Using Alternative Methods

A variety of techniques are available for the introduction of the genetic material into or transformation of the plant cell host. However, the particular manner of introduction of the plant vector into the host is not critical to the practice of the present invention, and any method which provides for efficient transformation may be employed. In addition to transformation using plant transformation vectors derived from the tumor-inducing (Ti) or root-inducing (Ri) plasmids of Agrobacterium, alternative methods could be used to insert the DNA constructs of the present invention into plant cells. Such methods may include, for example, the use of liposomes, transformation using viruses or pollen, chemicals that increase the direct uptake of DNA (Paszkowski et al., EMBO J., 3, 2717 (1984)), microinjection (Crossway et al., Mol. Gen. Genet., 202, 179 (1985)), electroporation (Fromm et al., Proc. Natl. Acad. Sci. US, 82, 824 (1985)), or high-velocity microprojectiles (Klein et al., Nature, 327, 70 (1987)).

7.4.14.1 Plant Tissue Source or Cultured Plant Cell

The choice of plant tissue source or cultured plant cells for transformation will depend on the nature of the host plant and the—transformation protocol. Useful tissue sources include callus, suspension culture cells, protoplasts, leaf segments, stem segments, tassels, pollen, embryos, hypocotyls, tuber segments, meristematic regions, and the like.

The tissue source is regenerable, in that it will retain the ability to regenerate whole, fertile plants following transformation.

7.4.14.2 Conditions During Transformation

The transformation is carried out under conditions directed to the plant tissue of choice. The plant cells or tissue are exposed to the DNA carrying the present multi-gene expression cassette for an effective period of time. This may range from a less-than-one-second pulse of electricity for electroporation, to a two-to-three day co-cultivation in the presence of plasmid-beazing Agrobacterium cells. Buffers and media used will also vary with the plant tissue source and transformation protocol. Many transformation protocols employ a feeder layer of suspended culture cells (tobacco or Black Mexican Sweet Corn, for example) on the surface of solid media plates, separated by a sterile filter paper disk from the plant cells or tissues being transformed.

Following treatment with DNA, the plant cells or tissue may be cultivated for varying lengths of time prior to selection, or may be immediately exposed to a selective agent such as those described hereinabove.

7.4.14.3 Inhibitory Agent

Protocols involving exposure to Agrobacterium will also include an agent inhibitory to the growth of the Agrobacterium cells. Commonly used compounds are antibiotics such as cefotaxime and carbenicillin. The media used in the selection may be formulated to maintain transformed callus or suspension culture cells in an undifferentiated state, or to allow production of shoots from callus, leaf or stem segments, tuber disks, and the like.

7.4.15 Method for Transformation of the Target Plant

The methods used for the actual transformation of the target plant are not critical to this invention. The transformation of the plant is preferably permanent, e.g. by integration of introduced sequences into the plant genome, so that the introduced sequences are passed onto successive plant generations. There are many plant transformation techniques well-known to workers in the art, and new techniques are continually becoming known. Any technique that is suitable for the target plant can be employed with this invention. For example, the sequences can be introduced in a variety of forms, such as a strand of DNA, in a plasmid, or in an artificial chromosome, to name a few. The introduction of the sequences into the target plant cells can be accomplished by a variety of techniques, as well, such as calcium phosphate-DNA co-precipitation, electroporation, microinjection, Agrobacterium infection, liposomes or microprojectile transformation. Those of ordinary skill in the art can refer to the literature for details, and select suitable techniques without undue experimentation.

7.4.15.1 Introduction of Sequences into Target Plant Cells

It is possible to introduce the recombinase gene, in particular, into the transgenic plant in a number of ways. The gene can be introduced along with all of the other basic sequences, as in the first preferred embodiment described above. The repressible promoter/recombinase construct can be also introduced directly via a viral vector into a transgenic plant that contains the other sequence components of the system. Still another method of introducing all the necessary sequences into a single plant is the second preferred embodiment described above, involving a first transgenic plant containing the transiently-active promoter/structural gene sequences and the blocking sequence, and a second transgenic plant containing the recombinase gene linked to a germination-specific plant-active promotor, the two plants being hybridized by conventional to produce hybrid progeny containing all the necessary sequences.

It is also possible to introduce the recombinase itself directly into a transgenic plant as a conjugate with a compound such as biotin, that is transported into the cell. See Horn, et al. (1990).

7.4.15.2 Direct or Vectored Transformation

Various methods for direct or vectored transformation of plant cells, e. g., plant protoplast cells, have been described, e.g., in above-cited PCT application WO 95/14099. As noted in that reference, promoters directing expression of selectable markers used for plant transformation (e.g., nptII) should operate effectively in plant hosts. One such promoter is the nos promoter from native Ti plasmids (Heffera-Estrella, et al., Nature 303:209–213 (1983). Others include the 35S and 19S promoters of cauliflower mosaic virus (Odell, et al., Nature 313:810–812 (1985) and the 2' promoter (Velten, et al., EMBO J. 3:2723–2730 (1984).

In one preferred embodiment, the embryo and endosperm. of mature seeds are removed to exposed scutulum tissue cells. The cells may be transformed by DNA bombardment or injection, or by vectored transformation, e.g., by Agrobacteriwn infection after bombarding the scuteller cells with microparticles to make them susceptible to Agrobacteriwn infection (Bidney et al., Plant Mol. Biol. 18:301–313, 1992).

One preferred transformation follows the methods detailed generally in Sivamani, E. et al., Plant Cell Reports 15:465 (1996); Zhang, S., et al., Plant Cell Reports 15:465 (1996); and Li, L., et al., Plant Cell Reports 12:250 (1993). Briefly, rice seeds are sterilized by standard methods, and callus induction from the seeds is carried out on MB media with 2,41). During a first incubation period, callus tissue forms around the embryo of the seed. By the end of the incubation period, (e.g., 14 days at 28° C.) the calli are about 0.25 to 0.5 cm in diameter. Callus mass is then detached from the seed, and placed on fresh NB media, and incubated again for about 14 days at 28° C. After the second incubation period, satellite calli developed around the original "mother" callus mass.

These satellite calli were slightly smaller, more compact and defined than the original tissue. It was these calli were transferred to fresh media. The "mother" calli was not transferred. The goal was to select only the strongest, most vigorous growing tissue for fiwffier culture.

Calli to be bombarded are selected from 14-day-old subcultures. The size, shape, color and density are all important in selecting calli in the optimal physiological condition for transformation. The calli should be between 0.8 and 1.1 mm in diameter. The calli should appear as spherical masses with a rough exterior.

Transformation is by particle bombardment, as detailed in the references cited above. After the transformation steps, the cells are typically grown under conditions that permit expression of the selectable marker gene. In a preferred embodiment, the selectable marker gene is HPH. It is preferred to culture the transformed cells under multiple rounds of selection to produce a uniformly stable transformed cell line.

7.4.16 Subculturing Cells or Callus Growing in Normally Inhibitory Concentrations of the Selective Agents Cells or callus observed to be growing in the presence of normally inhibitory concentrations of the selective agents are presumed to be transformed and may be subcultured several additional times on the same medium to remove non-resistant sections. The cells or calli can then be assayed for the presence of the viral gene cassette, or may be subjected to known plant regeneration protocols. In protocols involving the direct production of shoots, those shoots appearing on the selective media are presumed to be transformed and may be excised and rooted, either on selective medium suitable for the production of roots, or by simply dipping the excised shoot in a root-inducing compound and directly planting it in vermiculite.

7.4.17 Selecting for Multi-Viral Resistance

In order to produce transgenic plants exhibiting multi-viral resistance, the viral genes must be taken up into the plant cell and stably integrated within the plant genome. Plant cells and tissues selected for their resistance to an inhibitory agent are presumed to have acquired the selectable marker gene encoding this resistance during the transformation treatment.

Since the marker gene is commonly linked to the viral genes, it can be assumed that the viral genes have similarly been acquired. Southern blot hybridization analysis using a probe specific to the viral genes can then be used to confirm that the foreign genes have been taken up and integrated into the genome of the plant cell. This technique may also give some indication of the number of copies of the gene that have been incorporated. Successful transcription of the foreign gene into mRNA can likewise be assayed using Northern blot hybridization analysis of total cellular RNA and/or cellular RNA that has been enriched in a polyadenylated region. mRNA molecules encompassed within the scope of the invention are those which contain viral specific sequences derived from the viral genes present in the transformed vector which are of the same polarity to that of the viral genomic RNA such that they are capable of base pairing with viral specific RNA of the opposite polarity to that of viral genomic RNA under conditions described in Chapter 7 of Sambrook et al. (1989). mRNA molecules also encompassed within the scope of the invention are those which contain viral specific sequences derived from the viral genes present in the transformed vector which are of the opposite polarity to that of the viral genomic RNA such that they are capable of base pairing with viral genomic RNA under conditions described in Chapter 7 of Sambrook et al. (1 989).

The presence of a viral gene can also be detected by immunological assays, such as the double-antibody sandwich assays described by Namba, et al., Gene, 107, 181 (1991) as modified by Clark et al., J. Gen. Virol., 34, 475 (1979). See also, Namba et al., Phytopathology, 82, 940 (1992).

Virus resistance can be assayed via infectivity studies as generally disclosed by Namba et al., ibid., wherein plants are scored as symptomatic when any inoculated leaf shows veinclearing, mosaic or necrotic symptoms.

It is understood that the invention is operable when either sense or anti-sense viral specific RNA is transcribed from the expression cassettes described above. That is, there is no specific molecular mechanism attributed to the desired phenotype and/or genotype exhibited by the transgenic plants. Thus, protection against viral challenge can occur by any one or any number of mechanisms.

It is also understood that virus resistance can occur by the expression of any virally encoded gene. Thus, transgenic plants expressing a coat protein gene or a non-coat protein gene can be resistant to challenge with a homologous or heterologous virus.

7.4.18 Cell Culture Production of Mature Heterologous Protein

Transgenic cells, typically callus cells, are cultured under conditions that favor plant cell growth, until the cells reach a desired cell density, then under conditions that favor expression of the mature protein under the control of the given promoter. Preferred culture conditions are described herein. Purification of the mature protein secreted into the medium is by standard techniques known by those of skill in the art.

In one embodiment of the invention, in which BPN' is secreted as the proBPN' form of the enzyme, the chaperon "pro" moiety of the enzyme facilitates enzyme folding and is cleaved from the enzyme, leaving the active mature form of BPN'. In another embodiment, the mature enzyme is co-expressed and co-secreted with the "pro" chaperon moiety, with conversion of the enzyme to active form occurring in presence of the free chaperon (Eder et al., Biochem. (1993) L2:18–26; Eder et al, (1993) J. Mol. Biol.

223:293–304). In yet another embodiment of the invention, the BPN' is secreted in inactive form at a pH that may be in the 6–8 range, with subsequent activation of the inactive form, e.g., after enzyme isolation, by exposure. to the "pro" chaperon moiety, e.g., immobilized to a solid support. In both of these embodiments, the culture medium is maintained at a pH of between 5 and 6, preferably about 5.5 during the period of active expression and secretion of BPN', to keep the BPN', which is normally active at alkaline pH, at a pH below optimal activity.

7.4.18.1 Production of Mature Heterologous Protein in Germinatin Seeds

In this embodiment, monocot cells transformed as above are used to regenerate plants, seeds from the plants are harvested and then germinated, and the mature protein is isolated from the germinated seeds.

Plant regeneration from cultured protoplasts or callus tissue is carried by standard methods, e.g., as described in Evans et al., HANDBOOK OF PLANT CELL CULTURE Vol. 1: (MacMillan Publishing Co. New York, 1983); and Vasil I. R. (ed.), CELL CULTURE AND SOMATIC CELL GENETICS OF PLANTS, Acad. Press, Orlando, Vol. 1, 1984, and Vol. 111, 1986, and as described in the above-cited PCT application.

7.4.18.2 Seed Germination Conditions

The transgenic seeds obtained from the regenerated plants are harvested, and prepared for germination by an initial steeping step, in which the seeds immersed in or sprayed with water to increase the moisture content of the seed to between 35–45%. This initiates germination. Steeping— typically takes place in a steep tank which is typically fitted with a conical end to allow the seed to flow freely out. The addition of compressed air to oxygenate the steeping process is an option.

The temperature is controlled at approximately 22-C. depending on the seed.

After steeping, the seeds are transferred to a germination compartment which contains air saturated with water and is under controlled temperature and air flows. The typical temperatures are between 12–25-C. and germination is permitted to continue for from 3 to 7 days.

Where the heterologous protein coding gene is operably linked to a inducible promoter requiring a metabolite such as sugar or plant hormone, e.g., 2 to 100 µM gibberellic acid, this metabolite is added, removed or depleted from the steeping water medium and/or is added to the water saturated air used during germination. The seed absorbs the aqueous medium and begins to germinate, expressing the heterologous protein. The medium may then be withdrawn and the malting begun, by maintaining the seeds in a moist temperature controlled aerated environment. In this way, the seeds may begin growth prior to expression, so that the expressed product is less likely to be partially degraded or denatured during the process.

More specifically, the temperature during the imbibition or steeping phase will be maintained in the range of about 15–25° C., while the temperature during the germination will usually be about 20° C. The time for the imbibition will usually be from about 1 to 4 days, while the germination time will usually be an additional 1 to 10 days, more usually 3 to 7 days. Usually, the time for the malting does not exceed about ten days. The period for the malting can be reduced by using plant hormones during the imbibition, particularly gibberellic acid.

To achieve maximum production of recombinant protein from malting, the malting procedure may be modified to accommodate de-hulled and de-embryonated seeds, as described in above-cited PCT application WO 95/14099. In the absence of sugars from the endosperm, there is expected to be a 5 to 10 fold increase in RAmy3D promoter activity and thus expression of heterologous protein. Alternatively when embryoless half-seeds are incubated in 10 mM $CaCl_2$ and 5 µM gibberellic acid, there is a 50 fold increase in RAmy1A promoter activity.

7.4.18.3 Production of Mature HAS

Following the germination conditions as outlined above and further detailed herein, supernatant was analyzed by Western blot. Western blot analysis shows production of HSA in germinating rice seeds, with seed samples taken 24, 72, and 120 hours after induction with gibberellin. HSA production was highest approximately 24 hours post-induction. Bilirubin binding, a measure of correct folding of plant-produced HSA, is assayed according to the method presented herein.

7.4.19 Production of Mature Heterologous Protein in Maturing Seeds

In this embodiment, monocot cells transformed as above are used to regenerate plants, and seeds from the plants are allowed to mature, typically in the field, with consequent production of heterologous protein in the seeds.

Following seed maturation, the seeds and their heterologous proteins may be used directly, that is, without protein isolation, where for example, the heterologous protein is intended to confer a benefit on the seed as a whole, for example, to enrich the seed in the selected protein.

Alternatively, the seeds may be fractionated by standard methods to obtain the heterologous protein in enriched or purified form. In one general approach, the seed is first milled, then suspended in a suitable extraction medium, e.g., an aqueous or an organic solvent, to extract the protein or metabolite of interest. If desired the heterologous protein can be further fractionated and purified, using standard purification methods.

The following examples are provided by way of illustration only and not by way of limitation. Those of skill will readily recognize a variety of noncritical parameters which could be changed or modified to yield essentially similar results.

7.4.20 Regeneration of the Transformed Plant Cells

After transformation, the transformed plant cells must be regenerated.

The methods used to regenerate transformed cells into whole plants are not critical to this invention, and any method suitable for the target plant can be employed. The literature describes numerous techniques for regenerating specific plant types, (e.g., via somatic embryogenesis, Umbeck, et al., 1987) and more are continually becoming known. Those of ordinary skill in the art can refer to the literature for details and select suitable techniques without undue experimentation.

Plant regeneration from cultured protoplasts is described in Evans et al., Handbook of Plant Cell Cultures, Vol. 1: (MacMillan Publishing Co., New York, 1983); and Vasil I. R. (ed.), Cell Culture and Somatic Cell Genetics of Plants, Acad. Press, Orlando, Vol. I, 1984, and Vol.-III (1986), which are hereby incorporated is by reference.

It is known that practically all plants can be regenerated from cultured cells or tissues, including but not limited to, all major species of sugarcane, sugar beets, cotton, fruit trees, and legumes.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

7.4.21 Breeding Techniques

After the expression cassette is stably incorporated in transgenic plants, it can be transferred to other plants by sexual crossing. Any of a number of standard breeding techniques can be used, depending upon the species to be crossed.

Seed from plants regenerated from tissue culture is grown in the field and self-pollinated to generate true breeding plants. The progeny from these plants become true breeding lines which are evaluated for viral resistance in the field under a range of environmental conditions. The commercial value of viral-resistant plants is greatest if many different hybrid combinations with resistance are available for sale. The farmer typically grows more than one kind of hybrid based on such differences as maturity, disease and insect resistance, color or other agronomic traits. Additionally, hybrids adapted to one part of a country are not adapted to another part because of differences in such traits as maturity, disease and insect tolerance, or public demand for specific varieties in given geographic locations.

Because of this, it is necessary to breed viral resistance into a large number of parental lines so that many hybrid combinations can be produced.

Adding viral resistance to agronomically elite lines is most efficiently accomplished when the genetic control of viral resistance is understood. This requires crossing resistant and sensitive plants and studying the pattern of inheritance in segregating generations to ascertain whether the trait is expressed as dominant or recessive, the number of genes involved, and any possible interaction between genes if more than one are required for expression. With respect to transgenic plants of the type disclosed herein, the transgenes exhibit dominant, single gene Mendelian behavior. This genetic analysis can be part of the initial efforts to covert agronomically elite, yet sensitive lines to resistant lines. A conversion process (backcrossing) is carried out by crossing the original resistant line with a sensitive elite line and crossing the progeny back to the sensitive parent. The progeny from this cross will segregate such that some plants carry the resistance gene(s) whereas some do not. Plants carrying the resistance gene(s) will be crossed again to the sensitive parent resulting in progeny which segregate for resistance and sensitivity once more. This is repeated until the original sensitive parent has been converted to a resistant line, yet possesses all of the other important attributes originally found in the sensitive parent. A separate backcrossing program is implemented for every sensitive elite line that is to be converted to a virus resistant line.

Subsequent to the backcrossing, the new resistant lines and the appropriate combinations of lines which make good commercial hybrids are evaluated for viral resistance, as well as for a battery of important agronomic traits. Resistant lines and hybrids are produced which are true to type of the original sensitive lines and hybrids. This requires evaluation under a range of environmental conditions under which the lines or hybrids will be grown commercially. Parental lines of hybrids that perform satisfactorily are increased and utilized for hybrid production using standard hybrid production practices.

7.4.21.1 Use of Conventional Cultivation

Once transgenic plants of this type are produced, the plants themselves can be cultivated in accordance with conventional procedure so that the DNA construct is present in the resulting plants. Alternatively, transgenic seeds are recovered from the transgenic plants. These seeds can then be planted in the soil and cultivated using conventional procedures to produce transgenic plants.

7.4.21.2 Plant Varieties

The present invention can be used to make a variety of transgenic plants. The method is particularly suited for use with plants that are planted as a yearly crop from seed. These include, but are not limited to, fiber crops such as cotton and flax; dicotyledonous seed crops such as soybean, sunflower and peanut; annual ornamental flowers; monocotyledonous grain crops such as maize, wheat and sorghum; leaf crops such as tobacco; vegetable crops such as lettuce, carrot, broccoli, cabbage and cauliflower; and fruit crops such as tomato, zucchini, watermelon, cantaloupe and pumpkin.

The present invention can be utilized in conjunction with a wide variety of plants or their seeds.

Suitable plants include dicots and monocots. More particularly, useful crop plants can include: alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, papaya, and sugarcane.

Examples of suitable ornamental plants are: Arabidopsis thaliana, Saintpaulia, petunia, pelargonium, poinsettia, chrysanthemum, carnation, and zinnia.

The plants used in the process of the present invention are derived from monocots, particularly the members of the taxonomic family known as the Gramineae. This family includes all members of the grass family of which the edible varieties are known as cereals. The cereals include a wide variety of species such as wheat (Triticwn sps.), rice (Oryza sps.) barley (Hordewn sps.) oats, (Avena sps.) rye (Secale sps.), corn (Zea sps.) and millet (Pennisettum sps.). In the present invention, preferred family members are rice and barley.

7.4.22 Identification and Localization and Introgression into Plants of Desired Multigenic Traits with RFLP Technology The invention typically involves genetic linkage maps constructed with RFLP technology and the use of RFLP probes to correlate those probes with Quantitative Trait Loci (QTL) and the degree of inheritance of particular multigenic traits.

7.4.22.1 Determining the Degree of Inheritance of Particular Multigenic Traits In one embodiment, a plant source (designated $P_1$) having a desired multigenic trait—for example, increased height—is recovered and crossed with a second plant (designated $P_2$) having essentially or substantially opposite characteristics, that is, decreased height. Heterozygote plants from the $F_1$ population are selfed to create a segregating ($F_2$) plant population which exhibit a gradient with respect to height, i.e., with respect to the degree of expression of the multigenic or quantitative trait of interest.

7.4.22.1.1 RFLP Probe Tests

Quantitative values for the trait of interest (height) are determined and assigned to each individual parent plant, $F_1$ population plant, and $F_2$ segregation plant and a genomic DNA sample from each plant is prepared for Southern blotting. Following preparation for a Southern blot—which may be constructed to contain, for example, DNA from 25 to 50 or more different $F_2$ plants—an RFLP probe is randomly chosen or selected from an RFLP genetic linkage map and hybridized to create the blot. Additional Southern blots are constructed using other RFLP probes. As indicated above, the RFLPs to be used for this purpose, i.e., the indirect selection of a QTL, may but need not be randomly chosen. They can be selected in systematic fashion from the RFLP genetic linkage map. For example, for a trait of completely unknown location, several spaced RFLPs from each of the 10 chromosomes of maize may be selected for Southern blot testing for the location of DNA associated with a desired height. Alternatively, of course, all mapped RFLPs may be used.

Following these Southern blot constructs, a matrix may be prepared having an identification of each plant that has been tested, followed by its quantitative trait measurement (height) and the genotype as revealed by each RFLP probe tested. Typically, only three genotypes will be seen: $P_1$, $P_2$ and $F_1$, the latter being heterozygous and having one chromosome from each parent. Thus, from the matrix all plants can be grouped into one of three RFLP genotypic categories: $P_1P_1$, $P_1P_2$ or $P_2 P_2$. If, with one or more RFLPs, the so-grouped plants, when averaged, all show approximately equal expression of the trait of interest, i.e., the average height of plants in all groups is about the same, that RFLP is deemed noninformative. In other words, there was no association between the trait of interest and that particular RFLP or RFLPs. The genotype of the plant at the location of the RFLP was not relevant to the trait of interest.

7.4.22.1.2 Alteration of Experiment

Another RFLP, however, may show association with height. For example, the average height of the maize plants, respectively, in each of the $P_1P_1$, $P_1P_2$ and $P_2P_2$ groups for a different RFLP, respectively, may be 3 feet, 4 feet and 5 feet. With this information, it may be presumed that this RFLP, as revealed by the degree of its correlation to the $P_2 P_2$ genotype, hybridizes to maize DNA in the area of a gene for height.

7.4.22.1.3 Use of a Genetic Linkage Map

In the above-described manner, it is possible to review results from a first group of RFLP probes used to screen for association to the trait of interest. Use of an RFLP genetic linkage map allows the selection of further RFLPs to be tested on an objective, rather than random, basis. Correlation may be improved by testing RFLPs located on either side of that RFLP or RFLPs which initially showed the strongest association. Once the best probe or probes are identified they may then be utilized, by way of example, in a breeding program to select plants having a desired height.

It is to be noted, of course, that in a multigenic system, there may be three, four, or more different genes contributing to one trait. In such a situation there may, therefore, be many different quantitative expressions of that trait and no one gene can account for, or be relied upon to predict, that expression. We have further determined that the relative importance of each correlating RFLP can be determined. Particular values can be assigned to those. RFLPs and utilized in a mathematical model to assist in predicting the degree of trait expression in a particular plant.

7.4.22.1.4 Analysis of Variance

In the case of RFLP analysis, there are three different genotypic classes, i.e., AA, Aa and aa. Among three classes there are two possible contrasts and, hence, there are 2 degrees of freedom among genotypic classes. Moreover, the two possible contrasts among genotypes can be specifically partitioned into linear and quadratic sources, each with one degree of freedom. The linear contrast would have the values −1, 0 and +1 for the three genotypic classes AA, Aa and aa, respectively. This effectively compares the difference between the AA class and the aa class, i.e., the parental classes. The values for the quadratic contrast are 1, −2 and 1 for the three genotypic classes and, therefore, compare the difference between the mean of the parental AA and aa classes to the heterozygote class Aa.

The error, or deviation from regression, reflects the failure of the observed points to be exactly on the regression line. In the case of RFLP "A" we can observe that the mean square for the linear contrast is approximately 100 times larger that of the quadratic contrast and about 10 times larger than the error mean square. The magnitudes of the mean squares from the analysis of variance indicates that linear regression can account for the majority of the variance among the plant heights. The $r^2$ (coefficient of determination) value can be defined as the sums of the linear and quadratic mean squares divided by the total phenotypic variance (the total sums of squares of deviations from mean). The $r^2$ value for "A" indicates that 89% of the observed variance for plant height can be explained as due to differences among RFLP "A" genotypic classes. Similarly, the analysis of variance for RFLP "B" indicates that none of the variance for plant height can be explained due to differences among genotypic classes. The analysis of variance for RFLP "C" indicates that 53% of the variance can be explained due to differences among genotypic classes and that both the linear and quadratic contrast are important. Thus, the relative magnitudes of mean squares from the analysis of variance provides a description of the relationship between RFLPs and plant height. The conclusions coincide with those obtained from observation of the plots of plant height by genotypic classes.

The means for each genotypic class are also presented in Table 2. These means represent the average phenotypic performance for each of the 3 genotypic classes. For RFLP "A", the mean of the parent 1 class (aa) is 12.5, the mean for the heterozygous class (Aa) is 62.5, and the mean for the homozygous parent 2 class (AA) is 100 plant height units. The linear regression line slope (b1) is also presented for each RFLP. Thus, the linear regression of plant height on genotypic classes for RFLP "A" is 45. This, as noted above, can be interpreted as indicating that each time an "A" allele is substituted for an a allele that plant height will increase 45 units. The slope thus permits comparisons among RFLPs and helps to identify those RFLPs most strongly associated with the expression of a trait of interest.

Once the RFLPs most strongly associated with the expression of a trait are identified, the effects of each RFLP may be combined into a multiple regression model which will permit prediction of expression of the trait of interest based on knowledge of the genotypes of specific RFLP. The effects of each RFLP are not strictly additive because the effects of RFLP may be correlated. For example, in this case, RFLP "A" and "C" may each provide some unique information, but part of the information provided by one RFLP may also be provided by another. Thus, the average effects of allelic substitutions may not be simply added together to provide a predictive model.

7.4.22.2 General Form of Multiple Regression Model

The general form of a useful multiple regression predictive model is shown below:

$$y = \mu + b_1 \text{ (genotype of RFLP locus 1)} + b_2 \text{ (genotype of RFLP locus 2)}$$

where y is the predicted expression of a trait, $\mu$ is the weighted mean expression of the trait for the population, $b_1$ is the coefficient associated with a specific RFLP and so on. The genotype of a RFLP will be −1, 0 or 1 for genotypic classes AA, Aa and aa if the RFLP is additive (linear), or 1, −2 or 1 if the RFLP is quadratic (non-additive).

Determination of the "best" multiple regression model requires an interative process of substitution of RFLPs into and out of the model and the evaluation of interaction (epistatic) effects of RFLPs. For example, if two independent genes act together to provide expression of a trait, the genotypic class may involve the products of linear and/or quadratic genotypic values. The process for determination of the "best" multiple regression model can be done using stepwise regression procedures or by comparison of partial and sequential sums of squares from the regression models.

7.1.4.22.2.1 Example of Model Building

For example, in the present hypothetical, the logical RFLPs to include in the model would be the linear contrast for RFLP "A" and both the linear and quadratic contrasts for RFLP "C". The partial and sequential sums of squares (SS) for a model including RFLP A and C are the following:

| Source | sequential SS | partial SS |
|---|---|---|
| linear "A" | 5580 | 2812 |
| linear "C" | 62 | 236 |
| quadratic "C" | 503 | 503 |

The magnitudes of the sums of squares indicates that linear "A" is the most important determinate in explaining the variance for plant height. However, the reduction in partial SS (2812) vs. sequential SS (5580) for linear "A" suggests that much of the effect of linear "A" is accounted for by the linear and quadratic effects of "C". It should be noted that if the effects of each locus were completely independent there would be no differences in the partial and sequential sums of squares. Changes in the magnitudes of these sums of squares in an analysis of variance indicates that the effects of the different RFLP are correlated.

7.4.22.2.2 Another Model Constructed (Eliminate Linear Contrast)

The iterative process of substituting linear and quadratic contrasts for different RFLPs can continue until a final predictive model is constructed. The objective of the model is to maximize the r.sup.2 (coefficient of determination) value using as few RFLP as possible as predictive variables. The final model will generally eliminate RFLP which might flank a particular gene of interest because both RFLP will typically be contributing the same information. In addition, the final model might contain effects with reflect interactions between RFLPs.

In the present hypothetical, the next step in the process of model building might be to eliminate the linear contrast for RFLP "C". The results of this model are the following:

| Source | sequential SS | partial SS |
|---|---|---|
| linear "A" | 5580 | 5127 |
| quadratic "C" | 328 | 328 |

7.4.22.3 Final Mathematical Model

The general agreement in magnitude between partial and sequential SS suggest that the effects of linear "A" and quadratic "C" are relatively independent. The r.sup.2 value for this model is 0.95. Thus, 95% of the variance for plant height can be explained as due to differences among genotypic classes at RFLP "A" and "C". The final prediction equation would, therefore, be written as follows:

Plant height=61.4+43 (linear code RFLP A)−7.0 (quadratic code for RFLP C).

Thus, if the genotypes of RFLP A and C are known for a particular plant, the height of that plant can be predicted without having to measure its height following growth to maturity. In a breeding program, the breeder can analyze the genotypes of specific RFLP of seedling plants grown in a greenhouse during the winter and need only evaluate those plants predicted to have the desired plant height in the field the following summer.

7.4.22.3.1 Explanation of the Mathematical Model

TABLE 6

Hypothetical Raw data

| Genotype Observed | "A" (Linear Code) | | "B" (Linear Code) | | "C" (Linear Code) | (Quadratic Code) | Plant Height |
|---|---|---|---|---|---|---|---|
| 1 | AA | 1 | bb | −1 | CC | 1 | 1 | 100 |
| 2 | aa | −1 | bb | −1 | cc | −1 | 1 | 0 |
| 3 | Aa | 0 | BB | 1 | C | c | 0 | −275 |
| 4 | Aa | 0 | Bb | 0 | CC | 1 | 1 | 50 |
| 5 | aa | −1 | BB | 1 | CC | 1 | 1 | 25 |

TABLE 7

Analysis of Variance

| | | RFLP locus | | |
| | | A | B | C |
| Source of Variance | Degrees of Freedom | Mean Squares | | |
|---|---|---|---|---|
| Genotype | 2 | | | |
| Linear | 1 | 5104 | 0.0 | 2552 |
| Quadratic | 1 | 44 | 0.0 | 1575 |
| Error (deviations from regression) | 2 | 625 | 6250 | 1458 |
| r² | | 0.89 | 0.0 | 0.53 |
| Genotypes | (code) | Means | | |
| Homozygous Parent 1 | (−1) | 12.5 | 50 | 0 |
| Heterozygote | (0) | 62.5 | 50 | 75 |
| Homozygous Parent 2 | (+1) | 100.0 | 50 | 58 |
| Slope (b1) | | 45 | 0 | 23 |

7.4.22.3.2 Analyzing Result Using Mathematical Model

The breeding value of an RFLP as an indirect selection criteria is a function of the additive genetic correlation between the RFLP marker and a QTL. This genetic association is presumed to be due to linkage disequilibrium rather than due to pleiotropism. The problem of recombination between an RFLP and an associated QTL can be minimized if two RFLP are identified which flank the QTL. In that instance, the probability of a double crossover would be, assuming no interference, the product of their recombination frequencies. Nevertheless, localizing a target QTL between a pair of linked RFLP can be problematic, and the complexity of the analyses increased. One possible solution to the analysis using flanking RFLPs is to use multivariate analysis and derive one or more orthogonal vectors which include information from linked (correlated) RFLP loci. Alternatively, if crossovers are detected between the two flanking RFLPs for specific entries, the RFLPs linked to the QTL can be determined and information from the other RFLP discounted.

The rate of gain from indirect selection in a population is a function of the magnitude of the phenotypic variance of the desired trait, the selection differential, the heritability of the indirect criteria, and the genetic correlation between the direct and indirect criteria. Indirect selection for RFLPs will have an advantage over direct selection if the heritability of RFLPs is higher than the desired character and the additive genetic correlation between them is high.

The "heritability" of the RFLP phenotype is 1.0, i.e., genotype=phenotype. Hence, if the correlation between RFLPs and the desired trait is greater than the heritability of the desired trait, then RFLP-facilitated selection can be advantageous. In the evaluation of 2-tridecanone ("2TD") mediated insect resistance in tomatoes, for example, the development of the colorimetric assay has contributed to increased efficiency of selection.

As noted above, quantitative differences between genotypes are usually, but not always, influenced by genes at many loci, the effects of which are small in relation to the variation arising from other causes (Falconer, D.C., "Introduction to Quantitative Genetics" (2d Edition 1981)). Consequently, the individual genes involved in the expression of a quantitative trait are difficult to identify and Mendelian analysis cannot be applied. Id. Quantitative genetic analysis has therefore focused on estimation of breeding value which is the sum of the effects of the alleles at many loci. Nevertheless, a basic premise of quantitative genetics is that the laws which govern the inheritance of quantitative loci are the same as those which govern qualitative loci. The magnitude of the individual allelic effects which can be resolved through RFLP analysis will be a function of experimental error and recombination frequencies. As RFLP maps are developed which more completely saturate the genome, identification of more loci with smaller individual effects should be possible. Thus, RFLP analysis also offers the opportunity to determine the effects of individual loci (alleles) with major effects, and thereby to reduce the analysis of complex quantitative traits to classical Mendelian segregation ratios of individual alleles.

8. Mutagenizing Organisms—Engineering Aspects
8.1.1 General Considerations

In one aspect, this invention applies the technical field of molecular genetics to evolve the genomes of cells and organisms to acquire new and improved properties.

Cells have a number of well-established uses in molecular biology. For example, cells are commonly used as hosts for manipulating DNA in processes such as transformation and recombination. Cells are also used for expression of recombinant proteins encoded by DNA transformed into the cells. Some types of cells are also used as progenitors for generation of transgenic animals and plants. Although all of these processes are now routine, in general, the genomes of the cells used in these processes have evolved little from the genomes of natural cells, and particularly not toward acquisition of new or improved properties for use in the above processes.

The traditional approach to artificial or forced molecular evolution focuses on optimization of an individual gene having a discrete and selectable phenotype. The strategy is to clone a gene, identify a discrete function for the gene and an assay by which it can be selected, mutate selected positions in the gene (e.g., by error-prone PCR or cassette mutagenesis) and select variants of the gene for improvement in the known function of the gene. A variant having improved function can then be expressed in a desired cell type. This approach has a number of limitations. First, it is only applicable to genes that have been isolated and functionally characterized. Second, the approach is usually only applicable to genes that have a discrete function. In other words, multiple genes that cooperatively confer a single phenotype cannot usually be optimized in this manner.

Probably, most genes do have cooperative functions. Finally, this approach can only explore a very limited number of the total number of permutations even for a single gene. For example, varying even ten positions in a protein with every possible amino acid would generate $20^{10}$ variants, which is more than can be accommodated by existing methods of transfection and screening.

In view of these limitations, the traditional approach is inadequate for improving cellular genomes in many useful properties. For example, to improve a cell's capacity to express a recombinant protein might require modification in any or all of a substantial number of genes, known and unknown, having roles in transcription, translation, post-translational modification, secretion or proteolytic degradation, among others. Attempting individually to optimize even all the known genes having such functions would be a virtually impossible task, let alone optimizing hitherto unknown genes which may contribute to expression in manners not yet understood.

The present invention provides inter alia novel methods for evolving the genome of whole cells and organisms which overcome the difficulties and limitations of prior methods.

This ability to evolve genes artificially is of fundamental importance. For example, cells have a number of well-established uses in molecular biology, medicine and industrial processes. For example, cells are commonly used as hosts for manipulating DNA in processes such as transformation and recombination. Cells are used for expression of recombinant proteins encoded by DNA transformed/ transfected or otherwise introduced into the cells. Some types of cells are used as progenitors for generation of transgenic animals and plants. The genomes of the cells used in these processes had evolved little from the genomes of natural cells, and particularly not toward acquisition of new or improved properties for use in the above processes.

Additional methods of recursively recombining nucleic acids in vivo and selecting resulting recombinants would be of use. The present invention provides a number of new and valuable methods and compositions for whole and partial genome evolution.

Metabolic engineering is the manipulation of intermediary metabolism through the use of both classical genetics and genetic engineering techniques. Cellular engineering is generally a more inclusive term referring to the modification of cellular properties. Cameron et al. (Applied Biochem. Biotech. 38:105–140 (1993)) provide a summary of equivalent terms to describe this type of engineering, including "metabolic engineering", which is most often used in the context of industrial microbiology and bioprocess engineering, "in vitro evolution" or "directed evolution", most often used in the context of environmental microbiology, "molecular breeding", most often used by Japanese researchers, "cellular engineering", which is used to describe modifications of bacteria, animal, and plant cells, "rational strain development", and "metabolic pathway evolution". In this application, the terms "metabolic engineering" and "cellular engineering" are used preferentially for clarity; the term "evolved" genes is used as discussed below.

Metabolic engineering can be divided into two basic categories: modification of genes endogenous to the host organism to alter metabolite flux and introduction of foreign genes into an organism. Such introduction can create new metabolic pathways leading to modified cell properties including but not limited to synthesis of known compounds not normally made by the host cell, production of novel compounds (e.g. polymers, antibiotics, etc.) and the ability to utilize new nutrient sources. Specific applications of metabolic engineering can include the production of specialty and novel chemicals, including antibiotics, extension of the range of substrates used for growth and product formation, the production of new catabolic activities in an organism for toxic chemical degradation, and modification of cell properties such as resistance to salt and other environmental factors.

Bailey (Science 252:1668–1674 (1991)) describes the application of metabolic engineering to the recruitment of heterologous genes for the improvement of a strain, with the caveat that such introduction can result in new compounds that may subsequently undergo further reactions, or that expression of a heterologous protein can result in proteolysis, improper folding, improper modification, or unsuitable intracellular location of the protein, or lack of access to required substrates. Bailey recommends careful configuration of a desired genetic change with minimal perturbation of the host. Liao (Curr. Opin. Biotech. 4:211–216 (1993)) reviews mathematical modeling and analysis of metabolic pathways, pointing out that in many cases the kinetic parameters of enzymes are unavailable or inaccurate.

Stephanopoulos et al. (Trends. Biotechnol. 11:392–396 (1993)) describe attempts to improve productivity of cellular systems or effect radical alteration of the flux through primary metabolic pathways as having difficulty in that control architectures at key branch points have evolved to resist flux changes. They conclude that identification and characterization of these metabolic nodes is a prerequisite to rational metabolic engineering. Similarly, Stephanopoulos (Curr. Opin. Biotech. 5:196–200 (1994)) concludes that rather than modifying the "rate limiting step" in metabolic engineering, it is necessary to systematically elucidate the control architecture of bioreaction networks. The present invention is generally directed to the evolution of new metabolic pathways and the enhancement of bioprocessing through a process herein termed recursive sequence recombination. Recursive sequence recombination entails performing iterative cycles of recombination and screening or selection to "evolve" individual genes, whole plasmids or viruses, multigene clusters, or even whole genomes (Stemmer, Bio/Technolog 13:549–553 (1995)). Such techniques do not require the extensive analysis and computation required by conventional methods for metabolic engineering. Recursive sequence recombination allows the recombination of large numbers of mutations in a minimum number of selection cycles, in contrast to traditional, pairwise recombination events.

Thus, because metabolic and cellular engineering can pose the particular problem of the interaction of many gene products and regulatory mechanisms, recursive sequence recombination (RSR) techniques provide particular advantages in that they provide recombination between mutations in any or all of these, thereby providing a very fast way of exploring the manner in which different combinations of mutations can affect a desired result, whether that result is increased yield of a metabolite, altered catalytic activity or substrate specificity of an enzyme or an entire metabolic pathway, or altered response of a cell to its environment.

8.1.2 The Evolutionary Importance of Recombination

Strain improvement is the directed evolution of an organism to be more "fit" for a desired task. In nature, adaptation is facilitated by sexual recombination. Sexual recombination allows a population to exploit the genetic diversity within it, e.g., by consolidating useful mutations and discarding deleterious ones. In this way, adaptation and evolution can proceed in leaps. In the absence of a sexual cycle, members of a population must evolve independently by accumulating random mutations sequentially. Many useful mutations are lost while deleterious mutations can accumulate. Adaptation and evolution in this way proceeds slowly as compared to sexual evolution.

A sexual evolution is a slow and inefficient process. Populations move as individuals rather than as groups. A diverse population is generated by the mutagenesis of a single parent resulting in a distribution of fit and unfit individuals. In the absence of a sexual cycle, each piece of genetic information of the surviving population remains in the individual mutants. Selection of the "fittest" results in many "fit" individuals being discarded along with the useful genetic information they carry. A sexual evolution proceeds one genetic event at a time and is thus limited by the intrinsic value of a single genetic event. Sexual evolution moves more quickly and efficiently. Mating within a population consolidates genetic information within the population and results in useful mutations being combined together. The combining of useful genetic information results in progeny that are much more fit than their parents. Sexual evolution thus proceeds much faster by multiple genetic events.

Years of plant and animal breeding has demonstrated the power of employing sexual recombination to effect the rapid evolution of complex genomes towards a particular task. This general principle is further demonstrated by using DNA stochastic &/or non-stochastic mutagenesis to recombine DNA molecules in vitro to accelerate the rate of directed molecular evolution. The strain improvement efforts of the fermentation industry rely on the directed evolution of microorganisms by sequential random mutagenesis. Incorporation of recombination into this iterative process greatly accelerates the strain improvement process, which in turn increases the profitability of current fermentation processes and facilitates the development of new products.

8.1.2.1 DNA Stochastic &/or Non-Stochastic Mutagenesis vs Natural Recombination

DNA stochastic &/or non-stochastic mutagenesis includes the recursive recombination of DNA sequences. A significant difference between DNA stochastic &/or non-stochastic mutagenesis and natural sexual recombination is that DNA stochastic &/or non-stochastic mutagenesis can produce DNA sequences originating from multiple parental sequences while sexual recombination produces DNA sequences originating from only two parental sequences.

The rate of evolution is in part limited by the number of useful mutations that a member of a population can accumulate between selection events.

In sequential random mutagenesis, useful mutations are accumulated one per selection event. Many useful mutations are discarded each cycle in favor of the best performer, and neutral or deleterious mutations which survive are as difficult to lose as they were to gain and thus accumulate. In sexual evolution pairwise recombination allows mutations from two different parents to segregate and recombine in different combinations. Useful mutations can accumulate and deleterious mutations can be lost. Poolwise recombination, such as that effected by DNA stochastic &/or non-stochastic mutagenesis, has the same advantages as pairwise recombination but allows mutations from many parents to consolidate into a single progeny. Thus poolwise recombination provides a means for increasing the number of useful mutations that can accumulate each selection event. One can plot the potential number of mutations an individual can accumulate by each of these processes. Recombination is exponentially superior to sequential random mutagenesis, and this advantage increases exponentially with the number of parents that can recombine. Sexual recombination is thus more conservative. In nature, the pairwise nature of sexual recombination may provide important stability within a population by impeding the large changes in DNA sequence that can result from poolwise recombination. For the purposes of directed evolution, however, poolwise recombination is more efficient.

The potential diversity that can be generated from a population is greater as a result of poolwise recombination as compared to that resulting from pairwise recombination. Further, poolwise recombination enables the combining of multiple beneficial mutations originating from multiple parental sequences. To demonstrate the importance of poolwise recombination vs pairwise recombination in the generation of molecular diversity consider the breeding of ten independent DNA sequences each containing only one unique mutation. There are $2^{10}$=1024 different combinations of those ten mutations ranging from a single sequence having no mutations (the consensus) to that having all ten mutations. If this pool were recombined together by pairwise recombination, a population containing the consensus, the parents, and the 45 different combinations of any two of the mutations would result in 56 or ca. 5% of the possible 1024 mutant combinations. Alternatively, if the pool were recombined together in a poolwise fashion, all 1024 would be theoretically generated, resulting in an approximately 20 fold increase in library diversity. When looking for a unique solution to a problem in molecular evolution, the more complex the library, the more complex the possible solution. Indeed, the most fit member of a stochastic &/or non-stochastic mutagenized library often contains several mutations originating from several independent starting sequences.

8.1.2.2 DNA Stochastic &/or Non-Stochastic Mutagenesis Provides Recursive Pairwise Recombination In vitro DNA stochastic &/or non-stochastic mutagenesis results in the efficient production of combinatorial genetic libraries by catalyzing the recombination of multiple DNA sequences. While the result of DNA stochastic &/or non-stochastic mutagenesis is a population representing the poolwise recombination of multiple sequences, the process does not rely on the recombination of multiple DNA sequences simultaneously, but rather on their recursive pairwise recombination. The assembly of complete genes from a mixed pool of small gene fragments requires multiple annealing and elongation cycles, the thermal cycles of the primerless PCR reaction. During each thermal cycle many pairs of fragments anneal and are extended to form a combinatorial population of larger chimeric DNA fragments. After the first cycle of stochastic &/or non-stochastic mutagenesis, chimeric fragments contain sequence originating from predominantly two different parent genes, with all possible pairs of "parental" sequence theoretically represented. This is similar to the result of a single sexual cycle within a population. During the second cycle, these chimeric fragments anneal with each other or with other small fragments, resulting in chimeras originating from up to four of the different starting sequences, again with all possible combinations of the four parental sequences theoretically represented. This second cycle is analogous to the entire population resulting from a single sexual cross, both parents and offspring, inbreeding.

Further cycles result in chimeras originating from 8, 16, 32, etc parental sequences and are analogous to further inbreedings of the preceding population. This could be considered similar to the diversity generated from a small population of birds that are isolated on an island, breeding with each other for many generations. The result mimics the outcome of "poolwise" recombination, but the path is via recursive pairwise recombination. For this reason, the DNA molecules generated from in vitro DNA stochastic &/or non-stochastic mutagenesis are not the "progeny" of the starting "parental" sequences, but rather the great, great great, greats, (n=number of thermal cycles) grand progeny of the starting "ancestor" molecules. 8.1.3 Definitions The term "cognate" refers to a gene sequence that is evolutionarily and functionally related between species. For example, in the human genome, the human CD4 gene is the cognate gene to the mouse CD4 gene, since the sequences and structures of these two genes indicate that they are homologous and that both genes encode a protein which functions in signaling T-cell activation through MHC class II-restricted antigen recognition. Screening is, in general, a two-step process in which one first determines which cells do and do not express a screening marker or phenotype (or a selected level of marker or phenotype), and then physically separates the cells having the desired property. Selection is a form of screening in which identification and physical separation are achieved simultaneously by expression of a selection marker, which, in some genetic circumstances, allows cells expressing the marker to survive while other cells die (or vice versa). Screening markers include luciferase, P-galactosidase, and green fluorescent protein. Selection markers include drug and toxin resistance genes.

An exogenous DNA segment is one foreign (or heterologous) to the cell or homologous to the cell but in a position within the host cell nucleic acid in which the element is not ordinarily found. Exogenous DNA segments can be expressed to yield exogenous polypeptides.

The term "gene" is used broadly to refer to any segment of DNA associated with a biological function. Thus, genes include coding sequences and/or the regulatory sequences required for their expression. Genes also include nonexpressed DNA segments that, for example, form recognition sequences for other proteins.

The terms "identical" or "percent identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl Math. 2:482 (1981), by the homology alignment algorithm of Needleman & Wunsch, J Mol Biot 48:443 (1970), by the search for similarity method of Pearson & Lipman, Proc. Natl. Acad. Sci. USA 85:2444 (1988), by computerized implementations of algorithms GAP, BESTFIT, FASTA, and TFASTA in the Wisconsin Genetics Software Package Release 7.0, Genetics Computer Group, 575 Science Dr., Madison, Wis.

Another example of a useful alignment algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J Mol. Evol. 35:351–360 (1987). The method used is similar to the method described by Higgins & Sharp, CABIOS 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., J Mol. Biol. 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff& Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Natl. Acad. Sci. USA 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions.

Another indication that two nucleic acid sequences are substantially identical is that the two molecules hybridize to each other under stringent conditions.

The term "naturally-occurring" is used to describe an object that can be found in nature. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

A sexual recombination is recombination occurring without the fusion of gametes to form a zygote.

A "mismatch repair deficient strain" can include any mutants in any organism impaired in the functions of mismatch repair. These include mutant gene products of mutS, mutT, mutH, mutL, ovrD, dcm, vsr, umuC, umuD, sbcB, recj, etc. The impairment is achieved by genetic mutation, allelic replacement, selective inhibition by an added reagent such as a small compound or an expressed antisense RNA, or other techniques. Impairment can be of the genes noted, or of homologous genes in any organism.

8.2. Strategies 8.2.1. Evolving a Cell to Acquire a Desired Function 8.2.1.1. Desired Function is Secretion of a Protein Optionally, the desired function is secretion of a protein, and the plurality of cells further comprises a construct encoding the protein. The protein is optionally inactive unless secreted, and further modified cells are optionally selected for protein function.

Optionally, the protein is toxic to the plurality of cells, unless secreted. In this case, the modified or further modified cells which evolve toward acquisition of the desired function are screened by propagating the cells and recovering surviving cells.

8.2.1.2. Desired Function is Enhanced Recombination

In some methods, the desired function is enhanced recombination. In such methods, the library of fragments sometimes comprises a cluster of genes collectively conferring recombination capacity. Screening can be achieved using cells carrying a gene encoding a marker whose expression is prevented by a mutation removable by recombination. The cells are screened by their expression of the marker resulting from removal of the mutation by recombination.

8.2.13. Desired Function is Improved Resistance in Plant Cells

In some methods, the plurality of cells are plant cells and the desired property is improved resistance to a chemical or microbe. The modified or further modified cells (or whole plants) are exposed to the chemical or microbe and modified or further modified cells having evolved toward the acquisition of the desired function are selected by their capacity to survive the exposure.

8.2.1.4. Desired Function is Predictiong Efficacy of a Drug

8.2.1.4.1. A Drug Treating a Viral Infection

The invention further provides methods of predicting efficacy of a drug in treating a viral infection. Such methods entail recombining a nucleic acid segment from a virus, whose infection is inhibited by a drug, with at least a second nucleic acid segment from the virus, the second nucleic acid segment differing from the first nucleic acid segment in at least two nucleotides, to produce a library of recombinant nucleic acid segments. Host cells are then contacted with a collection of viruses having genomes including the recombinant nucleic acid segments in a media containing the drug, and progeny viruses resulting from infection of the host cells are collected.

A recombinant DNA segment from a first progeny virus recombines with at least a recombinant DNA segment from a second progeny virus to produce a further library of recombinant nucleic acid segments. Host cells are contacted with a collection of viruses having genomes including the further library or recombinant nucleic acid segments, in media containing the drug, and further progeny viruses are produced by the host cells. The recombination and selection steps are repeated, as desired, until a further progeny virus has acquired a desired degree of resistance to the drug, whereby the degree of resistance acquired and the number of repetitions needed to acquire it provide a measure of the efficacy of the drug in treating the virus. Viruses are optionally adapted to grow on particular cell lines.

8.2.1.4.2. A Drug Treating Infection by a Pathogenic Microorganism

The invention further provides methods of predicting efficacy of a drug in treating an infection by a pathogenic microorganism. These methods entail delivering a library of DNA fragments into a plurality of microorganism cells, at least some of which undergo recombination with segments in the genome of the cells to produce modified microorganism cells. Modified microorganisms are propagated in a media containing the drug, and surviving microorganisms are recovered. DNA from surviving microorganisms is recombined with a further library of DNA fragments at least some of which undergo recombination with cognate segments in the DNA from the surviving microorganisms to produce further modified microorganisms cells. Further modified microorganisms are propagated in media containing the drug, and further surviving microorganisms are collected. The recombination and selection steps are repeated as needed, until a further surviving microorganism has acquired a desired degree of resistance to the drug. The degree of resistance acquired and the number of repetitions needed to acquire it provide a measure of the efficacy of the drug in killing the pathogenic microorganism.

8.2.1.3. Method 8.2.1.3.1 Modify or Recombine Cells

In one aspect, the invention provides methods of evolving a cell to acquire a desired function. Such methods entail, e.g., introducing a library of DNA fragments into a plurality of cells, whereby at least one of the fragments undergoes recombination with a segment in the genome or an episome of the cells to produce modified cells. Optionally, these modified cells are bred to increase the diversity of the resulting recombined cellular population. The modified cells, or the recombined cellular population are then screened for modified or recombined cells that have evolved toward acquisition of the desired function. DNA from the modified cells that have evolved toward the desired function is then optionally recombined with a further library of DNA fragments, at least one of which undergoes recombination with a segment in the genome or the episome of the modified cells to produce further modified cells. The further modified cells are then screened for further modified cells that have further evolved toward acquisition of the desired function. Steps of recombination and screening/selection are repeated as required until the further modified cells have acquired the desired function. In one preferred embodiment, modified cells are recursively recombined to increase diversity of the cells prior to performing any selection steps on any resulting cells.

8.2.1.3.2 Coat with RecA

In some methods, the library or further library of DNA fragments is coated with recA protein to stimulate recombination with the segment of the genome. The library of fragments is optionally denatured to produce single-stranded DNA, which are annealed to produce duplexes, some of which contain mismatches at points of variation in the fragments. Duplexes containing mismatches are optionally selected by affinity chromatography to immobilized MutS.

8.2.1.3.3 Perform In Vivo Recombination

The invention further provides methods for performing in vivo recombination. At least first and second segments from at least one gene are introduced into a cell, the segments differing from each other in at least two nucleotides, whereby the segments recombine to produce a library of chimeric genes. A chimeric gene is selected from the library having acquired a desired function.

The invention further provides methods of evolving a cell to acquire a desired function. These methods entail providing a populating of different cells. The cells are cultured under conditions whereby DNA is exchanged between cells, forming cells with hybrid genomes. The cells are then screened or selected for cells that have evolved toward acquisition of a desired property. The DNA exchange and screening/selecting steps are repeated, as needed, with the screened/selected cells from one cycle forming the population of different cells in the next cycle, until a cell has acquired the desired property.

Mechanisms of DNA exchange include conjugation, phage-mediated transduction, liposome delivery, protoplast fusion, and sexual recombination of the cells. Optionally, a library of DNA fragments can be transformed or electroporated into the cells.

8.2.1.3.4 Protopoast-Mediated Exchange

As noted, some methods of evolving a cell to acquire a desired property are effected by protoplast-mediated exchange of DNA between cells. Such methods entail forming protoplasts of a population of different cells. The protoplasts are then fused to form hybrid protoplasts, in which genomes from the protoplasts recombine to form hybrid genomes. The hybrid protoplasts are incubated under conditions promoting regeneration of cells. The regenerated cells can be recombined one or more times (i.e., via protoplasting or any other method than combines genomes of cells) to increase the diversity of any resulting cells. Preferably, regenerated cells are recombined several times, e.g., by protoplast fusion to generate a diverse population of cells. The next step is to select or screen to isolate regenerated cells that have evolved toward acquisition of the desired property. DNA exchange and selection/screening steps are repeated, as needed, with regenerated cells in one cycle being used to form protoplasts in the next cycle until the regenerated cells have acquired the desired property. Industrial microorganisms are a preferred class of organisms for conducting the above methods. Some methods further comprise a step of selecting or screening for fused protoplasts free from unfused protoplasts of parental cells. Some methods further comprise a step of selecting or screening for fused protoplasts with hybrid genomes free from cells with parental genomes. In some methods, protoplasts are provided by treating individual cells, mycelia or spores with an enzyme that degrades cell walls. In some methods, the strain is a mutant that is lacking capacity for intact cell wall synthesis, and protoplasts form spontaneously. In some methods, protoplasts are formed by treating growing cells with an inhibitor of cell wall formation to generate protoplasts. In some methods, the desired property is expression and/or secretion of a protein or secondary metabolite, such as an industrial enzyme, a therapeutic protein, a primary metabolite such as lactic acid or ethanol, or a secondary metabolite such as erythromycin cyclosporin A or taxol. In other methods it is the ability of the cell to convert compounds provided to the cell to different compounds. In yet other methods, the desired property is capacity for meiosis. In some methods, the desired property is compatibility to form a heterokaryon with another strain.

The invention further provides methods of evolving a cell toward acquisition of a desired property. These methods entail providing a population of different cells. DNA is isolated from a first subpopulation of the different cells and encapsulated in liposomes. Protoplasts are formed from a second subpopulation of the different cells. Liposomes are fused with the protoplasts, whereby DNA from the liposomes is taken up by the protoplasts and recombines with the genomes of the protoplasts. The protoplasts are incubated under regenerating conditions. Regenerating or regenerated cells are then selected or screened for evolution toward the desired property.

8.2.1.3.4 Reiterative Pooling and Breeding of Higher Organisms

The method also provides methods of reiterative pooling and breeding of higher organisms. In the methods, a library of diverse multicellular organisms are produced (e.g., plants, animals or the like). A pool of male gametes is provided along with a pool of female gametes. At least one of the male pool or the female pool comprises a plurality of different gametes derived from different strains of a species or different species. The male gametes are used to fertilize the female gametes. At least a portion of the resulting fertilized gametes grow into reproductively viable organisms. These reproductively viable organisms are crossed (e.g., by pairwise pooling and joining of the male and female gametes as before) to produce a library of diverse organisms. The library is then selected for a desired trait or property.

The library of diverse organisms can comprise a plurality of plants such as Gramineae, Fetucoideae, Poacoideae, Agrostis, Phleum, Dactylis, Sorgum, Setaria, Zea, Oryza, Triticurn, Secale, Avena, Hordeurn, Saccharum, Poa, Festuca, Stenotaphrum, Cynodon, Coix, Olyreae, Phareae, Compositae or Leguminosae. For example, the plants can be e.g., corn, rice, wheat, rye, oats, barley, pea, beans, lentil, peanut, yam bean, cowpeas, velvet beans, soybean, clover, alfalfa, lupine, vetch, lotus, sweet clover, wisteria, sweet pea, sorghum, millet, sunflower, canola or the like.

Similarly, the library of diverse organisms can include a plurality of animals such as non-human mammals, fish, insects, or the like.

Optionally, a plurality of selected library members can be crossed by pooling gametes from the selected members and repeatedly crossing any resulting additional reproductively viable organisms to produce a second library of diverse organisms (e.g., by split pair wise pooling and rejoining of the male and female gametes). Here again, the second library can be selected for a desired trait or property, with the resulting selected members forming the basis for additional poolwise breeding and selection. A feature of the invention is the libraries made by these (or any preceding) method.

8.3. Origin of Cells 8.3.1 Embryonic Cells of an Animal

In some methods, the plurality of cells are embryonic cells of an animal, and the method further comprises propagating the transformed cells to transgenic animals. The plurality of cells can be a plurality of industrial microorganisms that are enriched for microorganisms which are tolerant to desired process conditions (heat, light, radiation, selected pFL presence of detergents or other denaturants, presence of alcohols or other organic molecules, etc.).

8.3.2 Artificial Chromosomes

The invention further provides methods of evolving a cell toward acquisition of a desired property using artificial chromosomes. Such methods entail introducing a DNA fragment library cloned into an artificial chromosome into a population of cells. The cells are then cultured under conditions whereby sexual recombination occurs between the cells, and DNA fragments cloned into the artificial chromosome recombines by homologous recombination with corresponding segments of endogenous chromosomes of the populations of cells, and endogenous chromosomes recombine with each other. Cells can also be recombined via conjugation. Any resulting cells can be recombined via any method noted herein, as many times as desired, to generate a desired level of diversity in the resulting recombinant cells. In any case, after generating a diverse library of cells, the cells that have evolved toward acquisition of the desired property are screened and/or selected for a desired property. The method is then repeated with cells that have evolved toward the desired property in one cycle forming the population of different cells in the next cycle. Here again, multiple cycles of in vivo recombination are optionally performed prior to any additional selection or screening steps.

The invention further provides methods of evolving a DNA segment cloned into an artificial chromosome for acquisition of a desired property. These methods entail providing a library of variants of the segment, each variant cloned into separate copies of an artificial chromosome. The copies of the artificial chromosome are introduced into a population of cells. The cells are cultured under conditions whereby sexual recombination occurs between cells and homologous recombination occurs between copies of the artificial chromosome bearing the variants. Variants are then screened or selected for evolution toward acquisition of the desired property.

The invention further provides hyperrecombinogenic recA proteins.

8.4. Method to Acquire a Biocatalytic Activity

One aspect of the invention is a method of evolving a biocatalytic activity of a cell, comprising:
- (a) recombining at least a first and second DNA segment from at least one gene conferring ability to catalyze a reaction of interest, the segments differing from each other in at least two nucleotides, to produce a library of recombinant genes;
- (b) screening at least one recombinant gene from the library that confers enhanced ability to catalyze the reaction of interest by the cell relative to a wild type form of the gene;
- (c) recombining at least a segment from at least one recombinant gene with a further DNA segment from at least one gene, the same or different from the first and second segments, to produce a further library of recombinant genes;
- (d) screening at least one further recombinant gene from the further library of recombinant genes that confers enhanced ability to catalyze the reaction of interest in the cell relative to a previous recombinant gene;
- (e) repeating (c) and (d), as necessary, until the further recombinant gene confers a desired level of enhanced ability to catalyze the reaction of interest by the cell.

8.4.1. Method to Evolve a Gene to Catalyze a RXN of Interest

Another aspect of the invention is a method of evolving a gene to confer ability to catalyze a reaction of interest, the method comprising:
- (1) recombining at least first and second DNA segments from at least one gene conferring ability to catalyze a reaction of interest, the segments differing from each other in at least two nucleotides, to produce a library of recombinant genes;
- (2) screening at least one recombinant gene from the library that confers enhanced ability to catalyze a reaction of interest relative to a wild type form of the gene;
- (3) recombining at least a segment from the at least one recombinant gene with a further DNA segment from the at least one gene, the same or different from the first and second segments, to produce a further library of recombinant genes;
- (4) screening at least one further recombinant gene from the further library of recombinant genes that confers enhanced ability to catalyze a reaction of interest relative to a previous recombinant gene;
- (5) repeating (3) and (4), as necessary, until the further recombinant gene confers a desired level of enhanced ability to catalyze a reaction of interest.

8.4.2. Method to Generate a New Biocatalytic Activity in a Cell

A further aspect of the invention is a method of generating a new biocatalytic activity in a cell, comprising:
- (1) recombining at least first and second DNA segments from at least one gene conferring ability to catalyze a first reaction related to a second reaction of interest, the segments differing from each other in at least two nucleotides, to produce a library of recombinant genes;
- (2) screening at least one recombinant gene from the library that confers a new ability to catalyze the second reaction of interest;
- (3) recombining at least a segment from at least one recombinant gene with a further DNA segment from the at least one gene, the same or different from the first and second segments, to produce a further library of recombinant genes;
- (4) screening at least one further recombinant gene from the further library of recombinant genes that confers enhanced ability to catalyze the second reaction of interest in the cell relative to a previous recombinant gene;
- (5) repeating (3) and (4), as necessary, until the further recombinant gene confers a desired level of enhanced ability to catalyze the second reaction of interest in the cell.

8.4.3. Method to Modify a Metabolic Pathway Evolved by Recursive Sequence Recombination Another aspect of the invention is a modified form of a cell, wherein the modification comprises a metabolic pathway evolved by recursive sequence recombination.

A further aspect of the invention is a method of optimizing expression of a gene product, the method comprising:
- (1) recombining at least first and second DNA segments from at least one gene conferring ability to produce the gene product, the segments differing from each other in at least two nucleotides, to produce a library of recombinant genes;
- (2) screening at least one recombinant gene from the library that confers optimized expression of the gene product relative to a wild type form of the gene;
- (3) recombining at least a segment from the at least one recombinant gene with a further DNA segment from the at least one gene, the same or different from the first and second segments, to produce a further library of recombinant genes;
- (4) screening at least one further recombinant gene from the further library of recombinant genes that confers optimized ability to produce the gene product relative to a previous recombinant gene;
- (5) repeating (3) and (4), as necessary, until the further recombinant gene confers a desired level of optimized ability to express the gene product.

8.4.4. Method to Evolve a Biosensor

A further aspect of the invention is a method of evolving a biosensor for a compound A of interest, the method comprising:
- (1) recombining at least first and second DNA segments from at least one gene conferring ability to detect a related compound B, the segments differing from each other in at least two nucleotides, to produce a library of recombinant genes;
- (2) screening at least one recombinant gene from the library that confers optimized ability to detect compound A relative to a wild type form of the gene;
- (3) recombining at least a segment from the at least one recombinant gene with a further DNA segment from the at least one gene, the same or different from the first and second segments, to produce a further library of recombinant genes;
- (4) screening at least one further recombinant gene from the further library of recombinant genes that confers optimized ability to detect compound A relative to a previous recombinant gene;
- (5) repeating (3) and (4), as necessary, until the further recombinant gene confers a desired level of optimized ability to detect compound A.

8.5. Fermentation of Micro-Organisms

The fermentation of microorganisms for the production of natural products is the oldest and most sophisticated application of biocatalysis. Industrial microorganisms effect the multistep conversion of renewable feedstocks to high value chemical products in a single reactor and in so doing catalyze a multi-billion dollar industry. Fermentation products range from fine and commodity chemicals such as ethanol, lactic acid, amino acids and vitamins, to high value small molecule pharmaceuticals, protein pharmaceuticals, and industrial enzymes. (See, e.g., McCoy (1998) C&EN 13–19) for an introduction to biocatalysis. Success in bringing these products to market and success in competing in the market depends on continuous improvement of the whole cell biocatalysts. Improvements include increased yield of desired products, removal of unwanted co-metabolites, improved utilization of inexpensive carbon and nitrogen sources, and adaptation to fermenter conditions, increased production of a primary metabolite, increased production of a secondary metabolite, increased tolerance to acidic conditions, increased tolerance to basic conditions, increased tolerance to organic solvents, increased tolerance to high salt conditions and increased tolerance to high or low temperatures. Shortcomings in any of these areas can result in high manufacturing costs, inability to capture or maintain market share, and failure of bringing promising products to market. For this reason, the fermentation industry invests significant financial and personnel resources in the improvement of production strains. Current strategies for strain improvement rely on the empirical and iterative modification of fermenter conditions and genetic manipulation of the producing organism.

While advances in the molecular biology of established industrial organisms have been made, rational metabolic engineering is information intensive and is not broadly applicable to less characterized industrial strains. The most widely practiced strategy for strain improvement employs random mutagenesis of the producing strain and screening for mutants having improved properties. For mature strains, those subjected to many rounds of improvement, these efforts routinely provide a 10% increase in product titre per year. Although effective, this classic strategy is slow, laborious, and expensive. Technological advances in this area are aimed at automation and increasing sample screening throughput in hopes of reducing the cost of strain improvement. However, the real technical barrier resides in the intrinsic limitation of single mutations to effect significant strain improvement. The methods herein overcome this limitation and provide access to multiple useful mutations per cycle which can be used to complement automation technologies and catalyze strain improvement processes.

The methods herein allow biocatalysts to be improved at a faster pace than conventional methods. Whole genome stochastic &/or non-stochastic mutagenesis can at least double the rate of strain improvement for microorganisms used in fermentation as compared to traditional methods. This provides for a relative decrease in the cost of fermentation processes. New products can enter the market sooner, producers can increase profits as well as market share, and consumers gain access to more products of higher quality and at lower prices. Further, increased efficiency of production processes translates to less waste production and more frugal use of resources. Whole genome stochastic &/or non-stochastic mutagenesis provides a means of accumulating multiple useful mutation per cycle and thus eliminate the inherent limitation of current strain improvement programs (SIPs).

DNA stochastic &/or non-stochastic mutagenesis provides recursive mutagenesis, recombination, and selection of DNA sequences. A key difference between DNA stochastic &/or non-stochastic mutagenesis-mediated recombination and natural sexual recombination is that DNA stochastic &/or non-stochastic mutagenesis effects both the pairwise (two parents) and the poolwise (multiple parents) recombination of parent molecules, as described Supra. Natural recombination is more conservative and is limited to pairwise recombination. In nature, pairwise recombination provides stability within a population by preventing large leaps in sequences or genomic structure that can result from poolwise recombination. However, for the purposes of directed evolution, poolwise recombination is appealing since the beneficial mutations of multiple parents can be combined during a single cross to produce a superior offspring. Poolwise recombination is analogous to the cross-breeding of inbred strains in classic strain improvement, except that the crosses occur between many strains at once. In essence, poolwise recombination is a sequence of events that effects the recombination of a population of nucleic acid sequences that results in the generation of new nucleic acids that contains genetic information from more than two of the original nucleic acids. The power of in vitro DNA stochastic &/or non-stochastic mutagenesis is that large combinatorial libraries can be generated from a small pool of DNA fragments stochastic &/or non-stochastic mutagenized by recursive pairwise annealing and extension reactions, "matings." Many of the in vivo recombination formats described (such as plasmid-plasmid, plasmid-chromosome, phage-phage, phage-chromosome, phage-plasmid, conjugal DNA-chromosome, exogenous DNA-chromosome, chromosome-chromosome, with the DNA being introduced into the cell by natural and non-natural competence, transduction, transfection, conjugation, protoplast fusion, etc.) result primarily in the pairwise recombination of two DNA molecules. Thus, these formats when executed for only a single cycle of recombination are inherently limited in their potential to generate molecular diversity. To generate the level of diversity obtained by in vitro DNA stochastic &/or non-stochastic mutagenesis methods, pairwise mating formats must be carried out recursively, i.e for many generations, prior to screening for improved sequences.

Thus a pool of DNA sequences, such as four independent chromosomes, must be recombined, for example by protoplast fusion, and the progeny of that recombination (each representing a unique outcome of the pairwise mating) must then be pooled, without selection, and then recombined again, and again, and again. This process should be repeated for a sufficient number of cycles to result in progeny having the desired complexity. Only once sufficient diversity has been generated, should the resulting population be screened for new and improved sequences.

There are a few general methods for effecting efficient recombination in prokaryotes. Bacteria have no known sexual cycle per se, but there are natural mechanisms by which the genomes of these organisms undergo recombination. These mechanisms include natural competence, phage-mediated transduction, and cell-cell conjugation. Bacteria that are naturally competent are capable of efficiently taking up naked DNA from the environment. If homologous, this DNA undergoes recombination with the genome of the cell, resulting in genetic exchange. Bacillus subtilis, the primary production organism of the enzyme industry, is known for the efficiency with which it carries out this process.

In generalized transduction, a bacteriophage mediates genetic exchange. A transducing phage will often package headfulls of the host genome. These phage can infect a new host and deliver a fragment of the former host genome which is frequently integrated via homologous recombination.

Cells can also transfer DNA between themselves by conjugation. Cells containing the appropriate mating factors transfer episomes as well as entire chromosomes to an appropriate acceptor cell where it can recombine with the acceptor genome. Conjugation resembles sexual recombination for microbes and can be intraspecific, interspecific, and intergeneric. For example, an efficient means of transforming Streptomyces sp., a genera responsible for producing many commercial antibiotics, is by the conjugal transfer of plasmids from *Escherichia coli* .

For many industrial microorganisms, knowledge of competence, transducing phage, or fertility factors is lacking. Protoplast fusion has been developed as a versatile and general alternative to these natural methods of recombination. Protoplasts are prepared by removing the cell wall by treating cells with lytic enzymes in the presence of osmotic stabilizers. In the presence of a fusogenic agent, such as polyethylene glycol (PEG), protoplasts are induced to fuse and form transient hybrids or "fusants." During this hybrid state, genetic recombination occurs at high frequency allowing the genomes to reassort. The final crucial step is the successful segregation and regeneration of viable cells from the fused protoplasts. Protoplast fusion can be intraspecific, interspecific, and intergeneric and has been applied to both prokaryotes and eukaryotes. In addition, it is possible to fuse more than two cells, thus providing a mechanism for effecting poolwise recombination. While no fertility factors, transducing phages or competency development is needed for protoplast fusion, a method for the formation fusing, and regeneration of protoplasts is typically optimized for each organism. Protoplast fusion as applied to poolwise recombination is described in more detail, supra.

One key to SIP is having an assay that can be dependably used to identify a few mutants out of thousands that have subtle increases in product yield. The limiting factor in many assay formats is the uniformity of cell growth. This variation is the source of baseline variability in subsequent assays. Inoculum size and culture environment (temperature/humidity) are sources of cell growth variation. Automation of all aspects of establishing initial cultures and state-of-the-art temperature and humidity controlled incubators are useful in reducing variability.

Mutant cells or spores are separated on solid media to produce individual sporulating colonies. Using an automated colony picker (Q-bot, Genefix, U.K.), colonies are identified, picked, and 10,000 different mutants inoculated into 96 well microtitre dishes containing two 3 mm. glass balls/well. The Q-bot does not pick an entire colony but rather inserts a pin through the center of the colony and exits with a small sampling of cells (or mycelia) and spores. The time the pin is in the colony, the number of dips to inoculate the culture medium, and the time the pin is in that medium each effect inoculum size, and each can be controlled and optimized. The uniform process of the Q-bot decreases human handling error and increases the rate of establishing cultures (roughly 10,000/4 hours). These cultures are then shaken in a temperature and humidity controlled incubator. The glass balls act to promote uniform aeration of cells and the dispersal of mycelial fragments similar to the blades of a fermenter.

1. Prescreen The ability to detect a subtle increase in the performance of a mutant over that of a parent strain relies on the sensitivity of the assay. The chance of finding the organisms having an improvement is increased by the number of individual mutants that can be screened by the assay. To increase the chances of identifying a pool of sufficient size a prescreen that increases the number of mutants processed by 10-fold can be used. The goal of the primary screen will be to quickly identify mutants having equal or better product titres than the parent strain(s) and to move only these mutants forward to liquid cell culture. The primary screen is an agar plate screen is analyzed by the Q-bot colony picker. Although assays can be fundamentally different, many result, e.g., in the production of colony halos. For example, antibiotic production is assayed on plates using an overlay of a sensitive indicator strain, such as B. subtilis. Antibiotic production is typically assayed as a zone of clearing (inhibited growth of the indicator organism) around the producing organism. Similarly, enzyme production can be assayed on plates containing the enzyme substrate, with activity being detected as a zone of substrate modification around the producing colony. Product titre is correlated with the ratio of halo area to colony area.

The Q-bot or other automated system is instructed to only pick colonies having a halo ratio in the top 10% of the population i.e. 10,000 mutants from the 100,000 entering the plate prescreen. This increases the number of improved clones in the secondary assay and eliminates the wasted effort of screening knock-out and low producers. This improves the "hit rate" of the secondary assay.

8.6. Experimental Applications
8.6.1 Stochastic &/or Non-Stochastic Mutagenesis
8.6.1.1 General Techniques
8.6.1.1.1 Starting Materials Thus, a general method for recursive sequence recombination for the embodiments herein is to begin with a gene encoding an enzyme or enzyme subunit and to evolve that gene either for ability to act on a new substrate, or for enhanced catalytic properties with an old substrate, either alone or in combination with other genes in a multistep pathway. The term "gene" is used herein broadly to refer to any segment or sequence of DNA associated with a biological function. Genes can be obtained from a variety of sources, including cloning from a source of interest or synthesizing from known or predicted sequence information, and may include sequences designed to have desired parameters. The ability to use a new substrate can be assayed in some instances by the ability to grow on a substrate as a nutrient source. In other circumstances such ability can be assayed by decreased toxicity of a substrate for a host cell, hence allowing the host to grow in the presence of that substrate. Biosynthesis of new compounds, such as antibiotics, can be assayed similarly by growth of an indicator organism in the presence of the host expressing the evolved genes. For example, when an indicator organism used in an overlay of the host expressing the evolved gene(s), wherein the indicator organism is sensitive or expected to be sensitive to the desired antibiotic, growth of the indicator organism would be inhibited in a zone around the host cell or colony expressing the evolved gene(s).

Another method of identifying new compounds is the use of standard analytical techniques such as mass spectroscopy, nuclear magnetic resonance, high performance liquid chromatography, etc. Recombinant microorganisms can be pooled and extracts or media supernatants assayed from these pools. Any positive pool can then be subdivided and the procedure repeated until the single positive is identified ("sib-selection").

In some instances, the starting material for recursive sequence recombination is a discrete gene, cluster of genes, or family of genes known or thought to be associated with metabolism of a particular class of substrates. One of the advantages of the instant invention is that structural information is not required to estimate which parts of a sequence should be mutated to produce a functional hybrid enzyme.

In some embodiments of the invention, an initial screening of enzyme activities in a particular assay can be useful in identifying candidate enzymes as starting materials. For example, high throughput screening can be used to screen enzymes for dioxygenase-type activities using aromatic acids as substrates. Dioxygenases typically transform indole-2-carboxylate and indole-3-carboxylate to colored products, including indigo (Eaton et. al. J. Bacteriol. 177:6983–6988 (1995)). DNA encoding enzymes that give some activity in the initial assay can then be recombined by the recursive techniques of the invention and rescreened. The use of such initial screening for candidate enzymes against a desired target molecule or analog of the target molecule can be especially useful to generate enzymes that catalyze reactions of interest such as catabolism of man-made pollutants.

This type of high throughput screening can also be used during each round of recursive sequence recombination to identify mutants that possess the highest level of the desired activity. For example, penicillin G acylases have been isolated by looking for clones that allow a leucine auxotroph to hydrolyse penicillin G analogue phenylacetyl-L-leucine, thereby producing leucine and allowing cell growth (Martin, L. et al., FEMS Microbiology Lett. 125:287–292 (1995)). Positives from this selection are then screened by a more labour-intensive method for ability to hydrolyse penicillin G.

This same selection on phenylacetyl-L-leucine can be used when evolving penicillin G acylase for greater activity by recursive sequence recombination. After each round of recombination the library of acylase genes is transformed into a leucine auxotroph. Those that grow fastest are picked as probably having the most active acylase. The acylases are then be tested against the real substrate, penicillin G, by a more laborious screen such as HPLC. Thus, even if there is no convenient high throughput screen for an enzyme or a metabolic pathway, it is often possible to find a rapid detection method that can approximately measure the desired phenotype, thereby reducing the numbers of colonies that must be screened more accurately.

The starting material can also be a segment of such a gene or cluster that is recombined in isolation of its surrounding DNA, but is relinked to its surrounding DNA before screening/selection of recombination products. In other instances, the starting material for recombination is a larger segment of DNA that includes a coding sequence or other locus associated with metabolism of a particular substrate at an unknown location. For example, the starting material can be a chromosome, episome, YAC, cosmid, or phage P1 clone. In still other instances, the starting material is the whole genome of an organism that is known to have desirable metabolic properties, but for which no information localizing the genes associated with these characteristics is available.

In general any type of cells can be used as a recipient of evolved genes. Cells of particular interest include many bacterial cell types, both gram-negative and gram-positive, such as Rhodococcus, Streptomycetes, Actinomycetes, Corynebacteria, Penicillium, Bacillus, Escherichia coli, Pseudomonas, Salmonella, and Erwinia. Cells of interest also include eukaryotic cells, particularly mammalian cells (e.g., mouse, hamster, primate, human), both cell lines and primary cultures. Such cells include stem cells, including embryonic stem cells, zygotes, fibroblasts, lymphocytes, Chinese hamster ovary (CHO), mouse fibroblasts (NIHM), kidney, liver, muscle, and skin cells. Other eukaryotic cells of interest include plant cells, such as maize, rice, wheat, cotton, soybean, sugarcane, tobacco, and arabidopsis; fish, algae, fungi (Penicillium, Fusarium, Aspergillus, Podospora, Neurospora), insects, yeasts (Picchia and Saccharomyces).

The choice of host will depend on a number of factors, depending on the intended use of the engineered host, including pathogenicity, substrate range, environmental hardiness, presence of key intermediates, ease of genetic manipulation, and likelihood of promiscuous transfer of genetic information to other organisms. Particularly advantageous hosts are E. coli, lactobacilli, Streptomycetes, Actinomycetes and filamentous fungi.

The breeding procedure starts with at least two substrates, which generally show substantial sequence identity to each other (i.e., at least about 50%, 70%, 80% or 90% sequence identity) but differ from each other at certain positions. The difference can be any type of mutation, for example, substitutions, insertions and deletions. Often, different segments differ from each other in perhaps 5–20 positions. For recombination to generate increased diversity relative to the starting materials, the starting materials must differ from each other in at least two nucleotide positions. That is, if there are only two substrates, there should be at least two divergent positions. If there are three substrates, for example, one substrate can differ from the second as a single position, and the second can differ from the third at a different single position. The starting DNA segments can be natural variants of each other, for example, allelic or species variants. The segments can also be from nonallelic genes showing some degree of structural and is usually functional relatedness (e.g., different genes within a superfamily such as the immunoglobulin superfamily). The starting DNA segments can also be induced variants of each other. For example, one DNA segment can be produced by error-prone PCR replication of the other, or by substitution of a mutagenic cassette. Induced mutants can also be prepared by propagating one (or both) of the segments in a mutagenic strain. In these situations, strictly speaking, the second DNA segment is not a single segment but a large family of related segments. The different segments forming the starting materials are often the same length or substantially the same length. However, this need not be the case; for example; one segment can be a subsequence of another. The segments can be present as part of larger molecules, such as vectors, or can be in isolated form. The starting DNA segments are recombined by any of the recursive sequence recombination formats described above to generate a diverse library of recombinant DNA segments.

Such a library can vary widely in size from having fewer than to more than $10^5$, $10^7$, or $10^9$ members. In general, the starting segments and the recombinant libraries generated include full-length coding sequences and any essential regulatory sequences, such as a promoter and polyadenylation sequence, required for expression. However, if this is not the case, the recombinant DNA segments in the library can be inserted into a common vector providing the missing sequences before performing screening/selection.

If the recursive sequence recombination format employed is an in vivo format, the library of recombinant DNA segments generated already exists in a cell, which is usually the cell type in which expression of the enzyme with altered substrate specificity is desired. If recursive sequence recombination is performed in vitro, the recombinant library is preferably introduced into the desired cell type before screening/selection. The members of the recombinant library can be linked to an episome or virus before introduction or can be introduced directly. In some embodiments of the is invention, the library is amplified in a first host, and is then recovered from that host and introduced to a second host more amenable to expression, selection, or screening, or any other desirable parameter. The manner in which the library is introduced into the cell type depends on the DNA-uptake characteristics of the cell type, e.g., having viral receptors, being capable of conjugation, or being naturally competent. If the cell type is insusceptible to natural and chemical-induced competence, but susceptible to electroporation, one would usually employ electroporation. If the cell type is insusceptible to electroporation as well, one can employ biolistics. The biolistic PDS-1000 Gene Gun (Biorad, Hercules, Calif.) uses helium pressure to accelerate DNA-coated gold or tungsten microcarriers toward target cells.

The process is applicable to a wide range of tissues, including plants, bacteria, fungi, algae, intact animal tissues, tissue culture cells, and animal embryos. One can employ electronic pulse delivery, which is essentially a mild electroporation format for live tissues in animals and patients. Zhao, Advanced Drug Delivery Reviews 17:257–262 (1995). After introduction of the library of recombinant DNA genes, the cells are optionally propagated to allow expression of genes to occur.

8.6.1.1.2 Selection and Screening

Screening is, in general, a two-step process in which one first determines which cells do and do not express a screening marker and then physically separates the cells having the desired property. Selection is a form of screening in which identification and physical separation are achieved simultaneously, for example, by expression of a selectable marker, which, in some genetic circumstances, allows cells expressing the marker to survive while other cells die (or vice versa). Screening markers include, for example, luciferase, β-galactosidase, and green fluorescent protein.

Screening can also be done by observing such aspects of growth as colony size, halo formation, etc. Additionally, screening for production of a desired compound, such as a therapeutic drug or "designer chemical" can be accomplished by observing binding of cell products to a receptor or ligand, such as on a solid support or on a column. Such screening can additionally be accomplished by binding to antibodies, as in an ELISA. In some instances the screening process is preferably automated so as to allow screening of suitable numbers of colonies or cells. Some examples of automated screening devices include fluorescence activated cell sorting, especially in conjunction with cells immobilized in agarose (see Powell et. al. Bio/Technology 8:333–337 (1990); Weaver et. al. Methods 2:234–247 (1991)), automated ELISA assays, scintillation proximity assays (Hart, H. E. et al., Molecular Immunol. 16:265–267 (1979)) and the formation of fluorescent, coloured or UV absorbing compounds on agar plates or in microtitre wells (Krawiec, S., Devel. Indust. Microbiology 31:103–114 (1990)).

Selectable markers can include, for example, drug, toxin resistance, or nutrient synthesis genes. Selection is also done by such techniques as growth on a toxic substrate to select for hosts having the ability to detoxify a substrate, growth on a new nutrient source to select for hosts having the ability to utilize that nutrient source, competitive growth in culture based on ability to utilize a nutrient source, etc.

In particular, uncloned but differentially expressed proteins (e.g., those induced in response to new compounds, such as biodegradable pollutants in the medium) can be screened by differential display (Appleyard et al. Mol. Gen. Gent. 247:338–342 (1995)). Hopwood (Phil Trans R. Soc. Lond B 324:549–562) provides a review of screens for antibiotic production. Omura (Microbio. Rev. 50:259–279 (1986) and Nisbet (Ann Rev. Med. Chem. 21:149–157 (1986)) disclose screens for antimicrobial agents, including supersensitive bacteria, detection of beta-lactamase and D,D-carboxypeptidase inhibition, beta-lactamase induction, chromogenic substrates and monoclonal antibody screens.

Antibiotic targets can also be used as screening targets in high throughput screening. Antifungals are typically screened by inhibition of fungal growth. Pharmacological agents can be identified as enzyme inhibitors using plates containing the enzyme and a chromogenic substrate, or by automated receptor assays. Hydrolytic enzymes (e.g., proteases, amylases) can be screened by including the substrate in an agar plate and scoring for a hydrolytic clear zone or by using a colorimetric indicator (Steele et al. Ann. Rev. Microbiol. 45:89–106 (1991)). This can be coupled with the use of stains to detect the effects of enzyme action (such as congo red to detect the extent of degradation of celluloses and hemicelluloses).

Tagged substrates can also be used. For example, lipases and esterases can be screened using different lengths of fatty acids linked to umbelliferyl. The action of lipases or esterases removes this tag from the fatty acid, resulting in a quenching or enhancement of umbelliferyl fluorescence. These enzymes can be screened in microtiter plates by a robotic device.

8.6.1.1.3 FACS

Fluorescence activated cell sorting (FACS) methods are also a powerful tool for selection/screening. In some instances a fluorescent molecule is made within a cell (e.g., green fluorescent protein). The cells producing the protein can simply be sorted by FACS. Gel microdrop technology allows screening of cells encapsulated in agarose microdrops (Weaver et al. Methods 2:234–247 (1991)). In this technique products secreted by the cell (such as antibodies or antigens) are immobilized with the cell that generated them. Sorting and collection of the drops containing the desired product thus also collects the cells that made the product, and provides a ready source for the cloning of the genes encoding the desired functions. Desired products can be detected by incubating the encapsulated cells with fluorescent antibodies (Powell et al. Bio/Technology 8:333–337 (1990)). FACS sorting can also be used by this technique to assay resistance to toxic compounds and antibiotics by selecting droplets that contain multiple cells (i.e., the product of continued division in the presence of a cytotoxic compound; Goguen et al. Nature 363:189–190 (1995)). This method can select for any enzyme that can change the fluorescence of a substrate that can be immobilized in the agarose droplet. 8.6.1.1.4 Reporter Molecule In some embodiments of the invention, screening can be accomplished by assaying reactivity with a reporter molecule reactive with a desired feature of, for example, a gene product. Thus, specific functionalities such as antigenic domains can be screened with antibodies specific for those determinants. 8.6.1.1.5 Cell-Cell Indicator In other embodiments of the invention, screening is preferably done with a cell-cell indicator assay. In this assay format, separate library cells (Cell A, the cell being assayed) and reporter cells (Cell B, the assay cell) are used.

Only one component of the system, the library cells, is allowed to evolve. The screening is generally carried out in a two-dimensional immobilized format, such as on plates. The products of the metabolic pathways encoded by these genes (in this case, usually secondary metabolites such as antibiotics, polyketides, carotenoids, etc.) diffuse out of the library cell to the reporter cell. The product of the library cell may affect the reporter cell in one of a number of ways.

The assay system (indicator cell) can have a simple readout (e.g., green fluorescent protein, luciferase, β-galactosidase) which is induced by the library cell product but which does not affect the library cell. In these examples the desired product can be detected by colorimetric changes in the reporter cells adjacent to the library cell.

8.6.1.1.6 Feedback Mechanism

In other embodiments, indicator cells can in turn produce something that modifies the growth rate of the library cells via a feedback mechanism. Growth rate feedback can detect and accumulate very small differences. For example, if the library and reporter cells are competing for nutrients, library cells producing compounds to inhibit the growth of the reporter cells will have more available nutrients, and thus will have more opportunity for growth. This is a useful screen for antibiotics or a library of polyketide synthesis gene clusters where each of the library cells is expressing and exporting a different polyketide gene product.

8.6.1.1.7 Secretion

Another variation of this theme is that the reporter cell for an antibiotic selection can itself secrete a toxin or antibiotic that inhibits growth of the library cell. Production by the library cell of an antibiotic that is able to suppress growth of the reporter cell will thus allow uninhibited growth of the library cell.

Conversely, if the library is being screened for production of a compound that stimulates the growth of the reporter cell (for example, in improving chemical syntheses, the library cell may supply nutrients such as amino acids to an auxotrophic reporter, or growth factors to a growth-factor-dependent reporter. The reporter cell in turn should produce a compound that stimulates the growth of the library cell. Interleukins, growth factors, and nutrients are possibilities. Further possibilities include competition based on ability to kill surrounding cells, positive feedback loops in which the desired product made by the evolved cell stimulates the indicator cell to produce a positive growth factor for cell A, thus indirectly selecting for increased product formation.

In some embodiments of the invention it can be advantageous to use a different organism (or genetic background) for screening than the one that will be used in the final product. For example, markers can be added to DNA constructs used for recursive sequence recombination to make the microorganism dependent on the constructs during the improvement process, even though those markers may be undesirable in the final recombinant microorganism.

Likewise, in some embodiments it is advantageous to use a different substrate for screening an evolved enzyme than the one that will be used in the final product. For example, Evnin et al. (Proc. Natl. Acad. Sci. U.S.A. 87:6659–6663 (1990)) selected trypsin variants with altered substrate specificity by requiring that variant trypsin generate an essential amino acid for an arginine auxotroph by cleaving arginine-naphthylamide. This is thus a selection for arginine-specific trypsin, with the growth rate of the host being proportional to that of the enzyme activity.

The pool of cells surviving screening and/or selection is enriched for recombinant genes conferring the desired phenotype (e.g. altered substrate specificity, altered biosynthetic ability, etc.). Further enrichment can be obtained, if desired, by performing a second round of screening and/or selection without generating additional diversity.

The recombinant gene or pool of such genes surviving one round of screening/selection forms one or more of the substrates for a second round of recombination. Again, recombination can be performed in vivo or in vitro by any of the recursive sequence recombination formats described above.

If recursive sequence recombination is performed in vitro, the recombinant gene or genes to form the substrate for recombination should be extracted from the cells in which screening/selection was performed. Optionally, a subsequence of such gene or genes can be excised for more targeted subsequent recombination. If the recombinant gene(s) are contained within episomes, their isolation presents no difficulties. If the recombinant genes are chromosomally integrated, they can be isolated by amplification primed from known sequences flanking the regions in which recombination has occurred. Alternatively, whole genomic DNA can be isolated, optionally amplified, and used as the substrate for recombination. Small samples of genomic DNA can be amplified by whole genome amplification with degenerate primers (Barrett et al. Nucleic Acids Research 23:3488–3492 (1995)). These primers result in a large amount of random 3' ends, which can undergo homologous recombination when reintroduced into cells.

If the second round of recombination is to be performed in vivo, as is often the case, it can be performed in the cell surviving screening/selection, or the recombinant genes can be transferred to another cell type (e.g., a cell is type having a high frequency of mutation and/or recombination). In this situation, recombination can be effected by introducing additional DNA segment(s) into cells bearing the recombinant genes. In other methods, the cells can be induced to exchange genetic information with each other by, for example, electroporation. In some methods, the second round of recombination is performed by dividing a pool of cells surviving screening/selection in the first round into two subpopulations. DNA from one subpopulation is isolated and transfected into the other population, where the recombinant gene(s) from the two subpopulations recombine to form a further library of recombinant genes. In these methods, it is not necessary to isolate particular genes from the first subpopulation or to take steps to avoid random shearing of DNA during extraction. Rather, the whole genome of DNA sheared or otherwise cleaved into manageable sized fragments is transfected into the second subpopulation. This approach is particularly useful when several genes are being evolved simultaneously and/or the location and identity of such genes within chromosome are not known.

The second round of recombination is sometimes performed exclusively among the recombinant molecules surviving selection. However, in other embodiments, additional substrates can be introduced. The additional substrates can be of the same form as the substrates used in the first round of recombination, i.e., additional natural or induced mutants of the gene or cluster of genes, forming the substrates for the first round. Alternatively, the additional substrate(s) in the second round of recombination can be exactly the same as the substrate(s) in the first round of replication.

After the second round of recombination, recombinant genes conferring the desired phenotype are again selected. The selection process proceeds essentially as before. If a suicide vector bearing a selective marker was used in the first round of selection, the same vector can be used again. Again, a cell or pool of cells surviving selection is selected. If a pool of cells, the cells can be subject to further enrichment.

8.6.1.2 General Methods 8.6.1.2.1 In vitro

In Vitro Formats one format for recursive sequence recombination in vitro is illustrated herein. The initial substrates for recombination are a pool of related sequences. The X's show where the sequences diverge. The sequences can be DNA or RNA and can be of various lengths depending on the size of the gene or DNA fragment to be recombined or stochastic &/or non-stochastic mutagenized. Preferably the sequences are from 50 bp to 100 kb.

The pool of related substrates are converted into overlapping fragments, e.g., from about 5 bp to 5 kb or more, as shown herein. Often, the size of the fragments is from about 10 bp to 1000 bp, and sometimes the size of the DNA fragments is from about 100 bp to 500 bp. The conversion can be effected by a number of different methods, such as DNaseI or RNase digestion, random shearing or partial restriction enzyme digestion.

Alternatively, the conversion of substrates to fragments can be effected by incomplete PCR amplification of substrates or PCR primed from a single primer. Alternatively, appropriate single-stranded fragments can be generated on a nucleic acid synthesizer. The concentration of nucleic acid fragments of a particular length and sequence is often less than 0.1% or 1% by weight of the total nucleic acid. The number of different specific nucleic acid fragments in the mixture is usually at least about 100, 500 or 1000.

The mixed population of nucleic acid fragments are converted to at least partially single-stranded form. Conversion can be effected by heating to about 80 C. to 100 C., more preferably from 90 C. to 96 C., to form single-stranded nucleic acid fragments and then reannealing. Conversion can also be effected by treatment with single-stranded DNA binding protein or recA protein. Single-stranded nucleic acid fragments having regions of sequence identity with other single-stranded nucleic acid fragments can then be reannealed by cooling to 4 C. to 75 C., and preferably from 40 C. to 65 C. Renaturation can be accelerated by the addition of polyethylene glycol (PEG), other volume-excluding reagents or salt. The salt concentration is preferably from 0 mM to 200 mM more preferably the salt concentration is from 10 mM to 100 mM. The salt may be KCl or NaCl. The concentration of PEG is preferably from 0% to 20%, more preferably from 5% to 10%. The fragments that reanneal can be from different substrates as shown herein. The annealed nucleic acid fragments are incubated in the presence of a nucleic acid polymerase, such as Taq or Klenow, or proofreading polymerases, such as pfu or pwo, and dNTP's (i.e. dATP, dCTP, dGTP and dTTP). If regions of sequence identity are large, Taq polymerase can be used with an annealing temperature of between 45–65 C. If the areas of identity are small, Klenow polymerase can be used with an annealing temperature of between 20–30 T (Stemmer, Proc. Natl. Acad. Sci. USA (1994), supra). The polymerase can be added to the random nucleic acid fragments prior to annealing, simultaneously with annealing or after annealing.

The process of denaturation, renaturation and incubation in the presence of polymerase of overlapping fragments to generate a collection of polynucleotides containing different permutations of fragments is sometimes referred to as stochastic &/or non-stochastic mutagenesis of the nucleic acid in vitro. This cycle is repeated for a desired number of times. Preferably the cycle is repeated from 2 to 100 times, more preferably the sequence is repeated from 10 to 40 times. The resulting nucleic acids are a family of double-stranded polynucleotides of from about 50 bp to about 100 kb, preferably from 500 bp to 50 kb, as shown herein. The population represents variants of the starting substrates showing substantial sequence identity thereto but also diverging at several positions. The population has many more members than the starting substrates. The population of fragments resulting from stochastic &/or non-stochastic mutagenesis is used to transform host cells, optionally after cloning into a vector.

8.6.1.2.1.1 Full Length Sequences

In a variation of in vitro stochastic &/or non-stochastic mutagenesis, subsequences of recombination substrates can be generated by amplifying the full-length sequences under conditions which produce a substantial fraction, typically at least 20 percent or more, of incompletely extended amplification products. The amplification products, including the incompletely extended amplification products are denatured and subjected to at least one additional cycle of reannealing and amplification. This variation, wherein at least one cycle of reannealing and amplification provides a substantial fraction of incompletely extended products, is termed "stuttering." In the subsequent amplification round, the incompletely extended products anneal to and prime extension on different sequence-related template species.

8.6.1.2.1.2 Overlapping Single Stranded DNA Fragments

In a further variation, at least one cycle of amplification can be conducted using a collection of overlapping single-stranded DNA fragments of related sequence, and different lengths. Each fragment can hybridize to and prime polynucleotide chain extension of a second fragment from the collection, thus forming sequence-recombined polynucleotides. In a further variation, single-stranded DNA fragments of variable length can be generated from a single primer by Vent DNA polymerase on a first DNA template. The single stranded DNA fragments are used as primers for a second, Kunkel-type template, consisting of a uracil-containing circular single-stranded DNA. This results in multiple substitutions of the first template into the second (see Levichkin et al. Mol. Biology 29:572–577 (1995)).

8.6.1.2.1.3 Gene Clusters

Gene clusters such as those involved in polyketide synthesis (or indeed any multi-enzyme pathways catalyzing is analogous metabolic reactions) can be recombined by recursive sequence recombination even if they lack DNA sequence homology. Homology can be introduced using synthetic oligonucleotides as PCR primers. In addition to the specific sequences for the gene being amplified, all of the primers used to amplify one type of enzyme (for example the acyl carrier protein in polyketide synthesis) are synthesized to contain an additional sequence of 20–40 bases 51 to the gene (sequence A) and a different 20–40 base sequence 31 to the gene (sequence B). The adjacent gene (in this case the keto-synthase) is amplified using a 51 primer which contains the complementary strand of sequence B (sequence B'), and a 31 primer containing a different 20–40 base sequence (C). Similarly, primers for the next adjacent gene (keto-reductases) contain sequences C' (complementary to C) and D. If 5 different polyketide gene clusters are being stochastic &/or non-stochastic mutagenized, all five acyl carrier proteins are flanked by sequences A and B following their PCR amplification. In this way, small regions of homology are introduced, making the gene clusters into site specific recombination cassettes. Subsequent to the initial amplification of individual genes, the amplified genes can then be mixed and subjected to primerless PCR. Sequence B at the 3' end of all of the five acyl carrier protein genes can anneal with and prime DNA synthesis from sequence BI at the 5' end of all five keto reductase genes. In this way all possible combinations of genes within the cluster can be obtained. Oligonucleotides allow such recombinants to be obtained in the absence of sufficient sequence homology for recursive sequence recombination described above. Only homology of function is required to produce functional gene clusters.

8.6.1.2.1.4 Multi Subunit Enzymes

This method is also useful for exploring permutations of any other multi-subunit enzymes. An example of such enzymes composed of multiple polypeptides that have shown novel functions when the subunits are combined in novel ways are dioxygenases. Directed recombination between the four protein subunits of biphenyl and toluene dioxygenases produced functional dioxygenases with increased activity against trichloroethylene (Furukawa et. al. J. Bacteriol. 176: 2121–2123 (1994)). This combination of subunits from the two dioxygenases could also have been produced by cassette-stochastic &/or non-stochastic mutagenesis of the dioxygenases as described above, followed by selection for degradation of trichloroethylene.

In some polyketide synthases, the separate functions of the acyl carrier protein, keto-synthase, keto-reductase, etc. reside in a single polypeptide. In these cases domains within the single polypeptide may be stochastic &/or non-stochastic mutagenized, even if sufficient homology does not exist naturally, by introducing regions of homology as described above for entire genes. In this case, it may not be possible to introduce additional flanking sequences to the domains, due to the constraint of maintaining a continuous open reading frame.

Instead, groups of oligonucleotides are synthesized that are homologous to the 3' end of the first domain encoded by one of the genes to be stochastic &/or non-stochastic mutagenized, and the 5' ends of the second domains encoded by all of the other genes to be stochastic &/or non-stochastic mutagenized together. This is repeated with all domains, thus providing sequences that allow recombination between protein domains while maintaining their order.

8.6.1.2.1.5 Cassette-Based

The cassette-based recombination method can be combined with recursive sequence recombination by including gene fragments (generated by DNase, physical shearing, DNA stuttering, etc.) for one or more of the genes. Thus, in addition to different combinations of entire genes within a cluster (e.g., for polyketide synthesis), individual genes can be stochastic &/or non-stochastic mutagenized at the same time (e.g., all acyl carrier protein genes can also be provided as fragmented DNA), allowing a more thorough search of sequence space.

8.6.1.2.1.6 In vitro Whole Genome Stochastic &/or Non-Stochastic Mutagenesis

The stochastic &/or non-stochastic mutagenesis of large DNA sequences, such as eukaryotic chromosomes, is difficult by prior art in vitro stochastic &/or non-stochastic mutagenesis methods. A method for overcoming this limitation is described herein.

The cells of related eukaryotic species are gently lysed and the intact chromosomes are liberated. The liberated chromosomes are then sorted by FACS or similar method (such as pulse field electrophoresis) with chromosomes of similar size being sequestered together. Each size fraction of the sorted chromosomes generally will represent a pool of analogous chromosomes, for example the Y chromosome of related mammals. The goal is to isolate intact chromosomes that have not been irreversibly damaged.

The fragmentation and stochastic &/or non-stochastic mutagenesis of such large complex pieces of DNA employing DNA polymerases is difficult and would likely introduce an unacceptably high level of random mutations. An alternative approach that employs restriction enzymes and DNA ligase provides a feasible less destructive solution. A chromosomal fraction is digested with one or more restriction enzymes that recognize long DNA sequences (about 15–20 bp), such as the intron and intein encoded endonucleases (I-Ppo 1, I-Ceu I, PI-Psp 1, PI-Tli 1, PI-Sce I (VDE).

These enzymes each cut, at most, a few times within each chromosome, resulting in a combinatorial mixture of large fragments, each having overhanging single stranded termini that are complementary to other sites cleaved by the same enzyme.

The digest is further modified by very short incubation with a single stranded exonuclease. The polarity of the nuclease chosen is dependent on the single stranded overhang resulting from the restriction enzyme chosen. 5'–3' exonuclease for 3+-overhangs, and 3'–5'-exonuclease for 5' overhangs. This digestion results in significantly long regions of ssDNA overhang on each dsDNA termini. The purpose of this incubation is to generate regions of DNA that define specific regions of DNA where recombination can occur. The fragments are then incubated under condition where the ends of the fragments anneal with other fragments having homologous ssDNA termini. Often, the two fragments annealing will have originated from different chromosomes and in the presence of DNA ligase are covalently linked to form a chimeric chromosome. This generates genetic diversity mimicking the crossing over of homologous chromosomes. The complete ligation reaction will contain a combinatorial mixture of all possible ligations of fragments having homologous overhanging termini. A subset of this population will be complete chimeric chromosomes.

To screen the stochastic &/or non-stochastic mutagenized library, the chromosomes are delivered to a suitable host in a manner allowing for the uptake and expression of entire chromosomes. For example, YACs (yeast artificial chromosomes) can be delivered to eukaryotic cells by protoplast fusion.

Thus, the reassemble library could be encapsulated in liposomes and fused with protoplasts of the appropriate host cell. The resulting transformants would be propagated and screened for the desired cellular improvements. Once an improved population was identified, the chromosomes would be isolated, stochastic &/or non-stochastic mutagenized, and screened recursively.

8.6.1.2.1.7 Whole Genome Stochastic &/or Non-Stochastic Mutagenesis of Naturally Competent Microorganisms Natural competence is a phenomenon observed for some microbial species whereby individual cells take up DNA from the environment and incorporate it into their genome by homologous recombination. *Bacillus subtilis* and Acetinetobacter Spp. are known to be particularly efficient at this process. A method for the whole genome stochastic &/or non-stochastic mutagenesis of these and analogous organisms is described employing this process.

One goal of whole genome stochastic &/or non-stochastic mutagenesis is the rapid accumulation of useful mutations from a population of individual strains into one superior strain. If the organisms to be evolved are naturally competent, then a split pooled strategy for the recursive transformation of naturally competent cells with DNA originating from the pool will effect this process. An example procedure is as follows.

A population of naturally competent organisms that demonstrates a variety of useful traits (such as increased protein secretion) is identified. The strains are pooled, and the pool is split. One half of the pool is used as a source of gDNA, while the other is used to generate a pool of naturally competent cells.

The competent cells are grown in the presence of the pooled gDNA to allow DNA uptake and recombination. Cells of one genotype uptake and incorporate gDNA from cells of a different type generating cells having chimeric genomes. The result is a population of cells representing a combinatorial mixture of the genetic variations originating in the original pool. These cells are pooled again and transformed with the same source of DNA again. This process is carried out recursively to increase the diversity of the genomes of cells resulting from transformation. Once sufficient diversity has been generated, the cell population is screened for new chimeric organisms demonstrating desired improvements.

This process is enhanced by increasing the natural competence of the host organism. COMS is a protein that, when expressed in *B. subtilis*, enhances the efficiency of natural competence mediated transformation more than an order of magnitude.

It was demonstrated that approximately 100% of the cells harboring the plasmid pCOMS uptake and recombine genomic DNA fragments into their genomes. In general, approximately 10% of the genome is recombined into any given transformed cell. This observation was demonstrated by the following.

A strain of *B. subtilis* pCOMS auxotrophic for two nutritional markers was transformed with genomic DNA (gDNA) isolated from a prototrophic strain of the same organism. 10% of the cells exposed to the DNA were prototrophic for one of the two nutrient markers. The average size of the DNA strand taken up by *B. subtilis* is approximately 50 kb or about 2% of the genome. Thus 1 of every ten cells had recombined a marker that was represented 1 in every fifty molecules of uptaken gDNA. Thus, most of the cells take up and recombine with approximately five 50 kb molecules or 10% of the genome. This method represents a powerful tool for rapidly and efficiently recombining whole microbial genomes.

In the absence of pCOMS, only 0.3% of the cells prepared for natural competency uptake and integrate a specific marker. This suggested that about 15% of the cells actually underwent recombination with a single genomic fragment. Thus, a recursive transformation strategy as described above produces a whole genome stochastic &/or non-stochastic mutagenized library, even in the absence of pCOMS. In the absence of pCOMS, however, the complex genomes will represent a smaller, but still screenable percentage of the transformed or stochastic &/or non-stochastic mutagenized population.

8.6.1.2.1.8 Congression

Congression is the integration of two independent unlinked markers into a cell. 0.3% of naturally competent *B. subtilis* cells integrate a single marker (described above). Of these, about 10% have taken up an additional marker. Thus, if one selects or screens for the integration of one specific marker, 10% of the resulting population will have integrated another specific marker. This provides a way of enriching for specific integration events.

For example, if one is looking for the integration of a gene for which there is no easy screen or selection, it will exist as 0.3% of the cell population. If the population is first selected for a specific integration event, then the desired integration will be found in 10% of the population. This represents a significant (about 30-fold) enrichment for the desired event. This enrichment is defined as the "congression effect." The congression effect is not influenced by the presence of pCOMS, thus the "pCOMS effect" is simply to increase the percentage of naturally competent cells that are truly naturally competent from about 15% in its absence to 100% in its presence. All competent cells still uptake about the same amount of DNA or about 10% of the *Bacillus genome*.

The congression effect can be used in the following examples to enhance whole genome stochastic &/or non-stochastic mutagenesis as well, as the targeted integration of stochastic &/or non-stochastic mutagenized genes to the chromosome.

8.6.1.2.1.9 *B. Subtilis* Stochastic &/or Non-Stochastic Mutagenesis

A population of *B. subtilis* cells having desired properties are identified, pooled and stochastic &/or non-stochastic mutagenized as described above with one exception: once the pooled population is split, half of the population is transformed with an antibiotic selection marker that is flanked by sequence that targets its integration and disruption of a specific nutritional gene, for example, one involved in amino biosynthesis. Transformants resistant to the drug are auxotrophic for that nutrient. The resistant population is pooled and grown under conditions rendering them naturally competent (or optionally first transformed with pCOMS).

The competent cells are then transformed with gDNA isolated from the original pool, and prototrophs are selected. The prototrophic population will have undergone recombination with genomic fragments encoding a functional copy of the nutritional marker, and thus will be enriched for cells having undergone recombination at other genetic loci by the congression effect.

8.6.1.2.1.10 Targeting of Genes and Gene Libraries to the Chromosome

It is useful to be able to efficiently deliver genes or gene libraries directly to a specific location in a cells chromosome. As above, target cells are transformed with a positive selection marker flanked by sequences that target its homologous recombination into the chromosome. Selected cells harboring the marker are made naturally competent (with or without pCOMS, but preferably the former) and transformed with a mixture of two sets of DNA fragments. The first set contains a gene or a stochastic &/or non-stochastic mutagenized library of genes each flanked with sequence to target its integration to a specific chromosomal loci. The second set contains a positive selection marker (different from that first integrated into the cells) flanked by sequence that will target its integration and replacement of the first positive selection marker.

Under optimal conditions, the mixture is such that the gene or gene library is in molar excess over the positive selection marker. Transformants are then selected for cells containing the new positive marker. These cells are enriched for cells having integrated a copy of the desired gene or gene library by the congression effect and can be directly screened for cells harboring the gene or gene variants of interest. This process was carried out using PCR fragments <10 kb, and it was found that, employing the congression effect, a population can be enriched such that 50% of the cells are congregants. Thus, one in two cells contained a gene or gene variant.

Alternatively, the expression host can be absent of the first positive selection marker, and the competent cells are transformed with a mixture of the target genes and a limiting amount of the first positive selection marker fragment. Cells selected for the positive marker are screened for the desired properties in the targeted genes. The improved genes are amplified by the PCR, stochastic &/or non-stochastic mutagenized again, and then returned to the original host again with the first positive selection marker. This process is carried out recursively until the desired function of the genes are obtained. This process obviates the need to construct a primary host strain and the need for two positive markers.

8.6.1.2.1.11 Conjugation-Mediated Genetic Exchange

Conjugation can be employed in the evolution of cell genomes in several ways. Conjugative transfer of DNA occurs during contact between cells. See Guiney(1993)in: Bacterial Conjugation (Clewell, ed., Plenum Press, New York), pp. 75–104; Reimmann & Haas in Bacterial Conjugation (Clewell, ed., Plenum Press, New York 1993), at pp. 137–188 (incorporated by reference in their entirety for all purposes). Conjugation occurs between many types of gram negative bacteria, and some types of gram positive bacteria. Conjugative transfer is also known between bacteria and plant cells (*Agrobacterium tumefaciens*) or yeast. As discussed in U.S. Pat. No. 5,837,458, the genes responsible for conjugative transfer can themselves be evolved to expand the range of cell types (e.g., from bacteria to mammals) between which such transfer can occur.

Conjugative transfer is effected by an origin of transfer (oriT) and flanking genes (MOB A, B and C, and 15–25 genes, termed tra, encoding the structures and enzymes necessary for conjugation to occur. The transfer origin is defined as the site required in cis for DNA transfer. Tra genes include tra A, B, C, D, E, F, G, H, I, J, K, L, M, N, P, Q, R, S, T, U, V, W, X, Y,Z, virAB(allelesl-ll),C,D,E,G,IHF, and-FinOP. Tra genes can be expressed in cis or trans to oriT. Other cellular enzymes, including those of the RecBCD pathway, RecA, SSB protein, DNA gyrase, DNA poll, and DNA ligase, are also involved in conjugative transfer. RecE or recF pathways can substitute for RecBCD.

One structural protein encoded by a tra gene is the sex pilus, a filament constructed of an aggregate of a single polypeptide protruding from the cell surface. The sex pilus binds to a polysaccharide on recipient cells and forms a conjugative bridge through which DNA can transfer. This process activates a site-specific nuclease encoded by a MOB gene, which specifically cleaves DNA to be transferred at oriT. The cleaved DNA is then threaded through the conjugation bridge by the action of other tra enzymes.

Mobilizable vectors can exist in episomal form or integrated into the chromosome. Episomal mobilizable vectors can be used to exchange fragments inserted into the vectors between cells. Integrated mobilizable vectors can be used to mobilize adjacent genes from the chromosome.

8.6.1.2.1.12 Use of Integrated Mobilized Vectors to Promote Exchange of Genomic DNA The F plasmid of *E. coli* integrates into the chromosome at high frequency and mobilizes genes unidirectional from the site of integration (Clewell, 1993, supra; Firth et al., in *Escherichia coli* and Salmonella Cellular and Molecular Biology 2, 23 77–2401 (1996); Frost et al., Microbiol. Rev. 58, 162–210 (1994)). Other mobilizable vectors do not spontaneously integrate into a host chromosome at high efficiency, but can be induced to do so by growth under particular conditions (e.g., treatment with a mutagenic agent, growth at a nonpermissive temperature for plasmid replication). See Reimann & Haas in Bacterial Conjugation (ed. Clewell, Plenum Press, NY 1993), Ch. 6. Of particular interest is the IncP group of conjugal plasmids which are typified by their broad host range (Clewell, 1993, supra. Donor "male" bacteria which bear a chromosomal insertion of a conjugal plasmid, such as the *E. coli* F factor can efficiently donate chromosomal DNA to recipient "female" enteric bacteria which lack F (F−). Conjugal transfer from donor to recipient is initiated at oriT. Transfer of the nicked single strand to the recipient occurs in a 5' to 3' direction by a rolling circle mechanisms which allows mobilization of tandem chromosomal copies. Upon entering the recipient, the donor strand is discontinuously replicated. The linear, single-stranded donor DNA strand is a potent substrate for initiation of recA-mediated homologous recombination within the recipient. Recombination between the donor strand and recipient chromosomes can result in the inheritance of donor traits. Accordingly, strains which bear a chromosomal copy of F are designated Hfr (for high frequency of recombination) (Low, 1996 in *Escherichia coli* and Salmonella Cellular and Molecular Biology Vol. 2, pp. 2402–2405; Sanderson, in *Escherichia coli* and Salmonella Cellular and Molecular Biology 2, 2406–2412 (1996)).

The ability of strains with integrated mobilizable vector to transfer chromosomal DNA provides a rapid and efficient-means of exchanging genetic material between a population of bacteria thereby allowing combination of positive mutations and dilution of negative mutations. Such stochastic &/or non-stochastic mutagenesis methods typically start with a population of strains with an integrated mobilizable vector encompassing at least some genetic diversity.

The genetic diversity can be the result of natural variation, exposure to a mutagenic agent or introduction of a fragment library. The population of cells is cultured without selection to allow genetic exchange, recombination and expression of recombinant genes. The cells are then screened or selected for evolution toward a desired property. The population surviving selection/screening can then be subject to a further round of stochastic &/or non-stochastic mutagenesis by IVR-mediated genetic exchange, or otherwise.

The natural efficiency of Hfr and other strains with integrated mob vectors as recipients of conjugal transfer can be improved by several means. The relatively low recipient efficiency of natural BFR strains is attributable to the products of traS and traT genes of F (Clewell, 1993, supra; Firth et al., 1996, supra.—Frost et al., 1994; supra; Achtman et al., J Mol. Biol. 138, 779–795 (1980). These products are localized to the inner and outer membranes of F+ strains, respectively, where they serve to inhibit redundant matings between two strains which are both capable of donating DNA. The effects of traS and traT, and cognate genes in other conjugal plasmids, can be eliminated by use of knockout cells incapable of expressing these enzymes or reduced by propagating cells on a carbon-limited source. (Peters et al., J Bacteriol., 178, 3037–3043 (1996)).

In some methods, the starting population of cells has a mobilizable vector integrated at different genomic sites. Directional transfer from oriT typically results in more frequent inheritance of traits proximal to oriT. This is because mating pairs are fragile and tend to dissociate (particularly when in liquid medium) resulting in the interruption of transfer.

In a population of cells having a mobilizable vector integrated at different sites, chromosomal exchange occurs in a more random fashion. Kits of Hfr strains are available from the *E coli*. Genetic Stock Center and the Salmonella Genetic Stock Centre (Frost et al., 1994, supra).

Alternatively, a library of strains with oriT at random sites and orientations can be produced by insertion mutagenesis using a transposon which bears oriT. The use of a transposon bearing an oriT [e.g., the Tn5-oriT described by Yakobson E A, et al. J. Bacteriol. October 1984; 160(1): 451–453] provides a quick method of generating such a library. Transfer functions for mobilization from the transposon-borne oriT sites are provided by a helper vector in trans. It is possible to generate similar genetic constructs using other sequences known to one of skill as well.

In one aspect, a recursive scheme for genomic stochastic &/or non-stochastic mutagenesis using Tn-oriT elements is provided. A prototrophic bacterial strain or set of related strains bearing a conjugal plasmid, such as the F fertility factor or a member of the IncP group of broad host range plasmids is mutagenized and screened for the desired properties. Individuals with the desired properties are mutagenized with a Tn-oriT element and screened for acquisition of an auxotrophy (e.g., by replica-plating to a minimal and complete media) resulting from insertion of the Tn-oriT element in any one of many biosynthetic gene scattered across the genome. The resulting auxotrophs are pooled and allowed to mate under conditions promoting male-to-male matings, e.g., during growth in close proximity on a filter membrane. Note that transfer functions are provided by the helper conjugal plasmid present in the original strain set. Recombinant transconjugants are selected on minimal medium and screened for further improvement.

Optionally, strains bearing integrated mobilizable vectors are defective in mismatch repair gene(s). Inheritance of donor traits which arise from sequence heterologies increases in strains lacking the methyl-directed mismatch repair system. Optionally, the gene products which decrease recombination efficiency can be inhibited by small molecules.

Intergenic conjugal transfer between species such as $E.$ $coli$ and Salmonella typhimurium, which are 20% divergent at the DNA level, is also possible if the recipient strain is muth, mutL or mutS (see Rayssiguier et al., Nature 342, 396–401 (1989)). Such transfer can be used to obtain recombination at several points as shown by the following example.

One example uses an S. typhimurium Hfr donor strain having markers thr557 at map position 0, pyrF2690 at 33 min, serA13 at 62 min and hfrK5 at 43 min. MutS+/−, F− $E.$ $coli.$ recipient strains had markers pyrD68 at 21 min aroC355 at 51 min, ilv3164 at 85 min and mutS215 at 59 min. The triauxotrophic S. typhimurium Hfr donor and isogenic mutS+/− triauxotrophic $E.$ $coli$ recipient were inoculated into 3 ml of Lb broth and shaken at 37 C. until fully grown. 100 ul of the donor and each recipient were mixed in 10 ml fresh LB broth, and then deposited to a sterile Millipore 0.45 uM HA filter using a Nalgene 250 ml reusable filtration device. The donor and recipients alone were similarly diluted and deposited to check for reversion. The filters with cells were placed cell-side-up on the surface of an LB agar plate which was incubated overnight at 37 C. The filters were removed with the aid of a sterile forceps and placed in a sterile 50 ml tube containing 5 ml of minimal salts broth. Vigorous vortexing was used to wash the cells from the filters. 100 ul of mating mixtures, as well as donor and recipient controls were spread to LB for viable cell counts and minimal glucose supplemented with either two of the three recipient requirements for single recombinant counts, one of the three requirements for double recombinant counts, or none of the three requirements for triple recombinant counts. The plates were incubated for 48 hr at 37 C. after which colonies were counted.

Frequencies are further enhanced by increasing the ratio of donor to recipient cells, or by repeatedly mating the original donor strains with the previously generated recombinant progeny.

8.6.1.2.1.13 Introduction of Fragments by Conjugation

Sobilizable vectors can also be used to transfer fragment libraries into cells to be evolved. This approach is particularly useful in situations in which the cells to be evolved cannot be efficiently transformed directly with the fragment library but can undergo conjugation with primary cells that can be transformed with the fragment library. DNA fragments to be introduced into host cells encompasses diversity relative to the host cell genome. The diversity can be the result of natural diversity or mutagenesis.

The DNA fragment library is cloned into a mobilizable vector having an origin of transfer. Some such vectors also contain mob genes although alternatively these functions can also be provided in trans. The vector should be capable of efficient conjugal transfer between primary cells and the intended host cells. The vector should also confer a selectable phenotype. This 96 phenotype can be the same as the phenotype being evolved or can be conferred by a marker, such as a drug resistance marker. The vector should preferably allow self-elimination in the intended host cells thereby allowing selection for cells in which a cloned fragment has undergone genetic exchange with a homologous host segment rather than duplication. Such can be achieved by use of vector lacking an origin of replication functional in the intended host type or inclusion of a negative selection marker in the vector.

One suitable vector is the broad host range conjugation plasmid described by Simon et al., Bio/Technology 1, 784–791 (1983); TrieuCuot et al., Gene 102, 99–104 (1991); Bierman et al., Gene 116, 43–49 (1992). These plasmids can be transformed into $E.$ $coli$ and then force-mated into bacteria that are difficult or impossible to transform by chemical or electrical induction of competence. These plasmids contain the origin of the IncP plasmid, oriT Mobilization functions are supplied in trans by chromosomally-integrated copies of the necessary genes. Conjugal transfer of DNA can in some cases be assisted by treatment of the recipient (if gram-positive) with sub-inhibitory concentrations of penicillins (Trieu-Cuot et al., 1993 FEMS Microbiol. Lett. 109, 19–23). To increase diversity in populations, recursive conjugal mating prior to screening is performed.

Cells that have undergone allelic exchange with library fragments can be screened or selected for evolution toward a desired phenotype. Subsequent rounds of recombination can be performed by repeating the conjugal transfer step. The library of fragments can be fresh or can be obtained from some (but not all) of the cells surviving a previous round of selection/screening. Conjugation-mediated stochastic &/or non-stochastic mutagenesis can be combined with other methods of stochastic &/or non-stochastic mutagenesis.

8.6.1.2.1.14 Genetic Exchange Promoted by Transducing Phage in Cells Suseptible to Phage Phage transduction can include the transfer, from one cell to another, of nonviral genetic material within a viral coat (Masters, in $Escherichia$ $coli$ and Salmonella Cellular and Molecular Biology 2, 2421–2442 (1996). Perhaps the two best examples of generalized transducing phage are bacteriophages PI and P22 of $E.$ $coli$ and $S.$ $typhimurium$, respectively. Generalized transducing bacteriophage particles are formed at a low frequency during lytic infection when viral-genome-sized, doubled-stranded fragments of host (which serves as donor) chromosomal DNA are packaged into phage heads. Promiscuous high transducing (HT) mutants of bacteriophage P22 which efficiently package DNA with little sequence specificity have been isolated. Infection of a susceptible host results in a lysate in which up to 50% of the phage are transducing particles. Adsorption of the generalized transducing particle to a susceptible recipient cell results in the injection of the donor chromosomal fragment. RecA-mediated homologous recombination following injection of the donor fragment can result in the inheritance of donor traits. Another type of phage which achieves quasi random insertion of DNA into the host chromosome is Mu. For an overview of Mu biology, see, Groisman (1991) in Methods in Enzymology v. 204. Mu can generate a variety of chromosomal rearrangements including deletions, inversions, duplications and transpositions. In addition, elements which combine the features of P22 and Mu are available, including Mud-P22, which contains the ends of the Mu genome in place of the P22 att site and int gene. See, Berg, supra.

Generalized transducing phage can be used to exchange genetic material between a population of cells encompassing genetic diversity and susceptible to infection by the phage. Genetic diversity can be the result of natural variation between cells, induced mutation of cells or the introduction of fragment libraries into cells. DNA is then exchanged between cells by generalized transduction. If the phage does not cause lysis of cells, the entire population of cells can be propagated in the presence of phage. If the phage results in lytic infection, transduction is performed on a split pool basis. That is, the starting population of cells is divided into two. One subpopulation is used to prepare transducing phage. The transducing phage are then infected into the other subpopulation. Preferably, infection is performed at high multiplicity of phage per cell so that few cells remain uninfected. Cells surviving infection are propagated and screened or selected for evolution toward a desired property. The pool of cells surviving screening/selection can then be stochastic &/or non-stochastic mutagenized by a further round of generalized transduction or by other stochastic &/or non-stochastic mutagenesis methods. Recursive split pool tranduction is optionally performed prior to selection to increase the diversity of any population to be screened.

The efficiency of the above methods can be increased by reducing infection of cells by infectious (nontransducing phage) and by reducing lysogen formation. The former can be achieved by inclusion of chelators of divalent cations, such as citrate and EDTA in culture media. Tail defective transducing phages can be used to allow only a single round of infection.

Divalent cations are required for phage absorption and the inclusion of chelating agents therefore provides a means of preventing unwanted infection. Integration defective (int) derivatives of generalized transducing phage can be used to prevent lysogen formation. In a further variation, host cells with defects in mismatch repair gene(s) can be used to increase recombination between transduced DNA and genomic DNA.

8.6.1.2.1.15 Use of Locked in Prophages to Facilitate DNA Stochastic &/or Non-Stochastic Mutagenesis The use of a hybrid, mobile genetic element (locked-in prophages) as a means to facilitate whole genome stochastic &/or non-stochastic mutagenesis of organisms using phage transduction as a means to transfer DNA from donor to recipient is a preferred embodiment. One such element (Mud-P22) based on the temperate Salmonella phage P22 has been described for use in genetic and physical mapping of mutations. See, Youderian et al. (1988) Genetics 118:581–592, and Benson and Goldman (1992) J Bacteriol. 174(5):1673–1681. Individual Mud-P22 insertions package specific regions of the Salmonella chromosome into phage P22 particles.

Libraries of random Mud-P22 insertions can be readily isolated and induced to create pools of phage particles packaging random chromosomal DNA fragments. These phage particles can be used to infect new cells and transfer the DNA from the host into the recipient in the process of transduction. Alternatively, the packaged chromosomal DNA can be isolated and manipulated further by techniques such as DNA stochastic &/or non-stochastic mutagenesis or any other mutagenesis technique prior to being reintroduced into cells (especially recD cells for linear DNA) by transformation or electroporation, where they integrate into the chromosome. Either the intact transducing phage particles or isolated DNA can be subjected to a variety of mutagens prior to reintroduction into cells to enhance the mutation rate.

Mutator cell fines such as mutD can also be used for phage growth. Either method can be used recursively in a process to create genes or strains with desired properties. E. coli cells carrying a cosmid clone of Salmonella LPS genes are infectable by P22 phage. It is possible to develop similar genetic elements using other combinations of transposable elements and bacteriophages or viruses as well. P22 is a lambdoid phage that packages its DNA into pstochastic &/or non-stochastic mutagenized phage particles (heads) by a "headful" mechanism. Packaging of phage DNA is initiated at a specific site (pac) and proceeds unidirectionally along a linear, double stranded normally concatameric molecule. When the phage head is full (about 43 kb), the DNA strand is cleaved, and packaging of the next phage head is initiated. Locked-in or excision-defective P22 prophages, however, initiate packaging at their pac site, and then proceed unidirectionally along the chromosome, packaging successive headfuls of chromosomal DNA (rather than phage DNA). When these transducing phages infect new Salmonella cells they inject the chromosomal DNA from the original host into the recipient cell, where it can recombine into the chromosome by homologous recombination creating a chimeric chromosome. Upon infection of recipient cells at a high multiplicity of infection, recombination can also occur between incoming transducing fragments prior to recombination into the chromosome.

Integration of such locked-in P22 prophages at various sites in the chromosome allows flanking regions to be amplified and packaged into phage particles. The Mud-P22 mobile genetic element contains an excision-defective P22 prophage flanked by the ends of phage/transposon Mu. The entire Mud-P22 element can transpose to virtually any location in the chromosome or other episome (eg. F', BAC clone) when the Mu A and B proteins are provided in trans.

A number of embodiments for this type of genetic element are available. In one example, the locked in prophage are used as generalized transducing phage to transfer random fragments of a donor chromosome into a recipient. The Mud-P22 element acts as a transposon when Mu A and B transposase proteins are provided in trans and integrate copies of itself at random locations in the chromosome. In this way, a library of random chromosomal Mud-P22 insertions can be generated in a suitable host. When the Mud-P22 prophages in this library are induced, random fragments of chromosomal DNA will be packaged into phage particles. When these phages infect recipient cells, the chromosomal DNA is injected and can recombine into the chromosome of the recipient. These recipient cells are screened for a desired property and cells showing improvement are then propagated.

The process can be repeated, since the Mud-P22 genetic element is not transferred to the recipient in this process. Infection at a high multiplicity allows for multiple chromosomal fragments to be injected and recombined into the recipient chromosome. Locked in prophages can also be used as specialized transducing phage.

Individual insertions near a gene of interest can be isolated from a random insertion library by a variety of methods. Induction of these specific prophages results in packaging of flanking chromosomal DNA including the gene(s) of interest into phage particles. Infection of recipient cells with these phages and recombination of the packaged DNA into the chromosome creates chimeric genes that can be screened for desired properties. Infection at a high multiplicity of infection can allow recombination between incoming transducing fragments prior to recombination into the chromosome.

These specialized transducing phage can also be used to isolate large quantities of high quality DNA containing specific genes of interest without any prior knowledge of the DNA sequence. Cloning of specific genes is not required. Insertion of such an element nearby a biosynthetic operon for example allows for large amounts of DNA from that operon to be isolated for use in DNA stochastic &/or non-stochastic mutagenesis (in vitro and/or in vivo), cloning, sequencing, or other uses as set forth herein. DNA isolated from similar insertions in other organisms containing homologous operons are optionally mixed for use in family stochastic &/or non-stochastic mutagenesis formats as described, herein, in which homologous genes from different organisms (or different chromosomal locations within a single species, or both). Alternatively, the transduced population is recursively transduced with pooled transducing phage or new transducing phage generated from the previously transduced cells. This can be carried out recursively to optimize the diversity of the genes prior to stochastic &/or non-stochastic mutagenesis.

Phage isolated from insertions in a variety of strains or organisms containing homologous operons are optionally mixed and used to coinfect cells at a high MOI allowing for recombination between incoming transducing fragments prior to recombination into the chromosome.

Locked in prophage are useful for mapping of genes, operons, and/or specific mutations with either desirable or undesirable phenotypes. Locked-in prophages can also provide a means to separate and map multiple mutations in a given host. If one is looking for beneficial mutations outside a gene or operon of interest, then an unmodified gene or operon can be transduced into a mutagenized or stochastic &/or non-stochastic mutagenized host then screened for the presence of desired secondary mutations. Alternatively, the gene/operon of interest can be readily moved from a mutagenized/stochastic &/or non-stochastic mutagenized host into a different background to screen/select for modifications in the gene/operon itself. It is also possible to develop similar genetic elements using other combinations of transposable elements and bacteriophages or viruses as well. Similar systems are set up in other organisms, e.g., that do not allow replication of P22 or P1. Broad host range phages and transposable elements are especially useful. Similar genetic elements are derived from other temperate phages that also package by a headful mechanism. In general, these are the phages that are capable of generalized transduction. Viruses infecting eukaryotic cells may be adapted for similar purposes. Examples of generalized transducing phages that are useful are described in: Green et al., "Isolation and preliminary characterization of lytic and lysogenic phages with wide host range within the streptomycetes", J Gen Microbiol 131(9):2459–2465 (1985); Studdard et al., "Genome structure in Streptomyces spp.: adjacent genes on the *S. coelicolor* A3(2) linkage map have cotransducible analogs in *S. venezuelae*", J Bacteriol 169(8):3 814–3 816 (1987); Wang et al., "High frequency generalized transduction by miniMu plasmid phage", Genetics 116(2):201–206, (1987); Welker, N. E., "Transduction in *Bacillus stearothertnophilus*", J Bacteriol, 176(11):3354–3359, (1988); Darzins et al., "Mini-D3112 bacteriophage transposable elements for genetic analysis of *Pseudomonas aeruginosa*, J Bacteriol 171(7):3909–3916 (1989); Hugouvieux-Cotte-Pattat et al., "Expanded linkage map of *Erwinia chrysanthemi* strain 3937", Mol Microbiol 3(5):573–581, (1989); Ichige et al. "Establishment of gene transfer systems for and construction of the genetic map of a marine Vibrio strain", J Bacteriol 171(4):1825–1834 (1989); Murainatsu et al., "Two generalized transducing phages in Vibrio parahaemolyticus and Vibrio alginolyticus", Microbiol Immunol (12):1073–1084 (1991); Regue et al., "A generalized transducing bacteriophage for *Serratia marcescens*", Res Microbiol 42(1):23–27, (199 1)-Kiesel et al , "Phage Acm I-mediated transduction in the facultatively methanol-utilizing A cetobacter methanolicus MB 58/4", J Gen Virol 74(9):1741–1745 (1993); Blahova et al., "Transduction of imipenem resistance by the phage F-116 from a nosocornial strain of *Pseudomonas aeruginosa* isolated in Slovakia", Acta Virol 38(5):247–250 (1994); Kidambi et al., "Evidence for phage-mediated gene transfer among *Pseudomonas aeruginosa* strains on the phylloplane", Appl Environ Microbiol 60:(2)496–500 (1994); Weiss et al., "Isolation and characterization of a generalized transducing phage for *Xanthomonas campestris* pv.campestris", J Bacteriol 176(11):3 3 54–3359 (1994); Matsumoto et al., "Clustering of the trp genes in Burkholderia (formerly Pseudomonas) cepacia", FEMS Microbiol Lett 134(2–3):265–271 (1995); Schicklmaier et al., "Frequency of generalized transducing phages in natural isolates of the *Salmonella typhimurium* complex", Appl Environ Microbiol 61(4): 61(4):163 7–1640 (1995); Humphrey et al., "Purification and characterization of VSH-1, a generalized transducing bacteriophage of Serpulina hyodysenteriae", J Bacteriol 179(2):323–329 (1997); Willi et al, "Transduction of antibiotic resistance markers among *Actinobacillus actinomycetemcomitans* strains by temperate bacteriophages Aa phi 23", Cell Mol Life Sci 53 (11–12):904–910 (1997); Jensen et al., "Prevalence of broad-host-range lytic bacteriophages of *Sphaerofilus natans, Escherichia coli*, and *Pseudomonas aeruginosa*", Appl Environ Microbiol 64(2):575–580 (1998), and Nedelmann el al., "Generalized transduction for genetic linkage analysis and transfer of transposon insertions in different *Staphylococcus epidermidis* strains", Zentiviralaffil Bakteriol 287(1–2):85–92 (1998).

A Mud-PI/Tn-P1 system comparable to Mud-P22 is developed using phage P1. Phage PI has an advantage of packaging much larger (about 110 kb) fragments per headful. Phage PI is currently used to create bacterial artificial chromosomes or BAC's. P I-based BAC vectors are designed along these principles so that cloned DNA is packaged into phage particles, rather than the current system, which requires DNA preparation from single-copy episomes. This combines the advantages of both systems in having the genes cloned in a stable single-copy format, while allowing for amplification and specific packaging of cloned DNA upon induction of the prophage.

8.6.1.2.1.16 Random Placement of Genes or Improved Genes Throughout the Genome for Optimization of Gene Context The placement and orientation of genes in a host chromosome (the "context" of the gene in a chromosome) or episome has large effects on gene expression and activity. Random integration of plasmid or other episomal sequences into a host chromosome by non-homologous recombination, followed by selection or screening for the desired phenotype, is a preferred way of identifying optimal chromosomal positions for expression of a target. This strategy is illustrated herein.

A variety of transposon mediated delivery systems can be employed to deliver genes of interest, either individual genes, genomic libraries, or a library of stochastic &/or non-stochastic mutagenized gene(s) randomly throughout the genome of a host. Thus, in one preferred embodiment, the improvement of a cellular function is achieved by cloning a gene of interest, for example a gene encoding a desired metabolic pathway, within a transposon delivery vehicle.

Such transposon vehicles are available for both Gram-negative and Gram-positive bacteria. De Lorenzo and Timis (1994) Methods in Enzymology 235:385404 describe the analysis and construction of stable phenotypes in gram-negative Bacteria with Tn5- and Tn 10-derived minitransposons. Kleckner et al. (1991) Methods in Enzymology 204, chapter 7 describe uses of transposons such as Tn 10, including for use in gram positive bacteria. Petit el al. (1990) Journal of Bacteriology, 172(12):6736–6740 describe Tn10 derived transposons active in *Bacillus Subtilis*. The transposon delivery vehicle is introduced into a cell population, which is then selected for recombinant cells that have incorporated the transposon into the genome.

The selection is typically by any of a variety of drug resistant markers also carried within the transposon. The selected subpopulation is screened for cells having improved expression of the gene(s) of interest. Once cells harboring the genes of interest in the optimal location are isolated, the genes are amplified from within the genome using PCR, stochastic &/or non-stochastic mutagenized, and cloned back into a similar transposon delivery vehicle which contains a different selection marker within the transposon and lacks the transposon integrase gene.

This stochastic &/or non-stochastic mutagenized library is then transformed back into the strain harboring the original transposon, and the cells are selected for the presence of the new resistance marker and the loss of the previous selection marker. Selected cells are enriched for those that have exchanged by homologous recombination the original transposon for the new transposon carrying members of the stochastic &/or non-stochastic mutagenized library. The surviving cells are then screened for further improvements in the expression of the desired phenotype. The genes from the improved cells are then amplified by the PCR and stochastic &/or non-stochastic mutagenized again. This process is carried out recursively, oscillating each cycle between the different selection markers. Once the gene(s) of interest are optimized to a desired level, the fragment can be amplified and again randomly distributed throughout the genome as described above to identify the optimal location of the improved genes.

Alternatively, the gene(s) conferring a desired property may not be known. In this case the DNA fragments cloned within the transposon delivery vehicle could be a library of genomic fragments originating from a population of cells derived from one or more strains having the desired property(ies). The library is delivered to a population of cells derived from one or more strains having or lacking the desired property(ies) and cells incorporating the transposon are selected. The surviving cells are then screened for acquisition or improvement of the desired property. The fragments contained within the surviving cells are amplified by PCR and then cloned as a pool into a similar transposon delivery vector harboring a different selection marker from the first delivery vector. This library is then delivered to the pool of surviving cells, and the population having acquired the new selective marker is selected. The selected cells are then screened for further acquisition or improvement of the desired property.

In this way the different possible combinations of genes conferring or improving a desired phenotype are explored in a combinatorial fashion. This process is carried out repetitively with each new cycle employing an additional selection marker. Alternatively, PCR fragments are cloned into a pool of transposon vectors having different selective markers. These are delivered to cells and selected for 1, 2, 3, or more markers.

Alternatively, the amplified fragments from each improved cell are stochastic &/or non-stochastic mutagenized independently. The stochastic &/or non-stochastic mutagenized libraries are then cloned back into a transposon delivery vehicle similar to the original vector but containing a different selection marker and lacking the transposase gene. Selection is then for acquisition of the new marker and loss of the previous marker. Selected cells are enriched for those incorporating the stochastic &/or non-stochastic mutagenized variants of the amplified genes by homologous recombination. This process is carried out recursively, oscillating each cycle between the two selective markers.

8.6.1.2.1.17 Improvement of Overexpressed Genes for a Desired Phenotype

The improvement of a cellular property or phenotype is often enhanced by increasing the copy number or expression of gene(s) participating in the expression of that property. Genes that have such an effect on a desired property can also be improved by DNA stochastic &/or non-stochastic mutagenesis to have a similar effect. A genomic DNA library is cloned into an overexpression vector and transformed into a target cell population such that the genomic fragments are highly expressed in cells selected for the presence of the overexpression vector. The selected cells are then screened for improvement of a desired property. The overexpression vector from the improved cells are isolated and the cloned genomic fragments stochastic &/or non-stochastic mutagenized. The genomic fragment carried in the vector from each improved isolate is stochastic &/or non-stochastic mutagenized independently or with identified homologous genes (family stochastic &/or non-stochastic mutagenesis). The stochastic &/or non-stochastic mutagenized libraries are then delivered back to a population of cells and the selected transformants rescreened for further improvements in the desired property. This stochastic &/or non-stochastic mutagenesis/screening process is cycled recursively until the desired property has been optimized to the desired level. As stated above, gene dosage can greatly enhance a desired cellular property.

One method of increasing gene copy number of unknown genes is using a method of random amplification (see also, Mavingui et. al. (1997) Nature Biotech, 15, 5 64). In this method, a genomic library is cloned into a suicide vector containing a selective marker that also at higher dosage provides an enhanced phenotype. An example of such a marker is the kanamycin resistance gene. At successively higher copy number, resistance to successively higher levels of kanamycin is achieved. The genomic library is delivered to a target cell by any of a variety of methods including transformation, transduction, conjugation, etc. Cells that have incorporated the vector into the chromosome by homologous recombination between the vector and chromosomal copies of the cloned genes can be selected by requiring expression of the selection marker under conditions where the vector does not replicate. This recombination event results in the duplication of the cloned DNA fragment in the host chromosome with a copy of the vector and selection marker separating the two copies. The population of surviving cells are screened for improvement of a desired cellular property resulting form the gene duplication event. Further gene duplication events resulting in additional copies of the original cloned DNA fragments can be generated by further propagating the cells under successively more stringent selective conditions i.e. increased concentrations of kanamycin. In this case selection requires increased copies of the selective marker, but increased copies of the desired gene fragment is also concomitant. Surviving cells are further screened for an improvement in the desired phenotype. The resulting population of cells likely resulted in the amplification of different genes since often many genes effect a given phenotype. To generate a library of the possible combinations of these genes, the original selected library showing phenotypic improvements are recombined, using the methods described herein, e.g., protoplast fusion, split pool transduction, transformation, conjugation, etc.

The recombined cells are selected for increased expression of the selective marker. Survivors are enriched for cells having incorporated additional copies of the vector sequence by homologous recombination, and these cells will be enriched for those having combined duplications of different genes. In other words, the duplication from one cell of enhanced phenotype becomes combined with the duplication of another cell of enhanced phenotype. These survivors are screened for further improvements in the desired phenotype. This procedure is repeated recursively until the desired level of phenotypic expression is achieved.

Alternatively, genes that have been identified or are suspected as being beneficial in increased copy number are cloned in tandem into appropriate plasmid vectors. These vectors are then transformed and propagated in an appropriate host organism. Plasmid-plasmid recombination between the cloned gene fragments result in further duplication of the genes. Resolution of the plasmid doublet can result in the uneven distribution of the gene copies, with some plasmids having additional gene copies and others having fewer gene copies. Cells carrying this distribution of plasmids are then screened for an improvement in the phenotype effected by the gene duplications.

In summary, a method of selecting for increased copy number of a nucleic acid sequence by the above procedure is provided. In the method, a genomic library in a suicide vector comprising a dose-sensitive selectable marker is provided, as noted above. The genomic library is transduced into a population of target cells. The target cells are selected in a population of target cells for increasing doses of the selective marker under conditions in which the suicide vector does not replicate episomally. A plurality of target cells are selected for the desired phenotype, recombined and reselected. The process is recursively repeated, if desired, until the desired phenotype is obtained.

8.6.1.2.1.18 Strategies for Improving Genomic Stochastic &/or Non-Stochastic Mutagenesis Via Transformation of Linear DNA Fragments Wild-type members of the Enterobacteriaceae (e.g., *Escherichia coli*) are typically resistant to genetic exchange following transformation of linear DNA molecules.

This is due, at least in part, to the Exonuclease V (Exo V) activity of the RecBCD holoenzyme which rapidly degrades linear DNA molecules following transformation. Production of ExoV has been traced to the recD gene, which encodes the D subunit of the holoenzyme. As demonstrated by Russel et al. (1989) Journal of Bacteriology 2609–2613, homologous recombination between a transformed linear donor DNA molecule and the chromosome of recipient is readily detected in a strains bearing a loss of function mutation in a recD mutant.

The use of recD strains provides a simple means for genomic stochastic &/or non-stochastic mutagenesis of the Enterobacteriaceae. For example, a bacterial strain or set of related strains bearing a recD null mutation (e.g., the *E. coli* recD1903::mini-Tet allele) is mutagenized and screened for the desired properties. In a split-pool fashion, chromosomal DNA prepared on one aliquot could be used to transform (e.g., via electroporation or chemically induced competence) the second aliquot. The resulting transformants are then screened for improvement, or recursively transformed prior to screening.

The use of RecE/recT as described supra, can improve homologous recombination of linear DNA fragments. The RecBCD holoezyme plays an important role in initiation of RecA-dependent homologous recombination. Upon recognizing a dsDNA end, the RecBCD enzyme unwinds and degrades the DNA asymmetrically in a 5' to 3' direction until it encounters a chi (or 'X')-site (consensus 5'-GCTGGTGG-3) which attenuates the nuclease activity. This results in the generation of a ssDNA terminating near the c site with a 3'-ssDNA tail that is preferred for RecA loading and subsequent invasion of dsDNA for homologous recombination. Accordingly, preprocessing of transforming fragments with a 5' to 3' specific ssDNA Exonuclease, such as Lamda ( ) exonuclease (available, e.g., from Boeringer Mannheim) prior to transformation may serve to stimulate homologous recombination in recD-strain by providing ssDNA invasive end for RecA loading and subsequent strand invasion.

The addition of DNA sequence encoding chi-sites (consensus 5'-GCTGGTGG-3') to DNA fragments can serve to both attenuate Exonuclease V activity and stimulate homologous recombination, thereby obviating the need for a recD mutation (see also, Kowalczykowski, et al. (1994) "Biochemistry of homologous recombination in *Escherichia coli*," Microbiol. Rev. 58:401–465 and Jessen, et al. (1998) "Modification of bacterial artificial chromosomes through Chi-stimulated homologous recombination and its application in zebrafish transgenesis." Proc. Natl. Acad. Sci. 95:5121–5126). Chi sites are optionally included in linkers ligated to the ends of transforming fragments or incorporated into the external primers used to generate DNA fragments to be transformed. The use of recombination-stimulatory sequences such as chi is a generally useful approach for evolution of a broad range of cell types by fragment transformation. Methods to inhibit or mutate analogs of Exo V or other nucleases (such as, Exonucleases I (endA 1), 111 (nth), IV (nfo), VII, and VIII of *E. coli*) is similarly useful.

Inhibition or elimination of nucleases, or modification of ends of transforming DNA fragments to render them resistant to exonuclease activity has applications in evolution of a broad range of cell types.

8.6.1.2.1.19 Stochastic &/or Non-Stochastic Mutagenesis to Optimize Unknown Interactions Many observed traits are the result of complex interactions of multiple genes or gene products. Most such interactions are still uncharacterized. Accordingly, it is often unclear which genes need to be optimized to achieve a desired trait, even if some of the genes contributing to the trait are known.

This lack of characterization is not an issue during DNA stochastic &/or non-stochastic mutagenesis, which produces solutions that optimize whatever is selected for. An alternative approach, which has the potential to solve not only this problem, but also anticipated future rate limiting factors, is complementation by overexpression of unknown genomic sequences.

A library of genomic DNA is first made as described, supra. This is transformed into the cell to be optimized and transformants are screened for increases in a desired property. Genomic fragments which result in an improved property are evolved by DNA stochastic &/or non-stochastic mutagenesis to further increase their beneficial effect. This approach requires no sequence information, nor any knowledge or assumptions about the nature of protein or pathway interactions, or even of what steps are rate-limiting; it relies only on detection of the desired phenotype. This sort of random cloning and subsequent evolution by DNA stochastic &/or non-stochastic mutagenesis of positively interacting genomic sequences is extremely powerful and generic. A variety of sources of genomic DNA are used, from isogenic strains to more distantly related species with potentially desirable properties. In addition, the technique is applicable to any cell for which the molecular biology basics of transformation and cloning vectors are available, and for any property which can be assayed (preferably in a high-throughput format). Alternatively, once optimized, the evolved DNA can be returned to the chromosome by homologous recombination or randomly by phage mediated site-specific recombination.

8.6.1.2.1.20 Homologous Recombination within the Chromosome

Homologous recombination within the chromosome is used to circumvent the limitations of plasmid based evolution and size restrictions. The strategy is similar to that described above for stochastic &/or non-stochastic mutagenesis genes within their chromosomal context, except that no in vitro stochastic &/or non-stochastic mutagenesis occurs. Instead, the parent strain is treated with mutagens such as ultraviolet light or nitrosoguanidine, and improved mutants are selected. The improved mutants are pooled and split. Half of the pool is used to generate random genomic fragments for cloning into a homologous recombination vector. Additional genomic fragments are optionally derived from related species with desirable properties. The cloned genomic fragments are homologously recombined into the genomes of the remaining half of the mutant pool, and variants with improved properties are selected. These are subjected to a further round of mutagenesis, selection and recombination. Again this process is entirely generic for the improvement of any whole cell biocatalyst for which a recombination vector and an assay can be developed. Here again, it should be noted that recombination can be performed recursively prior to screening.

8.6.1.2.1.21 Methods for Recursive Sequence Recombination

As shown herein, DNA Stochastic &/or non-stochastic mutagenesis provides most rapid technology for evolution of complex new functions. As shown herein, recombination in DNA stochastic &/or non-stochastic mutagenesis achieves accumulation of multiple beneficial mutations in a few cycles. In contrast, because of the high frequency of deleterious mutations relative to beneficial ones, iterative point mutation must build beneficial mutations one at a time, and consequently requires many cycles to reach the same point. As shown herein, rather than a simple linear sequence of mutation accumulation, DNA stochastic &/or non-stochastic mutagenesis is a parallel process where multiple problems may be solved independently, and then combined.

8.6.1.2.2 In Vivo Formats 8.6.1.2.2.1 Plasmid-Plasmid Recombination

The initial substrates for recombination are a collection of polynucleotides comprising variant forms of a gene. The variant forms usually show substantial sequence identity to each other sufficient to allow homologous recombination between substrates. The diversity between the polynucleotides can be natural (e.g., allelic or species variants), induced (e.g., error-prone PCR or error-prone recursive sequence recombination), or the result of in vitro recombination. Diversity can also result from resynthesizing genes encoding natural proteins with alternative codon usage.

There should be at least sufficient diversity between substrates that recombination can generate more diverse products than there are starting materials. There must be at least two substrates differing in at least two positions.

However, commonly a library of substrates of $10^3$–$10^8$ members is employed. The degree of diversity depends on the length of the substrate being recombined and the extent of the functional change to be evolved. Diversity at between 0.1–25%. of positions is typical. The diverse substrates are incorporated into plasmids. The plasmids are often standard cloning vectors, e.g., bacterial multicopy plasmids. However, in some methods to be described below, the plasmids include mobilization (MOB) functions. The substrates can be incorporated into the same or different plasmids. Often at least two different types of plasmid having different types of selectable markers are used to allow selection for cells containing at least two types of vector. Also, where different types of plasmid are employed, the different plasmids can come from two distinct incompatibility groups to S allow stable co-existence of two different plasmids within the cell. Nevertheless, plasmids from the same incompatibility group can still co-exist within the same cell for sufficient time to allow homologous recombination to occur.

Plasmids containing diverse substrates are initially introduced into cells by any method (e.g., chemical transformation, natural competence, electroporation, biolistics, packaging into phage or viral systems). Often, the plasmids are present at or near saturating concentration (with respect to maximum transfection capacity) to increase the probability of more than one plasmid entering the same cell. The plasmids containing the various substrates can be transfected simultaneously or in multiple rounds. For example, in the latter approach cells can be transfected with a first aliquot of plasmid, transfectants selected and propagated, and then infected with a second aliquot of plasmid.

Having introduced the plasmids into cells, recombination between substrates to generate recombinant genes occurs within cells containing multiple different plasmids merely by propagating the cells. However, cells that receive only one plasmid are unable to participate in recombination and the potential contribution of substrates on such plasmids to evolution is not fully exploited (although these plasmids may contribute to some extent if they are propagated in mutator cells). The rate of evolution can be increased by allowing all substrates to participate in recombination. Such can be achieved by subjecting transfected cells to electroporation. The conditions for electroporation are the same as those conventionally used for introducing exogenous DNA into cells (e.g., 1,000–2,500 volts, 400 uF and a 1–2 mM gap). Under these conditions, plasmids are exchanged between cells allowing all substrates to participate in recombination.

In addition the products of recombination can undergo further rounds of recombination with each other or with the original substrate. The rate of evolution can also be increased by use of conjugative transfer. To exploit conjugative transfer, substrates can be cloned into plasmids having MOB genes, and tra genes are also provided in cis or in trans to the MOB gene s. The effect of conjugative transfer is very similar to electroporation in that it allows plasmids to move between cells and allows recombination between any substrate and the products of previous recombination to occur, merely by propagating the culture. The rate of evolution can also be increased by fusing cells to induce exchange of plasmids or chromosomes. Fusion can be induced by chemical agents, such as PEG, or viral proteins, such as influenza virus hemagglutinin, HSV-1 gB and gD. The rate of evolution can also be increased by use of mutator host cells (e.g., Mut L, S, D, T, H in bacteria and Ataxia telangiectasia human cell lines).

The time for which cells are propagated and recombination is allowed to occur, of course, varies with the cell type but is generally not critical, because even a small degree of recombination can substantially increase diversity relative to the starting materials. Cells bearing plasmids containing recombined genes are subject to screening or selection for a desired function. For example, if the substrate being evolved contains a drug resistance gene, one would select for drug resistance. Cells surviving screening or selection can be subjected to one or more rounds of screening/selection followed by recombination or can be subjected directly to an additional round of recombination. The next round of recombination can be achieved by several different formats independently of the previous round. For example, a further round of recombination can be effected simply by resuming the electroporation or conjugation-mediated intercellular transfer of plasmids described above.

Alternatively, a fresh substrate or substrates, the same or different from previous substrates, can be transfected into cells surviving selection/screening. Optionally, the new substrates are included in plasmid vectors bearing a different selective marker and/or from a different incompatibility group than the original plasmids. As a further alternative, cells surviving selection/screening can be subdivided into two subpopulations, and plasmid DNA from one subpopulation transfected into the other, where the substrates from the plasmids from the two subpopulations undergo a further round of recombination. In either of the latter two options, the rate of evolution can be increased by employing DNA extraction, electroporation, conjugation or mutator cells, as described above. In a still further variation, DNA from cells surviving screening/selection can be extracted and subjected to in vitro recursive sequence recombination. After the second round of recombination, a second round of screening/selection is performed, preferably under conditions of increased stringency. If desired, further rounds of recombination and selection/screening can be performed using the same strategy as for the second round.

With successive rounds of recombination and selection/screening, the surviving recombined substrates evolve toward acquisition of a desired phenotype. Typically, in this and other methods of recursive recombination, the final product of recombination that has acquired the desired phenotype differs from starting substrates at 0.1%–50% of positions and has evolved at a rate orders of magnitude in excess (e.g., by at least 10-fold, 100-fold, 1000-fold, or 10,000 fold) of the rate of naturally acquired mutation of about 1 mutation per $10^{-9}$ positions per generation (see Anderson et al. Proc. Natl. Acad. Sci. U.S.A. 93:906–907 (1996)). The "final product" may be transferred to another host more desirable for utilization of the "stochastic &/or non-stochastic mutagenized" DNA.

This is particularly advantageous in situations where the more desirable host is less efficient as a host for the many cycles of mutation/recombination due to the lack of molecular biology or genetic tools available for other organisms such as *E. coli*.

8.6.1.2.2.2 Virus Plasmid Recombination

The strategy used for plasmid-plasmid recombination can also be used for virus-plasmid recombination; usually, phage-plasmid recombination. However, some additional comments particular to the use of viruses are appropriate.

The initial substrates for recombination are cloned into both plasmid and viral vectors. It is usually not critical which substrate(s) are inserted into the viral vector and which into the plasmid, although usually the viral vector should contain different substrate(s) from the plasmid. As before, the plasmid (and the virus) typically contains a selective marker.

The plasmid and viral vectors can both be introduced into cells by transfection as described above. However, a more efficient procedure is to transfect the cells with plasmid, select transfectants and infect the transfectants with virus. Because the efficiency of infection of many viruses approaches 100% of cells, most cells transfected and infected by this route contain both a plasmid and virus bearing different substrates.

Homologous recombination occurs between plasmid and virus generating both recombined plasmids and recombined virus. For some viruses, such as filamentous phage, in which intracellular DNA exists in both double-stranded and single-stranded forms, both can participate in recombination.

Provided that the virus is not one that rapidly kills cells, recombination can be augmented by use of electroporation or conjugation to transfer plasmids between cells. Recombination can also be augmented for some types of virus by allowing the progeny virus from one cell to reinfect other cells. For some types of virus, virus infected-cells show resistance to superinfection. However, such resistance can be overcome by infecting at high multiplicity and/or using mutant strains of the virus in which resistance to superinfection is reduced.

The result of infecting plasmid-containing cells with virus depends on the nature of the virus. Some viruses, such as filamentous phage, stably exist with a plasmid in the cell and also extrude progeny phage from the cell. Other viruses, such as lambda having a cosmid genome, stably exist in a cell like plasmids without producing progeny virions.

Other viruses, such as the T-phage and lytic lambda, undergo recombination with the plasmid but ultimately kill the host S cell and destroy plasmid DNA. For viruses that infect cells without killing the host, cells containing recombinant plasmids and virus can be screened/selected using the same approach as for plasmid-plasmid recombination. Progeny virus extruded by cells surviving selection/screening can also be collected and used as substrates in subsequent rounds of recombination. For viruses that kill their host cells, recombinant genes resulting from recombination reside only in the progeny virus. If the screening or selective assay requires expression of recombinant genes in a cell, the IS recombinant genes should be transferred from the progeny virus to another vector, e.g., a plasmid vector, and retransfected into cells before selection/screening is performed.

For filamentous phage, the products of recombination are present in both cells surviving recombination and in phage extruded from these cells. The dual source of recombinant products provides some additional options relative to the plasmid-plasmid recombination. For example, DNA can be isolated from phage particles for use in a round of in vitro recombination. Alternatively, the progeny 2S phage can be used to transfect or infect cells surviving a previous round of screening/selection, or fresh cells transfected with fresh substrates for recombination.

8.6.1.2.2.3 Virus-Virus Recombination

The principles described for plasmid-plasmid and plasmid-viral recombination can be applied to virus-virus recombination with a few modifications. The initial substrates for recombination are cloned into a viral vector. Usually, the same vector is used for all substrates.

Preferably, the virus is one that, naturally or as a result of mutation, does not kill cells. After insertion, some viral genomes can be packaged in vitro or using a packaging cell line. The packaged viruses are used to infect cells at high multiplicity such that there is a high probability that a cell will receive multiple viruses bearing different substrates.

After the initial round of infection, subsequent steps depend on the nature of infection as discussed in the previous section. For example, if the viruses have phagemid genomes such as lambda cosmids or M13, F1 or Fd phagemids, the phagemids behave as plasmids within the cell and undergo recombination simply by propagating the cells. Recombination is particularly efficient between single-stranded forms of intracellular DNA. Recombination can be augmented by electroporation of cells.

Following selection/screening, cosmids containing recombinant genes can be recovered from surviving cells, e.g., by heat induction of a cos-lysogenic host cell, or extraction of DNA by standard procedures, followed by repackaging cosmid DNA in vitro.

If the viruses are filamentous phage, recombination of replicating form DNA occurs by propagating the culture of infected cells. Selection/screening identifies colonies of cells containing viral vectors having recombinant genes with improved properties, together with phage extruded from such cells. Subsequent options are essentially the same as for plasmid-viral recombination.

8.6.1.2.2.4 Chromosome Recombination

This format can be used to especially evolve chromosomal substrates. The format is particularly useful in situations in which many chromosomal genes contribute to a phenotype or one does not know the exact location of the chromosomal gene(s) to be evolved. The initial substrates for recombination are cloned into a plasmid vector. If the chromosomal gene(s) to be evolved are known, the substrates constitute a family of sequences showing a high degree of sequence identity but some divergence from the chromosomal gene. If the chromosomal genes to be evolved have not been located, the initial substrates usually constitute a library of DNA segments of which only a small number show sequence identity to the gene or gene(s) to be evolved. Divergence between plasmid-borne substrate and the chromosomal gene(s) can be induced by mutagenesis or by obtaining the plasmid-borne substrates from a different species than that of the cells bearing the chromosome.

The plasmids bearing substrates for recombination are transfected into cells having chromosomal gene(s) to be evolved. Evolution can occur simply by propagating the culture, and can be accelerated by transferring plasmids between cells by conjugation or electroporation. Evolution can be further accelerated by use of mutator host cells or by seeding a culture of nonmutator host cells being evolved with mutator host cells and inducing intercellular transfer of plasmids by electroporation or conjugation. Preferably, mutator host cells used for seeding contain a negative selectable marker to facilitate isolation of a pure culture of the nonmutator cells being evolved. Selection/screening identifies cells bearing chromosomes and/or plasmids that have evolved toward acquisition of a desired function.

Subsequent rounds of recombination and selection/screening proceed in similar fashion to those described for plasmid-plasmid recombination. For example, further recombination can be effected by propagating cells surviving recombination in combination with electroporation or conjugative transfer of plasmids. Alternatively, plasmids bearing additional substrates for recombination can be introduced into the surviving cells. Preferably, such plasmids are from a different incompatibility group and bear a different selective marker than the original plasmids to allow selection for cells containing at least two different plasmids. As a further alternative, plasmid and/or chromosomal DNA can be isolated from a subpopulation of surviving cells and transfected into a second subpopulation. Chromosomal DNA can be cloned into a plasmid vector before transfection.

8.6.1.2.2.5 Virus-Chromosome Recombination

As in the other methods described above, the virus is usually one that does not kill the cells, and is often a phage or phagemid. The procedure is substantially the same as for plasmid-chromosome recombination. Substrates for recombination are cloned into the vector. Vectors including the substrates can then be transfected into cells or in vitro packaged and introduced into cells by infection. Viral genomes recombine with host chromosomes merely by propagating a culture. Evolution can be accelerated by allowing intercellular transfer of viral genomes by electroporation, or reinfection of cells by progeny virions. Screening/selection identifies cells having chromosomes and/or viral genomes that have evolved toward acquisition of a desired function.

There are several options for subsequent rounds of recombination. For example, viral genomes can be transferred between cells surviving selection/recombination by electroporation. Alternatively, viruses extruded from cells surviving selection/screening can be pooled and used to superinfect the cells at high multiplicity. Alternatively, fresh substrates for recombination can be introduced into the cells, either on plasmid or viral vectors.

8.6.1.2.2.6 Poolwise Whole Genome Recombination

Asexual evolution is a slow and inefficient process. Populations move as individuals rather than as a group. A diverse population is generated by mutagenesis of a single parent, resulting in a distribution of fit and unfit individuals. In the absence of a sexual cycle, each piece of genetic information for the surviving population remains in the individual mutants. Selection of the fittest results in many fit individuals being discarded, along with the genetically useful information they carry. Asexual evolution proceeds one genetic event at a time, and is thus limited by the intrinsic value of a single genetic event. Sexual evolution moves more quickly and efficiently. Mating within a population consolidates genetic information within the population and results in useful information being combined together.

The combining of useful genetic information results in progeny that are much more fit than their parents. Sexual evolution thus proceeds much faster by multiple genetic events. These differences are further illustrated herein. In contrast to sexual evolution, DNA stochastic &/or non-stochastic mutagenesis is the recursive mutagenesis, recombination, and selection of DNA sequences.

Sexual recombination in nature effects pairwise recombination and results in progeny that are genetic hybrids of two parents. In contrast, DNA stochastic &/or non-stochastic mutagenesis in vitro effects poolwise recombination, in which progeny are hybrids of multiple parental molecules. This is because DNA stochastic &/or non-stochastic mutagenesis effects many individual pairwise recombination events with each thermal cycle. After many cycles the result is a repetitively inbred population, with the "progeny" being the Fx (for X cycles of stochastic &/or non-stochastic mutagenesis) of the original parental molecules. These progeny are potentially descendants of many or all of the original parents. One can graph to show a plot of the potential number of mutations an individual can accumulate by sequential, pairwise and poolwise recombination.

Poolwise recombination is an important feature to DNA stochastic &/or non-stochastic mutagenesis in that it provides a means of generating a greater proportion of the possible combinations of mutations from a single "breeding" experiment. In this way, the "genetic potential" of a population can be readily assessed by screening the progeny of a single DNA shufflmig experiment.

For example, if a population consists of 10 single mutant parents, there are $2^{10}=1024$ possible combinations of those mutations ranging from progeny having 0–10 mutations. Of these 1024, only 56 will result from a single pairwise cross (i.e those having 0, 1, and 2 mutations). In nature the multiparent combinations will eventually arise after multiple random sexual matings, assuming no selection is imparted to remove some mutations from the population. In this way, sex effects the consolidation and sampling of all useful mutant combinations possible within a population. For the purposes of directed evolution, having the greatest number of mutant combinations entering a screen or selection is desirable so that the best progeny (i.e., according to the selection criteria used in the selection screen) is identified in the shortest possible time.

One challenge to in vivo and whole genome stochastic &/or non-stochastic mutagenesis is devising methods for effecting poolwise recombination or multiple repetitive pairwise recombination events. In crosses with a single pairwise cross per cycle before screening, the ability to screen the "genetic potential" of the starting population is limited. For this reason, the rate of in vivo and whole genome stochastic &/or non-stochastic mutagenesis mediated cellular evolution would be facilitated by effecting poolwise recombination. Two strategies for poolwise recombination are described below (protoplast fusion and transduction).

8.6.1.2.2.7 Protoplast Fusion

Protoplast fusion (discussed supra) mediated whole genome stochastic &/or non-stochastic mutagenesis is one format that can directly effect poolwise recombination. Whole gene stochastic &/or non-stochastic mutagenesis is the recursive recombination of whole genomes, in the form of one or more nucleic acid molecule(s) (fragments, chromosomes, episomes, etc), from a population of organisms, resulting in the production of new organisms having distributed genetic information from at least two of the starting population of organisms. The process of protoplast fusion is further illustrated in herein.

Progeny resulting from the fusion of multiple parent protoplasts have been observed (Hopwood & Wright, 1978), however, these progeny are rare ($10^{-4}$–$10^{-6}$). The low frequency is attributed to the distribution of fusants arising from two, three, four, etc parents and the likelihood of the multiple recombination events (6 crossovers for a four parent cross) that would have to occur for multiparent progeny to arise. Thus, it is useful to enrich for the multiparent progeny. This can be accomplished, e.g., by repetitive fusion or enrichment for multiply fused protoplasts. The process of poolwise fusion and recombination is further illustrated herein.

8.6.1.2.2.8 Repetitive Fusion

Protoplasts of identified parental cells are prepared, fused and regenerated. Protoplasts of the regenerated progeny are then, without screening or enrichment, formed, fused and regenerated. This can be carried out for two, three, or more cycles before screening to increase the representation of multiparent progeny. The number of possible mutations/progeny doubles for each cycle. For example, if one cross produces predominantly progeny with 0, 1, and 2 mutations, a breeding of this population with itself will produce progeny with 0, 1, 2, 3, and 4 mutations, the third cross up to eight, etc. The representation of the multiparent progeny from these subsequent crosses will not be as high as the single and double parent progeny, but it will be detectable and much higher than from a single cross. The repetitive fusion prior to screening is analogous to many sexual crosses within a population, and the individual thermal cycles of in vitro DNA stochastic &/or non-stochastic mutagenesis described supra. A factor effecting the value of this approach is the starting size of the parental population. As the population grows, it becomes more likely that a multiparent fusion will arise from repetitive fusions. For example, if 4 parents are fused twice, the 4 parent progeny will make up approximately 0.2% of the total progeny. This is sufficient to find in a population of 3000 (95% confidence), but better representation is preferable. If ten parents are fused twice >20% of the progeny will be four parent offspring.

8.6.1.2.2.9 Enrichment for Multiple Fused Protoplasts

After the fusion of a population of protoplasts, the fusants are typically diluted into hypotonic medium, to dilute out the fusing agent (e.g., 50% PEG). The fused cells can be grown for a short period to regenerate cell walls or separated directly and are then separated on the basis of size. This is carried out, e.g., by cell sorting, using fight dispersion as an estimate of size, to isolate the largest fusants. Alternatively the fusants can be sorted by FACS on the basis of DNA content. The large fusants or those containing more DNA result from the fusion of multiple parents and are more likely to segregate to multiparent progeny. The enriched fusants are regenerated and screened directly or the progeny are fused recursively as above to further enrich the population for diverse mutant combinations.

8.6.1.2.2.10 Transduction

Transduction can theoretically effect poolwise recombination, if the transducing phage particles contain predominantly host genomic DNA rather than phage DNA. If phage DNA is overly represented, then most cells will receive at least one undesired phage genome.

Phage particles generated from locked-in-prophage (supra) are useful for this purpose. A population of cells is infected with an appropriate transducing phage, and the lysate is collected and used to infect the same starting population. A high multiplicity of infection is employed to deliver multiple genomic fragments to each infected cell, thereby increasing the chance of producing recombinants containing mutations from more than two parent genomes.

The resulting transductants are recovered under conditions where phage can not propagate e.g., in the presence of citrate. This population is then screened directly or infected again with phage, with the resulting transducing particles being used to transduce the first progeny. This would mimic recursive protoplast fusion, multiple sexual recombination, and in vitro DNA stochastic &/or non-stochastic mutagenesis.

8.6.1.2.2.11 Methods for Whole Genome Stochastic &/or Non-Stochastic Mutagenesis by Blind Family Stochastic &/or Non-Stochastic Mutagenesis of Parsed Genomes and Recursive Cycles of Forced Integration and Excision by Homologous Recombination, and Screening for Improved Phenotypes In vitro methods have been developed to reassemble single genes and operons, as set forth, e.g., herein. "Family" stochastic &/or non-stochastic mutagenesis of homologous genes within species and from different species is also an effective methods for accelerating molecular evolution. This section describes additional methods for extending these methods such that they can be applied to whole genomes.

In some cases, the genes that encode rate limiting steps in a biochemical process, or that contribute to a phenotype of interest are known. This method can be used to target family stochastic &/or non-stochastic mutagenized libraries to such loci, generating libraries of organisms with high quality family stochastic &/or non-stochastic mutagenized libraries of alleles at the locus of interest. An example of such a gene would be the evolution of a host chaperonin to more efficiently chaperone the folding of an overexpressed protein in E. coli.

The goals of this process are to reassemble homologous genes from two or more species and to then integrate the stochastic &/or non-stochastic mutagenized genes into the chromosome of a target organism.

Integration of multiple stochastic &/or non-stochastic mutagenized genes at multiple loci can be achieved using recursive cycles of integration (generating duplications), excision (leaving the improved allele in the chromosome) and transfer of additional evolved genes by serially applying the same procedure.

In the first step, genes to be stochastic &/or non-stochastic mutagenized into suitable bacterial vectors are subcloned. These vectors can be plasmids, cosmids, BACS or the like. Thus, fragments from 100 bp to 100 kb can be handled. Homologous fragments are then "family stochastic &/or non-stochastic mutagenized" together (i.e. homologous fragments from different species or chromosomal locations are homologously recombined). As a simple case, homologs from two species (say, E. coli and Salmonella) are cloned, family stochastic &/or non-stochastic mutagenized in vitro and cloned into an allele replacement vector (e.g., a vector with a positively selectable marker, a negatively selectable marker and conditionally active origin of replication). The basic strategy for whole genome family stochastic &/or non-stochastic mutagenesis of parsed (subcloned) genomes is additionally set forth herein.

The vectors are transfected into E. coli and selected, e.g., for drug resistance. Most drug resistant cells should arise by homologous recombination between a family stochastic &/or non-stochastic mutagenized insert and a chromosomal copy of the cloned insert. Colonies with improved phenotype are screened (e.g., by mass spectroscopy for enzyme activity or small molecule production, or a chromogenic screen, or the like, depending on the phenotype to be assayed). Negative selection (i.e. sue selection) is imposed to force excision of tandem duplication. Roughly half C, of the colonies should retain the improved phenotype. Importantly, this process regenerates a "clean" chromosome in which the wild type locus is replaced with a family stochastic &/or non-stochastic mutagenized fragment that encodes a beneficial allele. Since the chromosome is "clean" (i.e., has no vector sequences), other improved alleles can also be moved into this point on the chromosome by homologous recombination.

Selection or screening for improved phenotype can occur either after step 3 or step 4. If selection or screening takes place after step 3, then the improved allele can be conveniently moved to other strains by, for example, PI transduction. One can then regenerate a strain containing the improved allele but lacking vector sequences by "negative selection" against the suc marker. In subsequent rounds, independently identified improved variants of the gene can be sequentially moved into the improved strain (e.g., by PI transduction of the drug marked tandem duplication above). Transductants are screened for further improvement in phenotype by virtue of receiving the transduced tandem duplication, which itself contains the family stochastic &/or non-stochastic mutagenized genetic material. Negative selection is again imposed and the process of stochastic &/or non-stochastic mutagenesis the improved strain is recursively repeated as desired.

Although this process was described with reference to targeting a gene or genes of interest, it can be used "blindly," making no assumptions about which locus is to be targeted. This procedure is set forth herein. For example, the whole genome of an organism of interest is cloned into manageable fragments (e.g., 10 kb for plasmid-based methods). Homologous fragments are then isolated from related species. Forced recombination with chromosomal homologs creates chimeras.

8.6.1.2.2.12 Methods for High throughput Family Stochastic &/or Non-Stochastic Mutagenesis of Genes For E. coli., cloning the genome in 10 kb fragments requires about 300 clones. The homologous fragments are isolated, e.g., from Salmonella. This gives roughly three hundred pairs of homologous fragments. Each pair is family stochastic &/or non-stochastic mutagenized and the stochastic &/or non-stochastic mutagenized fragments are cloned into an allele replacement vector. The inserts are integrated into the E. coli genome as described above. A global screen is made to identify variants with an improved phenotype. This serves as the basis collection of improvements that are to be stochastic &/or non-stochastic mutagenized to produce a desired strain. The stochastic &/or non-stochastic mutagenesis of these independently identified variants into one super strain is done as described above.

Family stochastic &/or non-stochastic mutagenesis has been shown to be an efficient method for creating high quality libraries of genetic variants. Given a cloned gene from one species, it is of interest to quickly and rapidly isolate homologs from other species, and this process can be rate limiting. For example, if one wants to perform family stochastic &/or non-stochastic mutagenesis on an entire genome, one may need to construct hundreds to thousands of individual family stochastic &/or non-stochastic mutagenized libraries.

In this embodiment, a gene of interest is optionally cloned into a vector in which ssDNA can be made. An example of such a vector is a phagemid vector with an M13 origin of replication. Genomic DNA or cDNA from a species of interest is isolated, denatured, annealed to the phagemid, and then enzymatically manipulated to clone it. The cloned DNA is then used to family reassemble with the original gene of interest. PCR based formats are also available. These formats require no intermediate cloning steps, and are, therefore, of particular interest for high throughput applications.

Alternatively, the gene of interest can be fished out using purified RecA protein. The gene of interest is PCR amplified using primers that are tagged with an affinity tag such as biotin, denatured, then coated with RecA protein (or an improved variant thereof). The coated ssDNA is then mixed with a gDNA plasmid library. Under the appropriate conditions, such as in the presence of non-hydrolyzable rATP analogs, RecA will catalyze the hybridization of the RecA coated gene (ssDNA) in the plasmid library. The heteroduplex is then affinity purified from the non-hybridizing plasmids of the gene library by adsorbtion of the labeled PCR products and its associated homologous DNA to an appropriate affinity matrix.

The homologous DNA is used in a family stochastic &/or non-stochastic mutagenesis reaction for improvement of the desired function. Stochastic &/or non-stochastic mutagenesis the E. coli chaperonin gene DnaJ with other homologs is described below as an example. The example can be generalized to any other gene, including eukaryotic genes such as plant or animal genes (including mammalian genes), by following the format described.

As a first step, the E. coli DnaJ gene is cloned into an M13 phagemid vector. ssDNA is then produced, preferably in a dut(−) ung(−) strain so that Kunkel site directed mutagenesis protocols can be applied. Genomic DNA is then isolated from a non-E. coil source, such as Salmonella and Yersinia Pestis. The bacterial genomic DNAs are denatured and reannealed to the phagemid ssDNA (e.g., about 1 microgram of ssDNA). The reannealed product is treated with an enzyme such as Mung Bean nuclease that degrades ssDNA as an exonuclease but not as an endonuclease (the nuclease does not degrade mismatched DNA that is embedded in a larger annealed fragment). The standard Kunkel site directed mutagenesis protocol is used to extend the fragment and the target cells are transformed with the resulting mutagenized DNA.

In a first variation on the above, the procedure is adapted to the situation where the target gene or genes of interest are unknown. In this variation, the whole genome of the organism of interest is cloned in fragments (e.g., of about 10 kb each) into a phagemid. Single stranded phagemid DNA is then produced. Genomic DNA from the related species is denatured and annealed to the phagemids. Mung bean nuclease is used to trim away unhybridized DNA ends. Polymerase plus ligase is used to fill in the resulting gapped circles.

These clones are transformed into a mismatch repair deficient strain. When the mismatched molecules are replicated in the bacteria, most colonies contain both the E. coli and the homologous fragment. The two homologous genes are then isolated from the colonies (e.g., either by standard plasmid purification or colony PCR) and stochastic &/or non-stochastic mutagenized.

Another approach to generating chimeras that requires no in vitro stochastic &/or non-stochastic mutagenesis is simply to clone the Salmonella genome into an allele replacement vector, transform E. coli, and select for chromosomal integrants. Homologous recombination between Salmonella genes and E. coli homologs generate stochastic &/or non-stochastic mutagenized chimeras. A global screen is done to screen for improved phenotypes. Alternately, recursive transformation and recombination is performed to increase diversity prior to screening. If colonies with improved phenotypes are obtained, it is verified that the improvement is due to allele replacement by P1 transduction into a fresh strain and counterscreening for improved phenotype. A collection of such improved alleles can then be combined into one strain using the methods for whole genome stochastic &/or non-stochastic mutagenesis by blind family stochastic &/or non-stochastic mutagenesis of parsed genomes as set forth herein. Additionally, once these loci are identified, it is likely that further rounds of stochastic &/or non-stochastic mutagenesis and screening will yield further improvements. This could be done by cloning the chimeric gene and then using the methods described in this disclosure to breed the gene with homologs from many different strains of bacteria.

In general, the transformants contain clones of the homologue of the target gene (e.g., E. coli DnaJ in the example above). Mismatch repair in vivo results in a decrease in diversity of the gene. There are at least two solutions to this. First, transduction can be performed into a mismatch repair deficient strain. Alternatively or in addition, the M13 template DNA can be selectively degraded, leaving the cloned homologue. This can be done using methods similar to the standard Eckstein site directed mutagenesis technique (General texts which describe general molecular biological techniques useful herein, including mutagenesis, include Sambrook et al., Molecular Cloning—A Laboratory Manual (2nd Ed.), Vol. 1–3, Cold Spring Harbor Laboratory, Cold Spring Harbor, N.Y. 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1998) ("Ausubel")).

This method relies on incorporation of alpha thiol modified dNTPs during synthesis of the new strand followed by selective degradation of the template and resynthesis of the template strand. In one embodiment, the template strand is grown in a dut(−) ung(−) strain so that uracil is incorporated into the phagemid DNA. After extension as noted above (and before transformation) the DNA is treated with uracil glycosylate and an apurinic site endonuclease such as Endo III or Endo IV. The treated DNA is then treated with a processive exonuclease that resects from the resulting gaps while leaving the other strand intact (as in Eckstein mutagenesis). The DNA is polymerized and ligated. Target cells are then transformed. This process enriches for clones encoding the homologue which is not derived from the target (i.e., in the example above, the non-E. coli. homologue).

An analogous procedure is optionally performed in a PCR format. As applied to the DnaJ illustration above, DnaJ DNA is amplified by PCR with primers that build 30-mer priming sites on each end. The PCR is denatured and annealed with an excess of Salmonella genomic DNA. The Salmonella DnaJ gene hybridizes with the E. coli homologue. After treatment with Mung Bean nuclease, the resulting mismatched hybrid is PCR amplified with the flanking 30-mer primers. This PCR product can be used directly for family stochastic &/or non-stochastic mutagenesis. As genomics provides an increasing amount of sequence information, it is increasingly possible to directly PCR amplify homologs with designed primers. For example, given the sequence of the E. coli genome and of a related genome (i.e. Salmonella), each genome can be PCR amplified with designed primers in, e.g., 5 kb fragments. The homologous fragments can be put together in a pairwise fashion for stochastic &/or non-stochastic mutagenesis. For genome stochastic &/or non-stochastic mutagenesis, the stochastic &/or non-stochastic mutagenized products are cloned into the allele replacement vector and bred into the genome as described supra.

8.6.1.2.2.13 Hyper-Recombinogenic RecA Clones

The invention further provides hyper-recombinogenic RecA proteins (see, the examples below). It is fully expected that one of skill can make a variety of related recombinogenic proteins given the disclosed sequences.

Standard molecular biological techniques can be used to make nucleic acids which comprise the given nucleic acids, e.g., by cloning the nucleic acids into any known vector. Examples of appropriate cloning and sequencing techniques, and instructions sufficient to direct persons of skill through many cloning exercises are found in Berger and Kimmel, Guide to Molecular Cloning Techniques, Methods in Enzymology volume 152 Academic Press, Inc., San Diego, Calif. (Berger); Sambrook et al. (1989) Molecular Cloning —A Laboratory Manual (2nd ed.) Vol. 1–3, Cold Spring Harbor Laboratory, Cold Spring Harbor Press, NY, (Sambrook); and Current Protocols in Molecular Biology, F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Mich.)), Fluka Chernica-Biochemika Analytika (Fluka Chemie AG, Buchs, Switzerland), Invitrogen, San Diego, Calif., and Applied Biosystems (Foster City, Calif.), as well as many other commercial sources known to one of skill.

It will be appreciated that conservative substitutions of the given sequences can be used to produce nucleic acids which encode hyperrecombinogenic clones. "Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon, for methionine) can be modified to yield a functionally identical molecule by standard techniques. Accordingly, each "silent variation" of a nucleic acid which encodes a polypeptide is implicit in any described sequence. Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (1), Leucine (L), Methionine (M), Valine (V); and 6) Phenylalanine (F), Tyrosine (Y), Tryptophan (W). See also, Creighton (1984) Proteins W.H. Freeman and Company. Finally, the addition of sequences which do not alter the encoded activity of a nucleic acid molecule, such as a non-functional sequence is a conservative modification of the basic nucleic acid.

One of skill will appreciate that many conservative variations of the nucleic acid constructs disclosed yield a functionally identical construct. For example, due to the degeneracy of the genetic code, "silent substitutions" (ie., substitutions of a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence of a packaging or packageable construct are substituted with different amino acids with highly similar properties, are also readily identified as being highly similar to a disclosed construct. Such conservatively substituted variations of each explicitly disclosed sequence are a feature of the present invention.

Nucleic acids which hybridize under stringent conditions to the nucleic acids in the figures are a feature of the invention. "Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) Laboratory Techniques in Biochemistry and Molecular Biology-Hybridization with Nucleic Acid Probes part I chapter 2 "overview of principles of hybridization and the strategy of nucleic acid probe assays", Elsevier, N.Y. Generally, highly stringent hybridization and wash conditions are selected to be about 5C. lower than the thermal melting point (T.) for the specific sequence at a defined ionic strength and ph. The T. is the temperature (under defined ionic strength and pH) at which 50% of the target sequence hybridizes to a perfectly matched probe. Very stringent conditions are selected to be equal to the T. for a particular probe. In general, a signal to noise ratio of 2×(or higher) than that observed for an unrelated probe in the particular hybridization assay indicates detection of a specific hybridization.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Finally, preferred nucleic acids encode hyperrecombinogenic RecA proteins which are at least one order of magnitude (10 times) as active as a wild-type RecA protein in a standard assay for Rec A activity.

8.6.1.2.2.14 RecE/RecT Mediated Stochastic &/or Non-Stochastic Mutagenesis in Vivo Like recA, recE and recT (or their homologues, for example the lambda recombination proteins red and red ) can stimulate homologous recombination in vivo. See, Muyrers et al. (1999) Nucleic Acids Res 27(6):1555–7 and Zhang et al. (1998) Nat Genet (2):123–8 Hyperrecombinogenic recE and recT are evolved by the same method as described for recA. Alternatively, variants with increased recombinogenicity are selected by their ability to cause recombination between a suicide vector (lacking an origin of replication) carrying a selectable marker, and a homologous region in either the chromosome or a stably-maintained episome.

A plasmid containing recA and recE genes is stochastic &/or non-stochastic mutagenized (either using these genes as single starting points, or by family stochastic &/or non-stochastic mutagenesis (with for example red and red, or other homologous genes identified from available sequence databases). This stochastic &/or non-stochastic mutagenized library is then cloned into a vector with a selectable marker and transformed into an appropriate recombination-deficient strain. The library of cells would then be transformed with a second selectable marker, either borne on a suicide vector or as a linear DNA fragment with regions at its ends that are homologous to a target sequence (either in the plasmid or in the host chromosome). Integration of this marker by homologous recombination is a selectable event, dependent on the activity of the recE and recT gene products. The recE/recT genes are isolated from cells in which homologous recombination has occurred. The process is repeated several times to enrich for the most efficient variants before the next round of stochastic &/or non-stochastic mutagenesis is performed. In addition, cycles of recombination without selection can be performed to increase the diversity of a cell population prior to selection.

Once hyper-recombinogenic recE/recT genes are isolated they are used as described for hyper-recombinogenic recA. For example they are expressed (constitutively or conditionally) in a host cell to facilitate homologous recombination between variant gene fragments and homologues within the host cell. They are alternatively introduced by microinjection, biolistics, lipofection or other means into a host cell at the same time as the variant genes.

Hyper-recombinogenic recE/recT (either of bacterial/phage origin, or from plant homologues) are useful for facilitating homologous recombination in plants. They are, for example, cloned into the Agrobacterium cloning vector, where they are expressed upon entry into the plant, thereby stimulating homologous recombination in the recipient cell.

In a preferred embodiment, recE/recT are used and or generated in mutS strains.

8.6.1.2.2.15 Multi-Cyclic Recombination

As noted, protoplast fusion is an efficient means of recombining two microbial genomes. The process reproducibly results in about 10% of a non-selected population being recombinant chimeric organisms.

Protoplasts are cells that have been stripped of their cell walls by treatment in hypotonic medium with cell wall degrading enzymes. Protoplast fusion is the induced fusion of the membranes of two or more of these protoplasts by fusogenic agents such as polyethylene glycol. Fusion results in cytoplasmic mixing and places the genomes of the fused cells within the same membrane. Under these conditions recombination between the genomes is frequent.

The fused protoplasts are regenerated, and, during cell division, single genomes segregate into each daughter cell. Typically, 10% of these daughter cells have genomes that originate partially from more than one of the original parental protoplast genomes.

This result is similar to that of the crossing over of sister chromatids in eukaryotic cells during prophase of meiosis II. The percentage of daughter cells that are recombinant is just lower after protoplast fusion. While protoplast fusion does result in efficient recombination, the recombination predominantly occurs between two cells as in sexual recombination.

In order to efficiently generate libraries of whole genome stochastic &/or non-stochastic mutagenized libraries, daughter cells having genetic information originating from multiple parents are made.

In vitro DNA stochastic &/or non-stochastic mutagenesis results in the efficient poolwise recombination of multiple homologous DNA sequences. The stochastic &/or non-stochastic mutagenesis of full length genes from a mixed pool of small gene fragments requires multiple annealing and elongation cycles, the thermal cycles of the primerless PCR reaction. During each thermal cycle, many pairs of fragments anneal and are extended to form a combinatorial population of larger chimeric DNA fragments. After the first cycle of stochastic &/or non-stochastic mutagenesis, chimeric fragments contain sequences originating from two different parent genes. This is similar to the result of a single sexual cycle within a population, pairwise cross, or protoplast fusion. During the second cycle, these chimeric fragments can anneal with each other, or with other small fragments, resulting in chimeras originating from up to four different parental sequences.

This second cycle is analogous to the entire progeny from a single sexual cross inbreeding with itself. Further cycles will result in chimeras originating from 8, 16, 32, etc parental sequences and are analogous to further inbreedings of the progeny population. The power of in vitro DNA stochastic &/or non-stochastic mutagenesis is that a large combinatorial library can be generated from a single pool of DNA fragments stochastic &/or non-stochastic mutagenized by these recursive pairwise "matings." As described above, in vivo stochastic &/or non-stochastic mutagenesis strategies, such as protoplast fusion, result in a single pairwise mating reaction. Thus, to generate the level of diversity obtained by in vitro methods, in vivo methods are carried out recursively. That is, a pool of organisms is recombined and the progeny pooled, without selection, and then recombined again. This process is repeated for sufficient cycles to result in progeny having multiple parental sequences.

Described below is a method used to reassemble four strains of Streptomyces coelicolor. From the initial four strains each containing a unique nutritional marker, three to four rounds of recursive pooled protoplast fusion was sufficient to generate a population of stochastic &/or non-stochastic mutagenized organisms containing all 16 possible combinations of the four markers. This represents a $10^6$ fold improvement in the generation of four parent progeny as compared to a single pooled fusion of the four strains.

Protoplasts were generated from several strains of *S. coelicolor*, pooled and fused. Mycelia were regenerated and allowed to sporulate. The spores were collected, allowed to grow into Mycelia, formed into protoplasts, pooled and fused and the process repeated for three to four rounds. the resulting spores were then subject to screening.

The basic protocol for generating a whole genome stochastic &/or non-stochastic mutagenized library from four *S. coelicolor* strains, each having one of four distinct markers, was as follows. Four mycelial cultures, each of a strain having one of four different markers, were grown to early stationary phase. The mycelia from each were harvested by centrifugation and washed. Protoplasts from each culture were prepared as follows. Approximately $10^9$ *S. coelicolor* spores were inoculated into 50 ml YEME with 0.5% Glycine in a 250 ml baffled flask. The spores were incubated at 30 C. for 36–40 hours in an orbital shaker. Mycelium were verified using a microscope. Some strains needed an additional day of growth. The culture was transferred into a 50 ml tube and centrifuged at 4,000 rpm for 10 min. The mycelium were twice washed with 10.3% sucrose and centrifuged at 4,000 rpm for 10 min. (mycelium can be stored at about 80 C. after wash). 5 ml of lysozyme was added to the about 0.5 g of mycelium pellet. The pellet was suspended and incubated at 30 C. for 20–60 min., with gentle shaking every 10 min. The microscope was checked for protoplasting every 20 min. Once the majority were protoplasts, protoplasting was stopped by adding 10 ml of P buffer. The protoplasts were filtered through cotton and the protoplast spun down at 3,000 rpm for 7 min at room temperature. The supernatant was discarded and the protoplast gently resuspended, adding a suitable amount of P buffer according to the pellet size (usually about 500 W). Ten-fold serial dilutions were made in P buffer, and the protoplasts counted at a $10^{-2}$ dilution. Protoplasts were adjusted to $10^{10}$ protoplasts per ml.

The protoplasts from each culture were quantitated by microscopy. $10^8$ protoplast from each culture were mixed in the same tube, washed, and then fused by the addition of 50% PEG. The fused protoplasts were diluted and plated regeneration medium and incubated until the colonies were sporulating (four days). Spores were harvested and washed. These spores represent a pool of all the recombinants and parents form the fusion.

A sample of the pooled spores was then used to inoculate a single liquid culture. The culture was grown to early stationary phase, the myclelia harvested, and protoplasts prepared. $10^8$ protoplasts from this "mycelial library" were then fused with themselves by the addition of 50%PEG. The protoplast fusion/regeneration/harvesting/protoplast preparation steps were repeated two times. The spores resulting from the fourth round of fusion were considered the "whole genome stochastic &/or non-stochastic mutagenized library" and they were screened for the frequency of the 16 possible combinations of the four markers.

In particular, adding rounds of recombination prior to selection produced significant increases in the number of clones which incorporated all four of the relevant selectable markers, indicating that the population became increasingly diverse be recursive pooling and sporulation.

The four strains of the four parent stochastic &/or non-stochastic mutagenesis were each auxotrophic for three and prototrophic for one of four possible nutritional markers: arginine (A), cystine (C), proline (P), and/or uracil (U). Spores from each fusion were plated in each of the 16 possible combinations of these four nutrients, and the percent of the population growing on a particulate medium was calculated as the ration of those colonies form a selective plate to those growing on a plate having all four nutrients (all variants grow on the medium having all four nutrients, thus the colonies from this plate thus represent the total viable population). The corrected percentages for each of the no, one, two, and three marker phenotypes were determined by subtracting the percentage of cells having additional markers that might grow on the medium having "unnecessary" nutrients. For example, the number of colonies growing on no additional nutrients (the prototroph) was subtracted from the number of colonies growing on any plate requiring nutrients.

8.6.1.2.2.16 Whole Genome Stochastic &/or Non-Stochastic Mutagenesis through Organized Heteroduplex Stochastic &/or Non-Stochastic Mutagenesis A new procedure to optimize phenotypes of interests by heteroduplex stochastic &/or non-stochastic mutagenesis of cosmids libraries of the organism of choice, is provided. This procedure does not require protoplast fusion and is applicable to bacteria for which well-established genetic systems are available, including cosmid cloning, transformation, in vitro packaging/transfection and plasmid transfer/mobilization. Microorganism that can be improved by these methods include *Escherichia coli, Pseudomonas aeruginosa, Pseudomonas putida,* Pseudomonas spp., Rhizobium spp., Xanthomonas spp., and other gram-negative organisms. This method is also applicable to Gram-positive microorganisms.

In step A, Chromosomal DNA of the organism to be improved is digested with suitable restriction enzymes and ligated into a cosmid. The cosmid used for cosmid-based heteroduplex guided whole genome stochastic &/or non-stochastic mutagenesis has at least two rare restriction enzyme recognition sites (e.g. Sfr and NotI) to be used for linearization in subsequent steps. Sufficient cosmids to represent the complete chromosome are purified and stored in 96-well microtiter dishes. In step B, small samples of the library are mutagenized in vitro using hydroxylamine or other mutagenic chemicals. In step C, a sample from each well of the mutagenized collection is used to transfect the target cells. In step D, the transfectants are assayed (as a pool from each mutagenized sample-well) for phenotypic improvements. Positives from this assay indicate that a cosmid from a particular well can confer phenotypic improvements and thus contain large genomic fragments that are suitable targets for heteroduplex mediated stochastic &/or non-stochastic mutagenesis. In step E, the transfected cells harboring a mutant library of the identified cosmid(s) are separated by plating on solid media and screened for independent mutants conferring an improved phenotype. In step F, DNA from positive cells is isolated and pooled by origin. In step G, the selected cosmid pools are divided so that one sample can be digested with Sfr and the other with NotI. These samples are pooled, denatured, reannealed, and religated.

In step K target cells are transfected with the resulting heteroduplexes and propagated to allow "recombination" to occur between the strands of the heteroduplexes in vivo. The transfectants can be screened (the population will represent the pairwise recombinants) or, commonly, as represented by step 1, the recombined cosmids are further stochastic &/or non-stochastic mutagenized by recursive in vitro heteroduplex formation and in vivo recombination (to generate a complete combinatorial library of the possible mutations) prior to screening. An additional mutagenesis step could also be added for increased diversity during the stochastic &/or non-stochastic mutagenesis process.

In step J, once several cosmids harboring different distributed loci have been improved, they are combined into the same host by chromosome integration. This organism can be used directly or subjected to a new round of heteroduplex guided whole genome stochastic &/or non-stochastic mutagenesis.

8.7. Specialized Methods
8.7.1 Targeted Stochastic &/or Non-Stochastic Mutagenesis-Hot Spots In one aspect, targeted homologous genes are cloned into specific regions of the genome (e.g., by homologous recombination or other targeting procedures) which are known to be recombination "hot spots" (i.e., regions showing elevated levels of recombination compared to the average level of recombination observed across an entire genome), or known to be proximal to such hot spots. The resulting recombinant strains are mated recursively. During meiotic recombination, homologous recombinant genes recombine, thereby increasing the diversity of the genes. After several cycles of recombination by recursive mating, the resulting cells are screened.

8.7.2 Stochastic &/or Non-Stochastic Mutagenesis Using Yeasts

Yeasts are subspecies of fungi that grow as single cells. Yeasts are used for the production of fermented beverages and leavening, for production of ethanol as a fuel, low molecular weight compounds, and for the heterologous production of proteins and enzymes (see accompanying list of yeast strains and their uses). Commonly used strains of yeast include *Saccharomyces cerevisiae,* Pichia sp., Canidia sp. and *Schizosaccharomyces pombe.*

Several types of vectors are available for cloning in yeast including integrative plasmid (YIp), yeast replicating plasmid (YRp, such as the 2 circle based vectors), yeast episomal plasmid (YEp), yeast centromeric plasmid (YCp), or yeast artificial chromosome (YAC). Each vector can carry markers useful to select for the presence of the plasmid such as LUE2, URA3, and H1S3, or the absence of the plasmid such as URA3 (a gene that is toxic to cells grown in the presence of 5-fluoro orotic acid.

Many yeasts have a sexual cycle and asexual (vegetative) cycles. The sexual cycle involves the recombination of the whole genome of the organism each time the cell passes through meiosis. For example, when diploid cells of *S. cerevisiae* are exposed to nitrogen and carbon limiting conditions, diploid cells undergo meiosis to form asci. Each ascus holds four haploid spores, two of mating type "a" and two of mating type " ". Upon return to rich medium, haploid spores of opposite mating type mate to form diploid cells once again. Asiospores of opposite mating type can mate within the ascus, or if the ascus is degraded, for example with zymolase, the haploid cells are liberated and can mate with spores from other asci. This sexual cycle provides a format to reassemble endogenous genomes of yeast and/or exogenous fragment libraries inserted into yeast vectors. This process results in swapping or accumulation of hybrid genes, and for the stochastic &/or non-stochastic mutagenesis of homologous sequences shared by mating cells.

Yeast strains having mutations in several known genes have properties useful for stochastic &/or non-stochastic mutagenesis. These properties include increasing the frequency of recombination and increasing the frequency of spontaneous mutations within a cell. These properties can be the result of mutation of a coding sequence or altered expression (usually overexpression) of a wildtype coding sequence. The HO nuclease effects the transposition of HMLa/ and HMRa/ to the MAT locus resulting in mating type switching. Mutants in the gene encoding this enzyme do not switch their mating type and can be employed to force crossing between strains of defined genotype, such as ones that harbor a library or have a desired phenotype and to prevent in breeding of starter strains. PMS 1, MLH 1, MSH2, MSH6 are involved in mismatch repair. Mutations in these genes all have a mutator phenotype (Chambers et al., Mol. Cell. Biol. 16, 6110–6120 (1996)). Mutations in TOP3 DNA topoisomerase have a 6-fold enhancement of inter-chromosomal homologous recombination (Bailis et al., Molecular and Cellular Biology 12, 4988–4993 (1992)). The RAD50–57 genes confer resistance to radiation. Rad3 functions in excision of pyrimidine dimers. RAD52 functions in gene conversion. RAD50, MRE11, XRS2 function in both homologous recombination and illegitimate recombination. HOP1, RED1 function in early meiotic recombination (Mao-Draayer, Genetics 144, 71–86) Mutations in either HOP1 or RED1 reduce double stranded breaks at the HIS2 recombination hotspot. Strains deficient in these genes are useful for maintaining stability in hyper recombinogenic constructs such as tandem expression libraries carried on YACs. Mutations in HPR1 are hyperrecombinogenic. HDF1 has DNA end binding activity and is involved in double stranded break repair and V(D)J recombination.

Strains bearing this mutation are useful for transformation with random genomic fragments by either protoplast fusion or electroporation. Kar-1 is a dominant mutation that prevents karyogamy. Kar-1 mutants are useful for the directed transfer of single chromosomes from a donor to a recipient strain. This technique has been widely used in the transfer of YACs between strains, and is also useful in the transfer of evolved genes/chromosomes to other organisms (Markie, YAC Protocols, (Humana Press, Totowa, N.J., 1996). HOT1 is an *S. cerevisiae* recombination hotspot within the promoter and enhancer region of the rDNA repeat sequences. This locus induces mitotic recombination at adjacent sequences-presumably due to its high level transcription. Genes and/or pathways inserted under the transcriptional control of this region undergo increased mitotic recombination. The regions surrounding the arg 4 and his 4 genes are also recombination hot spots, and genes cloned in these regions have an increased probability of undergoing recombination during meiosis.

Homologous genes can be cloned in these regions and stochastic &/or non-stochastic mutagenized in vivo by recursively mating the recombinant strains. CDC2 encodes polymerase and is necessary for mitotic gene conversion. Overexpression of this gene can be used in a reassembler or mutator strain. A temperature sensitive mutation in CDC4 halts the cell cycle at G1 at the restrictive temperature and could be used to synchronize protoplasts for optimized fusion and subsequent recombination.

As with filamentous fungi, the general goals of stochastic &/or non-stochastic mutagenesis yeast include improvement in yeast as a host organism for genetic manipulation, and as a production apparatus for various compounds. One desired property in either case is to improve the capacity of yeast to express and secrete a heterologous protein. The following example describes the use of stochastic &/or non-stochastic mutagenesis to evolve yeast to express and secrete increased amounts of RNase A.

RNase A catalyzes the cleavage of the $P-O_{5'}$ bond of RNA specifically after pyrimidine nucleotides. The enzyme is a basic 124 amino acid polypeptide that has 8 half cystine residues, each required for catalysis. YEpWL-RNase A is a vector that effects the expression and secretion of RNaseA from the yeast *S. cerevisiae*, and yeast harboring this vector secrete 1–2 mg of recombinant RNase A per liter of culture medium (del Cardayre et al., Protein Engineering 8(3):26, 1–273 (1995)). This overall yield is poor for a protein heterologously expressed in yeast and can be improved at least 10–100 fold by stochastic &/or non-stochastic mutagenesis. The expression of RNaseA is easily detected by several plate and microtitre plate assays (del Cardayre & Raines, Biochemistry 33, 6031–6037 1994)). Each of the described formats for whole genome stochastic &/or non-stochastic mutagenesis can be used to reassemble a strain of *S. cerevisiae* harboring YepWL-RNase A, and the resulting cells can be screened for the increased secretion of RNase A into the medium. The new strains are cycled recursively through the stochastic &/or non-stochastic mutagenesis format, until sufficiently high levels of RNase A secretion is observed. The use of RNase A is particularly useful since it not only requires proper folding and disulfide bond formation but also proper glycosylation. Thus numerous components of the expression, folding, and secretion systems can be optimized. The resulting strain is also evolved for improved secretion of other heterologous proteins.

8.7.3 Ressemble to Increase Tolerance of Yeast to Ethanol

Another goal of stochastic &/or non-stochastic mutagenesis yeast is to increase the tolerance of yeast to ethanol. Such is useful both for the commercial production of ethanol, and for the production of more alcoholic beers and wines. The yeast strain to be stochastic &/or non-stochastic mutagenized acquires genetic material by exchange or transformation with other strain(s) of yeast, which may or may not be know to have superior resistance to ethanol. The strain to be evolved is stochastic &/or non-stochastic mutagenized and shufflants are selected for capacity to survive exposure to ethanol. Increasing concentrations of ethanol can be used in successive rounds of stochastic &/or non-stochastic mutagenesis. The same principles can be used to reassemble baking yeasts for improved osmotolerance.

8.7.4 Capacity to Grow Under Desired Nutritional Conditions

Another desired property of stochastic &/or non-stochastic mutagenesis yeast is capacity to grow under desired nutritional conditions. For example, it is useful to yeast to grow on cheap carbon sources such as methanol, starch, molasses, cellulose, cellobiose, or xylose depending on availability. The principles of stochastic &/or non-stochastic mutagenesis and selection are similar to those discussed for filamentous fungi.

8.7.5 To Produce Secondary Metabolites

Another desired property is capacity to produce secondary metabolites naturally produced by filamentous fungi or bacteria, Examples of such secondary metabolites are cyclosporin A, taxol, and cephalosporins. The yeast to be evolved undergoes genetic exchange or is transformed with DNA from organism(s) that produce the secondary metabolite. For example, fungi producing taxol include Taxomyces andreanae and Pestalotopis microspora (Stierle et al., Science 260, 214–216 (1993); Strobel et al., Microbiol. 142, 435440 (1996)). DNA can also be obtained from trees that naturally produce taxol, such as Taxus brevifolia. DNA encoding one enzyme in the taxol pathway, taxadiene synthase, which it is believed catalyzes the committed step in taxol biosynthesis and may be rate limiting in overall taxol production, has been cloned (Wildung & Croteau, J Biol Chem. 271, 9201–4 (1996). The DNA is then stochastic &/or non-stochastic mutagenized, and shufflants are screened/selected for production of the secondary metabolite. For example, taxol production can be monitored using antibodies to taxol, by mass spectroscopy or UV spectrophotometry. Alternatively, production of intermediates in taxol synthesis or enzymes in the taxol synthetic pathway can be monitored. Concetti & Ripani, Biol Chem. Hoppe Seyler 375, 419–23 (1994). Other examples of secondary metabolites are polyols, amino acids, polyketides, non-ribosomal polypeptides, ergosterol, carotenoids, terpinoids, sterols, vitamin E, and the like.

8.7.6 Increase Ability to Separate in Ethanol

Another desired property is to increase the flocculence of yeast to facilitate separation in preparation of ethanol. Yeast can be stochastic &/or non-stochastic mutagenized by any of the procedures noted above with selection for stochastic &/or non-stochastic mutagenized yeast forming the largest clumps.

8.7.6.1 Exemplary Procedure for Yeast Protoplasting

Protoplast preparation in yeast is reviewed by Morgan, in Protoplasts (Birkhauser Verlag, Basel, 1983). Fresh cells ($\sim 10^8$) are washed with buffer, for example 0.1 M potassium phosphate, then resuspended in this same buffer containing a reducing agent, such as 50 mM DTT, incubated for 1 h at 30° C. with gentle agitation, and then washed again with buffer to remove the reducing agent. These cells are then resuspended in buffer containing a cell wall degrading enzyme, such as Novozyme 234 (1 mg/mL), and any of a variety of osmotic stabilizers, such as sucrose, sorbitol, NaCl, KCl, $MgSO_4$, $MgCl_2$, or $NH_4Cl$ at any of a variety of concentrations. These suspensions are then incubated at 30° C. with gentle shaking (~60 rpm) until protoplasts are released. To generate protoplasts that are more likely to produce productive fusants several strategies are possible.

Protoplast formation can be increased if the cell cycle of the protoplasts have been synchronized to be halted at G1. In the case of S. cerevisiae this can be accomplished by the addition of mating factors, either a or alpha (Curran & Carter, J Gen. Microbiol. 129, 1589–1591 (1983)). These peptides act as adenylate cyclase inhibitors which by decreasing the cellular level of cAMP arrest the cell cycle at G1. In addition, sex factors have been shown to induce the weakening of the cell wall in preparation for the sexual fusion of a and alpha cells (Crandall & Brock, Bacteriol. Rev. 32, 139–163 (1968); Osumi et al., Arch. Microbiol 97, 27–38 (1974)). Thus in the preparation of protoplasts, cells can be treated with mating factors or other known inhibitors of adenylate cyclase, such as leflunomide or the killer toxin from K. lactis, to arrest them at G1 (Sugisaki et al., Nature 304, 464–466 (1983)). Then after fusing of the protoplasts (step 2), cAMP can be added to the regeneration medium to induce S-phase and DNA synthesis. Alternatively, yeast strains having a temperature sensitive mutation in the CDC4 gene can be used, such that cells could be synchronized and arrested at G1. After fusion cells are returned to the permissive temperature so that DNA synthesis and growth resumes.

Once suitable protoplasts have been prepared, it is necessary to induce fusion by physical or chemical means. An equal number of protoplasts of each cell type is mixed in phosphate buffer (0.2 M, pH 5.8, $2 \times 10^8$ cells/mL) containing an osmotic stabilizer, for example 0.8 M NaCl, and PEG 6000 (33% w/v) and then incubated at 30° C. for 5 min while fusion occurs. Polyols, or other compounds that bind water, can be employed. The fusants are then washed and resuspended in the osmotically stabilized buffer lacking PEG, and transferred to osmotically stabilized regeneration medium on/in which the cells can be selected or screened for a desired property.

8.7.7 Stochastic &/or Non-Stochastic Mutagenesis Using Artificial Chromosomes Yeast artificial chromosomes (Yacs) are yeast vectors into which very large DNA fragments (e.g., 50–2000 kb) can be cloned (see, e.g., Monaco & Larin, Trends. Biotech. 12(7), 280–286 (1994); Ramsay, Mol Biotechnol 1(2), 181–201 1994; Huxley, Genet. Eng. 16, 65–91 (1994); Jakobovits, Curr. Biol. 4(8), 761–3 (1994); Lamb & Gearhart, Curr. Opin. Genet. Dev. 5(3), 342–8 (1995); Montoliu et al., Reprod Fertil. Dev. 6, 577–84 (1994)). These vectors have telomeres (Tel), a centromere (Cen), an autonomously replicating sequence (ARS), and can have genes for positive (e.g., TRPI) and negative (e.g., URA3) selection. YACs are maintained, replicated, and segregate as other yeast chromosomes through both meiosis and mitosis thereby providing a means to expose cloned DNA to true meiotic recombination.

YACs provide a vehicle for the stochastic &/or non-stochastic mutagenesis of libraries of large DNA fragments in vivo. The substrates for stochastic &/or non-stochastic mutagenesis are typically large fragments from 20 kb to 2 Mb. The fragments can be random fragments or can be fragments known to encode a desirable property. For example, a fragment might include an operon of genes involved in production of antibiotics. Libraries can also include whole genomes or chromosomes. Viral genomes and some bacterial genomes can be cloned intact into a single YAC. In some libraries, fragments are obtained from a single organism. Other libraries include fragment variants, as where some libraries are obtained from different individuals or species. Fragment variants can also be generated by induced mutation. Typically, genes within fragments are expressed from naturally associated regulatory sequences within yeast. However, alternatively, individual genes can be linked to yeast regulatory elements to form an expression cassette, and a concatemer of such cassettes, each containing a different gene, can be inserted into a YAC.

In some instances, fragments are incorporated into the yeast genome, and stochastic &/or non-stochastic mutagenesis is used to evolve improved yeast strains. In other instances, fragments remain as components of YACs throughout the stochastic &/or non-stochastic mutagenesis process, and after acquisition of a desired property, the YACs are transferred to a desired recipient cell.

8.7.8 Stochastic &/or Non-Stochastic Mutagenesis of Genes for Bioremediation Modern industry generates many pollutants for which the environment can no longer be considered an infinite sink. Naturally occurring microorganisms are able to metabolize thousands of organic compounds, including many not found in nature (e.g xenobiotics). Bioremediation, the deliberate use of microorganisms for the biodegradation of man-made wastes, is an emerging technology that offers cost and practicality advantages over traditional methods of disposal. The success of bioremediation depends on the availability of organisms that are able to detoxify or mineralize pollutants.

Microorganisms capable of degrading specific pollutants can be generated by genetic engineering and recursive sequence recombination. Although bioremediation is an aspect of pollution control, a more useful approach in the long term is one of prevention before industrial waste is pumped into the environment. Exposure of industrial waste streams to recursive sequence recombination-generated microorganisms capable of degrading the pollutants they contain would result in detoxification of mineralization of these pollutants before the waste stream enters the environment. Issues of releasing recombinant organisms can be avoided by containing them within bioreactors fitted to the industrial effluent pipes. This approach would also allow the microbial mixture used to be adjusted to best degrade the particular wastes being produced. Finally, this method would avoid the problems of adapting to the outside world and dealing with competition that face many laboratory microorganisms.

In the wild, microorganisms have evolved new catabolic activities enabling them to exploit pollutants as nutrient sources for which there is no competition. However, pollutants that are present at low is concentrations in the environment may not provide a sufficient advantage to stimulate the evolution of catabolic enzymes. For a review of such naturally occurring evolution of biodegradative pathways and the manipulation of some of microorganisms by classical techniques, see Ramos et al., Bio/Technology "12:1349–1355 (1994).

Generation of new catabolic enzymes or pathways for bioremediation has thus relied upon deliberate transfer of specific genes between organisms (Wackett et al., supra), forced matings between bacteria with specific catabolic capabilities (Brenner et al. Biodegradation 5:359–377 (1994)), or prolonged selection in a chemostat. Some researchers have attempted to facilitate evolution via naturally occurring genetic mechanisms in their chemostat selections by including microorganisms with a variety of catabolic pathways (Kellogg et. al. Science 214:1133–1135 (1981); Chakrabarty American Society of Micro. Biol. News 62:130–137 (1996)). For a review of efforts in this area, see Cameron et al. Applied Biochem. Biotech 38:105–140 (1993).

Current efforts in improving organisms for bioremediation take a labor-intensive approach in which many parameters are optimized independently, including transcription efficiency from native and heterologous promoters, regulatory circuits and translational efficiency as well as improvement of protein stability and activity (Timmis et al. Ann. Rev. Microbiol. 48:525–527 (1994)).

A recursive sequence recombination approach overcomes a number of limitations in the bioremediation capabilities of naturally occurring microorganisms. Both enzyme activity and specificity can be altered, simultaneously or sequentially, by the methods of the invention. For example, catabolic enzymes can be evolved to increase the rate at which they act on a substrate. Although knowledge of a rate-limiting step in a metabolic pathway is not required to practice the invention, rate-limiting proteins in pathways can be evolved to have increased expression and/or activity, the requirement for inducing substances can be eliminated, and enzymes can be evolved that catalyze novel reactions.

Some examples of chemical targets for bioremediation include but are not limited to benzene, xylene, and toluene, camphor, naphthalene, halogenated hydrocarbons, polychlorinated biphenyls (PCBs), trichlorethylene, pesticides such as pentachlorophenyls (PCPs), and herbicides such as atrazine.

8.7.8.1 Aromatic Hydrocarbons

Preferably, when an enzyme is "evolved" to have a new catalytic function, that function is expressed, either constitutively or in response to the new substrate. Recursive sequence recombination subjects both structural and regulatory elements (including the structure of regulatory proteins) of a protein to recombinogenic mutagenesis simultaneously. Selection of mutants that are efficiently able to use the new substrate as a nutrient source will be sufficient to ensure that both the enzyme and its regulation are optimized, without detailed analysis of either protein structure or operon regulation.

Examples of aromatic hydrocarbons include but are not limited to benzene, xylene, toluene, biphenyl, and polycyclic aromatic hydrocarbons such as pyrene and naphthalene. These compounds are metabolized via catechol intermediates. Degradation of catechol by Pseudomonas putida requires induction of the catabolic operon by cis, cis-muconate which acts on the CatR regulatory protein. The binding site for the CatR protein is $G-N_{11}-A$, while the optimal sequence for the LysR class of activators (of which CatR is a member) is $T-N_{11}-A$. Mutation of the G to a T in the CatR binding site enhances the expression of catechol metabolizing genes (Chakrabarty, American Society of Microbiology News 62:130–137 (1996)). This demonstrates that the control of existing catabolic pathways is not optimized for the metabolism of specific xenobiotics. It is also an example of a type of mutant that would be expected from recursive sequence recombination of the operon followed by selection of bacteria that are better able to degrade the target compound.

As an example of starting materials, dioxygenases are required for many pathways in which aromatic compounds are catabolized. Even small differences in dioxygenase sequence can lead to significant differences in substrate specificity (Furukawa et al. J. Bact. 175:5224–5232 (1993); Erickson et al. App. Environ. Micro. 59:3858–3862 (1993)). A hybrid enzyme made using sequences derived from two "parental" enzymes may possess catalytic activities that are intermediate between the parents (Erickson, ibid.), or may actually be better than either parent for a specific reaction (Furukawa et al. J. Bact. 176:2121–2123 (1994)). In one of these cases site directed mutagenesis was used to generate a single polypeptide with hybrid sequence (Erickson, ibid.); in the other, a four subunit enzyme was produced by expressing two subunits from each of two different dioxygenases (Furukawa, ibid.). Thus, sequences from one or more genes encoding dioxygenases can be used in the recursive sequence recombination techniques of the instant invention, to generate enzymes with new specificities. In addition, other features of the catabolic pathway can also be evolved using these techniques, simultaneously or sequentially, to optimize the metabolic pathway for an activity of interest.

8.7.8.2 Halogenated Hydrocarbons

Large quantities of halogenated hydrocarbons are produced annually for uses as solvents and biocides. These include, in the United States alone, over 5 million tons of both 1,2-dichloroethane and vinyl chloride used in PVC production in the U.S. alone. The compounds are largely not biodegradable by processes in single organisms, although in principle haloaromatic catabolic pathways can be constructed by combining genes from different microorganisms. Enzymes can be manipulated to change their substrate specificities. Recursive sequence recombination offers the possibility of tailoring enzyme specificity to new substrates without needing detailed structural analysis of the enzymes.

As an example of possible starting materials for the methods of the instant invention, Wackett et al. (Nature 368:627–629 (1994)) recently demonstrated that through classical techniques a recombinant Pseudomonas strain in which seven genes encoding two multi-component oxygenases are combined, generated a single host that can metabolize polyhalogenated compounds by sequential reductive and oxidative techniques to yield non-toxic products. These and/or related materials can be subjected to the techniques discussed above so as to evolve and optimize a biodegradative pathway in a single organism.

Trichloroethylene is a significant groundwater contaminant. It is degraded by microorganisms in a cometabolic way (i.e., no energy or nutrients are derived). The enzyme must be induced by a different compound (e.g., *Pseudomonas cepacia* uses toluene-4-monoxygenase, which requires induction by toluene, to destroy trichloroethylene). Furthermore, the degradation pathway involves formation of highly reactive epoxides that can inactivate the enzyme (Timmis et al. Ann. Rev. Microbiol. 48:525–557 (1994)). The recursive sequence recombination techniques of the invention could be used to mutate the enzyme and its regulatory region such that it is produced constitutively, and is less susceptible to epoxide inactivation. In some embodiments of the invention, selection of hosts constitutively producing the enzyme and less susceptible to the epoxides can be accomplished by demanding growth in the presence of increasing concentrations of trichloroethylene in the absence of inducing substances.

8.7.8.3 Polychlorinated Biphenyls and Polycyclic Aromatic Hydrocarbons

Polychlorinated Biphenyls (PCBs) an Polycyclic Aromatic Hydrocarbons (PAHs) PCBs and PAHs are families of structurally related compounds that are major pollutants at many Superfund sites. Bacteria transformed with plasmids encoding enzymes with broader substrate specificity have been used commercially. In nature, no known pathways have been generated in a single host that degrade the larger PAHs or more heavily chlorinated PCBs. Indeed, often the collaboration of anaerobic and aerobic bacteria are required for complete metabolism.

Thus, likely sources for starting material for recursive sequence recombination include identified genes encoding PAH-degrading catabolic pathways on large (20–100 KB) plasmids (Sanseverino et al. Applied Environ. Micro. 59:1931–1937 (1993); Simon et al. Gene 127:31–37 (1993); Zylstra et al. Annals of the NY Acad. Sci. 721:386–398 (1994)); while biphenyl and PCB-metabolizing enzymes are encoded by chromosomal gene clusters, and in a number of cases have been cloned onto plasmids (Hayase et al. J. Bacteriol. 172:1160–1164 (1990); Furukawa et al. Gene 98:21–28 (1992); Hofer et al. Gene 144:9–16 (1994)). The materials can be subjected to the techniques discussed above so as to evolve a biodegradative pathway in a single organism.

Substrate specificity in the PCB pathway largely results from enzymes involved in initial dioxygenation reactions, and can be significantly altered by mutations in those enzymes (Erickson et al. Applied Environ. Micro. 59:3858–38662 (1993); Furukawa et al. J. Bact. 175:5224–5232 (1993). Mineralization of PAHs and PCBs requires that the downstream pathway is able to metabolize the products of the initial reaction (Brenner et al. Biodegradation 5:359–377 (1994)). In this case, recursive sequence recombination of the entire pathway with selection for bacteria able to use the PCE or PAH as the sole carbon source will allow production of novel PCB and PAH degrading bacteria.

8.7.8.4 Herbicides

A general method for evolving genes for the catabolism of insoluble herbicides is exemplified as follows for atrazine. Atrazine [2-chloro-4-(ethylamino)-6-(isopropylamino)-1,3, 5-triazine] is a moderately persistent herbicide which is frequently detected in ground and surface water at concentrations exceeding the 3 ppb health advisory level set by the EPA. Atrazine can be slowly metabolized by a Pseudomonas species (Mandelbaum et al. Appl. Environ.Micro. 61:1451–1457 (1995)). The enzymes catalyzing the first two steps in atrazine metabolism by Pseudomonas are encoded by genes AtzA and AtzB (de Souza et al. Appl. Environ. Micro. 61:3373–3378 (1995)). These genes have been cloned in a 6.8 kb fragment into pUC18 (AtzAB-pUC). *E. coli* carrying this plasmid converts atrazine to much more soluble metabolites. It is thus possible to screen for enzyme activity by growing bacteria on plates containing atrazine. The herbicide forms an opaque precipitate in the plates, but cells containing AtzAB-pU18 secrete atrazine degrading enzymes, leading to a clear halo around those cells or colonies. Typically, the size of the halo and the rate of its formation can be used to assess the level of activity so that picking colonies with the largest halos allows selection of the more active or highly produced atrazine degrading enzymes.

Thus, the plasmids carrying these genes can be subjected is to the recursive sequence recombination formats described above to optimize the catabolism of atrazine in *E. coli* or another host of choice, including Pseudomonas. After each round of recombination, screening of host colonies expressing the evolved genes can be done on agar plates containing atrazine to observe halo formation. This is a generally applicable method for screening enzymes that metabolize insoluble compounds to those that are soluble (e.g., polycyclicaromatic hydrocarbons). Additionally, catabolism of atrazine can provide a source of nitrogen for the cell; if no other nitrogen is available, cell growth will be limited by the rate at which the cells can catabolize nitrogen. Cells able to utilize atrazine as a nitrogen source can thus be selected from a background of non-utilizers or poor-utilizers.

8.7.8.5 Heavy Metal Detoxification

Bacteria are used commercially to detoxify arsenate waste generated by the mining of arsenopyrite gold ores. As well as mining effluent, industrial waste water is often contaminated with heavy metals (e.g., those used in the manufacture of electronic components and plastics). Thus, simply to be able to perform other bioremedial functions, microorganisms must be resistant to the levels of heavy metals present, including mercury, arsenate, chromate, cadmium, silver, etc.

A strong selective pressure is the ability to metabolize a toxic compound to one less toxic. Heavy metals are toxic largely by virtue of their ability to denature proteins (Ford et al. Bioextraction and Biodeterioration of Metals, p. 1–23). Detoxification of heavy metal contamination can be effected in a number of ways including changing the solubility or bioavailability of the metal, changing its redox state (e.g. toxic mercuric chloride is detoxified by reduction to the much more volatile elemental mercury) and even by bioaccumulation of the metal by immobilized bacteria or is plants. The accumulation of metals to a sufficiently high concentration allows metal to be recycled; smelting burns off the organic part of the organism, leaving behind reusable accumulated metal. Resistances to a number of heavy metals (arsenate, cadmium, cobalt, chromium, copper, mercury, nickel, lead, silver, and zinc) are plasmid encoded in a number of species including Staphylococcus and Pseudomonas (Silver et al. Environ. Health Perspect. 102:107–113 (1994); Ji et al. J. Ind. Micro. 14:61–75 (1995). These genes also confer heavy metal resistance on other species as well (e.g., E. coli). The recursive sequence recombination techniques of the instant invention (RSR) can be used to increase microbial heavy metal tolerances, as well as to increase the extent to which cells will accumulate heavy metals. For example, the ability of E. coli to detoxify arsenate can be improved at least 100-fold by RSR.

Cyanide is very efficiently used to extract gold from rock containing as little as 0.2 oz per ton. This cyanide can be microbially neutralized and used as a nitrogen source by fungi or bacteria such as Pseudomonas fluorescens. A problem with microbial cyanide degradation is the presence of toxic heavy metals in the leachate. RSR can be used to increase the resistance of bioremedial microorganisms to toxic heavy metals, so that they will be able to survive the levels present in many industrial and Superfund sites. This will allow them to biodegrade organic pollutants including but not limited to aromatic hydrocarbons, halogenated hydrocarbons, and biocides.

8.7.8.6 Microbial Mining

"Bioleaching" is the process by which microbes convert insoluble metal deposits (usually metal sulfides or oxides) into soluble metal sulfates. Bioleaching is commercially important in the mining of arsenopyrite, but has additional potential in the detoxification and recovery of metals and acids from waste dumps. Naturally occurring bacteria capable of bioleaching are reviewed by Rawlings and Silver (Bio/Technology 13:773–778 (1995)).

These bacteria are typically divided into groups by their preferred temperatures for growth. The more important mesophiles are Thiobacillus and Leptospirillum species. Moderate thermophiles include Sulfobacillus species. Extreme thermophiles include Sulfolobus species. Many of these organisms are difficult to grow in commercial industrial settings, making their catabolic abilities attractive candidates for transfer to and optimization in other organisms such as Pseudomonas, Rhodococcus, T. ferrooxidans or E. coli. Genetic systems are available for at least one strain of T. ferrooxidans, allowing the manipulation of its genetic material on plasmids.

The recursive sequence recombination methods described above can be used to optimize the catalytic abilities in native hosts or heterologous hosts for evolved bioleaching genes or pathways, such as the ability to convert metals from insoluble to soluble salts. In addition, leach rates of particular ores can be improved as a result of, for example, increased resistance to toxic compounds in the ore concentrate, increased specificity for certain substrates, ability to use different substrates as nutrient sources, and so on.

8.7.8.7 Oil Desulfurization

The presence of sulfur in fossil fuels has been correlated with corrosion of pipelines, pumping, and refining equipment, and with the premature breakdown of combustion engines. Sulfur also poisons many catalysts used in the refining of fossil fuels. The atmospheric emission of sulfur combustion products is known as acid rain.

Microbial desulfurization is an appealing bioremediation application. Several bacteria have been is reported that are capable of catabolizing dibenzothiophene (DBT), which is the representative compound of the class of sulfur compounds found in fossil fuels. U.S. Pat. No. 5,356,801 discloses the cloning of a DNA molecule from Rhodococcus rhodochrous capable of biocatalyzing the desulfurization of oil. Denome et al. (Gene 175:6890–6901 (1995)) disclose the cloning of a 9.8 kb DNA fragment from Pseudomonas encoding the upper naphthalene catabolizing pathway which also degrades dibenzothiophene. Other genes have been identified that perform similar functions (disclosed in U.S. Pat. No. 5,356,801).

The activity of these enzymes is currently too low to be commercially viable, but the pathway could be increased in efficiency using the recursive sequence recombination techniques of the invention. The desired property of the genes of interest is their ability to desulfurize dibenzothiophene or its alkyl or aryl substituted analogues. In some embodiments of the invention, selection is preferably accomplished by coupling this pathway to one providing a nutrient to the bacteria. Thus, for example, desulfurization of dibenzothiophene results in formation of hydroxybiphenyl.

This is a substrate for the biphenyl-catabolizing pathway which provides carbon and energy. Selection would thus be done by "stochastic &/or non-stochastic mutagenesis" the dibenzothiophene genes and transforming them into a host containing the biphenyl-catabolizing pathway. Increased dibenzothiophene desulfurization will result in increased nutrient availability and increased growth rate. Once the genes have been evolved they are easily separated from the biphenyl degrading genes. The latter are undesirable in the final product since the object is to desulfurize without decreasing the energy content of the oil. Alkyl or aryl substituted dibenzothiophenes can be detected by changes in fluorescence (Krawiec, S., Devel. Indus. Microbiology 31:103–114 (1990)) or by detection of phenol groups formed as a result of desulfurization (Dacre, J. C. Anal. Chem. 43:589–591 (1971)).

8.7.8.8 Organo-Nitro Compounds

Organo-nitro compounds are used as explosives, dyes, drugs, polymers and antimicrobial agents. Biodegradation of these compounds occurs usually by way of reduction of the nitrate group, catalyzed by nitroreductases, a family of broadly-specific enzymes. Partial reduction of organo-nitro compounds often results in the formation of a compound more toxic than the original (Hassan et al. 1979 Arch Bioch Biop. 196:385–395). Recursive sequence recombination of nitroreductases can produce enzymes that are more specific, and able to more completely reduce (and thus detoxify) their target compounds (examples of which include but are not limited to nitrotoluenes and nitrobenzenes). Nitroreductases can be isolated from bacteria isolated from explosive-contaminated soils, such as Morganella morganii and Enterobacter cloacae (Bryant et. al., 1991. J. Biol Chem. 266:4126–4130). A preferred selection method is to look for increased resistance to the organo-nitro compound of interest, since that will indicate that the enzyme is also able to reduce any toxic partial reduction products of the original compound.

8.7.8.9 Alternative Substrates for Chemical Synthesis

Metabolic engineering can be used to alter microorganisms that produce industrially useful chemicals, so that they will grow using alternate and more abundant sources of nutrients, including human-produced industrial wastes. This typically involves providing both a transport system to get the alternative substrate into the engineered cells and catabolic enzymes from the natural host organisms to the engineered cells.

In some instances, enzymes can be secreted into the medium by engineered cells to degrade the alternate is substrate into a form that can more readily be taken up by the engineered cells; in other instances, a batch of engineered cells can be grown on one preferred substrate, then lysed to liberate hydrolytic enzymes for the alternate substrate into the medium, while a second inoculum of the same engineered host or a second host is added to utilize the hydrolyzate.

The starting materials for recursive sequence recombination will typically be genes for utilization of a substrate or its transport. Examples of nutrient sources of interest include but are not limited to lactose, whey, galactose, mannitol, xylan, cellobiose, cellulose and sucrose, thus allowing cheaper production of compounds including but not limited to ethanol, tryptophan, rhamnolipid surfactants, xanthan gum, and polyhydroxylalkanoate. For a review of such substrates as desired target substances, see Cameron et al. (Appl. Biochem. Biotechnol. 38:105–140 (1993)). The recursive sequence recombination methods described above can be used to optimize the ability of native hosts or heterologous hosts to utilize a substrate of interest, to evolve more efficient transport systems, to increase or alter specificity for certain substrates, and so on.

8.7.8.10 Modification of Cell Properties

Although not strictly examples of manipulation of intermediary metabolism, recursive sequence recombination techniques can be used to improve or alter other aspects of cell properties, from growth rate to ability to secrete certain desired compounds to ability to tolerate increased temperature or other environmental stresses. Some examples of traits engineered by traditional methods include expression of heterologous proteins in bacteria, yeast, and other eukaryotic cells, antibiotic resistance, and phage resistance. Any of these traits is advantageously evolved by the recursive sequence recombination techniques of the instant invention. Examples include replacement of one nutrient uptake system (e.g. ammonia in Methylophilus methylotrophus) with another that is more energy efficient; expression of haemoglobin to improve growth under conditions of limiting oxygen; redirection of toxic metabolic end products to less toxic compounds; expression of genes conferring tolerance to salt, drought and toxic compounds and resistance to pathogens, antibiotics and bacteriophage, reviewed in Cameron et. al. Appl Biochem Biotechnol, 38:105–140 (1993).

The heterologous genes encoding these functions all have the potential for further optimization in their new hosts by existing recursive sequence recombination technology. Since these functions increase cell growth rates under the desired growth conditions, optimization of the genes by evolution simply involves recombining the DNA recursively and selecting the recombinants that grow faster with limiting oxygen, higher toxic compound concentration, or whatever is the appropriate growth condition for the parameter being improved.

Since these functions increase cell growth rates under the desired growth conditions, optimization of the genes by "evolution" can simply involve "stochastic &/or non-stochastic mutagenesis" the DNA and selecting the recombinants that grow faster with limiting oxygen, higher toxic compound concentration or whatever restrictive condition is being overcome. Cultured mammalian cells also require essential amino acids to be present in the growth medium. This requirement could also be circumvented by expression of heterclogous metabolic pathways that synthesize these amino acids (Rees et al. , Biotechnology 8:629–633 (1990). Recursive sequence recombination would provide a mechanism for optimizing the expression of these genes in mammalian cells. Once again, a preferred selection would be for cells that can grow in the absence of added amino acids.

Yet another candidate for improvement through the techniques of the invention is symbiotic nitrogen fixation. Genes involved in nodulation (nod, ndv), nitrogen reduction (nif, fix), host range determination (nod, hsp), bacteriocin production (tfx), surface polysaccharide synthesis (exo) and energy utilization (dct, hup) which have been identified (Paau, Biotech. Adv. 9:173–184 (1991)). The main function of recursive sequence recombination in this case is in improving the survival of strains that are already known to be better nitrogen fixers. These strains tend to be less good at competing with strains already present in the environment, even though they are better at nitrogen fixation. Targets for recursive sequence recombination such as nodulation and host range determination genes can be modified and selected for by their ability to grow on the new host.

Similarly any bacteriocin or energy utilization genes that will improve the competitiveness of the strain will also result in greater growth rates. Selection can simply be performed by subjecting the target genes to recursive sequence recombination and forcing the inoculant to compete with wild type nitrogen fixing bacteria. The better the nitrogen fixing bacteria grow in the new host, the more copies of their recombined genes will be present for the next round of recombination. This growth rate differentiating selection is described above in detail.

8.7.8.11 Biodetectors/Biosensors

Bioluminescence or fluorescence genes can be used as reporters by fusing them to specific regulatory genes (Cameron et. al. Appl. Biochem Biotechnol, 38:105–140 (1993)). A specific example is one in which the luciferase genes luxCDABE of Vibrio fischeri were fused to the regulatory region of the isopropylbenzene catabolism operon from Pseudomonas putida RE204.

Transformation of this fusion construct into E. coli resulted in a strain which produced light in response to a variety of hydrophobic compound such as substituted benzenes, chlorinated solvents and naphthalene (Selifonova et. al., Appl Environ Microbiol 62:778–783 (1996)). This type of construct is useful for the detection of pollutant levels, and has the added benefit of only measuring those pollutants that are bioavailable (and therefore potentially toxic). other signal molecules such as jellyfish green fluorescent protein could also be fused to genetic regulatory regions that respond to chemicals in the environment. This should allow a variety of molecules to be detected by their ability to induce expression of a protein or proteins which result in light, fluorescence or some other easily detected signal. Recursive sequence recombination can be used in several ways to modify this type of biodetection system. It can be used to increase the amplitude of the response, for example by increasing the fluorescence of the green fluorescent protein. Recursive sequence recombination could also be used to increase induced expression levels or catalytic activities of other signal-generating systems, for example of the luciferase genes.

Recursive sequence recombination can also be used to alter the specificity of biosensors. The regulatory region, and transcriptional activators that interact with this region and with the chemicals that induce transcription can also be stochastic &/or non-stochastic mutagenized. This should generate regulatory systems in which transcription is activated by analogues of the normal inducer, so that biodetectors for different chemicals can be developed.

In this case, selection would be for constructs that are activated by the (new) specific chemical to be detected. Screening could be done simply with fluorescence (or light) activated cell sorting, since the desired improvement is in light production. In addition to detection of environmental pollutants, biosensors can be developed that will respond to any chemical for which there are receptors, or for which receptors can be evolved by recursive sequence recombination, such as hormones, growth factors, metals and drugs. These receptors may be intracellular and direct activators of transcription, or they may be membrane bound receptors that activate transcription of the signal indirectly, for example by a phosphorylation cascade. They may also not act on transcription at all, but may produce a signal by some post-transcriptional modification of a component of the signal generating pathway. These receptors may also be generated by fusing domains responsible for binding different ligands with different signaling domains. Again, recursive sequence recombination can be used to increase the amplitude of the signal generated to optimize expression and functioning of chimeric receptors, and to alter the specificity of the chemicals detected by the receptor.

8.8 Promoting Genetic Exchange

Some methods of the invention effect recombination of cellular DNA by propagating cells under conditions inducing exchange of DNA between cells. DNA exchange can be promoted by generally applicable methods such as electroporation, biolistics, cell fusion, or in some instances, by conjugation, transduction, or agrobacterium mediated transfer and meiosis. For example, Agrobacterium can transform S. cerevisiae with T-DNA, which is incorporated into the yeast genome by both homologous recombination and a gap repair mechanism. (Piers et al., Proc. Natl. Acad. Sci. USA 93(4),1613–8 (1996)).

In some methods, initial diversity between cells (i.e., before genome exchange) is induced by chemical or radiation-induced mutagenesis of a progenitor cell type, optionally followed by screening for a desired phenotype. In other methods, diversity is natural as where cells are obtained from different individuals, strains or species.

In some stochastic &/or non-stochastic mutagenesis methods, induced exchange of DNA is used as the sole means of effecting recombination in each cycle of recombination. In other methods, induced exchange is used in combination with natural sexual recombination of an organism. In other methods, induced exchange and/or natural sexual recombination are used in combination with the introduction of a fragment library. Such a fragment library can be a whole genome, a whole chromosome, a group of functionally or genetically linked genes, a plasmid, a cosmid, a mitochondrial genome, a viral genome (replicative and nonreplicative) or specific or random fragments of any of these. The DNA can be linked to a vector or can be in free form. Some vectors contain sequences promoting homologous or nonhomologous recombination with the host genome. Some fragments contain double stranded breaks such as caused by shearing with glass beads, sonication, or chemical or enzymatic fragmentation, to stimulate recombination. In each case, DNA can be exchanged between cells after which it can undergo recombination to form hybrid genomes. Generally, cells are recursively subject to recombination to increase the diversity of the population prior to screening. Cells bearing hybrid genomes, e.g., generated after at least one, and usually several cycles of recombination are screened for a desired phenotype, and cells having this phenotype are isolated. These cells can additionally form starting materials for additional cycles of recombination in a recursive recombination/selection scheme.

8.8.1 Protoplast Fusion

One means of promoting exchange of DNA between cells is by fusion of cells, such as by protoplast fusion. A protoplast results from the removal from a cell of its cell wall, leaving a membrane-bound cell that depends on an isotonic or hypertonic medium for maintaining its integrity. If the cell wall is partially removed, the resulting cell is strictly referred to as a spheroplast and if it is completely removed, as a protoplast. However, here the term protoplast includes spheroplasts unless otherwise indicated.

Protoplast fusion is described by Shaffner et al., Proc. Natl. Acad Sci. USA 77, 2163 (1980) and other exemplary procedures are described by Yoakum et al. , U.S. Pat. No. 4,608,339, Takahashi et al., U.S. Pat. No. 4,677,066 and Sambrooke et al., at Ch. 16. Protoplast fusion has been reported between strains, species, and genera (e.g., yeast and chicken erythrocyte). Protoplasts can be prepared for both bacterial and eukaryotic cells, including mammalian cells and plant cells, by several means including chemical treatment to strip cell walls. For example, cell walls can be stripped by digestion with a cell wall degrading enzyme such as lysozyme in a 10–20% sucrose, 50 mM EDTA buffer. Conversion of cells to spherical protoplasts can be monitored by phase-contrast microscopy. Protoplasts can also be prepared by propagation of cells in. media supplemented with an inhibitor of cell wall synthesis, or use of mutant strains lacking capacity for cell wall formation. Preferably, eukaryotic cells are synchronized in G1 phase by arrest with inhibitors such as –factor, K. lactis killer toxin, leflonamide and adenylate cyclase inhibitors. Optionally, some but not all, protoplasts to be fused can be killed and/or have their DNA fragmented by treatment with ultraviolet irradiation, hydroxylamine or cupferon (Reeves et al., FFMS Microbiol. Lett. 99, 193–198 (1992)). In this situation, killed protoplasts are referred to as donors, and viable protoplasts as acceptors.

Using dead donors cells can be advantageous in subsequently recognizing fused cells with hybrid genomes, as described below. Further, breaking up DNA in donor cells is advantageous for stimulating recombination with acceptor DNA. Optionally, acceptor and/or fused cells can also be briefly, but nonlethally, exposed to UV irradiation further to stimulate recombination.

Once formed, protoplasts can be stabilized in a variety of osmolytes and compounds such as sodium chloride, potassium chloride, sodium phosphate, potassium phosphate, sucrose, sorbitol in the presence of DTT. The combination of buffer, pH, reducing agent, and osmotic stabilizer can be optimized for different cell types. Protoplasts can be induced to fuse by treatment with a chemical such as PEG, calcium chloride or calcium propionate or electrofusion (Tsoneva, Acta Microbiologica Bulgaria 24, 53–59 (1989)). A method of cell fusion employing electric fields has also been described. See Chang U.S. Pat. No. 4,970,154. Conditions can be optimized for different strains.

The fused cells are heterokaryons containing genomes from two or more component protoplasts. Fused cells can be enriched from unfused parental cells by sucrose gradient sedimentation or cell sorting. The two nuclei in the heterokaryons can fuse (karyogamy) and homologous recombination can occur between the genomes. The chromosomes can also segregate asymmetrically resulting in regenerated protoplasts that have lost or gained whole chromosomes.

The frequency of recombination can be increased by treatment with ultraviolet irradiation or by use of strains overexpressing recA or other recombination genes, or the yeast rad genes, and cognate variants thereof in other species, or by the inhibition of gene products of MutS, MutL, or MutD. Overexpression can be either the result of introduction of exogenous recombination genes or the result of selecting strains, which as a result of natural variation or induced mutation, overexpress endogenous recombination genes. The fused protoplasts are propagated under conditions allowing regeneration of cell walls, recombination and segregation of recombinant genomes into progeny cells from the heterokaryon and expression of recombinant genes. This process can be reiteratively repeated to increase the diversity of any set of protoplasts or cells. After, or occasionally before or during, recovery of fused cells, the cells are screened or selected for evolution toward a desired property.

Thereafter a subsequent round of recombination can be performed by preparing protoplasts from the cells surviving selection/screening in a previous round. The protoplasts are fused, recombination occurs in fused protoplasts, and cells are regenerated from the fused protoplasts. This process can again be reiteratively repeated to increase the diversity of the starting population. Protoplasts, regenerated or regenerating cells are subject to further selection or screening.

Subsequent rounds of recombination can be performed on a split pool basis as described above. That is, a first subpopulation of cells surviving selection/screening from a previous round are used for protoplast formation. A second subpopulation of cells surviving selection/screening from a previous round are used as a source for DNA library preparation.

The DNA library from the second subpopulation of cells is then transformed into the protoplasts from the first subpopulation. The library undergoes recombination with the genomes of the protoplasts to form recombinant genomes. This process can be repeated several times in the absence of a selection event to increase the diversity of the cell population. Cells are regenerated from protoplasts, and selection/screening is applied to regenerating or regenerated cells. In a further variation, a fresh library of nucleic acid fragments is introduced into protoplasts surviving selection/screening from a previous round.

Protoplast formation of donor and recipient strains, heterokaryon formation, karyogamy, recombination, and segregation of recombinant genomes into separate cells. Optionally, the recombinant genomes, if having a sexual cycle, can undergo further recombination with each other as a result of meiosis and mating. Recursive cycles of protoplast fusion, or recursive mating/meiosis is often used to increase the diversity of a cell population. After achieving a sufficiently diverse population via one of these forms of recombination, cells are screened or selected for a desired property. Cells surviving selection/screening can then used as the starting materials in a further cycle of protoplasting or other recombination methods as noted herein.

8.8.2 Parasexual Reproduction

Parasexual reproduction provides a further means for stochastic &/or non-stochastic mutagenesis genetic material between cells. This process allows recombination of parental DNA without involvement of mating types or gametes. Parasexual fusion occurs by hyphal fusion giving rise to a common cytoplasm containing different nuclei. The two nuclei can divide independently in the resulting heterokaryon but occasionally fuse. Fusion is followed by haploidization, which can involve loss of chromosomes and mitotic crossing over between homolgous chromosomes. Protoplast fusion is a form of parasexual reproduction.

8.8.3 Selection for Hybrid Strains 8.8.3.1 Identifying Cells Formed By the Fusion of Components of Parental Cells from Two or More Distinct Subpopulations The invention provides selection strategies to identify cells formed by fusion of components from parental cells from two or more distinct subpopulations. Selection for hybrid cells is usually performed before selecting or screening for cells that have evolved (as a result of genetic exchange) to acquisition of a desired property. A basic premise of most such selection schemes is that two initial subpopulations have two distinct markers. Cells with hybrid genomes can thus be identified by selection for both markers.

8.8.3.2 Method Where One Subpopulation Has a Marker

In one such scheme, at least one subpopulation of cells bears a selective marker attached to its cell membrane. Examples of suitable membrane markers include biotin, fluorescein and rhodamine. The markers can be linked to amide or thiol groups or through more specific derivatization chemistries, such as iodo-acetates, iodoacetamides, maleimides.

For example, a marker can be attached as follows. Cells or protoplasts are washed with a buffer (e.g., PBS), which does not interfere with the chemical coupling of a chemically active ligand which reacts with amino groups of lysines or N-terminal amino groups of membrane proteins. The ligand is either amine reactive itself (e.g., isothiocyanates, succinimidyl esters, sulfonyl chlorides) or is activated by a heterobifunctional linker (e.g. EMCS, SLAB, SPDP, SMB) to become amine reactive. The ligand is a molecule which is easily bound by protein derivatized magnetic beads or other capturing solid supports. For example, the ligand can be succinimidyl activated biotin (Molecular Probes Inc.: B-1606, B-2603, S-1515, S-1582). This linker is reacted with amino groups of proteins residing in and on the surface of a cell. The cells are then washed to remove excess labeling agent before contacting with cells from the second subpopulation bearing a second selective marker.

The second subpopulation of cells can also bear a membrane marker, albeit a different membrane marker from the first subpopulation. Alternatively, the second subpopulation can bear a genetic marker. The genetic marker can confer a selective property such as drug resistance or a screenable property, such as expression of green fluorescent protein.

After fusion of first and second subpopulations of cells and recovery, cells are screened or selected for the presence of markers on both parental subpopulations. For example, fusants are enriched for one population by adsorbtion to specific beads and these are then sorted by FACS for those expressing a marker. Cells surviving both screens for both markers are those having undergone protoplast fusion, and are therefore more likely to have recombined genomes. Usually, the markers are screened or selected separately. Membrane-bound markers, such as biotin, can be screened by affinity enrichment for the cell membrane marker (e.g., by panning fused cells on an affinity matrix). For example, for a biotin membrane label, cells can be affinity purified using streptavidin-coated magnetic beads (Dynal). These beads are washed several times to remove the non-fused host cells.

Alternatively, cells can be panned against an antibody to the membrane marker. In a further variation, if the membrane marker is fluorescent, cells bearing the marker can be identified by FACS. Screens for genetic markers depend on the nature of the markers, and include capacity to grow on drug-treated media or FACS selection for green fluorescent protein. If first and second cell populations have fluorescent markers of different wavelengths, both markers can be screened simultaneously by FACS sorting.

In a further selection scheme for hybrid cells, first and second populations of cells to be fused express different subunits of a heteromultimeric enzyme. Usually, the heteromultimeric enzyme has two different subunits, but heteromultimeric enzymes having three, four or more different subunits can be used. If an enzyme has more than two different subunits, each subunit can be expressed in a different subpopulation of cells (e.g., three subunits in three subpopulations), or more than one subunit can be expressed in the same subpopulation of cells (e.g., one subunit in one subpopulation, two subunits in a second subpopulation). In the case where more than two subunits are used, selection for the poolwise recombination of more than two protoplasts can be achieved.

Hybrid cells representing a combination of genomes of first, second or more subpopulation component cells can then be recognized by an assay for intact enzyme. Such an assay can be a binding assay, but is more typically a functional assay (e.g., capacity to metabolize a substrate of the enzyme). Enzymatic activity can be detected for example by processing of a substrate to a product with a fluorescent or otherwise easily detectable absorbance or emission spectrum. The individual subunits of a heteromultimeric enzyme used in such an assay preferably have no enzymic activity in dissociated form, or at least have significantly less activity in dissociated form than associated form. Preferably, the cells used for fusion lack an endogenous form of the heteromultimeric enzyme, or at least have significantly less endogenous activity than results from heteromultimeric enzyme formed by fusion of cells.

Penicillin acylase enzymes, cephalosporin acylase and penicillin acyltransferase are examples of suitable heteromultimeric enzymes. These enzymes are encoded by a single gene, which is translated as a proenzyme and cleaved by posttranslational autocatalytic proteolysis to remove a spacer endopeptide and generate two subunits, which associate to form the active heterodimeric enzyme. Neither subunit is active in the absence of the other subunit. However, activity can be reconstituted if these separated gene portions are expressed in the same cell by co-transformation. Other enzymes that can be used have subunits that are encoded by distinct genes (e.g., faoA and faoB genes encode 3-oxoacyl-CoA thiolase of *Pseudoumonas fragi* (Biochem. J 328, 815–820 (1997)).

An exemplary enzyme is penicillin G acylase from *Escherichia coli*, which has two subunits encoded by a single gene. Fragments of the gene encoding the two subunits operably linked to appropriate expression regulation sequences are transfected into first and second subpopulations of cells, which lack endogenous penicillin acylase activity. A cell formed by fusion of component cells from the first and second subpopulations expresses the two subunits, which assemble to form functional enzyme, e.g., penicillin acylase. Fused cells can then be selected on agar plates containing penicillin G, which is degraded by penicillin acylase.

In another variation, fused cells are identified by complementation of auxotrophic mutants. Parental subpopulations of cells can be selected for known auxotrophic mutations. Alternatively, auxotrophic mutations in a starting population of cells can be generated spontaneously by exposure to a mutagenic agent. Cells with auxotrophic mutations are selected by replica plating on minimal and complete media. Lesions resulting in auxotrophy are expected to be scattered throughout the genome, in genes for amino acid, nucleotide, and vitamin biosynthetic pathways. After fusion of parental cells, cells resulting from fusion can be identified by their capacity to grow on minimal media. These cells can then be screened or selected for evolution toward a desired property. Further steps of mutagenesis generating fresh auxotrophic mutations can be incorporated in subsequent cycles of recombination and screening/selection.

In variations of the above method, de novo generation of auxotrophic mutations in each round of stochastic &/or non-stochastic mutagenesis can be avoided by reusing the same auxotrophs. For example, auxotrophs can be generated by transposon mutagenesis using a transposon bearing selective marker. Auxotrophs are identified by a screen such as replica plating. Auxotrophs are pooled, and a generalized transducing phage lysate is prepared by growth of phage on a population of auxotrophic cells. A separate population of auxtrophic cells is subjected to genetic exchange, and complementation is used to selected cells that have undergone genetic exchange and recombination. These cells are then screened or selected for acquisition of a desired property. Cells surviving screening or selection then have auxotrophic markers regenerated by introduction of the transducing transposon library. The newly generated auxotrophic cells can then be subject to further genetic exchange and screening/selection.

In a further variation, auxotrophic mutations are generated by homologous recombination with a targeting vector comprising a selective marker flanked by regions of homology with a biosynthetic region of the genome of cells to be evolved. Recombination between the vector and the genome inserts the positive selection marker into the genome causing an auxotrophic mutation. The vector is in linear form before introduction of cells.

Optionally, the frequency of introduction of the vector can be increased by capping its ends with self-complementarity oligonucleotides annealed in a hair pin formation. Genetic exchange and screening/selection proceed as described above. In each round, targeting vectors are reintroduced regenerating the same population of auxotrophic markers.

In another variation, fused cells are identified by screening for a genomic marker present on one subpopulation of parental cells and an episomal marker present on a second subpopulation of cells. For example, a first subpopulation of yeast containing mitochondria can be used to complement a second subpopulation of yeast having a petite phenotype (i.e., lacking mitochondria).

In a further variation, genetic exchange is performed between two subpopulations of cells, one of which is dead. Cells are preferably killed by brief exposure to DNA fragmenting agents such as hydroxylamine, cupferon, or irradiation. Viable cells are then screened for a marker present on the dead parental subpopulation.

8.8.4 Liposome Mediated Transfers 8.8.4.1 Nucleic Acid Fragment Libraries Are Introduced into Protoplasts 8.8.4.1.1 The Nucleic Acids Are Encapsulated in Liposomes to Help Uptake by Protoplasts In the methods noted above, in which nucleic acid fragment libraries are introduced into protoplasts, the nucleic acids are sometimes encapsulated in liposomes to facilitate uptake by protoplasts. Liposome-mediated uptake of DNA by protoplasts is described in Redford et al., Mol. Gen. Genet. 184, 567–569 (1981). Liposomes can efficiently deliver large volumes of DNA to protoplasts (see Deshayes et al., FMBO J. 4, 2731–2737 (1985)).

See also, Philippot and Schuber (eds) (1995) Liposomes as Tools in Basic Research and Industry CRC press, Boca Raton, e.g., Chapter 9, Remy et al. "Gene Transfer with Cationic Amphiphiles." Further, the DNA can be delivered as linear fragments, which are often more recombinogenic that whole genomes. In some methods, fragments are mutated prior to encapsulation in liposomes. In some methods, fragments are combined with RecA and homologs, or nucleases (e.g., restriction endonucleases) before encapsulation in liposomes to promote recombination. Alternatively, protoplasts can be treated with lethal doses of nicking reagents and then fused. Cells which survive are those which are repaired by recombination with other genomic fragments, thereby providing a selection mechanism to select for recombinant (and therefore desirably diverse) protoplasts.

8.9 Shuffling Using Filamentous Fungi

Filamentous fungi are particularly suited to performing the stochastic &/or non-stochastic mutagenesis methods described above. Filamentous fungi are divided into four main classifications based on their structures for sexual reproduction: Phycomycetes, Ascomycetes, Basidiomycetes and the Fungi Imperfecti. Phycomycetes (e-g., Rhizopus, Mucor) form sexual spores in sporangium.

The spores can be uni or multinucleate and often lack septated hyphae (coenocytic).

Ascomycetes (e.g., Aspergillus, Neurospora, Penicillum) produce sexual spores in an ascus as a result of meiotic division. Asci typically contain 4 meiotic products, but some contain 8 as a result of additional mitotic division. Basidiomycetes include mushrooms, and smuts and form sexual spores on the surface of a basidium. In holobasidiomycetes, such as mushrooms, the basidium is undivided. In hemibasidiomycetes, such as ruts (Uredinales) and smut fungi (Ustilaginales), the basidium is divided. Fungi imperfecti, which include most human pathogens, have no known sexual stage.

Fungi can reproduce by asexual, sexual or parasexual means. Asexual reproduction, involves vegetative growth of mycelia, nuclear division and cell division without involvement of gametes and without nuclear fusion. Cell division can occur by sporulation, budding or fragmentation of hyphae.

8.9.1 Evolve Fungi from Stochastic &/or Non-Stochastic Mutagenesis to Become Useful Hosts for Genetic Engineering of Unrelated Genes 8.9.2 To Improve the Capacity of Fungi to Make Specific Compounds One general goal of stochastic &/or non-stochastic mutagenesis is to evolve fungi to become useful hosts for genetic engineering, in particular for the stochastic &/or non-stochastic mutagenesis of unrelated genes. *A. nidulans* and neurospora are generally the fungal organisms of choice to serve as a hosts for such manipulations because of their sexual cycles and well-established use in classical and molecular genetics. Another general goal is to improve the capacity of fungi to make specific compounds (e.g. antibacterials (penicillins, cephalosporins), antifungals (e.g. echinocandins, aureobasidins), and wood-degrading enzymes). There is some overlap between these general goals, and thus, some desired properties are useful for achieving both goals.

8.9.3 Mutator Strain

Another desired property is the production of a mutator strain of fungi. Such a fungus can be produced by stochastic &/or non-stochastic mutagenesis a fungal strain containing a marker gene with one or more mutations that impair or prevent expression of a functional product. Shufflants are propagated under conditions that select for expression of the positive marker (while allowing a small amount of residual growth without expression). Shufflants growing fastest are selected to form the starting materials for the next round of stochastic &/or non-stochastic mutagenesis.

8.9.4 Expanded Host Range So Able to Form Heterokaryons with More Strains

Another desired property is to expand the host range of a fungus so it can form heterokaryons with fungi from other vegetative compatibility groups. Incompatability between species results from the interactions of specific alleles at different incompatability loci (such as the "het" loci). If two strains undergo hyphal anastomosis, a lethal cytoplasmic incomparability reaction may occur if the strains differ at these loci. Strains must carry identical loci to be entirely compatible. Several of these loci have been identified in various species, and the incompatibility effect is somewhat additive (hence, "partial incompatibility" can occur). Some tolerant and het-negative mutants have been described for these organisms (e.g. Dales & Croft, J Gen. Microbiol. 136, 1717–1724 (1990)). Further, a tolerance gene (tol) has been reported, which suppresses mating-type heterokaryon incompatability. Stochastic &/or non-stochastic mutagenesis is performed between protoplasts of strains from different incompatibility groups. A preferred format uses a five acceptor strain and a UV-irradiated dead acceptor strain. The UV irradiation serves to introduce mutations into DNA inactivating het genes. The two strains should bear different genetic markers. Protoplasts of the strain are fused, cells are regenerated and screened for complementation of markers. Subsequent rounds of stochastic &/or non-stochastic mutagenesis and selection can be performed in the same manner by fusing the cells surviving screening with protoplasts of a fresh population of donor cells. Similar to other procedures noted herein, the cells resulting from regeneration of the protoplasts are optionally refused by protoplasting and regenerated into cells one or more times prior to any selection step to increase the diversity of the resulting population of cells to be screened.

8.9.5 Ability to Outbreed without Self-Breeding

Another desired property is the introduction of multiple-allelomorph heterothallism into Ascomyceles and Fungi imperfecti, which do not normally exhibit this property. This mating system allows outbreeding without self-breeding. Such a mating system can be introduced by stochastic &/or non-stochastic mutagenesis Ascomycetes and Fungi imperfecti with DNA from Gasteromycetes or Hymenomycetes, which have such a system.

8.9.6 Spontaneous Formation of Protoplasts

Another desired property is spontaneous formation of protoplasts to facilitate use of a fungal strain as a stochastic &/or non-stochastic mutagenesis host. Here, the fungus to be evolved is typically mutagenized. Spores of the fungus to be evolved are briefly treated with a cell-wall degrading agent for a time insufficient for complete protoplast formation, and are mixed with protoplasts from other strain(s) of fungi. Protoplasts formed by fusion of the two different subpopulations are identified by genetic or other selection/or screening as described above. These protoplasts are used to regenerate mycelia and then spores, which form the starting material for the next round of stochastic &/or non-stochastic mutagenesis. In the next round, at least some of the surviving spores are treated with cell-wall removing enzyme but for a shorter time than the previous round. After treatment, the partially stripped cells are labeled with a first label. These cells are then mixed with protoplasts, which may derive from other cells surviving selection in a previous round, or from a fresh strain of fungi. These protoplasts are physically labeled with a second label. After incubating the cells under conditions for protoplast fusion fusants with both labels are selected.

These fusants are used to generate mycelia and spores for the next round of stochastic &/or non-stochastic mutagenesis, and so forth. Eventually, progeny that spontaneously form protoplasts (i.e., without addition of cell wall degrading agent) are identified. As with other procedures noted herein, cells or protoplasts can be reiteratively fused and regenerated prior to performing any selection step to increase the diversity of the resulting cells or protoplasts to be screened. Similarly, selected cells or protoplasts can be reiteratively fused and regenerated for one or several cycles without imposing selection on the resulting cellular or protoplast populations, thereby increasing the diversity of cells or protoplasts which are eventually screened. This process of performing multiple cycles of recombination interspersed with selection steps can be reiteratively repeated as desired.

8.9.7 Acquisition or Improvement of Genes Encoding in Biosynthetic Pathways; Transporter Proteins; and Metabolic Flux Another desired property is the acquisition and/or improvement of genes encoding enzymes in biosynthetic pathways, genes encoding transporter proteins, and genes encoding proteins involved in metabolic flux control. In this situation, genes of the pathway can be introduced into the fungus to be evolved either by genetic exchange with another strain of fungus possessing the pathway or by introduction of a fragment library from an organism possessing the pathway. Genetic material of these fungi can then be subjected to further stochastic &/or non-stochastic mutagenesis and screening/selection by the various procedures discussed in this application.

Shufflant strains of fungi are selected/screened for production of the compound produced by the metabolic pathway or precursors thereof.

8.9.8 Increased Stability to Extreme Conditions

Another desired property is increasing the stability of fungi to extreme conditions such as heat. In this situation, genes conferring stability can be acquired by exchanging DNA with or transforming DNA from a strain that already has such properties.

Alternatively, the strain to be evolved can be subjected to random mutagenesis. Genetic material of the fungus to be evolved can be stochastic &/or non-stochastic mutagenized by any of the procedures described in this application, with shufflants being selected by surviving exposure to extreme conditions.

8.9.9 Growth Under Altered Nutritional Requirements

Another desired property is capacity of a fungus to grow under altered nutritional requirements (e.g., growth on particular carbon or nitrogen sources). Altering nutritional requirements is particularly valuable, e.g., for natural isolates of fungi that produce valuable commercial products but have esoteric and therefore expensive nutritional requirement. The strain to be evolved undergoes genetic exchange and/or transformation with DNA from a strain that has the desired nutritional requirements. The fungus to be evolved can then optionally be subjected to further stochastic &/or non-stochastic mutagenesis as described in this application and with recombinant strains being selected for capacity to grow in the desired nutritional circumstances. Optionally, the nutritional circumstances can be varied in successive rounds of stochastic &/or non-stochastic mutagenesis starting at close to the natural requirements of the fungus to be evolved and in subsequent rounds approaching the desired nutritional requirements.

8.9.10 Natural Competance to Take Up a Plasmid Bearing a Selective Marker

Another desired property is acquisition of natural competence in a fungus. The procedure for acquisition of natural competence by stochastic &/or non-stochastic mutagenesis is generally described in PCT/US97/04494. The fungus to be evolved typically undergoes genetic exchange or transformation with DNA from a bacterial strain or fungal strain that already has this property.

Cells with recombinant genomes are then selected by capacity to take up a plasmid bearing a selective marker. Further rounds of recombination and selection can be performed using any of the procedures described above.

8.9.11 Reduced or Increased Secretion of Proteases and DNases

Another desired property is reduced or increased secretion of proteases and DNase. In this situation, the fungus to be evolved can acquire DNA by exchange or transformation from another strain known to have the desired property. Alternatively, the fungus to be evolved can be subject to random mutagenesis. The fungus to be evolved is stochastic &/or non-stochastic mutagenized as above. The presence of such enzymes, or lack thereof, can be assayed by contacting the culture media from individual isolates with a fluorescent molecule tethered to a support via a peptide or DNA linkage. Cleavage of the linkage releases detectable fluorescence to the media.

8.9.12 Altered Transporters to Use Secondary Components

Another desired property is producing fungi with altered transporters (e. g., MDR). Such altered transporters are useful, for example, in fungi that have been evolved to produce new secondary metabolites, to allow entry of precursors required for synthesis of the new secondary metabolites into a cell, or to allow efflux of the secondary metabolite from the cell. Transporters can be evolved by introduction of a library of transporter variants into fungal cells and allowing the cells to recombine by sexual or parasexual recombination. To evolve a transporter with capacity to transport a precursor into the cells, cells are propagated in the present of precursor, and cells are then screened for production of metabolite. To evolve a transporter with capacity to export a metabolite, cells are propagated under conditions supporting production of the metabolite, and screened for export of metabolite to culture medium.

A general method of fungal stochastic &/or non-stochastic mutagenesis is shown herein. Spores from a frozen stock, a lyophilized stock, or fresh from an agar plate are used to inoculate suitable liquid medium (1). Spores are germinated resulting in hyphal growth (2). Mycelia are harvested, and washed by filtration and/or centrifugation. Optionally the sample is pretreated with DTT to enhance protoplast formation (3). Protoplasting is performed in an osmotically stabling medium (e.g., 1 m NaCl/20 mM MgSO4, pH 5.8) by the addition of cell wall-degrading enzyme (e.g., Novozyme 234) (4). Cell wall degrading enzyme is removed by repeated washing with osmotically stabilizing solution (5). Protoplasts can be separated from mycelia, debris and spores by filtration through miracloth, and density centrifugation (6). Protoplasts are harvested by centrifugation and resuspended to the appropriate concentration. This step may lead to some protoplast fusion (7). Fusion can be stimulated by addition of PEG (e.g., PEG 3350), and/or repeated centrifugation and resuspension with or without PEG. Electrofusion can also be performed (8). Fused protoplasts can optionally be enriched from unfused protoplasts by sucrose gradient sedimentation (or other methods of screening described above). Fused protoplasts can optionally be treated with ultraviolet irradiation to stimulate recombination (9). Protoplasts are cultured on osmotically stabilized agar plates to regenerate cell walls and form mycelia (10). The mycelia are used to generate spores (11), which are used as the starting material in the next round of stochastic &/or non-stochastic mutagenesis (12). Selection for a desired property can be performed either on regenerated mycelia or spores derived therefrom.

In an alternative method, protoplasts are formed by inhibition of one or more enzymes required for cell wall synthesis. The inhibitor should be fungistatic rather than fungicidal under the conditions of use. Examples of inhibitors include antifungal compounds described by (e.g., Georgopapadakou & Walsh, Antimicrob. Ag. Chemother. 40, 279–291 (1996); Lyman & Walsh, Drugs 44, 9–35 (1992)). Other examples include chitin synthase inhibitors (polyoxin or nikkomycin compounds) and/or glucan synthase inhibitors (e.g. echinocandins, papulocandins, pneumocandins). Inhibitors should be applied in osmotically stabilized medium. Cells stripped of their cell walls can be fused or otherwise employed as donors or hosts in genetic transformation/strain development programs.

In a further variation, protoplasts are prepared using strains of fungi, which are genetically deficient or compromised in their ability to synthesize intact cell walls. Such mutants are generally referred to as fragile, osmotic-remedial, or cell wall-less, and are obtainable from strain depositories. Examples of such strains include *Neurospora crassa* os mutants (Selitrennikoff, Antimicrob. Agents. Chemother. 23, 757–765 (1983)). Some such mutations are temperature-sensitive. Temperature-sensitive strains can be propagated at the permissive temperature for purposes of selection and amplification and at a nonpermissive temperature for purposes of protoplast formation and fusion. A temperature sensitive strain *Neurospora crassa* os strain has been described which propagates as protoplasts when growth in osmotically stabilizing medium containing sorbose and polyoxin at nonpermissive temperature but generates whole cells on transfer to medium containing sorbitol at a permissive temperature. See U.S. Pat. No. 4,873,196.

Other suitable strains can be produced by targeted mutagenesis of genes involved in chitin synthesis, glucan synthesis and other cell wall-related processes. Examples of such genes include CHTI, CHT2 and CALI (or CSD2) of *Saccharomyces cerevisiae* and *Candida spp.* (Georgopapadakou & Walsh 1996); ETGI/FKSI/CNDI/CWH53/PB RI and homologs in *S. cerevisiae, Candida albicans, Cryptococcus neoformans, Aspergillus fumigatus,* ChvAINdvA Agrobacterium and Rhizobium. Other examples are M4, orlB, orlC, MD, tsE, and bimG of *Aspergillus nidulans* (Borgia, J Bacteriol. 174, 3 77–3 89 (1992)).

Strains of *A. nidulans* containing OrlA1 or tse1 mutations lyse at restrictive temperatures. Lysis of these strains may be prevented by osmotic stabilization, and the mutations may be complemented by the addition of N-acetylglucosimine (GlcNac). BimG11 mutations are ts for a type 1 protein phosphatase (germlines of strains carrying this mutation lack chitin, and condia swell and lyse). Other suitable genes are chsA, chsB, chsC, chsD and chsE of *Aspergillus fumigatus*; chs1 and chs2 of *Neurospora crassa;* Phycomyces blakesleeanus MM and chs 1, 2 and 3 of *S. cerevisiae.* Chs 1 is a non-essential repair enzyme; chs2 is involved in septum formation and chs3 is involved in cell wall maturation and bud ring formation.

Other useful strains include *S. cerevisiae* CLY (cell lysis) mutants such as ts strains (Paravicini et al., Mol. Cell Biol 12, 4896–4905 (1992)), and the CLY 15 strain which harbors a PKC 1 gene deletion. Other useful strains include strain VY 1160 containing a ts mutation in srb (encoding actin) (Schade et al. Acta Histochem. Suppl. 41, 193–200 (1991)), and a strain with an ses mutation which results in increased sensitivity to cell-wall digesting enzymes isolated from snail gut (Metha & Gregory, AppL Environ. Microbiol 41, 992–999 (1981)). Useful strains of *C albicans* include those with mutations in chs1, chs2, or chs3 (encoding chitin synthetases), such as osmotic remedial conditional lethal mutants described by Payton & de Tiani, Curr. Genet. 17, 293–296 (1990); *C. utilis* mutants with increased sensitivity to cell-wall digesting enzymes isolated from snail gut (Metha & Gregory, 1981, supra); and X crassa mutants os-1, os-2, os-3, os-4, os-5, and os-6. See, Selitrennikoff, Antimicrob. Agents Chemother. 23, 757–765 (1983). Such mutants grow and divide without a cell wall at 37 C., but at 22 C. produce a cell wall.

Targeted mutagenesis can be achieved by transforming cells with a positive-negative selection vector containing homologous regions flanking a segment to be targeted, a positive selection marker between the homologous regions and a negative selection marker outside the homologous regions (see Capecchi, U.S. Pat. No. 5,627,059). In a variation, the negative selection marker can be an antisense transcript of the positive selection marker (see U.S. Pat. No. 5,527,674).

Other suitable cells can be selected by random mutagenesis or stochastic &/or non-stochastic mutagenesis procedures in combination with selection. For example, a first subpopulation of cells are mutagenized, allowed to recover from mutagenesis, subjected to incomplete degradation of cell walls and then contacted with protoplasts of a second subpopulation of cells. Hybrids cells bearing markers from both subpopulations are identified (as described above) and used as the starting materials in a subsequent round of stochastic &/or non-stochastic mutagenesis. This selection scheme selects both for cells with capacity for spontaneous protoplast formation and for cells with enhanced recombinogenicity.

In a further variation, cells having capacity for spontaneous protoplast formation can be crossed with cells having enhanced recombinogenicity evolved using other methods of the invention. The hybrid cells are particularly suitable hosts for whole genome stochastic &/or non-stochastic mutagenesis.

Cells with mutations in enzymes involved in cell wall synthesis or maintenance can undergo fusion simply as a result of propagating the cells in osmotic-protected culture due to spontaneous protoplast formation. If the mutation is conditional, cells are shifted to a nonpermissive condition. Protoplast formation and fusion can be accelerated by addition of promoting agents, such as PEG or an electric field (See Philipova & Venkov, Yeast 6, 205–212 (1990); Tsoneva et al., FFMS Microbiol Lett. 51, 61–65 (1989)).

8.10 Process of Sexual Reproduction

Sexual reproduction provides a mechanism for stochastic &/or non-stochastic mutagenesis genetic material between cells. A sexual reproductive cycle is characterized by an alteration of a haploid phase and a diploid phase. Diploidy occurs when two haploid gamete nuclei fuse (karyogamy). The gamete nuclei can come from the same parental strains (self-fertile), such as in the homothallic fungi. In heterothallic fungi, the parental strains come from strains of different mating type.

A diploid cell converts to haploidy via meiosis, which essentially consists of two divisions of the nucleus accompanied by one division of the chromosomes. The products of one meiosis are a tetrad (4 haploid nuclei). In some cases, a mitotic division occurs after meiosis, giving rise to eight product cells. The arrangement of the resultant cells (usually enclosed in spores) resembles that of the parental strains. The length of the haploid and diploid stages differs in various fungi: for example, the Basidiomycetes and many of the Ascomycetes have a mostly haploid life cycle (that is, meiosis occurs immediately after karyogamy), whereas others (e.g., *Saccharomyces cerevisiae*) are diploid for most of their life cycle (karyogamy occurs soon after meiosis). Sexual reproduction can occur between cells in the same strain (selfing) or between cells from different strains (outcrossing).

Sexual dimorphism (dioecism) is the separate production of male and female organs on different mycelia. This is a rare phenomenon among the fungi, although a few examples are known. Heterothallism (one locus-two alleles) allows for outcrossing between crosscompatable strains which are self-incompatable. The simplest form is the two allele-one locus system of mating types/factors, illustrated by the following organisms: A and a in Neurospora; a and in Saccharomyces, plus and minus in Schizzosaccharomyces and Zygomycetes; $_1$ and $_2$ in Ustilago.

Multiple-allelomorph heterothallism is exhibited by some of the higher Basidiomycetes (e.g. Gasteromycetes and Hymenomycetes), which are heterothallic and have several mating types determined by multiple alleles. Heterothallism. In these organisms is either bipolar with one mating type factor, or tetrapolar with two unlinked factors, A and B. Stable, fertile heterokaryon formation depends on the presence of different A factors and, in the case of tetrapolar organisms, of different B factors as well. This system is effective in the promotion of outbreeding and the prevention of self-breeding. The number of different mating factors may be very large (i.e. thousands) (Kothe, FEMS Microbiol Rev. 18, 65–87 (1996)), and non-parental mating factors may arise by recombination.

8.10.1 Introducing Sexual Cycles 8.10.2 Meiosis 8.10.2.1 Heterokaryon-A Cell or Hypha Containing Two or More Nuclei of Different Genetic Constitutions One desired property is the introduction of meiotic apparatus into fungi presently lacking a sexual cycle (see Sharon et al., Mol. Gen. Genet. 251, 60–68 (1996)). A scheme for introducing a sexual cycle into the fungi *P. chrysogenum* (a fungus imperfecti) is shown herein. Subpopulations of protoplasts are formed from.4. nidulans (which has a sexual cycle) and *P. chrysogenum*, which does not. The two strains preferably bear different markers. The *A. nidulans* protoplasts are killed by treatment with UV or hydroxylamine. The two subpopulations are fused to form heterokaryons. In some heterokaryons, nuclei fuse, and some recombination occurs. Fused cells are cultured under conditions to generate new cell walls and then to allow sexual recombination to occur. Cells with recombinant genomes are then selected (e.g., by selecting for complementation of auxotrophic markers present on the respective parent strains). Cells with hybrid genomes are more likely to have acquired the genes necessary for a sexual cycle. Protoplasts of cells can then be crossed with killed protoplasts of a further population of cells known to have a sexual cycle (the same or different as the previous round) in the same manner, followed by selection for cells with hybrid genomes.

8.10.2.2 Vegetative Compatibility Between Classes of Fungi

Within the above four classes, fungi are also classified by vegetative compatibility group. Fungi within a vegetative compatibility group can form heterokaryons with each other. Thus, for exchange of genetic material between different strains of fungi, the fungi are usually prepared from the same vegetative compatibility group. However, some genetic exchange can occur between fungi from different incompatibility groups as a result of parasexual reproduction (see Timberlake et al., U.S. Pat. No. 5,605,820). Further, as discussed elsewhere, the natural vegetative compatibility group of fungi can be expanded as a result of stochastic &/or non-stochastic mutagenesis.

Several isolates of *Aspergillus nidulans, A. flavus, A. fumigatus, Penicillium chrysogenum, P. notatum, Cephalosporium chrysogenum, Neurospora crassa, Aureobasidium pullulans* have been karyotyped. Genome sizes generally range between 20 and 50 Mb among the Aspergilli. Differences in karyotypes often exist between similar strains and are also caused by transformation with exogenous DNA. Filamentous fungal genes contain introns, usually ~50–100 bp in size, with similar consensus 5' and 3' splice sequences. Promotion and termination signals are often cross-recognizable, enabling the expression of a gene/pathway from one fungus (e.g. *A. nidulans*) in another (e.g. *P. chrysogenum*). The major components of the fungal cell wall are chitin (or chitosan), beta-glucan, and mannoproteins. Chitin and beta-glucan form the scaffolding, mannoproteins are interstitial components which dictate the wall's porosity, antigenicity and adhesion. Chitin synthetase catalyzes the polymerization of beta-(1,4)-linked N-acetylglucosamine (GlcNAc) residues, forming linear strands running antiparallel; beta-(1,3)-glucan synthetase catalyze the homopolymerization of glucose.

8.11 Evolution 8.11.1 Artificially Evolving Cells to Acquire a New or Improved Property by Stochastic &/or Non-Stochastic Mutagenesis The invention provides a number of strategies for evolving metabolic and bioprocessing pathways through the technique of recursive sequence recombination. One strategy entails evolving genes that confer the ability to use a particular substrate of interest as a nutrient source in one species to confer either more efficient use of that substrate in that species, or comparable or more efficient use of that substrate in a second species. Another strategy entails evolving genes that confer the ability to detoxify a compound of interest in one or more species of organisms. Another strategy entails evolving new metabolic pathways by evolving an enzyme or metabolic pathway for biosynthesis or degradation of a compound A related to a compound B for the ability to biosynthesize or degrade compound B, either in the host of origin or a new host. A further strategy entails evolving a gene or metabolic pathway for more efficient or optimized expression of a particular metabolite or gene product. A further strategy entails evolving a host/vector system for expression of a desired heterologous product. These strategies may involve using all the genes in a multi-step pathway, one or several genes, genes from different organisms, or one or more fragments of a gene.

The strategies generally entail evolution of gene(s) or segment(s) thereof to allow retention of function in a heterologous cell or improvement of function in a homologous or heterologous cell. Evolution is effected generally by a process termed recursive sequence recombination. Recursive sequence recombination can be achieved in many different formats and permutations of formats, as described in further detail below. These formats share some common principles. Recursive sequence recombination entails successive cycles of recombination to generate molecular diversity, i.e., the creation of a family of nucleic acid molecules showing substantial sequence identity to each other but differing in the presence of mutations. Each recombination cycle is followed by at least one cycle of screening or selection for molecules having a desired characteristic. The molecule(s) selected in one round form the starting materials for generating diversity in the next round. In any given cycle, recombination can occur in vivo or in vitro. Furthermore, diversity resulting from recombination can be augmented in any cycle by applying prior methods of mutagenesis (e.g., error-prone PCR or cassette mutagenesis, passage through bacterial mutator strains, treatment with chemical mutagens) to either the substrates for or products of recombination.

8.11.2 Basic Approach 8.11.2.1 Successive Cycles of Recombination and Screening/Selection The invention provides methods for artificially evolving cells to acquire a new or improved property by recursive sequence recombination. Briefly, recursive sequence recombination entails successive cycles of recombination to generate molecular diversity and screening/selection to take advantage of that molecular diversity. That is, a family of nucleic acid molecules is created showing substantial sequence and/or structural identity but differing as to the presence of mutations. These sequences are then recombined in any of the described formats so as to optimize the diversity of mutant combinations represented in the resulting recombined library. Typically, any resulting recombinant nucleic acids or genomes are recursively recombined for one or more cycles of recombination to increase the diversity of resulting products. After this recursive recombination procedure, the final resulting products are screened and/or selected for a desired trait or property.

Alternatively, each recombination cycle can followed by at least one cycle of screening or selection for molecules having a desired characteristic. In this embodiment, the molecule(s) selected in one round form the starting materials for generating diversity in the next round.

The cells to be evolved can be bacteria, archaebacteria, or eukaryotic cells and can constitute a homogeneous cell line or mixed culture. Suitable cells for evolution include the bacterial and eukaryotic, cell lines commonly used in genetic engineering, protein expression, or the industrial production or conversion of proteins, enzymes, primary metabolites, secondary metabolites, fine, specialty or commodity chemicals. Suitable mammalian cells include those from, e.g., mouse, rat, hamster, primate, and human, both cell fines and primary cultures. Such cells include stem cells, including embryonic stem cells and hemopoietic stem cells, zygotes, fibroblasts, lymphocytes, Chinese hamster ovary (CHO), mouse fibroblasts (NIHM), kidney, liver, muscle, and skin cells. Other eukaryotic cells of interest include plant cells, such as maize, rice, wheat, cotton, soybean, sugarcane, tobacco, and arabidopsis; fish, algae, fungi (penicillium, aspergillus, podospora, neurospora, saccharomyces), insect (e.g., baculo lepidoptera), yeast (picchia and saccharomyces, Schizosaccharomycespombe). Also of interest are many bacterial cell types, both gramnegative and gram-positive, such as *Bacillus subtilis, B. licehniformis, B. cereus, Escherichia coli,* Streptomyces, Pseudomonas, Salmonella, Actinomycetes, Lactobacillius, Acelonitcbacter, Deinococcus, and Erwinia. The complete genome sequences of *E. coli* and *Bacillus subtilis* are described by Blattner et al., Science 277, 1454–1462 (1997); Kunst et al., Nature 390, 249–256 (1997)

8.11.2.1.1 Goal Is to Achieve Variaton

Evolution commences by generating a population of variant cells. Typically, the cells in the population are of the same type but represent variants of a progenitor cell. in some instances, the variation is natural as when different cells are obtained from different individuals within a species, from different species or from different genera. in other instances, variation is induced by mutagenesis of a progenitor cell. Mutagenesis can be effected by subjecting the cell to mutagenic agents, or if the cell is a mutator cell (e.g., has mutations in genes involved in DNA replication, recombination and/or repair which favor introduction of mutations) simply by propagating the mutator cells. Mutator cells can be generated from successive selections for simple phenotypic changes (e.g., acquisition of rifampicin-resistance, then nalidixic acid resistance then lac– to lac+ (see Mao et al., J Bacteriol 179, 417–422 (1997)), or mutator cells can be generated by exposure to specific inhibitors of cellular factors that result in the mutator phenotype. These could be inhibitors of mutS, mutL, mutD, recD, mutY, mutM, dam, uvrD and the like.

More generally, mutations are induced in cell populations using any available mutation technique. Common mechanisms for inducing mutations include, but are not limited to, the use of strains comprising mutations such as those involved in mismatch repair. e.g. mutations in mutS, mutT, mutL and mutH; exposure to UV light; Chemical mutagenesis, e.g. use of inhibitors of MMR, DNA damage inducible genes, or SOS inducers; overproduction/ underproduction/mutation of any component of the homologous recombination complex/pathway, e.g. RecA, ssb, etc. overproduction/underproduction/mutation of genes 9 involved in DNA synthesis/homeostasis; overproduction/ underproduction/mutation of recombination-stimulating genes from bacteria, phage (e.g. Lambda Red function ), or other organisms; addition of chi sites into/flanking the donor DNA fragments; coating the DNA fragments with RecA/ssb and the like.

In other instances, variation is the result of transferring a library of DNA fragments into the cells (e.g., by conjugation, protoplast fusion, liposome fusion, transformation, transduction or natural competence). At least one, and usually many of the fragments in the library, show some, but not complete, sequence or structural identity with a cognate or allelic gene within the cells sufficient to allow homologous recombination to occur.

For example, in one embodiment, homologous integration of a plasmid carrying a stochastic &/or non-stochastic mutagenized gene or metabolic pathway leads to insertion of the plasmid-borne sequences adjacent to the genomic copy. Optionally, a counter-selectable marker strategy is used to select for recombinants in which recombination occurred between the homologous sequences, leading to elimination of the counter-selectable marker. A variety of selectable and counter selectable markers are amply illustrated in the art. For a fist of useful markers, see, Berg and Berg (1996), Transposable element tools for microbial genetics, *Escherichia coli* and *Salmonella Neidhardt.* Washington, D.C., ASM Press. 2: 2588–2612; La Rossa, ibid., 2527–2587. This strategy can be recursively repeated to maximize sequence diversity of targeted genes prior to screening/selection for a desired trait or property.

The library of fragments can derive from one or more sources. One source of fragments is a genomic library of fragments from a different species, cell type, organism or individual from the cells being transfected. In this situation, many of the fragments in the library have a cognate or allelic gene in the cells being transformed but differ from that gene due to the presence of naturally occurring species variation, polymorphisms, mutations, and the presence of multiple copies of some homologous genes in the genome. Alternatively, the library can be derived from DNA from the same cell type as is being transformed after that DNA has been subject to induced mutation, by conventional methods, such as radiation, error-prone PCR, growth in a mutator organism, transposon mutagenesis, or cassette mutagenesis.

Alternatively, the library can derive from a genomic library of fragments generated from the pooled genomic DNA of a population of cells having the desired characteristics. Alternatively, the library can derive from a genomic library of fragments generated from the pooled genomic DNA of a population of cells having desired characteristics.

In any of these situations, the genomic library can be a complete genomic library or subgenome & library deriving, for example, from a selected chromosome, or part of a chromosome or an episomal element within a cell. As well as, or instead of these sources of DNA fragments, the library can contain fragments representing natural or selected variants of selected genes of known function (i.e., focused libraries).

The number of fragments in a library can vary from a single fragment to about $10^{10}$ with libraries having from $10^3$ to $10^8$ fragments being common. The fragments should be sufficiently long that they can undergo homologous recombination and sufficiently short that they can be introduced into a cell, and if necessary, manipulated before introduction. Fragment sizes can range from about 10 b to about 20 mb. Fragments can be double- or single-stranded. The fragments can be introduced into cells as whole genomes or as components of viruses, plasmids, YACS, HACs or BACs or can be introduced as they are, in which case all or most of the fragments lack an origin of replication. Use of viral fragments with single-stranded genomes offer the advantage of delivering fragments in single stranded form, which promotes recombination. The fragments can also be joined to a selective marker before introduction. Inclusion of fragments in a vector having an origin of replication affords a longer period of time after introduction into the cell in which fragments can undergo recombination with a cognate gene before being degraded or selected against and lost from the cell, thereby increasing the proportion of cells with recombinant genomes. Optionally, the vector is a suicide vector capable of a longer existence than an isolated DNA fragment but not capable of permanent retention in the cell line. Such a vector can transiently express a marker for a sufficient time to screen for or select a cell bearing the vector (e.g., because cells transduced by the vector are the target cell type to be screened in subsequent selection assays), but is then degraded or otherwise rendered incapable of expressing the marker. The use of such vectors can be advantageous in performing optional subsequent rounds of recombination to be discussed below. For example, some suicide vectors express a long-lived toxin which is neutralized by a short-lived molecule expressed from the same vector. Expression of the toxin alone will not allow vector to be established. Jense & Gerdes, Mol. Microbiol, 17, 205–210 (1995); Bernard et al., Gene 162, 159–160. Alternatively, a vector can be rendered suicidal by incorporation of a defective origin of replication (e.g. a temperature-sensitive origin of replication) or by omission of an origin of replication. Vectors can also be rendered suicidal by inclusion of negative selection markers, such as ura3 in yeast or sacB in many bacteria.

These genes become toxic only in the presence of specific compounds. Such vectors can be selected to have a wide range of stabilities. A list of conditional replication defects for vectors which can be used, e.g., to render the vector replication defective is found, e.g., in Berg and Berg (1996), "Transposable element tools for microbial genetics" *Escherichia coli* and *Salmonella Neidhardt*. Washington, D.C., ASM Press. 2: 2588–2612. Similarly, a fist of counter selectable markers, generally applicable to vector selection is also found in Berg and Berg, id. See also, LaRossa (1996), "Mutant selections linking physiology, inhibitors, and genotypes" *Escherichia coli* and Salmonella F. C. *Neidhardt*, Washington, D.C., ASM Press. 2: 2527–2587.

After introduction into cells, the fragments can recombine with DNA present in the genome, or episomes of the cells by homologous, nonhomologous or site-specific recombination. For present purposes, homologous recombination makes the most significant contribution to evolution of the cells because this form of recombination amplifies the existing diversity between the DNA of the cells being transfected and the DNA fragments. For example, if a DNA fragment being transfected differs from a cognate or allelic gene at two positions, there are four possible recombination products, and each of these recombination products can be formed in different cells in the transformed population. Thus, homologous recombination of the fragment doubles the initial diversity in this gene. When many fragments recombine with corresponding cognate or allelic genes, the diversity of recombination products with respect to starting products increases exponentially with the number of mutations. Recombination results in modified cells having modified genomes and/or episomes. Recursive recombination prior to selection further increases diversity of resulting modified cells.

The variant cells, whether the result of natural variation, mutagenesis, or recombination are screened or selected to identify a subset of cells that have evolved toward acquisition of a new or improved property. The nature of the screen, of course, depends on the property and several examples will be discussed below. Typically, recombination is repeated before initial screening. Optionally, however, the screening can also be repeated before performing subsequent cycles of recombination. Stringency can be increased in repeated cycles of screening. The subpopulation of cells surviving screening are optionally subjected to a further round of recombination. In some instances, the further round of recombination is effected by propagating the cells under conditions allowing exchange of DNA between cells. For example, protoplasts can be formed from the cells, allowed to fuse, and regenerated. Cells with recombinant genomes are propagated from the fused protoplasts. Alternatively, exchange of DNA can be promoted by propagation of cells or protoplasts in an electric field. For cells having a conjugative transfer apparatus, exchange of DNA can be promoted simply by propagating the cells.

8.11.2.1.2 Using Two Separate Pools: Amplify First Pool and Add to Second Pool

In other methods, the further round of recombination is performed by a split and pool approach. That is, the surviving cells are divided into two pools. DNA is isolated from one pool, and if necessary amplified, and then transformed into the other pool.

Accordingly, DNA fragments from the first pool constitute a further library of fragments and recombine with cognate fragments in the second pool resulting in further diversity. As shown, a pool of mutant bacteria with improvements in a desired phenotype is obtained and split. Genes are obtained from one half, e.g., by PCR, by cloning of random genomic fragments, by infection with a transducing phage and harvesting transducing particles, or by the introduction of an origin of transfer (OriT) randomly into the relevant chromosome to create a donor population of cells capable of transferring random fragments by conjugation to an acceptor population. These genes are then stochastic &/or non-stochastic mutagenized (in vitro by known methods or in vivo as taught herein), or simply cloned into an allele replacement vector (e.g., one carrying selectable and counter-selectable markers). The gene pool is then transformed into the other half of the original mutant pool and recombinants are selected and screened for further improvements in phenotype. These best variants are used as the starting point for the next cycle. Alternatively, recursive recombination by any of the methods noted can be performed prior to screening, thereby increasing the diversity of the population of cells to be screened.

8.11.2.1.3 Surviving Cells are Transfected into Fresh DNA

In other methods, some or all of the cells surviving screening are transfected with a fresh library of DNA fragments, which can be the same or different from the library used in the first round of recombination. In this situation, the genes in the fresh library undergo recombination with cognate genes in the surviving cells. If genes are introduced as components of a vector, compatibility of this vector with any vector used in a previous round of transfection should be considered. If the vector used in a previous round was a suicide vector, there is no problem of incompatibility. If, however, the vector used in a previous round was not a suicide vector, a vector having a different incompatibility origin should be used in the subsequent round. In all of these formats, further recombination generates additional diversity in the DNA component of the cells resulting in further modified cells.

The further modified cells are subjected to another round of screening/selection according to the same principles as the first round. Screening/selection identifies a subpopulation of further modified cells that have further evolved toward acquisition of the property. This subpopulation of cells can be subjected to further rounds of recombination and screening according to the same principles, optionally with the stringency of screening being increased at each round. Eventually, cells are identified that have acquired the desired property.

8.11.3 Variations 8.11.3.1 Coating with RecA to Enrich Diversity of Homologous Recombination The frequency of homologous recombination between library fragments and cognate endogenous genes can be increased by coating the fragments with a recombinogenic protein before introduction into cells. See Pati et al., Molecular Biology of Cancer 1, 1 (1996); Sena & Zarling, Nature Genetics 3, 365 (1996); Revet et al., J Mol. Biol. 232, 779–791 (1993); Kowalczkowski & Zarling in Gene Targeting (CRC 1995), Ch. 7. The recombinogenic protein promotes homologous pairing and/or strand exchange. The best characterized recA protein is from E. coli and is available from Pharmacia (Piscataway, N.J.).

In addition to the wild-type protein, a number of mutant recA-like proteins have been identified (e.g., recA803). Further, many organisms have recA-like recombinases with strand-transfer activities (e.g., Ogawa et al., Cold Spring Harbor Symposium on Quantitative Biology 18, 567–576 (1993); Johnson & Symington, Mol. Cell. Biol. 15, 4843–4850 (1995); Fugisawa et al., Nucl. Acids Res. 13, 7473 (1985); Hsieh et al., Cell 44, 885 (1986); Hsieh et al., J Biol. Chem. 264, 5089 (1989); Fishel et al., Proc. Nail. Acad. Sci. USA 85, 3683 (1988); Cassuto et al., Mol. Gen. Genet. 208, 10 (1987); Ganea et al., Mol. Cell Biol. 7, 3124 (1987); Moore et al., J Biol. Chem. 19, 11108 (1990); Keene et al., Nucl. Acids Res. 12, 3057 (1984); Kimiec, Cold Spring Harbor Symp. 48, 675 (1984); Kimeic, Cell 44, 545 (1986); Kolodner et al., Proc. Nad. Acad Sci. USA 84, 5560 (1987); Sugino et al., Proc. Natl Acad Sci. USA 85, 3683 (1985). Halbrook et al., J. Biol Chem. 264, 21403 (1989); Eisen et al., Proc. Natl. Acad. Sci. USA 85, 7481 (1988); McCarthy et al., Proc. Natl. Acad Sci. USA 85, 5854 (1988). Lowenhaupt et al., J Biol. Chem. 264, 20568 (1989). Examples of such recombinase proteins include recA, recA803, uvsX, (Roca, A. I., Crit. Rev. Biochem. Molec. Biol. 25, 415 (1990)), sepI (Kolodner et al., Proc. Natl. Acad. Sci. (U.S.A.) 84, 5560 (1987); Tishkoffetal., Molec. Cell. Biol 11, 2593), RuvC (Dunderdale et al., Nature 354, 506 (1991)), DS72, KEMI, XRATI (Dykstra et al., Molec. Cell. Biol 11, 25 83 (1991)), STP/DST1 (Clark et al., Molec. Cell. Biol 11, 2576 (1991)), HPP-I (Moore et al., Proc. Natl. Acad. Sci. (U.S.A.) 88, 9067 (1991)), other eukaryotic recombinases (Bishop et al., Cell 69, 439 (1992); Shinohara et al., Cell 69, 457. RecA protein forms a nucleoprotein filament when it coats a single-stranded DNA. In this nucleoprotein filament, one monomer of recA protein is bound to about 3 nucleotides. This property of recA to coat single-stranded DNA is essentially sequence independent, although particular sequences favor initial loading of recA onto a polynucleotide (e.g., nucleation sequences). The nucleoprotein filament(s) can be formed on essentially any DNA to be stochastic &/or non-stochastic mutagenized and can form complexes with both single-stranded and double-stranded DNA in prokaryotic and eukaryotic cells.

Before contacting with recA or other recombinase, fragments are often denatured, e.g., by heat-treatment. RecA protein is then added at a concentration of about 1–10 gM. After incubation, the recA-coated single-stranded DNA is introduced into recipient cells by conventional methods, such as chemical transformation or electroporation. In general, it can be desirable to coat the DNA with a RecA homolog isolated from the organism into which the coated DNA is being delivered. Recombination involves several cellular factors and the host RecA equivalent generally interacts better with other host factors than less closely related RecA molecules. The fragments undergo homologous recombination with cognate endogenous genes. Because of the increased frequency of recombination due to recombinase coating, the fragments need not be introduced as components of vectors. Fragments are sometimes coated with other nucleic acid binding proteins that promote recombination, protect nucleic acids from degradation, or target nucleic acids to the nucleus. Examples of such proteins includes Agrobacterium virE2 (Duffenberger et al., Proc. Natl. Acad. Sci. USA 86, 9154–9158 (1989)). Alternatively, the recipient strains are deficient in RecD activity. Single stranded ends can also be generated by 3'–5' exonuclease activity or restriction enzymes producing 5' overhangs.

8.11.3.2 Affinity Chromatography with Muts to Enrich for Fragments Having at Least One Mismatch The E. coli mismatch repair protein MutS can be used in affinity chromatography to enrich for fragments of double-stranded DNA containing at least one base of mismatch. The MutS protein recognizes the bubble formed by the individual strands about the point of the mismatch. See, e.g., Hsu & Chang, WO 9320233. The strategy of affinity enriching for partially mismatched duplexes can be incorporated into the present methods to increase the diversity between an incoming library of fragments and corresponding cognate or allelic genes in recipient cells.

MutS is used to increase diversity. The DNA substrates for enrichment are substantially similar to each other but differ at a few sites.

For example, the DNA substrates can represent complete or partial genomes (e.g., a chromosome library) from different individuals with the differences being due to polymorphisms. The substrates can also represent induced mutants of a wild type sequence.

The DNA substrates are pooled, restriction digested, and denatured to produce fragments of single-stranded DNA. The single-stranded DNA is then allowed to reanneal. Some single-stranded fragments reanneal with a perfectly matched complementary strand to generate perfectly matched duplexes. Other single-stranded fragments anneal to generate mismatched duplexes. The mismatched duplexes are enriched from perfectly matched duplexes by MutS chromatography (e.g., with MutS immobilized to beads). The mismatched duplexes recovered by chromatography are introduced into recipient cells for recombination with cognate endogenous genes as described above. MutS affinity chromatography increases the proportion of fragments differing from each other and the cognate endogenous gene. Thus, recombination between the incoming fragments and endogenous genes results in greater diversity.

A second strategy for MutS enrichment. In this strategy, the substrates for MutS enrichment represent variants of a relatively short segment, for example, a gene or cluster of genes, in which most of the different variants differ at no more than a single nucleotide. The goal of MutS enrichment is to produce substrates for recombination that contain more variations than sequences occurring in nature. This is achieved by fragmenting the substrates at random to produce overlapping fragments. The fragments are denatured and reannealed as in the first strategy. Reannealing generates some mismatched duplexes which can be separated from perfectly matched duplexes by MutS affinity chromatography. As before, MutS chromatography enriches for duplexes bearing at least a single mismatch. The mismatched duplexes are then stochastic &/or non-stochastic mutagenized into longer fragments. This is accomplished by cycles of denaturation, reannealing, and chain extension of partially annealed duplexes. After several such cycles, fragments of the same length as the original substrates are achieved, except that these fragments differ from each other at multiple sites. These fragments are then introduced into cells where they undergo recombination with cognate endogenous genes.

8.11.3.3 Suicide Vector Enriches Mutations for Cells that Have Integrated the Vector into the Host Chromosome The invention further provides methods of enriching for cells bearing modified genes relative to the starting cells. This can be achieved by introducing a DNA fragment library (e.g., a single specific segment or a whole or partial genomic library) in a suicide vector (i.e., lacking a functional replication origin in the recipient cell type) containing both positive and negative selection markers. Optionally, multiple fragment libraries from different sources (e.g., *B. sublilis, B. lichenifonnis and B. cereus*) can be cloned into different vectors bearing different selection markers. Suitable positive selection markers include $neo^R$, $kanamycin^R$, hyg, hisD, gpt, ble, $tet^R$. Suitable negative selection markers include hsv-tk, hprt, gpt, SacB ura3 and cytosine deaminase. A variety of examples of conditional replication vectors, mutations affecting vector replication, limited host range vectors, and counterselectable markers are found in Berg and Berg, supra, and LaRossa, ibid. and the references therein.

In one example, a plasmid with R6K and fl origins of replication, a positively selectable marker (beta-lactamase), and a counterselectable marker (*B. subtilis* sacB) was used. M13 transduction of plasmids containing cloned genes were efficiently recombined into the chromosomal copy of that gene in a rep mutant *E. coli* strain.

Another strategy for applying negative selection is to include a wild type rpsL gene (encoding ribosomal protein S12) in a vector for use in cells having a mutant rpsL gene conferring streptomycin resistance. The mutant form of rpsL is recessive in cells having wild type rpsL. Thus, selection for Sm resistance selects against cells having a wild type copy of rpsL. See Skorupski & Taylor, Gene 169, 47–52 (1 996). Alternatively, vectors bearing only a positive selection marker can be used with one round of selection for cells expressing the marker, and a subsequent round of screening for cells that have lost the marker (e.g., screening for drug sensitivity). The screen for cells that have lost the positive selection marker is equivalent to screening against expression of a negative selection marker. For example, Bacillus can be transformed with a vector bearing a CAT gene and a sequence to be integrated. See Harwood & Cutting, Molecular Biological Methods for Bacillus, at pp. 31–33. Selection for chloramphenicol resistance isolates cells that have taken up vector. After a suitable period to allow recombination, selection for CAT sensitivity isolates cells which have lost the CAT gene. About 50% of such cells will have undergone recombination with the sequence to be integrated.

Suicide vectors bearing a positive selection marker and optionally, a negative selection marker and a DNA fragment can integrate into host chromosomal DNA by a single crossover at a site in chromosomal DNA homologous to the fragment. Recombination generates an integrated vector flanked by direct repeats of the homologous sequence. In some cells, subsequent recombination between the repeats results in excision of the vector and either acquisition of a desired mutation from the vector by the genome or restoration of the genome to wild type.

In the present methods, after transfer of the gene library cloned in a suitable vector, positive selection is applied for expression of the positive selection marker. Because nonintegrated copies of the suicide vector are rapidly eliminated from cells, this selection enriches for cells that have integrated the vector into the host chromosome. The cells surviving positive selection can then be propagated and subjected to negative selection, or screened for loss of the positive selection marker. Negative selection selects against cells expressing the negative selection marker. Thus, cells that have retained the integrated vector express the negative marker and are selectively eliminated. The cells surviving both rounds of selection are those that initially integrated and then eliminated the vector. These cells are enriched for cells having genes modified by homologous recombination with the vector. This process diversifies by a single exchange of genetic information. However, if the process is repeated either with the same vectors or with a library of fragments generated by PCR of pooled DNA from the enriched recombinant population, resulting in the diversity of targeted genes being enhanced exponentially each round of recombination. This process can be repeated recursively, with selection being performed as desired.

8.11.3.4 Exploiting Known Information Such as Map Location or Function

In general, the above methods do not require knowledge of the number of genes to be optimized, their map location or their function. However, in some instances, where this information is available for one or more gene, it can be exploited. For example, if the property to be acquired by evolution is enhanced recombination of cells, one gene likely to be important is recA, even though many other genes, known and unknown, may make additional contributions. In this situation, the recA gene can be evolved, at least in part, separately from other candidate genes. The recA gene can be evolved by any of the methods of recursive recombination described in Section V. Briefly, this approach entails obtaining, diverse forms of a recA gene, allowing the forms to recombine, selecting recombinants having improved properties, and subjecting the recombinants to further cycles of recombination and selection. At any point in the individualized improvement of recA, the diverse forms of recA can be pooled with fragments encoding other genes in a library to be used in the general methods described herein. In this way, the library is seeded to contain a higher proportion of variants in a gene known to be important to the property sought to be acquired than would otherwise be the case.

In one example, a plasmid is constructed carrying a non-functional (mutated) version of a chromosomal gene such as URA3, where the wild-type gene confers sensitivity to a drug (in this case 5-fluoro orotic acid). The plasmid also carries a selectable marker (resistance to another drug such as kanamycin), and a library of recA variants. Transformation of the plasmid into the cell results in expression of the recA variants, some of which will catalyze homologous recombination at an increased rate. Those cells in which homologous recombination occurred are resistant to the selectable drug on the plasmid, and to 5-fluoro orotic acid because of the disruption of the chromosomal copy of this gene.

The recA variants which give the highest rates of homologous recombination are the most highly represented in a pool of homologous recombinants. The mutant recA genes can be isolated from this pool by PCR, re-stochastic &/or non-stochastic mutagenized, cloned back into the plasmid and the process repeated. Other sequences can be inserted in place of recA to evolve other components of the homologous recombination system.

8.11.3.5 Using Own Harvest of Cells So No Impurities

In some stochastic &/or non-stochastic mutagenesis methods, DNA substrates are isolated from natural sources and are not easily manipulated by DNA modifying or polymerizing enzymes due to recacitrant impurities, which poison enzymatic reactions. Such difficulties can be avoided by processing DNA substrates through a harvesting strain. The harvesting strain is typically a cell type with natural competence and a capacity for homologous recombination between sequences with substantial diversity (e.g., sequences exhibiting only 75% sequence identity). The harvesting strain bears a vector encoding a negative selection marker flanked by two segments respectively complementary to two segments flanking a gene or other region of interest in the DNA from a target organism. The harvesting strain is contacted with fragments of DNA from the target organism. Fragments are taken up by natural competence, or other methods described herein, and a fragment of interest from the target organism recombines with the vector of the harvesting strain causing loss of the negative selection marker. Selection against the negative marker allows isolation of cells that have taken up the fragment of interest.

Stochastic &/or non-stochastic mutagenesis can be carried out in the harvester strain (e.g., a RecE/T strain) or vector can be isolated from the harvester strain for in vitro stochastic &/or non-stochastic mutagenesis or transfer to a different cell type for in vivo stochastic &/or non-stochastic mutagenesis. Alternatively, the vector can be transferred to a different cell type by conjugation, protoplast fusion or electrofusion. An example of a suitable harvester strain is Acinelobacter calcoaceticus mutS. Melnikov and Youngman, (1999) Nucl Acid Res 27(4):1056–1062. This strain is naturally competent and takes up DNA in a nonsequence-specific manner. Also, because of the mutS mutation, this strain is capable of homologous recombination of sequences showing only 75% sequence identity.

8.12 Further Applications 8.12.1 Improved Recombinancy

One goal of whole cell evolution is to generate cells having improved capacity for recombination. Such cells are useful for a variety of purposes in molecular genetics including the in vivo formats of recursive sequence recombination described in Section V. Almost thirty genes (e.g., recA, recB, recC, recD, recE, recF, recG, recO, recQ, recR, recT, ruvA, ruvB, ruvC, sbcB, ssb, topA, gyrA and B, lig, polA, uvrD, E, recL, mutD, mutH, mutL, mutT, mutU, helD) and DNA sites (e.g., chi, recN, sbcC) involved in genetic recombination have been identified in E. coli, and cognate forms of several of these genes have been found in other organisms (e.g., rad51, rad55-rad57, Dmc1 in yeast (see Kowalczykowski et al., Microbiol. Rev. 58, 401–465 (1994); Kowalczkowski & Zarling, supra) and human homologs of Rad51 and Dmc1 have been identified (see Sandier et al., Nucl. Acids Res. 24, 2125–2132 (1996)). At least some of the E. coli genes, including recA are functional in mammalian cells, and can be targeted to the nucleus as a fusion with SV40 large T antigen nuclear targeting sequence (Reiss et al., Proc. Mad. Acad. Sci. USA, 93, 3094–3098 (1996)). Further, mutations in mismatch repair genes, such as mutL, mutS, mutH mutT relax homology requirements and allow recombination between more diverged sequences (Rayssiguier et al., Nature 342, 396–401 (1989)). The extent of recombination between divergent strains can be enhanced by impairing mismatch repair genes and stimulating SOS genes. Such can be achieved by use of appropriate mutant strains and/or growth under conditions of metabolic stress, which have been found to stimulate SOS and inhibit mismatch repair genes. Vulic et al., Proc. Mad. Acad. Sci. USA 94 (1997). In addition, this can be achieved by impairing the products of mismatch repair genes by exposure to selective inhibitors.

Starting substrates for recombination are selected according to the general principles described above. That is, the substrates can be whole genomes or fractions thereof containing recombination genes or sites. Large libraries of essentially random fragments can be seeded with collections of fragments constituting variants of one or more known recombination genes, such as recA. Alternatively, libraries can be formed by mixing variant forms of the various known recombination genes and sites.

8.12.2 Expression of GFP Indicates Cell is Capable of Homologous Recombination

The library of fragments is introduced into the recipient cells to be improved and recombination occurs, generating modified cells. The recipient cells preferably contain a marker gene whose expression has been disabled in a manner that can be corrected by recombination. For example, the cells can contain two copies of a marker gene bearing mutations at different sites, which copies can recombine to generate the wild type gene. A suitable marker gene is green fluorescent protein. A vector can be constructed encoding one copy of GFP having stop codons near the N-terminus, and another copy of GFP having stop codons near the C-terminus of the protein. The distance between the stop codons at the respective ends of the molecule is 500 bp and about 25% of recombination events result in active GFP. Expression of GFP in a cell signals that a cell is capable of homologous recombination to recombine in between the stop codons to generate a contiguous coding sequence. By screening for cells expressing GFP, one enriches for cells having the highest capacity for recombination. The same type of screen can be used following subsequent rounds of recombination. However, unless the selection marker used in previous round(s) was present on a suicide vector, subsequent round(s) should employ a second disabled screening marker within a second vector bearing a different origin of replication or a different positive selection marker to vectors used in the previous rounds.

8.12.3 Increased Genome Copy Number So More Chromosomes Per Bacterial Cell to Make Evolution Quicker The majority of bacterial cells in stationary phase cultures grown in rich media contain two, four or eight genomes. In minimal medium the cells contain one or two genomes. The number of genomes per bacterial cell thus depends on the growth rate of the cell as it enters stationary phase. This is because rapidly growing cells contain multiple replication forks, resulting in several genomes in the cells after termination. The number of genomes is strain dependent, although all strains tested have more than one chromosome in stationary phase. The number of genomes in stationary phase cells decreases with time. This appears to be due to fragmentation and degradation of entire chromosomes, similar to apoptosis in mammalian cells. This fragmentation of genomes in cells containing multiple genome copies results in massive recombination and mutagenesis. Useful mutants may find ways to use energy sources that will allow them to continue growing. Multigenome or gene-redundant cells are much more resistant to mutagenesis and can be improved for a selected trait faster.

Some cell types, such as Deinococcus radians (Daly and Minton J Bacteriol 177, 5495–5505 (1995)) exhibit polyploidy throughout the cell cycle. This cell type is highly radiation resistant due to the presence of many copies of the genome. High frequency recombination between the genomes allows rapid removal of mutations induced by a variety of DNA damaging agents.

A goal of the present methods is to evolve other cell types to have increased genome copy number akin to that of Deinoccocus radians. Preferably, the increased copy number is maintained through all or most of its cell cycle in all or most growth conditions. The presence of multiple genome copies in such cells results in a higher frequency of homologous recombination in these cells, both between copies of a gene in different genomes within the cell, and between a genome within the cell and a transfected fragment. The increased frequency of recombination allows the cells to be evolved more quickly to acquire other useful characteristics.

Starting substrates for recombination can be a diverse library of genes only a few of which are relevant to genomic copy number, a focused library formed from variants of gene(s) known or suspected to have a role in genomic copy number or a combination of the two. As a general rule one would expect increased copy number would be achieved by evolution of genes involved in replication and cell septation such that cell septation is inhibited without impairing replication. Genes involved in replication include tus, xerC, xerD, dif, gyrA, gyrB, parE, parC, dif, TerA, TerB, TerC, TerD, TerE, TerF, and genes influencing chromosome partitioning and gene copy number include minD, mukA (tolC), mukb, mukC, mukD, spoOJ, spoIIIE (Wake & Errington, Annu. Rev. Genet. 29, 41–67 (1995)). A useful source of substrates is the genome of a cell type such as Deinoccocus radians known to have the desired phenotype of multigenomic copy number. As well as, or instead of, the above substrates, fragments encoding protein or antisense RNA inhibitors to genes known to be involved in cell septation can also be used. In nature, the existence of multiple genomic copies in a cell type would usually not be advantageous due to the greater nutritional requirements needed to maintain this copy number. However, artificial conditions can be devised to select for high copy number.

Modified cells having recombinant genomes are grown in rich media (in which conditions, multicopy number should not be a disadvantage) and exposed to a mutagen, such as ultraviolet or gamma irradiation or a chemical mutagen, e.g., mitomycin, nitrous acid, photoactivated psoralens, alone or in combination, which induces DNA breaks amenable to repair by recombination. These conditions select for cells having multicopy number due to the greater efficiency with which mutations can be excised. Modified cells surviving exposure to mutagen are enriched for cells with multiple genome copies. If desired, selected cells can be individually analyzed for genome copy number (e.g., by quantitative hybridization with appropriate controls). Some or all of the collection of cells surviving selection provide the substrates for the next round of recombination. In addition, individual cells can be sorted using a cell sorter for those cells containing more DNA, e.g., using DNA specific fluorescent compounds or sorting for increased size using light dispersion. Eventually cells are evolved that have at least 2, 4, 6, 8 or 10 copies of the genome throughout the cell cycle. In a similar manner, protoplasts can also be recombined.

8.12.4 Evolve Secretion Pathways for Better Efficiency 8.12.5 Evolve to Manufacture Drugs or Chemicals The protein (or metabolite) secretion pathways of bacterial and eukaryotic cells can be evolved to export desired molecules more efficiently, such as for the manufacturing of protein pharmaceuticals, small molecule drugs or specialty chemicals. Improvements in efficiency are particularly desirable for proteins requiring multisubunit assembly (such as antibodies) or extensive posttranslational modification before secretion.

The efficiency of secretion may depend on a number of genetic sequences including a signal peptide coding sequence, sequences encoding protein(s) that cleave or otherwise recognize the coding sequence, and the coding sequence of the protein being secreted. The latter may affect folding of the protein and the ease with which it can integrate into and traverse membranes. The bacterial secretion pathway in *E. coli* include the SecA, SecB, SecE, SecD and SecF genes. In *Bacillus subtilis,* the major genes are secA, secD, secE, secF, secY, ffh, ftsy together with five signal peptidase genes (sipS, sipT, sipU, sipV and sipW) (Kunst et al, supra). For proteins requiring posttranslational modification, evolution of genes effecting such modification may contribute to improved secretion. Likewise genes with expression products having a role in assembly of multisubunit proteins (e.g., chaperonins) may also contribute to improved secretion.

Selection of substrates for recombination follows the general principles discussed above. In this case, the focused libraries referred to above comprise variants of the known secretion genes. For evolution of prokaryotic cells to express eukaryotic proteins, the initial substrates for recombination are often obtained at least in part from eukaryotic sources.

Incoming fragments can undergo recombination both with chromosomal DNA in recipient cells and with the screening marker construct present in such cells (see below). The latter form of recombination is important for evolution of the signal coding sequence incorporated in the screening marker construct. Improved secretion can be screened by the inclusion of marker construct in the cells being evolved. The marker construct encodes a marker gene, operably linked to expression sequences, and usually operably linked to a signal peptide coding sequence. The marker gene is sometimes expressed as a fusion protein with a recombinant protein of interest. This approach is useful when one wants to evolve the recombinant protein coding sequence together with secretion genes.

8.12.6 Evolve So Product is Toxic to Cell Unless Secreted

In one variation, the marker gene encodes a product that is toxic to the cell containing the construct unless the product is secreted. Suitable toxin proteins include diphtheria toxin and ricin toxin. Propagation of modified cells bearing such a construct selects for cells that have evolved to improve secretion of the toxin. Alternatively, the marker gene can encode a ligand to a known receptor, and cells bearing the ligand can be detected by FACS using labeled receptor. Optionally, such a ligand can be operably linked to a phospholipid anchoring sequence that binds the ligand to the cell membrane surface following secretion. In a further variation, secreted marker protein can be maintained in proximity with the cell secreting it by distributing individual cells into agar drops. This is done, e.g., by droplet formation of a cell suspension. Secreted protein is confined within the agar matrix and can be detected by e.g., FACS. In another variation, a protein of interest is expressed as a fusion protein together with beta-lactamase or alkaline phosphatase. These enzymes metabolize commercially available chromogenic substrates (e.g., X-gal), but do so only after secretion into the periplasm. Appearance of colored substrate in a colony of cells therefore indicates capacity to secrete the fusion protein and the intensity of color is related to the efficiency of secretion.

The cells identified by these screening and selection methods have the capacity to secrete increased amounts of protein. This capacity may be attributable to increased secretion and increased expression, or from increased secretion alone.

8.12.7 Evolve to Acquire Increased Expression of Recombinant Protein

Expression Cells can also be evolved to acquire increased expression of a recombinant protein. The level of expression is, of course, highly dependent on the construct from which the recombinant protein is expressed and the regulatory sequences, such as the promoter, enhancer(s) and transcription termination site contained therein. Expression can also be affected by a large number of host genes having roles in transcription, posttranslational modification and translation. In addition, host genes involved in synthesis of ribonucleotide and amino acid monomers for transcription and translation may have indirect effects on efficiency of expression. Selection of substrates for recombination follows the general principles discussed above. In this case, focused libraries comprise variants of genes known to have roles in expression. For evolution of prokaryotic cells to express eukaryotic proteins, the initial substrates for recombination are often obtained, at least in part, from eukaryotic sources; that is eukaryotic genes encoding proteins such as chaperonins involved in secretion and/assembly of proteins. Incoming fragments can undergo recombination both with chromosomal DNA in recipient cells and with the screening marker construct present in such cells (see below).

Screening for improved expression can be effected by including a reporter construct in the cells being evolved. The reporter construct expresses (and usually secretes) a reporter protein, such as GFP, which is easily detected and nontoxic. The reporter protein can be expressed alone or together with a protein of interest as a fusion protein. If the reporter gene is secreted, the screening effectively selects for cells having either improved secretion or improved expression, or both.

8.12.8 Evolve Plant Cells to Acquire Resistance

A further application of recursive sequence recombination is the evolution of plant cells, and transgenic plants derived from the same, to acquire resistance to pathogenic diseases (fungi, viruses and bacteria), insects, chemicals (such as salt, selenium, pollutants, pesticides, herbicides, or the like), including, e.g., atrazine or glyphosate, or to modify chemical composition, yield or the like. The substrates for recombination can again be whole genomic libraries, fractions thereof or focused libraries containing variants of gene(s) known or suspected to confer resistance to one of the above agents. Frequently, library fragments are obtained from a different species to the plant being evolved.

The DNA fragments are introduced into plant tissues, cultured plant cells, plant microspores, or plant protoplasts by standard methods including electroporation (From et al., Proc. Natl. Acad. Sci. USA 82, 5824 (1985), infection by viral vectors such as cauliflower mosaic virus (CaMV) (Hohn et al., Molecular Biology of Plant Tumors, (Academic Press, New York, 1982) pp. 549–560; Howell, U.S. Pat. No. 4,407,956), high velocity ballistic penetration by small particles with the nucleic acid either within the matrix of small beads or particles, or on the surface (Klein et al., Nature 327, 70–73 (1987)), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al., Science 233, 496–498 (1984); Fraley et al., Proc. Natl. Acad. Sci. USA 80, 4803 (1983)).

Diversity can also be generated by genetic exchange between plant protoplasts according to the same principles described below for fungal protoplasts. Procedures for formation and fusion of plant protoplasts are described by Takahashi et al., U.S. Pat. No. 4,677,066; Akagi et al., U.S. Pat. No. 5,360,725; Shimamoto et al., U.S. Pat. No. 5,250, 433; Cheney et al., U.S. Pat. No. 5,426,040.

8.12.9 Plant Genome Stochastic &/or Non-Stochastic Mutagensis

Plant genome stochastic &/or non-stochastic mutagenesis allows recursive cycles to be used for the introduction and recombination of genes or pathways that confer improved properties to desired plant species. Any plant species, including weeds and wild cultivars, showing a desired trait, such as herbicide resistance, salt tolerance, pest resistance, or temperature tolerance, can be used as the source of DNA that is introduced into the crop or horticultural host plant species.

Genomic DNA prepared from the source plant is fragmented (e.g. by DNase1, restriction enzymes, or mechanically) and cloned into a vector suitable for making plant genomic libraries, such as pGA482 (An. G., 1995, Methods Mol. Biol. 44:47–58). This vector contains the *A. tumefaciens* left and right borders needed for gene transfer to plant cells and antibiotic markers for selection in *E. coli*, Agrobacterium, and plant cells. A multicloning site is provided for insertion of the genomic, fragments. A cos sequence is present for the efficient packaging of DNA into bacteriophage lambda heads for transfection of the primary library into *E. coli*. The vector accepts DNA fragments of 25–40 kb.

The primary library can also be directly electroporated into an *A. tumefaciens* or *A. rhizogenes* strain that is used to infect and transform host plant cells (Main, G D et al., 1995, Methods Mol. Biol. 44:405–412). Alternatively, DNA can be introduced by electroporation or PEG-mediated uptake into protoplasts of the recipient plant species (Bilang et al. (1994) Plant Mol. Biol Manual, Kluwer Academic Publishers, Al: 1–16) or by particle bombardment of cells or tissues (Christou, ibid, A2:1–15). If necessary, antibiotic markers in the T-DNA region can be eliminated, as long as selection for the trait is possible, so that the final plant products contain no antibiotic genes.

Stably transformed whole cells acquiring the trait are selected on solid or liquid media containing the agent to which the introduced DNA confers resistance or tolerance. If the trait in question cannot be selected for directly, transformed cells can be selected with antibiotics and allowed to form callus or regenerated to whole plants and then screened for the desired property.

The second and further cycles consist of isolating genomic DNA from each transgenic line and introducing it into one or more of the other transgenic fines. In each round, transformed cells are selected or screened for incremental improvement. To speed the process of using multiple cycles of transformation, plant regeneration can be deferred until the last round. Callus tissue generated from the protoplasts or transformed tissues can serve as a source of genomic DNA and new host cells. After the final round, fertile plants are regenerated and the progeny are selected for homozygosity of the inserted DNAs. Ultimately, a new plant is created that carries multiple inserts which additively or synergistically combine to confer high levels of the desired trait. Alternatively, microspores can be isolated as homozygotes generated from spontaneous diploids.

In addition, the introduced DNA that confers the desired trait can be traced because it is flanked by known sequences in the vector. Either PCR or plasmid rescue is used to isolate the sequences and characterize them in more detail. Long PCR (Foord, O S and Rose, E A, 1995, PCR Primer: A Laboratory Manual, CSBL Press, pp 63–77) of the full 25–40 kb insert is achieved with the proper reagents and techniques using as primers the T-DNA border sequences. If the vector is modified to contain the *E. coli* origin of replication and an antibiotic marker between the T-DNA borders, a rare cutting restriction enzyme, such as NotI or SfiI, that cuts only at the ends of the inserted DNA is used to create fragments containing the source plant DNA that are then self-ligated and transformed into *E. coli* where they replicate as plasmids. The total DNA or subfragment of it that is responsible for the transferred trait can be subjected to in vitro evolution by DNA stochastic &/or non-stochastic mutagenesis. The stochastic &/or non-stochastic mutagenized library can be reiteratively recombined by any method herein and then introduced into host plant cells and screened for improvement of the trait. In this way, single and multigene traits can be transferred from one species to another and optimized for higher expression or activity leading to whole organism improvement. This entire process can also be reiteratively repeated. Alternatively, the cells can be transformed microspores with the regenerated haploid plants being screened directly for improved traits as noted below.

8.12.10 Plant Cell is Put into Contact with Agent to See Which Cells Survive

After a suitable period of incubation to allow recombination to occur and for expression of recombinant genes, the plant cells are contacted with the agent to which resistance is to be acquired, and surviving plant cells are collected. Some or all of these plant cells can be subject to a further round of recombination and screening. Eventually, plant cells having the required degree of resistance are obtained.

These cells can then be cultured into transgenic plants. Plant regeneration from cultured protoplasts is described in Evans et al., "Protoplast Isolation and Culture," Handbook of Plant Cell Cultures 1, 124–176 (MacMillan Publishing Co., New York, 1983); Davey, "Recent Developments in the Culture and Regeneration of Plant Protoplasts," Protoplasts, (1983) pp. 12–29, (Birkhauser, Basal 1983); Dale, "Protoplast Culture and Plant Regeneration of Cereals and Other Recalcitrant Crops," Protoplasts (1983) pp. 31–41, (Birkhauser, Basel 1983); Binding, "Regeneration of Plants," Plant Protoplasts, pp. 21–73, (CRC Press, Boca Raton, 1985).

8.12.11 Start in Bacterial Cell Since Faster Evolution and Transform into Plant

In a variation of the above method, one or more preliminary rounds of recombination and screening can be performed in bacterial cells according to the same general strategy as described for plant cells. More rapid evolution can be achieved in bacterial cells due to their greater growth rate and the greater efficiency with which DNA can be introduced into such cells. After one or more rounds of recombination/screening, a DNA fragment library is recovered from bacteria and transformed into the plant cells. The library can either be a complete library or a focused library. A focused library can be produced by amplification from primers specific for plant sequences, particularly plant sequences known or suspected to have a role in conferring resistance.

8.12.12 Microspore Manipulation

Microspores are haploid (ln) male spores that develop into pollen grains. Anthers contain a large numbers of microspores in early-uninucleate to first-mitosis stages. Microspores have been successfully induced to develop into plants for most species, such as, e.g., rice (Chen, CC 1977 In vitro. 13: 484–489), tobacco (Atanassov, 1. et al. 1998 Plant Mol Biol. 38:1169–1178), Tradescantia (Savage J R K and Papworth D G. 1998 Mutat Res. 422:313–322), Arabidopsis (Park S K et al. 1998 Development. 125:3789–3799), sugar beet (Majewska-Sawka A and Rodrigues-Garcia N E 1996 J Cell Sci. 109:859–866), Barley (Olsen F L 1991 Hereditas 115:255–266) and oilseed rape (Boutillier K A et al. 1994 Plant Mol Biol. 26:1711–1723).

The plants derived from microspores are predominantly haploid or diploid (infrequently polyploid and aneuploid). The diploid plants are homozygous and fertile and can be generated in a relatively short time. Microspores obtained from F I hybrid plants represent great diversity, thus being an excellent model for studying recombination. In addition, microspores can be transformed with T-DNA introduced by agrobacterium or other available means and then regenerated into individual plants. Furthermore, protoplasts can be made from microspores and they can be fused similar to what occur in fungi and bacteria.

Microspores, due to their complex ploidy and regenerating ability, provide a tool for plant whole genome stochastic &/or non-stochastic mutagenesis. For example, if pollens from 4 parents are collected 4 and pooled, and then used to randomly pollinate the parents, the progenies should have $2^4=16$ possible combinations. Assuming this plant has 7 chromosomes, microspores collected from the 16 progenies will represent $2^7 \times 16 = 2048$ possible chromosomal combinations. This number is even greater if meiotic processes occur. When diploid, homozygous embryos are generated from these microspores, in many cases, they are screened for desired phenotypes, such as herbicide- or disease-resistant. In addition, for plant oil composition these embryos can be dissected into two halves: one for analysis the other for regeneration into a viable plant. Protoplasts generated from microspores (especially the haploid ones) are pooled and fused. Microspores obtained from plants generated by protoplast fusion are pooled and fused again, increasing the genetic diversity of the resulting microspores. Microspores can be subjected to mutagenesis in various ways, such as by chemical mutagenesis, radiation-induced mutagenesis and, e.g., t-DNA transformation, prior to fusion or regeneration. New mutations which are generated can be recombined through the recursive processes described above and herein.

8.12.13 Acquistion of Salt Tolerance

DNA from a salt tolerant plant is isolated and used to create a genomic library. Protoplasts made from the recipient species are transformed/transfected with the genomic library (e.g., by electroporation, agrobacterium, etc.). Cells are selected on media with a normally inhibitory level of NaCl. Only the cells with newly acquired salt tolerance will grow into callus tissue. The best lines are chosen and genomic libraries are made from their pooled DNA. These libraries are transformed into protoplasts made from the first round transformed calli. Again, cells are selected on increased salt concentrations. After the desired level of salt tolerance is achieved, the callus tissue can be induced to regenerate whole plants. Progeny of these plants are typically analyzed for homozygosity of the inserts to ensure stability of the acquired trait. At the indicated steps, plant regeneration or isolation and stochastic &/or non-stochastic mutagenesis of the introduced genes can be added to the overall protocol.

8.13 Evolve Transgenic Animals 8.13.1 Optimize Transgene

One goal of transgenesis is to produce transgenic animals, such as mice, rabbits, sheep, pigs, goats, and cattle, secreting a recombinant protein in the milk. A transgene for this purpose typically comprises in operable linkage a promoter and an enhancer from a milk-protein gene (e.g., alpha, beta, or gamma casein, beta-lactoglobulin, acid whey protein or alpha-lactalbumin), a signal sequence, a recombinant protein coding sequence and a transcription termination site.

Optionally, a transgene can encode multiple chains of a multichain protein, such as an immunoglobulin, in which case, the two chains are usually individually operably linked to sets of regulatory sequences. Transgenes can be optimized for expression and secretion by recursive sequence recombination. Suitable substrates for recombination include regulatory sequences such as promoters and enhancers from milk-protein genes from different species or individual animals. Cycles of recombination can be performed in vitro or in vivo by any of the formats discussed. Screening is performed in vivo on cultures of mammary-gland derived cells, such as HC11 or MacT, transfected with transgenes and reporter constructs such as those discussed above. After several cycles of recombination and screening, transgenes resulting in the highest levels of expression and secretion are extracted from the mammary gland tissue culture cells and used to transfect embryonic cells, such as zygotes and embryonic stem cells, which are matured into transgenic animals.

8.13.2 Optimize Whole Animal By Transforming into Embryonic Cells Gene of Desired Trait 8.13.2.1 Growth Hormone In this approach, libraries of incoming fragments are transformed into embryonic cells, such as ES cells or zygotes. The fragments can be variants of a gene known to confer a desired property, such as growth hormone. Alternatively, the fragments can be partial or complete genomic libraries including many genes. Fragments are usually introduced into zygotes by microinjection as described by Gordon et al., Methods Enzymol. 10 1, 414 (1984); Hogan et al., Manipulation of the Mouse Embryo: A Laboratory Manual (C.S.H.L. N.Y., 1986) (mouse embryo),— and Hammer et al., Nature 315, 680 (1985) (rabbit and porcine embryos); Gandolfi et al., J Reprod. Fert. 81, 23–28 (1987); Rexroad et al., J Anim. Sci. 66, 947–953 (1988) (ovine embryos) and Eyestone et al., J Reprod. Fert. 85, 715–720 (1989); Camous et al., J Reprod. Fert. 72, 779–785 (1984); and Heyman et al., Theriogenology 27, 5968 (1987) (bovine embryos). Zygotes are then matured and introduced into recipient female animals which gestate the embryo and give birth to a transgenic offspring.

Alternatively, transgenes can be introduced into embryonic stem cells (ES).

These cells are obtained from preimplantation embryos cultured in vitro. Bradley et al., Nature 309, 255–258 (1984). Transgenes can be introduced into such cells by electroporation or microinjection. Transformed ES cells are combined with blastocysts from a non-human animal. The ES cells colonize the embryo and in some embryos form the germ line of the resulting chimeric animal. See Jaenisch, Science, 240, 1468–1474 (1988).

Regardless whether zygotes or ES are used, screening is performed on whole animals for a desired property, such as increased size and/or growth rate. DNA is extracted from animals having evolved toward acquisition of the desired property. This DNA is then used to transfect further embryonic cells. These cells can also be obtained from animals that have acquired toward the desired property in a split and pool approach. That is, DNA from one subset of such animals is transformed into embryonic cells prepared from another subset of the animals. Alternatively, the DNA from animals that have evolved toward acquisition of the desired property can be transfected into fresh embryonic cells. In either alternative, transfected cells are matured into transgenic animals, and the animals subjected to a further round of screening for the desired property.

Initially, a library is prepared of variants of a growth hormone gene. The variants can be natural or induced. The library is coated with recA protein and transfected into fertilized fish eggs. The fish eggs then mature into fish of different sizes. The growth hormone gene fragment of genomic DNA from large fish is then amplified by PCR and used in the next round of recombination. Alternatively, fish—IFN is evolved to enhance resistance to viral infections as described below.

8.13.2.2 Evolution of Improved Hormones for Expression in Transgenic Animals 8.13.3 To Create Animals with Improved Traits Evolution of improved hormones for expression in transgenic animals (e.g., Fish) to create animals with improved traits. Hormones and cytokines are key regulators of size, body weight, viral resistance and many other commercially important traits. DNA stochastic &/or non-stochastic mutagenesis is used to rapidly evolve the genes for these proteins using in vitro assays. This was demonstrated with the evolution of the human alpha interferon genes to have potent antiviral activity on murine cells. Large improvements in activity were achieved in two cycles of family stochastic &/or non-stochastic mutagenesis of the human IFN genes.

In general, a method of increasing resistance to virus infection in cells can be performed by first introducing a stochastic &/or non-stochastic mutagenized library comprising at least one stochastic &/or non-stochastic mutagenized interferon gene into animal cells to create an initial library of animal cells or animals. The initial library is then challenged with the virus. Animal cells or animals are selected from the initial library which are resistant to the virus and a plurality of transgenes from a plurality of animal cells or animals which are resistant to the virus are recovered. The plurality of transgenes is recovered to produce an evolved library of animal cells or animals which is again challenged with the virus. Cells or animals are selected from the evolved library the which are resistant to the virus.

For example, genes evolved with in vitro assays are introduced into the germplasm of animals or plants to create improved strains. One limitation of this procedure is that in vitro assays are often only crude predictors of in vivo activity. However, with improving methods for the production of transgenic plants and animals, one can now marry whole organism breeding with molecular breeding. The approach is to introduce stochastic &/or non-stochastic mutagenized libraries of hormone genes into the species of interest. This can be done with a single gene per transgenic or with pools of genes per transgenic. Progeny are then screened for the phenotype of interest. In this case, stochastic &/or non-stochastic mutagenized libraries of interferon genes (alpha IFN for example). are introduced into transgenic fish. The library of transgenic fish are challenged with a virus. The most resistant fish are identified (i.e. either survivors of a lethal challenge; or those that are deemed most 'healthy' after the challenge). The IFN transgenes are recovered by PCR and stochastic &/or non-stochastic mutagenized in either a poolwise or a pairwise fashion. This generates an evolved library of IFN genes. A second library of transgenic fish is created and the process is repeated. In this way, IFN is evolved for improved antiviral activity in a whole organism assay. This procedure is general and can be applied to any trait that is affected by a gene or gene family of interest and which can be quantitatively measured.

Fish interferon sequence data is available for the Japanese flatfish (*Paralichthys olivaceus*) as mRNA sequence (Tamai et al (1993) "Cloning and expression of flatfish (*Paralichthys olivaceus*) interferon cDNA." Biochem. Biophs. Act 1174, 182–186; Y see also, Tami et al. (1993) "Purification and characterization of interferon-like antiviral protein derived from flatfish (*Paralichthys olivaceus*) lymphocytes immortalized by oncogenes." Cytotechnology 1993; 11 (2):121–131). This sequence can be used to clone out IFN genes from this species. This sequence can also be used as a probe to clone homologous interferons from additional species of fish. As well, additional sequence information can be utilized to clone out more species of fish interferons. Once a library of interferons has been cloned, these can be family stochastic &/or non-stochastic mutagenized to generate a library of variants.

In one embodiment, BHK-21 (A fibroblast cell line from hamster) can be transfected with the stochastic &/or non-stochastic mutagenized WN-expression plasmids. Active recombinant IFN is produced and then purified by WGA agarose affinity chromatography (Tamai, et al. 1993 Biochim Ciophys Acta. supra). The antiviral activity of IFN can be measured on fish cells challenged by rhabdovirus. Tami et al. (1993) "Purification and characterization of interferon-like antiviral protein derived from flatfish (*Paralichthys olivaceus*) lymphocytes immortalized by oncogenes." Cytotechnolgy 1993; 11 (2):121–131).

8.13.4 Whole Genome Stochastic &/or Non-Stochastic Mutagenesis in Higher Organisms POOLWISE RECURSIVE BREEDING The present invention provides a procedure for generating large combinatorial libraries of higher eukaryotes, plants, fish, domesticated animals, etc. In addition to the procedures outlined above, poolwise combination of male and female gametes can also be used to generate large diverse molecular libraries.

In one aspect, the process includes recursive poolwise matings for several generations without any deliberate screening. This is similar to classical breeding, except that pools of organisms, rather than pairs of organisms, are mated, thereby accelerating the generation of genetic diversity. This method is similar to recursive fusion of a diverse population of bacterial protoplasts resulting in the generation of multiparent progeny harboring genetic information from all of the starting population of bacteria. The process described here is to perform analogous artificial or natural matings of large populations of natural isolates, imparting a split pool mating strategy. Before mating, all of the male gametes i.e. pollen, sperm, etc., are isolated from the starting population and pooled. These are then used to "self" fertilize a mixed pool of the female gametes from the same population.

The process is repeated with the subsequent progeny for several generations, with the final progeny being a combinatorial organism library with each member having genetic information originating from many if not all of the starting "parents." This process generates large diverse organism libraries on which many selections and or screens can be imparted, and it does not require sophisticated in vitro manipulation of genes. However, it results in the creation of useful new strains (perhaps well diluted in the population) in a much shorter time frame than such organisms could be generated using a classical targeted breeding approach.

These libraries are generated relatively quickly (e.g., typically in less than three years for most plants of commercial interest, with six cycles or less of recursive breeding being sufficient to generate desired diversity). An additional benefit of these methods is that the resulting libraries provide organismal diversity in areas, such as agriculture, aquaculture, and animal husbandry, that are currently genetically homogeneous.

Examples of these methods for several organisms are described below.

8.13.5 Plants

Plants A population of plants, for example all of the different corn strains in a commercial seed/germplasm collection, are grown and the pollen from the entire population is harvested and pooled. This mixed pollen population is then used to "self" fertilize the same population. Self pollination is prevented, so that the fertilization is combinatorial. The cross results in all pairwise crosses possible within the population, and the resulting seeds result in many of the possible outcomes of each of these pairwise crosses. The seeds from the fertilized plants are then harvested, pooled, planted, and the pollen is again harvested, pooled, and used to "self" fertilize the population. After only several generations, the resulting population is a very diverse combinatorial library of corn. The seeds from this library are harvested and screened for desirable traits, e.g., salt tolerance, growth rate, productivity, yield, disease resistance, etc. Essentially any plant collection can be modified by this approach. Important commercial crops include both monocots and dicots. Monocots include plants in the grass family (Gramineae), such as plants in the sub families Fetucoideae and Poacoideae, which together include several hundred genera including plants in the genera Agrostis, Phleum, Dactylis, Sorgum, Setaria, Zea (e.g., corn), Oryza (e.g., rice), Triticum (e.g., wheat), Secale (e.g., rye), Avena (e.g., oats), Hordeum (e.g., barley), Saccharum, Poa, Festuca, Stenotaphrum, Cynodon, Coix, the Olyreae, Phareae and many others. Plants in the family Gramineae are a particularly preferred target plants for the methods of the invention.

Additional preferred targets include other commercially important crops, e.g., from the families Compositae (the largest family of vascular plants, including at least 1,000 genera, including important commercial crops such as sunflower), and Leguminosae or "pea family," which includes several hundred genera, including many commercially valuable crops such as pea, beans, lentil, peanut, yam bean, cowpeas, velvet beans, soybean, clover, alfalfa, lupine, vetch, lotus, sweet clover, wisteria, and sweetpea. Common crops applicable to the methods of the invention include Zea mays, rice, soybean, sorghum, wheat, oats, barley, millet, sunflower, and canola.

This process can also be carried out using pollen from different species or more divergent strains (e.g., crossing the ancient grasses with corn). Different plant species can be forced to cross. Only a few plants from an initial cross would have to result in order to make the process viable. These few progeny, e.g., from a cross between soy bean and corn, would generate pollen and eggs, each of which would represent a different meiotic outcome from the recombination of the two genomes. The pollen would be harvested and used to "self pollinate the original progeny. This process would then be carried out recursively. This would generate a large family stochastic &/or non-stochastic mutagenized library of two or more species, which could be subsequently screened.

8.13.6 Fish

Fish The natural tendency of fish to lay their eggs outside of the body and to have a male cover those eggs with sperm provides another opportunity for a split pooled breeding strategy. The eggs from many different fish, e.g., salmon from different fisheries about the world, can be harvested, pooled, and then fertilized with similarly collected and pooled salmon sperm. The fertilization will result in all of the possible pairwise matings of the starting population. The resulting progeny is then grown and again the sperm and eggs are harvested, and pooled, with each egg and sperm representing a different meiotic outcome of the different crosses. The pooled sperm are then used to fertilize the pooled eggs and the process is carried out recursively. After several generations the resulting progeny can then be subjected to selections and screens for desired properties, such as size, disease resistance, etc.

8.13.7 Animals

Animals The advent of in vitro fertilization and surrogate motherhood provides a means of whole genome stochastic &/or non-stochastic mutagenesis in animals such as mammals. As with fish, the eggs and the sperm from a population, for example from all slaughter cows, are collected and pooled. The pooled eggs are then in vitro fertilized with the pooled sperm. The resulting embryos are then returned to surrogate mothers for development. As above, this process is repeated recursively until a large diverse population is generated that can be screened for desirable traits.

A technically feasible approach would be similar to that used for plants. In this case, sperm from the males of the starting population is collected and pooled, and then this pooled sample is used to artificially inseminate multiple females from each of the starting populations. Only one (or a few) sperm would succeed in each animal, but these should be different for each fertilization. The process is reiterated by harvesting the sperm from all of the male progeny, pooling it, and using it to fertilize all of the female progeny. The process is carried out recursively for several generations to generate the organism library, which can then be screened.

8.14 Predictive Tool in Looking for Drugs

Recursive sequence recombination can be used to simulate natural evolution of pathogenic microorganisms in response to exposure to a drug under test. Using recursive sequence recombination, evolution proceeds at a faster rate than in natural evolution. One measure of the rate of evolution is the number of cycles of recombination and screening required until the microorganism acquires a defined level of resistance to the drug. The information from this analysis is of value in comparing the relative merits of different drugs and in particular, in predicting their long term efficacy on repeated administration.

The pathogenic microorganisms used in this analysis include the bacteria that are a common source of human infections, such as chlamydia, rickettsial bacteria, mycobacteria, staphylococci, streplocci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lymes disease bacteria.

Evolution is effected by transforming an isolate of bacteria that is sensitive to a drug under test with a library of DNA fragments. The fragments can be a mutated version of the genome of the bacteria being evolved. If the target of the drug is a known protein or nucleic acid, a focused library containing variants of the corresponding gene can be used. Alternatively, the library can come from other kinds of bacteria, especially bacteria typically found inhabiting human tissues, thereby simulating the source material available for recombination in vivo. The library can also come from bacteria known to be resistant to the drug. After transformation and propagation of bacteria for an appropriate period to allow for recombination to occur and recombinant genes to be expressed, the bacteria are screened by exposing them to the drug under test and then collecting survivors. Surviving bacteria are subject to further rounds of recombination. The subsequent round can be effected by a split and pool approach in which DNA from one subset of surviving bacteria is introduced into a second subset of bacteria. Alternatively, a fresh library of DNA fragments can be introduced into surviving bacteria. Subsequent round(s) of selection can be performed at increasing concentrations of drug, thereby increasing the stringency of selection.

8.14.1 Biosynthesis

Metabolic engineering can be used to alter organisms to optimize the production of practically any metabolic intermediate, including antibiotics, vitamins, amino acids such as phenylalanine and aromatic amino acids, ethanol, butanol, polymers such as xanthan gum and bacterial cellulose, peptides, and lipids. When such compounds are already produced by a host, the recursive sequence recombination techniques described above can be used to optimize production of the desired metabolic intermediate, including such features as increasing enzyme substrate specificity and turnover number, altering metabolic fluxes to reduce the concentrations of toxic substrates or intermediates, increasing resistance of the host to such toxic compounds, eliminating, reducing or altering the need for inducers of gene expression/activity, increasing the production of enzymes necessary for metabolism, etc.

Enzymes can also be evolved for improved activity in solvents other than water. This is useful because intermediates in chemical syntheses are often protected by blocking groups which dramatically affect the solubility of the compound in aqueous solvents. Many compounds can be produced by a combination of pure chemical and enzymically catalyzed reactions. Performing enzymic reactions on almost insoluble substrates is clearly very inefficient, so the availability of enzymes that are active in other solvents will be of great use. One example of such a scheme is the evolution of a para-nitrobenzyl esterase to remove protecting groups from an intermediate in loracarbef synthesis (Moore, J. C. and Arnold, F. H. Nature Biotechnology 14:458467 (1996)). In this case alternating rounds of error-prone PCR and colony screening for production of a fluorescent reporter from a substrate analogue were used to generate a mutant esterase that was 16-fold more active than the parent molecule in 30%. dimethylformamide. No individual mutation was found to contribute more than a 2-fold increase in activity, but it was the combination of a number of mutations which led to the overall increase.

Structural analysis of the mutant protein showed that the amino acid changes were distributed throughout the length of the protein in a manner that could not have been rationally predicted. Sequential rounds of error-prone PCR have the problem that after each round all but one mutant is discarded, with a concomitant loss of information contained in all the other beneficial mutations. Recursive sequence recombination avoids this problem, and would thus be ideally suited to evolving enzymes for catalysis in other solvents, as well as in conditions where salt concentrations or pH were different from the original enzyme optimas.

In addition, the yield of almost any metabolic pathway can be increased, whether consisting entirely of genes endogenous to the host organisms or all or partly heterologous genes. Optimization of the expression levels of the enzymes in a pathway is more complex than simply maximizing expression. In some cases regulation, rather than constitutive expression of an enzyme may be advantageous for cell growth and therefore for product yield, as seen for production of phenylalanine (Backman et al. Ann. NY Acad. Sci. 589:16–24 (1990)) and 2-keto-L-gluconic acid (Anderson et al. U.S. Pat. No. 5,032,514). In addition, it is often advantageous for industrial purposes to express proteins in organisms other than their original hosts. New host strains may be preferable for a variety of reasons, including ease of cloning and transformation, pathogenicity, ability to survive in particular environments and a knowledge of the physiology and genetics of the organisms. However, proteins expressed in heterologous organisms often show markedly reduced activity for a variety of reasons including inability to fold properly in the new host (Sarthy et al. Appl. Environ. Micro. 53:1996–2000 (1987)). Such difficulties can indeed be overcome by the recursive sequence recombination strategies of the instant invention.

8.14.2 Antibotics

The range of natural small molecule antibiotics includes but is not limited to peptides, peptidolactones, thiopeptides, beta-lactams, glycopeptides, lantibiotics, microcins, polyketide-derived antibiotics (anthracyclins, tetracyclins, macrolides, avermectins, polyethers and ansamycins), chloramphenicol, aminoglycosides, aminocyclitols, polyoxins, agrocins and isoprenoids. There are at least three ways in which recursive sequence recombination techniques of the instant invention can be used to facilitate novel drug synthesis, or to improve biosynthesis of existing antibiotics.

First, antibiotic synthesis enzymes can be "evolved" together with transport systems that allow entry of compounds used as antibiotic precursors to improve uptake and incorporation of function-altering artificial side chain precursors. For example, penicillin V is produced by feeding Penicillium the artificial side chain precursor phenoxyacetic acid, and LY146032 by feeding Streptomyces roseosporus decanoic acid (Hopwood, Phil. Trans. R. Soc. Lond. B 324:549–562 (1989)). Poor precursor uptake and poor incorporation by the synthesizing enzyme often lead to inefficient formation of the desired product. Recursive sequence recombination of these two systems can increase the yield of desired product.

Furthermore, a combinatorial approach can be taken in which an enzyme is stochastic &/or non-stochastic mutagenized for novel catalytic activity/substrate recognition (perhaps by including randomizing oligonucleotides in key positions such as the active site). A number of different substrates (for example, analogues of side chains that are normally incorporated into the antibiotic) can then be tested in combination with all the different enzymes and tested for biological activity. In this embodiment, plates are made containing different potential antibiotic precursors (such as the side chain analogues). The microorganisms containing the stochastic &/or non-stochastic mutagenized library (the library strain) are replicated onto those plates, together with a competing, antibiotic sensitive, microorganism (the indicator strain). Library cells that are able to incorporate the new side chain to produce an effective antibiotic will thus be able to compete with the indicator strain, and will be selected for.

Second, the expression of heterologous genes transferred from one antibiotic synthesizing organism to another can be optimized. The newly introduced enzyme(s) act on secondary metabolites in the host cell, transforming them into new compounds with novel properties. Using traditional methods, introduction of foreign genes into antibiotic synthesizing hosts has already resulted in the production of novel hybrid antibiotics. Examples include mederrhodin, dihydrogranatirhodin, 6-deoxyerythromycin A, isovalerylspiramycin and other hybrid macrolides (Cameron et. al. Appl. Biochem. Biotechnol. 38:105–140 (1993)). The recursive sequence recombination techniques of the instant invention can be used to optimize expression of the foreign genes, to stabilize the enzyme in the new host cell, and to increase the activity of the introduced enzyme against its new substrates in the new host cell. In some embodiments of the invention, the host genome may also be so optimized.

Third, the substrate specificity of an enzyme involved in secondary metabolism can be altered so that it will act on and modify a new compound or so that its so activity is changed and it acts at a different subset of positions of its normal substrate. Recursive sequence recombination can be used to alter the substrate specificities of enzymes. Furthermore, in addition to recursive sequence recombination of individual enzymes being a strategy to generate novel antibiotics, recursive sequence recombination of entire pathways, by altering enzyme ratios, will alter metabolite fluxes and may result, not only in increased antibiotic synthesis, but also in the synthesis of different antibiotics. This can be deduced from the observation that expression of different genes from the same cluster in a foreign host leads to different products being formed (see p. 80 in Hutchinson et. al., (1991) Ann NY Acad Sci, 646:78–93).

Recursive sequence recombination of the introduced gene clusters may result in a variety of expression levels of different proteins within the cluster (because it produces different combinations of, in this case regulatory, mutations). This in turn may lead to a variety of different end products. Thus, "evolution" of an existing antibiotic synthesizing pathway could be used to generate novel antibiotics either by modifying the rates or substrate specificities of enzymes in that pathway.

Additionally, antibiotics can also be produced in vitro by the action of a purified enzyme on a precursor. For example isopenicillin N synthase catalyses the cyclization of many analogues of its normal substrate (d-(L-a-aminoadipyl)-L-cysteinyl-D-valine) (Hutchinson, Med. Res. Rev. 8:557–567 (1988)). Many of these products are active as antibiotics. A wide variety of substrate analogues can be tested for incorporation by secondary metabolite synthesizing enzymes without concern for the initial efficiency of the reaction. Recursive sequence recombination can be used subsequently to increase the rate of reaction with a promising new substrate.

Thus, organisms already producing a desired antibiotic can be evolved with the recursive sequence recombination techniques described above to maximize production of that antibiotic. Additionally, new antibiotics can be evolved by manipulation of genetic material from the host by the recursive sequence recombination techniques described above. Genes for antibiotic production can be transferred to a preferred host after cycles of recursive sequence recombination or can be evolved in the preferred host as described above.

Antibiotic genes are generally clustered and are often positively regulated, making them especially attractive candidates for the recursive sequence recombination techniques of the instant invention. Additionally, some genes of related pathways show cross-hybridization, making them preferred candidates for the generation of new pathways for new antibiotics by the recursive sequence recombination techniques of the invention.

Furthermore, increases in secondary metabolite production including enhancement of substrate fluxes (by increasing the rate of a rate limiting enzyme, deregulation of the pathway by suppression of negative control elements or over expression of activators and the relief of feedback controls by mutation of the regulated enzyme to a feedback-insensitive deregulated protein) can be achieved by recursive sequence recombination without exhaustive analysis of the regulatory mechanisms governing expression of the relevant gene clusters.

The host chosen for expression of evolved genes is preferably resistant to the antibiotic produced, although in some instances production methods can be designed so as to sacrifice host cells when the amount of antibiotic produced is commercially significant yet lethal to the host. Similarly, bioreactors can be designed so that the growth medium is continually replenished, thereby "drawing off" antibiotic produced and sparing the lives of the producing cells. Preferably, the mechanism of resistance is not the degradation of the antibiotic produced.

Numerous screening methods for increased antibiotic expression are known in the art, as discussed above, including screening for organisms that are more resistant to the antibiotic that they produce. This may result from linkage between expression of the antibiotic synthesis and antibiotic resistance genes (Chater, Bio/Technology 8:115–121 (1990)). Another screening method is to fuse a reporter gene (e.g. xylE from the Pseudomonas TOL plasmid) to the antibiotic production genes. Antibiotic synthesis gene expression can then be measured by looking for expression of the reporter (e.g. xylE encodes a catechol dioxygenase which produces yellow muconic semialdehyde when colonies are sprayed with catechol (Zukowski et al. Proc. Natl. Acad. Sci. U.S.A. 80:1101–1105 (1983)). The wide variety of cloned antibiotic genes provides a wealth of starting materials for the recursive sequence recombination techniques of the instant invention. For example, genes have been cloned from Streptomyces cattleya which direct cephamycin C synthesis in the non-antibiotic producer Streptomyces lividans (Chen et al. Bio/Technology 6:1222–1224 (1988)). Clustered genes for penicillin biosynthesis (-(L-aminoadipyl)-L-cysteinyl-D-valine synthetase; isopenicillin N synthetase and acyl coenzyme A:6-aminopenicillanic acid acyltransferase) have been cloned from Penicillium chrysogenum. Transfer of these genes into Neurospora crassa and Aspergillus niger result in the synthesis of active penicillin V (Smith et al. Bio/Technology 8:3941 (1990)). For a review of cloned genes involved in Cephalosporin C, Penicillins G and V and Cephamycin C biosynthesis, see Piepersberg, Crit. Rev. Biotechnol. 14:251–285 (1994). For a review of cloned clusters of antibiotic-producing genes, see Chater Bio/Technology 8:115–121 (1990).Other examples of antibiotic synthesis genes transferred to industrial producing strains, or over expression of genes, include tylosin, cephamycin C, cephalosporin C, LL-E33288 complex (an antitumor and antibacterial agent), doxorubicin, spiramycin and other macrolide antibiotics, reviewed in Cameron et al. Appl. Biochem. Biotechnol. 38:105–140 (1993).

8.14.3 Biosynthesis to Replace Chemical Synthesis of Antibiotics

Some antibiotics are currently made by chemical modifications of biologically produced starting compounds. Complete biosynthesis of the desired molecules may currently be impractical because of the lack of an enzyme with the required enzymatic activity and substrate specificity. For example, 7-aminodeacetooxycephalosporanic acid (7-ADCA) is a precursor for semi-synthetically produced cephalosporins. 7-ADCA is made by a chemical ring expansion from penicillin V followed by enzymatic deacylation of the phenoxyacetal group. Cephalosporins could in principle be produced biologically from their corresponding penicillins (e.g., cephalosporin V or G from penicillin V or G) using penicillin N expandase, but other penicillins (such as penicillin V or G) are not used as substrates by known expandases. The recursive sequence recombination techniques of the invention can be used to alter the enzyme so that it will use penicillin V as a substrate. Similarly, penicillin transacylase could be so modified to accept cephalosporins or cephamycins as substrates.

In yet another example, penicillin amidase expressed in *E. coli* is a key enzyme in the production of penicillin G derivatives. The enzyme is generated from a precursor peptide and tends to accumulate as insoluble aggregates in the periplasm unless non-metabolizable sugars are present in the medium (Scherrer et al. , Appl. Microbiol. Biotechnol. 42:85–91 (1994)). Evolution of this enzyme through the methods of the instant invention could be used to generate an enzyme that folds better, leading to a higher level of active enzyme expression.

In yet another example, Penicillin G acylase covalently linked to agarose is used in the synthesis of penicillin G derivatives. The enzyme can be stabilized for increased activity, longevity and/or thermal stability by chemical modification (Femandez-Lafuente et. al. Enzyme Microb. Technol. 14:489495 (1992). Increased thermal stability is an especially attractive application of the recursive sequence recombination techniques of the instant invention, which can obviate the need for the chemical modification of such enzymes. Selection for thermostability can be performed in vivo in *E. coli* or in thermophiles at higher temperatures. In general, thermostability is a good first step in enhancing general stabilization of enzymes. Random mutagenesis and selection can also be used to adapt enzymes to function in non-aqueous solvents (Arnold Curr Opin Biotechnol, 4:450–455 (1993); Chen et. al. Proc. Natl. Acad. Sci. U.S.A., 90:5618–5622 (1993)). Recursive sequence recombination represents a more powerful (since recombinogenic) method of generating mutant enzymes that are stable and active in non-aqueous environments. Additional screening can be done on the basis of enzyme stability in solvents.

8.14.4 Polyketides

Polyketides include antibiotics such as tetracycline and erytlromycin, anti-cancer agents such as daunomycin, immunosuppressants such as FK506 and rapamycin and veterinary products such as monesin and avermectin. Polyketide synthases (PKS's) are multifunctional enzymes that control the chain length, choice of chain-building units and reductive cycle that generates the huge variation in naturally occurring polyketides. Polyketides are built up by sequential transfers of "extender units" (fatty acyl CoA groups) onto the appropriate starter unit (examples are acetate, coumarate, propionate and malonamide). The PKS's determine the number of condensation reactions and the type of extender groups added and may also fold and cyclize the polyketide precursor. PKS's reduce specific—keto groups and may dehydrate the resultant—hydroxyls to form double bonds. Modifications of the nature or number of building blocks used, positions at which—keto groups are reduced, the extent of reduction and different positions of possible cyclizations, result in formation of different final products. Polyketide research is currently focused on modification and inhibitor studies, site directed mutagenesis and 3-D structure elucidation to lay the groundwork for rational changes in enzymes that will lead to new polyketide products.

Recently, McDaniel et al. (Science 262:1546–1550 (1995)) have developed a Streptomyces host-vector system for efficient construction and expression of recombinant PKSs. Hutchinson (Bio/Technolo 12:375–308 (1994)) reviewed targeted mutation of specific biosynthetic genes and suggested that microbial isolates can be screened by DNA hybridization for genes associated with known pharmacologically active agents so as to provide new metabolites or increased yields of metabolites already being produced. In particular, that review focuses on polyketide synthase and pathways to aminoglycoside and oligopeptide antibiotics.

The recursive sequence recombination techniques of the instant invention can be used to generate modified enzymes that produce novel polyketides without such detailed analytical effort. The availability of the PKS genes on plasmids and the existence of *E. coli*-Streptomyces shuttle vectors (Wehmeier Gene 165:149–150 (1995)) makes the process of recursive sequence recombination especially attractive by the techniques described above. Techniques for selection of antibiotic producing organisms can be used as described above; additionally, in some embodiments screening for a particular desired polyketide activity or compound is preferable.

8.14.5 Isoprenoids

Isoprenoids result from cyclization of farnesyl pyrophosphate by sesquiterpene synthases. The diversity of isoprenoids is generated not by the backbone, but by control of cyclization. Cloned examples of isoprenoid synthesis genes include trichodiene synthase from Fusarium sprorotrichioides, pentalene synthase from Streptomyces, aristolochene synthase from Penicillium roquefortii, and epi-aristolochene synthase from N. tabacum (Cane, D. E. (1995). Isoprenoid antibiotics, pages 633–655, in "Genetics and Biochemistry of Antibiotic Production" edited by Vining, L. C. & Stuttard, C., published by Butterworth-Heinemann). Recursive sequence recombination of sesquiterpene synthases will be of use both in allowing expression of these enzymes in heterologous hosts (such as plants and industrial microbial strains) and in alteration of enzymes to change the cyclized product made. A large number of isoprenoids are active as antiviral, antibacterial, antifungal, herbicidal, insecticidal or cytostatic agents. Antibacterial and antifingal isoprenoids could thus be preferably screened for using the indicator cell type system described above, with the producing cell competing with bacteria or fungi for nutrients. Antiviral isoprenoids could be screened for preferably by their ability to confer resistance to viral attack on the producing cell.

8.14.6 Bioactive Peptide Derivatives

Examples of bioactive non-ribosomally synthesized peptides include the antibiotics cyclosporin, pepstatin, actinomycin, gramicidin, depsipeptides, vancomycin, etc. These peptide derivatives are synthesized by complex enzymes rather than ribosomes. Again, increasing the yield of such non-ribosomally synthesized peptide antibiotics has thus far been done by genetic identification of biosynthetic "bottlenecks" and over expression of specific enzymes (See, for example, p. 133–135 in "Genetics and Biochemistry of Antibiotic Production" edited by Vining, L. C. & Stuttard, C., published by Butterworth-Heinemann). Recursive sequence recombination of the enzyme clusters can be used to improve the yields of existing bioactive non-ribosomally made peptides in both natural and heterologous hosts.

Like polyketide synthases, peptide synthases are modular and multifunctional enzymes catalyzing condensation reactions between activated building blocks (in this case amino acids) followed by modifications of those building blocks (see Kleinkauf, H. and von Dohren, H. Eur. J. Biochem. 236:335–351 (1996)). Thus, as for polyketide synthases, recursive sequence recombination can also be used to alter peptide synthases: modifying the specificity of the amino acid recognized by each binding site on the enzyme and altering the activity or substrate specificities of sites that modify these amino acids to produce novel compounds with antibiotic activity. other peptide antibiotics are made ribosomally and then post-translationally modified. Examples of this type of antibiotics are lantibiotics (produced by gram positive bacteria such Staphylococcus, Streptomyces, Bacillus, and Actinoplanes) and microcins (produced by Enterobacteriaceae). Modifications of the original peptide include (in lantibiotics) dehydration of serine and threonine, condensation of dehydroamino acids with cysteine, or simple N- and C-terminal blocking (microcins). For ribosomally made antibiotics both the peptide-encoding sequence and the modifying enzymes may have their expression levels modified by recursive sequence recombination. Again, this will lead to both increased levels of antibiotic synthesis, and by modulation of the levels of the modifying enzymes (and the sequence of the ribosomally synthesized peptide itself) novel antibiotics.

Screening can be done as for other antibiotics as described above, including competition with a sensitive (or even initially insensitive) microbial species. Use of competing bacteria that have resistances to the antibiotic being produced will select strongly either for greatly elevated levels of that antibiotic (so that it swamps out the resistance mechanism) or for novel derivatives of that antibiotic that are not neutralized by the resistance mechanism.

8.14.7 Polymers

Several examples of metabolic engineering to produce biopolymers have been reported, including the production of the biodegradable plastic polyhydroxybutarate (PHB), and the polysaccharide xanthan gum. For a review, see Cameron et al. Applied Biochem. Biotech. 38:105–140 (1993). Genes for these pathways have been cloned, making them excellent candidates for the recursive sequence recombination techniques described above. Expression of such evolved genes in a commercially viable host such as E. coli is an especially attractive application of this technology.

Examples of starting materials for recursive sequence recombination include but are not limited to genes from bacteria such as Alcaligenes, Zoogloea, Rhizobium, Bacillus, and Azobacter, which produce polyhydroxyalkanoates (PHAs) such as polyhyroxybutyrate (PHB) intracellularly as energy reserve materials in response to stress. Genes from Alcaligenes eutrophus that encode enzymes catalyzing the conversion of acetoacetyl CoA to PHB have been transferred both to E. coli and to the plant Arabidopsis thaliana (Poirier et al. Science 256:520–523 (1992)). Two of these genes (phbB and phbC, encoding acetoacetyl-CoA reductase and PHB synthase respectively) allow production of PHE in Arabidopsis. The plants producing the plastic are stunted, probably because of adverse interactions between the new metabolic pathway and the plants' original metabolism (i.e., depletion of substrate from the mevalonate pathway). Improved production of PHB in plants has been attempted by localization of the pathway enzymes to organelles such as plastids. Other strategies such as regulation of tissue specificity, expression timing and cellular localization have been suggested to solve the deleterious effects of PHB expression in plants. The recursive sequence recombination techniques of the invention can be used to modify such heterologous genes as well as specific cloned interacting pathways (e.g., mevalonate), and to optimize PHB synthesis in industrial microbial strains, for example to remove the requirement for stresses (such as nitrogen limitation) in growth conditions.

Additionally, other microbial polyesters are made by different bacteria in which additional monomers are incorporated into the polymer (Peoples et al. in Novel Biodegradable Microbial Polymers, E A Dawes, ed., pp191–202 (1990) ). Recursive sequence recombination of these genes or pathways singly or in combination into a heterologous host will allow the production of a variety of polymers with differing properties, including variation of the monomer subunit ratios in the polymer.

Another polymer whose synthesis may be manipulated by recursive sequence recombination is cellulose. The genes for cellulose biosynthesis have been cloned from Agrobacterium tumefaciens (Matthysse, A. G. et. al. J. Bacteriol. 177:1069–1075 (1995)). Recursive sequence recombination of this biosynthetic pathway could be used either to increase synthesis of cellulose, or to produce mutants in which alternative sugars are incorporated into the polymer.

8.14.8 Carotenoids

Carotenoids are a family of over 600 terpenoids produced in the general isoprenoid biosynthetic pathway by bacteria, fungi and plants (for a review, see Armstrong, J. Bact. 176:4795–4802 (1994)). These pigments protect organisms against photooxidative damage as well as functioning as anti-tumor agents, free radical-scavenging anti-oxidants, and enhancers of the immune response. Additionally, they are used commercially in pigmentation of cultured fish and shellfish. Examples of carotenoids include but are not limited to myxobacton, spheroidene, spheroidenone, lutein, astaxanthin, violaxanthin, 4-ketorulene, myxoxanthrophyll, echinenone, lycopene, zeaxanthin and its mono- and di-glucosides, alpha-, beta-, gamma- and sigma-carotene, beta-cryptoxanthin monoglucoside and neoxanthin.

Carotenoid synthesis is catalyzed by relatively small numbers of clustered genes: 11 different genes within 12 kb of DNA from Myxococcus xanthus (Botella et al. Eur. J. Biochem. 233:238–248 (1995)) and 8 genes within 9 kb of DNA from Rhodobacter sphaeroides (Lang et. al. J. Bact. 177:2064–2073 (1995)). In some microorganisms, such as Thermus thermophilus, these genes are plasmid-borne (Tabata et al. FEBS Letts 341:251–255 (1994)). These features make carotenoid synthetic pathways especially attractive candidates for recursive sequence recombination.

Transfer of some carotenoid genes into heterologous organisms results in expression. For example, genes from Erwina uredovora and Haematococcus pluvialis will function together in E. coli (Kajiwara et al. Plant Mol. Biol. 29:343–352 (1995)). E. herbicola genes will function in R. sphaeroides (Hunter et al. J. Bact. 176:3692–3697 (1994)). However, some other genes do not; for example, R. capsulatus genes do not direct carotenoid synthesis in E. coli (Marrs, J. Bact. 146:1003–1012 (1981)).

In an embodiment of the invention, the recursive sequence recombination techniques of the invention can be used to generate variants in the regulatory and/or structural elements of genes in the carotenoid synthesis pathway, allowing increased expression in heterologous hosts. Indeed, traditional techniques have been used to increase carotenoid production by increasing expression of a rate limiting enzyme in Thermus thermophilus (Hoshino et al. Appl. Environ. Micro. 59:3150–3153 (1993)). Furthermore, mutation of regulatory genes can cause constitutive expression of carotenoid synthesis in actinomycetes, where carotenoid photoinducibility is otherwise unstable and lost at a relatively high frequency in some species (Kato et al. Mol. Gen. Genet. 247:387–390 (1995)). These are both mutations that can be obtained by recursive sequence recombination.

The recursive sequence recombination techniques of the invention as described above can be used to evolve one or more carotenoid synthesis genes in a desired host without the need for analysis of regulatory mechanisms. Since carotenoids are colored, a colorimetric assay in microtiter plates, or even on growth media plates, can be used for screening for increased production.

In addition to increasing expression of carotenoids, carotenogenic biosynthetic pathways have the potential to produce a wide diversity of carotenoids, as the enzymes involved appear to be specific for the type of reaction they will catalyze, but not for the substrate that they modify. For example, two enzymes from the marine bacterium Agrobacterium aurantiacum (CrtW and CrtZ) synthesize six different ketocarotenoids from beta-carotene (Misawa et al. J. Bact. 177:6576–6584 (1995)). This relaxed substrate specificity means that a diversity of substrates can be transformed into an even greater diversity of products. Introduction of foreign carotenoid genes into a cell can lead to novel and functional carotenoid-protein complexes, for example in photosynthetic complexes (Hunter et al. J. Bact. 176:3692–3697 (1994)). Thus, the deliberate recombination of enzymes through the recursive sequence recombination techniques of the invention is likely to generate novel compounds. Screening for such compounds can be accomplished, for example, by the cell competition/survival techniques discussed above and by a calorimetric assay for pigmented compounds.

Another method of identifying new compounds is to use standard analytical techniques such as mass spectroscopy, nuclear magnetic resonance, high performance liquid chromatography, etc. Recombinant microorganisms can be pooled and extracts or media supernatants assayed from these pools. Any positive pool can then be subdivided and the procedure repeated until the single positive is identified ("sib-selection").

8.14.9 Indigo Biosynthesis

Many dyes, i.e. agents for imparting color, are specialty chemicals with significant markets. As an example, indigo is currently produced chemically. However, nine genes have been combined in *E. coli* to allow the synthesis of indigo from glucose via the tryptophan/indole pathway (Murdock et al. Bio/Technology 11:381–386 (1993)). A number of manipulations were performed to optimize indigo synthesis: cloning of nine genes, modification of the fermentation medium and directed changes in two operons to increase reaction rates and catalytic activities of several enzymes.

Nevertheless, bacterially produced indigo is not currently an economic proposition. The recursive sequence recombination techniques of the instant invention could be used to optimize indigo synthesizing enzyme expression levels and catalytic activities, leading to increased indigo production, thereby making the process commercially viable and reducing the environmental impact of indigo manufacture. Screening for increased indigo production can be done by calorimetric assays of cultures in microtiter plates.

8.14.10 Amino Acids

Amino acids of particular commercial importance include but are not limited to phenylalanine, monosodium glutamate, glycine, lysine, threonine, tryptophan and methionine. Backman et al. (Ann. NY Acad. Sci. 589:16–24 (1990)) disclosed the enhanced production of phenylalanine in *E. coli* via a systematic and downstream strategy covering organism selection, optimization of biosynthetic capacity, and development of fermentation and recovery processes. As described in Simpson et al. (Biochem Soc Trans, 23:381–387 (1995)), current work in the field of amino acid production is focused on understanding the regulation of these pathways in great molecular detail.

The recursive sequence recombination techniques of the instant invention would obviate the need for this analysis to obtain bacterial strains with higher secreted amino acid yields. Amino acid production could be optimized for expression using recursive sequence recombination of the amino acid synthesis and secretion genes as well as enzymes at the regulatory phosphoenolpyruvate branchpoint, from such organisms as Serratia marcescens, Bacillus, and the Corynebacterium -Brevibacterium group. In some embodiments of the invention, screening for enhanced production is preferably done in microtiter wells, using chemical tests well known in the art that are specific for the desired amino acid. Screening/selection for amino acid synthesis can also be done by using auxotrophic reporter cells that are themselves unable to synthesize the amino acid in question. If these reporter cells also produce a compound that stimulates the growth of the amino acid producer (this could be a growth factor, or even a different amino acid), then library cells that produce more amino acid will in turn receive more growth stimulant and will therefore grow more rapidly.

8.14.11 Vitamin C Synthesis

L-Ascorbic acid (vitamin C) is a commercially important vitamin with a world production of over 35,000 tons in 1984. Most vitamin C is currently manufactured chemically by the Reichstein process, although recently bacteria have been engineered that are able to transform glucose to 2,5-keto-gluconic acid, and that product to 2-keto-L-idonic acid, the precursor to L-ascorbic acid (Boudrant, Enzyme Microb. Technol. 12:322–329 (1990)).

The efficiencies of these enzymatic steps in bacteria are currently low. Using the recursive sequence recombination techniques of the instant invention, the genes can be genetically engineered to create one or more operons followed by expression optimization of such a hybrid L-ascorbic acid synthetic pathway to result in commercially viable microbial vitamin C biosynthesis. In some embodiments, screening for enhanced L-ascorbic acid production is preferably done in microtiter plates, using assays well known in the art.

8.15 Test for Resistance to Drugs 8.15.1 Find Drugs That Induce Resistance Slowly A similar strategy can be used to simulate viral acquisition of drug resistance. The object is to identify drugs for which resistance can be acquired only slowly, if at all. The viruses to be evolved are those that cause infections in humans for which at least modestly effective drugs are available. Substrates for recombination can come from induced mutants, natural variants of the same viral strain or different viruses. If the target of the drug is known (e.g., nucleotide analogs which inhibit the reverse transcriptase gene of HIV), focused libraries containing variants of the target gene can be produced. Recombination of a viral genome with a library of fragments is usually performed in vitro. However, in situations in which the library of fragments constitutes variants of viral genomes or fragments that can be encompassed in such genomes, recombination can also be performed in vivo, e.g., by transfecting cells with multiple substrate copies (see Section V). For screening, recombinant viral genomes are introduced into host cells susceptible to infection by the virus and the cells are exposed to a drug effective against the virus (initially at low concentration). The cells can be spun to remove any noninfected virus. After a period of infection, progeny viruses can be collected from the culture medium, the progeny viruses being enriched for viruses that have acquired at least partial resistance to the drug. Alternatively, virally infected cells can be plated in a soft agar lawn and resistant viruses isolated from plaques. Plaque size provides some indication of the degree of viral resistance.

Progeny viruses surviving screening are subject to additional rounds of recombination and screening at increased stringency until a predetermined level of drug resistance has been acquired. The predetermined level of drug resistance may reflect the maximum dosage of a drug practical to administer to a patient without intolerable side effects. The analysis is particularly valuable for investigating acquisition of resistance to various combination of drugs, such as the growing list of approved anti-HIV drugs (e.g., AZT, ddI, ddC, d4T, TIBO 82150, nevaripine, 3TC, crixivan and ritonavir).

8.15.2 Method to Evolve Yeast Strains

Fragments are cloned into a YAC vector, and the resulting YAC library is transformed into competent yeast cells. Transformants containing a YAC are identified by selecting for a positive selection marker present on the YAC. The cells are allowed to recover and are then pooled. Thereafter, the cells are induced to sporulate by transferring the cells from rich medium, to nitrogen and carbon limiting medium. In the course of sporulation, cells undergo meiosis. Spores are then induced to mate by return to rich media. Optionally, asci are lysed to liberate spores, so that the spores can mate with other spores originating from other asci. Mating results in recombination between YACs bearing different inserts, and between YACs and natural yeast chromosomes. The latter can be promoted by irradiating spores with ultra violet light. Recombination can give rise to new phenotypes either as a result of genes expressed by fragments on the YACs or as a result of recombination with host genes, or both.

After induction of recombination between YACs and natural yeast chromosomes, YACs are often eliminated by selecting against a negative selection marker on the YACs. For example, YACs containing the marker URA3 can be selected against by propagation on media containing 5-fluro orotic acid. Any exogenous or altered genetic material that remains is contained within natural yeast chromosomes. Optionally, further rounds of recombination between natural yeast chromosomes can be performed after elimination of YACs. Optionally, the same or different library of YACs can be transformed into the cells, and the above steps repeated. By recursively repeating this process, the diversity of the population is increased prior to screening.

After elimination of YACs, yeast are then screened or selected for a desired property. The property can be a new property conferred by transferred fragments, such as production of an antibiotic. The property can also be an improved property of the yeast such as improved capacity to express or secrete an exogenous protein, improved recombinogenicity, improved stability to temperature or solvents, or other property required of commercial or research strains of yeast.

Yeast strains surviving selection/screening are then subject to a further round of recombination. Recombination can be exclusively between the chromosomes of yeast surviving selection/screening. Alternatively, a library of fragments can be introduced into the yeast cells and recombined with endogenous yeast chromosomes as before. This library of fragments can be the same or different from the library used in the previous round of transformation. For example, the YACs could contain a library of genomic DNA isolated from a pool of the improved strains obtained in the earlier steps. YACs are eliminated as before, followed by additional rounds of recombination and/or transformation with further YAC libraries. Recombination is followed by another round of selection/screening, as above.

Further rounds of recombination/screening can be performed as needed until a yeast strain has evolved to acquire the desired property.

An exemplary scheme for evolving yeast by introduction of a YAC library is yeast containing an endogenous diploid genome and a YAC library of fragments representing variants of a sequence. The library is transformed into the cells to yield 100–1000 colonies per μg DNA. Most transformed yeast cells now harbor a single YAC as well as endogenous chromosomes. Meiosis is induced by growth on nitrogen and carbon limiting medium. In the course of meiosis the YACs recombine with other chromosomes in the same cell. Haploid spores resulting from meiosis mate and regenerated diploid forms. The diploid forms now harbor recombinant chromosomes, parts of which come from endogenous chromosomes and parts from YACs.

Optionally, the YACs can now be cured from the cells by selecting against a negative selection marker present on the YACS. Irrespective whether YACS are selected against, cells are then screened or selected for a desired property. Cells surviving selection/screening are transformed with another YAC library to start another stochastic &/or non-stochastic mutagenesis cycle.

8.15.3 Evolve YACs for Transfer into Recipient Strain

These methods are based in part on the fact that multiple YACs can be harbored in the same yeast cell, and YAC-YAC recombination is known to occur (Green & Olson, Science 250, 94–98 1990)). Inter-YAC recombination provides a format for which families of homologous genes harbored on fragments of >20 kb can be stochastic &/or non-stochastic mutagenized in vivo.

The starting population of DNA fragments show sequence similarity with each other but differ as a result of for example, induced, allelic or species diversity. Often DNA fragments are known or suspected to encode multiple genes that function in a common pathway.

The fragments are cloned into a Yac and transformed into yeast, typically with positive selection for transformants. The transformants are induced to sporulate, as a result of which chromosomes undergo meiosis. The cells are then mated. Most of the resulting diploid cells now carry two YACs each having a different insert. These are again induced to sporulate and mated. The resulting cells harbor YACs of recombined sequence. The cells can then be screened or selected for a desired property. Typically, such selection occurs in the yeast strain used for stochastic &/or non-stochastic mutagenesis. However, if fragments being stochastic &/or non-stochastic mutagenized are not expressed in yeast, YACs can be isolated and transferred to an appropriate cell type in which they are expressed for screening. Examples of such properties include the synthesis or degradation of a desired compound, increased secretion of a desired gene product, or other detectable phenotype.

Preferably, the YAC library is transformed into haploid a and haploid a cells. These cells are then induced to mate with each other, i.e., they are pooled and induced to mate by growth on rich medium. The diploid cells, each carrying two YACs, are then transferred to sporulation medium. During sporulation, the cells undergo meiosis, and homologous chromosomes recombine. In this case, the genes harbored in the YACs will recombine, diversifying their sequences. The resulting haploid acospores are then liberated from the asci by enzymatic degradation of the asci wall or other available means and the pooled liberated haploid acospores are induced to mate by transfer to rich medium. This process is repeated for several cycles to increase the diversity of the DNA cloned into the YACs. The resulting population of yeast cells, preferably in the haploid state, are either screened for improved properties, or the diversified DNA is delivered to another host cell or organism for screening.

Cells surviving selection/screening are subjected to successive cycles of pooling, sporulation, mating and selection/screening until the desired phenotype has been observed. Recombination can be achieved simply by transferring cells from rich medium to carbon and nitrogen limited medium to induce sporulation, and then returning the spores to rich media to induce mating. Asci can be lysed to stimulate mating of spores originating from different asci.

After YACs have been evolved to encode a desired property they can be transferred to other cell types. Transfer can be by protoplast fusion, or retransformation with isolated DNA. For example, transfer of YACs from yeast to mammalian cells is discussed by Monaco & Larin, Trends in BiotechnoloSy 12, 280–286 (1994); Montoliu et al., Reprod. Fertil. Dev. 6, 577–84 (1994); Lamb et al., Curr. Opin. Genet. Dev. 5, 342–8 (1995). An exemplary scheme for stochastic &/or non-stochastic mutagenesis a YAC fragment library in yeast is shown herein. A library of YAC fragments representing genetic variants are transformed into yeast that have diploid endogenous chromosomes. The transformed yeast continue to have diploid endogenous chromosomes, plus a single YAC. The yeast are induced to undergo meiosis and sporulate. The spores contain haploid genomes and are selected for those which contain a YAC, using the YAC selective marker. The spores are induced to mate generating diploid cells. The diploid cells now contain two YACs bearing different inserts as well as diploid endogenous chromosomes. The cells are again induced to undergo meiosis and sporulate. during meiosis, recombination occurs between the YAC inserts, and recombinant YACs are segregated to ascoytes. Some ascoytes thus contain haploid endogenous chromosomes plus a YAC chromosome with a recombinant insert. The ascoytes mature to spores, which can mate again generating diploid cells. Some diploid cells now possess a diploid complement of endogenous chromosomes plus two recombinant YACs. These cells can then be taken through further cycles of meiosis, sporulation and mating. In each cycle, further recombination occurs between YAC inserts and further recombinant forms of inserts are generated. After one or several cycles of recombination has occurred, cells can be tested for acquisition of a desired property. Further cycles of recombination, followed by selection, can then be performed in similar fashion.

8.15.4 In Vivo Stochastic &/or Non-Stochastic Mutagensis of Genes By the Recursive Mating of Yeast Cells Harboring Homologous Genes in Identical Loci A goal of DNA stochastic &/or non-stochastic mutagenesis is to mimic and expand the combinatorial capabilities of sexual recombination. In vitro DNA stochastic &/or non-stochastic mutagenesis succeeds in this process. However, by changing the mechanism of recombination and altering the conditions under which recombination occurs, naturally in vitro recombination methods may jeopardize intrinsic information in a DNA sequence that renders it "evolvable." Stochastic &/or non-stochastic mutagenesis in vivo by employing the natural crossing over mechanisms that occur during meiosis may access inherent natural sequence information and provide a means of creating higher quality stochastic &/or non-stochastic mutagenized libraries. Described here is a method for the in vivo stochastic &/or non-stochastic mutagenesis of DNA that utilizes the natural mechanisms of meiotic recombination and provides an alternative method for DNA stochastic &/or non-stochastic mutagenesis.

The basic strategy is to clone genes to be stochastic &/or non-stochastic mutagenized into identical loci within the haploid genome of yeast. The haploid cells are then recursively induced to mate and to sporulate. The process subjects the cloned genes to recursive recombination during recursive cycles of meiosis. The resulting stochastic &/or non-stochastic mutagenized genes are then screened in in situ or isolated and screened under different conditions.

For example, if one wished to reassemble a family of five lipase genes, the following provides a means of doing so in vivo.

The open reading frame of each lipase is amplified by the PCR such that each ORF is flanked by identical 3' and 5' sequences. The 5' flanking sequence is identical to a region within the 5' coding sequence of the *S. cerevisiae* ura 3 gene and the 3' flanking sequence is identical to a region within the 3' of the ura 3 gene. The flanking sequences are chosen such that homologous recombination of the PCR product with the ura 3 gene results in the incorporation of the lipase gene and the disruption of the ura 3 ORF. Both *S. cerevisiae* a and haploid cells are then transformed with each of the PCR amplified lipase ORFs, and cells having incorporated a lipase gene into the ura 3 locus are selected by growth on 5 fluoro orotic acid (5FOA is lethal to cells expressing functional URA3). The result is 10 cell types, two different mating types each harboring one of the five lipase genes in the disrupted ura 3 locus. These cells are then pooled and grown under conditions where mating between the a and cells are favored, e.g. in rich medium. Mating results in a combinatorial mixture of diploid cells having all 32 possible combinations of lipase genes in the two ura 3 loci. The cells are then induced to sporulate by growth under carbon and nitrogen limited conditions. During sporulation the diploid cells undergo meiosis to form four (two a and two ) haploid ascospores housed in an ascus.

During meiosis II of the sporulation process sister chromatids align and crossover. The lipase genes cloned into the ura 3 loci will also align and recombine. Thus the resulting haploid ascospores will represent a library of cells each harboring a different possible chimeric lipase gene, each a unique result of the meiotic recombination of the two lipase genes in the original diploid cell. The walls of asci are degraded by treatment with zymolase to liberate and allow the mixing of the individual ascospores. This mixture is then grown under conditions that promote the mating of the a and h aploid cells. It is important to liberate the individual ascospores, since mating will otherwise occur between the ascospores within an ascus.

Mixing of the haploid cells allows recombination between more than two lipase genes, enabling "poolwise recombination." Mating brings together new combinations of chimeric genes that can then undergo recombination upon sporulation. The cells are recursively cycled through sporulation, ascospore mixing, and mating until sufficient diversity has been generated by the recursive pairwise recombination of the five lipase genes. The individual chimeric lipase genes either can be screened directly in the haploid yeast cells or transferred to an appropriate expression host.

The process is described above for lipases and yeast; however, any sexual organisms into which genes can be directed can be employed, and any genes, of course, could be substituted for lipases. This process is analogous to the method of stochastic &/or non-stochastic mutagenesis whole genomes by recursive pairwise mating. The diversity, however, in the whole genome case is distributed throughout the host genome rather than localized to specific loci.

8.15.5 Using YACs to Clone Unlinked Genes But Functionally Important Genes from One Species into Another Stochastic &/or non-stochastic mutagenesis of YACs is particularly amenable to transfer of unlinked but functionally related genes from one species to another, particularly where such genes have not been identified. Such is the case for several commercially important natural products, such as taxol. Transfer of the genes in the metabolic pathway to a different organism is often desirable because organisms naturally producing such compounds are not well suited for mass culturing.

Clusters of such genes can be isolated by cloning a total genomic library of DNA from an organisms producing a useful compound into a YAC library. The YAC library is then transformed into yeast. The yeast is sporulated and mated such that recombination occurs between YACs and/or between YACs and natural yeast chromosomes.

Selection/screening is then performed for expression of the desired collection of genes. If the genes encode a biosynthetic pathway, expression can be detected from the appearance of product of the pathway. Production of individual enzymes in the pathway, or intermediates of the final expression product or capacity of cells to metabolize such intermediates indicates partial acquisition of the synthetic pathway. The original library or a different library can be introduced into cells surviving/selection screening, and further rounds of recombination and selection/screening can be performed until the end product of the desired metabolic pathway is produced.

8.15.6 YAC-YAC Stochastic &/or Non-Stochastic Mutagenesis

If a phenotype of interest can be isolated to a single stretch of genomic DNA less than 2 megabases in length, it can be cloned into a YAC and replicated in *S. cerevisiae*. The cloning of similar stretches of DNA from related hosts into an identical YAC results in a population of yeast cells each harboring a YAC having a homologous insert effecting a desired phenotype. The recursive breeding of these yeast cells allows the homologous regions of these YACs to recombine during meiosis, allowing genes, pathways, and clusters to recombine during each cycle of meiosis. After several cycles of mating and segregation, the YAC inserts are well stochastic &/or non-stochastic mutagenized. The now very diverse yeast library could then be screened for phenotypic improvements resulting from the stochastic &/or non-stochastic mutagenesis of the YAC inserts.

8.15.7 YAC-Chromosome Stochastic &/or Non-Stochastic Mutagenesis

"Mitotic" recombination occurs during cell division and results from the recombination of genes during replication. This type of recombination is not limited to that between sister chromatids and can be enhanced by agents that induce recombination machinery, such as nicking chemicals and ultraviolet irradiation. Since it is often difficult to directly mate across a species barrier, it is possible to induce the recombination of homologous genes originating from different species by providing the target genes to a desired host organism as a YAC library. The genes harbored in this library are then induced to recombine with homologous genes on the host chromosome by enhanced mitotic recombination. This process is carried out recursively to generate a library of diverse organisms and then screened for those having the desired phenotypic improvements. The improved subpopulation is then mated recursively as above to identify new strains having accumulated multiple useful genetic alterations.

8.15.8 Accumlation of Multiple YACs Harboring Useful Genes

The accumulation of multiple unlinked genes that are required for the acquisition or improvement of a given phenotype can be accomplished by the stochastic &/or non-stochastic mutagenesis of YAC libraries. Genomic DNA from organisms having desired phenotypes, such as ethanol tolerance, thermotolerance, and the ability to ferment pentose sugars are pooled, fragmented and cloned into several different YAC vectors, each having a different selective marker (his, ura, ade, etc). *S. cerevisiae* are transformed with these libraries, and selected for their presence (using selective media i.e uracil dropout media for the YAC containing the ura3 selective marker) and then screened for having acquired or improved a desired phenotype.

Surviving cells are pooled, mated recursively, and selected for the accumulation of multiple YACs (by propagation in medium with multiple nutritional dropouts). Cells that acquire multiple YACs harboring useful genomic inserts are identified by further screening. Optimized strains can be used directly, however, due to the burden a YAC may pose to a cell, the relevant YAC inserts can be minimized, subcloned, and recombined into the host chromosome, to generate a more stable production strain.

8.15.9 Choice of Host SSF Organism

One example use for the present invention is to create an improved yeast for the production of ethanol from lignocellulosic biomass. Specifically, a yeast strain with improved ethanol tolerance and thermostability/thermotolerance is desirable. Parent yeast strains known for good behavior in a Simultaneous Saccharification and Fermentation (SSF) process are identified. These strains are combined with others known to possess ethanol," tolerance and/or thermostability.

*S. cerevisiae* is highly amenable to development for optimized SSF processes. It inherently possesses several traits for this use, including the ability to import and ferment a variety of sugars such as sucrose, glucose, galactose, maltose and maltriose. Also, yeast has the capability to flocculate, enabling recovery of the yeast biomass at the end of a fermentation cycle, and allowing its re-use in subsequent bioprocesses. This is an important property in that it optimizes the use of nutrients in the growth medium. S. cerevisiae is also highly amenable to laboratory manipulation, has highly characterized genetics and possesses a sexual reproductive cycle. *S. cerevisiae* may be grown under either aerobic or anaerobic conditions, in contrast to some other potential SSF organisms that are strict anaerobes (e.g. Clostridium spp.), making them very difficult to handle in the laboratory. *S. cerevisiae* are also "generally regarded as safe" ("GRAS"), and, due to its widespread use for the production of important comestibles for the general public (e.g. beer, wine, bread, etc), is generally familiar and well known. *S. cerevisiae* is commonly used in fermentative processes, and the familiarity in its handling by fermentation experts eases the introduction of novel improved yeast strains into the industrial setting. *S. cerevisiae* strains that previously have been identified as particularly good SSF organisms, for example, *S. cerevisiae* $D_5A$ (ATCC200062) (South C R and Lynd L R. (1994) Appl. Biochem. Biotechnol. 45/46: 467–481; Ranatunga T D et al. (1997) Biotechnol. Lett. 19:1125–1127) can be used for starting materials. In addition, other industrially used S. cerevisiae strains are optionally used as host strains, particularly those showing desirable fermentative characteristics, such as *S. cerevisiae* Y567 (ATCC24858) (Sitton OC et al. (1979) Process Biochem. 14(9): 7–10; Sitton OC et al. (1981) Adv. Biotechnol. 2: 231–237; McMurrough I et al. (1971) Folia Microbiol. 16: 346–349) and *S. cerevisiae* ACA 174 (ATCC 60868) (Benitez T et al. (1983) Appl. Environ. Microbiol. 45: 1429–1436; Chem. Eng. J. 50: B I 7-B22, 1992), which have been shown to have desirable traits for large-scale fermentation.

8.15.10 Choice of Ethanol Tolerant Strains

Many strains of *S. cerevisiae* have been isolated from high-ethanol environments, and have survived in the ethanol-rich environment by adaptive evolution. For example, strains from Sherry wine aging ("Flor" strains) have evolved highly functional mitochondria to enable their survival in a high-ethanol environment. It has been shown that transfer of these wine yeast mitochondria to other strains increases the recipient's resistance to high ethanol concentration, as well as thermotolerance (Jimenez, J. and Benitez, T (1988) Curr. Genet. 13: 461–469). There are several flor strains deposited in the ATCC, for example *S. cerevisiae* MY91 (ATCC 201301), MY138 (ATCC 201302), C5 (ATCC 201298), ET7 (ATCC 201299), LA6 (ATCC 201300), OSB21 (ATCC 201303), F23 (S. globosus ATCC 90920). Also, several flor strains of *S. uvarum* and *Torulaspora pretoriensis* have been deposited. Other ethanol-tolerant wine strains include *S. cerevisiae* ACA 174 (ATCC 60868), 15% ethanol, and *S. cerevisiae* A54 (ATCC 90921), isolated from wine containing 18% (v/v) ethanol, and NRCC 202036 (ATCC 46534), also a wine yeast. Other *S. cerevisiae* ethanologens that additionally exhibit enhanced ethanol tolerance include ATCC 24858, ATCC 24858, G 3706 (ATCC 42594), NRRL Y-265 (ATCC 60593), and ATCC 24845 - ATCC 24860. A strain of *S. pastorianus* (*S. carls-* bergensis ATCC 2345) has high ethanol-tolerance (13% v/v). *S. cerevisiae* Sa28 (ATCC 26603), from Jamaican cane juice sample, produces high levels of alcohol from molasses, is sugar tolerant, and produces ethanol from wood acid hydrolyzate. Several of the listed strains, as well as additional strains can be used as starting materials for breeding ethanol tolerance.

8.15.11 Choice of Temperature Tolerant Strains

A few temperature tolerant strains have been reported, including the highly flocculent strain *S. pastorianus* SA 23 (*S. carlsbergensis* ATCC 26602), which produces ethanol at elevated temperatures, and *S. cerevisiae* Kyokai 7 (*S. sake*, ATCC 26422), a sake yeast tolerant to brief heat and oxidative stress. Ballesteros et al ((1 991) Appl. Biochem. Biotechnol. 28/29: 307–315) examined 27 strains of yeast for their ability to grow and ferment glucose in the 32–45° C. temperature range, including Saccharomyces, Kluyveromyces and Candida spp. Of these, the best thermotolerant clones were *Kluyveromyces marxianus* LG and *Kluyveromyces fragilis* 2671 (Ballesteros et al (1993) Appl. Biochem. Biotechnol. 39/40: 201–211). *S. cerevisiae*-pretoriensis FDHI was somewhat thermotolerant, however was poor in ethanol tolerance. Recursive recombination of this strain with others that display ethanol tolerance can be used to acquire the thermotolerant characteristics of the strain in progeny which also display ethanol tolerance. *Candida acidothermophilum* (*Issatchenlaa orientalis*, ATCC 203 8 1) is a good SSF strain that also exhibits improved performance in ethanol production from lignocellulosic biomass at higher SSF temperatures than *S. cerevisiae* $D_5A$ (Kadam, K L, Schmidt, S L (1997) Appl. Microbial. Biotechnol. 48: 709–713). This strain can also be a genetic contributor to an improved SSF strain.

8.15.12 Stochastic &/or Non-Stochastic Mutagenesis of Strains

In those instances where strains are highly related, a recursive mating strategy may be pursued. For example, a population of haploid *S. cerevisiae* (a and ) a r e mutagenized and screened for improved EtOH or thermal tolerance. The improved haploid subpopulation are mixed together and mated as a pool and induced to sporulate. The resulting haploid spores are freed by degrading the asci wall and mixed. The freed spores are then induced to mate and sporulate recursively. This process is repeated a sufficient number of times to generate all possible mutant combinations. The whole genome stochastic &/or non-stochastic mutagenized population (haploid) is then screened for further EtOH or thermal tolerance.

When strains are not sufficiently related for recursive mating, formats based on protoplast fusion may be employed. Recursive and poolwise protoplast fusion can be performed to generate chimeric populations of diverse parental strains. The resultant pool of progeny is selected and screened to identify improved ethanol and thermal tolerant strains.

Alternatively, a YAC-based Whole Genome Stochastic &/or non-stochastic mutagenesis format can be used. In this format, YACs are used to shuttle large chromosomal fragments between strains. As detailed earlier, recombination occurs between YACs or between YACs, and the host chromosomes. Genomic DNA from organisms having desired phenotypes are pooled, fragmented and cloned into several different YAC vectors, each having a different selective marker (his, ura, ade, etc). *S. cerevisiae* are transformed with these libraries, and selected for their presence (using selective media, i.e. uracil dropout media for the YAC containing the Ura 3 selective marker) and then screened for having acquired or improved a desired phenotype. Surviving cells are pooled, mated recursively (as above), and selected for the accumulation of multiple YACs (by propagation in medium with multiple nutritional dropouts). Cells that acquire multiple YACs harboring useful genomic inserts are identified by further screening (see below).

8.15.13 Selection for Improved Strains

Having produced large libraries of novel strains by mutagenesis and recombination, a first task is to isolate those strains that possess improvements in the desired phenotypes. Identification of the organism libraries is facilitated where the desired key traits are selectable phenotypes. For example, ethanol has different effects on the growth rate of a yeast population, viability, and fermentation rate. Inhibition of cell growth and viability increases with ethanol concentration, but high fermentative capacity is only inhibited at higher ethanol concentrations. Hence, selection of growing cells in ethanol is a viable approach to isolate ethanol-tolerant strains. Subsequently, the selected strains may be analyzed for their fermentative capacity to produce ethanol. Provided that growth and media conditions are the same for all strains (parents and progeny), a hierarchy of ethanol tolerance may be constructed.

Simple selection schemes for identification of thermal tolerant and ethanol tolerant strains are available and, in this case, are based on those previously designed to identify potentially useful SSF strains. Selection of ethanol tolerance is performed by exposing the population to ethanol, then plating the population and looking for growth. Colonies capable of growing after exposure to ethanol can be re-exposed to a higher concentration of ethanol and the cycle repeated until the most tolerant strains are selected. In order to discern strains possessing heritable ethanol tolerance from with temporarily acquired adaptations, these cycles may be punctuated with cycles of growth in the absence of selection (e.g. no ethanol).

Alternatively, the mixed population can be grown directly at increasing concentrations of ethanol, and the most tolerant strains enriched (Aguilera and Benitez, 1986, Arch Microbiol 4:337–44). For example this enrichment could be carried out in a chemostat or turbidostat. Similar selections can be developed for thermal tolerance, in which strains are identified by their ability to grow after a heat treatment, or directly for growth at elevated temperatures (Ballesteros et al., 1991, Applied Biochem and Biotech, 28:307–315). The best strains identified by these selections will be assayed more thoroughly in subsequent screens for ethanol, thermal tolerance or other properties of interest.

In one aspect, organisms having increased ethanol tolerance are selected for. A population of natural *S. cerevisiae* isolates are mutagenized. This population is then grown under fermentor conditions under low initial ethanol concentrations. Once the culture has reached saturation, the culture is diluted into fresh medium having a slightly higher ethanol content. This process of successive dilution into medium of incrementally increasing ethanol concentration is continued until a threshold of ethanol tolerance is reached. The surviving mutant population having the highest ethanol tolerance are then pooled and their genomes recombined by any method noted herein. Enrichment could also be achieved by a continuous culture in a chemostat or turbidostat in which temperature or ethanol concentrations are progressively elevated. The resulting stochastic &/or non-stochastic mutagenized population are then exposed once again to the enrichment strategy but at a higher starting medium ethanol concentration. This strategy is optionally applied for the enrichment of thermotolerant cells and for the enrichment of cells having combined thermo- and ethanol tolerance.

8.15.14 Screening for Improved Strains

Strains showing viability in initial selections are assayed more quantitatively for improvements in the desired properties before being restochastic &/or non-stochastic mutagenized with other strains.

Progeny resulting from mutagenesis of a strain, or those pre-selected for their ethanol tolerance and/or thermostability, can be plated on non-selective agar. Colonies can be picked robotically into microtiter dishes and grown. Cultures are replicated to fresh microtiter plates, and the replicates are incubated under the appropriate stress condition(s). The growth or metabolic activity of individual clones may be monitored and ranked. Indicators of viability can range from the size of growing colonies on solid media, density of growing cultures, or color change of a metabolic activity indicator added to liquid media. Strains that show the greatest viability are then mixed and stochastic &/or non-stochastic mutagenized, and the resulting progeny are rescreened under more stringent conditions.

8.15.15 Development of a Yeast Strain Capable of Converting Cellulose to Monomeric Sugars Once a strain of yeast exhibiting thermotolerance and ethanol tolerance is developed, the degradation of cellulose to monomeric sugars is provided by the inclusion to the host strain of an efficient cellulase degradation pathway.

Additional desirable characteristic can be useful to enhance the production of ethanol by the host. For example, inclusion of heterologous enzymes and pathways that broaden the substrate sugar range may be performed. "Tuning" of the strain can be accomplished by the addition of various other traits, or the restoration of certain endogenous traits that are desirable, but lost during the recombination procedures.

8.15.16 Conferring of Cellulase Activity

A vast number of cellulases and cellulase degradation systems have been characterized from fungi, bacteria and yeast (see reviews by Beguin, P and Aubert, J-P (1994) FEMS Microbial. Rev. 13: 25–58; Ohima, K. et al. (1 997) Biotechnol. Genet. Eng. Rev. 14: 365414). An enzymatic pathway required for efficient saccharification of cellulose involves the synergistic action of endoglucanases (endo-1, 4-D-glucanases, EC 3.2.1.4), exocellobiohydrolases (exo-1, 4-D-glucanases, EC 3.2.1.91), and -glucosidases (cellobiases, 1,4-D-glucanases EC 3.2.1.21). The heterologous production of cellulase enzymes in the ethanologen would enable the saccharification of cellulose, producing monomeric sugars that may be used by the organism for ethanol production. There are several advantages to the heterologous expression of a functional cellulase pathway in the ethanologen. For example, the SSF process would eliminate the need for a separate bioprocess step for saccharification, and would ameliorate end-product inhibition of cellulase enzymes by accumulated intermediate and product sugars.

Naturally occurring cellulase pathways are inserted into the ethanologen, or one may choose to use custom improved "hybrid" cellulase pathways, employing the coordinate action of cellulases derived from different natural sources, including thermophiles.

Several cellulases from non-Saccharomyces have been produced and secreted from this organism successfully, including bacterial, fungal, and yeast enzymes, for example *T. reesei* CBH I ((Shoemaker (1994), in "The Cellulase System of *Trichoderma reesei:* Trichoderma strain improvement and Expression of *Trichoderma cellulases* in Yeast," Online, Pinner, UK, 593-600). It is possible to employ straightforward metabolic engineering techniques to engender cellulase activity in Saccharomyces. Also, yeast have been forced to acquire elements of cellulose degradation pathways by protoplast fusion (e.g. intergeneric hybrids of *Saccharomyces cerevisiae* and *Zygosaccharomyces fermentati,* a cellobiase-producing yeast, have been created (Pina A, et. al. (1986) Appl. Environ. Microbial. 51: 995–1003). In general, any cellulase component enzyme that derives from a closely related yeast organism could be transferred by protoplast fusion. Cellobiases produced by a somewhat broader range of yeast may be accessed by whole genome stochastic &/or non-stochastic mutagenesis in one of its many formats (e.g. whole, fragmented, YAC-based).

Optimally, the cellulase enzymes to be used should exhibit good synergy, an appropriate level of expression and secretion from the host, good specific activity (i.e. resistance to host degradation factors and enzyme modification) and stability in the desired SSF environment. An example of a hybrid cellulose degradation pathway having excellent synergy includes the following enzymes: CBH I exocellobiohydrolase of *Trichoderma reesei,* the Acidothermus cellulolyticus E1 endoglucanase, and the *Thermomonospora fusca* E3 exocellulase (Baker, et. al. (1998) Appl. Biochem. Biotechnol. 70–72: 395–403).

It is suggested here that these enzymes (or improved mutants thereof) be considered for use in the SSF organism, along with a cellobiase (-glucosidase), such as that from *Candida peltata.* Other possible cellulase systems to be considered should possess particularly good activity against crystalline cellulose, such as the *T. reesei* cellulase system (Teeri, TT, et. al. (1998) Biochem. Soc, Trans. 26: 173-178), or possess particularly good thermostability characteristics (e.g. cellulase systems from thermophilic organisms, such as *Thermomonospora fusca* (Zhang, S., et. al. (1995) Biochem.. 34:33 86–335).

A rational approach to the cloning of cellulases in the ethanologenic yeast host could be used. For example, known cellulase genes are cloned into expression cassettes utilizing *S. cerevisiae* promoter sequences, and the resultant linear fragments of DNA may be transformed into the recipient host by placing short yeast sequences at the termini to encourage site-specific integration into the genome. This is preferred to plasmidic transformation for reasons of genetic stability and maintenance of the transforming DNA.

If an entire cellulose degradative pathway were introduced, a selection could be implemented in an agar-plate-based format, and a large number of clones could be assayed for cellulase activity in a short period of time. For example, selection for an exocellulase may be accessible by providing a soluble oligocellulose substrate or carboxymethy I cellulose (CMC) as a sole carbon source to the host, otherwise unable to grow on agar containing this sole carbon source. Clones producing active cellulase pathways would grow by virtue of their ability to produce glucose.

Alternatively, if the different cellulases were to be introduced sequentially, it would be useful to first introduce a cellobiase, enabling a selection using commercially available cellobiose as a sole carbon source. Several strains of *S. cerevisiae* that are able to grow on cellobiose have been created by introduction of a cellobiase gene (e.g. Rajoka M I, et. al. (1998) Floia Microbiol. (Praha) 43, 129–135; Skory, C D, et. al. (1996) Curr. Genet. 30, 417–422; D'Auria, S, et. al. (1996) Appl. Biochem. Biotechnol. 61, 157–166; Adam, A C, et. al. (1995) Yeast 11, 395–406; Adam, A C (1991) Cuff. Genet. 20, 5–8).

Subsequent transformation of this organism with CBHI exocellulase can be selected for by growth on a cellulose substrate such as carboxymethylcellulose (CMC). Finally, addition of an endoglucanase creates a yeast strain with improved crystalline degradation capacity.

8.15.17 Conferring of Pentose Sugar Utilization

Inclusion of pentose sugar utilization pathways is an important facet to a potentially useful SSF organism. The successful expression of xylose sugar utilization pathways for ethanol production has been reported in Saccharomyces (e.g. Chen, Z D and Ho, N W Y (1993) Appl. Biochem. Biotechnol. 39/40 135–147).

It would also be useful to accomplish L-arabinose substrate utilization for ethanol production in the Saccharomyces host. Yeast strains that utilize L-arabinose include some Candida and Pichia spp. (McMillan J D and Boynton B L (1994) Appl. Biochem. Biotechnol. 45–46: 569–584; Dien B S, et al. (1996) Appl. Biochem. Biotechnol. 57–58: 233–242). Genes necessary for arabinose fermentation in *E. coli* could also be introduced by rational means (e.g. as has been performed previously in *Z. mobilis* (Deanda K, et. al. (1996) Appl. Environ. Microbial. 62: 4465–4470))

8.15.18 Conferring of Other Useful Activites

Several other traits that are important for optimization of an SSF strain have been shown to be transferable to *S. cerevisiae*. Like thermal tolerance, cellulase activity and pentose sugar utilization, these traits may not normally be exhibited by Saccharomyces (or the particular strain of Saccharomyces being used as a host), and may be added by genetic means.

For example, expression of human muscle acylphosphatase in *S. cerevisiae* has been suggested to increase ethanol production (Rougei, G., et. al. (1996) Biotechnol. App. Biochem. 23: 273–278).

It can occur that evolved stress-tolerant SSF strain acquire some undesirable mutations in the course of the evolution strategy. Indeed, this is a pervasive problem in strain improvement strategies that rely on mutagenesis techniques, and can result in highly unstable or fragile production strains. It is possible to restore some of these desirable traits by rational methods such as cloning of specific genes that have been knocked out or negatively influenced in the previous rounds of strain improvement. The advantage to this approach is specificity the offending gene may be targeted directly. The disadvantage is that it may be time-consuming and repetitious if several genes have been compromised, and it only addresses problems that have been characterized. A preferred (and more traditional) approach to the removal of undesirable/deleterious mutations is to backcross the evolved strain to a desirable parent strain (e.g. the original "host" SSF strain). This strategy has been employed successfully throughout strain improvement where accessible (i.e. for organisms that have sexual cycles of reproduction). When lacking the advantage of a sexual process, it has been accomplished by using other methods, such as parasexual recombination or protoplast fusion.

For example, the ability to flocculate was conferred on a non-flocculating strain of *S. cerevisiae* by protoplast fusion with a flocculation competent *S. cerevisiae* (Watari, J., et. al (1990) Agric. Biol. Chem. 54: 1677–1681).

8.16 Method of In vivo and In vitro DNA Shuffling

8.16.1 Applications

Disclosed is a method of producing random polynucleotides by introducing two or more related polynucleotides into a suitable host cell such that a hybrid polynucleotide is generated by recombination and reductive reassortment. Also provided are vector and expression vehicles including such polynucleotides, polypeptides expressed by the hybrid polynucleotides and a method for screening for hybrid polypeptides

8.16.2 Experimental Applications

This invention relates generally to recombination and more specifically to a method for preparing polynucleotides encoding a polypeptide by a method of in vivo re-assortment of polynucleotide sequences containing regions of partial homology, assembling the polynucleotides to form at least one polynucleotide and screening the polynucleotides for the production of polypeptide(s) having a useful property.

8.16.3 History

An exceedingly large number of possibilities exist for purposeful and random combinations of amino acids within a protein to produce useful hybrid proteins and their corresponding biological molecules encoding for these hybrid proteins, i.e., DNA, RNA. Accordingly, there is a need to produce and screen a wide variety of such hybrid proteins for a useful utility, particularly widely varying random proteins.

The complexity of an active sequence of a biological macromolecule (e.g., proteins, DNA) has been called its information content ("IC"), which has been defined as the resistance of the active protein to amino acid sequence variation (calculated from the minimum number of invariable amino acids (bits) required to describe a family of related sequences with the same function. Proteins that are more sensitive to random mutagenesis have a high information content.

Molecular biology developments, such as molecular libraries, have allowed the identification of quite a large number of variable bases, and even provide ways to select functional sequences from random libraries. In such libraries, most residues can be varied (although typically not all at the same time) depending on compensating changes in the context. Thus, while a 100 amino acid protein can contain only 2,000 different mutations, $20^{100}$ sequence combinations are possible.

Information density is the IC per unit length of a sequence. Active sites of enzymes tend to have a high information density. By contrast, flexible linkers of information in enzymes have a low information density.

Current methods in widespread use for creating alternative proteins in a library format are error-prone polymerase chain reactions and cassette mutagenesis, in which the specific region to be optimized is replaced with a synthetically mutagenized oligonucleotide. In both cases, a substantial number of mutant sites are generated around certain sites in the original sequence.

8.16.3.1 Error-prone PCR

Error-prone PCR uses low-fidelity polymerization conditions to introduce a low level of point mutations randomly over a long sequence. In a mixture of fragments of unknown sequence, error-prone PCR can be used to mutagenize the mixture. The published error-prone PCR protocols suffer from a low processivity of the polymerase. Therefore, the protocol is unable to result in the random mutagenesis of an average-sized gene. This inability limits the practical application of error-prone PCR. Some computer simulations have suggested that point mutagenesis alone may often be too gradual to allow the large-scale block changes that are required for continued and dramatic sequence evolution. Further, the published error-prone PCR protocols do not allow for amplification of DNA fragments greater than 0.5 to 1.0 kb, limiting their practical application. In addition, repeated cycles of error-prone PCR can lead to an accumulation of neutral mutations with undesired results, such as affecting a protein's immunogenicity but not its binding affinity.

8.16.3.2 Oligonucleotide-Directed Mutagenesis

In oligonucleotide-directed mutagenesis, a short sequence is replaced with a synthetically mutagenized oligonucleotide. This approach does not generate combinations of distant mutations and is thus not combinatorial. The limited library size relative to the vast sequence length means that many rounds of selection are unavoidable for protein optimization. Mutagenesis with synthetic oligonucleotides requires sequencing of individual clones after each selection round followed by grouping them into families, arbitrarily choosing a single family, and reducing it to a consensus motif. Such motif is resynthesized and reinserted into a single gene followed by additional selection. This step process constitutes a statistical bottleneck, is labor intensive, and is not practical for many rounds of mutagenesis.

Error-prone PCR and oligonucleotide-directed mutagenesis are thus useful for single cycles of sequence fine tuning, but rapidly become too limiting when they are applied for multiple cycles.

Another limitation of error-prone PCR is that the rate of down-mutations grows with the information content of the sequence. As the information content, library size, and mutagenesis rate increase, the balance of down-mutations to up-mutations will statistically prevent the selection of further improvements (statistical ceiling).

8.16.3.3 Cassette Mutagenesis

In cassette mutagenesis, a sequence block of a single template is typically replaced by a (partially) randomized sequence. Therefore, the maximum information content that can be obtained is statistically limited by the number of random sequences (i.e., library size). This eliminates other sequence families which are not currently best, but which may have greater long term potential.

Also, mutagenesis with synthetic oligonucleotides requires sequencing of individual clones after each selection round. Thus, such an approach is tedious and impractical for many rounds of mutagenesis.

Thus, error-prone PCR and cassette mutagenesis are best suited, and have been widely used, for fine-tuning areas of comparatively low information content. One apparent exception is the selection of an RNA ligase ribozyme from a random library using many rounds of amplification by error-prone PCR and selection.

In nature, the evolution of most organisms occurs by natural selection and sexual reproduction. Sexual reproduction ensures mixing and combining of the genes in the offspring of the selected individuals. During meiosis, homologous chromosomes from the parents line up with one another and cross-over part way along their length, thus randomly swapping genetic material. Such swapping or shuffling of the DNA allows organisms to evolve more rapidly.

In recombination, because the inserted sequences were of proven utility in a homologous environment, the inserted sequences are likely to still have substantial information content once they are inserted into the new sequence.

8.16.3.4 Applied Molecular Evolution

The term Applied Molecular Evolution ("AME") means the application of an evolutionary design algorithm to a specific, useful goal. While many different library formats for AME have been reported for polynucleotides, peptides and proteins (phage, lacI and polysomes), none of these formats have provided for recombination by random cross-overs to deliberately create a combinatorial library.

Theoretically there are 2,000 different single mutants of a 100 amino acid protein. However, a protein of 100 amino acids has $20^{100}$ possible sequence combinations, a number which is too large to exhaustively explore by conventional methods. It would be advantageous to develop a system which would allow generation and screening of all of these possible combination mutations.

8.16.3.5 Reported in vivo Recombination Systems

Some workers in the art have utilized an in vivo site specific recombination system to generate hybrids of combine light chain antibody genes with heavy chain antibody genes for expression in a phage system. However, their system relies on specific sites of recombination and is limited accordingly. Simultaneous mutagenesis of antibody CDR regions in single chain antibodies (scFv) by overlapping extension and PCR have been reported.

Others have described a method for generating a large population of multiple hybrids using random in vivo recombination. This method requires the recombination of two different libraries of plasmids, each library having a different selectable marker. The method is limited to a finite number of recombinations equal to the number of selectable markers existing, and produces a concomitant linear increase in the number of marker genes linked to the selected sequence(s).

In vivo recombination between two homologous, but truncated, insect-toxin genes on a plasmid has been reported as a method of producing a hybrid gene. The in vivo recombination of substantially mismatched DNA sequences in a host cell having defective mismatch repair enzymes, resulting in hybrid molecule formation has been reported.

8.16.4 Strategies

In one aspect this invention provides a method that utilizes the natural property of cells to recombine molecules and/or to mediate reductive processes that reduce the complexity of sequences and extent of repeated or consecutive sequences possessing regions of homology.

It is an object of the present invention to provide a method for generating hybrid polynucleotides encoding biologically active hybrid polypeptides with enhanced activities. In accomplishing these and other objects, there has been provided, in accordance with one aspect of the invention, a method for introducing polynucleotides into a suitable host cell and growing the host cell under conditions which produce a hybrid polynucleotide.

In another aspect of the invention, the invention provides a method for screening for biologically active hybrid polypeptides encoded by hybrid polynucleotides. The present method allows for the identification of biologically active hybrid polypeptides with enhanced biological activities.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

8.16.5 Possible Uses

The invention described herein is directed to the use of repeated cycles of reductive reassortment, recombination and selection which allow for the directed molecular evolution of highly complex linear sequences, such as DNA, RNA or proteins thorough recombination.

In vivo shuffling of molecules can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

8.16.5.1 Production of a Hybrid Polynucleotide

In a preferred embodiment, the invention relates to a method for producing a hybrid polynucleotide from at least a first polynucleotide and a second polynucleotide. The present invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

The invention provides a means for generating hybrid polynucleotides which may encode biologically active hybrid polypeptides. In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism may, for example, function effectively under a particular environmental condition, e.g. high salinity. An enzyme encoded by a second polynucleotide from a different organism may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

8.16.5.1.1 Encoded Enzymes

Enzymes encoded by the original polynucleotides of the invention include, but are not limited to; oxidoreductases, transferases, hydrolases, lyases, isomerases and ligases. A hybrid-polypeptide resulting from the method of the invention may exhibit specialized enzyme activity not displayed in the original enzymes. For example, following recombination and/or reductive reassortment of polynucleotides encoding hydrolase activities, the resulting hybrid polypeptide encoded by a hybrid polynucleotide can be screened for specialized hydrolase activities obtained from each of the original enzymes, i.e. the type of bond on which the hydrolase acts and the temperature at which the hydrolase functions. Thus, for example, the hydrolase may be screened to ascertain those chemical functionalities which distinguish the hybrid hydrolase from the original hydrolyases, such as: (a) amide (peptide bonds), i.e. proteases; (b) ester bonds, i.e. esterases and lipases; (c) acetals, i.e., glycosidases and, for example, the temperature, pH or salt concentration at which the hybrid polypeptide functions.

8.16.5.1.2 Sources of the Original Polynucleotides

Sources of the original polynucleotides may be isolated from individual organisms ("isolates"), collections of organisms that have been grown in defined media ("enrichment cultures"), or, most preferably, uncultivated organisms ("environmental samples"). The use of a culture-independent approach to derive polynucleotides encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

The microorganisms from which the polynucleotide may be prepared include prokaryotic microorganisms, such as Eubacteria and Archaebacteria, and lower eukaryotic microorganisms such as fungi, some algae and protozoa. Polynucleotides may be isolated from environmental samples in which case the nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. Polynucleotides encoding enzymes isolated from extremophilic microorganisms are particularly preferred. Such enzymes may function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. For example, several esterases and lipases cloned and expressed from extremophilic organisms show high activity throughout a wide range of temperatures and pHs.

8.16.5.1.3 Suitable Host Cells

Polynucleotides selected and isolated as hereinabove described are introduced into a suitable host cell. A suitable host cell is any cell which is capable of promoting recombination and/or reductive reassortment. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

As representative examples of appropriate hosts, there may be mentioned: bacterial cells, such as E. coli, Streptomyces, Salmonella typhimurium; fungal cells, such as yeast; insect cells such as Drosophila S2 and Spodoptera SJ9; animal cells such as CHO, COS or Bowes melanoma; adenoviruses; and plant cells. The selection of an appropriate host is deemed to be within the scope of those skilled in the art from the teachings herein.

8.16.5.1.3.1 Mammalian Cell Culture Systems

With particular references to various mammalian cell culture systems that can be employed to express recombinant protein, examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified enzyme activity may then be sequenced to identify the polynucleotide sequence encoding an enzyme having the enhanced activity.

8.16.5.1.4 Generation of Polynucleotides Encoding Biochemical Pathways

In another aspect, it is envisioned the method of the present invention can be used to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function. An example of a biochemical pathway encoded by gene clusters are polyketides. Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of an enormous variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

The ability to select and combine desired components from a library of polyketides, or fragments thereof, and postpolyketide biosynthesis genes for generation of novel polyketides for study is appealing. The method of the present invention makes it possible to facilitate the production of novel polyketide synthases through intermolecular recombination.

8.16.5.1.5 Gene Cluster DNA

Preferably, gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of E. coli. This f-factor of E. coli is a plasmid which affect high-frequency transfer of itself during conjugation and is ideal to achieve and stably propagate large DNA fragments, such as gene clusters from mixed microbial samples. Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Therefore, in a preferred embodiment, the present invention relates to a method for producing a biologically active hybrid polypeptide and screening such a polypeptide for enhanced activity by:

introducing at least a first polynucleotide in operable linkage and a second polynucleotide in operable linkage, said at least first polynucleotide and second polynucleotide sharing at least one region of partial sequence homology, into a suitable host cell;

growing the host cell under conditions which promote sequence reorganization resulting in a hybrid polynucleotide in operable linkage;

expressing a hybrid polypeptide encoded by the hybrid polynucleotide;

screening the hybrid polypeptide under conditions which promote identification of enhanced biological activity; and isolating the a polynucleotide encoding the hybrid polypeptide.

Methods for screening for various enzyme activities are known to those of skill in the art and discussed throughout the present specification. Such methods may be employed when isolating the polypeptides and polynucleotides of the present invention.

The term "isolated" means that material is removed from its original environment (e.g., the natural environment if it is naturally occurring). For example, a naturally-occurring polynucleotide or polypeptide present in a living animal is not isolated, but the same polynucleotide or polypeptide separated from some or all of the coexisting materials in the natural system, is isolated.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

8.16.5.1.6 Expression Vectors

As representative examples of expression vectors which may be used there may be mentioned viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus and yeast) Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used as long as they are replicable and viable in the host. Low copy number or high copy number vectors may be employed with the present invention.

A preferred type of vector for use in the present invention contains an f-factor origin replication. The f-factor (or fertility factor) in $E.$ $coli$ is a plasmid which effects high frequency transfer of itself during conjugation and less frequent transfer of the bacterial chromosome itself. A particularly preferred embodiment is to use cloning vectors, referred to as "fosmids" or bacterial artificial chromosome (BAC) vectors. These are derived from $E.$ $coli$ f-factor which is able to stably integrate large segments of genomic DNA. When integrated with DNA from a mixed uncultured environmental sample, this makes it possible to achieve large genomic fragments in the form of a stable "environmental DNA library."

Another preferred type of vector for use in the present invention is a cosmid vector. Cosmid vectors were originally designed to clone and propagate large segments of genomic DNA. Cloning into cosmid vectors is described in detail in Sambrook, et al., Molecular Cloning A Laboratory Manual, Second Edition, Cold Spring Harbor Laboratory Press, 1989.

8.16.5.1.6.1 Expression Control Sequence

The DNA sequence in the expression vector is operatively linked to an appropriate expression control sequence(s) (promoter) to direct RNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

8.16.5.1.6.2 Selectable Marker Genes

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ Generally, recombinant expression vectors will include origins of replication and selectable markers permitting transformation of the host cell, e.g., the ampicillin resistance gene of $E.$ $coli$ and $S.$ $cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), -factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

The cloning strategy permits expression via both vector driven and endogenous promoters; vector promotion may be important with expression of genes whose endogenous promoter will not function in $E.$ $coli.$ 8.16.5.1.7 Insertion into a Vector or Plasmid The DNA isolated or derived from microorganisms can preferably be inserted into a vector or a plasmid prior to probing for selected DNA. Such vectors or plasmids are preferably those containing expression regulatory sequences, including promoters, enhancers and the like. Such polynucleotides can be part of a vector and/or a composition and still be isolated, in that such vector or composition is not part of its natural environment. Particularly preferred phage or plasmid and methods for introduction and packaging into them are described in detail in the protocol set forth herein.

The selection of the cloning vector depends upon the approach taken, for example, the vector can be any cloning vector with an adequate capacity for multiply repeated copies of a sequence, or multiple sequences that can be successfully transformed and selected in a host cell. One example of such a vector is described in "Polycos vectors: a system for packaging filamentous phage and phagemid vectors using lambda phage packaging extracts", Alting-Mecs MA, Short J M, Gene, Dec 27, 1993 137:1, 93–100. Propagation/maintenance can be by an antibiotic resistance carried by the cloning vector. After a period of growth, the naturally abbreviated molecules are recovered and identified by size fractionation on a gel or column, or amplified directly. The cloning vector utilized may contain a selectable gene that is disrupted by the insertion of the lengthy construct. As reductive reassortment progresses, the number of repeated units is reduced and the interrupted gene is again expressed and hence selection for the processed construct can be applied. The vector may be an expression/selection vector which will allow for the selection of an expressed product possessing desirable biologically properties. The insert may be positioned downstream of a functional promotor and the desirable property screened by appropriate means.

8.16.5.1.8 Reductive Reassortment

In vivo reassortment is focused on "inter-molecular" processes collectively referred to as "recombination" which in bacteria, is generally viewed as a "RecA-dependent" phenomenon. The present invention can rely on recombination processes of a host cell to recombine and re-assort sequences, or the cells ability to mediate reductive processes to decrease the complexity of quasi-repeated sequences in the cell by deletion. This process of "reductive reassortment" occurs by an "intra-molecular", RecA-independent process.

Therefore, in another aspect of the present invention, novel polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

8.16.5.1.9 Repeated or "Quasi-Repeated" Sequences

Repeated or "quasi-repeated" sequences play a role in genetic instability. In the present invention, "quasi-repeats" are repeats. that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

8.16.5.1.10 Assembly of Sequences in a Head to Tail Orientation

Sequences can be assembled in a head to tail orientation using any of a variety of methods, including the following:

a) Primers that include a poly-A head and poly-T tail which when made single-stranded would provide orientation can be utilized. This is accomplished by having the first few bases of the primers made from RNA and hence easily removed RNAseH.

b) Primers that include unique restriction cleavage sites can be utilized. Multiple sites, a battery of unique sequences, and repeated synthesis and ligation steps would be required.

c) The inner few bases of the primer could be thiolated and an exonuclease used to produce properly tailed molecules.

8.16.5.1.11 The Recovery of the Re-assorted Sequences

The recovery of the re-assorted sequences relies on the identification of cloning vectors with a reduced RI. The re-assorted encoding sequences can then be recovered by amplification. The products are re-cloned and expressed. The recovery of cloning vectors with reduced RI can be effected by:

1) The use of vectors only stably maintained when the construct is reduced in complexity.
2) The physical recovery of shortened vectors by physical procedures. In this case, the cloning vector would be recovered using standard plasmid isolation procedures and size fractionated on either an agarose gel, or column with a low molecular weight cut off utilizing standard procedures.
3) The recovery of vectors containing interrupted genes which can be selected when insert size decreases.
4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates the method of the invention. Encoding nucleic acid sequences (quasi-repeats) derived from three (3) unique species are depicted. Each sequence encodes a protein with a distinct set of properties. Each of the sequences differs by a single or a few base pairs at a unique position in the sequence which are designated "A", "B" and "C". The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may, or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations.

Optionally, the method comprises the additional step of screening the library members of the shuffled pool to identify individual shuffled library members having the ability to bind or otherwise interact (e.g., such as catalytic antibodies)

with a predetermined macromolecule, such as for example a proteinaceous receptor, peptide oligosaccharide, viron, or other predetermined compound or structure.

The displayed polypeptides, antibodies, peptidomimetic antibodies, and variable region sequences that are identified from such libraries can be used for therapeutic, diagnostic, research and related purposes (e.g., catalysts, solutes for increasing osmolarity of an aqueous solution, and the like), and/or can be subjected to one or more additional cycles of shuffling and/or affinity selection. The method can be modified such that the step of selecting for a phenotypic characteristic can be other than of binding affinity for a predetermined molecule (e.g., for catalytic activity, stability oxidation resistance, drug resistance, or detectable phenotype conferred upon a host cell).

8.16.5.1.12 Providing Antibodies Suitable for Affinity Interactions Screening

The present invention provides a method for generating libraries of displayed antibodies suitable for affinity interactions screening. The method comprises (1) obtaining first a plurality of selected library members comprising a displayed antibody and an associated polynucleotide encoding said displayed antibody, and obtaining said associated polynucleotide encoding for said displayed antibody and obtaining said associated polynucleotides or copies thereof, wherein said associated polynucleotides comprise a region of substantially identical variable region framework sequence, and (2) introducing said polynucleotides into a suitable host cell and growing the cells under conditions which promote recombination and reductive reassortment resulting in shuffled polynucleotides. CDR combinations comprised by the shuffled pool are not present in the first plurality of selected library members, said shuffled pool composing a library of displayed antibodies comprising CDR permutations and suitable for affinity interaction screening. Optionally, the shuffled pool is subjected to affinity screening to select shuffled library members which bind to a predetermined epitope (antigen) and thereby selecting a plurality of selected shuffled library members. Further, the plurality of selectively shuffled library members can be shuffled and screened iteratively, from 1 to about 1000 cycles or as desired until library members having a desired binding affinity are obtained.

8.16.5.1.13 Introduction of Mutations into the Original Polynucleotides

In another aspect of the invention, it is envisioned that prior to or during recombination or reassortment, polynucleotides generated by the method of the present invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N3-Adenine), (see. Biochem. 31, 2822–2829 (1992)); a N-acelylated or deacetylated 4'-fluro-4-aminobiphenyl adduct capable of inhibiting DNA synthesis (see, for example, Carcinogenesis vol. 13, No. 5, 751–758 (1992); or a N-acetylated or deacetylated 4-aminobiphenyl adduct capable of inhibiting DNA synthesis (see also, Id. 751–758); trivalent chromium, a trivalent chromium salt, a polycyclic aromatic hydrocarbon ("PAH") DNA adduct capable of inhibiting DNA replication, such as 7-bromomethyl-benz[α]anthracene ("BMA"), tris(2,3-dibrromopropyl)phosphate ("Tris-BP"), 1,2-dibromo-3-chloropropane ("DBCP"), 2-bromoacrolein (2BA), benzo[a]pyrene-7,8-dihydrodiol-9-10-epoxide ("BPDE"), a platinum(II) halogen salt, N-hydroxy-2-amino-3-methylimidazo[4,5-f]-quinoline ("N-hydroxy-IQ"), and N-hydroxy-2-amino-1-methyl-6-phenylimidazo[4,5-f]-pyridine ("N-hydroxy-PhIP"). Especially preferred "means for slowing or halting PCR amplification consist of UV light (+)-CC-1065 and (+)-CC-1065-(N3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

8.16.5.1.14 Production of Hybrid or Re-Assorted Polynucleotides

In another aspect the present invention is directed to a method of producing recombinant proteins having biological activity by treating a sample comprising double-stranded template polynucleotides encoding a wild-type protein under conditions according to the present invention which provide for the production of hybrid or re-assorted polynucleotides.

8.16.5.1.15 Shuffling a Population of Viral Genes of Viral Genomes

The invention also provides the use of polynucleotide shuffling to shuffle a population of viral genes (e.g., capsid proteins, spike glycoproteins, polymerases, and proteases) or viral genomes (e.g., paramyxoviridae, orthomyxoviridae, herpesviruses, retroviruses, reoviruses and rhinoviruses). In an embodiment, the invention provides a method for shuffling sequences encoding all or portions of immunogenic viral proteins to generate novel combinations of epitopes as well as novel epitopes created by recombination; such shuffled viral proteins may comprise epitopes or combinations of epitopes as well as novel epitopes created by recombination; such shuffled viral proteins may comprise epitopes or combinations of epitopes which are likely to arise in the natural environment as a consequence of viral evolution; (e.g., such as recombination of influenza virus strains).

8.16.5.1.16 Generation of Gene Therapy Vectors and Replication-Defective Gene Therapy Constructs The invention also provides a method suitable for shuffling polynucleotide sequences for generating gene therapy vectors and replication-defective gene therapy constructs, such as may be used for human gene therapy, including but not limited to vaccination vectors for DNA-based vaccination, as well as anti-neoplastic gene therapy and other general therapy formats.

8.16.5.2 Definitions

The term "DNA shuffling" is used herein to indicate recombination between substantially homologous but non-identical sequences, in some embodiments DNA shuffling may involve crossover via non-homologous recombination, such as via cer/lox and/or flp/frt systems and the like.

The term "amplification" means that the number of copies of a polynucleotide is increased.

The term "identical" or "identity" means that two nucleic acid sequences have the same sequence or a complementary sequence. Thus, "areas of identity" means that regions or areas of a polynucleotide or the overall polynucleotide are identical or complementary to areas of another polynucleotide or the polynucleotide.

The term "corresponds to" is used herein to mean that a polynucleotide sequence is homologous (ie., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference "TATAC" and is complementary to a reference sequence "GTATA."

Genetic instability, as used herein, refers to the natural tendency of highly repetitive sequences to be lost through a process of reductive events generally involving sequence simplification through the loss of repeated sequences. Deletions tend to involve the loss of one copy of a repeat and everything between the repeats.

Quasi-repeated units, as used herein, refers to the repeats to be re-assorted and are by definition not identical. Indeed the method is proposed not only for practically identical encoding units produced by mutagenesis of the identical starting sequence, but also the reassortment of similar or related sequences which may diverge significantly in some regions. Nevertheless, if the sequences contain sufficient homologies to be reassorted by this approach, they can be referred to as "quasi-repeated" units.

Reductive reassortment, as used herein, refers to the increase in molecular diversity that is accrued through deletion (and/or insertion) events that are mediated by repeated sequences.

Repetitive Index (RI), as used herein, is the average number of copies of the quasi-repeated units contained in the cloning vector.

The term "related polynucleotides" means that regions or areas of the polynucleotides are identical and regions or areas of the polynucleotides are heterologous.

The term "population" as used herein means a collection of components such as polynucleotides, portions or polynucleotides or proteins. A "mixed population: means a collection of components which belong to the same family of nucleic acids or proteins (i.e., are related) but which differ in their sequence (i.e., are not identical) and hence in their biological activity.

The term "specific polynucleotide" means a polynucleotide having certain end points and having a certain nucleic acid sequence. Two polynucleotides wherein one polynucleotide has the identical sequence as a portion of the second polynucleotide but different ends comprises two different specific polynucleotides.

The following terms are used to describe the sequence relationships between two or more polynucleotides: "reference sequence," "comparison window," "sequence identity," "percentage of sequence identity," and "substantial identity." A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482 by the homology alignment algorithm of Needlemen and Wuncsch *J. Mol. Biol.* 48: 443 (1970), by the search of similarity method of Pearson and Lipman *Proc. Natl. Acad. Sci. (U.S.A.)* 85: 2444 (1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. This "substantial identity", as used herein, denotes a characteristic of a polynucleotide sequence, wherein the polynucleotide comprises a sequence having at least 80 percent sequence identity, preferably at least 85 percent identity, often 90 to 95 percent sequence identity, and most commonly at least 99 percent sequence identity as compared to a reference sequence of a comparison window of at least 25–50 nucleotides, wherein the percentage of sequence identity is calculated by comparing the reference sequence to the polynucleotide sequence which may include deletions or additions which total 20 percent or less of the reference sequence over the window of comparison.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are : valine-leucine-isoleucine, phenylalanine-tyrosine, lysine-arginine, alanine-valine, and asparagine-glutamine.

The term "homologous" or "homeologous" means that one single-stranded nucleic acid nucleic acid sequence may hybridize to a complementary single-stranded nucleic acid sequence. The degree of hybridization may depend on a number of factors including the amount of identity between the sequences and the hybridization conditions such as temperature and salt concentrations as discussed later. Preferably the region of identity is greater than about 5 bp, more preferably the region of identity is greater than 10 bp.

The term "heterologous" means that one single-stranded nucleic acid sequence is unable to hybridize to another single-stranded nucleic acid sequence or its complement. Thus areas of heterology means that areas of polynucleotides or polynucleotides have areas or regions within their sequence which are unable to hybridize to another nucleic acid or polynucleotide. Such regions or areas are, for example areas of mutations.

The term "cognate" as used herein refers to a gene sequence that is evolutionarily and functionally related between species. For example but not limitation, in the human genome the human CD4 gene is the cognate gene to the mouse 3d4 gene, since the sequences and structures of these two genes indicate that they are highly homologous and both genes encode a protein which fumctions in signaling T cell activation through MHC class II-restricted antigen recognition.

The term "wild-type" means that the polynucleotide does not comprise any mutations. A "wild type" protein means that the protein will be active at a level of activity found in nature and will comprise the amino acid sequence found in nature.

The term "mutations" means changes in the sequence of a wild-type nucleic acid sequence or changes in the sequence of a peptide. Such mutations may be point mutations such as transitions or transversions. The mutations may be deletions, insertions or duplications.

In the polypeptide notation used herein, the left-hand direction is the amino terminal direction and the right-hand direction is the carboxy-terminal direction, in accordance with standard usage and convention. Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the coding RNA transcript are referred to as "downstream sequences".

The term "naturally-occurring" as used herein as applied to the object refers to the fact that an object can be found in nature. For example, a polypeptide or polynucleotide sequence that is present in an organism (including viruses) that can be isolated from a source in nature and which has not been intentionally modified by man in the laboratory is naturally occurring. Generally, the term naturally occurring refers to an object as present in a non-pathological (undiseased) individual, such as would be typical for the species.

The term "agent" is used herein to denote a chemical compound, a mixture of chemical compounds, an array of spatially localized compounds (e.g., a VLSIPS peptide array, polynucleotide array, and/or combinatorial small molecule array), biological macromolecule, a bacteriophage peptide display library, a bacteriophage antibody (e.g., scFv) display library, a polysome peptide display library, or an extract made form biological materials such as bacteria, plants, fungi, or animal (particular mammalian) cells or tissues. Agents are evaluated for potential activity as anti-neoplastics, anti-inflammatories or apoptosis modulators by inclusion in screening assays described hereinbelow. Agents are evaluated for potential activity as specific protein interaction inhibitors (i.e., an agent which selectively inhibits a binding interaction between two predetermined polypeptides but which doe snot substantially interfere with cell viability) by inclusion in screening assays described hereinbelow.

As used herein, "substantially pure" means an object species is the predominant species present (i.e., on a molar basis it is more abundant than any other individual macromolecular species in the composition), and preferably substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50-200 mM NaCl or KCl, pH 6.5–8.5, 20–45 C. and 0.001–10 mM divalent cation (e.g., $Mg^{++}$, $Ca^{++}$); preferably about 150 mM NaCl or KCl, pH 7.2–7.6, 5 mM divalent cation, and often include 0.01–1.0 percent nonspecific protein (e.g., BSA). A non-ionic detergent (Tween, NP-40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s) and/or metal chelators and/or non-ionic detergents and/or membrane fractions and/or anti-foam agents and/or scintillants.

"Specific hybridization" is defined herein as the formation of hybrids between a first polynucleotide and a second polynucleotide (e.g., a polynucleotide having a distinct but substantially identical sequence to the first polynucleotide), wherein substantially unrelated polynucleotide sequences do not form hybrids in the mixture.

As used herein, the term "single-chain antibody" refers to a polypeptide comprising a VH domain and a VL domain in polypeptide linkage, generally liked via a spacer peptide (e.g., [Gly-Gly-Gly-Gly-Ser]$_x$), and which may comprise additional amino acid sequences at the amino- and/or carboxy- termini. For example, a single-chain antibody may comprise a tether segment for linking to the encoding polynucleotide. As an example, a scFv is a single-chain antibody. Single-chain antibodies are generally proteins consisting of one or more polypeptide segments of at least 10 contiguous amino substantially encoded by genes of the immunoglobulin superfamily (e.g., see *The Immunoglobulin Gene Superfamily*, A. F. Williams and A. N. Barclay, in *Immunoglobulin Genes*, T. Honjo, F. W. Alt, and THE.

Rabbits, eds., (1989) Academic press: San Diego, Calif., pp. 361–368, which is incorporated herein by reference), most frequently encoded by a rodent, non-human primate, avian, porcine bovine, ovine, goat, or human heavy chain or light chain gene sequence. A fuictional single-chain antibody generally contains a sufficient portion of an immunoglobulin superfamily gene product so as to retain the property of binding to a specific target molecule, typically a receptor or antigen (epitope).

As used herein, the term "complementarity-determining region" and "CDR" refer to the art-recognized term as exemplified by the Kabat and Chothia CDR definitions also generally known as supervariable regions or hypervariable loops (Chothia and Leks (1987) *J. Mol. Biol.* 19; 901; Clothia et al. (1989) *Nature* 342; 877; E.A. Kabat et al., Sequences of Proteins of Immunological Interest (national Institutes of Health, Bethesda, Md.) (1987); and Tramontano et al. (1990) *J. Mol. Biolog.* 215; 175). Variable region domains typically comprise the amino-terminal approximately 105-115 amino acids of a naturally-occurring immunoglobulin chain (e.g., amino acids 1–110), although variable domains somewhat shorter or longer are also suitable for forming single-chain antibodies.

An immunoglobulin light or heavy chain variable region consists of a "framework" region interrupted by three hypervariable regions, also called CDR's. The extent of the framework region and CDR's have been precisely defined (see, "Sequences of Proteins of Immunological Interest," E. Kabat et al., 4th Ed., U.S. Department of Health and human services, Bethesda, Md. (1987)). The sequences of the framework regions of different light or heavy chains are relatively conserved within a specie. As used herein, a "human framework region" is a framework region that is substantially identical (about 85 or more, usually 90–95 or more) to the framework region of a naturally occurring human immunoglobulin. the framework region of an antibody, that is the combined framework regions of the constituent light and heavy chains, serves to position and align the CDR's. The CDR's are primarily responsible for binding to an epitope of an antigen.

As used herein, the term "variable segment" refers to a portion of a nascent peptide which comprises a random, pseudorandom, or defined kernal sequence. A variable segment" refers to a portion of a nascent peptide which comprises a random pseudorandom, or defined kernal sequence. A variable segment can comprise both variant and invariant residue positions, and the degree of residue variation at a variant residue position may be limited: both options are selected at the discretion of the practitioner. Typically, variable segments are about 5 to 20 amino acid residues in length (e.g., 8 to 10), although variable segments may be longer and may comprise antibody portions or receptor proteins, such as an antibody fragment, a nucleic acid binding protein, a receptor protein, and the like.

As used herein, "random peptide sequence" refers to an amino acid sequence composed of two or more amino acid monomers and constructed by a stochastic or random process. A random peptide can include framework or scaffolding motifs, which may comprise invariant sequences.

As used herein "random peptide library" refers to a set of polynucleotide sequences that encodes a set of random peptides, and to the set of random peptides encoded by those polynucleotide sequences, as well as the fusion proteins contain those random peptides.

As used herein, the term "pseudorandom" refers to a set of sequences that have limited variability, such that, for example, the degree of residue variability at another position, but any pseudorandom position is allowed some degree of residue variation, however circumscribed.

As used herein, the term "defined sequence framework" refers to a set of defined sequences that are selected on a non-random basis, generally on the basis of experimental data or structural data; for example, a defined sequence framework may comprise a set of amino acid sequences that are predicted to form a β-sheet structure or may comprise a leucine zipper heptad repeat motif, a zinc-finger domain, among other variations. A "defined sequence kernal" is a set of sequences which encompass a limited scope of variability. Whereas (1) a completely random 10-mer sequence of the 20 conventional amino acids can be any of $(20)^{10}$ sequences, and (2) a pseudorandom 10-mer sequence of the 20 conventional amino acids can be any of $(20)^{10}$ sequences but will exhibit a bias for certain residues at certain positions and/or overall, (3) a defined sequence kernal is a subset of sequences if each residue position was allowed to be any of the allowable 20 conventional amino acids (and/or allowable unconventional amino/imino acids). A defined sequence kernal generally comprises variant and invariant residue positions and/or comprises variant residue positions which can comprise a residue selected from a defined subset of amino acid residues), and the like, either segmentally or over the entire length of the individual selected library member sequence. Defined sequence kernels can refer to either amino acid sequences or polynucleotide sequences. Of illustration and not limitation, the sequences $(NNK)_{10}$ and $(NNM)_{10}$, wherein N represents A, T, G, or C; K represents G or T; and M represents A or C, are defined sequence kernels.

As used herein "epitope" refers to that portion of an antigen or other macromolecule capable of forming a binding interaction that interacts with the variable region binding body of an antibody. Typically, such binding interaction is manifested as an intermolecular contact with one or more amino acid residues of a CDR.

As used herein, "receptor" refers to a molecule that has an affinity for a given ligand. Receptors can be naturally occurring or synthetic molecules. Receptors can be employed in an unaltered state or as aggregates with other species. Receptors can be attached, covalently or non-covalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

As used herein "ligand" refers to a molecule, such as a random peptide or variable segment sequence, that is recognized by a particular receptor. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

As used herein, "linker" or "spacer" refers to a molecule or group of molecules that connects two molecules, such as a DNA binding protein and a random peptide, and serves to place the two molecules in a preferred configuration, e.g., so that the random peptide can bind to a receptor with minimal steric hindrance from the DNA binding protein.

8.16.5.3 Methodology

Nucleic acid shuffling is a method for in vitro or in vivo homologous recombination of pools of shorter or smaller polynucleotides to produce a polynucleotide or polynucleotides. Mixtures of related nucleic acid sequences or polynucleotides are subjected to sexual PCR to provide random polynucleotides, and reassembled to yield a library or mixed population of recombinant hybrid nucleic acid molecules or polynucleotides.

In contrast to cassette mutagenesis, only shuffling and error-prone PCR allow one to mutate a pool of sequences blindly (without sequence information other than primers).

8.16.5.3.1 Advantage of the Mutagenic Shuffling

The advantage of the mutagenic shuffling of this invention over error-prone PCR alone for repeated selection can best be explained with an example from antibody engineering.

8.16.5.3.2 Inverse Chain Reaction

This method differs from error-prone PCR, in that it is an inverse chain reaction. In error-prone PCR, the number of polymerase start sites and the number of molecules grows exponentially. However, the sequence of the polymerase start sites and the sequence of the molecules remains essentially the same. In contrast, in nucleic acid reassembly or shuffling of random polynucleotides the number of start sites and the number (but not size) of the random polynucleotides decreases over time. For polynucleotides derived from whole plasmids the theoretical endpoint is a single, large concatemeric molecule.

Since crossovers occur at regions of homology, recombination will primarily occur between members of the same sequence family. This discourages combinations of CDRs that are grossly incompatible (e.g., directed against different epitopes of the same antigen). It is contemplated that multiple families of sequences can be shuffled in the same reaction. Further, shuffling generally conserves the relative order, such that, for example, CDR1 will not be found in the position of CDR2.

Rare shufflants will contain a large number of the best (eg. highest affinity) CDRs and these rare shufflants may be selected based on their superior affinity.

CDRs from a pool of 100 different selected antibody sequences can be permutated in up to 1006 different ways. This large number of permutations cannot be represented in a single library of DNA sequences. Accordingly, it is contemplated that multiple cycles of DNA shuffling and selection may be required depending on the length of the sequence and the sequence diversity desired.

Error-prone PCR, in contrast, keeps all the selected CDRs in the same relative sequence, generating a much smaller mutant cloud.

8.16.5.3.3 The Template Polynucleotide

The template polynucleotide which may be used in the methods of this invention may be DNA or RNA. It may be of various lengths depending on the size of the gene or shorter or smaller polynucleotide to be recombined or reassembled. Preferably, the template polynucleotide is from 50 bp to 50 kb. It is contemplated that entire vectors containing the nucleic acid encoding the protein of interest can be used in the methods of this invention, and in fact have been successfully used.

The template polynucleotide may be obtained by amplification using the PCR reaction (U.S. Pat. Nos. 4,683,202 and 4,683,195) or other amplification or cloning methods. However, the removal of free primers from the PCR products before subjecting them to pooling of the PCR products and sexual PCR may provide more efficient results. Failure to adequately remove the primers from the original pool before sexual PCR can lead to a low frequency of crossover clones.

The template polynucleotide often should be double-staanded. A double-stranded nucleic acid molecule is recommended to ensure that regions of the resulting single-stranded polynucleotides are complementary to each other and thus can hybridize to form a double-stranded molecule.

It is contemplated that single-stranded or double-stranded nucleic acid polynucleotides having regions of identity to the template polynucleotide and regions of heterology to the template polynucleotide may be added to the template polynucleotide, at this step. It is also contemplated that two different but related polynucleotide templates can be mixed at this step.

The double-stranded polynucleotide template and any added double-or single-stranded polynucleotides are subjected to sexual PCR which includes slowing or halting to provide a mixture of from about 5 bp to 5 kb or more. Preferably the size of the random polynucleotides is from about 10 bp to 1000 bp, more preferably the size of the polynucleotides is from about 20 bp to 500 bp.

8.16.5.3.4 Use of Double-Stranded Nucleic Acid Having Multiple Nicks

Alternatively, it is also contemplated that double-stranded nucleic acid having multiple nicks may be used in the methods of this invention. A nick is a break in one strand of the double-stranded nucleic acid. The distance between such nicks is preferably 5 bp to 5 kb, more preferably between 10 bp to 1000 bp. This can provide areas of self-priming to produce shorter or smaller polynucleotides to be included with the polynucleotides resulting from random primers, for example.

The concentration of any one specific polynucleotide will not be greater than 1% by weight of the total polynucleotides, more preferably the concentration of any one specific nucleic acid sequence will not be greater than 0.1% by weight of the total nucleic acid.

The number of different specific polyncletides in the mixture will be at least about 100, preferably at least about 500, and more preferably at least about 1000.

8.16.5.3.5 Increasing the Heterogeneity of the Mixture of Polynucleotides

At this step single-stranded or double-stranded polynucleotides, either synthetic or natural, may be added to the random double-stranded shorter or smaller polynucleotides in order to increase the heterogeneity of the mixture of polynucleotides.

It is also contemplated that populations of double-stranded randomly broken polynucleotides may be mixed or combined at this step with the polynucleotides from the sexual PCR process and optionally subjected to one or more additional sexual PCR cycles.

Where insertion of mutations into the template polynucleotide is desired, single-stranded or double-stranded polynucleotides having a region of identity to the template polynucleotide and a region of heterology to the template polynucleotide may be added in a 20 fold excess by weight as compared to the total nucleic acid, more preferably the single-stranded polynucleotides may be added in a 10 fold excess by weight as compared to the total nucleic acid.

Where a mixture of different but related template polynucleotides is desired, populations of polynucleotides from each of the templates may be combined at a ratio of less than about 1:100, more preferably the ratio is less than about 1:40. For example, a backcross of the wild-type polynucleotide with a population of mutated polynucleotide may be desired to eliminate neutral mutations (e.g., mutations yielding an insubstantial alteration in the phenotypic property being selected for). In such an example, the ratio of randomly provided wild-type polynucleotides which may be added to the randomly provided sexual PCR cycle hybrid polynucleotides is approximately 1:1 to about 100:1, and more preferably from 1:1 to 40:1.

8.16.5.3.5.1 Denaturing and Re-annealing

The mixed population of random polynucleotides are denatured to form single-stranded polynucleotides and then re-annealed. Only those single-stranded polynucleotides having regions of homology with other single-stranded polynucleotides will re-anneal.

The random polynucleotides may be denatured by heating. One skilled in the art could determine the conditions necessary to completely denature the double-stranded nucleic acid. Preferably the temperature is from 80 C. to 100 C., more preferably the temperature is from 90 C. to 96 C. other methods which may be used to denature the polynucleotides include pressure (36) and pH.

The polynucleotides may be re-annealed by cooling. Preferably the temperature is from 20 C. to 75 C., more preferably the temperature is from 40 C. to 65 C. If a high frequency of crossovers is needed based on an average of only 4 consecutive bases of homology, recombination can be forced by using a low annealing temperature, although the process becomes more difficult. The degree of renaturation which occurs will depend on the degree of homology between the population of single-stranded polynucleotides.

Renaturation can be accelerated by the addition of polyethylene glycol ("PEG") or salt. The salt concentration is preferably from 0 mM to 200 mM, more preferably the salt concentration is from 10 mM to 100 mm. The salt may be KCl or NaCl. The concentration of PEG is preferably from 0% to 20%, more preferably from 5% to 10%.

8.16.5.3.5.2 Incubation

The annealed polynucleotides are next incubated in the presence of a nucleic acid polymerase and dNTP's (i.e. dATP, dCTP, DGTP and dTTP). The nucleic acid polymerase may be the Klenow fragment, the Taq polymerase or any other DNA polymerase known in the art.

The approach to be used for the assembly depends on the minimum degree of homology that should still yield crossovers. If the areas of identity are large, Taq polymerase can be used with an annealing temperature of between 45–65 C. If the areas of identity are small, Klenow polymerase can be used with an annealing temperature of between 20–30 C. One skilled in the art could vary the temperature of annealing to increase the number of cross-overs achieved.

The polymerase may be added to the random polynucleotides prior to annealing, simultaneously with annealing or after annealing.

The cycle of denaturation, renaturation and incubation in the presence of polymerase is referred to herein as shuffling or reassembly of the nucleic acid. This cycle is repeated for a desired number of times. Preferably the cycle is repeated from 2 to 50 times, more preferably the sequence is repeated from 10 to 40 times.

8.16.5.3.6 The Resulting Nucleic Acid

The resulting nucleic acid is a larger double-stranded polynucleotide of from about 50 bp to about 100 kb, preferably the larger polynucleotide is from 500 bp to 50 kb.

This larger polynucleotides may contain a number of copies of a polynucleotide having the same size as the template polynucleotide in tandem. This concatemeric polynucleotide is then denatured into single copies of the template polynucleotide. The result will be a population of polynucleotides of approximately the same size as the template polynucleotide. The population will be a mixed population where single or double-stranded polynucleotides having an area of identity and an area of heterology have been added to the template polynucleotide prior to shuffling.

These polynucleotides are then cloned into the appropriate vector and the ligation mixture used to transform bacteria.

It is contemplated that the single polynucleotides may be obtained from the larger concatemeric polynucleotide by amplification of the single polynucleotide prior to cloning by a variety of methods including PCR (U.S. Pat. Nos. 4,683,195 and 4,683,202), rather than by digestion of the concatemer.

8.16.5.3.7 Vectors Used for Cloning

The vector used for cloning is not critical provided that it will accept a polynucleotide of the desired size. If expression of the particular polynucleotide is desired, the cloning vehicle should further comprise transcription and translation signals next to the site of insertion of the polynucleotide to allow expression of the polynucleotide in the host cell. Preferred vectors include the pUC series and the pBR series of plasmids.

8.16.5.3.8 The Resulting Bacterial Population

The resulting bacterial population will include a number of recombinant polynucleotides having random mutations. This mixed population may be tested to identify the desired recombinant polynucleotides. The method of selection will depend on the polynucleotide desired.

For example, if a polynucleotide which encodes a protein with increased binding efficiency to a ligand is desired, the proteins expressed by each of the portions of the polynucleotides in the population or library may be tested for their ability to bind to the ligand by methods known in the art (i.e. panning, affinity chromatography). If a polynucleotide which encodes for a protein with increased drug resistance is desired, the proteins expressed by each of the polynucleotides in the population or library may be tested for their ability to confer drug resistance to the host organism. One skilled in the art, given knowledge of the desired protein, could readily test the population to identify polynucleotides which confer the desired properties onto the protein.

It is contemplated that one skilled in the art could use a phage display system in which fragments of the protein are expressed as fusion proteins on the phage surface (Pharmacia, Milwaukee Wis.). The recombinant DNA molecules are cloned into the phage DNA at a site which results in the transcription of a fusion protein a portion of which is encoded by the recombinant DNA molecule. The phage containing the recombinant nucleic acid molecule undergoes replication and transcription in the cell. The leader sequence of the fusion protein directs the transport of the fusion protein to the tip of the phage particle. Thus the fusion protein which is partially encoded by the recombinant DNA molecule is displayed on the phage particle for detection and selection by the methods described above.

8.16.5.3.9 Cycles of Nucleic Acid Shuffling

It is further contemplated that a number of cycles of nucleic acid shuffling may be conducted with polynucleotides from a sub-population of the first population, which sub-population contains DNA encoding the desired recombinant protein. In this manner, proteins with even higher binding affinities or enzymatic activity could be achieved.

It is also contemplated that a number of cycles of nucleic acid shuffling may be conducted with a mixture of wild-type polynucleotides and a sub-population of nucleic acid from the first or subsequent rounds of nucleic acid shuffling in order to remove any silent mutations from the sub-population.

8.16.5.3.10 The Starting Nucleic Acid

Any source of nucleic acid, in purified form can be utilized as the starting nucleic acid. Thus the process may employ DNA or RNA including messenger RNA, which DNA or RNA may be single or double stranded. In addition, a DNA-RNA hybrid which contains one strand of each may be utilized. The nucleic acid sequence may be of various lengths depending on the size of the nucleic acid sequence to be mutated. Preferably the specific nucleic acid sequence is from 50 to 50000 base pairs. It is contemplated that entire vectors containing the nucleic acid encoding the protein of interest may be used in the methods of this invention.

The nucleic acid may be obtained from any source, for example, from plasmids such a pBR322, from cloned DNA or RNA or from natural DNA or RNA from any source including bacteria, yeast, viruses and higher organisms such as plants or animals. DNA or RNA may be extracted from blood or tissue material. The template polynucleotide may be obtained by amplification using the polynucleotide chain reaction (PCR) (U.S. Pat. Nos. 4,683,202 and 4,683,195). Alternatively, the polynucleotide may be present in a vector present in a cell and sufficient nucleic acid may be obtained by culturing the cell and extracting the nucleic acid from the cell by methods known in the art.

Any specific nucleic acid sequence can be used to produce the population of hybrids by the present process. It is only necessary that a small population of hybrid sequences of the specific nucleic acid sequence exist or be created prior to the present process.

8.16.5.3.11 Creation of the Initial Population of Sequences

The initial small population of the specific nucleic acid sequences having mutations may be created by a number of different methods. Mutations may be created by error-prone PCR. Error-prone PCR uses low-fidelity polymerization conditions to introduce a low level of point mutations randomly over a long sequence. Alternatively, mutations can be introduced into the template polynucleotide by oligonucleotide-directed mutagenesis. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be altered by chemical mutagenesis. Chemical mutagens include, for example, sodium bisulfite, nitrous acid, hydroxylamine, hydrazine or formic acid. other agents which ate analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light. Generally, plasmid polynucleotides so mutagenized are introduced into *E. coli* and propagated as a pool or library of hybrid plasmids.

Alternatively the small mixed population of specific nucleic acids may be found in nature in that they may consist of different alleles of the same gene or the same gene from different related species (i.e., cognate genes). Alternatively, they may be related DNA sequences found within one species, for example, the immunoglobulin genes.

Once the mixed population of the specific nucleic acid sequences is generated, the polynucleotides can be used directly or inserted into an appropriate cloning vector, using techniques well-known in,the art.

8.16.5.3.11.1 The Choice of Vector

The choice of vector depends on the size of the polynucleotide sequence and the host cell to be employed in the methods of this invention. The templates of this invention may be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are preferred where the specific nucleic acid sequence to be mutated is larger because these vectors are able to stably propagate large polynucleotides.

8.16.5.3.11.2 Clonal Amplification

If the mixed population of the specific nucleic acid sequence is cloned into a vector it can be clonally amplified by inserting each vector into a host cell and allowing the host cell to amplify the vector. This is referred to as clonal amplification because while the absolute number of nucleic acid sequences increases, the number of hybrids does not increase. Utility can be readily determined by screening expressed polypeptides.

8.16.5.3.12 Incorporation of Any Sequence Mixture at Any Specific Position

The DNA shuffling method of this invention can be performed blindly on a pool of unknown sequences. By adding to the reassembly mixture oligonucleotides (with ends that are homologous to the sequences being reassembled) any sequence mixture can be incorporated at any specific position into another sequence mixture. Thus, it is contemplated that mixtures of synthetic oligonucleotides, PCR polynucleotides or even whole genes can be mixed into another sequence library at defined positions. The insertion of one sequence (mixture) is independent from the insertion of a sequence in another part of the template. Thus, the degree of recombination, the homology required, and the diversity of the library can be independently and simultaneously varied along the length of the reassembled DNA.

This approach of mixing two genes may be useful for the humanization of antibodies from murine hybridomas. The approach of mixing two genes or inserting alternative sequences into genes may be useful for any therapeutically used protein, for example, interleukin I, antibodies, tPA and growth hormone. The approach may also be useful in any nucleic acid for example, promoters or introns or 3' untranslated region or 5' untranslated regions of genes to increase expression or alter specificity of expression of proteins. The approach may also be used to mutate ribozymes or aptamers.

8.16.5.3.13 Creation of Scaffold-like Proteins

Shuffling requires the presence of homologous regions separating regions of diversity. Scaffold-like protein structures may be particularly suitable for shuffling. The conserved scaffold determines the overall folding by self-association, while displaying relatively unrestricted loops that mediate the specific binding. Examples of such scaffolds are the immunoglobulin beta-barrel, and the four-helix bundle which are well-known in the art. This shuffling can be used to create scaffold-like proteins with various combinations of mutated sequences for binding.

8.16.5.4 In vitro Shuffling

The equivalents of some standard genetic matings may also be performed by shuffling in vitro. For example, a "molecular backcross" can be performed by repeatedly mixing the hybrid's nucleic acid with the wild-type nucleic acid while selecting for the mutations of interest. As in traditional breeding, this approach can be used to combine phenotypes from different sources into a background of choice. It is useful, for example, for the removal of neutral mutations that affect unselected characteristics (i.e. immunogenicity). Thus it can be useful to determine which mutations in a protein are involved in the enhanced biological activity and which are not, an advantage which cannot be achieved by error-prone mutagenesis or cassette mutagenesis methods.

Large, functional genes can be assembled correctly from a mixture of small random polynucleotides. This reaction may be of use for the reassembly of genes from the highly fragmented DNA of fossils. In addition random nucleic acid fragments from fossils may be combined with polynucleotides from similar genes from related species.

8.16.5.4.1 In vitro Amplification of a Genome

It is also contemplated that the method of this invention can be used for the in vitro amplification of a whole genome from a single cell as is needed for a variety of research and diagnostic applications. DNA amplification by PCR is in practice limited to a length of about 40 kb. Amplification of a whole genome such as that of E. coli (5,000 kb) by PCR would require about 250 primers yielding 125 forty kb polynucleotides. This approach is not practical due to the unavailability of sufficient sequence data. On the other hand, random production of polynucleotides of the genome with sexual PCR cycles, followed by gel purification of small polynucleotides will provide a multitude of possible primers. Use of this mix of random small polynucleotides as primers in a PCR reaction alone or with the whole genome as the template should result in an inverse chain reaction with the theoretical endpoint of a single concatemer containing many copies of the genome.

100 fold amplification in the copy number and an average polynucleotide size of greater than 50 kb may be obtained when only random polynucleotides are used. It is thought that the larger concatemer is generated by overlap of many smaller polynucleotides. The quality of specific PCR products obtained using synthetic primers will be indistinguishable from the product obtained from unamplified DNA. It is expected that this approach will be useful for the mapping of genomes.

The polynucleotide to be shuffled can be produced as random or non-random polynucleotides, at the discretion of the practitioner.

8.16.5.5 In vivo Shuffling

In an embodiment of in vivo shuffling, the mixed population of the specific nucleic acid sequence is introduced into bacterial or eukaryotic cells under conditions such that at least two different nucleic acid sequences are present in each host cell. The polynucleotides can be introduced into the host cells by a variety of different methods. The host cells can be transformed with the smaller polynucleotides using methods known in the art, for example treatment with calcium chloride. If the polynucleotides are inserted into a phage genome, the host cell can be transfected with the recombinant phage genome having the specific nucleic acid sequences. Alternatively, the nucleic acid sequences can be introduced into the host cell using electroporation, transfection, lipofection, biolistics, conjugation, and the like.

In general, in this embodiment, the specific nucleic acids sequences will be present in vectors which are capable of stably replicating the sequence in the host cell. In addition, it is contemplated that the vectors will encode a marker gene such that host cells having the vector can be selected. This ensures that the mutated specific nucleic acid sequence can be recovered after introduction into the host cell. However, it is contemplated that the entire mixed population of the specific nucleic acid sequences need not be present on a vector sequence. Rather only a sufficient number of sequences need be cloned into vectors to ensure that after introduction of the polynucleotides into the host cells each host cell contains one vector having at least one specific nucleic acid sequence present therein. It is also contemplated that rather than having a subset of the population of the specific nucleic acids sequences cloned into vectors, this subset may be already stably integrated into the host cell.

8.16.5.5.1 Homologous Recombination

It has been found that when two polynucleotides which have regions of identity are inserted into the host cells homologous recombination occurs between the two polynucleotides. Such recombination between the two mutated specific nucleic acid sequences will result in the production of double or triple hybrids in some situations.

8.16.5.5.2 Increase in the Frequency of Recombination

It has also been found that the frequency of recombination is increased if some of the mutated specific nucleic acid sequences are present on linear nucleic acid molecules. Therefore, in a preferred embodiment, some of the specific nucleic acid sequences are present on linear polynucleotides.

8.16.5.5.3 Identification of Host Cell Transformants Containing Desired Sequences After transformation, the host cell transformants are placed under selection to identify those host cell transformants which contain mutated specific nucleic acid sequences having the qualities desired. For example, if increased resistance to a particular drug is desired then the transformed host cells may be subjected to increased concentrations of the particular drug and those transformants producing mutated proteins able to confer increased drug resistance will be selected. If the enhanced ability of a particular protein to bind to a receptor is desired, then expression of the protein can be induced from the transformants and the resulting protein assayed in a ligand binding assay by methods known in the art to identify that subset of the mutated population which shows enhanced binding to the ligand. Alternatively, the protein can be expressed in another system to ensure proper processing.

Once a subset of the first recombined specific nucleic acid sequences (daughter sequences) having the desired characteristics are identified, they are then subject to a second round of recombination.

8.16.5.5.4 The Second Cycle of Recombination

In the second cycle of recombination, the recombined specific nucleic acid sequences may be mixed with the original mutated specific nucleic acid sequences (parent sequences) and the cycle repeated as described above. In this way a set of second recombined specific nucleic acids sequences can be identified which have enhanced characteristics or encode for proteins having enhanced properties. This cycle can be repeated a number of times as desired.

It is also contemplated th at in the second or subsequent recombination cycle, a backcross can be performed. A molecular backcross can be performed by mixing the desired specific nucleic acid sequences with a large number of the wild-type sequence, such that at least one wild-type nucleic acid sequence and a mutated nucleic acid sequence are present in the same host cell after transformation. Recombination with the wild-type specific nucleic acid sequence will eliminate those neutral mutations that may affect unselected characteristics such as immunogenicity but not the selected characteristics.

8.16.5.5.5 Generation of a Subset of the Specific Nucleic Acid Sequences

In another embodiment of this invention, it is contemplated that during the first round a subset of the specific nucleic acid sequences can be generated as smaller polynucleotides by slowing or halting their PCR amplification prior to introduction into the host cell. The size of the polynucleotides must .be large enough to contain some regions of identity with the other sequences so as to homologously recombine with the other sequences. The size of the polynucleotides will range from 0.03 kb to 100 kb more preferably from 0. 2 kb to 10 kb. It is also contemplated that in subsequent rounds, all of the specific nucleic acid sequences other than the sequences selected from the previous round may be utilized to generate PCR polynucleotides prior to introduction into the host cells.

The shorter polynucleotide sequences can be single-stranded or double-stranded. If the sequences were originally single-stranded and have become double-stranded they can be denatured with heat, chemicals or enzymes prior to insertion into the host cell. The reaction conditions suitable for separating the strands of nucleic acid are well known in the art.

The steps of this process can be repeated indefinitely, being limited only by the number of possible hybrids which can be achieved. After a certain number of cycles, all possible hybrids will have been achieved and further cycles are redundant.

In an embodiment the same mutated template nucleic acid is repeatedly recombined and the resulting recombinants selected for the desired characteristic.

8.16.5.5.6 Cloning into a Vector Capable of Replicating in a Bacteria

Therefore, the initial pool or population of mutated template nucleic acid is cloned into a vector capable of replicating in a bacteria such as E. coli. The particular vector is not essential, so long as it is capable of autonomous replication in E. coli. In a preferred embodiment, the vector is designed to allow the expression and production of any protein encoded by the mutated specific nucleic acid linked to the vector. It is also preferred that the vector contain a gene encoding for a selectable marker.

The population of vectors containing the pool of mutated nucleic acid sequences is introduced into the E. coli host cells. The vector nucleic acid sequences may be introduced by transformation, transfection or infection in the case of phage. The concentration of vectors used to transform the bacteria is such that a number of vectors is introduced into each cell. Once present in the cell, the efficiency of homologous recombination is such that homologous recombination occurs between the various vectors. This results in the generation of hybrids (daughters) having a combination of mutations which differ from the original parent mutated sequences.

The host cells are then clonally replicated and selected for the marker gene present on the vector. Only those cells having a plasmid will grow under the selection.

8.16.5.5.7 Testing for the Presence of Favorable Mutations

The host cells which contain a vector are then tested for the presence of favorable mutations. Such testing may consist of placing the cells under selective pressure, for example, if the gene to be selected is an improved drug resistance gene. If the vector allows expression of the protein encoded by the mutated nucleic acid sequence, then such selection may include allowing expression of the protein so encoded, isolation of the protein and testing of the protein to determine whether, for example, it binds with increased efficiency to the ligand of interest.

8.16.5.5.8 Isolation of the Desired Nucleic Acid Sequence

Once a particular daughter mutated nucleic acid sequence has been identified which confers the desired characteristics, the nucleic acid is isolated either already linked to the vector or separated from the vector. This nucleic acid is then mixed with the first or parent population of nucleic acids and the cycle is repeated.

It has been shown that by this method nucleic acid sequences having enhanced desired properties can be selected.

8.16.5.5.9 Addition of Parental Mutated Sequences to the Cells Containing the First Generation of Hybrids In an alternate embodiment, the first generation of hybrids are retained in the cells and the parental mutated sequences are added again to the cells. Accordingly, the first cycle of Embodiment I is conducted as described above. However, after the daughter nucleic acid sequences are identified, the host cells containing these sequences are retained.

The parent mutated specific nucleic acid population, either as polynucleotides or cloned into the same vector is introduced into the host cells already containing the daughter nucleic acids. Recombination is allowed to occur in the cells and the next generation of recombinants, or granddaughters are selected by the methods described above.

This cycle can be repeated a number of times until the nucleic acid or peptide having the desired characteristics is obtained. It is contemplated that in subsequent cycles, the population of mutated sequences which are added to the preferred hybrids may come from the parental hybrids or any subsequent generation.

8.16.5.5.10 "Molecular" Backcross to Eliminate Any Neutral Mutations

In an alternative embodiment, the invention provides a method of conducting a "molecular" backcross of the obtained recombinant specific nucleic acid in order to eliminate any neutral mutations. Neutral mutations are those mutations which do not confer onto the nucleic acid or peptide the desired properties. Such mutations may however confer on the nucleic acid or peptide undesirable characteristics. Accordingly, it is desirable to eliminate such neutral mutations. The method of this invention provide a means of doing so.

In this embodiment, after the hybrid nucleic acid, having the desired characteristics, is obtained by the methods of the embodiments, the nucleic acid, the vector having the nucleic acid or the host cell containing the vector and nucleic acid is isolated.

The nucleic acid or vector is then introduced into the host cell with a large excess of the wild-type nucleic acid. The nucleic acid of the hybrid and the nucleic acid of the wild-type sequence are allowed to recombine. The resulting recombinants are placed under the same selection as the hybrid nucleic acid. Only those recombinants which retained the desired characteristics will be selected. Any silent mutations which do not provide the desired characteristics will be lost through recombination with the wild-type DNA. This cycle can be repeated a number of times until all of the silent mutations are eliminated.

Thus the methods of this invention can be used in a molecular backcross to eliminate unnecessary or silent mutations.

8.16.5.6 Utility

The in vivo recombination method of this invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of express ion. This approach may also be useful in the study of repetitive DNA sequences. Finally, this approach may be useful to mutate ribozymes or aptamers.

Scaffold-like regions separating regions of diversity in proteins may be particularly suitable for the methods of this invention. The conserved scaffold determines the overall folding by self-association, while displaying relatively unrestricted loops that mediate the specific binding. Examples of such scaffolds are the immunoglobulin beta barrel, and the four-helix bundle. The methods of this invention can be used to create scaffold-like proteins with various combinations of mutated sequences for binding.

The equivalents of some standard genetic matings may also be per formed by the methods of this invention. For example, a "molecular" backcross can be performed by repeated mixing of the hybrid's nucleic acid with the wild-type nucleic acid while selecting for the mutations of interest. As in traditional breeding, this approach can be used to combine phenotypes from different sources into a background of choice. It is useful, for example, for the removal of neutral mutations that affect unselected characteristics (i.e. immunogenicity). Thus it can be useful to determine which mutations in a protein are involved in th e enhanced biological activity and which are not.

8.16.5.7 Peptide Display Methods

The present method can be used to shuffle, by in vitro and/or in vivo recombination by any of the disclosed methods, and in any combination, polynucleotide sequences selected by peptide display methods, wherein an associated polynucleotide encodes a displayed peptide which is screened for a phenotype (e.g., for affinity for a predetermined receptor (ligand).

A n increasingly important aspect of bio-pharmaceutical drug development and molecular biology is the identification of peptide structures, including the primary amino acid sequences, of peptides or peptidomimetics that interact with biological macromolecules. one method of identifying peptides that possess a desired structure or functional property, such as binding to a predetermined biological macromolecule (e.g., a receptor), involves the screening of a large library or peptides for individual library members which possess the desired structure or functional property conferred by the amino acid sequence of the peptide.

In addition to direct chemical synthesis methods for generating peptide libraries, several recombinant DNA methods also have been reported. One type involves the display of a peptide sequence, antibody, or other protein on the surface of a bacteriophage particle or cell. Generally, in these methods each bacteriophage particle or cell serves as an individual library member displaying a single species of displayed peptide in addition to the natural bacteriophage or cell protein sequences. Each bacteriophage or cell contains the nucleotide sequence information encoding the particular displayed peptide sequence; thus, the displayed peptide sequence can be ascertained by nucleotide sequence determination of an isolated library member.

A well-known peptide display method involves the presentation of a peptide sequence on the surface of a filamentous bacteriophage, typically as a fusion with a bacteriophage coat protein. The bacteriophage library can be incubated with an immobilized, predetermined macromolecule or small molecule (e.g., a receptor) so that bacteriophage particles which present a peptide sequence that binds to the immobilized macromolecule can be differentially partitioned from those that do not present peptide sequences that bind to the predetermined macromolecule. The bacteriophage particles (i.e., library members) which are bound to the immobilized macromolecule are then recovered and replicated to amplify the selected bacteriophage sub-population for a subsequent round of affinity enrichment and phage replication. After several rounds of affinity enrichment and phage replication, the bacteriophage library members that are thus selected are isolated and the nucleotide sequence encoding the displayed peptide sequence is determined, thereby identifying the sequence(s) of peptides that bind to the predetermined macromolecule (e.g., receptor). Such methods are further described in PCT patent publication Nos. 91/17271, 91/18980, and 91/19818 and 93/08278.

The latter PCT publication describes a recombinant DNA method for the display of peptide ligands that involves the production of a library of fusion proteins with each fusion protein composed of a first polypeptide portion, typically comprising a variable sequence, that is available for potential binding to a predetermined macromolecule, and a second polypeptide portion that binds to DNA, such as the DNA vector encoding the individual fusion protein. When transformed host cells are cultured under conditions that allow for expression of the fusion protein, the fusion protein binds to the DNA vector encoding it. Upon lysis of the host cell, the fusion protein/vector DNA complexes can be screened against a predetermined macromolecule in much the same way as bacteriophage particles are screened in the phage-based display system, with the replication and sequencing of the DNA vectors in the selected fusion protein/vector DNA complexes serving as the basis for identification of the selected library peptide sequence(s).

8.16.5.7.1 Hybrid Methods for Generating Libraries of Peptides and Like Polymers Other systems for generating libraries of peptides and like polymers have aspects of both the recombinant and in vitro chemical synthesis methods. In these hybrid methods, cell-free enzymatic machinery is employed to accomplish the in vitro synthesis of the library members (i.e., peptides or polynucleotides). In one type of method, RNA molecules with the ability to bind a predetermined protein or a predetermined dye molecule were selected by alternate rounds of selection and PCR amplification (Tuerk and Gold (1990) *Science* 249: 505; Ellington and Szostak (1990) *Nature* 346: 818). A similar technique was used to identify DNA sequences which bind a predetermined human transcription factor (Thiesen and Bach (1990) *Nucleic Acids Res.* 18: 3203; Beaudry and Joyce (1992) *Science* 257: 635; PCT patent publication Nos. 92/05258 and 92/14843). In a similar fashion, the technique of in vitro translation has been used to synthesize proteins of interest and has been proposed as a method for generating large libraries of peptides. These methods which rely upon in vitro translation, generally comprising stabilized polysome complexes, are described further in PCT patent publication Nos. 88/08453, 90/05785, 90/07003, 91/02076, 91/05058, and 92/02536. Applicants have described methods in which library members comprise a fusion protein having a first polypeptide portion with DNA binding activity and a second polypeptide portion having the library member unique peptide sequence; such methods are suitable for use in cell-free in vitro selection formats, among others.

8.16.5.7.2 The Displayed Peptide Sequences

The displayed peptide sequences can be of varying lengths, typically from 3–5000 amino acids long or longer, frequently from 5–100 amino acids long, and often from about 8–15 amino acids long. A library can comprise library members having varying lengths of displayed peptide sequence, or may comprise library members having a fixed length of displayed peptide sequence. Portions or all of the displayed peptide sequence(s) can be random, pseudorandom, defined set kernal, fixed, or the like. The present display methods include methods for in vitro and in vivo display of single-chain antibodies, such as nascent scFv on polysomes or scfv displayed on phage, which enable large-scale screening of scfv libraries having broad diversity of variable region sequences and binding specificities.

8.16.5.7.3 Sequence Framework Peptide Libraries

The present invention also provides random, pseudorandom, and defined sequence framework peptide libraries and methods for generating and screening those libraries to identify useful compounds (e.g., peptides, including single-chain antibodies) that bind to receptor molecules or epitopes of interest or gene products that modify peptides or RNA in a desired fashion. The random, pseudorandom, and defined sequence framework peptides are produced from libraries of peptide library members that comprise displayed peptides or displayed single-chain antibodies attached to a polynucleotide template from which the displayed peptide was synthesized. The mode of attachment may vary according to the specific embodiment of the invention selected, and can include encapsulation in a phage particle or incorporation in a cell.

8.16.5.7.4 Selecting for the Desired Peptide Using Affinity Enrichment

A method of affinity enrichment allows a very large library of peptides and single-chain antibodies to be screened and the polynucleotide sequence encoding the desired peptide(s) or single-chain antibodies to be selected. The polynucleotide can then be isolated and shuffled to recombine combinatorially the amino acid sequence of the selected peptide(s) (or predetermined portions thereof) or single-chain antibodies (or just VHI, VLI or CDR portions thereof). Using these methods, one can identify a peptide or single-chain antibody as having a desired binding affinity for a molecule and can exploit the process of shuffling to converge rapidly to a desired high-affinity peptide or scfv. The peptide or antibody can then be synthesized in bulk by conventional means for any suitable use (e.g., as a therapeutic or diagnostic agent).

A significant advantage of the present invention is that no prior information regarding an expected ligand structure is required to isolate peptide ligands or antibodies of interest. The peptide identified can have biological activity, which is meant to include at least specific binding affinity for a selected receptor molecule and, in some instances, will further include the ability to block the binding of other compounds, to stimulate or inhibit metabolic pathways, to act as a signal or messenger, to stimulate or inhibit cellular activity, and the like.

8.16.5.7.5 Shuffling Sequences Selected by Affinity Screening

The present invention also provides a method for shuffling a pool of polynucleotide sequences selected by affinity screening a library of polysomes displaying nascent peptides (including single-chain antibodies) for library members which bind to a predetermined receptor (e.g., a mammalian proteinaceous receptor such as, for example, a peptidergic hormone receptor, a cell surface receptor, an intracellular protein which binds to other protein(s) to form intracellular protein complexes such as hetero-dimers and the like) or epitope (e.g., an immobilized protein, glycoprotein, oligosaccharide, and the like).

Polynucleotide sequences selected in a first selection round (typically by affinity selection for binding to a receptor (e.g., a ligand)) by any of these methods are pooled and the pool(s) is/are shuffled by in vitro and/or in vivo recombination to produce a shuffled pool comprising a population of recombined selected polynucleotide sequences. The recombined selected polynucleotide sequences are subjected to at least one subsequent selection round. The polynucleotide sequences selected in the subsequent selection round(s) can be used directly, sequenced, and/or subjected to one or more additional rounds of shuffling and subsequent selection. Selected sequences can also be back-crossed with polynucleotide sequences encoding neutral sequences (i.e., having insubstantial functional effect on binding), such as for example by back-crossing with a wild-type or naturally-occurring sequence substantially identical to a selected sequence to produce native-like functional peptides, which may be less immunogenic. Generally, during back-crossing subsequent selection is applied to retain the property of binding to the predetermined receptor (ligand).

Prior to or concomitant with the shuffling of selected sequences, the sequences can be mutagenized. In one embodiment, selected library members are cloned in a prokaryotic vector (e.g., plasmid, phagemid, or bacteriophage) wherein a collection of individual colonies (or plaques) representing discrete library members are produced. Individual selected library members can then be manipulated (e.g., by site-directed mutagenesis, cassette mutagenesis, chemical mutagenesis, PCR mutagenesis, and the like) to generate a collection of library members representing a kernal of sequence diversity based on the sequence of the selected library member. The sequence of an individual selected library member or pool can be manipulated to incorporate random mutation, pseudorandom mutation, defined kernal mutation (i.e., comprising variant and invariant residue positions and/or comprising variant residue positions which can comprise a residue selected from a defined subset of amino acid residues), codon-based mutation, and the like, either segmentally or over the entire length of the individual selected library member sequence. The mutagenized selected library members are then shuffled by in vitro and/or in vivo recombinatorial shuffling as disclosed herein.

8.16.5.7.6 Peptide Libraries Comprising a Plurality of Individual Library Members The invention also provides peptide libraries comprising a plurality of individual library members of the invention, wherein (1) each individual library member of said plurality comprises a sequence produced by shuffling of a pool of selected sequences, and (2) each individual library member comprises a variable peptide segment sequence or single-chain antibody segment sequence which is distinct from the variable peptide segment sequences or single-chain antibody sequences of other individual library members in said plurality (although some library members may be present in more than one copy per library due to uneven amplification, stochastic probability, or the like).

8.16.5.7.7 Product-by-Process

The invention also provides a product-by-process, wherein selected polynucleotide sequences having (or encoding a peptide having) a predetermined binding specificity are formed by the process of: (1) screening a displayed peptide or displayed single-chain antibody library against a predetermined receptor (e.g., ligand) or epitope (e.g., antigen macromolecule) and identifying and/or enriching library members which bind to the predetermined receptor or epitope to produce a pool of selected library members, (2) shuffling by recombination the selected library members (or amplified or cloned copies thereof) which binds the predetermined epitope and has been thereby isolated and/or enriched from the library to generate a shuffled library, and (3) screening the shuffled library against the predetermined receptor (e.g., ligand) or epitope (e.g., antigen macromolecule) and identifying and/or enriching shuffled library members which bind to the predetermined receptor or epitope to produce a pool of selected shuffled library members.

8.16.5.8 Antibody Display and Screening Methods The present method can be used to shuffle, by in vitro and/or in vivo recombination by any of the disclosed methods, and in any combination, polynucleotide sequences selected by antibody display methods, wherein an associated polynucleotide encodes a displayed antibody which is screened for a phenotype (e.g., for affinity for binding a predetermined antigen (ligand).

Various molecular genetic approaches have been devised to capture the vast immunological repertoire represented by the extremely large number of distinct variable regions which can be present in immunoglobulin chains. The naturally-occurring germ line immunoglobulin heavy chain locus is composed of separate tandem arrays of variable segment genes located upstream of a tandem array of diversity segment genes, which are themselves located upstream of a tandem array of joining (i) region genes, which are located upstream of the constant region genes. During B lymphocyte development, V-D-J rearrangement occurs wherein a heavy chain variable region gene (VH) is formed by rearrangement to form a fused D segment followed by rearrangement with a V segment to form a V-D-J joined product gene which, if productively rearranged, encodes a functional variable region (VH) of a heavy chain. Similarly, light chain loci rearrange one of several V segments with one of several J segments to form a gene encoding the variable region (VL) of a light chain.

8.16.5.8.1 Sequence Diversity

The vast repertoire of variable regions possible in immunoglobulins derives in part from the numerous combinatorial possibilities of joining V and i segments (and, in the case of heavy chain loci, D segments) during rearrangement in B cell development. Additional sequence diversity in the heavy chain variable regions arises from non-uniform rearrangements of the D segments during V-D-J joining and from N region addition. Further, antigen-selection of specific B cell clones selects for higher affinity variants having non-germline mutations in one or both of the heavy and light chain variable regions; a phenomenon referred to as "affinity maturation" or "affinity sharpening". Typically, these "affinity sharpening" mutations cluster in specific areas of the variable region, most commonly in the complementarity-determining regions (CDRs).

8.16.5.8.2 Prokaryotic Epression Systems

In order to overcome many of the limitations in producing and identifying high-affinity immunoglobulins through antigen-stimulated β cell development (i.e., immunization), various prokaryotic expression systems have been developed that can be manipulated to produce combinatorial antibody libraries which may be screened for high-affinity antibodies to specific antigens. Recent advances in the expression of antibodies in Escherichia coli and bacteriophage systems (see, "Alternative Peptide Display Methods", infra) have raised the possibility that virtually any specificity can be obtained by either cloning antibody genes from characterized hybridomas or by de novo selection using antibody gene libraries (e.g., from Ig CDNA).

Combinatorial libraries of antibodies have been generated in bacteriophage lambda expression systems which may be screened as bacteriophage plaques or as colonies of lysogens (Huse et al. (1 989) Science 246: 1275; Caton and Koprowski (1990) Proc. Natl Acad. Sci. (U.S.A.) 87: 6450; Mullinax et al (1990) Proc. Natl. Acad. Sci. (U.S.A.) 87: 8095; Persson et al (1991) Proc. Natl. Acad. Sci. (TJ.S.A.) 88: 2432). Various embodiments of bacteriophage antibody display libraries and lambda phage expression libraries have been described (Kang et al. (1991) Proc. Nat. Acad. Sci. (U.S.A.) 88: 4363; Clackson et al. (1991) Nature 352: 624; McCafferty et al. (1990) Nature 348: 552; Burton et al. (1991) Proc. Natl- Acad. Sci. (U.S.A.) 88: 10134; Hoogenboom et al. (1991) Nucleic Acids Res. 19: 4133; Chang et al. (1991) J. Immunol. 147: 3610; Breitling et al. (1991) Gene 104: 147; Marks et al. (1991) J. Mol. Biol. 222@: 581; Barbas et al. (1992) Proc. Natl. Acad. Sci. (U.S.A.) 89: 4457; Hawkins and Winter (1992) J. Immunol. 22: 867; Marks et al. (1992) Biotechnology 10: 779; Marks et al. (1992) J. Biol. Chem. 267: 16007; Lowman et al (1991) Biochemistry 30: 10832; Lerner et al. (1992) Science. 258: 1313, incorporated herein by reference). Typically, a bacteriophage antibody display library is screened with a receptor (e.g., polypeptide, carbohydrate, glycoprotein, nucleic acid) that is immobilized (e.g., by covalent linkage to a chromatography resin to enrich for reactive phage by affinity chromatography) and/or labeled (e.g., to screen plaque or colony lifts).

8.16.5.8.3 Single-Chain Fragment Variable Libraries

One particularly advantageous approach has been the use of so-called single-chain fragment variable (scfv) libraries (Marks et al. (1992) Biotechnology 10: 779; Winter G and Milstein C (1991) Nature 349: 293; Clackson et al. (1991) op. cit.: Marks et al. (1991) J. Mol. Biol. 222: 581; Chaudhary et al. (1990) Proc. Natl. Acad. Sci. (USA) 87: 1066; Chiswell et al. (1992) TIBTECH 10: 80; McCafferty et al. (1990) op. cit.: and Huston et al- (1988) Proc. Natl. Acad. Sci, (USA) 85: 5879). Various embodiments of scfv libraries displayed on bacteriophage coat proteins have been described.

Beginning in 1988, single-chain analogues of Fv fragments and their fusion proteins have been reliably generated by antibody engineering methods. The first step generally involves obtaining the genes encoding VH and VL domains with desired binding properties; these V genes may be isolated from a specific hybridoma cell line, selected from a combinatorial V-gene library, or made by V gene synthesis. The single-chain Fv is formed by connecting the component V genes with an oligonucleotide that encodes an appropriately designed linker peptide, such as (Gly-Gly-Gly-Gly-Ser)3 or equivalent linker peptide(s). The linker bridges the C-terminus of the first V region and N-terminus of the second, ordered as either VH-linker-VL or VL-linker-VH' In principle, the scfv binding site can faithfully replicate both the affinity and specificity of its parent antibody combining site.

Thus, scfv fragments are comprised of VH and VL domains linked into a single polypeptide chain by a flexible linker peptide. After the scfv genes are assembled, they are cloned into a phagemid and expressed at the tip of the M13 phage (or similar filamentous bacteriophage) as fusion proteins with the bacteriophage PIII (gene 3) coat protein. Enriching for phage expressing an antibody of interest is accomplished by panning the recombinant phage displaying a population scfv for binding to a predetermined epitope (e.g., target antigen, receptor).

The linked polynucleotide of a library member provides the basis for replication of the library member after a screening or selection procedure, and also provides the basis for the determination, by nucleotide sequencing, of the identity of the displayed peptide sequence or VH and VL amino acid sequence. The displayed peptide (s) or single-chain antibody (e. g., scfv) and/or its VH and VL domains or their CDRs can be cloned and expressed in a suitable expression system. often polynucleotides encoding the isolated VH and VL domains will be ligated to polynucleotides encoding constant regions (CH and CL) to form polynucleotides encoding complete antibodies (e.g., chimeric or fully-human), antibody fragments, and the like. Often polynucleotides encoding the isolated CDRs will be grafted into polynucleotides encoding a suitable variable region framework (and optionally constant regions) to form polynucleotides encoding complete antibodies (e.g., humanized or fully-human), antibody fragments, and the like. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like.

8.16.5.8.4 Increasing the Combinatorial Diversity of a SCFV Library

Various methods have been reported for increasing the combinatorial diversity of a scfv library to broaden the repertoire of binding species (idiotype spectrum) The use of PCR has permitted the variable regions to be rapidly cloned either from a specific hybridoma source or as a gene library from non-immunized cells, affording combinatorial diversity in the assortment of VH and VL cassettes which can be combined. Furthermore, the VH and VL cassettes can themselves be diversified, such as by random, pseudorandom, or directed mutagenesis. Typically, VH and VL cassettes are diversified in or near the complementarity-determining regions (CDRS), often the third CDR, CDR3. Enzymatic inverse PCR mutagenesis has been shown to be a simple and reliable method for constructing relatively large libraries of scfv site-directed hybrids (Stemmer et al. (1993) *Biotechniques* 14: 256), as has error-prone PCR and chemical mutagenesis (Deng et al. (1994) *J. Biol. Chem.* 269: 953 3). Riechmann et al. (1993) *Biochemistry* 32: 8848 showed semi-rational design of an antibody scfv fragment using site-directed randomization by degenerate oligonucleotide PCR and subsequent phage display of the resultant scfv hybrids. Barbas et al. (1992) on. cit. attempted to circumvent the problem of limited repertoire sizes resulting from using biased variable region sequences by randomizing the sequence in a synthetic CDR region of a human tetanus toxoid-binding Fab.

CDR randomization has the potential to create approximately $1 \times 10^{20}$ CDRs for the heavy chain CDR3 alone, and a roughly similar number of variants of the heavy chain CDR1 and CDR2, and light chain CDR1–3 variants. Taken individually or together, the combination possibilities of CDR randomization of heavy and/or light chains requires generating a prohibitive number of bacteriophage clones to produce a clone library representing all possible combinations, the vast majority of which will be non-binding. Generation of such large numbers of primary transformants is not feasible with current transformation technology and bacteriophage display systems. For example, Barbas et al. (1992) op cit. only generated $5 \times 10^7$ transformants, which represents only a tiny fraction of the potential diversity of a library of thoroughly randomized CDRS.

Despite these substantial limitations, bacteriophage. display of scfv have already yielded a variety of useful antibodies and antibody fusion proteins. A bispecific single chain antibody has been shown to mediate efficient tumor cell lysis (Gruber et al. (1994) *J. Immunol.* 152: 5368). Intracellular expression of an anti-Rev scfv has been shown to inhibit HIV-1 virus replication in vitro (Duan et al. (1994) *Proc. Natl. Acad. Sci.* (*USA*) 91: 5075), and intracellular expression of an anti-p21rar, scfv has been shown to inhibit meiotic maturation of Xenopus oocytes (Biocca et al. (1993) *Biochem. Bioshys. Res. Commun.* 197: 422. Recombinant scfv which can be used to diagnose HIV infection have also been reported, demonstrating the diagnostic utility of scfv (Lilley et al. (1994) *J. Immunol. Meth.* 171: 211). Fusion proteins wherein an scFv is linked to a second polypeptide, such as a toxin or fibrinolytic activator protein, have also been reported (Holvost et al. (1992) *Eur. J. Biochess.* 210: 945; Nicholls et al. (1993) J. Biol. Chem. 268: 5302).

8.16.5.8.5 Use of in vitro and in vivo Shuffling Methods to Recombine CDRs

If it were possible to generate scfv libraries having broader antibody diversity and overcoming many of the limitations of conventional CDR mutagenesis and randomization methods which can cover only a very tiny fraction of the potential sequence combinations, the number and quality of scfv antibodies suitable for therapeutic and diagnostic use could be vastly improved. To address this, the in vitro and in vivo shuffling methods of the invention are used to recombine CDRs which have been obtained (typically via PCR amplification or cloning) from nucleic acids obtained from selected displayed antibodies. Such displayed antibodies can be displayed on cells, on bacteriophage particles, on polysomes, or any suitable antibody display system wherein the antibody is associated with its encoding nucleic acid(s). In a variation, the CDRs are initially obtained from mRNA (or CDNA) from antibody-producing cells (e.g., plasma cells/splenocytes from an immunized wild-type mouse, a human, or a transgenic mouse capable of making a human antibody as in W092/03918, W093/12227, and W094/25585), including hybridomas derived therefrom.

Polynucleotide sequences selected in a first selection round (typically by affinity selection for displayed antibody binding to an antigen (e.g., a ligand) by any of these methods are pooled and the pool(s) is/are shuffled by in vitro and/or in vivo recombination, especially shuffling of CDRs (typically shuffling heavy chain CDRs with other heavy chain CDRs and light chain CDRs with other light chain CDRS) to produce a shuffled pool comprising a population of recombined selected polynucleotide sequences. The recombined selected polynucleotide sequences are expressed in a selection format as a displayed antibody and subjected to at least one subsequent selection round. The polynucleotide sequences selected in the subsequent selection round(s) can be used directly, sequenced, and/or subjected to one or more additional rounds of shuffling and subsequent selection until an antibody of the desired binding affinity is obtained. Selected sequences can also be back-crossed with polynucleotide sequences encoding neutral antibody framework sequences (i.e., having insubstantial functional effect on antigen binding), such as for example by back-crossing with a human variable region framework to produce human-like sequence antibodies. Generally, during back-crossing subsequent selection is applied to retain the property of binding to the predetermined antigen.

8.16.5.8.6 Controlling the Average Binding Affinity of Selected SCFV Library Members Alternatively, or in combination with the noted variations, the valency of the target epitope may be varied to control the average binding affinity of selected scfv library members. The target epitope can be bound to a surface or substrate at varying densities, such as by including a competitor epitope, by dilution, or by other method known to those in the art. A high density (valency) of predetermined epitope can be used to enrich for scfv library members which have relatively low affinity, whereas a low density (valency) can preferentially enrich for higher affinity scfv library members.

8.16.5.8.7 Generating Diverse Variable Segments

For generating diverse variable segments, a collection of synthetic oligonucleotides encoding random, pseudorandom, or a defined sequence kernal set of peptide sequences can be inserted by ligation into a predetermined site (e.g., a CDR). Similarly, the sequence diversity of one or more CDRs of the single-chain antibody cassette(s) can be expanded by mutating the CDR(s) with site-directed mutagenesis, CDR-replacement, and the like. The resultant DNA molecules can be propagated in a host for cloning and amplification prior to shuffling, or can be used directly (ie., may avoid loss of diversity which may occur upon propagation in a host cell) and the selected library members subsequently shuffled.

Displayed peptide/polynucleotide complexes (library members) which encode a variable segment peptide sequence of interest or a single-chain antibody of interest are selected from the library by an affinity enrichment technique. This is accomplished by means of a immobilized macromolecule or epitope specific for the peptide sequence of interest, such as a receptor, other macromolecule, or other epitope species. Repeating the affinity selection procedure provides an enrichment of library members encoding the desired sequences, which may then be isolated for pooling and shuffling, for sequencing, and/or for further propagation and affinity enrichment.

The library members without the desired specificity are removed by washing. The degree and stringency of washing required will be determined for each peptide sequence or single-chain antibody of interest and the immobilized predetermined macromolecule or epitope. A certain degree of control can be exerted over the binding characteristics of the nascent peptide/DNA complexes recovered by adjusting the conditions of the binding incubation and the subsequent washing. The temperature, pH, ionic strength, divalent cations concentration, and the volume and duration of the washing will select for nascent peptide/DNA complexes within particular ranges of affinity for the immobilized macromolecule. Selection based on slow dissociation rate, which is usually predictive of high affinity, is often the most practical route. This may be done either by continued incubation in the presence of a saturating amount of free predetermined macromolecule, or by increasing the volume, number, and length of the washes. In each case, the rebinding of dissociated nascent peptide/DNA or peptide/RNA complex is prevented, and with increasing time, nascent peptide/DNA or peptide/RNA complexes of higher and higher affinity are recovered.

Additional modifications of the binding and washing procedures may be applied to find peptides with special characteristics. The affinities of some peptides are dependent on ionic strength or cation concentration. This is a useful characteristic for peptides that will be used in affinity purification of various proteins when gentle conditions for removing the protein from the peptides are required.

One variation involves the use of multiple binding targets (multiple epitope species, multiple receptor species), such that a scfv library can be simultaneously screened for a multiplicity of scfv which have different binding specificities. Given that the size of a scfv library often limits the diversity of potential scfv sequences, it is typically desirable to us scfv libraries of as large a size as possible. The time and economic considerations of generating a number of very large polysome scFv-display libraries can become prohibitive. To avoid this substantial problem, multiple predetermined epitope species (receptor species) can be concomitantly screened in a single library, or sequential screening against a number of epitope species can be used. In one variation, multiple target epitope species, each encoded on a separate bead (or subset of beads), can be mixed and incubated with a polysome-display scfv library under suitable binding conditions. The collection of beads, comprising multiple epitope species, can then be used to isolate, by affinity selection, scfv library members. Generally, subsequent affinity screening rounds can include the same mixture of beads, subsets thereof, or beads containing only one or two individual epitope species. This approach affords efficient screening, and is compatible with laboratory automation, batch processing, and high throughput screening methods.

8.16.5.8.8 Techniques Used to Diversify a Peptide Library or Single-Chain Antibody Library A variety of techniques can be used in the present invention to diversify a peptide library or single-chain antibody library, or to diversify, prior to or concomitant with shuffling, around variable segment peptides found in early rounds of panning to have sufficient binding activity to the predetermined macromolecule or epitope. In one approach, the positive selected peptide/polynucleotide complexes (those identified in an early round of affinity enrichment) are sequenced to determine the identity of the active peptides. Oligonucleotides are then synthesized based on these active peptide sequences, employing a low level of all bases incorporated at each step to produce slight variations of the primary oligonucleotide sequences. This mixture of (slightly) degenerate oligonucleotides is then cloned into the variable segment sequences at the appropriate locations. This method produces systematic, controlled variations of the starting peptide sequences, which can then be shuffled. It requires, however, that individual positive nascent peptide/polynucleotide complexes be sequenced before mutagenesis, and thus is useful for expanding the diversity of small numbers of recovered complexes and selecting variants having higher binding affinity and/or higher binding specificity. In a variation, mutagenic PCR amplification of positive selected peptide/polynucleotide complexes (especially of the variable region sequences, the amplification products of which are shuffled in vitro and/or in vivo and one or more additional rounds of screening is done prior to sequencing. The same general approach can be employed with single-chain antibodies in order to expand the diversity and enhance the binding affinity/specificity, typically by diversifying CDRs or adjacent framework regions prior to or concomitant with shuffling. If desired, shuffling reactions can be spiked with mutagenic oligonucleotides capable of in vitro recombination with the selected library members can be included. Thus, mixtures of synthetic oligonucleotides and PCR produced polynucleotides (synthesized by error-prone or high-fidelity methods) can be added to the in vitro shuffling mix and be incorporated into resulting shuffled library members (shufflants).

8.16.5.8.9 Generation of a Library of CDR-Varient Single-Chain Antibodies

The present invention of shuffling enables the generation of a vast library of CDR-variant single-chain antibodies. One way to generate such antibodies is to insert synthetic CDRs into the single-chain antibody and/or CDR randomization prior to or concomitant with shuffling. The sequences of the synthetic CDR cassettes are selected by referring to known sequence data of human CDR and are selected in the discretion of the practitioner according to the following guidelines: synthetic CDRs will have at least 40 percent positional sequence identity to known CDR sequences, and preferably will have at least 50 to 70 percent positional sequence identity to known CDR sequences. For example, a collection of synthetic CDR sequences can be generated by synthesizing a collection of oligonucleotide sequences on the basis of naturally-occurring human CDR sequences listed in Kabat et al. (1991) op. cit.; the pool (s) of synthetic CDR sequences are calculated to encode CDR peptide sequences having at least 40 percent sequence identity to at least one known naturally-occurring human CDR sequence. Alternatively, a collection of naturally-occurring CDR sequences may be compared to generate consensus sequences so that amino acids used at a residue position frequently (i.e., in at least 5 percent of known CDR sequences) are incorporated into the synthetic CDRs at the corresponding position(s). Typically, several (e.g., 3 to about 50) known CDR sequences are compared and observed natural sequence variations between the known CDRs are tabulated, and a collection of oligonucleotides encoding CDR peptide sequences encompassing all or most permutations of the observed natural sequence variations is synthesized. For example but not for limitation, if a collection of human VH CDR sequences have carboxy-terminal amino acids which are either Tyr, Val, Phe, or Asp, then the pool(s) of synthetic CDR oligonucleotide sequences are designed to allow the carboxy-terminal CDR residue to be any of these amino acids. In some embodiments, residues other than those which naturally-occur at a residue position in the collection of CDR sequences are incorporated: conservative amino acid substitutions are frequently incorporated and up to 5 residue positions may be varied to incorporate non-conservative amino acid substitutions as compared to known naturally-occurring CDR sequences. Such CDR sequences can be used in primary library members (prior to first round screening) and/or can be used to spike in vitro shuffling reactions of selected library member sequences. Construction of such pools of defined and/or degenerate sequences will be readily accomplished by those of ordinary skill in the art.

The collection of synthetic CDR sequences comprises at least one member that is not known to be a naturally-occurring CDR sequence. It is within the discretion of the practitioner to include or not include a portion of random or pseudorandom sequence corresponding to N region addition in the heavy chain CDR; the N region sequence ranges from 1 nucleotide to about 4 nucleotides occurring at V-D and D-J junctions. A collection of synthetic heavy chain CDR sequences comprises at least about 100 unique CDR sequences, typically at least about 1,000 unique CDR sequences, preferably at least about 10,000 unique CDR sequences, frequently more than 50,000 unique CDR sequences; however, usually not more than about $1\times10^6$ unique CDR sequences are included in the collection, although occasionally $1\times10^7$ to $1\times10^8$ unique CDR sequences are present, especially if conservative amino acid substitutions are permitted at positions where the conservative amino acid substituent is not present or is rare (i.e., less than 0.1 percent) in that position in naturally-occurring human CDRS. In general, the number of unique CDR sequences included in a library should not exceed the expected number of primary transformants in the library by more than a factor of 10. Such single-chain antibodies generally bind of about at least $1\times10$ m-, preferably with an affinity of about at least $5\times10^7$ M-1, more preferably with an affinity of at least $1\times10^8$ M-1 to $1\times10^9$ M-1 or more, sometimes up to $1\times10^{10}$ M-1 or more. Frequently, the predetermined antigen is a human protein, such as for example a human cell surface antigen (e. g., CD4, CD8, IL-2 receptor, EGF receptor, PDGF receptor), other human biological macromolecule (e.g., thrombomodulin, protein C, carbohydrate antigen, sialyl Lewis antigen, Lselectin), or nonhuman disease associated macromolecule (e.g., bacterial LPS, virion capsid protein or envelope glycoprotein) and the like.

8.16.5.8.10 Expression Systems

High affinity single-chain antibodies of the desired specificity can be engineered and expressed in a variety of systems. For example, scfv have been produced in plants (Firek et al. (1993) *Plant Mol. Biol.* 23: 861) and can be readily made in prokaryotic systems (Owens R J and Young R J (1994) *J. Immunol. Meth.* 168: 149; Johnson S and Bird R E (1991) *Methods Enzymol* 203: 88). Furthermore, the single-chain antibodies can be used as a basis for constructing whole antibodies or various fragments thereof (Kettleborough et al. (1994) *Eur. J. Immunol.* 24: 952). The variable region encoding sequence may be isolated (e.g., by PCR amplification or subcloning) and spliced to a sequence encoding a desired human constant region to encode a human sequence antibody more suitable for human therapeutic uses where immunogenicity is preferably minimized. The polynucleotide(s) having the resultant fully human encoding sequence(s) can be expressed in a host cell (e.g., from an expression vector in a mammalian cell) and purified for pharmaceutical formulation.

The DNA expression constructs will typically include an expression control DNA sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the mutant' "engineered" antibodies.

As stated previously, the DNA sequences will be expressed in hosts after the sequences have been operably linked to an expression control sequence (i.e., positioned to ensure the transcription and translation of the structural gene). These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

8.16.5.8.11 Mammalian Tissue Cell Culture

In addition to eukaryotic microorganisms such as yeast, mammalian tissue cell culture may also be used to produce the polypeptides of the present invention (see, Winnacker, "From Genes to Clones," VCH Publishers, N.i., N.Y. (1987), which is incorporated herein by reference). Eukaryotic cells are actually preferred, because a number of suitable host cell lines capable of secreting intact immunoglobulins have been developed in the art, and include the CHO cell lines, various COS cell lines, HeLa cells, and myeloma cell lines, but preferably transformed Bcells or hybridomas. Expression vectors for these cells can include expression control sequences, such as an origin of replication, a promoter, an enhancer (Queen et al. (1986) Immunol. Rev. 89: 49), and necessary processing information sites, such as ribosome binding sites, RNA splice sites, polyadenylation sites, and transcriptional terminator sequences. Preferred expression control sequences are promoters derived from immunoglobulin genes, cytomegalovirus, SV40, Adenovirus, Bovine Papilloma Virus, and the like.

Eukaryotic DNA transcription can be increased by inserting an enhancer sequence into the vector. Enhancers are cis-acting sequences of between 10 to 300 bp that increase transcription by a promoter. Enhancers can effectively increase transcription when either 51 or 31 to the transcription unit. They are also effective if located within an intron or within the coding sequence itself. Typically, viral enhancers are used, including SV40 enhancers, cytomegalovirus enhancers, polyoma enhancers, and adenovirus enhancers. Enhancer sequences from mammalian systems are also commonly used, such as the mouse immunoglobulin heavy chain enhancer.

Mammalian expression vector systems will also typically include a selectable marker gene. Examples of suitable markers include, the dihydrofolate reductase gene (DHFR), the thymidine kinase gene (TK), or prokaryotic genes conferring drug resistance. The first two marker genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The vectors containing the DNA segments of interest can be transferred into the host cell by well-known methods, depending on the type of cellular host. For example, calcium chloride transfection is commonly utilized for prokaryotic cells, whereas calcium phosphate treatment. lipofection, or electroporation may be used for other cellular hosts. Other methods used to transform mammalian cells include the use of Polybrene, protoplast fusion, liposomes, electroporation, and micro-injection (see, generally, Sambrook et al., supra).

Once expressed, the antibodies, individual mutated immunoglobulin chains, mutated antibody fragments, and other immunoglobulin polypeptides of the invention can be purified according to standard procedures of the art, including ammonium sulfate precipitation, fraction column chromatography, gel electrophoresis and the like (see, generally, Scopes, R., *Protein* Purification, Springer-Verlag, N.Y. (1982)). once purified, partially or to homogeneity as desired, the polypeptides may then be used therapeutically or in developing and performing assay procedures, immunofluorescent stainings, and the like (see, generally, *Immunological Methods*, Vols. I and II, Eds. Lefkovits and Pernis, Academic Press, New York, N.Y. (1979 and 1981)).

The antibodies generated by the method of the present invention can be used for diagnosis and therapy. By way of illustration and not limitation, they can be used to treat cancer, autoimmune diseases, or viral infections. For treatment of cancer, the antibodies will typically bind to an antigen expressed preferentially on cancer cells, such as erbB-2, CEA, CD33, and many other antigens and binding members well known to those skilled in the art.

8.16.5.9 Yeast Two-Hybrid Screening Assays

Shuffling can also be used to recombinatorially diversify a pool of selected library members obtained by screening a two-hybrid screening system to identify library members which bind a predetermined polypeptide sequence. The selected library members are pooled and shuffled by in vitro and/or in vivo recombination. The shuffled pool can then be screened in a yeast two hybrid system to select library members which bind said predetermined polypeptide sequence (e. g., and SH2 domain) or which bind an alternate predetermined polypeptide sequence (e.g., an SH2 domain from another protein species).

An approach to identifying polypeptide sequences which bind to a predetermined polypeptide sequence has been to use a so-called "two-hybrid" system wherein the predetermined polypeptide sequence is present in a fusion protein (Chien et al. (1991) *Proc. Natl. Acad. Sci. (USA)* 88: 9578). This approach identifies protein-protein interactions in vivo through reconstitution of a transcriptional activator (Fields S and Song 0 (1989) *Nature* 340: 245), the yeast Gal4 transcription protein. Typically, the method is based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacz, HIS3) which is operably linked to a Gal4 binding site. Typically, the two-hybrid method is used to identify novel polypeptide sequences which interact with a known protein (Silver SC and Hunt SW (1993) *Mol. Biol. Rep.* 17: 155; Durfee et al. (1993) *Genes Devel.* 7: 555; Yang et al. (1992) *Science* 257: 680; Luban et al. (1993) *Cell* 73: 1067; Hardy et al(1992) *Genes Devel.* 6: 801; Bartel et al. (1993) *Biotechniques* 14: 920; and Vojtek et al. (1993) *Cell* 74: 205). However, variations of the two-hybrid method have been used to identify mutations of a known protein that affect its binding to a second known protein (Li B and Fields S (1993) *FASEB J.* 7: 957; Lalo et al. (1993) *Proc. Natl. Acad. Sci.* (*USA*) 90: 5524; Jackson et al(1993) *Mol. Cell. Biol.* 13: 2899; and Madura et al. (1993) *J. Biol-Chem.* 268: 12046). Two-hybrid systems have also been used to identify interacting structural domains of two known proteins (Bardwell et al. (1993) med. *Microbial.* 8: 1177; Chakrabarty et al. (1992) *J. Biol. Chem.* 267: 17498; Staudinger et al. (1993) *J. Biol. Chem.* 268: 4608; and Milne G T. and Weaver D T (1993) *Genes Devel.* 7: 1755) or domains responsible for oligomerization of a single protein (Iwabuchi et al. (1993) *Oncogene* 8: 1693; Bogerd et al. (1993) *J. Virol.* 67: 5030). Variations of two-hybrid systems have been used to study the in vivo activity of a proteolytic enzyme (Dasmahapatra et al. (1992) *Proc. Natl. Acad. Sci.* (*USA*) 89: 4159). Alternatively, an *E. coli*/BCCP interactive screening system (Germino et al. (1993) *Proc. Natl. Acad. Sci.* (*U.S.A.*) 90: 933; Guarente L (1993) *Proc. Natl. Acad. Sci.* (*U.S.A.*) 90: 1639) can be used to identify interacting protein sequences (i.e., protein sequences which heterodimerize or form higher order heteromultimers). Sequences selected by a two-hybrid system can be pooled and shuffled and introduced into a two-hybrid system for one or more subsequent rounds of screening to identify polypeptide sequences which bind to the hybrid containing the predetermined binding sequence. The sequences thus identified can be compared to identify consensus sequence(s) and consensus sequence kernals.

In general, standard techniques of recombination DNA technology are described in various publications, e.g Sambrook et al., 1989, Molecular Cloning: A Laboratory Manual, Cold Spring Harbor Laboratory; Ausubel et al., 1987, Current Protocols in Molecular Biology, vols. 1 and 2 and supplements, and Berger and Kimmel, *Methods in Enzymology, Volume* 152. *Guide to Molecular Cloning Tech-*

*nicrues* (1987), Academic Press, Inc., San Diego, Calif., each of which is incorporated herein in their entirety by reference. Polynucleotide modifying enzymes were used according to the manufacturers recommendations. Oligonucleotides were synthesized on an Applied Biosystems Inc. Model 394 DNA synthesizer using ABI chemicals. If desired, PCR amplimers for amplifying a predetermined DNA sequence may be selected at the discretion of the practitioner.

8.16.5.9.1 Formation of Dimers

One microgram samples of template DNA are obtained and treated with U.V. light to cause the formation of dimers, including TT dimers, particularly purine dimers. U.V. exposure is limited so that only a few photoproducts are generated per gene on the template DNA sample. Multiple samples are treated with U.V. light for varying periods of time to obtain template DNA samples with varying numbers of dimers from U.V. exposure.

8.16.5.9.2 Random Priming Kit

A random priming kit which utilizes a non-proofreading polymease (for example, Prime-It II Random Primer Labeling kit by Stratagene Cloning Systems) is utilized to generate different size polynucleotides by priming at random sites on templates which are prepared by U.V. light (as described above) and extending along the templates. The priming protocols such as described in the Prime-It II Random Primer Labeling kit may be utilized to extend the primers. The dimers formed by U.V. exposure serve as a roadblock for the extension by the non-proofreading polymerase. Thus, a pool of random size polynucleotides is present after extension with the random primers is finished.

8.16.5.9.3 Generation of a Selected Mutant Polynucleotide Sequence

The present invention is further directed to a method for generating a selected mutant polynucleotide sequence (or a population of selected polynucleotide sequences) typically in the form of amplified and/or cloned polynucleotides, whereby the selected polynucleotide sequences(s) possess at least one desired phenotypic. characteristic (e.g., encodes a polypeptide, promotes transcription of linked polynucleotides, binds a protein, and the like) which can be selected for. One method for identifying hybrid polypeptides that possess a desired structure or functional property, such as binding to a predetermined biological macromolecule (e.g., a receptor), involves the screening of a large library of polypeptides for individual library members which possess the desired structure or functional property conferred by the amino acid sequence of the polypeptide.

8.16.5.9.4 Generating Libraries Suitable for Affinity Interaction Screening or Phenotypic Screening In one embodiment, the present invention provides a method for generating libraries of displayed polypeptides or displayed antibodies suitable for affinity interaction screening or phenotypic screening. The method comprises (1) obtaining a first plurality of selected library members comprising a displayed polypeptide or displayed antibody and an associated polynucleotide encoding said displayed polypeptide or displayed antibody, and obtaining said associated polynucleotides or copies thereof wherein said associated polynucleotides comprise a region of substantially identical sequences, optimally introducing mutations into said polynucleotides or copies, (2) pooling the polynucleotides or copies, (3) producing smaller or shorter polynucleotides by interrupting a random or particularized priming and synthesis process or an amplification process, and (4) performing amplification, preferably PCR amplification, and optionally mutagenesis to homologously recombine the newly synthesized polynucleotides.

8.16.5.9.5 Producing Hybrid Polynucleotides Which Express a Useful Hybrid Polypeptide It is a particularly preferred object of the invention to provide a process for producing hybrid polynucleotides which express a useful hybrid polypeptide by a series of steps comprising:

(a) producing polynucleotides by interrupting a polynucleotide amplification or synthesis process with a means for blocking or interrupting the amplification or synthesis process and thus providing a plurality of smaller or shorter polynucleotides due to the replication of the polynucleotide being in various stages of completion;

(b) adding to the resultant population of single- or double-stranded polynucleotides one or more single- or double-stranded oligonucleotides, wherein said added oligonucleotides comprise an area of identity in an area of heterology to one or more of the single- or double-stranded polynucleotides of the population;

(c) denaturing the resulting single- or double-stranded oligonucleotides to produce a mixture of single-stranded polynucleotides, optionally separating the shorter or smaller polynucleotides into pools of polynucleotides having various lengths and further optionally subjecting said polynucleotides to a PCR procedure to amplify one or more oligonucleotides comprised by at least one of said polynucleotide pools;

(d) incubating a plurality of said polynucleotides or at least one pool of said polynucleotides with a polymerase under conditions which result in annealing of said single-stranded polynucleotides at regions of identity between the single-stranded polynucleotides and thus forming of a mutagenized double-stranded polynucleotide chain;

(e) optionally repeating steps (c) and (d);

(f) expressing at least one hybrid polypeptide from said polynucleotide chain, or chains; and (g) screening said at least one hybrid polypeptide for a useful activity.

In a preferred aspect of the invention, the means for blocking or interrupting the amplification or synthesis process is by utilization of uv light, DNA adducts, DNA binding proteins.

In one embodiment of the invention, the DNA adducts, or polynucleotides comprising the DNA adducts, are removed from the polynucleotides or polynucleotide pool, such as by a process including heating the solution comprising the DNA fragments prior to further processing.

Having thus disclosed exemplary embodiments of the present invention, it should be noted by those skilled in the art that the disclosures are exemplary only and that various other alternatives, adaptations and modifications may be made within the scope of the present invention. Accordingly, the present invention is not limited to the specific embodiments as illustrated herein.

Without further elaboration, it is believed that one skilled in the art can, using the preceding description, utilize the present invention to its fullest extent. The following examples are to be considered illustrative and thus are not limiting of the remainder of the disclosure in any way whatsoever.

REFERENCES

Unless otherwise indicated, all references cited herein (supra and infra) are incorporated by reference in their entirety.

Alting-Mecs MA and Short JM: Polycos vectors: a system for packaging filamentous phage and phagemid vectors using lambda phage packaging extracts. *Gene* 137:1, 93–100, 1993.

Arkin AP and Youvan DC: An algorithm for protein engineering: simulations of recursive ensemble mutagenesis. *Proc Natl Acad Sci USA* 89(16):7811–7815, (Aug. 15) 1992.

Arnold FH: Protein engineering for unusual environments. *Current Opinion in Biotechnology* 4(4):450–455, 1993.

Ausubel FM, et al Editors. *Current Protocols in Molecular Biology*, Vols. 1 and 2 and supplements. (a.k.a. "The Red Book") Greene Publishing Assoc., Brooklyn, NY, ©1987.

Ausubel FM, et al Editors. *Current Protocols in Molecular Biology*, Vols. 1 and 2 and supplements. (a.k.a. "The Red Book") Greene Publishing Assoc., Brooklyn, NY, ©1989.

Ausubel FM, et al Editors. *Short Protocols in Molecular Biology: A Compendium of Methods from Current Protocols in Molecular Biology*. Greene Publishing Assoc., Brooklyn, NY, ©1989.

Ausubel FM, et al Editors. *Short Protocols in Molecular Biology: A Compendium of Methods from Current Protocols in Molecular Biology*, $2^{nd}$ Edition. Greene Publishing Assoc., Brooklyn, NY, ©1992.

Barbas CF 3d, Barn JD, Hoekstra DM, Lerner RA: Semisynthetic combinatorial antibody libraries: a chemical solution to the diversity problem. *Proc Natl Acad Sci USA* 89(10):4457–4461, 1992.

Bardwell AJ, Bardwell L, Johnson DK, Friedberg EC: Yeast DNA recombination and repair proteins Rad1 and Rad10 constitute a complex in vivo mediated by localized hydrophobic domains. *Mol Microbiol* 8(6):1177–1188, 1993.

Barret AJ, et al., eds.: *Enzyme Nomenclature: Recommendations of the Nomenclature Committee of the International Union of Biochemistry and Molecular Biology*. San Diego: Academic Press, Inc., 1992.

Bartel P, Chien CT, Sternglanz R, Fields S: Elimination of false positives that arise in using the two-hybrid system. *Biotechniques* 14(6):920–924, 1993.

Beaudry AA and Joyce GF: Directed evolution of an RNA enzyme. *Science* 257(5070):635–641, 1992.

Berger and Kimmel, *Methods in Enzymology*, Vol. 152, Guide to Molecular Cloning Techniques. Academic Press, Inc., San Diego, CA, ©1987. (Cumulative Subject Index: Vols. 135–139, 141–167, 1990, 272 pp.)

Bevan M: Binary Agrobacterium vectors for plant transformation. *Nucleic Acids Research* 12(22):8711–21, 1984.

Biocca 5, Pierandrei-Amaldi P, Cattaneo A: Intracellular expression of anti-p21ras single chain Fv fragments inhibits meiotic maturation of xenopus oocytes. *Biochem Biophys Res Commun* 197(2):422–427, 1993.

Bird et al. *Plant Mol Biol* 11:651, 1988.

Bogerd HP, Fridell RA, Blair WS, Cullen BR: Genetic evidence that the Tat proteins of human immunodeficiency virus types 1 and 2 can multimerize in the eukaryotic cell nucleus. *J Virol* 67(8):5030–5034, 1993.

Boyce COL, ed.: *Novo's Handbook of Practical Biotechnology*. $2^{nd}$ ed. Bagsvaerd, Denmark, 1986.

Brederode FT. Koper-Zawrthoff EC, Bol JF: Complete nucleotide sequence of alfalfa mosaic virus RNA 4. *Nucleic Acids Research* 8(10):2213–23, 1980.

Breitling F, Dubel S, Seehaus T, Klewinghaus I, Little M: A surface expression vector for antibody screening. *Gene* 104(2):147–153, 1991.

Brown NL, Smith M: Cleavage specificity of the restriction endonuclease isolated from Haemophilus gallinarum (Hga I). *Proc Natl Acad Sci USA* 74(8):3213–6, (Aug.) 1977.

Burton DR. Barbas CF 3d, Persson MA, Koenig S, Chanock RM, Lerner RA: A large array of human monoclonal antibodies to type 1 human immunodeficiency virus from combinatorial libraries of asymptomatic seropositive individuals. *Proc Natl Acad Sci USA* 88(22):10134–7, (Nov. 15) 1991.

Caldwell RC and Joyce GF: Randomization of genes by PCR mutagenesis. *PCR Methods Appl* 2(10):28–33, 1992.

Caton AJ and Koprowski H: Influenze virus hemagglutinin-specific antibodies isolatedf froma combinatorial expression library are closely related to the immune response of the donor. *Proc Natl Acad Sci USA* 87(16):6450–6454, 1990.

Chakraborty T, Martin JF, Olson EN: Analysis of the oligomerization of myogenin and E2A products in vivo using a two-hybrid assay system. *J Biol Chem* 267(25): 17498–501, 1992.

Chang CN, Landolfi NF, Queen C: Expression of antibody Fab domains on bacteriophage surfaces. Potential use for antibody selection. *J Immunol* 147(10):3610–4, (Nov. 15) 1991.

Chaudhary VK, Batra JK, Gallo MG, Willingham MC, FitzGerald DJ, Pastan I: A rapid method of cloning functional variable-region antibody genes in *Escherichia coli* as single-chain immunotoxins. *Proc Natl Acad Sci USA* 87(3):1066–1070, 1990.

Chien CT, Bartel PL, Sternglanz R, Fields S: The two-hybrid system: a method to identify and clone genes for proteins that interact with a protein of interest. Proc Natl Acad Sci USA 88(21):9578–9582, 1991.

Chiswell DJ, McCafferty J: Phage antibodies: will new 'coliclonal' antibodies replace monoclonal antibodies! *Trends Biotechnol* 10(3):80–84, 1992.

Chothia C and Lesk AM: Canonical structures for the hypervariable regions of immunoglobulins. *J Mol Biol* 196)4):901–917, 1987.

Chothia C, Lesk AM, Tramontano A, Levitt M, Smith-Gill SJ, Air G, Sheriff S, Padlan EA, Davies D, Tulip WR, et al: Conformations of immunoglobulin hypervariable regions. *Nature* 342(6252):877–883, 1989.

Clackson T, Hoogenboom HR, Griffiths AD, Winter G: Making antibody fragments using phage display libraries. *Nature* 352(6336):624–628, 1991.

Conrad M, Topal MD: DNA and spermidine provide a switch mechanism to regulate the activity of restriction enzyme *Nae I*. *Proc Natl Acad Sci USA* 86(24):9707–11, (Dec.) 1989.

Coruzzi G, Broglie R, Edwards C, Chua NH: Tissue-specific and light-regulated expression of a pea nuclear gene encoding the small subunit of ribulose-1,5-bisphosphate carboxylase. *EMBO J* 3(8): 1671–9, 1984.

Dasmahapatra B, DiDomenico B, Dwyer S, Ma J, Sadowski I, Schwartz J: A genetic system for studying the activity of a proteolytic enzyme. *Proc Natl Acad Sci USA* 89(9) :4159–4162, 1992.

Davis LG, Dibner MD, Battey JF. *Basic Methods in Molecular Biology*. Elsevier, New York, NY ©1986.

Delegrave S and Youvan DC. Biotechnology Research 11:1548–1552, 1993.

DeLong EF, Wu KY, Prezelin BB, Jovine RV: High abundance of Archaea in Antarctic marine picoplankton. *Nature* 371(6499):695–697, 1994.

Deng SJ, MacKenzie CR, Sadowska J, Michniewicz J, Young NM, Bundle Dr, Narang SA: Selection of antibody single-chain variable fragments with improved carbohydrate binding by phage display. *J Biol Chem* 269(13) :9533–9538, 1994.

Drauz K, Waldman H, eds.: *Enzyme Catalysis in Organic Synthesis: A Comprehensive Handbook.* Vol. 1. New York: VCH Publishers, 1995.

Drauz K, Waldman H, eds.: *Enzyme Catalysis in Organic Synthesis: A Comprehensive Handbook.* Vol. 2. New York: VCH Publishers, 1995.

Duan L, Bagasra O, Laughlin MA, Oakes JW, Pomerantz RJ: Potent inhibition of human immunodeficiency virus type 1 replication by an intracellular anti-Rev single-chain antibody. *Proc Natl Acad Sci USA* 91(11):5075–5079, 1994.

Durfee T, Becherer K, Chen PL, Yeh SH, Yang Y, Kilburn AE, Lee WH, Elledge SJ: The retinoblastoma protein associates with the protein phosphatase type I catalytic subunit. *Genes Dev* 7(4):555–569, 1993.

Ellington AD and Szostak JW: In vitro selection of RNA molecules that bind specific ligands. *Nature* 346(6287): 818–822, 1990.

Fields S and Song 0: A novel genetic system to detect protein-protein interactions. *Nature* 340(6230):245–246, 1989.

Firek S, Draper J, Owen MR. Gandecha A, Cockburn B, Whitelam GC: Secretion of a functional single-chain Fv protein in trmnsgenic tobacco plants and cell suspension cultures. *Plant Mol Biol* 23(4):861–870, 1993.

Forsblom S, Rigler R, Ehrenberg M, Philipson L: Kinetic studies on the cleavage of adenovirus DNA by restriction endonuclease Eco RI. *Nucleic Acids Res* 3(12):3255–69, (Dec.) 1976.

Foster GD, Taylor SC, eds.: *Plant Virology Protocols: From Virus Isolation to Transgenic Resistance. Methods in Molecular Biology,* Vol. 81. New Jersey: Humana Press Inc., 1998.

Franks F, ed.; *Protein Biotechnology; Isolation. Characterization, and Stabilization.* New Jersey: Humana Press Inc., 1993.

Germino FJ, Wang ZX, Weissman SM: Screening or in viva protein-protein interactions. *Proc Natl Acad Sci USA* 90(3):933–937, 1993.

Gingeras TR, Brooks JE: Cloned restriction/modification system from Pseudomonas aeruginosa. *Proc Natl Acad Sci USA* 80(2):402–6, 1983 (Jan).

Godfrey T, West S, eds.: *Industrial Enzymology.* 2nd ed. London: Macmillan Press Ltd, 1996.

Gottschalk G: *Bacterial Metabolism.* 2nd ed. New York: Springer-*Verlag Inc.*, 1986.

Gresshoff PM, ed.: *Technology Transfer of Plant Biotechnology.* Current Topics in Plant Molecular Biology. Boca Raton: CRC Press, 1997.

Griffin HG, Griffin AM, eds.: PCR Technology: *Current Innovations.* Boca Raton: CRC Press, Inc., 1994.

Gruber M, Schodin BA, Wilson ER, Kranz DM: Efficient tumor cell lysis mediated by a bispecific single chain antibody expressed in Escherichia coli. *J Immunol* 152 (11):5368–5374, 1994.

Guarente L: Strategies for the identification of interacting proteins. *Proc Natl Acad Sci USA* 90(5): 1639–1641, 1993.

Guilley H, Dudley RK, Jonard G, Balazs E, Richards KE: Transcription of Cauliflower mosaic virus DNA: detection of promoter sequences, and characterization of transcripts. *Cell* 30(3):763–73, 1982.

Hansen G, Chilton MD: Lessons in gene transfer to plants by a gifted microbe. *Curr Top Microbiol Immunol* 240:21–57, 1999.

Hardy CF, Sussel L. Shore D: A RAP1-interacting protein involved in transcriptional silencing and telomere length regulation. *Genes Dev* 6(5):801–814, 1992.

Hartman HT, et al.: *Plant Propagation: Principles and Practices.* 6th ed. New Jersey: Prentice Hall, Inc., 1997.

Hawkins RE and Winter G: Cell selection strategies for making antibodies from variable gene libraries: trapping the memoly pool. *Eur J Immunol* 22(3):867–870, 1992.

Holvoet P, Laroche Y, Lijnen HR, Van Hoef B, Brouwers E, De Cock F, Lauwereys M, Gansemans Y, Collen D: Biochemical characterization of single-chain chimeric plasminogen activators consisting of a single-chain Fv fragment of a fibrin-specific antibody and single-chain urokinase. *Eur J Biochem* 210(3):945–952, 1992.

Honjo T, Alt FW, Rabbitts Th (eds): *Immunoglobulin genes.* Academic Press: San Diego, CA, pp. 361–368, ©1989.

Hoogenboom HR, Griffiths AD, Johnson KS, Chiswell DJ, Judson P, Winter G: Multi-subunit proteins on the surface of filarnentous phage: methodologies for displaying antibody (Fab) heavy and light chains. *NucleicAcids Res* 19(15):4133–4137, 1991.

Huse WD, Sastry L, Iverson SA, Kang AS, Alting-Mees M, Burton DR. Benkovic Si, Lerner RA: Generation of a large combinatorial library of the inununoglobulin repertoire in phage lambda. *Science* 246(4935):1275–1281, 1989.

Huston JS, Levinson D, Mudgett-Hunter M, Tai MS. Novotney J, Margolies MN, Ridge RI, Bruccoleri RE, Haber E, Crea R, et al: Protein engineering of antibody binding sites: recovery of specific activity in an anti-digoxin single-chain Fv analogue produced in Escherichia coli. *Proc Natl Acad Sci USA* 85(16):5879–5883, 1988.

Ivan Lefkovits, Editor. Immunology methods manual : the comprehensive sourcebook of techniques. Academic Press, San Diego, ©1997.

Iwabuchi K, Li B, Bartel P, Fields S: Use of the two-hybrid system to identify the domain of p53 involved in oligomerization. *Oncogene* 8(6):1693–1696, 1993.

Jackson AL, Pahl PM, Harrison K, Rosamond J, Sclafani RA: Cell cycle regulation of the yeast Cdc7 protein kinase by association with the Dbf4 protein, *Mol Cell Biol* 13(5):2899–2908, 1993.

Johnson S and Bird RE: *Methods Enzymol* 203:88, 1991.

Kabat et al: *Sequences of Proteins of Immunological Interest,* 4th Ed. U.S. Department of Health and Human Services, Bethesda, MD (1987)

Kang AS, Barbas CF, Janda KD, Benkovic SJ, Lerner RA: Linkage of recognition and replication functions by assembling combinatorial antibody Fab libraries along phage surfaces. *Proc Natl Acad Sci USA* 88(10): 4363–4366, 1991.

Kettleborougji CA, Ansell Ku, Alien RW, Rosell-Vives E, Gussow DH, Bendig MM: Isolation of tumor cell-specific single-chain Fv from immunized mice using phage-antibody libraries and the re-construction of whole antibodies from these antibody fragments. *Eur J Immunol* 24(4):952–958, 1994.

Kruger DH, Barcak GJ, Reuter M, Smith HO: EcoRII can be activated to cleave refractory DNA recognition sites. *Nucleic Acids Res.* 16(9):3997–4008, (May 11)1988.

Lalo D, Carles C, Sentenac A, Thuriaux P: Interactions between three common subunits of yeast RNA polymerases I and III. *Proc Natl Acad Sci USA* 90(12) :5524–5528, 1993.

Laskowski M Sr: Purification and properties of venom phosphodiesterase. *Methods Enzymol* 65(1):276–84, 1980.

Lefkovits I and Pernis B, Editors. *Immunological Methods,* Vols. I and II. Academic Press, New York, NY. Also Vol. III published in Orlando and Vol. IV published in San Diego. ©1979-.

Lerner RA, Kang AS, Bain JD, Burton DR, Barbas CF 3d: Antibodies without immunization. *Science*258(5086) :1313–1314, 1992.

Leung, D.W., et al, *Technique*, 1:11–15, 1989.

Li B and Fields S: Identification of mutations in p53 that affect its binding to SV40 large T antigen by using the yeast two-hybrid system. FASEBJ 7(10):957–963, 1993.

Lilley GG, Doelzal O, Hillyard CJ, Bernard C, Hudson PJ: Recombinant single-chain antibody peptide conjugates expressed in Escherichia coli for the rapid diagnosis of HIV. *J Immunol Methods* 171(2):211–226, 1994.

Lowman HB, Bass SH, Simpson N, Wells JA: Selecting high-affinity binding proteins by monovalent phage display. *Biochemistry* 30(45):10832–10838, 1991.

Luban I, Bossolt KL, Franke EK, Kalpana GV, Goff SP: Human immunodeficiency virus type 1 Gag protein binds to cyclophilins A and B. *Cell* 73(6):1067–1078, 1993.

Madura K, Dohrnen lU, Varshavsky A: N-recognin/Ubc2 interactions in the N-end rule pathway. *J Biol Chem* 268(16):12046–54, (Jun. 5)1993.

Marks JD, Griffiths Ad, Malmqvist M, Clackson TP, Bye JM, Winter G: By-passing immunization: building high affinity human antibodies by chain shuffling. *Biotechnology* (N Y) 10(7):779–783, 1992.

Marks JD, Hoogenboom HR, Bonnert TP, McCafferty J, Griffiths AD, Winter G: By-passing immunization. Human antibodies from V-gene libraries displayed on phage. *J Mol Biol* 222(3):581–597, 1991.

Marks JD, Hoogenboom HR, Griffiths AD, Winter G: Molecular evolution of proteins on filamentous phage. Mimicking the strategy of the immune system. *J Biol Chem* 267(23):16007–16010, 1992.

Maxam AM, Gilbert W: Sequencing end-labeled DNA with base-specific chemical cleavages. *Methods Enzymol* 65(1): 499–560, 1980.

McCafferty J, Griffiths AD, Winter G, Chiswell DJ: Phage antibodies: filamentous phage displaying antibody variable domains. *Nature* 348(6301):552–554, 1990.

Method of DNA sequencing.

Miller JH. *A Short Course in Bacterial Genetics: A Laboratory Manual and Handbook for Escherichia coli and Related Bacteria* (see inclusively p. 445). Cold Spring Harbor Laboratory Press, Plainview, NY, ©1992.

Milne GT and Weaver DT: Dominant negative alleles of RAD52 reveal a DNA repair/recombination complex including Rad5I and Rad52. *Genes Dev* 7(9):1755–1765, 1993.

Mullinax RL, Gross EA, Amberg JR. Hay BN, Hogrefe HH, Kubtiz MM, Greener A, Alting-Mees M, Ardourel D, Short 3M, et al: Identification of human antibody fragment clones specific for tetanus toxoid in a bacteriophage lambda immunoexpression library. *Proc natl Acad Sci USA* 87(20):8095–9099, 1990.

Nath K, Azzolina BA: in *Gene Amplification and Analysis* (ed. Chirikjian JG), vol. 1, p. 113, Elsevier North Holland, Inc., New York, New York, ©1981.

Needleman SB and Wunsch CD: A general method applicable to the search for similarities in the amino acid sequence of two proteins. J Mol Biol 48(3):443–453, 1970.

Nelson M, Christ C, Schildkraut I: Alteration of apparent restriction endonuclease recognition specificities by DNA methylases. *Nucleic Acids Res* 12(13):5165–73, 1984 (Jul. 11).

Nicholls PJ, Johnson VG, Andrew SM, Hoogenboom HR, Raus JC, Youle RJ: Characterization of single-chain antibody (sFv)-toxin fusion proteins produced in vitro in rabbit reticulocyte lysate. *J Biol Chem* 268(7):5302–5308, 1993.

Oller AR, Vanden Broek W, Conrad M, Topal MD: Ability of DNA and spermidine to affect the activity of restriction endonucleases from several bacterial species. *Biochemistry* 30(9):2543–9, (Mar. 5)1991.

Owen MRL, Pen J:i Transgenic Plants: A Production System for Industrial and Pharmaceutical Proteins. Chichester: John Wiley & Sons, 1996.

Owens RJ and Young RJ: The genetic engineenng a monoclonal antibodies. *J Immunol Methods* 168(2):149–165, 1994.

Pearson WR and Lipman DJ: Improved tools for biological sequence comparison. *Proc Natl Acad Sci USA* 85(8): 2444–2448, 1988.

Pein CD, Reuter M, Meisel A, Cech D, Kruger DH: Activation of restriction endonuclease EcoRII does not depend on the cleavage of stimulator DNA. *Nucleic Acids Re s* 19(19):5139–42, (Oct. 11)1991.

Persson MA, Caothien RH, Burton DR: Generation of diverse high-affinity human monoclonal antibodies by repertoire cloning. *Proc Natl Acad Sci USA* 88(6): 2432–2436, 1991.

Perun TJ, Propst CL, eds.: *Computer-Aided Drug Design: Methods and Applications*. New York: Marcel Dekker, Inc., 1989.

Qiang BQ, McClelland M, Poddar S, Spokauskas A, Nelson M: The apparent specificity of NotI (5'-GCGGCCGC-3') is enhanced by M.FnuDII or M.BepI methyltransferases (5'-mCGCG-3'): cutting bacterial chromosomes into a few large pieces. *Gene* 88(1):101–5, (Mar. 30) 1990.

Queen C, Foster J, Stauber C, Stafford J: Cell-type specific regulation of a kappa immunoglobulin gene by promoter and enhance elements. *Immunol Rev* 89:49–68, 1986.

Raleigh EA, Wilson G: *Escherichia coli* K-12 restricts DNA containing 5-methylcytosine. *Proc Natl Acad Sci USA* 83(23):9070–4, (Dec.) 1986.

Reidhaar-Olson JF and Sauer RT: Combinatorial cassette mutagenesis as a probe of the informational content of protein sequences. *Science* 241(4861):53–57, 1988.

Riechmann L and Weill M: Phage display and selection of a site-directed randomized single-chain antibody Fv fragment for its affinity improvement. *Biochemistry* 32(34): 8848–8855, 1993.

Roberts RJ, Macelis D: REBASE—restriction enzymes and methylases. *Nucleic Acids Res* 24(1):223–35, (Jan 1)1996.

Ryan AJ, Royal CL, Hutchinson J, Shaw CH: Genomic sequence of a 12S seed storage protein from oilseed rape (Brassica napus c.v. jet neuf). *Nucl Acids Res* 17(9):3584, 1989.

Sambrook J, Fritsch EF, Maniatis T. *Molecular Cloning: A Laboratory Manual*. Cold Spring Harbor Laboratory Press, Cold Spring Harbor, NY, ©1982.

Sambrook J, Fritsch EF, Maniatis T. *Molecular Cloning: A Laboratory Manual*. Second Edition. Cold Spring Harbor Laboratory Press, Cold Spring Harbor, NY, ©1989.

Scopes RK. *Protein Purification: Principles and Practice*. Springer-Verlag, New York, NY, ©1982.

Segel IH: *Enzyme Kinetics: Behavior and Analysis of Rapid Equilibrium and Steady-State Enzyme Systems*. New York: John Wiley & Sons, Inc., 1993.

Silver SC and Hunt SW 3d: Techniques for cloning cDNAs encoding interactive transcriptional regulatory proteins. *Med Biol Rep* 17(3):155–165, 1993.

Smith TF, Waterman MS, Fitch WM: Comparative biosequence metrics. *J Mol Evol* S18(1):38–46, 1981.

Smith TF, Waterman MS. *Adv Appl Math* 2: 482-end of article, 1981.

Smith TF, Waterman MS: Identification of common molecular subsequences. *J Mol Biol* 147(1):195–7, (Mar. 25) 1981.

Smith TF, Waterman MS; Overlapping genes and information theory. *J Theor Biol* 91(2):379–80, (Jul. 21) 1981.

Staudinger J, Perry M, Elledge SJ, Olson EN: Interactions among vertebrate helix-loop-helix proteins in yeast using the two-hybrid system. *J Biol Chem* 26(7):4608–4611, 1993.

Stemmer WP, Morris SK, Wilson BS: Selection of an active single chain Fv antibody from a protein linker library prepared by enzymatic inverse PCR. *Biotechniques* 14(2):256–265, 1993.

Stemmer WP: DNA shuffling by random fragmentation and reassembly: in vitro recombination for molecular evolution. *Proc Natl Acad Sci USA* 91(22):10747–10751, 1994.

Sun D, Hurley LH: Effect of the (+)-CC-1065-(N3-adenine) DNA adduct on in vitro DNA synthesis mediated by *Escherichia coli* DNA polymerase. *Biochemistry* 31:10, 2822-9, (Mar. 17) 1992, Tague BW, Dickinson CD, Chrispeels MJ: A short domain of the plant vacuolar protein phytohemagglutinin targets invertase to the yeast vacuole. *Plant Cell* 2(6):533–46, (Jun.) 1990.

Takahashi N, Kobayashi I: Evidence for the double-strand break repair model of bacteriophage lambda recombination. *Proc Natl Acad Sci USA* 87(7):2790–4, (Apr.) 1990.

Thiesen HJ and Bach C: Target Detection Assay (TDA): a versatile procedure to determine DNA binding sites as demonstrated on SP1 protein. *Nucleic Acids Res* 18(11):3203–3209, 1990.

Thomas M, Davis RW: Studies on the cleavage of bacteriophage lambda DNA with EcoRI Restriction endonuclease. *J Mol Biol* 91(3):315–28, (Jan. 25) 1975.

Tingey SV, Walker EL, Corruzzi GM: Glutamine synthetase genes of pea encode distinct polypeptides which are differentially expressed in leaves, roots and nodules. *EMBO J* 6(1):1–9, 1987.

Topal MD, Thresher RJ, Conrad M, Griffith J: NaeI endonuclease binding to pBR322 DNA induces looping. *Biochemistry* 30(7):2006–10, (Feb. 19) 1991.

Tramontano A, Chothia C, Lesk AM: Framework residue 71 is a major determinant of the position and conformation of the second hypervariable region in the VH domains of immunoglobulins. *J Mol Biol* 215(1):175–182, 1990.

Tuerk C and Gold L: Systematic evolution of ligands by exponential enrichment: RNA ligands to bacteriophage T4 DNA polymerase. *Science* 249(4968):505–510, 1990.

USPN 4,683,195; Filed Feb. 7, 1986, Issued Jul. 28. 1987. Mullis KB, Erlich HA, Arnheim N, Horn GT, Saiki RK, Scharf SJ: Process for Amplifying, Detecting, and/or Cloning Nucleic Acid Sequences.

USPN 4,683,202; Filed Oct. 25, 1985, Issued Jul. 28, 1987. Mullis KB: Process for Amplifying Nucleic Acid Sequences.

USPN 4,704,362; Filed Nov. 5, 1979, Issued Nov. 3, 1987. Itakura K, Riggs AD: Recombinant Cloning Vehicle Microbial Polypeptide Expression.

USPN 4,713,337; Filed Jan. 3, 1985, Issued Dec. 15, 1987. Jasin M, Schimmel PR: Method for deletion of a gene from a bacteria.

USPN 4,732,856; Filed Apr. 3, 1984, Issued Mar. 22, 1988. Federoff NV: Transposable elements and process for using same.

USPN 4,963,487; Filed Sep. 14, 1987, Issued Jan. 16, 1990. Schimmel PR: Method for deletion of a gene from a bacteria.

USPN 5,354,656; Filed Oct. 2, 1989, Issued Oct. 11, 1994. Sorge, Joseph A. ; Huse, William D.:

USPN 5,385,835; Filed May 19, 1994, Issued Jan. 31, 1995. Helentjaris, Timothy ; Nienhuis, James: Identification and localization and introgression into plants of desired multigenic traits.

USPN 5,453,247; Filed Nov. 23, 1993, Issued Sep. 26, 1995. Beavis, Ronald C. ; Chait, Brian T.: Instrument and method for the sequencing of genome.

USPN 5,604,100; Filed Jul. 19, 1995, Issued Feb. 18, 1997. Penn, Mark W.: Method and system for sequencing genomes.

USPN 5,670,321; Filed May 10, 1995, Issued Sep. 23, 1997. Kimmel, Bruce E. ; Ellis, Michael ; Ruddy, David: Efficient method to conduct large-scale genome sequencing.

USPN 5,925,808; Filed Dec. 19, 1997, Issued Jul. 20, 1999. Oliver, Melvin John ; Quisenberry, Jerry Edwin ; Trolinder, Norma Lee Glover ; Keim, Don Lee: Control of Plant Gene Expression.

USPN 5,953,727; Filed Mar. 6, 1997, Issued Sep. 14, 1999. Maslyn, Timothy J. ; Au-Young, Janice ; Hillman, Jennifer L. ; Hibbert, Harold ; Akerblom, Ingrid E. ; Cheng, Rachel J. ; Tang, Yuanhua T.:Project-based full-length biomolecular sequence database.

USPN 5,965,443; Filed Sep. 9, 1996, Issued Oct. 12, 1999. Reznikoff WS, Goryshin IY: System for in vitro transposition.

USPN 5,981,177; Filed Jan. 25, 1995, Issued Nov. 9, 1999. Demirjian DC, Casadaban MJ, Weber M, Gaines GL: Protein fusion method and constructs.

USPN 5,994,058; Filed Mar. 20, 1995, Issued Nov. 30, 1999. Senapathy, Periannan:Method For Contiguous Genome Sequencing.

USPN 6,023,659; Filed Mar. 6, 1997, Issued Feb. 8, 2000. Seilhamer, Jeffrey J. ; Akerblom, Ingrid E. ; Altus, Christina M. ; Klingler, Tod M. ; Russo, Frank ; Au-Young, Janice ; Hilhnan, Jennifer L. ; Maslyn, Timothy J.: Database System Employing Protein Function Hierarchies For Viewing Biomolecular Sequence Data.

van de Poll ML, Lafleur MV, van Gog F, Vrieling H, Meerman JH: N-acetylated and deacetylated ∝4'-fluoro-4-aminobiphenyl and 4-aminobiphenyl adducts differ in their ability to inhibit DNA replicatin of single-stranded M13 in vitro and of single-stranded phi X174 in *Escherichia coli*. *Carcinogenesis* 13(5):751–8, (May) 1992.

Vojtek AB, Hollenberg SM, Cooper JA: Mammalian Ras interacts directly with the serine/threonine kinase Raf. *Cell* 74(1):205–214, 1993.

Wenzler H, Mignery G, Fisher L, Park W: Sucrose-regulated expression of a chimeric potato tuber gene in leaves of transgenic tobacco plants. *Plant Mol Biol* 13(4):347–54, 1989.

White JS, White DC: *Source Book of Enzymes*. Boca Raton: CRC Press, 1997.

Williams and Barclay, in *Immunoglobulin Genes. The Immunoglobulin Gene Superfamily.*

Winnacker EL. *From Genes to Clones: Introduction to Gene Technology*. VCH Publishers, New York, NY, ©1987.

Winter G and Milstein C: Man-made antibodies. *Nature* 349(6307):293–299, 1991.

WO 00/04190; Filed Jul. 15, 1999, Published Jan. 27, 2000. Del Cardayre S, Tobin M, Stemmer WP, Ness JE, Minshull J, Patten PA, Subramanian V, Castle LA, Krebber CM, Bass S, Zhang Y, Cox T, Huisman G, Yuan L, Affholter JA: Evolution of whole cells and organisms by recursive sequence recombination.

WO 00/09755; Filed Aug. 12, 1999, Published Feb. 24, 2000. Zarling D, Reddy G, Pati S: Domain specific gene evolution.

WO 88/08453; Filed Apr. 14, 1988, Published Nov. 3, 1988. Alakhov JB. Baranov, VI, Ovodov SJ, Ryabova LA, Spirin AS: Method of Obtaining Polypeptides in Cell-Free Translation System.

WO 90/05785; Filed Nov. 15, 1989, Published May 31, 1990. Schultz P: Method for Site-Specifically Incorporating Unnatural Amino Acids into Proteins.

WO 90/07003; Filed Jan. 27, 1989, Published Jun. 28, 1990. Baranov VI, Morozov IJ, Spirin AS: Method for Preparative Expression of Genes in a Cell-free System of Conjugated Transcription/translation.

WO 91/02076; Filed Jun. 14, 1990, Published Feb. 21, 1991. Baranov VI, Ryabova LA, Yarchuk OB, Spirin AS: Method for Obtaining Polypeptides in a Cell-free System.

WO 91/05058; Filed Oct. 5, 1989, Published Apr. 18, 1991. Kawasaki G: Cell-free Synthesis and Isolation of Novel Genes and Polypeptides.

WO 91/17271; Filed May 1, 1990, Published Nov. 14, 1991. Dower WJ, Cwirla SE: Recombinant Library Screening Methods.

WO 91/18980; Filed May 13, 1991, Published Dec. 12, 1991. Devlin JJ: Compositions and Methods for Indentifying Biologically Active Molecules.

WO 91/19818; Filed Jun. 20, 1990, Published Dec. 26, 1991. Dower WJ, Cwirla SE, Barrett RW: Peptide Library and Screening Systems.

WO 92/02536; Filed Aug. 1, 1991, Published Feb. 20, 1992. Gold L, Tuerk C: Systematic Polypeptide Evolution by Reverse Translation.

WO 92/03918; Filed Aug. 28, 1991, Published Mar. 19, 1992. Lonberg N, Kay RM: Transgenic Non-human Animals Capable of Producing Heterologous Antibodies.

WO 92/05258; Filed Sep. 17, 1991, Published Apr. 2, 1992. Fincher GB: Gene Encoding Barley Enzyme.

WO 92/14843; Filed Feb. 21, 1992, Published Sep. 3, 1992. Toole JJ, Griffin LC, Bock LC, Latham JA, Muenchau DD, Krawczyk 5: Aptamers Specific for Biomolecules and Method of Making.

WO 93/08278; Filed Oct. 15, 1992, Published Apr. 29, 1993. Schatz PJ, Cull MG, Miller JF, Stemmer WP: Peptide Library and Screening Method.

WO 93/12227; Filed Dec. 17, 1992, Published Jun. 24, 1993. Lonberg N, Kay RM: Transgenic Non-human Animals Capable of Producing Heterologous Antibodies.

WO 94/25585; Filed Apr. 25, 1994, Published Nov. 10, 1994. Lonberg N, Kay RM: Transgenic Non-human Animals Capable of Producing Heterologous Antibodies.

WO 95/00530; Filed Jun. 6, 1994, Published Jan. 1, 1995. Fodor, Stephen, P., A. ; Lipshutz, Robert, J. ; Huang, Xiaohua ; Jevons, Luis, Carlos: Hybridization and Sequencing of Nucleic Acids.

WO 96/21031; Filed Jun. 7, 1995, Published Jul. 11, 1996. Tricoli, David, M. ; Carney, Kim, J. ; Russell, Paul, F. ; Quemada, Hector, D. ; Mcmaster, J., Russell ; Reynolds, John, F. ; Deng, Rosaline, Z.: Transgenic Plants Expressing DNA Constructs Containing A Plurality Of Genes To Impart Virus Resistance.

WO 96/27025; Filed Feb. 21, 1996, Published Sep. 6, 1996. Rabani, Ely, Michael:Device, Compounds, Algorithms, And Methods Of Molecular Characterization And Manipulation With Molecular Parallelism.

WO 97/17429; Filed Nov. 8, 1996. Published May 15, 1997. Oglevee-O'donovan, Wendy ; Arteca, Richard, N. ; Arteca, Jeannette ; Stoots, Eleanor: Method For The Commercial Production Of Transgenic Plants.

WO 97/35966; Filed Mar. 20, 1997, Published Oct. 2, 1997. Minshull J, Stemmer WP: Methods and compositions for cellular and metabolic engineering.

WO 97/37041; Filed Mar. 18, 1997, Published Oct. 9, 1997. Köster, Hubert: DNA Sequencing By Mass Spectrometry.

WO 97/42348; Filed May 5, 1997, Published Nov. 13, 1997. Köster, Hubert ; Van Den Boom, Dirk ; Ruppert, Andreas: Process For Direct Sequencing During Template Amplification.

WO 98/26407; Filed Dec. 11, 1997, Published Jun. 18, 1998. Sabatini, Cathryn, E. ; Heath, Joe, Don ; Covitz, Peter, A. ; Klinger, Tod, M. ; Russo, Frank, D. ; Berry, Stephanie, F.: Database And System For Storing, Comparing And Displaying Genomic Information.

WO 98/26408; Filed Dec. 11, 1997, Published Jun. 18, 1998. Sabatini, Cathryn, E. ; Heath, Joe, Don ; Covitz, Peter, A. ; Klingler, Tod, M. ; Russo, Frank, D. ; Berry, Stephanie, F.:Database And System For Determining, Storing And Displaying Gene Locus Information.

WO 98/31833; Filed Dec. 12, 1997, Published Jul. 23, 1998. Ju, Jingyue: Nucleic Acid Sequencing With Solid Phase Capturable Terminators.

WO 98/31834; Filed Dec. 12, 1997, Published Jul. 23, 1998. Ju, Jingyue: Sets Of Labeled Energy Transfer Fluorescent Primers And Their Use In Multi Component Analysis.

WO 98/31837; Filed Jan. 16, 1998, Published Jul. 23, 1998. Delcardayre SB, Tobin MB, Stemmer WP, Ness JE, Minshull J, Patten P: Evolution of whole cells and organisms by recursive sequence recombination.

WO 98/36085; Filed Feb. 13, 1998, Published Aug. 20, 1998. Sutliff, Thomas, D. ; Rodriguez, Raymond, L.: Production Of Mature Proteins In Plants.

WO 98/37223; Filed Feb. 18, 1998, Published Aug. 27, 1998. Pang, Sheng-Zhi ; Gonsalves, Dennis ; Jan, Fuh-Jyh: DNA Construct To Confer Multiple Traits On Plants.

WO 99/35494; Filed Jan. 8, 1999, Published Jul. 15, 1999. Tally FP, Tao J, Wendler PA, Connelly G, Gallant PL: Method for identifying validated target and assay combinations.

WO 99/37755; Filed Dec. 11, 1998, Published Jul. 29, 1999. Pati S, Zarling David, Lehman CW, Zeng H: The use of consensus sequences for targeted homologous gene isolation and recombination in gene families.

WO 99/49403; Filed Mar. 25, 1999, Published Sep. 30, 1999. Lincoln, Stephen, E. ; Hodgson, David, M. ; Spiro, Peter, A. ; Russo, Frank, D. ; Akerblom, Ingrid, E. ; Hillman, Jennifer, L. ; Jones, Anissa, Lee ; Bratcher, Shawn, Robert ; Cohen, Howard, Jerome ; Dufour, Gerard ; Wood, Michael, Peter ; Koleszar, Alexander, George ; Banville, Steven, C.: System And Methods For Analyzing Biomolecular Sequences.

WO95/11995; Filed Oct. 26, 1994, Published May 4, 1995. Chee M, Cronin MT, Fodor SP, Gingeras TR, Huang XC, Hubbell EA, Lipshutz RJ, Lobban PE, Miyada CG, Morris MS, Shah N, Sheldon EL: Arrays Of Nucleic Acid Probes On Biological Chips.

Wong CH, Whitesides GM: *Enzymes in Synthetic Organic Chemistry*. Vol. 12. New York: Elsevier Science Publications, 1995.

Yang X, Hubbard EJ, Carlson M: A protein kinase substrate identified by the two-hybrid system. *Science* 257(5070): 680–2, (Jul. 31)1992.

What is claimed is:

1. A method of producing an improved organism having a desirable trait, the method comprising:
   a) obtaining an initial population of organisms,
   b) generating a set of mutagenized organisms, from the initial population, wherein non-stochastic genetic mutations are represented in the set of mutagenized organisms, and
   c) identifying the desirable trait exhibited by one of the set of mutagenized organisms, thereby producing the improved organism.

2. The method of claim 1, wherein the set of substantial genetic mutations in step b) is comprised of a knocking out of at least 15 different genes.

3. The method of claim 1, wherein the set of substantial genetic mutations in step b) is comprised of a knocking out of at least 50 different genes.

4. The method of claim 1, wherein the set of substantial genetic mutations in step b) is comprised of a knocking out of at least 100 different genes.

5. The method of claim 1, wherein the set of substantial genetic mutations in step b) is comprised of an introduction of at least 15 different genes.

6. The method of claim 1, wherein the set of substantial genetic mutations in step b) is comprised of an introduction of at least 50 different genes.

7. The method of claim 1, wherein the set of substantial genetic mutations in step b) is comprised of an introduction of at least 100 different genes.

8. The method of claim 1, wherein the set of substantial genetic mutations in step b) is comprised of an alteration in the expression of at least 15 different genes.

9. The method of claim 1, wherein the set of substantial genetic mutations in step b) is comprised of an alteration in the expression of at least 50 different genes.

10. The method of claim 1, wherein the set of substantial genetic mutations in step b) is comprised of an alteration in the expression of at least 100 different genes.

11. A method of producing an improved organism having a desirable trait, the method comprising:
   a) obtaining an initial population of organisms,.
   b) generating a set of mutagenized organisms from the initial population, each having at least one genetic mutation, wherein non-stochastic genetic mutations are represented in the set of mutagenized organisms,
   c) detecting the manifestation of at least two genetic mutations which contribute to the desired trait,
   d) introducing the at least two detected genetic mutations into one organism, and
   e) optionally repeating any of the steps, thereby producing an improved organism having a desirable trait.

12. The method of claim 11, wherein step d) is comprised of a knocking out of at least 15 different genes in one organism.

13. The method of claim 11, wherein step d) is comprised of a knocking out of at least 50 different genes in one organism.

14. The method of claim 11, wherein step d) is comprised of a knocking out of at least 100 different genes in one organism.

15. The method of claim 11, wherein step d) is comprised of an introduction of at least 15 different genes into one organism.

16. The method of claim 11, wherein step d) is comprised of an introduction of at least 50 different genes into one organism.

17. The method of claim 11, wherein step d) is comprised of an introduction of at least 100 different genes into one organism.

18. The method of claim 11, wherein step d) is comprised of an alteration in the expression of at least 15 different genes in one organism.

19. The method of claim 11, wherein step d) is comprised of an alteration in the expression of at least 50 different genes in one organism.

20. The method of claim 11, wherein step d) is comprised of an alteration in the expression of at least 100 different genes in one organism.

21. A method for identifying a gene that alters a trait of an organism, the method comprising:

a) obtaining an initial population of organisms, b) generating a set of mutagenized organisms from the initial population of organisms, wherein non-stochastic genetic mutations are represented in the set of mutagenized organisms, and c) identifying a mutagenized organisms exhibiting the altered trait, and d) determining the nucleotide sequence of a gene having the genetic mutation in the organism identified in step (c), thereby identifying the gene that alters the trait of the organism.

22. A method for producing an organism with an improved trait, the method comprising:

a) functionally knocking out an endogenous gene in a substantially clonal population of organisms;

b) transferring a library of altered genes into the substantially clonal population of organisms, wherein each altered gene differs from the endogenous gene at only one codon to produce a population of mutagenized organisms;

c) detecting a mutagenized organism having an improved trait, thereby producing an organism with an improved trait.

23. The method of any one of claims 1, 11, 21 or 22, wherein the trait is selected from the group of: an ability to produce a substance, an ability to not produce a substance, an increased ability to produce a substance, a decreased ability to produce a substance, viability under pre-defined conditions, non-viability under pre-defined conditions, altered behavior, change in growth rate, change in size, change in morphology, an alteration in a morphological characteristic, and any combination thereof.

24. The method of any one of claims 1, 11, 21 or 22, wherein the improved trait comprises differential activation of selected inactive gene products in the organism.

* * * * *